(12) United States Patent
McAllister et al.

(10) Patent No.: US 12,257,247 B2
(45) Date of Patent: Mar. 25, 2025

(54) TARGETED DEGRADATION OF VAV1

(71) Applicant: Monte Rosa Therapeutics AG, Basel (CH)

(72) Inventors: Laura Ann McAllister, Basel (CH); Andreas Ritzen, Basel (CH); Vladimiras Oleinikovas, Basel (CH)

(73) Assignee: Monte Rosa Therapeutics AG, Basel (CH)

( * ) Notice: Subject to any disclaimer, the term of this patent is extended or adjusted under 35 U.S.C. 154(b) by 0 days.

(21) Appl. No.: 18/633,272

(22) Filed: Apr. 11, 2024

(65) Prior Publication Data

US 2024/0285604 A1 Aug. 29, 2024

Related U.S. Application Data

(63) Continuation of application No. PCT/US2024/010733, filed on Jan. 8, 2024.

(60) Provisional application No. 63/437,951, filed on Jan. 9, 2023.

(51) Int. Cl.
| | |
|---|---|
| *A61K 31/4545* | (2006.01) |
| *A61P 1/04* | (2006.01) |
| *A61P 19/02* | (2006.01) |
| *A61P 37/06* | (2006.01) |
| *C07D 401/10* | (2006.01) |

(52) U.S. Cl.
CPC ............ *A61K 31/4545* (2013.01); *A61P 1/04* (2018.01); *A61P 19/02* (2018.01); *A61P 37/06* (2018.01); *C07D 401/10* (2013.01)

(58) Field of Classification Search
CPC ........ A61K 31/4545; A61P 1/04; A61P 19/02; A61P 37/06; C07D 401/10
USPC ......................................................... 514/318
See application file for complete search history.

(56) References Cited

U.S. PATENT DOCUMENTS

| | | |
|---|---|---|
| 2006/0270686 A1 | 11/2006 | Kelly et al. |
| 2021/0386721 A1 | 12/2021 | Zhu et al. |
| 2022/0363671 A1 | 11/2022 | Axford et al. |

FOREIGN PATENT DOCUMENTS

| | | |
|---|---|---|
| CN | 115232125 A | 10/2022 |
| CN | 115536657 A | 12/2022 |
| WO | 2020156323 A1 | 8/2020 |
| WO | 2021011631 A1 | 1/2021 |
| WO | 2021180103 A1 | 9/2021 |
| WO | WO2022012622 A1 | 1/2022 |
| WO | 2022068849 A1 | 4/2022 |
| WO | 2022235945 A1 | 11/2022 |
| WO | 2022246025 A1 | 11/2022 |
| WO | 2024018403 A1 | 1/2024 |

OTHER PUBLICATIONS

Xue, Jiang-Hao et al., "Deaminative bromination, chlorination, and iodination of primary amines", iScience, 26 (106255):1-33, Mar. 17, 2023.

(Continued)

*Primary Examiner* — Taylor V Oh
(74) *Attorney, Agent, or Firm* — Goodwin Procter LLP

(57) ABSTRACT

This disclosure features chemical entities (e.g., a compound or a pharmaceutically acceptable salt thereof) that degrades Proto-oncogene VAV 1 protein (VAV1). The chemical entities are useful, e.g., for treating a subject (e.g., a human subject) having an inflammatory or autoimmune disorder.

12 Claims, 13 Drawing Sheets

(56) References Cited

OTHER PUBLICATIONS

International Search Report and Written Opinion for International Patent Application No. PCT/US2024/010733, mailed May 16, 2024.

Zhang, L., et al., "Highly Regio- and Chemoselective Oxidative C—H/C—H Cross-Couplings of Anilines and Phenols Enabled by a Co-Oxidant-Free Rh(I)/Zn (NTf2)2/Air Catalytic System", ACS Catalysis, 9(6):5358-5364, May 1, 2019.

Gerspacher, M., et al., "Discovery of selective low molecular weight VAV1 guanine nucleotide exchange factor inhibitors", Abstracts of Papers of the American Chemical Society, Meeting 2017, 254:1, abstract MEDI306, Aug. 20, 2017.

Razidlo, G. L., et al., "Dynamin 2 Potentiates Invasive Migration of Pancreatic Tumor Cells through Stabilization of the Rac1 GEF Vav1", Developmental Cell, 24(6):573-585, Mar. 25, 2013.

Haubert, D., et al., "Vav1 GEF activity is required for T cell mediated allograft rejection", Transplant Immunology, 26:212-219, (2012).

Schmidt, R., et al., "CRISPR activation and interference screens decode stimulation responses in primary human T cells", Science 375, 513: 1-12, Feb. 4, 2022.

Korn, T., et al., "Vav1-deficient mice are resistant to MOG-induced experimental autoimmune encephalomyelitis due to impaired antigen priming", Journal of Neuroimmunology, 139:17-26, (2003).

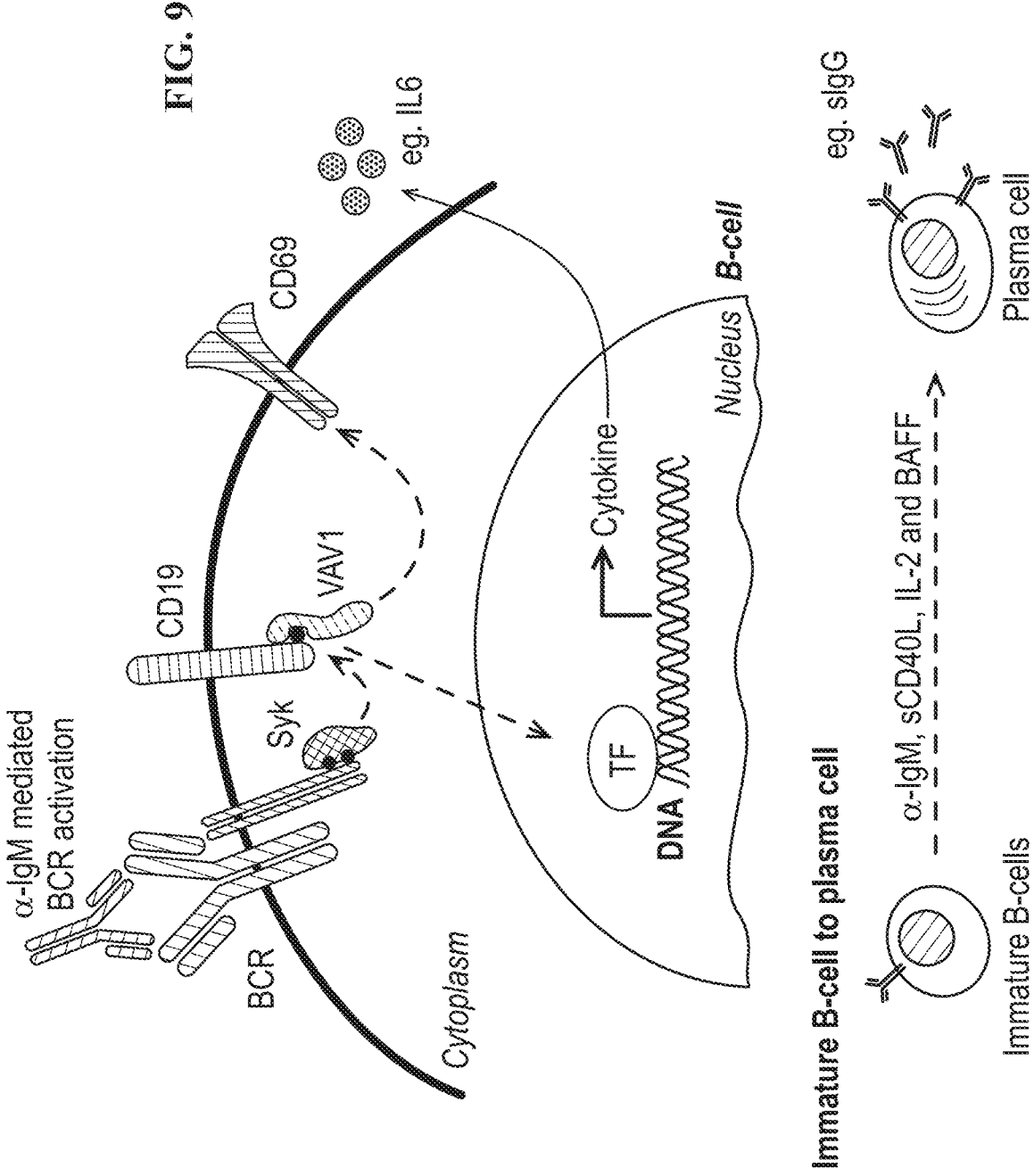

TARGETED DEGRADATION OF VAV1

CROSS-REFERENCE

This application is a continuation of International Patent Application No. PCT/US2024/010733, filed Jan. 8, 2024, which claims priority to U.S. Provisional Patent Application No. 63/437,951, filed Jan. 9, 2023, the entire contents of which are hereby incorporated by reference for all purposes.

TECHNICAL FIELD

This disclosure features chemical entities (e.g., a compound or a pharmaceutically acceptable salt thereof) that degrade human Proto-oncogene VAV 1 protein (VAV1). These chemical entities are useful, e.g., for treating a subject (e.g., a human subject) having a disorder or disease that can be treated by reducing the level of VAV1. This disclosure also features compositions containing these chemical entities as well as methods of using and making these chemical entities.

BACKGROUND

The ubiquitin proteasome system can be manipulated with different small molecules to trigger targeted degradation of specific proteins of interest. Promoting the targeted degradation of proteins using small molecule degraders is emerging as a new modality in the treatment of diseases. One such modality relies on redirecting the activity of E3 ligases such as cereblon (a phenomenon known as E3 reprogramming) using low molecular weight compounds, which have been termed molecular glues (also called molecular glue degraders; "MGDs"), to promote the poly-ubiquitination and ultimately proteasomal degradation of new protein substrates involved in the development of diseases. Molecular glues bind to both the E3 ligase and the target protein. It is believed that the interaction between the molecular glue and the E3 ligase creates a surface that promotes formation of a complex with the target protein, permitting subsequent degradation of the target protein. Examples of molecular glues for the E3 ligase cereblon include: Thalidomide, Lenalidomide and Pomalidomide, all of which are immunomodulatory imide drugs (IMiDs) approved by the FDA for use in hematological cancers.

VAV family proteins, including VAV1, VAV2 and VAV3, are guanine nucleotide exchange factors (GEFs) for Rho family GTPases. VAV1 is a 95 kDa protein that is a positive regulator of T cell receptor and B cell receptor signaling. VAV1 expression is normally highly restricted to hematopoietic cells. VAV1 becomes rapidly phosphorylated on tyrosine in response to a variety of stimuli, including stimulation of T-cell receptor (TCR), B cell receptor (BCR), and various cytokine receptors. VAV1 regulates multiple cellular functions and signaling pathways in hematopoietic-derived cells (e.g., T- and B-cells, natural killer cells, and osteoclasts) through activation of certain GTPases. VAV1-mediated functions include gene transcription, development and activation of immune cells (e.g., T- and B-cells). VAV1 is a positive regulator of (TCR) signaling including nuclear factor of activated T cells (NFAT), interferon gamma (IFNγ) and Interleukin-2 (IL-2) cytokine secretion.

Knock-in mice having a mutated VAV1 with disrupted GEF activity, but intact GEF-independent function, show reduced T cells proliferation and activation in response to allogeneic stimulation and showed reduced expansion of T cells in a systemic graft-versus-host model (Haubert et al. 2012 *Transplantation Immunology* 26: 212, 2012). VAV1 deficient mice are resistant to MOG(5-55)-induced experimental autoimmune encephalomyelitis (EAE), a commonly used model of multiple sclerosis (Korn et al. 2003 *Journal of Neuroimmunology* 139:17). Finally, genome-wide CRISPR activation (CRISPRa) and interference (CRISPRi) screens in primary human T cells identified VAV1 as an important positive regulator of T cell function (Schmidt et al. 2022 Science 375:6580).

SUMMARY

This disclosure features chemical entities (e.g., a compound or a pharmaceutically acceptable salt thereof) that degrade Proto-oncogene VAV 1 protein (VAV1). These chemical entities are useful, e.g., for treating a subject (e.g., a human subject) having a disorder or disease that can be treated by reducing the level of VAV1, thereby reducing VAV activity in cells. By reducing the level of VAV1, the chemical entities can reduce signaling in certain immune cell activation pathways. For example, the chemical entities may be used to reduce inflammation or autoimmune activity. They may be useful for treating, for example, multiple sclerosis, rheumatoid arthritis, myasthenia gravis, chronic lymphocytic leukemia, ulcerative colitis, psoriasis, cutaneous lupus, axial spondylarthritis and graft versus host disease. This disclosure also features compositions containing the chemical entities as well as methods of using and making the same.

VAV1 is a dominant signal transduction protein in the adaptive immune system. It is a positive regulator of immune receptor signaling in both T cells and B cells. Thus, reduction in VAV1 can reduce immune cell activation, immune cell proliferation and the production of various cytokines. For at least these reasons, degradation of VAV1 can be therapeutically beneficial in a variety of disease conditions.

In one aspect, this disclosure features compounds of Formula (I) or pharmaceutically acceptable salts thereof, Formula (I)

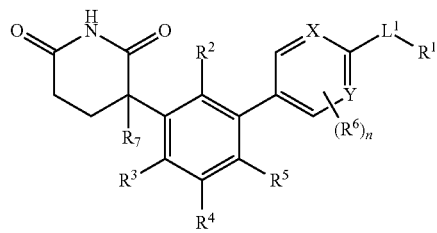

in which X, Y, $R^1$, $R^2$, $R^3$, $R^4$, $R^5$, $R^6$, $L^1$, and n can be as defined anywhere here.

In one aspect, this disclosure features compounds of Formula (II) or pharmaceutically acceptable salts thereof, Formula (II)

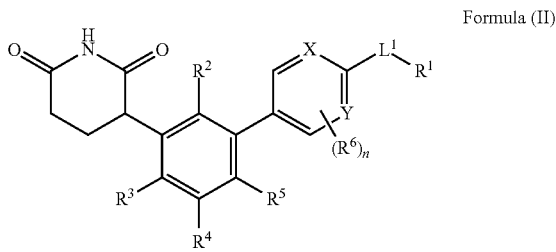

in which X, Y, $R^1$, $R^2$, $R^3$, $R^4$, $R^5$, $R^6$, $L^1$, and n can be as defined anywhere here.

In one aspect, this disclosure features compounds of Formula (III) or pharmaceutically acceptable salts thereof, Formula (III)

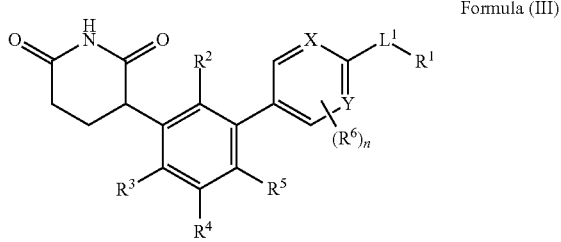

in which X, Y, $R^1$, $R^2$, $R^3$, $R^4$, $R^5$, $R^6$, $L^1$, and n can be as defined anywhere here.

In one aspect, this disclosure features compounds of Formula (IV) or pharmaceutically acceptable salts thereof, Formula (IV)

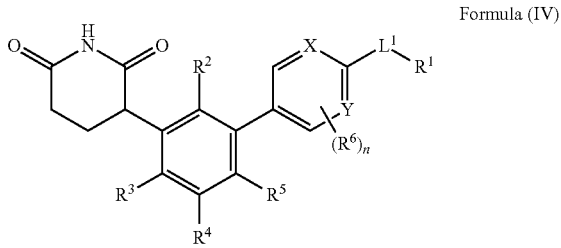

in which X, Y, $R^1$, $R^2$, $R^3$, $R^4$, $R^5$, $R^6$, $L^1$, and n can be as defined anywhere here.

Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, "VAV1" refers to naturally occurring VAV1, also known as Vav or p95vav, (e.g. mammalian, preferably human (*Homo sapiens*) VAV1) and encompasses naturally occurring variants, such as allelic variants and splice variants, which retain VAV1 functional activity.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment").

In general, the "effective amount" of a compound refers to an amount sufficient to elicit the desired biological response. As will be appreciated by those of ordinary skill in this art, the effective amount of a compound of the present disclosure may vary depending on such factors as the desired biological endpoint, the pharmacokinetics of the compound, the disease being treated, the mode of administration, and the age, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

The compounds described herein also include isotopically labeled compounds which are identical to those recited herein, except that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, sulfur, fluorine and chlorine, such as $^2H$ $^3H$, $^{13}C$, $^{14}C$, $^{15}N$, $^{18}O$, $^{17}O$ $^{31}P$, $^{32}P$, $^{35}S$, $^{18}F$, and $^{36}Cl$, respectively. For example, a compound of the disclosure may have one or more H atom replaced with deuterium.

The term "halo" refers to fluoro (F), chloro (Cl), bromo (Br), or iodo (I).

The term "alkyl" refers to a saturated acyclic hydrocarbon radical that may be a straight chain or branched chain, containing the indicated number of carbon atoms. For example, $C_{1-10}$ indicates that the group may have from 1 to 10 (inclusive) carbon atoms in it. Alkyl groups can either be unsubstituted or substituted with one or more substituents. Non-limiting examples include methyl, ethyl, iso-propyl, tert-butyl, n-hexyl. The term "saturated" as used in this context means only single bonds present between constituent carbon atoms and other available valences occupied by hydrogen and/or other substituents as defined herein.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a divalent alkyl (e.g., —CH$_2$—).

The term "alkenyl" refers to an acyclic hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it. Alkenyl groups can either be unsubstituted or substituted with one or more substituents.

The term "alkynyl" refers to an acyclic hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it. Alkynyl groups can either be unsubstituted or substituted with one or more substituents.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, dihydro-1H-indenyl and the like.

The term "cycloalkyl" as used herein refers to cyclic saturated hydrocarbon groups having, e.g., 3 to 20 ring carbons, preferably 3 to 16 ring carbons, and more preferably 3 to 12 ring carbons or 3-10 ring carbons or 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butanyl, bicyclo[2.1.0]pentanyl, bicyclo[1.1.1]pentanyl, bicyclo[3.1.0]hexanyl, bicyclo[2.1.1]hexanyl, bicyclo[3.2.0]heptanyl, bicyclo[4.1.0]heptanyl, bicyclo[2.2.1]heptanyl, bicyclo[3.1.1]heptanyl, bicyclo[4.2.0]octanyl, bicyclo[3.2.1]octanyl, bicyclo[2.2.2]octanyl, and the like. Cycloalkyl also includes spirocyclic rings (e.g., spirocyclic bicycle wherein two rings are connected through just one atom). Non-limiting examples of spirocyclic cycloalkyls include spiro[2.2]pentanyl, spiro[2.5]octanyl, spiro[3.5]nonanyl, spiro[3.5]nonanyl, spiro[3.5]nonanyl, spiro[4.4]nonanyl, spiro[2.6]nonanyl, spiro[4.5]decanyl, spiro[3.6]decanyl, spiro[5.5]undecanyl, and the like. The term "saturated" as used in this context means only single bonds present between constituent carbon atoms.

The term "cycloalkenyl" as used herein means partially unsaturated cyclic hydrocarbon groups having 3 to 20 ring carbons, preferably 3 to 16 ring carbons, and more preferably 3 to 12 ring carbons or 3-10 ring carbons or 3-6 ring carbons, wherein the cycloalkenyl group may be optionally substituted. Examples of cycloalkenyl groups include, without limitation, cyclopentenyl, cyclohexenyl, cycloheptenyl, and cyclooctenyl. As partially unsaturated cyclic hydrocarbon groups, cycloalkenyl groups may have any degree of unsaturation provided that one or more double bonds is present in the ring, none of the rings in the ring system are aromatic, and the cycloalkenyl group is not fully saturated overall. Cycloalkenyl may include multiple fused and/or bridged and/or spirocyclic rings.

The term "heteroaryl", as used herein, means a mono-, bi-, tri- or polycyclic group having 5 to 20 ring atoms, alternatively 5, 6, 9, 10, or 14 ring atoms; and having 6, 10, or 14 pi electrons shared in a cyclic array; wherein at least one ring in the system is aromatic, and at least one ring in the system contains one or more heteroatoms independently selected from the group consisting of N, O, and S (but does not have to be a ring which contains a heteroatom, e.g. tetrahydroisoquinolinyl, e.g., tetrahydroquinolinyl). Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridinyl, pyrazolo[4,3-b]pyridinyl, tetrazolyl, chromanyl, 2,3-dihydrobenzo[b][1,4]dioxinyl, benzo[d][1,3]dioxolyl, 2,3-dihydrobenzofuranyl, tetrahydroquinolinyl, 2,3-dihydrobenzo[b][1,4]oxathiinyl, isoindolinyl, and others. In some embodiments, the heteroaryl is selected from thienyl, pyridinyl, furyl, pyrazolyl, imidazolyl, isoindolinyl, pyranyl, pyrazinyl, and pyrimidinyl.

The term "heterocyclyl" refers to a mon-, bi-, tri-, or polycyclic saturated ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heterocyclyl includes: 2-azabicyclo[1.1.0]butanyl, 2-azabicyclo[2.1.0]pentanyl, 2-azabicyclo[1.1.1]pentanyl, 3-azabicyclo[3.1.0]hexanyl, 5-azabicyclo[2.1.1]hexanyl, 3-azabicyclo[3.2.0]heptanyl, octahydrocyclopenta[c]pyrrolyl, 3-azabicyclo[4.1.0]heptanyl, 7-azabicyclo[2.2.1]heptanyl, 6-azabicyclo[3.1.1]heptanyl, 7-azabicyclo[4.2.0]octanyl, 2-azabicyclo[2.2.2]octanyl, 3-azabicyclo[3.2.1]octanyl, 2-oxabicyclo[1.1.0]butanyl, 2-oxabicyclo[2.1.0]pentanyl, 2-oxabicyclo[1.1.1]pentanyl, 3-oxabicyclo[3.1.0]hexanyl, 5-oxabicyclo[2.1.1]hexanyl, 3-oxabicyclo[3.2.0]heptanyl, 3-oxabicyclo[4.1.0]heptanyl, 7-oxabicyclo[2.2.1]heptanyl, 6-oxabicyclo[3.1.1]heptanyl, 7-oxabicyclo[4.2.0]octanyl, 2-oxabicyclo[2.2.2]octanyl, 3-oxabicyclo[3.2.1]octanyl, and the like. Heterocyclyl also includes spirocyclic rings (e.g., spirocyclic bicycle wherein two rings are connected through just one atom).

Non-limiting examples of spirocyclic heterocyclyls include 2-azaspiro[2.2]pentanyl, 4-azaspiro[2.5]octanyl, 1-azaspiro[3.5]nonanyl, 2-azaspiro[3.5]nonanyl, 7-azaspiro[3.5]nonanyl, 2-azaspiro[4.4]nonanyl, 6-azaspiro[2.6] nonanyl, 1,7-diazaspiro[4.5]decanyl, 7-azaspiro[4.5]decanyl 2,5-diazaspiro[3.6]decanyl, 3-azaspiro[5.5]undecanyl, 2-oxaspiro[2.2]pentanyl, 4-oxaspiro[2.5]octanyl, 1-oxaspiro[3.5]nonanyl, 2-oxaspiro[3.5]nonanyl, 7-oxaspiro[3.5] nonanyl, 2-oxaspiro[4.4]nonanyl, 6-oxaspiro[2.6]nonane, 1,7-dioxaspiro[4.5]decanyl, 2,5-dioxaspiro[3.6]decanyl, 1-oxaspiro[5.5]undecanyl, 3-oxaspiro[5.5]undecanyl, 3-oxa-9-azaspiro[5.5]undecanyl and the like. The term "saturated" as used in this context means only single bonds present between constituent ring atoms and other available valences occupied by hydrogen and/or other substituents as defined herein.

The term "heterocycloalkenyl" as used herein means partially unsaturated cyclic ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent.

Examples of heterocycloalkenyl groups include, without limitation, tetrahydropyridyl, dihydropyrazinyl, dihydropyridyl, dihydropyrrolyl, dihydrofuranyl, dihydrothiophenyl. As partially unsaturated cyclic groups, heterocycloalkenyl groups may have any degree of unsaturation provided that one or more double bonds is present in the ring, none of the rings in the ring system are aromatic, and the heterocycloalkenyl group is not fully saturated overall. Heterocycloalkenyl may include multiple fused and/or bridged and/or spirocyclic rings.

Certain groups, such as

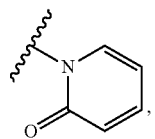 [SMILES: *n1ccccc1=O]

can be considered as either: (i) a heterocycloalkenyl which is substituted with an oxo group; or (ii) a heteroaryl group.

As used herein, when a ring is described as being "aromatic", it means said ring has a continuous, delocalized π-electron system. Typically, the number of out of plane π-electrons corresponds to the Hückel rule (4n+2). Examples of such rings include: benzene, pyridine, pyrimidine, pyrazine, pyridazine, pyridone, pyrrole, pyrazole, oxazole, thioazole, isoxazole, isothiazole, and the like.

As used herein, when a ring is described as being "partially unsaturated", it means said ring has one or more additional degrees of unsaturation (in addition to the degree of unsaturation attributed to the ring itself, e.g., one or more double or triple bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like.

For the avoidance of doubt, and unless otherwise specified, for rings and cyclic groups (e.g., aryl, heteroaryl, heterocyclyl, heterocycloalkenyl, cycloalkenyl, cycloalkyl, and the like described herein) containing a sufficient number of ring atoms to form bicyclic or higher order ring systems (e.g., tricyclic, polycyclic ring systems), it is understood that such rings and cyclic groups encompass those having fused rings, including those in which the points of fusion are located (i) on adjacent ring atoms (e.g., [x.x.0] ring systems, in which 0 represents a zero atom bridge (e.g.,

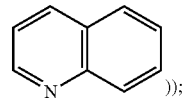

(ii) a single ring atom (spiro-fused ring systems) (e.g.,

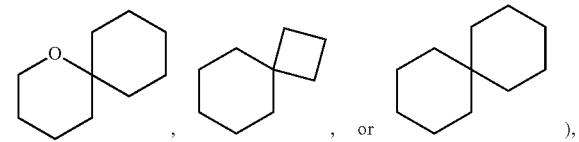

or (iii) a contiguous array of ring atoms (bridged ring systems having all bridge lengths>0) (e.g.,

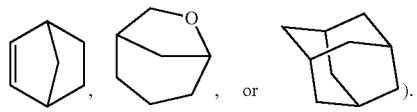

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In addition, the compounds generically or specifically disclosed herein include all tautomeric forms, or "tautomers" of said compounds. To give a non-limiting example, a disclosure of a compound with the group

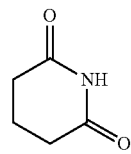

is also a disclosure of a compound with the group

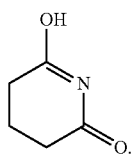

As another non-limiting example, a disclosure of a compound with the group

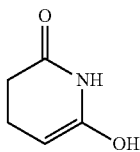

is also a disclosure of a compound with the group

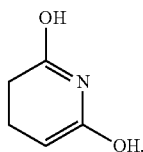

The compounds generically or specifically disclosed herein include all stereoisomeric forms, including all diastereomeric and enantiomeric forms, unless it is specifically stated or the context indicates otherwise. Compounds with chiral centers can occur as racemates, individual enantiomers (e.g. as the (R) enantiomer or (S) entantiomer) or diastereomers, and mixtures thereof. All such stereoisomeric forms are included within the embodiments disclosed herein, including mixtures thereof.

Further, compounds of one enantiomeric form may epimerise into the other enantiomeric form. Thus, unless it is specifically stated or the context indicates otherwise, disclosure of one enantiomer encompasses the isolated entantiomer and a mixture, such as a racemic mixture, of the (R) and (S) entantiomers if the enantiomers epimerise. For example, a disclosure of

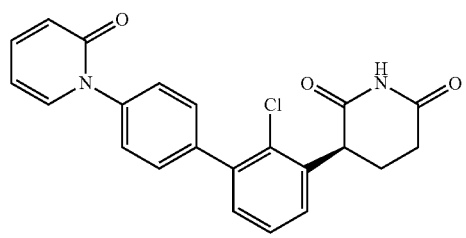 [SMILES: O=C1CC[C@@H](c2cccc(-c3ccc(-n4ccccc4=O)cc3)c2Cl)C(=O)N1]

encompasses both isolated

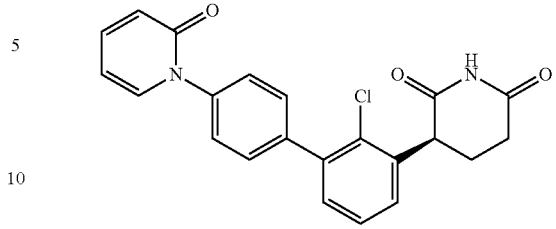

and a mixture of

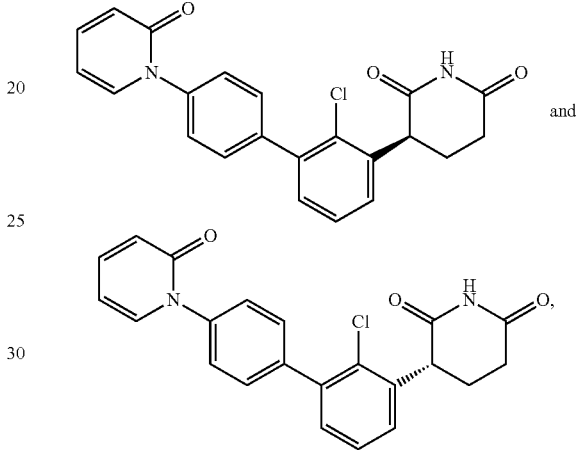

including a racemic mixture of the two enantiomers. Similarly, a compound comprising a chiral center disclosed herein without its enantiomeric form indicated encompasses the isolated entantiomer and a mixture, such as a racemic mixture, of the (R) and (S) entantiomers if the enantiomers epimerise. For example,

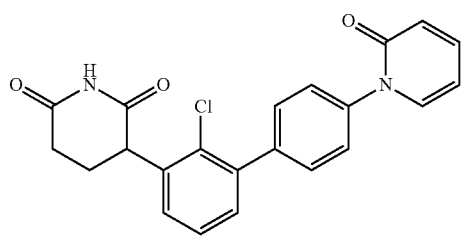 [SMILES: O=C1CCC(c2cccc(-c3ccc(-n4ccccc4=O)cc3)c2Cl)C(=O)N1]

encompasses both isolated

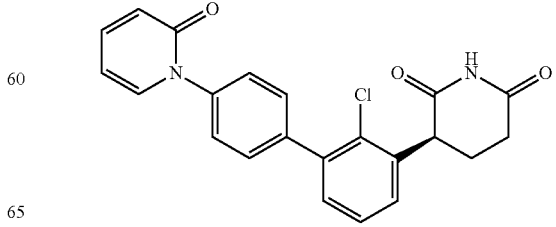

and a mixture of

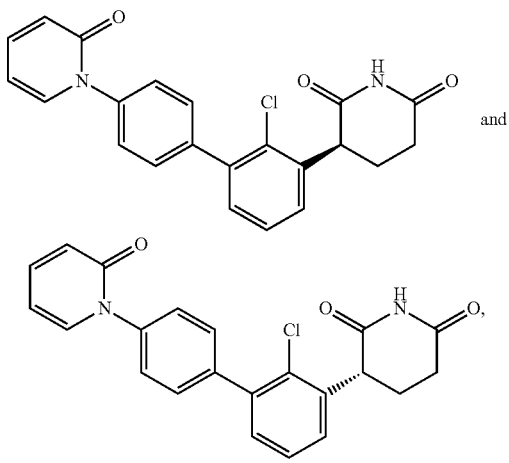

including a racemic mixture of the two enantiomers.

As used herein, the phrase "optionally substituted" when used in conjunction with a structural moiety (e.g., alkyl) is intended to encompass both the unsubstituted structural moiety (i.e., none of the substitutable hydrogen atoms are replaced with one or more non-hydrogen substituents) and substituted structural moieties substituted with the indicated range of non-hydrogen substituents. For example, "$C_1$-$C_4$ alkyl optionally substituted with 1-4 $R^a$" is intended to encompass both unsubstituted $C_1$-$C_4$ alkyl and $C_1$-$C_4$ alkyl substituted with 1-4 $R^a$.

As used herein, the term "hydrogen bond acceptor" is intended to include any functional group containing a heteroatom, usually oxygen or nitrogen, having one or more lone pairs suitable for formation of hydrogen bond with a polarized hydrogen atom. A more detailed discussion of hydrogen bond acceptors and a list of accepted hydrogen bond acceptors is found in Laurence et al., *J. Med. Chem.*, 2009, 52, 4073-4086 and Kenny et al., *J. Med Chem*. 2016, 59, 4278-4288, both of which are incorporated by reference in their entirety.

As used herein, the term "antibody" encompasses an immunoglobulin, whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)2, Fab, Fab', and F(ab')2, F(abl)2, Fv, dAb, and Fd fragments, diabodies, and antibody-related polypeptides. Antibody includes bispecific antibodies and multispecific antibodies so long as they exhibit the desired biological activity or function.

As used herein, an "antibody fragment" comprises a portion of an intact antibody, generally the antigen binding or variable region thereof. Examples of antibody fragments include Fab, Fab', F(ab').sub.2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

As used herein, the term "antibody-drug conjugate" refers to an antibody or antibody fragment linked, e.g., covalently, to a compound of the disclosure.

The details of one or more embodiments of the invention are set forth in the accompanying drawings and the description below. Other features and advantages of the invention will be apparent from the description and drawings, and from the claims.

DESCRIPTION OF DRAWINGS

FIG. 9 depicts VAV1 as a key mediator downstream of the B-cell receptor (BCR). Hallmarks of BCR pathway engagement include CD69 surface activation and secretion of IL-6 and IgG.

FIG. 10A shows CD69 expression which was then assessed on CD19+B cells by flow cytometry. CD69 expression is shown as a percentage (%) change relative to stimulated DMSO controls. Y-axis shows relative percentage of CD19+B cells expressing CD69 and x-axis shows concentration of VAV1 MGD.

FIG. 10B shows IL-6 secretion which was assessed in the supernatant by alphalisa. IL-6 secretion is shown as a percentage (%) change relative to stimulated DMSO controls. Y-axis shows relative percentage of IL-6 level and x-axis shows concentration of VAV1 MGD. FIG. 10C shows IgG secretion was assessed in the supernatant by alphalisa. IgG secretion is shown as a percentage (%) change relative to stimulated DMSO controls. Y-axis shows relative percentage of IgG level and x-axis shows concentration of VAV1 MGD.

DETAILED DESCRIPTION

Figure 1:
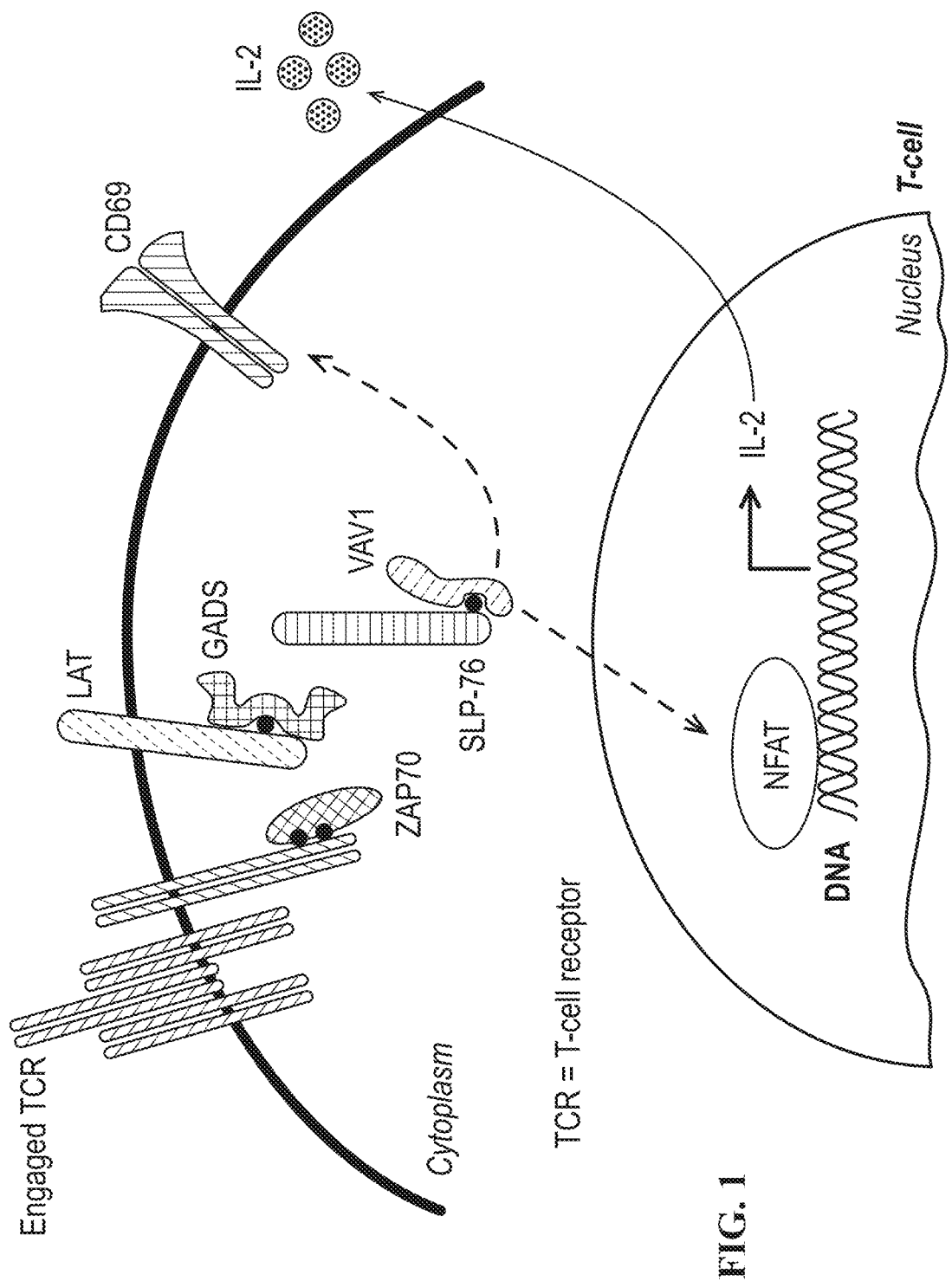
FIG. 1 is a schematic depiction of certain aspects of VAV1's relationship to certain proteins involved in T cell receptor activation. VAV1 is a positive regular of T cell receptor signaling, including interferon gamma production and IL-2 secretion.

This disclosure features chemical entities (e.g., a compound or a pharmaceutically acceptable salt thereof) that degrade and/or otherwise inhibit Proto-oncogene VAV 1 protein (VAV1). Said chemical entities are useful, e.g., for treating a subject (e.g., a human subject) having a disorder or disease associated with VAV1 polymorphisms or disregulated lymphocyte (e.g., T-cell). This disclosure also features compositions containing the same as well as methods of using and making the same.

Compounds

Compounds of Formulae (I), (II), (III) and (IV)

This disclosure features compounds of Formula (I) or pharmaceutically acceptable salts thereof,

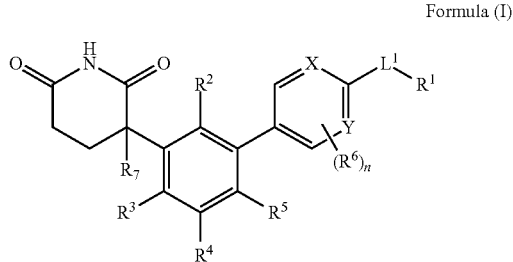

Formula (I)

wherein:

L¹ is:
  a bond;
  *—O(C₀-C₄ alkylene)-, *—S(C₀-C₄ alkylene)-, *—C₁-C₄ alkylene-, or *—NR'(C₀-C₄ alkylene)-, —(C₁-C₄ alkylene)-C(=O)—*, *—(C₁-C₄ alkylene)-C(=O)—, wherein the alkylene is optionally substituted with 1-2 R$^a$ and wherein * indicates the point of attachment of L¹ to the ring comprising X and Y;
  (C=O)—; or
  taken together with Y to form an additional ring fused with the ring containing X and Y, wherein the fused ring system includes 9 or 10 ring atoms, wherein from 1-4 ring atoms in the additional ring are heteroatoms, each independently selected from the group consisting of N, N(H), N(R$^d$) and O, wherein the additional ring is substituted with R₁ and is optionally further substituted with from 1-4 substituents independently selected from the group consisting of oxo and R$^c$; and each one of X and Y is independently selected from the group consisting of N and CH;

R¹ is selected from the group consisting of hydrogen, deuterium, R$^b$, —OR$^b$, —S(O)₀₋₂R$^b$, —N(R')R$^b$, CN, halo, and —NR'C(O)R";

R² is selected from the group consisting of hydrogen, deuterium, CH₃, CHF₂, CF₃, OMe, F, Cl and Br;

each of R³, R⁴ and R⁵ is independently selected from the group consisting of hydrogen and R$^c$;

each of R⁶ is independently selected from the group consisting of: deuterium, halo; cyano; C₁₋₁₀ alkyl which is optionally substituted with from 1-6 independently selected R$^a$; C₃₋₆ cycloalkyl which is optionally substituted with from 1-4 independently selected R$^a$; C₂₋₆ alkenyl; C₂₋₆ alkynyl; C₁₋₄ alkoxy; —S(O)₀₋₂(C₁₋₄ alkyl); —NR$^e$R$^f$; —OH; —S(O)₁₋₂NR'R"; —NO₂; —C(=O)(C₁₋₁₀ alkyl); —C(=O)O(C₁₋₄ alkyl); —C(=O)OH; —N(R')C(=O)(C₁₋₄ alkyl), —C(=O)NR'R", R$^g$, and —(CH₂)₁₋₂ R$^g$;

n is selected from 0, 1, 2 and 3;

R⁷ is selected from the group consisting of hydrogen, deuterium, CH₃, CHF₂, CF₃, OMe, F, Cl and Br;

each occurrence of R$^a$ is independently selected from the group consisting of: —OH; -halo; —NR$^e$R$^f$; C₁₋₄ alkoxy; C₁₋₄ haloalkoxy; —C(=O)O(C₁₋₄ alkyl); —C(=O)(C₁₋₄ alkyl); —C(=O)OH; —CONR'R"; —S(O)₁₋₂NR'R"; —S(O)₁₋₂(C₁₋₄ alkyl); and cyano;

each occurrence of R$^b$ is independently selected from the group consisting of:
  C₃₋₁₀ cycloalkyl or C₃₋₁₀ cycloalkenyl, each of which is optionally substituted with from 1-4 substituents independently selected from the group consisting of oxo and R$^c$;
  heterocyclyl or heterocycloalkenyl including 3-10 ring atoms, wherein from 1-3 ring atoms are heteroatoms, each independently selected from the group consisting of N, N(H), N(R$^d$), O, and S(O)₀₋₂, and wherein the heterocyclyl or heterocycloalkenyl is optionally substituted with from 1-4 substituents independently selected from the group consisting of oxo and R$^c$;
  heteroaryl including 5-10 ring atoms, wherein from 1-4 ring atoms are heteroatoms, each independently selected from the group consisting of N, N(H), N(R$^d$), O, and S(O)₀₋₂, wherein at least one ring in the system is aromatic and wherein the heteroaryl is optionally substituted with from 1-4 substituents independently selected from oxo and R$^c$; and
  C₆₋₁₀ aryl optionally substituted with from 1-4 substituents independently selected R$^c$;

each occurrence of R$^c$ is independently selected from the group consisting of: deuterium; halo; cyano; C₁₋₁₀ alkyl which is optionally substituted with from 1-6 independently selected R$^a$; C₃₋₆ cycloalkyl which is optionally substituted with from 1-4 independently selected R$^a$; C₂₋₆ alkenyl; C₂₋₆ alkynyl; C₁₋₄ alkoxy; —S(O)₀₋₂(C₁₋₄ alkyl); —NR$^e$R$^f$; —OH; —S(O)₁₋₂NR'R"; —NO₂; —C(=O)(C₁₋₁₀ alkyl); —C(=O)O(C₁₋₄ alkyl); —C(=O)OH; —N(R')C(=O)(C₁₋₄ alkyl), —C(=O)NR'R", R$^g$, and —(CH₂)₁₋₂ R$^g$;

each occurrence of R$^d$ is independently selected from the group consisting of: hydrogen, deuterium, C₁₋₆ alkyl optionally substituted with from 1-3 independently selected R$^a$; —C(O)(C₁₋₄ alkyl); —C(O)O(C₁₋₄ alkyl); —CONR'R"; —S(O)₁₋₂NR'R"; —S(O)₁₋₂(C₁₋₄ alkyl); —OH; and C₁₋₄ alkoxy;

each occurrence of R$^e$ and R$^f$ is independently selected from the group consisting of: H; deuterium; C₁₋₆ alkyl; —C(O)(C₁₋₄ alkyl); —C(O)O(C₁₋₄ alkyl); —CONR'R"; —S(O)₁₋₂NR'R"; —S(O)₁₋₂ (C₁₋₄ alkyl); —OH; and C₁₋₄ alkoxy; and each occurrence of R$^g$ is independently selected from the group consisting of:

C$_{3-7}$ cycloalkyl or C$_{3-7}$ cycloalkenyl, each of which is optionally substituted with from 1-4 substituents independently selected from the group consisting of oxo and R$^a$;

heterocyclyl or heterocycloalkenyl including 3-7 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and R$^a$;

heteroaryl including 5-10 ring atoms, wherein from 1-4 ring atoms are heteroatoms, each independently selected from the group consisting of N, N(H), N(R$^d$), O, and S(O)$_{0-2}$, wherein at least one ring in the system is aromatic and wherein the heteroaryl is optionally substituted with from 1-4 oxo or R$^a$; and C$_{6-10}$ aryl optionally substituted with from 1-4 R$^a$;

each occurrence of R' and R" is independently selected from the group consisting of: hydrogen; and C$_{1-4}$ alkyl.

This disclosure also features compounds of Formula (II) or pharmaceutically acceptable salts thereof, Formula (II)

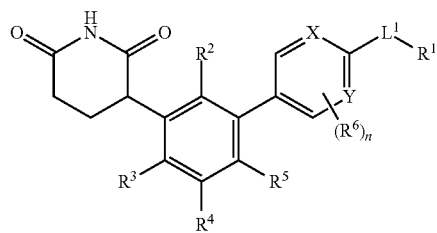

wherein:

L is:
a bond;
O(C$_0$-C$_4$ alkylene)-, *—S(C$_0$-C$_4$ alkylene)-, *—C$_1$-C$_4$ alkylene-, or *—NR'(C$_0$-C$_4$ alkylene)-, *—NR'(C=O)(C$_0$-C$_4$ alkylene)-, —(C$_1$-C$_4$ alkylene)-C(=O)—*, *—(C$_1$-C$_4$ alkylene)-C(=O)—, wherein the alkylene is optionally substituted with 1-2 R$^a$ and wherein * indicates the point of attachment of L$^1$ to the ring comprising X and Y;
—(C=O)—; or
taken together with Y to form an additional ring fused with the ring containing X and Y, wherein the fused ring system includes 9 or 10 ring atoms, wherein from 1-4 ring atoms in the additional ring are heteroatoms, each independently selected from the group consisting of N, N(H), N(R$^d$) and O, wherein the additional ring is substituted with R$_1$ and is optionally further substituted with from 1-4 substituents independently selected from the group consisting of oxo and R$^c$; and each one of X and Y is independently selected from the group consisting of N and CH;

R$^1$ is selected from the group consisting of hydrogen, deuterium, R$^b$, —OR$^b$, —S(O)$_{0-2}$R$^b$, —N(R')R$^b$, CN, halo, and —NR'C(O)R";

R$^2$ is selected from the group consisting of hydrogen, deuterium, CH$_3$, CHF$_2$, CF$_3$, OMe, F, Cl and Br;

each of R$^3$, R$^4$ and R$^5$ is independently selected from the group consisting of hydrogen and R$^c$;

each of R$^6$ is independently selected from the group consisting of: deuterium, halo; cyano; C$_{1-10}$ alkyl which is optionally substituted with from 1-6 independently selected R$^a$; C$_{3-6}$ cycloalkyl which is optionally substituted with from 1-4 independently selected R$^a$; C$_{2-6}$ alkenyl; C$_{2-6}$ alkynyl; C$_{1-4}$ alkoxy; —S(O)$_{0-2}$(C$_{1-4}$ alkyl); —NR$^e$R$^f$; —OH; —S(O)$_{1-2}$NR'R"; —NO$_2$; —C(=O)(C$_{1-10}$ alkyl); —C(=O)O(C$_{1-4}$ alkyl); —C(=O)OH; —N(R')C(=O)(C$_{1-4}$ alkyl), —C(=O)NR'R", R$^g$, and —(CH$_2$)$_{1-2}$ R$^g$;

n is selected from 0, 1, 2 and 3;

each occurrence of R$^a$ is independently selected from the group consisting of: —OH; -halo; —NR$^e$R$^f$; C$_{1-4}$ alkoxy; C$_{1-4}$ haloalkoxy; —C(=O)O(C$_{1-4}$ alkyl); —C(=O)(C$_{1-4}$ alkyl); —C(=O)OH; —CONR'R"; —S(O)$_{1-2}$NR'R"; —S(O)$_{1-2}$(C$_{1-4}$ alkyl); and cyano;

each occurrence of R$^b$ is independently selected from the group consisting of:
C$_{3-10}$ cycloalkyl or C$_{3-10}$ cycloalkenyl, each of which is optionally substituted with from 1-4 substituents independently selected from the group consisting of oxo and R$^c$;
heterocyclyl or heterocycloalkenyl including 3-10 ring atoms, wherein from 1-3 ring atoms are heteroatoms, each independently selected from the group consisting of N, N(H), 5 N(R$^d$), O, and S(O)$_{0-2}$, and wherein the heterocyclyl or heterocycloalkenyl is optionally substituted with from 1-4 substituents independently selected from the group consisting of oxo and R$^c$;
heteroaryl including 5-10 ring atoms, wherein from 1-4 ring atoms are heteroatoms, each independently selected from the group consisting of N, N(H), N(R$^d$), O, and S(O)$_{0-2}$, wherein at least one ring in the system is aromatic and wherein the heteroaryl is optionally substituted with from 1-4 substituents independently selected from oxo and R$^c$; and
C$_{6-10}$ aryl optionally substituted with from 1-4 substituents independently selected R$^c$;

each occurrence of R$^c$ is independently selected from the group consisting of: deuterium; halo; cyano; C$_{1-10}$ alkyl which is optionally substituted with from 1-6 independently selected R$^a$ C$_{3-6}$ cycloalkyl which is optionally substituted with from 1-4 independently selected R$^a$; C$_{2-6}$ alkenyl; C$_{2-6}$ alkynyl; C$_{1-4}$ alkoxy; —S(O)$_{0-2}$(C$_{1-4}$ alkyl); —NR$^e$R$^f$; —OH; —S(O)$_{1-2}$NR'R"; —NO$_2$; —C(=O)(C$_{1-10}$ alkyl); —C(=O)O(C$_{1-4}$ alkyl); —C(=O)OH; —N(R')C(=O)(C$_{1-4}$ alkyl), —C(=O)NR'R", R$^g$, and —(CH$_2$)$_{1-2}$ R$^g$;

each occurrence of R$^d$ is independently selected from the group consisting of: hydrogen, deuterium, C$_{1-6}$ alkyl optionally substituted with from 1-3 independently selected R$^a$; —C(O)(C$_{1-4}$ alkyl); —C(O)O(C$_{1-4}$ alkyl); —CONR'R"; —S(O)$_{1-2}$NR'R"; —S(O)$_{1-2}$(C$_{1-4}$ alkyl); —OH; and C$_{1-4}$ alkoxy;

each occurrence of R$^e$ and R$^f$ is independently selected from the group consisting of: H; deuterium; C$_{1-6}$ alkyl; —C(O)(C$_{1-4}$ alkyl); —C(O)O(C$_{1-4}$ alkyl); —CONR'R"; —S(O)$_{1-2}$NR'R"; —S(O)$_1$-2(C$_{1-4}$ alkyl); —OH; and C$_{1-4}$ alkoxy; and each occurrence of R$^g$ is independently selected from the group consisting of:
C$_{3-7}$ cycloalkyl or C$_{3-7}$ cycloalkenyl, each of which is optionally substituted with from 1-4 substituents independently selected from the group consisting of oxo and R$^a$;
heterocyclyl or heterocycloalkenyl including 3-7 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and R$^a$;

heteroaryl including 5-10 ring atoms, wherein from 1-4 ring atoms are heteroatoms, each independently selected from the group consisting of N, N(H), N(R$^d$), O, and S(O)$_{0-2}$, wherein at least one ring in the system is aromatic and wherein the heteroaryl is optionally substituted with from 1-4 oxo or R$^a$; and C$_{6-10}$ aryl optionally substituted with from 1-4 R$^a$;

each occurrence of R' and R" is independently selected from the group consisting of: hydrogen; and C$_{1-4}$ alkyl.

This disclosure also features compounds of Formula (III) or pharmaceutically acceptable salts thereof,

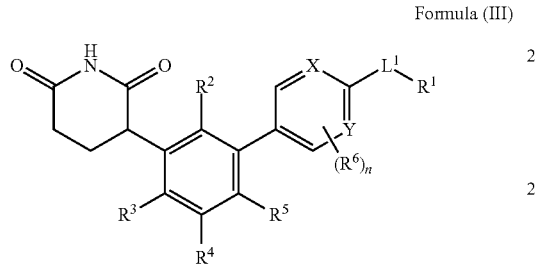

Formula (III)

wherein:

L$^1$:
  is a bond;
  is *—O(C$_0$-C$_4$ alkylene)-, *—S(C$_0$-C$_4$ alkylene)-, *—C$_1$-C$_4$ alkylene-, or *—NR'(C$_0$-C$_4$ alkylene)-, *—NR'(C═O)(C$_0$-C$_4$ alkylene)-, —(C$_1$-C$_4$ alkylene)-C(═O)—*, *—(C$_1$-C$_4$ alkylene)-C(═O)—, wherein the alkylene is optionally substituted with 1-2 R$^a$ and wherein * indicates the point of attachment of L$^1$ to the ring comprising X and Y;
  is —(C═O)—;

each one of X and Y is independently selected from the group consisting of N and CH;

R$^1$ is selected from the group consisting of hydrogen, deuterium, R$^b$, —OR$^b$, —S(O)$_{0-2}$R$^b$, —N(R')R$^b$, CN, halo, and —NR'C(O)R";

provided that -L$^1$-R$^1$ does not include O—O, N—O, N—N, O—S, S—S, or N—S bonds; further provided that L$^1$ must be a bond when R$^1$ is CN, halo, or —NR'C(O)R"; and further provided that L$^1$ cannot be a bond when R$^1$ is hydrogen;

R$^2$ is selected from the group consisting of hydrogen, deuterium, CH$_3$, CHF$_2$, CF$_3$, OMe, F, Cl and Br;

each of R$^3$, R$^4$ and R$^5$ is independently selected from the group consisting of hydrogen and R$^c$;

each of R$^6$ is independently selected from the group consisting of: deuterium; halo; cyano; C$_{1-10}$ alkyl which is optionally substituted with from 1-6 independently selected R$^a$; C$_{3-6}$ cycloalkyl which is optionally substituted with from 1-4 independently selected R$^a$; C$_{2-6}$ alkenyl; C$_{2-6}$ alkynyl; C$_{1-4}$ alkoxy; —S(O)$_{0-2}$(C$_{1-4}$ alkyl); —NR$^e$R$^f$; —OH; —S(O)$_{1-2}$NR'R"; —NO$_2$; —C(═O)(C$_{1-10}$ alkyl); —C(═O)O(C$_{1-4}$ alkyl); —C(═O)OH; —N(R')C(═O)(C$_{1-4}$ alkyl), —C(═O)NR'R", R$^g$, and —(CH$_2$)$_{1-2}$R$^g$;

n is selected from 0, 1, 2 and 3;

each occurrence of R$^a$ is independently selected from the group consisting of: —OH; -halo; —NR$^e$R$^f$; C$_{1-4}$ alkoxy; C$_{1-4}$ haloalkoxy; —C(═O)O(C$_{1-4}$ alkyl); —C(═O)(C$_{1-4}$ alkyl); —C(═O)OH; —CONR'R"; —S(O)$_{1-2}$NR'R"; —S(O)$_{1-2}$(C$_{1-4}$ alkyl); and cyano;

each occurrence of R$^b$ is independently selected from the group consisting of:

C$_{3-10}$ cycloalkyl or C$_{3-10}$ cycloalkenyl, each of which is optionally substituted with from 1-4 substituents independently selected from the group consisting of oxo and R$^c$;

heterocyclyl or heterocycloalkenyl including 3-10 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and R$^c$;

heteroaryl including 5-10 ring atoms, wherein from 1-4 ring atoms are heteroatoms, each independently selected from the group consisting of N, N(H), N(R$^d$), O, and S(O)$_{0-2}$, wherein at least one ring in the system is aromatic and wherein the heteroaryl is optionally substituted with from 1-4 substituents independently selected from oxo and R$^c$; and C$_{6-10}$ aryl optionally substituted with from 1-4 substituents independently selected R$^c$;

each occurrence of R$^c$ is independently selected from the group consisting of: deuterium; halo; cyano; C$_{1-10}$ alkyl which is optionally substituted with from 1-6 independently selected R$^a$ C$_{3-6}$ cycloalkyl which is optionally substituted with from 1-4 independently selected R$^a$; C$_{2-6}$ alkenyl; C$_{2-6}$ alkynyl; C$_{1-4}$ alkoxy; —S(O)$_{0-2}$(C$_{1-4}$ alkyl); —NR$^e$R$^f$; —OH; —S(O)$_{1-2}$NR'R"; —NO$_2$; —C(═O)(C$_{1-10}$ alkyl); —C(═O)O(C$_{1-4}$ alkyl); —C(═O)OH; —N(R')C(═O)(C$_{1-4}$ alkyl), —C(═O)NR'R", R$^g$, and —(CH$_2$)$_{1-2}$R$^g$;

each occurrence of R$^d$ is independently selected from the group consisting of: hydrogen, C$_{1-6}$ alkyl optionally substituted with from 1-3 independently selected R$^a$; —C(O)(C$_{1-4}$ alkyl); —C(O)O(C$_{1-4}$ alkyl); —CONR'R"; —S(O)$_{1-2}$NR'R"; —S(O)$_{1-2}$(C$_{1-4}$ alkyl); —OH; and C$_{1-4}$ alkoxy;

each occurrence of R$^e$ and R$^f$ is independently selected from the group consisting of: H; C1-6 alkyl; —C(O)(C$_{1-4}$ alkyl); —C(O)O(C$_{1-4}$ alkyl); —CONR'R"; —S(O)$_{1-2}$NR'R"; —S(O)$_{1-2}$(C$_{1-4}$ alkyl); —OH; and C$_{1-4}$ alkoxy; and each occurrence of R$^g$ is independently selected from the group consisting of:

C$_{3-7}$ cycloalkyl or C$_{3-7}$ cycloalkenyl, each of which is optionally substituted with from 1-4 substituents independently selected from the group consisting of oxo and R$^a$;

heterocyclyl or heterocycloalkenyl including 3-7 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and R$^a$;

heteroaryl including 5-10 ring atoms, wherein from 1-4 ring atoms are heteroatoms, each independently selected from the group consisting of N, N(H), N(R$^d$), O, and S(O)$_{0-2}$, wherein at least one ring in the system is aromatic and wherein the heteroaryl is optionally substituted with from 1-4 oxo or R$^a$; and C$_{6-10}$ aryl optionally substituted with from 1-4 R$^a$;

each occurrence of R' and R" is independently selected from the group consisting of: hydrogen; and C$_{1-4}$ alkyl.

This disclosure also features compounds of Formula (IV) or pharmaceutically acceptable salts thereof, Formula (IV)

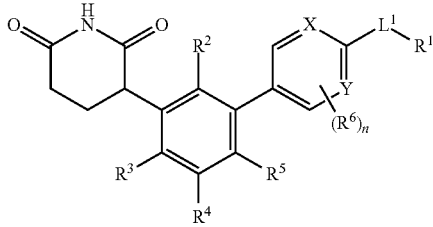

wherein:
L$^1$ is:
a bond;
*—O(C$_0$-C$_4$ alkylene)-, *—S(C$_0$-C$_4$ alkylene)-, *—C$_1$-C$_4$ alkylene-, or *—NR'(C$_0$-C$_4$ alkylene)-, *—NR'(C=O)(C$_0$-C$_4$ alkylene)-, —(C$_1$-C$_4$ alkylene)-C(=O)—*, *—(C$_1$-C$_4$ alkylene)-C(=O)—, wherein the alkylene is optionally substituted with 1-2 R$^a$ and wherein * indicates the point of attachment of L$^1$ to the ring comprising X and Y; or
—(C=O)—;
each one of X and Y is independently selected from the group consisting of N and CH;
R$^1$ is selected from the group consisting of hydrogen, R$^b$, —OR$^b$, —SR$^b$, —N(R')R$^b$, CN, halo, and —NR'C(O)R";
provided that -L$^1$-R$^1$ does not include O—O, N—O, N—N, O—S, S—S, or N—S bonds; further provided that L$^1$ must be a bond when R$^1$ is CN, halo, or —NR'C(O)R"; and further provided that L$^1$ cannot be a bond when R$^1$ is hydrogen;
R$^2$ is selected from the group consisting of hydrogen, CH$_3$, CHF$_2$, CF$_3$, OMe, F, and Cl;
each of R$^3$, R$^4$ and R$^5$ is independently selected from the group consisting of hydrogen and R$^c$;
each of R$^6$ is independently selected R$^c$;
n is selected from 0, 1, 2 and 3;
each occurrence of R$^a$ is independently selected from the group consisting of: —OH; -halo; —NR$^e$R$^f$; C$_{1-4}$ alkoxy; C$_{1-4}$ haloalkoxy; —C(=O)O(C$_{1-4}$ alkyl); —C(=O)(C$_{1-4}$ alkyl); —C(=O)OH; —CONR'R"; —S(O)$_{1-2}$NR'R"; —S(O)$_{1-2}$(C$_{1-4}$ alkyl); and cyano;
each occurrence of R$^b$ is independently selected from the group consisting of:
C$_{3-10}$ cycloalkyl or C$_{3-10}$ cycloalkenyl, each of which is optionally substituted with from 1-4 substituents independently selected from the group consisting of oxo and R$^c$;
heterocyclyl or heterocycloalkenyl including 3-10 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and R$^c$;
heteroaryl including 5-10 ring atoms, wherein from 1-4 ring atoms are heteroatoms, each independently selected from the group consisting of N, N(H), N(R$^d$), O, and S(O)$_{0-2}$, and wherein the heteroaryl is optionally substituted with from 1-4 substituents independently selected R$^c$; and
C$_{6-10}$ aryl optionally substituted with from 1-4 substituents independently selected R$^c$;
each occurrence of R$^c$ is independently selected from the group consisting of: halo; cyano; C$_{1-10}$ alkyl which is optionally substituted with from 1-6 independently selected R$^a$; C$_{2-6}$ alkenyl; C$_{2-6}$ alkynyl; C$_{1-4}$ alkoxy; —S(O)$_{0-2}$(C$_{1-4}$ alkyl); —NR$^e$R$^f$; —OH; —S(O)$_{1-2}$NR'R"; —NO$_2$; —C(=O)(C$_{1-10}$ alkyl); —C(=O)O(C$_{1-4}$ alkyl); —C(=O)OH; —N(R')C(=O)(C$_{1-4}$ alkyl), —C(=O)NR'R", R$^g$, and —(CH$_2$)$_{1-2}$R$^g$;
each occurrence of R$^d$ is independently selected from the group consisting of: hydrogen, C$_{1-6}$ alkyl optionally substituted with from 1-3 independently selected R$^a$; —C(O)(C$_{1-4}$ alkyl); —C(O)O(C$_{1-4}$ alkyl); —CONR'R"; —S(O)$_{1-2}$NR'R"; —S(O)$_{1-2}$(C$_{1-4}$ alkyl); —OH; and C$_{1-4}$ alkoxy;
each occurrence of R$^e$ and R$^f$ is independently selected from the group consisting of: H; C$_{1-6}$ alkyl; —C(O)(C$_{1-4}$ alkyl); —C(O)O(C$_{1-4}$ alkyl); —CONR'R"; —S(O)$_{1-2}$NR'R"; —S(O)$_{1-2}$(C$_{1-4}$ alkyl); —OH; and C$_{1-4}$ alkoxy; and each occurrence of R$^g$ is independently selected from the group consisting of:
C$_{3-7}$ cycloalkyl or C$_{3-7}$ cycloalkenyl, each of which is optionally substituted with from 1-4 substituents independently selected from the group consisting of oxo and R$^a$;
heterocyclyl or heterocycloalkenyl including 3-7 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and R$^a$;
heteroaryl including 5-10 ring atoms, wherein from 1-4 ring atoms are heteroatoms, each independently selected from the group consisting of N, N(H), N(R$^d$), O, and S(O)$_{0-2}$, and wherein the heteroaryl is optionally substituted with from 1-4 R$^a$; and
C$_{6-10}$ aryl optionally substituted with from 1-4 R$^a$;
each occurrence of R' and R" is independently selected from the group consisting of: hydrogen; and C$_{1-4}$ alkyl.
In certain embodiments, L$^1$-R$^1$ does not include O—O, N—O, N—N, O—S, S—S, or N—S bonds.
In certain embodiments, L$^1$ must be a bond when R$^1$ is CN, halo, or —NR'C(O)R".
In certain embodiments, L$^1$ cannot be a bond when R$^1$ is hydrogen.
In certain embodiments, L$^1$-R$^1$ does not include O—O, N—O, N—N, O—S, S—S, or N—S bonds, L$^1$ must be a bond when R$^1$ is CN, halo, or —NR'C(O)R"; and L$^1$ cannot be a bond when R$^1$ is hydrogen.
In certain embodiments:
L$^1$ is a bond, —(C=O)—, *—O(C$_0$-C$_4$ alkylene)-, *—C$_1$-C$_4$ alkylene-, *—NR'(C$_0$-C$_4$ alkylene)-, *—NR'(C=O)(C$_0$-C$_4$ alkylene)-, or *—(C$_1$-C$_4$ alkylene)-C(=O)—, wherein the alkylene is optionally substituted with 1-2 R$^a$ and wherein * indicates the point of attachment of L$^1$ to the ring; or
when taken together with Y forms a heteroaryl ring including 9 or 10 ring atoms, wherein from 1-4 ring atoms are heteroatoms, each independently selected from the group consisting of N, N(H), N(R$^d$) and O, wherein at least one ring in the system is aromatic and wherein the heteroaryl is optionally substituted with from 1-4 substituents independently selected from the group consisting of oxo and $R^c$;

X and Y are both CH or one of X and Y is N and the other is CH;

$R^1$ is $R^b$;

$R^2$ is hydrogen, chloro, fluoro or methyl;

$R^3$, $R^4$ and $R^5$ are hydrogen or halo;

$R^6$ is selected from the group consisting of deuterium, halo and unsubstituted $C_{1-10}$ alkyl; and $R^b$ is:

heterocyclyl or heterocycloalkenyl including 3-10 ring atoms, wherein from 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with from 1-4 substituents independently selected from the group consisting of oxo and $R^c$; or heteroaryl including 5-10 ring atoms, wherein from 1-4 ring atoms are heteroatoms, each independently selected from the group consisting of N, N(H), N($R^d$), O, and $S(O)_{0-2}$, wherein at least one ring in the system is aromatic and wherein the heteroaryl is optionally substituted with from 1-4 substituents independently selected from oxo and $R^c$.

In certain embodiments:

$L^1$ is a bond, —(C=O)—, *—O($C_0$-$C_4$ alkylene)-, *—$C_1$-$C_4$ alkylene-, *—NR'($C_0$-$C_4$ alkylene)-, *—NR'(C=O)($C_0$-$C_4$ alkylene)-, or *—($C_1$-$C_4$ alkylene)-C(=O)—, wherein the alkylene is optionally substituted with 1-2 $R^a$ and wherein * indicates the point of attachment of $L^1$ to the ring; or $L^1$ when taken together with Y forms a heteroaryl ring including 9 or 10 ring atoms, wherein from 1-4 ring atoms are heteroatoms, each independently selected from the group consisting of N, N(H), N($R^d$) and O, wherein at least one ring in the system is aromatic and wherein the heteroaryl is optionally substituted with from 1-4 substituents independently selected from the group consisting of oxo and $R^c$;

X and Y are both CH or one of X and Y is N and the other is CH;

$R^1$ is $R^b$;

$R^2$ is hydrogen, chloro, fluoro or methyl;

$R^3$, $R^4$ and $R^5$ are hydrogen or halo;

$R^6$ is selected from the group consisting of deuterium, halo and unsubstituted $C_{1-10}$ alkyl; and $R^b$ comprises a hydrogen bond acceptor within seven atoms of the carbon atom between X and Y.

In certain embodiments:

$L^1$ is a bond, —(C=O)—, *—O($C_0$-$C_4$ alkylene)-, *—$C_1$-$C_4$ alkylene-, *—NR'($C_0$-$C_4$ alkylene)-, *—NR'(C=O)($C_0$-$C_4$ alkylene)-, or *—($C_1$-$C_4$ alkylene)-C(=O)—, wherein the alkylene is optionally substituted with 1-2 $R^a$ and wherein * indicates the point of attachment of $L^1$ to the ring; or when taken together with Y forms a heteroaryl ring including 9 or 10 ring atoms, wherein from 1-4 ring atoms are heteroatoms, each independently selected from the group consisting of N, N(H), N($R^d$) and O, wherein at least one ring in the system is aromatic and wherein the heteroaryl is optionally substituted with from 1-4 substituents independently selected from the group consisting of oxo and $R^c$;

X and Y are both CH or one of X and Y is N and the other is CH;

$R^1$ is $R^b$;

$R^2$ is hydrogen, chloro, fluoro or methyl;

$R^3$, $R^4$ and $R^5$ are hydrogen or halo;

n is 0; and $R^b$ is:

heterocyclyl or heterocycloalkenyl including 5-10 ring atoms, wherein from 1-3 ring atoms are heteroatoms, each independently selected from the group consisting of N, N(H), N($R^d$), O, and $S(O)_{0-2}$, and wherein the heterocyclyl or heterocycloalkenyl is optionally substituted with from 1-4 substituents independently selected from the group consisting of oxo and $R^c$; or heteroaryl including 5-10 ring atoms, wherein from 1-4 ring atoms are heteroatoms, each independently selected from the group consisting of N, N(H), N($R^d$), O, and $S(O)_{0-2}$, wherein at least one ring in the system is aromatic and wherein the heteroaryl is optionally substituted with from 1-4 substituents independently selected from oxo and $R^c$.

Identity of $R^c$

In certain embodiments, $R^c$ is independently selected from the group consisting of: halo; $C_{1-10}$ alkyl which is optionally substituted with from 1-6 independently selected $R^a$; $C_{1-4}$ alkoxy; $R^g$, and —$(CH_2)_{1-2}$ $R^g$.

Identity of $L^1$

In certain embodiments, $L^1$ is a bond, —(C=O)—, *—O($C_0$-$C_4$ alkylene)-, *—$C_1$-$C_4$ alkylene-, *—NR'($C_0$-$C_4$ alkylene)-, *—NR'(C=O)($C_0$-$C_4$ alkylene)-, or *—($C_1$-$C_4$ alkylene)-C(=O)—, wherein the alkylene is optionally substituted with 1-2 $R^a$ and wherein * indicates the point of attachment of $L^1$ to the ring.

In certain embodiments, $L^1$ is a bond, —(C=O)—, *—O($C_0$-$C_4$ alkylene)-, *—$C_1$-$C_4$ alkylene-, *—NR'($C_0$-$C_4$ alkylene)-, *—NR'(C=O)($C_0$-$C_4$ alkylene)-, or *—($C_1$-$C_4$ alkylene)-C(=O)—.

In certain embodiments, $L^1$ is a bond, —(C=O)—, *—O($C_1$-$C_4$ alkylene, *—$C_1$-$C_4$ alkylene-, *—($C_1$-$C_4$ alkylene)-C(=O)—, *—NH'($C_0$-$C_4$ alkylene)-, or *—NH'(C=O)($C_0$-$C_4$ alkylene)-, wherein the alkylene is optionally substituted with 1-2 $R^a$, and wherein * indicates the point of attachment of $L^1$ to the ring.

In certain embodiments, $L^1$ is a bond, —(C=O)—, *—O($C_1$-$C_4$ alkylene, *—$C_1$-$C_4$ alkylene-, or *—($C_1$-$C_4$ alkylene)-C(=O)—.

In certain embodiments, $L^1$ is a bond, *—$OCH_2$—, *—$OCH_2CH_2$, —$CH_2$—, —$CH(CH_3)$—, —$C(CH_3)2$-, —$CH_2CH_2CH_2$—, —(C=O)— or *—$(CH_2)$—C(=O)—.

In certain embodiments, $L^1$ is a bond or —$CH_2$—.

In certain embodiments, $L^1$ is a bond.

In certain embodiments, $L^1$ is taken together with Y to form an additional ring fused with the ring containing X and Y, wherein the fused ring system includes 9 or 10 ring atoms, wherein from 1-4 ring atoms in the additional ring are heteroatoms, each independently selected from the group consisting of N, N(H), N($R^d$) and O, wherein the additional ring is substituted with $R^1$ and is optionally further substituted with from 1-4 substituents independently selected from the group consisting of oxo and $R^c$.

Identity of X and Y

In certain embodiments, X and Y are both CH or one of X and Y is N and the other is CH.

In certain embodiments, X and Y are both CH.

Identity of $R^1$

In certain embodiments, $R^1$ is $R^b$.

In certain embodiments, $R^b$ comprises a hydrogen bond acceptor within seven atoms of the carbon atom between X and Y.

In certain embodiments, $R^b$ comprises a hydrogen bond acceptor within seven atoms of the carbon atom between X and Y and the hydrogen bond acceptor is selected from a carbonyl group, a sulfonyl group, a nitrogen-containing heteroaromatic group, an oxygen-containing heteroaromatic group and an oxygen-containing aliphatic or cycloaliphatic group.

In certain embodiments, $R^b$ comprises a hydrogen bond acceptor within seven atoms of the carbon atom between X and Y and wherein the hydrogen bond acceptor is selected from an amide, a lactam, a carbamate, a pyridone, a pyrimidinone, a piperazinone, a piridazinone, a urea, a sulfonamide, a sulfone, a pyrimidine, a pyrazine, a pyridazine, a pyridine, an oxazole, an isoxazole, an oxadiazole, a thiazole, a thiadiazole, an imidazole, a pyrazole, an oxazole, an isoxazole, an oxadiazole, an oxetane, a tetrahydrofuran, a tetrahydropyran or a methoxy alkyl group.

In certain embodiments, $R^b$ is:
heterocyclyl or heterocycloalkenyl including 3-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$; or
heteroaryl including 5-10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 substituents independently selected from oxo and $R^c$.

In certain embodiments, $R^b$ is:
heterocyclyl or heterocycloalkenyl including 5-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$; or
heteroaryl including 5-10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 substituents independently selected from oxo and $R^c$.

In certain embodiments, $R^b$ is:
heterocyclyl or heterocycloalkenyl including 5-10 ring atoms, wherein from 1-3 ring atoms are heteroatoms each independently selected from the group consisting of N, N(H), N($R^d$), O, and S(O)$_{0-2}$, wherein at least one heteroatom is N or N($R^d$), and wherein the heterocyclyl or heterocycloalkenyl is optionally substituted with from 1-4 substituents independently selected from the group consisting of oxo and $R^c$; or
heteroaryl including 5-10 ring atoms, wherein from 1-4 ring atoms are heteroatoms, each independently selected from the group consisting of N, N(H), N($R^d$), O, and S(O)$_{0-2}$, wherein at least one heteroatom is N or N($R^d$), wherein at least one ring in the system is aromatic and wherein the heteroaryl is optionally substituted with from 1-4 substituents independently selected from oxo and $R^c$.

In certain embodiments, $R^c$ is independently selected from halo, $C_{1-4}$ alkyl which is optionally substituted with from 1-3 independently selected halo atoms and $C_{1-4}$ alkoxy.

In certain embodiments, $R^b$ is selected from the group consisting of:

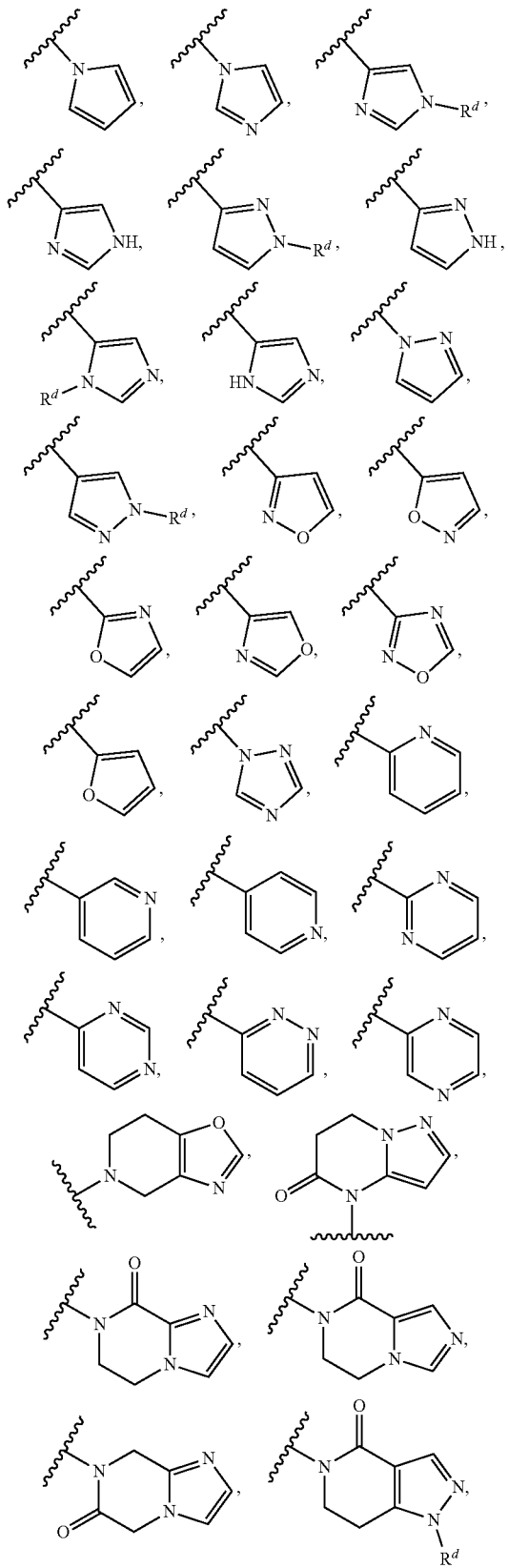

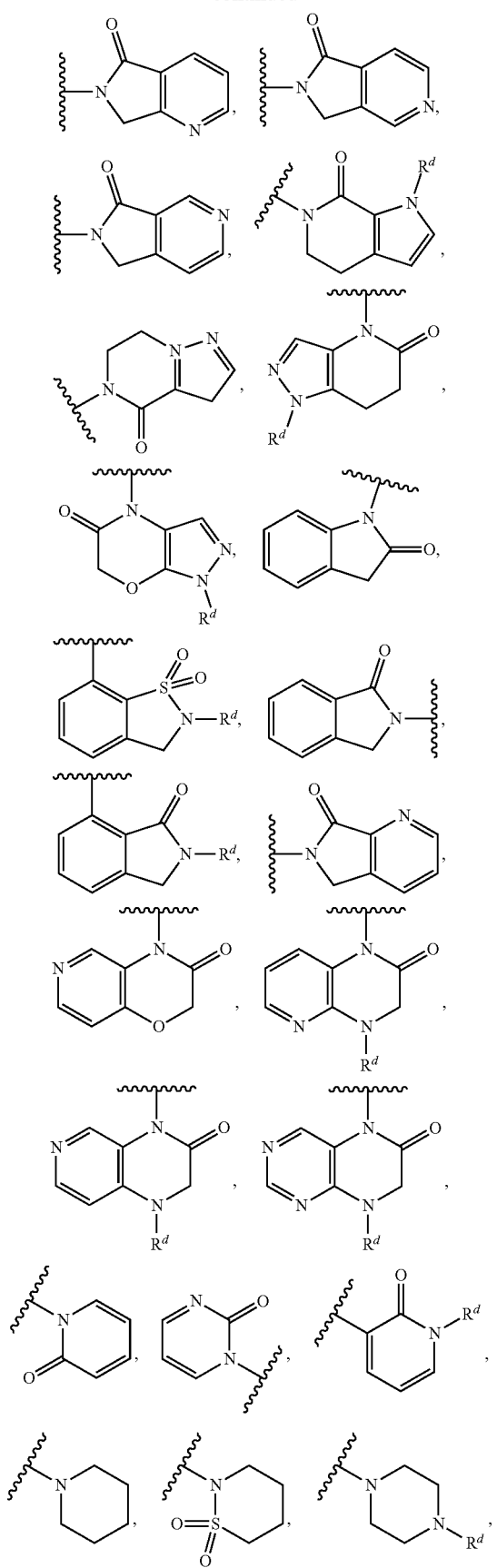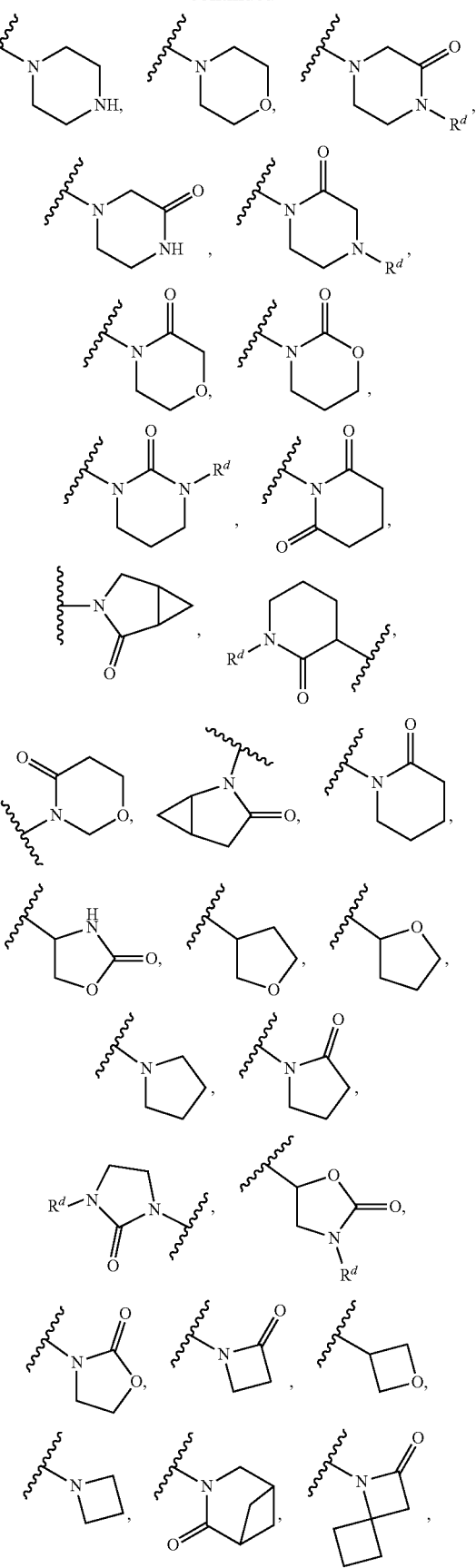

-continued

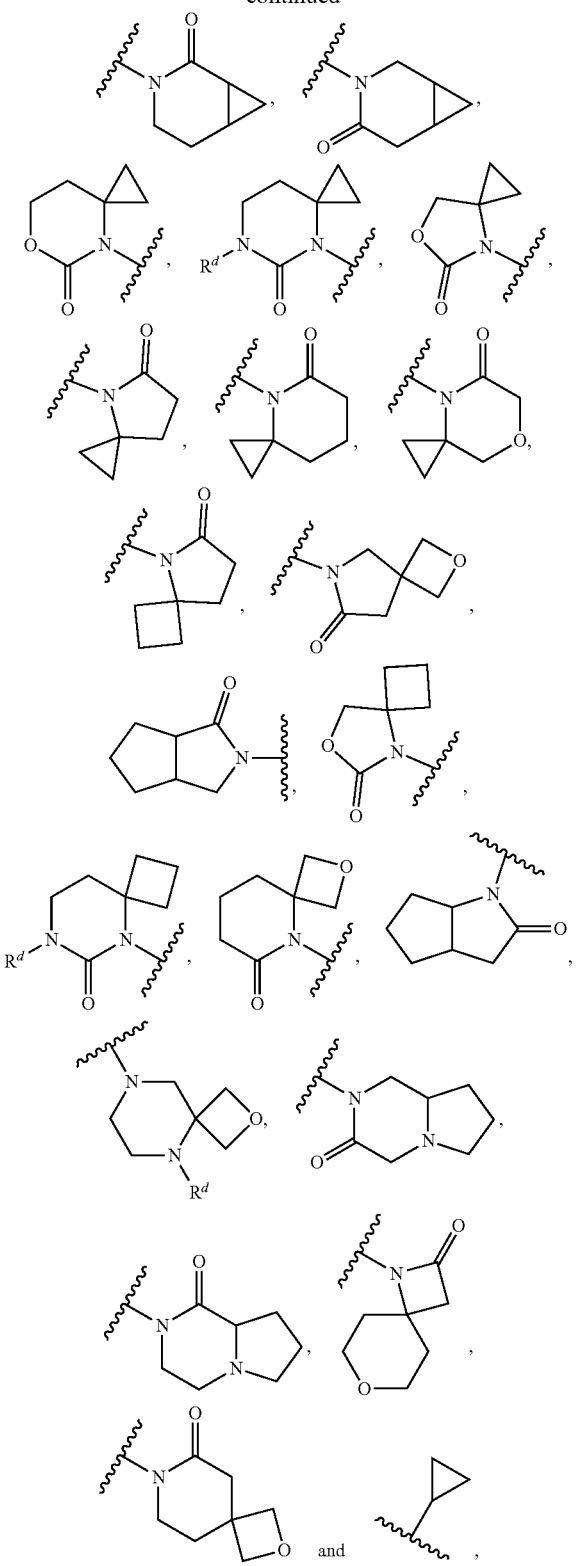

each of which is optionally substituted with from 1-4 substituents independently selected $R^c$.

In certain embodiments, $R^b$ is heteroaryl including 5-10 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$.

In certain embodiments, $R^b$ is heteroaryl including 5-6 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$.

In certain embodiments, R is heteroaryl including 5 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-2 independently selected $R^c$.

In certain embodiments, $R^b$ is heteroaryl including 5 ring atoms, wherein from 1-4 ring atoms are heteroatoms, each independently selected from the group consisting of N, N(H), N($R^d$), O, and S(O)$_{0-2}$.

In certain embodiments, $R^b$ is selected from the group consisting of

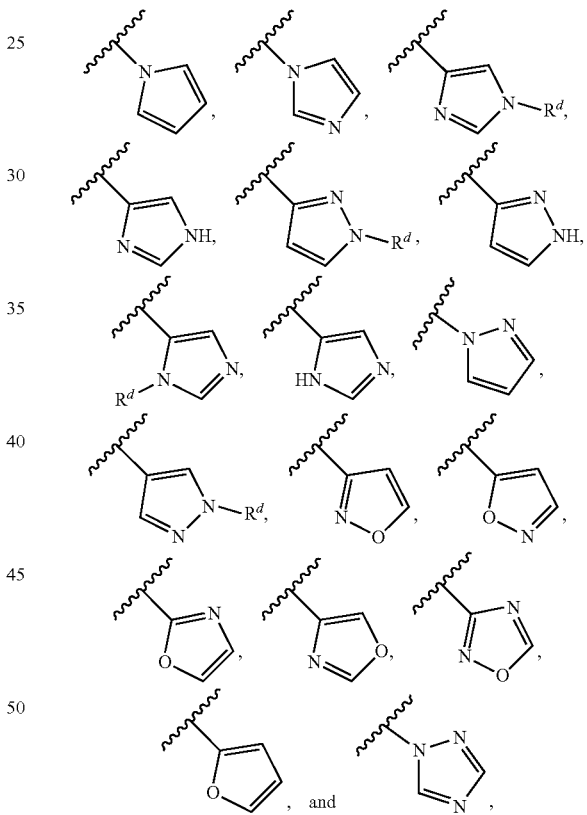

each of which is optionally substituted with from 1-2 independently selected $R^c$.

In certain embodiments, $R^b$ is selected from the group consisting of

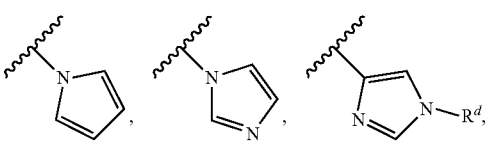

-continued

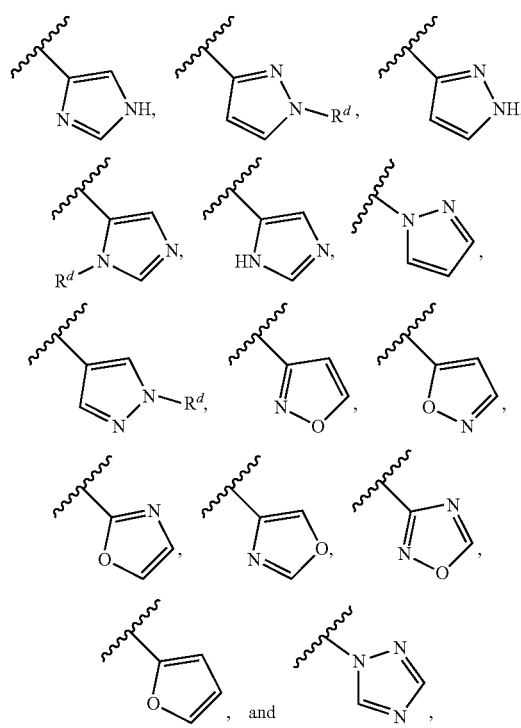

optionally wherein $R^d$ is CH$_3$.

In certain embodiments, $R^b$ is selected from the group consisting of

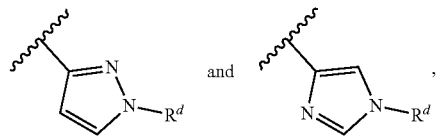

optionally wherein $R^d$ is CH$_3$.

In certain embodiments, R is selected from

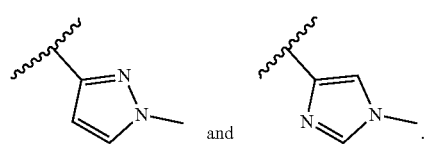

In certain embodiments, $R^b$ is

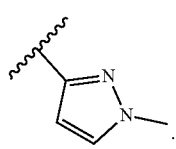 [SMILES: *c1ccn(C)n1]

In certain embodiments, $R^b$ is selected from the group consisting of

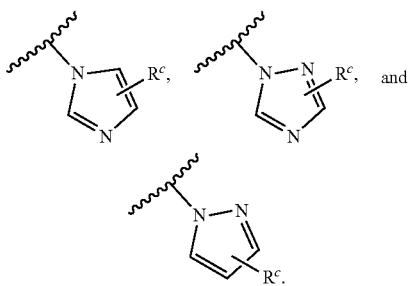

In certain embodiments, $R^b$ is selected from the group consisting of $R^c$

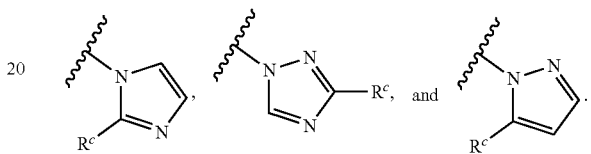

In certain embodiments, $R^c$ is selected from the group consisting of C$_{1-10}$ alkyl which is optionally substituted with from 1-6 independently selected $R^a$ and —NR$^e$R$^f$, optionally wherein RC is methyl, or —NH$_2$.

In certain embodiments, $R^b$ is selected from the group consisting of

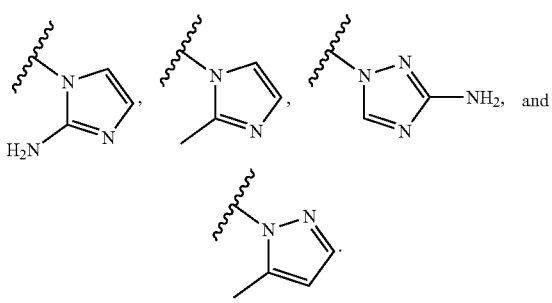

In certain embodiments, $R^b$ is

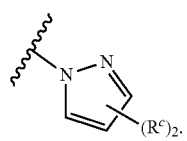

In certain embodiments, $R^b$ is

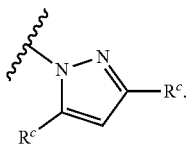

In certain embodiments, $R^c$ is C$_{1-10}$ alkyl which is optionally substituted with from 1-6 independently selected $R^a$ and —NR$^e$R$^f$, optionally wherein $R^c$ is methyl.

In certain embodiments, $R^b$ is

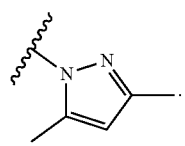 [SMILES: *n1nc(C)cc1C]

In certain embodiments, $R^b$ is heteroaryl including 6 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 substituents independently selected $R^c$.

In certain embodiments, $R^b$ is heteroaryl including 6 ring atoms, wherein from 1-4 ring atoms are heteroatoms, each independently selected from the group consisting of N, N(H), N($R^d$), O, and S(O)$_{0-2}$.

In certain embodiments, $R^b$ is selected from the group consisting of

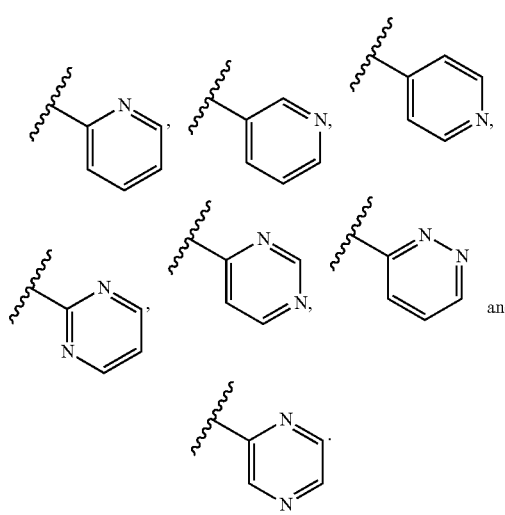

In certain embodiments, $R^b$ is

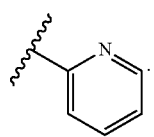 [SMILES: *c1ccccn1]

In certain embodiments, $R^b$ is heteroaryl including 7-10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 independently selected oxo or $R^c$.

In certain embodiments, $R^b$ is heteroaryl including 9-10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 independently selected oxo or $R^c$.

In certain embodiments, $R^b$ is heteroaryl including 9 ring atoms, wherein at least one ring in the system is aromatic, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected from the list consisting of oxo and $R^c$.

In certain embodiments, $R^b$ is selected from the group consisting of

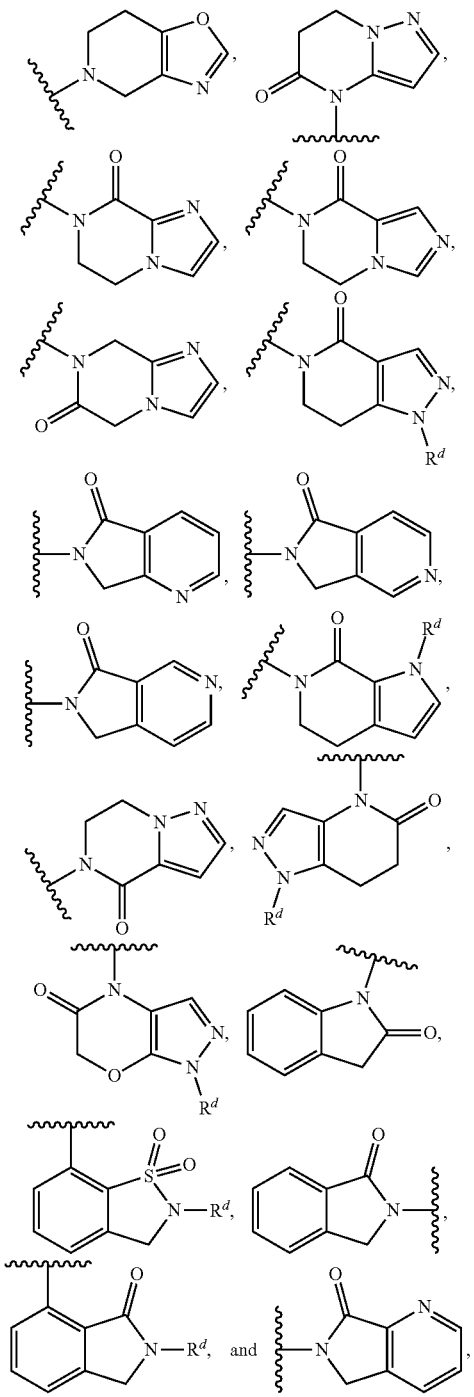

each of which is optionally substituted with from 1-4 independently selected $R^c$.

In certain embodiments, $R^b$ is selected from the group consisting of

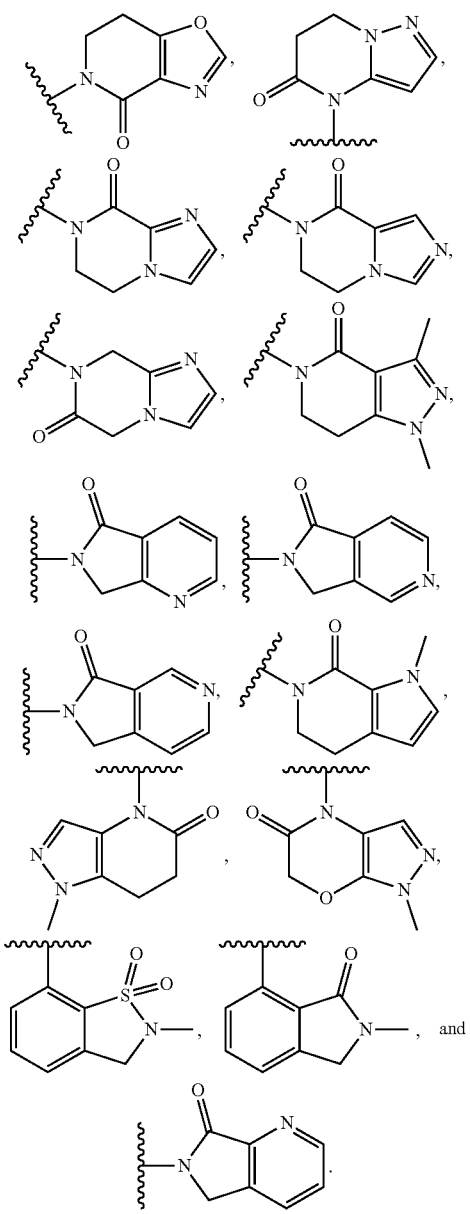

In certain embodiments, $R^b$ is heteroaryl including 10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 independently selected oxo or $R^c$.

In certain embodiments, $R^b$ is selected from the group consisting of

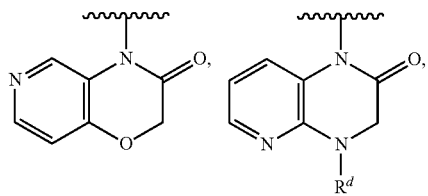

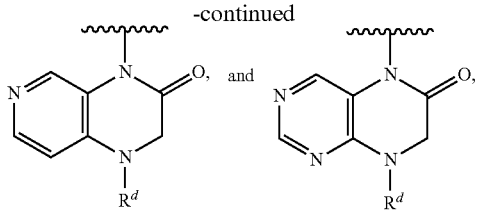

-continued each of which is optionally substituted with from 1-4 independently selected $R^c$.

In certain embodiments, $R^b$ is selected from the group consisting of

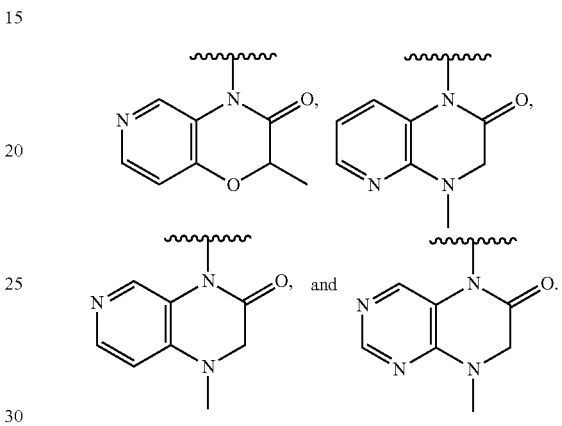

In certain embodiments, $R^b$ is heterocyclyl or heterocycloalkenyl including 3-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocyclyl or heterocycloalkenyl including 4-6 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocyclyl or heterocycloalkenyl including 5-6 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocyclyl or heterocycloalkenyl including 6 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocycloalkenyl including 6 ring atoms, wherein from 1-3 ring atoms are heteroatoms, each independently selected from the group consisting of N, N(H), N($R^d$), O, and S(O)$_{0-2}$, and wherein the heterocycloalkenyl is optionally substituted with from 1-4 substituents independently selected from the group consisting of oxo and $R^c$.

In certain embodiments, $R^b$ is or

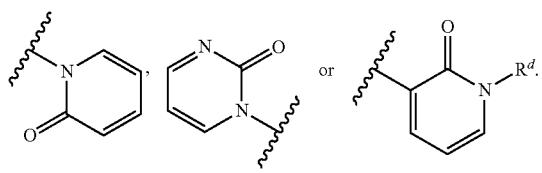

In certain embodiments, $R^d$ is $CH_3$.
In certain embodiments, $R^b$ is

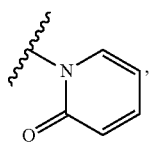

optionally substituted with from 1-2 independently selected $R^c$ substituents.

In certain embodiments, $R^b$ is

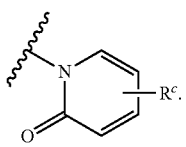

In certain embodiments, $R^b$ is

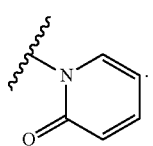 [SMILES: *n1ccccc1=O]

In certain embodiments, $R^c$ or each occurrence of $R^c$ is selected from the group consisting of $C_{1-10}$ alkyl optionally substituted with from 1-6 independently selected $R^a$, $C_{1-4}$ alkoxy, halo, and $-NR^eR^f$.

In certain embodiments, $R^c$ is selected from the group consisting of methyl, ethyl, $-CHF_2$, $-CF_3$, methoxy, fluoro, chloro, and $NH_2$.

In certain embodiments, $R^1$ is selected from the group consisting of

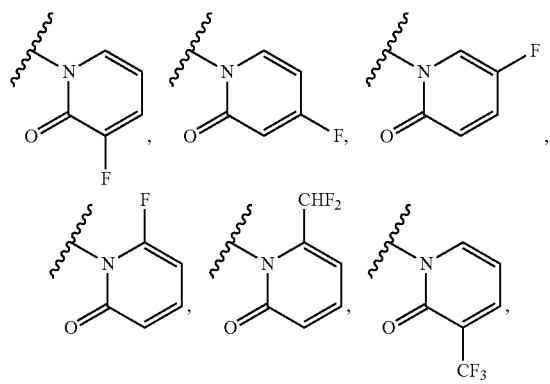

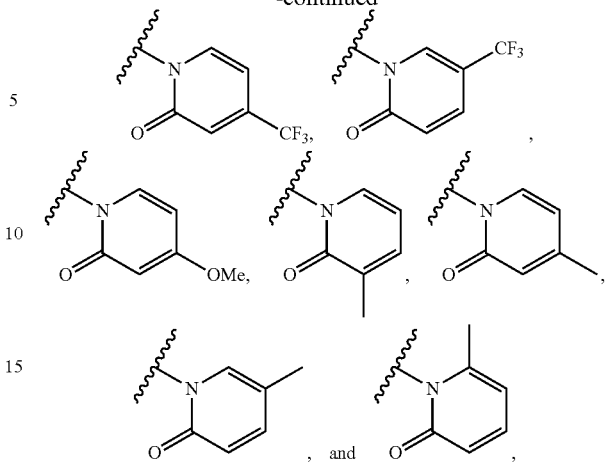

In certain embodiments, $R^b$ is heterocyclyl including 6 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$.

In certain embodiments, $R^b$ is selected from the group consisting of

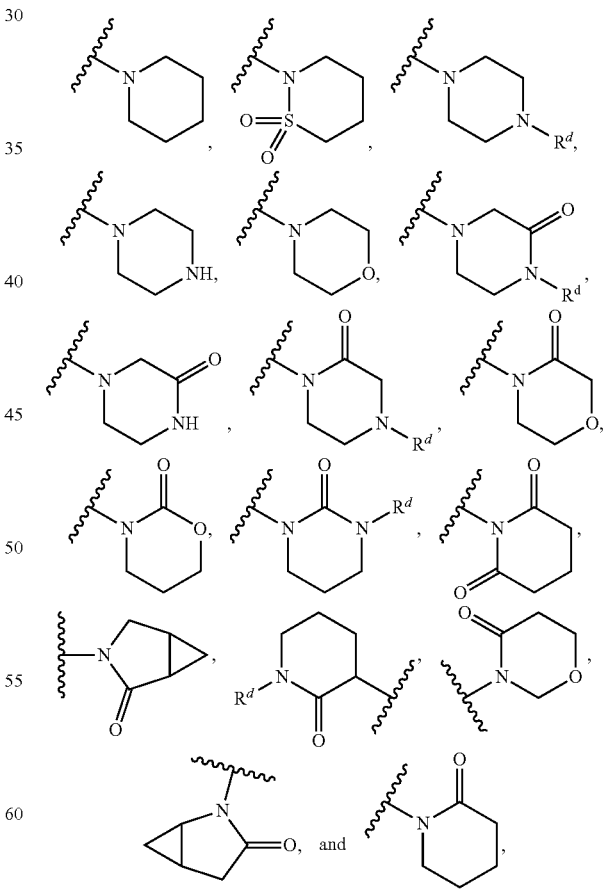

each of which is optionally substituted with 1-4 substituents independently selected from the group consisting of oxo and $R^c$.

In certain embodiments, $R^c$ is methyl, halo, methoxy or $CF_3$.

In certain embodiments, $R^b$ is selected from the group consisting of

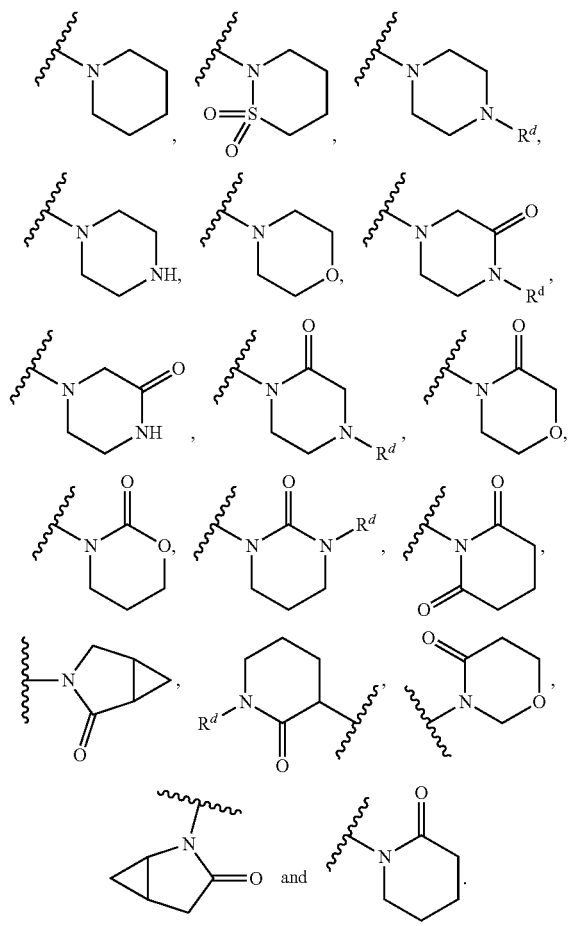

In certain embodiments, $R^b$ is selected from the group consisting of

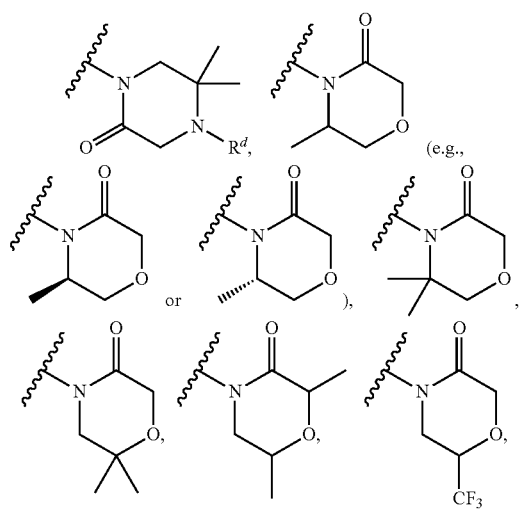

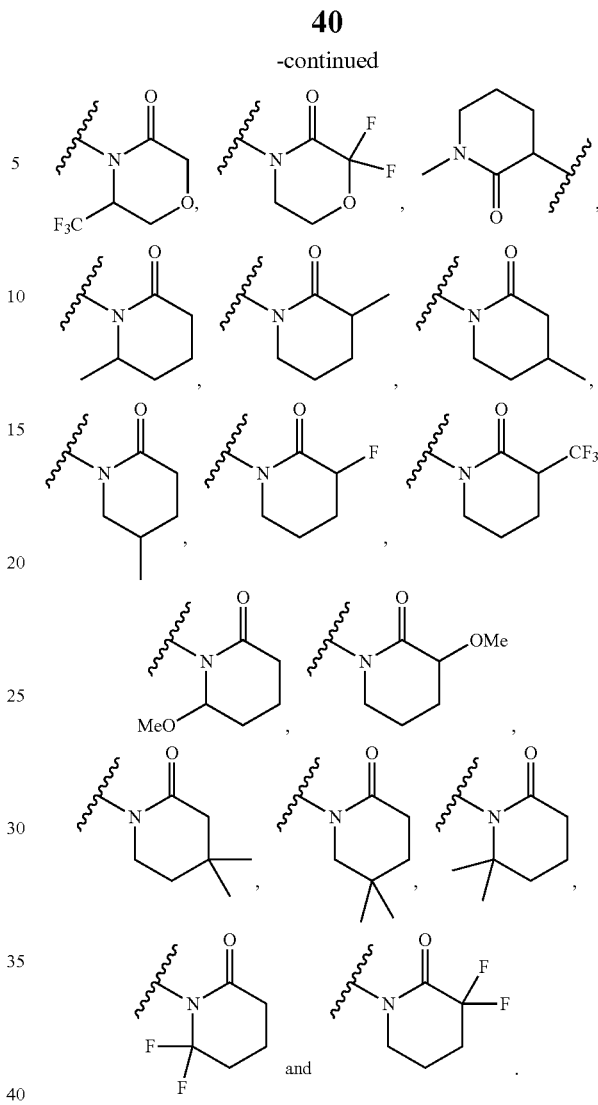

In certain embodiments, R is $CH_3$.

In certain embodiments, $R^b$ is

In certain embodiments, $R^b$ is heterocyclyl or heterocycloalkenyl including 5 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocyclyl including 5 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$.

In certain embodiments, $R^b$ is selected from the group consisting of

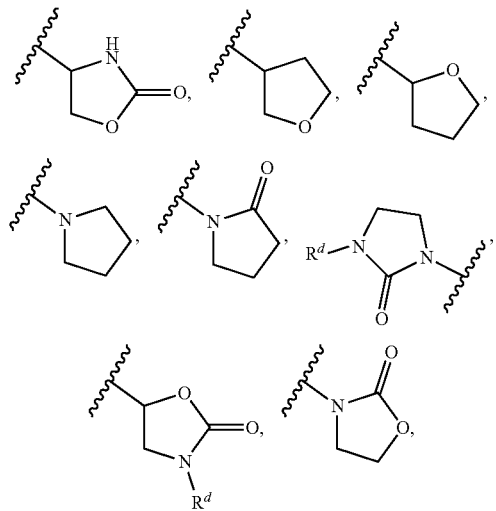

each of which is optionally substituted with 1-4 $R^c$.

In certain embodiments, $R^c$ is halo, or $C_{1-6}$ alkyl.

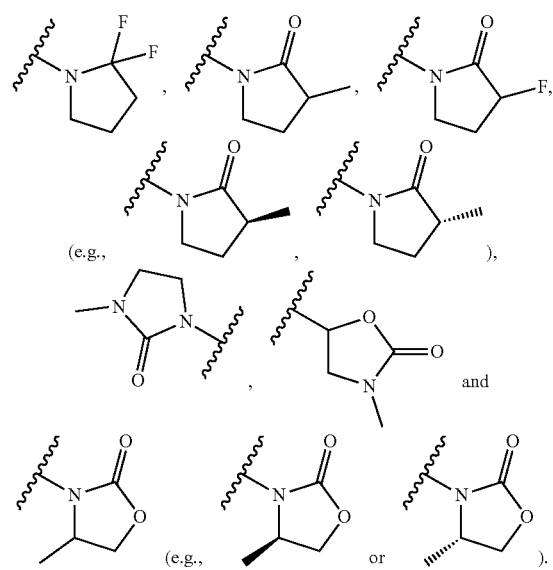

In certain embodiments, $R^b$ is selected from the group consisting of

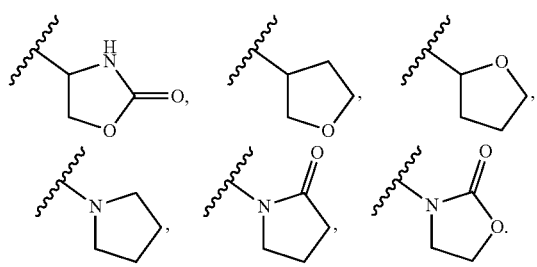

In certain embodiments, $R^b$ is

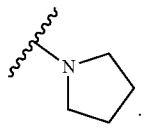 [SMILES: *N1CCCC1]

In certain embodiments, $R^b$ is heterocycloalkenyl including 5 ring atoms, wherein from 1-3 ring atoms are heteroatoms, each independently selected from the group consisting of N, N(H), N($R^d$), O, and S(O)$_{0-2}$, and wherein the heterocycloalkenyl is optionally substituted with from 1-4 substituents independently selected from the group consisting of oxo and $R^c$.

In certain embodiments, $R^b$ is

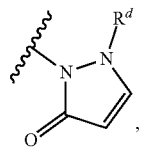

optionally wherein $R^b$ is

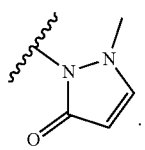 [SMILES: *n1c(=O)ccn1C]

In certain embodiments, $R^b$ is selected from the group consisting of N

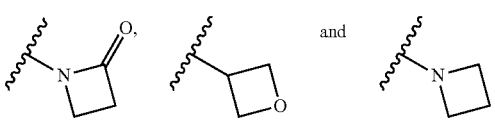

In certain embodiments, $R^b$ is heterocyclyl or heterocycloalkenyl including 7-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocyclyl including 7-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocyclyl including 7 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected $R^c$.

In certain embodiments, $R^b$ is selected from the group consisting of

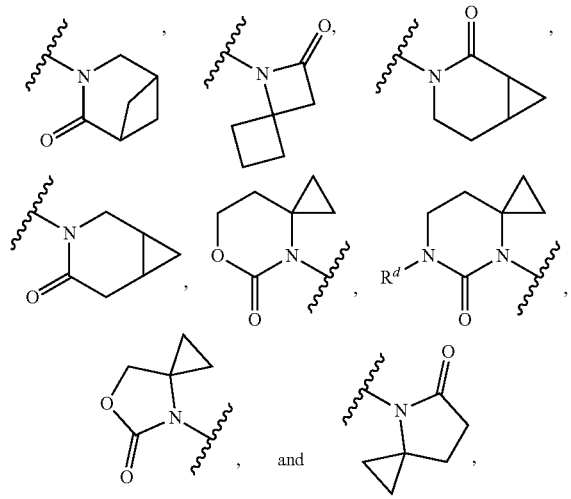

each of which is optionally substituted with from 1-4 substituents independently selected $R^c$.

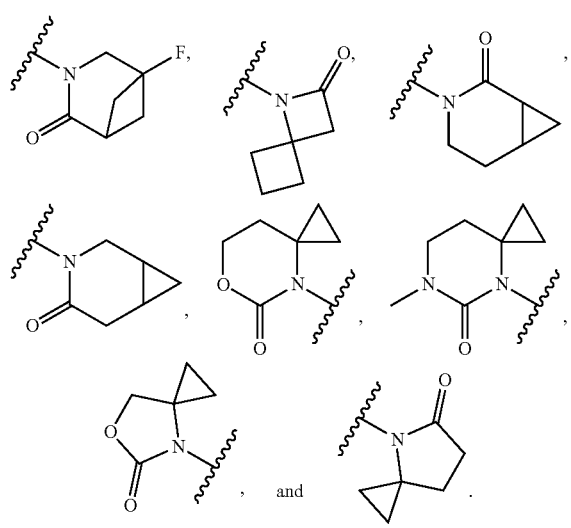

In certain embodiments, $R^b$ is selected from the group consisting of

In certain embodiments, $R^b$ is heterocyclyl including 8 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected $R^c$.

In certain embodiments, $R^b$ is selected from the group consisting of

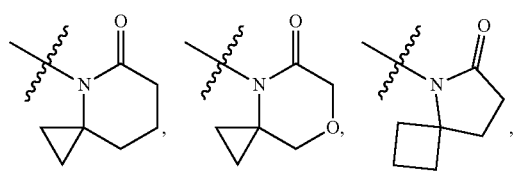

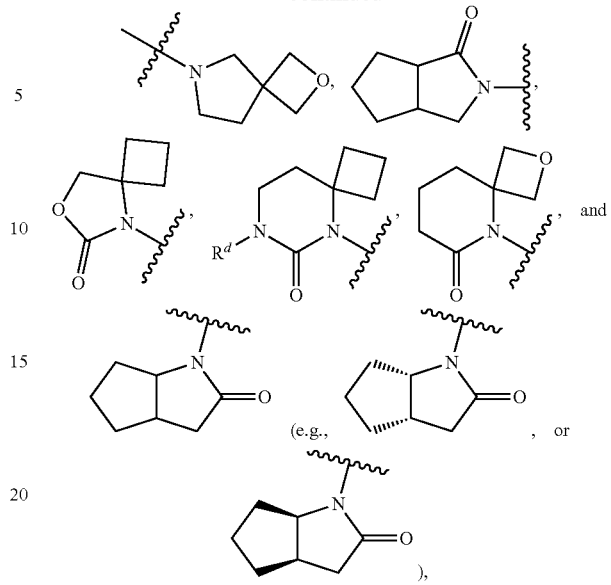

each of which is optionally substituted with from 1-4 substituents independently selected $R^c$.

In certain embodiments, $R^b$ is selected from the group consisting of

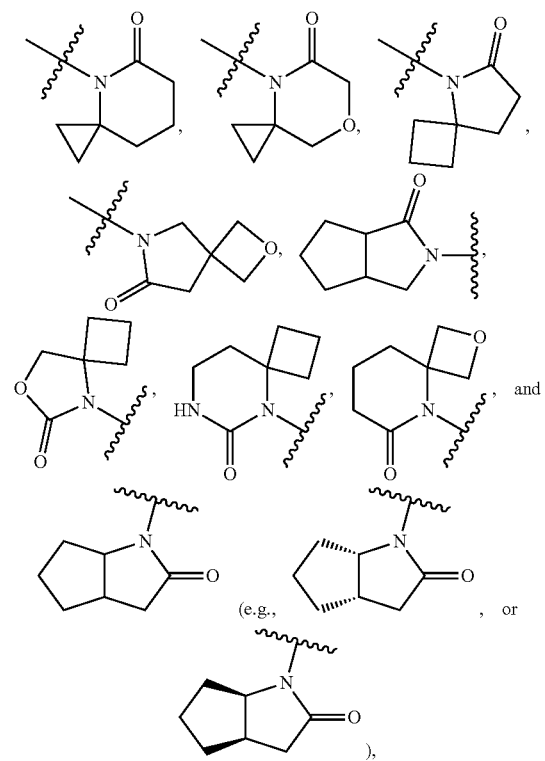

In certain embodiments, $R^b$ is heterocyclyl including 9 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$.

In certain embodiments, $R^b$ is selected from the group consisting of

[structures shown]

each of which is optionally substituted with from 1-4 substituents independently selected $R^c$.

In certain embodiments, $R^d$ is $CH_3$.

In certain embodiments, $R^b$ is selected from the group consisting of

[structures shown]

In certain embodiments, $R^b$ is $C_{3-10}$ cycloalkyl or $C_{3-10}$ cycloalkenyl, each of which is optionally substituted with from 1-4 substituents independently selected from the group consisting of oxo and $R^c$;

In certain embodiments, $R^b$ is

[cyclopropyl structure]

optionally substituted with one $R^c$.

Identity of $R^2$

In certain embodiments, $R^2$ is hydrogen, chloro, fluoro or methyl.

In certain embodiments, $R^2$ is chloro.

Identity of $R^2$, $R^3$, $R^4$ and $R^5$ and Value of n

In certain embodiments, $R^3$, $R^4$ and $R^5$ are hydrogen or halo.

In certain embodiments, $R^3$ is halo or hydrogen and $R^4$ and $R^5$ are hydrogen.

In certain embodiments, $R^3$, $R^4$ and $R^5$ are hydrogen.

In certain embodiments, $R^2$ is chloro, and $R^3$, $R^4$ and $R^5$ are hydrogen.

In certain embodiments, n is 0.

In certain embodiments, n is 0 and $R^3$, $R^4$ and $R^5$ are hydrogen; and/or $L^1$ is a bond, —(C=O)—, *—$C_1$-$C_4$ alkylene-, *—NR' ($C_0$-$C_4$ alkylene)-, *—NR'(C=O)($C_0$-$C_4$ alkylene)-, or *—($C_1$-$C_4$ alkylene)-C(=O)—, wherein the alkylene is optionally substituted with 1-2 $R^a$ and wherein * indicates the point of attachment of $L^1$ to the ring.

In certain embodiments, n is 1 or 2.

Identity of $R^6$

In certain embodiments, $R^6$ is selected from the group consisting of deuterium, halo; cyano; $C_{1-10}$ alkyl which is optionally substituted with from 1-6 independently selected $R^a$; $C_{1-4}$ alkoxy, $C_{1-4}$ haloalkoxy; and —NR$^e$R$^f$; optionally wherein $R^6$ is selected from the group consisting of deuterium, cyano, chloro, fluoro, methyl, ethyl, —CHF$_2$, methoxy, —OCHF$_2$, and —NH$_2$.

In certain embodiments, $R^6$ is selected from the group consisting of deuterium, halo and unsubstituted $C_{1-10}$ alkyl.

In certain embodiments, $R^6$ is selected from the group consisting of deuterium, fluoro and methyl.

In certain embodiments, $R^6$ is deuterium, optionally wherein n is 4.

Formulae I-1, I-2, I-3 and I-4

In certain embodiments, the compound is a compound of formula (I-1)

Formula (I-1)

[structure]

In certain embodiments, the compound is a compound of formula (I-2)

Formula (I-2)

[structure]

wherein X is —NH— or —O—.

In certain embodiments, X is —O—.

In certain embodiments, the compound is a compound of formula (I-3)

Formula (I-3)

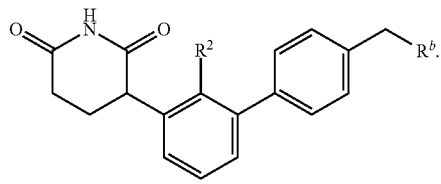

In certain embodiments, the compound is a compound of formula (I-4)

Formula (I-4)

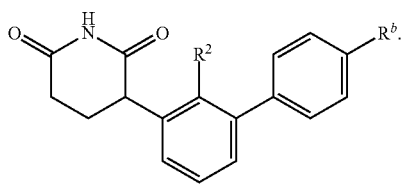

In certain embodiments, $R^2$ is chloro.

In certain embodiments, $R^b$ is heterocyclyl or heterocycloalkenyl including 3-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$; or heteroaryl including 5-10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 substituents independently selected from oxo and $R^c$.

In certain embodiments, $R^b$ is heterocycloalkenyl including 6 ring atoms, wherein from 1-3 ring atoms are heteroatoms, each independently selected from the group consisting of N, N(H), N($R^d$), O, and S(O)$_{0-2}$, and wherein the heterocycloalkenyl is optionally substituted with from 1-4 substituents independently selected from the group consisting of oxo and $R^c$.

In certain embodiments, $R^b$ is

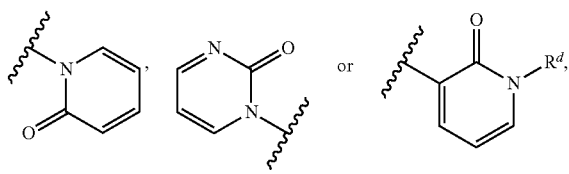

each of which is optionally substituted with from 1-2 substituents independently selected $R^c$ In certain embodiments, $R^b$ is

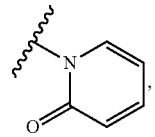 [SMILES: *n1ccccc1=O]

which is optionally substituted with from 1-2 independently selected $R^c$.

In certain embodiments, $R^b$ is

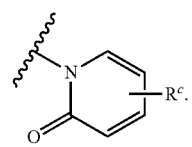

In certain embodiments, $R^c$ or each occurrence of $R^c$ is selected from the group consisting of $C_{1-10}$ alkyl optionally substituted with from 1-6 independently selected $R^a$, $C_{1-4}$ alkoxy, halo, and —N$R^e R^f$.

In certain embodiments, $R^c$ is selected from the group consisting of methyl, ethyl, —CHF$_2$, —CF$_3$, methoxy, fluoro, chloro, and NH$_2$.

In certain embodiments, $R^b$ is selected from the group consisting of

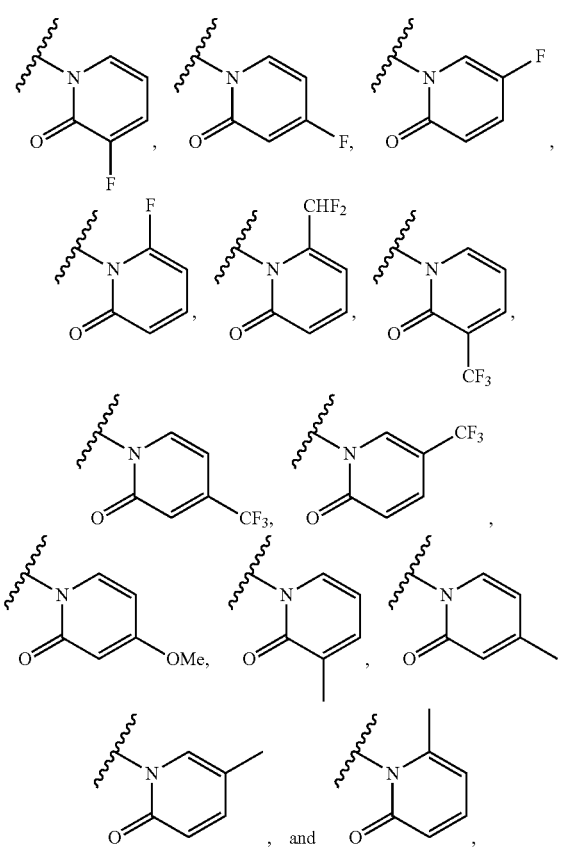

In certain embodiments, $R^b$ is

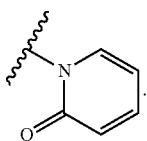

In certain embodiments, $R^b$ is heteroaryl including 5 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 substituents independently selected $R^c$.

In certain embodiments, R is selected from the group consisting of

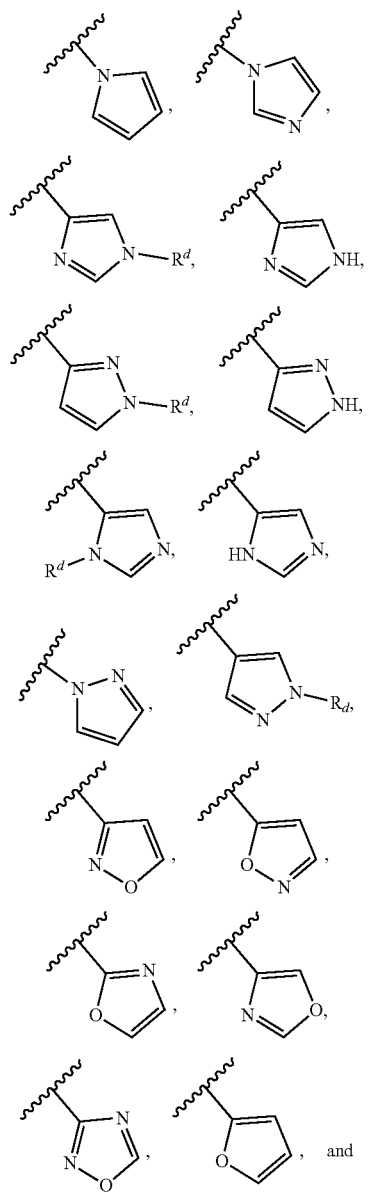

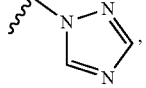

each of which is optionally substituted with from 1-2 independently selected $R^c$.

In certain embodiments, $R^b$ is selected from the group consisting of

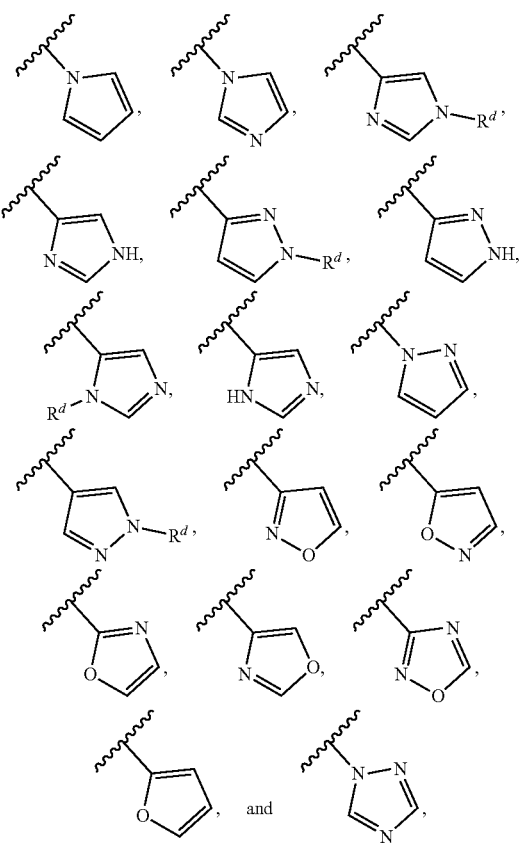

optionally wherein $R^d$ is CH$_3$.

In certain embodiments, $R^b$ is

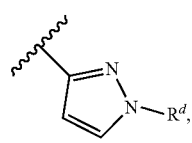

optionally wherein $R^d$ is CH$_3$.

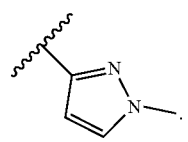 [SMILES: *c1ccn(C)n1]

In certain embodiments, $R^b$ is In certain embodiments, $R^b$ is heterocyclyl including 6 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$.

In certain embodiments, $R^b$ is selected from the group consisting of

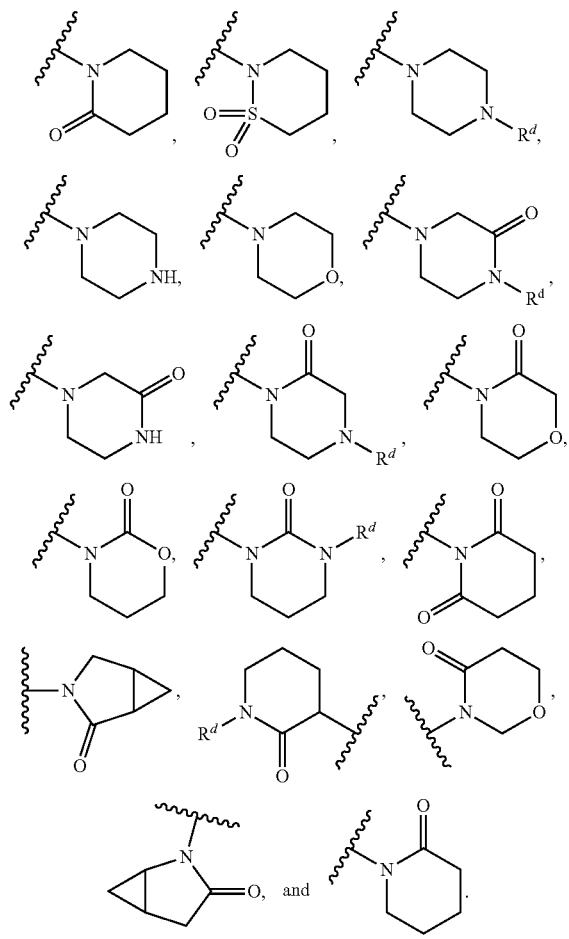

In certain embodiments, $R^b$ is selected from the group consisting of R

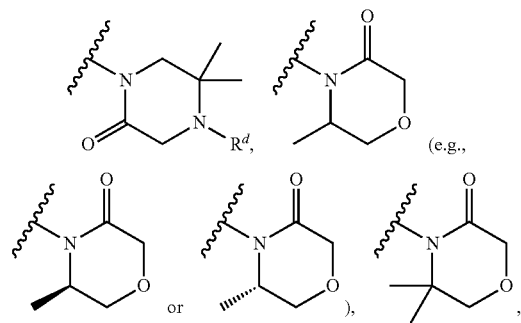

(e.g.,

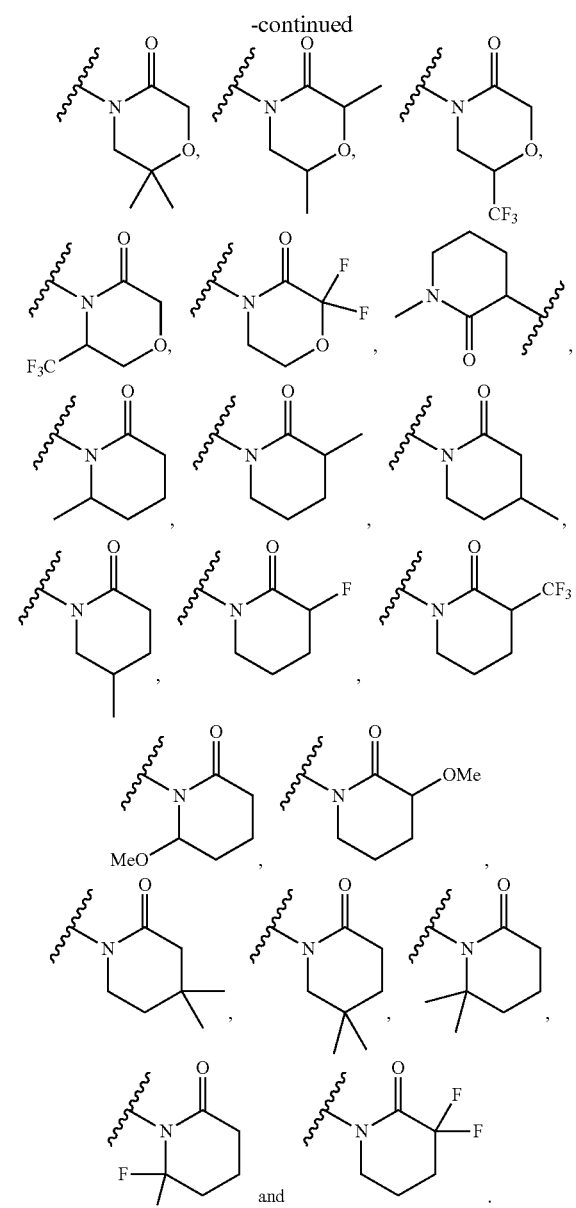

In certain embodiments, $R^d$ is CH$_3$.
In certain embodiments, $R^b$ is

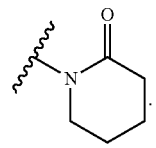 [SMILES: *N1CCCCC1=O]

In certain embodiments, $R^b$ is heteroaryl including 6 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$.

In certain embodiments, $R^b$ is heteroaryl including 6 ring atoms, wherein from 1-4 ring atoms are heteroatoms, each independently selected from the group consisting of N, N(H), N(R$^d$), O, and S(O)$_{0-2}$.

In certain embodiments, R$^b$ is selected from the group consisting of

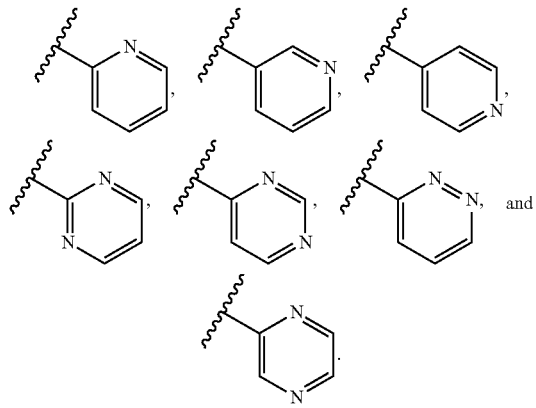

In certain embodiments, R$^b$ is

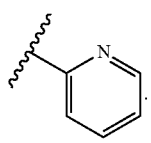 [SMILES: *c1ccccn1]

In certain embodiments, R$^b$ is heteroaryl including 9 ring atoms, wherein from 1-4 ring atoms are heteroatoms, each independently selected from the group consisting of N, N(H), N(R$^d$), O, and S(O)$_{0-2}$, wherein at least one ring in the system is aromatic and wherein the heteroaryl is optionally substituted with from 1-4 independently selected from the group consisting of oxo and R$^c$.

In certain embodiments, R$^b$ is selected from the group consisting of

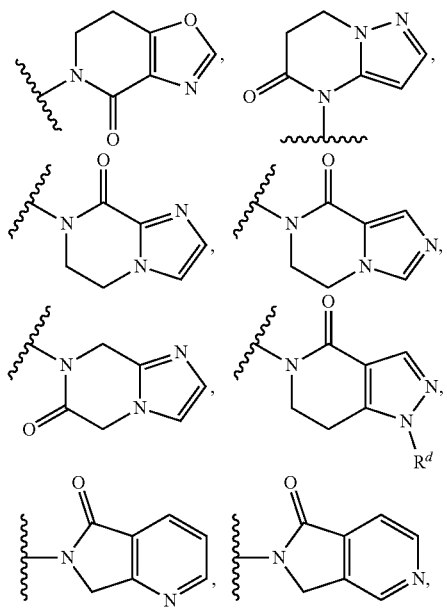

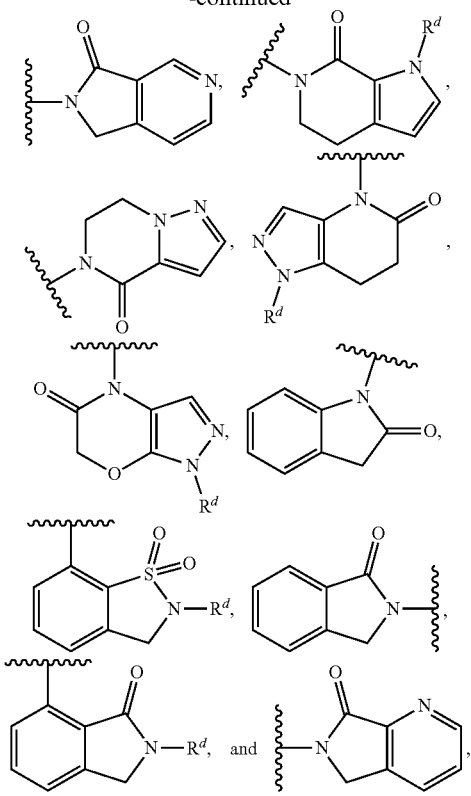

each of which is optionally substituted with from 1-4 independently selected R$^c$.

In certain embodiments, R$^b$ is selected from the group consisting of

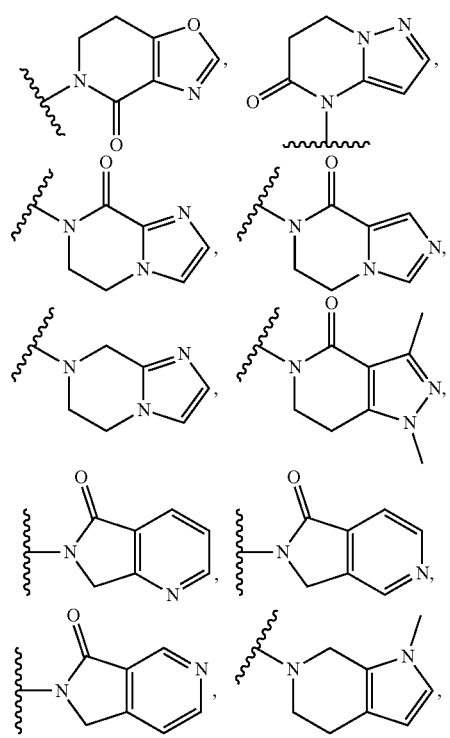

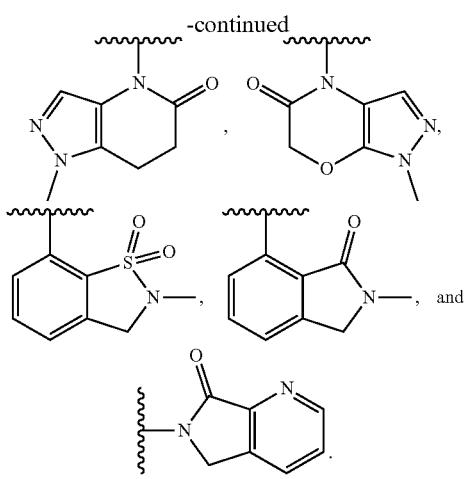

In certain embodiments, $R^b$ is heteroaryl including 10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 independently selected oxo and $R^c$.

In certain embodiments, $R^b$ is selected from the group consisting of

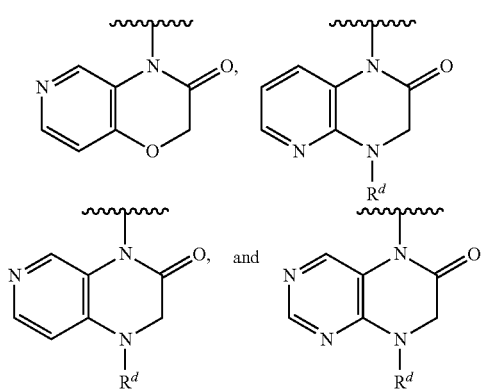

each of which is optionally substituted with from 1-4 independently selected $R^c$.

In certain embodiments, $R^b$ is selected from the group consisting of

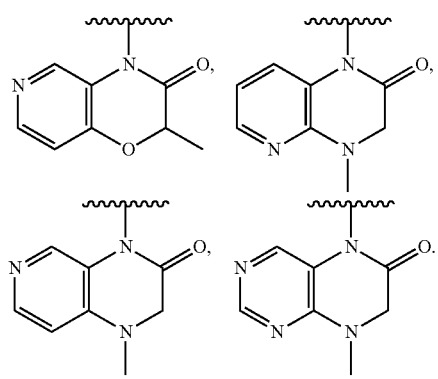

In certain embodiments, $R^b$ is heterocyclyl including 7-10 ring atoms, wherein from 1-3 ring atoms are heteroatoms, each independently selected from the group consisting of N, N(H), N($R^d$), O, and S(O)$_{0-2}$, wherein and wherein the heterocyclyl or heterocycloalkenyl is optionally substituted with from 1-4 substituents independently selected from the group consisting of oxo and $R^c$.

In certain embodiments, $R^b$ is heterocyclyl including 7 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected $R^c$.

In certain embodiments, $R^b$ is selected from the group consisting of


each of which is optionally substituted with from 1-4 substituents independently selected $R^c$.

In certain embodiments, $R^b$ is selected from the group consisting of


In certain embodiments, $R^b$ is heterocyclyl including 8 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected $R^c$.

In certain embodiments, $R^b$ is selected from the group consisting of

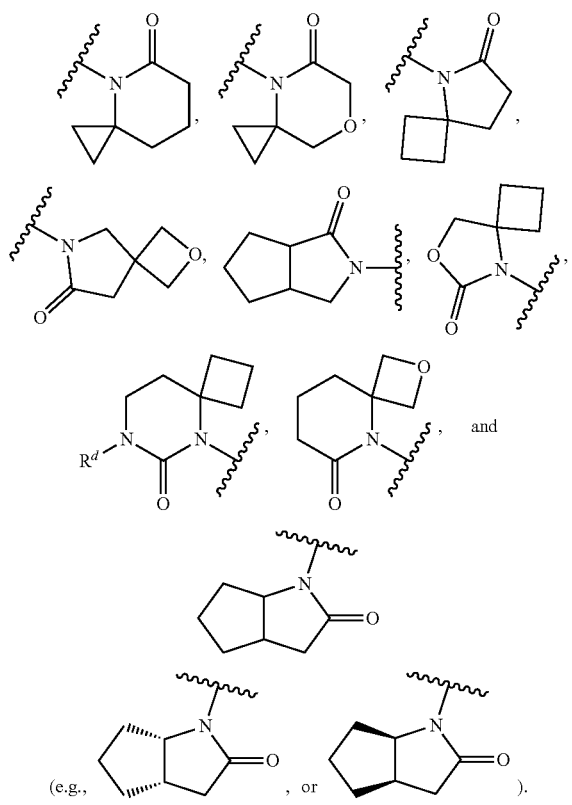

(e.g.,

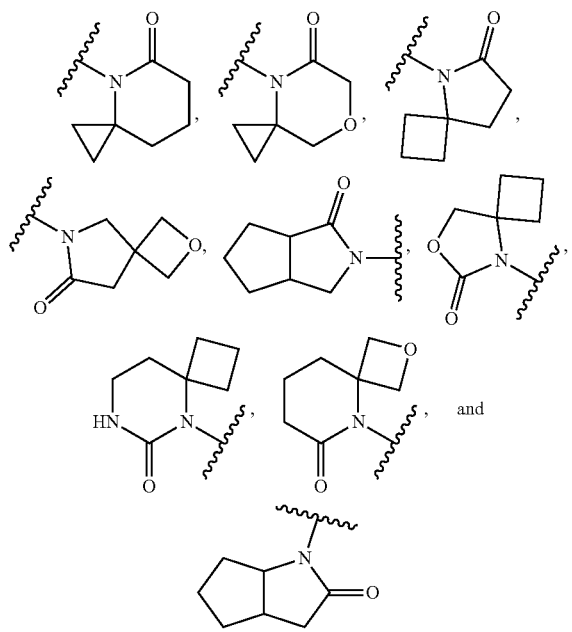

, or            ).

each of which is optionally substituted with from 1-4 substituents independently selected $R^c$.

In certain embodiments, $R^b$ is selected from the group consisting of

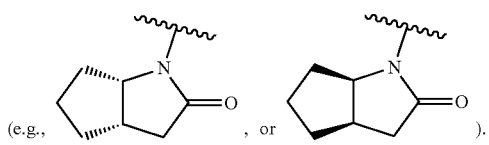

(e.g.,            , or            ).

In certain embodiments, $R^b$ is heterocyclyl including 9 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$.

In certain embodiments, $R^b$ is selected from the group consisting of

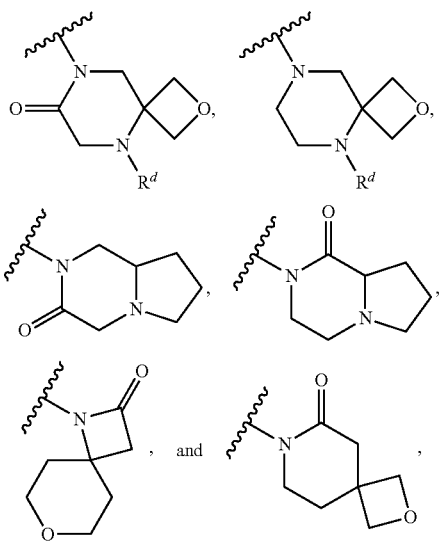

each of which is optionally substituted with from 1-4 substituents independently selected from the group consisting of oxo and $R^c$.

In certain embodiments, $R^d$ is CH$_3$.

In certain embodiments, $R^b$ is selected from the group consisting of

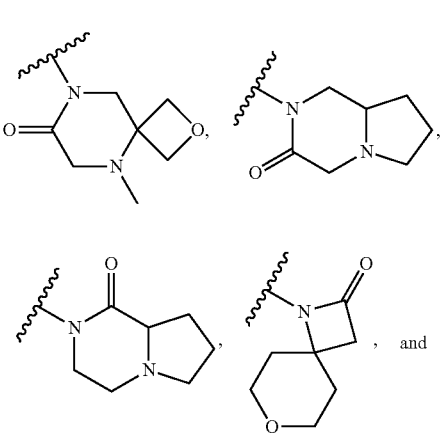

-continued

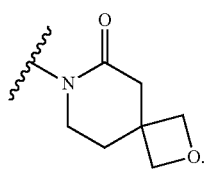

In certain embodiments, $R^2$ is chloro.

Formulae (Ia) and (Ib)

In certain embodiments, the compound is a compound of formula (Ia)

Formula (Ia)

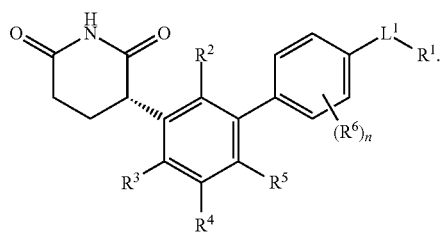

In certain embodiments, the compound is a compound of formula (Ib)

Formula (Ib)

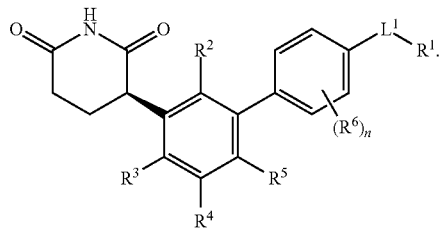

Particular Compounds of Formulae (I), (II), (III), (IV) and (V)

In certain embodiments, the compound is selected from the group consisting of the compounds in Table C1, or a pharmaceutically acceptable salt thereof.

In certain embodiments, the compound is

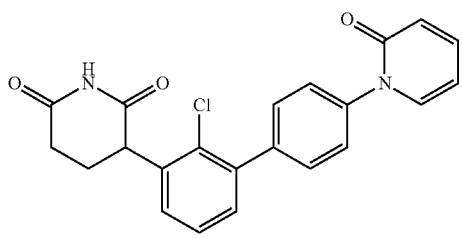 [SMILES: O=C1CCC(c2cccc(-c3ccc(-n4ccccc4=O)cc3)c2Cl)C(=O)N1]

or a pharmaceutically acceptable salt thereof.

In certain embodiments, the compound is

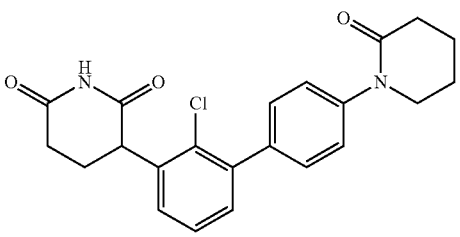 [SMILES: O=C1CCC(c2cccc(-c3ccc(N4CCCCC4=O)cc3)c2Cl)C(=O)N1]

or a pharmaceutically acceptable salt thereof.

In certain embodiments, the compound is

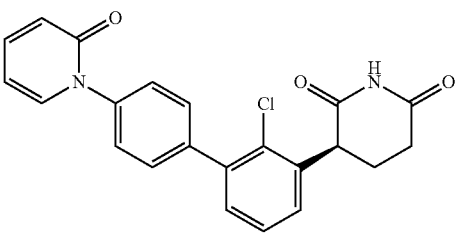 [SMILES: O=C1CC[C@@H](c2cccc(-c3ccc(-n4ccccc4=O)cc3)c2Cl)C(=O)N1]

or a pharmaceutically acceptable salt thereof.

In certain embodiments, the compound is

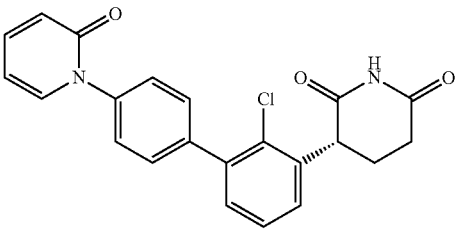 [SMILES: O=C1CC[C@H](c2cccc(-c3ccc(-n4ccccc4=O)cc3)c2Cl)C(=O)N1]

or a pharmaceutically acceptable salt thereof.

In certain embodiments, the compound exists in a racemic mixture. In certain embodiments, the compound in a racemic mixture is

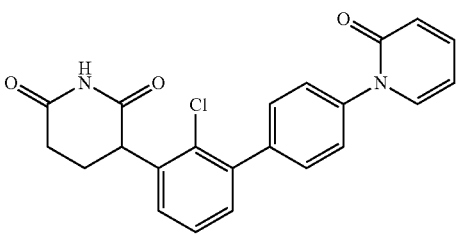 [SMILES: O=C1CCC(c2cccc(-c3ccc(-n4ccccc4=O)cc3)c2Cl)C(=O)N1]

or a pharmaceutically acceptable salt thereof.

In certain embodiments, this disclosure features a pharmaceutical composition comprising any of the compounds described herein, or pharmaceutically acceptable salt thereof, and a pharmaceutically acceptable excipient.

In some embodiments, the compound is not

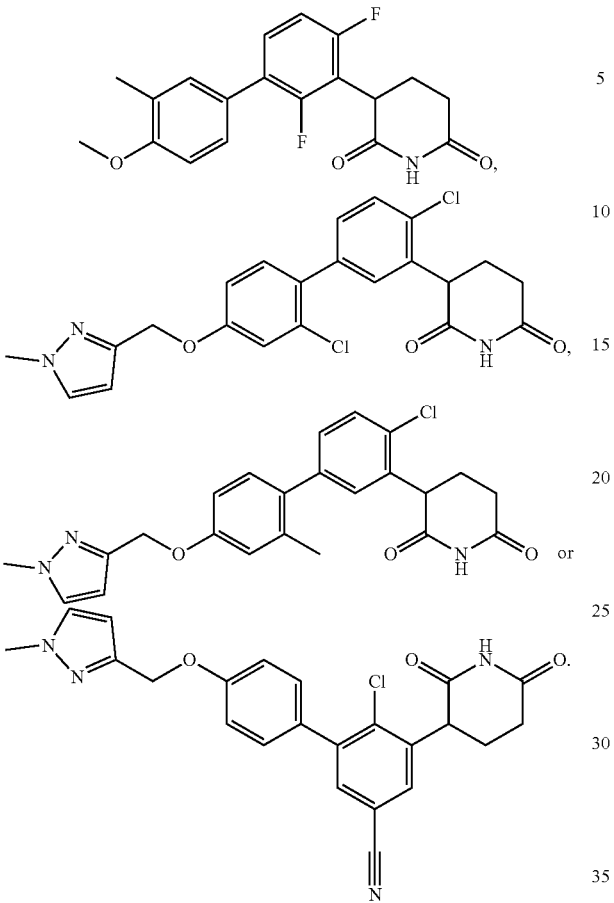

In some embodiments, the compound has a Dmax % of 20% or greater.

In some embodiments, the present disclosure provides a compound of Formula (V):

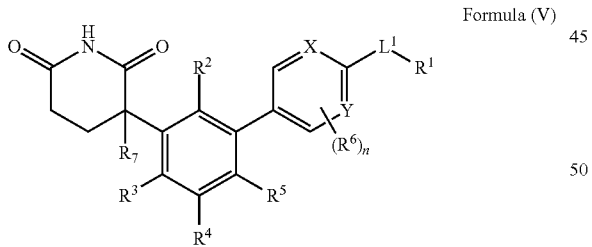

Formula (V)

or a pharmaceutically acceptable salt thereof, wherein:
$L^1$ is:
   a bond;
   *—O($C_0$-$C_4$ alkylene)-, *—S($C_0$-$C_4$ alkylene)-, *—$C_1$-$C_4$ alkylene-, or *—NR'($C_0$-$C_4$ alkylene)-, *—NR'(C=O)($C_0$-$C_4$ alkylene)-, —($C_1$-$C_4$ alkylene)-C(=O)—*, *—($C_1$-$C_4$ alkylene)-C(=O)—, wherein the alkylene is optionally substituted with 1-2 $R^a$ and wherein * indicates the point of attachment of $L^1$ to the ring comprising X and Y; —(C=O)—; or
   taken together with Y to form an additional ring fused with the ring containing X and Y, wherein the fused ring system includes 9 or 10 ring atoms, wherein from 1-4 ring atoms in the additional ring are heteroatoms, each independently selected from the group consisting of N, N(H), N($R^d$) and O, wherein the additional ring is substituted with $R_1$ and is optionally further substituted with from 1-4 substituents independently selected from the group consisting of oxo and R; and each one of X and Y is independently selected from the group consisting of N and CH;

$R^1$ is selected from the group consisting of hydrogen, deuterium, $R^b$, —$OR^b$, —S(O)$_{0-2}R^b$, —N(R')$R^b$, CN, halo, and —NR'C(O)R";

$R^2$ is selected from the group consisting of hydrogen, deuterium, $CH_3$, $CHF_2$, $CF_3$, OMe, F, Cl and Br;

each of $R^3$, $R^4$ and $R^5$ is independently selected from the group consisting of hydrogen and $R^c$;

each of $R^6$ is independently selected from the group consisting of: deuterium, halo; cyano; $C_{1-10}$ alkyl which is optionally substituted with from 1-6 independently selected $R^a$; $C_{3-6}$ cycloalkyl which is optionally substituted with from 1-4 independently selected $R^a$; $C_{2-6}$ alkenyl; $C_{2-6}$ alkynyl; $C_{1-4}$ alkoxy; —S(O)$_{0-2}$($C_{1-4}$ alkyl); —$NR^eR^f$; —OH; —S(O)$_{1-2}$NR'R"; —$NO_2$; —C(=O)($C_{1-10}$ alkyl); —C(=O)O($C_{1-4}$ alkyl); —C(=O)OH; —N(R')C(=O)($C_{1-4}$ alkyl), —C(=O)NR'R", $R^g$, and —(CH$_2$)$_{1-2}$ $R^g$;

n is selected from 0, 1, 2 and 3;

$R^7$ is selected from the group consisting of hydrogen, deuterium, $CH_3$, $CHF_2$, $CF_3$, Ome, F, Cl and Br;

each occurrence of $R^a$ is independently selected from the group consisting of: —OH; -halo; —$NR^eR^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CONR'R"; —S(O)$_{1-2}$NR'R"; —S(O)$_{1-2}$($C_{1-4}$ alkyl); and cyano;

each occurrence of $R^b$ comprises a hydrogen bond acceptor;

each occurrence of $R^c$ is independently selected from the group consisting of: deuterium; halo; cyano; $C_{1-10}$ alkyl which is optionally substituted with from 1-6 independently selected $R^a$; $C_{3-6}$ cycloalkyl which is optionally substituted with from 1-4 independently selected $R^a$; $C_{2-6}$ alkenyl; $C_{2-6}$ alkynyl; $C_{1-4}$ alkoxy; —S(O)$_{0-2}$($C_{1-4}$ alkyl); —$NR^eR^f$; —OH; —S(O)$_{1-2}$NR'R"; —$NO_2$; —C(=O)($C_{1-10}$ alkyl); —C(=O)O($C_{1-4}$ alkyl); —C(=O)OH; —N(R')C(=O)($C_{1-4}$ alkyl), —C(=O)NR'R", $R^g$, and —(CH$_2$)$_{1-2}$ $R^g$;

each occurrence of $R^d$ is independently selected from the group consisting of: hydrogen, deuterium, $C_{1-6}$ alkyl optionally substituted with from 1-3 independently selected $R^a$; —C(O)($C_{1-4}$ alkyl); —C(O)O($C_{1-4}$ alkyl); —CONR'R"; —S(O)$_{1-2}$NR'R"; —S(O)1-2($C_{1-4}$ alkyl); —OH; and $C_{1-4}$ alkoxy;

each occurrence of $R^e$ and $R^f$ is independently selected from the group consisting of: H; deuterium; $C_{1-6}$ alkyl; —C(O)($C_{1-4}$ alkyl); —C(O)O($C_{1-4}$ alkyl); —CONR'R"; —S(O)$_{1-2}$NR'R"; —S(O)$_{1-2}$ ($C_{1-4}$ alkyl); —OH; and $C_{1-4}$ alkoxy; and each occurrence of $R^g$ is independently selected from the group consisting of:
   $C_{3-7}$ cycloalkyl or $C_{3-7}$ cycloalkenyl, each of which is optionally substituted with from 1-4 substituents independently selected from the group consisting of oxo and $R^a$;
   heterocyclyl or heterocycloalkenyl including 3-7 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^a$;

heteroaryl including 5-10 ring atoms, wherein from 1-4 ring atoms are heteroatoms, each independently selected from the group consisting of N, N(H), N($R^d$), O, and S(O)$_{0-2}$, wherein at least one ring in the system is aromatic and wherein the heteroaryl is optionally substituted with from 1-4 oxo or $R^a$; and $C_{6-10}$ aryl optionally substituted with from 1-4 $R^a$;

each occurrence of R' and R" is independently selected from the group consisting of: hydrogen; and $C_{1-4}$ alkyl.

In some embodiments where $R^b$ comprises a hydrogen bond acceptor, $R^b$ comprises a hydrogen bond acceptor within seven atoms of the carbon atom between X and Y. In some embodiments, $R^b$ comprises a hydrogen bond acceptor within six atoms of the carbon atom between X and Y. In some embodiments, $R^b$ comprises a hydrogen bond acceptor within five atoms of the carbon atom between X and Y. In some embodiments, $R^b$ comprises a hydrogen bond acceptor within four atoms of the carbon atom between X and Y In some embodiments, $R^b$ comprises a hydrogen bond acceptor within three atoms of the carbon atom between X and Y.

Hydrogen Bond Acceptor Groups

In some embodiments where $R^b$ comprises a hydrogen bond acceptor, the hydrogen bond acceptor is selected from a carbonyl, sulfonyl group, nitrogen containing heteroaromatic group, oxygen containing heteroaromatic group and an oxygen containing aliphatic or cycloaliphatic group.

In some embodiments where $R^b$ comprises a hydrogen bond acceptor, the hydrogen bond acceptor is selected from an amide, lactam, carbamate, pyridone, pyrimidinone, piperazinone, piridazinone, urea, sulfonamide, sulfone, pyrimidine, pyrazine, pyridazine, pyridine, oxazole, isoxazole, oxadiazole, thiazole, thiadiazole, imidazole, pyrazole, oxazole, isoxazole, oxadiazole, oxetane, tetrahydrofuran, tetrahydropyran or methoxy alkyl group.

In some embodiments where $R^b$ comprises a hydrogen bond acceptor, the hydrogen bond acceptor is selected from:

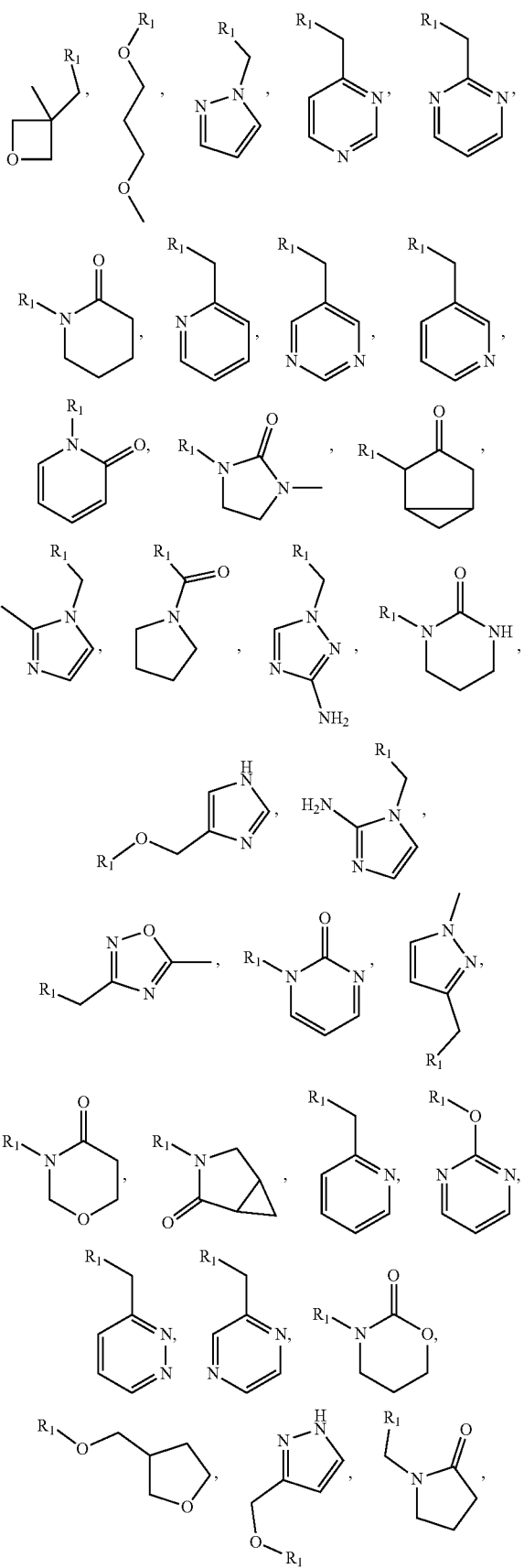

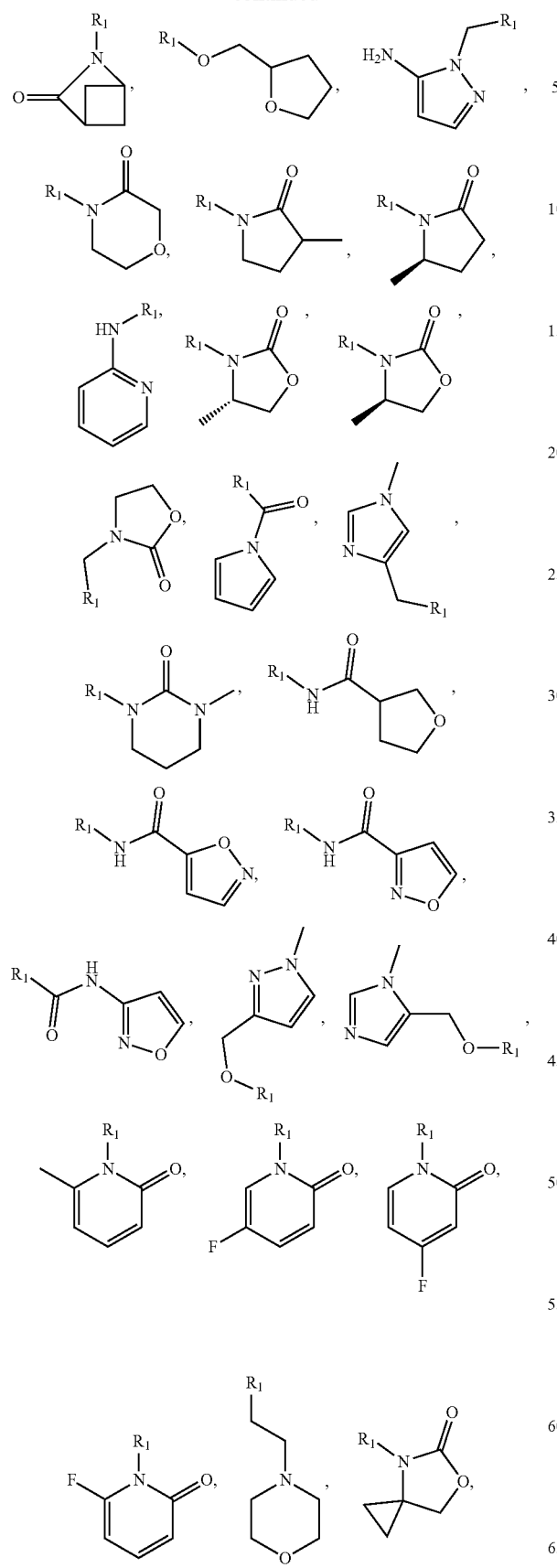
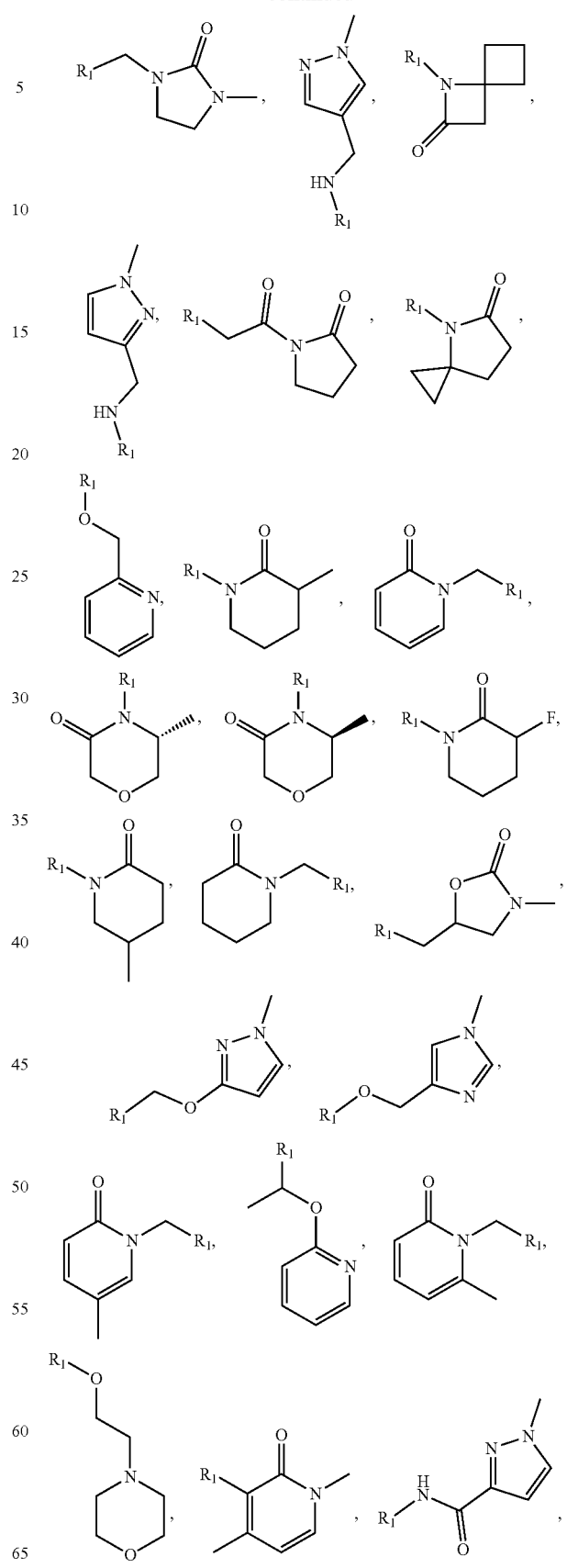

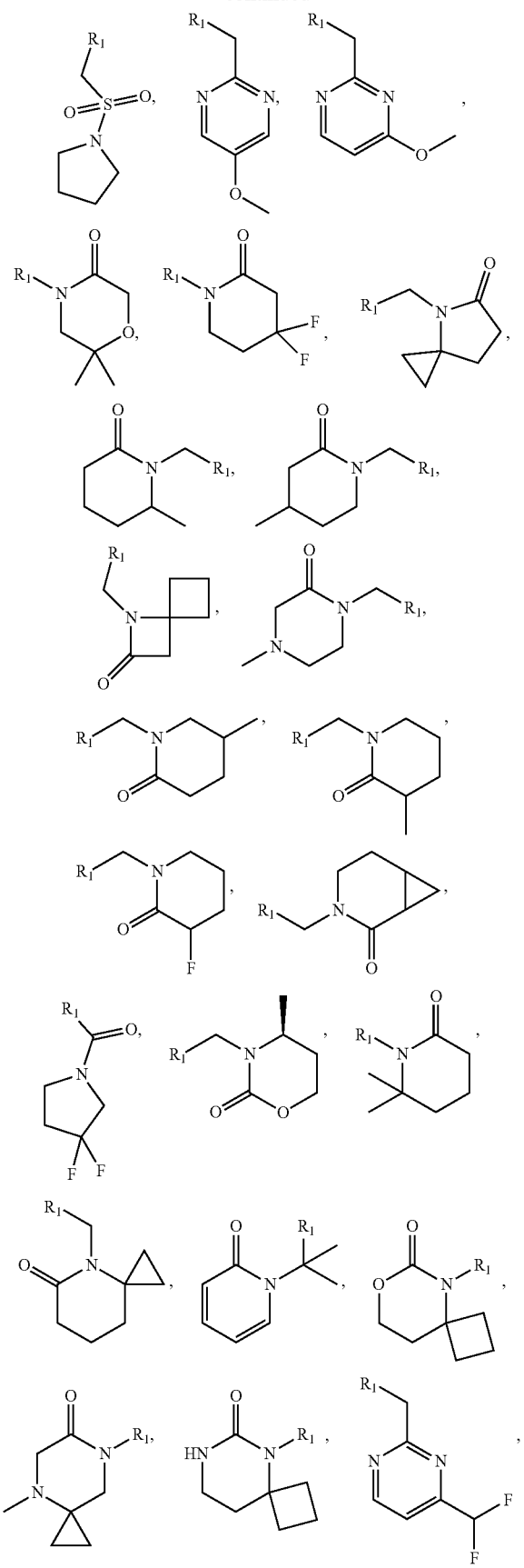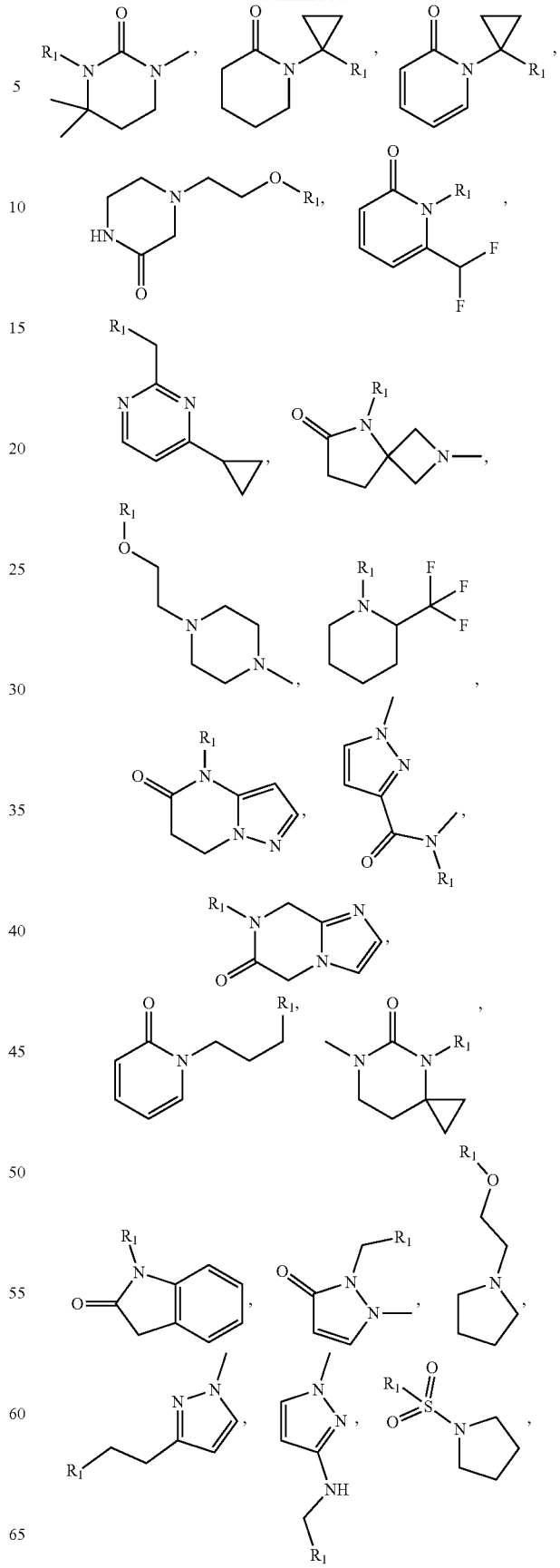

-continued
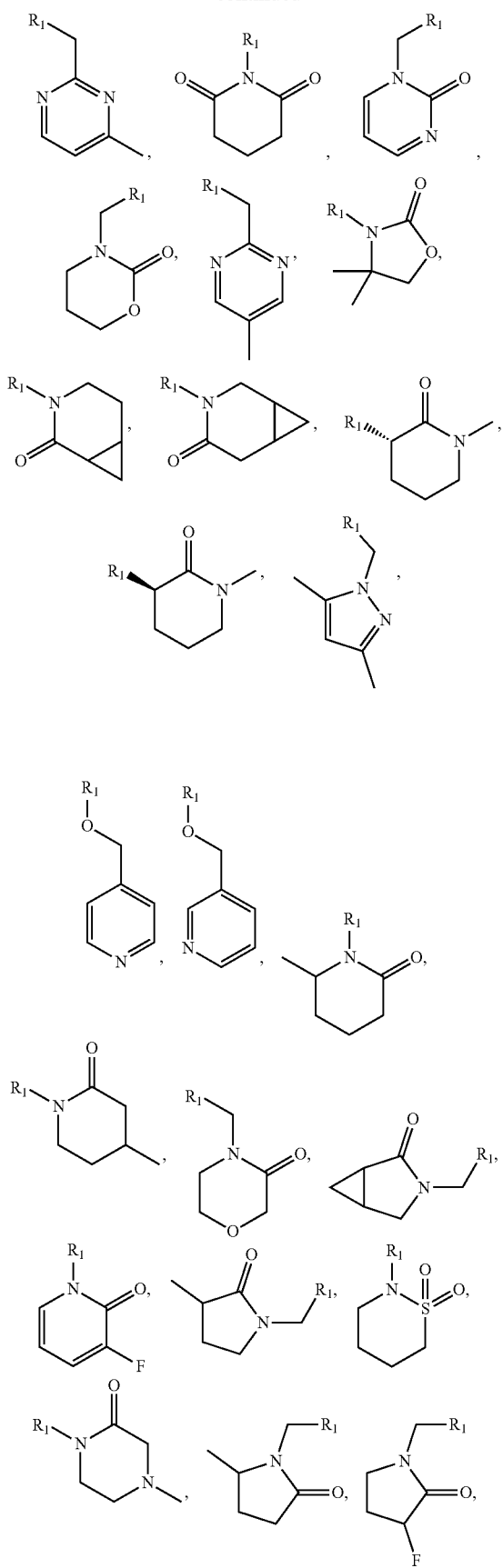
-continued
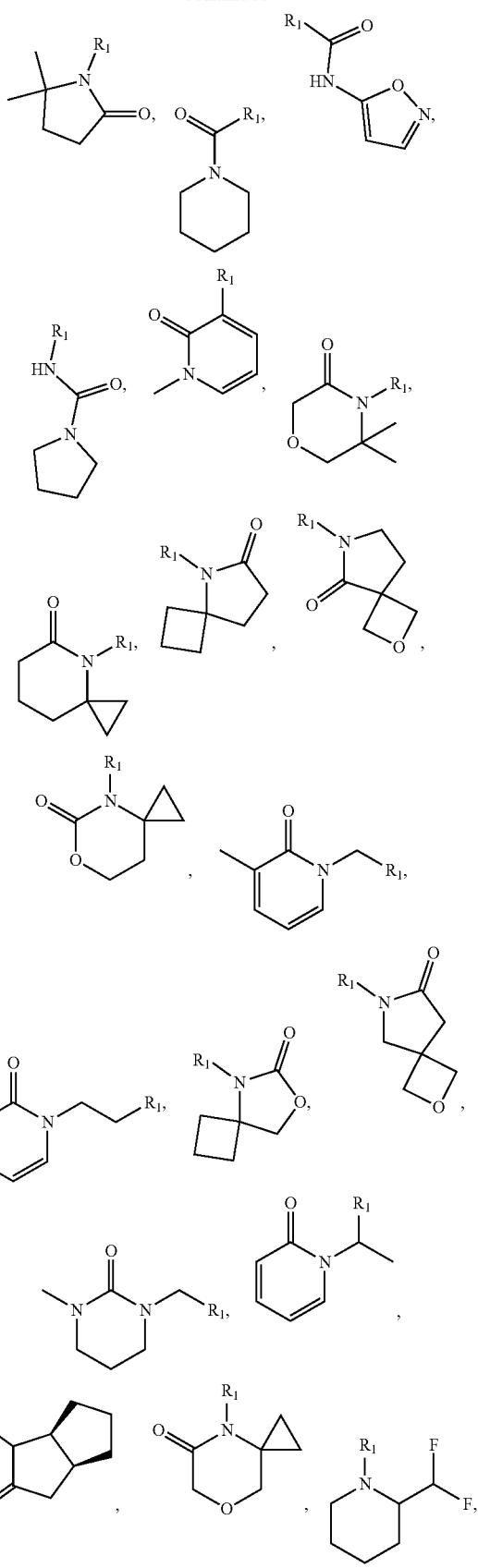

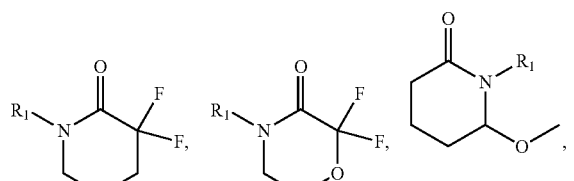
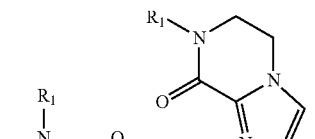
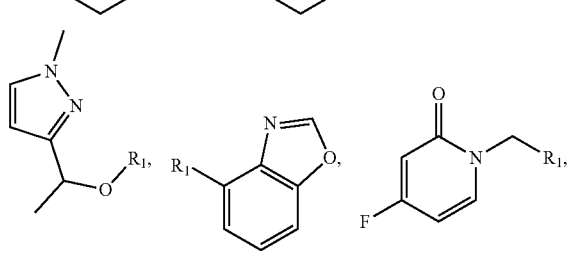
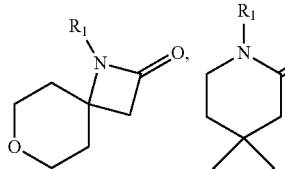
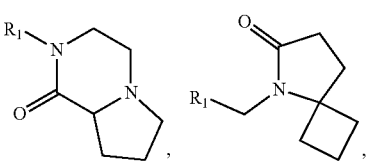
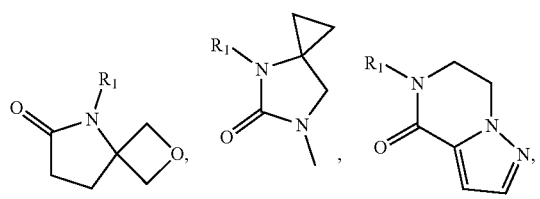
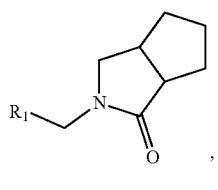
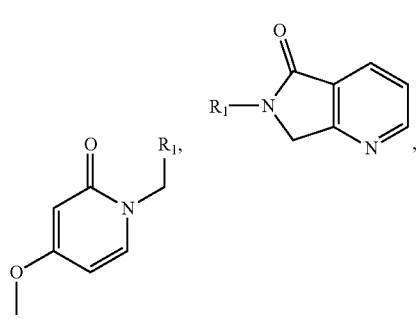
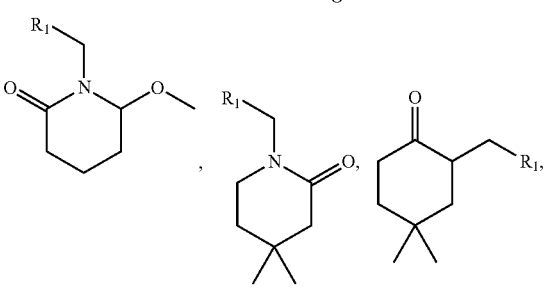
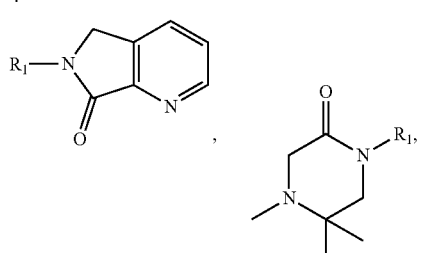
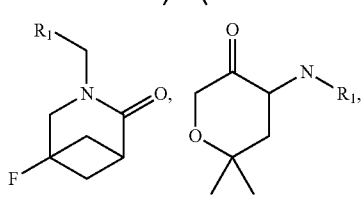
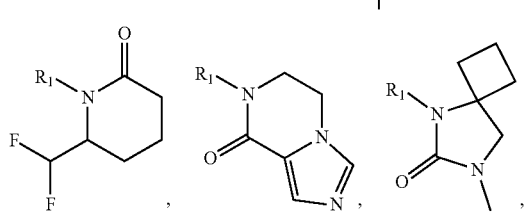
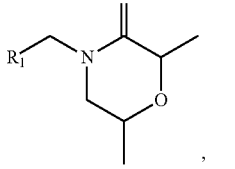
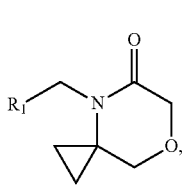
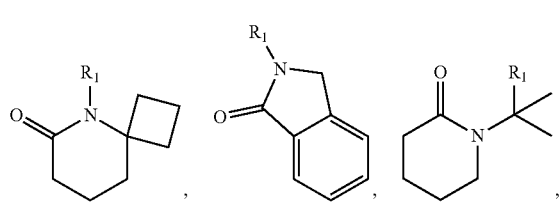
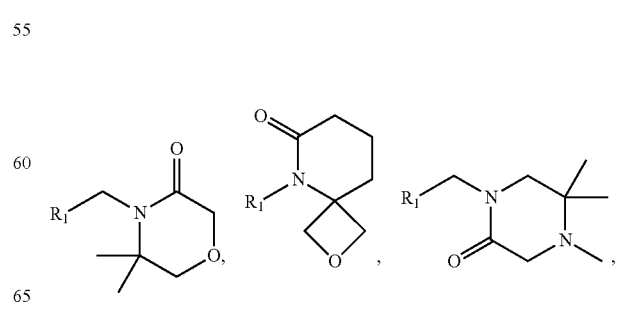

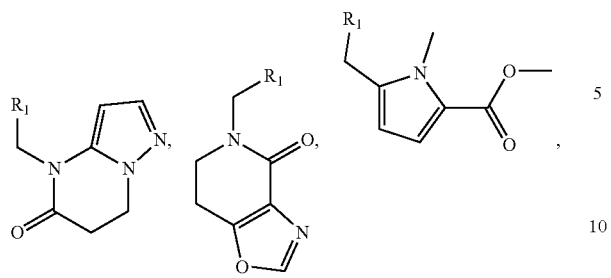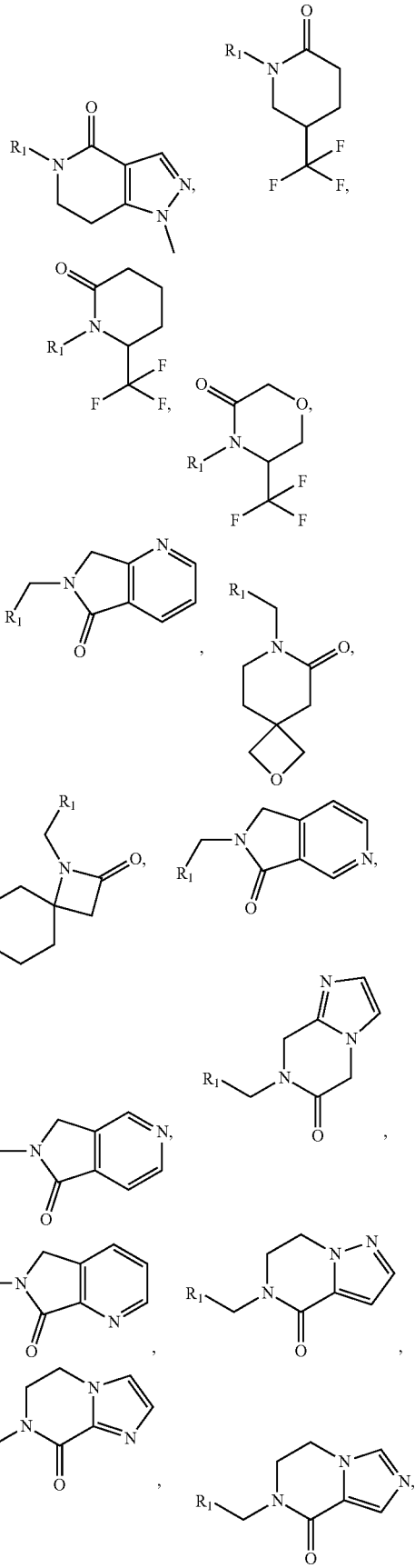

-continued

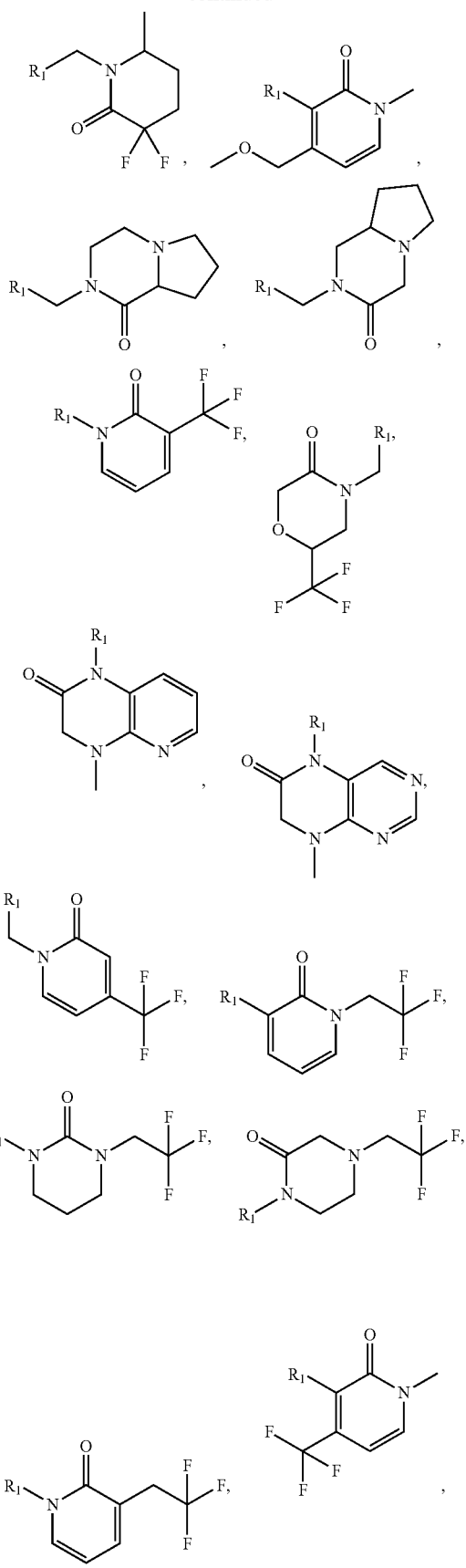

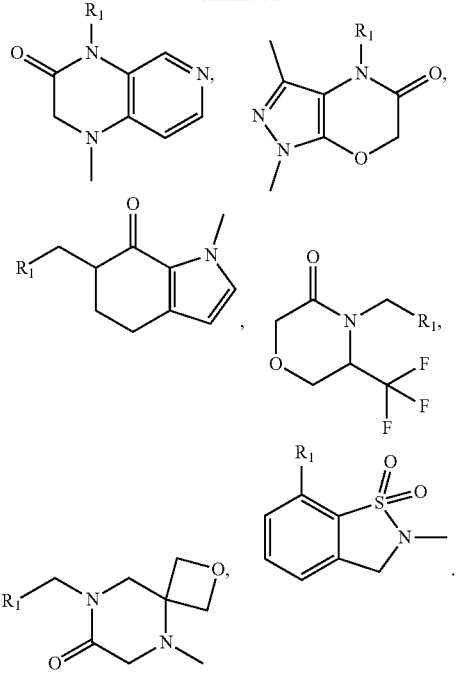

Compounds of Formula (IV)

In one aspect, this disclosure features compounds of Formula (IV) or pharmaceutically acceptable salts thereof,

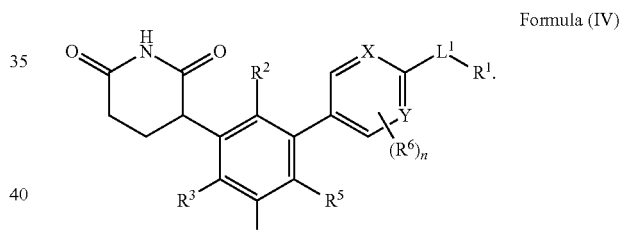

Formula (IV)

or a pharmaceutically acceptable salt thereof, wherein:

$L^1$ is:
  a bond;
  *—O($C_0$-$C_4$ alkylene)-, *—S($C_0$-$C_4$ alkylene)-, *—$C_1$-$C_4$ alkylene-, or *—NR'($C_0$-$C_4$ alkylene)-, *—NR'(C=O)($C_0$-$C_4$ alkylene)-, —($C_1$-$C_4$ alkylene)-C(=O)—*, *—($C_1$-$C_4$ alkylene)-C(=O)—, wherein the alkylene is optionally substituted with 1-2 $R^a$ and wherein * indicates the point of attachment of $L^1$ to the ring comprising X and Y; or
  —(C=O)—;

each one of X and Y is independently selected from the group consisting of N and CH;

$R^1$ is selected from the group consisting of hydrogen, $R^b$, —$OR^b$, —$SR^b$, —N(R')$R^b$, CN, halo, and —NR'C(O)R";

provided that -$L^1$-$R^1$ does not include O—O, N—O, N—N, O—S, S—S, or N—S bonds; further provided that $L^1$ must be a bond when $R^1$ is CN, halo, or —NR'C(O)R"; and further provided that $L^1$ cannot be a bond when $R^1$ is hydrogen;

$R^2$ is selected from the group consisting of hydrogen, $CH_3$, $CHF_2$, $CF_3$, OMe, F, and Cl;

each of $R^3$, $R^4$ and $R^5$ is independently selected from the group consisting of hydrogen and $R^c$;
each of $R^6$ is independently selected $R^c$;
n is selected from 0, 1, 2 and 3;
each occurrence of $R^a$ is independently selected from the group consisting of: —OH; -halo; —NR$^e$R$^f$; $C_{1-4}$ alkoxy; $C_{1-4}$ haloalkoxy; —C(=O)O($C_{1-4}$ alkyl); —C(=O)($C_{1-4}$ alkyl); —C(=O)OH; —CONR'R''; —S(O)$_{1-2}$NR'R''; —S(O)$_{1-2}$($C_{1-4}$ alkyl); and cyano;
each occurrence of $R^b$ is independently selected from the group consisting of:
  $C_{3-10}$ cycloalkyl or $C_{3-10}$ cycloalkenyl, each of which is optionally substituted with from 1-4 substituents independently selected from the group consisting of oxo and $R^c$;
  heterocyclyl or heterocycloalkenyl including 3-10 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and $R^c$;
  heteroaryl including 5-10 ring atoms, wherein from 1-4 ring atoms are heteroatoms, each independently selected from the group consisting of N, N(H), N(R$^d$), O, and S(O)$_{0-2}$, and wherein the heteroaryl is optionally substituted with from 1-4 substituents independently selected $R^c$; and
  $C_{6-10}$ aryl optionally substituted with from 1-4 substituents independently selected $R^c$;
each occurrence of $R^c$ is independently selected from the group consisting of: halo; cyano; $C_{1-10}$ alkyl which is optionally substituted with from 1-6 independently selected $R^a$; $C_{2-6}$ alkenyl; $C_{2-6}$ alkynyl; $C_{1-4}$ alkoxy; —S(O)$_{0-2}$($C_{1-4}$ alkyl); —NR$^e$R$^f$; —OH; —S(O)$_{1-2}$NR'R''; —NO$_2$; —C(=O)($C_{1-10}$ alkyl); —C(=O)O($C_{1-4}$ alkyl); —C(=O)OH; —N(R')C(=O)($C_{1-4}$ alkyl), —C(=O)NR'R'', $R^g$, and —(CH$_2$)$_{1-2}$ $R^g$;
each occurrence of $R^d$ is independently selected from the group consisting of: hydrogen, $C_{1-6}$ alkyl optionally substituted with from 1-3 independently selected $R^a$; —C(O)($C_{1-4}$ alkyl); —C(O)O($C_{1-4}$ alkyl); —CONR'R''; —S(O)$_{1-2}$NR'R''; —S(O)$_{1-2}$($C_{1-4}$ alkyl); —OH; and $C_{1-4}$ alkoxy;
each occurrence of $R^e$ and $R^f$ is independently selected from the group consisting of: H; $C_{1-6}$ alkyl; —C(O)($C_{1-4}$ alkyl); —C(O)O($C_{1-4}$ alkyl); —CONR'R''; —S(O)$_{1-2}$NR'R''; —S(O)$_{1-2}$($C_{1-4}$ alkyl); —OH; and $C_{1-4}$ alkoxy; and each occurrence of $R^g$ is independently selected from the group consisting of:
  $C_{3-7}$ cycloalkyl or $C_{3-7}$ cycloalkenyl, each of which is optionally substituted with from 1-4 substituents independently selected from the group consisting of oxo and $R^a$;
  heterocyclyl or heterocycloalkenyl including 3-7 ring atoms, wherein from 1-3 ring atoms are heteroatoms, each independently selected from the group consisting of N, N(H), N(R$^d$), O, and S(O)$_{0-2}$, and wherein the heterocyclyl or heterocycloalkenyl is optionally substituted with from 1-4 substituents independently selected from the group consisting of oxo and $R^a$;
  heteroaryl including 5-10 ring atoms, wherein from 1-4 ring atoms are heteroatoms, each independently selected from the group consisting of N, N(H), N(R$^d$), O, and S(O)$_{0-2}$, and wherein the heteroaryl is optionally substituted with from 1-4 $R^a$; and
  $C_{6-10}$ aryl optionally substituted with from 1-4 $R^a$;
each occurrence of R' and R'' is independently selected from the group consisting of: hydrogen; and $C_{1-4}$ alkyl.

Variable $L^1$

In some embodiments, $L^1$ is *—O(C$_0$-C$_4$ alkylene)-, *—S(C$_0$-C$_4$ alkylene)-, *—C$_1$-C$_4$ alkylene-, or *—NR'(C$_0$-C$_4$ alkylene)-, wherein the alkylene is optionally substituted with 1-2 $R^a$ and wherein * indicates the point of attachment of $L^1$ to the phenyl ring.

In some embodiments, $L^1$ is *—O(C$_0$-C$_4$ alkylene)-, wherein the alkylene portion is optionally substituted with from 1-2 $R^a$. In some embodiments, $L^1$ is *—O(C$_1$-C$_4$ alkylene)-, the alkylene portion is optionally substituted with from 1-2 $R^a$. In some embodiments, $L^1$ is unsubstituted *—O(C$_1$-C$_4$ alkylene)-. For example, $L^1$ can be *—OCH$_2$— or *—OCH$_2$CH$_2$.

In certain embodiments, $L^1$ is *—OCH$_2$—.

In certain embodiments, $L^1$ is *—C$_1$-C$_4$ alkylene- optionally substituted with from 1-2 $R^a$. In certain embodiments, $L^1$ is unsubstituted *—C$_1$-C$_4$ alkylene. In certain embodiments. $L^1$ is selected from the group consisting of —CH$_2$—, —CH(CH$_3$)—, —C(CH$_3$)$_2$—, and —CH$_2$CH$_2$CH$_2$—. For example, $L^1$ can be —CH$_2$—.

In certain embodiments, $L^1$ is *—NR'(C$_0$-C$_4$ alkylene)-, wherein the alkylene portion is optionally substituted with from 1-2 $R^a$. In certain embodiments, $L^1$ is *—NR'(C$_1$-C$_4$ alkylene)-, wherein the alkylene portion is optionally substituted with from 1-2 $R^a$. In certain embodiments, $L^1$ is *—NR'(C$_1$-C$_4$ alkylene)-, wherein the alkylene portion is unsubstituted. In certain embodiments, —R'— is H. For example, $L^1$ can be

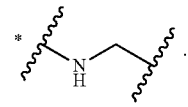 [SMILES: *CN*]

For still another example, $L^1$ can be —NH—.

In certain embodiments, $L^1$ is —(C=O)—.

Variables X and Y

In certain embodiments, X and Y are both CH.

In certain embodiments, one of X and Y is N, and the other one of X and Y is CH.

In certain embodiments, X is N, and Y is CH.

In certain embodiments, Y is N, and X is CH.

Variable $R^1$

In some embodiments, $R^1$ is hydrogen.

In some embodiments, $R^1$ is $R^b$.

In some embodiments, $R^1$ is selected from the group consisting of —OR$^b$, and —N(R')R$^b$.

In some embodiments, $R^b$ is heteroaryl including 5-10 ring atoms, wherein from 1-4 ring atoms are heteroatoms, each independently selected from the group consisting of N, N(H), N(R$^d$), O, and S(O)$_{0-2}$, and wherein the heteroaryl is optionally substituted with from 1-4 independently selected $R^c$. In some embodiments, $R^b$ is heteroaryl including 5-6 ring atoms, wherein from 1-4 ring atoms are heteroatoms, each independently selected from the group consisting of N, N(H), N(R$^d$), O, and S(O)$_{0-2}$, and wherein the heteroaryl is optionally substituted with from 1-4 independently selected $R^c$.

In certain embodiments, $R^b$ is heteroaryl including 5 ring atoms, wherein from 1-4 ring atoms are heteroatoms, each independently selected from the group consisting of N, N(H), N(R$^d$), O, and S(O)$_{0-2}$, and wherein the heteroaryl is optionally substituted with from 1-2 independently selected R$^c$.

In certain embodiments, R$^b$ is heteroaryl including 5 ring atoms, wherein from 1-4 ring atoms are heteroatoms, each independently selected from the group consisting of N, N(H), N(R$^d$), O, and S(O)$_{0-2}$. In certain embodiments, R$^b$ is selected from the group consisting of

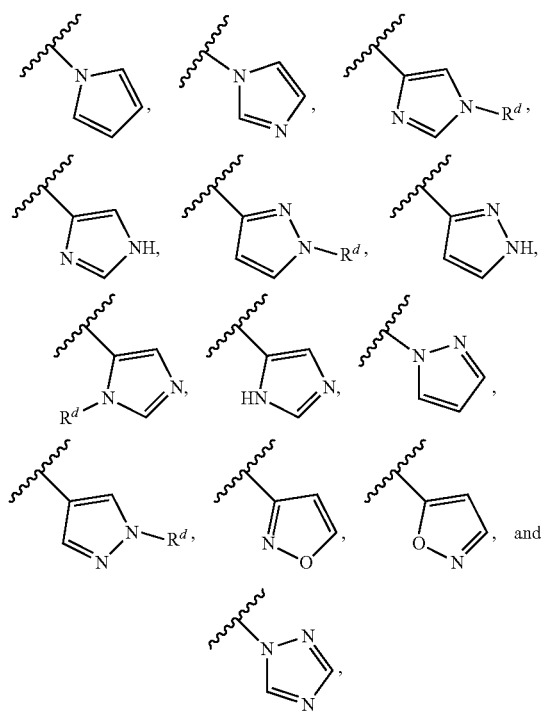

each of which is optionally substituted with from 1-2 independently selected R$^c$.

In certain embodiments, R$^b$ is selected from the group consisting of

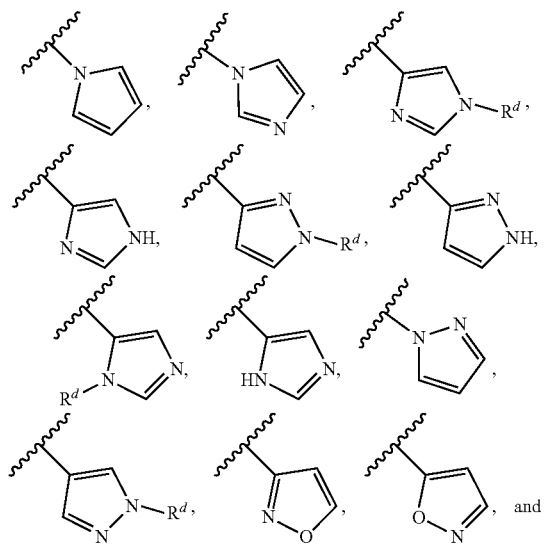

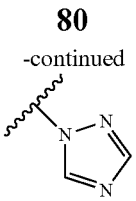

optionally wherein R$^d$ is CH$_3$.

In certain embodiments, R$^b$ is selected from the group consisting of

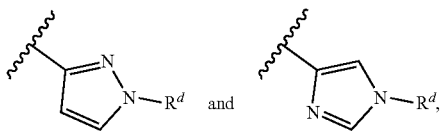

optionally wherein R$^d$ is CH$_3$.

In certain embodiments, R$^b$ is selected from

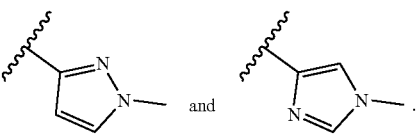

For example, R$^b$ can be

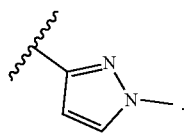

In certain embodiments, R$^b$ is selected from the group consisting of

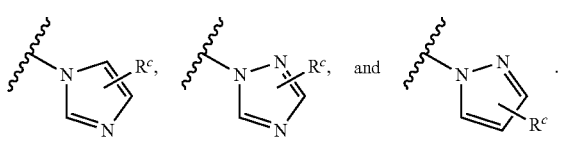

In certain embodiments, R$^b$ is selected from the group consisting of

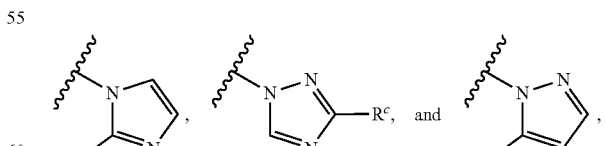

In certain embodiments, R$^c$ is selected from the group consisting of C$_{1-10}$ alkyl which is optionally substituted with from 1-6 independently selected R$^a$ and —NR$^e$R$^f$, optionally wherein R$^c$ is methyl or —NH$_2$. In certain embodiments, R$^b$ is selected from the group consisting of

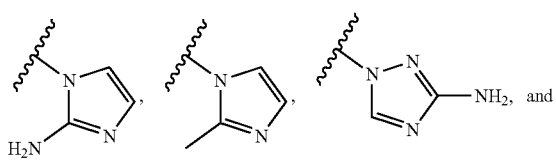

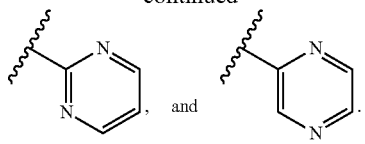

For example, R can be

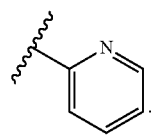

In certain embodiments, $R^b$ is

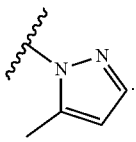

In certain embodiments, $R^b$ is

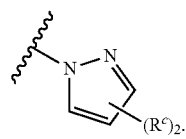

In certain embodiments, $R^c$ is $C_{1-10}$ alkyl which is optionally substituted with from 1-6 independently selected $R^a$ and —$NR^eR^f$, optionally wherein $R^c$ is methyl. In certain embodiments, $R^b$ is

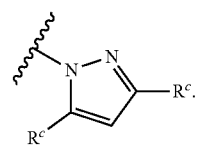

In some embodiments, $R^b$ is heteroaryl including 6 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 substituents independently selected $R^c$. In certain embodiments, $R^b$ is heteroaryl including 6 ring atoms, wherein from 1-4 ring atoms are heteroatoms, each independently selected from the group consisting of N, N(H), N($R^d$), O, and S(O)$_{0-2}$. In certain embodiments, $R^b$ is selected from the group consisting of

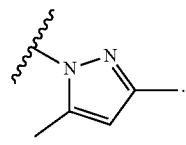 [SMILES: *n1nc(C)cc1C]

In some embodiments, $R^b$ is heteroaryl including 7-10 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$. In some embodiments, $R^b$ is heteroaryl including 9-10 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$.

In some embodiments, wherein $R^b$ is heteroaryl including 9 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected from the list consisting of oxo and $R^c$. In certain embodiments, $R^b$ is selected from the group consisting of

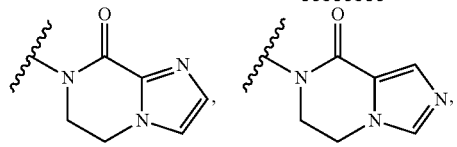

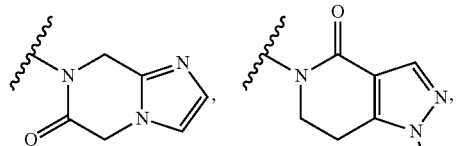

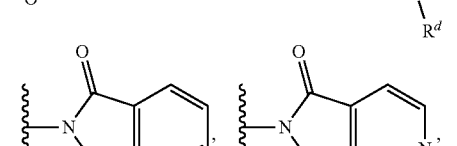

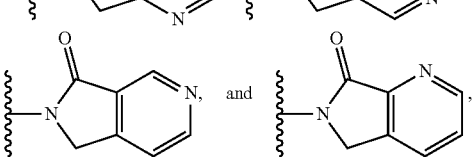

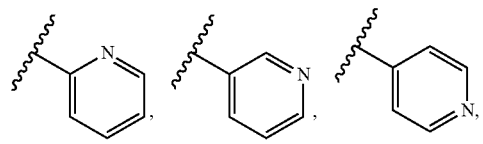

and each of which is optionally substituted with from 1-4 independently selected $R^c$.

In certain embodiments, $R^b$ is selected from the group consisting of

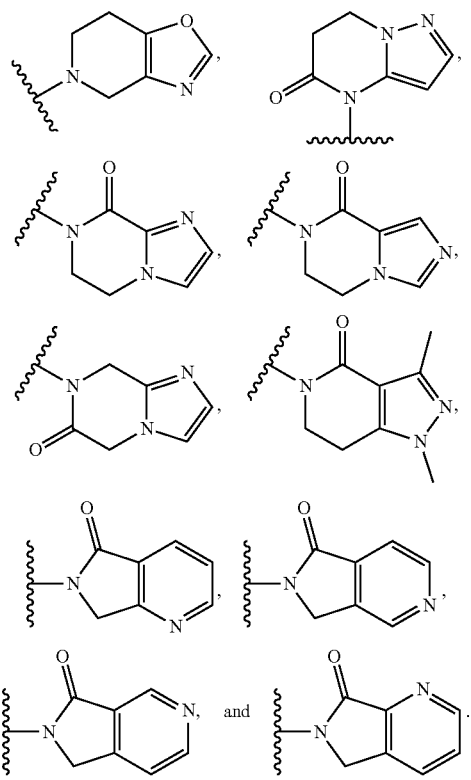

In some embodiments, $R^b$ is heteroaryl including 10 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$. In certain embodiments, $R^b$ is selected from the group consisting of

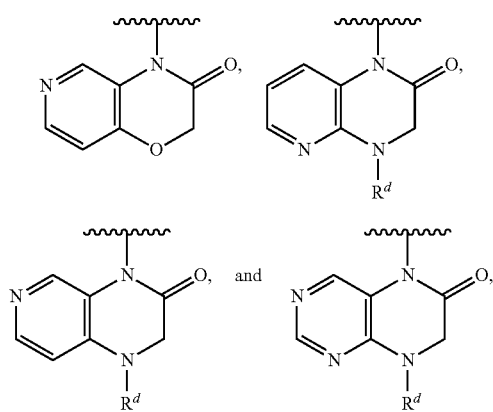

each of which is optionally substituted with from 1-4 independently selected $R^c$. In certain embodiments, $R^b$ is selected from the group consisting of

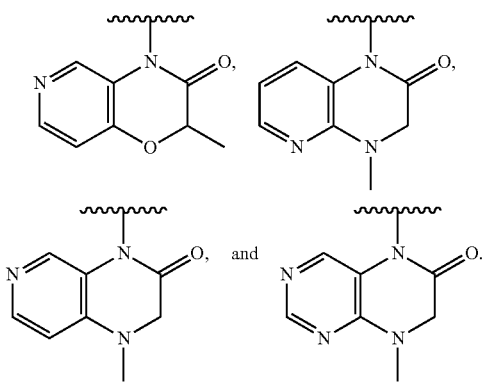

In some embodiments, $R^b$ is heterocyclyl or heterocycloalkenyl including 3-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In some embodiments, $R^b$ is heterocyclyl or heterocycloalkenyl including 4-6 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In some embodiments, $R^b$ is heterocyclyl or heterocycloalkenyl including 5-6 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocyclyl or heterocycloalkenyl including 6 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In certain embodiments, $R^b$ is heterocycloalkenyl including 6 ring atoms, wherein from 1-3 ring atoms are heteroatoms, each independently selected from the group consisting of N, N(H), N($R^d$), O, and S(O)$_{0-2}$, and wherein the heterocycloalkenyl is optionally substituted with from 1-4 substituents independently selected from the group consisting of oxo and $R^c$. In certain embodiments, $R^b$ is

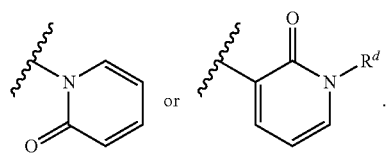

In certain embodiments, $R^d$ is CH$_3$.

For example, $R^b$ can be

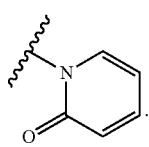 [SMILES: *n1ccccc1=O].

As another example, $R^b$ is

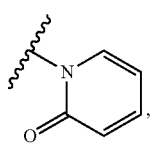, which is substituted with from 1-2 substituents independently selected $R^c$.

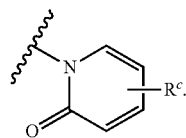

In certain embodiments. $R^b$ is

In certain of these embodiments, each occurrence of $R^c$ is selected from the group consisting of $C_{1-10}$ alkyl optionally substituted with from 1-6 independently selected $R^a$, $C_{1-4}$ alkoxy, halo, and —$NR^eR^f$. In certain embodiments, $R^c$ is selected from the group consisting of methyl, ethyl, —$CHF_2$, —$CF_3$, methoxy, fluoro, chloro, and $NH_2$. In certain embodiments, $R^b$ is selected from the group consisting of

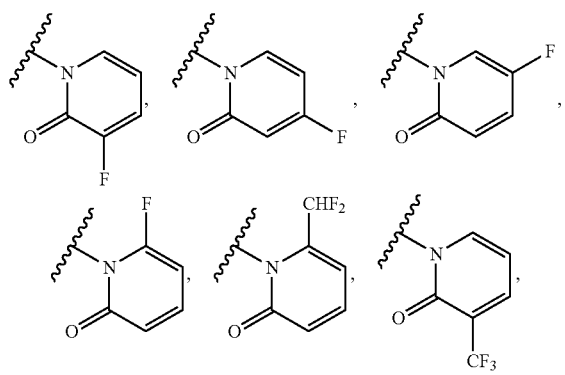

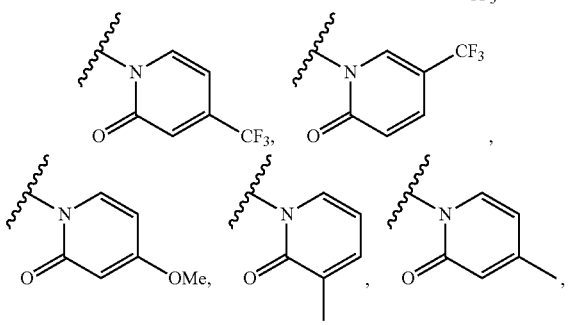

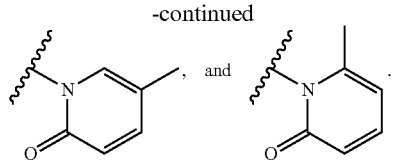

In some embodiments, $R^b$ is heterocyclyl including 6 ring atoms, wherein from 1-3 ring atoms are heteroatoms, each independently selected from the group consisting of N, N(H), N($R^d$), O, and $S(O)_{0-2}$, and wherein the heterocyclyl is optionally substituted with from 1-4 substituents independently selected from the group consisting of oxo and $R^c$. In certain embodiments, $R^b$ is selected from the group consisting of

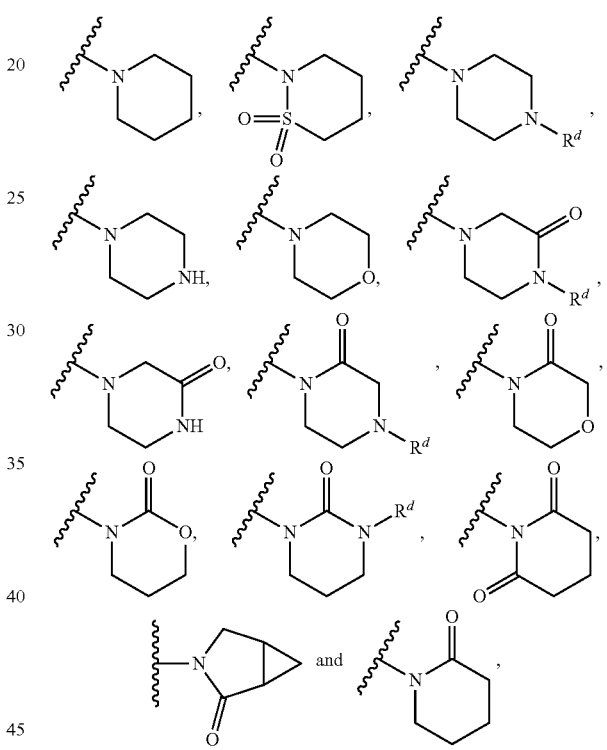

each of which is optionally substituted with 1-4 substituents independently selected from the group consisting of oxo and $R^c$. In certain of these embodiments, $R^c$ is methyl, halo, methoxy or $CF_3$.

In certain embodiments, $R^b$ is selected from the group consisting of

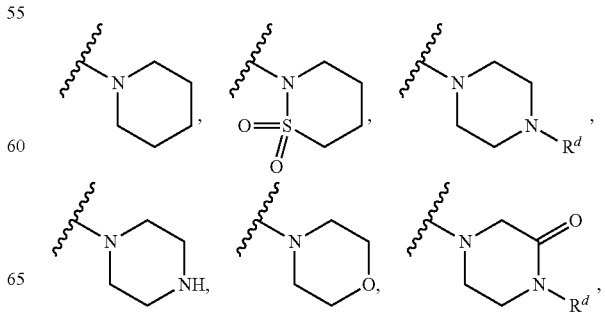

-continued

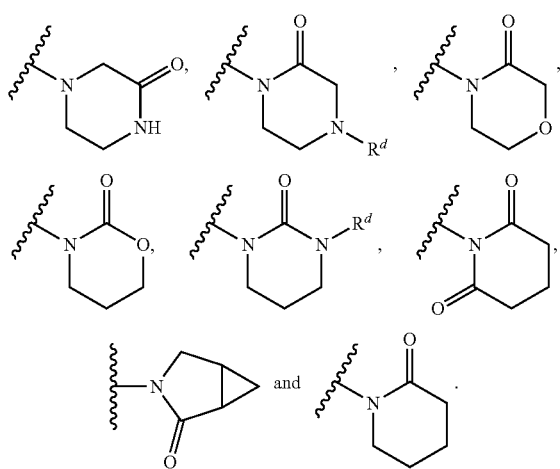

In certain embodiments, $R^b$ is selected from the group consisting of

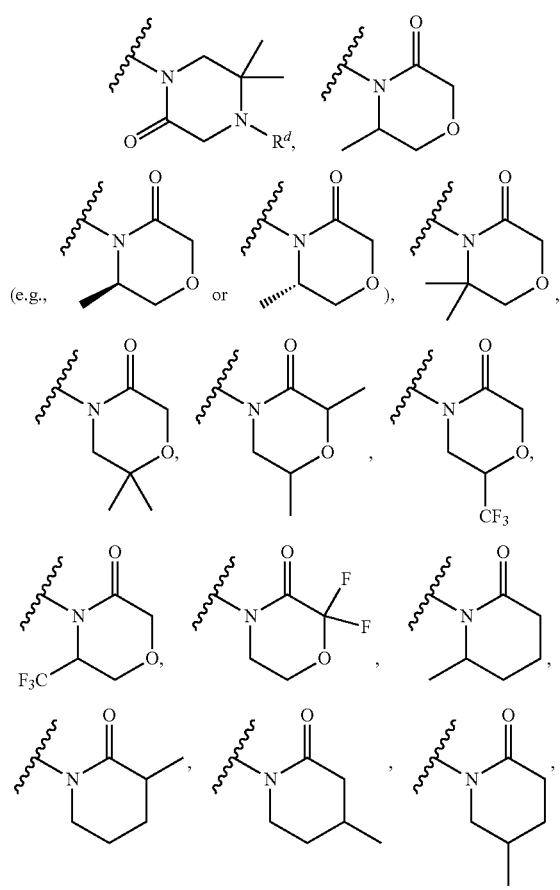

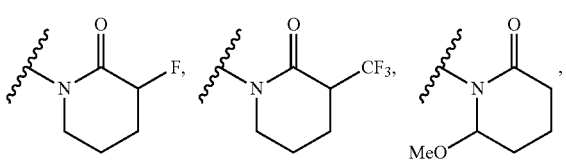

-continued

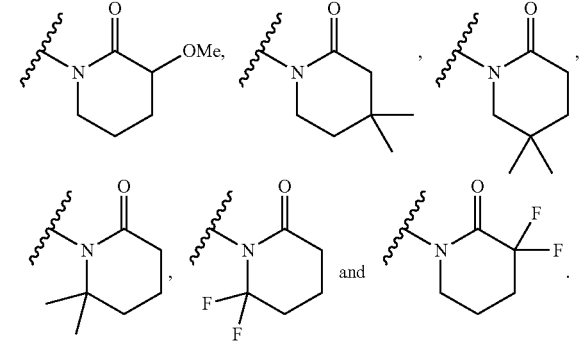

In certain of these embodiments, $R^d$ is $CH_3$.
For example, $R^b$ can be

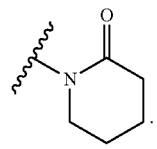

In some embodiments, $R^b$ is heterocyclyl or heterocycloalkenyl including 5 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In some embodiments, $R^b$ is heterocyclyl including 5 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$. In some embodiments, $R^b$ is selected from the group consisting of

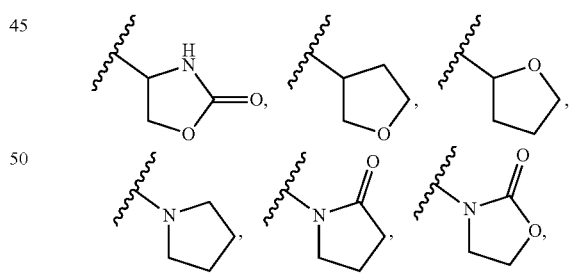

each of which is optionally substituted with 1-4 $R^c$. In certain of these embodiments, $R^c$ is halo, or $C_{1-6}$ alkyl.

In certain embodiments, $R^b$ is selected from the group consisting of

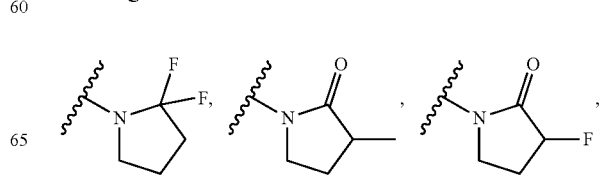

-continued (e.g., 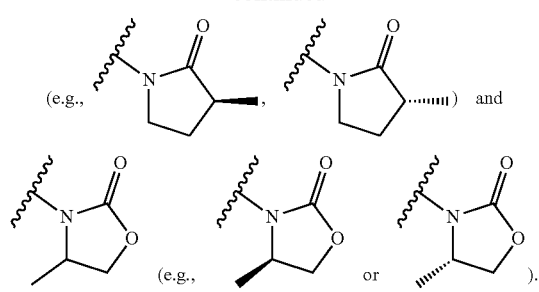 and (e.g., or ).

In some embodiments, $R^b$ is selected from the group consisting of

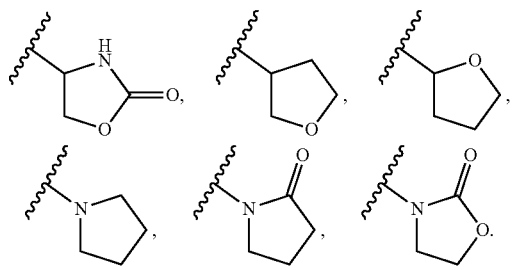

For example, $R^b$ can be

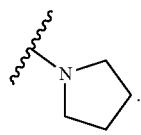 [SMILES: *N1CCCC1]

In some embodiments, wherein $R^b$ is heterocycloalkenyl including 5 ring atoms, wherein from 1-3 ring atoms are heteroatoms, each independently selected from the group consisting of N, N(H), N($R^d$), O, and S(O)$_{0-2}$, and wherein the heterocycloalkenyl is optionally substituted with from 1-4 substituents independently selected from the group consisting of oxo and $R^c$.

In certain embodiments, wherein $R^b$ is

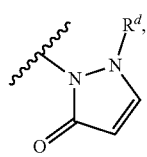

optionally wherein $R^b$ is

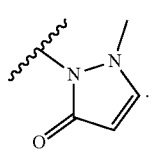 [SMILES: *n1c(=O)ccn1C]

In some embodiments, $R^b$ is selected from the group consisting of

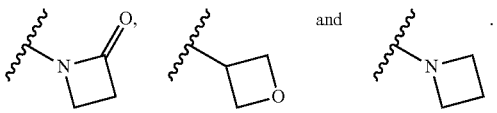 [SMILES: *N1CCC1=O ; *C1COC1 ; *N1CCC1]

In some embodiments, $R^b$ is heterocyclyl or heterocycloalkenyl including 7-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In some embodiments, $R^b$ is heterocyclyl including 7-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In some embodiments, $R^b$ is heterocyclyl including 7 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected $R^c$. In certain embodiments, $R^b$ is selected from the group consisting of

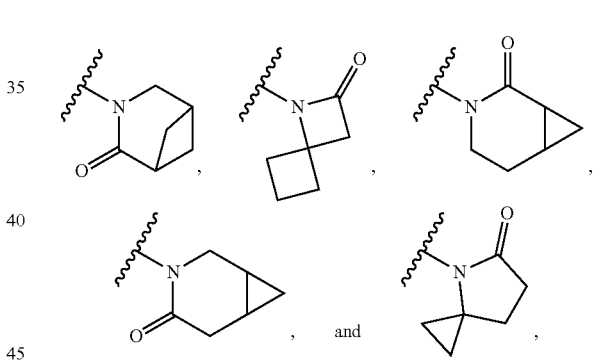

each of which is optionally substituted with from 1-4 substituents independently selected $R^c$. In certain embodiments, $R^b$ is selected from the group consisting of

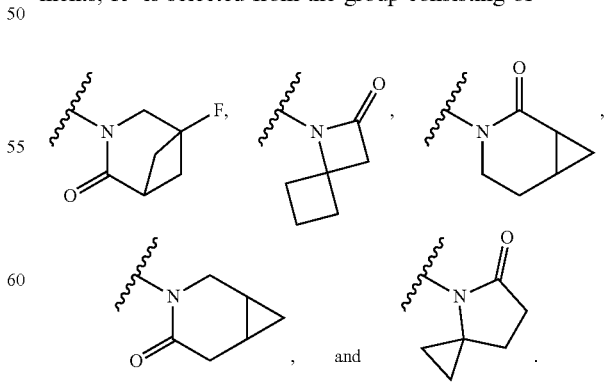

In some embodiments, $R^b$ is heterocyclyl including 8 ring atoms, wherein from 1-3 ring atoms are heteroatoms, each independently selected from the group consisting of N, N(H), N(R$^d$), O, and S(O)$_{0-2}$, and wherein the heterocyclyl is optionally substituted with from 1-4 substituents independently selected R$^c$. In certain embodiments, R$^b$ is selected from the group consisting of

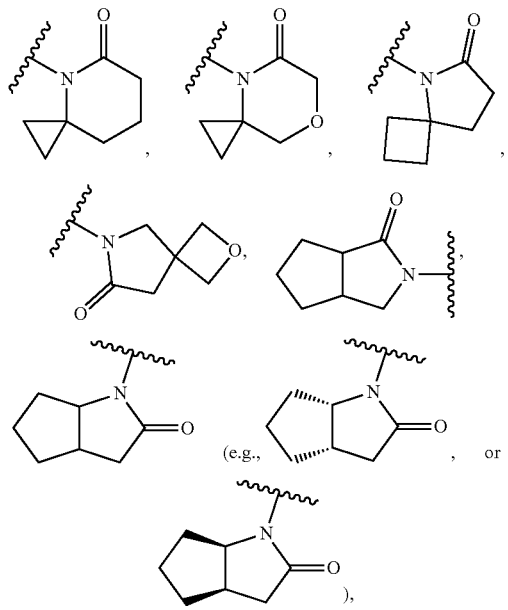

each of which is optionally substituted with from 1-4 substituents independently selected R$^c$. In certain embodiments, R$^b$ is selected from the group consisting of

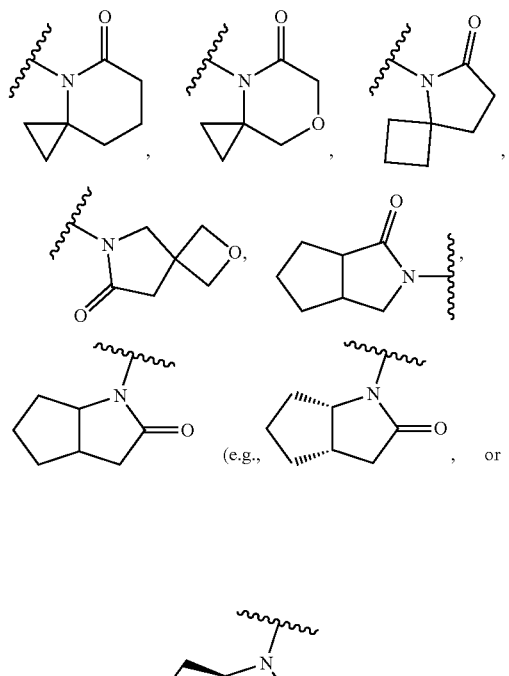

In some embodiments, R$^b$ is heterocyclyl including 9 ring atoms, wherein from 1-3 ring atoms are heteroatoms, each independently selected from the group consisting of N, N(H), N(R$^d$), O, and S(O)$_{0-2}$, and wherein the heterocyclyl is optionally substituted with from 1-4 substituents independently selected from the group consisting of oxo and R$^c$. In certain embodiments, R$^b$ is selected from the group consisting of


each of which is optionally substituted with from 1-4 substituents independently selected from the group consisting of oxo and R$^c$. in certain of these embodiments, R$^d$ is CH$_3$. In certain embodiments, R$^b$ is selected from the group consisting of


In some embodiments, $R^b$ is $C_{3-10}$ cycloalkyl or $C_{3-10}$ cycloalkenyl, each of which is optionally substituted with from 1-4 substituents independently selected from the group consisting of oxo and $R^c$. In certain embodiments, $R^b$ can be

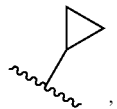 [SMILES: *C1CC1]

optionally substitute with one $R^c$

Variable $R^2$, $R^3$, $R^4$, and $R^5$

In some embodiments, $R^2$ is hydrogen.
In some embodiments, $R^2$ is chloro or fluoro. In certain embodiments, $R^2$ is chloro.
In some embodiments, $R^3$, $R^4$ and $R^5$ are hydrogen.
In some embodiments, $R^2$ is chloro, and $R^3$, $R^4$ and $R^5$ are hydrogen.

Variable n and $R^6$

In some embodiments, n is 0.
In some embodiments, n is 1 or 2.
In some embodiments, $R^6$ is selected from the group consisting of halo; cyano; $C_{1-10}$ alkyl which is optionally substituted with from 1-6 independently selected $R^a$; $C_{1-4}$ alkoxy, $C_{1-4}$ haloalkoxy; and $-NR^eR^f$; optionally wherein $R^6$ is selected from the group consisting of cyano, chloro, fluoro, methyl, ethyl, $-CHF_2$, methoxy, $-OCHF_2$, and $-NH_2$.

Non-Limiting Combinations

Formula (I-1)

In some embodiments, the compound of formula (IV) is a compound of formula (I-1)

Formula (I-1)

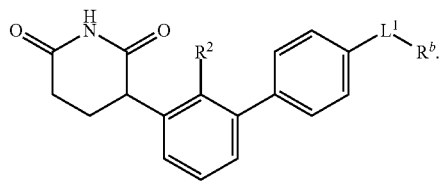

Formula (I-2)

In some embodiments, the compound of formula (IV) is a compound of formula (I-2)

Formula (I-2)

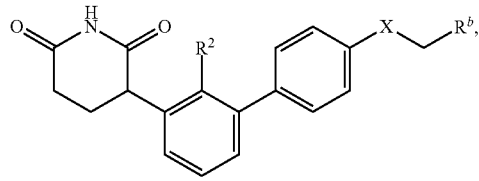

wherein X is $-NH-$ or $-O-$.

In certain embodiments of Formula (I-2), X is $-NH-$.
In certain embodiments of Formula (I-2), in X is $-O-$.
In certain embodiments of Formula (I-2), $R^2$ is chloro.
In certain embodiments of Formula (I-2), $R^b$ is a heteroaryl including 5 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$.

In certain embodiments of Formula (I-2), $R^b$ is selected from the group consisting of

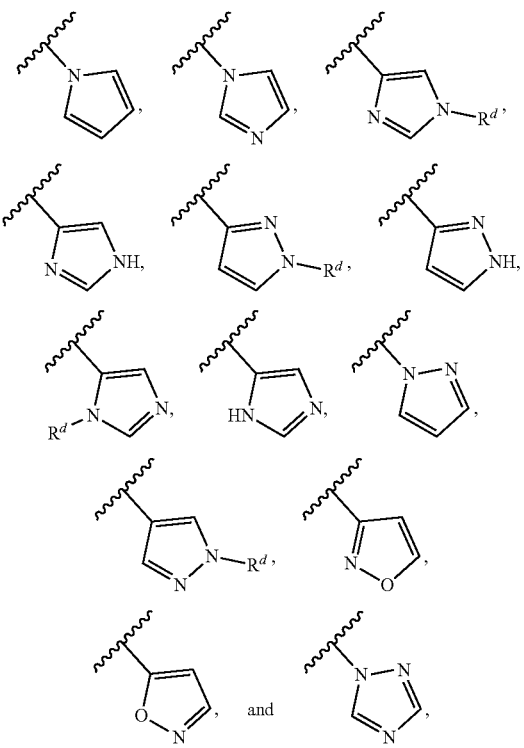

each of which is optionally substituted with from 1-2 substituents independently selected $R^c$. In certain embodiments of Formula (I-2), $R^b$ is selected from the group consisting of

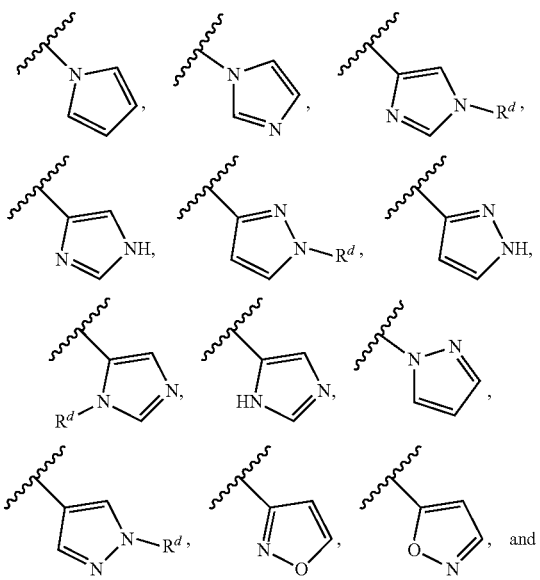

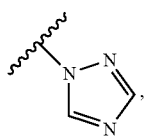

optionally wherein $R^d$ is $CH_3$. In certain embodiments of Formula (I-2), $R^b$ is selected from the group consisting of

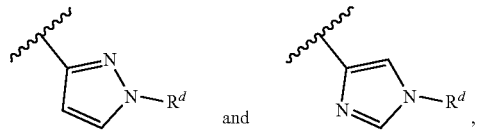

optionally wherein $R^d$ is $CH_3$.

In certain embodiments of Formula (I-2), $R^b$ is selected from the group consisting of

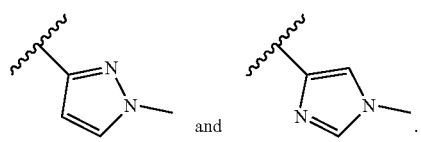

In certain embodiments of Formula (I-2), $R^b$ is

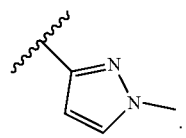 [SMILES: *c1ccn(C)n1]

Formula (I-3)

In some embodiments, the compound of formula (IV) is a compound of formula (I-3)

Formula (I-3)

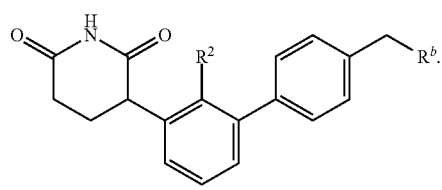

In certain embodiments of Formula (I-3), $R^2$ is chloro.

In certain embodiments of Formula (I-2), $R^b$ is heterocycloalkenyl including 6 ring atoms, wherein from 1-3 ring atoms are heteroatoms, each independently selected from the group consisting of N, N(H), N($R^d$), O, and S(O)$_{0-2}$, and wherein the heterocycloalkenyl is optionally substituted with from 1-4 substituents independently selected from the group consisting of oxo and $R^c$.

In certain embodiments of Formula (I-3), $R^b$ is

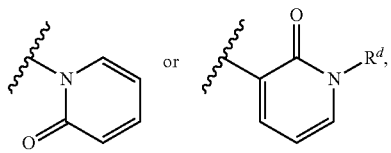

each of which is optionally substituted with from 1-2 substituents independently selected $R^c$. In certain embodiments of Formula (I-3), wherein $R^b$ is

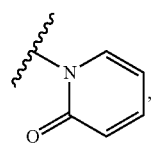 [SMILES: *n1ccccc1=O]

which is optionally substituted with from 1-2 independently selected $R^c$.

For example, $R^b$ can be

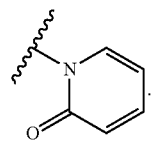

In certain embodiments of Formula (I-3), $R^b$ is

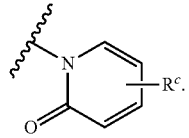

In certain of these embodiments, each occurrence of $R^c$ is selected from the group consisting of $C_{1-10}$ alkyl optionally substituted with from 1-6 independently selected $R^a$, $C_{1-4}$ alkoxy, halo, and —$NR^eR^f$. The compound of any one of claim 121 or 122, wherein $R^c$ is selected from the group consisting of methyl, ethyl, —$CHF_2$, —$CF_3$, methoxy, fluoro, chloro, and $NH_2$. In certain of these embodiments, $R^b$ is selected from the group consisting of

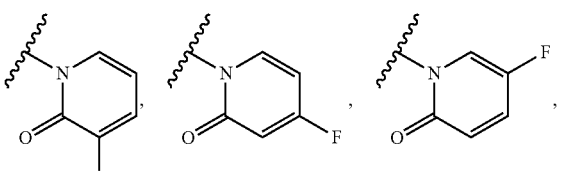

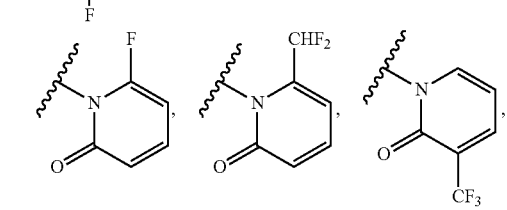

-continued

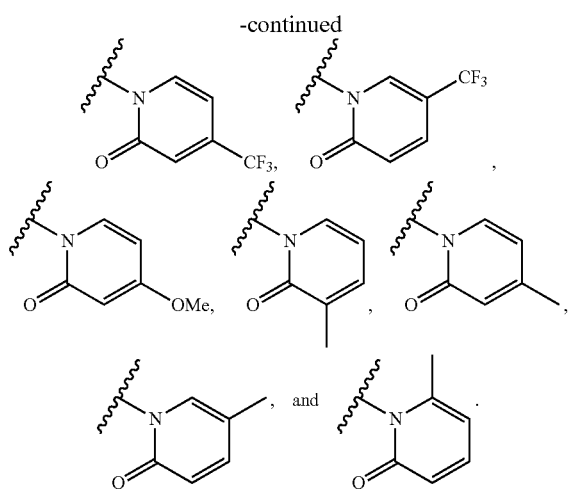

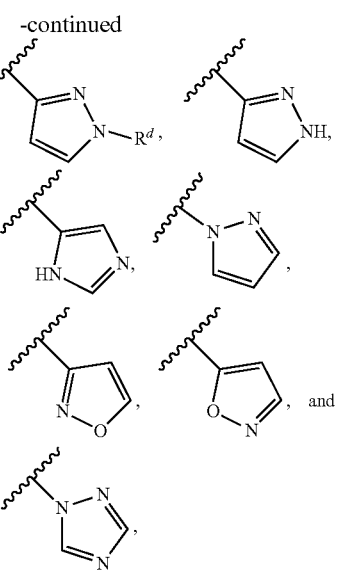

In certain embodiments of Formula (I-3), $R^b$ is heteroaryl including 5 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 substituents independently selected $R^c$. In certain embodiments of Formula (I-3), $R^b$ is selected from the group consisting of

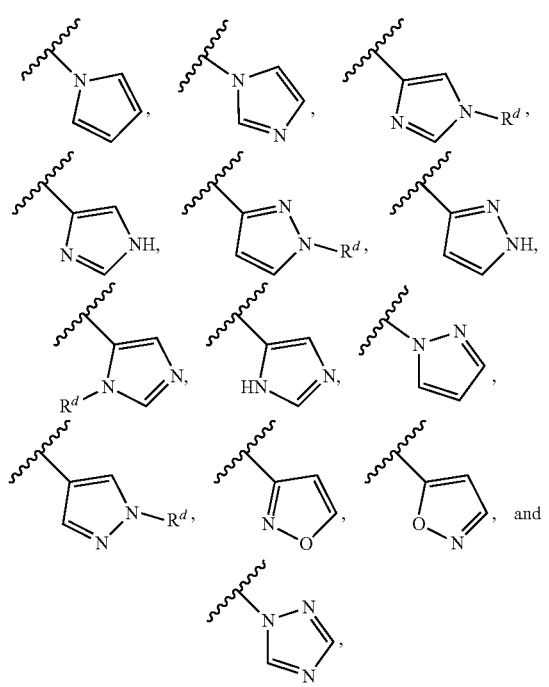

each of which is optionally substituted with from 1-2 independently selected $R^c$.

In certain of these embodiments, $R^b$ is selected from the group consisting of

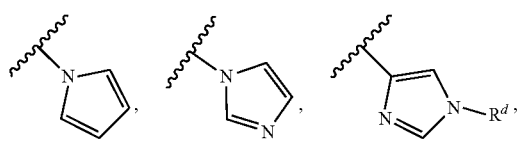

optionally wherein $R^d$ is CH$_3$.

For example, $R^b$ can be

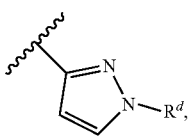

optionally wherein $R^d$ is CH$_3$.

For still another example, $R^b$ can be

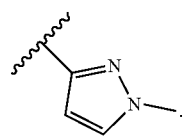

In certain embodiments of Formula (I-3), $R^b$ is heterocyclyl including 6 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$. In certain of these embodiments, $R^b$ is selected from the group consisting of

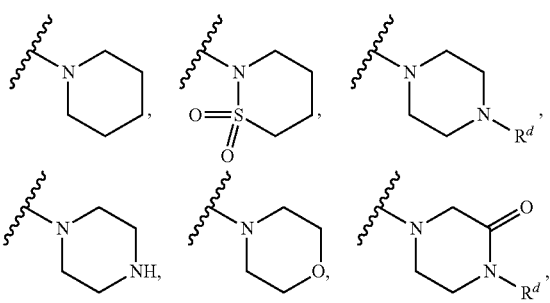

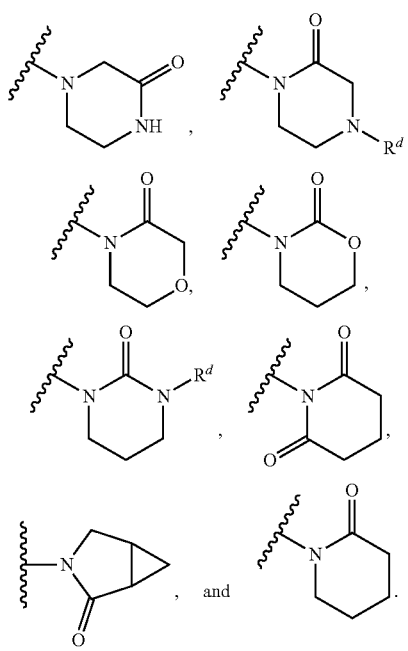

In certain of these embodiments, $R^b$ is selected from the group consisting of

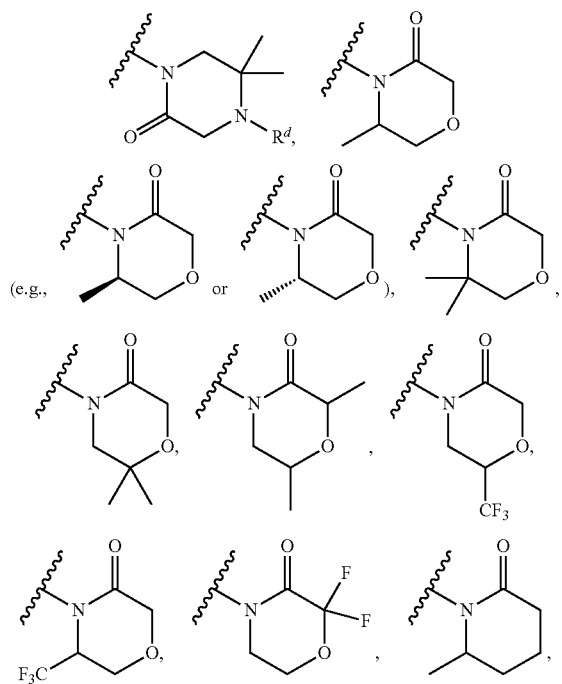

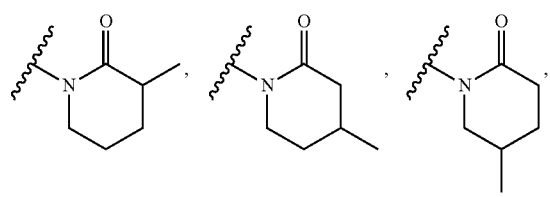

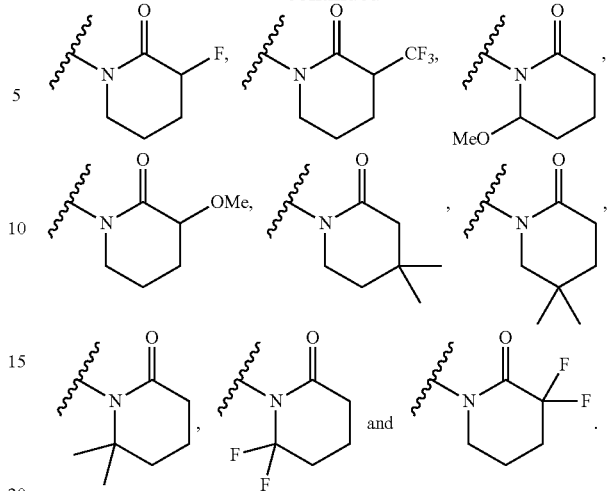

In certain of these embodiments, $R^A$ is CH$_3$.

For example, R can be

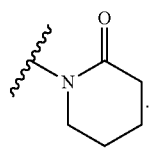 [SMILES: *N1CCCCC1=O]

In certain embodiments of Formula (I-3), R is heteroaryl including 6 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$.

In certain embodiments of Formula (I-3), $R^b$ is heteroaryl including 6 ring atoms, wherein from 1-4 ring atoms are heteroatoms, each independently selected from the group consisting of N, N(H), N($R^d$), O, and S(O)$_{0-2}$.

In certain embodiments of Formula (I-3), $R^b$ is selected from the group consisting of

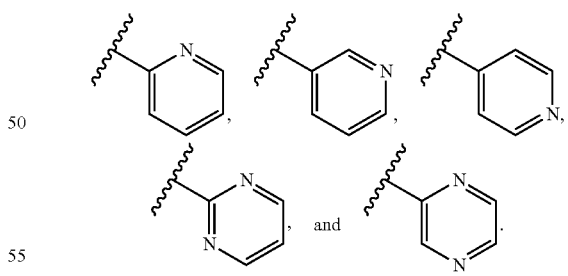

For example, $R^b$ can be

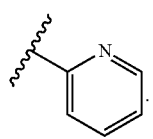 [SMILES: *c1ccccn1]

In certain embodiments of Formula (I-3), $R^2$ is chloro.

Formula (I-4)

In some embodiments, compound of formula (IV) is a compound of formula (I-4)

Formula (I-4)

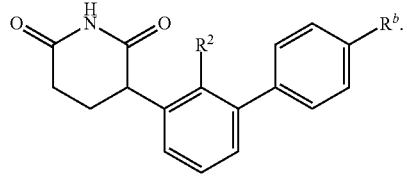

In some embodiments of Formula (I-4), $R^2$ is chloro.

In some embodiments of Formula (I-4), $R^b$ is heterocycloalkenyl including 6 ring atoms, wherein from 1-3 ring atoms are heteroatoms, each independently selected from the group consisting of N, N(H), N($R^d$), O, and S(O)$_{0-2}$, and wherein the heterocycloalkenyl is optionally substituted with from 1-4 substituents independently selected from the group consisting of oxo and $R^c$.

In some embodiments of Formula (I-4), $R^b$ is

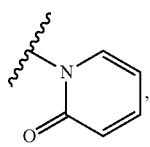 [SMILES: *n1ccccc1=O]

which is optionally substituted with from 1-4 s independently selected $R^c$. For example, $R^b$ is

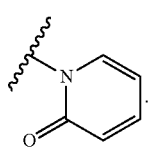

In some embodiments of Formula (I-4), $R^b$ is heterocyclyl including 6 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$.

In certain embodiments, $R^b$ is selected from the group consisting of

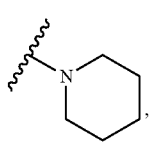 , 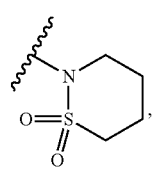 , 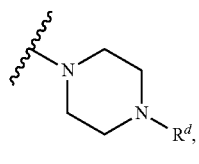

-continued

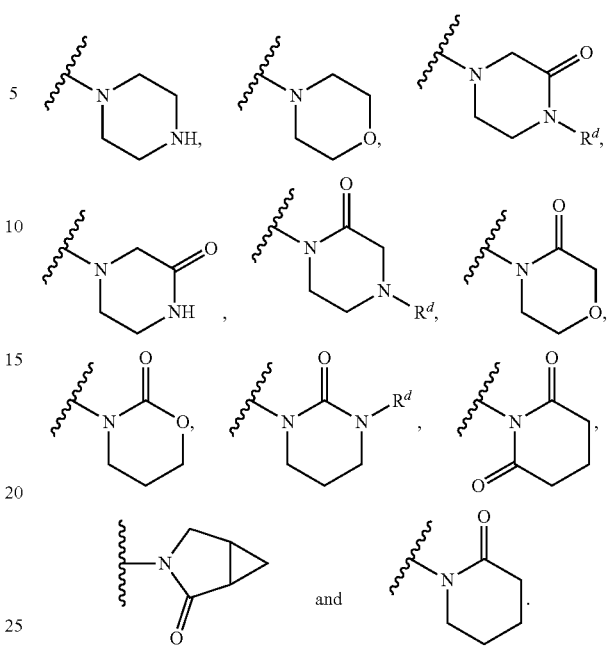

In certain embodiments, $R^b$ is selected from the group consisting of

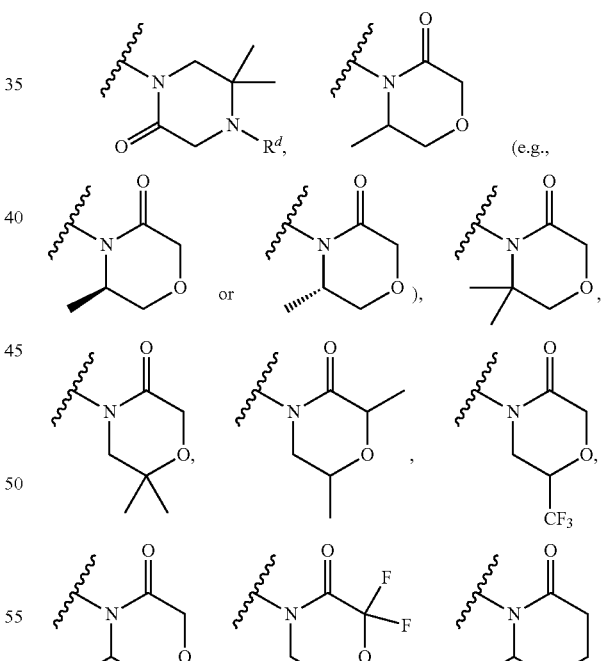

(e.g.,

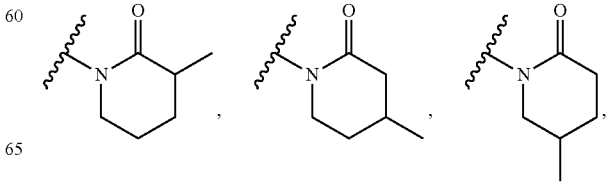

-continued

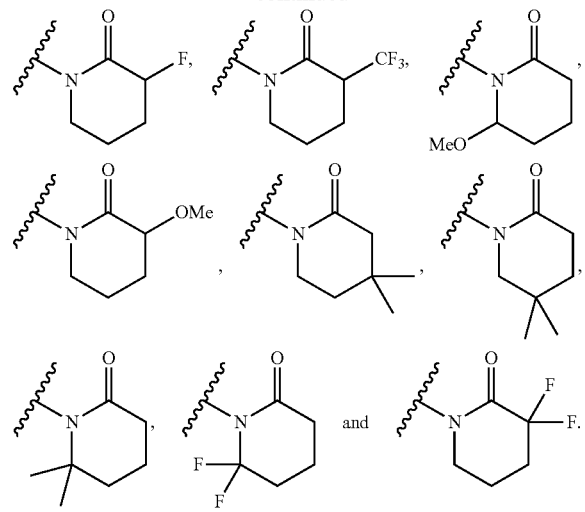

In certain of these embodiments, $R^d$ is CH$_3$.

For example, $R^b$ can be

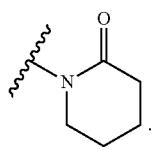

Formula (I-5)

In some embodiments, the compound of formula (IV) is a compound of formula (I-5)

Formula (I-5)

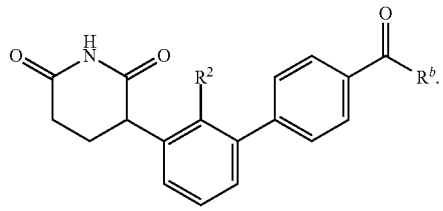

In some embodiments of Formula (I-5), $R^2$ is chloro.

In some embodiments of Formula (I-5), $R^b$ is heterocyclyl including 5 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$. In certain of these embodiments, $R^b$ is selected from the group consisting of

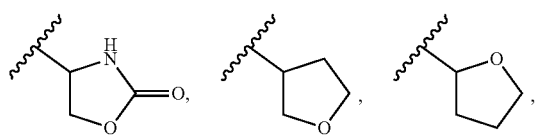

-continued

In certain of these embodiments, $R^b$ is selected from the group consisting of

For example, $R^b$ can be

In some embodiments of Formula (I-1), (I-2, (I-3) (I-4) or (I-5), $R^b$ is heteroaryl including 9 ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected from the group consisting of oxo and $R^c$.

In some embodiments of Formula (I-1), (I-2, (I-3) (I-4) or (I-5), $R^b$ is selected from the group consisting of

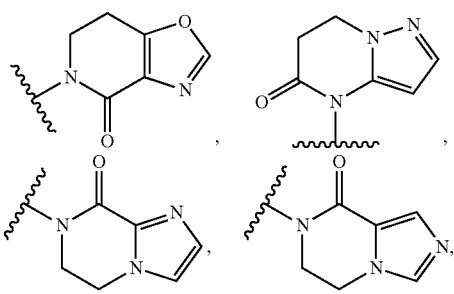

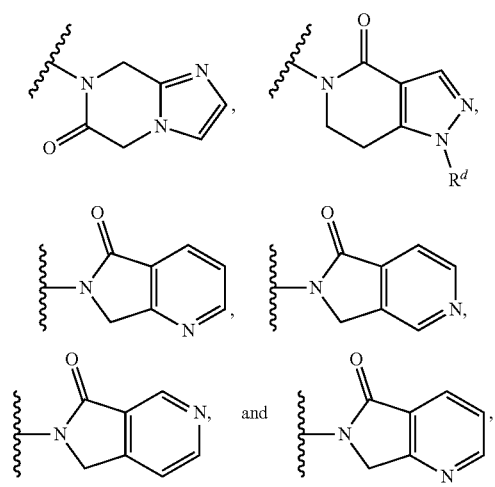

each of which is optionally substituted with from 1-4 independently selected $R^c$. In certain of these embodiments, $R^b$ is selected from the group consisting of

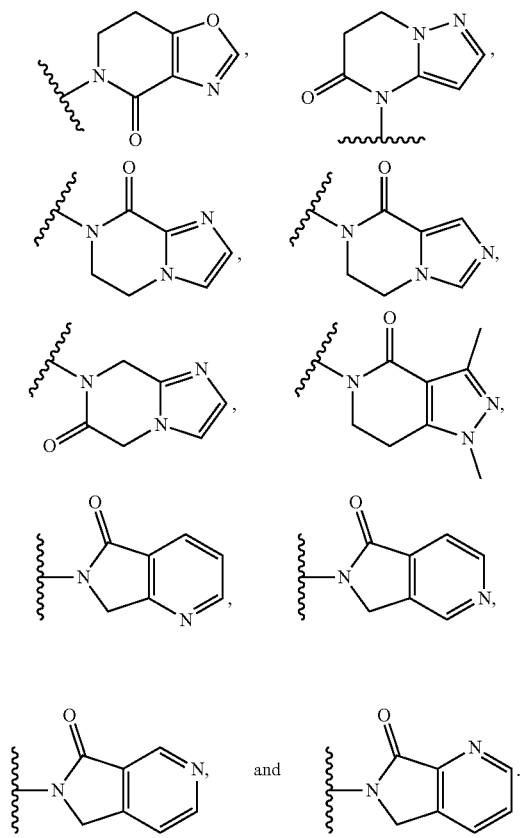

In some embodiments of Formula (I-1), (I-2, (I-3) (I-4) or (I-5), $R^b$ is heteroaryl including ring atoms, wherein from 1-4 ring atoms are heteroatoms, each independently selected from the group consisting of N, N(H), N($R^d$), O, and S(O)$_{0-2}$, and wherein the heteroaryl is optionally substituted with from 1-4 independently selected $R^c$. In certain of these embodiments, $R^b$ is selected from the group consisting of

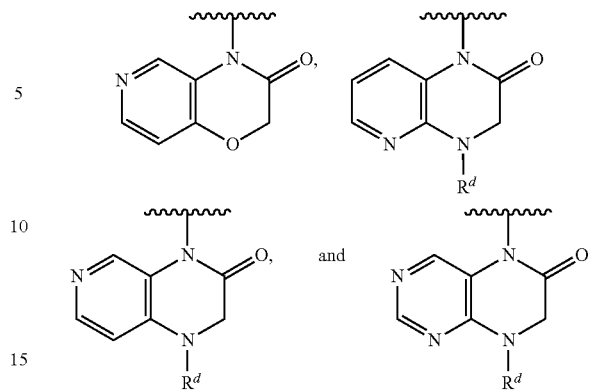

each of which is optionally substituted with from 1-4 independently selected $R^c$. In certain of these embodiments, $R^b$ is selected from the group consisting of

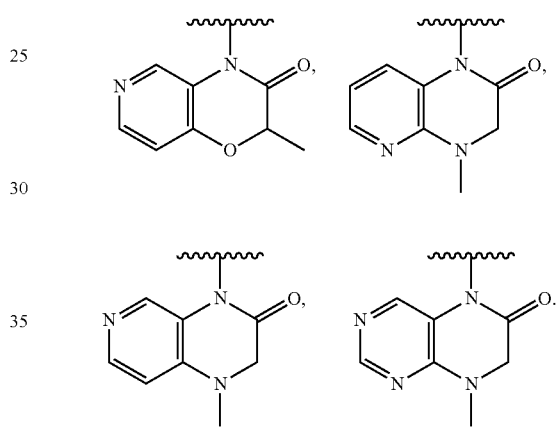

In some embodiments of Formula (I-1), (I-2, (I-3) (I-4) or (I-5), $R^b$ is heterocyclyl including 7-10 ring atoms, wherein from 1-3 ring atoms are heteroatoms, each independently selected from the group consisting of N, N(H), N($R^d$), O, and S(O)$_{0-2}$, and wherein the heterocyclyl or heterocycloalkenyl is optionally substituted with from 1-4 substituents independently selected from the group consisting of oxo and $R^c$.

In some embodiments of Formula (I-1), (I-2, (I-3) (I-4) or (I-5), $R^b$ is heterocyclyl including 7 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected $R^c$. In certain of these embodiments, $R^b$ is selected from the group consisting of

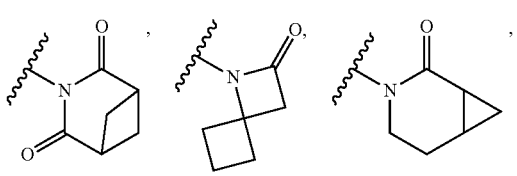

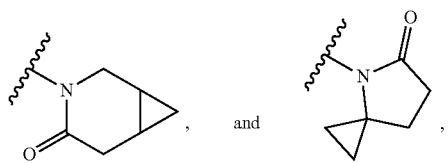

each of which is optionally substituted with from 1-4 substituents independently selected $R^c$. In certain of these embodiments, $R^b$ is selected from the group consisting of

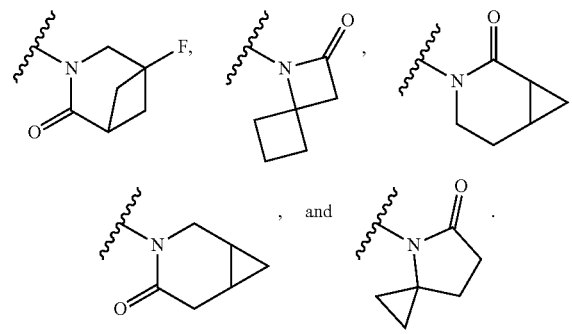

In some embodiments of Formula (I-1), (I-2, (I-3) (I-4) or (I-5), $R^b$ is heterocyclyl including 8 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected $R^c$. In certain of these embodiments, $R^b$ is selected from the group consisting of

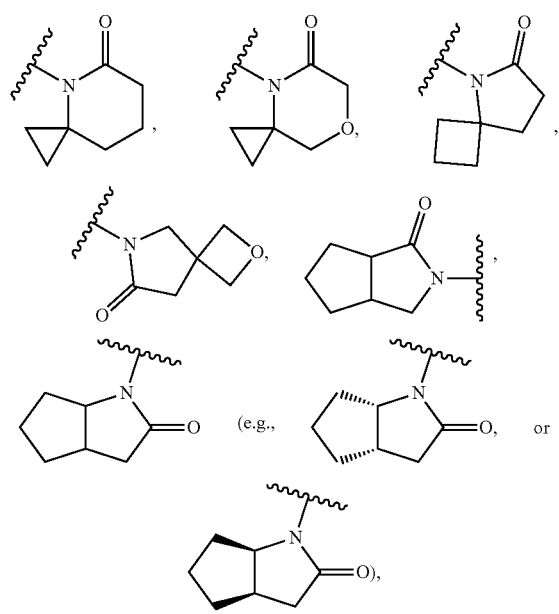

each of which is optionally substituted with from 1-4 substituents independently selected $R^c$. In certain of these embodiments, $R^b$ is selected from the group consisting of

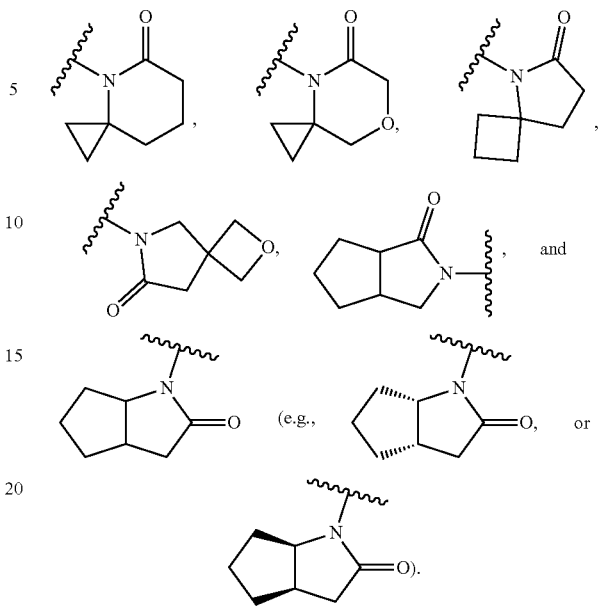

In some embodiments of Formula (I-1), (I-2, (I-3) (I-4) or (I-5), $R^b$ is heterocyclyl including 9 ring atoms, wherein from 1-3 ring atoms are heteroatoms, each independently selected from the group consisting of N, N(H), N($R^d$), O, and S(O)$_{0-2}$, and wherein the heterocyclyl is optionally substituted with from 1-4 substituents independently selected from the group consisting of oxo and $R^c$. In some embodiments of Formula (I-1), (I-2, (I-3) (I-4) or (I-5), $R^b$ is selected from the group consisting of

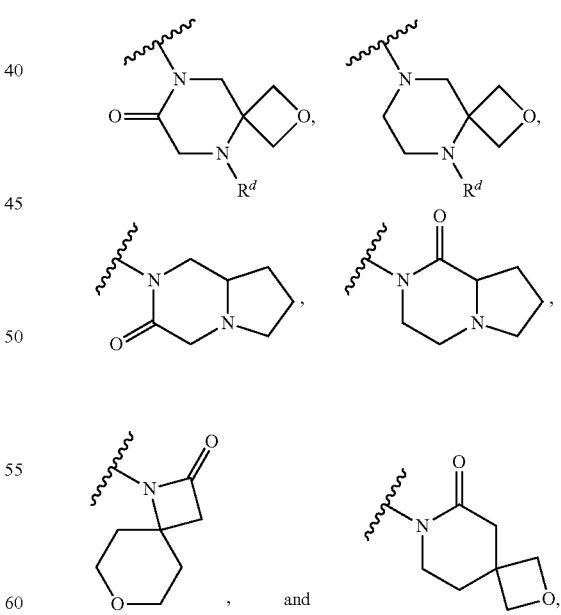

each of which is optionally substituted with from 1-4 substituents independently selected from the group consisting of oxo and $R^c$. In certain of these embodiments, $R^d$ is CH$_3$. In certain of these embodiments, $R^b$ is selected from the group consisting of

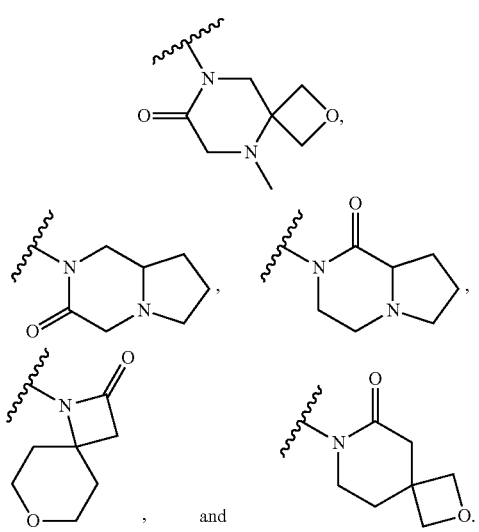

Formula (Ia) and (Ib)

In some embodiments, the compound of formula (IV) is a compound of formula (Ia)

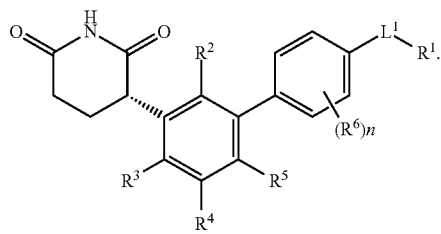

Formula (Ia)

In some embodiments, the wherein the compound of formula (IV) is a compound of formula (Ib)

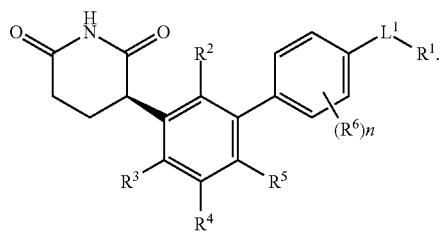

Formula (Ib)

Pharmaceutical Compositions

In another aspect, the present disclosure provides a pharmaceutical composition that includes any one of the compounds described herein, or a pharmaceutically acceptable salt thereof (e.g., a therapeutically effective amount of the compound or salt), and a pharmaceutically acceptable excipient.

The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

Compositions for oral administration can take the form of bulk liquid solutions or suspensions, or bulk powders. In some embodiments, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component with the remainder being various vehicles or excipients and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope of the disclosure provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pennsylvania, which is incorporated herein by reference.

Methods of Use In one aspect, this disclosure features methods of degrading VAV1 in a subject, which include administering to the subject an effective amount of a compound described herein, or pharmaceutically acceptable salt thereof. In some embodiments, the compound mediates the interaction of a VAV1 protein with an E3 ligase, thereby increasing degradation of the VAV1 protein. In some embodiments, VAV1 is a regulator of T-cells. In an embodiment, the compound interacts with the E3 ligase prior to the interaction of VAV1 with the E3 ligase. In some embodiments, the E3 ligase comprises cereblon.

In another aspect, this disclosure features methods of degrading VAV1, which include: (i) contacting a compound described herein or a pharmaceutically acceptable salt thereof with an E3 ligase; and (ii) interacting the contacted E3 ligase with VAV1, thereby degrading VAV1.

In some embodiments, the compounds described herein can bind to a specific amino acid sequence of VAV1, thereby causing degradation of VAV1. In other embodiments, such degradation of VAV1 is mediated by the compound interacting with both the specific amino acid sequence of VAV1 and an E3 ligase. In other embodiments, the E3 ligase comprises cereblon.

In a further aspect, this disclosure features methods of treating a variety of disorders which include administering the Compounds and pharmaceutical compositions described herein. Such disorders include, without limitation, autoimmune diseases (e.g., multiple sclerosis, rheumatoid arthritis, myasthenia gravis) and transplantation setting disease (e.g., graft-versus-host disease). Other disorders include those caused by or associated with deregulated lymphocyte development or activation.

In an aspect, this disclosure features methods of treating a disorder caused by or associated with deregulated lymphocyte development or activation in a subject in need thereof, comprising administering to the subject a therapeutically effective amount of a compound described herein or a pharmaceutically acceptable salt thereof. In some embodiments, the disorder is autoimmune diseases (e.g., multiple sclerosis, rheumatoid arthritis, myasthenia gravis). In some embodiments, the disorder is transplantation setting disease (e.g., graft-versus-host disease). In some embodiments, the disorder is a malignancy (e.g., T cell or B cell malignancy). In some embodiment, the lymphocyte is T-cell.

In an aspect, this disclosure features methods of treating a disorder caused by or associated with dysregulation of T-cell receptor signaling in a subject in need thereof, comprising administering to the subject a therapeutically effective amount of a compound described herein or a pharmaceutically acceptable salt thereof. In some embodiments, the T-cell receptor signaling are enhanced CD69 surface expression, IFNγ or IL-2.

In an aspect, this disclosure features methods of treating a disorder caused by or associated with VAV1 polymorphisms in a subject in need thereof, comprising administering to the subject a therapeutically effective amount of a compound described herein or a pharmaceutically acceptable salt thereof.

In an aspect, this disclosure features methods of treating a disorder caused by or associated with immunopathologies in a subject in need thereof, comprising administering to the subject a therapeutically effective amount of a compound described herein or a pharmaceutically acceptable salt thereof. In some embodiments, the disorder is autoimmune disorder. In some embodiments, the autoimmune disorder is selected from the group consisting of multiple sclerosis, rheumatoid arthritis, systemic lupus, erythematosus, Hashimoto's thyroiditis, myasthenia gravis, diabetes type I or II, and the disorders associated therewith, vasculitis, pernicious anemia, Sjoegren syndrome, uveitis, psoriasis, Graves ophthalmopathy, alopecia areata and others, allergic diseases (e.g., allergic asthma, atopic dermatitis, allergic rhinitis/conjunctivitis, allergic contact dermatitis), inflammatory diseases optionally with underlying aberrant reactions (e.g., inflammatory bowel disease, Crohn's disease or ulcerative colitis, intrinsic asthma, inflammatory lung injury, inflammatory liver injury, inflammatory glomerular injury), atherosclerosis, osteoarthritis, irritant contact dermatitis and further eczematous dermatitis, seborrheic dermatitis, cutaneous manifestations of immunologically-mediated disorders, inflammatory eye disease, keratoconjunctivitis, myocarditis or hepatitis. In some embodiments, the disorder is a cancer, tumour or other malignancy, optionally wherein the disorder is a T cell or B cell malignancy. In some embodiments, the disorder is selected from the group consisting of: leukemia, lymphoma, T-cell prolymphocytic leukemia, T-cell granular lymphocytic leukemia, aggressive NK cell leukemia, hairy-cell leukemia, nasal and nasal-type NK/T cell lymphoma, mycosis fungoides and Sezary syndrome, angioimmunoblastic T-cell lymphoma, peripheral T-cell lymphoma unspecified, adult T-cell leukemia/lymphoma (HTLV1+), anaplastic large cell lymphoma, primary cutaneous CD-30 positive T-cell lymphoproliferative disorders, cutaneous T-cell lymphoma, subcutaneous panniculitis like T-cell lymphoma, intestinal T-cell lymphoma (+enteropathy), hepatosplenic gamma/delta T-cell lymphoma, and non-Hodgkin lymphomas (e.g., B-cell non-Hodgkin lymphomas; e.g., Burkitt lymphoma, chronic lymphocytic leukemia/small lymphocytic lymphoma (CLL/SLL), diffuse large B-cell lymphoma, follicular lymphoma, and mantle cell lymphoma). Transplantation setting diseases include graft-versus-host disease, chronic graft rejection, acute graft rejection, transplant vasculopathy, graft vessel disease, graft atherosclerosis, and transplant coronary disease.

In an aspect, the disclosure features methods of treating a disorder caused by or associated with VAV1 polymorphisms in a subject in need thereof or caused by or associated with immunopathologies in a subject in need thereof, comprising administering to the subject a therapeutically effective amount of a therapeutically effective amount of a compound described herein or a pharmaceutically acceptable salt thereof.

In some embodiments, the disorder is T-cell mediated. In some embodiments, the disorder is selected from the group consisting of Diabetes Type I or II, pernicious anemia, uveitis, psoriasis, alopecia areata, ulcerative colitis, Chron's disease, atherosclerosis, myocarditis, pericarditis, pulmonary fibrosis, systemic sclerosis, morphea, Alzheimer's disease, Acute Graft-vs. Host Disease or T-cell mediated kidney disease.

In some embodiments, the disorder is T/B-cell mediated. In some embodiments, the disorder is selected from the group consisting of multiple sclerosis, rheumatoid arthritis, myasthenia gravis, Sjogren's syndrome, Grave's disease, an allergic disorder (e.g., asthma, allergic contact dermatitis, rhinitis or contact dermatitis), an autoimmune liver disease (e.g., biliary sclerosis or sclerosing cholangitis), chronic inflammatory demyelinating polyradiculoneuropathy, macular degeneration, systemic lupus erythematosus, Hashimoto's thyroiditis, amyloidosis, inflammatory eye diseases, pemphigus, systemic lupus erythematosus, Chronic Graft vs. Host Disease, lupus nephritis, pulmonary arterial hypertension or vasculitis.

In some embodiments, the disorder is selected from the group consisting of ulcerative colitis, rheumatoid arthritis, psoriasis, multiple sclerosis, myasthenia gravis, cutaneous lupus or axial spondylarthritis. In preferred embodiments, the disorder is ulcerative colitis.

In some embodiments, the disorder is selected from the group consisting of B-cell lymphoma, B-cell leukemia, T-cell lymphoma, T-cell leukemia or acute myeloid leukemia. In preferred embodiments, the disorder is chronic lymphocytic leukemia.

In an aspect, the disclosure relates to a method of treating an ulcerative colitis, rheumatoid arthritis, psoriasis, multiple sclerosis, myasthenia gravis, cutaneous lupus or axial spondylarthritis, the method comprising administering to the subject a therapeutically effective amount of a compound

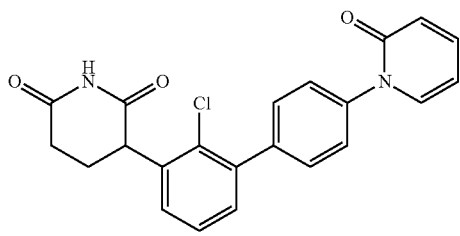

or a pharmaceutically acceptable salt thereof. In preferred embodiments, the disorder is ulcerative colitis.

In an aspect, the disclosure relates to a method of treating B-cell lymphoma, B-cell leukemia, T-cell lymphoma, T-cell leukemia or acute myeloid leukemia, the method comprising administering to the subject a therapeutically effective amount of a compound

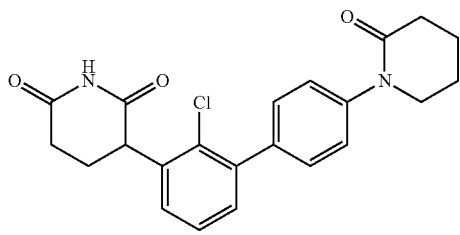 [SMILES: O=C1CCC(c2cccc(-c3ccc(N4CCCCC4=O)cc3)c2Cl)C(=O)N1]

or a pharmaceutically acceptable salt thereof. In preferred embodiments, the method is a method of treating chronic lymphocytic leukemia.

In some embodiments, the disclosure relates to a method of treating patients exhibiting CD226 overexpression.

In some embodiments, the disclosure relates to a method of treating patients having a CD226 risk variant.

In some embodiments, the disclosure relates to a method of treating patients having a CD226 polymorphism.

In some embodiments, the disclosure relates to a method of treating patients having a Gly307Ser (G307S) amino acid substitution in CD226 (rs763361T allele).

In an aspect, the disclosure relates to a method of treating a disorder caused by or associated with disregulation of lymphocyte development or activation in a subject in need thereof, comprising administering to the subject a therapeutically effective amount of a compound that binds cereblon and degrades VAV1 or a pharmaceutically acceptable salt thereof.

In some embodiments, the lymphocyte is T-cell.
In some embodiments, the lymphocyte is B-cell.

In an aspect, the disclosure relates to a method of treating a disorder caused by or associated with disregulation of T-cell receptor signaling in a subject in need thereof, comprising administering to the subject a therapeutically effective amount of a compound that binds cereblon and degrades VAV1 or a pharmaceutically acceptable salt thereof.

In an aspect, the disclosure relates to a method of treating a disorder caused by or associated with VAV1 polymorphisms in a subject in need thereof, comprising administering to the subject a therapeutically effective amount of a compound that binds cereblon and degrades VAV1 or a pharmaceutically acceptable salt thereof.

In an aspect, the disclosure relates to a method of treating a disorder caused by or associated with immunopathologies in a subject in need thereof, comprising administering to the subject a therapeutically effective amount of a compound that binds cereblon and degrades VAV1 or a pharmaceutically acceptable salt thereof.

In some embodiments, the disorder is autoimmune disorder.

In some embodiments, the autoimmune disorder is selected from the group consisting of multiple sclerosis, rheumatoid arthritis, systemic lupus, erythematosus, Hashimoto's thyroiditis, myasthenia gravis, diabetes type I or II, and the disorders associated therewith, vasculitis, pernicious anemia, Sjoegren syndrome, uveitis, psoriasis, Graves ophthalmopathy, alopecia areata and others, allergic diseases (e.g., allergic asthma, atopic dermatitis, allergic rhinitis/conjunctivitis, allergic contact dermatitis), inflammatory diseases optionally with underlying aberrant reactions (e.g., inflammatory bowel disease, Crohn's disease or ulcerative colitis, intrinsic asthma, inflammatory lung injury, inflammatory liver injury, inflammatory glomerular injury), atherosclerosis, osteoarthritis, irritant contact dermatitis and further eczematous dermatitis, seborrheic dermatitis, cutaneous manifestations of immunologically-mediated disorders, inflammatory eye disease, keratoconjunctivitis, myocarditis or hepatitis.

In an aspect, the disclosure provides a compound or pharmaceutically acceptable salt for use in any of the above-recited methods of treatment. In some embodiments, the compound or pharmaceutically acceptable salt thereof is a compound or pharmaceutically acceptable salt thereof as described herein. In a further aspect, the disclosure provides the use of a compound or pharmaceutically acceptable salt for the manufacture of a medicament for any of the above-recited methods of treatment. In some embodiments, the compound or pharmaceutically acceptable salt thereof is a compound or pharmaceutically acceptable salt thereof as described herein.

Process for Manufacturing Compound 185 and Intermediates Thereof

In an aspect, this disclosure provides a process for manufacturing an intermediate of compound 185, the process comprising:

(i) coupling a compound of formula

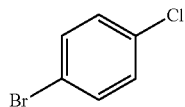

and a compound of formula

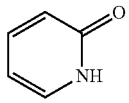

to form a compound

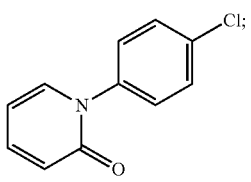

followed by
(ii) borylating

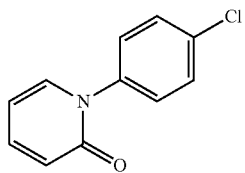 [SMILES: O=c1ccccn1-c1ccc(Cl)cc1]

to form

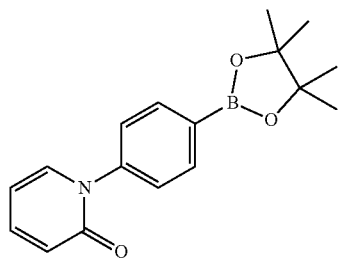 [SMILES: CC1(C)OB(c2ccc(-n3ccccc3=O)cc2)OC1(C)C]

(Intermediate I).

In some embodiments, step (i) comprises carrying out an Ullmann coupling. In some embodiments, step (i) comprises catalysing the reaction using copper (I) iodide. In some embodiments, step (i) comprises adding a ligand which is N1,N2-bis(furan-2-ylmethyl)oxalamide (BFMO). In some embodiments, step (i) comprises adding BFMO and copper (I) iodide.

In some embodiments, step (i) comprises dissolving the compound of formula

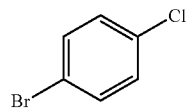

and a compound of formula

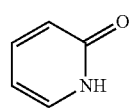

in a suitable solvent, followed by adding BFMO and then catalysing the reaction with copper (I) iodide.

In some embodiments, step (ii) comprises carrying out a Miyaura Borylation.

This process provides improved selectivity relative to other processes for manufacturing compound 185. In particular, the use of the starting material

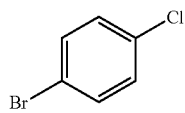

provides improved selectivity of the borylation step compared to the use of other substituted benzene rings, such as

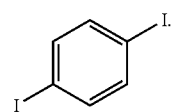

In an aspect, this disclosure provides a process for manufacturing an intermediate of compound 185, the process comprising:
(i) reacting a compound

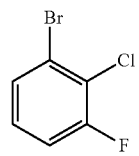

with a compound

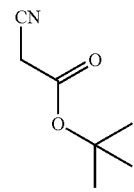

to form a compound

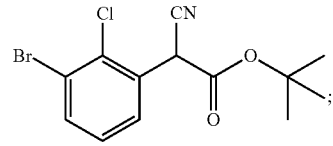 [SMILES: CC(C)(C)OC(=O)C(C#N)c1cccc(Br)c1Cl]

followed by
(ii) performing a deprotection of the compound

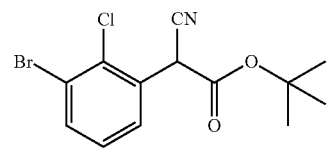 [SMILES: CC(C)(C)OC(=O)C(C#N)c1cccc(Br)c1Cl]

to form a compound

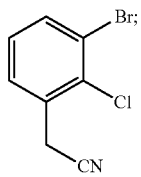 [SMILES: N#CCc1cccc(Br)c1Cl]

followed by
(iii) reacting the compound

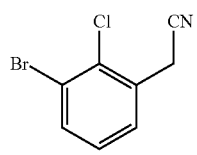

with a compound

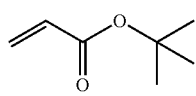

to form a compound

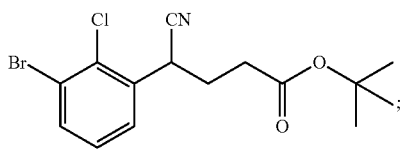

followed by
(iv) performing a cyclization of the compound

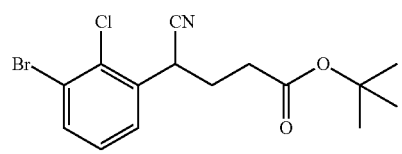 [SMILES: CC(C)(C)OC(=O)CCC(C#N)c1cccc(Br)c1Cl]

to provide

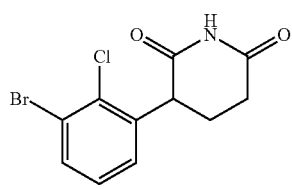 [SMILES: O=C1CCC(c2cccc(Br)c2Cl)C(=O)N1]

(Intermediate II).

In some embodiments, step (i) comprises carrying out a Hurtley arylation.

In some embodiments, step (iii) comprises carrying out a Michael addition.

Previously, intermediate II had been made starting from

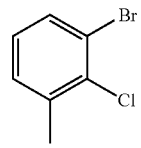

and reacting with N-bromosuccinimide and benzoyl peroxide to make

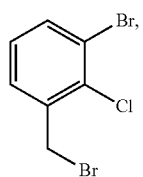

then adding TMSCN to form

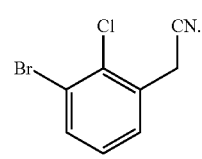

The present process is advantageous relative to the previous process because Intermediate II can be synthesized without the need for benzoyl peroxide, which may be explosive and is thus not a safe reagent for large-scale use. Further, Intermediate II can be synthesized without the need for TMSCN, which is toxic and is thus not appropriate for large-scale syntheses. In an aspect, this disclosure provides a process for manufacturing compound 185, the process (i) coupling a compound of formula

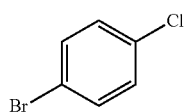

and a compound of formula

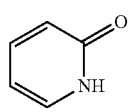

to form a compound

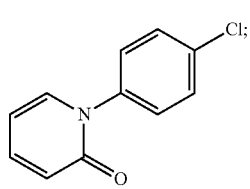 [SMILES: O=c1ccccn1-c1ccc(Cl)cc1]

followed by
(ii) borylating the compound

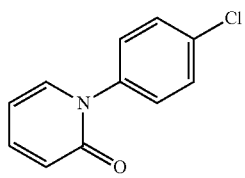 [SMILES: O=c1ccccn1-c1ccc(Cl)cc1]

to form

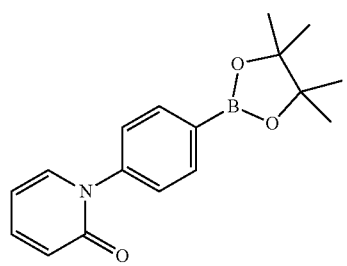 [SMILES: CC1(C)OB(c2ccc(-n3ccccc3=O)cc2)OC1(C)C]

(Intermediate I);
(iii) reacting a compound

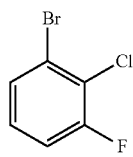

with a compound

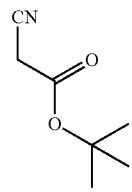

to form a compound

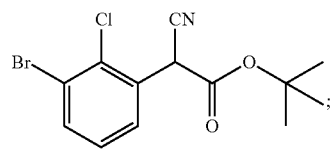 [SMILES: CC(C)(C)OC(=O)C(C#N)c1cccc(Br)c1Cl]

followed by
(iv) performing a deprotection of the compound

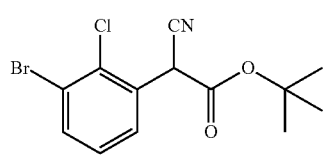 [SMILES: CC(C)(C)OC(=O)C(C#N)c1cccc(Br)c1Cl]

to form a compound

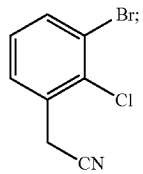

followed by
(v) reacting the compound

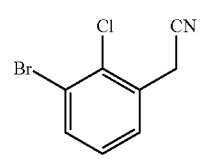 [SMILES: N#CCc1cccc(Br)c1Cl]

with a compound

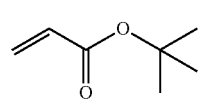

to form a compound

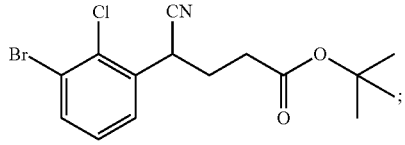 [SMILES: CC(C)(C)OC(=O)CCC(C#N)c1cccc(Br)c1Cl]

followed by
(vi) performing a cyclization of the compound

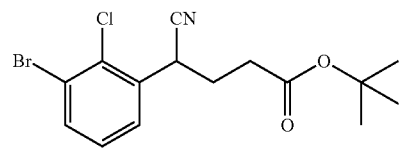 [SMILES: CC(C)(C)OC(=O)CCC(C#N)c1cccc(Br)c1Cl]

to provide

(Intermediate II); and
(vii) coupling Intermediate I and Intermediate II to provide compound 185.

This process harnesses the improved selectivity in the reaction to produce Intermediate I, as well as the improved safety and reduced toxicity of the reaction to produce Intermediate II.

In one embodiment, step (i) comprises at least one of the following steps:

(1) dissolving the compound of formula

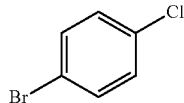

and the compound of formula

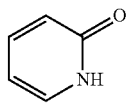

in a suitable solvent, for example a volume of N,N-dimethylacetamide (DMAc) three times the volume of the compound of formula

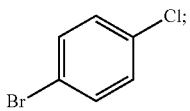

(2) adding N1,N2-bis(furan-2-ylmethyl)oxalamide (BFMO, 6 mol %) and tripotassium phosphate ($K_3PO_4$, 2 eq.) to the mixture obtained in (1);
(3) adding copper(I) iodide (CuI, 4 mol %) to the mixture obtained in (2), and stirring the resulting mixture at a temperature of 115° C. for 20 hours;
(4) quenching the mixture obtained in (3) with a suitable solvent, for example by the addition of a volume of aqueous ammonium hydroxide ($NH_4OH$) six times the volume of the compound of formula

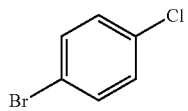

used in step (1), and stirring the resulting mixture at a temperature of 50° C. for 1 hour;
(5) filtering the mixture obtained in (4), and twice washing the solid obtained with a suitable solvent, for example a volume of $NH_4OH$ two times the volume of the compound of formula

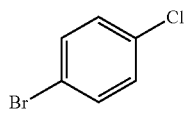

used in step (1);
(6) washing the solid obtained in (5) twice with a suitable solvent, for example a volume of water two times the volume of the compound of formula

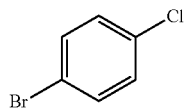

used in step (1);
(7) dissolving the solid obtained in (6) in a suitable solvent, for example a volume of dichloromethane (DCM) five times the volume of the compound of formula

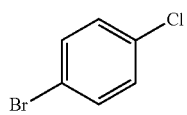

used in step (1);
(8) adding silica to the mixture obtained in (7), and stirring the resulting mixture for 2 hours;
(9) filtering the mixture obtained in (8), and washing the resulting solid with a suitable solvent, for example a volume of DCM seven times the volume of the compound of formula

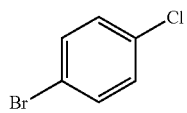

used in step (1).

In one embodiment, step (ii) comprises at least one of the following steps:
(1) dissolving [Pd cinnamyl Cl]$_2$ (0.2 mol %) and XPhos (0.8 mol %) in a suitable solvent, for example 0.4 volumes of iPrOH, to produce a preformed [Pd] solution, stirring the mixture for 30 to 60 minutes at a temperature of 30° C.;
(2) dissolving the compound of formula

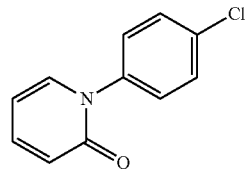 [SMILES: O=c1ccccn1-c1ccc(Cl)cc1]

in a suitable solvent, for example 9 volumes of iPrOH;
(3) adding potassium acetate (KOAc, 2.5 eq) to the mixture obtained in (2);
(4) adding a compound of formula

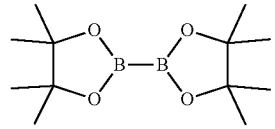

($B_2Pin_2$, 1.5 eq) to the mixture obtained in (3), and degassing the resulting mixture;

(5) adding the preformed [Pd] solution obtained in (1) to the mixture obtained in (4), and rinsing the resulting mixture with a suitable solvent, for example iPrOH (2 times 0.4 volumes);

(6) heating the mixture obtained in (5) to 80° C. for 2 hours;

(7) cooling the mixture obtained in (6) to 25° C., stirring for two hours;

(8) filtering the mixture obtained in (7) and rinsing the solid with a suitable solvent, for example iPrOH (2.4 volumes);

(9) distilling the combined filtrate and washings obtained in (8) to remove 10 volumes of solvent, for example iPrOH;

(10) precipitating the mixture obtained in (9) by addition of a suitable solvent, for example heptane (4 volumes);

(11) cooling the mixture obtained in (10) to 5° C., stirring for 1 hour;

(12) filtering the mixture obtained in (11) to obtain a solid comprising the compound of formula

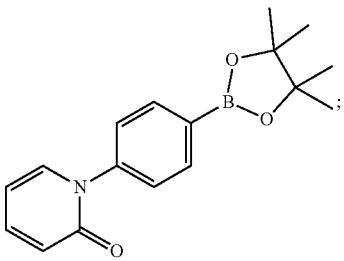 [SMILES: CC1(C)OB(c2ccc(-n3ccccc3=O)cc2)OC1(C)C]

(13) washing the solid obtained in (12) with a suitable solvent, for example cold heptane (2 times 2 volumes);

(14) dissolving the solid obtained in (13) in a suitable solvent, for example iPrOH (13 volumes), and adding a suitable scavenger (0.13 wt %), stirring for 2 hours at a temperature of 20° C.;

(15) filtering off the scavenger, and washing the resulting mixture with a suitable solvent, for example iPrOH (2 volumes);

(16) concentrating the mixture obtained in (15) to dryness at 45° C. under reduced pressure.

In one embodiment, step (iii) comprises at least one of the following steps:

(1) dissolving the compound of formula

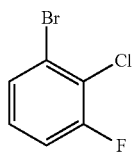

in a suitable solvent, for example DMAc (5 volumes, at 20° C.);

(2) adding $K_3PO_4$ (5 eq) to the mixture obtained in (1);

(3) adding the compound of formula

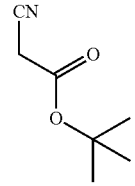

(0.6 eq) to the mixture obtained in (2) at 20° C.;

(4) stirring the mixture obtained in (3) for 2 hours at 120° C.;

(5) adding the compound of formula

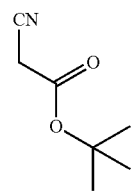

(0.6 eq) to the mixture obtained in (4) at 120° C.;

(6) stirring the mixture obtained in (5) for 16 hours at 120° C.;

(7) adding $H_2O$ (5 volumes) to the mixture obtained in (6) at 20° C. and allowing phase separation to obtain an organic phase;

(8) washing the organic phase obtained in (7) with $H_2O$ (1 volume) and 25% aq. NaCl (1 volume) at 20° C. and allowing phase separation to obtain an aqueous phase;

(9) washing the aqueous phase obtained in (8) with 8% aq. $NaHCO_3$ (6 volumes) and iPrOAc (5 volumes) at 20° C. and allowing phase separation to obtain an organic phase; (10) washing the organic phase obtained in (9) with 25% aq. $NH_4Cl$ (6 volumes) at 20° C. and allowing phase separation to obtain an organic phase;

(11) distilling the organic phase obtained in (10) to remove solvent;

(12) filtering the mixture obtained in (11) over a polish filter to obtain a compound of formula

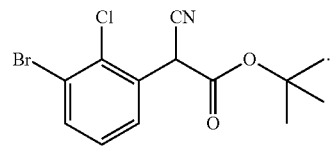 [SMILES: CC(C)(C)OC(=O)C(C#N)c1cccc(Br)c1Cl]

In one embodiment, step (iv) comprises at least one of the following steps:

(1) dissolving the compound of formula

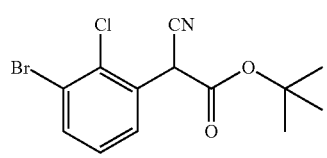 [SMILES: CC(C)(C)OC(=O)C(C#N)c1cccc(Br)c1Cl]

in a suitable solvent, for example toluene (3 volumes) at 20° C.;
(2) adding PTSA (p-toluenesulfonic acid, 0.17 eq) to the mixture obtained in (1) at 20° C.;
(3) heating the mixture obtained in (2) to 110° C. and stirring for 20 hours;
(4) washing the mixture obtained in (3) with 8% aq. NaHCO₃ (2 volumes) at 20° C. and allowing phase separation to obtain an organic phase;
(5) washing the organic phase obtained in (4) with 25% aq. NaCl (3 volumes);
(6) distilling the mixture obtained in (5) to remove solvent;
(7) filtering the mixture obtained in (6) over a polish filter to obtain a compound of formula

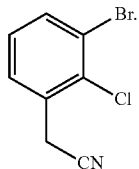 [SMILES: N#CCc1cccc(Br)c1Cl]

In one embodiment, step (v) comprises at least one of the following steps:
(1) dissolving the compound of formula

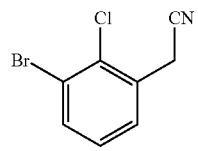

in a suitable solvent, for example THF (8 volumes, at 20° C.);
(2) adding NaOMe (0.05 eq) to the mixture obtained in (1);
(3) cooling the mixture obtained in (2) to 0° C.;
(4) adding the compound of formula

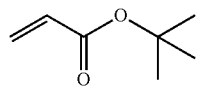

(1.00 eq dissolved in a suitable solvent, for example 2 volumes of THF) to the mixture obtained in (3);
(5) adding NaHCO₃ (8% aq., 1 volume) to the mixture obtained in (4);
(6) filtering the mixture obtained in (5) to obtain a filtrate;
(7) distilling the filtrate obtained in (6) under reduced pressure to remove solvent, for example 6 volumes of THF;
(8) dilution of the mixture obtained in (7) with suitable solvents, for example 4 volumes of toluene and 2 volumes of NaCl (25% aq.), allowing fast layer separation;
(9) washing the organic phase obtained in (8) with a suitable solvent, for example 1 volume of NaCl (25% aq.);
(10) distilling the mixture obtained in (9) under reduced pressure to remove 4 volumes of solvent;
(11) diluting the mixture obtained in (10) with 2 volumes of toluene;
(12) distilling the mixture obtained in (11) under reduced pressure to remove 2 volumes of solvent;
(13) polish filtering the mixture obtained in (12) to obtain the compound of formula

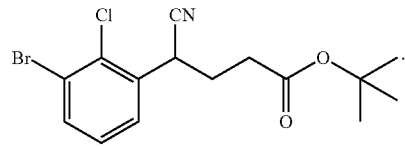 [SMILES: CC(C)(C)OC(=O)CCC(C#N)c1cccc(Br)c1Cl]

In one embodiment, step (vi) comprises at least one of the following steps:
(1) dissolving p-toluenesulfonic acid (PTSA) in a suitable solvent, for example toluene, at a temperature of 110° C.;
(2) adding the compound of formula

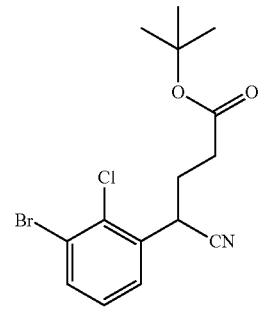 [SMILES: CC(C)(C)OC(=O)CCC(C#N)c1cccc(Br)c1Cl]

(dissolved in a suitable solvent, for example toluene) to the mixture obtained in (1) over an extended time period, for example 1.5 hours;
(3) diluting the mixture obtained in (2) by adding a suitable solvent, for example NaHCO₃ (8% aq., 1 volume) at a temperature of 75° C., and allowing phase separation of the resulting mixture;
(4) seeding the organic phase obtained in (3), then cooling the resulting mixture to 20° C. over 2 hours and maintaining a temperature of 20° C. for an extended time period, for example 14 hours;
(5) filtering the mixture obtained in (4), and washing the resulting solid of formula

with a suitable solvent, for example EtOH (1 volume);
(6) drying the solid obtained in (5) at 40-50° C. under reduced pressure.

In one embodiment, step (vii) comprises at least one of the following steps:
(1) dissolving the compound of formula

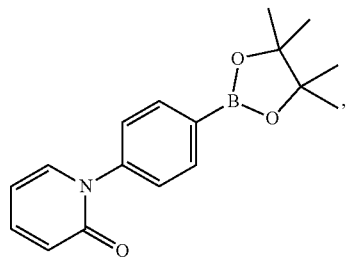 [SMILES: CC1(C)OB(c2ccc(-n3ccccc3=O)cc2)OC1(C)C]

the compound of formula

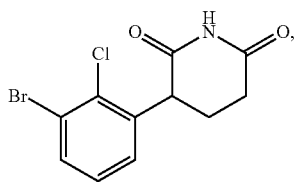 [SMILES: O=C1CCC(c2cccc(Br)c2Cl)C(=O)N1]

and Pd(dtbpf)Cl$_2$ in a suitable solvent, for example THF (10 volumes);

(2) adding Na$_2$CO$_3$ (5.5 volumes aq., i.e. 2.5 eq base) to the mixture obtained in (1), and stirring for an extended time period, for example 17 hours, at a temperature of 30° C.;

(3) quenching the reaction mixture obtained in (2) with a suitable solvent, for example 13 volumes of NH$_4$Cl;

(4) filtering the mixture obtained in (3) to produce a solid of formula

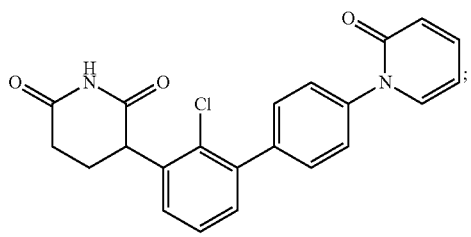 [SMILES: O=C1CCC(c2cccc(-c3ccc(-n4ccccc4=O)cc3)c2Cl)C(=O)N1]

(5) washing the solid obtained in (4) with suitable solvents, for example washing the solid with THF:H$_2$O in a ratio of 8:2, followed by washing with EtOH, and finally washing with heptane.

Polymorphic Form of Compound 185

In an aspect, this disclosure provides a crystalline form A of the free base of compound 185:

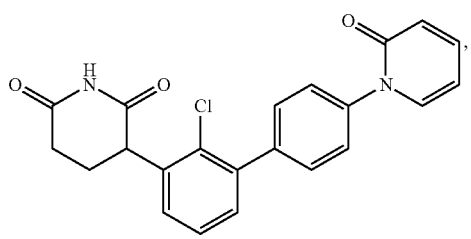 [SMILES: O=C1CCC(c2cccc(-c3ccc(-n4ccccc4=O)cc3)c2Cl)C(=O)N1]

wherein the Form A exhibits an XRPD pattern comprising peaks at about 16.5±0.5, 17±0.5 and 17.8±0.5 degrees two-theta using copper K-alpha radiation. In some embodiments, the Form A exhibits an XRPD pattern comprising peaks at about 14±0.5, 16.5±0.5, 17±0.5, 17.8±0.5 and 19.5±0.5 degrees two-theta using copper K-alpha radiation. In some embodiments, the Form A exhibits an XRPD pattern comprising peaks at about 14±0.5, 16.5±0.5, 17±0.5, 17.8±0.5 and 19.5±0.5 degrees two-theta using copper K-alpha radiation, as well as peaks between 21.5-23, 25.5-27, 27-28 and 29.5-31 degrees two-theta using copper K-alpha radiation. In some embodiments, the margin of error is ±0.4; ±0.3; ±0.2; ±0.1; or ±0.05.

In some embodiments, the crystalline form A exhibits an XRPD pattern comprising the peaks shown in Table 2 below.

TABLE 2

| XRPD Table of crystalline form A of compound 185 | |
| --- | --- |
| °2 Theta | Appearance |
| 14 | Single |
| 16.5 | Single |
| 17 | Single |
| 17.8 | Single |
| 19.5 | Single |
| 21.5-23 | Multiple |
| 25.5-27 | Multiple |
| 27-28 | Multiple |
| 29.5-31 | Multiple |

Figure 13:
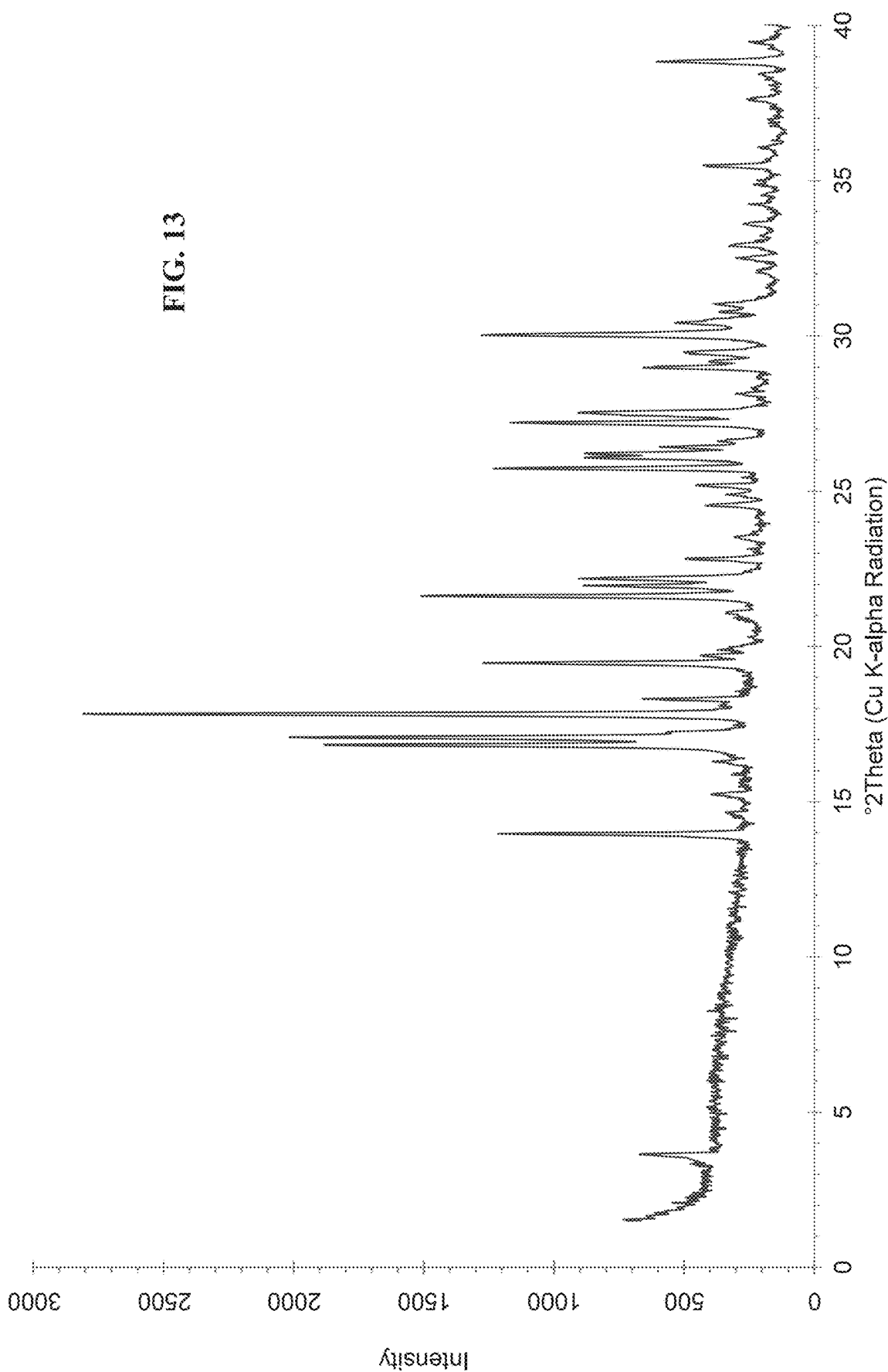
FIG. 13 shows an X-ray powder diffraction (XRPD) pattern of crystalline form A of compound 185.

In some embodiments, the crystalline form A of compound 185 exhibits an XRPD pattern which is substantially similar to FIG. 13.

Degrader Conjugates

In an aspect is a conjugate comprising a compound capable of degrading VAV1. For instance, in an aspect is an antibody-degrader conjugate or pharmaceutically acceptable salt thereof comprising a compound capable of degrading VAV1. The conjugate includes a compound capable of degrading VAV1 or pharmaceutically acceptable salt thereof which is conjugated to an antibody via a linker structure moiety. In some aspects, the compound is a compound of any of Formulae (I), (II), (III), (IV), (V), (I-1), (I-2), (I-3), (I-4), (Ia) and (Ib) or a pharmaceutically acceptable salt thereof.

In some embodiments, the conjugate has a structure according to Formula (A) below:

Bm-(-M-I)$_a$   Formula (A)

in which I is a compound that is capable of degrading VAV1, e.g., a compound of Formula (I), (II), (III), (IV), (V), (I-1), (I-2), (I-3), (I-4), (Ia) or (Ib) or a pharmaceutically acceptable salt thereof as defined herein, M is a linker moiety and Bm is a binding moiety that is capable of specifically binding to an antigen. The binding moiety may be an antibody, antibody fragment or an antibody-binding fragment.

In some embodiments, M is a linker as defined in WO 2021/198966, which is incorporated by reference in its entirety. The linker may be a cleavable linker or non-cleavable linker. In certain aspects, the linker can contain a heterobifunctional group. In the present disclosure, the term "heterobifunctional group" refers to a chemical moiety that connects the linker of which it is a part to the binding moiety. Heterobifunctional groups are characterized as having different reactive groups at either end of the chemical moiety. Attachment to Bm, can be accomplished through chemical or enzymatic conjugation, or a combination of both. Chemical conjugation involves the controlled reaction of accessible amino acid residues on the surface of the binding moiety with a reaction handle on the heterobifunctional group. Examples of chemical conjugation include, but are not limited to, lysine amide coupling, cysteine mediated coupling, and coupling via a non-natural amino acid incorporated by genetic engineering, wherein non-natural amino acid residues with a desired reaction handle are installed onto Bm. In enzymatic conjugation, an enzyme mediates the coupling of the linker with an accessible amino residue on the binding moiety.

Examples of enzymatic conjugation include, but are not limited to, transpeptidation using sortase, transpeptidation using microbial transglutaminase, and N-glycan engineering. Chemical conjugation and enzymatic conjugation may also be used sequentially. For example, enzymatic conjugation can also be used for installing unique reaction handles on Bm to be utilized in subsequent chemical conjugation.

In some embodiments, M is a linker as defined in WO 2023/037268, which is incorporated by reference in its entirety. In some embodiments, M is selected from the group consisting of

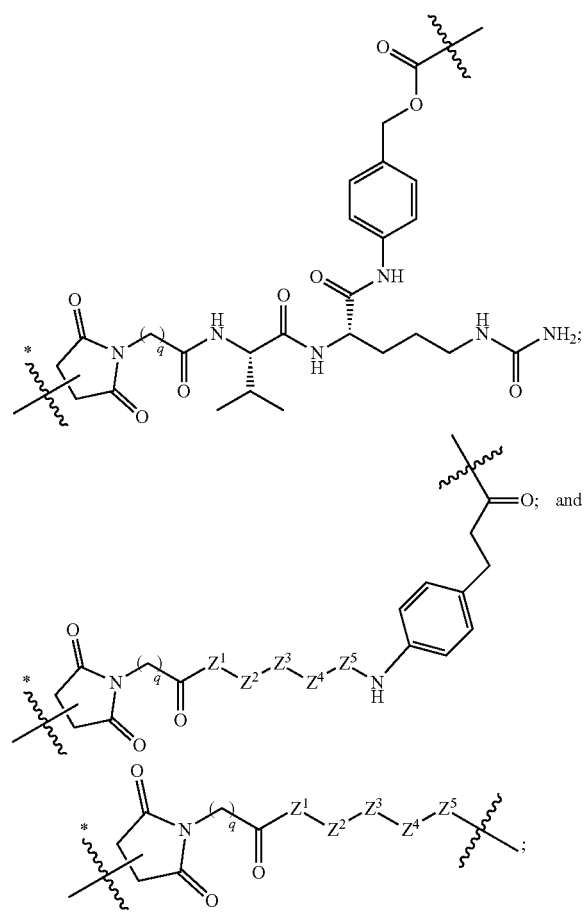

wherein
q is from 2 to 10;
$Z^1$, $Z^2$, $Z^3$, $Z^4$, and $Z^5$ are each independently absent or a naturally-occurring amino acid residue in the L- or D-configuration, provided that at least two of $Z^1$, $Z^2$, $Z^3$, $Z^4$, and $Z^5$ are amino acid residues;

⸺ is the point of attachment to the parent molecular (degrader) moiety; and

⸺ is the point of attachment to the binding moiety.

In some embodiments, $Z^1$, $Z^2$, $Z^3$, $Z^4$, and $Z^5$ are independently absent or selected from the group consisting of L-valine, D-valine, L-citrulline, D-citrulline, L-alanine, D-alanine, L-glutamine, D-glutamine, L-glutamic acid, D-glutamic acid, L-aspartic acid, D-aspartic acid, L-asparagine, D-asparagine, L-phenylalanine, D-phenylalanine, L-lysine, D-lysine, and glycine; provided that at least two of $Z^1$, $Z^2$, $Z^3$, $Z^4$, and $Z^5$ are amino acid residues.

The term "binding moiety" as used herein refers to any molecule that recognizes and binds to a cell surface marker or receptor. The binding moiety may be an antibody, antibody fragment, or an antigen-binding fragment. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. The term "antibody" herein is used in the broadest sense and specifically covers monoclonal antibodies, single domain antibodies, polyclonal antibodies, multispecific antibodies (e.g., bispecific antibodies), and antibody fragments, so long as they exhibit the desired biological activity. Antibodies may be murine, human, humanized, chimeric, or derived from other species. A monoclonal antibody (mAb) to an antigen-of-interest can be prepared by using any technique known in the art which provides for the production of antibody molecules by continuous cell lines in culture. These include, but are not limited to, the hybridoma technique, the human B cell hybridoma technique, and the EBV-hybridoma technique. Such antibodies may be of any immunoglobulin class including IgG, IgM, IgE, IgA, and IgD and any subclass thereof. The hybridoma producing the mAbs of use in this disclosure may be cultivated in vitro or in vivo.

The skilled person would understand how to provide an appropriate binding moiety for use in a conjugate depending on the intended therapeutic use. This is described, for example, in Nature Reviews Drug Discovery volume 22, pages 641-661 (2023), which is incorporated by reference in its entirety. In particular, an antibody, antibody fragment or an antibody-binding fragment used as a binding moiety must be capable of targeting a particular cell surface marker or receptor associated with the disorder to be treated. For example, the antibody trastuzumab can be employed if the desired target is HER2.

In some embodiments, the binding moiety is capable of binding to an antigen selected from α4β7, CD3, CD4, CD20, OX40, CD28, PD-1, ICOS, BCMA/TACl, CD52, CD30, CD19, CCR8, CD79b, CD22, CD4, CD7 and CD38 or combinations thereof.

In some embodiments, the binding moiety comprises an antibody selected from Vedolizumab, Etrolizumab, Teplizumab, Zanolimumab, Rituximab, Ublituximab, Ofatumumab, Ocrelizumab, Inebilizumab, Rocatinlimab, Nivolumab, Pembrolizumab, Alemtuzumab, Brentuximab vedotin, Tafasitamab, Loncastuximab, Mogamulizumab, Polatuzumab, Inotuzumab, Epratuzumab, Isatuximab and Daratumumab.

In some embodiments, the disclosure provides a method of treating ulcerative colitis (UC), Crohn's disease (CD), human immunodeficiency virus (HIV)/acquired immunodeficiency syndrome (AIDS), immune-mediated colitis (PhI open label), type 1 diabetes (T1D), pouchitis, graft-versus-host disease (GvHD), Celiac disease, rheumatoid arthritis (RA), psoriasis (PsO), late onset rejection, Pemphigus vulgaris, cutaneous lupus erythematosus (CLE), systemic sclerosis (SSc), Grave's disease, relapse-remitting/primary progressive multiple sclerosis (RR/PP MS), lupus nephritis, systemic lupus erythematosus (SLE), thrombotic thrombocytopenic purpura, nephrotic syndrome; idiopathic thrombocytopenic purpura, microscopic polyangiitis, atopic dermatitis (AD), transplant rejection, juvenile idiopathic arthritis, multiple sclerosis (MS), chronic lymphocytic leukemia (CLL), T-cell prolymphocytic leukemia, precursor cell lymphoblastic leukemia-lymphoma, Anaplastic large cell lymphoma; Hodgkin's disease; Mycosis fungoides; Peripheral T-cell lymphoma; Primary cutaneous anaplastic large cell lymphoma; T-cell lymphoma, adult T-cell leukemia-lymphoma; diffuse scleroderma; Germ cell cancer; malignant-mesothelioma; mastocytosis; non-Hodgkin's lymphoma; Sezary syndrome; Solid tumors, HIV-1 infections, Chronic lymphocytic leukemia; Follicular lymphoma; Granulomatosis with polyangiitis; idiopathic thrombocytopenic purpura; lymphoproliferative disorders; microscopic polyangiitis; marginal zone B-cell lymphoma, relapsed-refractory diffuse large B cell lymphoma (R/R DLBCL), B-cell lymphoma, precursor B-cell lymphoblastic leukemia-lymphoma, precursor cell lymphoblastic leukemia-lymphoma, mantle cell lymphoma, Waldenstrom's macroglobulinemia, cutaneous T-cell lymphoma; Richter's syndrome, relapsed/refractory acute lymphoblastic leukemia (R/R-ALL), precursor cell lymphoblastic leukemia-lymphoma, precursor B-cell lymphoblastic leukemia-lymphoma, chronic myelogenous leukemia (CML), cutaneous and peripheral T lymphoma, acute biphenotypic leukemia; Burkitt's lymphoma, T-cell acute lymphoblastic leukemia (T-ALL), relapsed/refractory multiple myeloma (R/R MM), melanoma, acute myeloid leukemia; chronic lymphocytic leukemia; Myelodysplastic syndromes; Plasmablastic lymphoma; precursor T-cell lymphoblastic leukemia-lymphoma; amyloid light-chain amyloidosis, multiple myeloma (M) and solid tumors in a subject in need thereof, wherein the method comprises administering the antibody-drug conjugate to the subject.

Exemplary combinations of antibodies, target antigens, and associated therapeutic indications are listed in the table below. In some embodiments, the binding moiety of the antibody-drug conjugate comprises an antibody listed in the table below and targets an antigen listed in the table below. In some aspects, the disclosure provides a method of treating a disorder listed in the table below, the method comprising administering to a subject in need thereof an antibody-drug conjugate comprising an antibody listed in the table below.

| Target | Indication | Commercial |
|---|---|---|
| α4β7 | Ulcerative colitis (UC), Crohn's disease (CD), human immunodeficiency virus/acquired immunodeficiency syndrome (HIV/AIDS), immune-mediated colitis (PhI open label), type 1 diabetes (T1D), pouchitis, graft-versus-host disease (GvHD), Celiac disease | Vedolizumab, Etrolizumab |
| CD3 | Type-1 diabetes (T1D) | Teplizumab |
| CD4 | Rheumatoid arthritis (RA), psoriasis (PsO), late onset transplant rejection | Zanolimumab |
| CD20 | Pemphigus vulgaris, cutaneous lupus erythematosus (CLE), systemic sclerosis (SSc), Grave's disease, relapse-remitting/primary-progressive multiple sclerosis (RR/PP MS), lupus nephritis, systemic lupus erythematosus (SLE), rheumatoid arthritis (RA), thrombotic thrombocytopenic purpura, nephrotic syndrome; idiopathic thrombocytopenic purpura, microscopic polyangiitis | Rituximab, Ublituximab, Ofatumumab, Ocrelizumab, Inebilizumab |
| OX40 | Atopic dermatitis (AD) | Rocatinlimab |
| CD28 | Transplant rejection, rheumatoid arthritis (RA), juvenile idiopathic arthritis | |
| PD-1 | Autoimmune/inflammatory disorders | Nivolumab, Pembrolizumab |
| ICOS | Autoimmune/inflammatory disorders | |
| BCMA/TACI | Autoimmune/inflammatory disorders | |
| CD52 | Multiple sclerosis (MS), chronic lymphocytic leukemia (CLL), T-cell prolymphocytic leukemia, precursor cell lymphoblastic leukemia-lymphoma | Alemtuzumab |
| CD30 | Anaplastic large cell lymphoma; Hodgkin's disease; mycosis fungoides; peripheral T-cell lymphoma; primary cutaneous anaplastic large cell lymphoma; T-cell lymphoma, diffuse large B cell lymphoma (DLBCL), adult T-cell leukemia-lymphoma; diffuse scleroderma; germ cell cancer; malignant-mesothelioma; Masto cytosis; non-Hodgkin's lymphoma; Sezary syndrome; Solid tumors, HIV-1 infections | Brentuximab vedotin |
| CD20 | Chronic lymphocytic leukemia; diffuse large B cell lymphoma; follicular lymphoma; granulomatosis with polyangiitis; idiopathic thrombocytopenic purpura; lymphoproliferative disorders; microscopic polyangiitis; non-Hodgkin's lymphoma, marginal zone B-cell lymphoma | Rituximab, Ublituximab, Ofatumumab, Ocrelizumab, Inebilizumab |

| Target | Indication | Commercial |
|---|---|---|
| CD19 | Relapsed-refractory diffuse large B cell lymphoma (R/R DLBCL), follicular lymphoma (FL), marginal zone B-cell lymphoma, B-cell lymphoma, chronic lymphocytic leukemia (CLL), non-Hodgkin lymphoma (NHL), precursor B-cell lymphoblastic leukemia-lymphoma, precursor cell lymphoblastic leukemia-lymphoma, mantle cell lymphoma, Waldenstrom's macroglobulinemia | Tafasitamab, Loncastuximab |
| CCR8 | Adult T-cell leukemia-lymphoma; Cutaneous T-cell lymphoma; mycosis fungoides; peripheral T-cell lymphoma; Sezary's syndrome | Mogamulizumab |
| CD79b | Diffuse large B cell lymphoma (DLBCL), non-Hodgkin lymphoma (NHL), follicular lymphoma, chronic lymphocytic leukemia (CLL), non-Hodgkin lymphoma (NHL), Richter's syndrome | Polatuzumab |
| CD22 | Relapsed/refractory acute lymphoblastic leukemia (R/R-ALL), precursor cell lymphoblastic leukemia-lymphoma, Precursor B-cell lymphoblastic leukemia-lymphoma, chronic myelogenous leukemia (CML), non-Hodgkin's lymphoma (NHL) | Inotuzumab, Epratuzumab |
| CD4 | Cutaneous and peripheral T lymphoma, acute biphenotypic leukemia; Burkitt's lymphoma | |
| CD7 | T-cell acute lymphoblastic leukemia (T-ALL) | |
| CD38 | Relapsed/refractory multiple myeloma (R/R MM), melanoma, acute myeloid leukemia; Chronic lymphocytic leukemia; diffuse large B cell lymphoma (DLBCL); follicular lymphoma; mantle-cell lymphoma; Myelodysplastic syndromes; plasmablastic lymphoma; precursor B-cell lymphoblastic leukemia-lymphoma; precursor T-cell lymphoblastic leukemia-lymphoma; T-cell lymphoma; Waldenstrom's macroglobulinemia, amyloid light-chain amyloidosis, multiple myeloma (MM), solid tumors | Isatuximab, Daratumumab |

In some embodiments, I is one of Compounds 101-510.

In some embodiments, the disclosure provides an antibody-drug conjugate or pharmaceutically acceptable salt thereof according to Formula (A1):

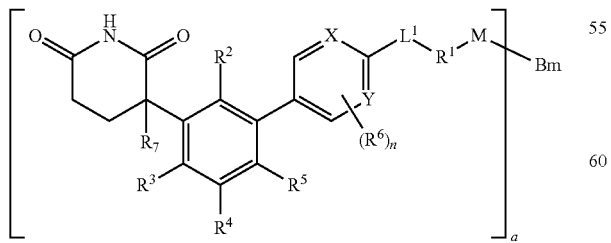

Formula (A1)

in which X, Y, $R^1$, $R^2$, $R^3$, $R^4$, $R^5$, $R^6$, $R^7$, $L^1$, and n can be as defined anywhere here, M is a linker moiety and Bm is a binding moiety that is capable of specifically binding to a protein, as defined above. In some embodiments, X, Y, $R^1$, $R^2$, $R^3$, $R^4$, $R^5$, $R^6$, $R^7$, $L^1$, and n are defined to provide a compound selected from any one of Compounds 101-510.

In some embodiments, the disclosure provides an antibody-drug conjugate or pharmaceutically acceptable salt thereof according to Formula (A2) or (A3).

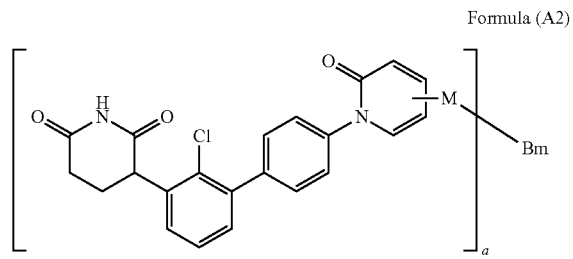

Formula (A2)

-continued

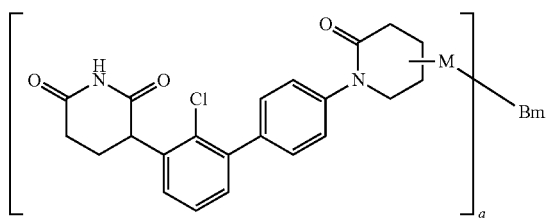

Formula (A3)

In some embodiments, the disclosure provides an antibody-drug conjugate or pharmaceutically acceptable salt thereof according to Formula (A4):

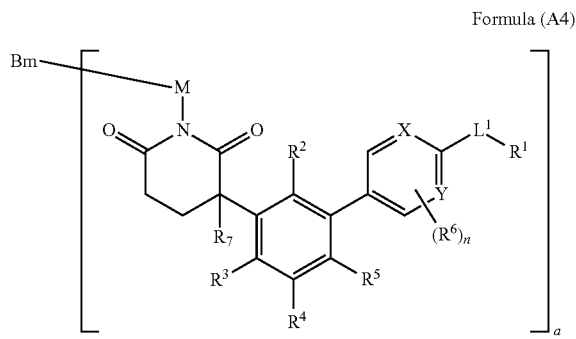

Formula (A4)

in which X, Y, $R^1$, $R^2$, $R^3$, $R^4$, $R^5$, $R^6$, $R^7$, $L^1$, and n can be as defined anywhere here, M is a linker moiety and Bm is a binding moiety that is capable of specifically binding to a protein, as defined above. In some embodiments, X, Y, $R^1$, $R^2$, $R^3$, $R^4$, $R^5$, $R^6$, $R^7$, $L^1$, and n are defined to provide a compound selected from any one of Compounds 101-510.

In some embodiments, the disclosure provides an antibody-drug conjugate or pharmaceutically acceptable salt thereof according to Formula (A5) or (A6).

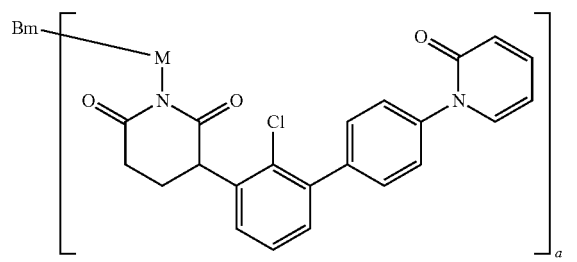

Formula (A5)

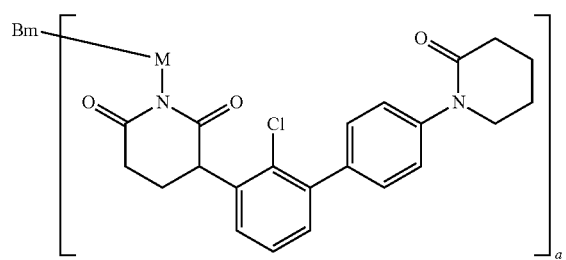

Formula (A6)

The antibody-drug conjugate may be administered as part of a pharmaceutical composition. The pharmaceutical composition may include excipients such as those recited herein.

Non-Limiting Exemplary Compounds

In some embodiments, the compound is selected from the group consisting of the compounds delineated in Table C1 or a pharmaceutically acceptable salt thereof.

Unless otherwise indicated, the symbol * at a chiral center denotes that this chiral center has been resolved (i.e., is a single epimer) and the absolute stereochemistry at that center has not been determined.

TABLE C1

| Compound No. | Structure |
|---|---|
| 101 | 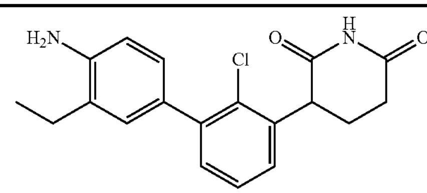 |
| 102 | 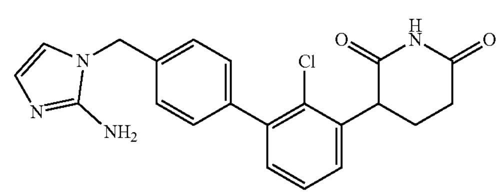 [SMILES: Nc1nccn1Cc1ccc(-c2cccc(C3CCC(=O)NC3=O)c2Cl)cc1] |
| 103 | 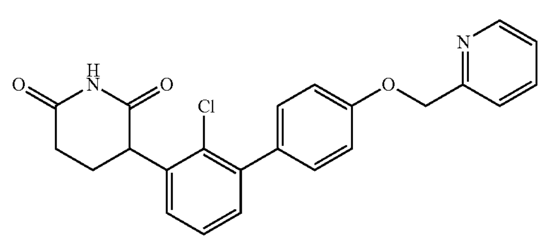 [SMILES: O=C1CCC(c2cccc(-c3ccc(OCc4ccccn4)cc3)c2Cl)C(=O)N1] |

TABLE C1-continued

| Compound No. | Structure |
| --- | --- |
| 104 | 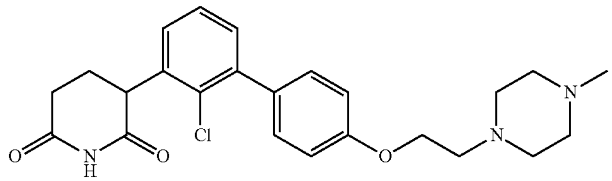 [SMILES: CN1CCN(CCOc2ccc(-c3cccc(C4CCC(=O)NC4=O)c3Cl)cc2)CC1] |
| 105 | 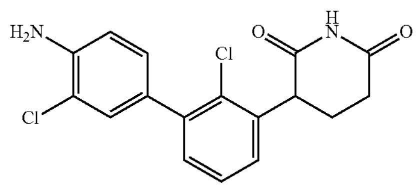 [SMILES: Nc1ccc(-c2cccc(C3CCC(=O)NC3=O)c2Cl)cc1Cl] |
| 106 | 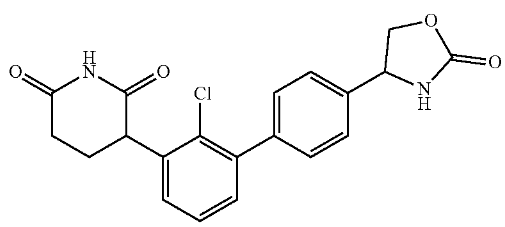 [SMILES: O=C1CCC(c2cccc(-c3ccc(C4COC(=O)N4)cc3)c2Cl)C(=O)N1] |
| 107 | 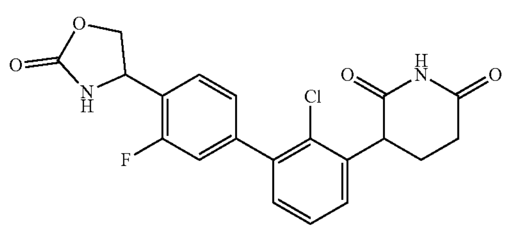 [SMILES: O=C1CCC(c2cccc(-c3ccc(C4COC(=O)N4)c(F)c3)c2Cl)C(=O)N1] |
| 108 | 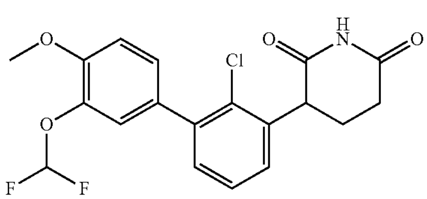 [SMILES: COc1ccc(-c2cccc(C3CCC(=O)NC3=O)c2Cl)cc1OC(F)F] |
| 109 | 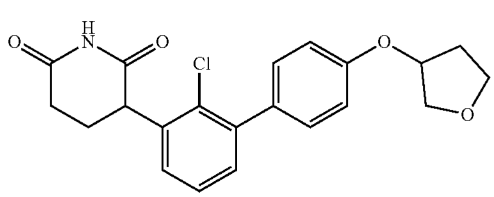 [SMILES: O=C1CCC(c2cccc(-c3ccc(OC4CCOC4)cc3)c2Cl)C(=O)N1] |
| 110 | 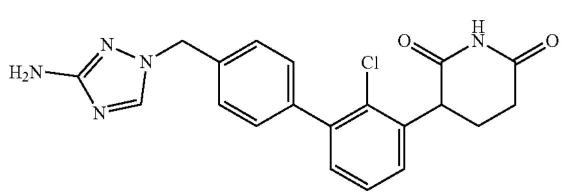 [SMILES: Nc1ncn(Cc2ccc(-c3cccc(C4CCC(=O)NC4=O)c3Cl)cc2)n1] |

TABLE C1-continued

| Compound No. | Structure |
| --- | --- |
| 111 | 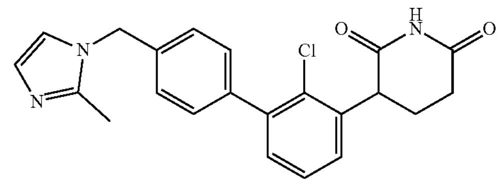 [SMILES: Cc1nccn1Cc1ccc(-c2cccc(C3CCC(=O)NC3=O)c2Cl)cc1] |
| 112 | 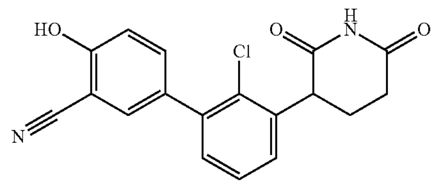 [SMILES: N#Cc1cc(-c2cccc(C3CCC(=O)NC3=O)c2Cl)ccc1O] |
| 113 | 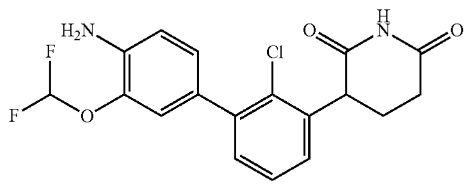 [SMILES: Nc1ccc(-c2cccc(C3CCC(=O)NC3=O)c2Cl)cc1OC(F)F] |
| 115 | 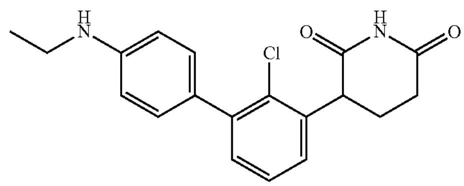 [SMILES: CCNc1ccc(-c2cccc(C3CCC(=O)NC3=O)c2Cl)cc1] |
| 116 | 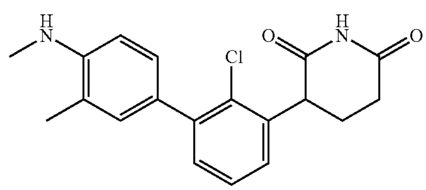 [SMILES: CNc1ccc(-c2cccc(C3CCC(=O)NC3=O)c2Cl)cc1C] |
| 117 | 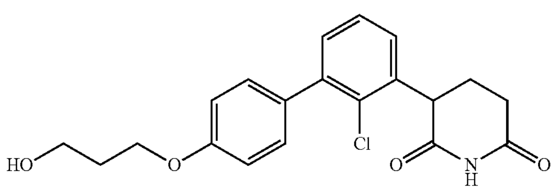 [SMILES: O=C1CCC(c2cccc(-c3ccc(OCCCO)cc3)c2Cl)C(=O)N1] |
| 118 | 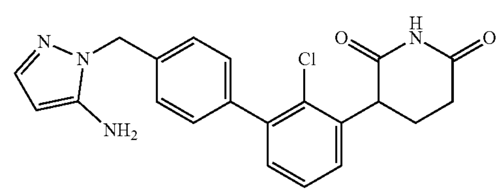 [SMILES: Nc1ccnn1Cc1ccc(-c2cccc(C3CCC(=O)NC3=O)c2Cl)cc1] |
| 119 | 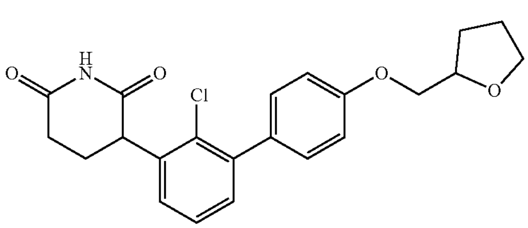 [SMILES: O=C1CCC(c2cccc(-c3ccc(OCC4CCCO4)cc3)c2Cl)C(=O)N1] |

TABLE C1-continued

| Compound No. | Structure |
|---|---|
| 120 | 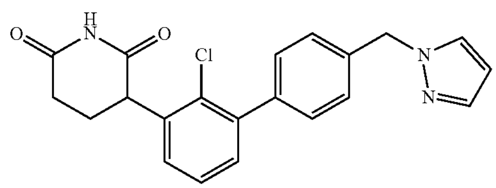 [SMILES: O=C1CCC(c2cccc(-c3ccc(Cn4cccn4)cc3)c2Cl)C(=O)N1] |
| 121 | 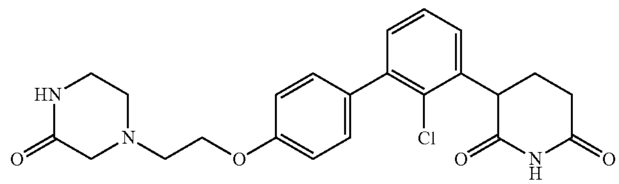 [SMILES: O=C1CN(CCOc2ccc(-c3cccc(C4CCC(=O)NC4=O)c3Cl)cc2)CCN1] |
| 122 | 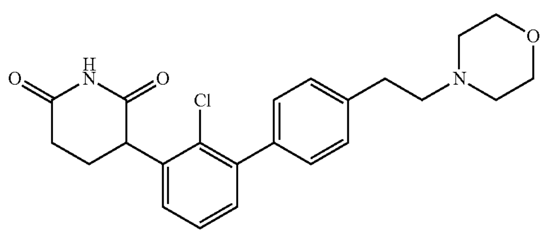 [SMILES: O=C1CCC(c2cccc(-c3ccc(CCN4CCOCC4)cc3)c2Cl)C(=O)N1] |
| 123 | 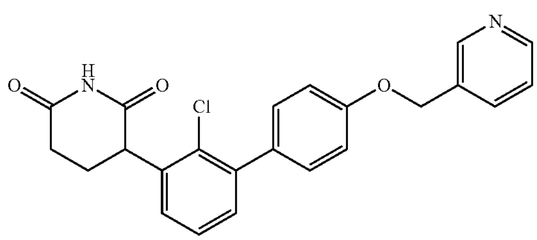 [SMILES: O=C1CCC(c2cccc(-c3ccc(OCc4cccnc4)cc3)c2Cl)C(=O)N1] |
| 124 | 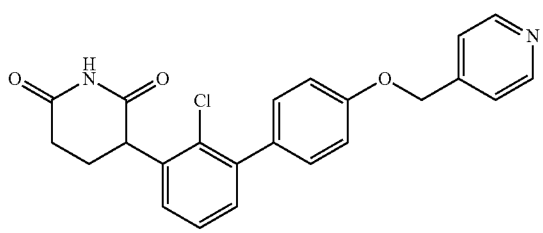 [SMILES: O=C1CCC(c2cccc(-c3ccc(OCc4ccncc4)cc3)c2Cl)C(=O)N1] |
| 125 | 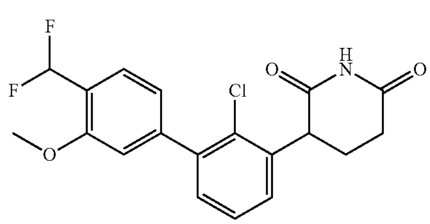 [SMILES: COc1cc(-c2cccc(C3CCC(=O)NC3=O)c2Cl)ccc1C(F)F] |
| 126 | 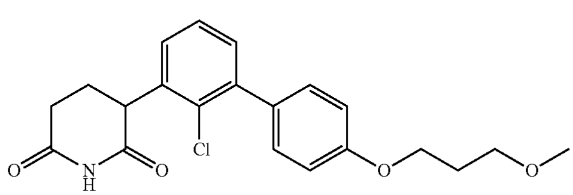 [SMILES: COCCCOc1ccc(-c2cccc(C3CCC(=O)NC3=O)c2Cl)cc1] |

TABLE C1-continued

| Compound No. | Structure |
|---|---|
| 127 | (3,5-dimethyl-1H-pyrazol-1-yl)methyl-substituted biphenyl-chloro-glutarimide |
| 128 | 4'-acetamido-biphenyl-chloro-glutarimide |
| 129 | 4'-(isopropylamino)-biphenyl-chloro-glutarimide |
| 130 | 4'-amino-biphenyl-chloro-glutarimide |
| 131 | 4'-amino-3'-methyl-biphenyl-chloro-glutarimide |
| 132 | 3'-methoxy-4'-methyl-biphenyl-chloro-glutarimide |
| 133 | 3'-amino-4'-cyano-biphenyl-chloro-glutarimide |
| 134 | 4'-(methylamino)-biphenyl-chloro-glutarimide |

TABLE C1-continued

| Compound No. | Structure |
| --- | --- |
| 135 | 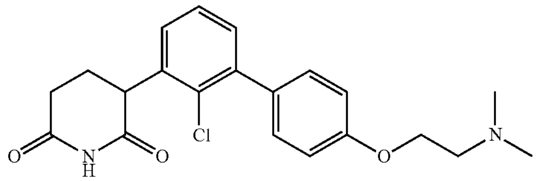 [SMILES: CN(C)CCOc1ccc(-c2cccc(C3CCC(=O)NC3=O)c2Cl)cc1] |
| 136 | 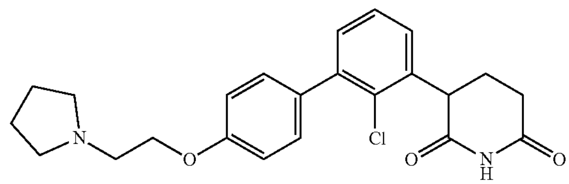 [SMILES: O=C1CCC(c2cccc(-c3ccc(OCCN4CCCC4)cc3)c2Cl)C(=O)N1] |
| 137 | 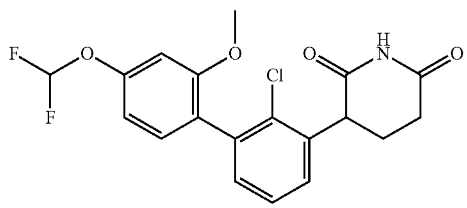 [SMILES: COc1cc(OC(F)F)ccc1-c1cccc(C2CCC(=O)NC2=O)c1Cl] |
| 138 | 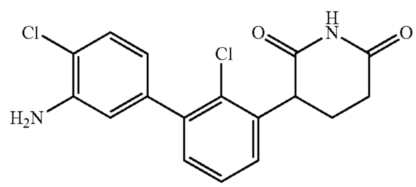 [SMILES: Nc1cc(-c2cccc(C3CCC(=O)NC3=O)c2Cl)ccc1Cl] |
| 139 | 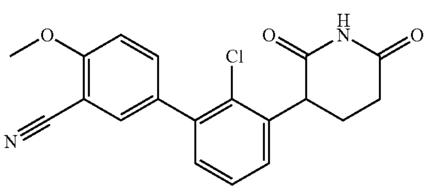 [SMILES: COc1ccc(-c2cccc(C3CCC(=O)NC3=O)c2Cl)cc1C#N] |
| 140 | 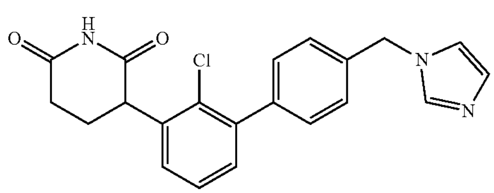 [SMILES: O=C1CCC(c2cccc(-c3ccc(Cn4ccnc4)cc3)c2Cl)C(=O)N1] |
| 141 | 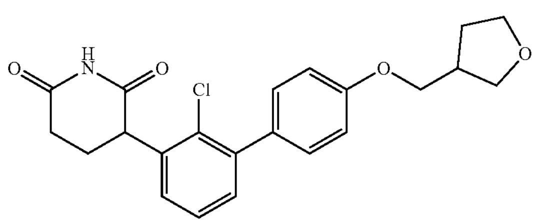 [SMILES: O=C1CCC(c2cccc(-c3ccc(OCC4CCOC4)cc3)c2Cl)C(=O)N1] |
| 142 | 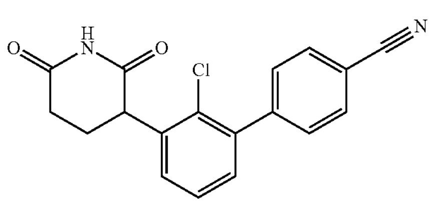 [SMILES: N#Cc1ccc(-c2cccc(C3CCC(=O)NC3=O)c2Cl)cc1] |

TABLE C1-continued

| Compound No. | Structure |
|---|---|
| 143 | 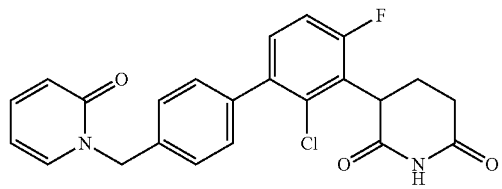 [SMILES: O=C1CCC(c2c(F)ccc(-c3ccc(Cn4ccccc4=O)cc3)c2Cl)C(=O)N1] |
| 144 | 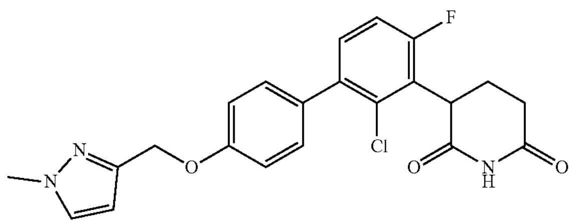 [SMILES: Cn1ccc(COc2ccc(-c3ccc(F)c(C4CCC(=O)NC4=O)c3Cl)cc2)n1] |
| 145 | 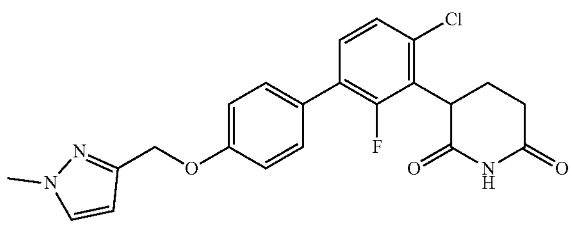 [SMILES: Cn1ccc(COc2ccc(-c3ccc(Cl)c(C4CCC(=O)NC4=O)c3F)cc2)n1] |
| 146 | 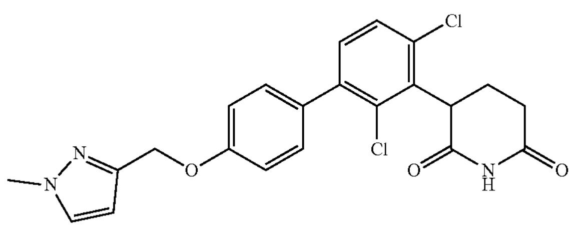 [SMILES: Cn1ccc(COc2ccc(-c3ccc(Cl)c(C4CCC(=O)NC4=O)c3Cl)cc2)n1] |
| 147 | 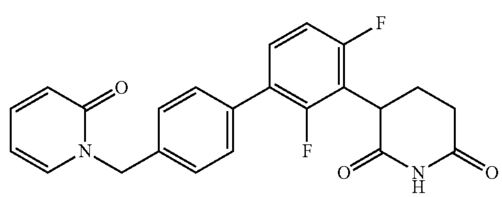 [SMILES: O=C1CCC(c2c(F)ccc(-c3ccc(Cn4ccccc4=O)cc3)c2F)C(=O)N1] |
| 148 | 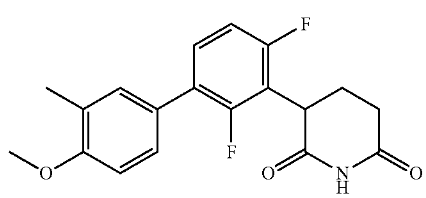 [SMILES: COc1ccc(-c2ccc(F)c(C3CCC(=O)NC3=O)c2F)cc1C] |
| 149 | 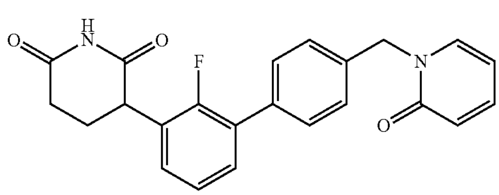 [SMILES: O=C1CCC(c2cccc(-c3ccc(Cn4ccccc4=O)cc3)c2F)C(=O)N1] |

TABLE C1-continued

| Compound No. | Structure |
| --- | --- |
| 150 | 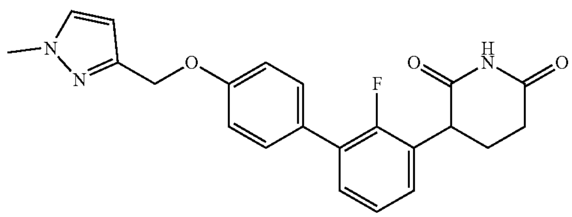 [SMILES: Cn1ccc(COc2ccc(-c3cccc(C4CCC(=O)NC4=O)c3F)cc2)n1] |
| 151 | 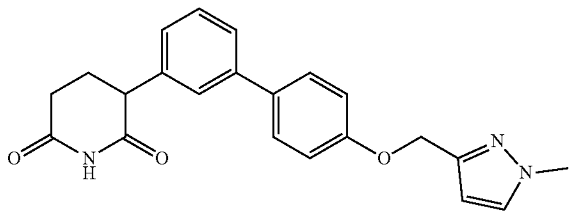 [SMILES: Cn1ccc(COc2ccc(-c3cccc(C4CCC(=O)NC4=O)c3)cc2)n1] |
| 152 | 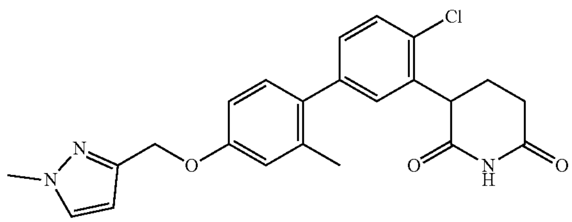 [SMILES: Cc1cc(OCc2ccn(C)n2)ccc1-c1ccc(Cl)c(C2CCC(=O)NC2=O)c1] |
| 153 | 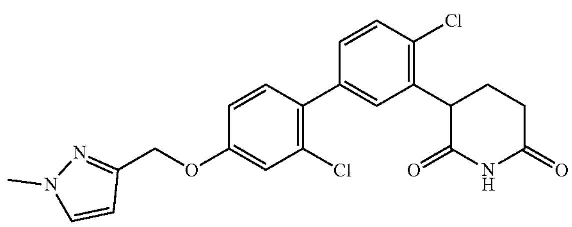 [SMILES: Cn1ccc(COc2ccc(-c3ccc(Cl)c(C4CCC(=O)NC4=O)c3)c(Cl)c2)n1] |
| 154 | 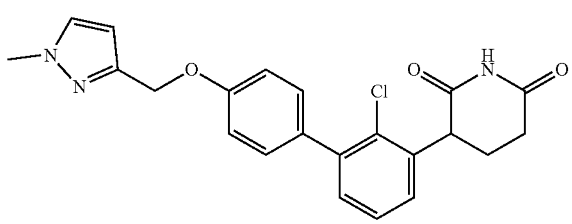 [SMILES: Cn1ccc(COc2ccc(-c3cccc(C4CCC(=O)NC4=O)c3Cl)cc2)n1] |
| 155 | 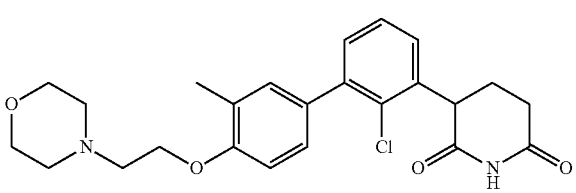 [SMILES: Cc1cc(-c2cccc(C3CCC(=O)NC3=O)c2Cl)ccc1OCCN1CCOCC1] |
| 156 | 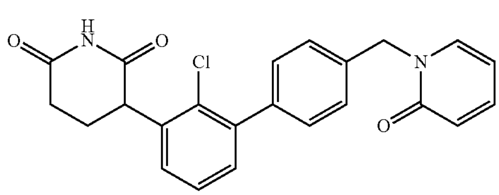 [SMILES: O=C1CCC(c2cccc(-c3ccc(Cn4ccccc4=O)cc3)c2Cl)C(=O)N1] |

TABLE C1-continued
| Compound No. | Structure |
|---|---|
| 157 | 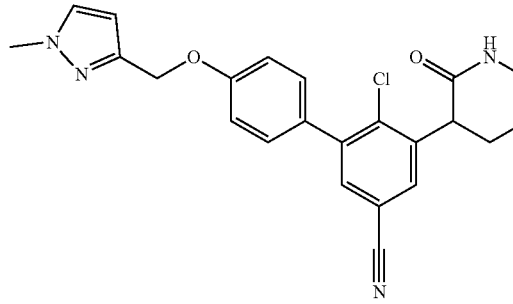 |
| 158 | 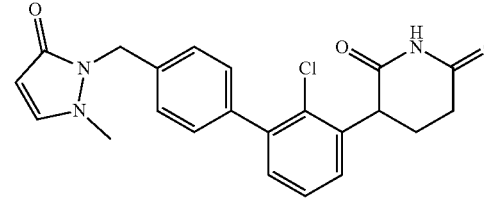 |
| 159 | 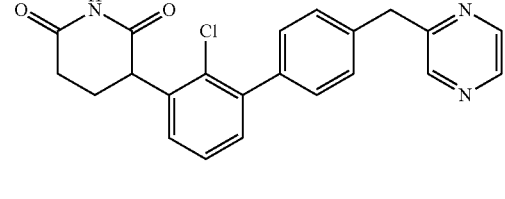 |
| 160 | 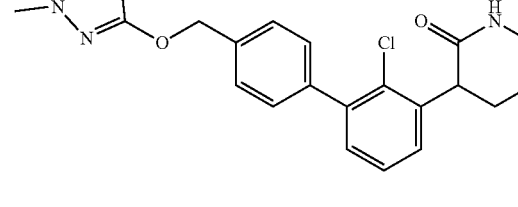 |
| 161 | 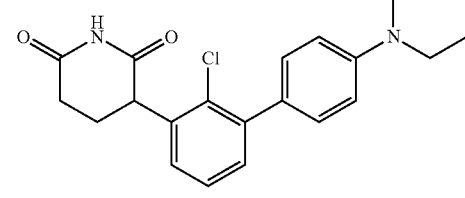 |
| 162 | 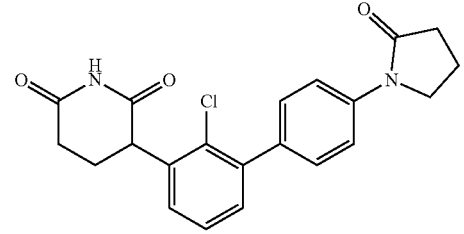 [SMILES: O=C1CCC(c2cccc(-c3ccc(N4CCCC4=O)cc3)c2Cl)C(=O)N1] |

TABLE C1-continued

| Compound No. | Structure |
| --- | --- |
| 163 | 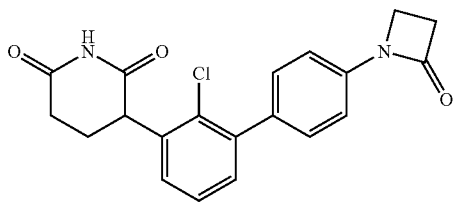 [SMILES: O=C1CCC(c2cccc(-c3ccc(N4CCC4=O)cc3)c2Cl)C(=O)N1] |
| 164 | 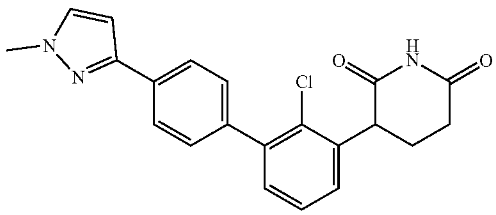 [SMILES: Cn1ccc(-c2ccc(-c3cccc(C4CCC(=O)NC4=O)c3Cl)cc2)n1] |
| 165 | 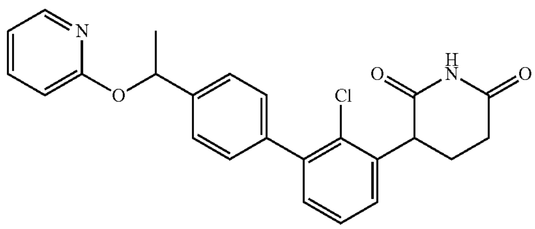 [SMILES: CC(Oc1ccccn1)c1ccc(-c2cccc(C3CCC(=O)NC3=O)c2Cl)cc1] |
| 166 | 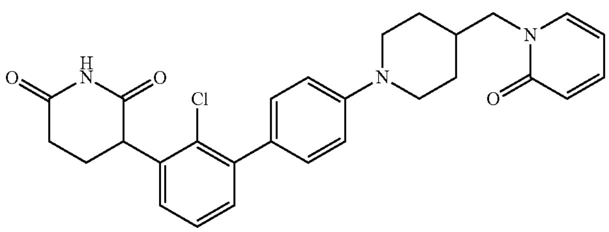 [SMILES: O=C1CCC(c2cccc(-c3ccc(N4CCC(Cn5ccccc5=O)CC4)cc3)c2Cl)C(=O)N1] |
| 167 | 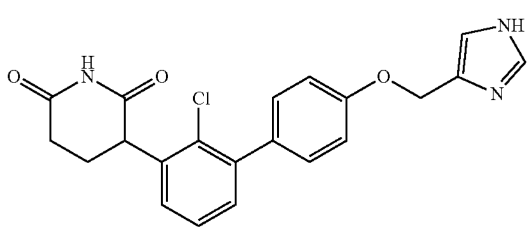 [SMILES: O=C1CCC(c2cccc(-c3ccc(OCc4c[nH]cn4)cc3)c2Cl)C(=O)N1] |
| 168 | 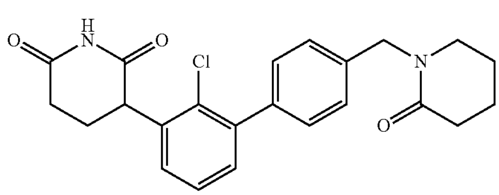 [SMILES: O=C1CCC(c2cccc(-c3ccc(CN4CCCCC4=O)cc3)c2Cl)C(=O)N1] |
| 169 | 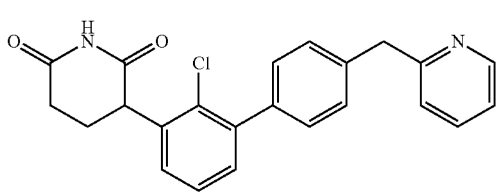 [SMILES: O=C1CCC(c2cccc(-c3ccc(Cc4ccccn4)cc3)c2Cl)C(=O)N1] |

TABLE C1-continued
| Compound No. | Structure |
|---|---|
| 170 | 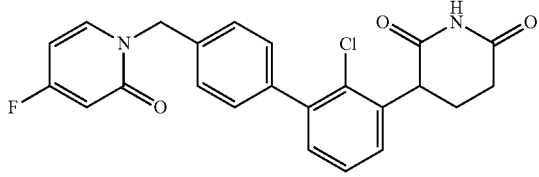 |
| 171 | 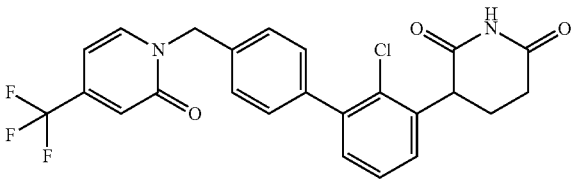 [SMILES: O=C1CCC(c2cccc(-c3ccc(Cn4ccc(C(F)(F)F)cc4=O)cc3)c2Cl)C(=O)N1] |
| 172 | 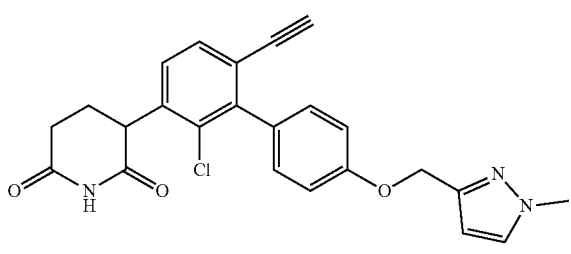 [SMILES: C#Cc1ccc(C2CCC(=O)NC2=O)c(Cl)c1-c1ccc(OCc2ccn(C)n2)cc1] |
| 173 | 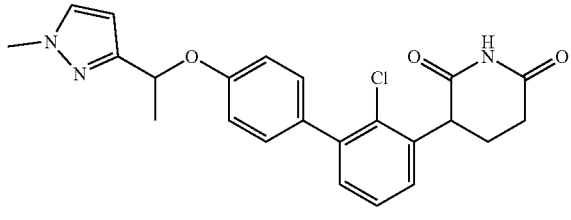 [SMILES: CC(Oc1ccc(-c2cccc(C3CCC(=O)NC3=O)c2Cl)cc1)c1ccn(C)n1] |
| 174 | 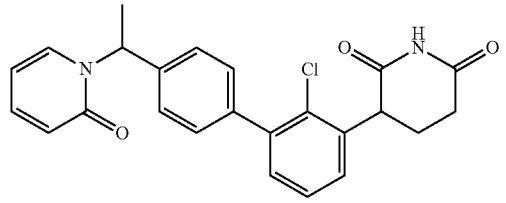 [SMILES: CC(c1ccc(-c2cccc(C3CCC(=O)NC3=O)c2Cl)cc1)n1ccccc1=O] |
| 175 | 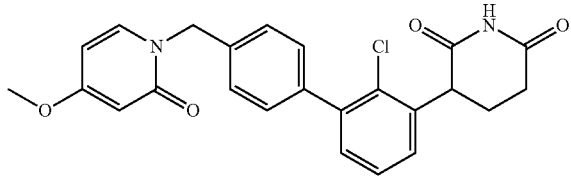 [SMILES: COc1ccn(Cc2ccc(-c3cccc(C4CCC(=O)NC4=O)c3Cl)cc2)c(=O)c1] |
| 176 | 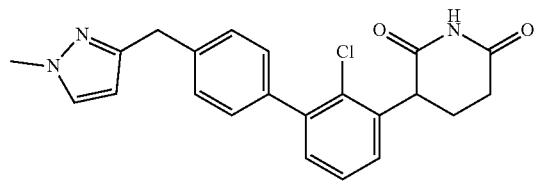 [SMILES: Cn1ccc(Cc2ccc(-c3cccc(C4CCC(=O)NC4=O)c3Cl)cc2)n1] |

TABLE C1-continued
| Compound No. | Structure |
|---|---|
| 177 | 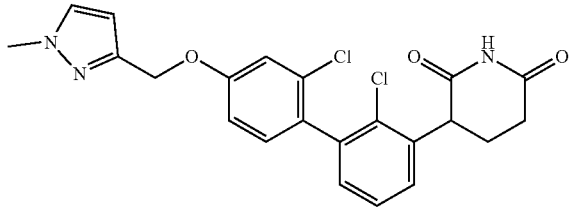 [SMILES: Cn1ccc(COc2ccc(-c3cccc(C4CCC(=O)NC4=O)c3Cl)c(Cl)c2)n1] |
| 178 | 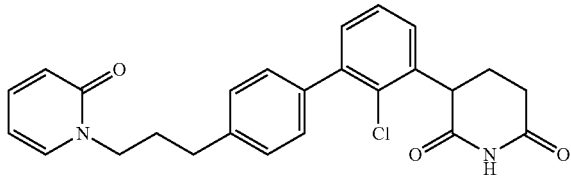 [SMILES: O=C1CCC(c2cccc(-c3ccc(CCCn4ccccc4=O)cc3)c2Cl)C(=O)N1] |
| 179 | 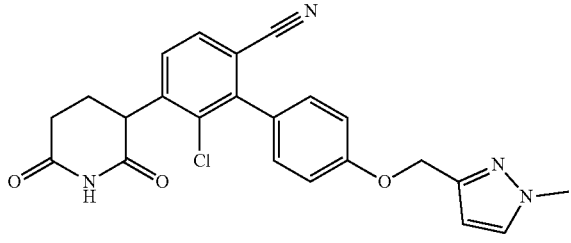 [SMILES: Cn1ccc(COc2ccc(-c3c(C#N)ccc(C4CCC(=O)NC4=O)c3Cl)cc2)n1] |
| 180 | 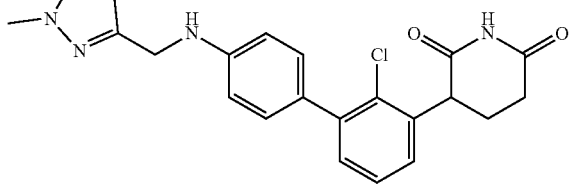 |
| 181 | 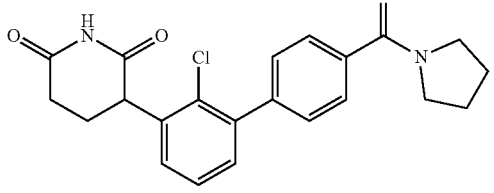 |
| 182 | 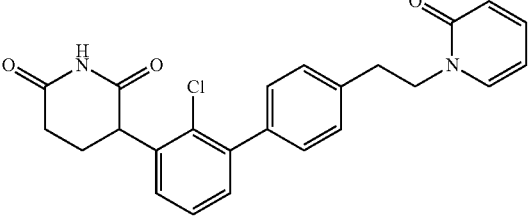 |
| 183 | 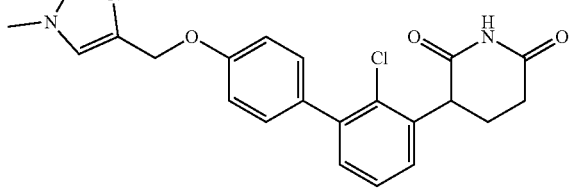 |

TABLE C1-continued

| Compound No. | Structure |
| --- | --- |
| 184 | 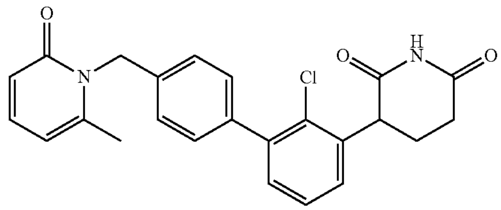 [SMILES: Cc1cccc(=O)n1Cc1ccc(-c2cccc(C3CCC(=O)NC3=O)c2Cl)cc1] |
| 185 | 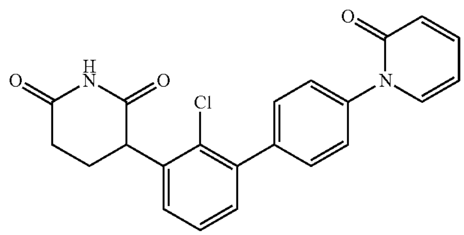 [SMILES: O=C1CCC(c2cccc(-c3ccc(-n4ccccc4=O)cc3)c2Cl)C(=O)N1] |
| 186 | 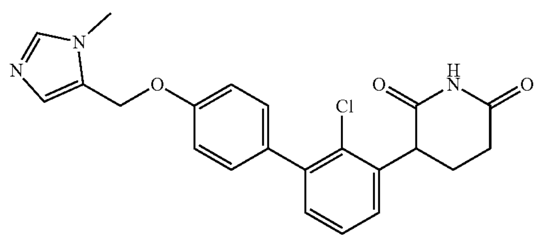 [SMILES: Cn1cncc1COc1ccc(-c2cccc(C3CCC(=O)NC3=O)c2Cl)cc1] |
| 187 | 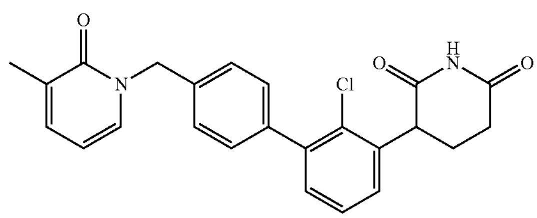 [SMILES: Cc1cccn(Cc2ccc(-c3cccc(C4CCC(=O)NC4=O)c3Cl)cc2)c1=O] |
| 188 | 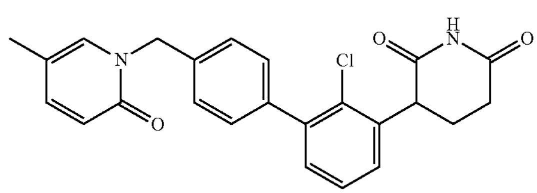 [SMILES: Cc1ccc(=O)n(Cc2ccc(-c3cccc(C4CCC(=O)NC4=O)c3Cl)cc2)c1] |
| 189 | 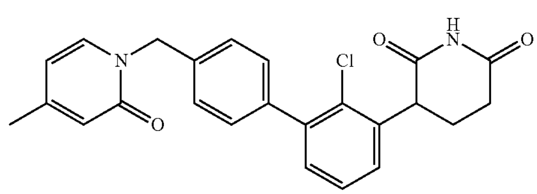 [SMILES: Cc1ccn(Cc2ccc(-c3cccc(C4CCC(=O)NC4=O)c3Cl)cc2)c(=O)c1] |
| 190 | 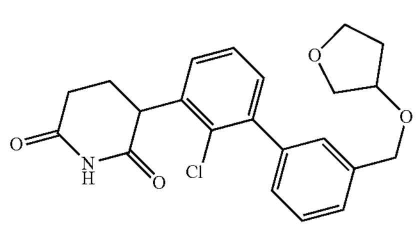 [SMILES: O=C1CCC(c2cccc(-c3cccc(COC4CCOC4)c3)c2Cl)C(=O)N1] |

TABLE C1-continued

| Compound No. | Structure |
| --- | --- |
| 191 | 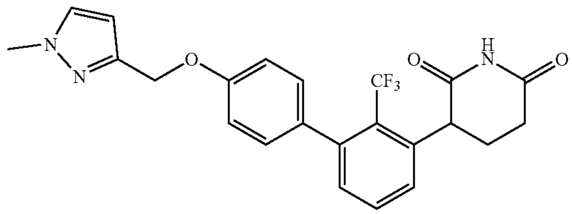 [SMILES: Cn1ccc(COc2ccc(-c3cccc(C4CCC(=O)NC4=O)c3C(F)(F)F)cc2)n1] |
| 192 | 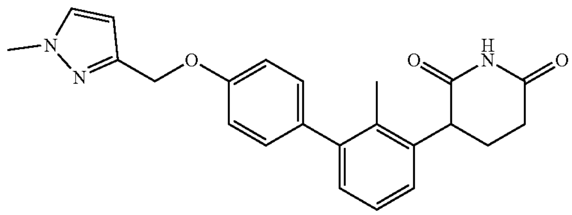 [SMILES: Cc1c(-c2ccc(OCc3ccn(C)n3)cc2)cccc1C1CCC(=O)NC1=O] |
| 193 | 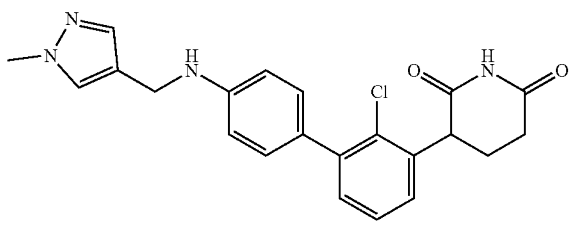 [SMILES: Cn1cc(CNc2ccc(-c3cccc(C4CCC(=O)NC4=O)c3Cl)cc2)cn1] |
| 194 | 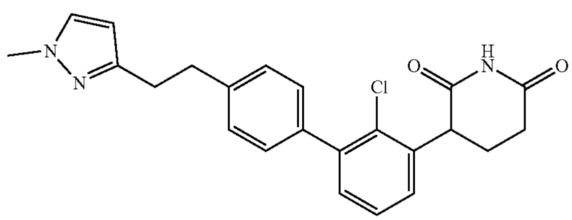 |
| 195 | 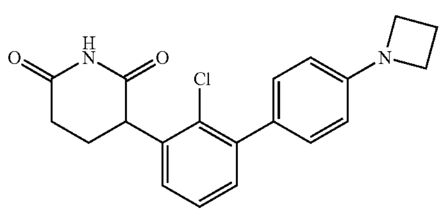 [SMILES: O=C1CCC(c2cccc(-c3ccc(N4CCC4)cc3)c2Cl)C(=O)N1] |
| 196 | 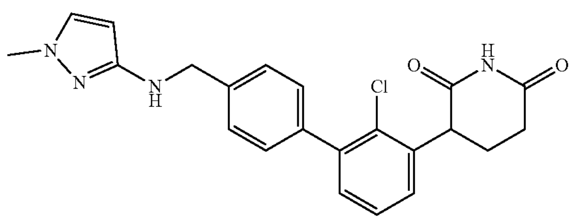 [SMILES: Cn1ccc(NCc2ccc(-c3cccc(C4CCC(=O)NC4=O)c3Cl)cc2)n1] |
| 197 | 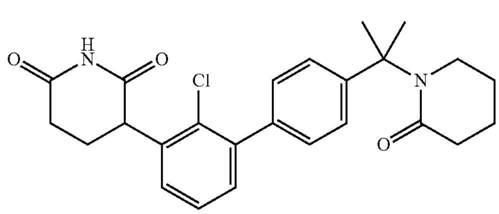 [SMILES: CC(C)(c1ccc(-c2cccc(C3CCC(=O)NC3=O)c2Cl)cc1)N1CCCCC1=O] |

TABLE C1-continued
| Compound No. | Structure |
|---|---|
| 198 | 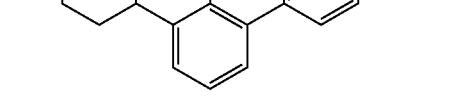 |
| 199 | 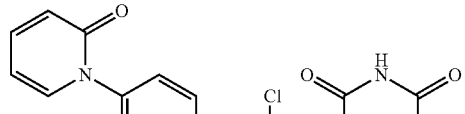 |
| 200 | 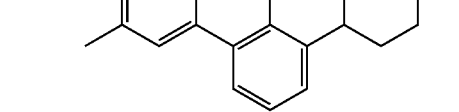 |
| 201 | 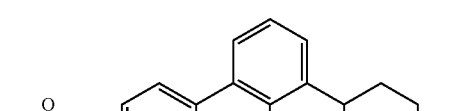 |
| 202 | 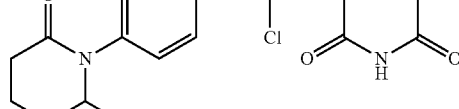 |
| 203 | 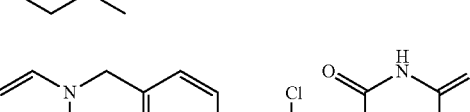 |
| 204 | 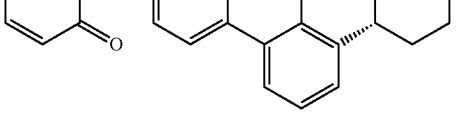 |

TABLE C1-continued

| Compound No. | Structure |
| --- | --- |
| 205 | 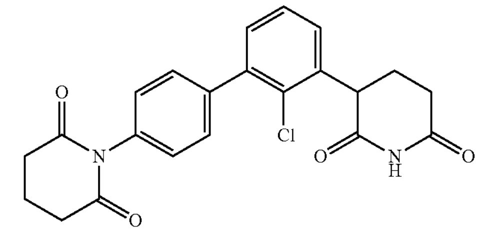 [SMILES: O=C1CCC(c2cccc(-c3ccc(N4C(=O)CCCC4=O)cc3)c2Cl)C(=O)N1] |
| 206 | 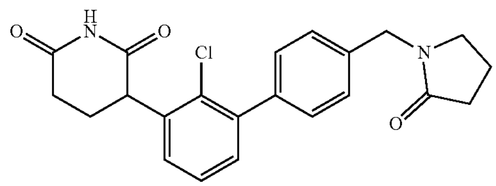 [SMILES: O=C1CCC(c2cccc(-c3ccc(CN4CCCC4=O)cc3)c2Cl)C(=O)N1] |
| 207 | 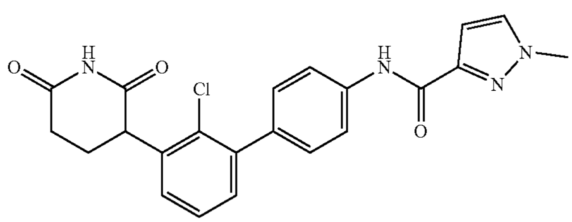 [SMILES: Cn1ccc(C(=O)Nc2ccc(-c3cccc(C4CCC(=O)NC4=O)c3Cl)cc2)n1] |
| 208 | 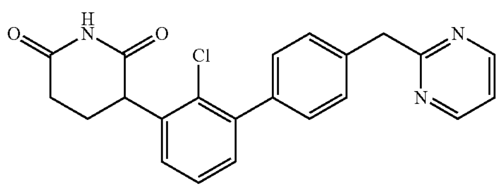 |
| 209 | 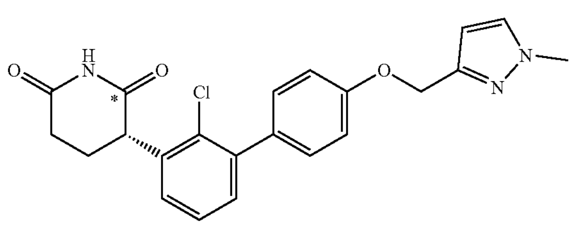 [SMILES: Cn1ccc(COc2ccc(-c3cccc([C@@H]4CCC(=O)NC4=O)c3Cl)cc2)n1] |
| 210 | 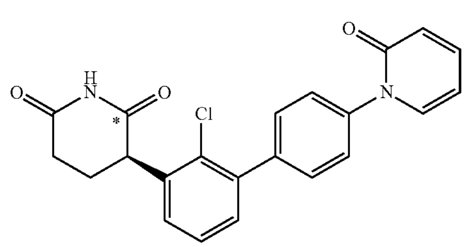 [SMILES: O=C1CC[C@H](c2cccc(-c3ccc(-n4ccccc4=O)cc3)c2Cl)C(=O)N1] |
| 211 | 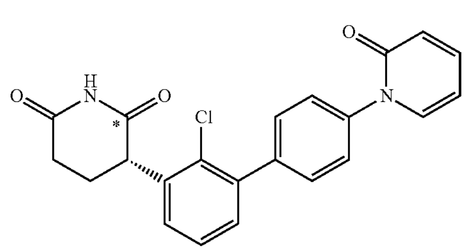 |

TABLE C1-continued

| Compound No. | Structure |
| --- | --- |
| 212 | 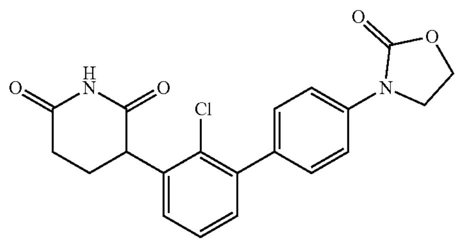 [SMILES: O=C1CCC(c2cccc(-c3ccc(N4CCOC4=O)cc3)c2Cl)C(=O)N1] |
| 213 | 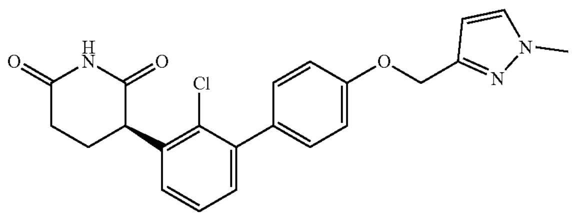 [SMILES: Cn1ccc(COc2ccc(-c3cccc([C@H]4CCC(=O)NC4=O)c3Cl)cc2)n1] |
| 214 | 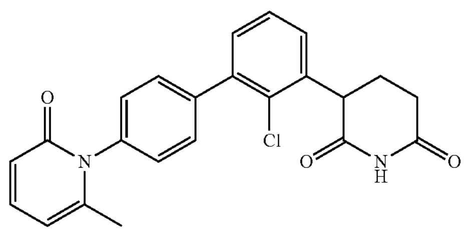 [SMILES: Cc1cccc(=O)n1-c1ccc(-c2cccc(C3CCC(=O)NC3=O)c2Cl)cc1] |
| 215 | 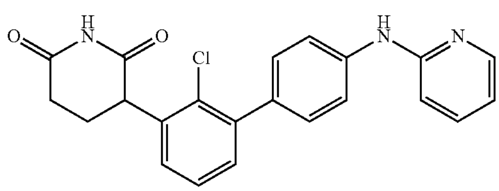 [SMILES: O=C1CCC(c2cccc(-c3ccc(Nc4ccccn4)cc3)c2Cl)C(=O)N1] |
| 216 | 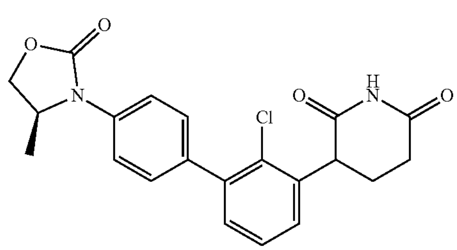 [SMILES: C[C@H]1COC(=O)N1c1ccc(-c2cccc(C3CCC(=O)NC3=O)c2Cl)cc1] |
| 217 | 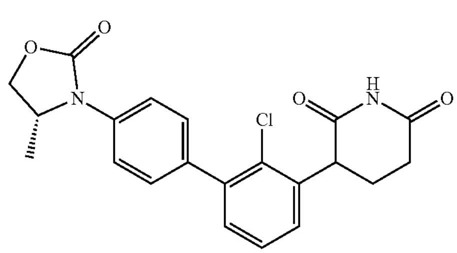 |

TABLE C1-continued

| Compound No. | Structure |
|---|---|
| 218 | 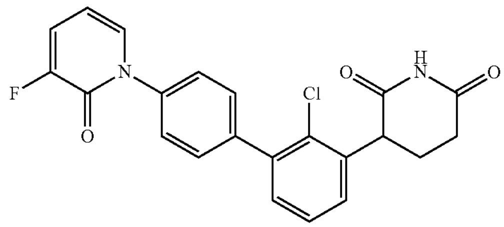 [SMILES: O=C1CCC(c2cccc(-c3ccc(-n4cccc(F)c4=O)cc3)c2Cl)C(=O)N1] |
| 219 | 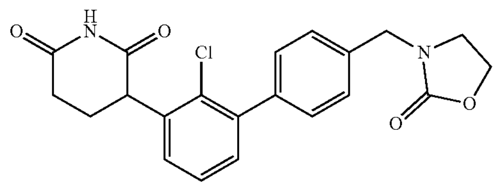 [SMILES: O=C1CCC(c2cccc(-c3ccc(CN4CCOC4=O)cc3)c2Cl)C(=O)N1] |
| 220 | 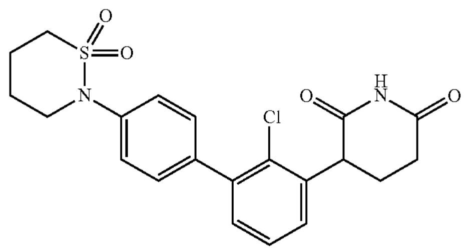 [SMILES: O=C1CCC(c2cccc(-c3ccc(N4CCCCS4(=O)=O)cc3)c2Cl)C(=O)N1] |
| 221 | 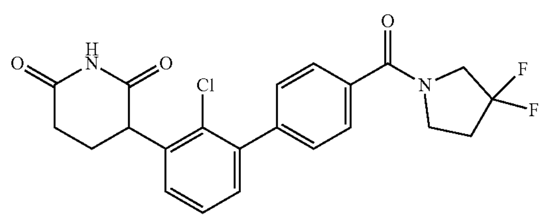 [SMILES: O=C1CCC(c2cccc(-c3ccc(C(=O)N4CCC(F)(F)C4)cc3)c2Cl)C(=O)N1] |
| 222 | 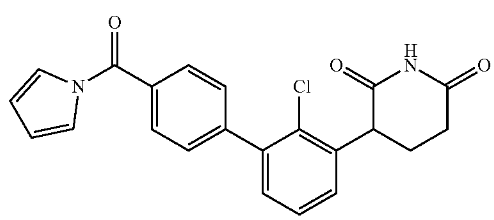 [SMILES: O=C1CCC(c2cccc(-c3ccc(C(=O)n4cccc4)cc3)c2Cl)C(=O)N1] |
| 223 | 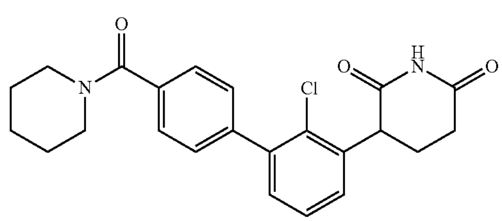 [SMILES: O=C1CCC(c2cccc(-c3ccc(C(=O)N4CCCCC4)cc3)c2Cl)C(=O)N1] |
| 224 | 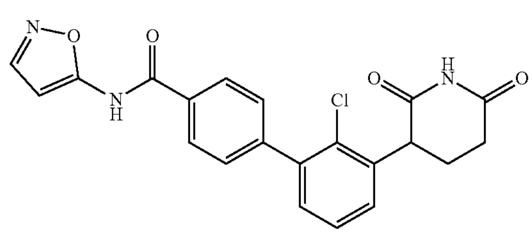 [SMILES: O=C1CCC(c2cccc(-c3ccc(C(=O)Nc4ccno4)cc3)c2Cl)C(=O)N1] |

TABLE C1-continued

| Compound No. | Structure |
|---|---|
| 225 | 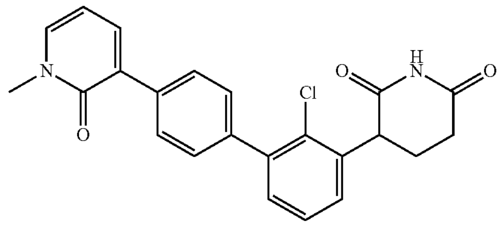 [SMILES: Cn1cccc(-c2ccc(-c3cccc(C4CCC(=O)NC4=O)c3Cl)cc2)c1=O] |
| 226 | 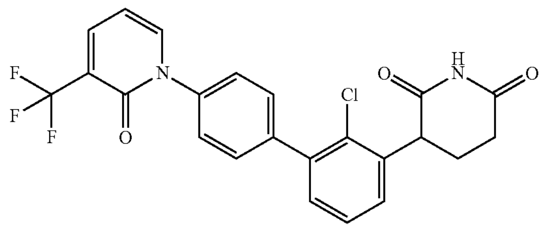 [SMILES: O=C1CCC(c2cccc(-c3ccc(-n4cccc(C(F)(F)F)c4=O)cc3)c2Cl)C(=O)N1] |
| 227 | 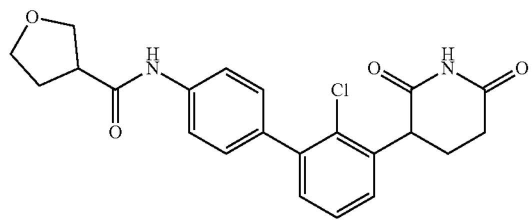 [SMILES: O=C1CCC(c2cccc(-c3ccc(NC(=O)C4CCOC4)cc3)c2Cl)C(=O)N1] |
| 228 | 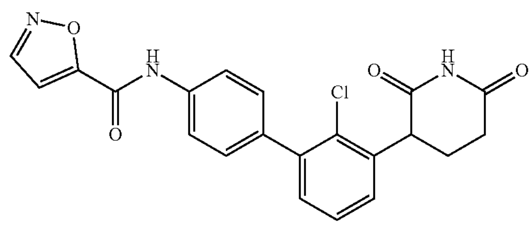 [SMILES: O=C1CCC(c2cccc(-c3ccc(NC(=O)c4ccno4)cc3)c2Cl)C(=O)N1] |
| 229 | 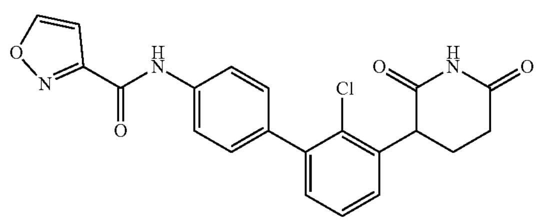 [SMILES: O=C1CCC(c2cccc(-c3ccc(NC(=O)c4ccon4)cc3)c2Cl)C(=O)N1] |
| 230 | 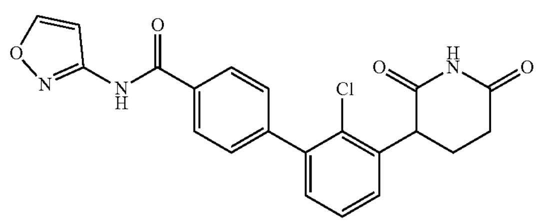 [SMILES: O=C1CCC(c2cccc(-c3ccc(C(=O)Nc4ccon4)cc3)c2Cl)C(=O)N1] |
| 231 | 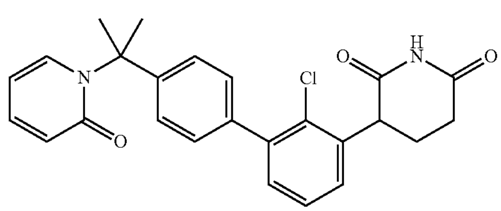 [SMILES: CC(C)(c1ccc(-c2cccc(C3CCC(=O)NC3=O)c2Cl)cc1)n1ccccc1=O] |

TABLE C1-continued
| Compound No. | Structure |
|---|---|
| 232 | 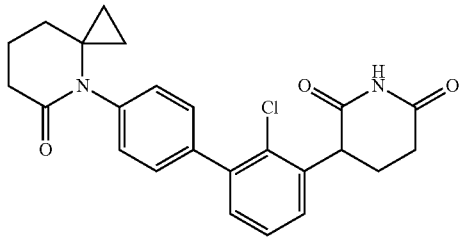 |
| 233 | 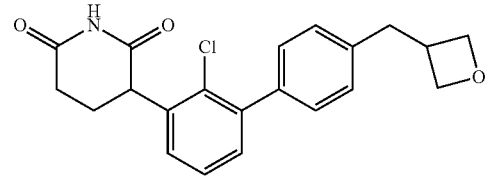 [SMILES: O=C1CCC(c2cccc(-c3ccc(CC4COC4)cc3)c2Cl)C(=O)N1] |
| 234 | 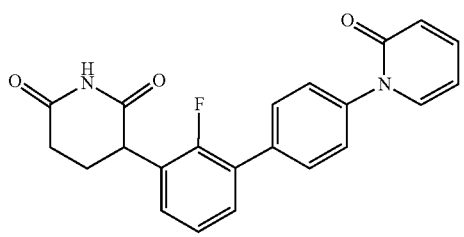 [SMILES: O=C1CCC(c2cccc(-c3ccc(-n4ccccc4=O)cc3)c2F)C(=O)N1] |
| 235 | 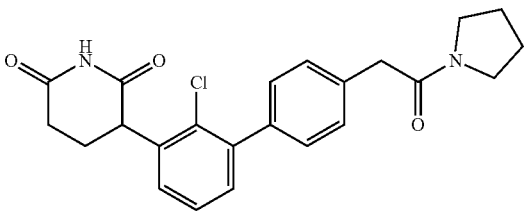 [SMILES: O=C1CCC(c2cccc(-c3ccc(CC(=O)N4CCCC4)cc3)c2Cl)C(=O)N1] |
| 236 | 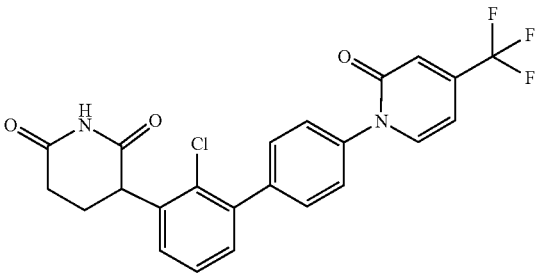 [SMILES: O=C1CCC(c2cccc(-c3ccc(-n4ccc(C(F)(F)F)cc4=O)cc3)c2Cl)C(=O)N1] |
| 237 | 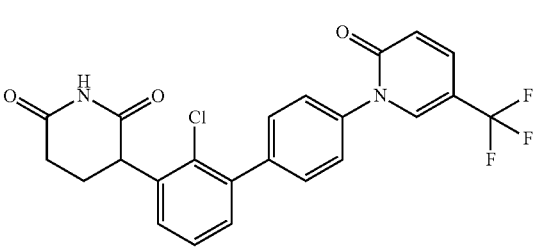 [SMILES: O=C1CCC(c2cccc(-c3ccc(-n4cc(C(F)(F)F)ccc4=O)cc3)c2Cl)C(=O)N1] |

TABLE C1-continued
| Compound No. | Structure |
| --- | --- |
| 238 | 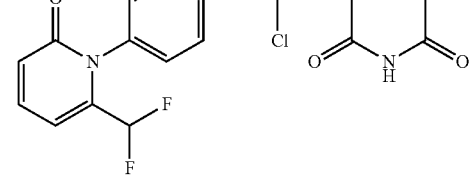 |
| 239 | 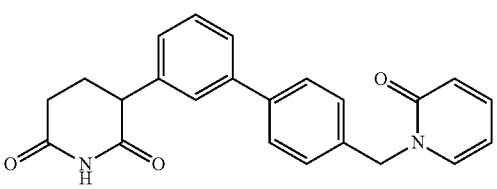 [SMILES: O=C1CCC(c2cccc(-c3ccc(Cn4ccccc4=O)cc3)c2)C(=O)N1] |
| 240 | 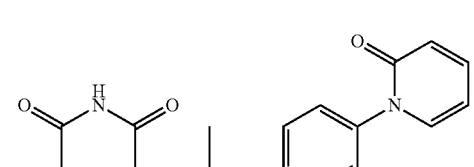 |
| 241 | 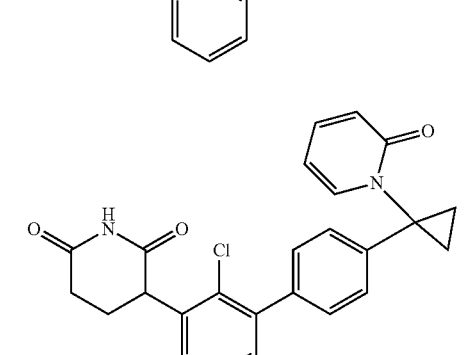 |
| 242 | 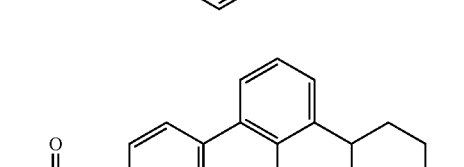 |
| 243 | 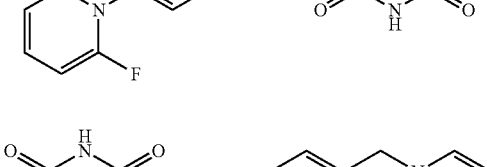 |

TABLE C1-continued

| Compound No. | Structure |
| --- | --- |
| 244 | 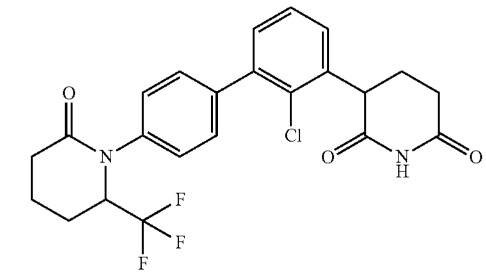 [SMILES: O=C1CCC(c2cccc(-c3ccc(N4C(=O)CCCC4C(F)(F)F)cc3)c2Cl)C(=O)N1] |
| 245 | 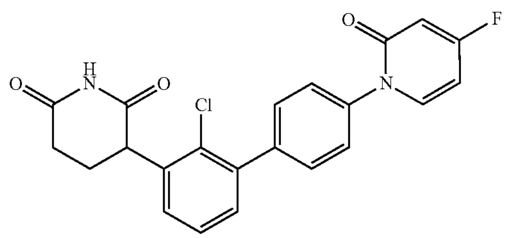 [SMILES: O=C1CCC(c2cccc(-c3ccc(-n4ccc(F)cc4=O)cc3)c2Cl)C(=O)N1] |
| 246 | 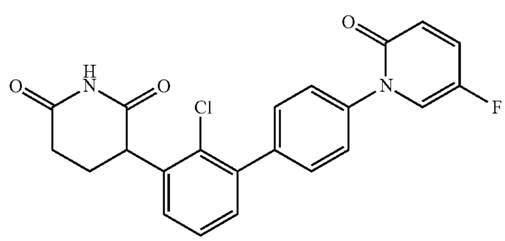 [SMILES: O=C1CCC(c2cccc(-c3ccc(-n4cc(F)ccc4=O)cc3)c2Cl)C(=O)N1] |
| 247 | 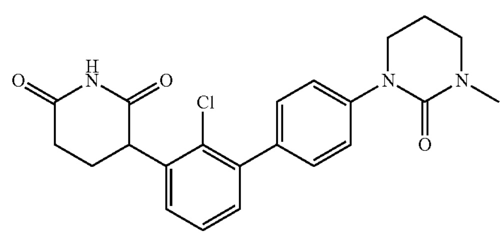 [SMILES: CN1CCCN(c2ccc(-c3cccc(C4CCC(=O)NC4=O)c3Cl)cc2)C1=O] |
| 248 | 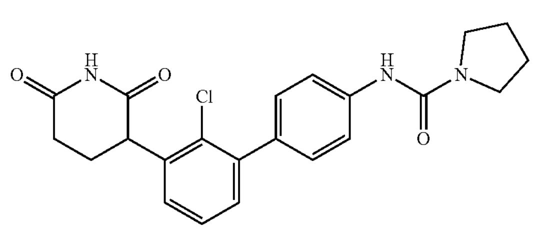 |
| 249 | 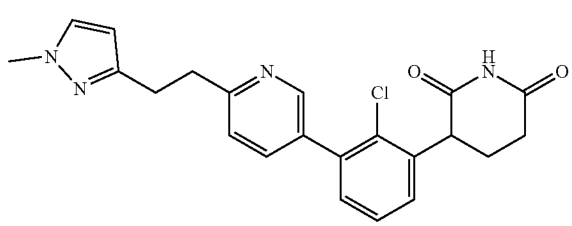 [SMILES: Cn1ccc(CCc2ccc(-c3cccc(C4CCC(=O)NC4=O)c3Cl)cn2)n1] |

TABLE C1-continued

| Compound No. | Structure |
| --- | --- |
| 251 | 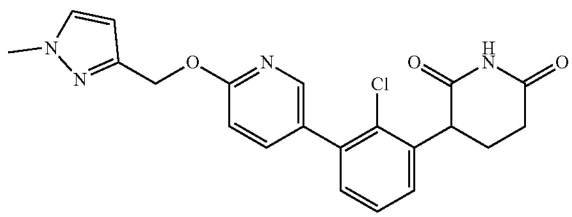 [SMILES: Cn1ccc(COc2ccc(-c3cccc(C4CCC(=O)NC4=O)c3Cl)cn2)n1] |
| 252 | 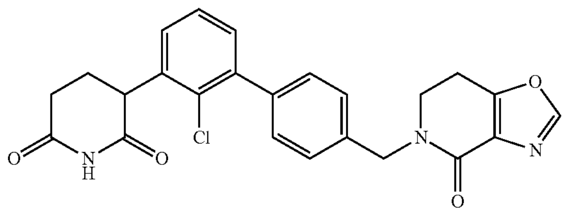 [SMILES: O=C1CCC(c2cccc(-c3ccc(CN4CCc5ocnc5C4=O)cc3)c2Cl)C(=O)N1] |
| 253 | 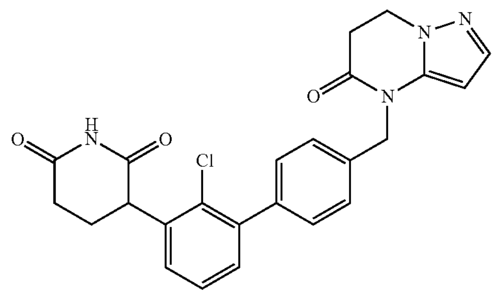 [SMILES: O=C1CCC(c2cccc(-c3ccc(CN4C(=O)CCn5nccc54)cc3)c2Cl)C(=O)N1] |
| 254 | 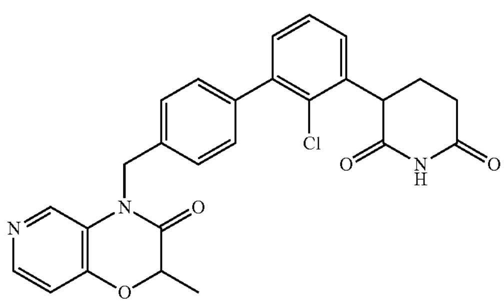 [SMILES: CC1Oc2ccncc2N(Cc2ccc(-c3cccc(C4CCC(=O)NC4=O)c3Cl)cc2)C1=O] |
| 255 | 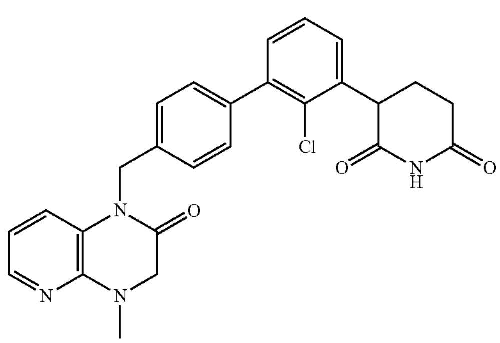 [SMILES: CN1CC(=O)N(Cc2ccc(-c3cccc(C4CCC(=O)NC4=O)c3Cl)cc2)c2cccnc21] |

181

TABLE C1-continued

| Compound No. | Structure |
| --- | --- |
| 256 | 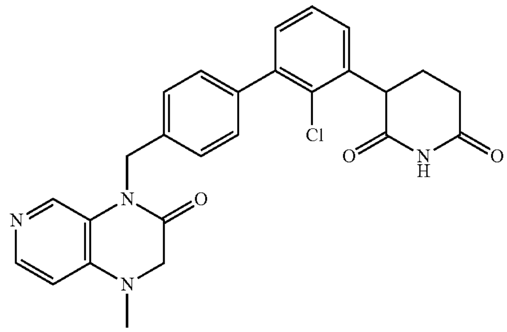 [SMILES: CN1CC(=O)N(Cc2ccc(-c3cccc(C4CCC(=O)NC4=O)c3Cl)cc2)c2cnccc21] |
| 257 | 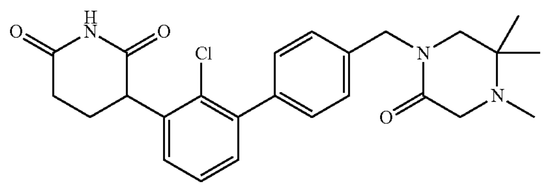 [SMILES: CN1CC(=O)N(Cc2ccc(-c3cccc(C4CCC(=O)NC4=O)c3Cl)cc2)CC1(C)C] |
| 258 | 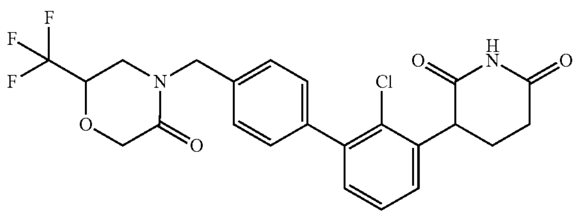 [SMILES: O=C1CCC(c2cccc(-c3ccc(CN4CC(C(F)(F)F)OCC4=O)cc3)c2Cl)C(=O)N1] |
| 259 | 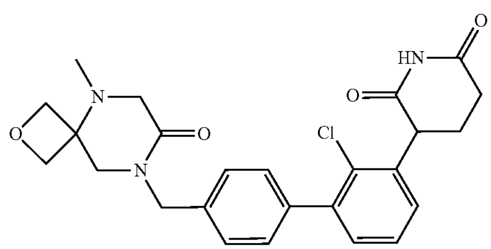 [SMILES: CN1CC(=O)N(Cc2ccc(-c3cccc(C4CCC(=O)NC4=O)c3Cl)cc2)CC12COC2] |
| 260 | 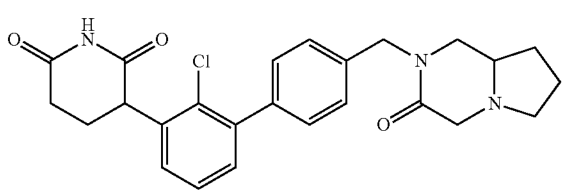 [SMILES: O=C1CCC(c2cccc(-c3ccc(CN4CC5CCCN5CC4=O)cc3)c2Cl)C(=O)N1] |
| 261 | 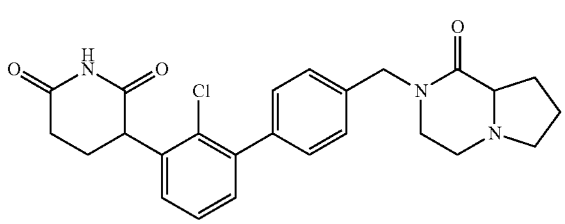 [SMILES: O=C1CCC(c2cccc(-c3ccc(CN4CCN5CCCC5C4=O)cc3)c2Cl)C(=O)N1] |

182

TABLE C1-continued

| Compound No. | Structure |
|---|---|
| 262 | 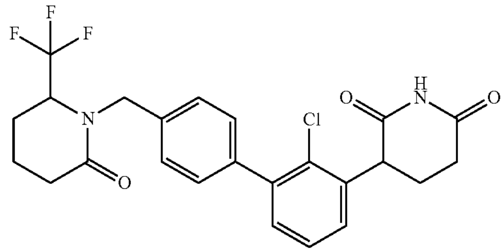 [SMILES: O=C1CCC(c2cccc(-c3ccc(CN4C(=O)CCCC4C(F)(F)F)cc3)c2Cl)C(=O)N1] |
| 263 | 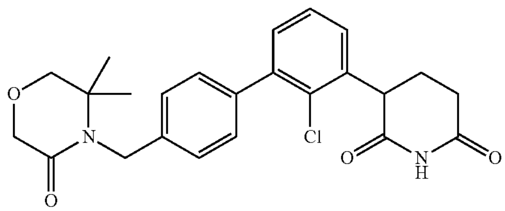 [SMILES: CC1(C)COCC(=O)N1Cc1ccc(-c2cccc(C3CCC(=O)NC3=O)c2Cl)cc1] |
| 264 | 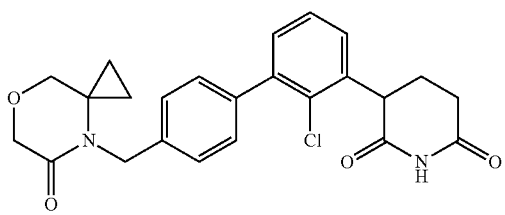 [SMILES: O=C1CCC(c2cccc(-c3ccc(CN4C(=O)COCC45CC5)cc3)c2Cl)C(=O)N1] |
| 265 | 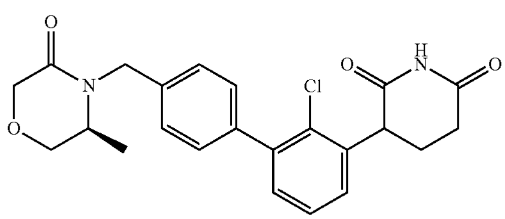 [SMILES: C[C@H]1COCC(=O)N1Cc1ccc(-c2cccc(C3CCC(=O)NC3=O)c2Cl)cc1] |
| 266 | 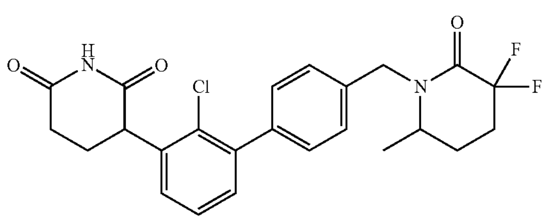 [SMILES: CC1CCC(F)(F)C(=O)N1Cc1ccc(-c2cccc(C3CCC(=O)NC3=O)c2Cl)cc1] |
| 267 | 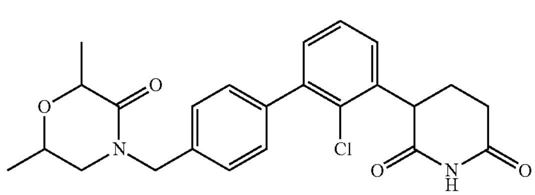 [SMILES: CC1CN(Cc2ccc(-c3cccc(C4CCC(=O)NC4=O)c3Cl)cc2)C(=O)C(C)O1] |
| 268 | 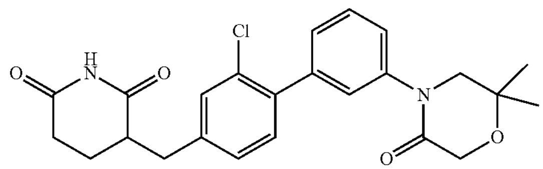 [SMILES: CC1(C)CN(c2cccc(-c3ccc(CC4CCC(=O)NC4=O)cc3Cl)c2)C(=O)CO1] |

TABLE C1-continued

| Compound No. | Structure |
| --- | --- |
| 269 | 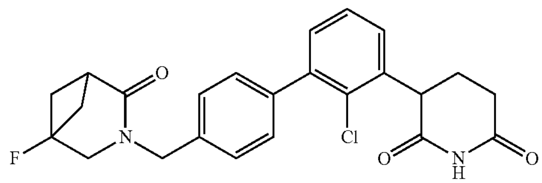 [SMILES: O=C1CCC(c2cccc(-c3ccc(CN4CC5(F)CC(C5)C4=O)cc3)c2Cl)C(=O)N1] |
| 270 | 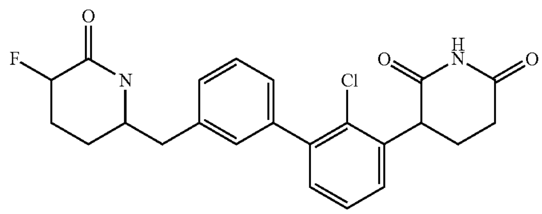 [SMILES: O=C1CCC(c2cccc(-c3cccc(CC4CCC(F)C(=O)N4)c3)c2Cl)C(=O)N1] |
| 271 | 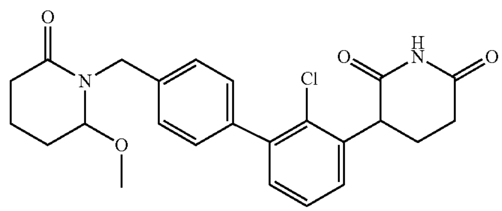 [SMILES: COC1CCCC(=O)N1Cc1ccc(-c2cccc(C3CCC(=O)NC3=O)c2Cl)cc1] |
| 272 | 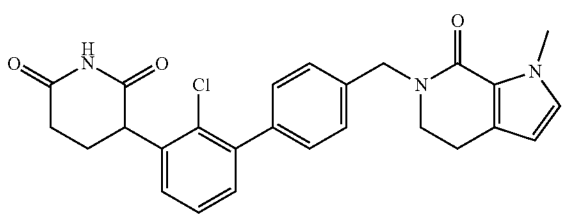 [SMILES: Cn1ccc2c1C(=O)N(Cc1ccc(-c3cccc(C4CCC(=O)NC4=O)c3Cl)cc1)CC2] |
| 273 | 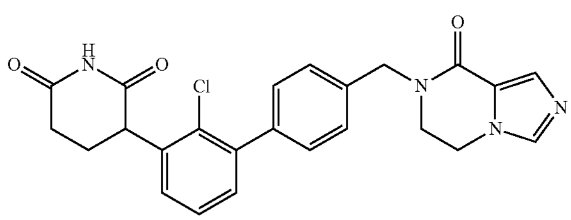 [SMILES: O=C1CCC(c2cccc(-c3ccc(CN4CCn5cncc5C4=O)cc3)c2Cl)C(=O)N1] |
| 274 | 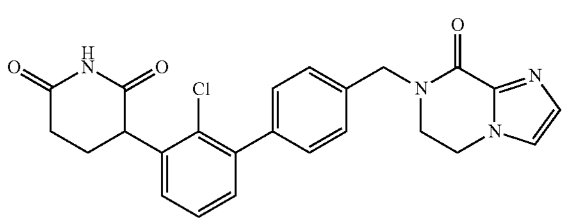 [SMILES: O=C1CCC(c2cccc(-c3ccc(CN4CCn5ccnc5C4=O)cc3)c2Cl)C(=O)N1] |
| 275 | 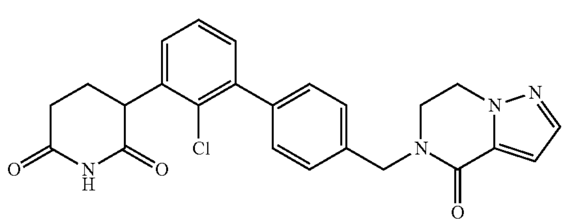 [SMILES: O=C1CCC(c2cccc(-c3ccc(CN4CCn5nccc5C4=O)cc3)c2Cl)C(=O)N1] |

TABLE C1-continued
| Compound No. | Structure |
|---|---|
| 276 | 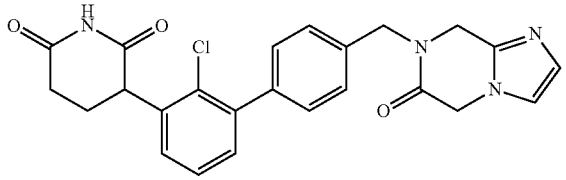 [SMILES: O=C1CCC(c2cccc(-c3ccc(CN4Cc5nccn5CC4=O)cc3)c2Cl)C(=O)N1] |
| 277 | 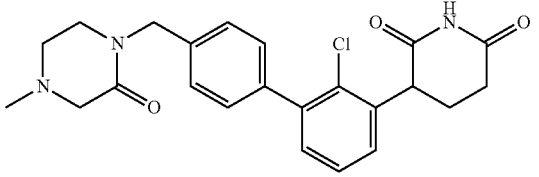 [SMILES: CN1CCN(Cc2ccc(-c3cccc(C4CCC(=O)NC4=O)c3Cl)cc2)C(=O)C1] |
| 278 | 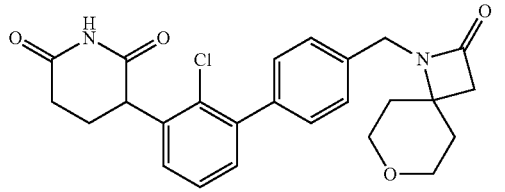 [SMILES: O=C1CCC(c2cccc(-c3ccc(CN4C(=O)CC45CCOCC5)cc3)c2Cl)C(=O)N1] |
| 279 | 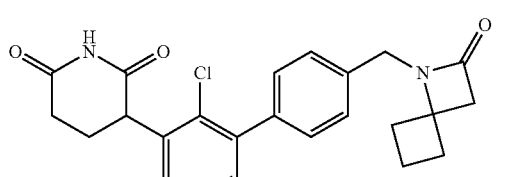 |
| 280 | 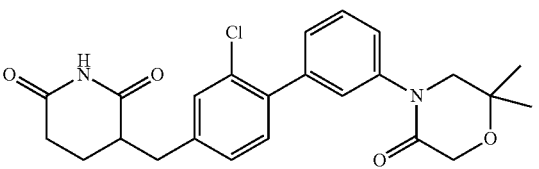 [SMILES: CC1(C)CN(c2cccc(-c3ccc(CC4CCC(=O)NC4=O)cc3Cl)c2)C(=O)CO1] |
| 281 | 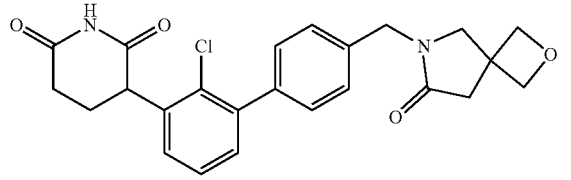 [SMILES: O=C1CCC(c2cccc(-c3ccc(CN4CC5(COC5)CC4=O)cc3)c2Cl)C(=O)N1] |
| 282 | 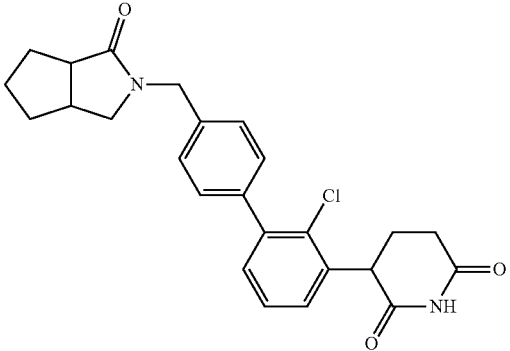 [SMILES: O=C1CCC(c2cccc(-c3ccc(CN4CC5CCCC5C4=O)cc3)c2Cl)C(=O)N1] |

TABLE C1-continued

| Compound No. | Structure |
| --- | --- |
| 283 | 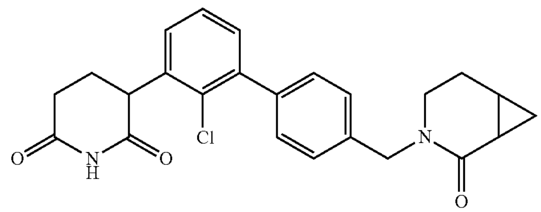 [SMILES: O=C1CCC(c2cccc(-c3ccc(CN4CCC5CC5C4=O)cc3)c2Cl)C(=O)N1] |
| 284 | 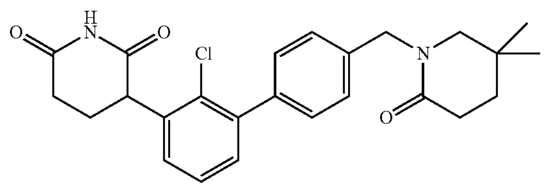 [SMILES: CC1(C)CCC(=O)N(Cc2ccc(-c3cccc(C4CCC(=O)NC4=O)c3Cl)cc2)C1] |
| 285 | 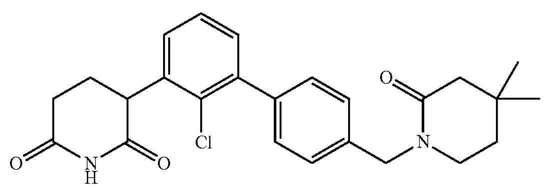 [SMILES: CC1(C)CCN(Cc2ccc(-c3cccc(C4CCC(=O)NC4=O)c3Cl)cc2)C(=O)C1] |
| 286 | 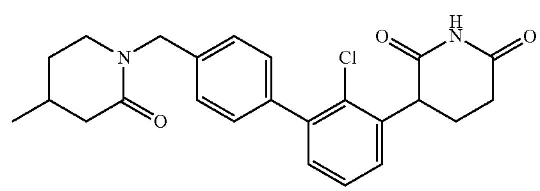 [SMILES: CC1CCN(Cc2ccc(-c3cccc(C4CCC(=O)NC4=O)c3Cl)cc2)C(=O)C1] |
| 287 | 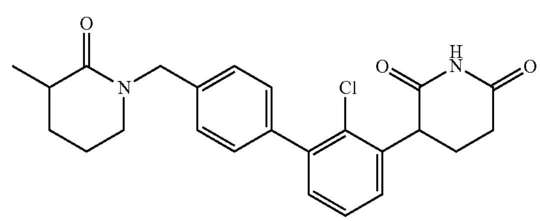 [SMILES: CC1CCCN(Cc2ccc(-c3cccc(C4CCC(=O)NC4=O)c3Cl)cc2)C1=O] |
| 288 | 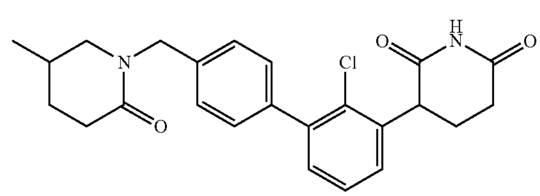 [SMILES: CC1CCC(=O)N(Cc2ccc(-c3cccc(C4CCC(=O)NC4=O)c3Cl)cc2)C1] |
| 289 | 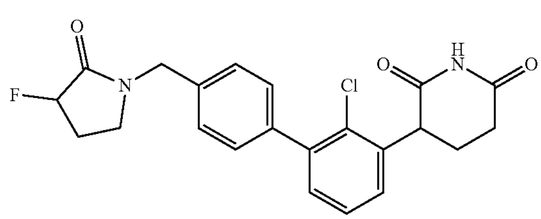 [SMILES: O=C1CCC(c2cccc(-c3ccc(CN4CCC(F)C4=O)cc3)c2Cl)C(=O)N1] |

TABLE C1-continued

| Compound No. | Structure |
| --- | --- |
| 290 | 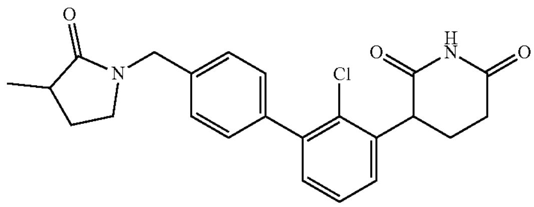 [SMILES: CC1CCN(Cc2ccc(-c3cccc(C4CCC(=O)NC4=O)c3Cl)cc2)C1=O] |
| 291 | 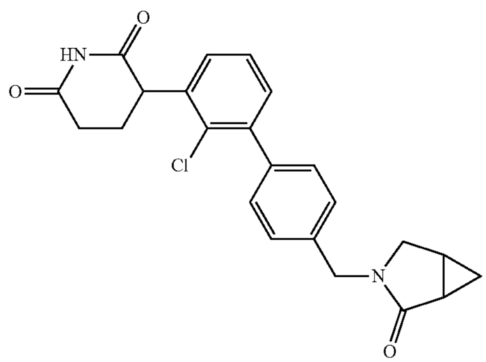 [SMILES: O=C1CCC(c2cccc(-c3ccc(CN4CC5CC5C4=O)cc3)c2Cl)C(=O)N1] |
| 292 | 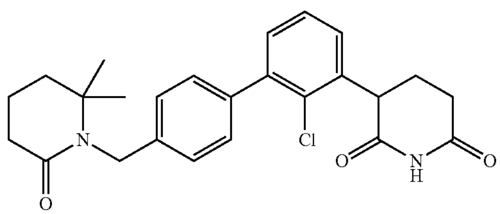 [SMILES: CC1(C)CCCC(=O)N1Cc1ccc(-c2cccc(C3CCC(=O)NC3=O)c2Cl)cc1] |
| 293 | 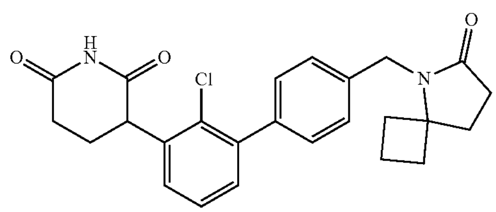 [SMILES: O=C1CCC(c2cccc(-c3ccc(CN4C(=O)CCC45CCC5)cc3)c2Cl)C(=O)N1] |
| 294 | 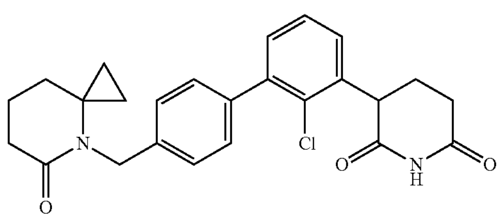 |
| 295 | 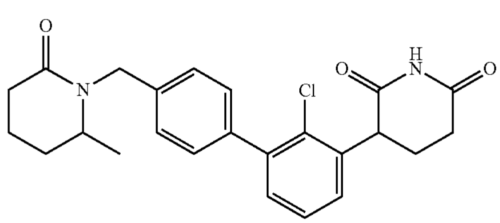 [SMILES: CC1CCCC(=O)N1Cc1ccc(-c2cccc(C3CCC(=O)NC3=O)c2Cl)cc1] |

TABLE C1-continued

| Compound No. | Structure |
| --- | --- |
| 296 | 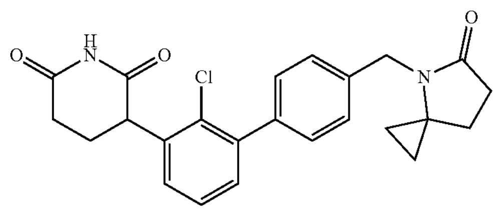 [SMILES: O=C1CCC(c2cccc(-c3ccc(CN4C(=O)CCC45CC5)cc3)c2Cl)C(=O)N1] |
| 297 | 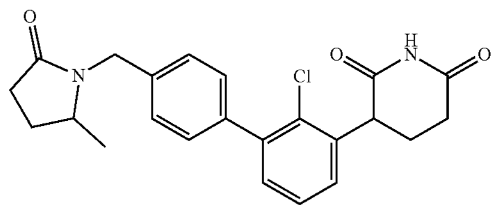 [SMILES: CC1CCC(=O)N1Cc1ccc(-c2cccc(C3CCC(=O)NC3=O)c2Cl)cc1] |
| 298 | 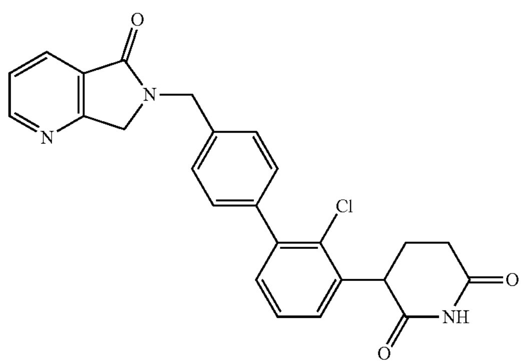 [SMILES: O=C1CCC(c2cccc(-c3ccc(CN4Cc5ncccc5C4=O)cc3)c2Cl)C(=O)N1] |
| 299 | 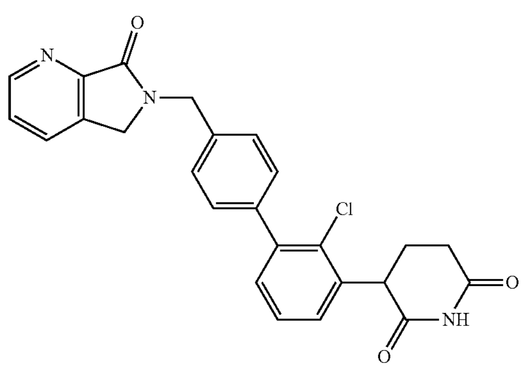 [SMILES: O=C1CCC(c2cccc(-c3ccc(CN4Cc5cccnc5C4=O)cc3)c2Cl)C(=O)N1] |
| 300 | 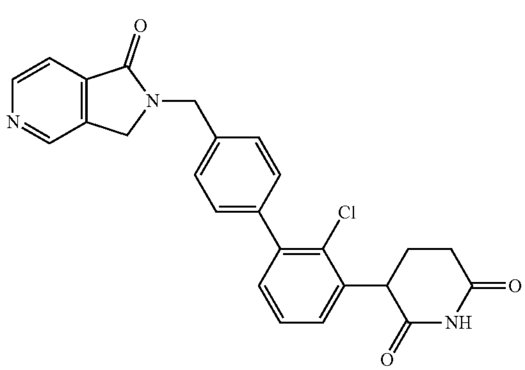 [SMILES: O=C1CCC(c2cccc(-c3ccc(CN4Cc5cnccc5C4=O)cc3)c2Cl)C(=O)N1] |

TABLE C1-continued

| Compound No. | Structure |
|---|---|
| 301 | 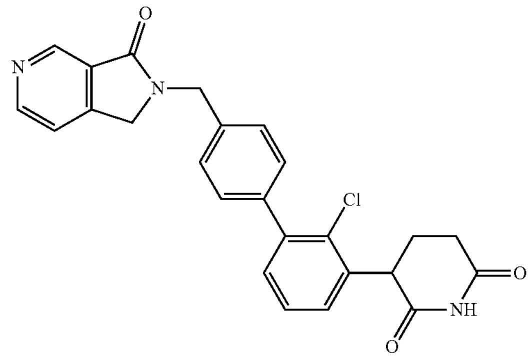 [SMILES: O=C1CCC(c2cccc(-c3ccc(CN4Cc5ccncc5C4=O)cc3)c2Cl)C(=O)N1] |
| 302 | 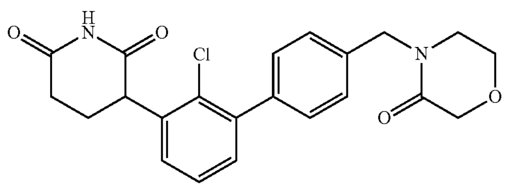 [SMILES: O=C1CCC(c2cccc(-c3ccc(CN4CCOCC4=O)cc3)c2Cl)C(=O)N1] |
| 303 | 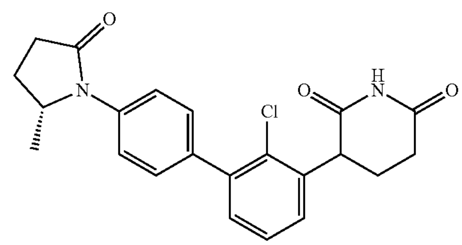 [SMILES: C[C@@H]1CCC(=O)N1c1ccc(-c2cccc(C3CCC(=O)NC3=O)c2Cl)cc1] |
| 304 | 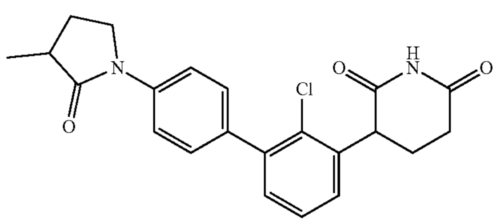 [SMILES: CC1CCN(c2ccc(-c3cccc(C4CCC(=O)NC4=O)c3Cl)cc2)C1=O] |
| 305 | 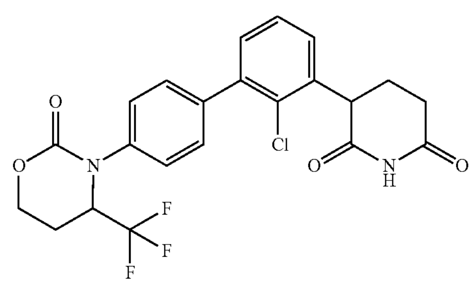 [SMILES: O=C1CCC(c2cccc(-c3ccc(N4C(=O)OCCC4C(F)(F)F)cc3)c2Cl)C(=O)N1] |
| 306 | 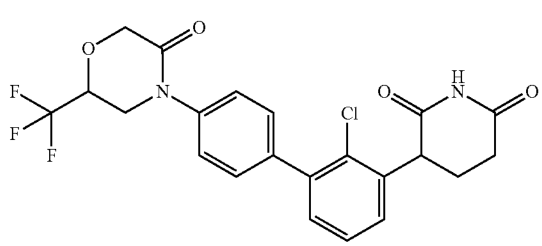 [SMILES: O=C1CCC(c2cccc(-c3ccc(N4CC(C(F)(F)F)OCC4=O)cc3)c2Cl)C(=O)N1] |

TABLE C1-continued

| Compound No. | Structure |
|---|---|
| 307 | 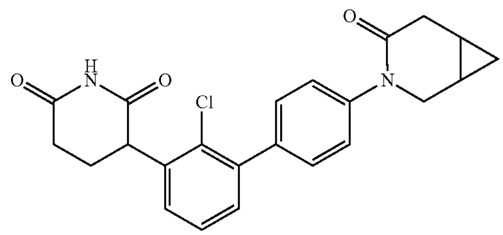 [SMILES: O=C1CCC(c2cccc(-c3ccc(N4CC5CC5CC4=O)cc3)c2Cl)C(=O)N1] |
| 308 | 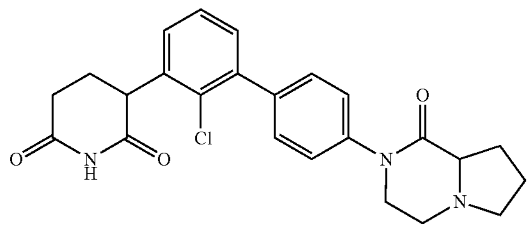 [SMILES: O=C1CCC(c2cccc(-c3ccc(N4CCN5CCCC5C4=O)cc3)c2Cl)C(=O)N1] |
| 309 | 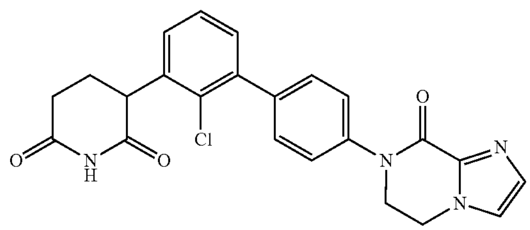 [SMILES: O=C1CCC(c2cccc(-c3ccc(N4CCn5ccnc5C4=O)cc3)c2Cl)C(=O)N1] |
| 310 | 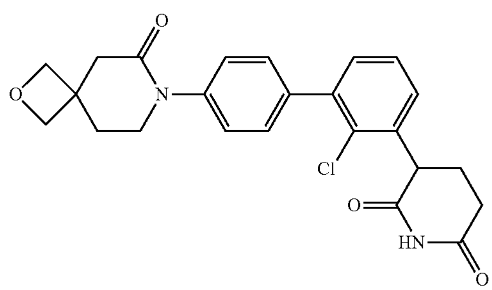 [SMILES: O=C1CCC(c2cccc(-c3ccc(N4CCC5(COC5)CC4=O)cc3)c2Cl)C(=O)N1] |
| 311 | 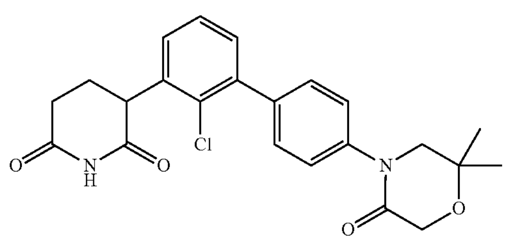 [SMILES: CC1(C)CN(c2ccc(-c3cccc(C4CCC(=O)NC4=O)c3Cl)cc2)C(=O)CO1] |
| 312 | 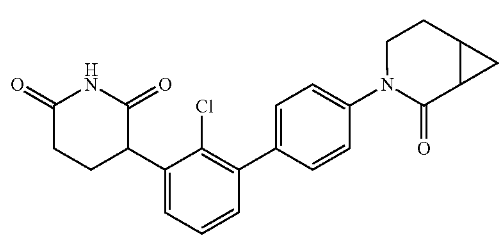 [SMILES: O=C1CCC(c2cccc(-c3ccc(N4CCC5CC5C4=O)cc3)c2Cl)C(=O)N1] |

TABLE C1-continued

| Compound No. | Structure |
| --- | --- |
| 313 | 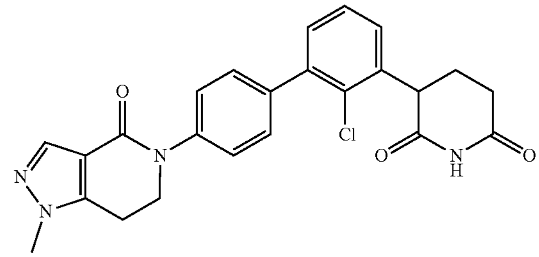 [SMILES: Cn1ncc2c1CCN(c1ccc(-c3cccc(C4CCC(=O)NC4=O)c3Cl)cc1)C2=O] |
| 314 | 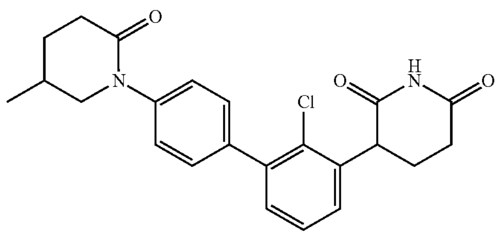 [SMILES: CC1CCC(=O)N(c2ccc(-c3cccc(C4CCC(=O)NC4=O)c3Cl)cc2)C1] |
| 315 | 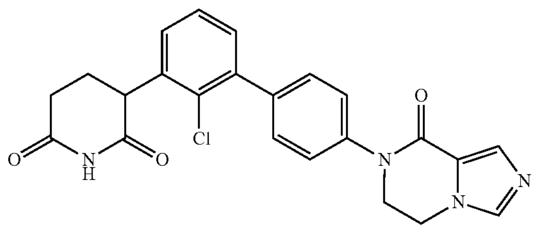 [SMILES: O=C1CCC(c2cccc(-c3ccc(N4CCn5cncc5C4=O)cc3)c2Cl)C(=O)N1] |
| 316 | 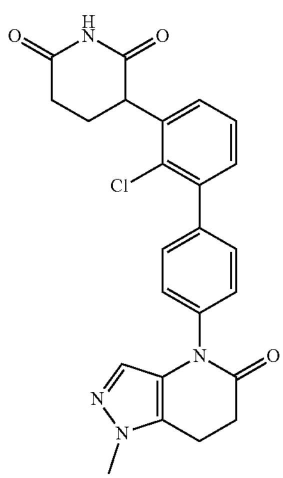 [SMILES: Cn1ncc2c1CCC(=O)N2c1ccc(-c2cccc(C3CCC(=O)NC3=O)c2Cl)cc1] |
| 317 | 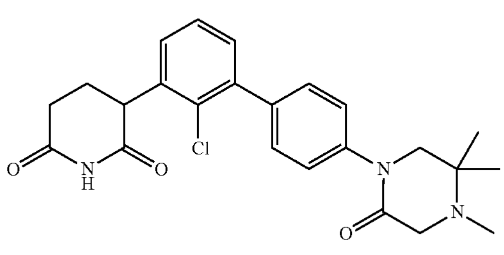 [SMILES: CN1CC(=O)N(c2ccc(-c3cccc(C4CCC(=O)NC4=O)c3Cl)cc2)CC1(C)C] |

TABLE C1-continued

| Compound No. | Structure |
| --- | --- |
| 318 | 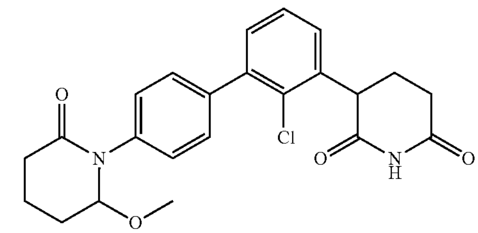 [SMILES: COC1CCCC(=O)N1c1ccc(-c2cccc(C3CCC(=O)NC3=O)c2Cl)cc1] |
| 319 | 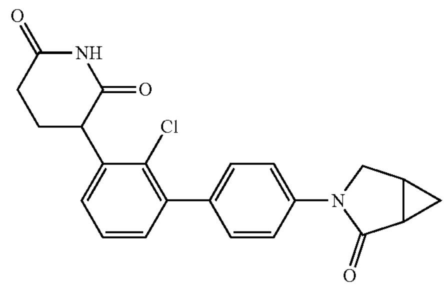 [SMILES: O=C1CCC(c2cccc(-c3ccc(N4CC5CC5C4=O)cc3)c2Cl)C(=O)N1] |
| 320 | 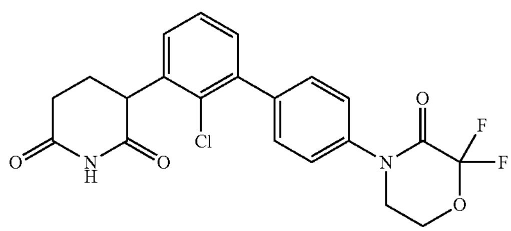 [SMILES: O=C1CCC(c2cccc(-c3ccc(N4CCOC(F)(F)C4=O)cc3)c2Cl)C(=O)N1] |
| 321 | 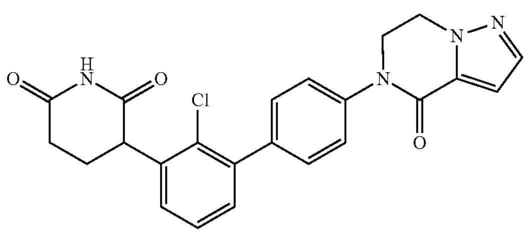 [SMILES: O=C1CCC(c2cccc(-c3ccc(N4CCn5nccc5C4=O)cc3)c2Cl)C(=O)N1] |
| 322 | 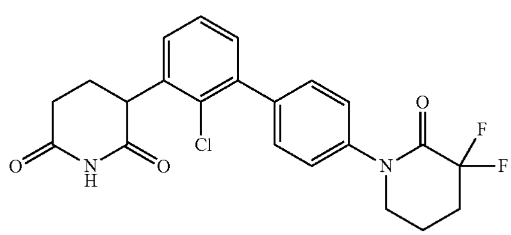 [SMILES: O=C1CCC(c2cccc(-c3ccc(N4CCCC(F)(F)C4=O)cc3)c2Cl)C(=O)N1] |
| 323 | 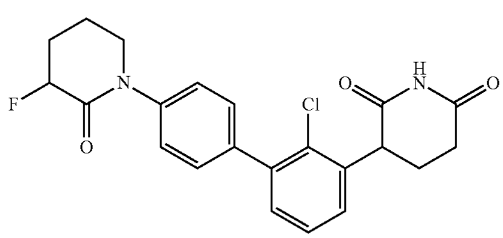 [SMILES: O=C1CCC(c2cccc(-c3ccc(N4CCCC(F)C4=O)cc3)c2Cl)C(=O)N1] |

TABLE C1-continued

| Compound No. | Structure |
| --- | --- |
| 324 | 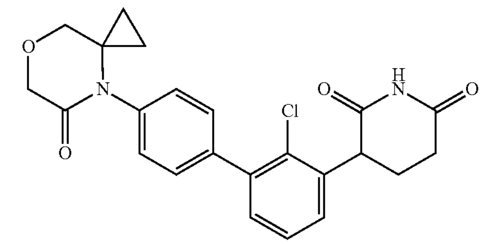 [SMILES: O=C1CCC(c2cccc(-c3ccc(N4C(=O)COCC45CC5)cc3)c2Cl)C(=O)N1] |
| 325 | 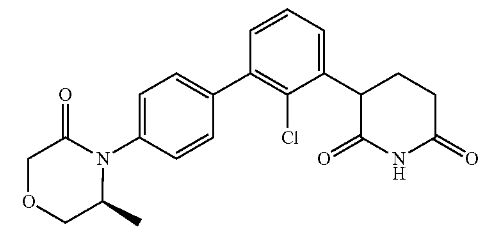 [SMILES: C[C@H]1COCC(=O)N1c1ccc(-c2cccc(C3CCC(=O)NC3=O)c2Cl)cc1] |
| 326 | 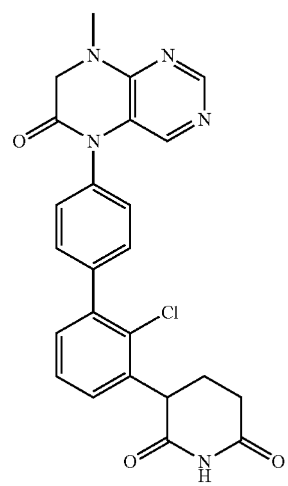 [SMILES: CN1CC(=O)N(c2ccc(-c3cccc(C4CCC(=O)NC4=O)c3Cl)cc2)c2cncnc21] |
| 327 | 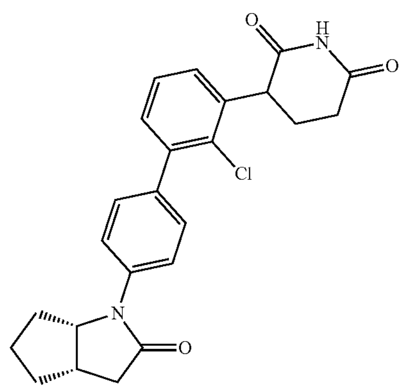 [SMILES: O=C1CCC(c2cccc(-c3ccc(N4C(=O)C[C@@H]5CCC[C@@H]54)cc3)c2Cl)C(=O)N1] |
| 328 | 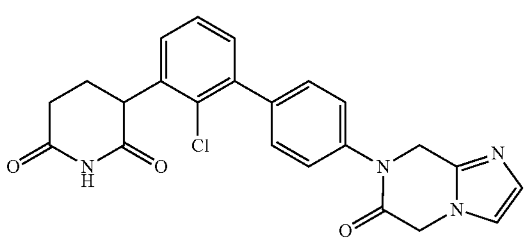 [SMILES: O=C1CCC(c2cccc(-c3ccc(N4Cc5nccn5CC4=O)cc3)c2Cl)C(=O)N1] |

TABLE C1-continued

| Compound No. | Structure |
| --- | --- |
| 329 | 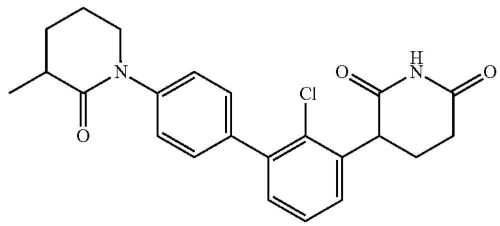 [SMILES: CC1CCCN(c2ccc(-c3cccc(C4CCC(=O)NC4=O)c3Cl)cc2)C1=O] |
| 330 | 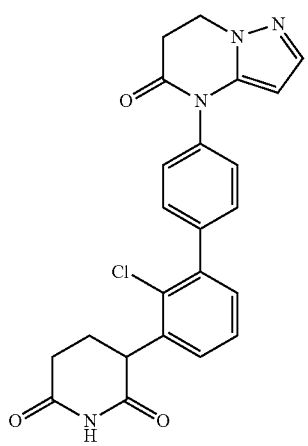 [SMILES: O=C1CCC(c2cccc(-c3ccc(N4C(=O)CCn5nccc54)cc3)c2Cl)C(=O)N1] |
| 331 | 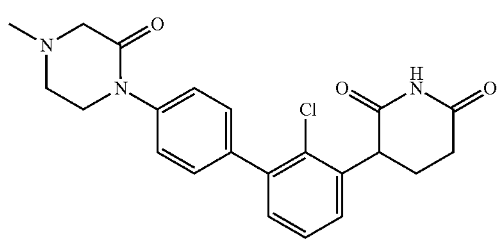 [SMILES: CN1CCN(c2ccc(-c3cccc(C4CCC(=O)NC4=O)c3Cl)cc2)C(=O)C1] |
| 332 | 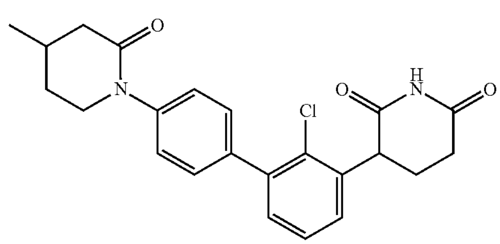 [SMILES: CC1CCN(c2ccc(-c3cccc(C4CCC(=O)NC4=O)c3Cl)cc2)C(=O)C1] |
| 333 | 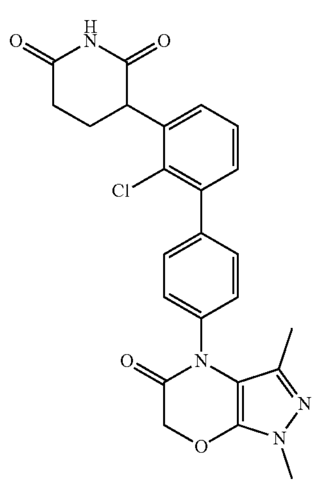 [SMILES: Cc1nn(C)c2c1N(c1ccc(-c3cccc(C4CCC(=O)NC4=O)c3Cl)cc1)C(=O)CO2] |

TABLE C1-continued
| Compound No. | Structure |
|---|---|
| 334 | 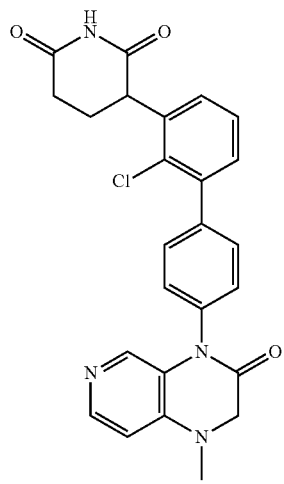 [SMILES: CN1CC(=O)N(c2ccc(-c3cccc(C4CCC(=O)NC4=O)c3Cl)cc2)c2cnccc21] |
| 335 | 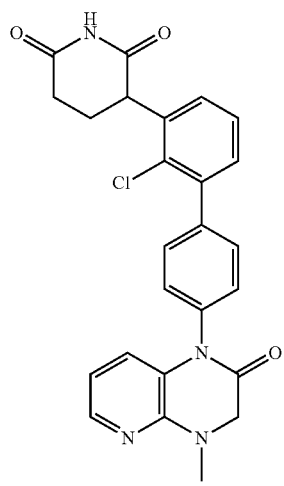 [SMILES: CN1CC(=O)N(c2ccc(-c3cccc(C4CCC(=O)NC4=O)c3Cl)cc2)c2cccnc21] |
| 336 | 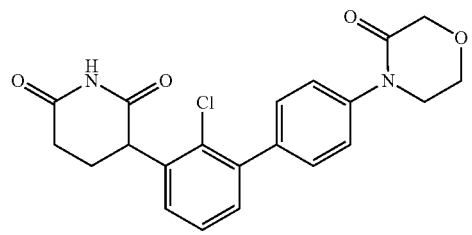 |

TABLE C1-continued
| Compound No. | Structure |
|---|---|
| 337 | 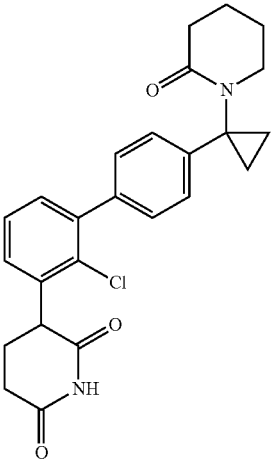 [SMILES: O=C1CCC(c2cccc(-c3ccc(C4(N5CCCCC5=O)CC4)cc3)c2Cl)C(=O)N1] |
| 338 | 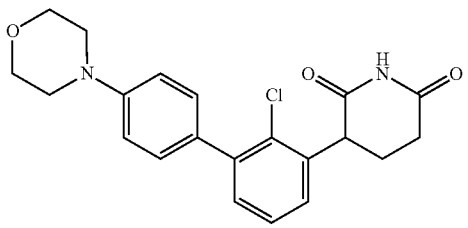 [SMILES: O=C1CCC(c2cccc(-c3ccc(N4CCOCC4)cc3)c2Cl)C(=O)N1] |
| 339 | 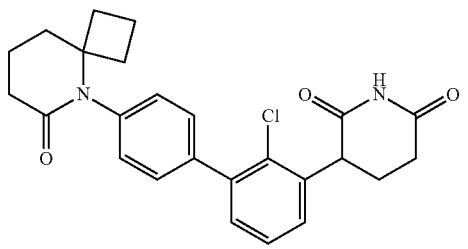 [SMILES: O=C1CCC(c2cccc(-c3ccc(N4C(=O)CCCC45CCC5)cc3)c2Cl)C(=O)N1] |
| 340 | 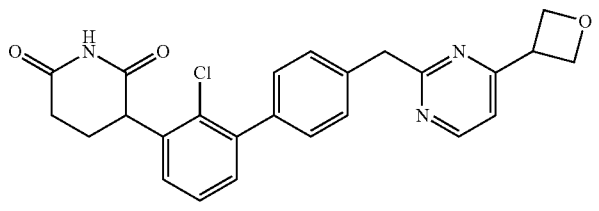 [SMILES: O=C1CCC(c2cccc(-c3ccc(Cc4nccc(C5COC5)n4)cc3)c2Cl)C(=O)N1] |
| 341 | 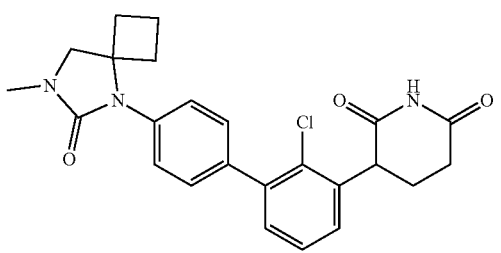 [SMILES: CN1CC2(CCC2)N(c2ccc(-c3cccc(C4CCC(=O)NC4=O)c3Cl)cc2)C1=O] |

TABLE C1-continued

| Compound No. | Structure |
|---|---|
| 342 | 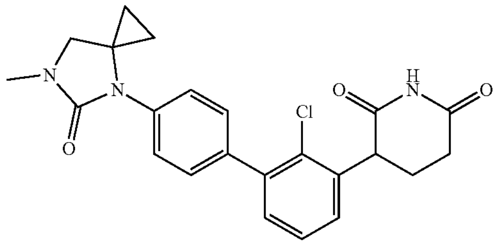 [SMILES: CN1CC2(CC2)N(c2ccc(-c3cccc(C4CCC(=O)NC4=O)c3Cl)cc2)C1=O] |
| 343 | 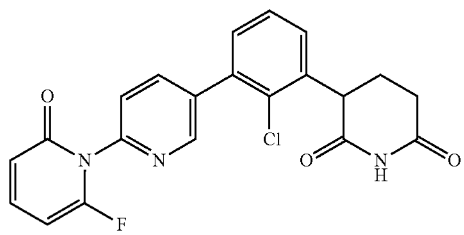 |
| 344 | 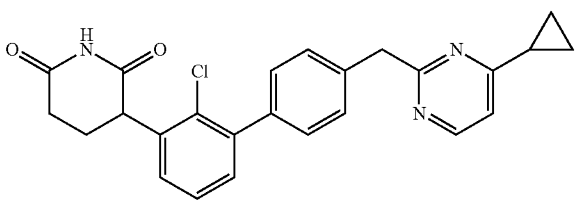 [SMILES: O=C1CCC(c2cccc(-c3ccc(Cc4nccc(C5CC5)n4)cc3)c2Cl)C(=O)N1] |
| 345 | 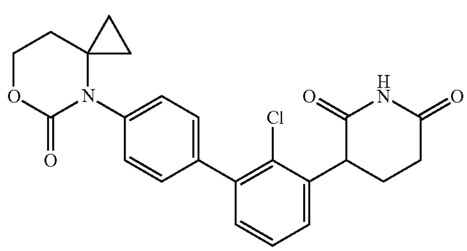 [SMILES: O=C1CCC(c2cccc(-c3ccc(N4C(=O)OCCC45CC5)cc3)c2Cl)C(=O)N1] |
| 346 | 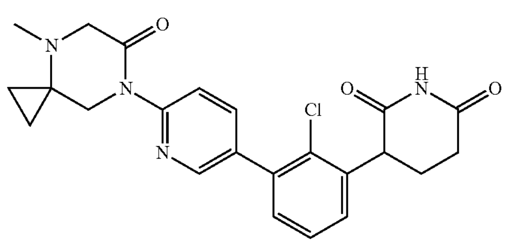 [SMILES: CN1CC(=O)N(c2ccc(-c3cccc(C4CCC(=O)NC4=O)c3Cl)cn2)CC12CC2] |
| 347 | 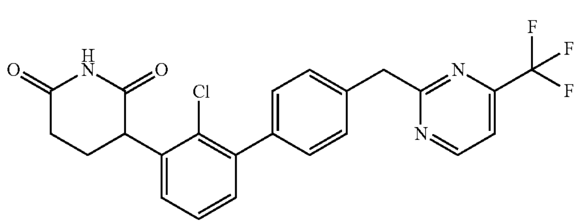 [SMILES: O=C1CCC(c2cccc(-c3ccc(Cc4nccc(C(F)(F)F)n4)cc3)c2Cl)C(=O)N1] |

TABLE C1-continued

| Compound No. | Structure |
|---|---|
| 348 | 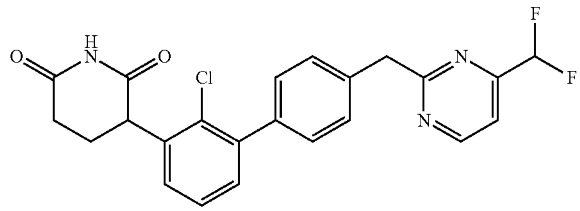 [SMILES: O=C1CCC(c2cccc(-c3ccc(Cc4nccc(C(F)F)n4)cc3)c2Cl)C(=O)N1] |
| 349 | 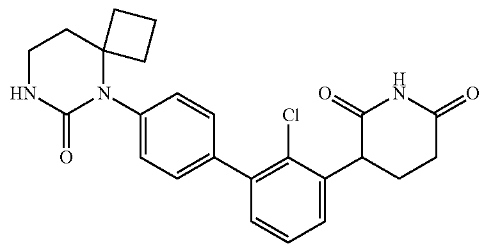 [SMILES: O=C1CCC(c2cccc(-c3ccc(N4C(=O)NCCC45CCC5)cc3)c2Cl)C(=O)N1] |
| 350 | 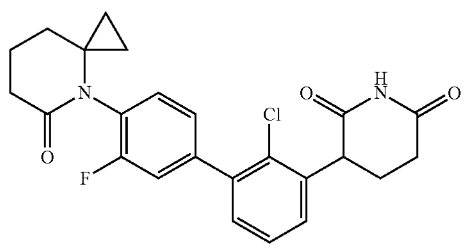 |
| 351 | 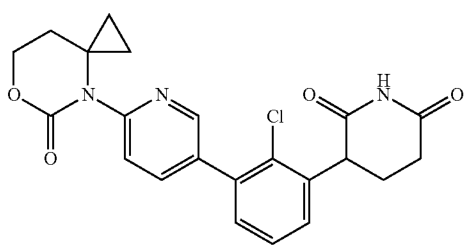 |
| 352 | 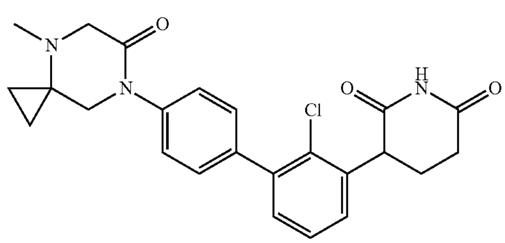 [SMILES: CN1CC(=O)N(c2ccc(-c3cccc(C4CCC(=O)NC4=O)c3Cl)cc2)CC12CC2] |
| 353 | 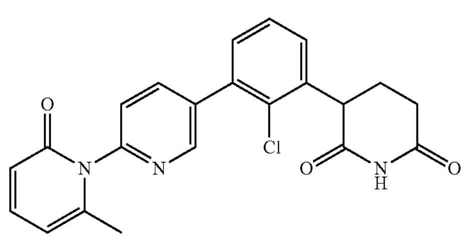 [SMILES: Cc1cccc(=O)n1-c1ccc(-c2cccc(C3CCC(=O)NC3=O)c2Cl)cn1] |

TABLE C1-continued
| Compound No. | Structure |
|---|---|
| 354 | 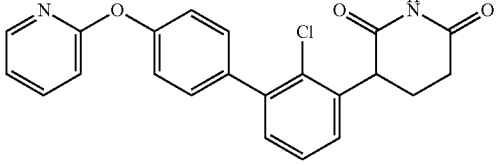 |
| 355 | 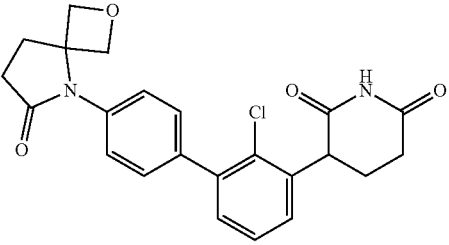 [SMILES: O=C1CCC(c2cccc(-c3ccc(N4C(=O)CCC45COC5)cc3)c2Cl)C(=O)N1] |
| 356 | 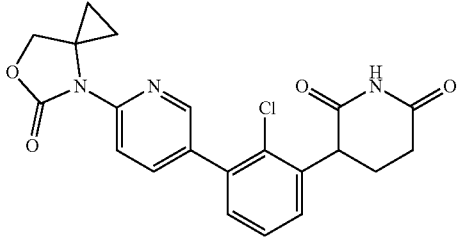 [SMILES: O=C1CCC(c2cccc(-c3ccc(N4C(=O)OCC45CC5)nc3)c2Cl)C(=O)N1] |
| 357 | 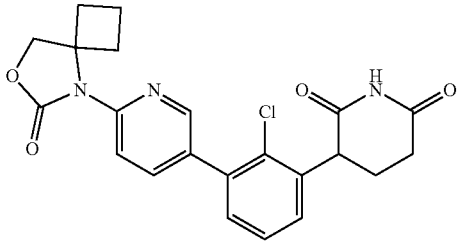 [SMILES: O=C1CCC(c2cccc(-c3ccc(N4C(=O)OCC45CCC5)nc3)c2Cl)C(=O)N1] |
| 358 | 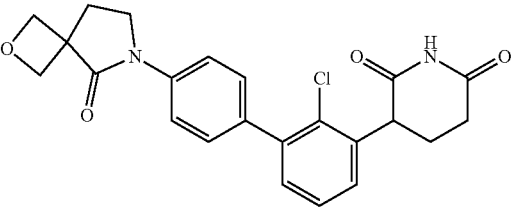 [SMILES: O=C1CCC(c2cccc(-c3ccc(N4CCC5(COC5)C4=O)cc3)c2Cl)C(=O)N1] |
| 359 | 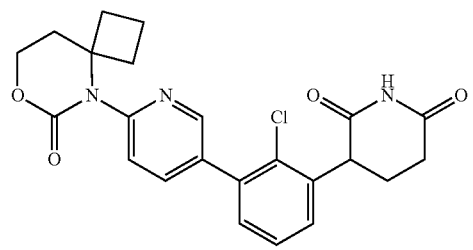 [SMILES: O=C1CCC(c2cccc(-c3ccc(N4C(=O)OCCC45CCC5)nc3)c2Cl)C(=O)N1] |

TABLE C1-continued

| Compound No. | Structure |
|---|---|
| 360 | 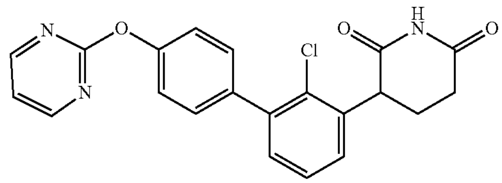 [SMILES: O=C1CCC(c2cccc(-c3ccc(Oc4ncccn4)cc3)c2Cl)C(=O)N1] |
| 361 | 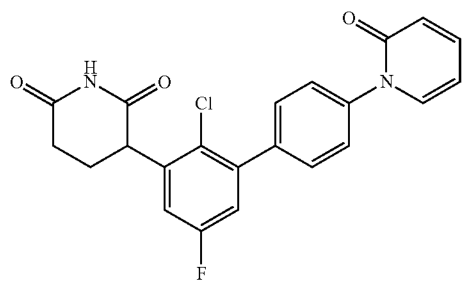 [SMILES: O=C1CCC(c2cc(F)cc(-c3ccc(-n4ccccc4=O)cc3)c2Cl)C(=O)N1] |
| 362 | 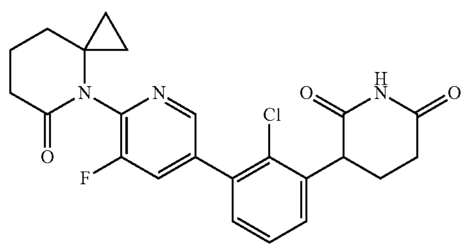 [SMILES: O=C1CCC(c2cccc(-c3cnc(N4C(=O)CCCC45CC5)c(F)c3)c2Cl)C(=O)N1] |
| 363 | 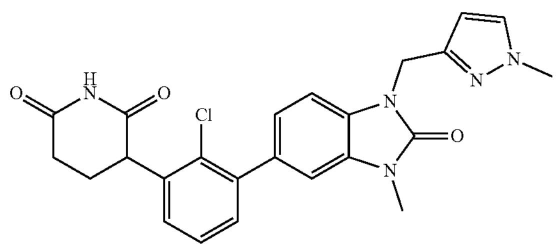 [SMILES: Cn1ccc(Cn2c(=O)n(C)c3cc(-c4cccc(C5CCC(=O)NC5=O)c4Cl)ccc32)n1] |
| 364 | 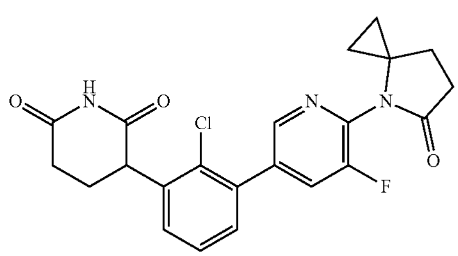 [SMILES: O=C1CCC(c2cccc(-c3cnc(N4C(=O)CCC45CC5)c(F)c3)c2Cl)C(=O)N1] |
| 365 | 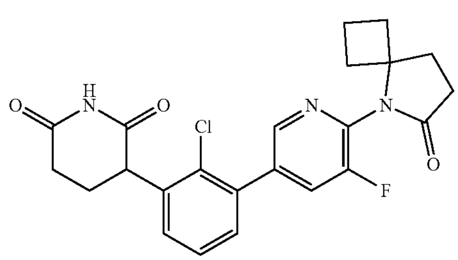 [SMILES: O=C1CCC(c2cccc(-c3cnc(N4C(=O)CCC45CCC5)c(F)c3)c2Cl)C(=O)N1] |

TABLE C1-continued
| Compound No. | Structure |
|---|---|
| 366 | 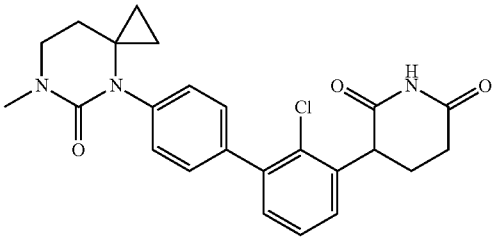 [SMILES: CN1CCC2(CC2)N(c2ccc(-c3cccc(C4CCC(=O)NC4=O)c3Cl)cc2)C1=O] |
| 367 | 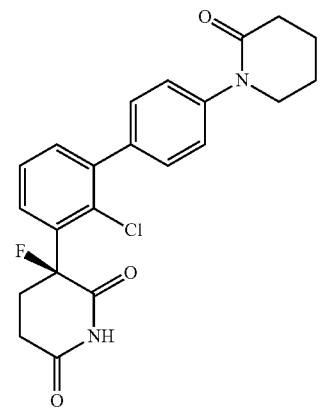 [SMILES: O=C1CC[C@](F)(c2cccc(-c3ccc(N4CCCCC4=O)cc3)c2Cl)C(=O)N1] |
| 368 | 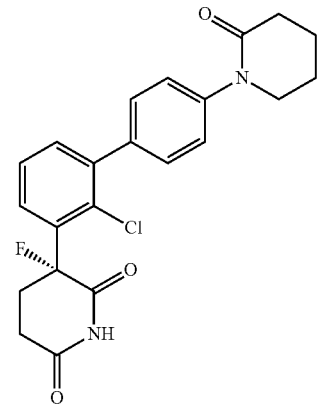 [SMILES: O=C1CC[C@@](F)(c2cccc(-c3ccc(N4CCCCC4=O)cc3)c2Cl)C(=O)N1] |
| 369 | 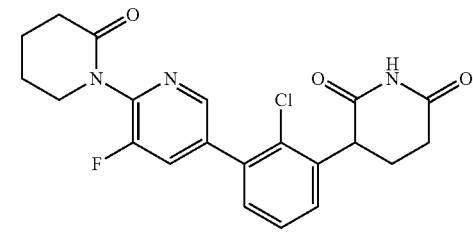 [SMILES: O=C1CCC(c2cccc(-c3cnc(N4CCCCC4=O)c(F)c3)c2Cl)C(=O)N1] |
| 370 | 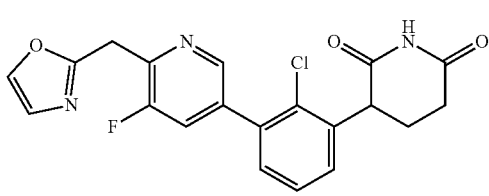 [SMILES: O=C1CCC(c2cccc(-c3cnc(Cc4ncco4)c(F)c3)c2Cl)C(=O)N1] |

TABLE C1-continued
| Compound No. | Structure |
| --- | --- |
| 371 | 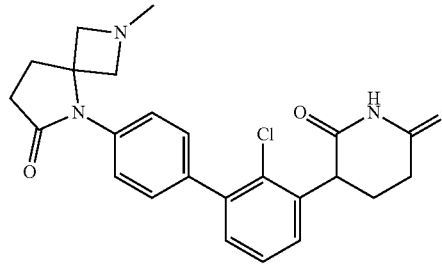 |
| 372 | 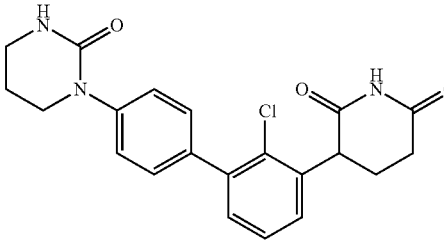 |
| 373 | 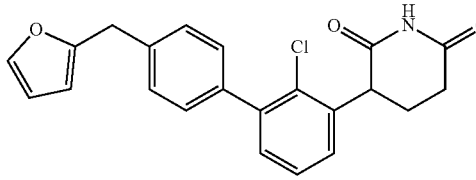 |
| 374 | 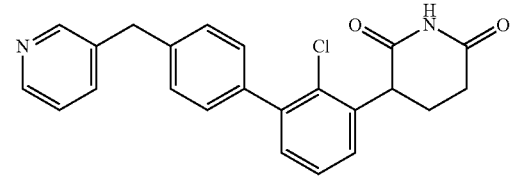 [SMILES: O=C1CCC(c2cccc(-c3ccc(Cc4cccnc4)cc3)c2Cl)C(=O)N1] |
| 375 | 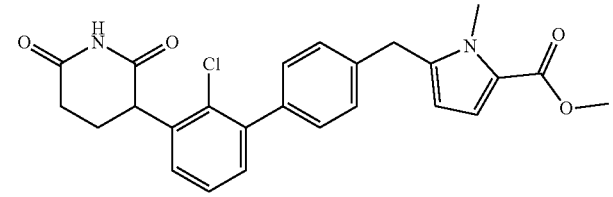 [SMILES: COC(=O)c1ccc(Cc2ccc(-c3cccc(C4CCC(=O)NC4=O)c3Cl)cc2)n1C] |
| 376 | 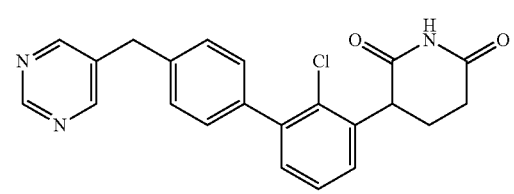 [SMILES: O=C1CCC(c2cccc(-c3ccc(Cc4cncnc4)cc3)c2Cl)C(=O)N1] |
| 377 | 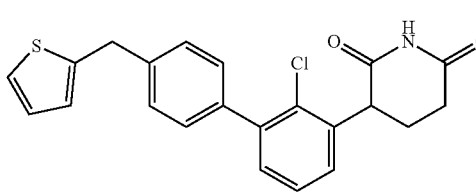 |

TABLE C1-continued

| Compound No. | Structure |
|---|---|
| 378 | 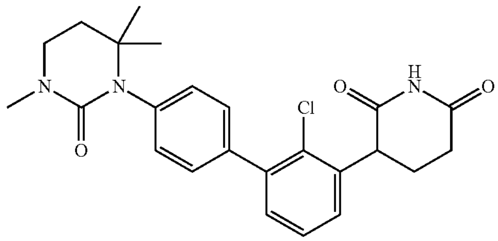 [SMILES: CN1CCC(C)(C)N(c2ccc(-c3cccc(C4CCC(=O)NC4=O)c3Cl)cc2)C1=O] |
| 379 | 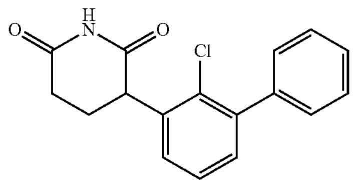 [SMILES: O=C1CCC(c2cccc(-c3ccccc3)c2Cl)C(=O)N1] |
| 380 | 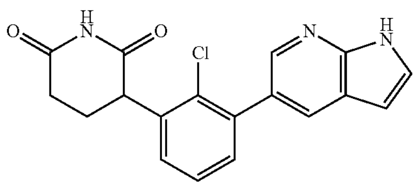 [SMILES: O=C1CCC(c2cccc(-c3cnc4[nH]ccc4c3)c2Cl)C(=O)N1] |
| 381 | 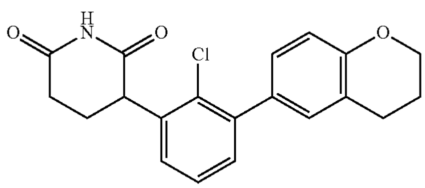 [SMILES: O=C1CCC(c2cccc(-c3ccc4c(c3)CCCO4)c2Cl)C(=O)N1] |
| 382 | 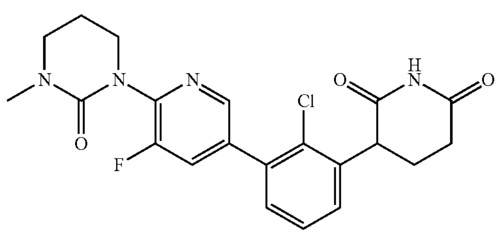 [SMILES: CN1CCCN(c2ncc(-c3cccc(C4CCC(=O)NC4=O)c3Cl)cc2F)C1=O] |
| 383 | 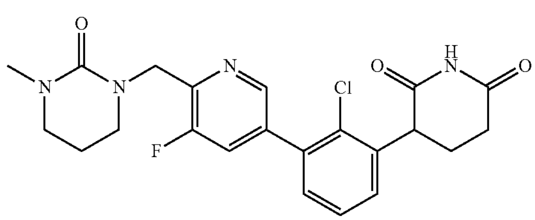 [SMILES: CN1CCCN(Cc2ncc(-c3cccc(C4CCC(=O)NC4=O)c3Cl)cc2F)C1=O] |
| 384 | 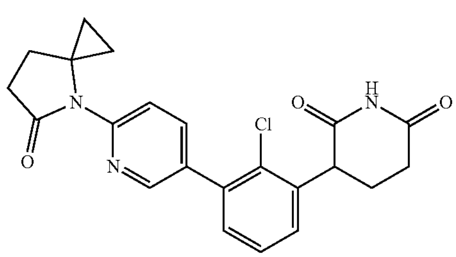 [SMILES: O=C1CCC(c2cccc(-c3ccc(N4C(=O)CCC45CC5)nc3)c2Cl)C(=O)N1] |

TABLE C1-continued
| Compound No. | Structure |
|---|---|
| 385 | 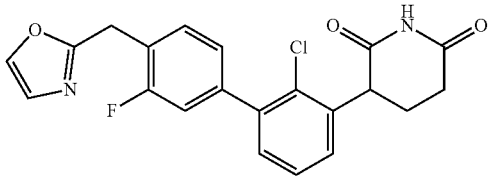 [SMILES: O=C1CCC(c2cccc(-c3ccc(Cc4ncco4)c(F)c3)c2Cl)C(=O)N1] |
| 386 | 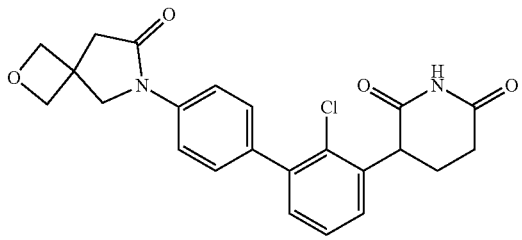 [SMILES: O=C1CCC(c2cccc(-c3ccc(N4CC5(COC5)CC4=O)cc3)c2Cl)C(=O)N1] |
| 387 | 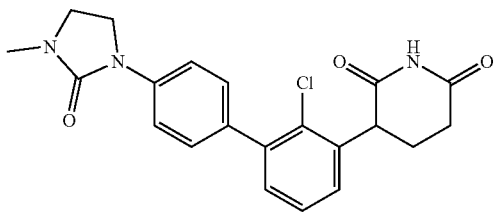 |
| 388 | 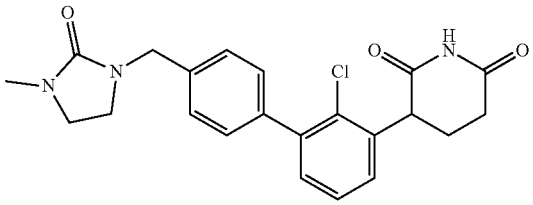 [SMILES: CN1CCN(Cc2ccc(-c3cccc(C4CCC(=O)NC4=O)c3Cl)cc2)C1=O] |
| 389 | 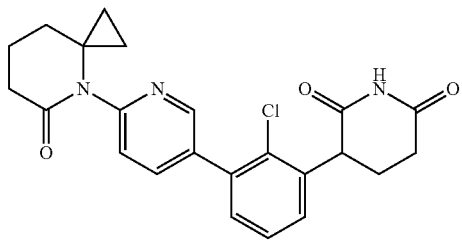 [SMILES: O=C1CCC(c2cccc(-c3ccc(N4C(=O)CCCC45CC5)nc3)c2Cl)C(=O)N1] |
| 390 | 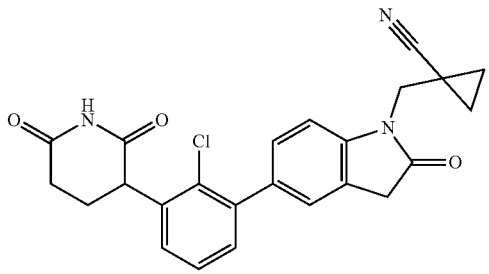 [SMILES: N#CC1(CN2C(=O)Cc3cc(-c4cccc(C5CCC(=O)NC5=O)c4Cl)ccc32)CC1] |

TABLE C1-continued

| Compound No. | Structure |
|---|---|
| 391 | 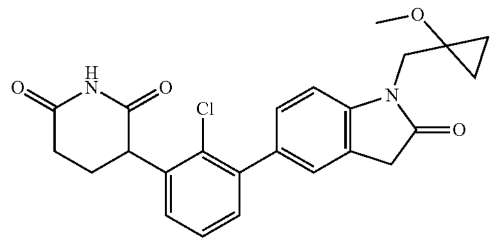 [SMILES: COC1(CN2C(=O)Cc3cc(-c4cccc(C5CCC(=O)NC5=O)c4Cl)ccc32)CC1] |
| 392 | 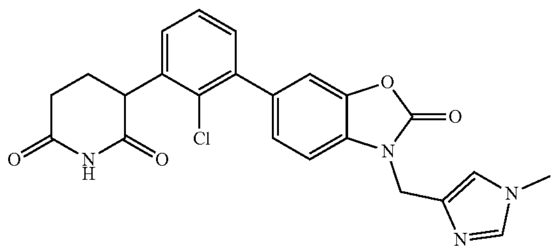 [SMILES: Cn1cnc(Cn2c(=O)oc3cc(-c4cccc(C5CCC(=O)NC5=O)c4Cl)ccc32)c1] |
| 393 | 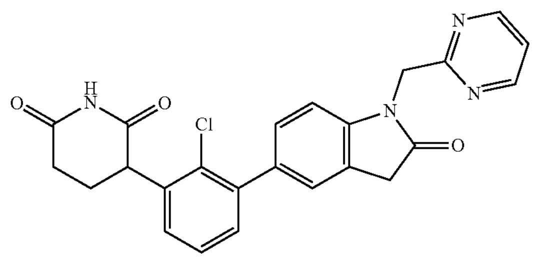 [SMILES: O=C1CCC(c2cccc(-c3ccc4c(c3)CC(=O)N4Cc3ncccn3)c2Cl)C(=O)N1] |
| 394 | 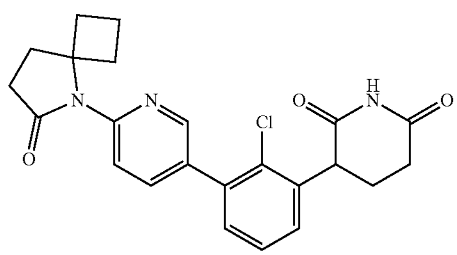 [SMILES: O=C1CCC(c2cccc(-c3ccc(N4C(=O)CCC45CCC5)nc3)c2Cl)C(=O)N1] |
| 395 | 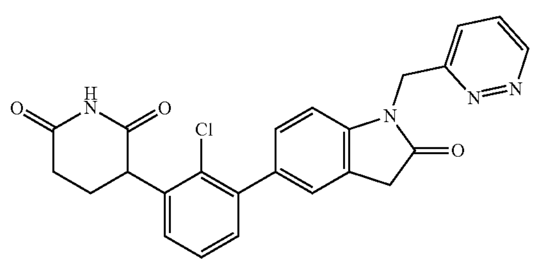 [SMILES: O=C1CCC(c2cccc(-c3ccc4c(c3)CC(=O)N4Cc3cccnn3)c2Cl)C(=O)N1] |
| 396 | 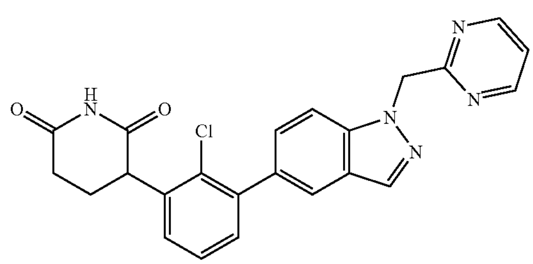 [SMILES: O=C1CCC(c2cccc(-c3ccc4c(cnn4Cc4ncccn4)c3)c2Cl)C(=O)N1] |

TABLE C1-continued
| Compound No. | Structure |
|---|---|
| 397 | 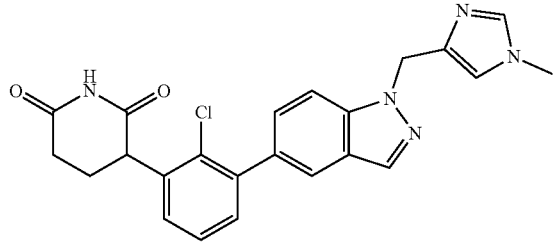 [SMILES: Cn1cnc(Cn2ncc3cc(-c4cccc(C5CCC(=O)NC5=O)c4Cl)ccc32)c1] |
| 398 | 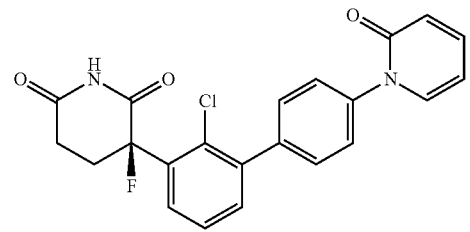 [SMILES: O=C1CC[C@@](F)(c2cccc(-c3ccc(-n4ccccc4=O)cc3)c2Cl)C(=O)N1] |
| 399 | 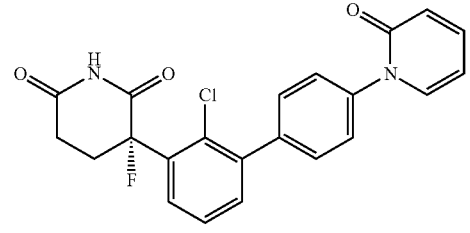 [SMILES: O=C1CC[C@](F)(c2cccc(-c3ccc(-n4ccccc4=O)cc3)c2Cl)C(=O)N1] |
| 400 | 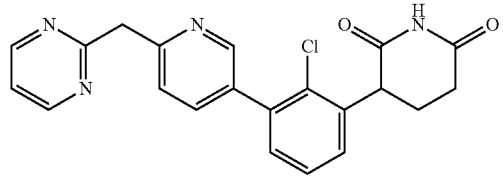 [SMILES: O=C1CCC(c2cccc(-c3ccc(Cc4ncccn4)nc3)c2Cl)C(=O)N1] |
| 401 | 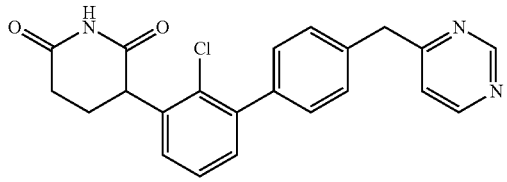 [SMILES: O=C1CCC(c2cccc(-c3ccc(Cc4ccncn4)cc3)c2Cl)C(=O)N1] |
| 402 | 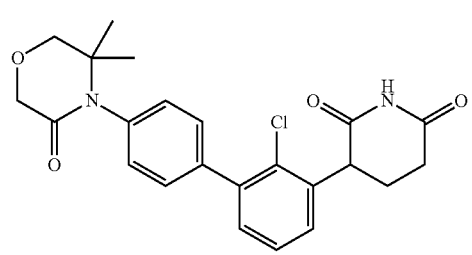 [SMILES: CC1(C)COCC(=O)N1c1ccc(-c2cccc(C3CCC(=O)NC3=O)c2Cl)cc1] |
| 403 | 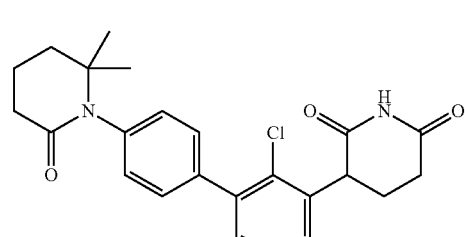 |

TABLE C1-continued

| Compound No. | Structure |
| --- | --- |
| 404 | 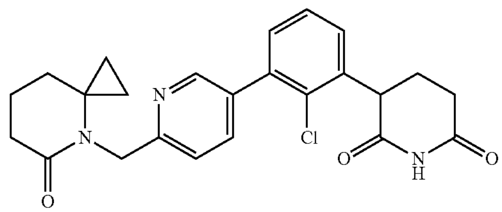 [SMILES: O=C1CCC(c2cccc(-c3ccc(CN4C(=O)CCCC45CC5)nc3)c2Cl)C(=O)N1] |
| 405 | 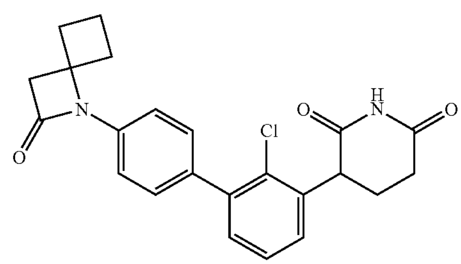 [SMILES: O=C1CCC(c2cccc(-c3ccc(N4C(=O)CC45CCC5)cc3)c2Cl)C(=O)N1] |
| 406 | 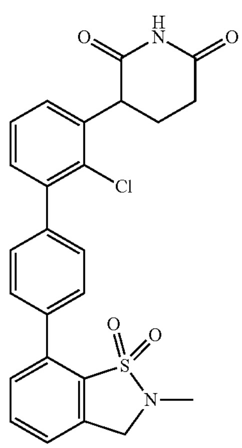 [SMILES: CN1Cc2cccc(-c3ccc(-c4cccc(C5CCC(=O)NC5=O)c4Cl)cc3)c2S1(=O)=O] |
| 407 | 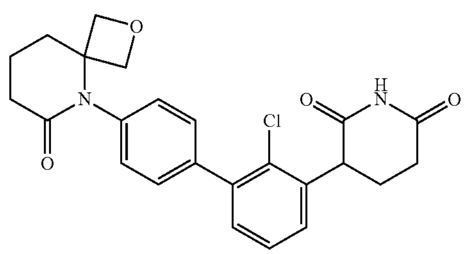 [SMILES: O=C1CCC(c2cccc(-c3ccc(N4C(=O)CCCC45COC5)cc3)c2Cl)C(=O)N1] |
| 408 | 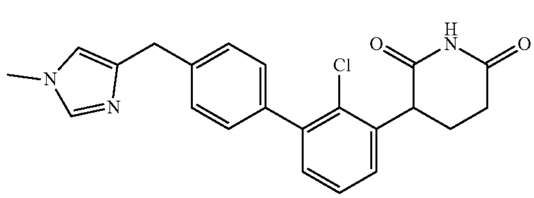 [SMILES: Cn1cnc(Cc2ccc(-c3cccc(C4CCC(=O)NC4=O)c3Cl)cc2)c1] |

TABLE C1-continued

| Compound No. | Structure |
|---|---|
| 409 | 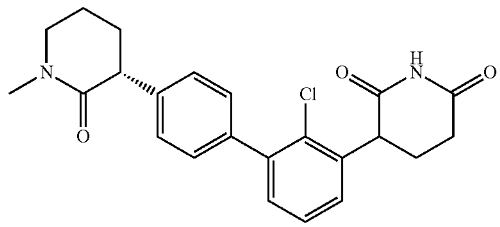 [SMILES: CN1CCC[C@H](c2ccc(-c3cccc(C4CCC(=O)NC4=O)c3Cl)cc2)C1=O] |
| 410 | 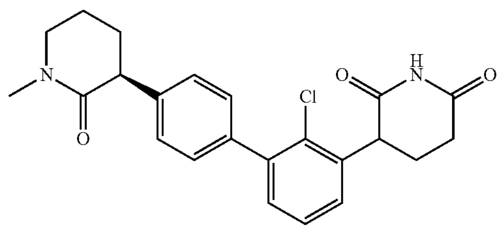 [SMILES: CN1CCC[C@@H](c2ccc(-c3cccc(C4CCC(=O)NC4=O)c3Cl)cc2)C1=O] |
| 411 | 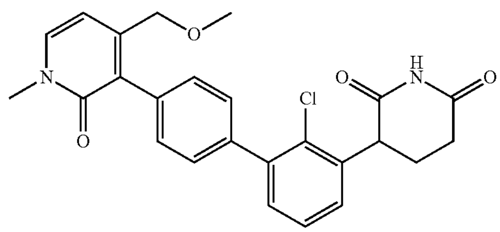 [SMILES: COCc1ccn(C)c(=O)c1-c1ccc(-c2cccc(C3CCC(=O)NC3=O)c2Cl)cc1] |
| 412 | 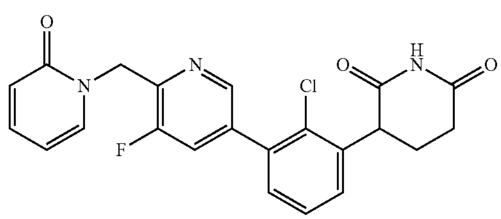 [SMILES: O=C1CCC(c2cccc(-c3cnc(Cn4ccccc4=O)c(F)c3)c2Cl)C(=O)N1] |
| 413 | 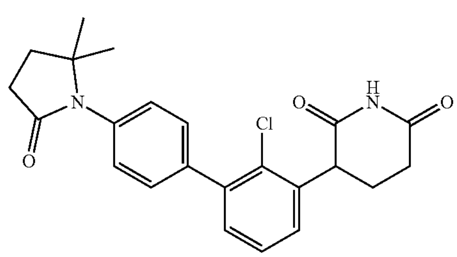 [SMILES: CC1(C)CCC(=O)N1c1ccc(-c2cccc(C3CCC(=O)NC3=O)c2Cl)cc1] |
| 414 | 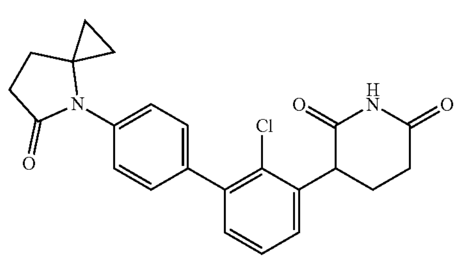 |

TABLE C1-continued

| Compound No. | Structure |
|---|---|
| 415 | 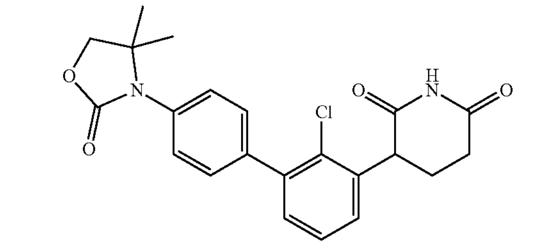 [SMILES: CC1(C)COC(=O)N1c1ccc(-c2cccc(C3CCC(=O)NC3=O)c2Cl)cc1] |
| 416 | 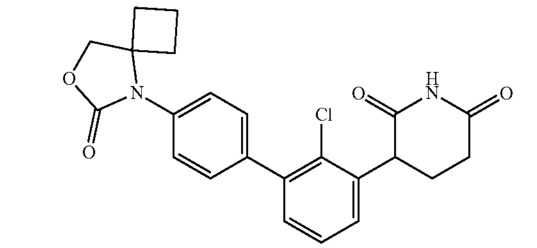 [SMILES: O=C1CCC(c2cccc(-c3ccc(N4C(=O)OCC45CCC5)cc3)c2Cl)C(=O)N1] |
| 417 | 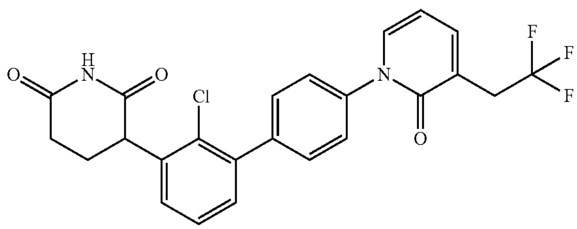 [SMILES: O=C1CCC(c2cccc(-c3ccc(-n4cccc(CC(F)(F)F)c4=O)cc3)c2Cl)C(=O)N1] |
| 418 | 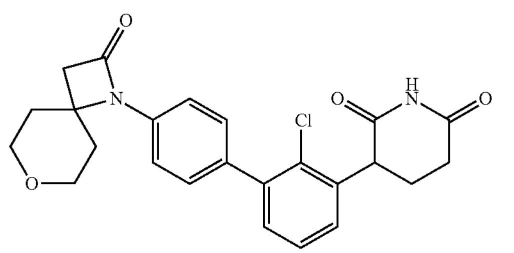 [SMILES: O=C1CCC(c2cccc(-c3ccc(N4C(=O)CC45CCOCC5)cc3)c2Cl)C(=O)N1] |
| 419 | 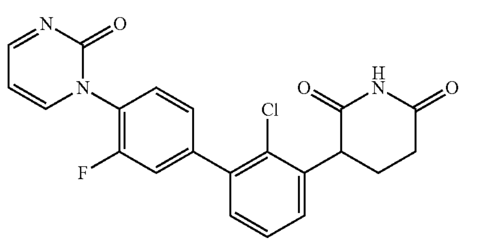 [SMILES: O=C1CCC(c2cccc(-c3ccc(-n4cccnc4=O)c(F)c3)c2Cl)C(=O)N1] |
| 420 | 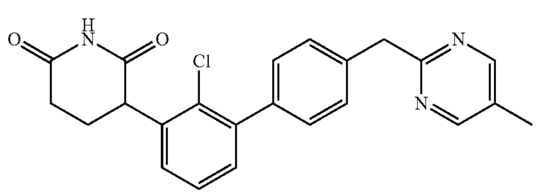 [SMILES: Cc1cnc(Cc2ccc(-c3cccc(C4CCC(=O)NC4=O)c3Cl)cc2)nc1] |
| 421 | 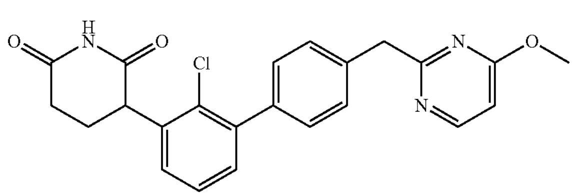 [SMILES: COc1ccnc(Cc2ccc(-c3cccc(C4CCC(=O)NC4=O)c3Cl)cc2)n1] |

TABLE C1-continued

| Compound No. | Structure |
|---|---|
| 422 | 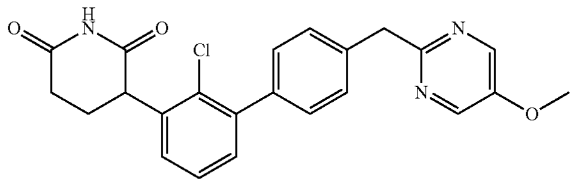 [SMILES: COc1cnc(Cc2ccc(-c3cccc(C4CCC(=O)NC4=O)c3Cl)cc2)nc1] |
| 423 | 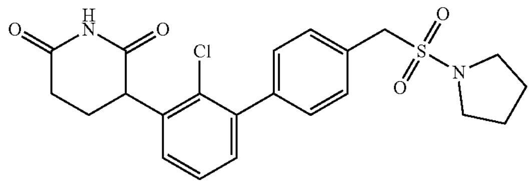 [SMILES: O=C1CCC(c2cccc(-c3ccc(CS(=O)(=O)N4CCCC4)cc3)c2Cl)C(=O)N1] |
| 424 | 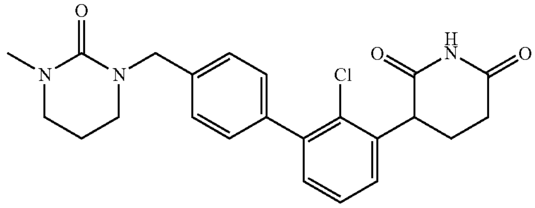 [SMILES: CN1CCCN(Cc2ccc(-c3cccc(C4CCC(=O)NC4=O)c3Cl)cc2)C1=O] |
| 425 | 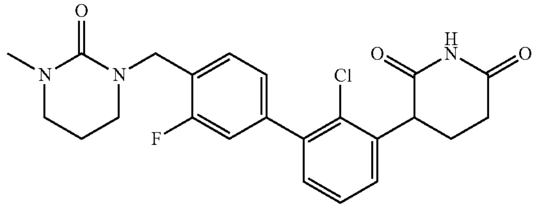 [SMILES: CN1CCCN(Cc2ccc(-c3cccc(C4CCC(=O)NC4=O)c3Cl)cc2F)C1=O] |
| 426 | 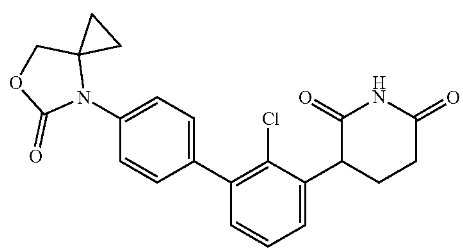 [SMILES: O=C1CCC(c2cccc(-c3ccc(N4C(=O)OCC45CC5)cc3)c2Cl)C(=O)N1] |
| 427 | 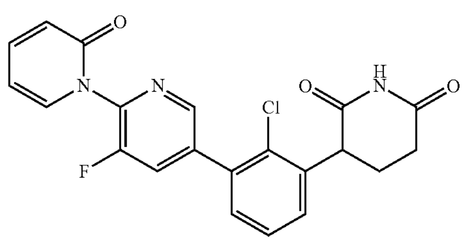 |
| 428 | 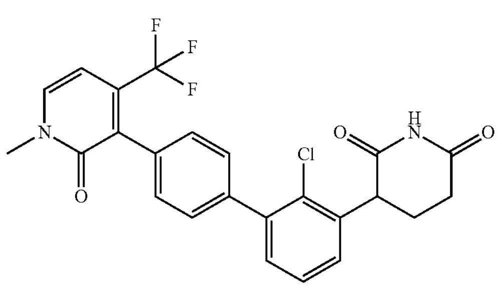 [SMILES: Cn1ccc(C(F)(F)F)c(-c2ccc(-c3cccc(C4CCC(=O)NC4=O)c3Cl)cc2)c1=O] |

US 12,257,247 B2
TABLE C1-continued
| Compound No. | Structure |
| --- | --- |
| 429 | 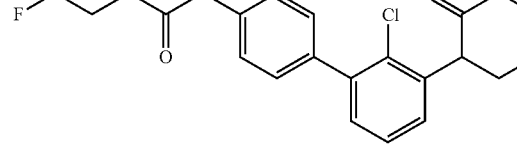 |
| 430 | 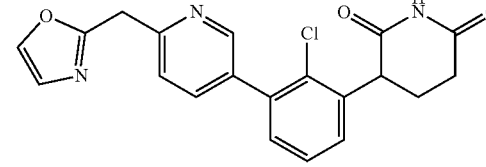 |
| 431 | 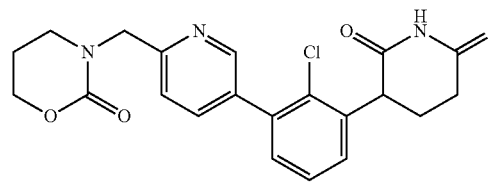 |
| 432 | 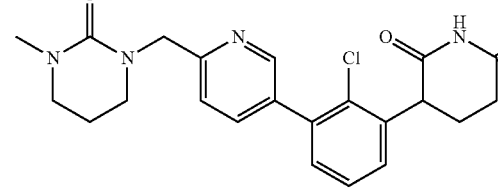 |
| 433 | 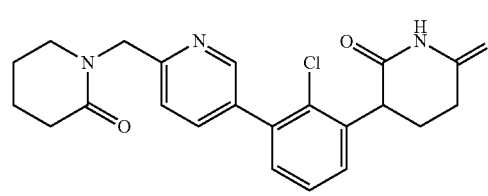 |
| 434 | 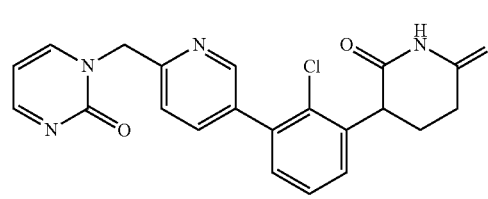 |
| 435 | 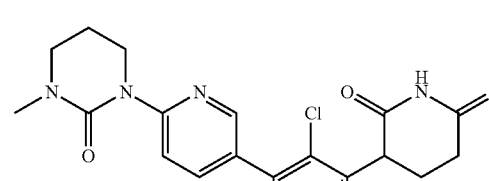 |

TABLE C1-continued

| Compound No. | Structure |
|---|---|
| 436 | 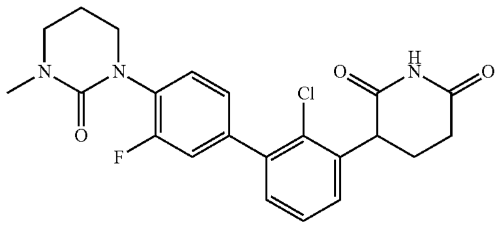 [SMILES: CN1CCCN(c2ccc(-c3cccc(C4CCC(=O)NC4=O)c3Cl)cc2F)C1=O] |
| 437 | 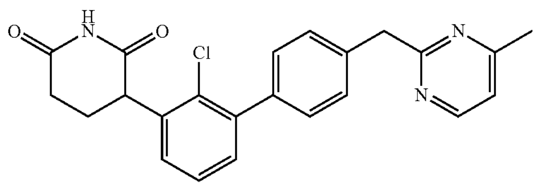 [SMILES: Cc1ccnc(Cc2ccc(-c3cccc(C4CCC(=O)NC4=O)c3Cl)cc2)n1] |
| 438 | 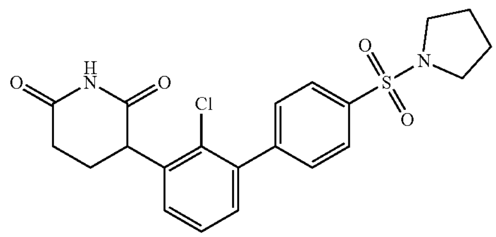 [SMILES: O=C1CCC(c2cccc(-c3ccc(S(=O)(=O)N4CCCC4)cc3)c2Cl)C(=O)N1] |
| 439 | 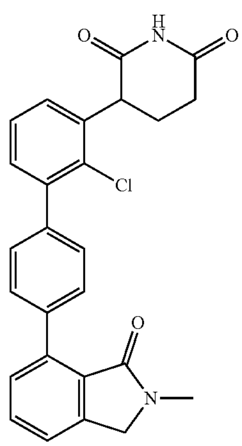 [SMILES: CN1Cc2cccc(-c3ccc(-c4cccc(C5CCC(=O)NC5=O)c4Cl)cc3)c2C1=O] |
| 440 | 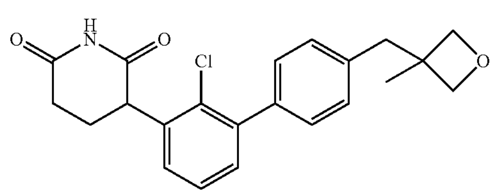 [SMILES: CC1(Cc2ccc(-c3cccc(C4CCC(=O)NC4=O)c3Cl)cc2)COC1] |
| 441 | 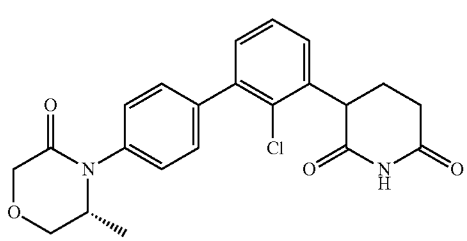 [SMILES: C[C@@H]1COCC(=O)N1c1ccc(-c2cccc(C3CCC(=O)NC3=O)c2Cl)cc1] |

TABLE C1-continued

| Compound No. | Structure |
|---|---|
| 442 | 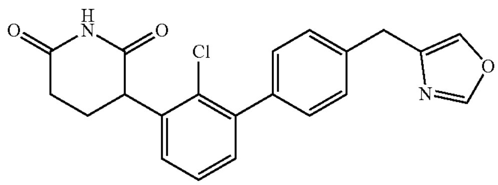 [SMILES: O=C1CCC(c2cccc(-c3ccc(Cc4cocn4)cc3)c2Cl)C(=O)N1] |
| 443 | 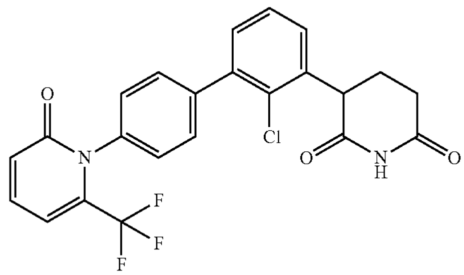 [SMILES: O=C1CCC(c2cccc(-c3ccc(-n4c(C(F)(F)F)cccc4=O)cc3)c2Cl)C(=O)N1] |
| 444 | 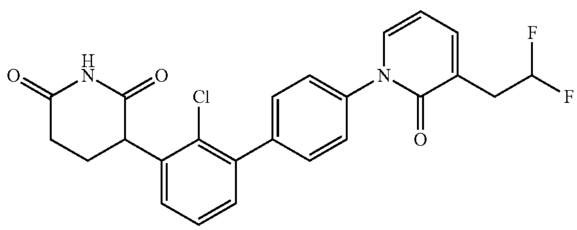 [SMILES: O=C1CCC(c2cccc(-c3ccc(-n4cccc(CC(F)F)c4=O)cc3)c2Cl)C(=O)N1] |
| 445 | 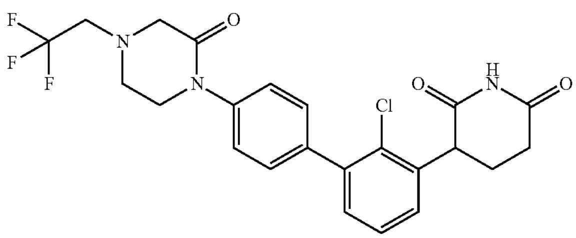 [SMILES: O=C1CCC(c2cccc(-c3ccc(N4CCN(CC(F)(F)F)CC4=O)cc3)c2Cl)C(=O)N1] |
| 446 | 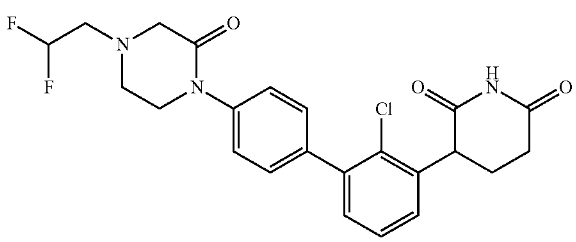 [SMILES: O=C1CCC(c2cccc(-c3ccc(N4CCN(CC(F)F)CC4=O)cc3)c2Cl)C(=O)N1] |
| 447 | 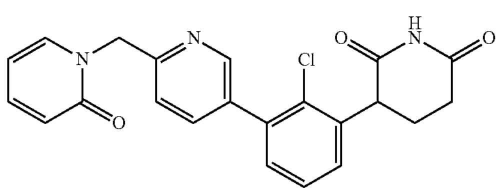 [SMILES: O=C1CCC(c2cccc(-c3ccc(Cn4ccccc4=O)nc3)c2Cl)C(=O)N1] |
| 448 | 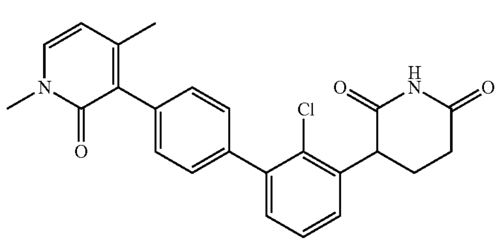 [SMILES: Cc1ccn(C)c(=O)c1-c1ccc(-c2cccc(C3CCC(=O)NC3=O)c2Cl)cc1] |

TABLE C1-continued
| Compound No. | Structure |
|---|---|
| 449 | 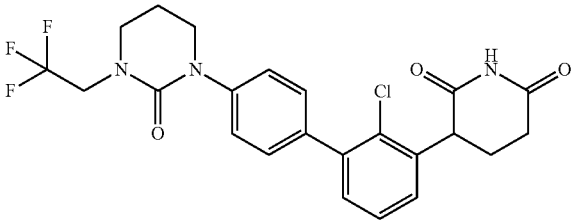 [SMILES: O=C1CCC(c2cccc(-c3ccc(N4CCCN(CC(F)(F)F)C4=O)cc3)c2Cl)C(=O)N1] |
| 450 | 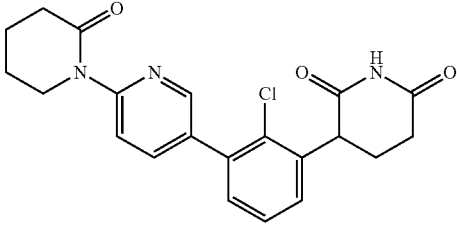 |
| 451 | 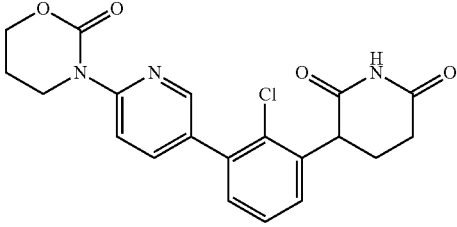 [SMILES: O=C1CCC(c2cccc(-c3ccc(N4CCCCC4=O)nc3)c2Cl)C(=O)N1] |
| 452 | 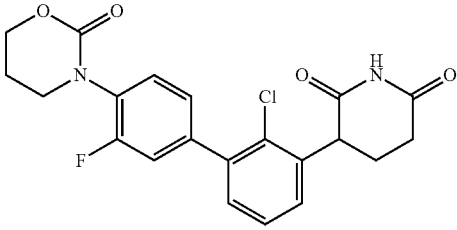 |
| 453 | 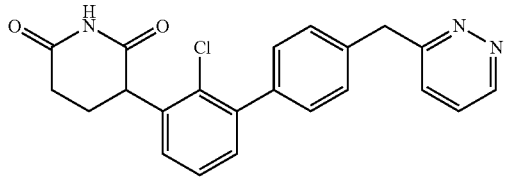 [SMILES: O=C1CCC(c2cccc(-c3ccc(Cc4cccnn4)cc3)c2Cl)C(=O)N1] |
| 454 | 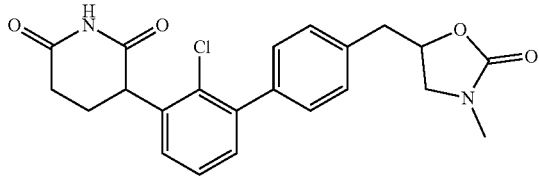 [SMILES: CN1CC(Cc2ccc(-c3cccc(C4CCC(=O)NC4=O)c3Cl)cc2)OC1=O] |
| 455 | 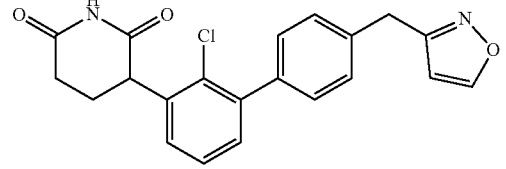 |

TABLE C1-continued
| Compound No. | Structure |
|---|---|
| 456 | 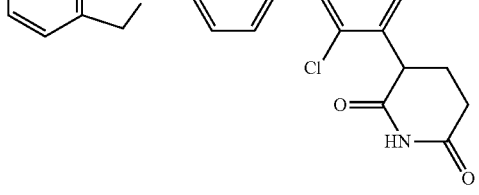 |
| 457 | 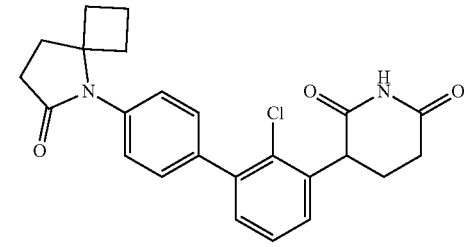 [SMILES: O=C1CCC(c2cccc(-c3ccc(N4C(=O)CCC45CCC5)cc3)c2Cl)C(=O)N1] |
| 458 | 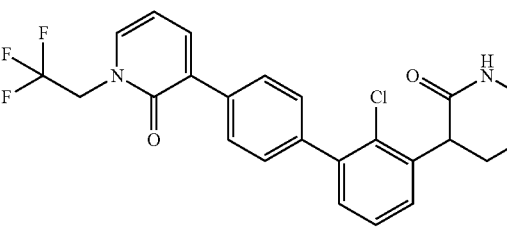 |
| 459 | 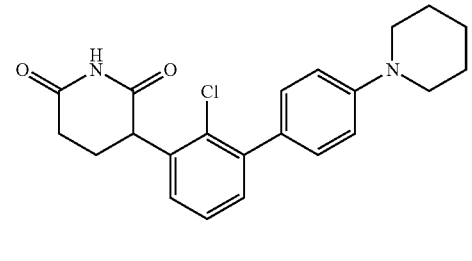 [SMILES: O=C1CCC(c2cccc(-c3ccc(N4CCCCC4)cc3)c2Cl)C(=O)N1] |
| 460 | 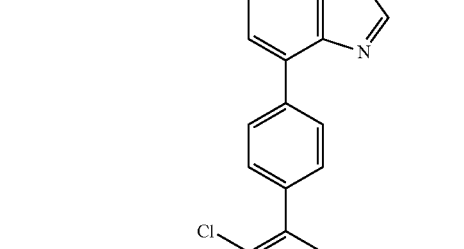 |

TABLE C1-continued

| Compound No. | Structure |
|---|---|
| 461 | 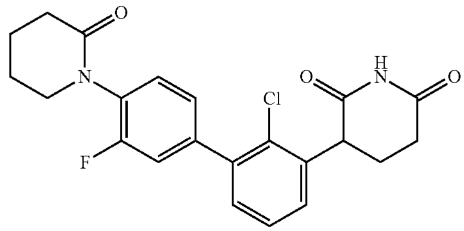 |
| 462 | 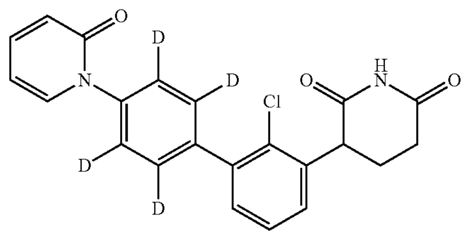 [SMILES: [2H]c1c([2H])c(-n2ccccc2=O)c([2H])c([2H])c1-c1cccc(C2CCC(=O)NC2=O)c1Cl] |
| 463 | 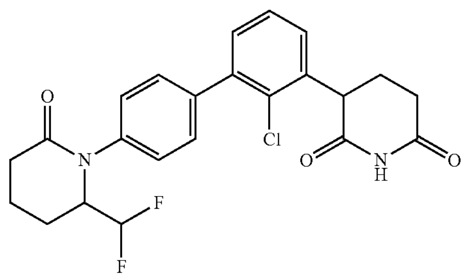 [SMILES: O=C1CCC(c2cccc(-c3ccc(N4C(=O)CCCC4C(F)F)cc3)c2Cl)C(=O)N1] |
| 464 | 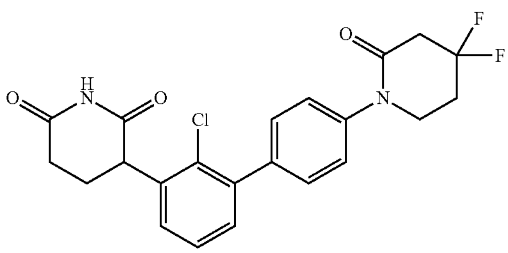 [SMILES: O=C1CCC(c2cccc(-c3ccc(N4CCC(F)(F)CC4=O)cc3)c2Cl)C(=O)N1] |
| 465 | 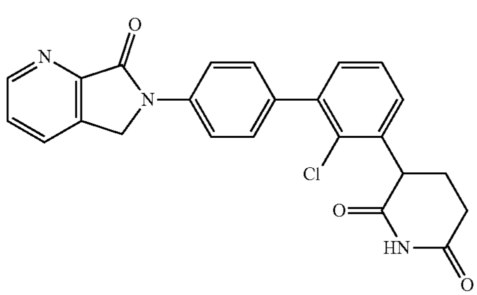 [SMILES: O=C1CCC(c2cccc(-c3ccc(N4Cc5cccnc5C4=O)cc3)c2Cl)C(=O)N1] |
| 466 | 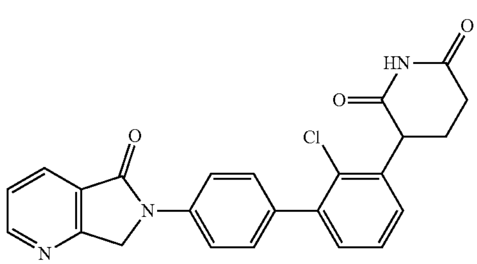 [SMILES: O=C1CCC(c2cccc(-c3ccc(N4Cc5ncccc5C4=O)cc3)c2Cl)C(=O)N1] |

TABLE C1-continued

| Compound No. | Structure |
|---|---|
| 467 | 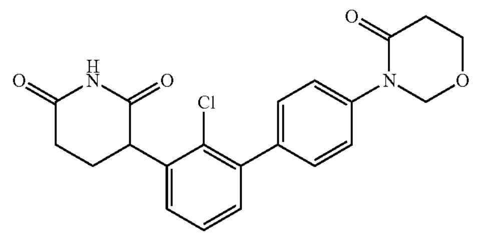 [SMILES: O=C1CCC(c2cccc(-c3ccc(N4COCCC4=O)cc3)c2Cl)C(=O)N1] |
| 468 | 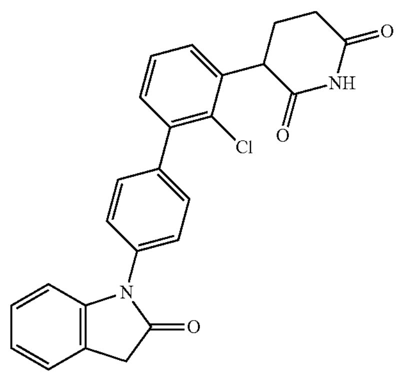 [SMILES: O=C1CCC(c2cccc(-c3ccc(N4C(=O)Cc5ccccc54)cc3)c2Cl)C(=O)N1] |
| 469 | 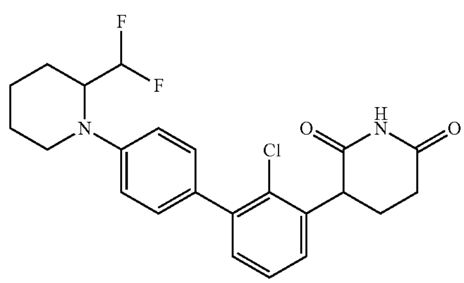 [SMILES: O=C1CCC(c2cccc(-c3ccc(N4CCCCC4C(F)F)cc3)c2Cl)C(=O)N1] |
| 470 | 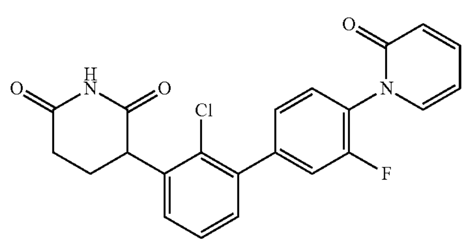 [SMILES: O=C1CCC(c2cccc(-c3ccc(-n4ccccc4=O)c(F)c3)c2Cl)C(=O)N1] |
| 471 | 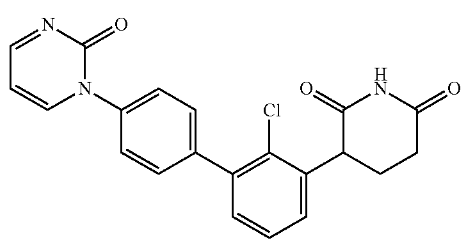 [SMILES: O=C1CCC(c2cccc(-c3ccc(-n4cccnc4=O)cc3)c2Cl)C(=O)N1] |
| 472 | 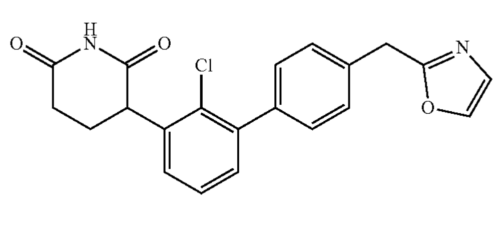 [SMILES: O=C1CCC(c2cccc(-c3ccc(Cc4ncco4)cc3)c2Cl)C(=O)N1] |

TABLE C1-continued

| Compound No. | Structure |
|---|---|
| 473 | 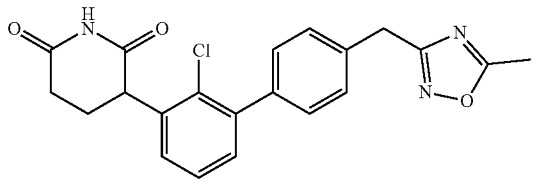 [SMILES: Cc1nc(Cc2ccc(-c3cccc(C4CCC(=O)NC4=O)c3Cl)cc2)no1] |
| 474 | 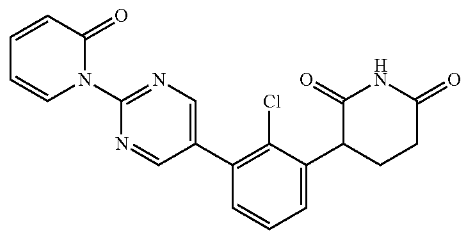 |
| 475 | 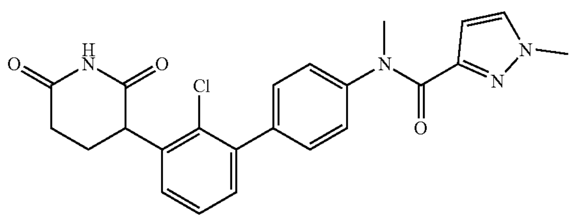 [SMILES: CN(C(=O)c1ccn(C)n1)c1ccc(-c2cccc(C3CCC(=O)NC3=O)c2Cl)cc1] |
| 476 | 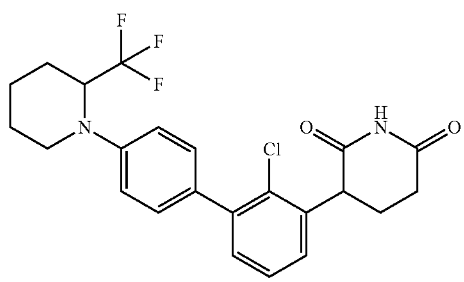 [SMILES: O=C1CCC(c2cccc(-c3ccc(N4CCCCC4C(F)(F)F)cc3)c2Cl)C(=O)N1] |
| 477 | 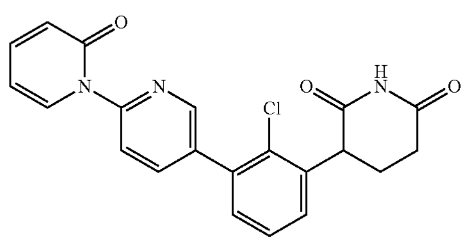 [SMILES: O=C1CCC(c2cccc(-c3ccc(-n4ccccc4=O)nc3)c2Cl)C(=O)N1] |
| 478 | 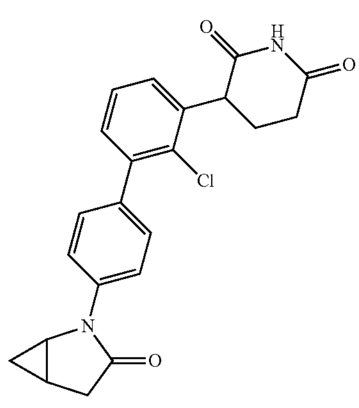 [SMILES: O=C1CCC(c2cccc(-c3ccc(N4C(=O)CC5CC54)cc3)c2Cl)C(=O)N1] |

TABLE C1-continued

| Compound No. | Structure |
|---|---|
| 479 | 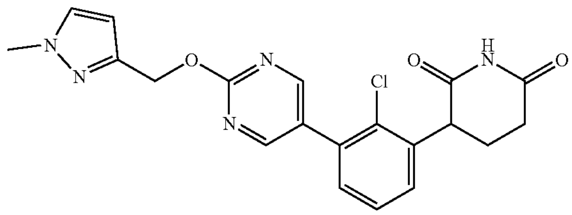 [SMILES: Cn1ccc(COc2ncc(-c3cccc(C4CCC(=O)NC4=O)c3Cl)cn2)n1] |
| 480 | 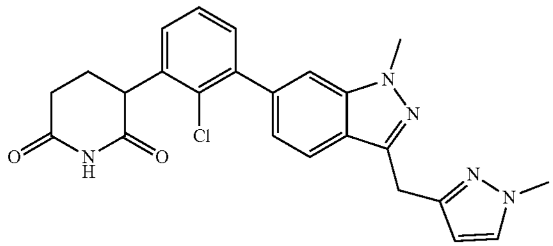 [SMILES: Cn1ccc(Cc2nn(C)c3cc(-c4cccc(C5CCC(=O)NC5=O)c4Cl)ccc23)n1] |
| 481 | 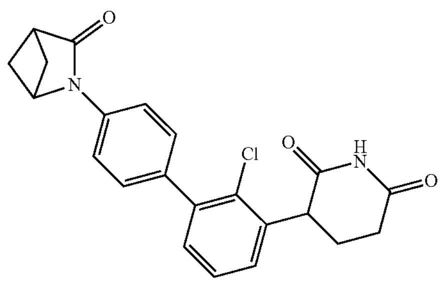 [SMILES: O=C1CCC(c2cccc(-c3ccc(N4C(=O)C5CC4C5)cc3)c2Cl)C(=O)N1] |
| 482 | 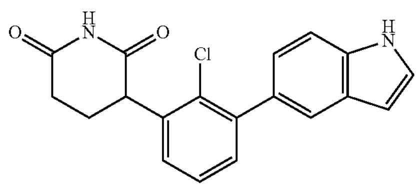 [SMILES: O=C1CCC(c2cccc(-c3ccc4[nH]ccc4c3)c2Cl)C(=O)N1] |
| 483 | 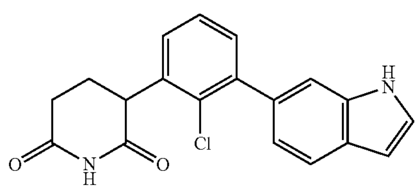 [SMILES: O=C1CCC(c2cccc(-c3ccc4cc[nH]c4c3)c2Cl)C(=O)N1] |
| 484 | 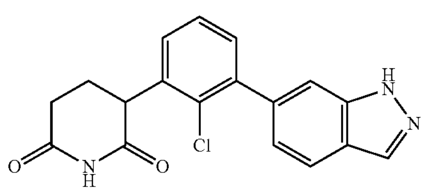 [SMILES: O=C1CCC(c2cccc(-c3ccc4cn[nH]c4c3)c2Cl)C(=O)N1] |
| 485 | 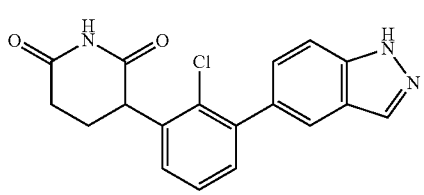 [SMILES: O=C1CCC(c2cccc(-c3ccc4[nH]ncc4c3)c2Cl)C(=O)N1] |

TABLE C1-continued

| Compound No. | Structure |
|---|---|
| 486 | 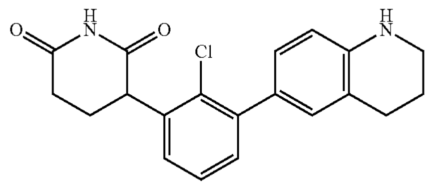 [SMILES: O=C1CCC(c2cccc(-c3ccc4c(c3)CCCN4)c2Cl)C(=O)N1] |
| 487 | 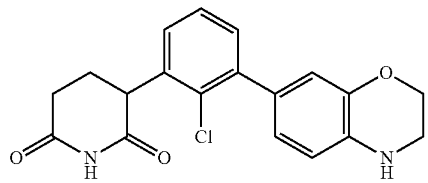 [SMILES: O=C1CCC(c2cccc(-c3ccc4c(c3)OCCN4)c2Cl)C(=O)N1] |
| 488 | 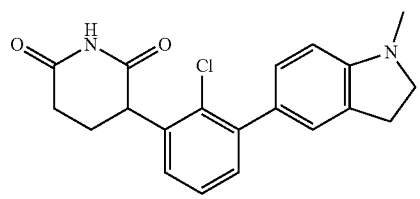 [SMILES: CN1CCc2cc(-c3cccc(C4CCC(=O)NC4=O)c3Cl)ccc21] |
| 489 | 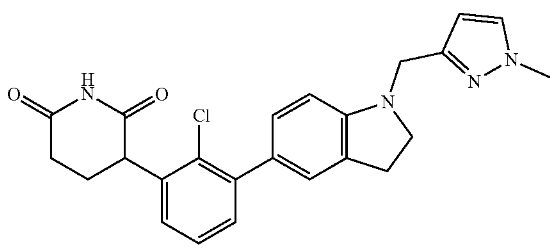 [SMILES: Cn1ccc(CN2CCc3cc(-c4cccc(C5CCC(=O)NC5=O)c4Cl)ccc32)n1] |
| 490 | 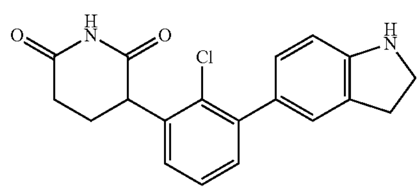 [SMILES: O=C1CCC(c2cccc(-c3ccc4c(c3)CCN4)c2Cl)C(=O)N1] |
| 491 | 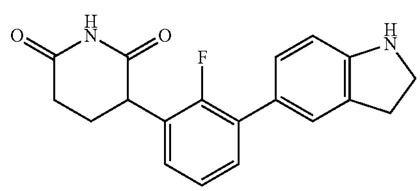 [SMILES: O=C1CCC(c2cccc(-c3ccc4c(c3)CCN4)c2F)C(=O)N1] |
| 492 | 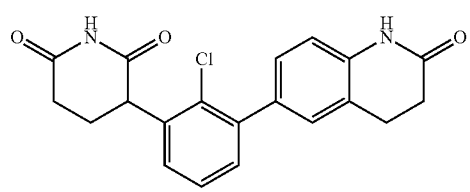 [SMILES: O=C1CCC(c2cccc(-c3ccc4c(c3)CCC(=O)N4)c2Cl)C(=O)N1] |
| 493 | 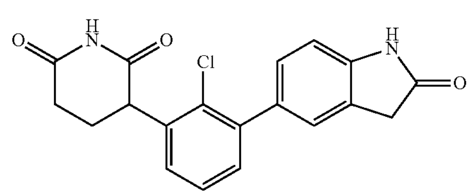 [SMILES: O=C1CCC(c2cccc(-c3ccc4c(c3)CC(=O)N4)c2Cl)C(=O)N1] |

TABLE C1-continued

| Compound No. | Structure |
| --- | --- |
| 494 | 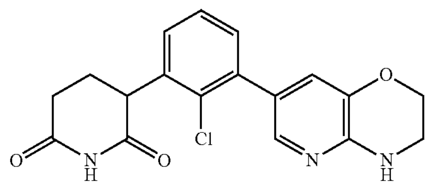 [SMILES: O=C1CCC(c2cccc(-c3cnc4c(c3)OCCN4)c2Cl)C(=O)N1] |
| 495 | 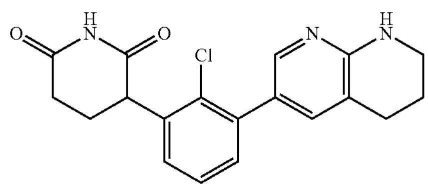 [SMILES: O=C1CCC(c2cccc(-c3cnc4c(c3)CCCN4)c2Cl)C(=O)N1] |
| 496 | 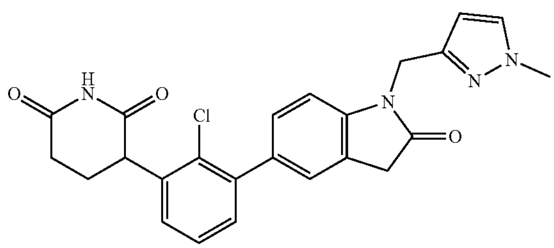 [SMILES: Cn1ccc(CN2C(=O)Cc3cc(-c4cccc(C5CCC(=O)NC5=O)c4Cl)ccc32)n1] |
| 497 | 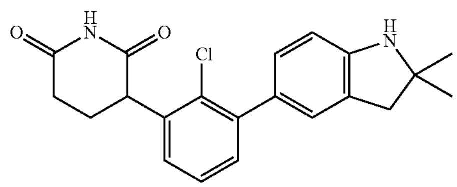 [SMILES: CC1(C)Cc2cc(-c3cccc(C4CCC(=O)NC4=O)c3Cl)ccc2N1] |
| 498 | 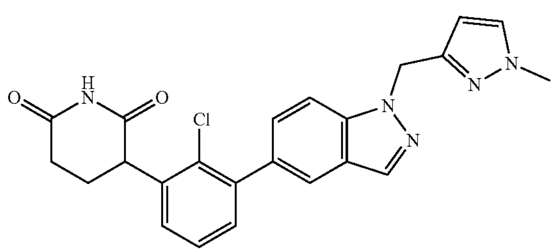 [SMILES: Cn1ccc(Cn2ncc3cc(-c4cccc(C5CCC(=O)NC5=O)c4Cl)ccc32)n1] |
| 499 | 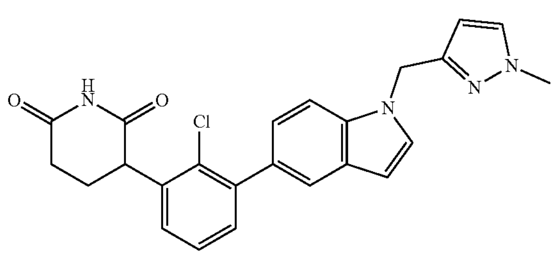 [SMILES: Cn1ccc(Cn2ccc3cc(-c4cccc(C5CCC(=O)NC5=O)c4Cl)ccc32)n1] |
| 500 | 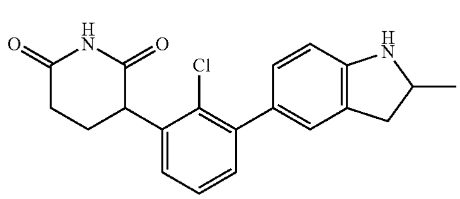 [SMILES: CC1Cc2cc(-c3cccc(C4CCC(=O)NC4=O)c3Cl)ccc2N1] |

TABLE C1-continued

| Compound No. | Structure |
|---|---|
| 501 | 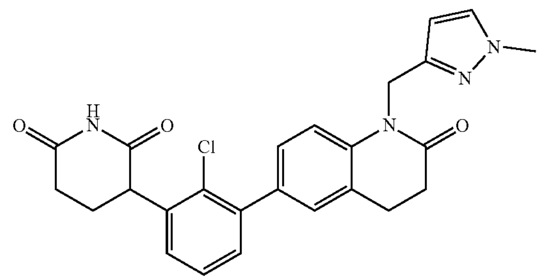 [SMILES: Cn1ccc(CN2C(=O)CCc3cc(-c4cccc(C5CCC(=O)NC5=O)c4Cl)ccc32)n1] |
| 502 | 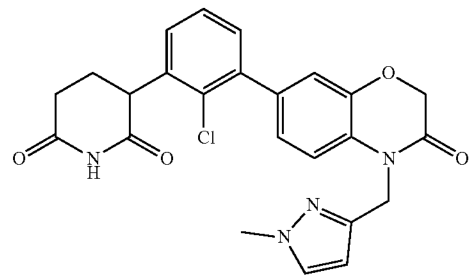 [SMILES: Cn1ccc(CN2C(=O)COc3cc(-c4cccc(C5CCC(=O)NC5=O)c4Cl)ccc32)n1] |
| 503 | 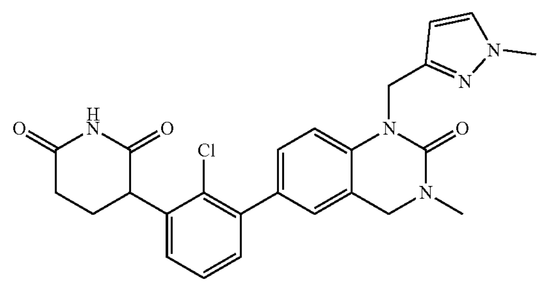 [SMILES: CN1Cc2cc(-c3cccc(C4CCC(=O)NC4=O)c3Cl)ccc2N(Cc2ccn(C)n2)C1=O] |
| 504 | 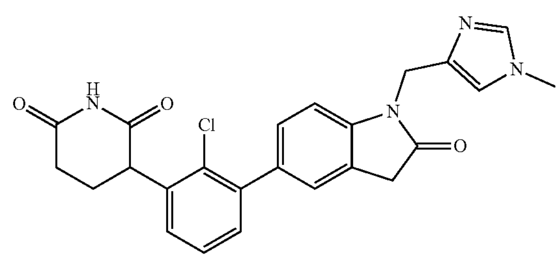 [SMILES: Cn1cnc(CN2C(=O)Cc3cc(-c4cccc(C5CCC(=O)NC5=O)c4Cl)ccc32)c1] |
| 505 | 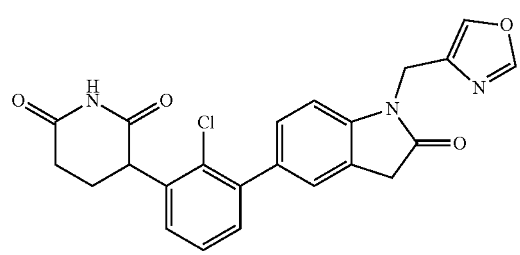 [SMILES: O=C1CCC(c2cccc(-c3ccc4c(c3)CC(=O)N4Cc3cocn3)c2Cl)C(=O)N1] |
| 506 | 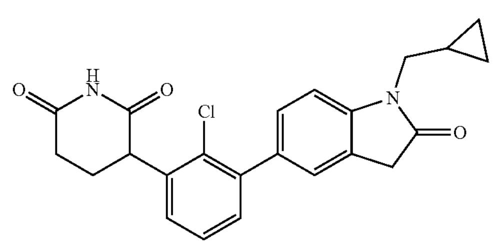 [SMILES: O=C1CCC(c2cccc(-c3ccc4c(c3)CC(=O)N4CC3CC3)c2Cl)C(=O)N1] |

TABLE C1-continued
| Compound No. | Structure |
|---|---|
| 507 | 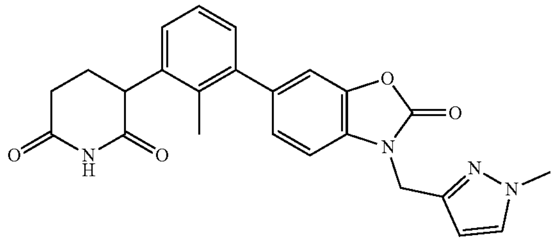 [SMILES: Cc1c(-c2ccc3c(c2)oc(=O)n3Cc2ccn(C)n2)cccc1C1CCC(=O)NC1=O] |
| 508 | 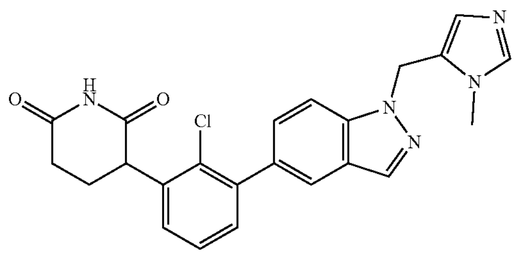 [SMILES: Cn1cncc1Cn1ncc2cc(-c3cccc(C4CCC(=O)NC4=O)c3Cl)ccc21] |
| 509 | 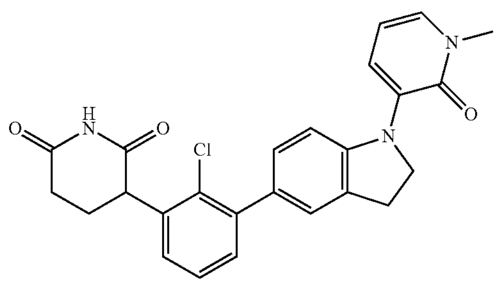 [SMILES: Cn1cccc(N2CCc3cc(-c4cccc(C5CCC(=O)NC5=O)c4Cl)ccc32)c1=O] |
| 510 | 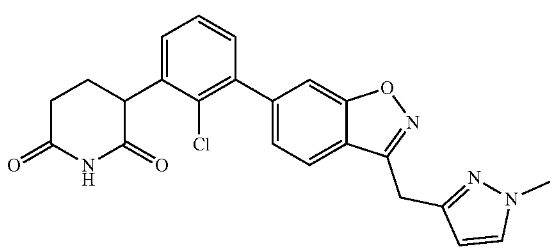 [SMILES: Cn1ccc(Cc2noc3cc(-c4cccc(C5CCC(=O)NC5=O)c4Cl)ccc23)n1] |
General Synthetic Schemes
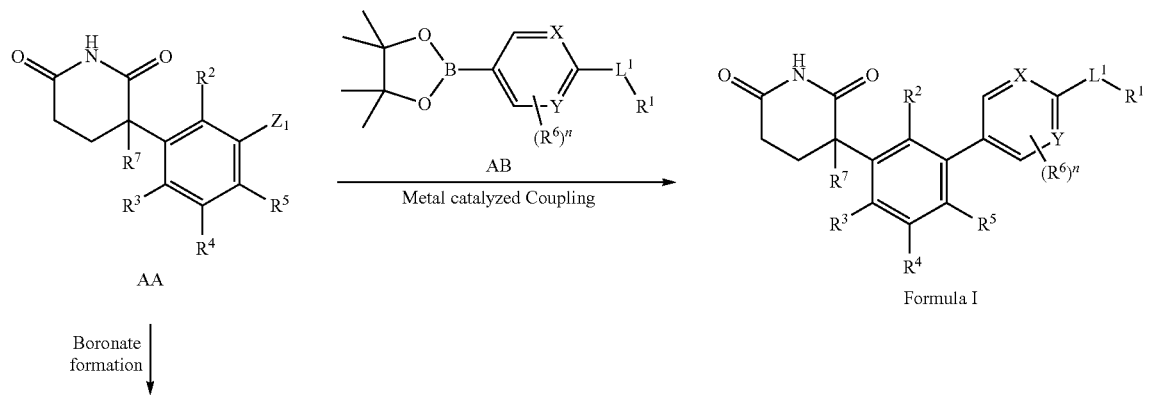
General Scheme 1

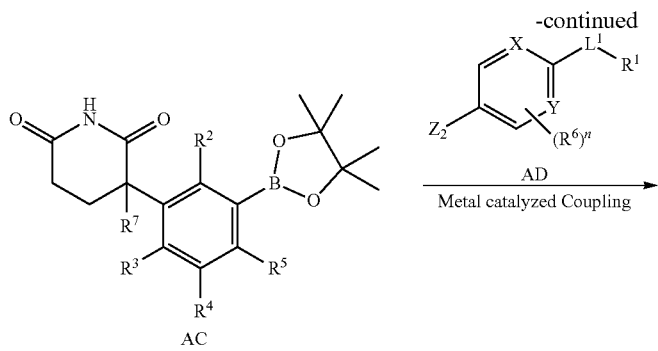

A general synthetic strategy that may be used to prepare compounds of Formula I is depicted in General Scheme 1. An aryl halide AA where $Z_1$ is any suitable halogen (e.g. Br or I) may be coupled with an aryl boronate AB using any suitable metal catalyzed coupling conditions. The specific groups X, Y, $L^1$, $R^1$, $R^2$, $R^3$, $R^4$, $R^5$, $R^6$ and $R^7$ are selected on the basis of the desired groups in the compound of formula I. The desired compound can be prepared using a Suzuki coupling reaction with palladium catalyst complex such as Pd(dtbpf)Cl$_2$(DBTF=1,1'-Bis(di-tert-butylphosphino)ferrocene) or Pd(dppf)Cl$_2$ (dppf=1,1'-Bis(diphenylphosphino)ferrocene) in the presence of a base such as potassium phosphate. A suitable solvent such as DMF (dimethylformamide) or dioxane may be used, or a suitable solvent mixture such as dioxane and water may be used.

Alternatively compounds of formula I may be prepared from reaction of an aryl boronate of formula AC and an aryl halide of formula AD using Suzuki cross-coupling conditions. $Z_2$ is any halide (Br, I, Cl) or triflate group which can be used in a metal catalyzed coupling reaction of AD to boronate AC. The desired compound can be prepared using a Suzuki coupling reaction with a palladium catalyst complex such as APhos Pd G3, Brettphos Pd G3, Pd(dppf)Cl$_2$ or Pd(dppf)Cl$_2$·CH$_2$Cl$_2$ in the presence of a suitable base such as K$_3$PO$_4$. A suitable solvent such as DMF (dimethylformamide) or dioxane may be used, or a suitable solvent mixture such as dioxane and water may be used.

Aryl boronate AC may be prepared from aryl halides AA using Bis(pinacolato)diboron, catalyst such as [Pdcinnamyl Cl]$_2$, and a ligand such as Xphos. A weak base such as sodium acetate, in solvent such as iPrOH may be used. The reaction may be performed at an elevated temperature, for example 60 degrees Celsius, 80 degrees Celsius or 100 degrees Celsius.

General Scheme 2

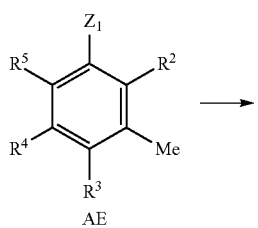

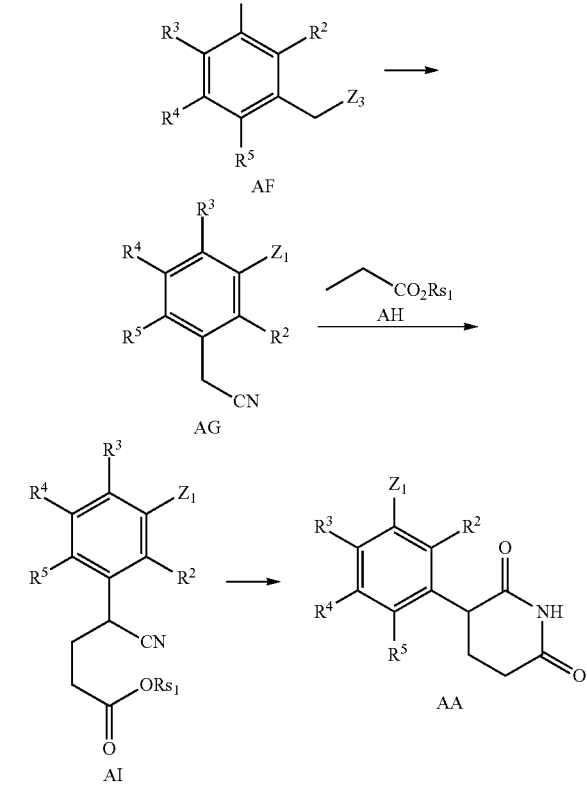

General Scheme 2 provides an exemplary synthetic procedure for the preparation of starting material AA used in General Scheme 1. Compound AE, where $Z_1$ is a suitable halogen atom (e.g. Br or I) may be converted into a benzylic halide of formula AF using conditions for benzylic halogenation. For example, N-bromosuccinimide and benzoyl peroxide in a solvent such as carbon tetrachloride at elevated temperatures (e.g. 80 degrees Celsius or 90 degrees Celsius) affords AF. A benzyl nitrile intermediate such as AG may be prepared from benzyl halide AF upon treatment with a cyanating reagent such as trimethylsilyl cyanide, in the presence of a desilylation reagent such as tert-butyl silyl fluoride or tetra-n-butylammonium fluoride (TBAF) and a solvent such as dichloromethane at a temperature such as 0-25 degrees Celsius.

Micheal addition of a compound of formula AG with an acrylate such as compound AH may be performed using a base such as sodium methoxide in a solvent such as tetrahydrofuran at room temperature. Rs1 is any suitable alkyl group which is labile to treatment with acid. For example, Rs1 may be tert-butyl at a temperature such as 0-25 degrees Celsius.

Compound AI may be converted to intermediate AA upon treatment with a strong acid such as sulfuric acid, in a solvent such as acetic acid, at elevated temperatures (for example, 90 degrees Celsius).

General Scheme 3 provides an alternative exemplary synthetic procedure for the preparation of starting material AA used in General Scheme 1. Compound AJ, where $Z_2$ is a suitable halide leaving group (e.g. fluorine), may be subjected to a nucleophilic aromatic substitution (Hurtley Arylation) with a reagent such as tert-Butyl cyano acetate AK. A solvent such as dimethylacetamide in the presence of a base such as potassium phosphate may be used to afford AL.

Benzyl nitriles of formula AG may be prepared by hydrolysis and decarboxylation of AL upon treatment with an acid such as p-toluene sulfonic acid, in a solvent such as toluene at 120 degrees Celsius.

Benzyl nitrile AG may be converted into AI by a Michael addition reaction to an acrylate reagent such as AH, where Rs1 is an alkyl group which forms an ester. The ester formed by Rs1 must be labile to hydrolysis upon treatment with acid. The Michael addition reaction may be performed by treatment with a base such as sodium methoxide in a solvent such as toluene at zero degrees Celsius.

Compound AA may be prepared from AI by treatment with an acid such as p-toluene sulfonic acid in a solvent such as toluene at elevated temperatures (for example, 110 degrees Celsius).

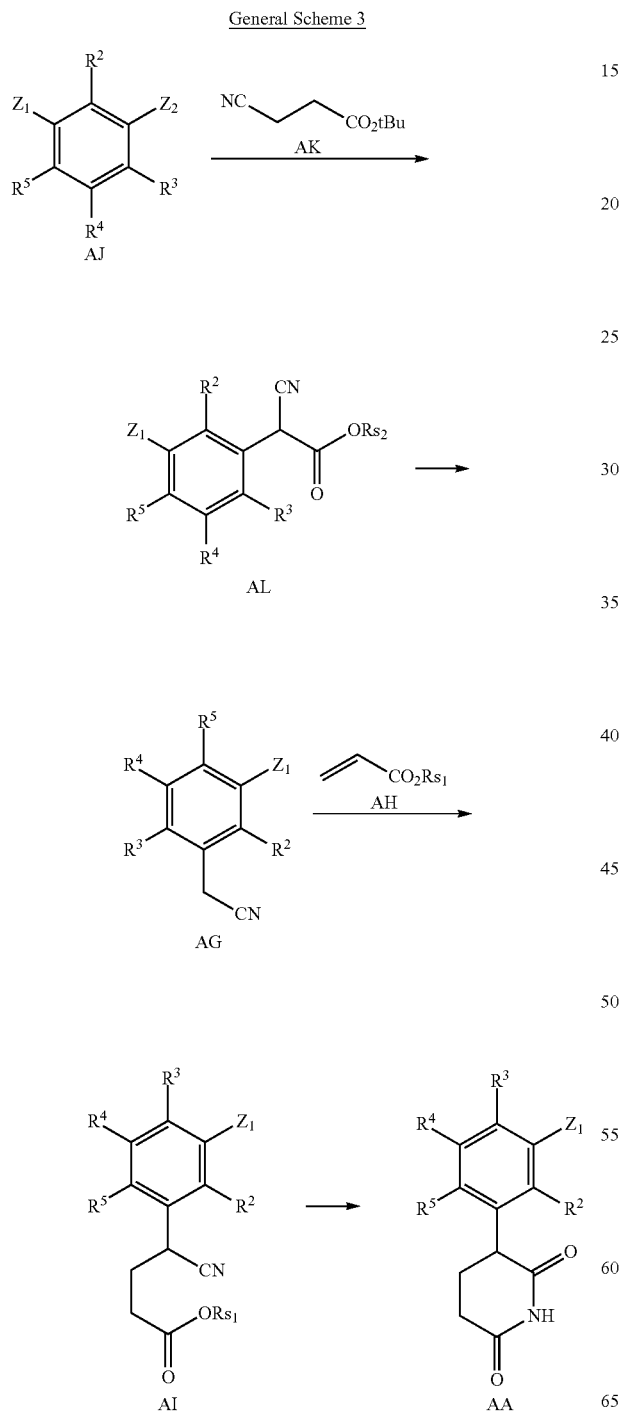

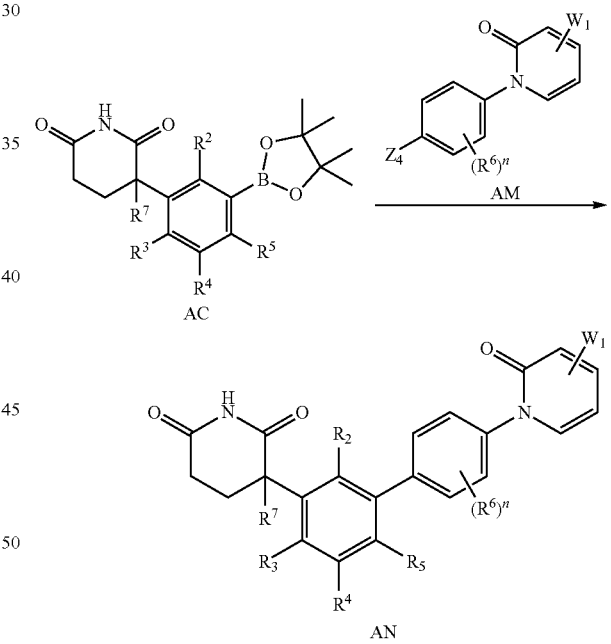

General Scheme 4 provides a specific exemplary synthetic strategy for the preparation of a compound of formula AN where aryl halide AM may be used as starting material AD in General Scheme 1. W1 is any suitable substituent which provides a compound of formula I. Compound AN may be prepared by coupling AC and AM under metal catalyzed conditions. For example, treatment with

[1,1'-Bis(diphenylphosphino)ferrocen]dichloropalladium (II) and a base such as potassium phosphate in a solvent such as dioxane. The reaction may be performed at temperature such as 80 degrees Celsius.

General Scheme 5

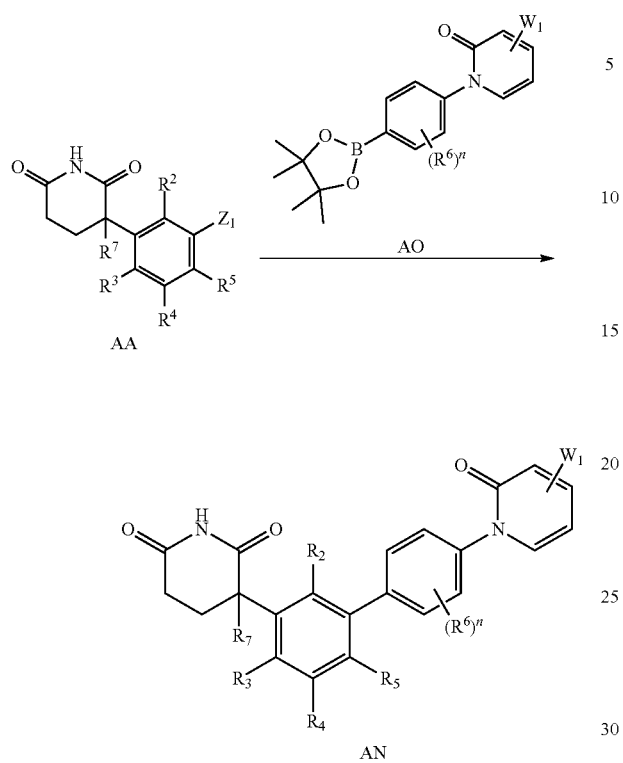

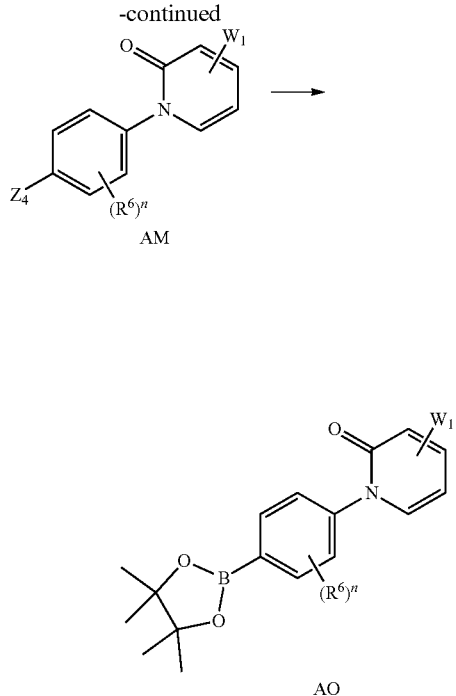

General Scheme 5 provides a specific exemplary synthetic strategy for the preparation of a compound of formula AN where aryl boronate AO may be used as starting material AD in General Scheme 1. Wi is any suitable substituent which provides a compound of formula I.

Compound AN may be prepared by coupling AA and AO under metal catalyzed conditions. For example, treatment with [1,1′-Bis(diphenylphosphino)ferrocen]dichloropalladium(II) and base such as potassium phosphate in a solvent such as dioxane. The reaction may be performed at an elevated temperature such as 80 degrees Celsius.

General Scheme 6

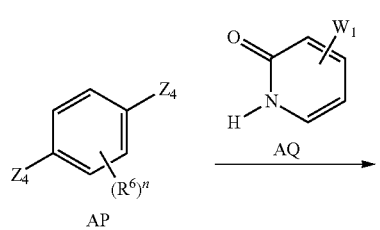

General Scheme 6 provides a specific exemplary synthetic strategy for the preparation of aryl halides of formula AM (where $Z^4$ is any suitable halide such as chlorine, bromine or iodine) and aryl boronates AO. Compounds AM and AO may be used as starting material AD and AB respectively in General Scheme 1. Wi is any suitable substituent which provides a compound of formula I.

A substituted pyridone of formula AQ may be coupled to a dihaloaryl compound AP using copper catalyzed conditions. One synthetic strategy involves treatment with copper iodide and base such as potassium phosphate in a solvent such as dimethyl acetamide. The reaction may be performed at 115 degrees Celsius for 20 hours. Alternative conditions involve copper iodide catalyst in the presence of a ligand. For example, N1,N2-Bis(furan-2-ylmethyl)oxalamide (BFMO) or 4,7-dimethoxy-1,10-phenanthroline ligand.

An aryl boronate of formula AO may be prepared from AM and a suitable borylating agent (such as Bis(pinacolato) diboron) using any metal catalyzed conditions for borylation. For example, cinnamyl palladium chloride dimer in the presence of 0.4 mol % Xphos ligand, or Pd(dppf)Cl$_2$ may be used. The reaction may be performed in a suitable solvent such as isopropanol or dioxane, at 80 degrees Celsius.

General Scheme 7

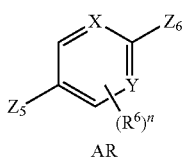

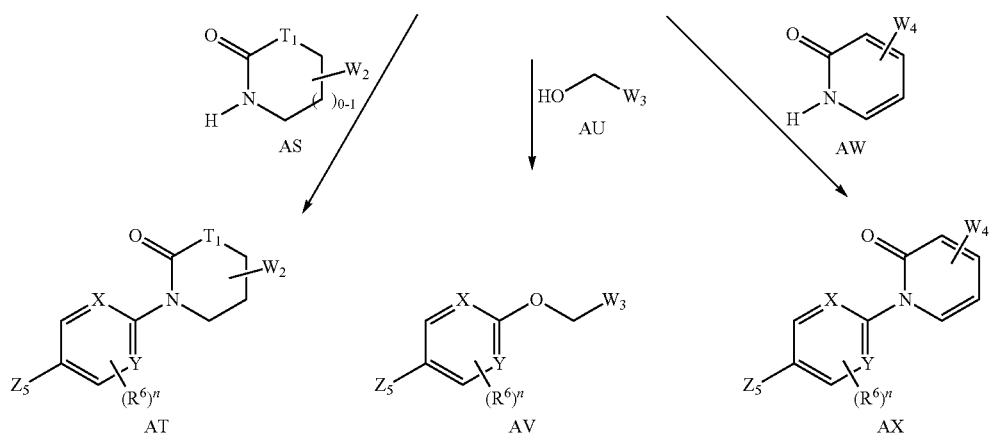

General Scheme 7 provides exemplary synthetic strategies for the preparation of diverse aryl halides of formula AT, AV and AX, which may be used as starting materials AD in General Scheme 1. In some instances, X and Y may be carbon, or X, y or both may be nitrogen depending on the desired substituents of formula I. $Z_5$ and $Z^6$ are any suitable halogens. $W_2$, $W_3$ and $W_4$ are any suitable substituents which provide a compound of formula I. $T_1$=C, O, or N-alkyl. A synthetic approach to a lactam, carbamate or pyrimidinone compound of formula AT involves a copper catalyzed coupling of lactams or pyrimidinone AS with aryl halides AR. Copper iodide and a ligand such as N,N'-Dimethylethylenediamine (DMEDA). The reaction may be performed in the presence of a base such as potassium phosphate or potassium carbonate, and a solvent such as toluene, DMSO, dioxane, DMF or NMP. Elevated temperature such as 90 degrees Celsius or 110 degrees Celsius may be required.

In some examples (where X and Y=N or X=N and Y=C and $Z_6$=Cl) an ether of formula AV may be prepared by treatment of halide AR with alcohols of formula AU under basic conditions. In some examples, pretreatment of AU with a base such as sodium hydride in a solvent such as THE followed by addition of AR at 0 degrees Celsius.

In some examples (where X=N and Y=C and $Z_6$=Cl), compounds of formula AX may be prepared from reaction of AW with AR using any suitable nucleophilic substitution conditions. A base such as cesium carbonate in a solvent such as dimethyl sulfoxide (DMSO) at 100 degrees Celsius may be applied.

General Scheme 8

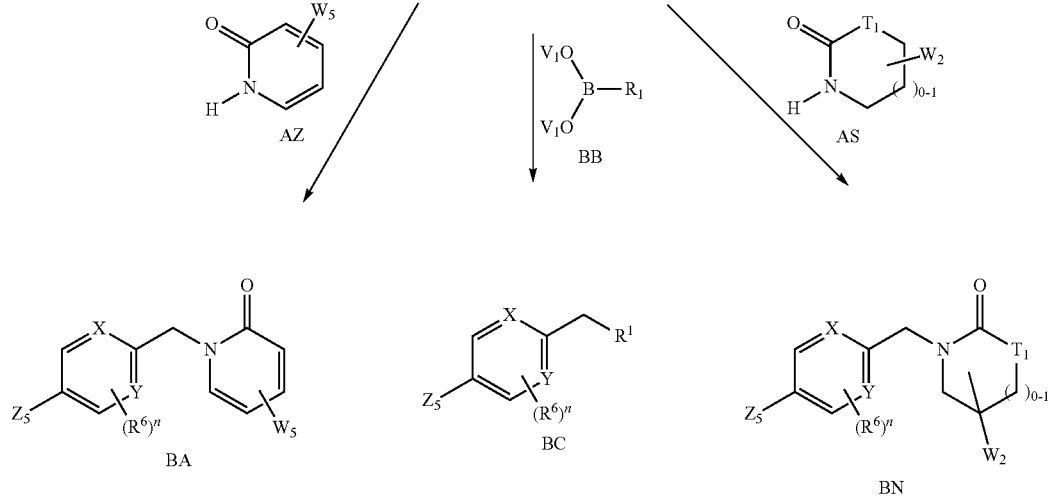

General Scheme 8 provides a representative synthetic strategy towards intermediates of formula BA from a benzyl halide of formula AY and pyridone AZ. $Z^7$ is a suitable halide such as bromine, chlorine or iodine. $W^5$ is any suitable substituent that results in a compound of formula I. N-Alkylation of pyridones AZ may be performed using a base such as potassium carbonate in the presence of phase transfer catalyst cetyl trimethyl ammonium bromide (CTAB) in a solvent such as water. The reaction may be performed at temperatures such as 50 degrees Celsius. A compound of formula BN may be similarly prepared from a compound of formula AS and AY.

A compound of formula BC may be prepared from AY and an aryl boronate or boronic acid of formula BB. $V_1$ may be hydrogen or any suitable alkyl that forms a boronate BB.

General Scheme 9

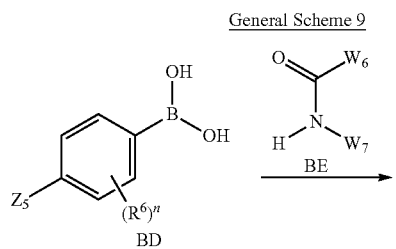

General Scheme 9 provides a representative synthetic strategy towards intermediates of formula BF which may be used as starting material AD in General Scheme 1. Boronic acid or a boronic ester of formula BD may undergo coupling with an amide or pyridone BE to afford BF. Some representative conditions for this reaction include copper acetate $(Cu(OAc)_2)$ in the presence of pyridine and 4 Å molecular sieves. The reaction may be performed in a solvent such as dichloromethane at ambient temperature (approx. 25 degrees Celsius).

General Scheme 10

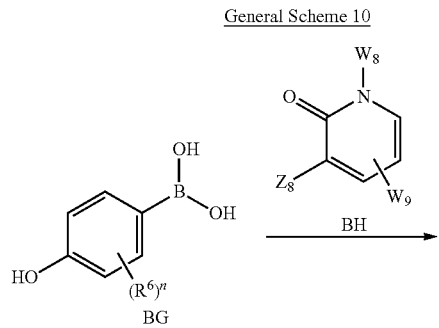

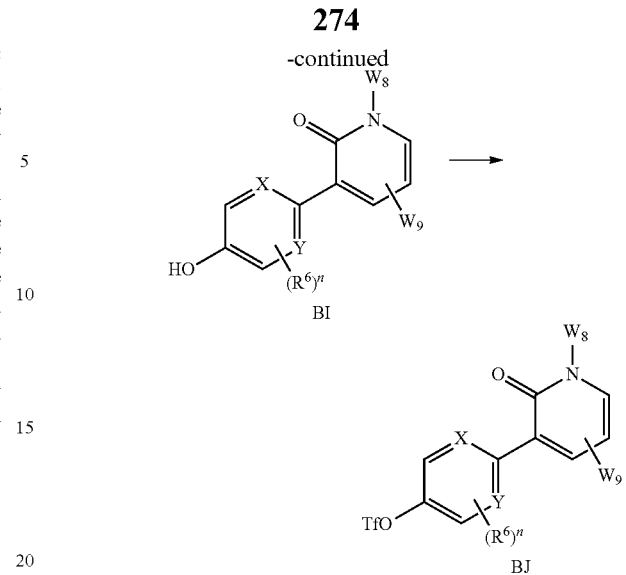

General Scheme 10 provides a general synthetic strategy towards intermediates of formula BJ which may be used as a starting material AD in General Scheme 1. $Z_8$ is any suitable halide. $W_8$ and $W_9$ are any suitable substituents which provide a compound of formula I. A compound of formula BI may be prepared by reaction of BG and BH in the presence of a catalyst such as [1,1'-Bis(diphenylphosphino)ferrocene]dichloropalladium(II) in the presence of a base such as potassium carbonate in a solvent mixture of dioxane and water. The reaction may be performed at a temperature of 100 degrees Celsius. A triflate of formula BJ may be prepared by treatment of alcohol BI with Trifluoromethanesulfonic anhydride and pyridine in dichloromethane at zero degrees Celsius.

General Scheme 11

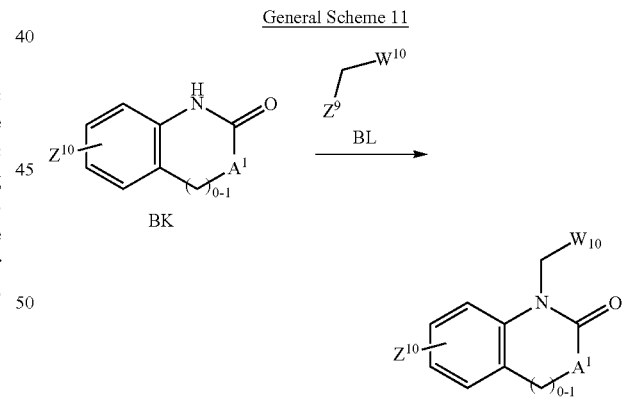

General Scheme 11 provides a general synthetic strategy towards intermediates of formula BM which may be used as a starting material AD in General Scheme 1. $Z^9$ and $Z^{10}$ are is any suitable halides. $A^1$ is any suitable atom or group suitable to provide a compound of formula I, for example, oxygen, NH or N-methyl. $W^{10}$ is heteroaryl or any suitable substituents which provide a compound of formula I. A compound of formula BM may be prepared by N-alkylation of BK with any aryl halide BL. The reaction may occur in the presence of base, such as Cesium carbonatite, in a polar solvent such as dimethylformamide at temperatures such as 80 degrees Celsius. Compound of formula BM may undergo cross coupling reactions with compounds of formula AD using a catalyst such as BrettPhos Pd3 complex in the presence of a base such as potassium phosphate. The reaction may be performed in a solvent such as dioxane at 100 degrees Celsius.

General Scheme 12

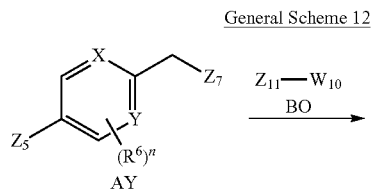

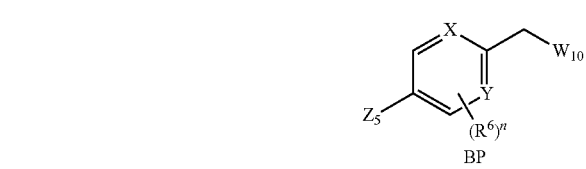

Scheme 12 provides a general synthetic approach to the preparation of compounds of formula BP which may be used as starting material AD in scheme 1. $W_{10}$ is any suitable Aryl or heteroaryl group which provides a compound of formula I. An organometallic zinc reagent may be prepared by treatment of compound AY with a Zn—Cu metal in the presence of a solvent such as toluene and dimethylacetamde mixture at elevated temperatures (e.g. 80 degrees Celsius). Addition of an aryl or heteroaryl halide such as BO and a palladium catalyst such as $Pd(PPh_3)_4$ in a solvent such as toluene, at room temperature may be used to generate compounds of formula BP.

EXAMPLES

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Abbreviations: DCM: dichloromethane; DIEA: N,N-diisopropylethylamine; DMF: dimethylformamide; DMSO: dimethyl sulfoxide; EtOH: ethanol; ESI: electrospray ionization; h: hours; HATU: 1-[bis(dimethylamino)methylene]-1H-1,2,3-triazolo[4,5-b]pyridinium 3-oxide hexafluorophosphate; HPLC: high-performance liquid chromatography; MeCN: acetonitrile; MS: mass spectrometry; NCS: N-chlorosuccinimide; NMR: nuclear magnetic resonance; TEA: triethylamine; and THF: tetrahydrofuran.

Synthesis of 3-(2-chloro-3-(4,4,5,5-tetramethyl-1,3,2-dioxaborolan-2-yl)phenyl)piperidine-2,6-dione (Intermediate A)

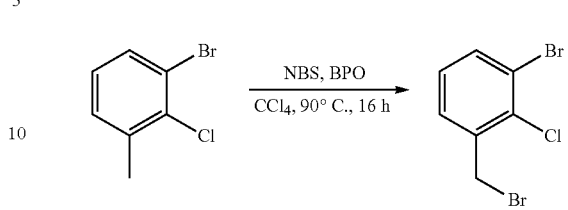

To a solution of 1-bromo-2-chloro-3-methylbenzene (30.0 g, 146 mmol, 1.00 eq) in tetrachloromethane (240 mL) was added N-bromosuccinimide (28.7 g, 161 mmol, 1.11 eq) and benzoyl peroxide (1.77 g, 7.30 mmol, 0.05 eq). The mixture was stirred at 90° C. for 16 hr. The reaction mixture was filtered and the filtered cake was washed with ethyl acetate (2×75 mL). The filtration was concentrated under reduced pressure. The residue was purified by flash silica gel chromatography (ISCO®; 200 g SepaFlash® Silica Flash Column, Eluent of 0~3% Ethyl acetate/Petroleum ether gradient @ 150 mL/min) to give 1-bromo-3-(bromomethyl)-2-chlorobenzene (20.8 g, 73.1 mmol, 50% yield) was obtained as colorless liquid.

$^1$H NMR (400 MHz, $CDCl_3$) δ=7.61 (dd, J=8.0, 1.6 Hz, 1H), 7.41 (dd, J=8.0, 1.6 Hz, 1H), 7.15-7.11 (m, 1H), 4.62 (s, 2H).

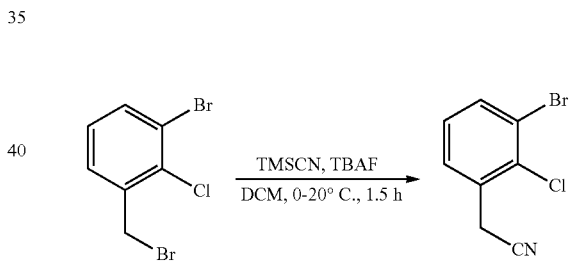

To a solution of 1-bromo-3-(bromomethyl)-2-chlorobenzene (20.0 g, 70.3 mmol, 1.00 eq) and trimethylsilcyane (10.5 g, 105 mmol, 1.76 mL, 1.50 eq) in dichloromethane (200 mL) was added tetrabutylammonium fluoride (1.0 M in THF, 105 mL, 1.50 eq) dropwise at 0° C. The mixture was stirred at 20° C. for 1.5 h. The reaction mixture was washed with water (3×150 mL), the organic layer was dried over sodium sulfate, filtered and concentrated under reduced pressure. The residue was purified by flash silica gel chromatography (ISCO®; 80 g SepaFlash® Silica Flash Column, Eluent of 0-60% Ethyl acetate/Petroleum ether gradient @ 60 mL/min) to give 2-(3-bromo-2-chlorophenyl)acetonitrile (13.2 g, 57.3 mmol, 81% yield) as a white solid.

$^1$H NMR (400 MHz, $CDCl_3$) δ=7.65 (d, J=8.0 Hz, 1H), 7.50 (dd, J=8.0, 0.8 Hz, 1H), 7.20 (t, J=8.0 Hz, 1H), 3.89 (s, 2H).

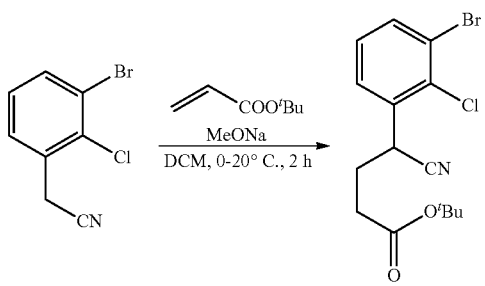

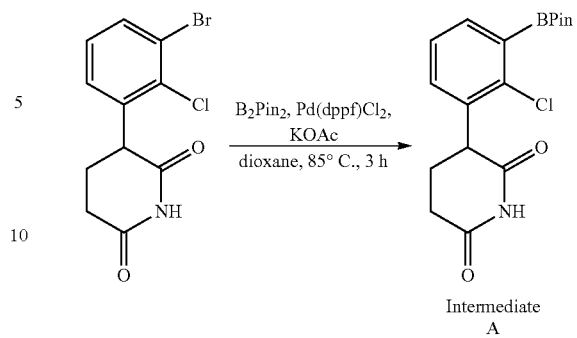

Intermediate A

To a solution of 2-(3-bromo-2-chlorophenyl)acetonitrile (13.2 g, 57.3 mmol, 1.00 eq) in tetrahydrofuran (130 mL) was added sodium methylate (620 mg, 11.5 mmol, 0.200 eq) and tert-butyl acrylate (7.34 g, 57.3 mmol, 8.31 mL, 1.00 eq) dropwise at 0° C. Then, the mixture was stirred at 20° C. for 2 hr. The reaction mixture was diluted with water (30 mL) and extracted with ethyl acetate (3×50 mL). The combined organic layers were washed with brine (3×80 mL), dried over sodium sulfate, filtered and concentrated under reduced pressure. The crude product was purified by reversed phase column (C18, 330 g, flow: 100 mL/min; gradient: from 10-65% water (0.1% formic acid) in acetonitrile over 40 min) to give tert-butyl 4-(3-bromo-2-chlorophenyl)-4-cyanobutanoate (7.50 g, 19.0 mmol, 33% yield) was obtained as colorless liquid.

$^1$H NMR (400 MHz, CDCl$_3$) δ=7.65 (dd, J=8.0, 1.6 Hz, 1H), 7.53 (dd, J=8.0, 1.6 Hz, 1H), 7.22 (t, J=8.0 Hz, 1H), 4.49 (dd, J=8.8, 5.6 Hz, 1H), 2.54-2.38 (m, 2H), 2.29-2.09 (m, 2H),

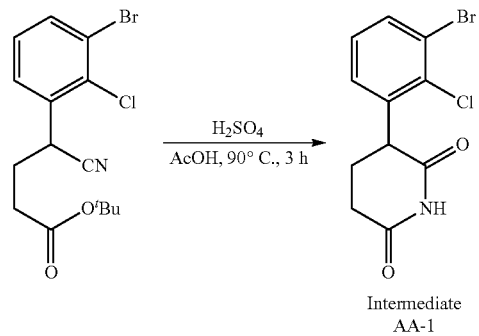

Intermediate AA-1

To a solution of tert-butyl 4-(3-bromo-2-chlorophenyl)-4-cyanobutanoate (4.70 g, 11.9 mmol, 1.00 eq) in acetic acid (30 mL) was added sulfuric acid (5.52 g, 56.3 mmol, 3.00 ml, 4.72 eq). The mixture was stirred at 90° C. for 3 hr. Cooled to room temperature, the reaction mixture was poured into ice water (120 mL) and filtered cake was washed with water (2×50 mL). The filter cake was dried under reduced pressure to afford 3-(3-bromo-2-chlorophenyl)piperidine-2,6-dione (2.89 g, 9.46 mmol, 79% yield, 99% purity) as a white solid.

$^1$H NMR (400 MHz, DMSO-d$_6$) δ=10.93 (s, 1H), 7.72 (dd, J=8.0, 0.8 Hz, 1H), 7.38 (dd, J=8.0, 1.2 Hz, 1H), 7.30-7.26 (m, 1H), 4.32 (dd, J=12.0, 4.8 Hz, 1H), 2.83-2.73 (m, 1H), 2.53-2.53 (m, 1H), 2.30-2.34 (m, 1H), 2.03-1.97 (m, 1H).

MS (ESI) m/z 303.9[M+H]$^+$

To a solution of 3-(3-bromo-2-chloro-phenyl)piperidine-2,6-dione (5.00 g, 16.5 mmol, 1.00 eq) in dioxane (80 mL) was added 4,4,5,5-tetramethyl-2-(4,4,5,5-tetramethyl-1,3,2-dioxaborolan-2-yl)-1,3,2-dioxaborolane (5.04 g, 19.8 mmol, 1.20 eq), [1,1'-bis(diphenylphosphino)ferrocene]dichloropalladium(II) (1.21 g, 1.65 mmol, 0.10 eq) and potassium acetate (4.87 g, 49.6 mmol, 3.00 eq) in one portion at 20° C. under nitrogen atmosphere. The mixture was stirred at 85° C. for 3 h. The mixture was filtered and the filter cake was washed with ethyl acetate (2×30 mL). The combined filtrate was concentrated under reduced pressure. The residue was purified by flash silica gel chromatography (ISCO®; 80 g SepaFlash® Silica Flash Column, eluent of 0~50% ethyl acetate/petroleum ether gradient @ 60 mL/min) to give 3-(2-chloro-3-(4,4,5,5-tetramethyl-1,3,2-dioxaborolan-2-yl)phenyl)-piperidine-2,6-dione (3.80 g, 8.70 mmol, 52% yield) as a white solid.

$^1$H NMR (400 MHz, DMSO-d$_6$) δ=10.90 (s, 1H), 7.52 (dd, J=2.0, 7.2 Hz, 1H), 7.41 (dd, J=2.0, 7.6 Hz, 1H), 7.32 (d, J=7.6 Hz, 1H), 4.26 (dd, J=5.2, 12.4 Hz, 1H), 2.81-2.70 (m, 1H), 2.59-2.53 (m, 1H), 2.33-2.23 (m, 1H), 1.99-1.93 (m, 1H), 1.31 (s, 12H).

MS (ESI) m/z 350.2/352.2 [M+H]$^+$

Synthesis of 3-(4'-(bromomethyl)-2-chloro-[1,1'-biphenyl]-3-yl)piperidine-2,6-dione (Intermediate B)

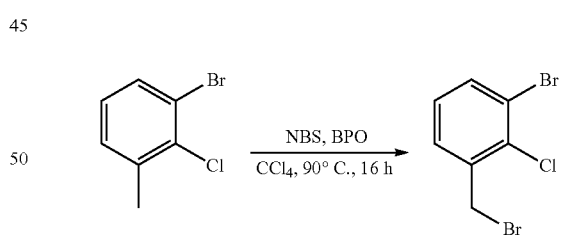

To a solution of 1-bromo-2-chloro-3-methylbenzene (30.0 g, 146 mmol, 1 eq) in carbon tetrachloride (240 mL) was added N-bromosuccinimide (28.8 g, 162 mmol, 1.11 eq) and benzoyl peroxide (1.77 g, 7.30 mmol, 0.0500 eq). The mixture was stirred at 90° C. for 16 h. The reaction mixture was filtered and the filtered cake was washed with ethyl acetate (2×75 mL).

The filtrate was concentrated under reduced pressure. The residue was purified by column chromatography on silica gel (petroleum ether/ethyl acetate=1/0 to 0/1) to give 1-bromo-3-(bromomethyl)-2-chlorobenzene (25.1 g, crude) and 1-bromo-3-(bromomethyl)-2-chlorobenzene (7.90 g, 26.3 mmol, 18% yield) as both colorless liquid.

¹H NMR (400 MHz, DMSO-d₆) δ=7.77 (dd, J=1.2, 8.0 Hz, 1H), 7.65 (dd, J=0.8, 7.6 Hz, 1H), 7.29 (t, J=8.0 Hz, 1H), 4.80 (s, 2H).

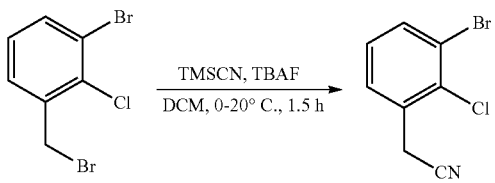 [SMILES: Clc1c(Br)cccc1CBr ; N#CCc1cccc(Br)c1Cl]

To a solution of 1-bromo-3-(bromomethyl)-2-chlorobenzene (33.0 g, 116 mmol, 1.00 eq) and trimethylsilylformonitrile (17.3 g, 174 mmol, 21.8 mL, 1.50 eq) in dichloromethane (330 mL) was added tris((1-benzyl-1H-1,2,3-triazol-4-yl)methyl)amine (1 M, 174 mL, 1.50 eq) (1.0 M in tetrahydrofuran, 105 mL, 1.50 eq) dropwise at 0° C. The mixture was stirred at 20° C. for 1.5 h. The reaction mixture was washed with water (3×150 mL), the organic layer was dried over sodium sulfate, filtered and concentrated under reduced pressure. The residue was purified by column chromatography on silica gel (petroleum ether/ethyl acetate=1/0 to 0/1) to give 2-(3-bromo-2-chlorophenyl)acetonitrile (5.80 g, 25.2 mmol, 21% yield) as a white solid.

¹H NMR (400 MHz, DMSO-d₆) δ=7.80 (dd, J=1.0, 8.0 Hz, 1H), 7.57 (dd, J=0.8, 7.6 Hz, 1H), 7.35 (t, J=8.0 Hz, 1H), 4.18 (s, 2H).

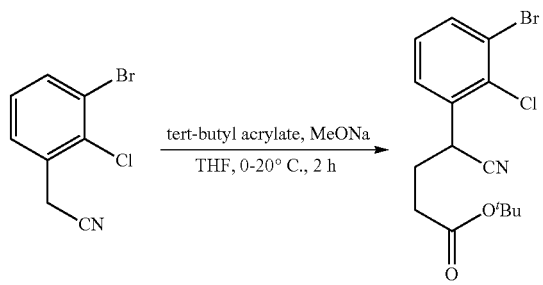 [SMILES: N#CCc1cccc(Br)c1Cl ; CC(C)(C)OC(=O)CCC(C#N)c1cccc(Br)c1Cl]

A mixture of 2-(3-bromo-2-chloro-phenyl)acetonitrile (13.3 g, 57.7 mmol, 1.00 eq), tert-butyl acrylate (7.40 g, 57.7 mmol, 8.38 mL, 1.00 eq) and sodium methoxide (623 mg, 11.5 mmol, 0.200 eq) in tetrahydrofuran (130 mL) was added at 0° C. The reaction was stirred at 20° C. for 2 h. The reaction mixture was diluted with water (30 mL) and extracted with ethyl acetate (3×50 mL). The combined organic layers were washed with brine (3×80 mL), dried over sodium sulfate, filtered and concentrated under reduced pressure. The residue was purified by column chromatography on silica gel (petroleum ether/ethyl acetate=1/0 to 0/1) to give tert-butyl 4-(3-bromo-2-chloro-phenyl)-4-cyano-butanoate (25.0 g, crude) as yellow oil.

¹H NMR (400 MHz, DMSO-d₆) δ=7.82 (dd, J=1.4, 8.0 Hz, 1H), 7.60 (dd, J=1.6, 8.0 Hz, 1H), 7.38 (t, J=8.0 Hz, 1H), 4.62 (dd, J=6.8, 8.0 Hz, 1H), 2.45-2.30 (m, 2H), 2.20-2.08 (m, 2H), 1.38 (s, 9H)

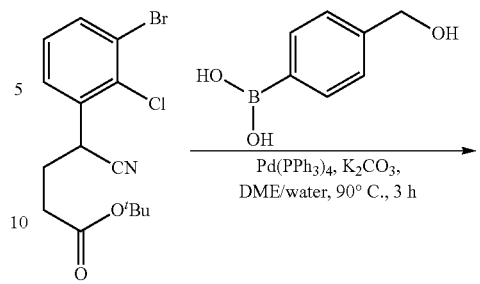

A mixture of tert-butyl 4-(3-bromo-2-chlorophenyl)-4-cyanobutanoate (10.0 g, 27.9 mmol, 1.00 eq), (4-(hydroxymethyl)phenyl)boronic acid (4.66 g, 30.7 mmol, 1.10 eq) and potassium carbonate (7.71 g, 55.7 mmol, 2.00 eq), palladium; triphenylphosphane (3.22 g, 2.79 mmol, 0.100 eq) in 1,2-dimethoxyethane (9.00 mL) and water (3.00 mL) was stirred at 90° C. for 3 h under nitrogen atmosphere. The mixture was cooled to room temperature and poured into water (30 mL), the two layers were separated. The aqueous phase was extracted with ethyl acetate (3×30 mL), the organic layer was washed with brine (30 mL). The combined extracts was dried over anhydrous sodium sulfate, filtered, and concentrated under vacuum. The residue was purified by column chromatography on silica gel (petroleum ether/ethyl acetate=1/0 to 0/1) to give tert-butyl 4-(2-chloro-4'-(hydroxymethyl)-[1,1'-biphenyl]-3-yl)-4-cyanobutanoate (6.07 g, 15.7 mmol, 56% yield) as yellow oil.

¹H NMR (400 MHz, DMSO-d₆) δ=7.60 (dd, J=1.6, 8.0 Hz, 1H), 7.51 (t, J=7.6 Hz, 1H), 7.45-7.34 (m, 5H), 5.25 (t, J=6.0 Hz, 1H), 4.63 (dd, J=6.8, 8.0 Hz, 1H), 4.56 (d, J=6.0 Hz, 2H), 2.46-2.37 (m, 2H), 2.23-2.14 (m, 2H), 1.39 (s, 9H)

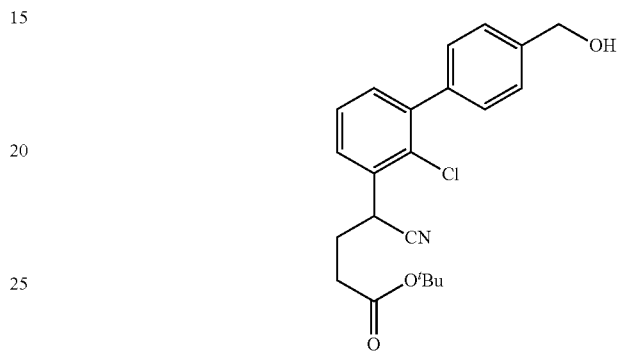

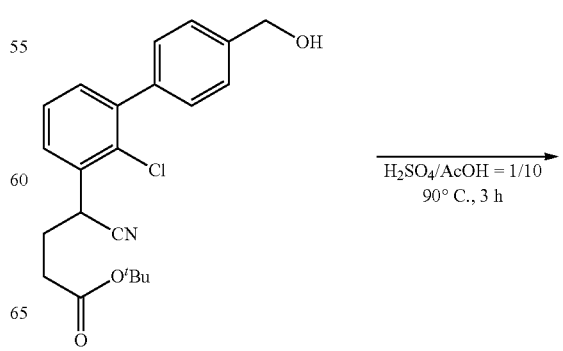

-continued

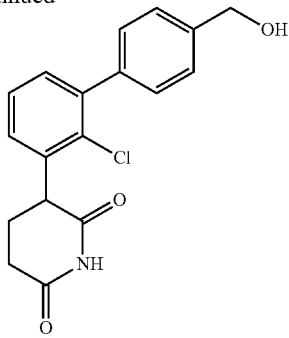

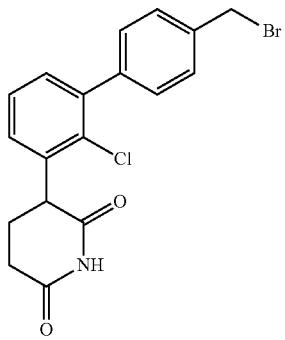

Intermediate B

A mixture of tert-butyl 4-(2-chloro-4'-(hydroxymethyl)-[1,1'-biphenyl]-3-yl)-4-cyanobutanoate (6.00 g, 15.6 mmol, 1.00 eq) and sulfuric acid (5.52 g, 56.3 mmol, 3.00 mL, 3.62 eq) in acetic acid (30.0 mL) was stirred at 90° C. for 3 h. After cooled to room temperature, the reaction mixture was poured water (120 mL) and filtered cake was washed with saturated sodium bicarbonate (3×20 mL). The filter cake was dried under reduced pressure to give the crude product. The crude product was purified by column chromatography on silica gel (petroleum ether/(ethyl acetate/methanol/dichloromethane=2/2/1)=I/O to 0/1), trituration with 2-methoxy-2-methylpropane (20 mL) at 25° C. for 15 min and filtered. The filter cake was dried to give 3-(2-chloro-4'-(hydroxymethyl)-[1,1'-biphenyl]-3-yl)piperidine-2,6-dione (2.78 g, 7.08 mmol, 45% yield, 84% purity) as a yellow solid.

$^1$H NMR (400 MHz, DMSO-d$_6$) δ=10.92 (s, 1H), 7.48-7.34 (m, 6H), 7.31 (dd, J=2.0, 7.2 Hz, 1H), 5.13 (s, 2H), 4.34 (dd, J=4.8, 12.0 Hz, 1H), 2.87-2.71 (m, 1H), 2.60-2.51 (m, 1H), 2.40-2.27 (m, 1H), 2.08-2.00 (m, 1H) MS (ESI) m/z 312.0 [M-17]+

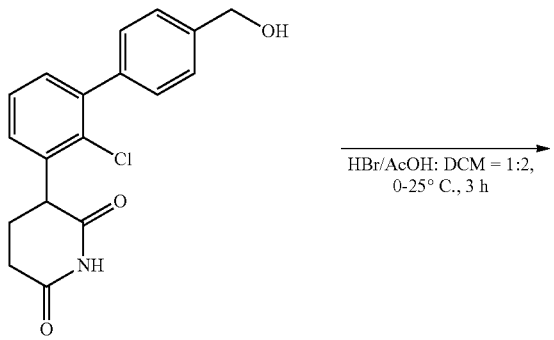

To a mixture of 3-(2-chloro-4'-(hydroxymethyl)-[1,1'-biphenyl]-3-yl)piperidine-2,6-dione (1.40 g, 4.25 mmol, 1.00 eq) in dichloromethane (5.00 mL) was added hydrogen bromide (2.98 g, 12.2 mmol, 2.00 mL, 33% purity in acetic acid, 2.86 eq) at 0° C. The reaction was warmed to 25° C. and stirred for 3 h. The mixture was poured into saturated sodium bicarbonate solution (30.0 mL) and filtered. The filter cake was dried under reduced pressure to give the crude product. The crude product was triturated with ethyl acetate (10 mL) at 20° C. for 10 min and filtered. The filter cake was dried under reduced pressure to afford 3-(4'-(bromomethyl)-2-chloro-[1,1'-biphenyl]-3-yl)piperidine-2,6-dione (1.33 g, 2.85 mmol, 670 yield, 84 O purity) as a white solid.

$^1$H NMR (400 MHz, DMSO-d$_6$) δ=10.92 (s, 1H), 7.57-7.51 (m, 2H), 7.43-7.35 (m, 4H), 7.34-7.30 (i, 1H), 4.77 (s, 2H), 4.40-4.30 (i, 1H), 2.85-2.74 (m, 1H), 2.54-2.51 (m, 1H), 2.40-2.27 (m, 1H), 2.09-2.02 (in, 1H)

MS (ESI) m/z 392.2 [M+H]$^+$

Characterization of Other Key Intermediates in the Preparation of Compounds of Formula I Characterization for Intermediates of general formula AA were used to prepare compound of formula I. Intermediates AA-2 to AA-9 were prepared according to general scheme 2 or 3, and analogously to 3-(3-bromo-2-chlorophenyl) piperidine-2,6-dione as described in the preparation of Intermediate A.

| Name | NMR |
| --- | --- |
| 3-(3-bromo-2-fluorophenyl)-piperidine-2,6-dione AA-2 | 1H NMR (400 MHz, DMSO-d6) δ = 10.94 (s, 1H), 7.66 - 7.62 (m, 1H), 7.35 - 7.33 (m, 1H), 7.17 - 7.13 (m, 1H), 4.15 - 4.11 (m, 1H), 2.80 - 2.71 (m, 1H), 2.58 - 2.56 (m, 1H), 2.28 - 2.18 (m, 1H), 2.05 - 1.98 (m, 1H). MS (ESI) m/z 285.9[M + H]+ |
| 3-(3-bromo-2,6-dichlorophenyl)piperidine-2,6-dione AA-3 | 1H NMR (400 MHz, DMSO-d6) δ = 11.02 (d, J = 3.6 Hz, 1H), 7.78 (dd, J = 4.0, 8.8 Hz, 1H), 7.54 - 7.40 (m, 1H), 4.87 - 4.60 (m, 1H), 2.93 - 2.80 (m, 1H), 2.59 - 2.53 (m, 1H), 2.41 - 2.31 (m, 1H), 2.01 - 1.88 (m, 1H) |
| 3-(3-bromo-2-chloro-6-fluorophenyl)piperidine-2,6-dione AA-4 | 1H NMR (400 MHz, DMSO-d6) δ = 11.02 (s, 1H), 7.82 (dd, J = 5.8, 9.2 Hz, 1H), 7.28 (t, J = 9.2 Hz, 1H), 4.55 - 4.46 (m, 1H), 2.90 - 2.78 (m, 1H), 2.58 - 2.54 (m, 1H), |

-continued

| Name | NMR |
|---|---|
| | 2.22 - 1.89 (m, 2H). MS (ESI) m/z 322.0 [M + 2H]+ |
| 3-(3-bromo-2,6-difluorophenyl)piperidine-2,6-dione AA-5 | 1H NMR (400 MHz, DMSO-d6) δ = 11.04 (s, 1H), 7.75 (dt, J = 6.0, 8.8 Hz, 1H), 7.18 (dt, J = 1.6, 9.2 Hz, 1H), 4.34 (dd, J = 5.2, 12.8 Hz, 1H), 2.91 - 2.75 (m, 1H), 2.63 - 2.54 (m, 1H), 2.23 - 2.10 (m, 1H), 2.09 - 2.01 (m, 1H). MS (ESI) m/z 304.0 [M + H]+ |
| 3-(3-bromo-6-chloro-2-fluorophenyl)piperidine-2,6-dione AA-6 | 1H NMR (400 MHz, DMSO-d6) δ = 11.03 (s, 1H), 7.72 (dd, J = 8.4, 7.6 Hz, 1H), 7.37 (d, J = 8.4 Hz, 1H), 4.45 (dd, J = 12.4, 5.2 Hz, 1H), 2.89-2.80 (m, 1H), 2.58-2.55 (m, 1H), 2.19-2.07 (m, 1H), 2.02-1.98 (m, 1H). MS (ESI) m/z 322.0 [M + H]+ |
| 3-(3-bromo-2-(trifluoromethyl)phenyl)piperidine-2,6-dione AA-7 | 1H NMR (400 MHz, CDCl3) δ = 8.27 (s, 1H), 7.74 (d, J = 8.0 Hz, 1H), 7.36 (t, J = 8.0 Hz, 1H), 7.22 (d, J = 7.6 Hz, 1H), 4.40 - 4.03 (m, 1H), 2.89 - 2.81 (m, 1H), 2.78 - 2.66 (m, 1H), 2.35 - 2.16 (m, 2H). MS (ESI) m/z 335.9 [M + H]+ |
| 3-(3-bromo-2-methyl-phenyl)piperidine-2,6-dione AA-8 | 1H NMR (400 MHz, DMSO-d6) δ = 10.87 (s, 1H), 7.52 (d, J = 7.6 Hz, 1H), 7.20 - 7.14 (m, 1H), 7.14 - 7.07 (m, 1H), 4.19 (dd, J = 12.0, 4.8 Hz, 1H), 2.81 - 2.69 (m, 1H), 2.54 (br d, J = 3.6 Hz, 1H), 2.22 (dq, J = 12.8, 4.0 Hz, 1H), 2.05 - 1.94 (m, 1H) MS (ESI) m/z 282.1 [M + H]+ |
| 3-(5-bromo-2-chlorophenyl)piperidine-2,6-dione AA-9 | 1H NMR (400 MHz, DMSO-d6) δ = 10.93 (s, 1H), 7.61 (d, J = 2.4 Hz, 1H), 7.55 - 7.50 (m, 1H), 7.45 - 7.41 (m, 1H), 4.23 (dd, J = 5.0, 12.8 Hz, 1H), 2.82 - 2.73 (m, 1H), 2.58 - 2.53 (m, 1H), 2.41 - 2.31 (m, 1H), 2.01 - 1.95 (m, 1H). |

General Synthetic Procedure for Preparation of Compounds of Formula I from Aryl Bromide Intermediate AA and Commercially Available or Synthetically Accessible Boronic Acids or Esters

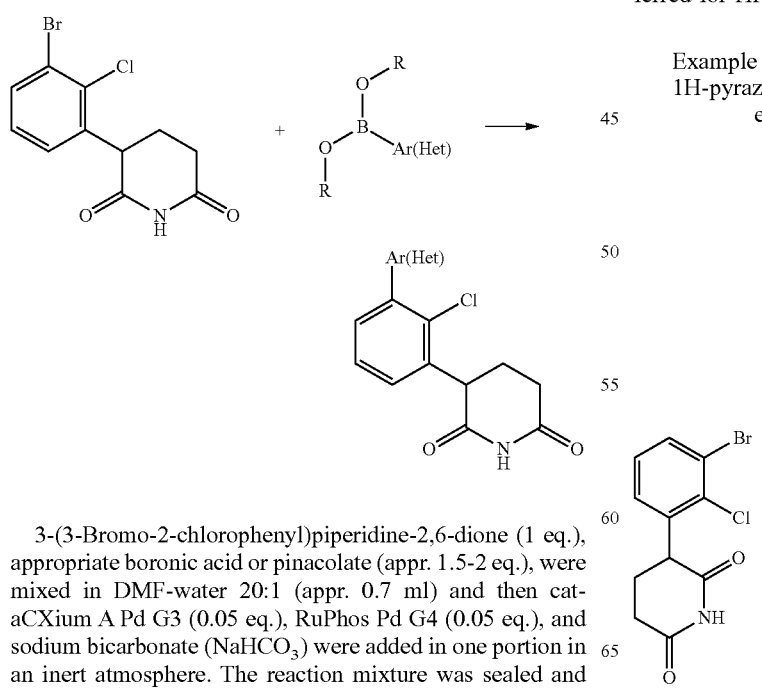

3-(3-Bromo-2-chlorophenyl)piperidine-2,6-dione (1 eq.), appropriate boronic acid or pinacolate (appr. 1.5-2 eq.), were mixed in DMF-water 20:1 (appr. 0.7 ml) and then cataCXium A Pd G3 (0.05 eq.), RuPhos Pd G4 (0.05 eq.), and sodium bicarbonate (NaHCO$_3$) were added in one portion in an inert atmosphere. The reaction mixture was sealed and heated for 15 hours at 90° C.

Then the mixture was cooled to the ambient temperature and trifluoroaceticacid (TFA) was added dropwise until neutral pH. The mixture was evaporated under reduced pressure and the residue was dissolved in the DMSO (appr. 0.7 ml). DMSO solution was treated with scavenger SiliaMetS DMT, filtered, analyzed by LCMS, and transferred for HPLC purification Example 1. Synthesis of 3-(2-chloro-4'-((1-methyl-1H-pyrazol-3-yl)methoxy)-[1,1'-biphenyl]-3-yl)piperidine-2,6-dione (compound 154)

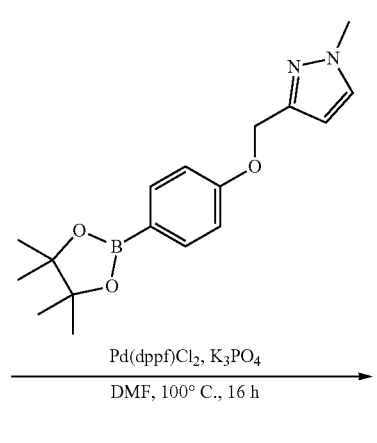

Example 2. Synthesis of 3-(2-chloro-4'-((2-oxopyridin-1(2H)-yl)methyl)-[1,1'-biphenyl]-3-yl)piperidine-2,6-dione (compound 156)

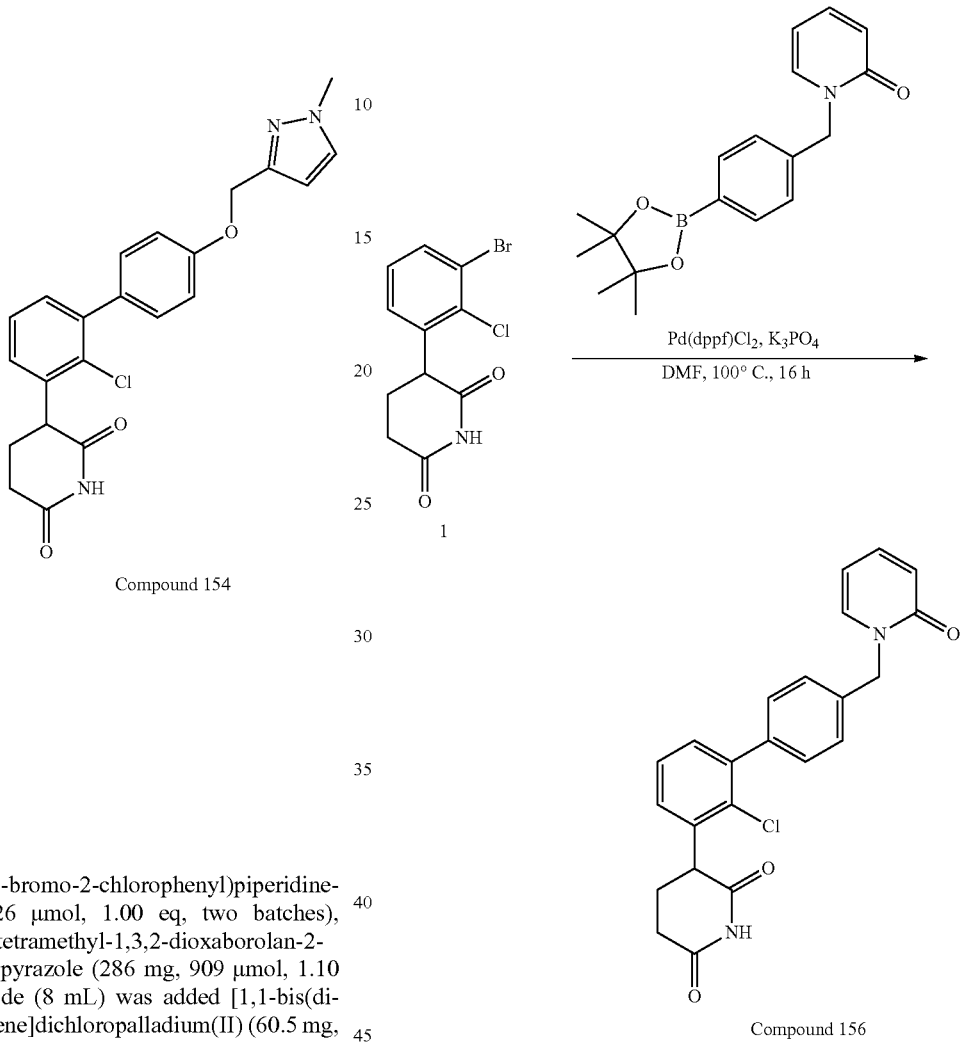

To a solution of 3-(3-bromo-2-chlorophenyl)piperidine-2,6-dione (250 mg, 826 µmol, 1.00 eq, two batches), 1-methyl-3-((4-(4,4,5,5-tetramethyl-1,3,2-dioxaborolan-2-yl)phenoxy)methyl)-1H-pyrazole (286 mg, 909 µmol, 1.10 eq) in dimethylformamide (8 mL) was added [1,1-bis(diphenylphosphino)ferrocene]dichloropalladium(II) (60.5 mg, 82.6 µmol, 0.10 eq) and potassium phosphate (526 mg, 2.48 mmol, 3.00 eq). The mixture was degassed and purged with nitrogen for three times, then stirred at 100° C. for 16 h. The reaction mixture was cooled to 25° C., and then filtered with Celite pad, washed with ethyl acetate (50 mL), the filtrate was concentrated under reduced pressure. The residue was purified by flash silica gel chromatography (ISCO®; 12 g SepaFlash® Silica Flash Column, Eluent of 0~80% Ethyl acetate/Petroleum ether gradient @60 mL/min). The desired fraction was collected and concentrated under reduced pressure, then the residue was triturated with dimethylformamide (4 mL) at 25° C. for 10 minutes, filtered, washed with n-hexane (5 mL), dried under reduced pressure to afford 3-(2-chloro-4'-((1-methyl-1H-pyrazol-3-yl)methoxy)-[1,1'-biphenyl]-3-yl)piperidine-2,6-dione (278.9 mg, 673.64 µmol, 41% yield) as a white solid.

$^1$H NMR (400 MHz, DMSO-$d_6$) δ=10.91 (s, 1H), 7.67 (d, J=2.0 Hz, 1H), 7.41-7.26 (m, 5H), 7.17-7.05 (m, 2H), 6.33 (d, J=2.0 Hz, 1H), 5.04 (s, 2H), 4.33 (dd, J=5.2, 12.0 Hz, 1H), 3.84 (s, 3H), 2.79 (m, 1H), 2.56 (m, 1H), 2.32 (m, 1H), 2.11-1.99 (m, 1H); MS (ESI) m/z 410.0 [M+H]+.

A mixture of 3-(3-bromo-2-chlorophenyl)piperidine-2,6-dione (450 mg, 1.34 mmol, 90% purity, 1.00 eq), 1-(4-(4,4,5,5-tetramethyl-1,3,2-dioxaborolan-2-yl)benzyl)pyridin-2(1H)-one (502 mg, 1.34 mmol, 83% purity, 1.00 eq), potassium phosphate (852 mg, 4.01 mmol, 3.00 eq) and [1,1-Bis(diphenylphosphino)ferrocene] dichloropalladium (II) (196 mg, 268 µmol, 0.20 eq) in N,N-dimethylformamide (23 mL) was degassed and purged with nitrogen for 3 times. The mixture was stirred at 100° C. for 16 h under nitrogen atmosphere. The reaction mixture was concentrated under reduced pressure. The residue was purified by flash silica gel chromatography (ISCO®; 40 g SepaFlash® Silica Flash Column, Eluent of 100~100% Ethyl acetate/Petroleum ether gradient @40 mL/min) followed by Prep-HPLC (column: Phenomenex Luna C18 150×25 mm×10 m; mobile phase: [water (formic acid)-acetonitrile]; B %: 24%-54%, 10 min) and lyophilized to afford 3-(2-chloro-4'-((2-oxopyridin-1(2H)-yl)methyl)-[1,1'-biphenyl]-3-yl)piperidine-2,6-dione (327 mg, 788 µmol, 59% yield) as an off-white solid.

$^1$H NMR (400 MHz, DMSO-$d_6$) δ=10.91 (s, 1H), 7.86 (dd, J=2.0, 6.8 Hz, 1H), 7.45 (ddd, J=2.0, 6.8, 9.2 Hz, 1H), 7.41-7.31 (m, 6H), 7.28 (dd, J=2.0, 7.2 Hz, 1H), 6.44 (d, J=9.2 Hz, 1H), 6.27 (dt, J=1.2, 6.8 Hz, 1H), 5.16 (s, 2H), 4.34 (dd, J=5.2, 12.0 Hz, 1H), 2.85-2.70 (m, 1H), 2.58-2.51 (m, 1H), 2.32 (dq, J=4.0, 12.8 Hz, 1H), 2.09-1.98 (m, 1H); MS (ESI) m/z 407.0 [M+H]+

Example 3. Synthesis of 3-(2-chloro-3'-(((tetrahydrofuran-3-yl)oxy)methyl)-[1,1'-biphenyl]-3-yl)piperidine-2,6-dione (compound 190)

3-(2-chloro-3'-(((tetrahydrofuran-3-yl)oxy)methyl)-[1,1'-biphenyl]-3-yl)piperidine-2,6-dione was prepared from 3-(3-bromo-2-chlorophenyl)piperidine-2,6-dione and 4,4,5,5-tetramethyl-2-(3-(((tetrahydrofuran-3-yl)oxy)methyl)phenyl)-1,3,2-dioxaborolane according to General Scheme 1.

$^1$H NMR (400 MHz, DMSO-$d_6$) δ=11.01-10.87 (m, 1H), 7.50-7.28 (m, 7H), 4.59-4.44 (m, 2H), 4.34 (dd, J=5.2, 12.0 Hz, 1H), 4.27-4.17 (m, 1H), 3.78-3.64 (m, 4H), 2.84-2.74 (m, 1H), 2.58-2.55 (m, 1H), 2.40-2.27 (m, 1H), 2.11-1.92 (m, 3H); MS (ESI) m/z 398.1 [M–H]−

Example 4. Synthesis of 3-(2-chloro-3'-methyl-4'-(2-morpholinoethoxy)-[1,1'-biphenyl]-3-yl)piperidine-2,6-dione (compound 155)

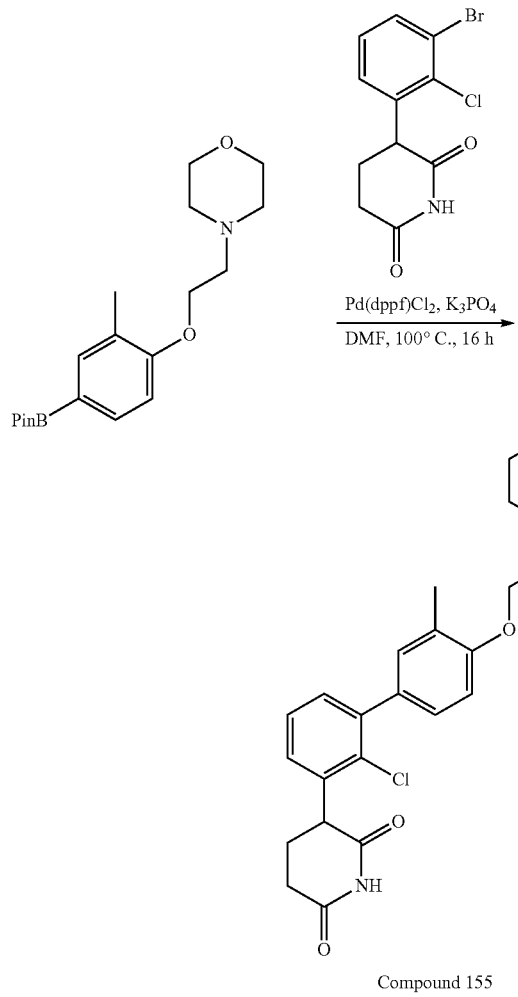

Compound 155

To a solution of 3-(3-bromo-2-chlorophenyl)piperidine-2,6-dione (141 mg, 0.466 mmol, 1.00 eq), 4-(2-(2-methyl-4-(4,4,5,5-tetramethyl-1,3,2-dioxaborolan-2-yl)phenoxy)ethyl)morpholine (178 mg, 0.512 mmol, 1.10 eq) in dimethylformamide (5 mL) was added [1,1-bis(diphenlphosphino)ferrocene]dichloropalladium(II) (34.1 mg, 46.6 umol, 0.10 eq) and tripotassium phosphate (296 mg, 1.40 mmol, 3.00 eq). The mixture was degassed and purged with nitrogen for three times, then stirred at 100° C. for 16 h. The reaction mixture was cooled to 25° C. and concentrated under reduced pressure. The residue was purified by flash silica gel chromatography (ISCO®; 12 g SepaFlash® Silica Flash Column, Eluent of 0~80% Ethyl acetate/Petroleum ether gradient @ 50 mL/min). The desired fraction was collected and concentrated under reduced pressure, then purified by Prep-HPLC (column: Phenomenex Luna C18 150*25 mm*10 μm; mobile phase: [water(formic acid)-acetonitrile]; B %: 8%-38%, 10 min) and lyophilized to afford 3-(2-chloro-3'-methyl-4'-(2-morpholinoethoxy)-[1,1'-biphenyl]-3-yl)piperidine-2,6-dione (82.6 mg, 185 μmol, 40% yield) as a white solid. 1H NMR (400 MHz, CDCl$_3$) δ=8.11 (s, 1H), 7.33-7.26 (m, 2H), 7.22-7.18 (m, 2H), 7.17-7.14 (m, 1H), 6.86 (d, J=9.0 Hz, 1H), 4.35-4.29 (m, 1H), 4.19 (t, J=5.6 Hz, 2H), 3.80-3.72 (m, 4H), 2.91 (t, J=5.6 Hz, 2H), 2.84-2.76 (m, 1H), 2.75-2.71 (m, 1H), 2.70-2.64 (m, 4H), 2.37-2.29 (m, 2H), 2.26 (s, 3H); MS (ESI) m/z 443.1 [M+H]+

Example 5. Synthesis of 3-(2-fluoro-4'-((1-methyl-1H-pyrazol-3-yl)methoxy)-[1,1'-biphenyl]-3-yl)piperidine-2,6-dione (compound 150)

(3-bromo-2-fluorophenyl)piperidine-2,6-dione was prepared from 1-bromo-2-fluoro-3-methyl-benzene according to General Scheme 2.

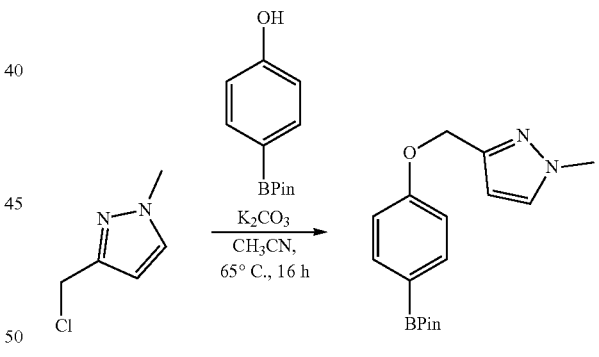

To a solution of 4-(4,4,5,5-tetramethyl-1,3,2-dioxaborolan-2-yl)phenol (2.53 g, 11.5 mmol, 1.50 eq) in acetic acid (20 mL) was added potassium carbonate (2.12 g, 15.3 mmol, 2.00 eq) and 3-(chloromethyl)-1-methyl-1H-pyrazole (1.00 g, 7.66 mmol, 1.00 eq). The mixture was stirred at 65° C. for 16 h. The reaction mixture was filtered with Celite pad, and the filtered cake was washed with acetonitrile (100 mL). The filtrate was concentrated under reduce pressure to give a residue. The residue was purified by flash silica gel chromatography (ISCO®; 12 g SepaFlash® Silica Flash Column, Eluent of 0~50% Ethyl acetate/Petroleum ether gradient @ 40 mL/min) to give 1-methyl-3-((4-(4,4,5,5-tetramethyl-1,3,2-dioxaborolan-2-yl)phenoxy)methyl)-1H-pyrazole (2.32 g, 7.09 mmol, 93% yield) as yellow oil.

3-(2-fluoro-4'-((1-methyl-1H-pyrazol-3-yl)methoxy)-[1,1'-biphenyl]-3-yl)piperidine-2,6-dione was prepared from 1-methyl-3-((4-(4,4,5,5-tetramethyl-1,3,2-dioxaborolan-2-yl)phenoxy)methyl)-1H-pyrazole and 3-(3-bromo-2-fluorophenyl) piperidine-2,6-dione according to General Scheme 1.

MS (ESI) m/z 394.3 [M+H]$^+$

Example 6. Synthesis of -3-(2,4-dichloro-4'-((1-methyl-1H-pyrazol-3-yl)methoxy)-[1,1'-biphenyl]-3-yl)piperidine-2,6-dione (compound 146)

3-(3-bromo-2,6-dichlorophenyl)piperidine-2,6-dione was prepared from 1-bromo-2,4-dichloro-3-methylbenzene according to General Scheme 2.

3-(2,4-dichloro-4'-((1-methyl-1H-pyrazol-3-yl)methoxy)-[1,1'-biphenyl]-3-yl)piperidine-2,6-dione was prepared from 3-(3-bromo-2,6-dichlorophenyl)piperidine-2,6-dione and 1-methyl-3-((4-(4,4,5,5-tetramethyl-1,3,2-dioxaborolan-2-yl)phenoxy)methyl)-1H-pyrazole according to General Scheme 1.

MS (ESI) m/z 444.1 [M+H]$^+$

Example 7. Synthesis of 3-(2-chloro-4-fluoro-4'-((1-methyl-1H-pyrazol-3-yl)methoxy)-[1,1'-biphenyl]-3-yl)piperidine-2,6-dione (Compound 144)

3-(3-bromo-2-chloro-6-fluorophenyl)piperidine-2,6-dione was prepared from 1-bromo-2-chloro-4-fluoro-3-methylbenzene according to General Scheme 2.

3-(2-chloro-4-fluoro-4'-((1-methyl-1H-pyrazol-3-yl)methoxy)-[1,1'-biphenyl]-3-yl)piperidine-2,6-dione was prepared from 3-(3-bromo-2-chloro-6-fluorophenyl)piperidine-2,6-dione and 1-methyl-3-((4-(4,4,5,5-tetramethyl-1,3,2-dioxaborolan-2-yl)phenoxy)methyl)-1H-pyrazole according to General Scheme 1.

$^1$H NMR (400 MHz, DMSO-d$_6$) δ=10.99 (s, 1H), 7.68 (d, J=2.0 Hz, 1H), 7.40-7.29 (m, 4H), 7.09 (d, J=8.8 Hz, 2H), 6.33 (d, J=2.0 Hz, 1H), 5.04 (s, 2H), 4.50 (dd, J=5.2, 12.0 Hz, 1H), 3.84 (s, 3H), 2.91-2.79 (m, 1H), 2.56 (s, 1H), 2.16-2.08 (m, 1H), 2.07 (s, 1H), 2.07-1.96 (m, 1H); MS (ESI) m/z 428.1 [M+H]$^+$

Example 8. Synthesis of 3-(4-chloro-2-fluoro-4'-((1-methyl-1H-pyrazol-3-yl)methoxy)-[1,1'-biphenyl]-3-yl)piperidine-2,6-dione (Compound 145)

3-(3-bromo-6-chloro-2-fluorophenyl)piperidine-2,6-dione was prepared from 1-bromo-4-chloro-3-(chloromethyl)-2-fluorobenzene according to General Scheme 2.

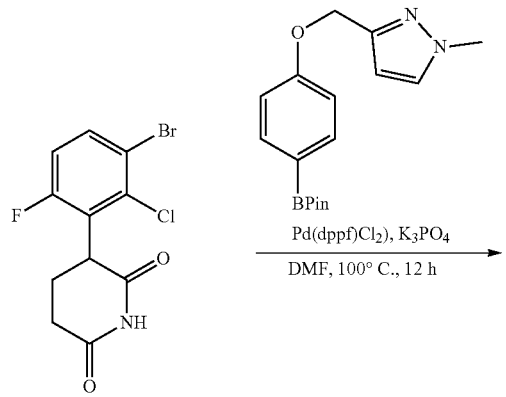

Compound 144

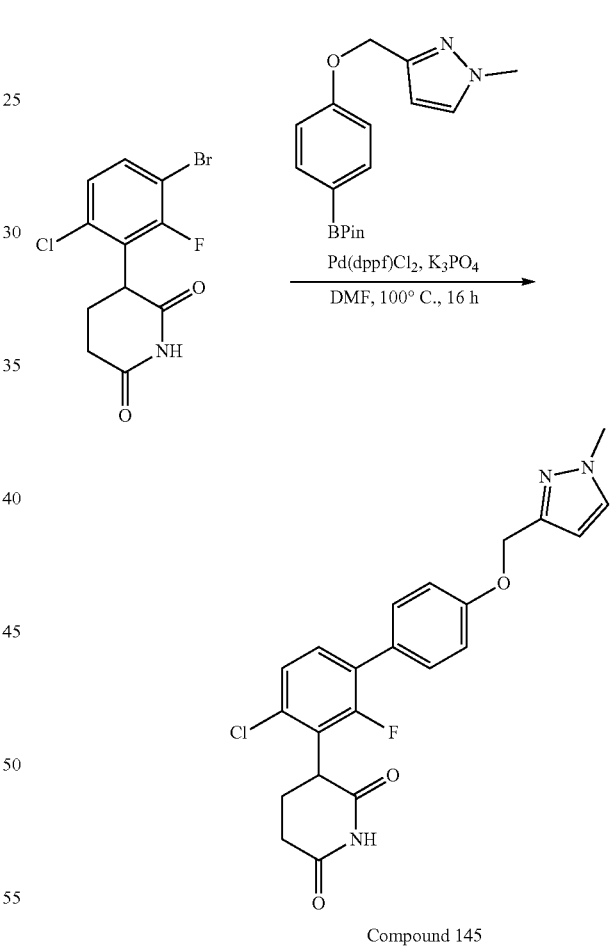

Compound 145

3-(4-chloro-2-fluoro-4'-((1-methyl-1H-pyrazol-3-yl)methoxy)-[1,1'-biphenyl]-3-yl)piperidine-2,6-dione was prepared from 3-(3-bromo-6-chloro-2-fluorophenyl)piperidine-2,6-dione and 1-methyl-3-((4-(4,4,5,5-tetramethyl-1,3,2-dioxaborolan-2-yl)phenoxy)methyl)-1H-pyrazole according to General Scheme 1.

$^1$H NMR (400 MHz, DMSO-d$_6$) δ=10.99 (s, 1H), 7.67 (d, J=2.0 Hz, 1H), 7.49-7.39 (m, 4H), 7.12 (d, J=8.4 Hz, 2H), 6.32 (d, J=2.0 Hz, 1H), 5.04 (s, 2H), 4.48-4.41 (m, 1H), 3.83

(s, 3H), 2.90-2.81 (m, 1H), 2.58-2.55 (m, 1H), 2.20-2.13 (m, 1H), 2.04-2.01 (m, 1H); MS (ESI) m/z 428.1 [M+H]+

Example 9. Synthesis of -3-(2',4-dichloro-4'-((1-methyl-1H-pyrazol-3-yl)methoxy)-[1,1'-biphenyl]-3-yl)piperidine-2,6-dione (compound 153)

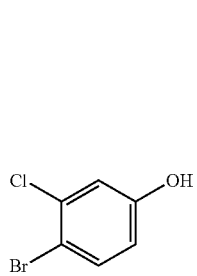
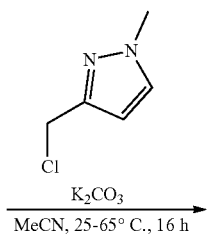
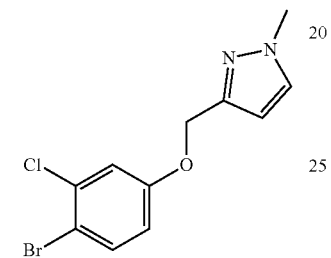

To a solution of 4-bromo-3-chlorophenol (715 mg, 3.45 mmol, 1.50 eq) in acetonitrile (150 mL) was added potassium carbonate (635 mg, 4.6 mmol, 2.00 eq). The mixture was stirred at 25° C. for 0.5 h. Then 1-3-(chloromethyl)-1-methyl-1H-pyrazole (300 mg, 2.30 mmol, 1.00 eq) was added, the reaction mixture was allowed to stir at 65° C. for 15.5 h. The reaction mixture was cooled to 25° C. and filtered through a pad of Celite and washed with ethyl acetate (10 mL), the filtration was concentrated under reduced pressure to give a residue. The residue was purified by flash silica gel chromatography (ISCO®; 12 g Sepa-Flash® Silica Flash Column, Eluent of 0-50% Ethyl acetate/Petroleum ether gradient @ 40 mL/min) to give 3-((4-bromo-3-chlorophenoxy)methyl)-1-methyl-1H-pyrazole (678 mg, 2.11 mmol, 92% yield) as white solid.

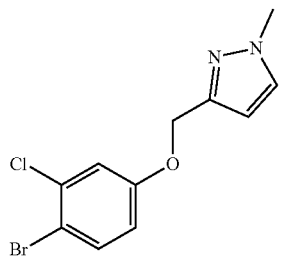
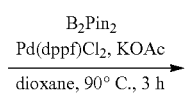
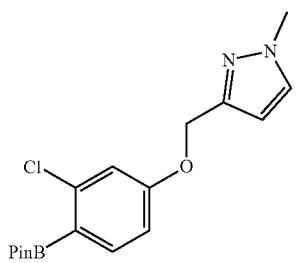

To a solution of 3-((4-bromo-3-chlorophenoxy)methyl)-1-methyl-1H-pyrazole (200 mg, 663 μmol, 1.00 eq), 4,4,4',4',5,5,5',5'-octamethyl-2,2'-bi(1,3,2-dioxaborolane) (185 mg, 730 μmol, 1.10 eq), potassium acetate (195 mg, 1.99 μmmol, 3.00 eq) and [1,1-bis(diphenylphosphino)ferrocene]dichloropalladium(II) (48.5 mg, 66.3 umol, 0.10 eq) in dioxane (8 mL). The mixture was degassed and purged with nitrogen for three times, then stirred at 100° C. for 3 h. The mixture was cooled to 20° C., filtered with Celite pad, washed with ethyl acetate (10 mL). The filtrate was concentrated under reduced pressure. The residue was purified by flash silica gel chromatography (ISCO®; 12 g Sepa-Flash® Silica Flash Column, Eluent of 0~50% Ethyl acetate/Petroleum ether gradient @ 40 mL/min) and then purified by reversed-phase column (0.1% formic acid condition) to give 3-((3-chloro-4-(4,4,5,5-tetramethyl-1,3,2-dioxaborolan-2-yl)phenoxy)methyl)-1-methyl-1H-pyrazole (62 mg, 128 μmol, 19% yield) as a white solid.

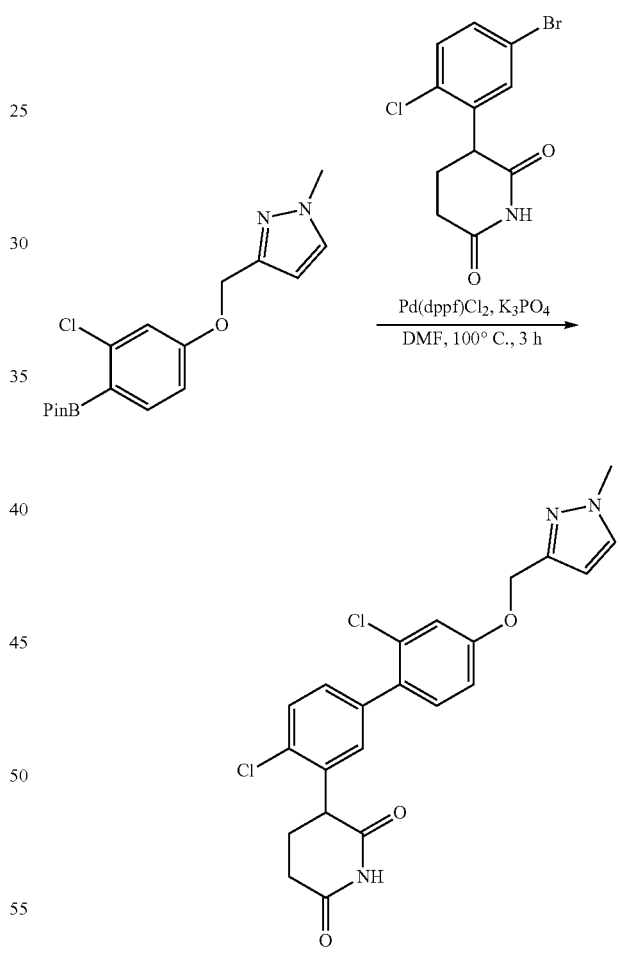

Compound 153

3-(2',4-dichloro-4'-((1-methyl-1H-pyrazol-3-yl)methoxy)-[1,1'-biphenyl]-3-yl)piperidine-2,6-dione was prepared from 3-(5-bromo-2-chlorophenyl)piperidine-2,6-dione and 3-((3-chloro-4-(4,4,5,5-tetramethyl-1,3,2-dioxaborolan-2-yl)phenoxy)methyl)-1-methyl-1H-pyrazole according to General Scheme 1.

MS (ESI) m/z 444.1 [M+H]+

Example 10. Synthesis of 3-(4-chloro-2-fluoro-4'-((1-methyl-1H-pyrazol-3-yl)methoxy)-[1,1'-biphenyl]-3-yl)piperidine-2,6-dione (Compound 152)

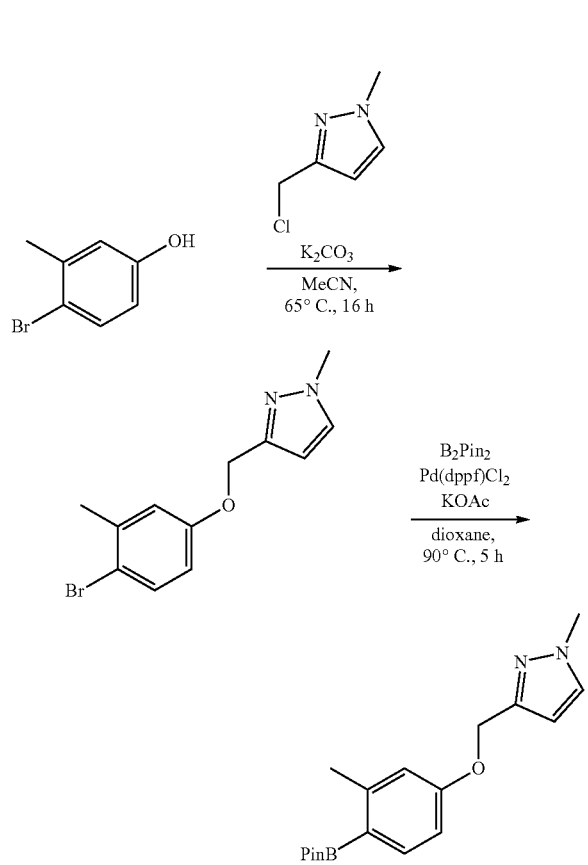

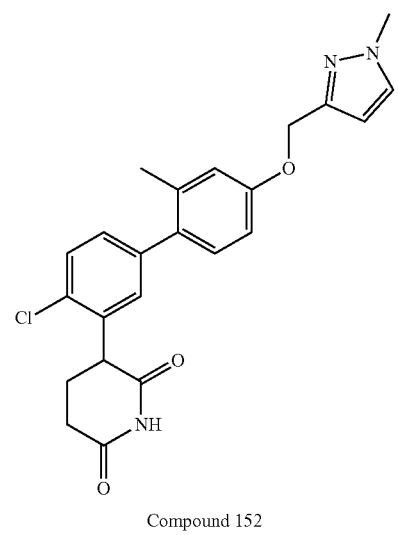

Compound 152

1-methyl-3-((3-methyl-4-(4,4,5,5-tetramethyl-1,3,2-dioxaborolan-2-yl)phenoxy)methyl)-1H-pyrazole was prepared from 4-bromo-3-methylphenol analogously to Example 9. $^1$H NMR (400 MHz, DMSO-$d_6$) δ=7.65 (d, J=2.0 Hz, 1H), 7.58-7.53 (m, 1H), 6.82-6.75 (m, 2H), 6.28 (d, J=2.0 Hz, 1H), 4.98 (s, 2H), 3.82 (s, 3H), 2.42 (s, 3H), 1.27 (s, 12H); MS (ESI) m/z 329.0 [M+H]$^+$ 3-(4-chloro-2-fluoro-4'-((1-methyl-1H-pyrazol-3-yl)methoxy)-[1,1'-biphenyl]-3-yl)piperidine-2,6-dione was prepared from 3-(5-bromo-2-chlorophenyl)piperidine-2,6-dione and 1-methyl-3-((3-methyl-4-(4,4,5,5-tetramethyl-1,3,2-dioxaborolan-2-yl)phenoxy)methyl)-1H-pyrazole according to General Scheme 1.

$^1$H NMR (400 MHz, DMSO-$d_6$) δ=10.89 (s, 1H), 7.66 (d, J=2.0 Hz, 1H), 7.49 (d, J=8.0 Hz, 1H), 7.30-7.22 (m, 2H), 7.12 (d, J=8.4 Hz, 1H), 6.95 (d, J=2.4 Hz, 1H), 6.93-6.87 (m, 1H), 6.30 (d, J=2.0 Hz, 1H), 5.01 (s, 2H), 4.25 (dd, J=5.2, 12.0 Hz, 1H), 3.83 (s, 3H), 2.84-2.71 (m, 1H), 2.56-2.53 (m, 1H), 2.38-2.32 (m, 1H), 2.21 (s, 3H), 2.07-1.96 (m, 1H).

MS (ESI) m/z 424.1 [M+H]$^+$

Example 11. Synthesis of 3-(4'-amino-2-chloro-[1,1'-biphenyl]-3-yl)piperidine-2,6-dione (compound 130)

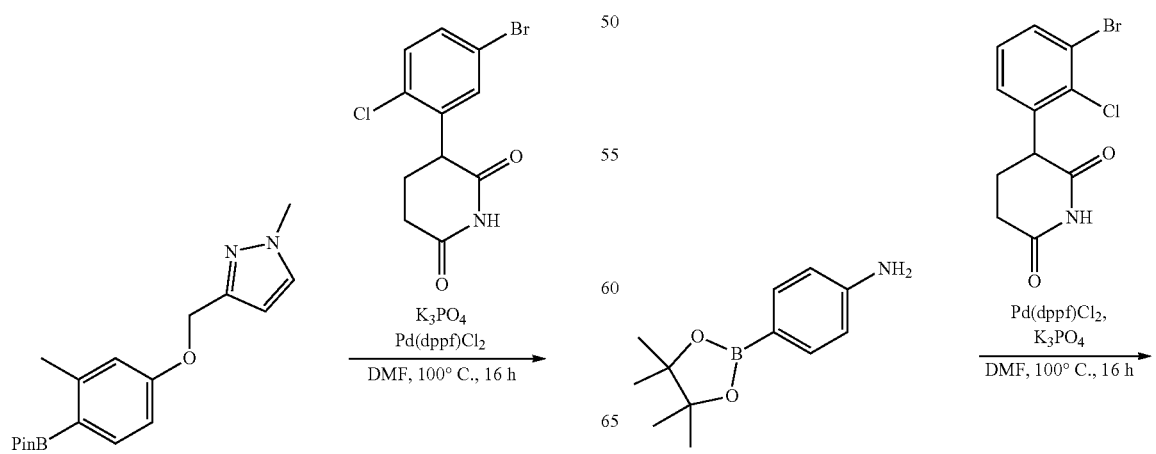

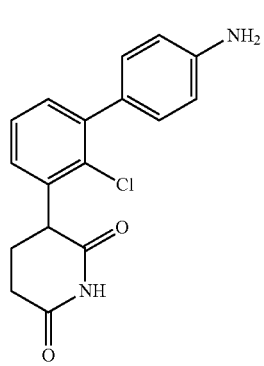

Compound 130

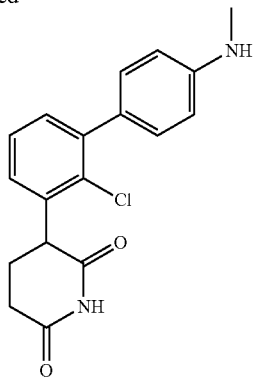

compound 134

3-(4'-amino-2-chloro-[1,1'-biphenyl]-3-yl)piperidine-2,6-dione was prepared form 4-(4,4,5,5-tetramethyl-1,3,2-dioxaborolan-2-yl)aniline and 3-(3-bromo-2-chloro-phenyl)piperidine-2,6-dione Add Back NMR according to General Scheme 1.

$^{1}$H NMR (400 MHz, DMSO-$d_6$) δ=10.89 (s, 1H), 7.28-7.35 (m, 1H), 7.19-7.27 (m, 2H), 7.07 (d, J=8.4 Hz, 2H), 6.61 (d, J=8.4 Hz, 2H), 5.24 (s, 2H), 4.31 (dd, J=12.0, 4.8 Hz, 1H), 2.71-2.83 (m, 1H), 2.57-2.63 (m, 1H), 2.30 (d, J=2.8 Hz, 1H), 1.98-2.08 (m, 1H); MS (ESI) m/z 314.9 [M+H]$^{+}$

Example 12. Synthesis of 3-(2-chloro-4'-(methylamino)-[1,1'-biphenyl]-3-yl)piperidine-2,6-dione (compound 134)

3-(2-chloro-4'-(methylamino)-[1,1'-biphenyl]-3-yl)piperidine-2,6-dione was prepared from 3-(3-bromo-2-chlorophenyl)piperidine-2,6-dione and N-methyl-4-(4,4,5,5-tetramethyl-1,3,2-dioxaborolan-2-yl)aniline according to General Scheme 1.

$^{1}$H NMR (400 MHz, DMSO-$d_6$) δ=10.9 (s, 1H), 7.38-7.29 (m, 1H), 7.28-7.19 (m, 2H), 7.15 (d, J=8.8 Hz, 2H), 6.59 (d, J=8.8 Hz, 2H), 5.83 (d, J=4.4 Hz, 1H), 4.31 (dd, J=5.2, 12.0 Hz, 1H), 2.82-2.73 (m, 1H), 2.73-2.67 (m, 3H), 2.55 (d, J=3.6 Hz, 1H), 2.37-2.27 (m, 1H), 2.08-1.98 (m, 1H).

MS (ESI) m/z 329.0 [M+H]$^{+}$

Example 13. Synthesis of 3-(2-chloro-4'-(isopropylamino)-[1,1'-biphenyl]-3-yl)piperidine-2,6-dione (compound 129)

3-(2-chloro-4'-(isopropylamino)-[1,1'-biphenyl]-3-yl)piperidine-2,6-dione was prepared from N-isopropyl-4-(4,4,5,5-tetramethyl-1,3,2-dioxaborolan-2-yl)aniline and 3-(3-bromo-2-chloro-phenyl)piperidine-2,6-dione according to General Scheme 1.

MS (ESI) m/z 357.2, 359.2 [M+H]$^{+}$

Example 14. Synthesis of 3-(2-chloro-6-iodo-4'-((1-methyl-1H-pyrazol-3-yl)methoxy)-[1,1'-biphenyl]-3-yl)piperidine-2,6-dione (compound 179)

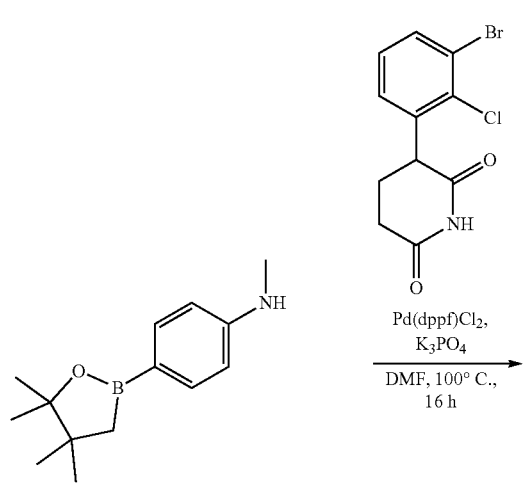

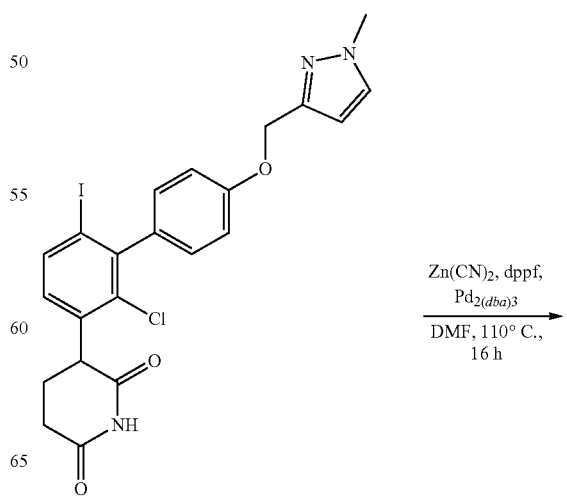

Example 15. Synthesis of 3-(2-chloro-6-ethynyl-4'-((1-methyl-1H-pyrazol-3-yl)methoxy)-[1,1'-biphenyl]-3-yl)piperidine-2,6-dione (compound 172)

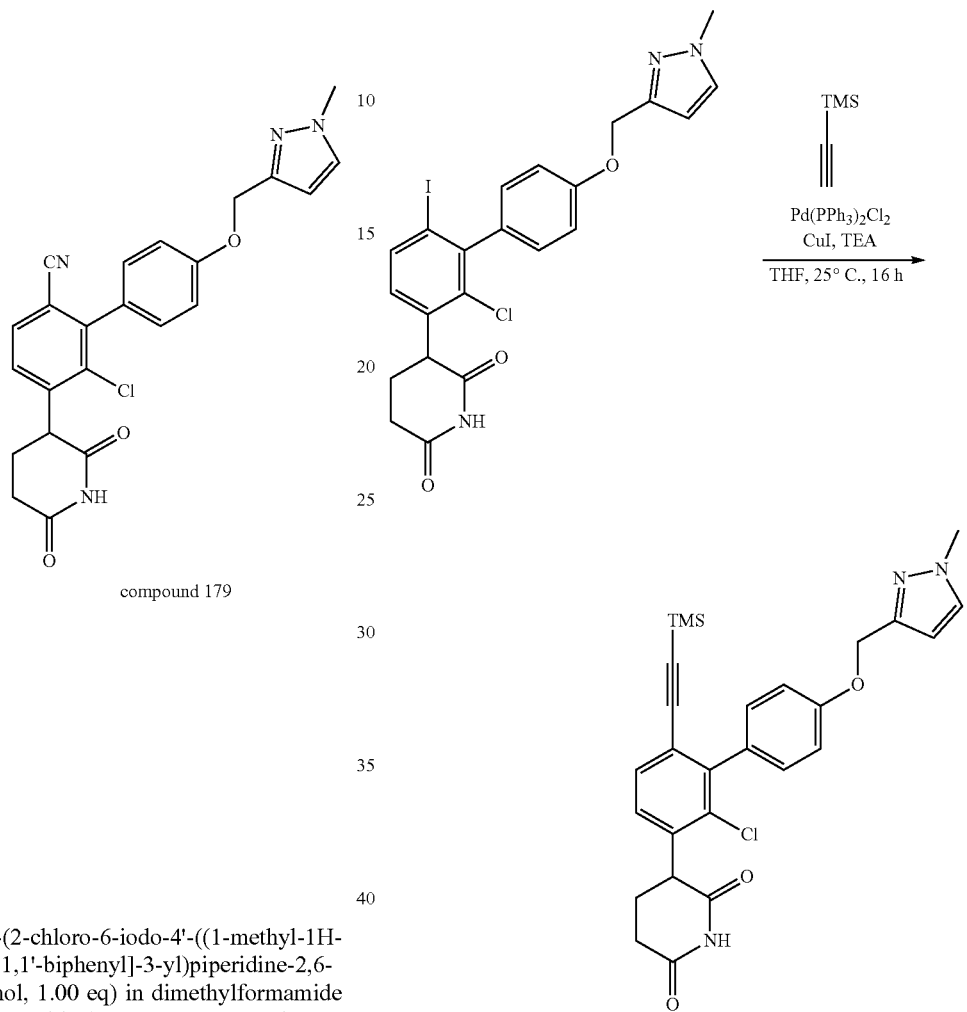

To a solution of 3-(2-chloro-6-iodo-4'-((1-methyl-1H-pyrazol-3-yl)methoxy)-[1,1'-biphenyl]-3-yl)piperidine-2,6-dione (70.0 mg, 130 μmol, 1.00 eq) in dimethylformamide (2 mL) was added zinc cyanide (170 mg, 1.45 mmol, 11.1 eq), tris(dibenzylideneacetone)dipalladium (23.9 mg, 26.1 μmol, 0.200 eq) and 1,1-Bis(diphenylphosphino)ferrocene (14.5 mg, 26.1 μmol, 0.200 eq). The mixture was stirred at 110° C. for 16 h under nitrogen atmosphere. The mixture was cooled to 25° C. and concentrated under reduced pressure. The residue was purified by flash silica gel chromatography (ISCO®; 4 g SepaFlash® Silica Flash Column, Eluent of 0~50% ethyl acetate/petroleum ether gradient @ 20 mL/min). And then the residue was purified by Prep-HPLC (column: Phenomenex luna C18 150*25 mm*10 um; mobile phase: [water (formic acid)-acetonitrile]; B %: 25%-58%, 9 min) to afford 3-(2-chloro-6-iodo-4'-((1-methyl-1H-pyrazol-3-yl)methoxy)-[1,1'-biphenyl]-3-yl)piperidine-2,6-dione (26.5 mg, 60.3 μmol, 46% yield) as a white solid.

$^1$H NMR (400 MHz, DMSO-$d_6$) δ=10.99 (s, 1H), 7.91 (d, J=8.0 Hz, 1H), 7.68 (d, J=2.0 Hz, 1H), 7.57 (d, J=8.0 Hz, 1H), 7.33 (t, J=8.0 Hz, 2H), 7.15 (d, J=8.8 Hz, 2H), 6.35 (d, J=2.0 Hz, 1H), 5.07 (s, 2H), 4.44 (dd, J=5.2, 12.4 Hz, 1H), 3.85 (s, 3H), 2.85-2.75 (m, 1H), 2.60-2.56 (m, 1H), 2.39-2.32 (m, 1H), 2.08-2.00 (m, 1H). MS (ESI) m/z 435.1 [M+H]$^+$ 3-(2-chloro-6-iodo-4'-((1-methyl-1H-pyrazol-3-yl)methoxy)-[1,1'-biphenyl]-3-yl)piperidine-2,6-dione was prepared analogously to Example 14. To a solution of 3-(2-chloro-6-iodo-4'-((1-methyl-1H-pyrazol-3-yl)methoxy)-[1,1'-biphenyl]-3-yl)piperidine-2,6-dione (200 mg, 373 μmol, 1.00 eq) and ethynyltrimethylsilane (110 mg, 1.12 mmol, 155 μL, 3.00 eq) in tetrahydrofuran (5 mL) was added bis(triphenylphosphine)palladium(II) chloride (52.4 mg, 74.7 μmol, 0.200 eq), copper iodide (35.6 mg, 187 μmol, 0.500 eq) and triethylamine (151 mg, 1.49 mmol, 208 μL, 4.00 eq).

The mixture was stirred at 25° C. for 16 h under nitrogen atmosphere. The mixture was concentrated under reduced pressure. The residue was purified by flash silica gel chromatography (ISCO®; 4 g SepaFlash® Silica Flash Column, Eluent of 0~50% ethyl acetate/petroleum ether gradient @ 18 mL/min) to afford 3-(2-chloro-4'-((1-methyl-1H-pyrazol-3-yl)methoxy)-6-((trimethylsilyl)ethynyl)-[1,1'-biphenyl]-3-yl)piperidine-2,6-dione (100 mg, 170 μmol, 46% yield) as brown gum.

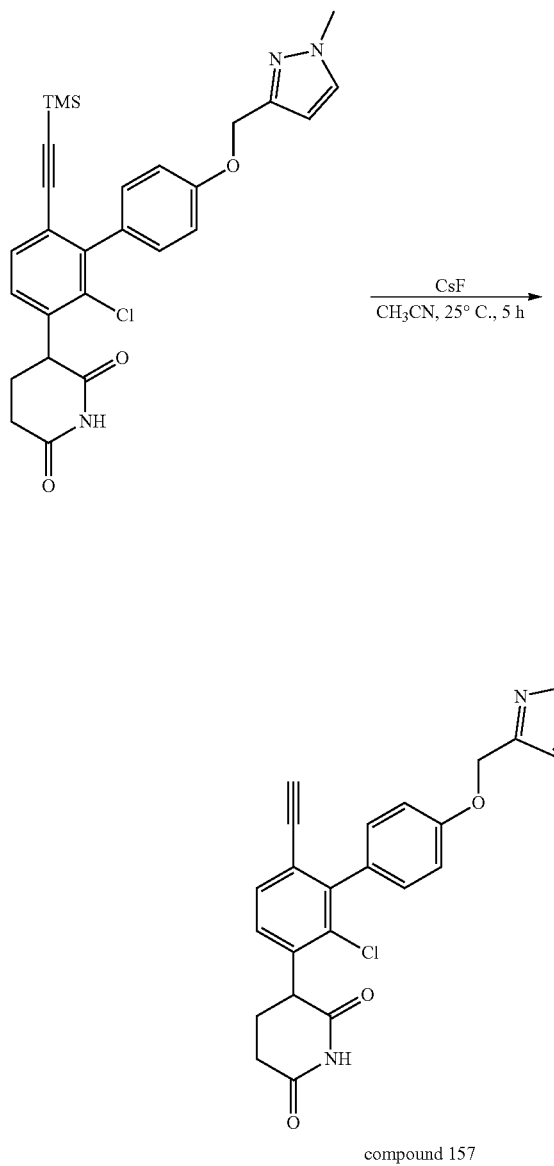

compound 157

To a solution of 3-(2-chloro-4'-((1-methyl-1H-pyrazol-3-yl)methoxy)-6-((trimethylsilyl)ethynyl)-[1,1'-biphenyl]-3-yl)piperidine-2,6-dione (100 mg, 170 μmol, 1.00 eq) in acetonitrile (4 mL) was added cesium fluoride (150 mg, 988 μmol, 5.00 eq). The mixture was stirred at 25° C. for 5 h. The mixture was filtered and concentrated under reduced pressure. The residue was purified by Prep-NPLC (column: Welch Ultimate XB-SiOH 250*50*10 μm; mobile phase: [Hexane-ethanol]; B %: 5%-45%, 15 min) to afford 3-(2-chloro-6-ethynyl-4'-((1-methyl-1H-pyrazol-3-yl)methoxy)-[1,1'-biphenyl]-3-yl)piperidine-2,6-dione (51.5 mg, 117 μmol, 59 yield, 99% purity) as a white solid.

$^1$H NMR (400 MHz, DMSO-$d_6$) δ=10.93 (s, 1H), 7.68 (d, J=2.0 Hz, 1H), 7.53 (d, J=8.0 Hz, 1H), 7.34 (d, J=8.0 Hz, 1H), 7.20 (t, J=7.6 Hz, 2H), 7.08 (d, J=8.4 Hz, 2H), 6.35 (d, J=2.0 Hz, 1H), 5.03 (s, 2H), 4.32 (dd, J=5.2, 12.0 Hz, 1H), 4.07 (s, 1H), 3.85 (s, 3H), 2.85-2.71 (m, 1H), 2.61-2.52 (m, 1H), 2.40-2.23 (m, 1H), 2.10-1.95 (m, 1H) MS (ESI) m/z 434.1 [M+H]$^+$

Example 16. Synthesis of 3-(4'-((1H-imidazol-4-yl)methoxy)-2-chloro-[1,1'-biphenyl]-3-yl)piperidine-2,6-dione (compound 167)

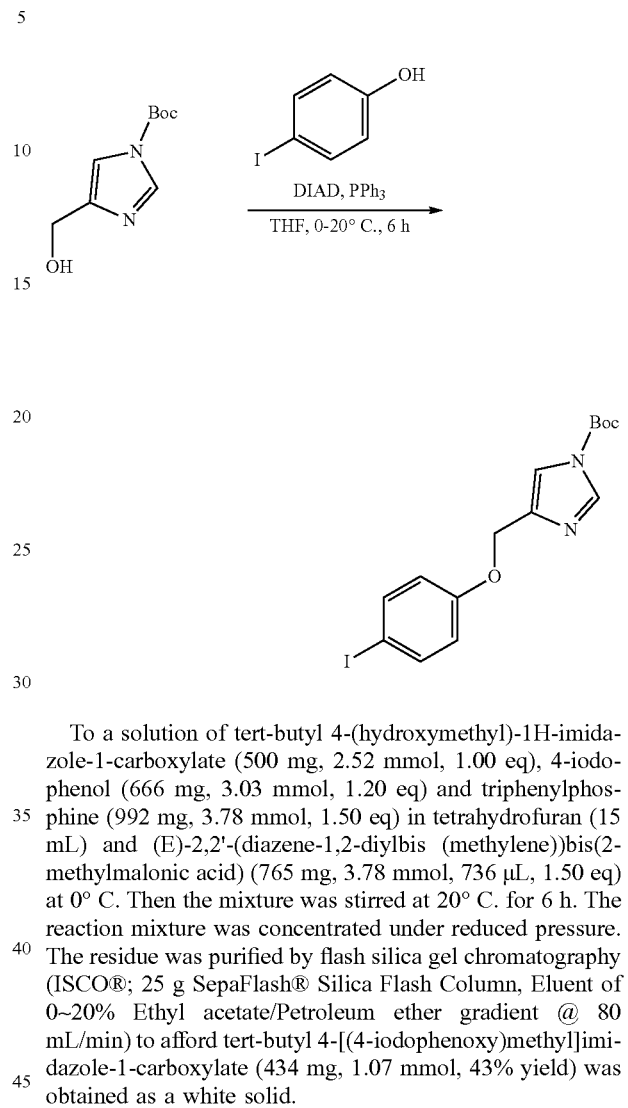

To a solution of tert-butyl 4-(hydroxymethyl)-1H-imidazole-1-carboxylate (500 mg, 2.52 mmol, 1.00 eq), 4-iodophenol (666 mg, 3.03 mmol, 1.20 eq) and triphenylphosphine (992 mg, 3.78 mmol, 1.50 eq) in tetrahydrofuran (15 mL) and (E)-2,2'-(diazene-1,2-diylbis (methylene))bis(2-methylmalonic acid) (765 mg, 3.78 mmol, 736 μL, 1.50 eq) at 0° C. Then the mixture was stirred at 20° C. for 6 h. The reaction mixture was concentrated under reduced pressure. The residue was purified by flash silica gel chromatography (ISCO®; 25 g SepaFlash® Silica Flash Column, Eluent of 0~20% Ethyl acetate/Petroleum ether gradient @ 80 mL/min) to afford tert-butyl 4-[(4-iodophenoxy)methyl]imidazole-1-carboxylate (434 mg, 1.07 mmol, 43% yield) was obtained as a white solid.

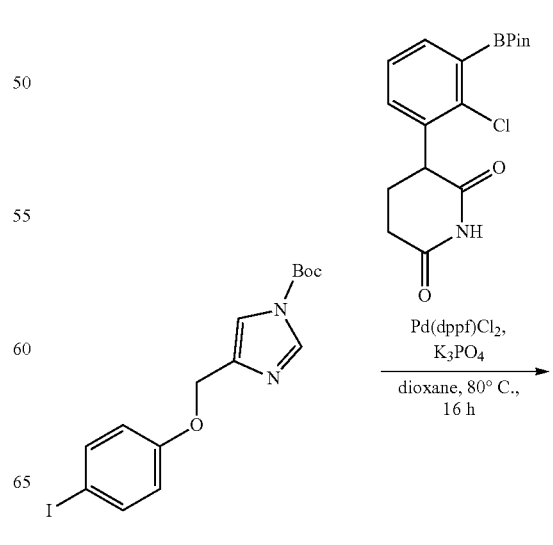

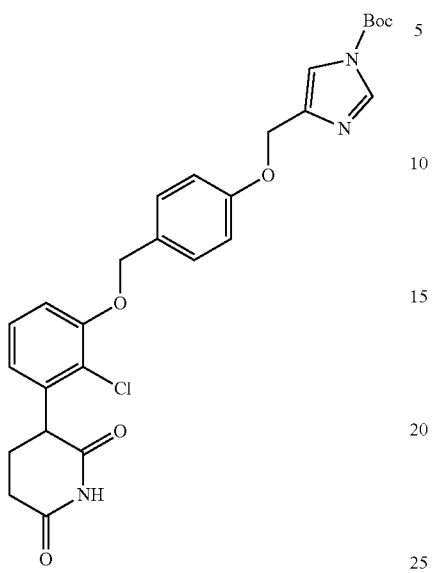

To a solution of tert-butyl 4-((4-iodophenoxy)methyl)-1H-imidazole-1-carboxylate (150 mg 0.375 μmmol, 1.00 eq), 3-(2-chloro-3-(4,4,5,5-tetramethyl-1,3,2-dioxaborolan-2-yl)phenyl)piperidine-2,6-dione (172 mg, 0.412 μmmol, 84% purity, 1.10 eq), [1,1'-bis(diphenylphosphino)ferrocene]dichloropalladium(II) (27.4 mg, 0.0375 mmol, 0.100 eq) and potassium phosphate (239 mg, 1.12 mmol, 3.00 eq) in 1,4-dioxane (5 mL). Then the mixture was degassed and purged with nitrogen for 3 times, and stirred at 80° C. for 16 h under nitrogen atmosphere. The reaction mixture was filtered and concentrated under reduced pressure to give a residue. The crude product (170 mg, 0.343 mmol) was obtained as a green solid, and used into next step without further purification.

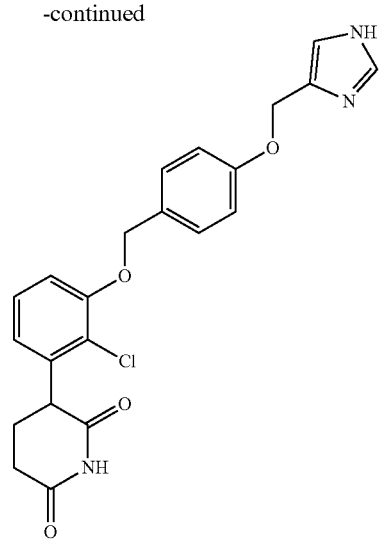

compound 167

To a solution of tert-butyl 4-[[4-[2-chloro-3-(2,6-dioxo-3-piperidyl)phenyl]phenoxy]methyl]imidazole-1-carboxylate (170 mg, 0.343 mmol, crude, 1.00 eq) in ethyl acetate (2 mL) was added dropwise chlorohydric acid/ethyl acetate (4 M, 2 mL, 23.3 eq) at 0° C. The mixture was stirred at 25° C. for 16 h. The reaction mixture was quenched by addition water 5 mL at 25° C., and then neutralized with saturated sodium bicarbonate (15 mL) and extracted with ethyl acetate (3×20 mL). The combined organic layers were dried over anhydrous sodium sulfate, filtered and concentrated under reduced pressure to give a residue. The residue was purified by flash silica gel chromatography (ISCO®; 12 g Sepa-Flash® Silica Flash Column, Eluent of 0-100% Ethyl acetate/Petroleum ether gradient @ 30 mL/min), followed by Prep-HPLC (column: Phenomenex luna C18 150*25 mm*10 um; mobile phase: [water (formic acid)-acetonitrile]; B %: 10%-30%, 9 min) to afford 3-(4'-((1H-imidazol-4-yl)methoxy)-2-chloro-[1,1'-biphenyl]-3-yl)piperidine-2,6-dione (10.4 mg, 0.0261 mmol, 8% yield, 99% purity) was obtained as a white solid.

$^1$H NMR (400 MHz, DMSO-$d_6$) δ=10.91 (s, 1H), 8.14 (s, 1H), 7.66 (s, 1H), 7.39-7.27 (m, 5H), 7.20 (s, 1H), 7.10 (d, J=8.8 Hz, 2H), 5.01 (s, 2H), 4.33 (dd, J=5.2, 12.0 Hz, 1H), 2.79 (s, 1H), 2.52-2.51 (m, 1H), 2.33-2.26 (m, 1H), 2.06 (s, 1H); MS (ESI) m/z 396.1[M+H]$^+$

Example 17. Synthesis of 3-(2-chloro-4'-((1-methyl-1H-imidazol-4-yl)methoxy)-[1,1'-biphenyl]-3-yl)piperidine-2,6-dione (compound 183)

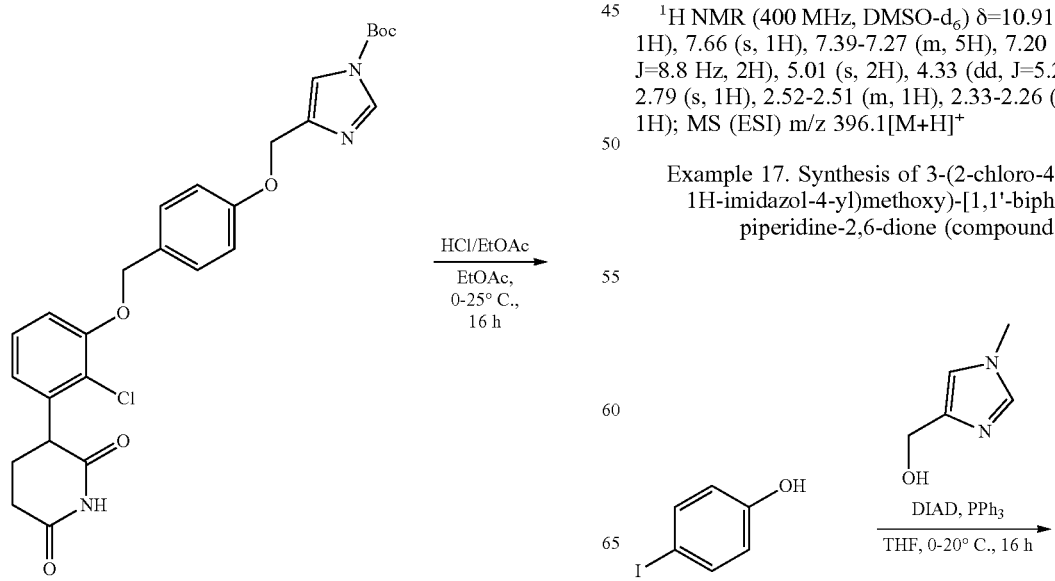

-continued

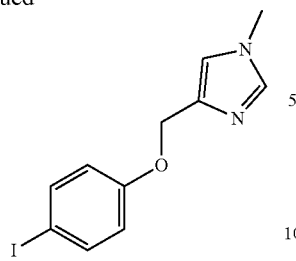

4-((4-iodophenoxy)methyl)-1-methyl-1H-imidazole was prepared from 4-iodophenol and (1-methyl-1H-imidazol-4-yl)methanol analogously to Example 16.

3-(2-fluoro-3-(indolin-5-yl)phenyl)piperidine-2,6-dione was prepared from 4-((4-iodophenoxy)methyl)-1-methyl-1H-imidazole and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.92 (s, 1H), 7.60 (s, 1H), 7.38-7.27 (m, 5H), 7.25 (s, 1H), 7.12-7.05 (m, 2H), 4.96 (s, 2H), 4.33 (dd, J=5.2, 12.0 Hz, 1H), 3.65 (s, 3H), 2.79 (ddd, J=5.2, 12.4, 17.6 Hz, 1H), 2.55 (br d, J=3.6 Hz, 1H), 2.39-2.26 (m, 1H), 2.10-2.00 (m, 1H);

MS (ESI) m/z 410.0 [M+H]$^+$

Example 18. Synthesis of 3-(2-chloro-4'-((1-methyl-1H-imidazol-5-yl)methoxy)-[1,1'-biphenyl]-3-yl)piperidine-2,6-dione (compound 186)

5-((4-iodophenoxy)methyl)-1-methyl-1H-imidazole was prepared from 4-iodophenol and (1-methyl-1H-imidazol-5-yl)methanol analogously to Example 16.

3-(2-chloro-4'-((1-methyl-1H-imidazol-5-yl)methoxy)-[1,1'-biphenyl]-3-yl)piperidine-2,6-dione was prepared from 5-[(4-iodophenoxy)methyl]-1-methyl-imidazole and 3-(2-chloro-3-(4,4,5,5-tetramethyl-1,3,2-dioxaborolan-2-yl)phenyl)piperidine-2,6-dione according to Scheme 1.

$^1$H NMR (400 MHz, DMSO-$d_6$) δ=10.92 (s, 1H), 8.17 (s, 1H), 7.66 (s, 1H), 7.40-7.32 (m, 4H), 7.32-7.28 (m, 1H), 7.15-7.10 (m, 2H), 7.06 (s, 1H), 5.15 (s, 2H), 4.33 (dd, J=4.8, 12.0 Hz, 1H), 3.66 (s, 3H), 2.83-2.73 (m, 1H), 2.56 (d, J=3.6 Hz, 1H), 2.39-2.27 (m, 1H), 2.09-2.00 (m, 1H); MS (ESI) m/z 410.0 [M+H]$^+$

Example 19. Synthesis of 3-(2-chloro-4'-(1-(1-methyl-1H-pyrazol-3-yl)ethoxy)-[1,1'-biphenyl]-3-yl)piperidine-2,6-dione (compound 173)

3-(2-chloro-4'-(1-(1-methyl-1H-pyrazol-3-yl)ethoxy)-[1,1'-biphenyl]-3-yl)piperidine-2,6-dione was prepared from 3-(1-(4-iodophenoxy)ethyl)-1-methyl-1H-pyrazole and 3-(2-chloro-3-(4,4,5,5-tetramethyl-1,3,2-dioxaborolan-2-yl)phenyl)piperidine-2,6-dione according to Scheme 1.

$^1$H NMR (400 MHz, DMSO-$d_6$) δ=10.91 (s, 1H), 7.61 (d, J=2.0 Hz, 1H), 7.38-7.24 (m, 5H), 7.06-7.00 (m, 2H), 6.25 (d, J=2.4 Hz, 1H), 5.51 (q, J=6.4 Hz, 1H), 4.32 (dd, J=5.2, 12.0 Hz, 1H), 3.81 (s, 3H), 2.85-2.71 (m, 1H), 2.58-2.53 (m, 1H), 2.38-2.24 (m, 1H), 2.09-1.99 (m, 1H), 1.59 (d, J=6.4 Hz, 3H); MS (ESI) m/z 424.1 [M+H]$^+$

Example 20. Synthesis of 3-(2-chloro-4'-((3-methyl-2-oxopyridin-1(2H)-yl)methyl)-[1,1'-biphenyl]-3-yl)piperidine-2,6-dione (compound 187)

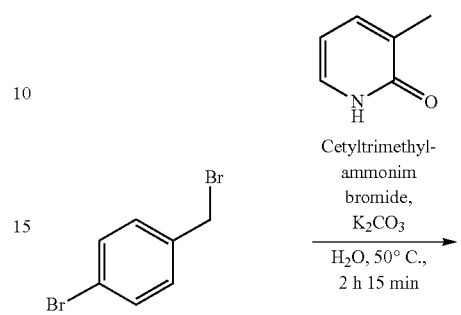

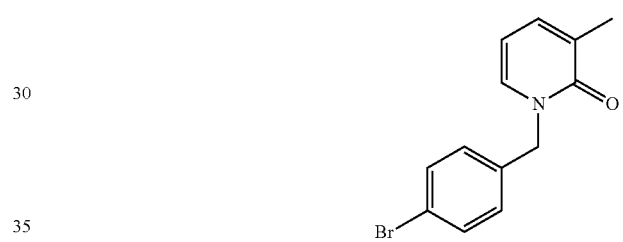

1-(4-bromobenzyl)-3-methylpyridin-2(1H)-one was prepared from 3-methylpyridin-2(1H)-one and 1-bromo-4-(bromomethyl)benzene according to General Scheme 8.

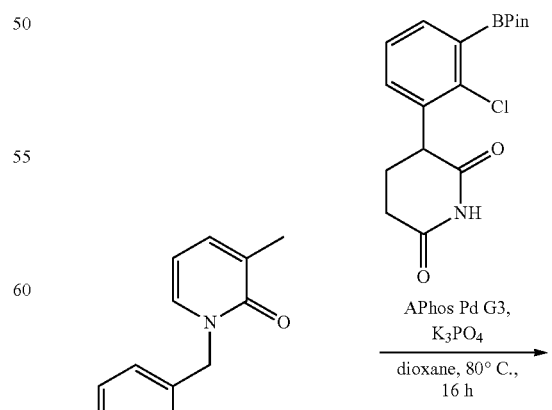

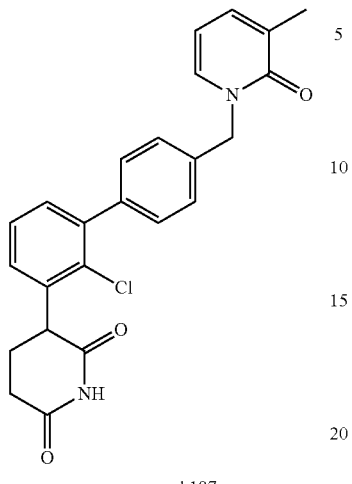

compound 187

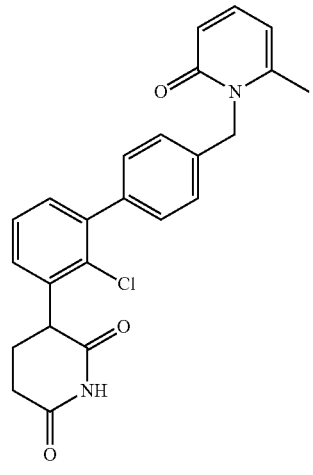

compound 184

3-(2-chloro-4'-((3-methyl-2-oxopyridin-1(2H)-yl)methyl)-[1,1'-biphenyl]-3-yl)piperidine-2,6-dione was prepared from 1-(4-bromobenzyl)-3-methylpyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-d$_6$) δ=10.92 (s, 1H), 7.76-7.69 (m, 1H), 7.43-7.32 (m, 7H), 7.31-7.25 (m, 1H), 6.20 (t, J=6.8 Hz, 1H), 5.17 (s, 2H), 4.38-4.27 (m, 1H), 2.86-2.72 (m, 1H), 2.56 (t, J=3.2 Hz, 1H), 2.34-2.25 (m, 1H), 2.11-1.95 (m, 4H); MS (ESI) m/z 421.2 [M+H]$^+$

Example 21. Synthesis of 3-(2-chloro-4'-((6-methyl-2-oxopyridin-1(2H)-yl)methyl)-[1,1'-biphenyl]-3-yl)piperidine-2,6-dione (compound 184)

1-(4-bromobenzyl)-6-methylpyridin-2(1H)-one was prepared from 1-bromo-4-(bromomethyl)benzene according to General Scheme 8.

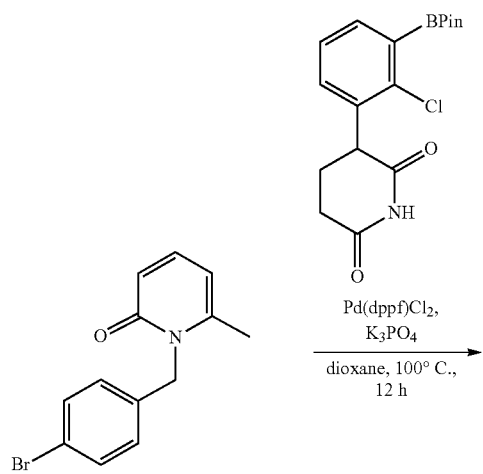

3-(2-chloro-4'-((6-methyl-2-oxopyridin-1(2H)-yl)methyl)-[1,1'-biphenyl]-3-yl)piperidine-2,6-dione was prepared from 1-(4-bromobenzyl)-6-methylpyridin-2(1H)-one and 1-(4-bromobenzyl)-6-methylpyridin-2(1H)-one according to General Scheme 1.

$^1$H NMR (400 MHz, DMSO-d$_6$) δ=10.91 (s, 1H), 7.43-7.32 (m, 5H), 7.29 (dd, J=2.0, 7.2 Hz, 1H), 7.19 (d, J=8.4 Hz, 2H), 6.37 (d, J=9.2 Hz, 1H), 6.18 (d, J=6.8 Hz, 1H), 5.34 (s, 2H), 4.33 (dd, J=5.2, 12.0 Hz, 1H), 2.79 (ddd, J=5.2, 12.0, 17.6 Hz, 1H), 2.55 (d, J=3.6 Hz, 1H), 2.38-2.32 (m, 1H), 2.31 (s, 3H), 2.08-1.99 (m, 1H); MS (ESI) m/z 421.0 [M+H]$^+$ Example 22. Synthesis of 3-(2-chloro-4'-((5-methyl-2-oxopyridin-1(2H)-yl)methyl)-[1,1'-biphenyl]-3-yl)piperidine-2,6-dione (compound 188)

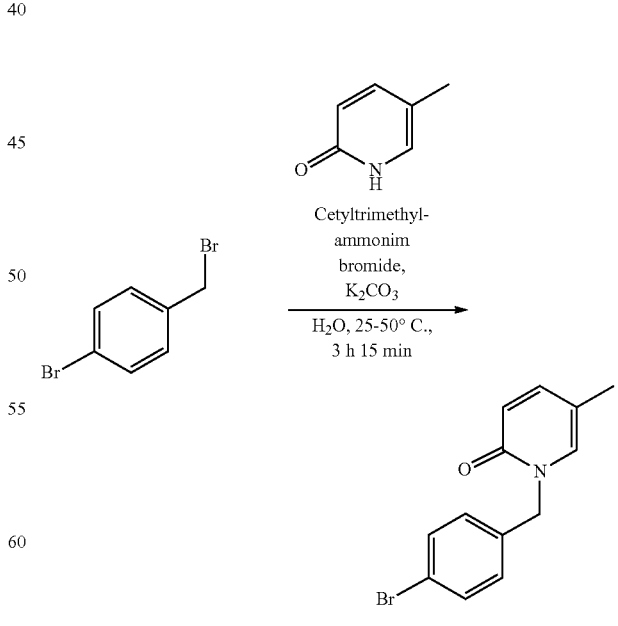

1-(4-bromobenzyl)-5-methylpyridin-2(1H)-one was prepared from 5-methylpyridin-2(1H)-one and 1-bromo-4-(bromomethyl)benzene according to General Scheme 8.

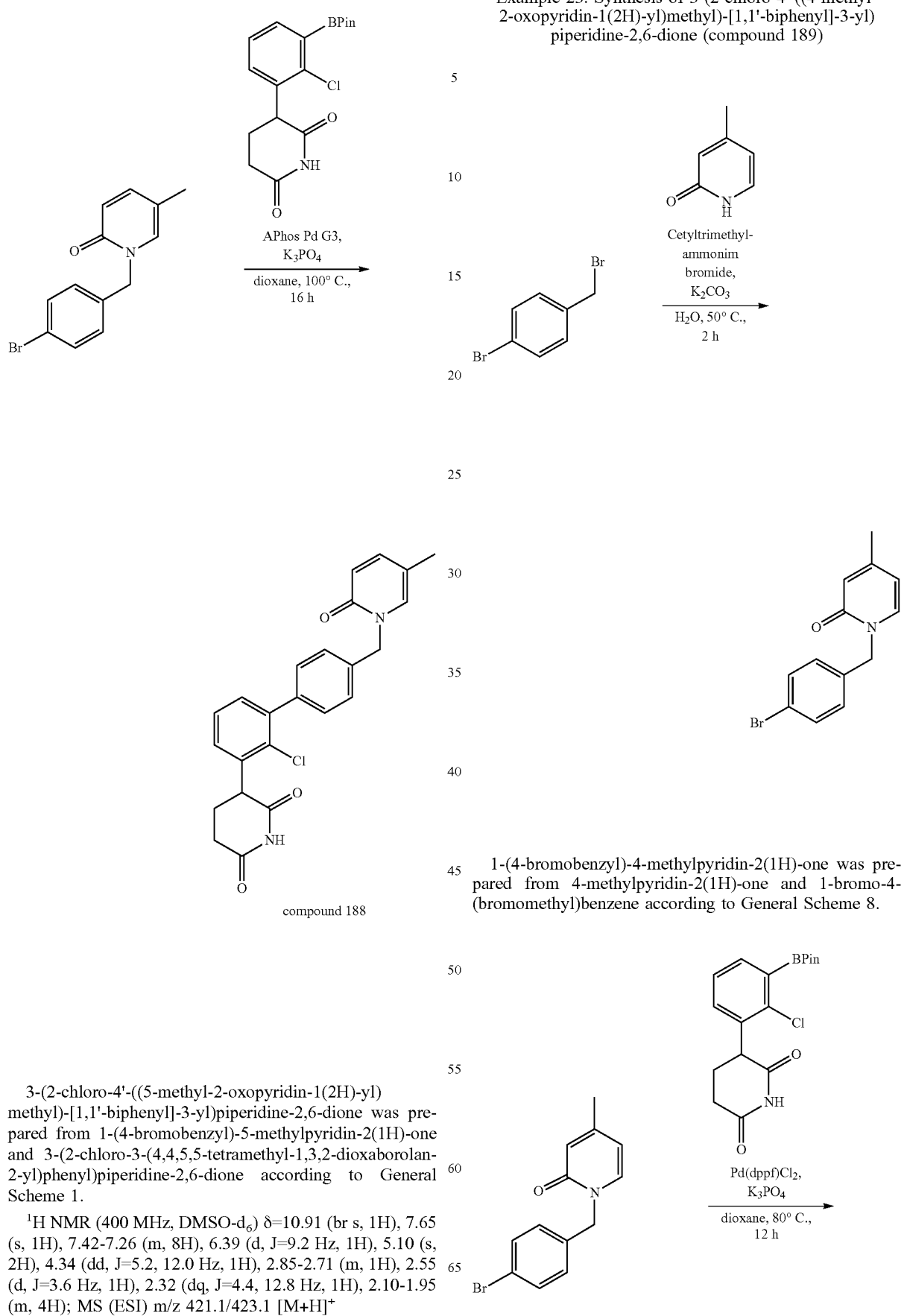

Example 23. Synthesis of 3-(2-chloro-4'-((4-methyl-2-oxopyridin-1(2H)-yl)methyl)-[1,1'-biphenyl]-3-yl)piperidine-2,6-dione (compound 189)

1-(4-bromobenzyl)-4-methylpyridin-2(1H)-one was prepared from 4-methylpyridin-2(1H)-one and 1-bromo-4-(bromomethyl)benzene according to General Scheme 8.

3-(2-chloro-4'-((5-methyl-2-oxopyridin-1(2H)-yl)methyl)-[1,1'-biphenyl]-3-yl)piperidine-2,6-dione was prepared from 1-(4-bromobenzyl)-5-methylpyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.91 (br s, 1H), 7.65 (s, 1H), 7.42-7.26 (m, 8H), 6.39 (d, J=9.2 Hz, 1H), 5.10 (s, 2H), 4.34 (dd, J=5.2, 12.0 Hz, 1H), 2.85-2.71 (m, 1H), 2.55 (d, J=3.6 Hz, 1H), 2.32 (dq, J=4.4, 12.8 Hz, 1H), 2.10-1.95 (m, 4H); MS (ESI) m/z 421.1/423.1 [M+H]$^+$

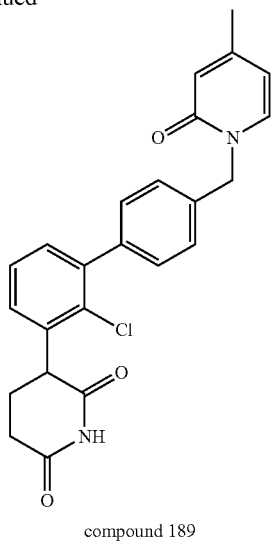

compound 189

3-(2-chloro-4'-((4-methyl-2-oxopyridin-1(2H)-yl)methyl)-[1,1'-biphenyl]-3-yl)piperidine-2,6-dione was prepared from 1-(4-bromobenzyl)-4-methylpyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.91 (br s, 1H), 7.72 (d, J=6.8 Hz, 1H), 7.38-7.27 (m, 7H), 6.25 (s, 1H), 6.13 (d, J=6.4 Hz, 1H), 5.11 (s, 2H), 4.35-4.31 (m, 1H), 2.82-2.76 (m, 1H), 2.55 (d, J=3.6 Hz, 1H), 2.33-2.31 (m, 1H), 2.14 (s, 3H), 2.07-2.02 (m, 1H); MS (ESI) m/z 421.1/423.0 [M+H, M+2+H]$^+$

Example 24. Synthesis of 3-(2-chloro-4'-(2-oxopyridin-1(2H)-yl)-[1,1'-biphenyl]-3-yl)piperidine-2,6-dione (compound 185)

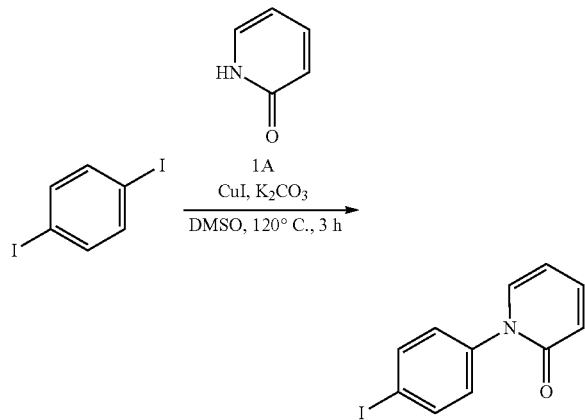

To a solution of 1,4-diiodobenzene (1.00 g, 3.03 mmol, 1.00 eq) and pyridin-2(1H)-one (28.26 mg, 3.03 mmol, 1.00 eq) in dimethyl sulfoxide (20 mL) was added copper(I) iodide (578 mg, 3.03 mmol, 1.00 eq) and potassium carbonate (2.01 g, 14.6 mmol, 4.80 eq) under nitrogen. The mixture was stirred at 120° C. for 3 h under nitrogen. The reaction mixture was partitioned between ethyl acetate (30 mL) and water (30 mL). The organic phase was separated, washed with water 60 mL (2×30 mL), dried over sodium sulfate, filtered and concentrated under reduced pressure to give a residue. The residue was purified by flash silica gel chromatography (ISCO®; 4 g SepaFlash® Silica Flash Column, Eluent of 0~10% Ethyl acetate/Petroleum ether gradient @ 20 mL/min) to give 1-(4-iodophenyl)pyridin-2(1H)-one (800 mg, 2.42 mmol, 79.9% yield) as a white solid.

$^1$H NMR (400 MHz, DMSO-$d_6$) δ=7.91-7.80 (m, 2H), 7.69-7.60 (m, 1H), 7.51 (ddd, J=2.0, 6.8, 9.2 Hz, 1H), 7.27-7.17 (m, 2H), 6.48 (d, J=9.2 Hz, 1H), 6.32 (dt, J=1.2, 6.8 Hz, 1H)
MS (ESI) m/z 298.0 [M+H]$^+$

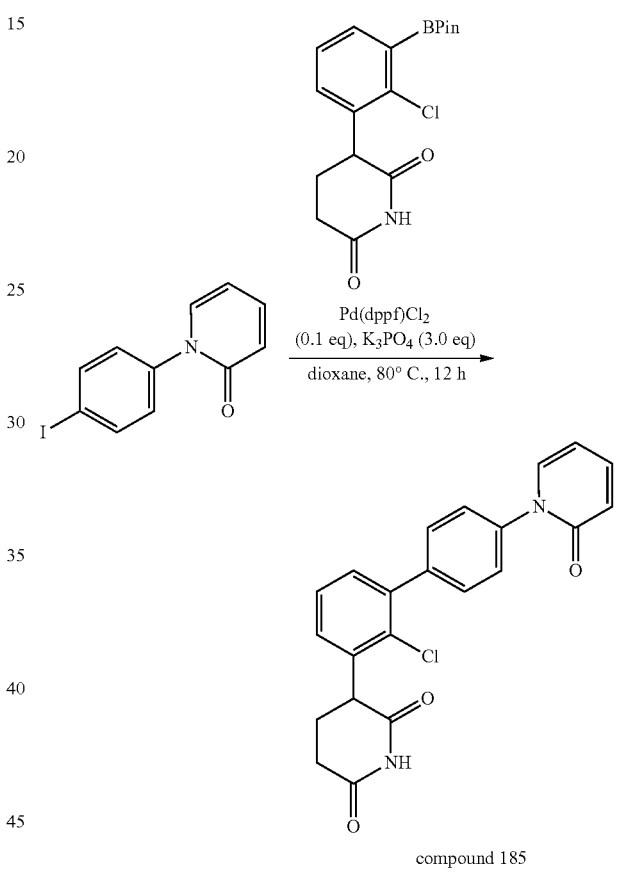

compound 185

To a solution of 3-(2-chloro-3-(4,4,5,5-tetramethyl-1,3,2-dioxaborolan-2-yl)phenyl)piperidine-2,6-dione (142 mg, 404 μmol, 1.20 eq) and 1-(4-iodophenyl)pyridin-2(1H)-one (100 mg, 337 uμmol, 1.00 eq) in dioxane (5 mL) was added potassium phosphate (215 mg, 1.01 mmol, 3.00 eq) and [1,1-Bis (diphenylphosphino) ferrocene]dichloropalladium (II) (25.0 mg, 34.0 μmol, 0.100 eq). The mixture was stirred at 80° C. for 12 h. The reaction mixture was filtered through a pad of Celite and washed with ethyl acetate (30 mL). The filtrate was concentrated in vacuo. The residue was purified by Prep-HPLC (column: Phenomenex luna C18 150*25 mm*10 μm; mobile phase: [water (formic acid)-acetonitrile]; B %: 36%-56%, 2 min). And then the residue was purified by Prep-HPLC (column: YMC Triart C18 150*25 mm*5 μm; mobile phase: [water (hydrochloric acid)-acetonitrile]; B %: 30%-60%, 10 min) to give 3-(2-chloro-4'-(2-oxopyridin-1(2H)-yl)-[1,1'-biphenyl]-3-yl)piperidine-2,6-dione (18.6 mg, 46.40 μmol, 13.79% yield) as a white solid.

$^1$H NMR (400 MHz, DMSO-d$_6$) δ=10.94 (s, 1H), 7.76-7.71 (m, 1H), 7.58-7.49 (m, 5H), 7.46-7.35 (m, 3H), 6.51 (d, J=9.2 Hz, 1H), 6.34 (t, J=6.8 Hz, 1H), 4.37 (dd, J=4.8, 12.0 Hz, 1H), 2.88-2.72 (m, 2H), 2.35 (dd, J=4.0, 12.8 Hz, 1H), 2.12-2.01 (m, 1H)

MS (ESI) m/z 393.0 [M+H]$^+$.

An alternative synthesis for Compound 185 is provided below.

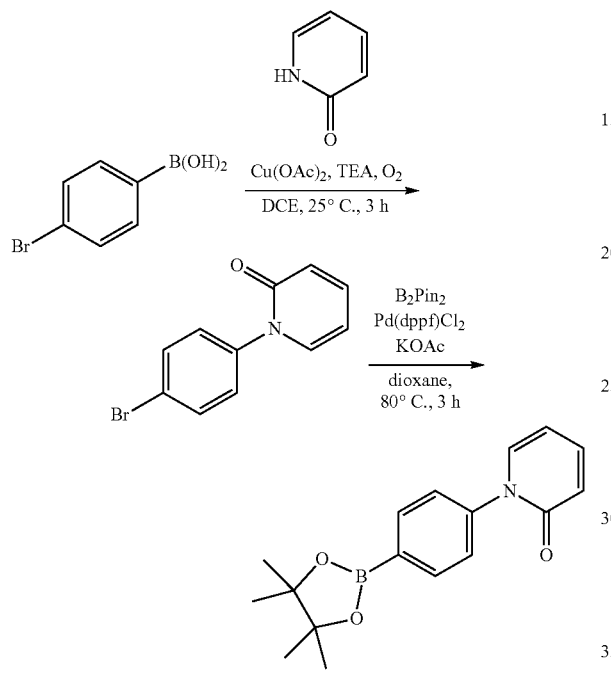

A mixture of (4-bromophenyl)boronic acid (3.00 g, 14.9 mmol, 1.00 eq), pyridin-2(1H)-one (1.70 g, 17.9 mmol, 1.20 eq), copper acetate (2.71 g, 14.9 mmol, 1.00 eq) and triethylamine (4.53 g, 44.8 mmol, 6.24 mL, 3.00 eq) in dichloroethane (5 mL) was degassed and purged with oxygen for 3 times, and then stirred at 25° C. for 3 hr. The reaction mixture was concentrated under reduced pressure to give a residue that was purified by flash silica gel chromatography (ISCO®; 20 g SepaFlash® Silica Flash Column, Eluent of 0~80% Ethyl acetate/Petroleum ether gradient @ 40 mL/min) to afford 1-(4-bromophenyl)pyridin-2(1H)-one (1.6 g, 6.33 mmol, 42% yield) as a white solid.

1H NMR (400 MHz, DMSO-d$_6$) δ=7.75-7.67 (m, 2H), 7.67-7.60 (m, 1H) 7.51 (ddd, J=9.2, 6.8, 2.0 Hz, 1H), 7.44-7.34 (m, 2H), 6.48 (d, J=9.2 Hz, 1H), 6.32 (dt, J=6.8, 1.2 Hz, 1H). MS (ESI) m/z 251.6 [M+H]$^+$ A mixture of 1-(4-bromophenyl)pyridin-2(1H)-one (500 mg, 2.00 mmol, 1.00 eq), 4,4,5,5-tetramethyl-2-(4,4,5,5-tetramethyl-1,3,2-dioxaborolan-2-yl)-1,3,2-dioxaborolane (558 mg, 2.20 mmol, 1.10 eq), [1,1-Bis(diphenylphosphino)ferrocene]dichloro-palladium(II) (146 mg, 199 umol, 0.100 eq) and potassium acetate (588 mg, 6.00 mmol, 3.00 eq) in dioxane (5 mL) was degassed and purged with nitrogen for 3 times, and then the mixture was stirred at 80° C. for 3 hr under nitrogen atmosphere. The reaction mixture was cooled to 25° C. and concentrated under reduced pressure to give a residue that was purified by flash silica gel chromatography (ISCO®; 25 g SepaFlash® Silica Flash Column, Eluent of 0~100% Ethyl acetate/Petroleum ether gradient @ 60 mL/min) to afford 1-(4-(4,4,5,5-tetramethyl-1,3,2-dioxaborolan-2-yl)phenyl)pyridin-2(1H)-one (500 mg, 1.53 mmol, 76% yield) as a white solid. 1H NMR (400 MHz, DMSO-d$_6$) δ=7.79 (d, J=7.6 Hz, 2H), 7.64-7.60 (m, 1H), 7.54-7.47 (m, 1H), 7.42 (d, J=7.6 Hz, 2H), 6.48 (d, J=9.2 Hz, 1H), 6.32 (t, J=6.8 Hz, 1H), 1.31 (s, 12H). MS (ESI) m/z 298.0 [M+H]$^+$

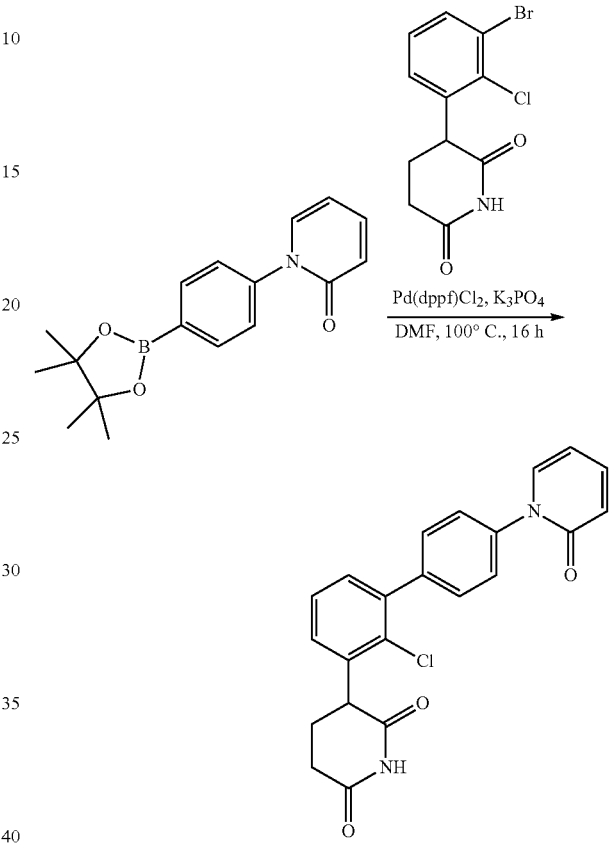

A mixture of 3-(3-bromo-2-chlorophenyl)piperidine-2,6-dione (2.78 g, 9.20 mmol, 1.00 eq), 1-(4-(4,4,5,5-tetramethyl-1,3,2-dioxaborolan-2-yl)phenyl)pyridin-2(1H)-one (3.00 g, 10.1 mmol, 1.10 eq) and [1,1-bis(diphenylphosphino)ferrocene]dichloropalladium(II) (672 mg, 918 µmol, 0.10 eq) and potassium phosphate (5.84 g, 27.5 mmol, 3.00 eq) in dimethylformamide (60 mL) was degassed and purged with nitrogen 3 times, then the mixture was stirred at 100° C. for 16 h under nitrogen atmosphere. The reaction mixture was filtered, the filtrate was concentrated under reduced pressure. The residue was purified by flash silica gel chromatography (ISCO®; 330 g SepaFlash® Silica Flash Column, Eluent of 100~100% Ethyl acetate and dichloromethane/Petroleum ether gradient @ 80 mL/min) followed by Prep-HPLC (column: Phenomenex luna C18 (250×70 mm, 10 m); mobile phase: [water (formic acid)-acetonitrile]; B %: 20%-50%, 20 min) and lyophilized to afford 3-(2-chloro-4'-(2-oxopyridin-1(2H)-yl)-[1,1'-biphenyl]-3-yl)piperidine-2,6-dione (926 mg, 2.33 mmol, 25% yield) as white solid. 1H NMR (400 MHz, DMSO-d$_6$) δ=10.94 (s, 1H), 7.73 (dd, J=1.6, 6.8 Hz, 1H), 7.58-7.49 (m, 5H), 7.47-7.35 (m, 3H), 6.51 (d, J=8.8 Hz, 1H), 6.34 (dt, J=1.6, 6.8 Hz, 1H), 4.43-4.33 (m, 1H), 2.87-2.74 (m, 1H), 2.60-2.54 (m, 1H), 2.42-2.29 (m, 1H), 2.12-2.02 (m, 1H); MS (ESI) m/z 392.9 [M+H]$^+$

Example 25. Synthesis of 3-(2,4-difluoro-4'-((2-oxopyridin-1(2H)-yl)methyl)-[1,1'-biphenyl]-3-yl)piperidine-2,6-dione (compound 147)

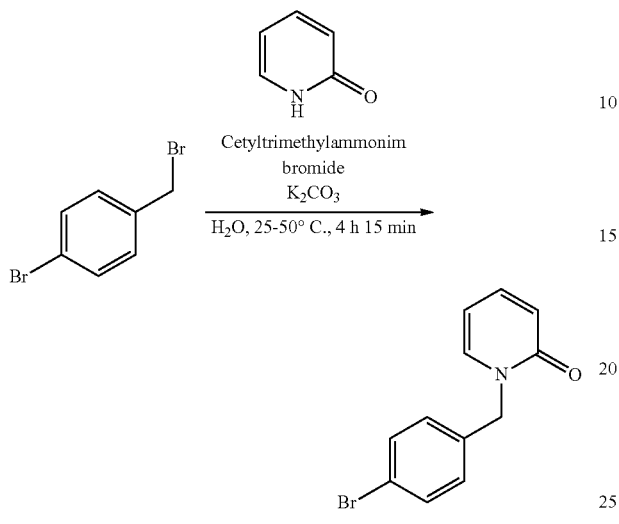

To a solution of N,N,N-trimethylhexadecan-1-aminium bromide (450 mg, 1.23 mmol, 0.08 eq) in water (20 mL) was added pyridin-2(1H)-one (1.50 g, 15.8 mmol, 1.00 eq) followed by potassium carbonate (3.27 g, 23.7 mmol, 1.50 eq). The mixture was stirred at 25° C. for 15 min. Then 1-bromo-4-(bromomethyl)benzene (4.34 g, 17.4 mmol, 1.10 eq) was added, the mixture was stirred at 50° C. for 4 h. The reaction mixture was cooled to 20° C. The reaction mixture was diluted with water (50 mL). The mixture was extracted with ethyl acetate (2×50 mL). The combined organic layers were washed with brine (50 mL), dried over sodium sulfate, filtered and concentrated under reduced pressure. The residue was triturated with petroleum ether/ethyl acetate=10/1 (66 mL) at 25° C. for 60 min. The mixture was filtered and the filter cake was dried under reduced pressure to afford 1-(4-bromobenzyl)pyridin-2(1H)-one (3.30 g, 12.4 mmol, 78% yield) as an off-white solid.

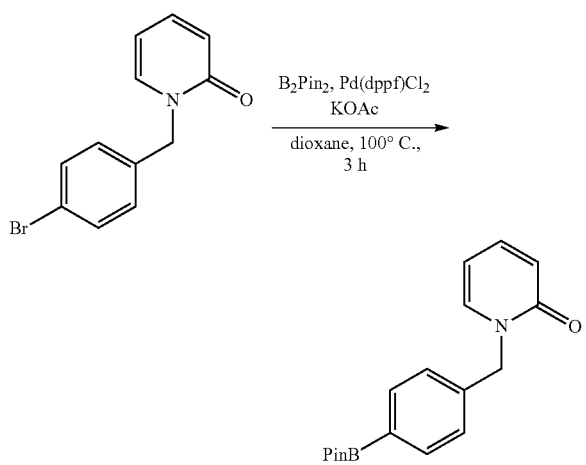

To a solution of 1-(4-bromobenzyl)pyridin-2(1H)-one (3.30 g, 12.5 mmol, 1.00 eq) and 4,4,4',4',5,5,5',5'-octamethyl-2,2'-bi(1,3,2-dioxaborolane) (3.48 g, 13.7 mmol, 1.10 eq) in dioxane (60 mL) were added potassium acetate (3.68 g, 37.5 mmol, 3.00 eq) and [1,1-bis(diphenylphosphino)ferrocene]dichloropalladium(II) (911 mg, 1.25 mmol, 0.10 eq). The mixture was stirred at 100° C. for 3 h under nitrogen atmosphere. The reaction mixture was cooled to 20° C., the reaction mixture was concentrated under reduced pressure. The residue was purified by flash silica gel chromatography (ISCO®; 120 g SepaFlash® Silica Flash Column, Eluent of 40~60% Ethyl acetate/Petroleum ether gradient @ 80 mL/min) to afford 1-(4-(4,4,5,5-tetramethyl-1,3,2-dioxaborolan-2-yl)benzyl)pyridin-2(1H)-one (3.03 g, 8.08 mmol, 65% yield, 83% purity) as yellow solid.

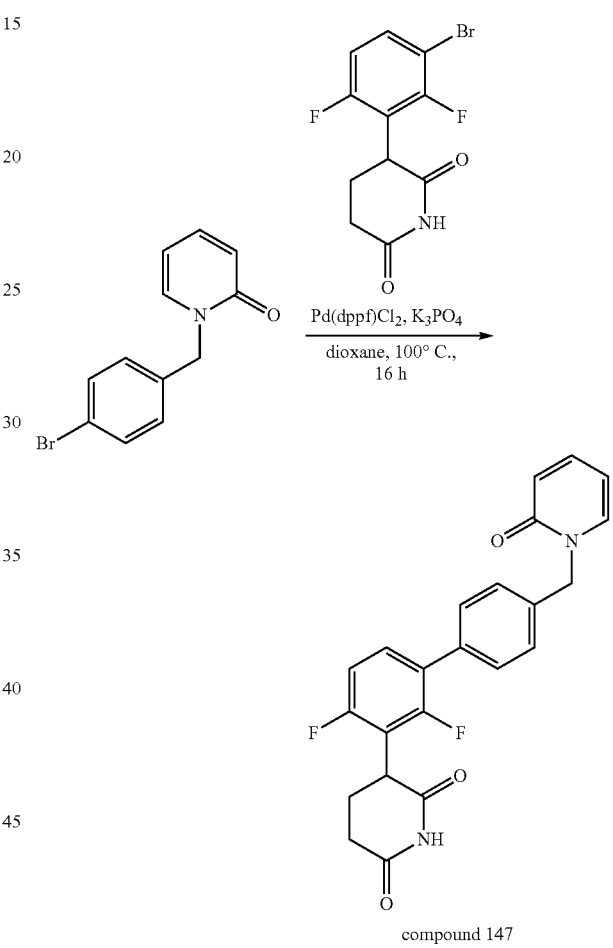

compound 147

To a solution of 3-(3-bromo-2,6-difluorophenyl)piperidine-2,6-dione (100 mg, 329 μmol, 1.00 eq) and 1-(4-(4,4,5,5-tetramethyl-1,3,2-dioxaborolan-2-yl)benzyl)pyridin-2(1H)-one (113 mg, 301 mol, 83% purity, 0.90 eq) in dioxane (3 mL) were added potassium phosphate (210 mg, 989 μmol, 3.01 eq) and [1,1-bis(diphenylphosphino)ferrocene]dichloropalladium(II) (25.0 mg, 34.2 μmol, 0.10 eq). The mixture was stirred at 100° C. for 16 h under nitrogen atmosphere. The reaction mixture was cooled to 25° C. and concentrated under reduced pressure. The residue was purified by flash silica gel chromatography (ISCO®; 4 g SepaFlash® Silica Flash Column, Eluent of 78~90% Ethyl acetate/Petroleum ether gradient @ 15 mL/min) followed by Prep-HPLC (column: Phenomenex luna C18 150×25 mm×10 m; mobile phase: [water (formic acid)-acetonitrile]; B %: 18%-38%, 10 min) and lyophilized to afford 3-(2,4-difluoro-4'-((2- oxopyridin-1(2H)-yl)methyl]-[1,1'-biphenyl]-3-yl)piperidine-2,6-dione (49.2 mg, 119 µmol, 36% yield) as an off-white solid.

$^1$H NMR (400 MHz, DMSO-d$_6$) δ=10.99 (s, 1H), 7.83 (dd, J=2.0, 6.8 Hz, 1H), 7.54-7.41 (m, 4H), 7.38 (d, J=8.4 Hz, 2H), 7.22 (t, J=9.2 Hz, 1H), 6.43 (d, J=9.2 Hz, 1H), 6.26 (dt, J=1.2, 6.8 Hz, 1H), 5.15 (s, 2H), 4.32 (dd, J=5.2, 12.4 Hz, 1H), 2.90-2.77 (m, 1H), 2.59-2.52 (m, 1H), 2.19 (dq, J=3.6, 13.2 Hz, 1H), 2.12-2.02 (m, 1H); MS (ESI) m/z 409.0 [M+H]$^+$

Example 26. Synthesis of 3-(2-chloro-4'-(((1-methyl-1H-pyrazol-3-yl)methyl)amino)-[1,1'-biphenyl]-3-yl)piperidine-2,6-dione (compound 180)

3-(2-chloro-4'-(((1-methyl-1H-pyrazol-3-yl)methyl)amino)-[1,1'-biphenyl]-3-yl)piperidine-2,6-dione was prepared from 4-iodo-N-((1-methyl-1H-pyrazol-3-yl)methyl)aniline and 3-(2-chloro-3-(4,4,5,5-tetramethyl-1,3,2-dioxaborolan-2-yl)phenyl)piperidine-2,6-dione according to General Scheme 1.

MS (ESI) m/z 409.1 [M+H]$^+$

Example 27. Synthesis of 3-(2-chloro-4'-(pyrrolidine-1-carbonyl)-[1,1'-biphenyl]-3-yl)piperidine-2,6-dione (compound 181)

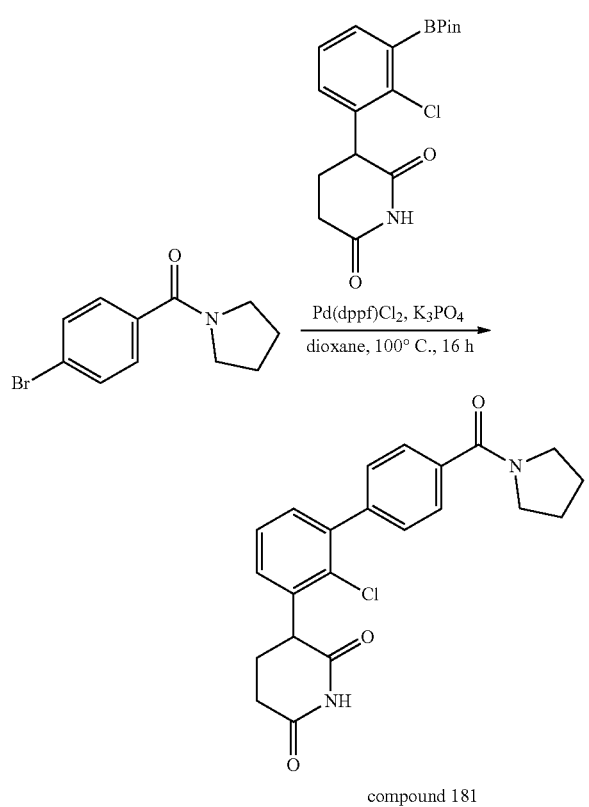

compound 181

A mixture of (4-bromophenyl)(pyrrolidin-1-yl)methanone (100 mg, 394 µmol, 1.00 eq), 3-(2-chloro-3-(4,4,5,5-tetramethyl-1,3,2-dioxaborolan-2-yl)phenyl)piperidine-2,6-dione (172 mg, 394 mol, 80% purity, 1.00 eq), potassium phosphate (251 mg, 1.18 mmol, 3.00 eq) and [1,1-Bis(diphenylphosphino)ferrocene] dichloropalladium(II) (29.0 mg, 39.6 µmol, 0.10 eq) in dioxane (3 mL) was degassed and purged with nitrogen for 3 times then the mixture was stirred at 100° C. for 16 h under nitrogen atmosphere. The mixture was concentrated under reduced pressure. The residue was purified by flash silica gel chromatography (ISCO®; 12 g SepaFlash® Silica Flash Column, Eluent of 85-95% Ethyl acetate/Petroleum ether gradient @ 40 mL/min) followed by Prep-HPLC (column: Phenomenex luna C18 150×25 mm×10 m; mobile phase: [water (formic acid)-acetonitrile]; B %: 26%-56%, 10 min) and lyophilized to afford 3-(2-chloro-4'-(pyrrolidine-1-carbonyl)-[1,1'-biphenyl]-3-yl)piperidine-2,6-dione (57.8 mg, 141 µmol, 36% yield) as a white solid.

$^1$H NMR (400 MHz, DMSO-d$_6$) δ=10.93 (br s, 1H), 7.60 (d, J=8.4 Hz, 2H), 7.50-7.43 (m, 2H), 7.43-7.37 (m, 2H), 7.36-7.31 (m, 1H), 4.36 (dd, J=4.8, 12.8 Hz, 1H), 3.47 (td, J=6.4, 18.0 Hz, 4H), 2.88-2.73 (m, 1H), 2.56 (d, J=3.2 Hz, 1H), 2.34 (dq, J=4.0, 12.8 Hz, 1H), 2.12-1.99 (m, 1H), 1.96-1.76 (m, 4H); MS (ESI) m/z 397.0 [M+H]$^+$

Example 28. Synthesis of 3-(2-chloro-4-fluoro-4'-((2-oxopyridin-1(2H)-yl)methyl)-[1,1'-biphenyl]-3-yl)piperidine-2,6-dione (compound 143)

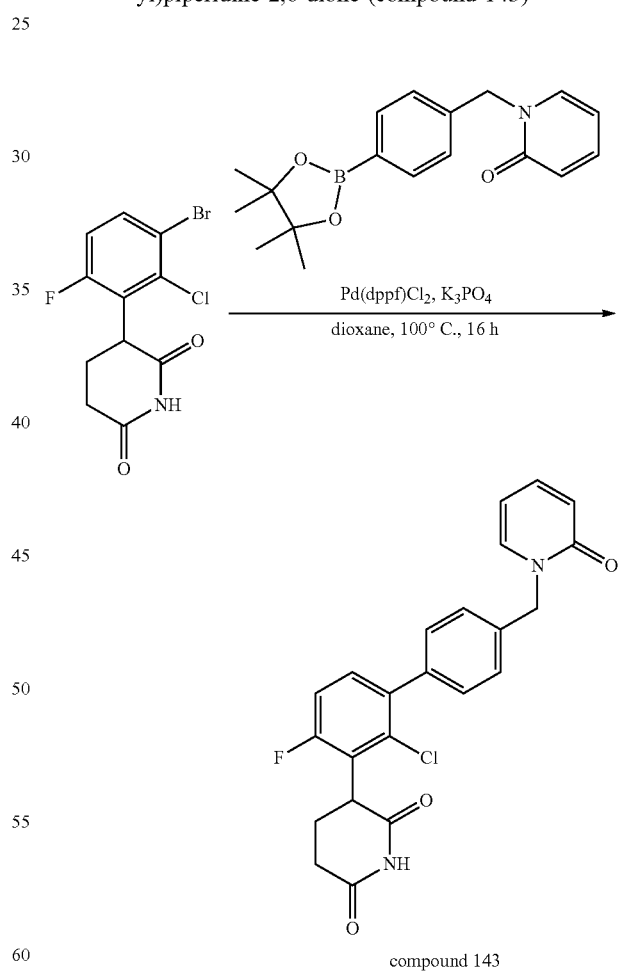

compound 143

3-(2-chloro-4-fluoro-4'-((2-oxopyridin-1(2H)-yl)methyl)-[1,1'-biphenyl]-3-yl)piperidine-2,6-dione was prepared from 3-(3-bromo-2-chloro-6-fluorophenyl)piperidine-2,6-dione and 1-(4-(4,4,5,5-tetramethyl-1,3,2-dioxaborolan-2-yl)benzyl)pyridin-2(1H)-one according to General Scheme 1.

¹H NMR (400 MHz, DMSO-d₆) δ=10.98 (d, J=6.4 Hz, 1H), 7.86 (dd, J=2.0, 6.8 Hz, 1H), 7.45 (ddd, J=2.0, 6.8, 9.2 Hz, 1H), 7.39 (s, 1H), 7.38-7.35 (m, 4H), 7.32 (s, 1H), 6.44 (d, J=9.2 Hz, 1H), 6.30-6.25 (m, 1H), 5.16 (s, 2H), 4.50 (dd, J=5.2, 12.4 Hz, 1H), 2.92-2.77 (m, 1H), 2.56 (d, J=3.2 Hz, 1H), 2.21-2.07 (m, 1H), 2.06-1.95 (m, 1H); MS (ESI) m/z 425.0 [M+H]⁺

Example 29. Synthesis of 3-(4'-((1-methyl-1H-pyrazol-3-yl)methoxy)-2-(trifluoromethyl)-[1,1'-biphenyl]-3-yl)piperidine-2,6-dione (compound 191)

3-(3-bromo-2-(trifluoromethyl)phenyl)piperidine-2,6-dione was prepared from 1-bromo-3-methyl-2-(trifluoromethyl)benzene according to General Scheme 2.
3-(4'-((1-methyl-1H-pyrazol-3-yl)methoxy)-2-(trifluoromethyl)-[1,1'-biphenyl]-3-yl)piperidine-2,6-dione was prepared from 3-(3-bromo-2-(trifluoromethyl)phenyl)piperidine-2,6-dione and 1-methyl-3-((4-(4,4,5,5-tetramethyl-1,3,2-dioxaborolan-2-yl)phenoxy)methyl)-1H-pyrazole according to General Scheme 1.
MS (ESI) m/z 444.3 [M+H]⁺

Example 30. Synthesis of 3-(2-methyl-4'-((1-methyl-1H-pyrazol-3-yl)methoxy)-[1,1'-biphenyl]-3-yl)piperidine-2,6-dione (Compound 192)

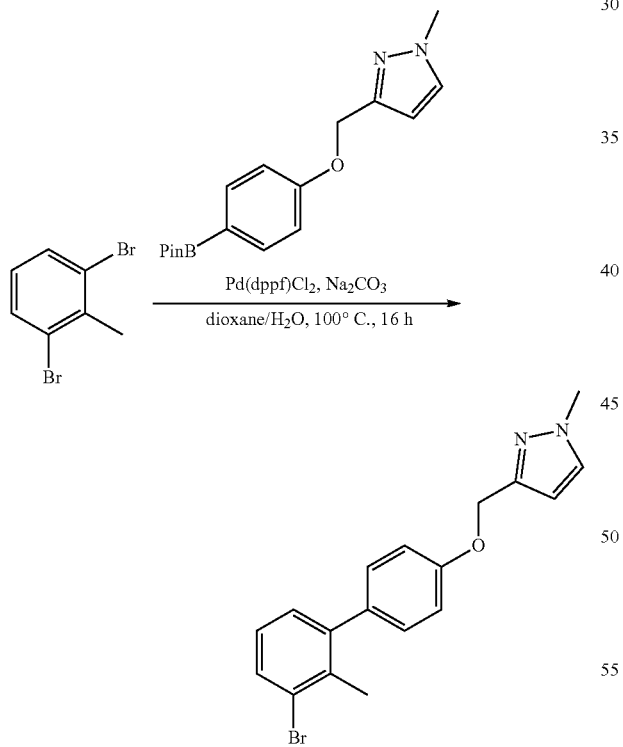

To a solution of 1,3-dibromo-2-methylbenzene (477 mg, 1.91 mmol, 3.00 eq), 1-methyl-3-((4-(4,4,5,5-tetramethyl-1,3,2-dioxaborolan-2-yl)phenoxy)methyl)-1H-pyrazole (200 mg, 0.636 mmol, 1.00 eq) in dioxane (4 mL) and water (1 mL) was added [1,1-Bis(diphenylphosphino)ferrocene]dichloropalladium(II) (46.6 mg, 63.7 μmol, 0.100 eq) and sodium carbonate (202 mg, 1.91 mmol, 3.00 eq). The reaction mixture was stirred at 100° C. for 16 h under nitrogen atmosphere. The mixture was diluted with water (30 mL) and extracted with ethyl acetate (3×30 mL). The combined organic layers were washed with brine (3×30 mL), dried over sodium sulfate, filtered and concentrated under reduced pressure. The residue was purified by flash silica gel chromatography (eluent of 0-30% ethyl acetate/petroleum ether gradient @ 25 mL/min) to afford 3-(((3'-bromo-2'-methyl-[1,1'-biphenyl]-4-yl)oxy)methyl)-1-methyl-1H-pyrazole (190 mg, 0.457 mmol, 72% yield) as yellow gum.
¹H NMR (400 MHz, DMSO-d₆) δ=7.67 (d, J=2.0 Hz, 1H), 7.58 (dd, J=2.4, 6.8 Hz, 1H), 7.24 (d, J=8.8 Hz, 2H), 7.21-7.14 (m, 2H), 7.08 (d, J=8.8 Hz, 2H), 6.33 (d, J=2.0 Hz, 1H), 5.03 (s, 2H), 3.84 (s, 3H), 2.26 (s, 3H); MS (ESI) m/z 357.0 [M+H]⁺

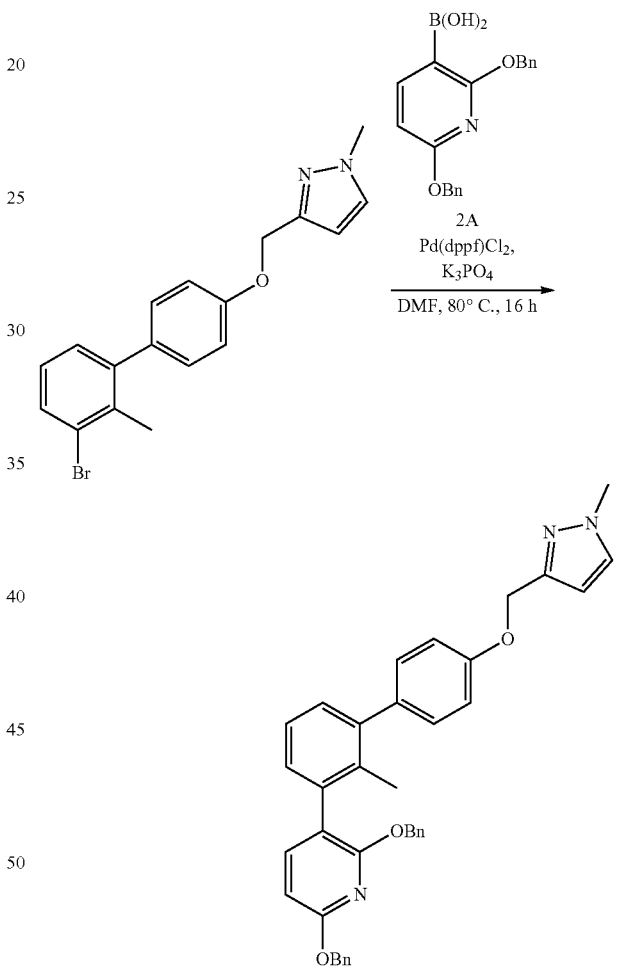

To a solution of (2,6-bis(benzyloxy)pyridin-3-yl)boronic acid (214 mg, 0.638 mmol, 1.20 eq), 3-(((3'-bromo-2'-methyl-[1,1'-biphenyl]-4-yl)oxy)methyl)-1-methyl-1H-pyrazole (190 mg, 0.532 mmol, 1.00 eq) in dimethylformamide (4 mL) was added [1,1-Bis(diphenylphosphino)ferrocene]dichloropalladium(II) (38.9 mg, 53.2 μmol, 0.100 eq) and sodium carbonate (339 mg, 1.60 mmol, 3.00 eq). The reaction mixture was stirred at 80° C. for 16 h under nitrogen atmosphere. The mixture was diluted with water (30 mL) and extracted with ethyl acetate (3×30 mL). The combined organic layers were washed with brine (3×30 mL), dried over sodium sulfate, filtered and concentrated under reduced pressure. The residue was purified by flash silica gel chromatography (eluent of 0-30% ethyl acetate/petroleum ether gradient @ 30 mL/min) to afford 2,6-bis(benzyloxy)-3-(2-methyl-4'-((1-methyl-1H-pyrazol-3-yl)methoxy)-[1,1'-biphenyl]-3-yl)pyridine (160 mg, 0.259 mmol, 49% yield) as a white solid.

$^1$H NMR (400 MHz, DMSO-d$_6$) δ=7.67 (d, J=2.0 Hz, 1H), 7.57 (d, J=8.0 Hz, 1H), 7.48-7.43 (m, 2H), 7.41-7.37 (m, 2H), 7.36-7.28 (m, 6H), 7.26-7.18 (m, 3H), 7.16-7.05 (m, 4H), 6.54 (d, J=8.0 Hz, 1H), 6.33 (d, J=2.0 Hz, 1H), 5.37 (s, 4H), 5.03 (s, 2H), 3.84 (s, 3H), 1.92 (s, 3H); MS (ESI) m/z 568.3 [M+H]$^+$ afford 3-(2-methyl-4'-((1-methyl-1H-pyrazol-3-yl)methoxy)-[1,1'-biphenyl]-3-yl)piperidine-2,6-dione (47.1 mg, 0.119 mmol, 85% yield, 99% purity) as a white solid.

$^1$H NMR (400 MHz, DMSO-d$_6$) δ=10.85 (s, 1H), 7.67 (d, J=2.0 Hz, 1H), 7.24-7.16 (m, 3H), 7.12-7.05 (m, 4H), 6.33 (d, J=2.0 Hz, 1H), 5.03 (s, 2H), 4.14 (dd, J=4.8, 11.6 Hz, 1H), 3.84 (s, 3H), 2.82-2.70 (m, 1H), 2.54 (d, J=4.0 Hz, 1H), 2.27-2.17 (m, 1H), 2.14 (s, 3H), 2.09-1.99 (m, 1H); MS (ESI) m/z 390.1 [M+H]$^+$

Example 31. Synthesis of 3-(2,2'-dichloro-4'-((1-methyl-1H-pyrazol-3-yl)methoxy)-[1,1'-biphenyl]-3-yl)piperidine-2,6-dione (compound 177)

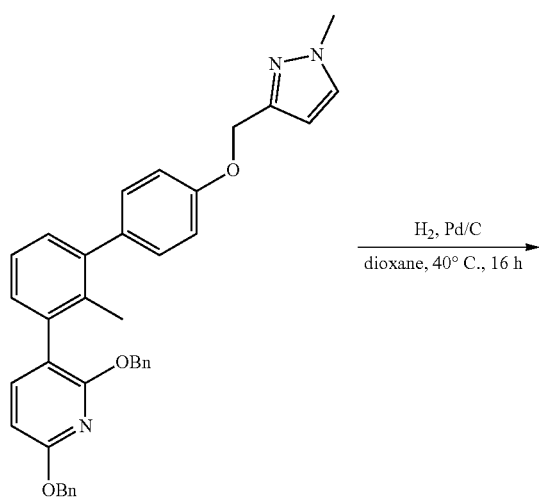

Compound 192

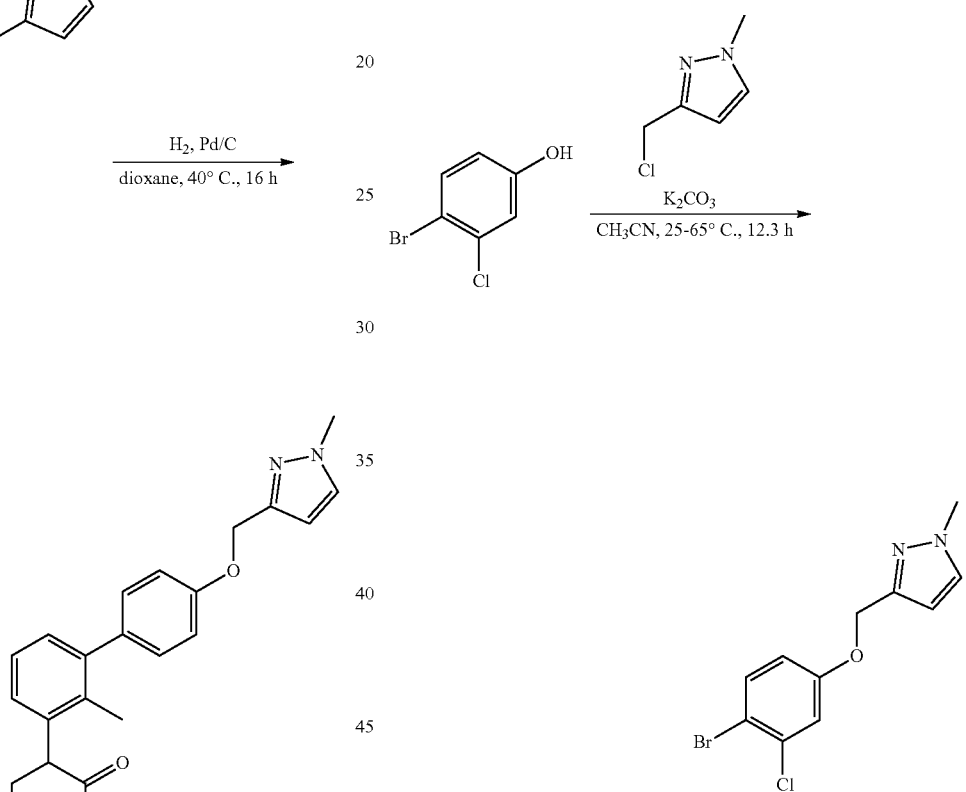

To a solution of 2,6-bis(benzyloxy)-3-(2-methyl-4'-((1-methyl-1H-pyrazol-3-yl)methoxy)-[1,1'-biphenyl]-3-yl)pyridine (80.0 mg, 0.141 mmol, 1.00 eq) in dioxane (2 mL) was added palladium on carbon (150 mg, 10% purity), then the mixture was degassed with nitrogen for three times and degassed with hydrogen for three times, the resulting mixture was stirred at 40° C. under hydrogen (15 psi) for 16 h. The reaction mixture was filtrated through diatomite, and the filter cake was washed with ethyl alcohol (50 mL), the filtrate was concentrated under reduced pressure. The residue was purified by Prep-HPLC (column: Phenomenex luna C18 150*40 mm*15 um; mobile phase: [water(formic acid)-acetonitrile]; B %: 31%-64%, 9 min) and lyophilized to To a solution of 4-bromo-3-chlorophenol (715 mg, 3.45 mmol, 1.50 eq) and potassium carbonate (635 mg, 4.60 mmol, 2.00 eq) in acetonitrile (5.00 mL) was stirred at 25° C. for 20 min, then 3-(chloromethyl)-1-methyl-1H-pyrazole (300 mg, 2.30 mmol, 1.00 eq) was added at 65° C. The mixture was stirred at 65° C. for 12 h. The reaction mixture was concentrated under reduced pressure to give a residue. The residue was purified by column chromatography (Petroleum ether/Ethyl acetate=10/1 to 3/1) to afford 3-((4-bromo-3-chlorophenoxy)methyl)-1-methyl-1H-pyrazole (708 mg, 90% purity) as a white solid. 3-(2,2'-dichloro-4'-((1-methyl-1H-pyrazol-3-yl)methoxy)-[1,1'-biphenyl]-3-yl)piperidine-2,6-dione was prepared from 3-((4-bromo-3-chlorophenoxy)methyl)-1-methyl-1H-pyrazole and 3-(2-chloro-3-(4,4,5,5-tetramethyl-1,3,2-dioxaborolan-2-yl)phenyl)piperidine-2,6-dione according to General Scheme 1.

MS (ESI) m/z 444.0 [M+H]$^+$

Example 32. Synthesis of 3-(4'-((1-methyl-1H-pyrazol-3-yl)methoxy)-[1,1'-biphenyl]-3-yl)piperidine-2,6-dione (compound 151)

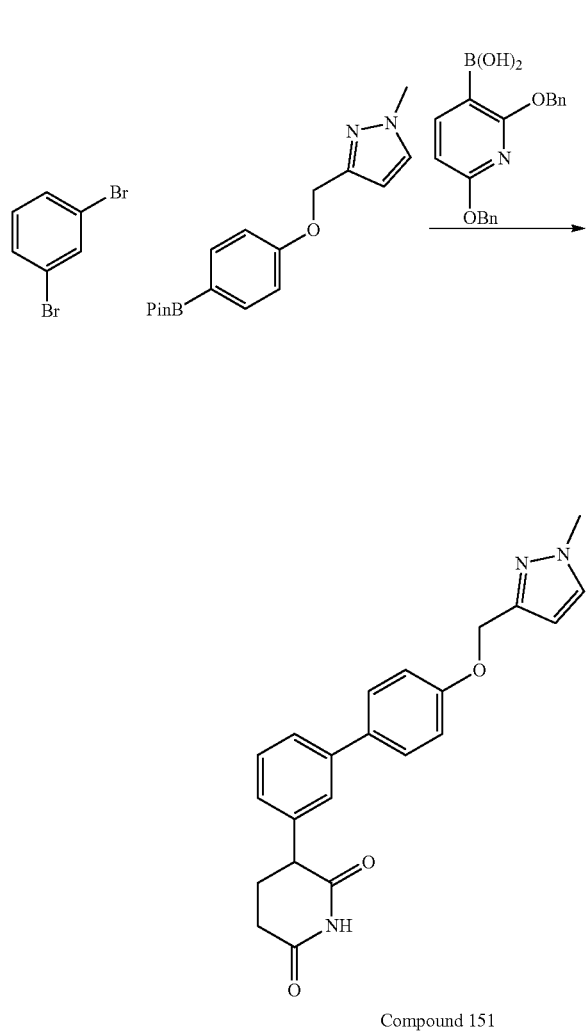

Compound 151

3-(4'-((1-methyl-1H-pyrazol-3-yl)methoxy)-[1,1'-biphenyl]-3-yl)piperidine-2,6-dione was prepared from 1,3-dibromobenzene, 1-methyl-3-((4-(4,4,5,5-tetramethyl-1,3,2-dioxaborolan-2-yl)phenoxy)methyl)-1H-pyrazole and (2,6-bis(benzyloxy)pyridin-3-yl)boronic acid analogously to Example 30.

MS (ESI) m/z 376.1 [M+H]$^+$

Example 33. Synthesis of 3-(2-chloro-4'-(2-(2-oxopyridin-1(2H)-yl)ethyl)-[1,1'-biphenyl]-3-yl)piperidine-2,6-dione (compound 182)

3-(2-chloro-4'-(2-(2-oxopyridin-1(2H)-yl)ethyl)-[1,1'-biphenyl]-3-yl)piperidine-2,6-dione was prepared from 1-(4-bromophenethyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

MS (ESI) m/z 421.1 [M+H]$^+$

Example 34. Synthesis of 3-(2-chloro-4'-(3-(2-oxopyridin-1(2H)-yl)propyl)-[1,1'-biphenyl]-3-yl)piperidine-2,6-dione (compound 178)

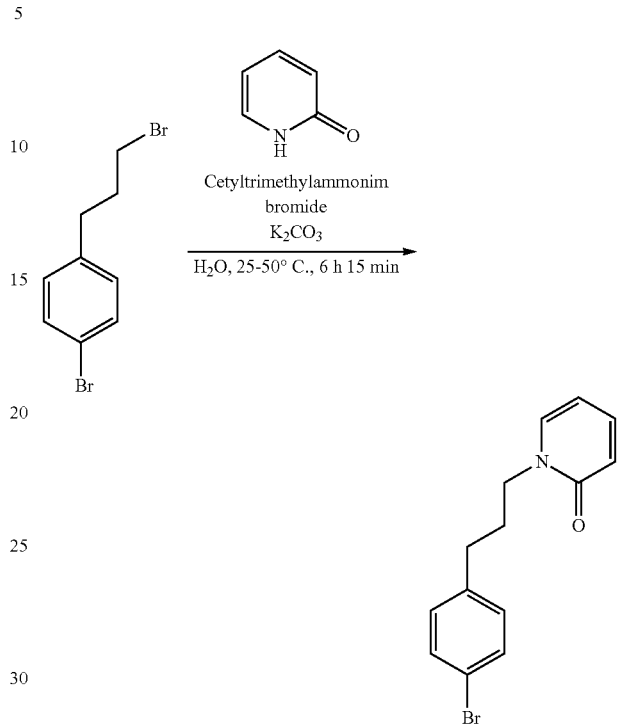

To a solution of N,N,N-trimethylhexadecan-1-aminium bromide (24.0 mg, 65.9 µmol, 0.09 eq) in water (4 mL) were added potassium carbonate (152 mg, 1.10 mmol, 1.53 eq) and pyridin-2(1H)-one (72.0 mg, 757 µmol, 1.05 eq). The mixture was stirred at 25° C. for 15 min. Then 1-bromo-4-(3-bromopropyl)benzene (200 mg, 720 µmol, 1.00 eq) was added. The mixture was stirred at 50° C. for 6 h. The reaction mixture was cooled to 25° C. and diluted with water (20 mL). The mixture was extracted with ethyl acetate (2×20 mL). The combined organic layers were washed with brine (30 mL), dried over sodium sulfate, filtered and concentrated under reduced pressure.

The residue was purified by flash silica gel chromatography (ISCO®; 4 g SepaFlash® Silica Flash Column, Eluent of 80~100% Ethyl acetate/Petroleum ether gradient @ 30 mL/min) to afford 1-(3-(4-bromophenyl)propyl)pyridin-2(1H)-one (90.0 mg, 260 µmol, 40% yield) as yellow solid. 3-(2-chloro-4'-(3-(2-oxopyridin-1(2H)-yl)propyl)-[1,1'-biphenyl]-3-yl)piperidine-2,6-dione was prepared from 1-(3-(4-bromophenyl)propyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-d$_6$) δ=10.92 (s, 1H), 7.69 (dd, J=2.0, 6.4 Hz, 1H), 7.43-7.25 (m, 8H), 6.37 (d, J=9.2 Hz, 1H), 6.21 (dt, J=1.2, 6.8 Hz, 1H), 4.34 (dd, J=5.2, 12.0 Hz, 1H), 3.95 (t, J=7.6 Hz, 2H), 2.85-2.72 (m, 1H), 2.69-2.62 (m, 2H), 2.59-2.52 (m, 1H), 2.40-2.25 (m, 1H), 2.09-1.93 (m, 3H); MS (ESI) m/z 435.1 [M+H]$^+$

Example 35. Synthesis of 3-(4'-((1H-imidazol-1-yl)methyl)-2-chloro-[1,1'-biphenyl]-3-yl)piperidine-2,6-dione (compound 140)

3-(4'-((1H-imidazol-1-yl)methyl)-2-chloro-[1,1'-biphenyl]-3-yl)piperidine-2,6-dione was prepared from 1-(4-bromobenzyl)-1H-imidazole and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-d$_6$) δ=10.92 (br d, J=2.4 Hz, 1H), 7.81 (s, 1H), 7.46-7.23 (m, 8H), 6.94 (s, 1H), 5.27 (s, 2H), 4.34 (dd, J=5.2, 12.4 Hz, 1H), 2.85-2.73 (m, 1H), 2.56 (br d, J=3.2 Hz, 1H), 2.34-2.27 (m, 1H), 2.09-1.98 (m, 1H); MS (ESI) m/z 380.0 [M+H]$^+$

Example 36. Synthesis of 3-(2-chloro-4'-((1-methyl-1H-pyrazol-3-yl)methyl)-[1,1'-biphenyl]-3-yl)piperidine-2,6-dione (compound 176)

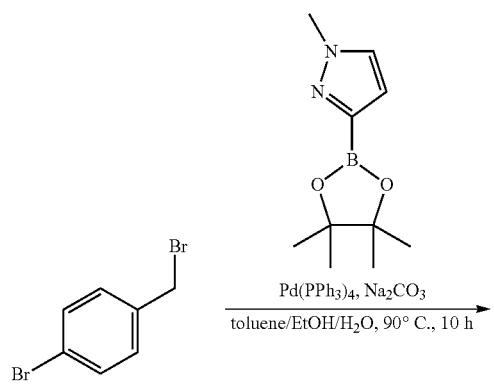

3-(4-bromobenzyl)-1-methyl-1H-pyrazole was prepared from 1-bromo-4-(bromomethyl)benzene and 1-methyl-3-(4,4,5,5-tetramethyl-1,3,2-dioxaborolan-2-yl)-1H-pyrazole according to General Scheme 8.

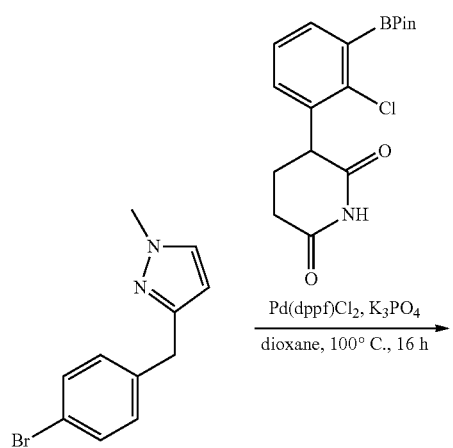

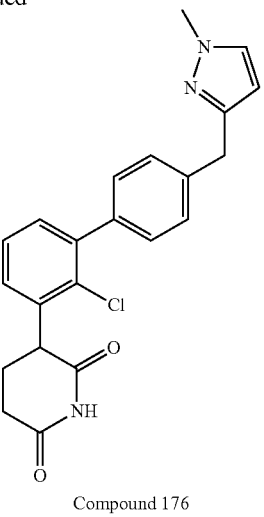

Compound 176

3-(2-chloro-4'-((1-methyl-1H-pyrazol-3-yl) methyl)-[1,1'-biphenyl]-3-yl) piperidine-2,6-dione was prepared from 3-(4-bromobenzyl)-1-methyl-1H-pyrazole and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-d$_6$) δ=10.91 (s, 1H), 7.57 (d, J=2.0 Hz, 1H), 7.37-7.26 (m, 7H), 6.07 (d, J=2.0 Hz, 1H), 4.34 (dd, J=5.2, 12.0 Hz, 1H), 3.91 (s, 2H), 3.79 (s, 3H), 2.79 (m, 1H), 2.56 (d, J=3.6 Hz, 1H), 2.33 (dd, J=4.0, 12.8 Hz, 1H), 2.11-1.97 (m, 1H); MS (ESI) m/z 394.0 [M+H]$^+$

Example 37. Synthesis of 3-(2-chloro-4'-(4-((2-oxopyridin-1(2H)-yl)methyl)piperidin-1-yl)-[1,1'-biphenyl]-3-yl)piperidine-2,6-dione (compound 166)

3-(2-chloro-4'-(4-((2-oxopyridin-1(2H)-yl)methyl)piperidin-1-yl)-[1,1'-biphenyl]-3-yl)piperidine-2,6-dione was prepared from 1-((1-(4-bromophenyl)piperidin-4-yl)methyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-d$_6$) δ=10.90 (s, 1H), 7.66 (dd, J=1.6, 6.8 Hz, 1H), 7.41 (ddd, J=2.0, 6.8, 8.8 Hz, 1H), 7.37-7.32 (m, 1H), 7.30-7.22 (m, 4H), 6.99 (d, J=8.8 Hz, 2H), 6.39 (d, J=8.8 Hz, 1H), 6.20 (dt, J=1.6, 6.8 Hz, 1H), 4.32 (dd, J=5.2, 12.0 Hz, 1H), 3.87-3.73 (m, 4H), 2.84-2.72 (m, 1H), 2.72-2.63 (m, 2H), 2.57-2.52 (m, 1H), 2.39-2.26 (m, 1H), 2.10-1.91 (m, 2H), 1.58 (d, J=11.2 Hz, 2H), 1.35 (dq, J=3.2, 12.4 Hz, 2H); MS (ESI) m/z 490.1 [M+H]$^+$ Example 38. Synthesis of 3-(2-chloro-4'-(1-(2-oxopyridin-1(2H)-yl)ethyl)-[1,1'-biphenyl]-3-yl) piperidine-2,6-dione (compound 174)

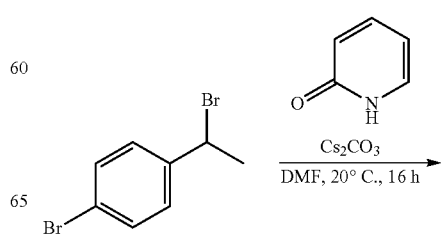

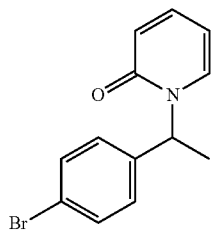

To a solution of 1-bromo-4-(1-bromoethyl)benzene (500 mg, 1.89 mmol, 1.00 eq) in dimethyl formamide (6 mL) was added cesium carbonate (1.23 g, 3.79 mmol, 2.00 eq) and pyridin-2(1H)-one (216 mg, 2.27 mmol, 1.20 eq). Then the mixture was stirred at 20° C. for 16 h. The reaction mixture was concentrated under reduced pressure to give a residue. The residue was purified by flash silica gel chromatography (ISCO®; 4 g SepaFlash® Silica Flash Column, Eluent of 0-50% Ethyl acetate/Petroleum ether gradient @ 20 mL/min). Compound 1-(1-(4-bromophenyl)ethyl)pyridin-2 (1H)-one (310 mg, 1.10 mmol, 58% yield) was obtained as a white solid.

3-(2-chloro-4'-(1-(2-oxopyridin-1(2H)-yl)ethyl)-[1,1'-biphenyl]-3-yl)piperidine-2,6-dione was prepared from 1-(1-(4-bromophenyl)ethyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

MS (ESI) m/z 421.1 [M+H]$^+$

Example 39. Synthesis of 3-(2-chloro-4'-(1-(pyridin-2-yloxy)ethyl)-[1,1'-biphenyl]-3-yl)piperidine-2, 6-dione (compound 165)

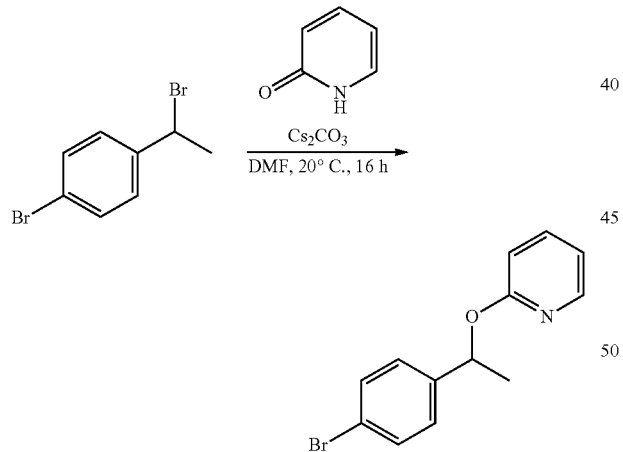

To a solution of 1-bromo-4-(1-bromoethyl)benzene (500 mg, 1.89 mmol, 1.00 eq) in dimethyl formamide (6 mL) was added cesium carbonate (1.23 g, 3.79 mmol, 2.00 eq) and pyridin-2(1H)-one (216 mg, 2.27 mmol, 1.20 eq). The mixture was degassed and purged with nitrogen for 3 times, and then the mixture was stirred at 20° C. for 16 hours under nitrogen atmosphere. The reaction mixture was concentrated under reduced pressure to give a residue. The residue was purified by flash silica gel chromatography (ISCO®; 4 g SepaFlash® Silica Flash Column, Eluent of 0~50% Ethyl acetate/Petroleum ether gradient @ 20 mL/min). 2-[1-(4-bromophenyl)ethoxy]pyridine (160 mg, 546 umol, 28.8% yield) was obtained as a colorless oil. 3-(2-chloro-4'-(1-(pyridin-2-yloxy)ethyl)-[1,1'-biphenyl]-3-yl)piperidine-2,6-dione was prepared from 2-(1-(4-bromophenyl)ethoxy)pyridine and 3-(2-chloro-3-(4,4,5,5-tetramethyl-1,3,2-dioxaborolan-2-yl)phenyl)piperidine-2,6-dione according to General Scheme 1; MS (ESI) m/z 443.1 [M+Na]$^+$ Example 40. Synthesis of 3-(2-chloro-4'-((2-oxopiperidin-1-yl)methyl)-[1,1'-biphenyl]-3-yl)piperidine-2,6-dione (compound 168)

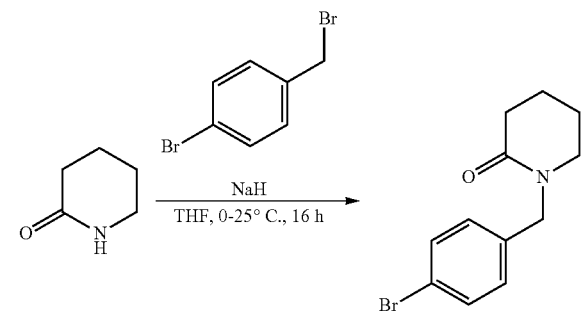

To a solution of piperidin-2-one (1.00 g, 10.0 mmol, 1.00 eq) and sodium hydride (806 mg, 20.1 mmol, 60% purity, 2.00 eq) in tetrahydrofuran (10.0 mL) was added 1-bromo-4-(bromomethyl)benzene (2.52 g, 10.0 mmol, 1.00 eq) in tetrahydrofuran (10.0 mL) at 0° C., the mixture was stirred at 25° C. for 16 h. The mixture was quenched with saturated ammonium chloride solution (150 mL) and extracted with ethyl acetate (3×30.0 mL). The combined organic layer was washed with brine (20.0 mL) and dried over anhydrous sodium sulfate, filtered and concentrated to give crude product. The crude product was purified by silica gel chromatography (petroleum ether/ethyl acetate=5/1 to 2/1) to give 1-(4-bromobenzyl)piperidin-2-one (1.54 g, 5.74 mmol, 56% yield) as colorless oil.

$^1$H NMR (400 MHz, DMSO-d$_6$) δ=7.57-7.43 (m, 2H), 7.18 (d, J=8.4 Hz, 2H), 4.46 (s, 2H), 3.14 (s, 2H), 2.37-2.21 (m, 2H), 1.68 (td, J=3.2, 6.4 Hz, 4H).

MS (ESI) m/z 270.0 [M+3H]$^+$

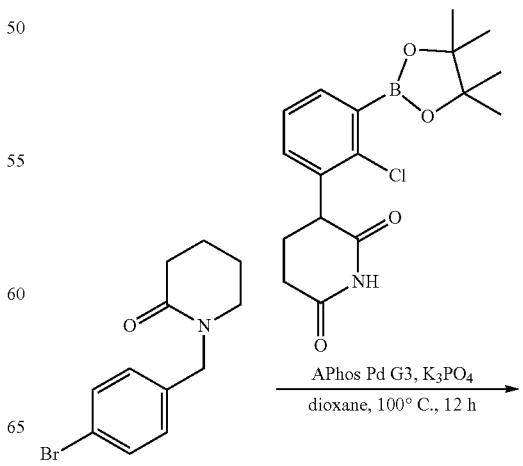

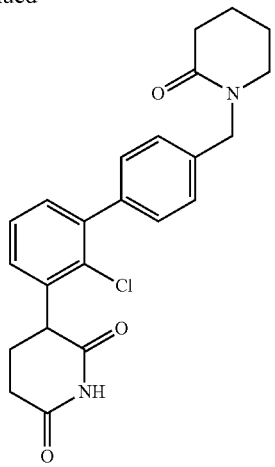

compound 168

To a solution of 1-(4-bromobenzyl)piperidin-2-one (100 mg, 372 umol, 1.00 eq), 3-(2-chloro-3-(4,4,5,5-tetramethyl-1,3,2-dioxaborolan-2-yl)phenyl)piperidine-2,6-dione (179 mg, 410 umol, 80% purity, 1.10 eq) and methanesulfonato ([4-(N,N-dimethylamino)phenyl]di-t-butylphosphino)(2-amino-1,1-biphenyl-2-yl)palladium(II) (47.3 mg, 74.5 umol, 0.200 eq) in dioxane (4.00 mL) was added tripotassium phosphate (237 mg, 1.12 mmol, 3.00 eq) in one portion under nitrogen atmosphere. The mixture was stirred at 100° C. for 12 h. The mixture was diluted with saturated ammonium chloride solution (10.0 mL) and extracted with ethyl acetate (3×10.0 mL). The combined organic layer was concentrated to give crude product. The crude product was purified by silica gel chromatography (petroleum ether/ethyl acetate=2/1 to 0/1) to give a crude product, which was purified by Prep-HPLC (column: Phenomenex luna C18 150*25 mm*10 um; mobile phase: [water (formic acid)-acetonitrile]; B %: 30%-60%, 10 min) and lyophilized to afford 3-(2-chloro-4'-((2-oxopiperidin-1-yl)methyl)-[1,1'-biphenyl]-3-yl)piperidine-2,6-dione (16.09 mg, 38.9 umol, 10% yield) as a white solid.

$^1$H NMR (400 MHz, DMSO-d$_6$) δ=10.92 (s, 1H), 7.43-7.33 (m, 4H), 7.32-7.26 (m, 3H), 4.55 (s, 2H), 4.34 (dd, J=5.2, 12.0 Hz, 1H), 3.28-3.22 (m, 2H), 2.86-2.72 (m, 1H), 2.64-2.64 (m, 1H), 2.56 (br t, J=3.6 Hz, 1H), 2.40-2.26 (m, 3H), 2.08-2.01 (m, 1H), 1.75 (br t, J=3.2 Hz, 4H).

MS (ESI) m/z 411.1 [M+H]$^+$

Example 41. Synthesis of 3-(2-chloro-4'-(pyridin-2-ylmethyl)-[1,1'-biphenyl]-3-yl)piperidine-2,6-dione (compound 169)

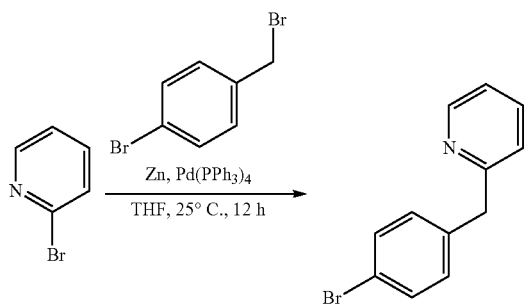

1-bromo-4-(bromomethyl)benzene (791 mg, 3.16 mmol, 1.00 eq) was added dropwise to a suspension of activated zinc (2.07 g, 31.7 mmol, 10.0 eq) in tetrahydrofuran (50.0 mL) under nitrogen. After the temperature reaches 25° C., then the mixture was added 2-bromopyridine (500 mg, 3.16 mmol, 301 uL, 1.00 eq) and tetrakis[triphenylphosphine]palladium(0) (731 mg, 633 umol, 0.200 eq) in portions under nitrogen. The mixture was stirred at 25° C. for 12 h. The mixture was filtered. The filtrate was diluted with water (30 mL) and extracted with ethyl acetate (3×30 mL). The combined organic layer was washed with brine (10 mL) and dried over anhydrous sodium sulfate, filtered and concentrated to give crude product, which was purified by reversed phase (C18, 120 g; condition: water/acetonitrile=100:0 to 0:100, 0.1% formic acid) to give 2-(4-bromobenzyl)pyridine (120 mg, 484 umol, 15% yield) as colorless oil.

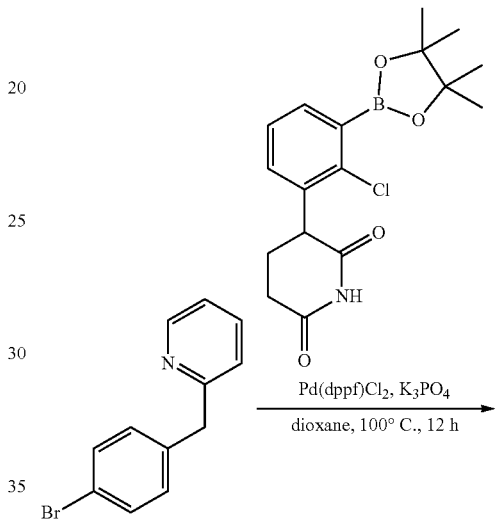

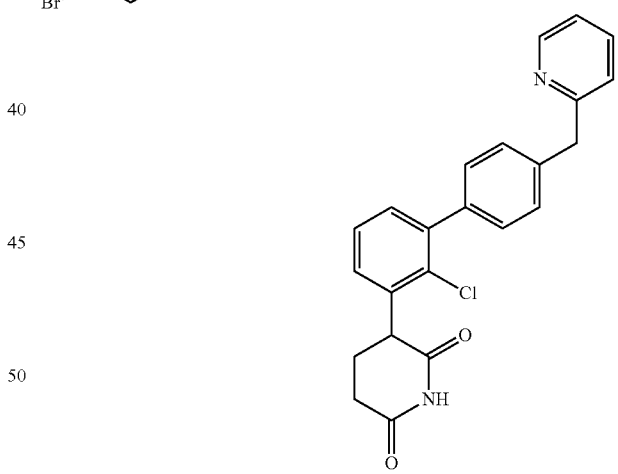

compound 169

3-(2-chloro-4'-(pyridin-2-ylmethyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 2-(4-bromobenzyl)pyridine according to General Scheme 1.

$^1$H NMR (400 MHz, DMSO-d$_6$) δ=10.92 (br s, 1H), 8.52 (d, J=4.0 Hz, 1H), 7.74 (dt, J=1.6, 7.6 Hz, 1H), 7.41-7.32 (m, 7H), 7.31-7.27 (m, 1H), 7.26-7.21 (m, 1H), 4.34 (dd, J=5.2, 12.0 Hz, 1H), 4.14 (s, 2H), 2.86-2.74 (m, 1H), 2.59-2.55 (m, 1H), 2.39-2.26 (m, 1H), 2.11-1.97 (m, 1H).

MS (ESI) m/z 391.1 [M+H]$^+$

Example 42. Synthesis of 3-(2-chloro-4'-(pyrazin-2-ylmethyl)-[1,1'-biphenyl]-3-yl)piperidine-2,6-dione (compound 159)

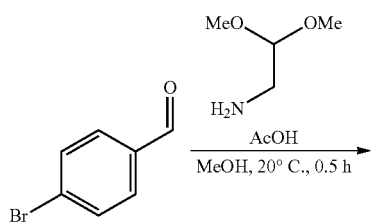

To a solution of 4-bromobenzaldehyde (2.00 g, 10.8 mmol, 1.00 eq) and 2,2-dimethoxyethanamine (1.25 g, 11.9 mmol, 1.30 mL, 1.10 eq) in methanol (20.0 mL) was added acetic acid (64.9 mg, 1.08 mmol, 61.8 uL, 0.100 eq). The mixture was stirred at 20° C. for 0.5 h. The mixture was concentrated under reduced pressure to afford (E)-N-(4-bromobenzylidene)-2,2-dimethoxyethanamine (2.94 g, crude) as colorless oil.

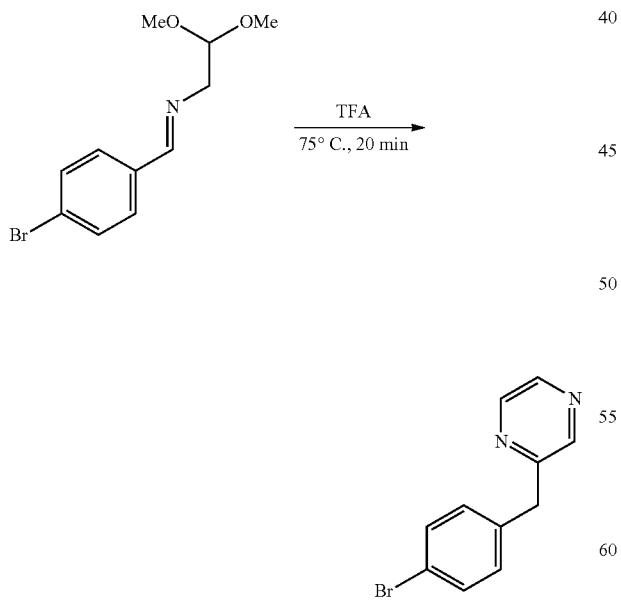

A solution of (E)-N-(4-bromobenzylidene)-2,2-dimethoxyethanamine (2.94 g, 10.8 mmol, 1.00 eq) in 2,2,2-trifluoroacetic acid (4.00 mL) was stirred at 75° C. for 20 min under nitrogen atmosphere. The reaction mixture was concentrated under reduced pressure to give a residue. The residue was added saturated sodium bicarbonate solution until pH=7 and then extracted with dichloromethane (3×80 mL). The combined organic layers were washed with saturated sodium bicarbonate solution (90 mL) and water (90 mL), dried over anhydrous sodium sulfate, filtered and concentrated under reduced pressure to give brown oil. The brown oil was purified by column chromatography (SiO$_2$, petroleum ether/ethyl acetate=1/0 to 10/1) to afford 2-(4-bromobenzyl)pyrazine (334 mg, 1.34 mmol, 12% yield) as a brown solid.

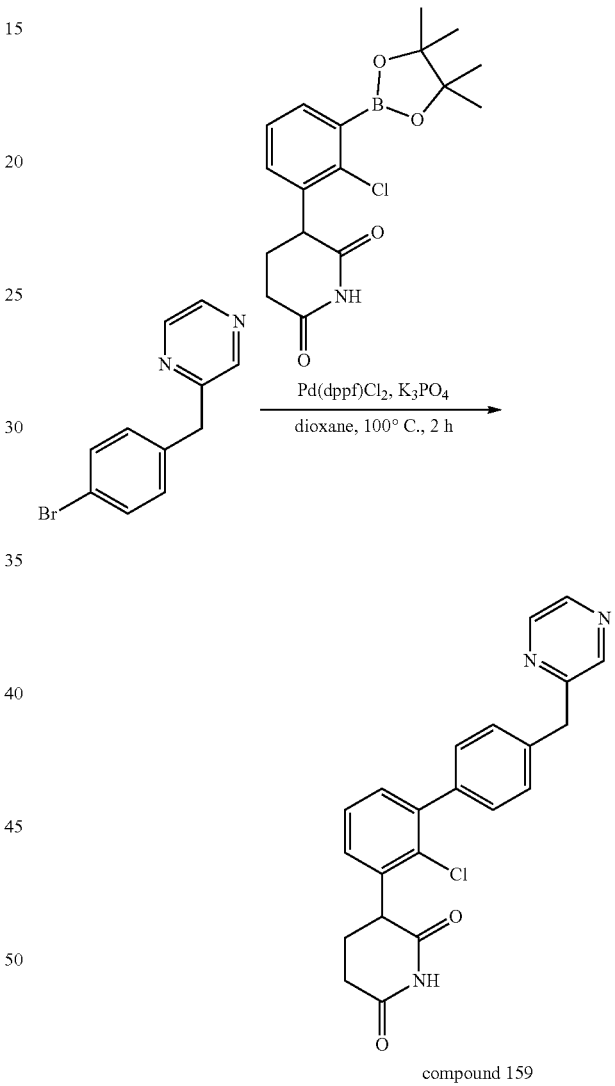

3-(2-chloro-4'-(pyrazin-2-ylmethyl)-[1,1'-biphenyl]-3-yl)piperidine-2,6-dione was prepared from 2-(4-bromobenzyl)pyrazine and 3-(2-chloro-3-(4,4,5,5-tetramethyl-1,3,2-dioxaborolan-2-yl)phenyl)piperidine-2,6-dione according to General Scheme 1.

1H NMR (400 MHz, DMSO-d$_6$) δ=10.88 (br s, 1H), 8.68 (d, J=1.2 Hz, 1H), 8.59-8.52 (m, 1H), 8.49 (d, J=2.4 Hz, 1H), 7.40-7.20 (m, 7H), 4.30 (dd, J=4.8, 12.0 Hz, 1H), 4.18 (s, 2H), 2.82-2.69 (m, 1H), 2.59-2.51 (m, 1H), 2.32-2.25 (m, 1H), 2.06-1.95 (m, 1H); MS (ESI) m/z 392.1 [M+H]$^+$

Example 43. Synthesis of 3-(2-chloro-4'-((4-fluoro-2-oxopyridin-1(2H)-yl)methyl)-[1,1'-biphenyl]-3-yl)piperidine-2,6-dione (compound 170)

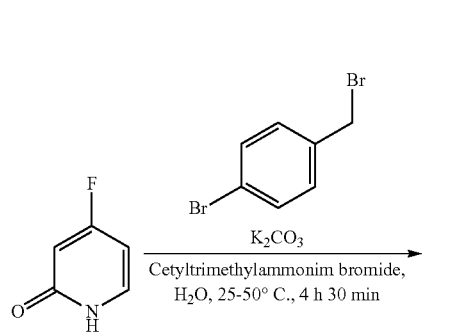

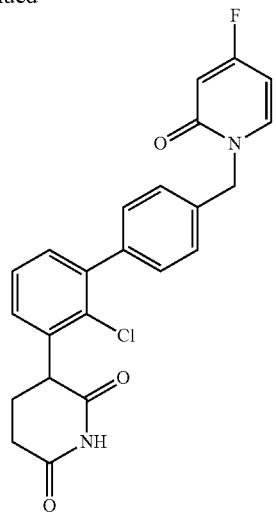

compound 170

3-(2-chloro-4'-((4-fluoro-2-oxopyridin-1(2H)-yl)methyl)-[1,1'-biphenyl]-3-yl)piperidine-2,6-dione was prepared from 1-(4-bromobenzyl)-4-fluoropyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.91 (br s, 1H), 8.06 (t, J=8.0 Hz, 1H), 7.40-7.33 (m, 6H), 7.29 (d, J=7.2 Hz, 1H), 6.41-6.35 (m, 1H), 6.26 (dd, J=2.4, 11.6 Hz, 1H), 5.16 (s, 2H), 4.33 (dd, J=4.8, 12.4 Hz, 1H), 2.80-2.75 (m, 1H), 2.68-2.55 (m, 1H), 2.33-2.27 (m, 1H), 2.06-2.02 (m, 1H); MS (ESI) m/z 425.1 [M+H]$^+$

Example 44. Synthesis of 3-[2-chloro-3-[4-[(4-methoxy-2-oxo-1-pyridyl)methyl]phenyl]phenyl]piperidine-2,6-dione (compound 175)

1-(4-bromobenzyl)-4-fluoropyridin-2(1H)-one was prepared from 4-fluoropyridin-2(1H)-one and 1-bromo-4-(bromomethyl)benzene according to General Scheme 8.

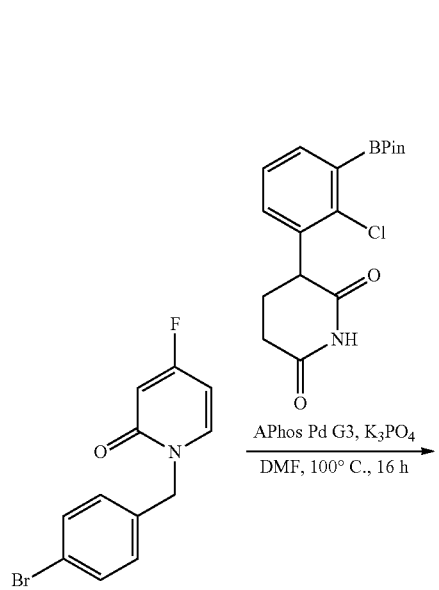

1-[(4-bromophenyl)methyl]-4-methoxy-pyridin-2-one was prepared from 4-methoxy-1H-pyridin-2-one and 1-bromo-4-(bromomethyl)benzene according to General Scheme 8.

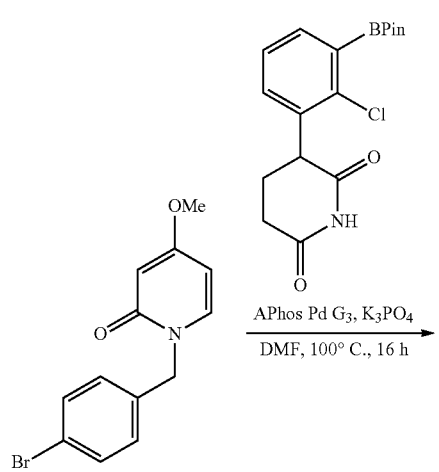

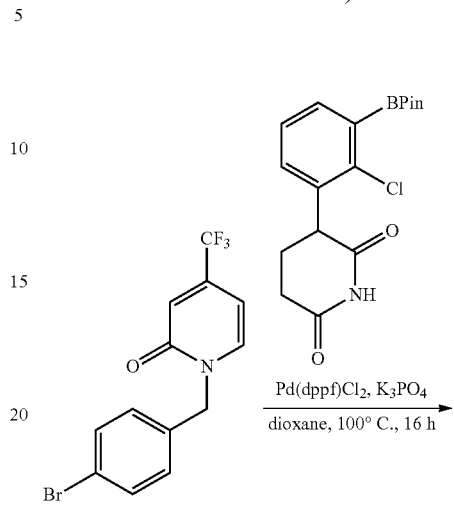

Example 45. Synthesis of 3-(2-chloro-4'-((2-oxo-4-(trifluoromethyl) pyridin-1(2H)-yl)methyl)-[1,1'-biphenyl]-3-yl)piperidine-2,6-dione (compound 171)

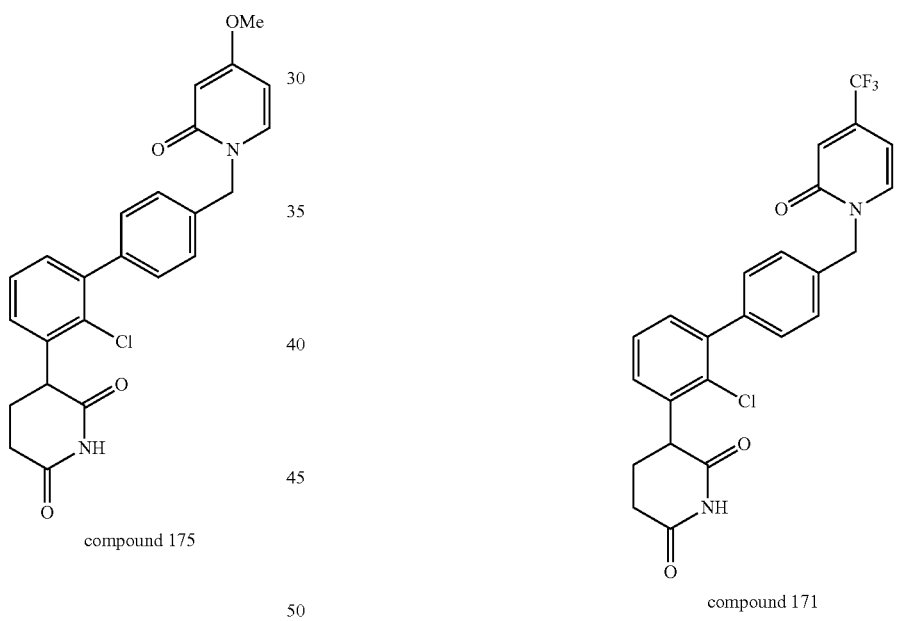

3-[2-chloro-3-[4-[(4-methoxy-2-oxo-1-pyridyl) methyl] phenyl] phenyl]piperidine-2,6-dione was prepared from 1-[(4-bromophenyl)methyl]-4-methoxy-pyridin-2-one and 3-[2-chloro-3-(4,4,5,5-tetramethyl-1,3,2-dioxaborolan-2-yl) phenyl]piperidine-2,6-dione according to General Scheme 1.

$^1$H NMR (400 MHz, DMSO-$d_6$) δ=10.91 (s, 1H), 7.74 (d, J=7.6 Hz, 1H), 7.41-7.33 (m, 4H), 7.33-7.26 (m, 3H), 6.01 (dd, J=2.8, 7.6 Hz, 1H), 5.85 (d, J=2.8 Hz, 1H), 5.09 (s, 2H), 4.40-4.28 (m, 1H), 3.74 (s, 3H), 2.86-2.70 (m, 1H), 2.58-2.52 (m, 1H), 2.36-2.29 (m, 1H), 2.10-1.98 (m, 1H); MS (ESI) m/z 437.2[M+H]$^+$ 3-(2-chloro-4'-((2-oxo-4-(trifluoromethyl)pyridin-1(2H)-yl)methyl)-[1,1'-biphenyl]-3-yl)piperidine-2,6-dione was prepared from 1-(4-bromobenzyl)-4-(trifluoromethyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.92 (s, 1H), 8.18 (d, J=7.2 Hz, 1H), 7.42-7.34 (m, 6H), 7.31-7.25 (m, 1H), 6.85 (s, 1H), 6.56 (dd, J=1.6, 7.2 Hz, 1H), 5.22 (s, 2H), 4.37-4.29 (m, 1H), 2.79-2.63 (m, 1H), 2.67-2.55 (m, 1H), 2.35-2.31 (m, 1H), 2.08-1.98 (m, 1H) MS (ESI) m/z 475.1 [M+H]$^+$

Example 46. Synthesis of 3-(2-chloro-4'-(((1-methyl-1H-pyrazol-3-yl)oxy)methyl)-[1,1'-biphenyl]-3-yl)piperidine-2,6-dione (compound 160)

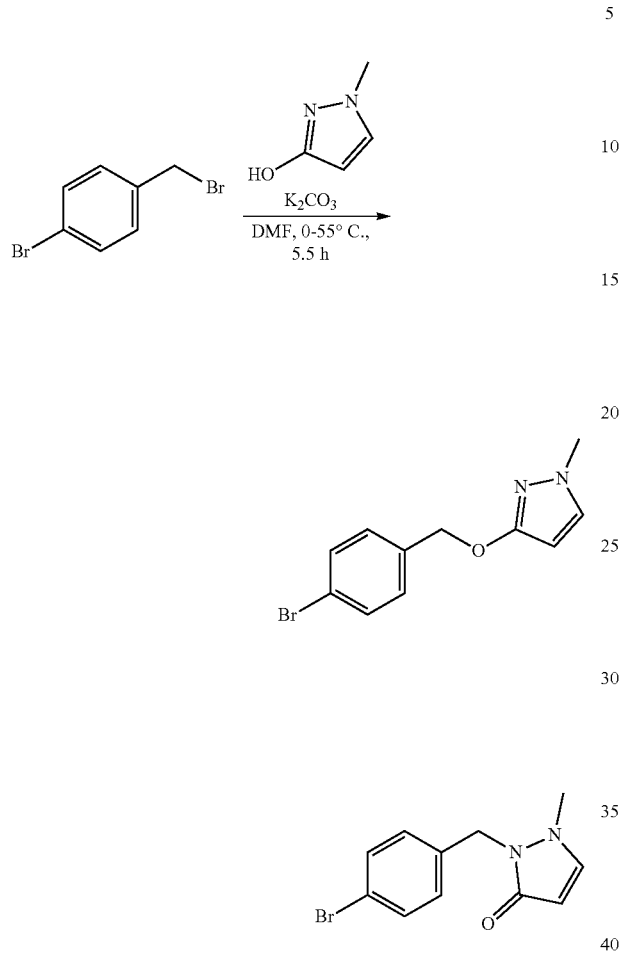

Example 47. Synthesis of 3-(2-chloro-4'-(2-oxopiperidin-1-yl)-[1,1'-biphenyl]-3-yl)piperidine-2,6-dione (compound 161)

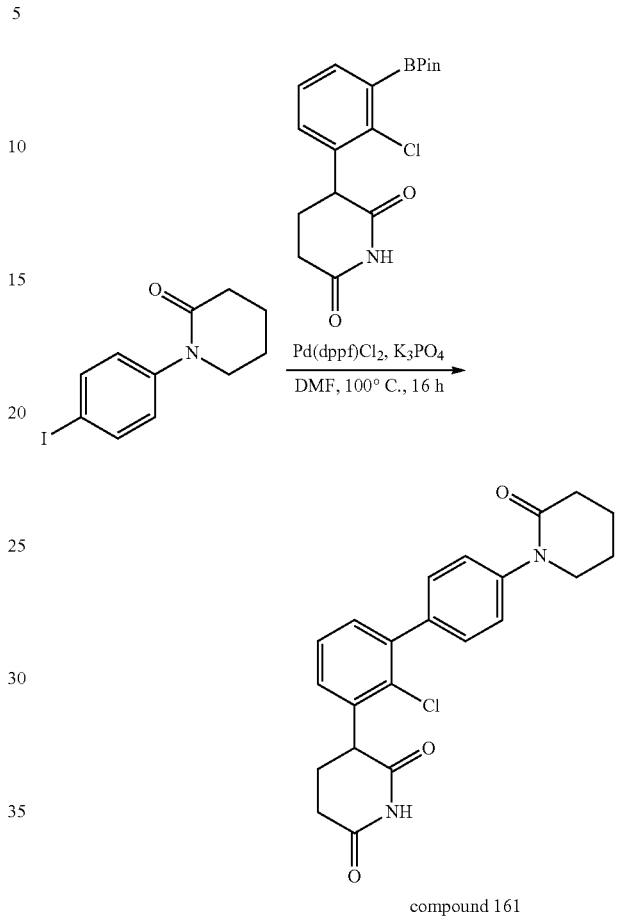

compound 161

To a solution of 1-bromo-4-(bromomethyl)benzene (3.06 g, 12.2 mmol, 1.20 eq) in N,N-dimethyl formamide (15.0 mL) was added 1-methyl-1H-pyrazol-3-ol (1.00 g, 10.2 mmol, 1.00 eq) and potassium carbonate (1.70 g, 12.3 mmol, 1.21 eq) at 0° C. The mixture was stirred at 25° C. for 1.5 h. Then the mixture was stirred at 55° C. for 4 h. The reaction mixture was partitioned between ethyl acetate (100 mL) and water (100 mL), and the organic layer was washed with brine (50 mL), dried over magnesium sulfate, filtered and concentrated in vacuo. The crude product was purified by reversed phase (C18, 80 g; condition: water/acetonitrile=100:0 to 0:100, 0.1% formic acid) and lyophilized to afford 3-((4-bromobenzyl)oxy)-1-methyl-1H-pyrazole (160 mg, 497 umol, 5% yield, 83% purity) as a white solid and 2-(4-bromobenzyl)-1-methyl-1,2-dihydro-3H-pyrazol-3-one (350 mg, 1.30 mmol, 13% yield, 99% purity) as a white solid. 3-(2-chloro-4'-(((1-methyl-1H-pyrazol-3-yl)oxy)methyl)-[1,1'-biphenyl]-3-yl)piperidine-2,6-dione was prepared from 3-((4-bromobenzyl)oxy)-1-methyl-1H-pyrazole and 3-(2-chloro-4'-(4,4,5,5-tetramethyl-1,3,2-dioxaborolan-2-yl)-[1,1'-biphenyl]-3-yl)piperidine-2,6-dione according to General Scheme 1.

MS (ESI) m/z 410.1 [M+H]$^+$

To a solution of 3-(2-chloro-3-(4,4,5,5-tetramethyl-1,3,2-dioxaborolan-2-yl)phenyl)piperidine-2,6-dione (139 mg, 399 umol, 1.20 eq) in dimethylformamide (4.00 mL) was added 1-(4-iodophenyl)piperidin-2-one (100 mg, 332 umol, 1.00 eq), potassium phosphate (211 mg, 996 umol, 3.00 eq) and [1,1-bis(diphenylphosphino)ferrocene]dichloropalladium(II) (24.3 mg, 33.2 umol, 0.100 eq). The reaction mixture was stirred at 100° C. for 16 h under nitrogen atmosphere. The reaction mixture was concentrated under reduced pressure to give a residue. The residue was purified by column chromatography (SiO$_2$, petroleum ether/ethyl acetate=1/0 to 2/1) and concentrated under reduced pressure to give a crude product. The crude product was purified by Prep-HPLC (column: Phenomenex luna C18 150*25 mm*10 um; mobile phase: [water (formic acid)-acetonitrile]; B %: 28%-58%, min) and lyophilized to afford 3-(2-chloro-4'-(2-oxopiperidin-1-yl)-[1,1'-biphenyl]-3-yl)piperidine-2,6-dione (9.92 mg, 24.5 umol, 7% yield, 98% purity) as an off-white solid.

$^1$H NMR (400 MHz, DMSO-d$_6$) δ=10.92 (br s, 1H), 7.45-7.30 (m, 7H), 4.35 (dd, J=4.8, 12.4 Hz, 1H), 3.66 (t, J=5.6 Hz, 2H), 2.80 (ddd, J=5.2, 12.4, 17.2 Hz, 1H), 2.59-2.53 (m, 1H), 2.42 (t, J=6.4 Hz, 2H), 2.37-2.27 (m, 1H), 2.10-2.01 (m, 1H), 1.94-1.81 (m, 4H); MS (ESI) m/z 397.1 [M+H]$^+$

Example 48. Synthesis of 3-(2-chloro-4'-(2-oxopyrrolidin-1-yl)-[1,1'-biphenyl]-3-yl)piperidine-2,6-dione (compound 162)

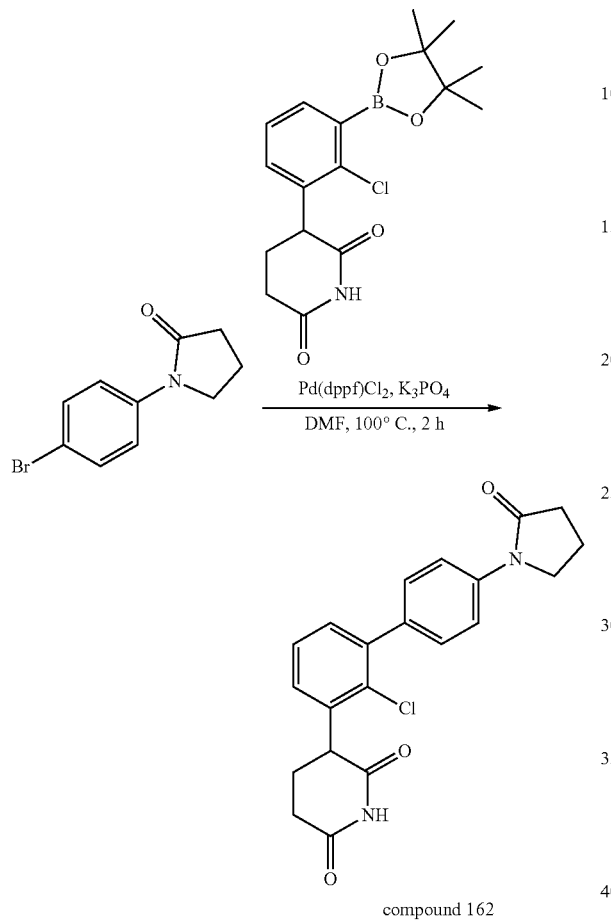

compound 162

3-(2-chloro-4'-(2-oxopyrrolidin-1-yl)-[1,1'-biphenyl]-3-yl)piperidine-2,6-dione was prepared from 1-(4-bromophenyl)pyrrolidin-2-one and 3-(2-chloro-3-(4,4,5,5-tetramethyl-1,3,2-dioxaborolan-2-yl)phenyl) piperidine-2,6-dione according to General Scheme 1.

$^1$H NMR (400 MHz, MeOD) δ=7.69 (d, J=8.8 Hz, 2H), 7.45-7.41 (m, 2H), 7.40-7.35 (m, 1H), 7.34-7.29 (m, 2H), 4.39 (dd, J=5.2, 12.0 Hz, 1H), 3.98 (t, J=7.2 Hz, 2H), 2.87-2.76 (m, 1H), 2.74-2.66 (m, 1H), 2.63 (t, J=8.0 Hz, 2H), 2.42 (dq, J=4.4, 12.4 Hz, 1H), 2.27-2.16 (m, 3H); MS (ESI) m/z 383.1 [M+H]$^+$

Example 49. Synthesis of 3-(2-chloro-4'-(2-oxoazetidin-1-yl)-[1,1'-biphenyl]-3-yl)piperidine-2,6-dione (compound 163)

3-(2-chloro-4'-(2-oxoazetidin-1-yl)-[1,1'-biphenyl]-3-yl) piperidine-2,6-dione was prepared from 1-(4-iodophenyl) azetidin-2-one and 3-[2-chloro-3-(4,4,5,5-tetramethyl-1,3,2-dioxaborolan-2-yl)phenyl]piperidine-2,6-dione according to General Scheme 1.

MS (ESI) m/z=369.0[M+H]$^+$

Example 50. Synthesis of 3-(2-chloro-4'-(1-methyl-1H-pyrazol-3-yl)-[1,1'-biphenyl]-3-yl)piperidine-2, 6-dione (compound 164)

3-(2-chloro-4'-(1-methyl-1H-pyrazol-3-yl)-[1,1'-biphenyl]-3-yl)piperidine-2,6-dione was prepared from 3-(4-bromophenyl)-1-methyl-1H-pyrazole and 3-[2-chloro-3-(4,4,5,5-tetramethyl-1,3,2-dioxaborolan-2-yl)phenyl]piperidine-2,6-dione according to General Scheme 1.

MS (ESI) m/z 380.1[M+H]$^+$

Example 51. Synthesis of 3-(2-chloro-4'-((2-methyl-5-oxo-2,5-dihydro-1H-pyrazol-1-yl)methyl)-[1,1'-biphenyl]-3-yl)piperidine-2,6-dione (compound 158)

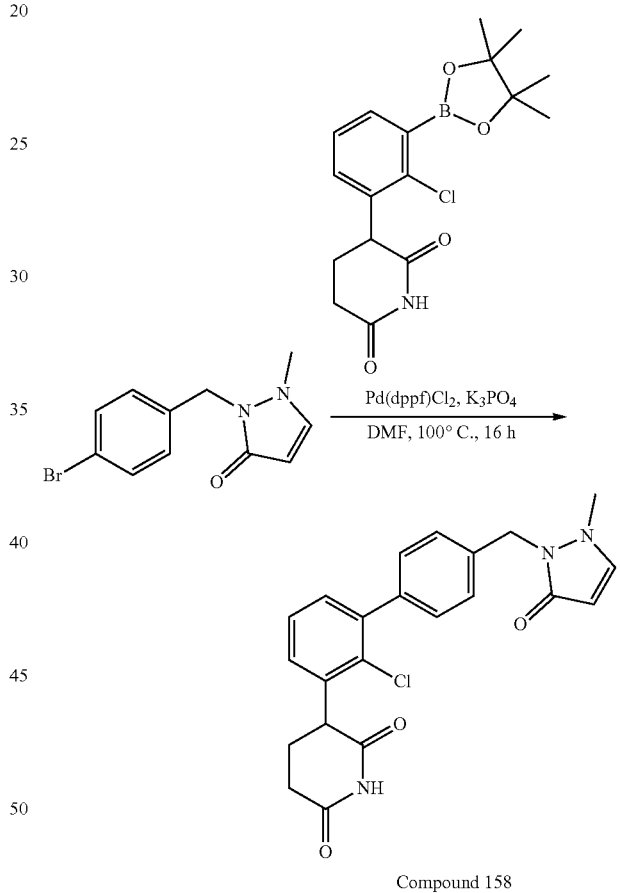

Compound 158

3-(2-chloro-4'-((2-methyl-5-oxo-2,5-dihydro-1H-pyrazol-1-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 2-(4-bromobenzyl)-1-methyl-1,2-dihydro-3H-pyrazol-3-one according to General Scheme 1.

$^1$H NMR (400 MHz, DMSO-d$_6$) δ=10.9 (br s, 1H), 7.68 (d, J=3.6 Hz, 1H), 7.41-7.33 (m, 4H), 7.31-7.27 (m, 1H), 7.24 (s, 1H), 7.22 (s, 1H), 5.28 (d, J=3.2 Hz, 1H), 5.03 (s, 2H), 4.33 (dd, J=5.2, 12.0 Hz, 1H), 3.32 (s, 3H), 2.85-2.72 (m, 1H), 2.57-2.53 (m, 1H), 2.36-2.26 (m, 1H), 2.09-1.99 (m, 1H); MS (ESI) m/z 410.1 [M+H]$^+$

Example 52. Synthesis of 3-(2-fluoro-4'-((2-oxopyridin-1(2H)-yl)methyl)-[1,1'-biphenyl]-3-yl)piperidine-2,6-dione (Compound 149)

3-(2-fluoro-4'-((2-oxopyridin-1(2H)-yl)methyl)-[1,1'-biphenyl]-3-yl)piperidine-2,6-dione was prepared from 3-(3-bromo-2-fluorophenyl)piperidine-2,6-dione and 1-(4-(4,4,5,5-tetramethyl-1,3,2-dioxaborolan-2-yl)benzyl)pyridin-2(1H)-one according to General Scheme 1.
MS (ESI) m/z 391.1 [M+H]⁺

Example 53. Synthesis of 3-(2-chloro-4'-(2-(2-oxopiperidin-1-yl)propan-2-yl)-[1,1'-biphenyl]-3-yl)piperidine-2,6-dione (Compound 197)

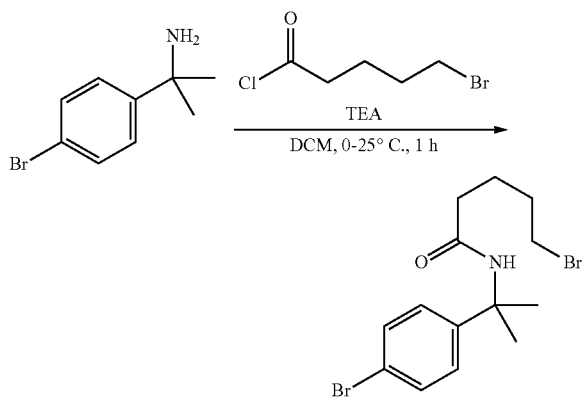

To a solution of 2-(4-bromophenyl)propan-2-amine (500 mg, 2.34 mmol, 1.00 eq) and triethylamine (473 mg, 4.67 mmol, 650 uL, 2.00 eq) in dichloromethane (6 mL) was added 5-bromopentanoyl chloride (559 mg, 2.80 mmol, 375 uL, 1.20 eq) at 0° C. Then the mixture was stirred at 25° C. for 1 h. The reaction mixture was concentrated under reduced pressure to give a residue. The residue was purified by flash silica gel chromatography (ISCO®; 12 g SepaFlash® Silica Flash Column, Eluent of 0~100% Ethylacetate/Petroleum ethergradient @ 60 mL/min) to afford compound 5-bromo-N-[1-(4-bromophenyl)-1-methyl-ethyl]pentanamide (1.71 g, 4.49 mmol, 96% yield) was obtained as a white solid.

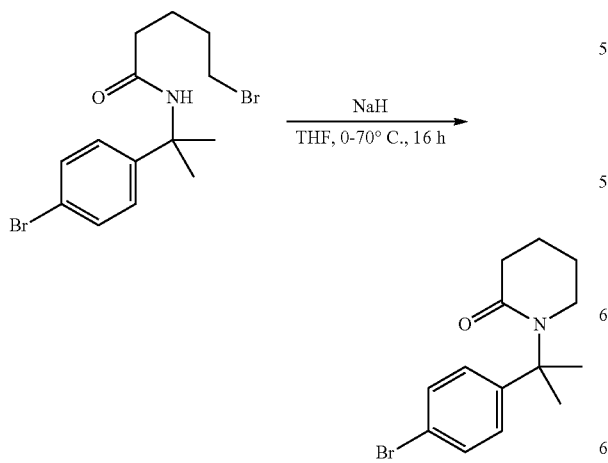

To a solution of sodium hydride (127 mg, 3.18 mmol, 60% purity, 1.20 eq) in tetrahydrofuran (5 mL) was added 5-bromo-N-(2-(4-bromophenyl)propan-2-yl)pentanamide (1.00 g, 2.65 mmol, 1.00 eq) at 0° C. Then the mixture was stirred at 70° C. for 16 h under nitrogen atmosphere. The reaction mixture was cooled to 25° C. and quenched with saturated ammonium chloride solution (15 mL) at 0° C. The reaction mixture was concentrated under reduced pressure to remove tetrahydrofuran and extracted with ethyl acetate (3×20 mL). The combined organic layers were washed with brine (30 mL), dried over sodium sulfate and concentrated under reduced pressure to give a residue. The residue was purified by flash silica gel chromatography (ISCO®; 12 g SepaFlash® Silica Flash Column, Eluent of 0~50% Ethyl acetate/Petroleum ether gradient @ 40 mL/min) to afford 1-(2-(4-bromophenyl)propan-2-yl)piperidin-2-one (550 mg, 1.84 mmol, 69% yield) as a colorless oil.

3-(2-chloro-4'-(2-(2-oxopiperidin-1-yl)propan-2-yl)-[1,1'-biphenyl]-3-yl)piperidine-2,6-dione was prepared from 1-(2-(4-bromophenyl)propan-2-yl)piperidin-2-one and 3-[2-chloro-3-(4,4,5,5-tetramethyl-1,3,2-dioxaborolan-2-yl)phenyl]piperidine-2,6-dione according to General Scheme 1.
MS (ESI) m/z=439.2 [M+H]⁺

Example 54. synthesis of 3-(4'-(azetidin-1-yl)-2-chloro-[1,1'-biphenyl]-3-yl)piperidine-2,6-dione (Compound 195)

3-(4'-(azetidin-1-yl)-2-chloro-[1,1'-biphenyl]-3-yl)piperidine-2,6-dione was prepared from 1-(4-bromophenyl)azetidine and 3-(2-chloro-3-(4,4,5,5-tetramethyl-1,3,2-dioxaborolan-2-yl)phenyl)piperidine-2,6-dione according to General Scheme 1. MS (ESI) m/z 355.1 [M+H]⁺

Example 55. Synthesis of 3-(2-chloro-4'-(2-(1-methyl-1H-pyrazol-3-yl)ethyl)-[1,1'-biphenyl]-3-yl)piperidine-2,6-dione (Compound 194)

3-(2-chloro-4'-(2-(1-methyl-1H-pyrazol-3-yl)ethyl)-[1,1'-biphenyl]-3-yl)piperidine-2,6-dione was prepared from 4-(2-(1-methyl-1H-pyrazol-3-yl)ethyl)phenyl trifluoromethanesulfonate and 3-(2-chloro-3-(4,4,5,5-tetramethyl-1,3,2-dioxaborolan-2-yl)phenyl)piperidine-2,6-dione according to General Scheme 1. MS (ESI) m/z 408.0 [M+H]⁺

Example 56. Synthesis of 3-(2-fluoro-4'-(2-oxopyridin-1(2H)-yl)-[1,1'-biphenyl]-3-yl)piperidine-2,6-dione (Compound 234)

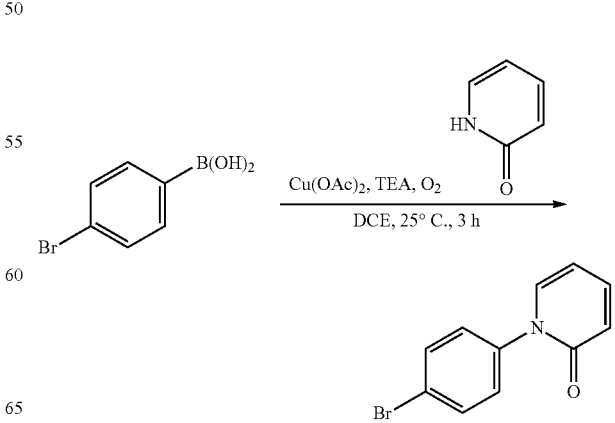

A mixture of (4-bromophenyl)boronic acid (3.00 g, 14.9 mmol, 1.00 eq), pyridin-2(1H)-one (1.70 g, 17.9 mmol, 1.20 eq), copper acetate (2.71 g, 14.9 mmol, 1.00 eq) and triethylamine (4.53 g, 44.8 mmol, 6.24 mL, 3.00 eq) in dichloroethane (5 mL) was degassed and purged with oxygen for 3 times, and then the mixture was stirred at 25° C. for 3 hr. The reaction mixture was concentrated under reduced pressure to give a residue. The residue was purified by flash silica gel chromatography (ISCO®; 20 g Sepa-Flash® Silica Flash Column, Eluent of 0~80% Ethyl acetate/Petroleum ether gradient @ 40 mL/min) to afford 1-(4-bromophenyl)pyridin-2(1H)-one (1.6 g, 6.33 mmol, 42% yield) as a white solid.

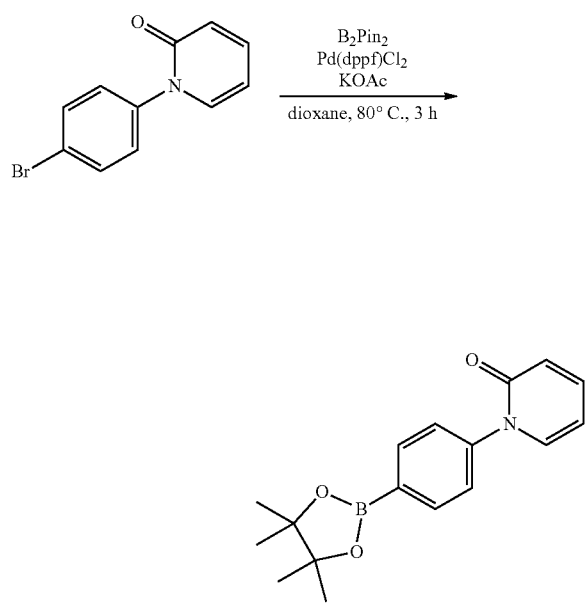

1-(4-(4,4,5,5-tetramethyl-1,3,2-dioxaborolan-2-yl)phenyl)pyridin-2(1H)-one was prepared from 1-(4-bromophenyl)pyridin-2(1H)-one and 4,4,5,5-tetramethyl-2-(4,4,5,5-tetramethyl-1,3,2-dioxaborolan-2-yl)-1,3,2-dioxaborolane according to General Scheme 6.

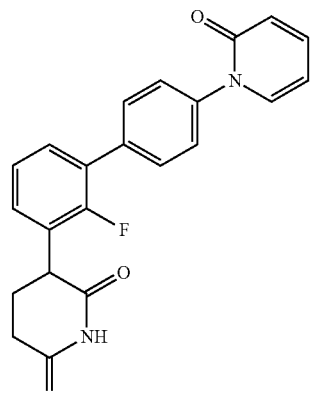

Compound 234

3-(2-fluoro-4'-(2-oxopyridin-1(2H)-yl)-[1,1'-biphenyl]-3-yl)piperidine-2,6-dione was prepared from 1-(4-(4,4,5,5-tetramethyl-1,3,2-dioxaborolan-2-yl)phenyl)pyridin-2(1H)-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-$d_6$) δ=10.92 (s, 1H), 7.74-7.63 (m, 3H), 7.56-7.48 (m, 4H), 7.41-7.35 (m, 1H), 7.34-7.28 (m, 1H), 6.51 (d, J=9.3 Hz, 1H), 6.34 (dt, J=6.8, 1.2 Hz, 1H), 4.16 (dd, J=12.4, 5.2, Hz, 1H), 2.84-2.72 (m, 1H), 2.62-2.55 (m, 1H), 2.35-2.21 (m, 1H), 2.14-2.02 (m, 1H)

MS (ESI) m/z 377.1 [M+H]$^+$

Example 57. synthesis of 3-(2-chloro-4'-(((1-methyl-1H-pyrazol-3-yl)amino)methyl)-[1,1'-biphenyl]-3-yl)piperidine-2,6-dione (Compound 196)

To a solution of 4-bromobenzaldehyde (1.00 g, 5.40 mmol, 1.00 eq) and 1-methyl-1H-pyrazol-3-amine (525 mg, 5.40 mmol, 1.00 eq) in dichloromethane (15.0 mL) was added acetic acid (325 mg, 5.40 mmol, 309 uL, 1.00 eq) dropwise at 25° C. The mixture was stirred at 25° C. for 1 h. Then the mixture was added sodium triacetoxyborohydride (2.29 g, 10.8 mmol, 2.00 eq) in portions at 25° C. The mixture was stirred at 25° C. for 11 h. The reaction mixture was quenched with saturated sodium bicarbonate solution and extracted with ethyl acetate (3×30.0 mL). The crude product was purified by silica gel chromatography (petroleum ether/ethyl acetate=5/1) to afford N-(4-bromobenzyl)-1-methyl-1H-pyrazol-3-amine (1.19 g, 4.47 mmol, 82% yield) as a white solid.

3-(2-chloro-4'-(((1-methyl-1H-pyrazol-3-yl)amino)methyl)-[1,1'-biphenyl]-3-yl)piperidine-2,6-dione was prepared from N-(4-bromobenzyl)-1-methyl-1H-pyrazol-3-amine and 3-(2-chloro-3-(4,4,5,5-tetramethyl-1,3,2-dioxaborolan-2-yl)phenyl)piperidine-2,6-dione according to General Scheme 1.

MS (ESI) m/z 409.0 [M+H]$^+$

Example 58. Synthesis of 3-(2-chloro-4'-(oxetan-3-yl)-[1,1'-biphenyl]-3-yl)piperidine-2,6-dione (Compound 198)

3-(2-chloro-4'-(oxetan-3-yl)-[1,1'-biphenyl]-3-yl)piperidine-2,6-dione was prepared from 3-(4-bromophenyl)oxetane and 3-(2-chloro-3-(4,4,5,5-tetramethyl-1,3,2-dioxaborolan-2-yl)phenyl)piperidine-2,6-dione according to General Scheme 1.

MS (ESI) m/z 356.0 [M+H]$^+$

Example 59. Synthesis of 3-(2-chloro-3'-methyl-4'-(2-oxopyridin-1(2H)-yl)-[1,1'-biphenyl]-3-yl)piperidine-2,6-dione (Compound 199)

1-(4-bromo-2-methylphenyl)pyridin-2(1H)-one was prepared from 4-bromo-1-iodo-2-methylbenzene and pyridin-2(1H)-one according to General Scheme 7.

3-(2-chloro-3'-methyl-4'-(2-oxopyridin-1(2H)-yl)-[1,1'-biphenyl]-3-yl)piperidine-2,6-dione was prepared from 1-(4-bromo-2-methylphenyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

MS (ESI) m/z 407.1 [M+H]$^+$

Example 60. Synthesis of 3-(2-chloro-4'-(2-methyl-6-oxopiperidin-1-yl)-[1,1'-biphenyl]-3-yl)piperidine-2,6-dione (Compound 200)

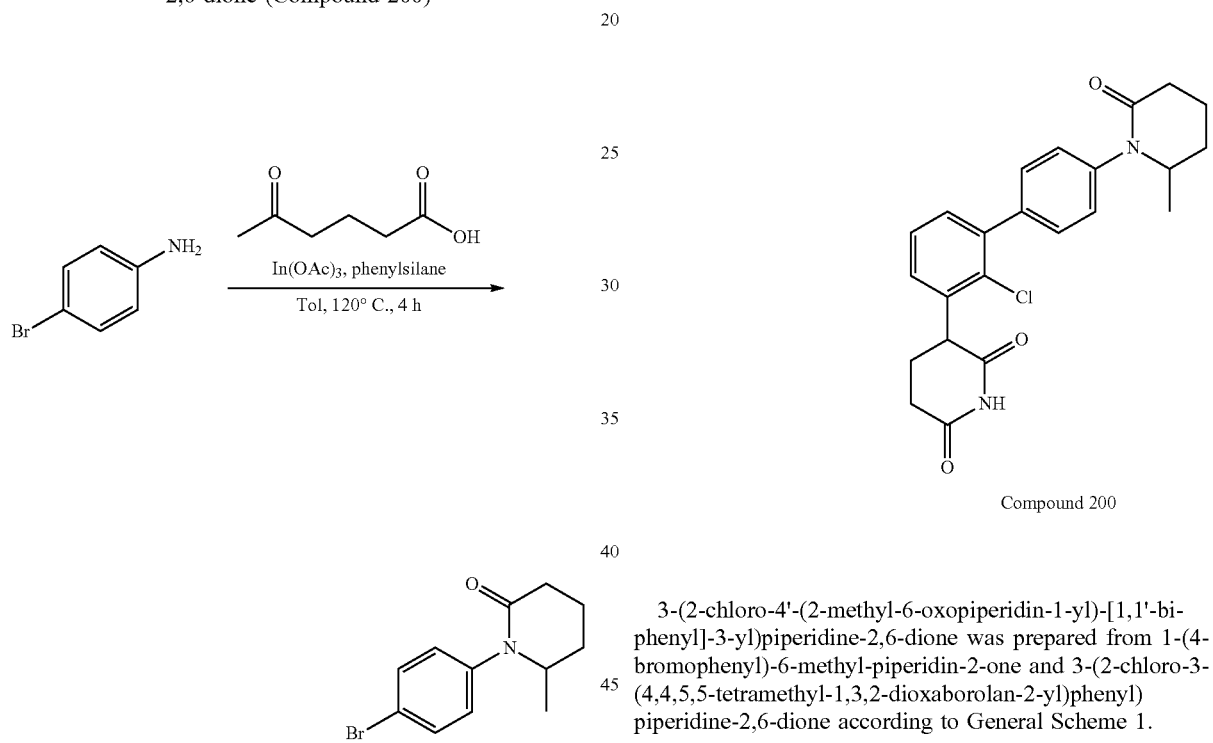

Compound 200

To a mixture of 4-bromoaniline (1.00 g, 5.81 mmol, 1.00 eq) in toluene (10.0 mL) was added 5-oxohexanoic acid (756 mg, 5.81 mmol, 694 uL, 1.00 eq), indiumacetate (17.0 mg, 58.1 umol, 0.0100 eq) and phenylsilane (629 mg, 5.81 mmol, 717 uL, 1.00 eq). The mixture was stirred at 120° C. for 4 h. The mixture was poured into water (80 mL) and extracted with ethyl acetate (3×60 mL). The combined organic layer was washed with brine (30 mL), dried over sodium sulfate, filtered and concentrated in vacuum. The residue was purified by silica gel chromatography (petroleum ether/ethyl acetate=0:1 to 3:1) to give 1-(4-bromophenyl)-6-methyl-piperidin-2-one (1.31 g, 4.89 mmol, 84% yield) as yellow oil.

3-(2-chloro-4'-(2-methyl-6-oxopiperidin-1-yl)-[1,1'-biphenyl]-3-yl)piperidine-2,6-dione was prepared from 1-(4-bromophenyl)-6-methyl-piperidin-2-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-d$_6$) δ=10.92 (s, 1H), 7.48-7.32 (m, 5H), 7.29-7.24 (m, 2H), 4.35 (dd, J=5.2, 12.0 Hz, 1H), 4.06-3.94 (m, 1H), 2.87-2.74 (m, 1H), 2.46-2.31 (m, 4H), 2.16-2.02 (m, 2H), 1.99-1.84 (m, 1H), 1.83-1.63 (m, 2H), 1.03 (d, J=6.4 Hz, 3H).

MS (ESI) m/z 411.2 [M+H]$^+$

Example 61. Synthesis of 3-(2-chloro-3-(6-(2-(1-methyl-1H-pyrazol-3-yl)ethyl)pyridin-3-yl)phenyl)piperidine-2,6-dione (Compound 249)

3-(2-chloro-3-(6-(2-(1-methyl-1H-pyrazol-3-yl)ethyl)pyridin-3-yl)phenyl)piperidine-2,6-dione was prepared from 3-(2-chloro-4'-(4,4,5,5-tetramethyl-1,3,2-dioxaborolan-2-yl)-[1,1'-biphenyl]-3-yl)piperidine-2,6-dione and 6-(2-(1-methyl-1H-pyrazol-3-yl)ethyl)pyridin-3-yl trifluoromethanesulfonate according to General Scheme 1.

MS (ESI) m/z 409.0 [M+H]$^+$

Example 62. Synthesis of (S)-3-(2-chloro-4'-((2-oxopyridin-1(2H)-yl)methyl)-[1,1'-biphenyl]-3-yl)piperidine-2,6-dione (Compound 202) and (R)-3-(2-chloro-4'-((2-oxopyridin-1(2H)-yl)methyl)-[1,1'-biphenyl]-3-yl)piperidine-2,6-dione (Compound 201)

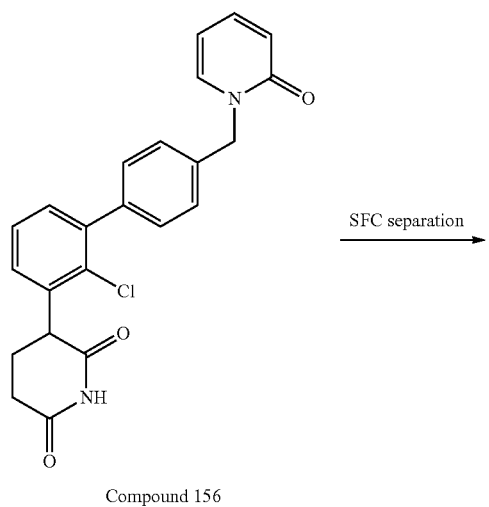

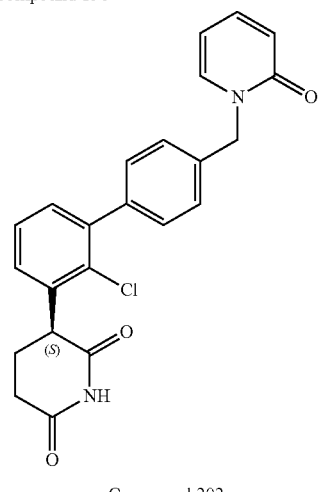

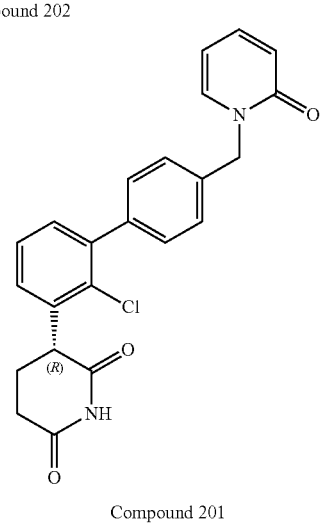

The 3-(2-chloro-4'-((2-oxopyridin-1(2H)-yl)methyl)-[1,1'-biphenyl]-3-yl)piperidine-2,6-dione (150 mg, 369 μmol, 1.00 eq) was separated by SFC (column: DAICEL CHIRALPAK AS(250 mm×30 mm, 10 m); mobile phase: [propan-2-ol/acetonitrile]; B %: 70%-70%, 6 min). The desired fraction was concentrated under reduced pressure to give two crude product. Crude product 1 was purified by Prep-HPLC (column: YMC-Actus Triart C18 150×30 mm×7 m; mobile phase: [water (formic acid)-acetonitrile]; B %: 35%-65%, 10 min) and lyophilized to afford (S)-3-(2-chloro-4'-((2-oxopyridin-1(2H)-yl)methyl)-[1,1'-biphenyl]-3-yl)piperidine-2,6-dione (46.4 mg, 113 μmol, 31% yield) as white solid. Crude product 2 was purified by Prep-HPLC (column: YMC-Actus Triart C18 150×30 mm×7 m; mobile phase: [water (formic acid)-acetonitrile]; B %: 35%-65%, 10 min) and lyophilized to afford (R)-3-(2-chloro-4'-((2-oxopyridin-1(2H)-yl)methyl)-[1,1'-biphenyl]-3-yl)piperidine-2,6-dione (47.8 mg, 116 μmol, 32% yield) as white solid.

Compound 202:
$^1$H NMR (400 MHz, DMSO-$d_6$) δ=10.91 (s, 1H), 7.86 (dd, J=1.6, 6.8 Hz, 1H), 7.45 (ddd, J=1.6, 6.8, 8.8 Hz, 1H), 7.41-7.32 (m, 6H), 7.28 (dd, J=1.6, 6.8 Hz, 1H), 6.44 (d, J=8.8 Hz, 1H), 6.27 (dt, J=1.2, 6.8 Hz, 1H), 5.16 (s, 2H), 4.33 (dd, J=4.8, 12.4 Hz, 1H), 2.85-2.70 (m, 1H), 2.58-2.52 (m, 1H), 2.40-2.26 (m, 1H), 2.09-1.97 (m, 1H).
MS (ESI) m/z 407.2 [M+H]$^+$ Compound 201:
$^1$H NMR (400 MHz, DMSO-$d_6$) δ=10.91 (br s, 1H), 7.86 (dd, J=1.6, 6.8 Hz, 1H), 7.45 (ddd, J=1.6, 6.8, 8.8 Hz, 1H), 7.41-7.31 (m, 6H), 7.28 (dd, J=1.6, 6.8 Hz, 1H), 6.44 (d, J=8.8 Hz, 1H), 6.27 (dt, J=1.2, 6.8 Hz, 1H), 5.16 (s, 2H), 4.33 (dd, J=4.8, 12.4 Hz, 1H), 2.86-2.71 (m, 1H), 2.58-2.52 (m, 1H), 2.39-2.26 (m, 1H), 2.10-1.97 (m, 1H).
MS (ESI) m/z 407.2 [M+H]$^+$ Example 63. Synthesis of 3-(4'-((1H-pyrazol-3-yl)methoxy)-2-chloro-[1,1'-biphenyl]-3-yl)piperidine-2,6-dione (Compound 203)

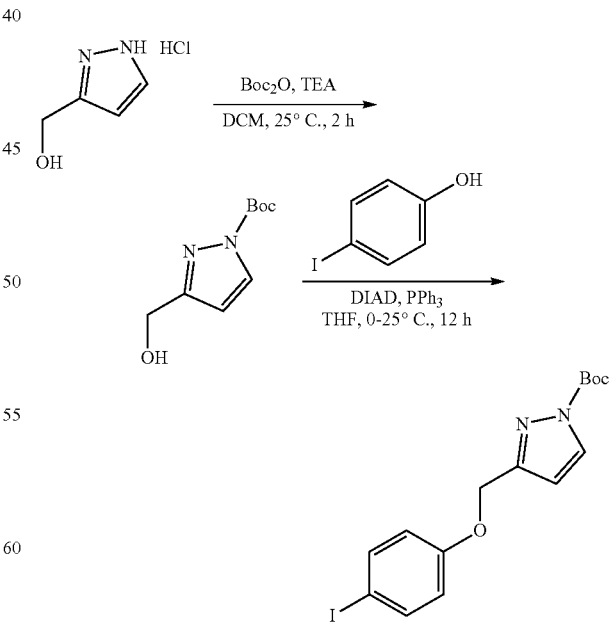

tert-butyl 3-((4-iodophenoxy)methyl)-1H-pyrazole-1-carboxylate was prepared from (1H-pyrazol-3-yl)methanol and 4-iodophenol analogously to Example 16.

tert-butyl 3-(((2'-chloro-3'-(2,6-dioxopiperidin-3-yl)-[1,1'-biphenyl]-4-yl)oxy)methyl)-1H-pyrazole-1-carboxylate was prepared from tert-butyl 3-((4-iodophenoxy)methyl)-1H-pyrazole-1-carboxylate and 3-(2-chloro-3-(4,4,5,5-tetramethyl-1,3,2-dioxaborolan-2-yl)phenyl)piperidine-2,6-dione according to General Scheme 1.

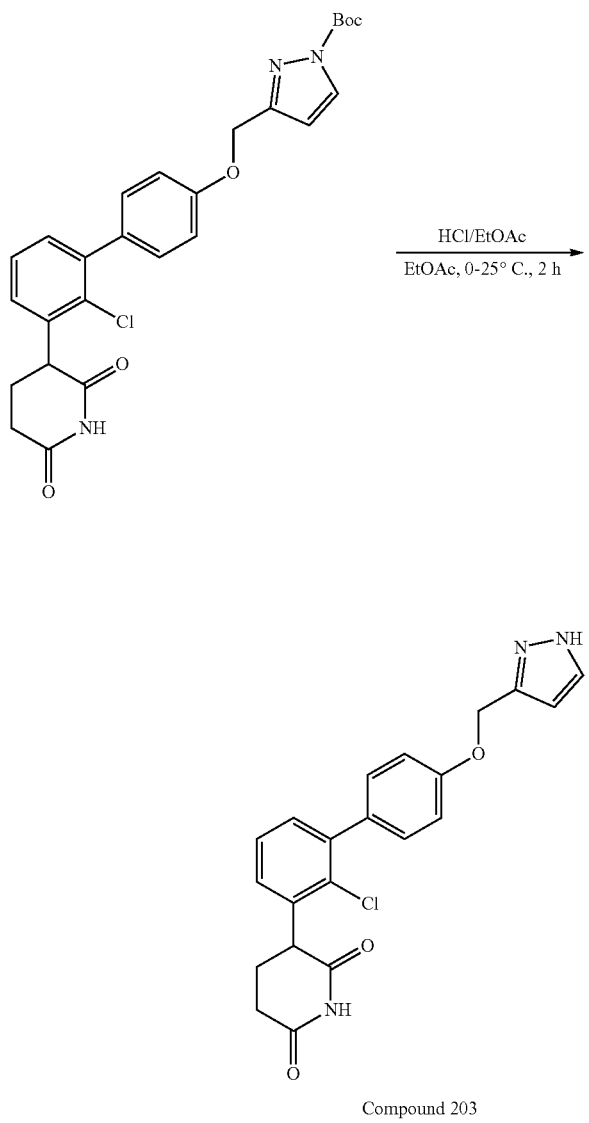

Compound 203

A mixture of tert-butyl 3-(((2'-chloro-3'-(2,6-dioxopiperidin-3-yl)-[1,1'-biphenyl]-4-yl)oxy)methyl)-1H-pyrazole-1-carboxylate (100 mg, 181 umol, 90% purity, 1.00 eq) in ethyl acetate (2.00 mL) was dropwise added hydrochloride acid/ethyl acetate (4M, 2 mL) at 0° C. The mixture was stirred at 25° C. for 2 h. The mixture was added saturated sodium bicarbonate solution (3 mL) and diluted with water (10 mL), extracted with ethyl acetate (3×20 mL). The organic layers were washed with brine (15 mL), dried over anhydrous sodium sulfate, filtered and concentrated to afford a residue. The residue was purified by Prep-HPLC (column: Phenomenex luna C18 150*25 mm*10 um; mobile phase: [water(formic acid)-acetonitrile]; B %: 28%-58%, 10 min) and lyophilized to afford 3-(4'-((1H-pyrazol-3-yl)methoxy)-2-chloro-[1,1'-biphenyl]-3-yl)piperidine-2,6-dione (25.43 mg, 63.6 umol, 35% yield, 99% purity) as a white solid.

MS (ESI) m/z 396.1[M+H]$^+$

Example 64. Synthesis of 3-(2-chloro-4'-(2-oxooxazolidin-3-yl)-[1,1'-biphenyl]-3-yl)piperidine-2,6-dione (Compound 212)

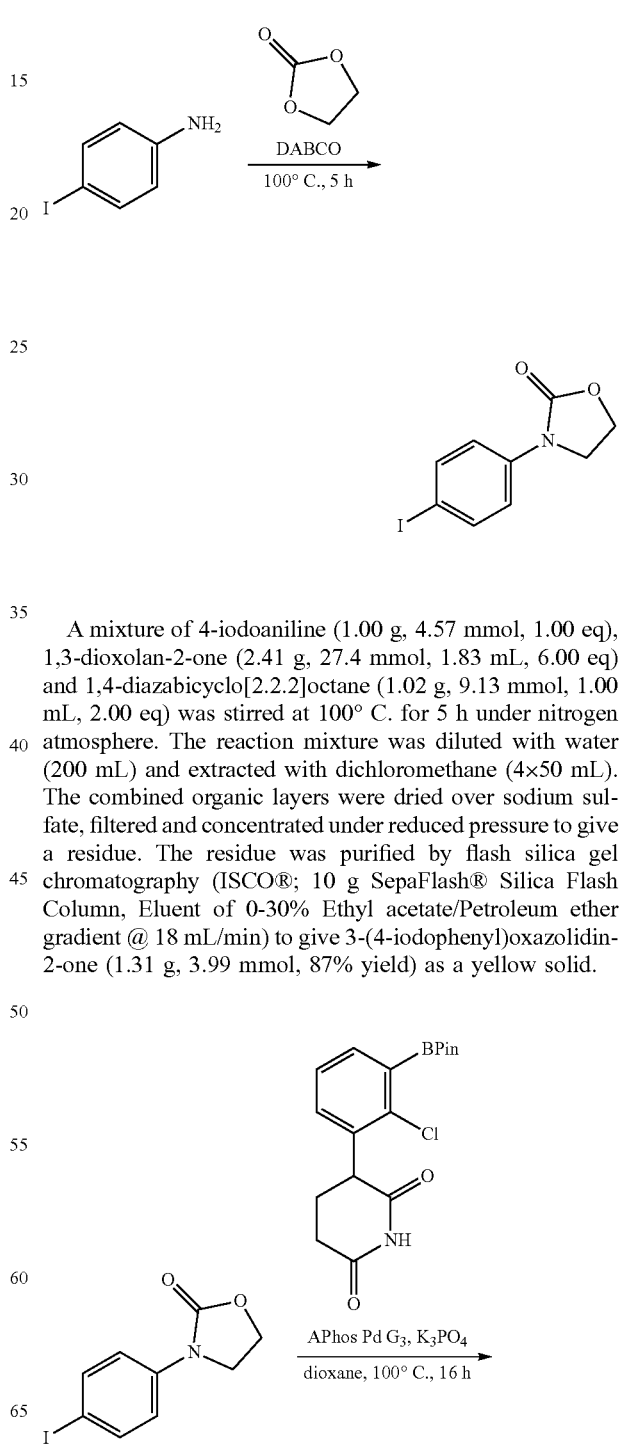

A mixture of 4-iodoaniline (1.00 g, 4.57 mmol, 1.00 eq), 1,3-dioxolan-2-one (2.41 g, 27.4 mmol, 1.83 mL, 6.00 eq) and 1,4-diazabicyclo[2.2.2]octane (1.02 g, 9.13 mmol, 1.00 mL, 2.00 eq) was stirred at 100° C. for 5 h under nitrogen atmosphere. The reaction mixture was diluted with water (200 mL) and extracted with dichloromethane (4×50 mL). The combined organic layers were dried over sodium sulfate, filtered and concentrated under reduced pressure to give a residue. The residue was purified by flash silica gel chromatography (ISCO®; 10 g SepaFlash® Silica Flash Column, Eluent of 0-30% Ethyl acetate/Petroleum ether gradient @ 18 mL/min) to give 3-(4-iodophenyl)oxazolidin-2-one (1.31 g, 3.99 mmol, 87% yield) as a yellow solid.

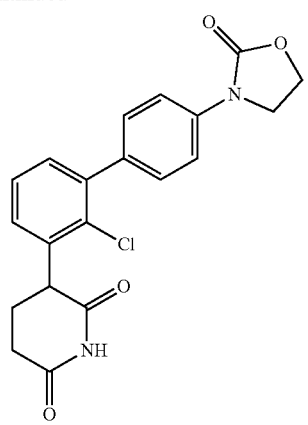

Compound 212

3-(2-chloro-4'-(2-oxooxazolidin-3-yl)-[1,1'-biphenyl]-3-yl)piperidine-2,6-dione was prepared from 3-(4-iodophenyl)oxazolidin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-$d_6$) δ=10.92 (s, 1H), 7.68 (d, J=8.4 Hz, 2H), 7.48-7.42 (m, 2H), 7.40-7.28 (m, 3H), 4.47 (t, J=8.0 Hz, 2H), 4.34 (dd, J=4.8, 12.0 Hz, 1H), 4.12 (t, J=8.0 Hz, 2H), 2.79 (ddd, J=5.2, 12.4, 17.6 Hz, 1H), 2.56 (d, J=3.6 Hz, 1H), 2.38-2.27 (m, 1H), 2.12-1.99 (m, 1H).

MS (ESI) m/z 385.1 [M+H]$^+$

Example 65. synthesis of 3-(2-chloro-4'-(6-methyl-2-oxopyridin-1(2H)-yl)-[1,1'-biphenyl]-3-yl)piperidine-2,6-dione (Compound 214)

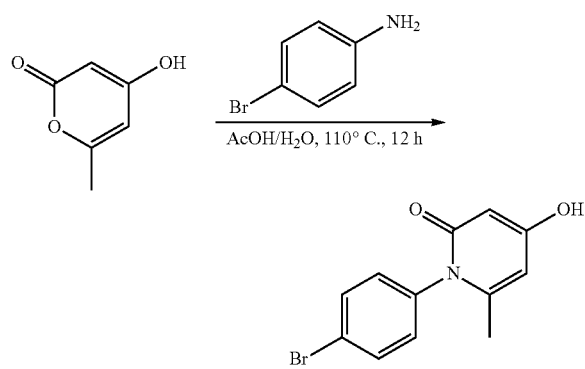

To a solution of 4-hydroxy-6-methyl-2H-pyran-2-one (5.00 g, 39.7 mmol, 1.00 eq) in water (10 mL) and acetic acid (10 mL) was added 4-bromoaniline (8.18 g, 47.6 mmol, 1.20 eq). The mixture was stirred at 110° C. for 12 h. The reaction mixture was cooled to 25° C., then filtered and concentrated under reduced pressure to give a residue. The residue was purified by reversed phase column (0.1% FA condition). Then the desired fraction was collected and lyophilized to afford 1-(4-bromophenyl)-4-hydroxy-6-methylpyridin-2(1H)-one (2.82 g, 9.67 mmol, 24% yield) as a yellow solid.

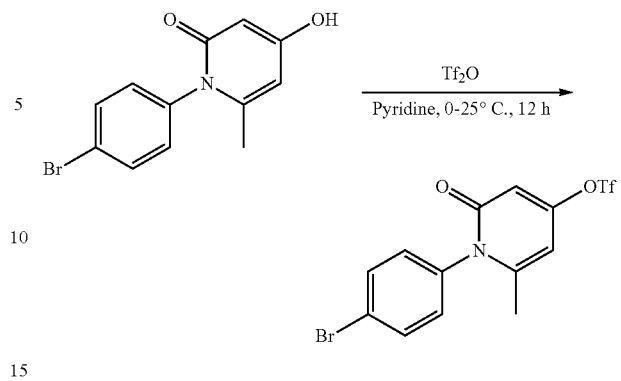

To a solution of 1-(4-bromophenyl)-4-hydroxy-6-methylpyridin-2-one (1.50 g, 4.71 mmol, 88% purity, 1.00 eq) in pyridine (10 mL) was added dropwise triflic anhydride (1.99 g, 7.07 mmol, 1.17 mL, 1.50 eq) at 0° C. After addition, the resulting mixture was stirred at 25° C. for 2 h. The reaction mixture was quenched by addition water (20 mL) at 25° C., and then extracted with dichloromethane (3×25 mL). The combined organic layers were washed with brine (15 mL), dried over anhydrous sodium sulfate, filtered and concentrated under reduced pressure to give a residue. The residue was purified by flash silica gel chromatography (ISCO®; 40 g SepaFlash® Silica Flash Column, Eluent of 0~100% Ethyl acetate/Petroleum ether gradient @ 35 mL/min) to afford 1-(4-bromophenyl)-6-methyl-2-oxo-1,2-dihydropyridin-4-yl trifluoromethanesulfonate (1.89 g, 4.54 mmol, 96% yield) as a light yellow solid.

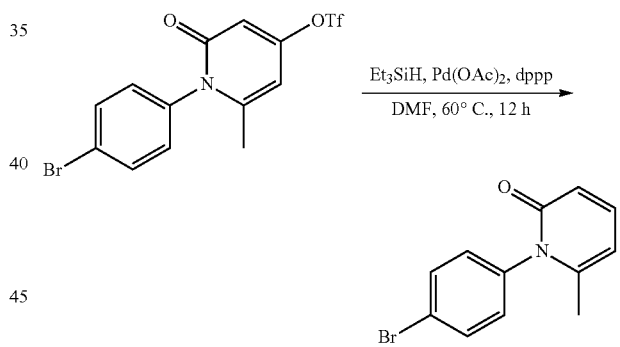

A mixture of [1-(4-bromophenyl)-2-methyl-6-oxo-4-pyridyl] trifluoromethanesulfonate (2.00 g, 4.80 mmol, 99% purity, 1.00 eq), palladium (II) acetate (53.9 mg, 240 μmol, 0.0500 eq) and 1,3-bis(diphenyphosphino)propane (99.1 mg, 240 μmol, 0.0500 eq) in dimethylformamide (20 mL) was degassed and purged with nitrogen for three times, and then the mixture was stirred at 60° C. for 10 minutes, followed by the addition of triethylsilane (1.40 g, 607 umol, 96.9 μL, 2.50 eq). Then the reaction mixture was stirred at 60° C. for another 12 h. The reaction mixture was concentrated under reduced pressure to remove dimethylformamide. The residue was diluted with ethyl acetate (30 mL) and filtered through a plug of Celite. To the mixture was added water (50 mL), the resulting mixture was extracted with ethyl acetate (3×30 mL). The combined organic layers were washed with brine (30 mL), dried over anhydrous sodium sulfate, filtered and concentrated under reduced pressure to give a residue. The residue was purified by flash silica gel chromatography (ISCO®; 40 g SepaFlash® Silica Flash Column, Eluent of 0-100% Ethyl acetate/Petroleum ether gradient @ 35 mL/min) to afford 1-(4-bromophenyl)-6-methyl-pyridin-2-one (660 mg, 2.47 mmol, 52% yield) as a white solid.

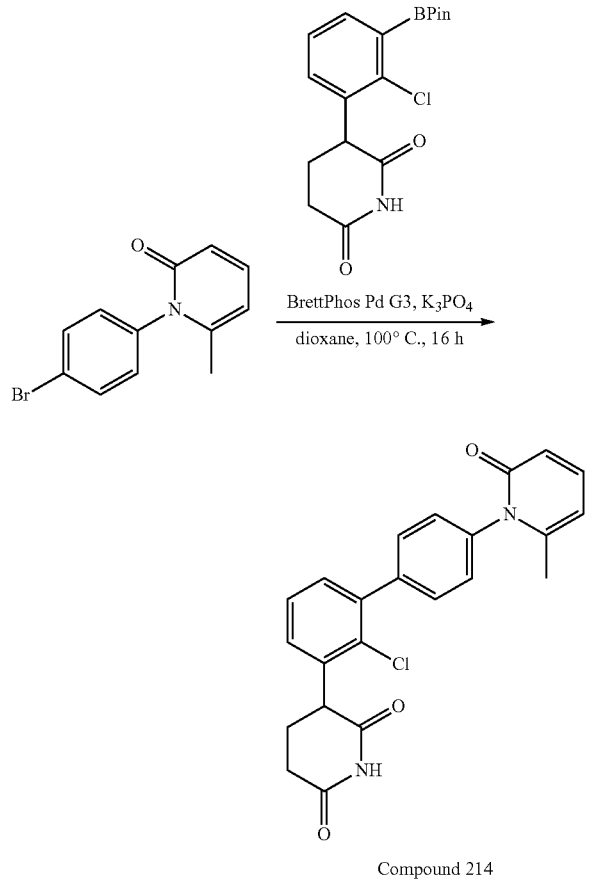

Compound 214

3-[2-chloro-3-[4-(2-methyl-6-oxo-1-pyridyl)phenyl]phenyl]piperidine-2,6-dione was prepared from 1-(4-bromophenyl)-6-methyl-pyridin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-$d_6$) δ 10.94 (s, 1H), 7.56 (d, J=8.0 Hz, 2H), 7.46-7.38 (m, 4H), 7.35 (d, J=8.4 Hz, 2H), 6.37 (d, J=9.2 Hz, 1H), 6.26 (d, J=6.4 Hz, 1H), 4.20-4.40 (m, 1H), 2.84-2.75 (m, 1H), 2.62-2.57 (m, 1H), 2.37-2.31 (m, 1H), 2.10-2.05 (m, 1H), 1.96 (s, 3H).

MS (ESI) m/z 407.1 [M+H]$^+$

Example 66. synthesis of 3-(2-chloro-4'-(((1-methyl-1H-pyrazol-4-yl)methyl)amino)-[1,1'-biphenyl]-3-yl)piperidine-2,6-dione (Compound 193)

3-(2-chloro-4'-(((1-methyl-1H-pyrazol-4-yl)methyl)amino)-[1,1'-biphenyl]-3-yl)piperidine-2,6-dione was prepared from 4-bromo-N-((1-methyl-1H-pyrazol-4-yl)methyl)aniline and 3-(2-chloro-3-(4,4,5,5-tetramethyl-1,3,2-dioxaborolan-2-yl)phenyl)piperidine-2,6-dione according to General Scheme 1.

MS (ESI) m/z 409.4 [M+H]$^+$

Example 67. synthesis of N-[4-[2-chloro-3-(2,6-dioxo-3-piperidyl)phenyl]phenyl]-1-methyl-pyrazole-3-carboxamide (Compound 207)

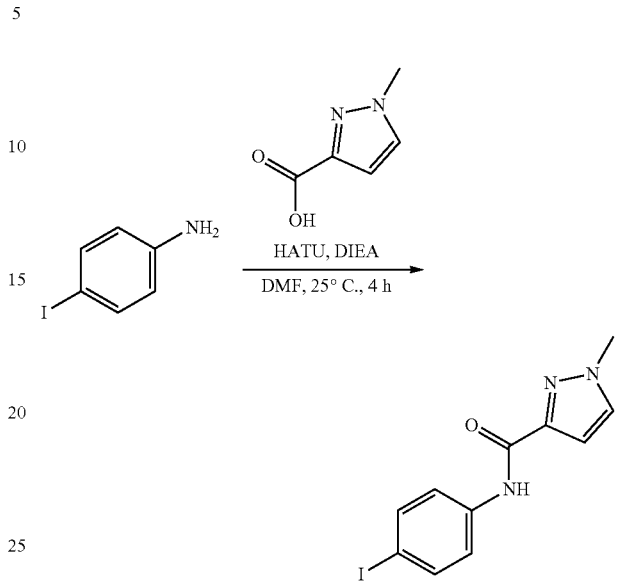

To a mixture of 4-iodoaniline (500 mg, 2.28 mmol, 1.00 eq), 1-methylpyrazole-3-carboxylic acid (302.30 mg, 2.40 μmmol, 1.05 eq), 2-(3H-[1,2,3]triazolo[4,5-b]pyridin-3-yl)-1,1,3,3-tetramethyluronium hexafluorophosphate(V) (1.30 g, 3.42 mmol, 1.50 eq) and N-ethyl-N-isopropylpropan-2-amine (885 mg, 6.85 mmol, 1.19 mL, 3.00 eq) in N,N-dimethylformamide (10 mL) was degassed and purged with nitrogen for 3 times, and then the mixture was stirred at 25° C. for 4 hr under nitrogen atmosphere. The reaction mixture was concentrated under reduced pressure to give a residue. The residue was purified by flash silica gel chromatography (ISCO®; 12 g SepaFlash® Silica Flash Column, Eluent of 0~100% Ethyl acetate/Petroleum ether gradient @ 40 mL/min). The desired fraction was collected and lyophilized to give N-(4-iodophenyl)-1-methyl-pyrazole-3-carboxamide (710 mg, 2.15 mmol, 94% yield, 99% purity) as a light yellow solid. N-[4-[2-chloro-3-(2,6-dioxo-3-piperidyl)phenyl]phenyl]-1-methyl-pyrazole-3-carboxamide was prepared from N-(4-iodophenyl)-1-methyl-pyrazole-3-carboxamide and 3-[2-chloro-3-(4,4,5,5-tetramethyl-1,3,2-dioxaborolan-2-yl)phenyl]piperidine-2,6-dione according to General Scheme 1.

MS (ESI) m/z 423.2 [M+H]$^+$

Example 68. Synthesis of 1-(2'-chloro-3'-(2,6-dioxopiperidin-3-yl)-[1,1'-biphenyl]-4-yl)piperidine-2,6-dione (Compound 205)

4-bromophenyl)piperidine-2,6-dione (2.24 g, 8.29 mmol, 79% yield) was obtained as a white solid. 1-(2'-chloro-3'-(2,6-dioxopiperidin-3-yl)-[1,1'-biphenyl]-4-yl)piperidine-2,6-dione was prepared from 1-(4-bromophenyl)piperidine-2,6-dione and 3-(2-chloro-3-(4,4,5,5-tetramethyl-1,3,2-dioxaborolan-2-yl)phenyl)piperidine-2,6-dione according to General Scheme 1.

MS (ESI) m/z 411.1 [M+H]$^+$

Example 69. Synthesis of 3-(2-chloro-4'-(2-oxo-1,3-oxazinan-3-yl)-[1,1'-biphenyl]-3-yl)piperidine-2,6-dione (Compound 204)

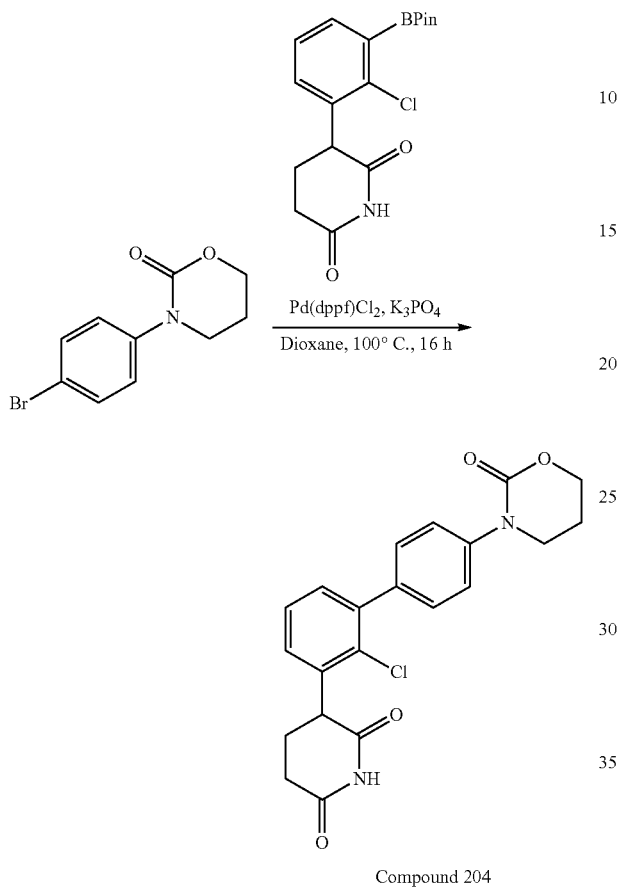

Compound 204

A mixture of 3-(4-bromophenyl)-1,3-oxazinan-2-one (100 mg, 390 μmol, 1.00 eq), 3-(2-chloro-3-(4,4,5,5-tetramethyl-1,3,2-dioxaborolan-2-yl)phenyl)piperidine-2,6-dione (170 mg, 390 μmol, 80% purity, 1.00 eq), potassium phosphate (249 mg, 1.17 mmol, 3.00 eq) and [1,1-bis(diphenylphosphino)ferrocene] dichloropalladium(II) (28.6 mg, 39.1 μmol, 0.100 eq) in dioxane (5 mL) was degassed and purged with nitrogen for 3 times, and then the mixture was stirred at 100° C. for 16 h. The mixture was cooled to 25° C., filtered and concentrated to give a residue. The residue was purified by flash silica gel chromatography (ISCO®; 20 g SepaFlash® Silica Flash Column, Eluent of 0~100% ethyl acetate/petroleum ether gradient @ 30 mL/min) followed by Prep-HPLC (column: Phenomenex luna C18 150×25 mm×10 μm; mobile phase: [water (formic acid)-acetonitrile]; B %: 30%-50%, 10 min) and lyophilized to give 3-(2-chloro-4'-(2-oxo-1,3-oxazinan-3-yl)-[1,1'-biphenyl]-3-yl)piperidine-2,6-dione (31.2 mg, 77.4 μmol, 20% yield) as a white solid.

$^1$H NMR (400 MHz, DMSO-d$_6$) δ=10.92 (s, 1H), 7.49-7.29 (m, 7H), 4.45-4.28 (m, 3H), 3.73 (t, J=6.0 Hz, 2H), 2.87-2.72 (m, 1H), 2.56 (d, J=3.6 Hz, 1H), 2.40-2.29 (m, 1H), 2.19-2.01 (m, 3H)

MS (ESI) m/z 399.1 [M+H]$^+$

Example 70. Synthesis of 3-(2-chloro-4'-((2-oxopyrrolidin-1-yl)methyl)-[1,1'-biphenyl]-3-yl)piperidine-2,6-dione (Compound 206)

3-(2-chloro-4'-((2-oxopyrrolidin-1-yl)methyl)-[1,1'-biphenyl]-3-yl)piperidine-2,6-dione was prepared from 1-(4-bromobenzyl)pyrrolidin-2-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-d$_6$) δ=10.92 (s, 1H), 7.44-7.33 (m, 4H), 7.33-7.26 (m, 3H), 4.43 (s, 2H), 4.34 (dd, J=5.2, 12.4 Hz, 1H), 3.33-3.29 (m, 2H), 2.79 (ddd, J=5.2, 12.4, 17.2 Hz, 1H), 2.59-2.53 (m, 1H), 2.40-2.26 (m, 3H), 2.09-2.01 (m, 1H), 1.96-1.87 (m, 2H); MS (ESI) m/z 397.3 [M+H]$^+$

Example 71. Synthesis of (S)-3-(2-chloro-4'-(2-oxopyridin-1(2H)-yl)-[1,1'-biphenyl]-3-yl)piperidine-2,6-dione (compound 211) and (R)-3-(2-chloro-4'-(2-oxopyridin-1(2H)-yl)-[1,1'-biphenyl]-3-yl)piperidine-2,6-dione (compound 210)

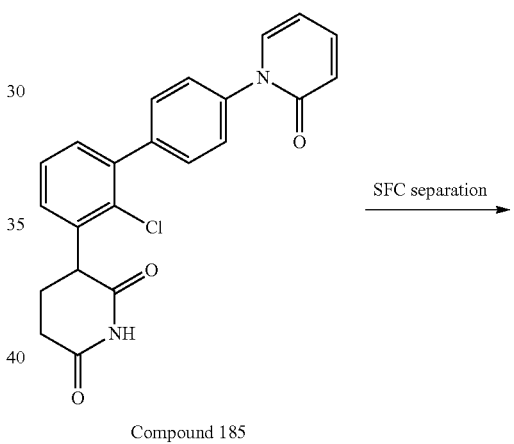

Compound 185

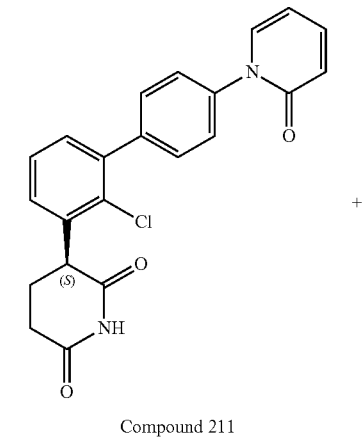

Compound 211

Example 72. Synthesis of (S)-3-(2-chloro-4'-((1-methyl-1H-pyrazol-3-yl)methoxy)-[1,1'-biphenyl]-3-yl)piperidine-2,6-dione (Compound 209)

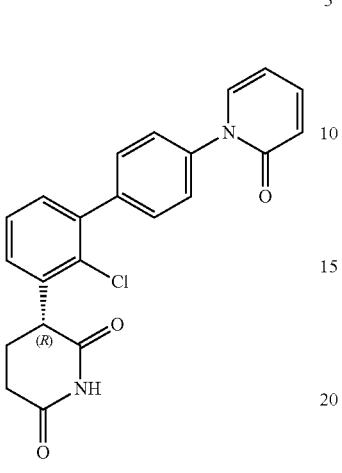

Compound 210

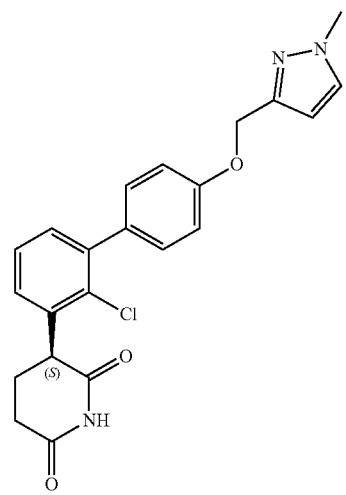

The 3-(2-chloro-4'-(2-oxopyridin-1(2H)-yl)-[1,1'-biphenyl]-3-yl)piperidine-2,6-dione (150 mg, 383 μmol, 1.00 eq) was separated by SFC (column: DAICEL CHIRALPAK IC (250 mm×30 mm, 10 μm); mobile phase: [Isopropyl alcohol-acetonitrile]; B %: 75%-75%, 4.7 min). The desired fraction was concentrated under reduced pressure to give two crude product. Crude product 1 was purified by Prep-HPLC (column: Welch Xtimate C18 150×25 mm×5 m; mobile phase: [water (formic acid)-acetonitrile]; B %: 25%-55%, 8 min) and lyophilized to afford (S)-3-(2-chloro-4'-(2-oxopyridin-1(2H)-yl)-[1,1'-biphenyl]-3-yl)piperidine-2,6-dione (37.0 mg, 93.2 μmol, 24% yield) as a white solid. Crude product 2 was purified by Prep-HPLC (column: YMC-Actus Triart C18 150×30 mm×7 m; mobile phase: [water (formic acid)-acetonitrile]; B %: 30%-60%, 10 min) and lyophilized to afford (R)-3-(2-chloro-4'-(2-oxopyridin-1(2H)-yl)-[1,1'-biphenyl]-3-yl)piperidine-2,6-dione (44.8 mg, 113 μmol, 30% yield) as a white solid.

Compound 211:

$^1$H NMR (400 MHz, DMSO-d$_6$) δ=10.94 (s, 1H), 7.73 (dd, J=1.6, 6.8 Hz, 1H), 7.59-7.48 (m, 5H), 7.47-7.33 (m, 3H), 6.51 (d, J=9.2 Hz, 1H), 6.34 (t, J=6.4 Hz, 1H), 4.38 (dd, J=5.2, 12.4 Hz, 1H), 2.88-2.73 (m, 1H), 2.61-2.53 (m, 1H), 2.38-2.28 (m, 1H), 2.11-2.02 (m, 1H).

MS (ESI) m/z 393.3 [M+H]$^+$

Compound 210:

$^1$H NMR (400 MHz, DMSO-d$_6$) δ=10.94 (s, 1H), 7.77-7.69 (m, 1H), 7.58-7.48 (m, 5H), 7.47-7.33 (m, 3H), 6.51 (d, J=9.2 Hz, 1H), 6.34 (t, J=6.4 Hz, 1H), 4.37 (dd, J=5.2, 12.4 Hz, 1H), 2.89-2.73 (m, 1H), 2.57 (d, J=3.6 Hz, 1H), 2.38-2.28 (m, 1H), 2.14-2.00 (m, 1H) MS (ESI) m/z 393.3 [M+H]$^+$

The 3-(2-chloro-4'-((1-methyl-1H-pyrazol-3-yl)methoxy)-[1,1'-biphenyl]-3-yl)piperidine-2,6-dione (150 mg, 366 μmol, 1.00 eq) was separated by SFC (column: DAICEL CHIRALPAK IC(250 mm×30 mm, 10 m); mobile phase: [propan-2-ol/acetonitrile]; B %: 50%-50%, 5.2 min). The desired fraction was concentrated under reduced pressure to give two crude product. Crude product 1 was purified by Prep-HPLC (column: YMC-Actus Triart C18 150×30 mm×7 m; mobile phase: [water (formic acid)-acetonitrile]; B %: 40%-70%, 10 min) and lyophilized to afford (S)-3-(2-chloro-4'-((1-methyl-1H-pyrazol-3-yl)methoxy)-[1,1'-biphenyl]-3-yl)piperidine-2,6-dione (43.0 mg, 104 μmol, 28% yield) as an off-white solid.

$^1$H NMR (400 MHz, DMSO-d$_6$) δ=10.92 (s, 1H), 7.67 (d, J=2.0 Hz, 1H), 7.40-7.26 (m, 5H), 7.13-7.04 (m, 2H), 6.33 (d, J=2.0 Hz, 1H), 5.04 (s, 2H), 4.33 (dd, J=4.8, 12.0 Hz, 1H), 3.84 (s, 3H), 2.85-2.72 (m, 1H), 2.58-2.52 (m, 1H), 2.40-2.26 (m, 1H), 2.08-1.99 (m, 1H); MS (ESI) m/z 410.2 [M+H]$^+$

Example 73. Synthesis of (R)-3-(2-chloro-4'-((1-methyl-1H-pyrazol-3-yl)methoxy)-[1,1'-biphenyl]-3-yl)piperidine-2,6-dione (Compound 213)

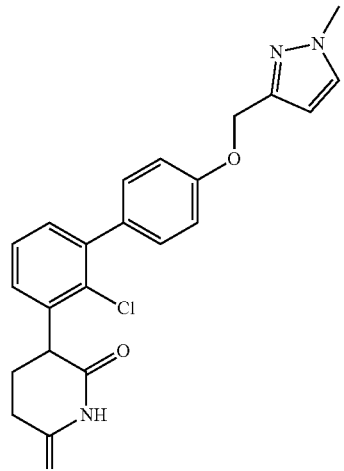

Compound 154

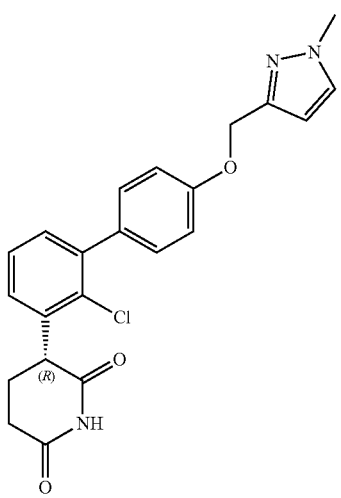

Compound 213

The 3-(2-chloro-4'-((1-methyl-1H-pyrazol-3-yl)methoxy)-[1,1'-biphenyl]-3-yl)piperidine-2,6-dione (150 mg, 366 μmol, 1.00 eq) was separated by SFC (column: DAICEL CHIRALPAK IC(250 mm×30 mm, 10 m); mobile phase: [propan-2-ol/acetonitrile]; B %: 60%-60%, 3.9 min) to give two crude products. Crude product 2 was purified by Prep-HPLC (column: YMC-Actus Triart C18 150×30 mm×7 m; mobile phase: [water (formic acid)-acetonitrile]; B %: 40%-70%, 10 min) and lyophilized to afford (R)-3-(2-chloro-4'-((1-methyl-1H-pyrazol-3-yl)methoxy)-[1,1'-biphenyl]-3-yl)piperidine-2,6-dione (62.6 mg, 151 μmol, 41% yield) as white solid.

$^1$H NMR (400 MHz, DMSO-$d_6$) δ=10.92 (s, 1H), 7.67 (d, J=2.0 Hz, 1H), 7.40-7.27 (m, 5H), 7.13-7.06 (m, 2H), 6.33 (d, J=2.0 Hz, 1H), 5.04 (s, 2H), 4.33 (dd, J=4.8, 12.0 Hz, 1H), 3.84 (s, 3H), 2.85-2.73 (m, 1H), 2.58-2.52 (m, 1H), 2.40-2.26 (m, 1H), 2.10-1.99 (m, 1H); MS (ESI) m/z 409.9 [M+H]$^+$

Example 74. Synthesis of 3-(2-chloro-4'-((R)-4-methyl-2-oxooxazolidin-3-yl)-[1,1'-biphenyl]-3-yl)piperidine-2,6-dione (Compound 217)

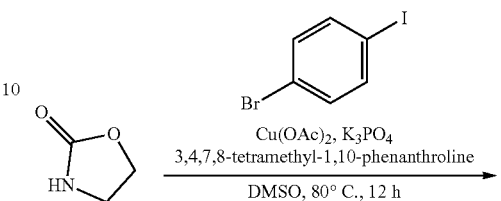

A mixture of 1-bromo-4-iodobenzene (923 mg, 3.26 mmol, 1.10 eq), (R)-4-methyloxazolidin-2-one (300 mg, 2.97 mmol, 1.00 eq), potassium phosphate (1.26 g, 5.93 mmol, 2.00 eq), copper (II) acetate (53.9 mg, 297 μmol, 0.100 eq) and 3,4,7,8-tetramethyl-1,10-phenanthroline (105 mg, 445 mol, 0.150 eq) in dimethyl sulfoxide (5 mL) was degassed and purged with nitrogen for three times, and then the mixture was stirred at 80° C. for 16 h under nitrogen atmosphere. The reaction mixture was concentrated under reduced pressure to remove dimethyl sulfoxide. The residue was diluted with water (20 mL) and extracted with ethyl acetate (2×30 mL). The combined organic layers were washed with brine (20 mL), dried over anhydrous sodium sulfate, filtered and concentrated under reduced pressure to give a residue. The residue was purified by flash silica gel chromatography (ISCO®; 10 g SepaFlash® Silica Flash Column, Eluent of 0~35% Ethyl acetate/Petroleum ether gradient @ 35 mL/min) to afford (R)-3-(4-bromophenyl)-4-methyloxazolidin-2-one (1.89 g, 4.54 mmol, 96% yield) as a light yellow solid.

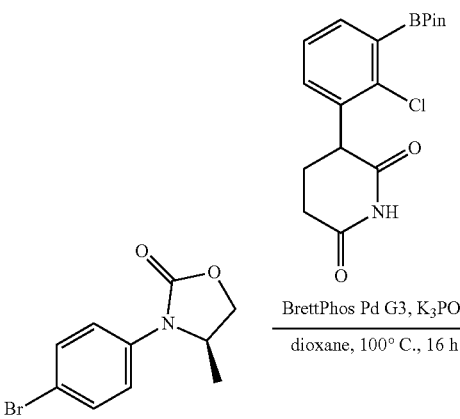

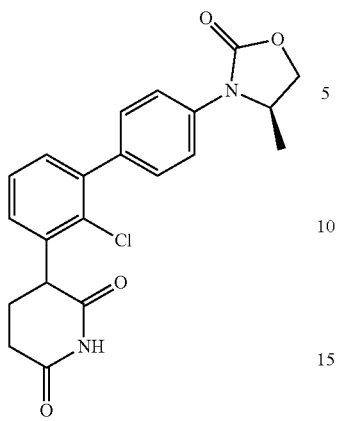

Compound 217

3-(2-chloro-4'-((R)-4-methyl-2-oxooxazolidin-3-yl)-[1,1'-biphenyl]-3-yl)piperidine-2,6-dione was prepared from (R)-3-(4-bromophenyl)-4-methyloxazolidin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-d$_6$) δ ppm 11.09-10.67 (m, 1H), 7.59 (d, J=8.4 Hz, 2H), 7.45 (d, J=8.8 Hz, 2H), 7.43-7.30 (m, 3H), 4.77-4.67 (m, 1H), 4.58 (t, J=8.4 Hz, 1H), 4.35 (dd, J=12.0, 8.8 Hz, 1H), 4.06 (dd, J=8.4, 5.6 Hz, 1H), 2.85-2.75 (m, 1H), 2.60-2.53 (m, 1H), 2.39-2.28 (m, 1H), 2.09-1.99 (m, 1H), 1.27 (d, J=6.4 Hz, 3H); MS (ESI) m/z 399.1 [M+H]$^+$ Example 75. synthesis of 3-(2-chloro-4'-((S)-4-methyl-2-oxooxazolidin-3-yl)-[1,1'-biphenyl]-3-yl)piperidine-2,6-dione (Compound 216)

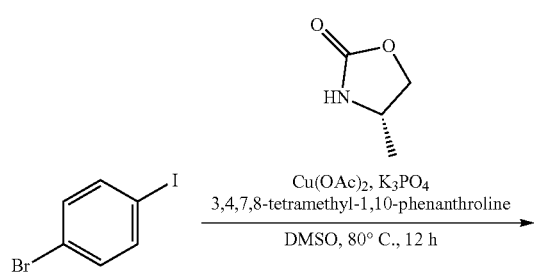

(S)-3-(4-bromophenyl)-4-methyloxazolidin-2-one was prepared from a 1-bromo-4-iodobenzene and (S)-4-methyl-oxazolidin-2-one using an analogous method to example 74.

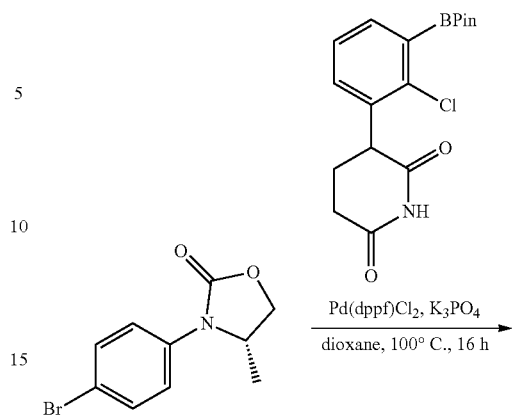

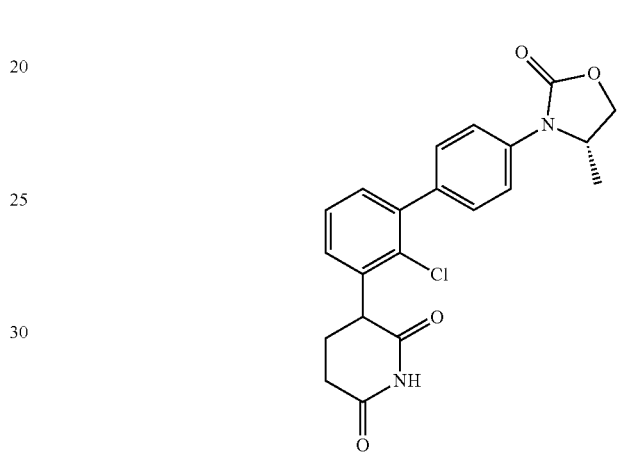

Compound 216

3-(2-chloro-4'-((S)-4-methyl-2-oxooxazolidin-3-yl)-[1,1'-biphenyl]-3-yl)piperidine-2,6-dione was prepared from (S)-3-(4-bromophenyl)-4-methyloxazolidin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-d$_6$) δ=10.92 (s, 1H), 7.62-7.55 (m, 2H), 7.48-7.43 (m, 2H), 7.42-7.30 (m, 3H), 4.77-4.65 (m, 1H), 4.58 (t, J=8.4 Hz, 1H), 4.35 (dd, J=12.4, 5.2 Hz, 1H), 4.06 (dd, J=8.4, 5.2 Hz, 1H), 2.85-2.73 (m, 1H), 2.60-2.52 (m, 1H), 2.38-2.29 (m, 1H), 2.10-2.00 (m, 1H), 1.27 (d, J=6.0 Hz, 3H); MS (ESI) m/z 399.1 [M+H]$^+$

Example 76. Synthesis of 3-(2-chloro-4'-(pyridin-2-ylamino)-[1,1'-biphenyl]-3-yl)piperidine-2,6-dione (Compound 215)

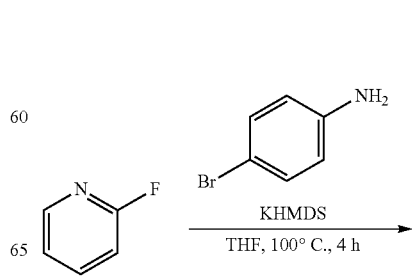

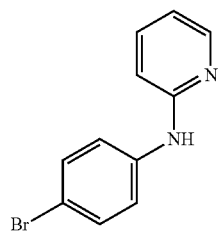

A solution of 2-fluoropyridine (1.00 g, 10.3 mmol, 885 μL, 1.00 eq) and 4-bromoaniline (2.66 g, 15.5 mmol, 1.50 eq) in tetrahydrofuran (10 mL) was added potassium bis(trimethylsilyl)amide (1.00 M, 15.5 mL, 1.50 eq), and then the mixture was stirred at 100° C. for 4 h under nitrogen atmosphere. The reaction mixture was filtered, washed with tetrahydrofuran (3×10 mL) and concentrated under reduced pressure to give a residue. The residue was purified by flash silica gel chromatography (ISCO®; 20 g SepaFlash® Silica Flash Column, Eluent of 0~60% Ethyl acetate/Petroleum ether gradient @ 18 mL/min) to give N-(4-bromophenyl)pyridin-2-amine (1.96 g, 7.16 mmol, 70% yield) as a brown solid. 3-(2-chloro-4'-(pyridin-2-ylamino)-[1,1'-biphenyl]-3-yl)piperidine-2,6-dione was prepared from N-(4-bromophenyl)pyridin-2-amine and 3-[2-chloro-3-(4,4,5,5-tetramethyl-1,3,2-dioxaborolan-2-yl)phenyl]piperidine-2,6-dione according to General Scheme 1.

MS (ESI) m/z 392.3 [M+H]$^+$

Example 77. Synthesis of 3-(2-chloro-4'-(3-fluoro-2-oxopyridin-1(2H)-yl)-[1,1'-biphenyl]-3-yl)piperidine-2,6-dione (Compound 247)

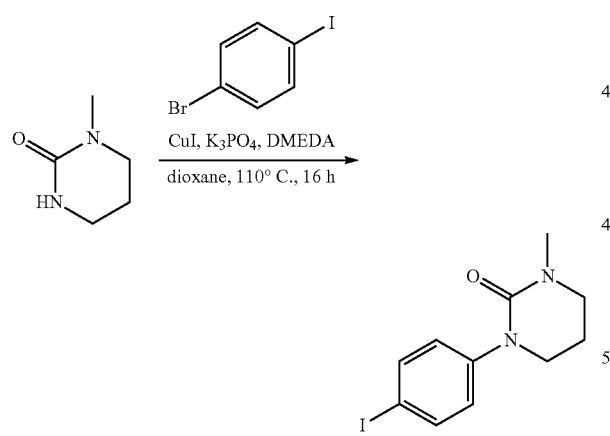

A mixture of 1-methyltetrahydropyrimidin-2(1H)-one (500 mg, 4.38 mmol, 1.00 eq), 1-bromo-4-iodobenzene (1.49 g, 5.26 mmol, 1.20 eq), copper iodide (167 mg, 876 μmol, 0.200 eq), potassium phosphate (1.86 g, 8.76 mmol, 2.00 eq) and N$^1$,N$^1$-dimethyl,ethane-1,2-diamine (154 mg, 1.75 mmol, 189 μL, 0.400 eq) in dioxane (7 mL) was degassed and purged with nitrogen for 3 times, and then the mixture was stirred at 110° C. for 16 h under nitrogen atmosphere. The reaction mixture was cooled to 25° C., then diluted with water (70 mL) and extracted with ethyl acetate (5×50 mL). The combined organic layers were washed with brine (50 mL), dried over anhydrous sodium sulfate, filtered and concentrated under reduced pressure to give a residue.

The residue was purified by flash silica gel chromatography (ISCO®; 10 g SepaFlash® Silica Flash Column, Eluent of 0~60% Ethyl acetate/Petroleum ether gradient @ 35 mL/min) to afford 1-(4-iodophenyl)-3-methyltetrahydropyrimidin-2(1H)-one (721 mg, 2.14 mmol, 49% yield) as a white solid. $^1$H NMR (400 MHz, CDCl$_3$) δ=7.65-7.59 (m, 1H), 7.45-7.40 (m, 1H), 7.20-7.13 (m, 1H), 7.08-7.02 (m, 1H), 3.72-3.64 (m, 2H), 3.38 (t, J=6.0 Hz, 2H), 3.00 (s, 3H), 2.17-2.08 (m, 2H) MS (ESI) m/z 317.0 [M+H]$^+$

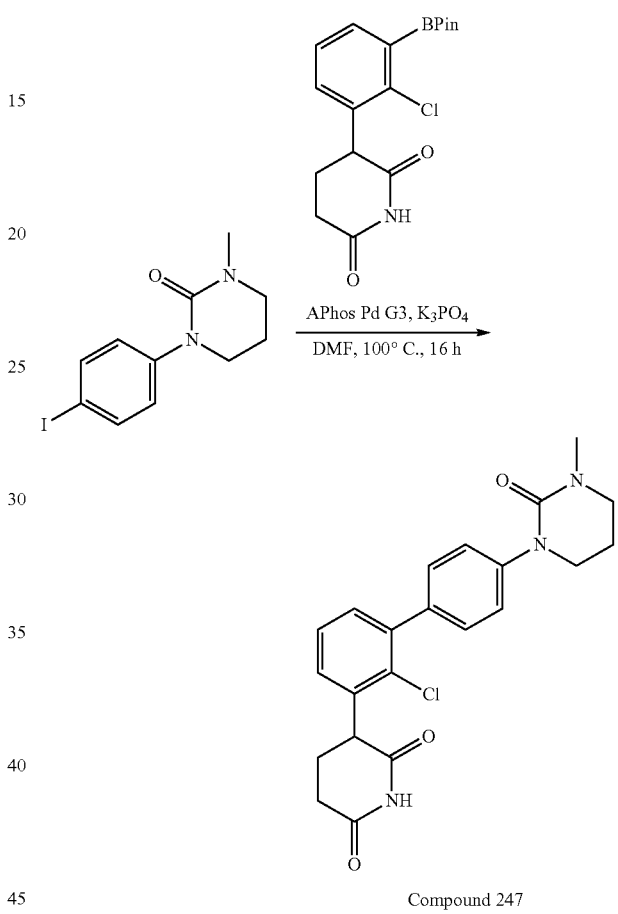

Compound 247

A mixture of 1-(4-iodophenyl)-3-methyltetrahydropyrimidin-2(1H)-one (200 mg, 633 μmol, 1.00 eq), 3-(2-chloro-3-(4,4,5,5-tetramethyl-1,3,2-dioxaborolan-2-yl)phenyl)piperidine-2,6-dione (309 mg, 759 μmol, 1.20 eq), potassium phosphate (403 mg, 1.90 mmol, 3.00 eq) and methanesulfonato[[4-(N,N-dimethylamino)phenyl]di-tert-butylphosphino](2'-amino-1,1'-biphenyl-2-yl) palladium(II) (80.4 mg, 127 μmol, 0.200 eq) in dimethylformamide (5 mL) was degassed and purged with nitrogen for three times, and then the mixture was stirred at 100° C. for 16 h under nitrogen atmosphere. The reaction mixture was cooled to 25° C., then diluted with water (20 mL) and extracted with ethyl acetate (4×50 mL). The combined organic layers were dried over anhydrous sodium sulfate, filtered and concentrated under reduced pressure to give a residue. The residue was purified by flash silica gel chromatography (ISCO®; 10 g SepaFlash® Silica Flash Column, Eluent of 0~100% Ethyl acetate/Petroleum ether gradient @ 40 mL/min) followed by Prep-HPLC (column: Phenomenex luna C18 150×25 mm×10 m; mobile phase: [water-acetonitrile]; B %: 25%-

55%, 10 min) to afford 3-(2-chloro-4'-(3-methyl-2-oxotetrahydropyrimidin-1(2H)-yl)-[1,1'-biphenyl]-3-yl)piperidine-2,6-dione (67.3 mg, 162 μmol, 22% yield) as a white solid.

$^1$H NMR (400 MHz, DMSO-$d_6$) δ=10.92 (s, 1H), 7.42-7.29 (m, 7H), 4.34 (dd, J=12.0, 5.2 Hz, 1H), 3.70 (t, J=5.6 Hz, 2H), 3.38-3.33 (m, 2H), 2.87 (s, 3H), 2.84-2.73 (m, 1H), 2.54-2.51 (m, 1H), 2.32 (d, J=4.0 Hz, 1H), 2.05 (td, J=11.6, 5.6 Hz, 3H)

Example 78. Synthesis of 3-(2-chloro-4'-(1-methyl-2-oxo-1,2-dihydropyridin-3-yl)-[1,1'-biphenyl]-3-yl)piperidine-2,6-dione (Compound 225)

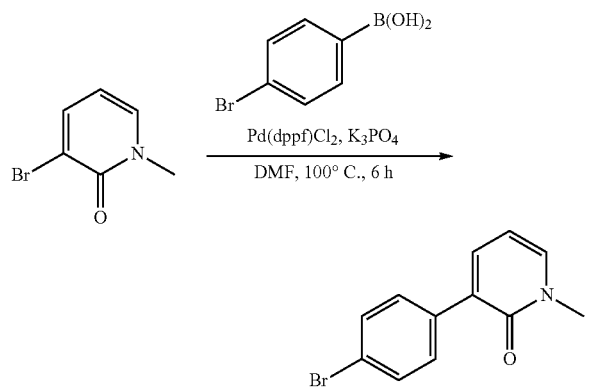

A mixture of 3-bromo-1-methyl-pyridin-2-one (500 mg, 2.66 mmol, 1.00 eq), (4-bromophenyl)boronic acid (641 mg, 3.19 mmol, 1.20 eq), potassium phosphate (1.69 g, 7.98 mmol, 3.00 eq) and [1,1-Bis(diphenylphosphino)ferrocene]dichloropalladium(II) (195 mg, 266 μmol, 0.100 eq) in N,N-dimethylformamide (20 mL) was degassed and purged with nitrogen for three times, and then the mixture was stirred at 100° C. for 6 h under nitrogen atmosphere. The reaction mixture was cooled to 25° C., and then filtered through a plug of Celite. The reaction mixture was concentrated under reduced pressure to remove solvent. The residue was purified by flash silica gel chromatography (ISCO®; 10 g SepaFlash® Silica Flash Column, Eluent of 0~60% Ethyl acetate/Petroleum ether gradient @ 35 mL/min) to afford 3-(4-bromophenyl)-1-methylpyridin-2(1H)-one (320 mg, 848 μmol, 32% yield) as a white solid.

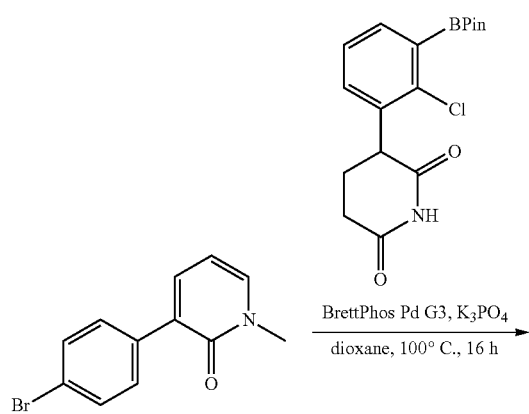

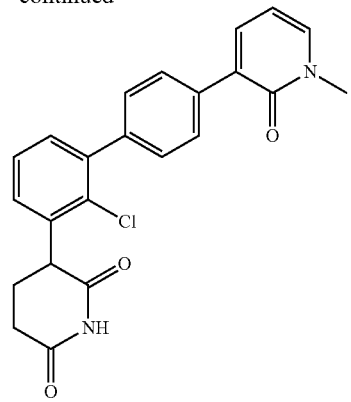

Compound 225

3-(2-chloro-4'-(1-methyl-2-oxo-1,2-dihydropyridin-3-yl)-[1,1'-biphenyl]-3-yl)piperidine-2,6-dione was prepared from 3-(4-bromophenyl)-1-methyl-pyridin-2(1H)-one and 3-[2-chloro-3-(4,4,5,5-tetramethyl-1,3,2-dioxaborolan-2-yl)phenyl]piperidine-2,6-dione according to General Scheme 1.

1H NMR (400 MHz, DMSO-$d_6$) δ=10.93 (s, 1H), 7.87-7.62 (m, 4H), 7.47-7.27 (m, 5H), 6.35 (t, J=6.8 Hz, 1H), 4.36 (dd, J=12.0, 5.2 Hz, 1H), 3.53 (s, 3H), 2.88-2.74 (m, 1H), 2.55-2.50 (m, 1H), 2.44-2.25 (m, 1H), 2.12-2.00 (m, 1H); MS (ESI) m/z 407.3 [M+H]$^+$

Example 79. Synthesis of 3-(2-chloro-4'-(2-oxo-3-(trifluoromethyl)pyridin-1(2H)-yl)-[1,1'-biphenyl]-3-yl)piperidine-2,6-dione (Compound 226)

A mixture of 3-(trifluoromethyl)-1H-pyridin-2-one (100 mg, 613 μmol, 1.00 eq), (4-bromophenyl)boronic acid (148 mg, 736 μmol, 1.20 eq), copper(II) acetate (111 mg, 613 μmol, 1.00 eq) and triethylamine (186 mg, 1.84 mmol, 256 μL, 3.00 eq) in 1,2-dichloroethane (2 mL) was degassed and purged with oxygen for three times, and then the mixture was stirred at 25° C. for 4 h under oxygen atmosphere. The reaction mixture was cooled to 25° C., and then filtered through a plug of Celite. The reaction mixture was filtered and concentrated under reduced pressure to give a residue. The residue was purified by flash silica gel chromatography (ISCO®; 10 g SepaFlash® Silica Flash Column, Eluent of 0~25% Ethyl acetate/Petroleum ether gradient @35 mL/min) to afford 1-(4-bromophenyl)-3-(trifluoromethyl)pyridin-2(1H)-one (95.0 mg, 293 mol, 48% yield) as a white solid.

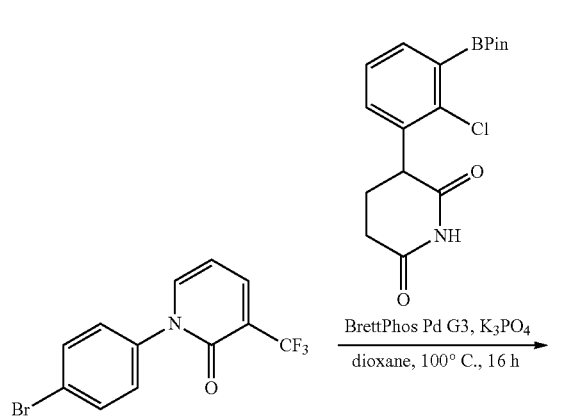

Compound 226

3-(2-chloro-4'-(2-oxo-3-(trifluoromethyl)pyridin-1(2H)-yl)-[1,1'-biphenyl]-3-yl)piperidine-2,6-dione was prepared from 1-(4-bromophenyl)-3-(trifluoromethyl)pyridin-2(1H)-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-d$_6$) δ=10.93 (s, 1H), 8.09 (dd, J=12.8, 7.2 Hz, 2H), 7.63-7.53 (m, 4H), 7.48-7.34 (m, 3H), 6.49 (t, J=7.2 Hz, 1H), 4.38 (dd, J=12.4, 5.2 Hz, 1H), 2.85-2.76 (m, 1H), 2.62-2.50 (m, 1H), 2.45-2.30 (m, 1H), 2.11-2.02 (m, 1H) MS (ESI) m/z 461.1 [M+H]$^+$

Example 80. Synthesis of 3-(2-chloro-4'-(3,3-difluoropyrrolidine-1-carbonyl)-[1,1'-biphenyl]-3-yl)piperidine-2,6-dione (Compound 221)

To a solution of 3,3-difluoropyrrolidine (1.00 g, 6.97 mmol, 1.00 eq, HCl) in dichloromethane (20 mL) was added triethylamine (2.82 g, 27.9 mmol, 3.88 mL, 4.00 eq) at 0° C. The reaction mixture was stirred at 0° C. for 10 minutes. Then 4-bromobenzoyl chloride (1.83 g, 8.36 mmol, 1.20 eq) was added dropwise at 0° C. After addition, the resulting mixture was stirred at 25° C. for 2 h. The reaction mixture was concentrated under reduced pressure to remove solvent. The residue was diluted with water (50 mL) and extracted with ethyl acetate (3×50 mL). The combined organic layers were washed with brine (2×30 mL), dried over anhydrous sodium sulfate, filtered and concentrated under reduced pressure to give a residue. The residue was purified by flash silica gel chromatography (ISCO®; 20 g SepaFlash® Silica Flash Column, Eluent of 0~30% Ethyl acetate/Petroleum ether gradient @ 35 mL/min) to afford (4-bromophenyl)-(3,3-difluoropyrrolidin-1-yl)methanone (1.80 g, 6.02 mmol, 86% yield) as a light yellow oil. 3-(2-chloro-4'-(3,3-difluoropyrrolidine-1-carbonyl)-[1,1'-biphenyl]-3-yl)piperidine-2,6-dione was prepared from (4-bromophenyl)-(3,3-difluoropyrrolidin-1-yl)methanone and 3-[2-chloro-3-(4,4,5,5-tetramethyl-1,3,2-dioxaborolan-2-yl)phenyl]piperidine-2,6-dione according to General Scheme 1.

MS (ESI) m/z 433.3 [M+H]$^+$

Example 81. Synthesis of 3-(2-chloro-4'-(piperidine-1-carbonyl)-[1,1'-biphenyl]-3-yl)piperidine-2,6-dione (Compound 223)

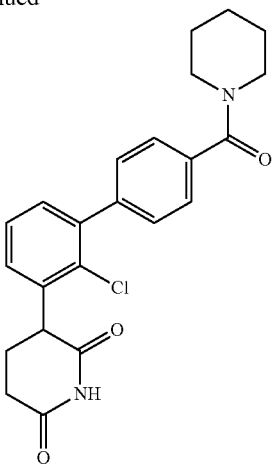

Compound 223

3-(2-chloro-4'-(piperidine-1-carbonyl)-[1,1'-biphenyl]-3-yl)piperidine-2,6-dione was prepared from (4-bromophenyl)(piperidin-1-yl)methanone and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-d$_6$) δ=10.92 (s, 1H), 7.48-7.36 (m, 7H), 4.36 (dd, J=12.0, 5.2 Hz, 1H), 3.63-3.57 (m, 2H), 2.79-2.56 (m, 1H), 2.53-2.51 (m, 1H), 2.51-2.49 (m, 2H), 2.35-2.33 (m, 1H), 2.07-2.05 (m, 1H), 1.64-1.53 (m, 6H).

$^1$H NMR (400 MHz, MeOD-d$_4$) δ=7.52-7.45 (m, 4H), 7.39-7.34 (m, 3H), 4.42-4.38 (m, 1H), 3.74-3.70 (m, 2H), 3.49-3.45 (m, 2H), 2.82-2.71 (m, 2H), 2.45-2.43 (m, 1H), 2.25-2.21 (m, 1H), 1.75-1.59 (m, 6H); MS (ESI) m/z 411.1 [M+H]$^+$

Example 82. Synthesis of 2'-chloro-3'-(2,6-dioxopiperidin-3-yl)-N-(isoxazol-5-yl)-[1,1'-biphenyl]-4-carboxamide (Compound 224)

were separated and the aqueous phase was extracted with dichloromethane (3×30 mL). The organic layer was dried over sodium sulfate, filtered and concentrated in vacuo. The residue was purified by flash silica gel chromatography (ISCO®; 20 g SepaFlash® Silica Flash Column, eluent of 0-50% ethyl acetate/petroleum ether gradient at 70 mL/min) to give 4-bromo-N-isoxazol-5-yl-benzamide (155 mg, 574 μmol, 63% yield) as a white solid. 2'-chloro-3'-(2,6-dioxopiperidin-3-yl)-N-(isoxazol-5-yl)-[1,1'-biphenyl]-4-carboxamide was prepared from 4-bromo-N-(isoxazol-5-yl)benzamide and 3-(2-chloro-3-(4,4,5,5-tetramethyl-1,3,2-dioxaborolan-2-yl)phenyl)piperidine-2,6-dione according to General Scheme 1.

MS (ESI) m/z 410.1 [M+H]$^+$

Example 83. Synthesis of 3-(2-chloro-4'-(1H-pyrrole-1-carbonyl)-[1,1'-biphenyl]-3-yl)piperidine-2,6-dione (Compound 222)

3-[2-chloro-3-[4-(pyrrole-1-carbonyl)phenyl]phenyl]piperidine-2,6-dione was prepared from 3-[2-chloro-3-(4,4,5,5-tetramethyl-1,3,2-dioxaborolan-2-yl)phenyl]piperidine-2,6-dione and (4-bromophenyl)-pyrrol-1-yl-methanone according to General Scheme 1.

MS (ESI) m/z 393.0 [M+H]$^+$

Example 84. Synthesis of N-(2'-chloro-3'-(2,6-dioxopiperidin-3-yl)-[1,1'-biphenyl]-4-yl)pyrrolidine-1-carboxamide (Compound 248)

N-[4-[2-chloro-3-(2,6-dioxo-3-piperidyl)phenyl]phenyl]pyrrolidine-1-carboxamide was prepared from N-(4-bromophenyl)pyrrolidine-1-carboxamide and 3-[2-chloro-3-(4,4,5,5-tetramethyl-1,3,2-dioxaborolan-2-yl)phenyl]piperidine-2,6-dione according to General Scheme 1. MS (ESI) m/z 412.2 [M+H]$^+$ Example 85. Synthesis of 3-(2-chloro-4'-(2-(2-oxopyridin-1(2H)-yl)propan-2-yl)-[1,1'-biphenyl]-3-yl)piperidine-2,6-dione (Compound 231)

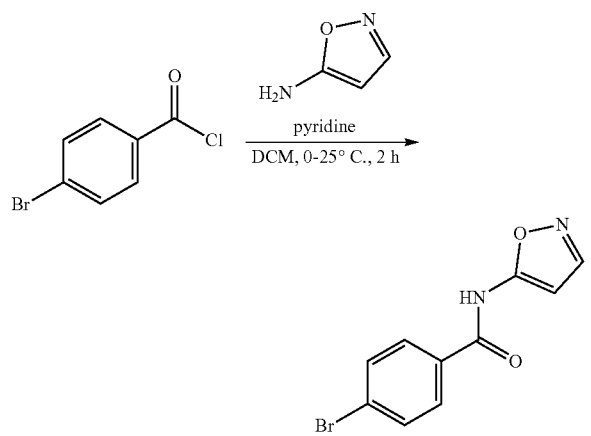

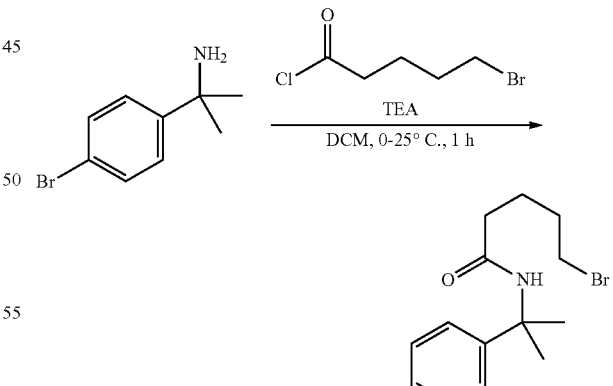

To a solution of pyridine (144 mg, 1.82 mmol, 2.00 eq) and isoxazol-5-amine (115 mg, 1.37 mmol, 1.50 eq) in dichloromethane (10 mL) was added 4-bromobenzoyl chloride (200 mg, 0.911 mmol, 1.00 eq) at 25° C. The mixture was stirred at 25° C. for 2 h. The mixture was diluted with dichloromethane (30 mL) and water (30 mL). The layers To a solution of 2-(4-bromophenyl)propan-2-amine (3.00 g, 14.0 mmol, 1.00 eq) and triethylamine (2.84 g, 28.0 mmol, 3.90 mL, 2.00 eq) in dichloromethane (30.0 mL) was added 5-bromopentanoyl chloride (3.35 g, 16.8 mmol, 2.25 mL, 1.20 eq) at 0° C. Then the mixture was stirred at 25° C. for 1 h. The mixture was diluted with water (50 mL) and extracted with ethyl acetate (3×30 mL). The combined organic layer was washed with brine (20 mL) and dried over anhydrous sodium sulfate, filtered and concentrated to give crude product. The crude product was purified by silica gel chromatography (petroleum ether/ethyl acetate=10/1 to 1/1) to give 5-bromo-N-(2-(4-bromophenyl)propan-2-yl)pentanamide (4.10 g, 10.8 mmol, 77% yield) as a white solid.

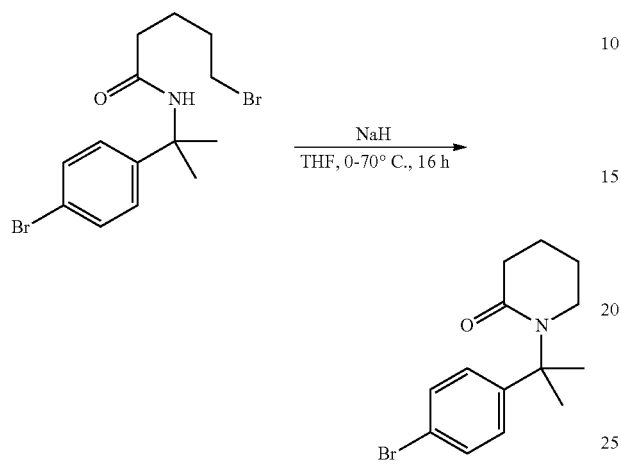

To a solution of 5-bromo-N-(2-(4-bromophenyl)propan-2-yl)pentanamide (4.10 g, 10.8 mmol, 1.00 eq) in tetrahydrofuran (50.0 mL) was added sodium hydride (521 mg, 13.0 mmol, 60% purity, 1.20 eq) in portions at 0° C. Then the mixture was stirred at 70° C. for 16 h. After the reaction was completed, the mixture was quenched by saturated ammonium chloride aqueous solution (15 mL) at 0° C. The mixture was concentrated to remove tetrahydrofuran and extracted with ethyl acetate (3×20 mL). The combined organic layer was washed with brine (30 mL), dried over anhydrous sodium sulfate and concentrated to give a residue. The crude product was purified by silica gel chromatography (petroleum ether/ethyl acetate=10/1 to 3/1) to give 1-(2-(4-bromophenyl)propan-2-yl)piperidin-2-one (2.40 g, 8.10 mmol, 74% yield) as a yellow solid.

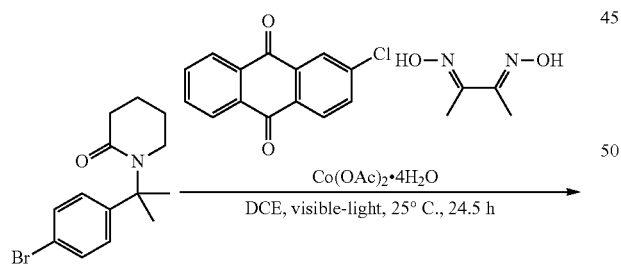

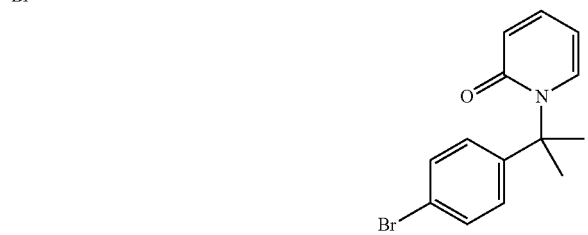

To a solution of 1-(2-(4-bromophenyl)propan-2-yl)piperidin-2-one (50.0 mg, 168 μmol, 1.00 eq) in dichloroethane (30.0 mL) was added cobalt(II) acetate tetrahydrate (2.99 mg, 16.9 μmol, 0.100 eq), (2E,3E)-butane-2,3-dione dioxime (9.80 mg, 84.4 μmol, 12.5 μL, 0.500 eq) and 2-chloroanthracene-9,10-dione (10.2 mg, 42.2 μmol, 0.250 eq) in portions. The mixture was sealed and stirred in dark for 30 min at 25° C. Then the mixture was irradiated with 20 W 420 nm LED (tube 2 cm away from light) and stirred at 25° C. for 24 h. The mixture was concentrated to give crude product, which was purified by reversed-phase column (column: spherical C18, 20-45 um, 100 Å, SW 120, mobile phase: [water (0.1% formic acid)-acetonitrile]) and lyophilized to give 1-(2-(4-bromophenyl)propan-2-yl)pyridin-2(1H)-one (140 mg, 479 μmol, 40% yield) as a yellow solid.

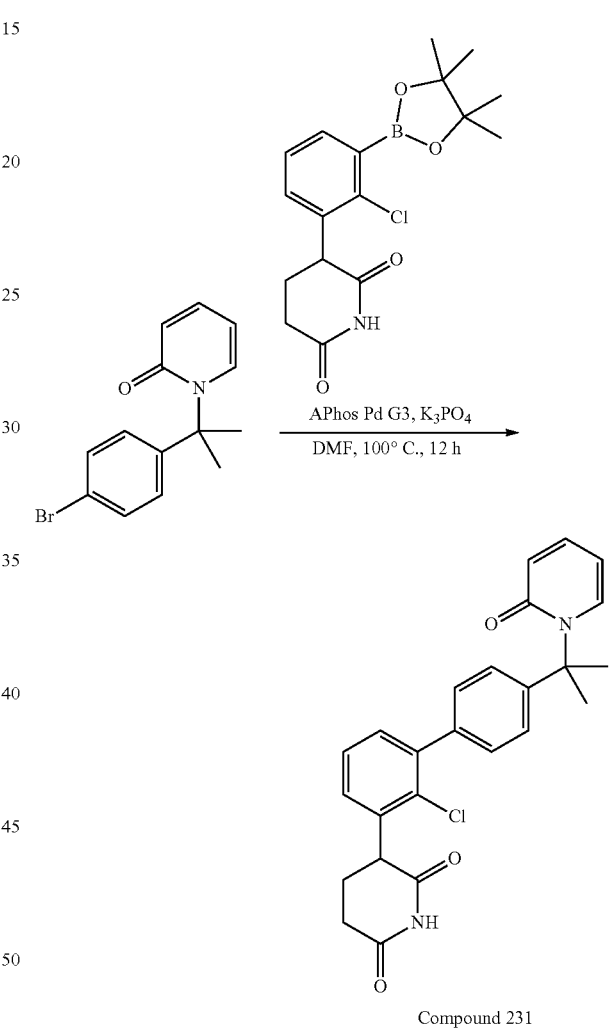

Compound 231

3-(2-chloro-4'-(2-(2-oxopyridin-1(2H)-yl)propan-2-yl)-[1,1'-biphenyl]-3-yl)piperidine-2,6-dione was prepared from 1-(2-(4-bromophenyl)propan-2-yl)pyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.91 (s, 1H), 7.99 (dd, J=1.6, 7.2 Hz, 1H), 7.45-7.40 (m, 1H), 7.39-7.26 (m, 5H), 7.16 (d, J=8.4 Hz, 2H), 6.34-6.17 (m, 2H), 4.34 (dd, J=5.2, 12.0 Hz, 1H), 2.87-2.73 (m, 1H), 2.55 (br d, J=3.6 Hz, 1H), 2.36-2.29 (m, 1H), 2.07-2.01 (m, 1H), 1.88 (s, 6H) MS (ESI) m/z 869.2 [2M+H]+

Example 86. Synthesis of 2'-chloro-3'-(2,6-dioxopiperidin-3-yl)-N-(isoxazol-3-yl)-[1,1'-biphenyl]-4-carboxamide (Compound 230)

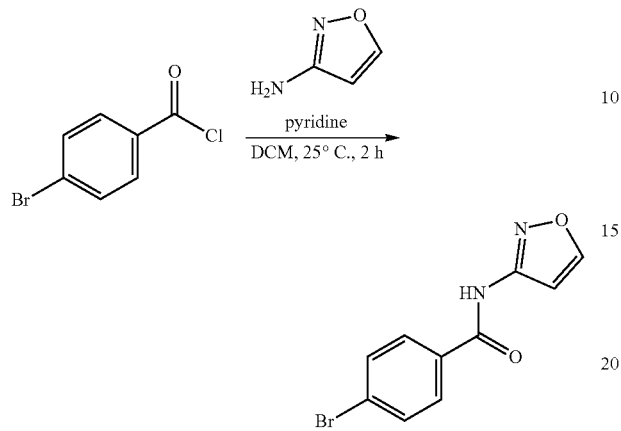

4-bromo-N-isoxazol-3-yl-benzamide was prepared from isoxazol-3-amine and 4-bromobenzoyl chloride analogously to Example 82. 2'-chloro-3'-(2,6-dioxopiperidin-3-yl)-N-(isoxazol-3-yl)-[1,1'-biphenyl]-4-carboxamide was prepared from 3-[2-chloro-3-(4,4,5,5-tetramethyl-1,3,2-dioxaborolan-2-yl)phenyl]piperidine-2,6-dione and 4-bromo-N-isoxazol-3-yl-benzamide according to General Scheme 1.

MS (ESI) m/z 410.2 [M+H]$^+$

Example 87. Synthesis of N-(2'-chloro-3'-(2,6-dioxopiperidin-3-yl)-[1,1'-biphenyl]-4-yl)isoxazole-3-carboxamide (Compound 229)

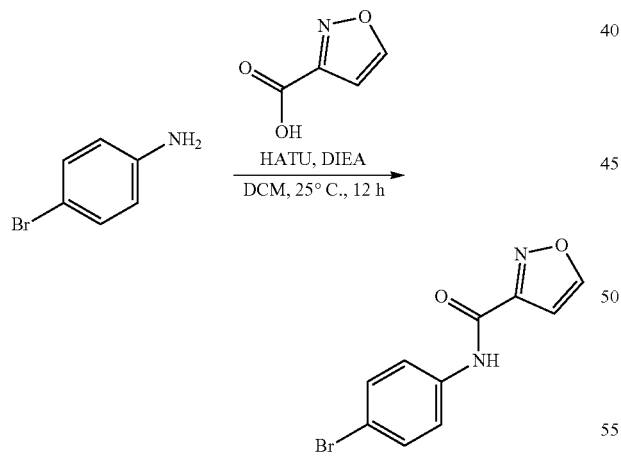

To a solution of isoxazole-3-carboxylic acid (316 mg, 2.79 mmol, 1.20 eq), O-(7-azabenzotriazol-1-yl)-N,N,N,N-tetramethyluroniumhexafluorophosphate (1.24 g, 3.26 mmol, 1.40 eq) and N,N-diisopropylethylamine (0.902 g, 6.98 mmol, 3.00 eq) in dichloromethane (8 mL) was added 4-bromoaniline (0.400 g, 2.33 mmol, 1.00 eq). The mixture was stirred at 25° C. for 12 h. The reaction mixture was diluted with dichloromethane (40 mL) and water (40 mL). The layers were separated and the aqueous phase was extracted with dichloromethane (2×40 mL). The organic layer was dried over sodium sulfate, filtered and concentrated in vacuo. The residue was purified by flash silica gel chromatography (ISCO®; 20 g SepaFlash® Silica Flash Column, eluent of 0-50% ethyl acetate/petroleum ether gradient at 40 mL/min) to give N-(4-bromophenyl)isoxazole-3-carboxamide (0.450 g, 1.67 mmol, 72% yield) as a yellow solid.

N-(2'-chloro-3'-(2,6-dioxopiperidin-3-yl)-[1,1'-biphenyl]-4-yl)isoxazole-3-carboxamide was prepared from N-(4-bromophenyl)isoxazole-3-carboxamide and 3-(2-chloro-3-(4,4,5,5-tetramethyl-1,3,2-dioxaborolan-2-yl)phenyl)piperidine-2,6-dione according to General Scheme 1.

MS (ESI) m/z 410.1 [M+H]$^+$

Example 88. Synthesis of N-(2'-chloro-3'-(2,6-dioxopiperidin-3-yl)-[1,1'-biphenyl]-4-yl)isoxazole-5-carboxamide (Compound 228)

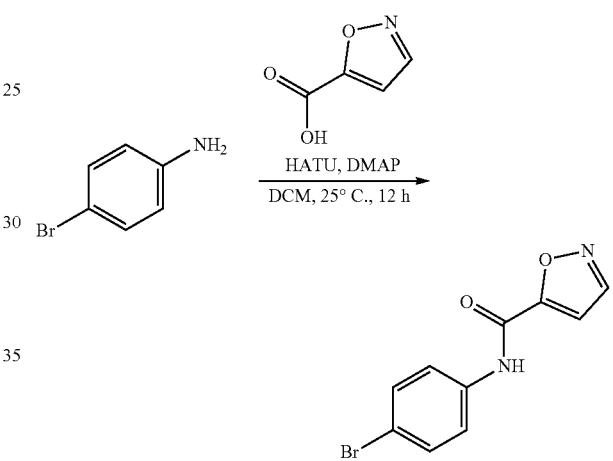

N-(4-bromophenyl)isoxazole-5-carboxamide was prepared from isoxazole-5-carboxylic acid and 4-bromoaniline analogously to Example 87.

N-(2'-chloro-3'-(2,6-dioxopiperidin-3-yl)-[1,1'-biphenyl]-4-yl)isoxazole-5-carboxamide was prepared from 3-[2-chloro-3-(4,4,5,5-tetramethyl-1,3,2-dioxaborolan-2-yl)phenyl]piperidine-2,6-dione and N-(4-bromophenyl)isoxazole-5-carboxamide according to General Scheme 1.

MS (ESI) m/z 410.0 [M+H]$^+$

Example 89. Synthesis of N-[4-[2-chloro-3-(2,6-dioxo-3-piperidyl)phenyl]phenyl]tetrahydrofuran-3-carboxamide (Compound 227)

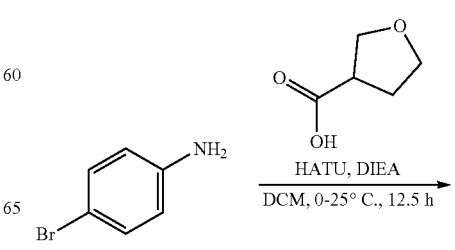

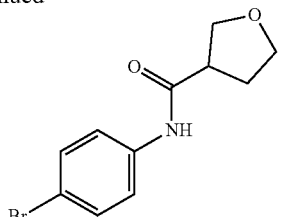

N-(4-bromophenyl)tetrahydrofuran-3-carboxamide was prepared from tetrahydrofuran-3-carboxylic acid and N-ethyl-N-isopropylpropan-2-amine analogously to Example 87.

N-[4-[2-chloro-3-(2,6-dioxo-3-piperidyl)phenyl]phenyl]tetrahydrofuran-3-carboxamide was prepared from N-[4-[2-chloro-3-(2,6-dioxo-3-piperidyl)phenyl]phenyl]tetrahydrofuran-3-carboxamide and 3-[2-chloro-3-(4,4,5,5-tetramethyl-1,3,2-dioxaborolan-2-yl)phenyl]piperidine-2,6-dione according to General Scheme 1.

MS (ESI) m/z 413.1 [M+H]$^+$

Example 90. Synthesis of 3-(2-chloro-4'-(5-oxo-4-azaspiro[2.5]octan-4-yl)-[1,1'-biphenyl]-3-yl)piperidine-2,6-dione (Compound 232)

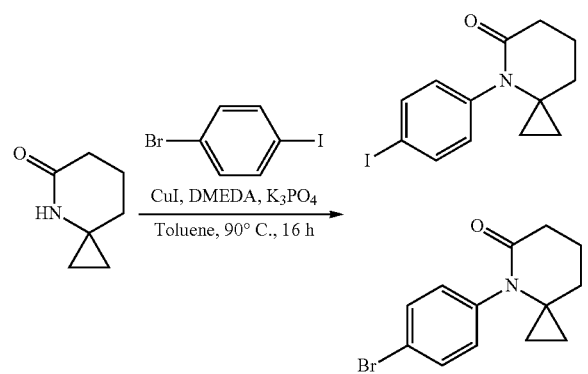

To a solution of 4-azaspiro[2.5]octan-5-one (0.500 g, 3.99 mmol, 1.00 eq) in toluene (2 mL) was added potassium phosphate (2.12 g, 9.99 mmol, 2.50 eq) and cuprous iodide (0.0761 g, 0.399 mmol, 0.100 eq) followed by 1-bromo-4-iodo-benzene (1.47 g, 5.19 mmol, 1.30 eq) and N,N-dimethylethane-1,2-diamine (0.0704 g, 0.799 mmol, 0.200 eq) at 25° C. under nitrogen atmosphere.

The reaction was stirred at 90° C. for 16 h. After being cooled to room temperature, the mixture was diluted with water (20 mL) and extracted with ethyl acetate (3×20 mL). The combined organic layers were washed with brine (3×20 mL), dried over anhydrous sodium sulfate, filtered and concentrated under vacuum. The residue was purified by column chromatography (silica, petroleum ether:ethyl acetate=5:1 to 1:2) to give 4-(4-bromophenyl)-4-azaspiro[2.5]octan-5-one (0.210 g, 0.346 mmol, 18% yield) as a yellow solid. $^1$H NMR (400 MHz, DMSO-d$_6$) δ=7.73-7.52 (m, 2H), 7.11-6.80 (m, 2H), 2.54-2.52 (m, 2H), 1.93 (q, J=6.8 Hz, 2H), 1.88-1.81 (m, 2H), 0.76-0.66 (m, 2H), 0.55-0.47 (m, 2H).

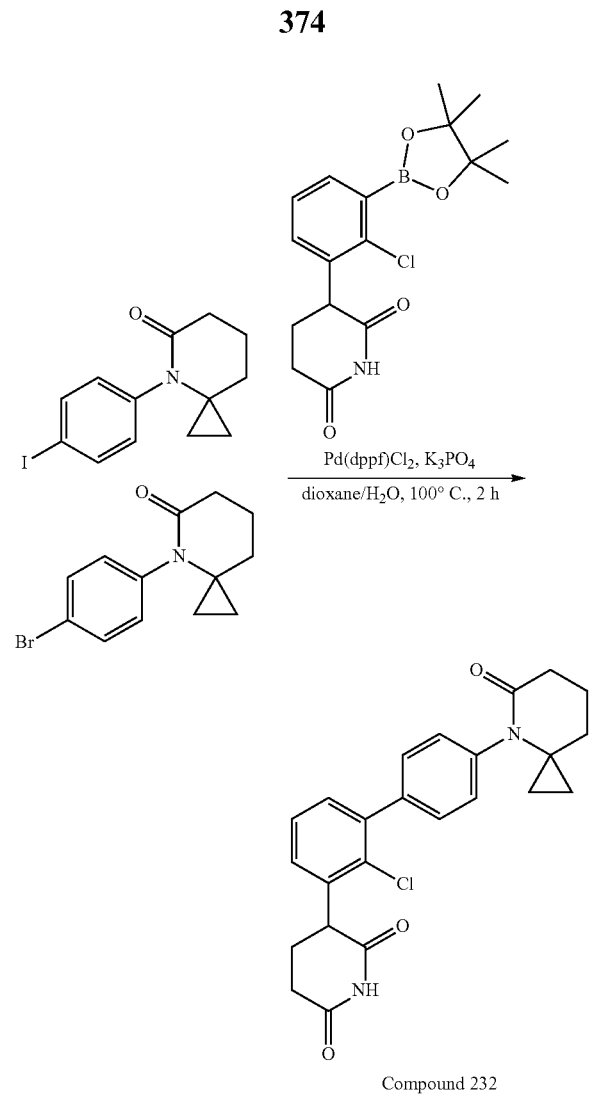

Compound 232

To a solution of 4-(4-bromophenyl)-4-azaspiro[2.5]octan-5-one (0.100 g, 0.357 mmol, 1.00 eq) in dioxane (10 mL) and water (1 mL) was added 3-(2-chloro-3-(4,4,5,5-tetramethyl-1,3,2-dioxaborolan-2-yl)phenyl)piperidine-2,6-dione (0.150 g, 0.428 mmol, 1.20 eq) and potassium phosphate (0.227 μg, 1.07 μmmol, 3.00 eq) followed by [1,1'-bis(diphenylphosphino)ferrocene]dichloropalladium(II) (0.0261 g, 0.0357 mmol, 0.100 eq) at 25° C. under nitrogen atmosphere. The reaction was stirred at 100° C. for 2 h. After being cooled to room temperature, the mixture was diluted with water (20 mL) and extracted with ethyl acetate (3×20 mL). The combined organic layers were washed with brine (3×20 mL), dried over anhydrous sodium sulfate and concentrated under vacuum. The residue was purified by column chromatography (silica, petroleum ether:ethyl acetate=5:1 to 1:2) and Prep-HPLC (column: Phenomenex luna C18 150 mm×25 mm×10 μm; mobile phase: [water (formic acid)-acetonitrile]; gradient: 35-65% B over 10 min) and lyophilized to afford 3-(2-chloro-4'-(5-oxo-4-azaspiro[2.5]octan-4-yl)-[1,1'-biphenyl]-3-yl)piperidine-2,6-dione (41.7 mg, 0.0976 mmol, 27% yield) as a white solid.

$^1$H NMR (400 MHz, DMSO-d$_6$) δ=10.92 (s, 1H), 7.46-7.29 (m, 5H), 7.17 (d, J=8.4 Hz, 2H), 4.43-4.29 (m, 1H), 2.86-2.74 (m, 1H), 2.58-2.54 (m, 3H), 2.42-2.32 (m, 1H), 2.09-2.01 (m, 1H), 2.00-1.92 (m, 2H), 1.92-1.84 (m, 2H), 0.78-0.71 (m, 2H), 0.62-0.53 (m, 2H); MS (ESI) m/z 423.3 [M+H]+

Example 91. Synthesis of 3-(2-chloro-4'-(oxetan-3-ylmethyl)-[1,1'-biphenyl]-3-yl)piperidine-2,6-dione (Compound 233)

3-(2-chloro-4'-(oxetan-3-ylmethyl)-[1,1'-biphenyl]-3-yl)piperidine-2,6-dione was prepared from 3-(4-bromobenzyl)oxetane and 3-(2-chloro-3-(4,4,5,5-tetramethyl-1,3,2-dioxaborolan-2-yl)phenyl)piperidine-2,6-dione according to General Scheme 1.
MS (ESI) m/z 739.1 [2M+H]+

Example 92. Synthesis of 3-(2-chloro-4'-(2-oxo-2-(pyrrolidin-1-yl)ethyl)-[1,1'-biphenyl]-3-yl)piperidine-2,6-dione (Compound 235)

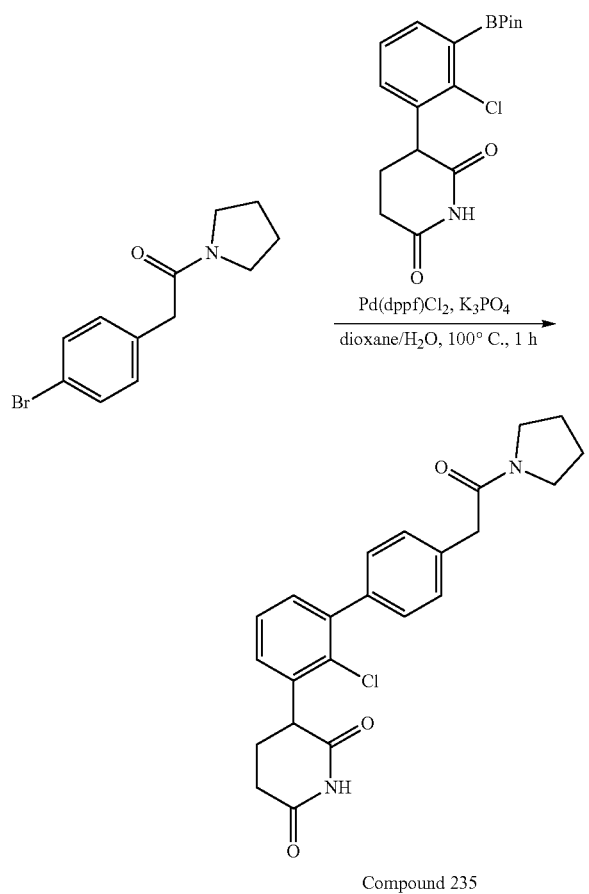

Compound 235

3-(2-chloro-4'-(2-oxo-2-(pyrrolidin-1-yl)ethyl)-[1,1'-biphenyl]-3-yl)piperidine-2,6-dione was prepared from 2-(4-bromophenyl)-1-pyrrolidin-1-yl-ethanone and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.92 (s, 1H), 7.43-7.27 (m, 7H), 4.34 (dd, J=12.0, 5.2 Hz, 1H), 3.68 (s, 2H), 3.52 (t, J=6.8 Hz, 2H), 3.30 (s, 2H), 2.86-2.72 (m, 1H), 2.58-2.52 (m, 1H), 2.42-2.25 (m, 1H), 2.11-1.99 (m, 1H), 1.94-1.84 (m, 2H), 1.83-1.73 (m, 2H).

$^1$H NMR (400 MHz, MeOD) δ=7.42-7.27 (m, 7H), 4.38 (dd, J=12.0, 5.2 Hz, 1H), 3.77 (s, 2H), 3.57 (t, J=6.8 Hz, 2H), 3.46 (t, J=6.8 Hz, 2H), 2.90-2.74 (m, 1H), 2.74-2.63 (m, 1H), 2.50-2.35 (m, 1H), 2.27-2.14 (m, 1H), 1.98 (q, J=6.8 Hz, 2H), 1.93-1.85 (m, 2H); MS (ESI) m/z 411.1, 413.1 [M+H]+

Example 93. Synthesis of 3-(2-chloro-4'-(2-oxo-4-(trifluoromethyl) pyridin-1(2H)-yl)-[1,1'-biphenyl]-3-yl)piperidine-2,6-dione (Compound 236)

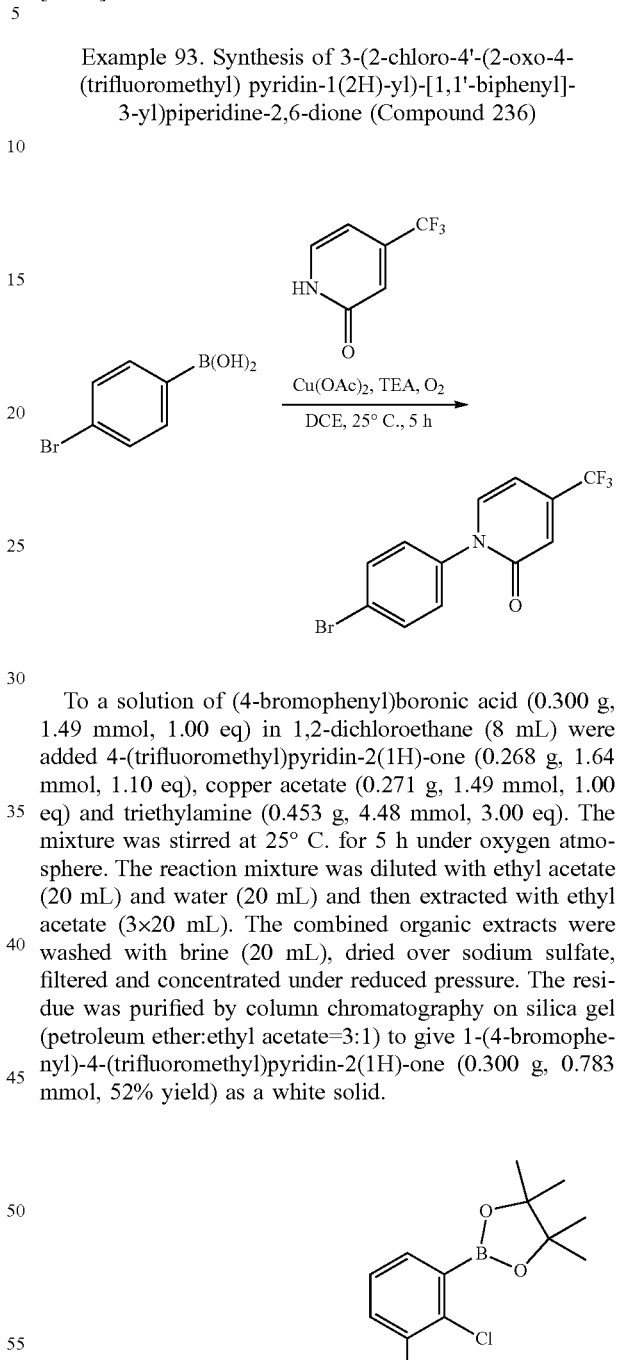

To a solution of (4-bromophenyl)boronic acid (0.300 g, 1.49 mmol, 1.00 eq) in 1,2-dichloroethane (8 mL) were added 4-(trifluoromethyl)pyridin-2(1H)-one (0.268 g, 1.64 mmol, 1.10 eq), copper acetate (0.271 g, 1.49 mmol, 1.00 eq) and triethylamine (0.453 g, 4.48 mmol, 3.00 eq). The mixture was stirred at 25° C. for 5 h under oxygen atmosphere. The reaction mixture was diluted with ethyl acetate (20 mL) and water (20 mL) and then extracted with ethyl acetate (3×20 mL). The combined organic extracts were washed with brine (20 mL), dried over sodium sulfate, filtered and concentrated under reduced pressure. The residue was purified by column chromatography on silica gel (petroleum ether:ethyl acetate=3:1) to give 1-(4-bromophenyl)-4-(trifluoromethyl)pyridin-2(1H)-one (0.300 g, 0.783 mmol, 52% yield) as a white solid.

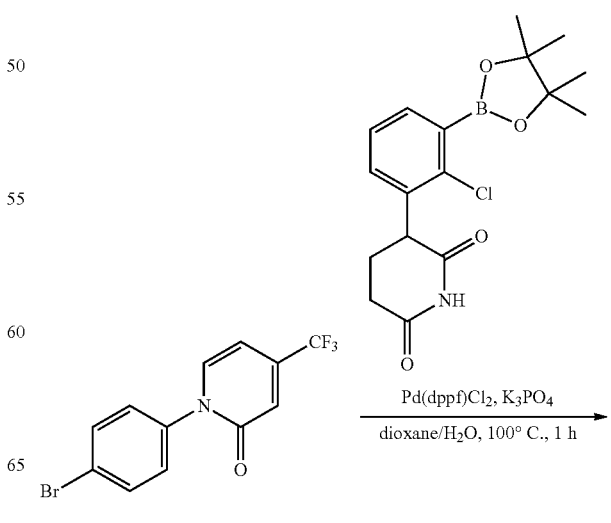

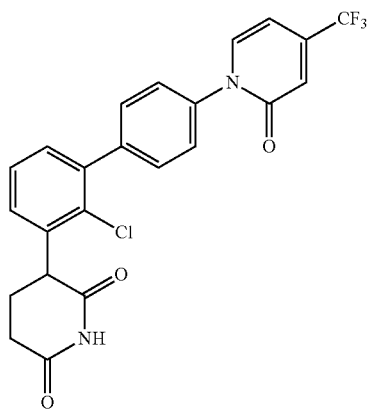

Compound 236

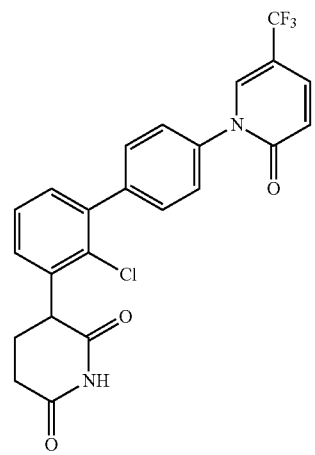

Compound 237

3-(2-chloro-4'-(2-oxo-4-(trifluoromethyl)pyridin-1(2H)-yl)-[1,1'-biphenyl]-3-yl)piperidine-2,6-dione was prepared from 1-(4-bromophenyl)-4-(trifluoromethyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.92 (s, 1H), 8.01 (d, J=7.2 Hz, 1H), 7.60-7.55 (m, 4H), 7.46-7.36 (m, 3H), 6.95 (s, 1H), 6.57 (d, J=7.2 Hz, 1H), 4.37 (dd, J=12.0, 4.8 Hz, 1H), 2.85-2.76 (m, 1H), 2.57 (d, J=3.6 Hz, 1H), 2.40-2.30 (m, 1H), 2.10-2.04 (m, 1H); MS (ESI) m/z 461.0, 463.0 [M+H]$^+$

Example 94. Synthesis of 3-(2-chloro-4'-(2-oxo-5-(trifluoromethyl)pyridin-1(2H)-yl)-[1,1'-biphenyl]-3-yl)piperidine-2,6-dione (Compound 237)

3-(2-chloro-4'-(2-oxo-5-(trifluoromethyl)pyridin-1(2H)-yl)-[1,1'-biphenyl]-3-yl)piperidine-2,6-dione was prepared from 1-(4-bromophenyl)-5-(trifluoromethyl)pyridin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-$d_6$) δ=10.94 (s, 1H), 8.36 (s, 1H), 7.79 (dd, J=9.6, 2.8 Hz, 1H), 7.59 (s, 4H), 7.50-7.35 (m, 3H), 6.69 (d, J=9.6 Hz, 1H), 4.39 (dd, J=12.2, 4.8 Hz, 1H), 2.86-2.77 (m, 1H), 2.58 (d, J=3.6 Hz, 1H), 2.43-2.30 (m, 1H), 2.14-2.02 (m, 1H); MS (ESI) m/z 399.1 [M+H]$^+$

Example 95. Synthesis of 3-[2-chloro-3-[4-(4-fluoro-2-oxo-1-pyridyl)phenyl]phenyl]piperidine-2,6-dione (Compound 245)

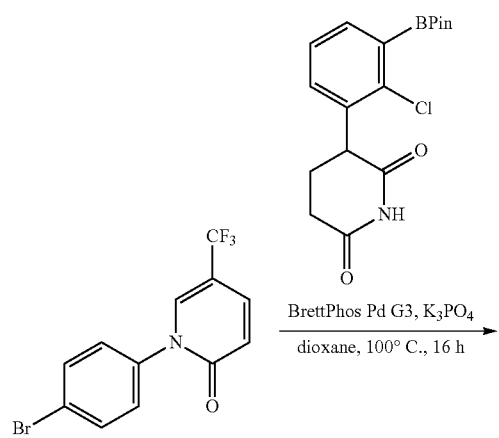

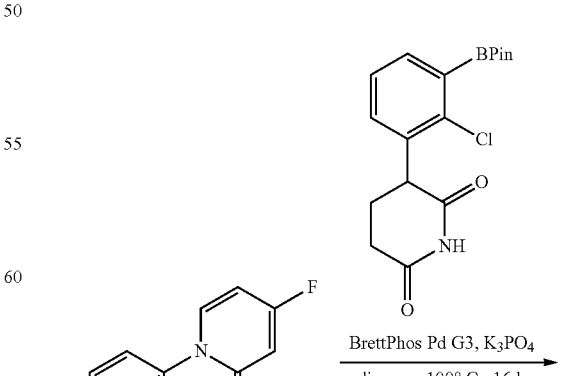

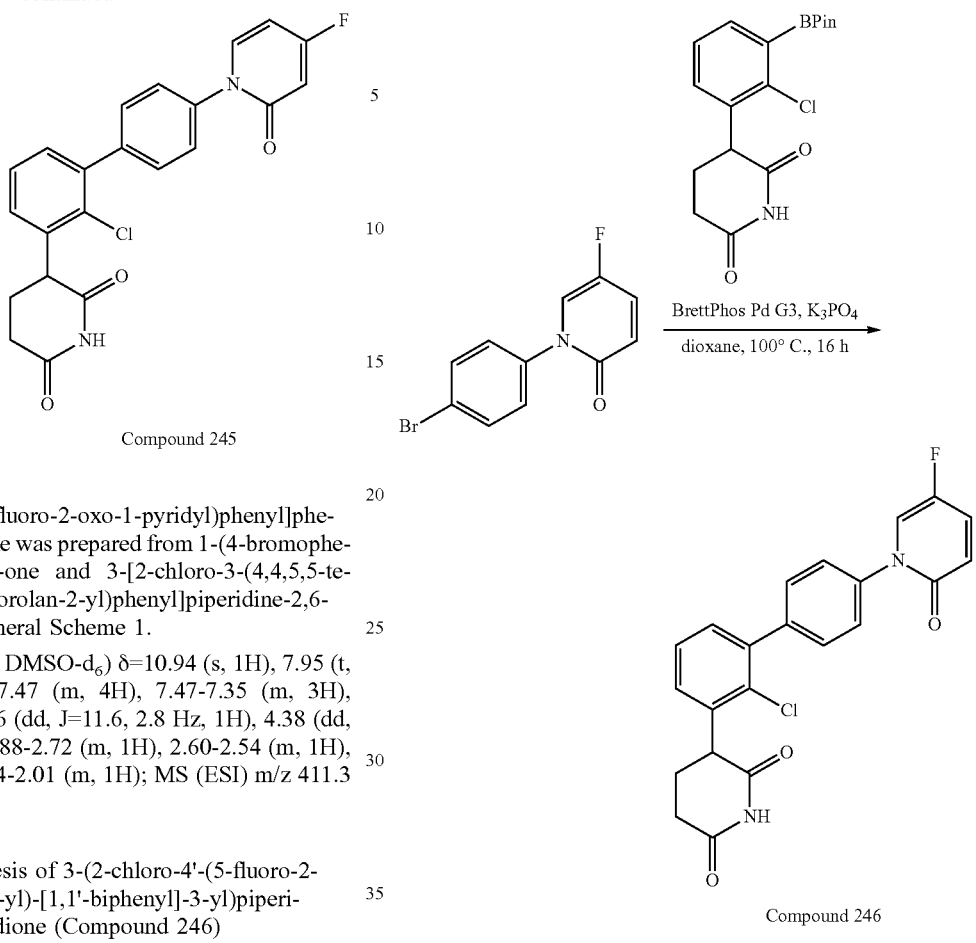

Compound 245

3-[2-chloro-3-[4-(4-fluoro-2-oxo-1-pyridyl)phenyl]phenyl]piperidine-2,6-dione was prepared from 1-(4-bromophenyl)-4-fluoro-pyridin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-$d_6$) δ=10.94 (s, 1H), 7.95 (t, J=8.0 Hz, 1H), 7.65-7.47 (m, 4H), 7.47-7.35 (m, 3H), 6.52-6.40 (m, 1H), 6.36 (dd, J=11.6, 2.8 Hz, 1H), 4.38 (dd, J=12.4, 4.8 Hz, 1H), 2.88-2.72 (m, 1H), 2.60-2.54 (m, 1H), 2.45-2.30 (m, 1H), 2.14-2.01 (m, 1H); MS (ESI) m/z 411.3 [M+H]$^+$

Example 96. synthesis of 3-(2-chloro-4'-(5-fluoro-2-oxopyridin-1(2H)-yl)-[1,1'-biphenyl]-3-yl)piperidine-2,6-dione (Compound 246)

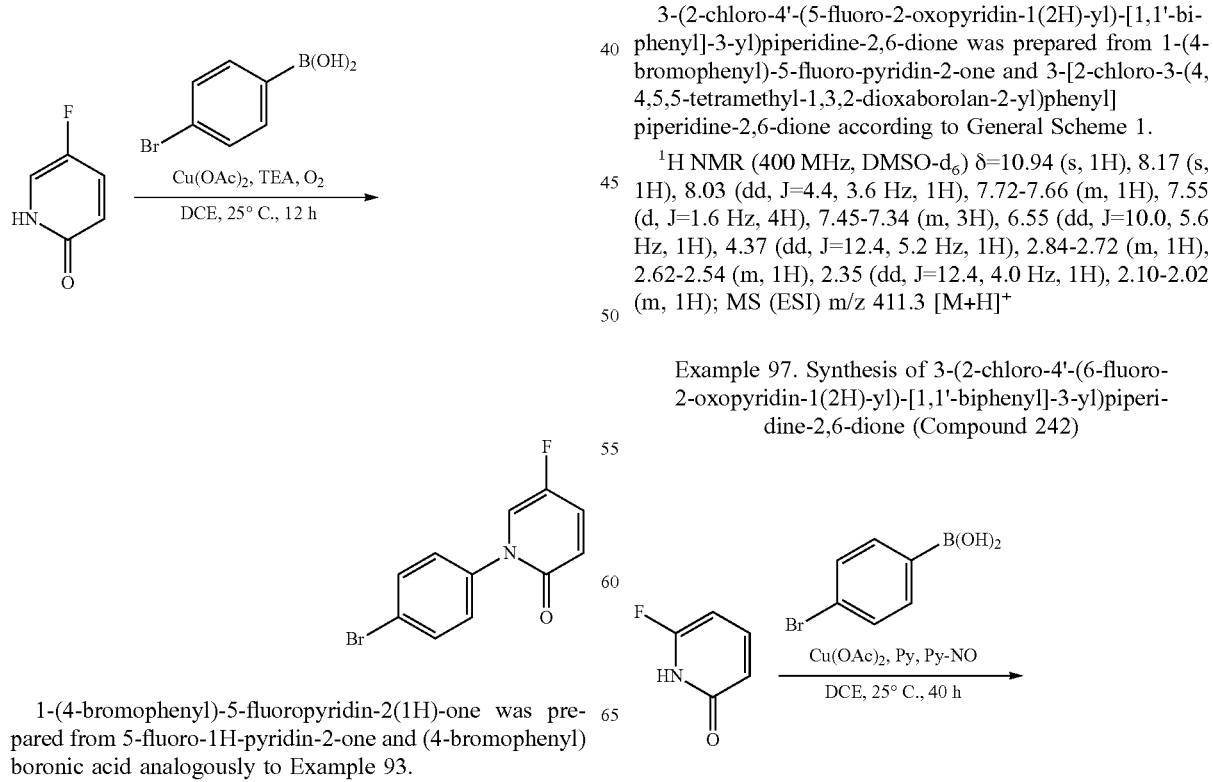

Compound 246

1-(4-bromophenyl)-5-fluoropyridin-2(1H)-one was prepared from 5-fluoro-1H-pyridin-2-one and (4-bromophenyl)boronic acid analogously to Example 93.

3-(2-chloro-4'-(5-fluoro-2-oxopyridin-1(2H)-yl)-[1,1'-biphenyl]-3-yl)piperidine-2,6-dione was prepared from 1-(4-bromophenyl)-5-fluoro-pyridin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-$d_6$) δ=10.94 (s, 1H), 8.17 (s, 1H), 8.03 (dd, J=4.4, 3.6 Hz, 1H), 7.72-7.66 (m, 1H), 7.55 (d, J=1.6 Hz, 4H), 7.45-7.34 (m, 3H), 6.55 (dd, J=10.0, 5.6 Hz, 1H), 4.37 (dd, J=12.4, 5.2 Hz, 1H), 2.84-2.72 (m, 1H), 2.62-2.54 (m, 1H), 2.35 (dd, J=12.4, 4.0 Hz, 1H), 2.10-2.02 (m, 1H); MS (ESI) m/z 411.3 [M+H]$^+$

Example 97. Synthesis of 3-(2-chloro-4'-(6-fluoro-2-oxopyridin-1(2H)-yl)-[1,1'-biphenyl]-3-yl)piperidine-2,6-dione (Compound 242)

-continued

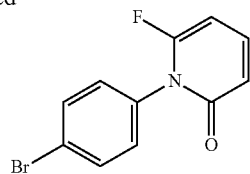

A mixture of 6-fluoropyridin-2(1H)-one (5.00 g, 44.2 mmol, 1.00 eq), (4-bromophenyl)boronic acid (17.8 g, 88.4 mmol, 2.00 eq), copper(II) acetate (803 mg, 4.42 mmol, 0.100 eq), pyridine (6.99 g, 88.4 mmol, 7.14 mL, 2.00 eq) and 4 Å MS (2.00 g, 44.2 mmol) and 1-oxidopyridin-1-ium (4.63 g, 48.6 mmol, 1.10 eq) in dichloromethane (100 mL) was degassed, and then the mixture was stirred at 25° C. for 40 h under air atmosphere. The reaction mixture was quenched by addition 1N hydrochloric acid (50 mL) at 25° C., and then concentrated under reduced pressure to remove dichloromethane. Then the mixture was extracted with ethyl acetate (4×100 mL). The combined organic layers were dried over sodium sulfate, filtered and concentrated under reduced pressure to give a residue. The residue was purified by flash silica gel chromatography (ISCO®; 40 g SepaFlash® Silica Flash Column, Eluent of 0~55% ethyl acetate/petroleum ether gradient @ 50 mL/min) followed by reversed phase column (condition; C18, flow: 40 mL/min; gradient: from 0-40% acetonitrile (0.1% formic acid) in water over 40 min) to afford 1-(4-bromophenyl)-6-fluoropyridin-2(1H)-one (190 mg, 687 μmol, 2% yield) as a white solid.

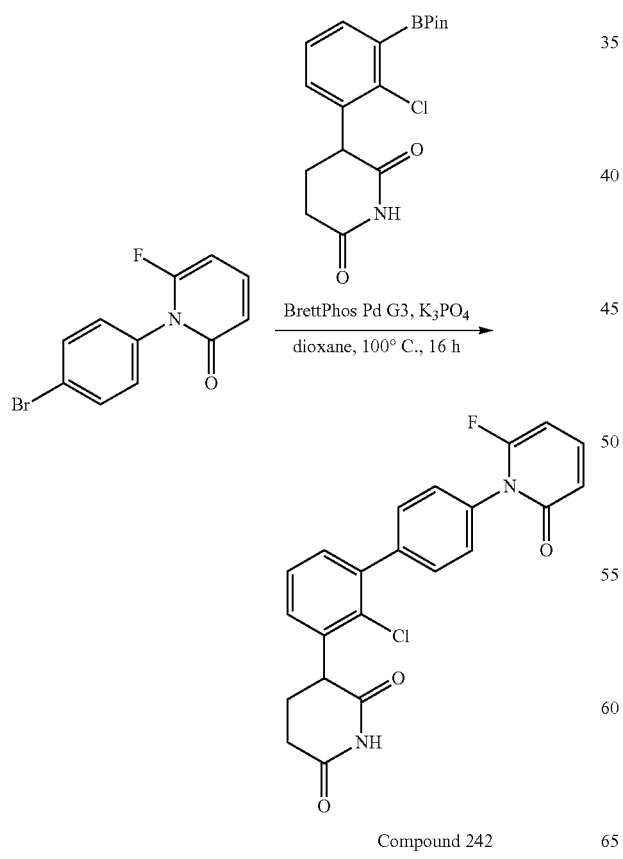

Compound 242

3-(2-chloro-4'-(6-fluoro-2-oxopyridin-1(2H)-yl)-[1,1'-biphenyl]-3-yl)piperidine-2,6-dione was prepared from 1-(4-bromophenyl)-6-fluoropyridin-2(1H)-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-d$_6$) δ=10.94 (s, 1H), 7.68-7.56 (m, 3H), 7.54-7.47 (m, 2H), 7.47-7.36 (m, 3H), 6.41 (dd, J=9.2, 0.8 Hz, 1H), 6.29-6.17 (m, 1H), 4.38 (dd, J=12.0, 5.2 Hz, 1H), 2.90-2.75 (m, 1H), 2.61-2.53 (m, 1H), 2.43-2.25 (m, 1H), 2.13-2.02 (m, 1H); MS (ESI) m/z 411.3 [M+H]$^+$

Example 98. Synthesis of 3-[2-methyl-3-[4-[(2-oxo-1-pyridyl)methyl]phenyl]phenyl]piperidine-2,6-dione (Compound 243)

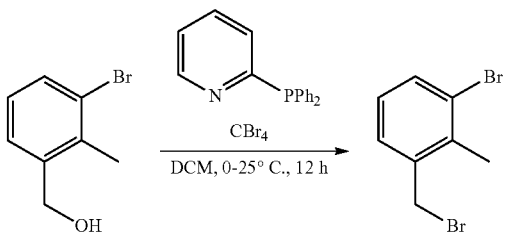

To a solution of (3-bromo-2-methyl-phenyl)methanol (10.0 g, 49.7 mmol, 1.00 eq) in dichloromethane (100 mL) was added diphenyl(2-pyridyl)phosphane (19.6 g, 74.6 mmol, 1.50 eq) and carbon tetrabromide (24.7 g, 74.6 mmol, 1.50 eq) at 0° C. Then the mixture was stirred at 25° C. for 16 h. The reaction mixture was concentrated under reduced pressure to remove dichloromethane, then filtered with silica gel and washed with Petroleum ether. Ethyl acetate=10:1 (200 mL), then concentrated under reduced pressure. The residue was purified by flash silica gel chromatography (ISCO®; 120 g SepaFlash® Silica Flash Column, eluent of 0-20% ethyl acetate/petroleum ether gradient @ 80 mL/min) to give 1-bromo-3-(bromomethyl)-2-methyl-benzene (4.80 g, 16.7 mmol, 33% yield) as a colorless oil. 3-(3-bromo-2-methyl-phenyl)piperidine-2,6-dione was prepared from 1-bromo-3-(bromomethyl)-2-methyl-benzene according to General Scheme 2.

3-[2-methyl-3-[4-[(2-oxo-1-pyridyl)methyl]phenyl]phenyl]piperidine-2,6-dione was prepared from 3-(3-bromo-2-methyl-phenyl)piperidine-2,6-dione and 1-[[4-(4,4,5,5-tetramethyl-1,3,2-dioxaborolan-2-yl)phenyl]methyl]pyridin-2-one according to General Scheme 1.

MS (ESI) m/z 387.3 [M+H]$^+$

Example 99. Synthesis of 3-(2-chloro-4'-(2-oxo-6-(trifluoromethyl)piperidin-1-yl)-[1,1'-biphenyl]-3-yl)piperidine-2,6-dione (Compound 244)

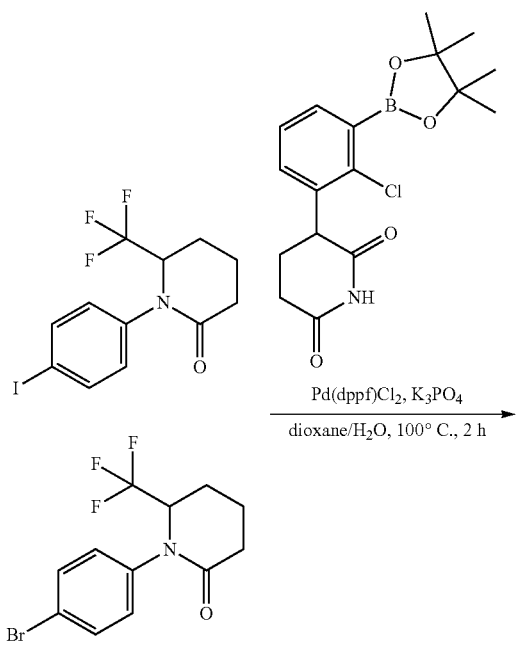

Compound 244

3-(2-chloro-4'-(2-oxo-6-(trifluoromethyl)piperidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and a mixture of 1-(4-bromophenyl)-6-(trifluoromethyl)piperidin-2-one and 1-(4-iodophenyl)-6-(trifluoromethyl)piperidin-2-one according to General Scheme 1.

$^1$H NMR (400 MHz, DMSO-$d_6$) δ=10.92 (s, 1H), 7.46-7.34 (m, 7H), 4.95-4.88 (m, 1H), 4.35 (dd, J=5.2, 12.4 Hz, 1H), 2.89-2.71 (m, 1H), 2.59-2.52 (m, 3H), 2.37-2.25 (m, 2H), 2.18-2.10 (m, 1H), 2.09-2.01 (m, 1H), 1.97-1.85 (m, 2H); MS (ESI) m/z 465.1 [M+H]$^+$

Example 100. Synthesis of 3-[2-chloro-3-[4-[1-(2-oxo-1-pyridyl)cyclopropyl]phenyl]phenyl]piperidine-2,6-dione (Compound 241) and 3-[2-chloro-3-[4-[1-(2-oxo-1-piperidyl)cyclopropyl]phenyl]phenyl]piperidine-2,6-dione (Compound 337)

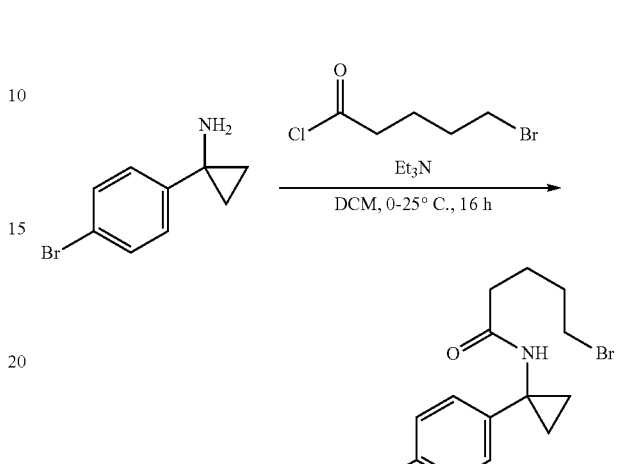

To a solution of 1-(4-bromophenyl)cyclopropanamine (2.00 g, 9.43 mmol, 1.00 eq) and triethylamine (1.91 g, 18.9 mmol, 2.63 mL, 2.00 eq) in dichloromethane (20 mL) was added dropwise 5-bromopentanoyl chloride (2.26 g, 11.3 mmol, 1.51 mL, 1.20 eq) at 0° C. The resulting mixture was stirred at 25° C. for 16 h. The reaction mixture was quenched by the addition of water (5 mL) at 25° C., and then diluted with water (20 mL) and extracted with dichloromethane (2×20 mL). The combined organic layers were washed with brine (20 mL), dried over anhydrous sodium sulfate, filtered and concentrated under reduced pressure to give a residue. The residue was purified by flash silica gel chromatography (ISCO®; 20 g SepaFlash® Silica Flash Column, Eluent of 0-50% Ethyl acetate/Petroleum ether gradient @ 35 mL/min) to afford 5-bromo-N-(1-(4-bromophenyl)cyclopropyl)pentanamide (1.35 g, 3.56 mmol, 38% yield) a light yellow solid.

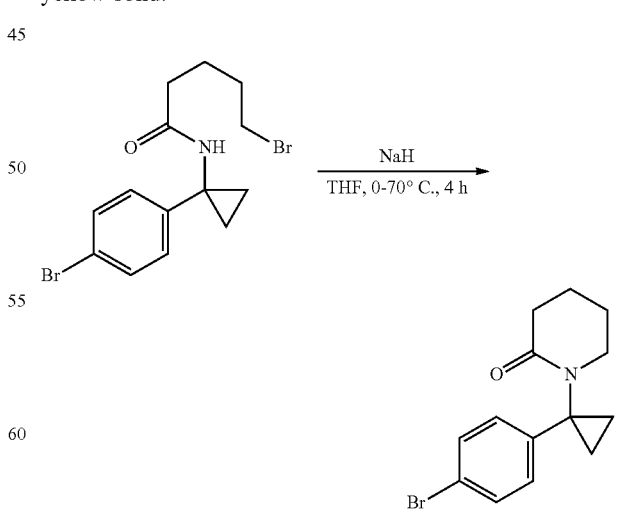

To a solution of sodium hydride (141 mg, 3.52 mmol, 60% purity, 1.10 eq) in tetrahydrofuran (10 mL) at 0° C. was added 5-bromo-N-(1-(4-bromophenyl)cyclopropyl)pentanamide (1.20 g, 3.20 mmol, 1.00 eq) in portions. The resulting mixture was stirred at 70° C. for 4 h. The reaction mixture was quenched by addition water (30 mL) at 0° C., and then diluted with water (50 mL) and extracted with ethyl acetate (3×50 mL). The combined organic layers were washed with brine (50 mL), dried over anhydrous sodium sulfate, filtered and concentrated under reduced pressure to give a residue. The residue was purified by flash silica gel chromatography (ISCO®; 20 g SepaFlash® Silica Flash Column, Eluent of 0-50% Ethyl acetate/Petroleum ether gradient @ 35 mL/min) to afford 1-(1-(4-bromophenyl)cyclopropyl)piperidin-2-one (650 mg, 1.97 mmol, 61% yield) as a light yellow oil.

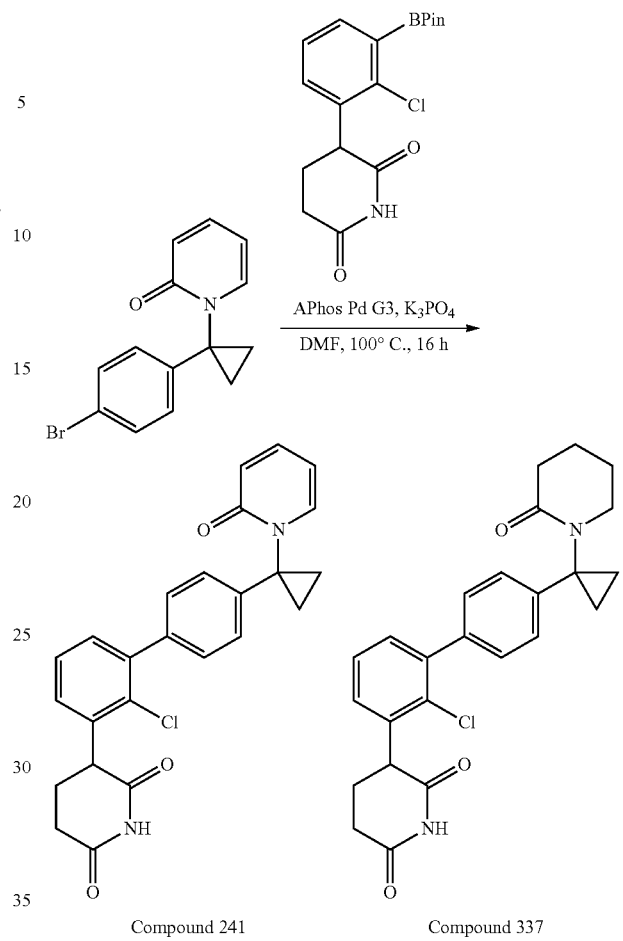

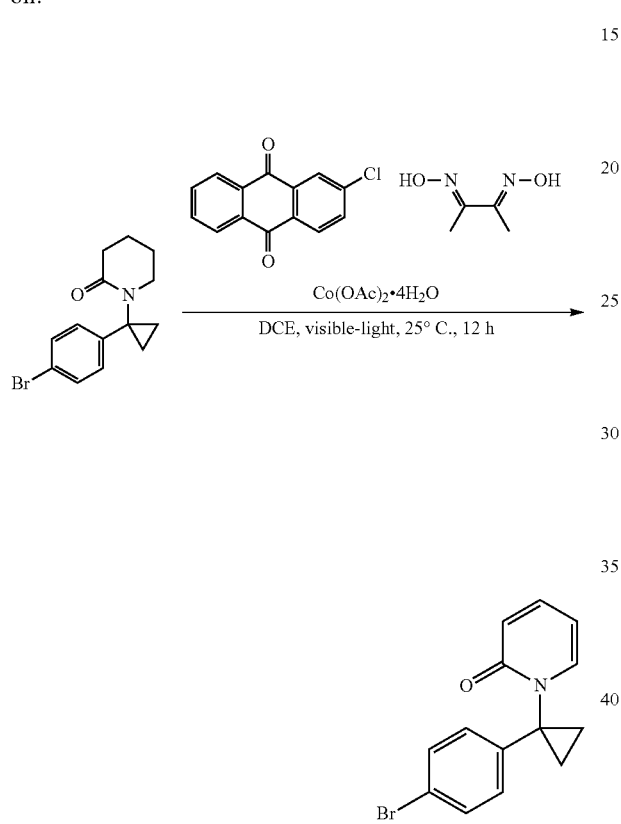

A mixture of 1-(1-(4-bromophenyl)cyclopropyl)piperidin-2-one (200 mg, 680 μmol, 1.00 eq), butane-2,3-dione oxime (39.5 mg, 340 μmol, 50.6 μL, 0.500 eq), 2-chloroanthracene-9,10-dione (41.2 mg, 170 μmol, 0.250 eq) and diacetoxycobalt (24.1 mg, 136 μmol, 0.200 eq) in dichloroethane (10 mL) was degassed and purged with nitrogen for three times, and then the mixture was stirred at 25° C. for 24 h under visible light (395 nm, 10 W). The reaction mixture was filtered through a plug of Celite and concentrated under reduced pressure to give a residue. The residue was purified by flash silica gel chromatography (ISCO®; 10 g SepaFlash® Silica Flash Column, Eluent of 0~50% Ethyl acetate/Petroleum ether gradient @ 45 mL/min) to afford 1-(1-(4-bromophenyl)cyclopropyl)pyridin-2(1H)-one (140 mg, 347 μmol, 51% yield, 72% purity) a brown oil.

Compound 241          Compound 337

A mixture of 1-(1-(4-bromophenyl)cyclopropyl)pyridin-2-one (210 mg, 282 μmol, 39% purity, 1.00 eq), 3-[2-chloro-3-(4,4,5,5-tetramethyl-1,3,2-dioxaborolan-2-yl)phenyl]piperidine-2,6-dione (138 mg, 339 μmol, 86% purity, 1.20 eq), methanesulfonato[[4-(N,N-dimethylamino)phenyl]di-tert-butylphosphino](2'-amino-1,1'-biphenyl-2-yl) palladium(II) (17.9 mg, 28.2 μmol, 0.100 eq), potassium phosphate (180 mg, 847 μmol, 3.00 eq) in dimethyl formamide (2 mL) was degassed and purged with nitrogen for three times, and then the mixture was stirred at 100° C. for 16 h under nitrogen atmosphere. The residue was purified by flash silica gel chromatography (ISCO®; 10 g SepaFlash® Silica Flash Column, Eluent of 0~50% Ethylacetate/Petroleum ether gradient @ 45 mL/min), followed by Prep-HPLC (column: Phenomenex luna C18 150×25 mm×m; mobile phase: [water (formic acid)-acetonitrile]; B %: 35%-65%, 7 min) and lyophilized to afford 3-[2-chloro-3-[4-[1-(2-oxo-1-pyridyl)cyclopropyl]phenyl]phenyl]piperidine-2,6-dione (64.2 mg, 147 μmol, 52% yield) as a white solid and 3-[2-chloro-3-[4-[1-(2-oxo-1-piperidyl)cyclopropyl]phenyl]phenyl]piperidine-2,6-dione (105 mg, 229 μmol, 81% yield) as a white solid respectively.

Compound 241:

$^1$H NMR (400 MHz, DMSO-d$_6$) δ 10.93 (s, 1H), 7.84 (dd, J=6.8, 1.6 Hz, 1H), 7.46 (ddd, J=9.2, 6.8, 2.0 Hz, 1H), 7.41-7.31 (m, 4H), 7.27 (dd, J=7.2, 2.0 Hz, 1H), 7.08 (d, J=8.4 Hz, 2H), 6.41 (d, J=9.2 Hz, 1H), 6.29 (td, J=6.8, 1.2 Hz, 1H), 4.34 (dd, J=12.0, 5.2 Hz, 1H), 2.84-2.74 (m, 1H), 2.61-2.53 (m, 1H), 2.38-2.28 (m, 1H), 2.08-2.00 (m, 1H), 1.66-1.56 (m, 2H), 1.56-1.48 (m, 2H); MS (ESI) m/z 433.2 [M+H]+

Compound 337:
¹H NMR (400 MHz, DMSO-d₆) δ 10.91 (s, 1H), 7.25-7.41 (m, 5H), 7.12 (d, J=8.4 Hz, 2H), 4.34 (dd, J=12.0, 4.8 Hz, 1H), 3.45-3.37 (m, 2H), 2.83-2.73 (m, 1H), 2.60-2.53 (m, 1H), 2.37-2.25 (m, 3H), 2.10-1.98 (m, 1H), 1.86-1.67 (m, 4H), 1.39-1.23 (m, 4H).
¹H NMR (400 MHz, MeOD) δ 7.38-7.30 (m, 4H), 7.29-7.25 (m, 1H), 7.24-7.17 (m, 2H) 4.38 (dd, J=11.6, 5.2 Hz, 1H) 3.48 (t, J=6.0 Hz, 2H), 2.87-2.75 (m, 1H), 2.74-2.64 (m, 1H), 2.51-2.43 (m, 2H) 2.43-2.33 (m, 1H), 2.25-2.14 (m, 1H), 1.96-1.79 (m, 4H), 1.47-1.31 (m, 4H); MS (ESI) m/z 437.1 [M+H]+

Example 101. Synthesis of 3-[2-methyl-3-[4-(2-oxo-1-pyridyl)phenyl]phenyl]piperidine-2,6-dione (Compound 240)

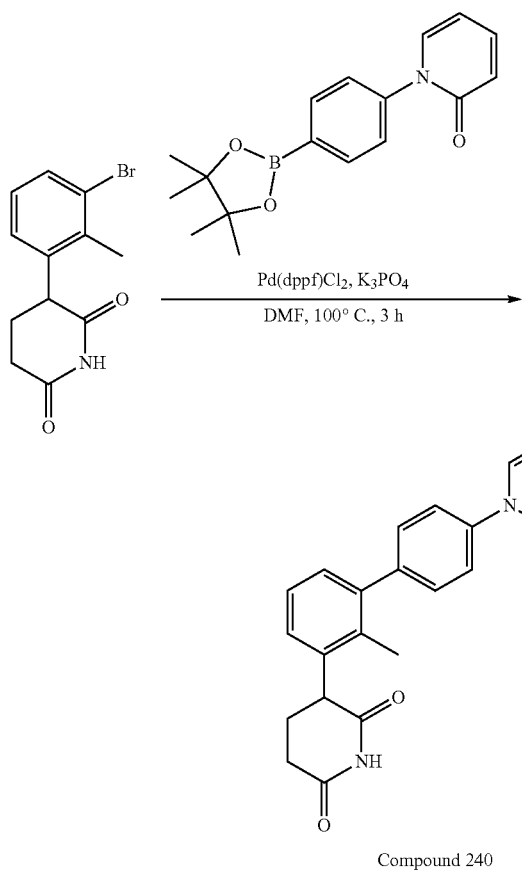

Compound 240

3-[2-methyl-3-[4-(2-oxo-1-pyridyl)phenyl]phenyl]piperidine-2,6-dione was prepared from 3-(3-bromo-2-methyl-phenyl)piperidine-2,6-dione and 1-[4-(4,4,5,5-tetramethyl-1,3,2-dioxaborolan-2-yl)phenyl]pyridin-2-one according to General Scheme 1.

¹H NMR (400 MHz, DMSO-d₆) δ=10.87 (s, 1H), 7.73 (d, J=6.4 Hz, 1H), 7.56-7.42 (m, 5H), 7.29-7.23 (m, 1H), 7.17 (dd, J=11.2, 7.6 Hz, 2H), 6.51 (d, J=9.2 Hz, 1H), 6.34 (t, J=6.8 Hz, 1H), 4.18 (dd, J=12.0, 4.8 Hz, 1H), 2.86-2.70 (m, 1H), 2.56 (s, 1H), 2.26 (s, 1H), 2.20 (s, 3H), 2.11-1.90 (m, 1H); MS (ESI) m/z 373.2 [M+H]+

Example 102. Synthesis of 3-(2-chloro-4'-(6-(difluoromethyl)-2-oxopyridin-1(2H)-yl)-[1,1'-biphenyl]-3-yl)piperidine-2,6-dione (Compound 238)

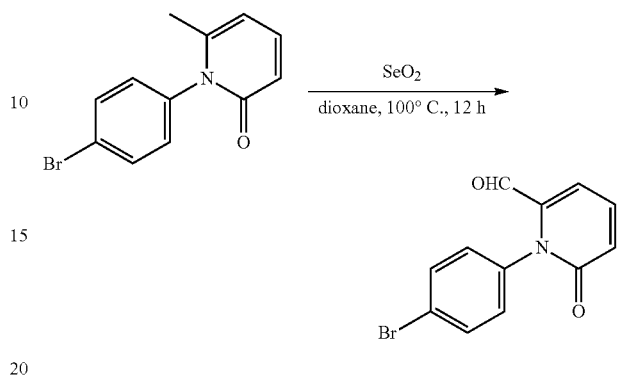

A mixture of 1-(4-bromophenyl)-6-methyl-pyridin-2-one (350 mg, 1.19 mmol, 1.00 eq), selenium dioxide (265 mg, 2.39 mmol, 259 μL, 2.00 eq) in dioxane (10 mL) was degassed and purged with nitrogen for three times, and then the mixture was stirred at 100° C. for 12 h under nitrogen atmosphere. The reaction mixture was cooled to 25° C., and then filtered through a plug of Celite and the filtrate was concentrated under reduced pressure to give a residue. The residue was purified by flash silica gel chromatography (ISCO®; 10 g SepaFlash® Silica Flash Column, Eluent of 0~50% Ethyl acetate/Petroleum ether gradient @ 45 mL/min) to afford 1-(4-bromophenyl)-6-oxo-1,6-dihydropyridine-2-carbaldehyde (253 mg, 819 μmol, 69% yield) as a yellow solid

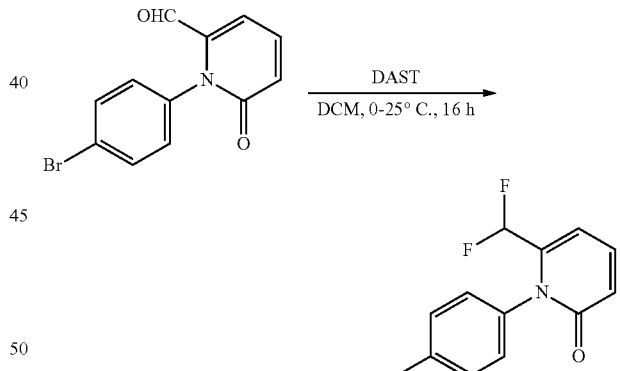

To a solution of 1-(4-bromophenyl)-6-oxo-pyridine-2-carbaldehyde (200 mg, 647 μmol, 1.00 eq) in dichloromethane (5 mL) was added diethylaminosulfur trifluoride (417 mg, 2.59 mmol, 342 μL, 4.00 eq) at 0° C. The mixture was stirred at 25° C. for 16 h. The reaction mixture was quenched by the slowly addition of saturated sodium bicarbonate solution (5 mL) at 0° C., and then diluted with dichloromethane (5 mL) and extracted with dichloromethane (2×10 mL). The combined organic layers were washed with brine (20 mL), dried over sodium sulfate, filtered and concentrated under reduced pressure to give a residue. The residue was purified by flash silica gel chromatography (ISCO®; 10 g SepaFlash® Silica Flash Column, Eluent of 0~40% Ethyl acetate/Petroleum ether gradient @ 35 mL/min) to afford 1-(4-bromophenyl)-6-(difluoromethyl)pyridin-2(1H)-one (190 mg, 627 μmol, 97% yield) as a white solid.

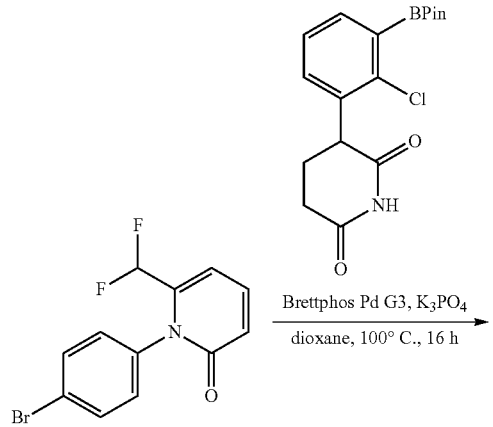

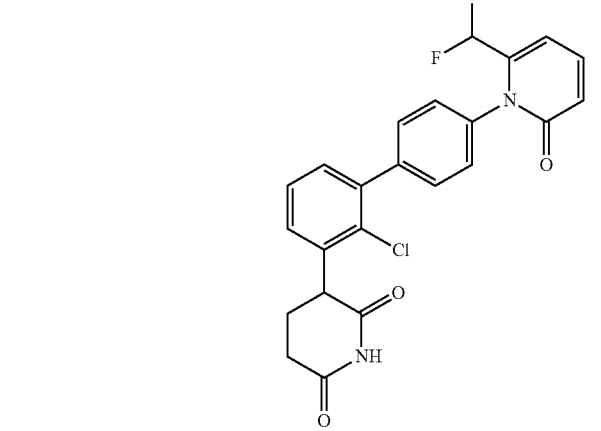

Compound 238

3-(2-chloro-4'-(6-(difluoromethyl)-2-oxopyridin-1(2H)-yl)-[1,1'-biphenyl]-3-yl)piperidine-2,6-dione was prepared from 1-(4-bromophenyl)-6-(difluoromethyl)pyridin-2-one and 3-[2-chloro-3-(4,4,5,5-tetramethyl-1,3,2-dioxaborolan-2-yl)phenyl]piperidine-2,6-dione according to General Scheme 1.

$^1$H NMR (400 MHz, DMSO-$d_6$) δ 10.94 (s, 1H), 7.65 (dd, J=9.2, 6.8 Hz, 1H), 7.57 (d, J=8.4 Hz, 2H), 7.47-7.37 (m, 5H), 6.76-6.69 (m, 2H), 6.55 (t, J=52.8 Hz, 1H), 4.38 (dd, J=12.4, 5.2 Hz, 1H), 2.87-2.75 (m, 1H), 2.59-2.53 (m, 1H), 2.40-2.28 (m, 1H), 2.13-1.99 (m, 1H); MS (ESI) m/z 443.1 [M+H]$^+$

Example 103. Synthesis of 3-(4'-((2-oxopyridin-1 (2H)-yl)methyl)-[1,1'-biphenyl]-3-yl)piperidine-2,6-dione (Compound 239)

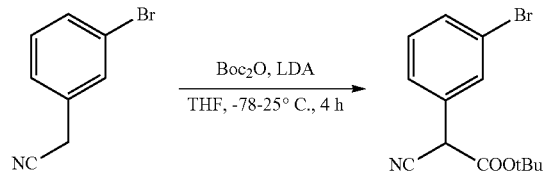

To a solution of 2-(3-bromophenyl)acetonitrile (5.00 g, 25.5 mmol, 1.00 eq) in tetrahydrofuran (80 mL) was added lithium diisopropylamide (2.00 M, 32.0 mL, 2.50 eq) at −78° C., then the reaction mixture was stirred at −78° C. for 1 h and 25° C. for 0.5 h. Di-tert-butyldicarbonate (6.12 g, 28.0 mmol, 6.45 mL, 1.10 eq) in tetrahydrofuran (20 mL) was added to the reaction mixture at −78° C., then the mixture was stirred at −78° C. for 2.5 h. The reaction mixture was quenched with saturated ammonium chloride (100 mL), then extracted with ethyl acetate (3×50 mL), the combined organic layers were washed with brine (100 mL), dried over sodium sulfate, filtered and concentrated under reduced pressure. The residue was purified by flash silica gel chromatography (ISCO®; 120 g SepaFlash® Silica Flash Column, Eluent of 0~4% Ethyl acetate/Petroleum ether gradient @ 150 mL/min) to give tert-butyl 2-(3-bromophenyl)-2-cyanoacetate (7.08 g, 23.7 mmol, 92% yield) as yellow oil.

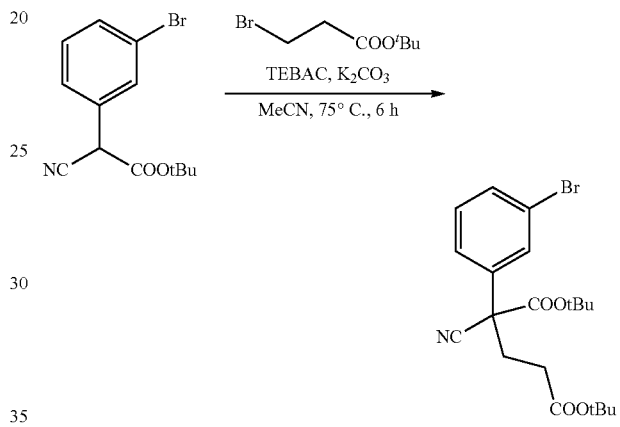

To a solution of tert-butyl 2-(3-bromophenyl)-2-cyanoacetate (5.00 g, 16.9 mmol, 1.00 eq) in acetonitrile (100 mL) was added tert-butyl 3-bromopropanoate (4.24 g, 20.3 mmol, 3.38 mL, 1.20 eq), N-benzyl-N,N,N-triethylammonium chloride (385 mg, 1.69 mmol, 0.100 eq) and potassium carbonate (4.67 g, 33.8 mmol, 2.00 eq). The mixture was stirred at 75° C. for 6 h. The reaction mixture was filtered and concentrated under reduced pressure. The residue was purified by flash silica gel chromatography (ISCO®; 20 g SepaFlash® Silica Flash Column, eluent of 0-5% ethyl acetate/petroleum ether gradient @ 40 mL/min) to give di-tert-butyl 2-(3-bromophenyl)-2-cyanopentanedioate (6.30 g, 14.1 mmol, 83% yield) as colorless oil.

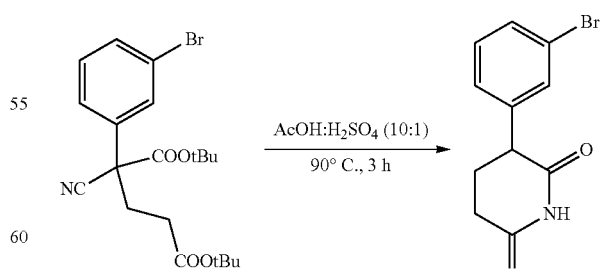

To a solution of di-tert-butyl 2-(3-bromophenyl)-2-cyanopentanedioate (3.00 g, 7.07 mmol, 1.00 eq) in acetic acid (50 mL) was added sulfuric acid (5.52 g, 56.3 mmol, 3.00 ml, 7.96 eq). The mixture was stirred at 90° C. for 3 h.

Cooled to room temperature, the reaction mixture was poured into ice water (200 mL) and the filtered cake was washed with water (3×50 mL) and Petroleum ether/Ethyl acetate (10:1; 3×50 mL). The filter cake was dried under reduced pressure to afford 3-(3-bromophenyl) piperidine-2,6-dione (770 mg, 2.81 mmol, 40% yield) as a white solid.

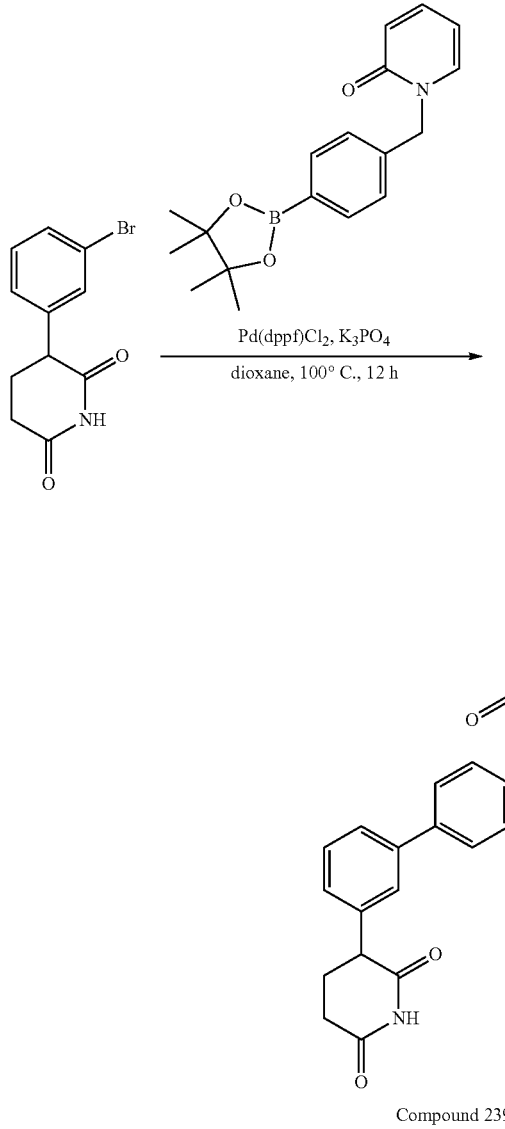

Compound 239

3-(4'-((2-oxopyridin-1(2H)-yl)methyl)-[1,1'-biphenyl]-3-yl)piperidine-2,6-dione was prepared from 3-(3-bromophenyl)piperidine-2,6-dione and 1-methyl-3-((4-(4,4,5,5-tetramethyl-1,3,2-dioxaborolan-2-yl)phenoxy)methyl)-1H-pyrazole according to General Scheme 1.

$^1$H NMR (400 MHz, DMSO-d$_6$) δ=10.85 (s, 1H), 7.82 (d, J=6.0 Hz, 1H), 7.62 (d, J=8.0 Hz, 2H), 7.55-7.49 (m, 2H), 7.40 (dd, J=17.2, 7.8 Hz, 4H), 7.21 (d, J=7.6 Hz, 1H), 6.43 (d, J=9.2 Hz, 1H), 6.25 (t, J=6.4 Hz, 1H), 5.14 (s, 2H), 3.92 (dd, J=11.6, 4.8 Hz, 1H), 2.73-2.65 (m, 1H), 2.56-2.52 (m, 1H), 2.34-2.23 (m, 1H), 2.12-2.03 (m, 1H); MS (ESI) m/z 373.1 [M+H]$^+$

Example 104. Synthesis of 3-(2-chloro-3-(6-((1-methyl-1H-pyrazol-3-yl)methoxy)pyridin-3-yl)phenyl)piperidine-2,6-dione (Compound 251)

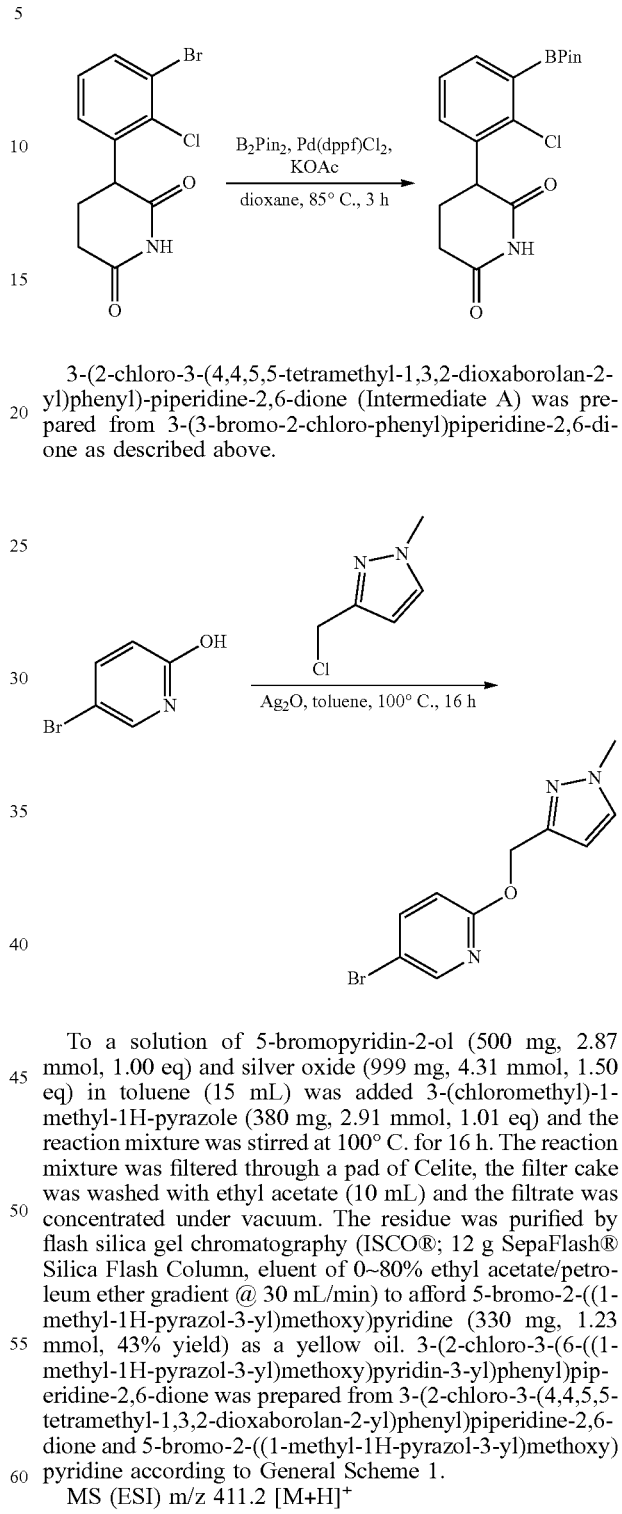

3-(2-chloro-3-(4,4,5,5-tetramethyl-1,3,2-dioxaborolan-2-yl)phenyl)-piperidine-2,6-dione (Intermediate A) was prepared from 3-(3-bromo-2-chloro-phenyl)piperidine-2,6-dione as described above.

To a solution of 5-bromopyridin-2-ol (500 mg, 2.87 mmol, 1.00 eq) and silver oxide (999 mg, 4.31 mmol, 1.50 eq) in toluene (15 mL) was added 3-(chloromethyl)-1-methyl-1H-pyrazole (380 mg, 2.91 mmol, 1.01 eq) and the reaction mixture was stirred at 100° C. for 16 h. The reaction mixture was filtered through a pad of Celite, the filter cake was washed with ethyl acetate (10 mL) and the filtrate was concentrated under vacuum. The residue was purified by flash silica gel chromatography (ISCO®; 12 g SepaFlash® Silica Flash Column, eluent of 0~80% ethyl acetate/petroleum ether gradient @ 30 mL/min) to afford 5-bromo-2-((1-methyl-1H-pyrazol-3-yl)methoxy)pyridine (330 mg, 1.23 mmol, 43% yield) as a yellow oil. 3-(2-chloro-3-(6-((1-methyl-1H-pyrazol-3-yl)methoxy)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-2-((1-methyl-1H-pyrazol-3-yl)methoxy)pyridine according to General Scheme 1.

MS (ESI) m/z 411.2 [M+H]$^+$

Example 105. Synthesis of 3-(2-chloro-4'-morpholino-[1,1'-biphenyl]-3-yl)piperidine-2,6-dione (Compound 338)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-morpholino-[1,1'-biphenyl]-3-yl)piperidine-2,6-dione was prepared from 4-(4-bromophenyl)morpholine and 3-(2-chloro-3-(4,4,5,5-tetramethyl-1,3,2-dioxaborolan-2-yl)phenyl)piperidine-2,6-dione according to General Scheme 1.

MS (ESI) m/z 385.2 [M+H]$^+$

Example 106. Synthesis of 3-(2-chloro-4'-(6-oxo-5-azaspiro[3.5]nonan-5-yl)-[1,1'-biphenyl]-3-yl)piperidine-2,6-dione (Compound 339)

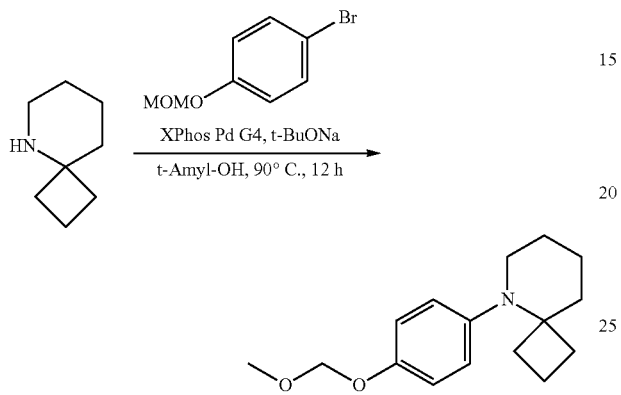

To a solution of 5-azaspiro[3.5]nonane (300 mg, 1.86 mmol, 1.00 eq, hydrochloride), 1-bromo-4-(methoxymethoxy)benzene (604 mg, 2.78 mmol, 1.50 eq) and sodium tert-butoxide (713 mg, 7.42 mmol, 4.00 eq) in 2-methylbutan-2-ol (4 mL) was added methanesulfonato(2-dicyclohexylphosphino-2,4,6-tri-i-propyl-1,1-biphenyl)(2-methylamino-1,1-biphenyl-2-yl)palladium(II) (319 mg, 0.371 mmol, 0.200 eq), the mixture was stirred at 90° C. for 12 h under nitrogen atmosphere. After being cooled to room temperature, the reaction mixture was poured into water (80 mL) and extracted with ethyl acetate (3×40 mL). The combined organic phase was washed with brine (100 mL), dried over anhydrous sodium sulfate, filtered and concentrated in vacuum. The residue was purified by flash silica gel chromatography (ISCO®; 10 g Sepa Flash® Silica Flash Column, eluent of 0%-50% ethyl acetate/petroleum ether gradient @ 30 mL/min) to give 5-(4-(methoxymethoxy)phenyl)-5-azaspiro[3.5]nonane (300 mg, 1.15 mmol, 62% yield) as a yellow solid. $^1$H NMR (400 MHz, DMSO-d$_6$) δ=6.92-6.85 (m, 2H), 6.83-6.76 (m, 2H), 5.09 (s, 2H), 3.36 (s, 3H), 3.01-2.99 (m, 2H), 1.94-1.85 (m, 4H), 1.80-1.73 (m, 2H), 1.66-1.56 (m, 3H), 1.38-1.37 (m, 3H)

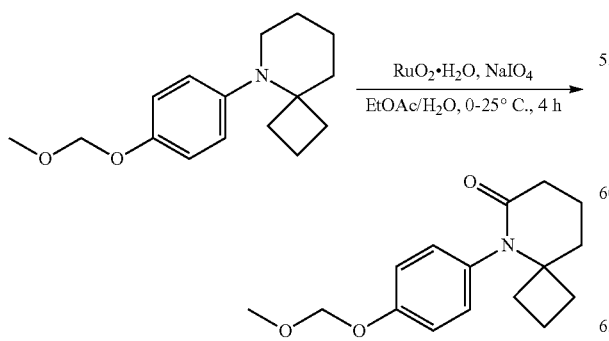

To a solution of sodium periodate (613 mg, 2.87 mmol, 5.00 eq) in water (3 mL) was added ruthenium(IV) oxide hydrate (26.0 mg, 172 pumol, 0.300 eq), the mixture was stirred at 25° C. for 5 min, then 5-(4-(methoxymethoxy)phenyl)-5-azaspiro[3.5]nonane (150 mg, 573 umol, 1.00 eq) in ethyl acetate (3 mL) was added at 0° C., the mixture was stirred at 25° C. for 4 h. The reaction mixture was quenched with saturated aqueous disodium sulfite (50 mL) and then poured into water (50 mL). The aqueous phase was extracted with ethyl acetate (3×60 mL). The combined organic phase was washed with brine (80 mL), dried over anhydrous sodium sulfate, filtered and concentrated in vacuum to give a residue. The residue was purified by Prep-HPLC (column: Phenomenex Luna C18 150 mm×25 mm×10 μm; mobile phase: [water (formic acid)-acetonitrile]; gradient: 38%-68% B over 9 min) to afford 5-(4-(methoxymethoxy)phenyl)-5-azaspiro[3.5]nonan-6-one (20.0 mg, 0.0730 mmol, 6% yield) as a yellow solid.

$^1$H NMR (400 MHz, DMSO-d$_6$) δ=7.09-7.05 (m, 2H), 6.99-6.95 (m, 2H), 5.22 (s, 2H), 3.41 (s, 3H), 2.36 (t, J=6.8 Hz, 2H), 2.15-2.05 (m, 4H), 1.89-1.78 (m, 4H), 1.63-1.51 (m, 1H), 1.40-1.30 (m, 1H)

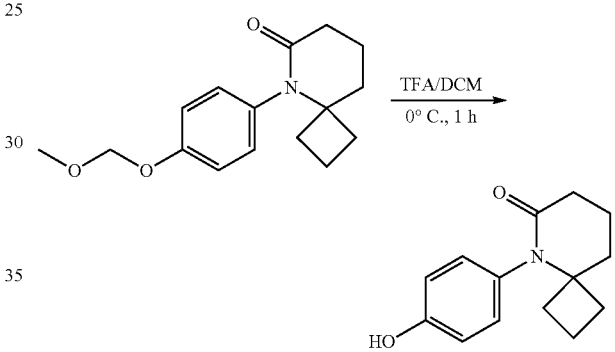

To a solution of 5-(4-(methoxymethoxy)phenyl)-5-azaspiro[3.5]nonan-6-one (20.0 mg, 0.0730 mmol, 1.00 eq) in dichloromethane (1 mL) was added trifluoroacetic acid (1 mL). The mixture was stirred at 0° C. for 1 h. The reaction mixture was concentrated to afford 5-(4-hydroxyphenyl)-5-azaspiro[3.5]nonan-6-one (20.0 mg, crude) as a yellow oil.

MS (ESI) m/z 232.2 [M+H]$^+$

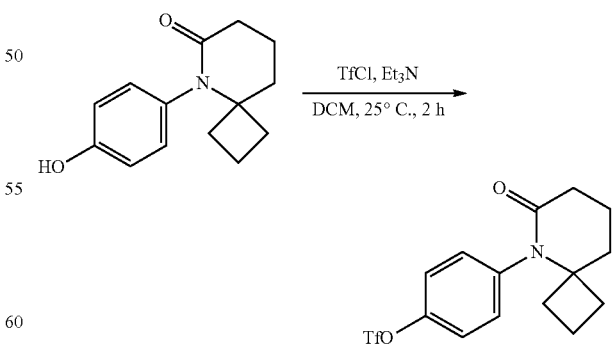

To a solution of 5-(4-hydroxyphenyl)-5-azaspiro[3.5]nonan-6-one (30.0 mg, 0.130 mmol, 1.00 eq) and triethylamine (52.5 mg, 0.519 mmol, 4.00 eq) in dichloromethane (1 mL) was added trifluoromethanesulfonyl chloride (66.0 mg, 0.389 mmol, 3.00 eq). The mixture was stirred at 25° C.

for 2 h. The mixture was concentrated under reduced pressure. The residue was purified by Prep-HPLC (column: Phenomenex luna C18 150 mm×25 mm×10 μm; mobile phase: [water (formic acid)-acetonitrile]; gradient: 45%-75% B over 10 min) to give 4-(6-oxo-5-azaspiro[3.5]nonan-5-yl)phenyl trifluoromethanesulfonate (30.0 mg, 0.0820 mmol, 64% yield) as a yellow solid.

$^1$H NMR (400 MHz, DMSO-d$_6$) δ=7.57 (d, J=8.8 Hz, 2H), 7.28 (d, J=8.8 Hz, 2H), 2.38 (t, J=6.8 Hz, 2H), 2.11-2.06 (m, 2H), 2.04-1.97 (m, 2H), 1.94-1.86 (m, 2H), 1.85-1.77 (m, 2H), 1.68-1.68 (m, 1H), 1.62-1.51 (m, 1H), 1.40-1.26 (m, 1H)

phase: [water (formic acid)-acetonitrile]; gradient: 40%-60% B over 10 min) and lyophilized to afford 3-(2-chloro-4'-(6-oxo-5-azaspiro[3.5]nonan-5-yl)-[1,1'-biphenyl]-3-yl)piperidine-2,6-dione (31.51 mg, 72.0 μmol, 52% yield) as an off white solid.

$^1$H NMR (400 MHz, DMSO-d$_6$) δ=10.92 (s, 1H), 7.48 (d, J=8.4 Hz, 2H), 7.45-7.35 (m, 3H), 7.15 (d, J=8.4 Hz, 2H), 4.36 (dd, J=5.2, 12.0 Hz, 1H), 2.80 (ddd, J=5.2, 12.4, 17.6 Hz, 1H), 2.54-2.51 (m, 1H), 2.39 (t, J=6.8 Hz, 2H), 2.37-2.30 (m, 1H), 2.19-2.02 (m, 5H), 1.96-1.77 (m, 4H), 1.65-1.50 (m, 1H), 1.42-1.28 (m, 1H). MS (ESI) m/z 437.2 [M+H]$^+$ Example 107. Synthesis of 3-(2-chloro-4'-((4-(oxetan-3-yl)pyrimidin-2-yl)methyl)-[1,1'-biphenyl]-3-yl)piperidine-2,6-dione (Compound 340)

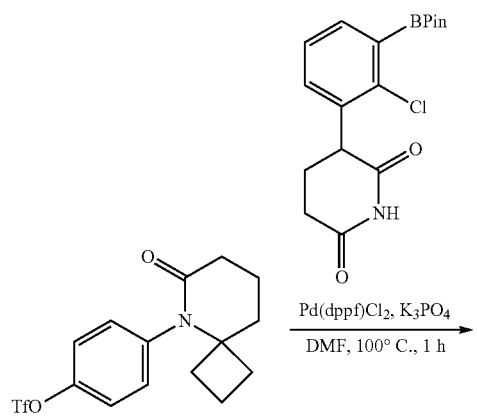

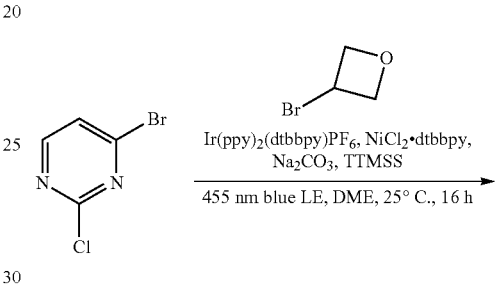

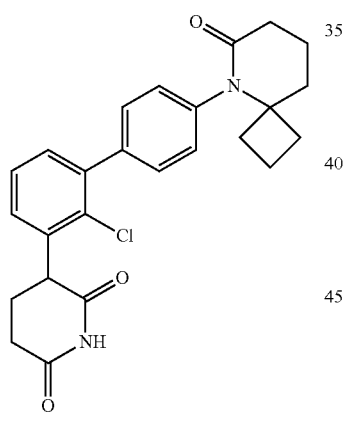

Compound 339

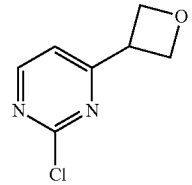

3-(2-chloro-3-(4,4,5,5-tetramethyl-1,3,2-dioxaborolan-2-yl)phenyl)piperidine-2,6-dione (intermediate A) was synthesized as described above. To a solution of 3-(2-chloro-3-(4,4,5,5-tetramethyl-1,3,2-dioxaborolan-2-yl)phenyl)piperidine-2,6-dione (35.0 mg, 0.100 mmol, 1.21 eq), 4-(6-oxo-5-azaspiro[3.5]nonan-5-yl)phenyl trifluoromethanesulfonate (30.0 mg, 0.0826 mmol, 1.00 eq) and potassium phosphate (53.0 mg, 0.250 mmol, 3.00 eq) in dimethylformamide (1 mL) was added [1,1-bis(diphenylphosphino)ferrocene]dichloropalladium(II) (6.00 mg, 8.26 μmol, 0.100 eq), the mixture was stirred at 100° C. for 1 h under nitrogen atmosphere. After being cooled to room temperature, the reaction mixture was filtered to give a filtrate. The residue was purified by Prep-HPLC (column: Phenomenex luna C18 150 mm×25 mm×10 μm; mobile To a solution of 4-bromo-2-chloropyrimidine (250 mg, 1.29 mmol, 1.00 eq) and 3-bromooxetane (230 mg, 1.68 mmol, 1.30 eq) in 1,2-dimethoxyethane (10 mL) was added [4,4'-bis(1,1-dimethylethyl)-2,2'-bipyridine-N,N']bis[3,5-difluoro-2-[5-(trifluoromethyl)-2-pyridinyl-N]phenyl-C] iridium(III) hexafluoro-phosphate (14.5 mg, 0.0129 mmol, 0.0100 eq), bis(trimethylsilyl)silyl-trimethyl-silane (321 mg, 1.29 mmol, 1.00 eq), sodium carbonate (274 mg, 2.58 mmol, 2.00 eq) and [4,4'-bis(1,1-dimethylethyl)-2,2'-bipyridine]nickel(II) dichloride (2.57 mg, 0.00646 mmol, 0.00500 eq). The reaction was stirred and irradiated with a 10 W blue LED lamp (455 nm), with cooling fan to keep the reaction temperature at 25° C. for 16 h. The reaction mixture was concentrated in vacuo. The residue was purified by flash silica gel chromatography (ISCO®; 10 g SepaFlash® Silica Flash Column, Eluent of 0%-100% ethyl acetate/petroleum ether gradient @ 20 mL/min) and Prep-HPLC (column: Phenomenex luna C18 150 mm×25 mm×10 μm; mobile phase: [water (formic acid)-acetonitrile]; gradient: 5%-35% B over 10 min). The desired fraction was collected and lyophilized to give 2-chloro-4-(oxetan-3-yl)pyrimidine (50.0 mg, 0.293 mmol, 23% yield) as a white solid.

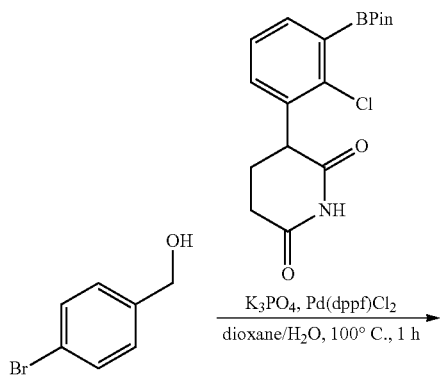
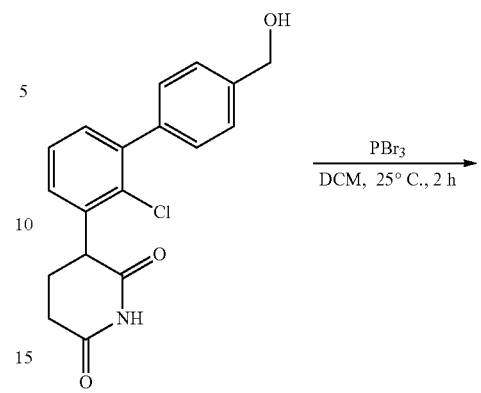

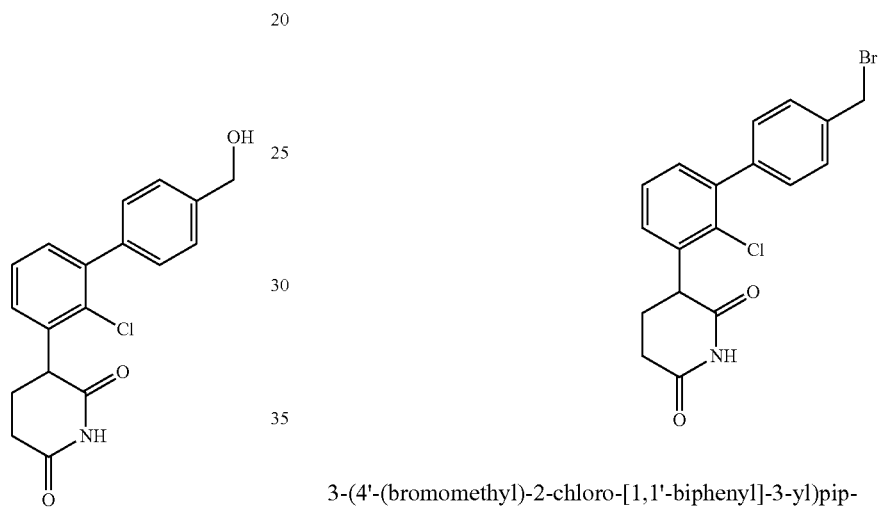

3-(4'-(bromomethyl)-2-chloro-[1,1'-biphenyl]-3-yl)piperidine-2,6-dione (intermediate B) was prepared as described above.

3-(2-chloro-3-(4,4,5,5-tetramethyl-1,3,2-dioxaborolan-2-yl)phenyl)piperidine-2,6-dione (intermediate A) was synthesized as described above. To a solution of 3-[2-chloro-3-(4,4,5,5-tetramethyl-1,3,2-dioxaborolan-2-yl)phenyl]piperidine-2,6-dione (0.880 g, 2.52 mmol, 1.18 eq) in dioxane (16 mL) and water (1.6 mL) was added (4-bromophenyl)methanol (400 mg, 2.14 mmol, 1.00 eq) and potassium phosphate (1.36 g, 6.41 mmol, 3.00 eq) followed by [1,1'-bis(diphenylphosphino)ferrocene]dichloropalladium (II) (0.160 g, 0.218 mmol, 0.100 eq) at 25° C. under nitrogen atmosphere. The reaction was stirred at 100° C. for 1 h. After being cooled to room temperature, the mixture was filtered over celite. The filtrate was concentrated under reduced pressure. The residue was purified by flash silica gel chromatography (ISCO®; 20 g SepaFlash® Silica Flash Column, eluent of 30-60% ethyl acetate/petroleum ether gradient @ 60 mL/min) to give 3-(2-chloro-4'-(hydroxymethyl)-[1,1'-biphenyl]-3-yl)piperidine-2,6-dione (0.150 g, 0.455 mmol, 21% yield) as a white solid.

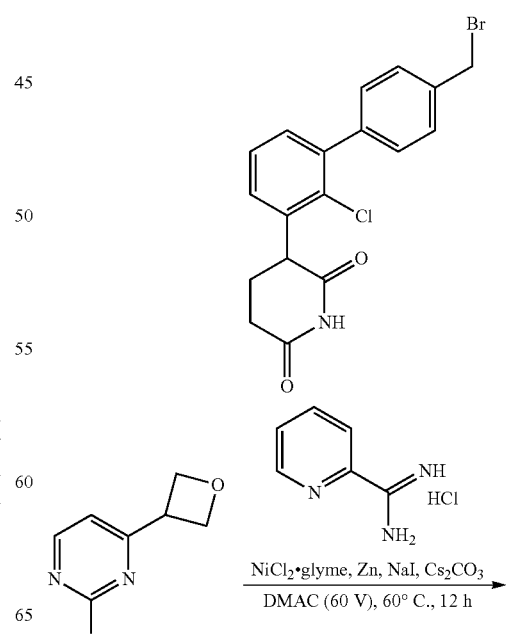

Example 108. Synthesis of 3-(2-chloro-4'-(7-methyl-6-oxo-5,7-diazaspiro[3.4]octan-5-yl)-[1,1'-biphenyl]-3-yl)piperidine-2,6-dione (Compound 341)

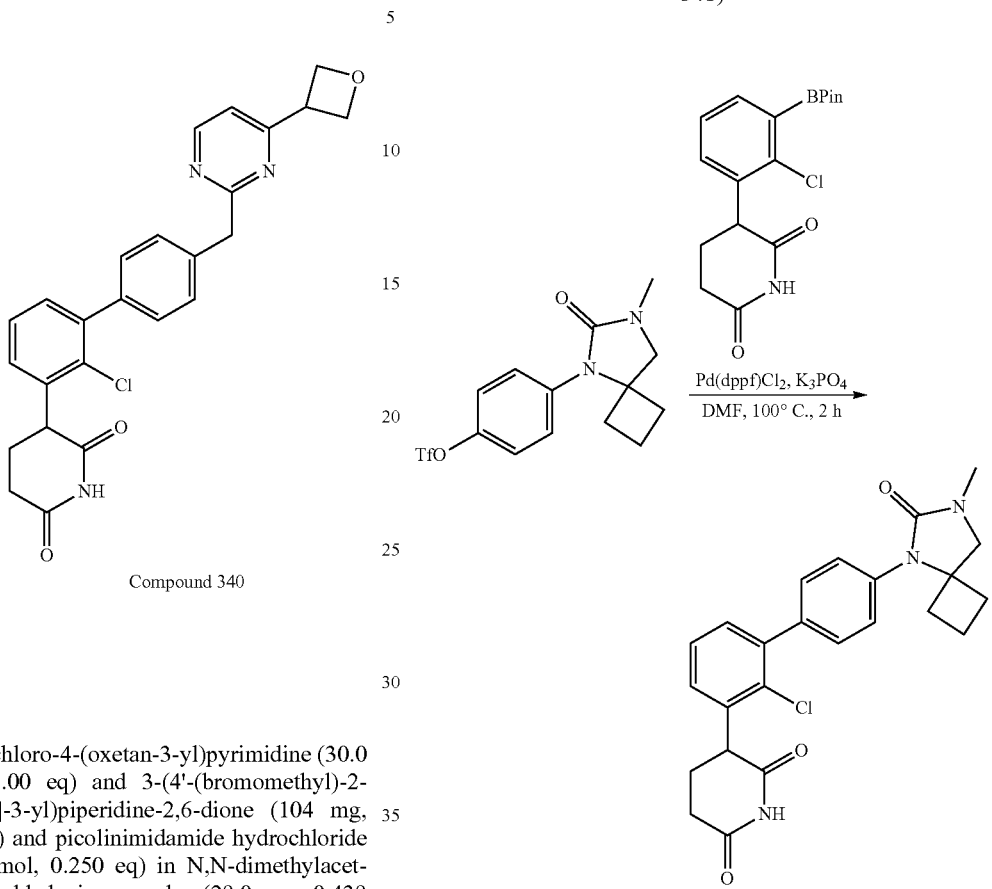

Compound 340

To a solution of 2-chloro-4-(oxetan-3-yl)pyrimidine (30.0 mg, 0.176 mmol, 1.00 eq) and 3-(4'-(bromomethyl)-2-chloro-[1,1'-biphenyl]-3-yl)piperidine-2,6-dione (104 mg, 0.264 mmol, 1.50 eq) and picolinimidamide hydrochloride (7.00 mg, 0.0439 mmol, 0.250 eq) in N,N-dimethylacetamide (2 mL) was added zinc powder (29.0 mg, 0.439 mmol, 2.50 eq), cesium carbonate (115 mg, 0.352 mmol, 2.00 eq), nickel(II) dichloride 1,2-dimethoxyethane (10.05 mg, 0.0457 mmol, 0.26 eq) and sodium iodide (10.0 mg, 0.0669 mmol, 0.380 eq). The mixture was stirred at 60° C. for 12 h under nitrogen. The reaction mixture was cooled to room temperature and filtered, the cake was washed with aqueous 1 M hydrogen chloride for quenching the zinc dust, and the filtrate was poured into water (20 mL). The aqueous phase was extracted with ethyl acetate (3×20 mL). The combined extracts was dried over sodium sulfate, filtered, and concentrated under vacuum. The residue was purified by flash silica gel chromatography (ISCO®; 10 g SepaFlash® Silica Flash Column, Eluent of 0%-100% ethyl acetate/petroleum ether gradient @ 20 mL/min) and prep-HPLC (column: Phenomenex luna C18 150 mm×25 mm×10 μm; mobile phase: [water (formic acid)-acetonitrile]; gradient: 30%-60% B over 10 min).

The desired fraction was collected and lyophilized to afford 3-(2-chloro-4'-((4-(oxetan-3-yl)pyrimidin-2-yl)methyl)-[1,1'-biphenyl]-3-yl)piperidine-2,6-dione (8.28 mg, 18.30 μmol, 10% yield, 99% purity) as a gray solid.

$^1$H NMR (400 MHz, DMSO-d$_6$) δ=10.91 (s, 1H), 8.71 (d, J=5.2 Hz, 1H), 7.44-7.26 (m, 8H), 4.90 (dd, J=5.6, 8.8 Hz, 2H), 4.78 (t, J=6.0 Hz, 2H), 4.43-4.37 (m, 1H), 4.37-4.33 (m, 1H), 4.32-4.27 (m, 2H), 2.80-2.76 (m, 1H), 2.58-2.54 (m, 1H), 2.38-2.29 (m, 1H), 2.11-1.97 (m, 1H); MS (ESI) m/z 448.2 [M+H]$^+$

Compound 341

3-(2-chloro-3-(4,4,5,5-tetramethyl-1,3,2-dioxaborolan-2-yl)phenyl)piperidine-2,6-dione (intermediate A) was synthesized as described above. A mixture of 4-(7-methyl-6-oxo-5,7-diazaspiro[3.4]octan-5-yl)phenyl trifluoromethanesulfonate (137 mg, 274 μmol, 1.00 eq), 3-(2-chloro-3-(4,4,5,5-tetramethyl-1,3,2-dioxaborolan-2-yl)phenyl)piperidine-2,6-dione (100 mg, 274 mol, 1.00 eq), potassium phosphate (174 mg, 823 μmol, 3.00 eq), [1,1-bis(diphenylphosphino)ferrocene]dichloropalladium(II) (20.0 mg, 27.4 μmol, 0.100 eq) in N,N-dimethylformamide (3.00 mL) was degassed and purged with nitrogen for 3 times, and then the mixture was stirred at 100° C. for 2 h. Under nitrogen atmosphere. The reaction mixture was filtered to give a filtrate. The filtrate was purified by reversed-phase column (0.1% formic acid condition) and Prep-HPLC (column: Phenomenex luna C18 150*25 mm*10 um; mobile phase: [water(formicacid condition)-acetonitrile]; gradient: 37%-67% B over 10 min) to afford 3-(2-chloro-4'-(7-methyl-6-oxo-5,7-diazaspiro[3.4]octan-5-yl)-[1,1'-biphenyl]-3-yl)piperidine-2,6-dione (18.84 mg, 42.1 μmol, 15% yield, 98% purity) as a white solid.

$^1$H NMR (400 MHz, DMSO-d$_6$) δ=10.93 (s, 1H), 7.49 (d, J=8.4 Hz, 2H), 7.45-7.36 (m, 3H), 7.26 (br d, J=8.4 Hz, 2H), 4.37 (br dd, J=4.4, 12.0 Hz, 1H), 3.61 (s, 2H), 2.86-2.79 (m, 1H), 2.77 (s, 3H), 2.57 (br d, J=3.2 Hz, 1H), 2.35 (br dd, J=4.0, 12.4 Hz, 1H), 2.25-2.18 (m, 2H), 2.08 (br t, J=4.0 Hz,

1H), 2.06-2.00 (m, 2H), 1.71-1.61 (m, 1H), 1.54-1.45 (m, 1H); MS (ESI) m/z 438.2 [M+H]

Example 109. Synthesis of 3-(2-chloro-4'-(6-methyl-5-oxo-4,6-diazaspiro[2.4]heptan-4-yl)-[1,1'-biphenyl]-3-yl)piperidine-2,6-dione (Compound 342)

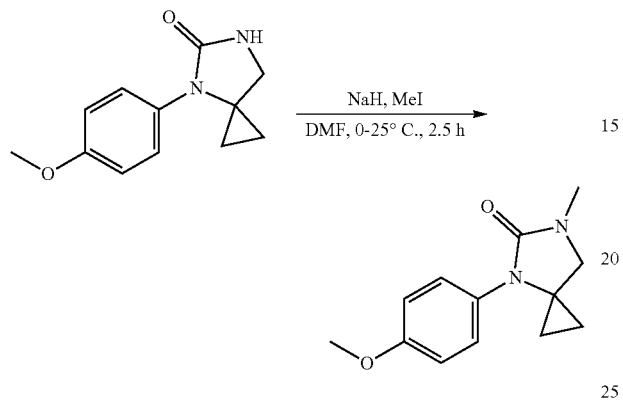

To a solution of 4-(4-methoxyphenyl)-4,6-diazaspiro[2.4]heptan-5-one (0.100 g, 458 µmol, 1.00 eq) in tetrahydrofuran (2.00 mL) was added sodium hydride (36.7 mg, 916 µmol, 60% purity, 2.00 eq) at 0° C. The mixture was stirred at 0° C. for 30 min. Then iodomethane (78.1 mg, 550 mol, 34.2 µL, 1.20 eq) was added at 0° C., the mixture was stirred at 25° C. for 2 hr. The reaction mixture was quenched by addition ammonium chloride 5 mL at 0° C., and then diluted with water 5 mL and extracted with ethyl acetate (3×10 mL). The combined organic layers were washed with brine (2×15 mL), dried over sodium sulfate, filtered and concentrated under reduced pressure to obtain 4-(4-methoxyphenyl)-6-methyl-4,6-diazaspiro[2.4]heptan-5-one (130 mg, crude) as brown oil.

MS (ESI) m/z 232.9 [M+H]⁺

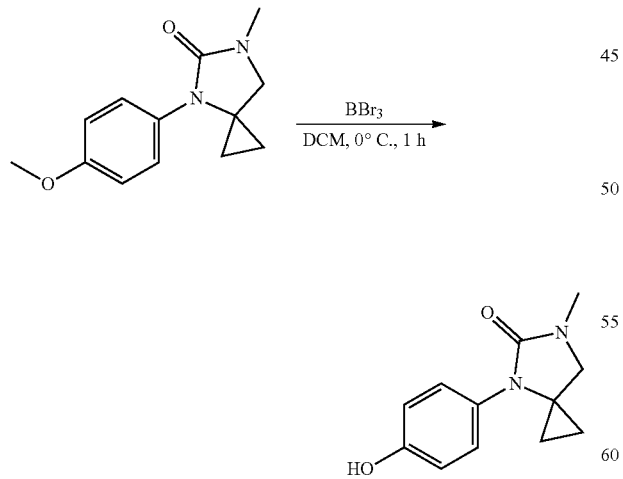

To a solution of 4-(4-methoxyphenyl)-6-methyl-4,6-diazaspiro[2.4]heptan-5-one (130 mg, 560 mol, 1.00 eq) in dichloromethane (1.00 mL) was added boron tribromide (2.00 M, 1.40 mL, 5.00 eq) at 0° C. The mixture was stirred at 0° C. for 1 hr. The reaction was quenched with water (20 mL) and extracted with dichloromethane (3×15 mL). The combined organic phase was separated, washed with brine (30 mL), dried over anhydrous sodium sulfate and concentrated under reduced pressure to obtain 4-(4-hydroxyphenyl)-6-methyl-4,6-diazaspiro[2.4]heptan-5-one (0.100 g, 458 µmol, 82% yield) as brown solid.

MS (ESI) m/z 219.0 [M+H]⁺

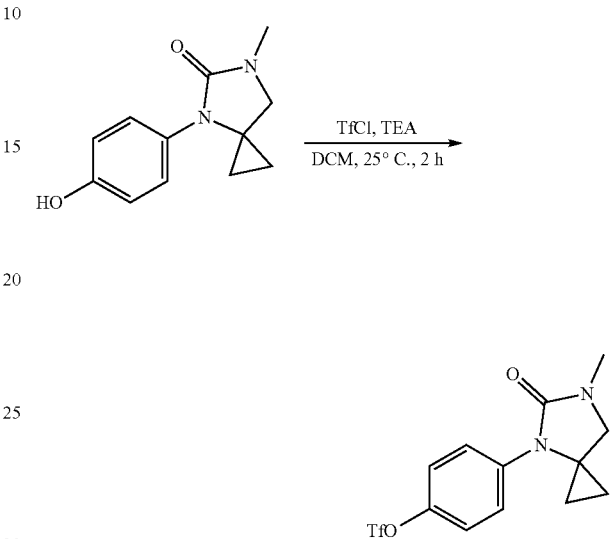

To a solution of 4-(4-hydroxyphenyl)-6-methyl-4,6-diazaspiro[2.4]heptan-5-one (100 mg, 458 mol, 1.00 eq) in dichloromethane (2.00 mL) was added triethylamine (140 mg, 1.37 mmol, 192 L, 3.00 eq) and trifluoromethanesulfonyl chloride (116 mg, 688 µmol, 72.7 µL, 1.50 eq). The mixture was stirred at 25° C. for 2 hr. The mixture was concentrated to give the residue. The crude product was purified by reversed-phase column (0.1% formic acid condition) to obtain 4-(6-methyl-5-oxo-4,6-diazaspiro[2.4]heptan-4-yl)phenyl trifluoromethanesulfonate (70.0 mg, 198 mol, 43% yield, 99% purity) as white solid.

¹H NMR (400 MHz, DMSO-d₆) δ=7.51 (d, J=8.8 Hz, 2H), 7.29 (d, J=9.2 Hz, 2H), 3.52 (s, 2H), 2.80 (s, 3H), 0.71 (s, 2H), 0.63-0.57 (m, 2H); MS (ESI) m/z 351.1 [M+H]⁺

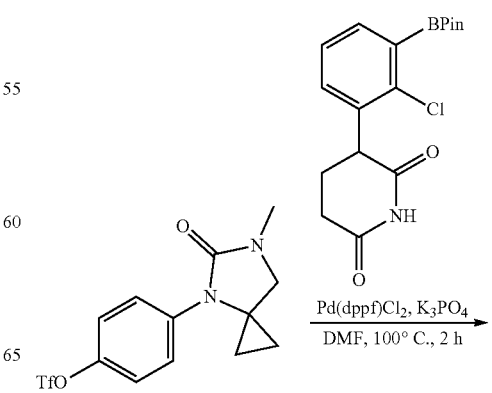

-continued

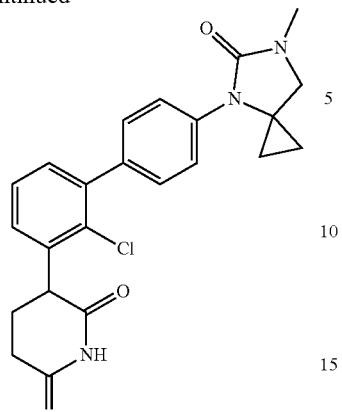

Compound 342

3-(2-chloro-3-(4,4,5,5-tetramethyl-1,3,2-dioxaborolan-2-yl)phenyl)piperidine-2,6-dione (intermediate A) was synthesized as described above. To a solution of 4-(6-methyl-5-oxo-4,6-diazaspiro[2.4]heptan-4-yl)phenyl trifluoromethanesulfonate (50.0 mg, 143 μmol, 1.00 eq) and 3-(2-chloro-3-(4,4,5,5-tetramethyl-1,3,2-dioxaborolan-2-yl)phenyl)piperidine-2,6-dione (74.9 mg, 214 μmol, 1.50 eq) in N,N-dimethylformamide (1.00 mL) was added potassium phosphate (90.9 mg, 428 μmol, 3.00 eq) and [1,1-bis(diphenylphosphino)ferrocene]dichloropalladium(II) (10.5 mg, 14.3 μmol, 0.100 eq). The mixture was stirred at 100° C. for 2 hr. The mixture was diluted with water (5 mL) and extracted with ethyl acetate 30 mL (10 mL×3). The combined organic layers were washed with brine 20 mL (2×10 mL), dried over sodium sulfate, filtered and concentrated under reduced pressure to give a residue. The residue was purified by Prep-HPLC (column: Phenomenex luna C18 150*25 mm*10 um; mobile phase: [water(FA)-MeOH]; gradient: 35%-55% B over 10 min) to obtain 3-(2-chloro-4'-(6-methyl-5-oxo-4,6-diazaspiro[2.4]heptan-4-yl)-[1,1'-biphenyl]-3-yl)piperidine-2,6-dione (20.6 mg, 48.0 μmol, 34% yield, 99% purity) as an off-white solid.

$^1$H NMR (400 MHz, DMSO-d$_6$) δ=10.93 (s, 1H), 7.44-7.32 (m, 5H), 7.17 (d, J=8.4 Hz, 2H), 4.36 (dd, J=4.8, 12.0 Hz, 1H), 3.53 (s, 2H), 2.81 (s, 4H), 2.57 (br d, J=3.2 Hz, 1H), 2.37-2.30 (m, 1H), 2.09-2.03 (m, 1H), 0.77-0.68 (m, 2H), 0.68-0.59 (m, 2H).

$^1$H NMR (400 MHz, CDCl$_3$) δ=8.00 (br s, 1H), 7.43 (d, J=8.4 Hz, 2H), 7.36-7.30 (m, 2H), 7.24-7.17 (m, 3H), 4.35 (dd, J=6.0, 10.4 Hz, 1H), 3.55 (s, 2H), 2.97 (s, 3H), 2.86-2.68 (m, 2H), 2.34 (br dd, J=5.2, 9.2 Hz, 2H), 0.93-0.78 (m, 2H), 0.71-0.57 (m, 2H); MS (ESI) m/z 424.2 [M+H]$^+$

Example 110. Synthesis of 3-(2-chloro-3-(6-fluoro-2-oxo-2H-[1,2'-bipyridin]-5'-yl)phenyl)piperidine-2,6-dione (Compound 343)

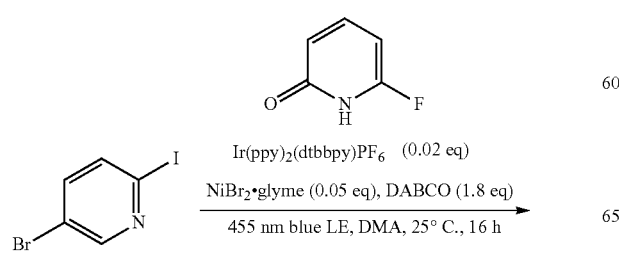

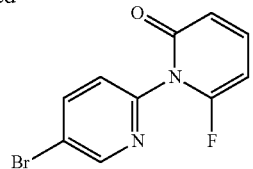

A mixture of 5-bromo-2-iodopyridine (2.00 g, 7.04 mmol, 1.00 eq), 6-fluoropyridin-2(1H)-one (1.59 g, 14.1 mmol, 2.00 eq), (4,4'-di-tert-butyl-2,2'-dipyridyl)-bis-(2-phenylpyridine(-1H))-iridium(III) hexafluorophosphate (129 mg, 141 μmol, 0.0200 eq), nickel(II) bromide dimethoxyethane (109 mg, 352 μmol, 0.0500 eq) and 1,4-diaza-bicyclo[2.2.2]octane (1.42 g, 12.7 mmol, 1.39 mL, 1.80 eq) in N,N-dimethylacetamide (120 mL) was degassed and purged with argon for 3 times, and then the mixture was stirred at 25° C. for 16 hr irradiated with a 455 nm blue LED. The mixture was filtered to obtained the filtrate. The crude product was purified by reversed-phase column (0.1% formic acid condition) to afford 5'-bromo-6-fluoro-2H-[1,2'-bipyridin]-2-one (180 mg, 669 μmol, 10% yield, 99% purity) as brown solid.

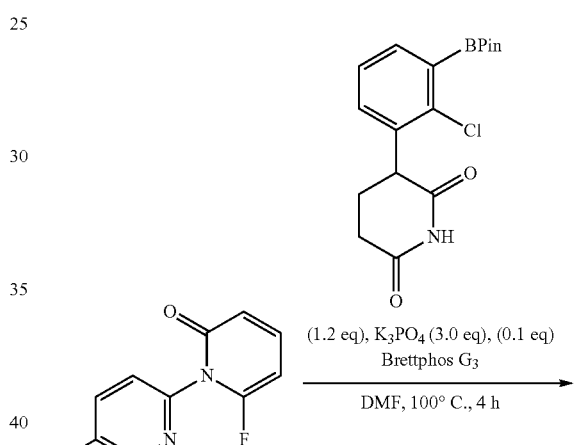

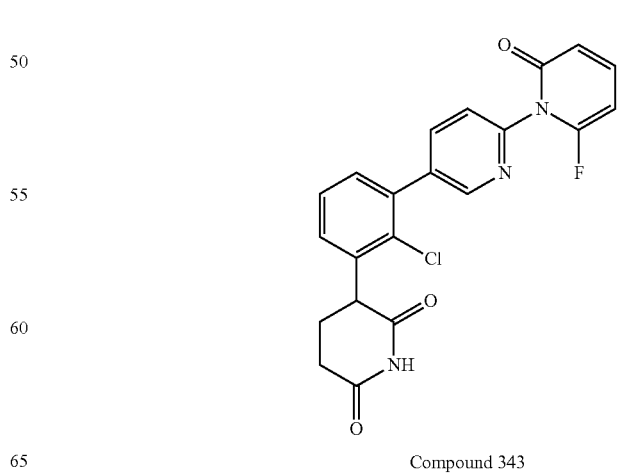

Compound 343

3-(2-chloro-3-(6-fluoro-2-oxo-2H-[1,2'-bipyridin]-5'-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5'-bromo-6-fluoro-2H-[1,2'-bipyridin]-2-one according to General Scheme 1.

$^1$H NMR (400 MHz, CDCl$_3$) δ=8.72 (d, J=2.0 Hz, 1H), 8.03 (dd, J=2.4, 8.0 Hz, 2H), 7.54-7.47 (m, 2H), 7.46-7.39 (m, 2H), 7.34 (dd, J=1.6, 7.6 Hz, 1H), 6.54 (d, J=9.6 Hz, 1H), 6.00 (dd, J=4.8, 7.6 Hz, 1H), 4.37 (dd, J=6.4, 10.4 Hz, 1H), 2.90-2.71 (m, 2H), 2.45-2.28 (m, 2H).

$^1$H NMR (400 MHz, DMSO-d$_6$) δ=10.96 (br s, 1H), 8.70 (d, J=2.4 Hz, 1H), 8.18 (dd, J=2.4, 8.4 Hz, 1H), 7.79-7.61 (m, 2H), 7.55-7.43 (m, 3H), 6.44 (d, J=9.6 Hz, 1H), 6.27 (dd, J=5.2, 7.2 Hz, 1H), 4.42-4.38 (m, 1H), 2.84-2.78 (m, 1H), 2.58 (br d, J=3.2 Hz, 1H), 2.39-2.32 (m, 1H), 2.12-2.06 (m, 1H); MS (ESI) m/z 412.1 [M+H]$^+$

Example 111. Synthesis of 3-(2-chloro-4'-((4-cyclopropylpyrimidin-2-yl)methyl)-[1,1'-biphenyl]-3-yl)piperidine-2,6-dione (Compound 344)

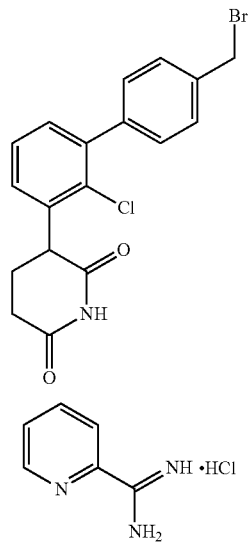

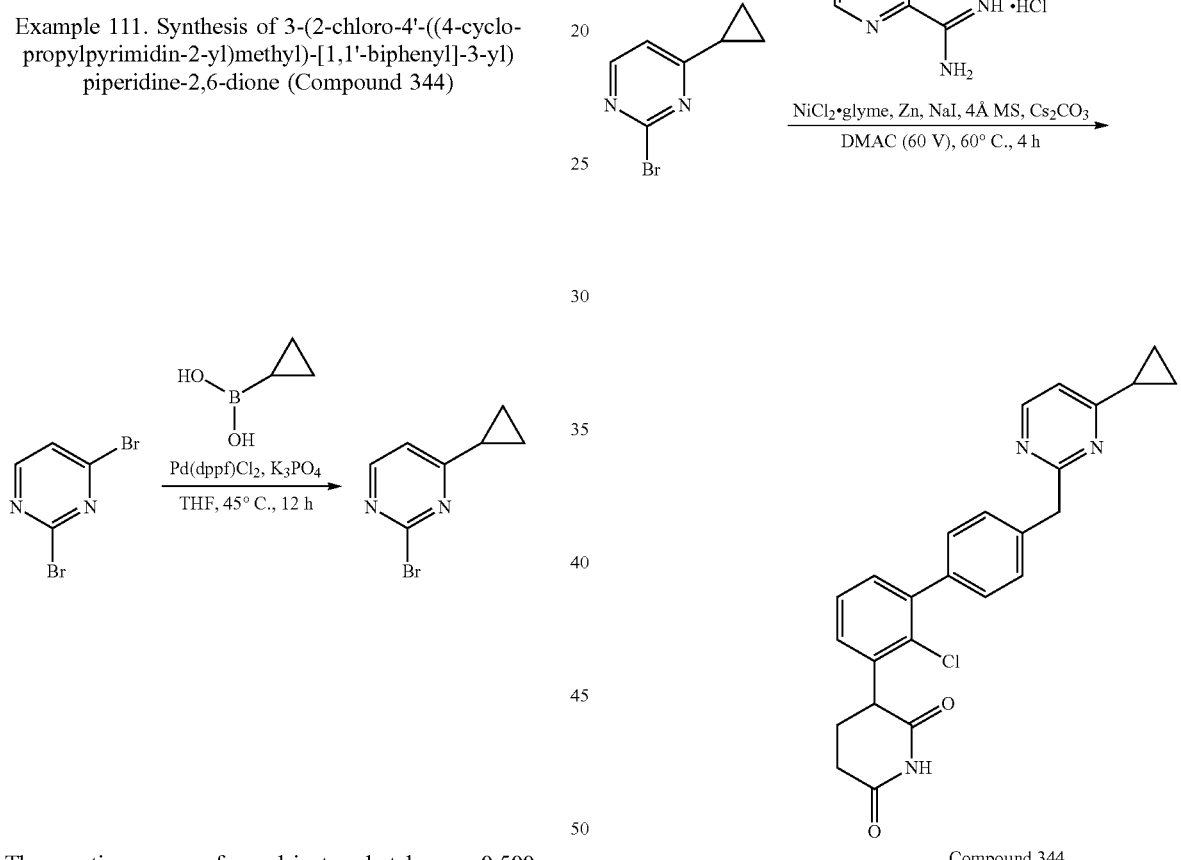

The reaction was performed in two batches on 0.500 g scale batch. To a solution of 2,4-dibromopyrimidine (0.500 g, 2.10 mmol, 1.00 eq) an cyclopropylboronic acid (0.171 g, 1.99 mmol, 0.90 eq) in tetrahydrofuran (15 mL) was added potassium phosphate (1.34 g, 6.31 mmol, 3.00 eq) followed by [1,1'-bis(diphenylphosphino)ferrocene]dichloropalladium(II) (0.172 g, 0.211 mmol, 0.100 eq) at 25° C. The reaction was stirred at 45° C. for 12 h under nitrogen atmosphere. After being cooled to room temperature, the reaction mixture was diluted with ethyl acetate (20 mL). The solvents were washed with brine (3×20 mL), dried over sodium sulfate and filtered. The filtrate was concentrated under reduced pressure. The residue was purified by column chromatography (silica, petroleum ether:ethyl acetate=1:0 to 10:1) to give 2-bromo-4-cyclopropylpyrimidine (0.300 g, 1.51 mmol, 36% yield) as colorless oil.

3-(2-chloro-4'-((4-cyclopropylpyrimidin-2-yl)methyl)-[1,1'-biphenyl]-3-yl)piperidine-2,6-dione was prepared from 3-(4'-(bromomethyl)-2-chloro-[1,1'-biphenyl]-3-yl)piperidine-2,6-dione and 2-bromo-4-cyclopropylpyrimidine analogously to Example 107.

$^1$H NMR (400 MHz, DMSO-d$_6$) δ=10.91 (s, 1H), 8.50 (d, J=5.2 Hz, 1H), 7.38-7.27 (m, 7H), 7.23 (d, J=5.2 Hz, 1H), 4.33 (dd, J=4.8, 12.0 Hz, 1H), 4.14 (s, 2H), 2.83-2.74 (m, 1H), 2.57-2.55 (m, 1H), 2.35-2.31 (m, 1H), 2.12-2.02 (m, 2H), 1.10-1.00 (m, 4H); MS (ESI) m/z 432.1 [M+H]$^+$

Example 112. Synthesis of 3-(2-chloro-4'-(5-oxo-6-oxa-4-azaspiro[2.5]octan-4-yl)-[1,1'-biphenyl]-3-yl)piperidine-2,6-dione (Compound 345)

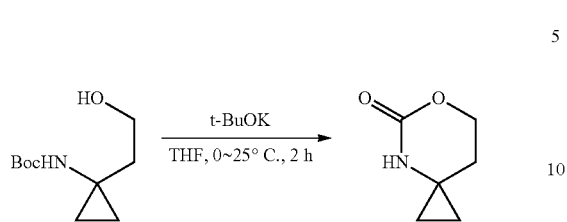

To a solution of tert-butyl (1-(2-hydroxyethyl)cyclopropyl)carbamate (200 mg, 993 μmol, 1.00 eq) in tetrahydrofuran (2.00 mL) was added potassium tert-butoxide (167 mg, 1.49 mmol, 1.50 eq) at 0° C. The reaction was stirred at 25° C. for 2 h. The reaction was concentrated under reduced pressure to give a residue. The residue was purified by column chromatography (SiO2, Petroleum ether/Ethyl acetate=2/1 to 1/1) to afford 6-oxa-4-azaspiro[2.5]octan-5-one (170 mg, 1.34 mmol, 67% yield) as a white solid.

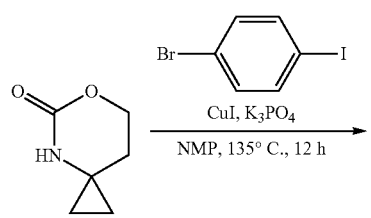

4-(4-bromophenyl)-6-oxa-4-azaspiro[2.5]octan-5-one was prepared from 6-oxa-4-azaspiro[2.5]octan-5-one and 1-bromo-4-iodobenzene according to General Scheme 7.

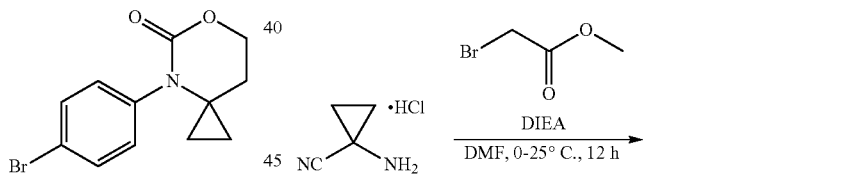

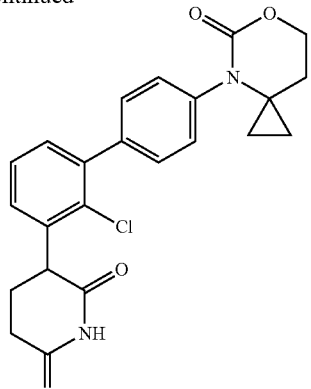

Compound 345

3-(2-chloro-4'-(5-oxo-6-oxa-4-azaspiro[2.5]octan-4-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(4-bromophenyl)-6-oxa-4-azaspiro[2.5]octan-5-one according to General Scheme 1.

$^1$H NMR (400 MHz, DMSO-d$_6$) δ=10.92 (s, 1H), 7.44-7.38 (m, 3H), 7.35-7.34 (m, 1H), 7.34-7.33 (m, 1H), 7.23 (d, J=8.4 Hz, 2H), 4.48 (t, J=5.6 Hz, 2H), 4.35 (dd, J=12.0, 4.8 Hz, 1H), 2.84-2.79 (m, 1H), 2.57-2.56 (m, 1H), 2.35-2.33 (m, 1H), 2.12 (t, J=5.6 Hz, 2H), 2.09-2.06 (m, 1H), 0.75-0.71 (m, 2H), 0.58-0.50 (m, 2H); MS (ESI) m/z 425.1 [M+H]$^+$

Example 113. Synthesis of 3-(2-chloro-3-(6-(4-methyl-6-oxo-4,7-diazaspiro[2.5]octan-7-yl)pyridin-3-yl)phenyl)piperidine-2,6-dione (Compound 346)

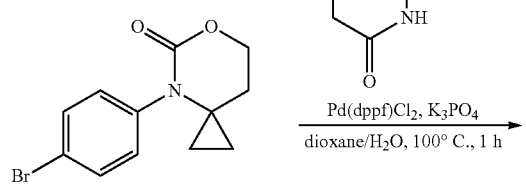

To a solution of 1-aminocyclopropane-1-carbonitrile hydrochloride (2.00 g, 16.87 mmol, 1.00 eq) and diisopropylethylamine (6.54 g, 50.6 mmol, 3.00 eq) in N,N-dimethylformamide (10 mL) was added methyl 2-bromoacetate (3.87 g, 25.3 mmol, 1.50 eq) at 0° C. The reaction was stirred at 25° C. for 12 h. The reaction was quenched with water (20 mL) and extracted with ethyl acetate (3×15 mL). The combined organic extracts were washed with saturated sodium bicarbonate (3×15 mL) and brine (2×10 mL), dried over sodium sulfate and filtered. The filtrate was concentrated under reduced pressure to give a residue. The residue was purified by flash silica gel chromatography (ISCO®; 20 g SepaFlash® Silica Flash Column, Eluent of 0%-50% ethyl acetate/petroleum ether gradient at 60 mL/min) to give methyl (1-cyanocyclopropyl)glycinate (1.00 g, 6.49 mmol, 38% yield) as colorless liquid.

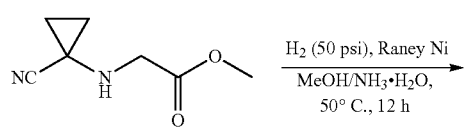

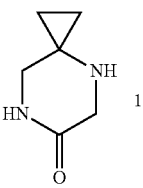

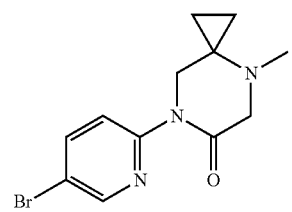

To a mixture of methyl (1-cyanocyclopropyl)glycinate (0.800 g, 5.19 mmol, 1.00 eq) in methanol (8 mL) and ammonium hydroxide (2 mL) was added Raney-nickel (0.800 g, 9.34 mmol, 1.80 eq) under nitrogen. The solution was purge with hydrogen for three times and then stirred at 50° C. for 12 h under hydrogen atmosphere (50 Psi). The reaction mixture was cooled to room temperature and filtered over Celite and the filtrate was concentrated under reduced pressure to give a residue. The residue was purified by flash silica gel chromatography (ISCO®; 12 g Sepa-Flash® Silica Flash Column, Eluent of 0%-10% methanol/ethyl acetate gradient at 50 mL/min) to give 4,7-diazaspiro[2.5]octan-6-one (0.350 g, 2.77 mmol, 53% yield) as a yellow solid.

To a solution of 7-(5-bromopyridin-2-yl)-4,7-diazaspiro[2.5]octan-6-one (0.150 g, 0.532 mmol, 1.00 eq) in methanol (2 mL) was added formaldehyde (0.216 g, 2.66 mmol, 37% purity, 5.00 eq) and sodium cyanoborohydride (0.100 g, 1.59 mmol, 3.00 eq). The mixture was stirred at 25° C. for 0.5 h. The reaction was concentrated under reduced pressure to give a residue. The residue was purified by Prep-HPLC (column: Phenomenex luna C18 150 mm×25 mm×10 µm; mobile phase: [water(formic acid)-acetonitrile]; gradient: 12%-32% B over 10 min) to give 7-(5-bromopyridin-2-yl)-4-methyl-4,7-diazaspiro[2.5]octan-6-one (0.0700 g, 0.236 mmol, 44% yield, 99% purity) as a white solid.

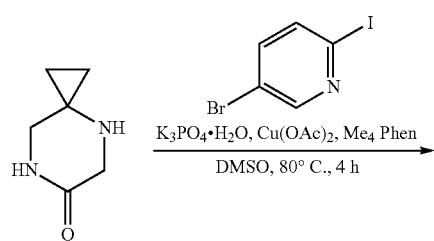

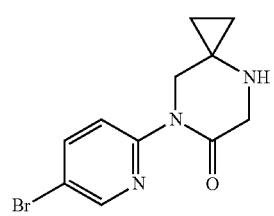

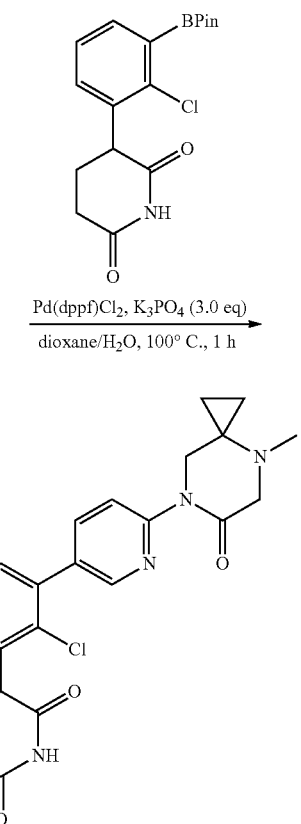

To a solution of 4,7-diazaspiro[2.5]octan-6-one (200 mg, 1.59 mmol, 1.00 eq) and 5-bromo-2-iodopyridine (502 mg, 1.77 mmol, 1.12 eq) in dimethylsulfoxide (2 mL) was added diacetoxycopper (28.8 mg, 0.159 mmol, 0.100 eq), potassium phosphate monohydrate (730 mg, 3.17 mmol, 2.00 eq) and 3,4,7,8-tetramethyl-1,10-phenanthroline (56.2 mg, 0.238 mmol, 0.15 eq). The mixture was stirred at 80° C. for 4 h under nitrogen. The reaction mixture was cooled to room temperature and filtered over Celite and the filtrate was concentrated under reduced pressure to give a residue. The residue was purified by flash silica gel chromatography (ISCO®; 12 g SepaFlash® Silica Flash Column, Eluent of 0%-50% ethyl acetate/petroleum ether gradient at 50 mL/min) to give 7-(5-bromopyridin-2-yl)-4,7-diazaspiro[2.5]octan-6-one (0.150 g, 0.532 mmol, 34% yield) as a white solid.

Compound 346

3-(2-chloro-3-(6-(4-methyl-6-oxo-4,7-diazaspiro[2.5]octan-7-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 7-(5-bromopyridin-2-yl)-4-methyl-4,7-diazaspiro[2.5]octan-6-one according to General Scheme 1.

$^1$H NMR (400 MHz, DMSO-$d_6$) δ=10.93 (s, 1H), 8.47 (d, J=2.0 Hz, 1H), 8.09 (d, J=8.8 Hz, 1H), 7.91-7.89 (m, 1H), 7.47-7.39 (m, 3H), 4.38-4.34 (m, 1H), 3.92 (s, 2H), 3.49 (s, 2H), 2.80-2.78 (m, 1H), 2.52 (s, 1H), 2.43 (s, 3H), 2.39-2.33 (m, 1H), 2.07-2.06 (m, 1H), 0.78-0.69 (m, 4H); MS (ESI) m/z 439.2 [M+H]$^+$

Example 114. Synthesis of 3-(2-chloro-4'-((4-(trifluoromethyl) pyrimidin-2-yl)methyl)-[1,1'-biphenyl]-3-yl)piperidine-2,6-dione (Compound 347)

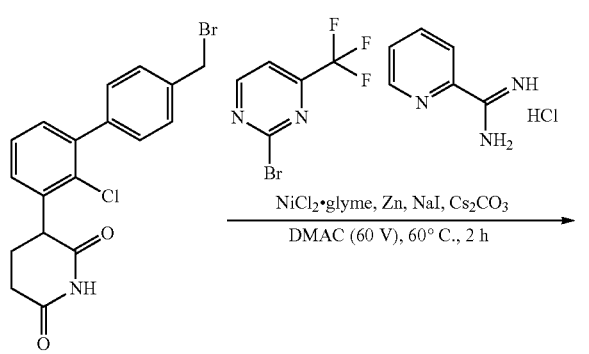

Compound 347

3-(2-chloro-4'-((4-(trifluoromethyl)pyrimidin-2-yl)methyl)-[1,1'-biphenyl]-3-yl)piperidine-2,6-dione was prepared from 3-(4'-(bromomethyl)-2-chloro-[1,1'-biphenyl]-3-yl)piperidine-2,6-dione and 2-bromo-4-(trifluoromethyl)pyrimidine analogously to Example 107.

$^1$H NMR (400 MHz, DMSO-$d_6$) δ=10.91 (s, 1H), 9.16 (d, J=4.8 Hz, 1H), 7.92 (d, J=4.8 Hz, 1H), 7.49-7.32 (m, 6H), 7.29 (dd, J=2.0, 6.4 Hz, 1H), 4.40 (s, 2H), 4.33 (dd, J=5.2, 12.4 Hz, 1H), 2.78-2.74 (m, 1H), 2.58-2.53 (m, 1H), 2.37-2.31 (m, 1H), 2.10-1.99 (m, 1H) MS (ESI) m/z 460.2 [M+H]$^+$

Example 115. Synthesis of 3-(2-chloro-4'-((4-(difluoromethyl)pyrimidin-2-yl)methyl)-[1,1'-biphenyl]-3-yl)piperidine-2,6-dione (Compound 348)

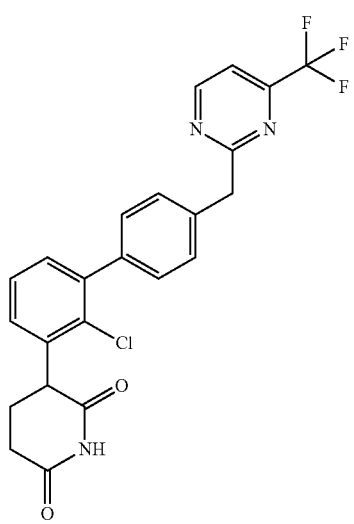

A mixture of 2-chloro-4-(difluoromethyl)pyrimidine (0.200 g, 1.22 mmol, 1.00 eq) in hydrobromic acid (1.20 mL, 7.29 mmol, 30 wt. % hydrobromic acid in the acetic acid, 6.00 eq) was stirred at 30° C. for 1.5 h. The mixture was stirred at 120° C. for 15 min. The reaction mixture was cooled to room temperature and quenched with ice water (10 mL). The pH was neutralized to 7 with saturated sodium bicarbonate solution. The mixture was extracted with ethyl acetate (3×10 mL). The organic phase was separated, washed with brine (10 mL) and then dried over sodium sulfate, filtered and concentrated under reduced pressure to give a residue. The residue was purified by flash silica gel chromatography (ISCO®; 10 g SepaFlash® Silica Flash Column, eluent of 0%-13% ethyl acetate/petroleum ether gradient @ 40 mL/min).

The desired fraction was collected and concentrated in vacuo to give 2-bromo-4-(difluoromethyl) pyrimidine (0.147 g, 0.703 mmol, 58% yield) as a white solid.

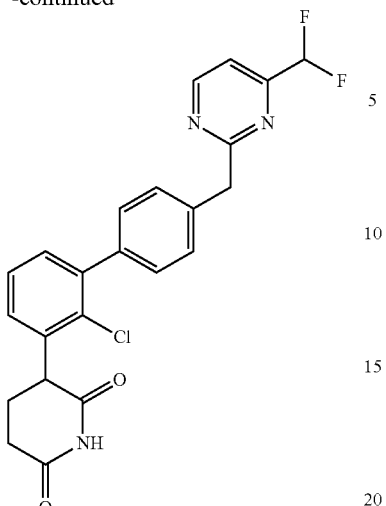

Compound 348

3-(2-chloro-4'-((4-(difluoromethyl)pyrimidin-2-yl)methyl)-[1,1'-biphenyl]-3-yl)piperidine-2,6-dione was prepared from 3-(4'-(bromomethyl)-2-chloro-[1,1'-biphenyl]-3-yl)piperidine-2,6-dione and 2-bromo-4-(difluoromethyl)pyrimidine analogously to Example 107.

$^1$H NMR (400 MHz, DMSO-d$_6$) δ=10.92 (s, 1H), 9.03 (d, J=5.2 Hz, 1H), 7.68 (d, J=5.2 Hz, 1H), 7.43-7.33 (m, 6H), 7.32-7.27 (m, 1H), 7.01 (t, J=54.0 Hz, 1H), 4.36 (s, 2H), 4.32 (br d, J=5.2 Hz, 1H), 2.85-2.74 (m, 1H), 2.58-2.55 (m, 1H), 2.36-2.31 (m, 1H), 2.10-2.00 (m, 1H); MS (ESI) m/z 442.2 [M+H]$^+$

Example 116. Synthesis of 3-(2-chloro-4'-(6-oxo-5,7-diazaspiro[3.5]nonan-5-yl)-[1,1'-biphenyl]-3-yl)piperidine-2,6-dione (Compound 349)

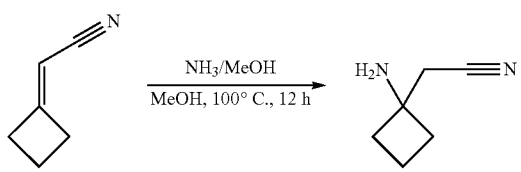 [SMILES: N#CC=C1CCC1 ; N#CCC1(N)CCC1]

A mixture of 2-cyclobutylideneacetonitrile (2.00 g, 21.5 mmol, 1.00 eq) in ammonia/methanol (7.00 M, 30.7 mL, 10.0 eq). The mixture was stirred at 100° C. for 12 h. The reaction mixture was concentrated in vacuum. The residue was purified by column chromatography (SiO$_2$, Petroleum ether/Ethyl acetate=5/1 to 0/1) and concentrated in vacuum to give 2-(1-aminocyclobutyl) acetonitrile (1.70 g, 15.4 mmol, 71% yield) as yellow oil.

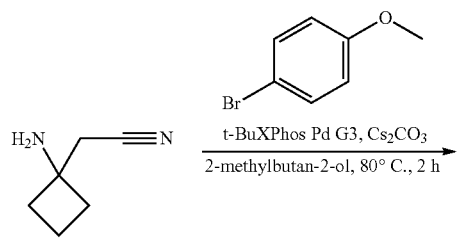

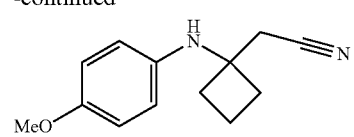

To a mixture of 1-bromo-4-methoxy-benzene (2.89 g, 15.4 mmol, 1.93 mL, 1.00 eq) and 2-(1-aminocyclobutyl)acetonitrile (1.70 g, 15.4 mmol, 1.00 eq) in 2-methylbutan-2-ol (20.0 mL) was added cesium carbonate (15.1 g, 46.3 mmol, 3.00 eq) and [2'-(Amino)[1,1'-biphenyl]-2-yl][bis(1,1-dimethylethyl)[2',4',6'-tris(1-methylethyl)[1,1'-biphenyl]-2-yl]phosphine](methanesulfonato)palladium(II) (1.23 g, 1.54 mmol, 0.100 eq). The mixture was stirred at 80° C. for 2 h under nitrogen atmosphere. The reaction mixture was filtered. The filtrate was purified by reversed phase HPLC (column: spherical C18, 20-45 um, 100 Å, SW 220, mobile phase: [water (0.1% formic acid)-acetonitrile) and lyophilized. The reverse collection was purified by column chromatography (SiO$_2$, Petroleum ether/Ethyl acetate=1/0 to 1/1) and to give 2-(1-((4-methoxyphenyl) amino)cyclobutyl) acetonitrile (700 mg, 3.24 mmol, 20% yield) as a white solid.

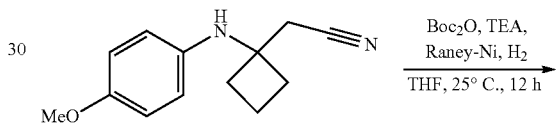

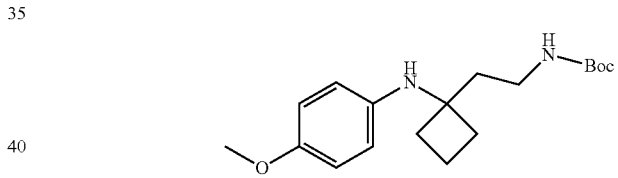

To a solution of raney nickel (70.0 mg) in tetrahydrofuran (10.0 mL) was added 2-(1-((4-methoxyphenyl)amino)cyclobutyl)acetonitrile (700 mg, 3.24 mmol, 1.00 eq), di-tert-butyldicarbonate (2.12 g, 9.71 mmol, 2.23 mL, 3.00 eq) and triethylamine (982 mg, 9.71 mmol, 1.35 mL, 3.00 eq) in tetrahydrofuran (10.0 mL) under nitrogen atmosphere. The suspension was degassed under vacuum and purged with hydrogen several times. The mixture was stirred under hydrogen at 25° C. for 12 h. The reaction mixture was filtered and the filtrate was concentrated under reduced pressure to give a residue. The residue was purified by Prep-TLC (SiO$_2$, Petroleum ether/Ethyl acetate=3:1) and concentrated in vacuum to give tert-butyl (2-(1-((4-methoxyphenyl)amino)cyclobutyl)ethyl)carbamate (970 mg, 3.03 mmol, 93% yield) as yellow oil.

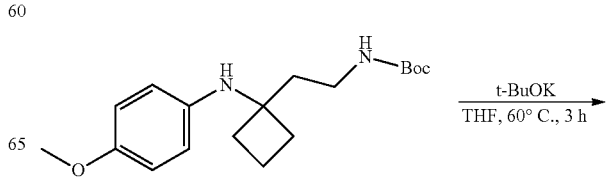

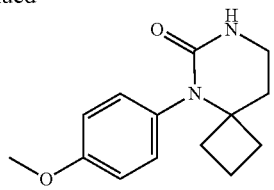

To a mixture of tert-butyl (2-(1-((4-methoxyphenyl) amino)cyclobutyl)ethyl)carbamate (970 mg, 3.03 mmol, 1.00 eq) in tetrahydrofuran (15.0 mL) was added potassium tert-butoxide (1.02 g, 9.08 mmol, 3.00 eq). The mixture was stirred at 60° C. for 3 h. The reaction mixture was diluted with water (50.0 mL) and extracted with ethyl acetate (3×60 mL). The combined organic layers were washed with brine (60 mL), dried over sodium sulfate, filtered and concentrated under reduced pressure to give 5-(4-methoxyphenyl)-5,7-diazaspiro[3.5]nonan-6-one (560 mg, 2.02 mmol, 66% yield, 89% purity) as a yellow solid.

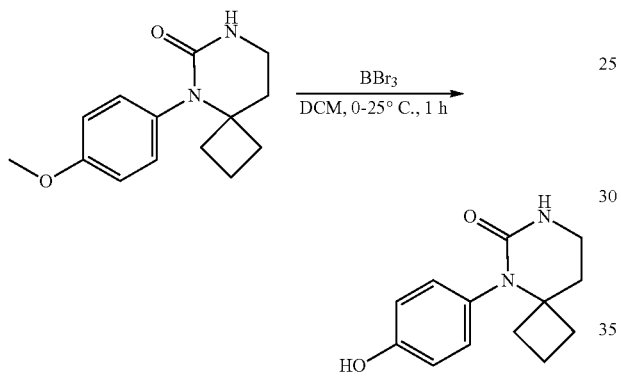

To a solution of 5-(4-methoxyphenyl)-5,7-diazaspiro[3.5]nonan-6-one (560 mg, 2.27 mmol, 1.00 eq) in dichloromethane (6.00 mL) was added boron tribromide (2.85 g, 11.4 mmol, 1.10 mL, 5.00 eq) at 0° C., then the mixture was stirred at 0° C. for 1 h. The reaction mixture was quenched by water (30 mL) and extracted with ethyl acetate (3×60 mL). The combined organic phase was separated, washed with brine (50 mL), dried over anhydrous sodium sulfate and concentrated to give 5-(4-hydroxyphenyl)-5,7-diazaspiro[3.5]nonan-6-one (440 mg, crude) as a brown solid.

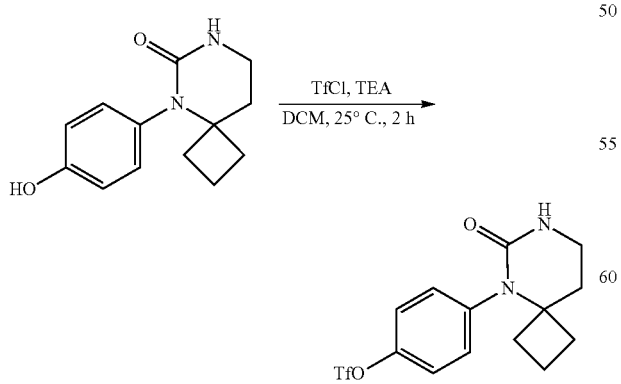

To a solution of 5-(4-hydroxyphenyl)-5,7-diazaspiro[3.5]nonan-6-one (440 mg, 1.89 mmol, 1.00 eq) in dichloromethane (5.00 mL) was added triethylamine (767 mg, 7.58 mmol, 1.05 mL, 4.00 eq) and trifluoromethanesulfonyl chloride (958 mg, 5.68 mmol, 601 µL, 3.00 eq), then the mixture was stirred at 25° C. for 2 h. The reaction mixture was concentrated in vacuum. The crude product was purified by reversed phase HPLC (column: spherical C18, 20-45 um, 100 Å, SW 120, mobile phase: [water (0.1% formic acid)-acetonitrile) and lyophilized to give 4-(6-oxo-5,7-diazaspiro[3.5]nonan-5-yl)phenyl trifluoromethanesulfonate (150 mg, 412 µmol, 21% yield) as a white solid.

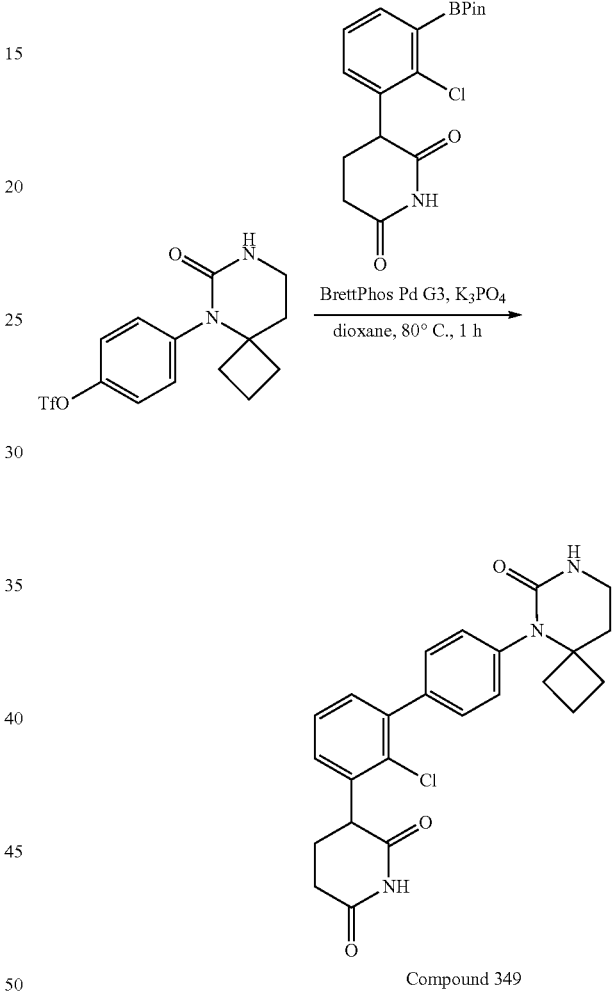

Compound 349

3-(2-chloro-4'-(6-oxo-5,7-diazaspiro[3.5]nonan-5-yl)-[1,1'-biphenyl]-3-yl)piperidine-2,6-dione was prepared from 3-(2-chloro-3-(4,4,5,5-tetramethyl-1,3,2-dioxaborolan-2-yl) phenyl)piperidine-2,6-dione (intermediate A) and 4-(6-oxo-5,7-diazaspiro[3.5]nonan-5-yl)phenyl trifluoromethanesulfonate according to General Scheme 1.

$^1$H NMR (400 MHz, DMSO-$d_6$) δ=10.92 (s, 1H), 7.45-7.43 (m, 1H), 7.43-7.39 (m, 2H), 7.37 (d, J=1.6 Hz, 1H), 7.36-7.34 (m, 1H), 7.18-7.13 (m, 2H), 6.59 (s, 1H), 4.36 (dd, J=5.2, 12.4 Hz, 1H), 3.28-3.22 (m, 2H), 2.86-2.75 (m, 1H), 2.59-2.52 (m, 1H), 2.34 (dq, J=4.0, 12.4 Hz, 1H), 2.13-2.03 (m, 5H), 1.86 (br t, J=9.2 Hz, 2H), 1.65-1.54 (m, 1H), 1.45-1.34 (m, 1H).

MS (ESI) m/z. 438.0 [M+H]$^+$

Example 117. Synthesis of 3-(2-chloro-3'-fluoro-4'-(5-oxo-4-azaspiro[2.5]octan-4-yl)-[1,1'-biphenyl]-3-yl)piperidine-2,6-dione (Compound 350)

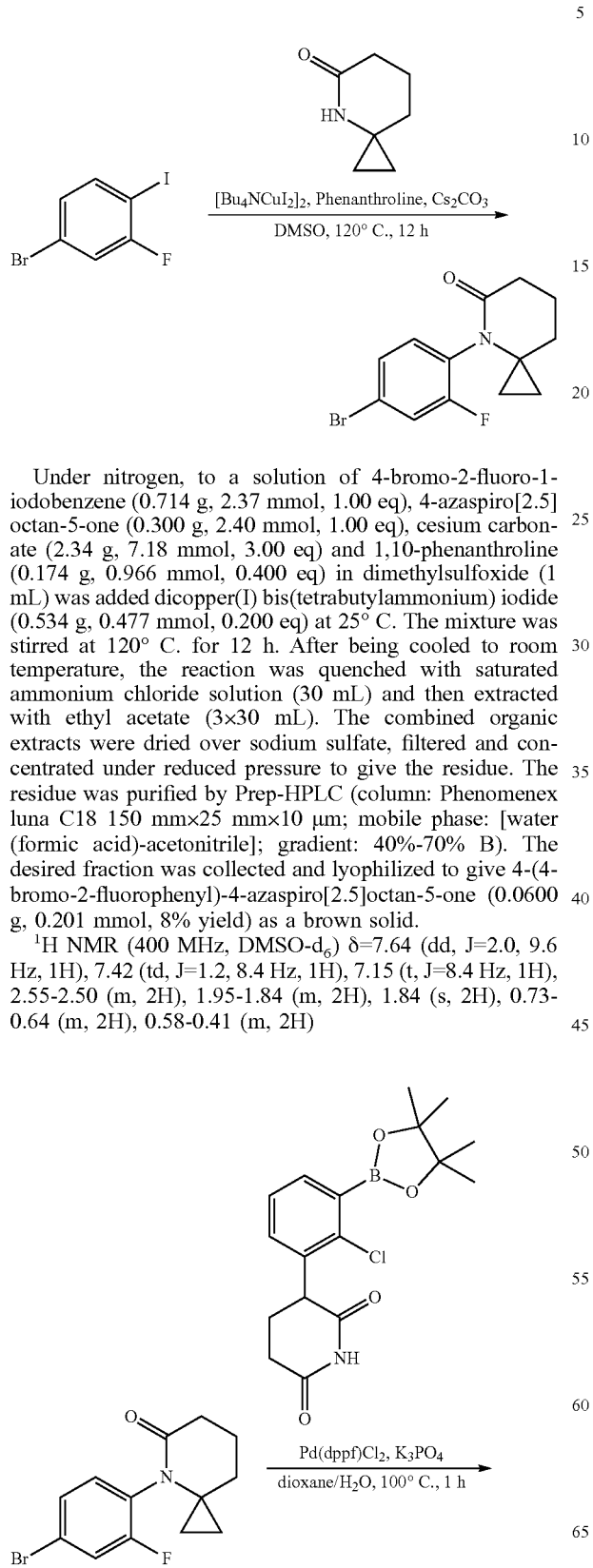

Under nitrogen, to a solution of 4-bromo-2-fluoro-1-iodobenzene (0.714 g, 2.37 mmol, 1.00 eq), 4-azaspiro[2.5]octan-5-one (0.300 g, 2.40 mmol, 1.00 eq), cesium carbonate (2.34 g, 7.18 mmol, 3.00 eq) and 1,10-phenanthroline (0.174 g, 0.966 mmol, 0.400 eq) in dimethylsulfoxide (1 mL) was added dicopper(I) bis(tetrabutylammonium) iodide (0.534 g, 0.477 mmol, 0.200 eq) at 25° C. The mixture was stirred at 120° C. for 12 h. After being cooled to room temperature, the reaction was quenched with saturated ammonium chloride solution (30 mL) and then extracted with ethyl acetate (3×30 mL). The combined organic extracts were dried over sodium sulfate, filtered and concentrated under reduced pressure to give the residue. The residue was purified by Prep-HPLC (column: Phenomenex luna C18 150 mm×25 mm×10 μm; mobile phase: [water (formic acid)-acetonitrile]; gradient: 40%-70% B). The desired fraction was collected and lyophilized to give 4-(4-bromo-2-fluorophenyl)-4-azaspiro[2.5]octan-5-one (0.0600 g, 0.201 mmol, 8% yield) as a brown solid.

$^1$H NMR (400 MHz, DMSO-$d_6$) δ=7.64 (dd, J=2.0, 9.6 Hz, 1H), 7.42 (td, J=1.2, 8.4 Hz, 1H), 7.15 (t, J=8.4 Hz, 1H), 2.55-2.50 (m, 2H), 1.95-1.84 (m, 2H), 1.84 (s, 2H), 0.73-0.64 (m, 2H), 0.58-0.41 (m, 2H)

3-(2-chloro-3-(4,4,5,5-tetramethyl-1,3,2-dioxaborolan-2-yl)phenyl)piperidine-2,6-dione (intermediate A) was synthesized as described above. Under nitrogen, to a solution of 4-(4-bromo-2-fluorophenyl)-4-azaspiro[2.5]octan-5-one (0.0600 g, 0.201 mmol, 1.00 eq) and 3-(2-chloro-3-(4,4,5,5-tetramethyl-1,3,2-dioxaborolan-2-yl)phenyl)piperidine-2,6-dione (0.132 g, 0.302 mmol, 1.50 eq) in dioxane (1 mL) and water (0.1 mL) was added potassium phosphate (0.128 g, 0.603 mmol, 3.00 eq) and [1,1'-bis(diphenylphosphino)ferrocene]dichloropalladium(II) (0.0150 g, 0.0205 mmol, 0.100 eq) at 25° C. The mixture was stirred at 100° C. for 1 h. After being cooled to room temperature, the mixture was concentrated under reduced pressure. The residue was purified by flash silica gel chromatography (ISCO®; 20 g SepaFlash® Silica Flash Column, eluent of 30%-100% ethyl acetate/petroleum ether gradient at 30 mL/min) and Prep-HPLC (column: Phenomenex luna C18 150 mm×25 mm×10 μm; mobile phase: [water (formic acid)-acetonitrile]; gradient: 36%-66% B over 10 min). The desired fraction was collected and lyophilized to afford 3-(2-chloro-3'-fluoro-4'-(5-oxo-4-azaspiro[2.5]octan-4-yl)-[1,1'-biphenyl]-3-yl)piperidine-2,6-dione (20.18 mg, 0.0453 mmol, 23% yield, 99% purity) as a white solid.

$^1$H NMR (400 MHz, DMSO-$d_6$) δ=10.93 (s, 1H), 7.42-7.36 (m, 4H), 7.34-7.25 (m, 2H), 4.36 (dd, J=4.8, 12.4 Hz, 1H), 2.80 (ddd, J=5.2, 12.4, 17.2 Hz, 1H), 2.59-2.55 (m, 3H), 2.40-2.27 (m, 1H), 2.09-2.02 (m, 1H), 1.98-1.95 (m, 2H), 1.89 (d, J=5.2 Hz, 2H), 0.72 (s, 2H), 0.63-0.48 (m, 2H); MS (ESI) m/z 441.1 [M+H]$^+$

Example 118. Synthesis of 3-(2-chloro-3-(6-(5-oxo-6-oxa-4-azaspiro[2.5]octan-4-yl)pyridin-3-yl)phenyl)piperidine-2,6-dione (Compound 351)

To a solution of tert-butyl (1-(2-hydroxyethyl)cyclopropyl)carbamate (500 mg, 2.48 mmol, 1.00 eq) in tetrahydrofuran (5 mL) was added potassium tert-butoxide (836 mg, 7.45 mmol, 3.00 eq) at 0° C. The reaction was stirred at 25° C. for 12 h. The reaction was concentrated under reduced pressure to give a residue. The residue was purified by column chromatography (SiO₂, Petroleum ether/ethyl acetate=1/1 to 1/2) to afford 6-oxa-4-azaspiro[2.5]octan-5-one (250 mg, 1.97 mmol, 79% yield) as a white solid.

¹H NMR (400 MHz, DMSO-d₆) δ=7.29 (s, 1H), 4.34-4.21 (m, 2H), 1.87-1.73 (m, 2H), 0.74-0.53 (m, 4H)

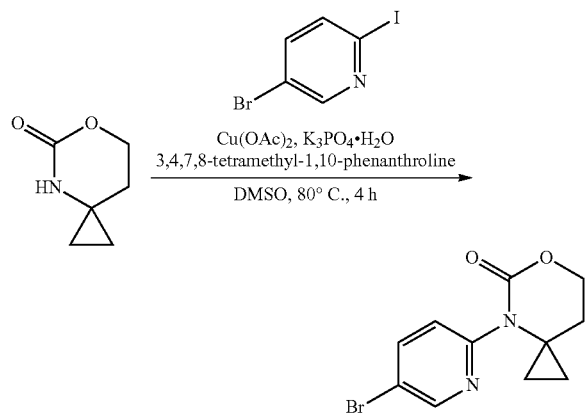

To a solution of 6-oxa-4-azaspiro[2.5]octan-5-one (200 mg, 1.57 mmol, 1.00 eq) and 5-bromo-2-iodopyridine (491 mg, 1.73 mmol, 1.10 eq) in dimethylsulfoxide (4 mL) were added potassium phosphate monohydrate (724 mg, 3.15 mmol, 2.00 eq), 3,4,7,8-tetramethyl-1,10-phenanthroline (56.0 mg, 0.236 mmol, 0.150 eq) and copper acetate (29.0 mg, 0.157 mmol, 0.100 eq). The reaction was stirred at 80° C. for 4 h under nitrogen atmosphere. After being cooled to room temperature, the reaction was quenched with water (10 mL) and extracted with ethyl acetate (3×10 mL). The combined organic extracts were washed with saturated sodium bicarbonate (3×5 mL) and brine (2×5 mL), dried over sodium sulfate and filtered. The filtrate was concentrated under reduced pressure to give a residue. The residue was purified by column chromatography (SiO2, petroleum ether/ethyl acetate=2/1 to 1/1) to afford 4-(5-bromopyridin-2-yl)-6-oxa-4-azaspiro[2.5]octan-5-one (220 mg, 0.777 mmol, 49% yield) as a white solid.

¹H NMR (400 MHz, DMSO-d₆) δ=8.61 (d, J=2.4 Hz, 1H), 8.15-8.09 (m, 1H), 7.30 (d, J=8.4 Hz, 1H), 4.48 (t, J=5.6 Hz, 2H), 2.07 (t, J=5.6 Hz, 2H), 0.75-0.67 (m, 2H), 0.66-0.58 (m, 2H)

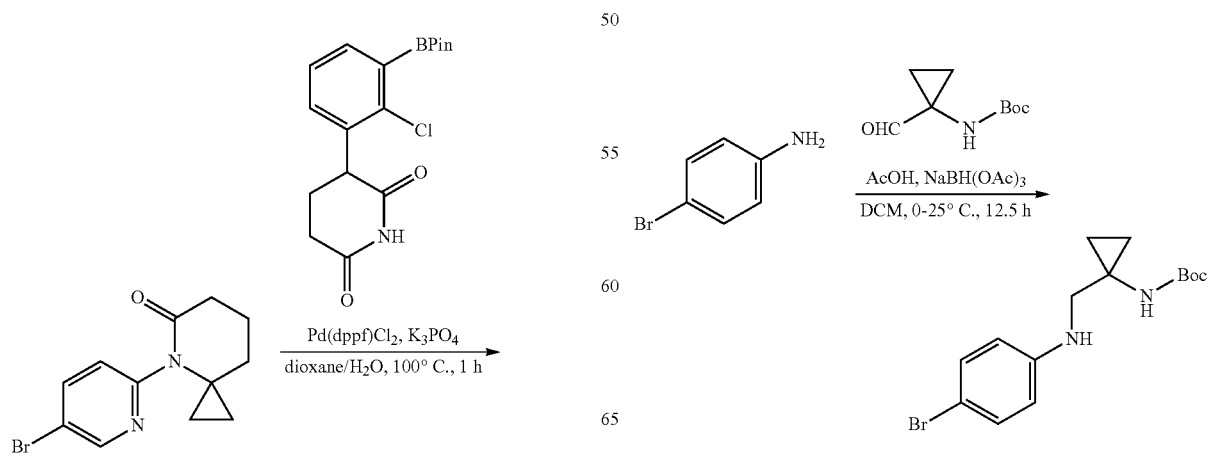

-continued

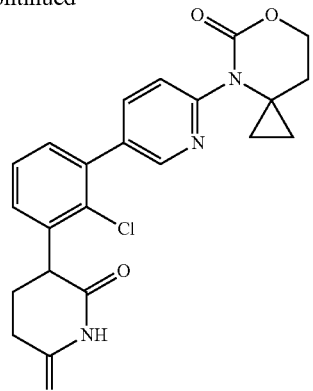

Compound 351

3-(2-chloro-3-(4,4,5,5-tetramethyl-1,3,2-dioxaborolan-2-yl)phenyl)piperidine-2,6-dione (intermediate A) was synthesized as described above. To a solution of 4-(5-bromopyridin-2-yl)-6-oxa-4-azaspiro[2.5]octan-5-one (100 mg, 0.353 mmol, 1.00 eq) and 3-(2-chloro-3-(4,4,5,5-tetramethyl-1,3,2-dioxaborolan-2-yl)phenyl)piperidine-2,6-dione (309 mg, 0.706 mmol, 2.00 eq, 80% purity) in dioxane (3 mL) and water (0.3 mL) was added potassium phosphate (225 mg, 1.06 mmol, 3.00 eq) and [1,1-bis(diphenylphosphino)ferrocene]dichloropalladium(II) (26.0 mg, 0.0353 mmol, 0.100 eq) under nitrogen atmosphere. The reaction was stirred at 100° C. for 1 h under nitrogen atmosphere. After being cooled to room temperature, the reaction was filtered through Celite and concentrated under reduced pressure to give a residue. The residue was purified by Prep-HPLC (column: Phenomenex luna C18 150 mm×25 mm×10 μm; gradient: 24%-44% B over 10 min) and lyophilized to afford 3-(2-chloro-3-(6-(5-oxo-6-oxa-4-azaspiro[2.5]octan-4-yl)pyridin-3-yl)phenyl)piperidine-2,6-dione (32.18 mg, 0.0748 mmol, 21% yield, 99% purity) as a white solid.

¹H NMR (400 MHz, DMSO-d₆) δ=10.93 (s, 1H), 8.50 (d, J=2.4 Hz, 1H), 8.06-7.85 (m, 1H), 7.55-7.29 (m, 4H), 4.51 (t, J=5.6 Hz, 2H), 4.41-4.33 (m, 1H), 2.86-2.74 (m, 1H), 2.60-2.54 (m, 1H), 2.33 (d, J=1.8 Hz, 1H), 2.14-2.00 (m, 3H), 0.79-0.63 (m, 4H); MS (ESI) m/z 426.1 [M+H]⁺

Example 119. Synthesis of 3-(2-chloro-4'-(4-methyl-6-oxo-4,7-diazaspiro[2.5]octan-7-yl)-[1,1'-biphenyl]-3-yl)piperidine-2,6-dione (Compound 352)

To a solution of 4-bromoaniline (1.00 g, 5.81 mmol, 1.00 eq), tert-butyl (1-formylcyclopropyl)carbamate (1.08 g, 5.81 mmol, 1.00 eq) and acetic acid (349 mg, 5.81 mmol, 1.00 eq) in dichloromethane (10 mL) was added sodium triacetoxy borohydride (1.48 g, 6.98 mmol, 1.20 eq) at 0° C. The mixture was stirred at 0° C. for 0.5 h. The mixture was stirred at 25° C. for additional 12 h. The mixture was concentrated under reduced pressure. The residue was purified by flash silica gel chromatography (ISCO®; 20 g SepaFlash® Silica Flash Column, eluent of 0%-27% ethyl acetate/petroleum ether gradient at 70 mL/min) to give tert-butyl (1-(((4-bromophenyl)amino)methyl)cyclopropyl) carbamate (1.60 g, 4.64 mmol, 80% yield, 99% purity) as a white solid.

$^1$H NMR (400 MHz, DMSO-d$_6$) δ=7.15 (d, J=8.8 Hz, 3H), 6.52 (d, J=8.8 Hz, 2H), 5.78 (t, J=5.6 Hz, 1H), 3.14 (d, J=6.0 Hz, 2H), 1.36 (s, 9H), 0.59 (d, J=13.9 Hz, 4H); MS (ESI) m/z 341.1, 343.1 [M+H]$^+$

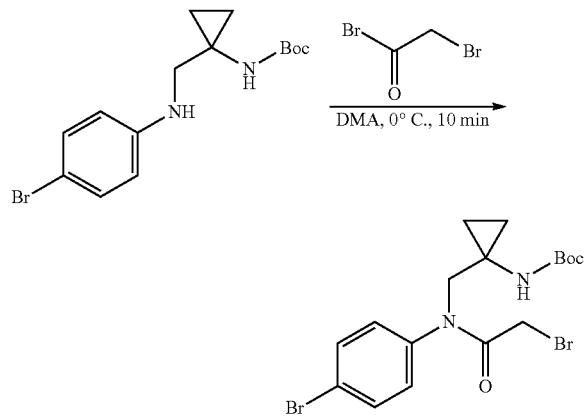

Under nitrogen atmosphere, to a solution of tert-butyl (1-(((4-bromophenyl)amino)methyl)cyclopropyl)-carbamate (800 mg, 2.34 mmol, 1.00 eq) in N,N-dimethylacetamide (10 mL) was added 2-bromoacetyl bromide (710 mg, 3.52 mmol, 1.50 eq) at 0° C. The mixture was stirred at 0° C. for 10 min. The reaction mixture was diluted with ethyl acetate (50 mL) and washed with saturated aqueous sodium bicarbonate (3×50 mL), dried over sodium sulfate and filtered. The filtrate was concentrated under reduced pressure to give tert-butyl (1-((2-bromo-N-(4-bromophenyl)acetamido) methyl)cyclopropyl)carbamate (890 mg, crude) as a brown solid.

$^1$H NMR (400 MHz, DMSO-d$_6$) δ=7.62 (d, J=8.0 Hz, 2H), 7.48 (d, J=7.6 Hz, 2H), 7.01 (s, 1H), 3.78 (d, J=4.0 Hz, 4H), 1.24 (s, 9H), 0.51 (s, 4H)

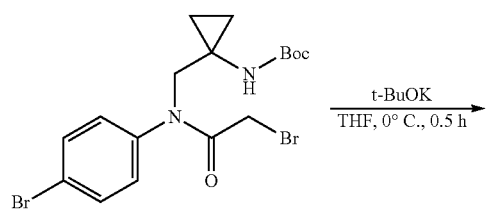

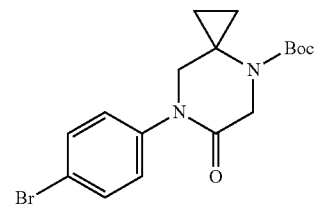

Under nitrogen atmosphere, to a solution of tert-butyl (1-((2-bromo-N-(4-bromophenyl)acetamido)-methyl)cyclopropyl)carbamate (890 mg, 2.32 mmol, 1.00 eq) in tetrahydrofuran (10 mL) was added potassium tert-butoxide (391 mg, 3.48 mmol, 1.50 eq) at 0° C. The mixture was stirred at 0° C. for 0.5 h. The mixture was poured into saturated aqueous ammonium chloride (100 mL) and extracted with ethyl acetate (3×100 mL). The combined organic layers were washed with brine (100 mL), dried over sodium sulfate and filtered. The filtrate was concentrated under reduced pressure. The residue was purified by flash silica gel chromatography (ISCO®; 40 g SepaFlash® Silica Flash Column, eluent of 0%-30% ethyl acetate/petroleum ether gradient at 70 mL/min) to give tert-butyl 7-(4-bromophenyl)-6-oxo-4,7-diazaspiro[2.5]octane-4-carboxylate (500 mg, 1.30 mmol, 56% yield, 99% purity) as a white solid.

$^1$H NMR (400 MHz, DMSO-d$_6$) δ=7.58 (d, J=8.8 Hz, 2H), 7.32 (d, J=8.8 Hz, 2H), 4.13 (s, 2H), 3.59 (s, 2H), 1.13-1.06 (m, 2H), 1.02-0.90 (m, 2H); MS (ESI) m/z 381.1, 383.1 [M+H]$^+$

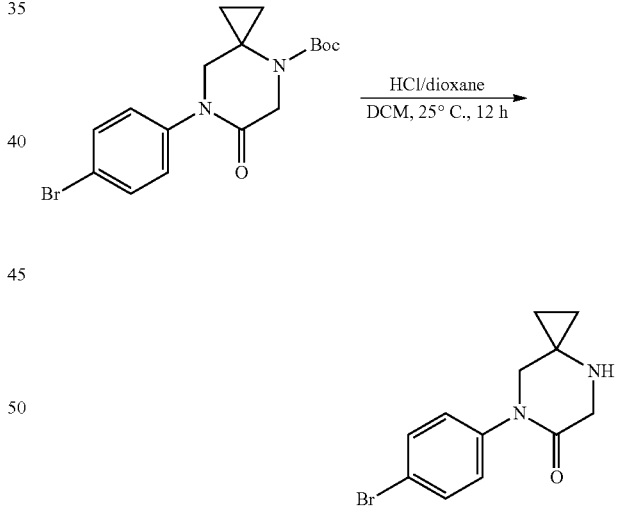

To a solution of tert-butyl 7-(4-bromophenyl)-6-oxo-4,7-diazaspiro[2.5]octane-4-carboxylate (200 mg, 525 μmol, 1.00 eq) in dichloromethane (2 mL) was added hydrogen chloride/dioxane (2 M, 2 mL) at 25° C. The mixture was stirred at 25° C. for 12 h. The mixture was concentrated under reduced pressure to give 7-(4-bromophenyl)-4,7-diazaspiro[2.5]octan-6-one (166 mg, 517 μmol, 99% yield, hydrochloride) as a white solid.

$^1$H NMR (400 MHz, DMSO-d$_6$) δ=10.39 (s, 2H), 7.68-7.59 (m, 2H), 7.37-7.28 (m, 2H), 3.96 (s, 2H), 3.85 (s, 2H), 1.34-1.25 (m, 2H), 1.11-1.01 (m, 2H)

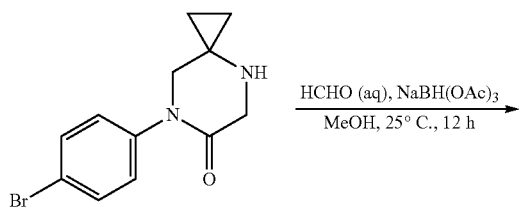

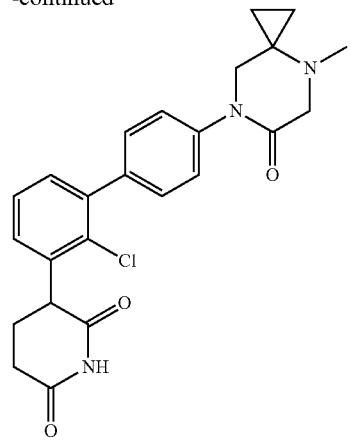

Compound 352

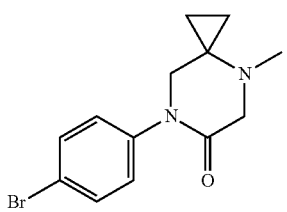

Under nitrogen atmosphere, to a solution of 7-(4-bromophenyl)-4,7-diazaspiro[2.5]octan-6-one (166 mg, 523 umol, 1.00 eq, hydrochloride) and formaldehyde (127 mg, 1.56 mmol, 2.99 eq) (37% in water) in methanol (5 mL) was added sodium triacetoxy borohydride (443 mg, 2.09 mmol, 4.00 eq) at 25° C. The mixture was stirred at 25° C. for 12 h. The mixture was concentrated under reduced pressure. The residue was purified by flash silica gel chromatography (ISCO®; 20 g SepaFlash® Silica Flash Column, eluent of 50%-100% ethyl acetate/petroleum ether gradient at 70 mL/min) to give 7-(4-bromophenyl)-4-methyl-4,7-diazaspiro[2.5]octan-6-one (130 mg, 440 µmol, 84% yield) as a white solid.

$^1$H NMR (400 MHz, DMSO-$d_6$) δ=7.58 (d, J=8.8 Hz, 2H), 7.35 (d, J=8.8 Hz, 2H), 3.62 (s, 2H), 3.36 (s, 2H), 2.43 (s, 3H), 0.76-0.70 (m, 2H), 0.69-0.63 (m, 2H); MS (ESI) m/z 295.0, 297.0 [M+H]$^+$ 3-(2-chloro-3-(4,4,5,5-tetramethyl-1,3,2-dioxaborolan-2-yl)phenyl)piperidine-2,6-dione (intermediate A) was synthesized as described above. Under nitrogen atmosphere, to a solution of 7-(4-bromophenyl)-4-methyl-4,7-diazaspiro[2.5] octan-6-one (130 mg, 440 µmol, 1.00 eq), 3-(2-chloro-3-(4, 4,5,5-tetramethyl-1,3,2-dioxaborolan-2-yl)phenyl)piperidine-2,6-dione (389 mg, 890 µmol, 2.02 eq) and potassium phosphate (284 mg, 1.34 mmol, 3.04 eq) in dioxane (4 mL) and water (0.4 mL) was added [1,1'-bis(diphenylphosphino) ferrocene]dichloropalladium(II) (32.0 mg, 43.7 umol, 0.0993 eq) at 25° C. Then the mixture was stirred at 100° C. for 1 h. After being cooled to room temperature, the mixture was concentrated under reduced pressure. The residue was purified by flash silica gel chromatography (ISCO®; 20 g SepaFlash® Silica Flash Column, eluent of 0%-60% ethyl acetate/petroleum ether gradient at 70 mL/min) and Prep-HPLC (column: Phenomenex luna C18 150 mm×25 mm×10 µm; mobile phase: [water (formic acid)-acetonitrile]; gradient: 11%-44% B over 11 min) and lyophilized to afford 3-(2-chloro-4'-(4-methyl-6-oxo-4,7-diazaspiro[2.5]octan-7-yl)-[1,1'-biphenyl]-3-yl)piperidine-2,6-dione (94.73 mg, 214 µmol, 49% yield, 99% purity) as a white solid.

$^1$H NMR (400 MHz, DMSO-$d_6$) δ=10.92 (s, 1H), 7.50-7.42 (m, 4H), 7.41-7.35 (m, 2H), 7.34-7.28 (m, 1H), 4.35 (dd, J=4.8, 12.0 Hz, 1H), 3.70 (s, 2H), 3.40 (s, 2H), 2.79 (ddd, J=5.2, 12.4, 17.2 Hz, 1H), 2.60-2.52 (m, 1H), 2.46 (s, 3H), 2.34 (dq, J=4.0, 12.4 Hz, 1H), 2.11-1.98 (m, 1H), 0.80-0.73 (m, 2H), 0.70 (d, J=3.6 Hz, 2H); MS (ESI) m/z 438.1 [M+H]$^+$ Example 120. Synthesis of 3-(2-chloro-3-(6-methyl-2-oxo-2H-[1,2'-bipyridin]-5'-yl)phenyl)piperidine-2, 6-dione (Compound 353)

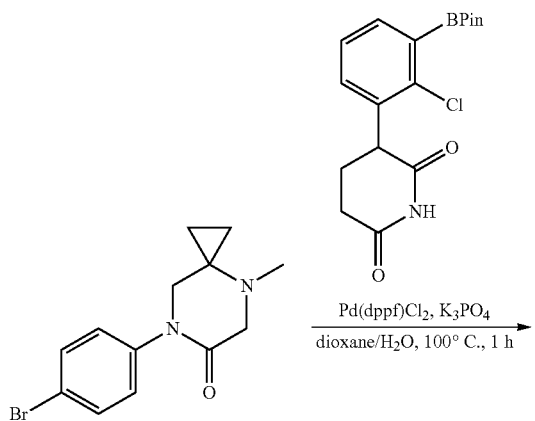

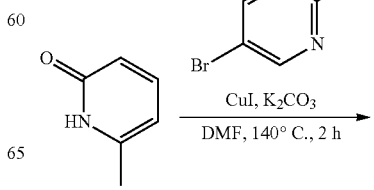

-continued

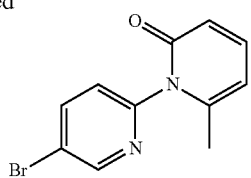

5'-bromo-6-methyl-2H-[1,2'-bipyridin]-2-one was prepared from 5-bromo-2-iodopyridine and 6-methylpyridin-2(1H)-one according to General Scheme 7.

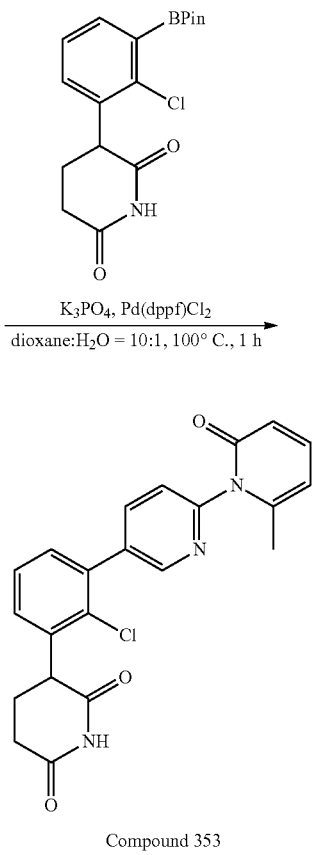

Compound 353

3-(2-chloro-3-(6-methyl-2-oxo-2H-[1,2'-bipyridin]-5'-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5'-bromo-6-methyl-2H-[1,2'-bipyridin]-2-one according to General Scheme 1.

¹H NMR (400 MHz, DMSO-d₆) δ=10.95 (s, 1H), 8.67 (s, 1H), 8.12 (br d, J=8.4 Hz, 1H), 7.58 (br d, J=8.0 Hz, 1H), 7.48 (br s, 4H), 6.39 (br d, J=9.2 Hz, 1H), 6.27 (br d, J=6.8 Hz, 1H), 4.39 (br dd, J=4.8, 12.0 Hz, 1H), 2.87-2.76 (m, 1H), 2.56 (br d, J=17.6 Hz, 1H), 2.41-2.32 (m, 1H), 2.12-2.03 (m, 1H), 1.94 (s, 3H); MS (ESI) m/z. 408.0 [M+H]⁺

Example 121. Synthesis of 3-(2-chloro-4'-(pyridin-2-yloxy)-[1,1'-biphenyl]-3-yl)piperidine-2,6-dione (Compound 354)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(pyridin-2-yloxy)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 2-(4-iodophenoxy)pyridine according to General Scheme 1.

MS (ESI) m/z 393.1 [M+H]⁺

Example 122. Synthesis of 3-(2-chloro-4'-(6-oxo-2-oxa-5-azaspiro[3.4]octan-5-yl)-[1,1'-biphenyl]-3-yl)piperidine-2,6-dione (Compound 355)

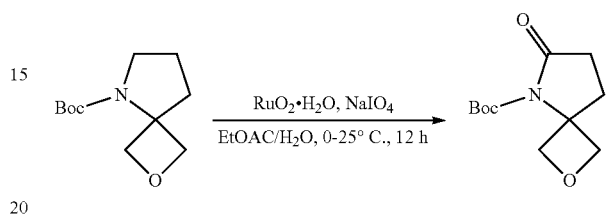

To a solution of tert-butyl 2-oxa-5-azaspiro[3.4]octane-5-carboxylate (500 mg, 2.34 mmol, 1.00 eq) in ethyl acetate (20.0 mL) was added sodium periodate (2.51 g, 11.7 mmol, 5.00 eq) and ruthenium(IV) oxide hydrate (106 mg, 703 µmol, 0.300 eq) in water (20.0 mL) at 0° C. The mixture was stirred at 25° C. for 12 h. The reaction mixture was diluted with water (20.0 mL) and extracted with ethyl acetate (3×20 mL). The combined organic layers were washed with brine (10 mL), dried over anhydrous sodium sulfate and filtered. The filtrate was concentrated under reduced pressure. The crude product was purified by reversed-phase column (column: spherical C18, 20-45 um, 100 Å, SW80, mobile phase: [water (0.1% formic acid)-acetonitrile) to get tert-butyl 6-oxo-2-oxa-5-azaspiro[3.4]octane-5-carboxylate (300 mg, 1.31 mmol, 56% yield, 99% purity) as a white solid.

¹H NMR (400 MHz, CDCl₃) δ=5.31 (d, J=6.4 Hz, 2H), 4.54 (d, J=6.4 Hz, 2H), 2.51-2.39 (m, 4H), 1.62 (s, 9H); MS (ESI) m/z. 128.1 [M+H]⁺

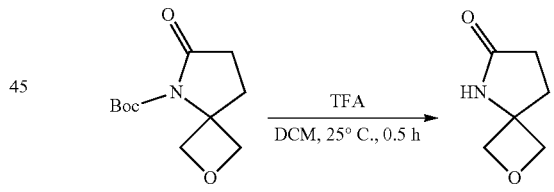

To a solution of tert-butyl 6-oxo-2-oxa-5-azaspiro[3.4]octane-5-carboxylate (300 mg, 1.32 mmol, 1.00 eq) in dichloromethane (3.00 mL) was added trifluoroacetic acid (576 mg, 5.05 mmol, 375 µL, 3.82 eq). The mixture was stirred at 25° C. for 0.5 h. The solvent was removed under reduced pressure to get 2-oxa-5-azaspiro[3.4]octan-6-one (200 mg, crude) as yellow oil.

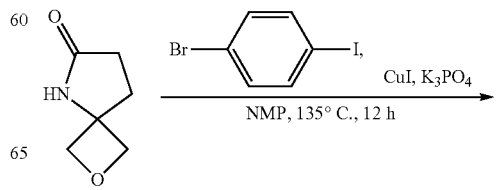

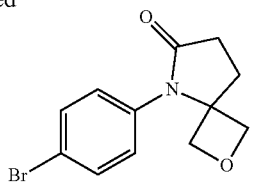

A mixture of 2-oxa-5-azaspiro[3.4]octan-6-one (200 mg, 1.57 mmol, 1.00 eq), 1-bromo-4-iodobenzene (579 mg, 2.04 mmol, 1.30 eq), copper(I) iodide (59.9 mg, 315 μmol, 0.200 eq), potassium phosphate (1.34 g, 6.29 mmol, 4.00 eq) in 1-methylpyrrolidin-2-one (4.00 mL) was degassed and purged with nitrogen for 3 times, and then the mixture was stirred at 135° C. for 12 h under nitrogen atmosphere. The reaction mixture filtered and filter liquor was collected. The crude product was purified by reversed-phase column (column: spherical C 18, 20-45 um, 100 Å, SW 80, mobile phase: [water(0.1% formic acid)-acetonitrile] to get 5-(4-bromophenyl)-2-oxa-5-azaspiro[3.4]octan-6-one (60.0 mg, 191 μmol, 12% yield, 90% purity) as a white solid.

$^1$H NMR (400 MHz, CDCl$_3$) δ=7.64 (d, J=8.4 Hz, 2H), 7.15 (d, J=8.4 Hz, 2H), 4.85 (d, J=7.2 Hz, 2H), 4.64 (d, J=7.2 Hz, 2H), 2.65-2.53 (m, 4H).

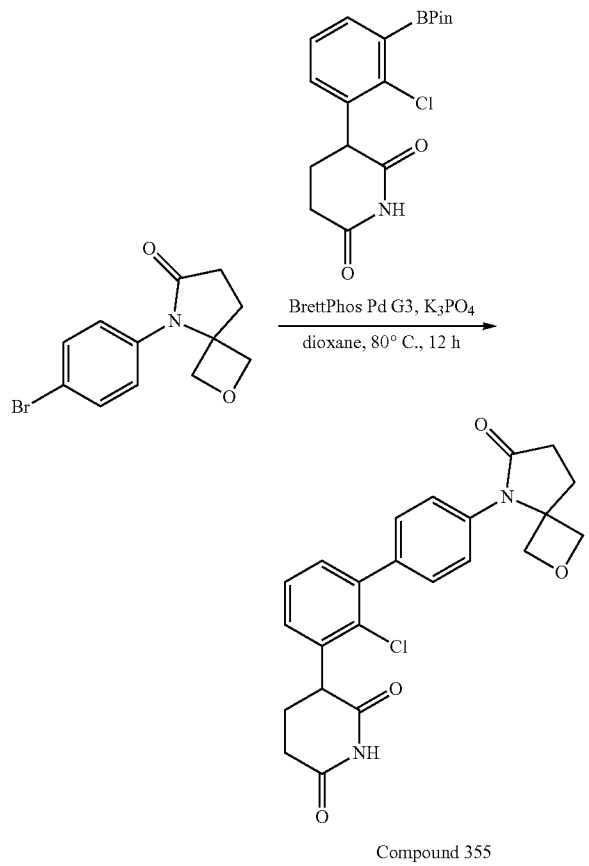

Compound 355

3-(2-chloro-3-(4,4,5,5-tetramethyl-1,3,2-dioxaborolan-2-yl)phenyl)piperidine-2,6-dione (intermediate A) was synthesized as described above. A mixture of 5-(4-bromophenyl)-2-oxa-5-azaspiro[3.4]octan-6-one (50.0 mg, 177 μmol, 1.00 eq), 3-(2-chloro-3-(4,4,5,5-tetramethyl-1,3,2-dioxaborolan-2-yl)phenyl)piperidine-2,6-dione (133 mg, 266 μmol, 1.50 eq), [(2-Di-cyclohexylphosphino-3,6-dimethoxy-2',4',6'-triisopropyl-1,1'-biphenyl)-2-(2'-amino-1,1'-biphenyl)]palladium(II) methanesulfonate (16.1 mg, 17.7 μmol, 0.100 eq), potassium phosphate (113 mg, 532 μmol, 3.00 eq) in dioxane (2.00 mL) was degassed and purged with nitrogen for 3 times, and then the mixture was stirred at 80° C. for 12 h under nitrogen atmosphere. The reaction mixture was filtered and filter liquor was concentrated in vacuum. The residue was purified by Prep-HPLC (column: Phenomenex luna C18 150*25 mm*10 um; mobile phase: [water (formic acid)-acetonitrile]; gradient: 13%-43% B over 10 min) to afford 3-(2-chloro-4'-(6-oxo-2-oxa-5-azaspiro[3.4]octan-5-yl)-[1,1'-biphenyl]-3-yl)piperidine-2,6-dione (11.6 mg, 26.0 mol, 15% yield, 95% purity) as a white solid.

$^1$H NMR (400 MHz, DMSO-d$_6$) δ=10.92 (br s, 1H), 7.56 (d, J=8.4 Hz, 2H), 7.46-7.37 (m, 5H), 4.71 (d, J=7.2 Hz, 2H), 4.59 (d, J=7.2 Hz, 2H), 4.37 (dd, J=4.8, 12.0 Hz, 1H), 2.85-2.76 (m, 1H), 2.57 (br s, 1H), 2.48-2.43 (m, 4H), 2.37 (br d, J=4.4 Hz, 1H), 2.12-2.03 (m, 1H).

$^1$H NMR (400 MHz, CDCl$_3$) δ=8.01 (br s, 1H), 7.56 (d, J=8.4 Hz, 2H), 7.40-7.30 (m, 4H), 7.24 (dd, J=2.0, 7.2 Hz, 1H), 4.97 (d, J=7.2 Hz, 2H), 4.66 (d, J=7.2 Hz, 2H), 4.36 (dd, J=6.0, 10.0 Hz, 1H), 2.87-2.69 (m, 2H), 2.68-2.58 (m, 4H), 2.41-2.28 (m, 2H); MS (ESI) m/z. 425.0 [M+H]$^+$

Example 123. Synthesis of 3-(2-chloro-3-(6-(5-oxo-6-oxa-4-azaspiro[2.4]heptan-4-yl)pyridin-3-yl)phenyl)piperidine-2,6-dione (Compound 356)

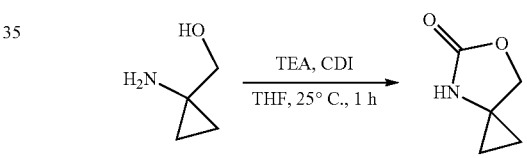

To a solution of (1-aminocyclopropyl)methanol (200 mg, 1.62 mmol, 1.00 eq, hydrochloride) in tetrahydrofuran (2 mL) was added triethylamine (328 mg, 3.24 mmol, 2.00 eq) and 1,1'-carbonyldiimidazole (315 mg, 1.94 mmol, 1.20 eq). The mixture was stirred at 25° C. for 1 h. The mixture was quenched with water (30 mL) and extracted with ethyl acetate (3×30 mL). The combined organic layers were washed with brine (30 mL), filtered and concentrated to give the residue. The residue was purified by flash silica gel chromatography (ISCO®; 4 g SepaFlash® Silica Flash Column, eluent of 0%-50% ethyl acetate/petroleum ether gradient at 18 mL/min) to give 6-oxa-4-azaspiro[2.4]heptan-5-one (60.0 mg, 0.530 mmol, 33% yield) as a white solid.

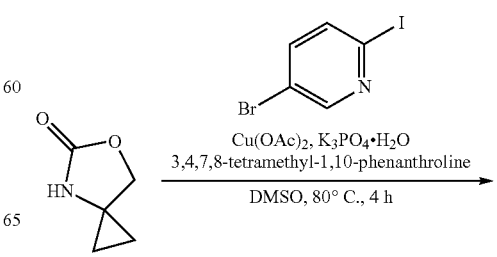

-continued

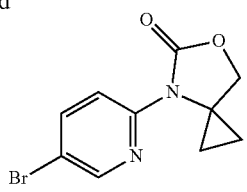

To a solution of 6-oxa-4-azaspiro[2.4]heptan-5-one (60.0 mg, 0.530 mmol, 1.00 eq) and 5-bromo-2-iodopyridine (156 mg, 0.549 mmol, 1.04 eq) in dimethylsulfoxide (2 mL) was added copper acetate (10.0 mg, 0.055 mmol, 0.100 eq), potassium phosphate monohydrate (244 mg, 1.06 mmol, 2.00 eq) and 3,4,7,8-tetramethyl-1,10-phenanthroline (19.0 mg, 0.0804 mmol, 0.150 eq). The mixture was stirred at 80° C. for 4 h under nitrogen. After being cooled to room temperature, ethyl acetate (60 mL) and water (60 mL) were added, layers were separated. The aqueous phase was extracted with ethyl acetate (3×60 mL). Combined extracts were washed with brine (60 mL), dried over sodium sulfate, filtered, and concentrated under vacuum. The residue was purified by flash silica gel chromatography (ISCO®; 4 g SepaFlash® Silica Flash Column, eluent of 0%-100% ethyl acetate/petroleum ether gradient at 18 mL/min) to give 4-(5-bromopyridin-2-yl)-6-oxa-4-azaspiro[2.4]heptan-5-one (130 mg, 0.483 mmol, 91% yield) as a white solid.

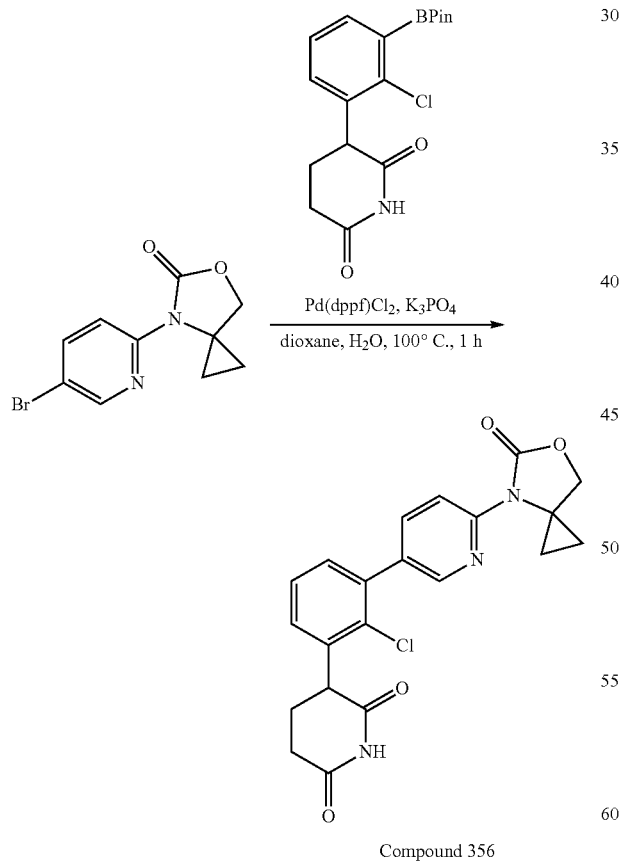

Compound 356 afford 3-(2-chloro-3-(6-(5-oxo-6-oxa-4-azaspiro[2.4]heptan-4-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(5-bromopyridin-2-yl)-6-oxa-4-azaspiro[2.4]heptan-5-one according to General Scheme 1.

$^1$H NMR (400 MHz, DMSO-d$_6$) δ=10.93 (s, 1H), 8.35 (d, J=2.4 Hz, 1H), 7.94 (dd, J=2.4, 8.8 Hz, 1H), 7.80 (d, J=8.8 Hz, 1H), 7.49-7.34 (m, 3H), 4.45 (s, 2H), 4.35 (dd, J=5.2, 12.4 Hz, 1H), 2.86-2.74 (m, 1H), 2.59-2.55 (m, 1H), 2.37-2.27 (m, 1H), 2.08-2.01 (m, 1H), 1.89-1.80 (m, 2H), 0.84-0.75 (m, 2H); MS (ESI) m/z 412.1 [M+H]$^+$

Example 124. Synthesis of 3-(2-chloro-3-(6-(6-oxo-7-oxa-5-azaspiro[3.4]octan-5-yl)pyridin-3-yl)phenyl)piperidine-2,6-dione (Compound 357)

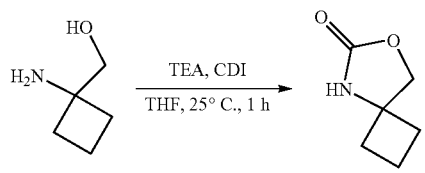 [SMILES: NC1(CO)CCC1 ; "TEA, CDI" ; "THF, 25° C., 1 h" ; O=C1NC2(CCC2)CO1]

To a solution of (1-aminocyclobutyl)methanol (0.500 g, 4.94 mmol, 1.00 eq) in tetrahydrofuran (5 mL) was added triethylamine (1.38 mL, 9.88 mmol, 2.00 eq) and 1,1'-carbonyldiimidazole (0.960 g, 5.92 mmol, 1.20 eq). The mixture was stirred at 25° C. for 1 h. The mixture was concentrated under reduced pressure. The residue was purified by flash silica gel chromatography (ISCO®; 20 g SepaFlash®Silica Flash Column, eluent of 0%-100% ethyl acetate/petroleum ether gradient at 30 mL/min) to give 7-oxa-5-azaspiro[3.4]octan-6-one (0.344 g, 2.71 mmol, 55% yield) as colorless oil.

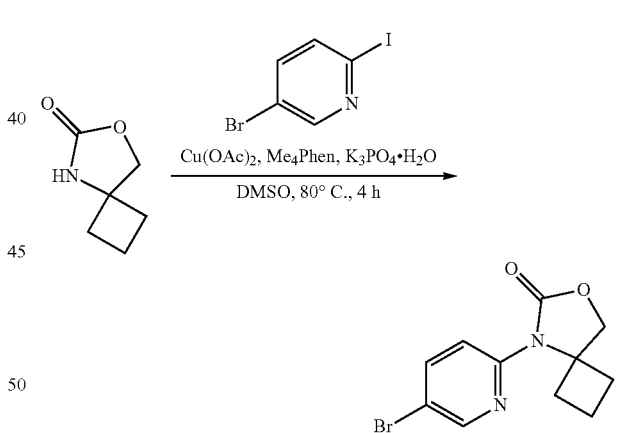

Under nitrogen, to a solution of 7-oxa-5-azaspiro[3.4]octan-6-one (0.200 g, 1.57 mmol, 1.00 eq), 5-bromo-2-iodopyridine (0.491 g, 1.73 mmol, 1.10 eq), 3,4,7,8-tetramethyl-1,10-phenanthroline (0.0560 g, 0.237 mmol, 0.500 eq) and potassium phosphate monohydrate (0.724 g, 3.14 mmol, 2.00 eq) in dimethylsulfoxide (2 mL) was added copper acetate (0.0290 g, 0.157 mmol, 0.100 eq) at 25° C. The mixture was stirred at 80° C. for 4 h. After being cooled to room temperature, the reaction mixture was diluted with water (20 mL) and extracted with ethyl acetate (3×20 mL). The combined organic extracts were washed with brine (20 mL), dried over sodium sulfate, filtered and concentrated under reduced pressure. The residue was purified by flash silica gel chromatography (ISCO®; 20 g SepaFlash®Silica Flash Column, eluent of 0%-50% ethyl acetate/petroleum ether gradient at 30 mL/min) to give 5-(5-bromopyridin-2-yl)-7-oxa-5-azaspiro[3.4]octan-6-one (0.350 g, 1.24 mmol, 79% yield) as a yellow solid.

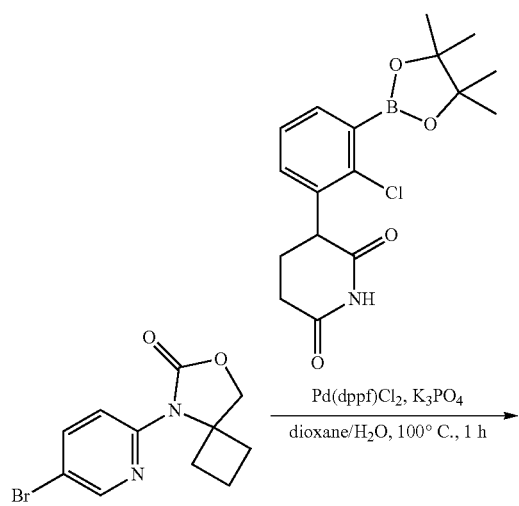

Compound 357

3-(2-chloro-3-(6-(6-oxo-7-oxa-5-azaspiro[3.4]octan-5-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5-(5-bromopyridin-2-yl)-7-oxa-5-azaspiro[3.4]octan-6-one according to General Scheme 1.

$^1$H NMR (400 MHz, DMSO-d$_6$) δ=10.94 (s, 1H), 8.51 (dd, J=0.8, 2.4 Hz, 1H), 7.96 (dd, J=2.4, 8.4 Hz, 1H), 7.84-7.82 (m, 1H), 7.46-7.42 (m, 3H), 4.58 (s, 2H), 4.37 (dd, J=4.8, 12.4 Hz, 1H), 3.26-3.20 (m, 2H), 2.84-2.76 (m, 1H), 2.57-2.56 (m, 1H), 2.40-2.30 (m, 1H), 2.16-2.13 (m, 2H), 2.11-2.07 (m, 1H), 1.91-1.85 (m, 1H), 1.78-1.71 (m, 1H); MS (ESI) m/z 426.0 [M+H]$^+$

Example 125. Synthesis of N-(2-(2,6-dioxopiperidin-3-yl)-1-oxoisoindolin-5-yl)-1-(methoxymethyl)-5-methylisoindoline-2-carboxamide (Compound 358)

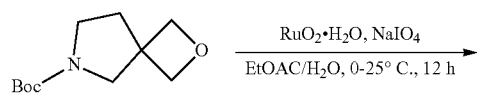

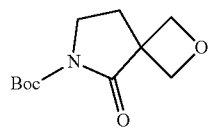

To a solution of ruthenium(iv)oxidehydrate (106 mg, 703 μmol, 0.300 eq) and sodium periodate (1.50 g, 7.03 mmol, 389 μL, 3.00 eq) in water (10.0 mL) was added tert-butyl 2-oxa-7-azaspiro[3.4]octane-7-carboxylate (500 mg, 2.34 mmol, 1.00 eq) in ethyl acetate (10.0 mL) dropwise at 0° C. The mixture was stirred at 25° C. for 12 h. The mixture was filtered and concentrated in vacuum to give a residue. The residue was purified by Prep-HPLC (column: Waters Xbridge BEH C18 150*25 mm*5 um; mobile phase: [water (ammonium bicarbonate)-acetonitrile]; gradient: 12%-42% B over 10 min) and lyophilized to get tert-butyl 5-oxo-2-oxa-6-azaspiro[3.4]octane-6-carboxylate (100 mg, 440 μmol, 9.38% yield) as a white solid.

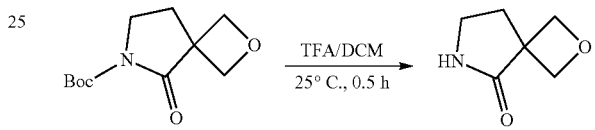

To a solution of tert-butyl 5-oxo-2-oxa-6-azaspiro[3.4]octane-6-carboxylate (100 mg, 440 μmol, 1.00 eq) in trifluoroacetic acid (0.100 mL) and dichloromethane (1.00 mL) was stirred at 25° C. for 30 min. The mixture was concentrated under reduced pressure to give 2-oxa-6-azaspiro[3.4]octan-5-one (80 mg, crude) was obtained as yellow oil and used into the next step without further purification.

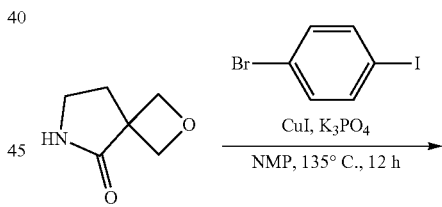

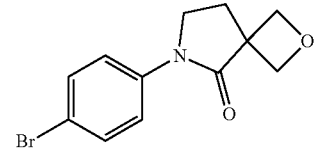

6-(4-bromophenyl)-2-oxa-6-azaspiro[3.4]octan-5-one was prepared from 1-bromo-4-iodo-benzene and 2-oxa-6-azaspiro[3.4]octan-5-one according to General Scheme 7.

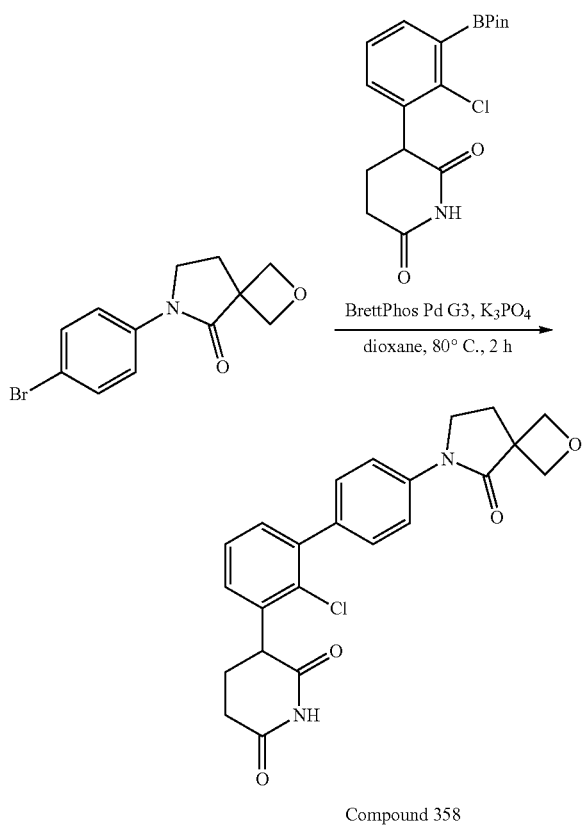

Compound 358

3-(2-chloro-4'-(5-oxo-2-oxa-6-azaspiro[3.4]octan-6-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 6-(4-bromophenyl)-2-oxa-6-azaspiro[3.4]octan-5-one according to General Scheme 1.

$^1$H NMR (400 MHz, DMSO-d$_6$) δ=10.92 (s, 1H), 7.79 (d, J=8.4 Hz, 2H), 7.43 (br d, J=8.4 Hz, 2H), 7.41-7.34 (m, 2H), 7.31 (br d, J=8.0 Hz, 1H), 4.76 (d, J=6.0 Hz, 2H), 4.52 (d, J=6.0 Hz, 2H), 4.34 (br dd, J=4.4, 12.0 Hz, 1H), 3.79 (br t, J=6.8 Hz, 2H), 2.85-2.74 (m, 1H), 2.59-2.55 (m, 1H), 2.53 (br s, 2H), 2.41-2.34 (m, 1H), 2.09-2.01 (m, 1H).

$^1$H NMR (400 MHz, CDCl$_3$) δ=8.00 (br s, 1H), 7.75 (d, J=8.8 Hz, 2H), 7.45 (d, J=8.8 Hz, 2H), 7.38-7.28 (m, 2H), 7.21 (dd, J=1.6, 7.2 Hz, 1H), 5.10 (d, J=6.0 Hz, 2H), 4.60 (d, J=6.0 Hz, 2H), 4.33 (dd, J=6.0, 10.4 Hz, 1H), 3.83 (t, J=6.8 Hz, 2H), 2.80 (t, J=4.4 Hz, 1H), 2.75 (dd, J=6.0, 10.8 Hz, 1H), 2.62 (t, J=6.8 Hz, 2H), 2.41-2.33 (m, 1H), 2.32 (br d, J=4.8 Hz, 1H); MS (ESI) m/z 425.1 [M+H]$^+$

Example 126. Synthesis of 3-(2-chloro-3-(6-(6-oxo-7-oxa-5-azaspiro-[3.5]nonan-5-yl)pyridin-3-yl)phenyl)piperidine-2,6-dione (Compound 359)

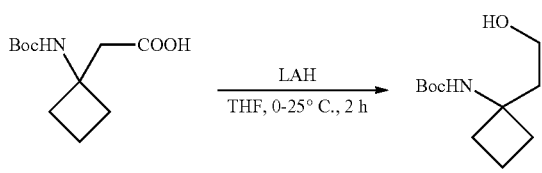 [SMILES: CC(C)(C)OC(=O)NC1(CC(=O)O)CCC1 ; "LAH" ; "THF, 0-25° C., 2 h" ; CC(C)(C)OC(=O)NC1(CCO)CCC1]

Under nitrogen atmosphere, to a solution of 2-(1-((tert-butoxycarbonyl)amino)cyclobutyl)acetic acid (900 mg, 3.93 mmol, 1.00 eq) in tetrahydrofuran (9 mL) was added lithium aluminum hydride (3.2 mL, 8.00 mmol, 2.04 eq, 2.5 M in tetrahydrofuran) at 0° C. Then the mixture was stirred at 0° C. for 0.5 h and stirred at 25° C. for 1.5 h. To the mixture was added sodium sulfate decahydrate until gas evolution ceased at 0° C. The reaction mixture was filtered, washed with ethyl acetate (100 mL). The filtrate was concentrated under reduced pressure to give tert-butyl (1-(2-hydroxyethyl)cyclobutyl)carbamate (608 mg, 2.54 mmol, 65% yield, 90% purity) as colorless oil.

$^1$H NMR (400 MHz, DMSO-d$_6$) δ=6.78 (s, 1H), 4.36 (s, 1H), 3.54-3.44 (m, 2H), 2.18 (d, J=5.2 Hz, 2H), 1.96-1.82 (m, 4H), 1.78-1.66 (m, 2H), 1.36 (s, 9H)

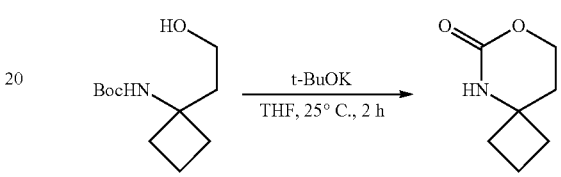

To a solution of tert-butyl (1-(2-hydroxyethyl)cyclobutyl)carbamate (200 mg, 836 μmol, 1.00 eq) in tetrahydrofuran (2 mL) was added potassium tert-butoxide (144 mg, 1.28 mmol, 1.53 eq) at 25° C. Then the mixture was stirred at 25° C. for 2 h. The mixture was concentrated under reduced pressure. The residue was purified by flash silica gel chromatography (ISCO®; 20 g SepaFlash® Silica Flash Column, eluent of 30%-80% ethyl acetate/petroleum ether gradient at 50 mL/min) to give 7-oxa-5-azaspiro[3.5]nonan-6-one (190 mg, 623 μmol, 18% yield) as a white solid.

$^1$H NMR (400 MHz, DMSO-d$_6$) δ=7.62 (s, 1H), 4.14-4.04 (m, 2H), 2.19-2.04 (m, 2H), 2.01-1.86 (m, 4H), 1.68-1.50 (m, 2H).

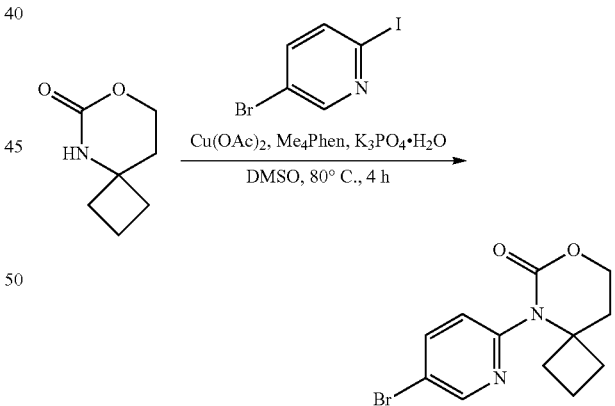

A mixture of 7-oxa-5-azaspiro[3.5]nonan-6-one (50.0 mg, 344 umol, 1.10 eq), 5-bromo-2-iodopyridine (88.0 mg, 310 μmol, 0.100 eq), potassium phosphate hydrate (144 mg, 625 μmol, 2.00 eq), 3,4,7,8-tetramethyl-1,10-phenanthroline (11.0 mg, 46.6 μmol, 0.150 eq) and copper(II) acetate (6.00 mg, 33.0 μmol, 0.100 eq) in dimethylsulfoxide (1 mL) was degassed and purged with nitrogen for three times, and then the mixture was stirred at 80° C. for 4 h under nitrogen atmosphere. After being cooled to room temperature, the mixture was concentrated under reduced pressure. The residue was purified by flash silica gel chromatography (ISCO®; 20 g SepaFlash® Silica Flash Column, eluent of 30%-70% ethyl acetate/petroleum ether gradient at 50 mL/min) to give 5-(5-bromopyridin-2-yl)-7-oxa-5-azaspiro[3.5]nonan-6-one (63.0 mg, 204 μmol, 65% yield, 96% purity) as a white solid.

$^1$H NMR (400 MHz, DMSO-d$_6$) δ=8.70 (d, J=2.4 Hz, 1H), 8.16 (dd, J=2.4, 8.4 Hz, 1H), 7.31 (d, J=8.4 Hz, 1H), 4.39-4.30 (m, 2H), 2.32-2.12 (m, 4H), 2.02-1.83 (m, 2H), 1.67-1.50 (m, 1H), 1.48-1.33 (m, 1H).

MS (ESI) m/z 297.0 [M+H]$^+$

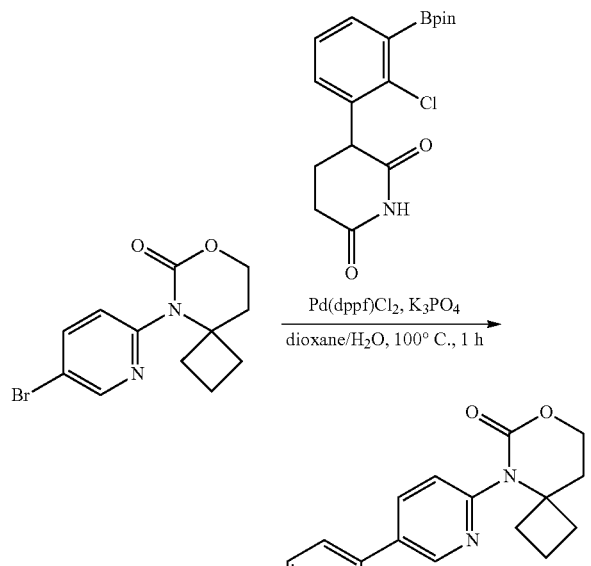

Compound 359

3-(2-chloro-3-(4,4,5,5-tetramethyl-1,3,2-dioxaborolan-2-yl)phenyl)piperidine-2,6-dione (intermediate A) was synthesized as described above. Under nitrogen atmosphere, to a solution of 5-(5-bromopyridin-2-yl)-7-oxa-5-azaspiro[3.5]nonan-6-one (81.0 mg, 262 μmol, 1.00 eq), 3-(2-chloro-3-(4,4,5,5-tetramethyl-1,3,2-dioxaborolan-2-yl)phenyl)-piperidine-2,6-dione (169 mg, 387 μmol, 1.48 eq) and potassium phosphate (166 mg, 782 μmol, 2.99 eq) in dioxane (2 mL) was added [1,1'-bis(diphenylphosphino)ferrocene]dichloropalladium(II) (19.0 mg, 26.0 μmol, 0.100 eq) and water (0.1 mL) at 25° C. The mixture was stirred at 100° C. for 1 h. After being cooled to room temperature, the mixture was concentrated under vacuum. The residue was purified by flash silica gel chromatography (ISCO®; 20 g SepaFlash® Silica Flash Column, eluent of 50%-80% ethyl acetate/petroleum ether gradient at 50 mL/min) and Prep-HPLC (column: Phenomenex luna C18 150 mm×25 mm×10 μm; mobile phase: [water (formic acid)-acetonitrile]; gradient: 24%-54% B over 10 min) and lyophilized to afford 3-(2-chloro-3-(6-(6-oxo-7-oxa-5-azaspiro[3.5]nonan-5-yl)pyridin-3-yl)phenyl)piperidine-2,6-dione (41.86 mg, 94.2 μmol, 36% yield, 99% purity) as a white solid.

$^1$H NMR (400 MHz, DMSO-d$_6$) δ=10.94 (s, 1H), 8.59 (d, J=2.4 Hz, 1H), 8.01 (dd, J=2.4, 8.4 Hz, 1H), 7.49-7.43 (m, 3H), 7.40 (d, J=8.4 Hz, 1H), 4.45-4.31 (m, 3H), 2.89-2.74 (m, 1H), 2.60-2.53 (m, 1H), 2.39-2.24 (m, 5H), 2.12-2.02 (m, 1H), 2.01-1.91 (m, 2H), 1.68-1.56 (m, 1H), 1.50-1.37 (m, 1H).

MS (ESI) m/z 440.1 [M+H]$^+$

Example 127. Synthesis of 3-(2-chloro-4'-(pyrimidin-2-yloxy)-[1,1'-biphenyl]-3-yl)piperidine-2,6-dione (Compound 360)

3-(2-chloro-4'-(pyrimidin-2-yloxy)-[1,1'-biphenyl]-3-yl)piperidine-2,6-dione was prepared from 2-(4-iodophenoxy)pyrimidine and 3-(2-chloro-3-(4,4,5,5-tetramethyl-1,3,2-dioxaborolan-2-yl)phenyl)piperidine-2,6-dione according to General Scheme 1.

MS (ESI) m/z 394.1 [M+H]$^+$

Example 128. Synthesis of 3-(2-chloro-5-fluoro-4'-(2-oxopyridin-1(2H)-yl)-[1,1'-biphenyl]-3-yl)piperidine-2,6-dione (Compound 361)

1-(4-(4,4,5,5-tetramethyl-1,3,2-dioxaborolan-2-yl)phenyl)pyridin-2(1H)-one was prepared from 1,4-dibromobenzene and pyridine-2(1H)-one according to General Scheme 6.

3-(3-bromo-2-chloro-5-fluorophenyl)piperidine-2,6-dione was prepared from 1-bromo-2-chloro-5-fluoro-3-methylbenzene according to General Scheme 2.

3-(2-chloro-5-fluoro-4'-(2-oxopyridin-1(2H)-yl)-[1,1'-biphenyl]-3-yl)piperidine-2,6-dione was prepared from 3-(3-bromo-2-chloro-5-fluorophenyl)piperidine-2,6-dione and 1-(4-(4,4,5,5-tetramethyl-1,3,2-dioxaborolan-2-yl)phenyl)pyridin-2(1H)-one according to General Scheme 5.

MS (ESI) m/z 411.2 [M+H]$^+$

Example 129. Synthesis of 3-(2-chloro-3-(5-fluoro-6-(5-oxo-4-azaspiro[2.5]octan-4-yl)pyridin-3-yl)phenyl)piperidine-2,6-dione (Compound 362)

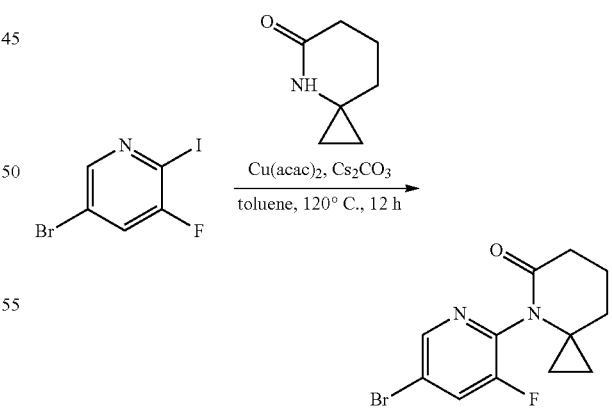

A mixture of 5-bromo-3-fluoro-2-iodopyridine (0.300 g, 0.994 mmol, 1.00 eq), 4-azaspiro[2.5]octan-5-one (0.0995 g, 0.795 mmol, 0.800 eq) and cesium carbonate (0.975 g, 2.99 mmol, 3.01 eq) in toluene (15 mL) was degassed and purged with nitrogen for 3 times, and then the bis[(Z)-1-methyl-3-oxo-but-1-enoxy]copper (0.0520 g, 0.198 mmol, 0.200 eq) was added. The resulting mixture was stirred at 120° C. for 12 h under nitrogen atmosphere. The mixture was cooled to 25° C. and concentrated under reduced pressure. The crude product was purified by flash silica gel chromatography (ISCO®; 20 g SepaFlash®Silica Flash Column, eluent of 20%-40% ethyl acetate/petroleum ether gradient at 100 mL/min) to give 4-(5-bromo-3-fluoropyridin-2-yl)-4-azaspiro[2.5]octan-5-one (0.100 g, 0.304 mmol, 31% yield) as white oil.

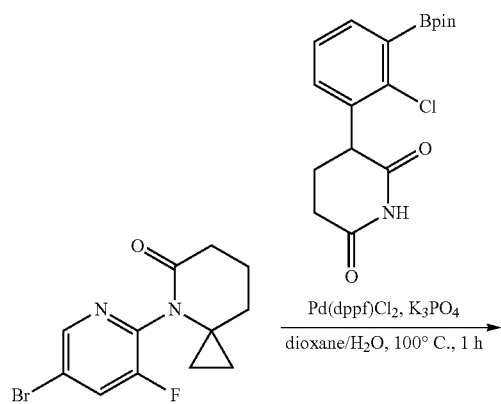

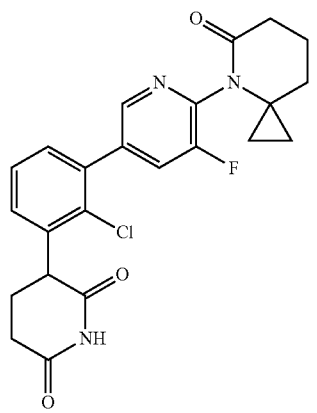

Compound 362

3-(2-chloro-3-(5-fluoro-6-(5-oxo-4-azaspiro [2.5] octan-4-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(5-bromo-3-fluoropyridin-2-yl)-4-azaspiro[2.5]octan-5-one according to General Scheme 1.

¹H NMR (400 MHz, DMSO-d₆) δ=10.94 (s, 1H), 8.38 (d, J=1.6 Hz, 1H), 7.98 (dd, J=2.0, 10.0 Hz, 1H), 7.46 (s, 3H), 4.37 (dd, J=4.8, 12.4 Hz, 1H), 2.87-2.75 (m, 1H), 2.63-2.58 (m, 2H), 2.54-2.52 (m, 1H), 2.41-2.27 (m, 1H), 2.09-2.02 (m, 1H), 1.99 (t, J=6.8 Hz, 2H), 1.91-1.83 (m, 2H), 0.74 (s, 2H), 0.63 (s, 2H)

¹H NMR (400 MHz, MeOD-d₄) δ=8.38 (d, J=1.6 Hz, 1H), 7.86 (dd, J=2.0, 9.6 Hz, 1H), 7.48-7.44 (m, 2H), 7.44-7.40 (m, 1H), 4.42 (dd, J=5.2, 12.0 Hz, 1H), 2.88-2.77 (m, 1H), 2.75-2.66 (m, 3H), 2.44 (dq, J=4.4, 12.8 Hz, 1H), 2.25-2.17 (m, 1H), 2.12 (q, J=6.8 Hz, 2H), 2.02-1.95 (m, 2H), 0.77 (s, 4H); MS (ESI) m/z 442.2 [M+H]⁺

Example 130. Synthesis of 3-(2-chloro-3-(5-(5-oxo-4-azaspiro[2.5]octan-4-yl)pyrimidin-2-yl)phenyl)piperidine-2,6-dione (Compound 364)

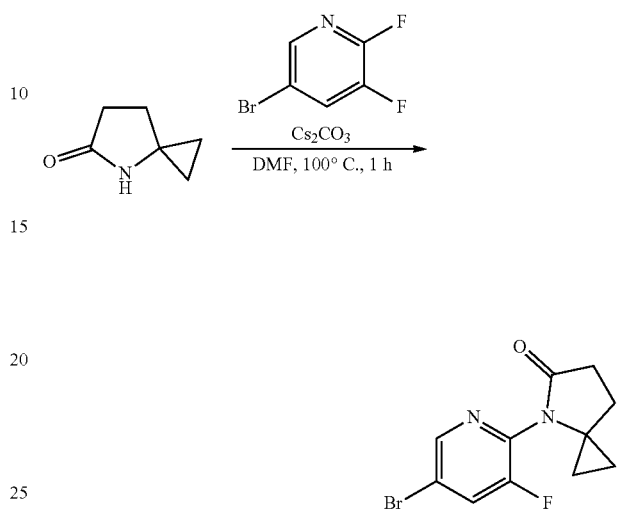

To a solution of 4-azaspiro[2.4]heptan-5-one (0.200 g, 1.80 mmol, 1.00 eq) in dimethyl formamide (10 mL) was added 5-bromo-2,3-difluoro-pyridine (0.419 g, 2.16 mmol, 1.20 eq) followed by cesium carbonate (1.17 g, 3.60 mmol, 2.00 eq) at 25° C. The reaction was stirred at 100° C. for 1 h. After being cooled to room temperature, the mixture was diluted with saturated ammonium chloride aqueous (20 mL) and extracted with ethyl acetate (3×20 mL). The combined organic layers were washed with brine (3×20 mL), dried over anhydrous sodium sulfate and concentrated under vacuum. The residue was purified by flash silica gel chromatography (ISCO®; 20 g SepaFlash® Silica Flash Column, eluent of 30%-50% ethyl acetate/petroleum ether gradient at 70 mL/min) to give 4-(5-bromo-3-fluoropyridin-2-yl)-4-azaspiro[2.4]heptan-5-one (150 mg, 526 umol, 29% yield) as a light yellow oil.

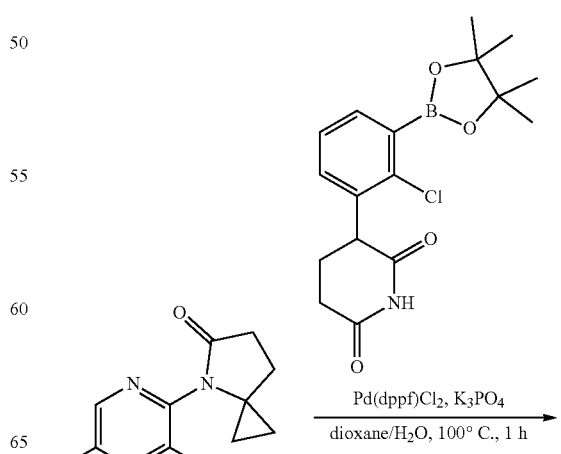

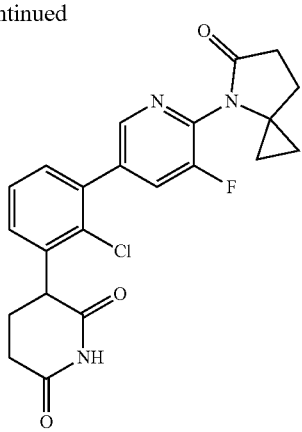

Compound 364

3-(2-chloro-3-(5-fluoro-6-(5-oxo-4-azaspiro[2.4]heptan-4-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(5-bromo-3-fluoropyridin-2-yl)-4-azaspiro[2.4]heptan-5-one according to General Scheme 1.

$^1$H NMR (400 MHz, DMSO-d$_6$) δ=10.94 (s, 1H), 8.36 (s, 1H), 8.08-8.01 (m, 1H), 7.46 (s, 3H), 4.37 (dd, J=4.8, 12.0 Hz, 1H), 2.87-2.73 (m, 1H), 2.65 (t, J=7.6 Hz, 2H), 2.58-2.55 (m, 1H), 2.36-2.25 (m, 3H), 2.08-2.00 (m, 1H), 0.98-0.82 (m, 2H), 0.76-0.69 (m, 2H); MS (ESI) m/z 428.1 [M+H]$^+$

Example 131. Synthesis of 3-(2-chloro-3-(5-fluoro-6-(6-oxo-5-azaspiro[3.4]octan-5-yl)pyridin-3-yl)phenyl)piperidine-2,6-dione (Compound 365)

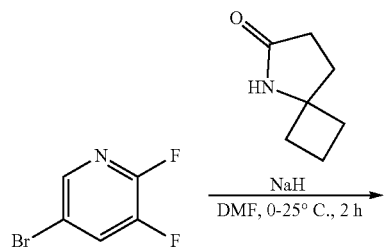

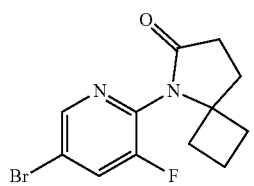

To a solution of 5-azaspiro[3.4]octan-6-one (240 mg, 1.92 mmol, 1.30 eq) and 5-bromo-2,3-difluoropyridine (286 mg, 1.47 mmol, 1.00 eq) in dimethylformamide (3.0 mL) was added sodium hydride (88.6 mg, 2.22 mmol, 60% purity, 1.50 eq) at 0° C. under nitrogen atmosphere. The reaction was stirred at 25° C. for 2 h. The reaction was quenched with 1M hydrochloric acid (50 mL) and extracted with ethyl acetate (3×50 mL), then the organic layers were wash with brine (50 mL), dried over sodium sulfate, filtered and concentrated under reduced pressure to give a residue. The residue was purified by column chromatography (SiO2, Petroleum ether/Ethyl acetate=5/1 to 3/1) to afford 5-(5-bromo-3-fluoropyridin-2-yl)-5-azaspiro[3.4]octan-6-one (50.0 mg, 167 μmol, 11% yield) as colourless oil.

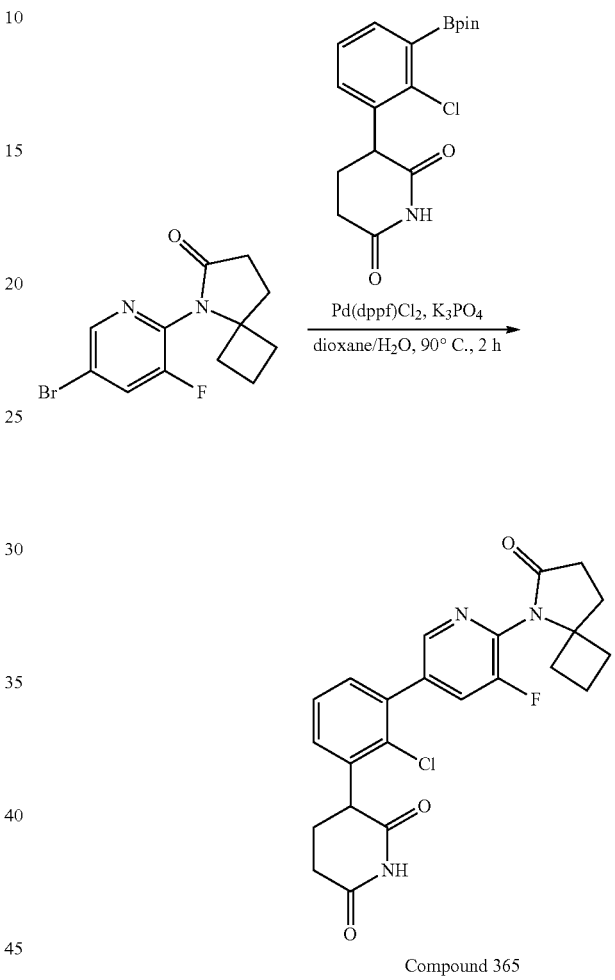

Compound 365

3-(2-chloro-3-(5-fluoro-6-(6-oxo-5-azaspiro[3.4]octan-5-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5-(5-bromo-3-fluoropyridin-2-yl)-5-azaspiro[3.4]octan-6-one according to General Scheme 1.

$^1$H NMR (400 MHz, DMSO-d$_6$) δ=10.95 (br s, 1H), 8.50 (d, J=1.6 Hz, 1H), 8.07 (dd, J=2.0, 10.0 Hz, 1H), 7.57-7.45 (m, 3H), 4.39 (dd, J=5.2, 12.0 Hz, 1H), 2.89-2.76 (m, 1H), 2.55-2.52 (m, 1H), 2.50-2.37 (m, 6H), 2.34 (br d, J=3.6 Hz, 1H), 2.12-2.06 (m, 2H), 2.05 (br d, J=2.8 Hz, 1H), 1.80-1.67 (m, 1H), 1.64-1.49 (m, 1H).

$^1$H NMR (400 MHz, CDCl$_3$) δ=8.47 (d, J=1.2 Hz, 1H), 8.04 (br s, 1H), 7.69 (dd, J=1.6, 9.6 Hz, 1H), 7.47-7.32 (m, 3H), 4.36 (dd, J=5.6, 10.4 Hz, 1H), 2.92-2.72 (m, 2H), 2.69-2.51 (m, 4H), 2.50-2.43 (m, 2H), 2.41-2.27 (m, 2H), 2.17-2.07 (m, 2H), 1.83-1.68 (m, 2H); MS (ESI) m/z 442.1 [M+H]$^+$

Example 132. Synthesis of 3-(2-chloro-4'-(6-methyl-5-oxo-4,6-diazaspiro[2.5]octan-4-yl)-[1,1'-biphenyl]-3-yl)piperidine-2,6-dione (Compound 366)

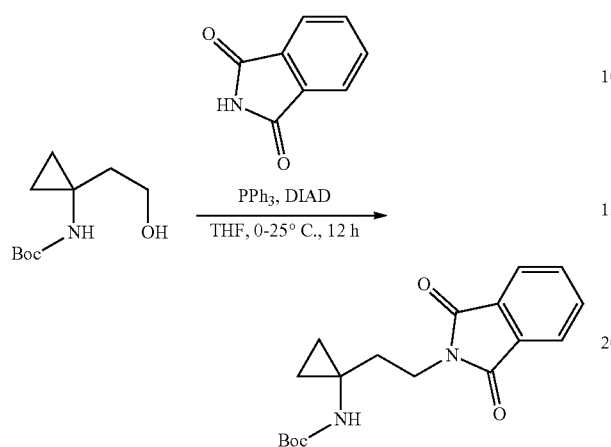

Under nitrogen atmosphere, to a solution of tert-butyl (1-(2-hydroxyethyl)cyclopropyl)carbamate (1.10 g, 5.47 mmol, 1.00 eq), isoindoline-1,3-dione (1.06 g, 7.18 mmol, 1.31 eq) and triphenylphosphine (1.87 g, 7.13 mmol, 1.30 eq) in tetrahydrofuran (10 mL) was added diisopropyl (E)-diazene-1,2-dicarboxylate (1.45 g, 7.18 mmol, 1.31 eq) at 0° C. Then the mixture was stirred at 25° C. for 12 h. The mixture was concentrated under reduced pressure. The residue was purified by flash silica gel chromatography (ISCO®; 20 g SepaFlash® Silica Flash Column, eluent of 0%-15% ethyl acetate/petroleum ether gradient at 70 mL/min) and reversed-phase column (column: C18, 80 g; mobile phase: [water (0.1% formic acid)-acetonitrile]; B %: 0%-50%) to give tert-butyl (1-(2-(1,3-dioxoisoindolin-2-yl)ethyl)cyclopropyl)carbamate (1.64 g, 4.72 mmol, 86% yield, 95% purity) as a white solid.

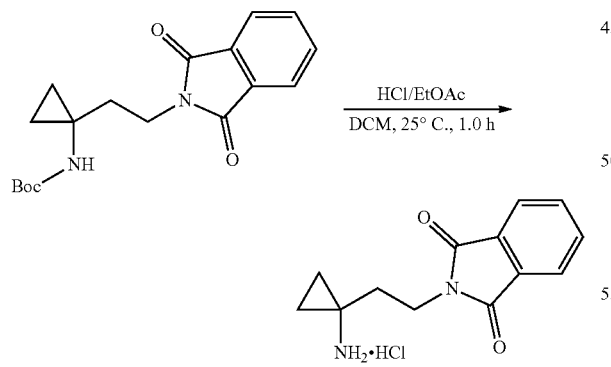

To a solution of tert-butyl (1-(2-(1,3-dioxoisoindolin-2-yl)ethyl)cyclopropyl)carbamate (1.64 g, 4.96 mmol, 1.00 eq) in dichloromethane (15 mL) was added hydrogen chloride/ethyl acetate (4 M, 15 mL) at 25° C. Then the mixture was stirred at 25° C. for 1 h. The mixture was concentrated under reduced pressure to give 2-(2-(1-aminocyclopropyl)ethyl)isoindoline-1,3-dione hydrochloride (1.32 g, 4.70 mmol, 95% yield, 95% purity) as a white solid.

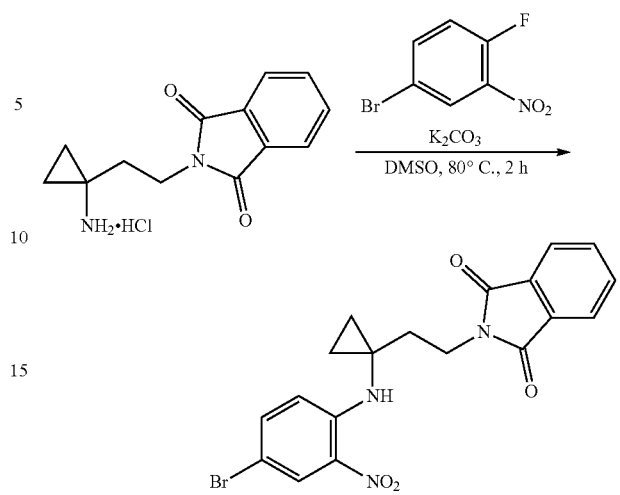

To a solution of 2-(2-(1-aminocyclopropyl)ethyl)isoindoline-1,3-dione hydrochloride (1.32 g, 4.70 mmol, 1.00 eq) and potassium carbonate (1.32 g, 9.53 mmol, 2.03 eq) in dimethylsulfoxide (10 mL) was added 4-bromo-1-fluoro-2-nitrobenzene (2.07 g, 9.41 mmol, 1.16 mL, 2.00 eq) at 25° C. Then the mixture was stirred at 80° C. for 2 h. After being cooled to room temperature, the reaction mixture was diluted with ethyl acetate (20 mL). The organic layer was washed with brine (3×20 mL), dried over sodium sulfate and filtered. The filtrate was concentrated under reduced pressure. The residue was purified by flash silica gel chromatography (ISCO®; 20 g SepaFlash® Silica Flash Column, eluent of 0%-30% ethyl acetate/petroleum ether gradient at 70 mL/min) to give 2-(2-(1-((4-bromo-2-nitrophenyl)amino)cyclopropyl)ethyl)isoindoline-1,3-dione (1.67 g, 3.69 mmol, 78% yield, 95% purity) as a yellow solid.

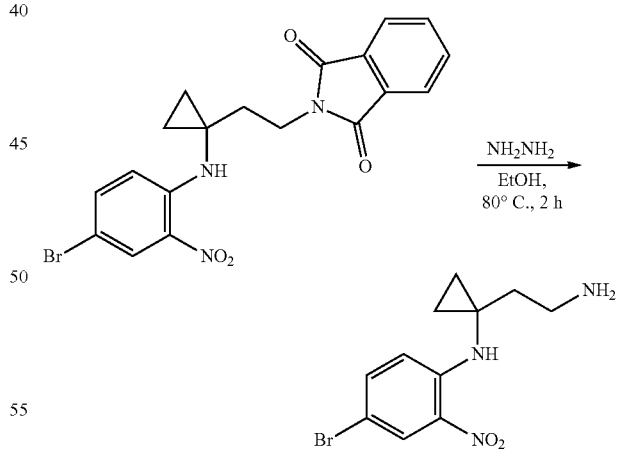

To a solution of 2-(2-(1-((4-bromo-2-nitrophenyl)amino)cyclopropyl)ethyl)isoindoline-1,3-dione (800 mg, 1.86 mmol, 1.00 eq) in ethanol (20 mL) was added hydrazine monohydrate (2.19 g, 43.8 mmol, 23.5 eq) at 25° C. Then the mixture was stirred at 80° C. for 2 h. After being cooled to room temperature, the reaction mixture was diluted with ethyl acetate (100 mL). The solvents were washed with brine (3×100 mL), dried over sodium sulfate and filtered. The filtrate was concentrated under reduced pressure to give N-(1-(2-aminoethyl)cyclopropyl)-4-bromo-2-nitroaniline (207 mg, 655 μmol, 35% yield, 95% purity) as a yellow solid.

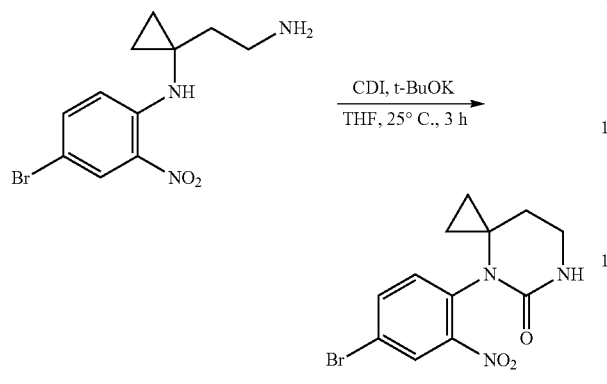

To a solution of N-(1-(2-aminoethyl)cyclopropyl)-4-bromo-2-nitroaniline (207 mg, 690 μmol, 1.00 eq) in tetrahydrofuran (2 mL) was added 1,1'-carbonyldiimidazole (134 mg, 826 umol, 1.20 eq) at 25° C. Then the mixture was stirred at 25° C. for 1 h. Then potassium tert-butoxide (154 mg, 1.37 mmol, 2.00 eq) was added at 25° C. Then the mixture was stirred at 25° C. for 2 h. The mixture was poured into brine (20 mL). The mixture was extracted with ethyl acetate (3×20 mL). The combined organic layers were washed with brine (20 mL), dried over sodium sulfate and filtered. The filtrate was concentrated under reduced pressure. The residue was purified by flash silica gel chromatography (ISCO®; 20 g SepaFlash® Silica Flash Column, eluent of 0%-50% ethyl acetate/petroleum ether gradient at 70 mL/min) to give 4-(4-bromo-2-nitrophenyl)-4,6-diazaspiro[2.5]octan-5-one (210 mg, 612 μmol, 89% yield, 95% purity) as a yellow solid.

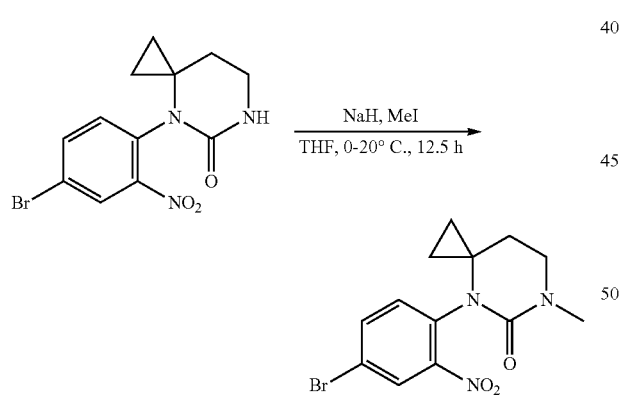

Under nitrogen atmosphere, to a solution of 4-(4-bromo-2-nitrophenyl)-4,6-diazaspiro[2.5]octan-5-one (220 mg, 675 umol, 1.00 eq) in tetrahydrofuran (5 mL) was added sodium hydride (33.0 mg, 825 umol, 60% purity, 1.22 eq) at 0° C. Then the mixture was stirred at 0° C. for 0.5 h. Then methyl iodide (193 mg, 1.36 mmol, 2.02 eq) was added at 0° C. The mixture was stirred at 25° C. for 12 h. The mixture was poured into brine (20 mL) and extracted with ethyl acetate (3×20 mL). The combined organic layers were washed with brine (20 mL), dried over sodium sulfate and filtered. The filtrate was concentrated under reduced pressure. The residue was purified by flash silica gel chromatography (ISCO®; 20 g SepaFlash® Silica Flash Column, eluent of 0%-20% ethyl acetate/petroleum ether gradient at 70 mL/min) to give 4-(4-bromo-2-nitrophenyl)-6-methyl-4,6-diazaspiro[2.5]octan-5-one (210 mg, 586 μmol, 87% yield, 95% purity) as a yellow solid.

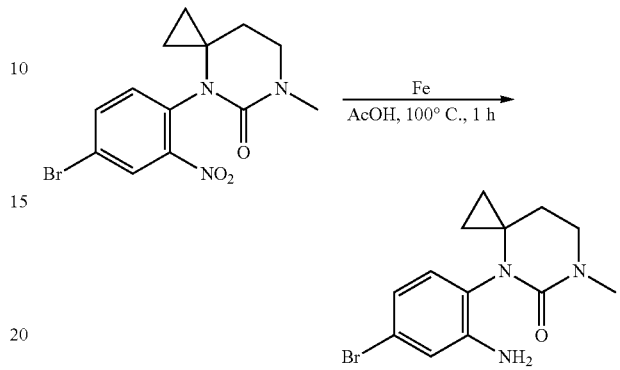

To a solution of 4-(4-bromo-2-nitrophenyl)-6-methyl-4,6-diazaspiro[2.5]octan-5-one (160 mg, 470 μmol, 1.00 eq) in acetic acid (2 mL) was added iron (263 mg, 4.70 mmol, 10.0 eq) at 25° C. The mixture was stirred at 100° C. for 1 h. After being cooled to room temperature, the mixture was diluted with ethyl acetate (50 mL). The mixture was filtered and the filtrate was washed with water (3×50 mL), dried over sodium sulfate, filtered and concentrated under reduced pressure. The residue was purified by flash silica gel chromatography (ISCO®; 20 g SepaFlash® Silica Flash Column, eluent of 0%-100% ethyl acetate/petroleum ether gradient at 70 mL/min) to give 4-(2-amino-4-bromophenyl)-6-methyl-4,6-diazaspiro[2.5]octan-5-one (90.0 mg, 276 μmol, 59% yield, 95% purity) as a yellow solid.

To a solution of 4-(2-amino-4-bromophenyl)-6-methyl-4,6-diazaspiro[2.5]octan-5-one (70.0 mg, 226 μmol, 1.00 eq) in water (1 mL) and hydrochloric acid (0.05 mL, 37% in water) was added sodium nitrite (19.0 mg, 275 μmol, 1.22 eq) and phosphinic acid (73.3 mg, 1.13 mmol, 5.00 eq) at 25° C. The mixture was stirred at 25° C. for 12 h. The reaction mixture was diluted with ethyl acetate (20 mL). The solvents were washed with brine (3×20 mL), dried over sodium sulfate and filtered. The filtrate was concentrated under reduced pressure. The residue was purified by flash silica gel chromatography (ISCO®; 20 g SepaFlash® Silica Flash Column, eluent of 0%-70% ethyl acetate/petroleum ether gradient at 70 mL/min) to give 4-(4-bromophenyl)-6- methyl-4,6-diazaspiro[2.5]octan-5-one (60.0 mg, 193 µmol, 70% yield, 95% purity) as a yellow solid.

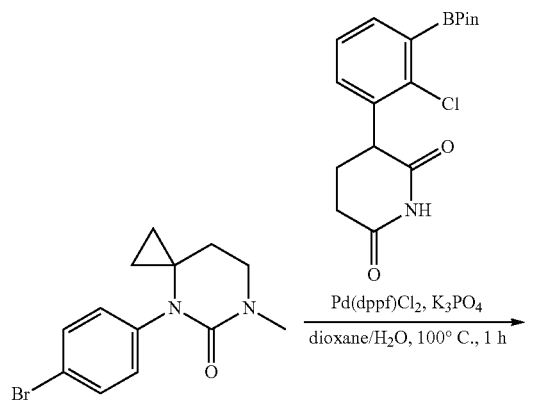

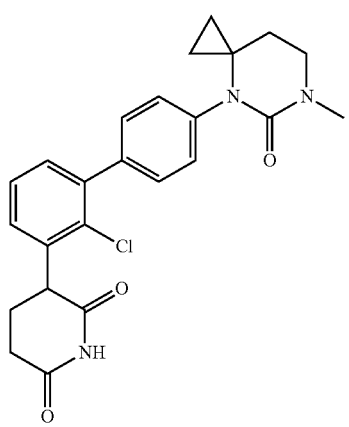

Compound 366

3-(2-chloro-4'-(6-methyl-5-oxo-4,6-diazaspiro[2.5]octan-4-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(4-bromophenyl)-6-methyl-4,6-diazaspiro[2.5]octan-5-one according to General Scheme 1.

$^1$H NMR (400 MHz, DMSO-d$_6$) δ=10.92 (s, 1H), 7.45-7.28 (m, 5H), 7.17 (d, J=8.4 Hz, 2H), 4.35 (dd, J=5.2, 12.0 Hz, 1H), 3.43 (t, J=6.0 Hz, 2H), 2.89 (s, 3H), 2.86-2.69 (m, 1H), 2.60-2.52 (m, 1H), 2.33 (dd, J=4.0, 12.4 Hz, 1H), 2.10-2.01 (m, 1H), 1.98 (t, J=6.0 Hz, 2H), 0.77-0.65 (m, 2H), 0.58-0.47 (m, 2H); MS (ESI) m/z 438.1 [M+H]$^+$

Example 133. Synthesis of 3-(2-chloro-3-(5-fluoro-6-(2-oxopiperidin-1-yl)pyridin-3-yl)phenyl)piperidine-2,6-dione (Compound 369)

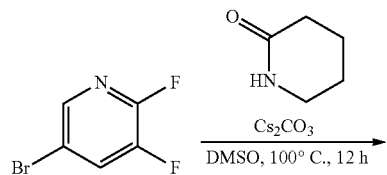

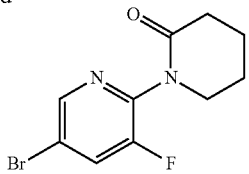

To a solution of 5-bromo-2,3-difluoropyridine (0.783 g, 4.04 mmol, 2.00 eq) and piperidin-2-one (0.200 g, 2.02 mmol, 1.00 eq) in dimethylsulfoxide (4.0 mL) was added cesium carbonate (1.31 g, 4.04 mmol, 2.00 eq) at 25° C. The mixture was stirred at 100° C. for 12 h. After being cooled to room temperature, the reaction mixture was diluted with water (20 mL) and ethyl acetate (20 mL) and then extracted with ethyl acetate (3×20 mL). The combined organic extracts were washed with brine (20 mL), dried over sodium sulfate, filtered and concentrated under reduced pressure. The residue was purified by flash silica gel chromatography (ISCO®; 20 g SepaFlash® Silica Flash Column, eluent of 0%-60% ethyl acetate/petroleum ether gradient at 30 mL/min) to give 1-(5-bromo-3-fluoropyridin-2-yl)piperidin-2-one (0.200 g, 0.732 mmol, 36% yield) as brown oil.

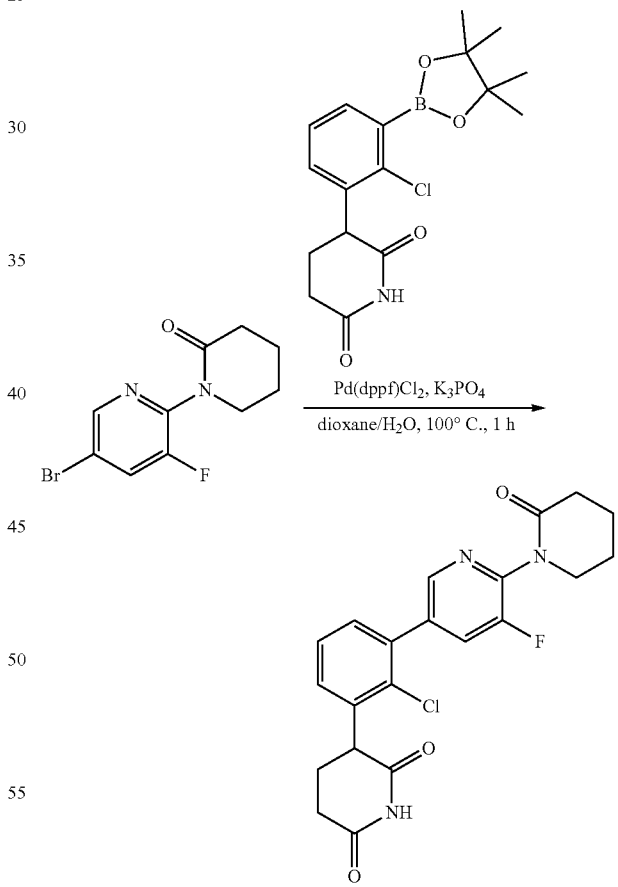

Compound 369

3-(2-chloro-3-(5-fluoro-6-(2-oxopiperidin-1-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(5-bromo-3-fluoropyridin-2-yl)piperidin-2-one according to General Scheme 1.

¹H NMR (400 MHz, DMSO-d₆) δ=10.94 (s, 1H), 8.38 (s, 1H), 7.94 (dd, J=1.6, 10.4 Hz, 1H), 7.47-7.45 (m, 3H), 4.37 (dd, J=5.2, 12.0 Hz, 1H), 3.77 (s, 2H), 2.84-2.76 (m, 1H), 2.57-2.53 (m, 1H), 2.47-2.46 (m, 2H), 2.33 (s, 1H), 2.07-2.03 (m, 1H), 1.92-1.87 (m, 4H); MS (ESI) m/z 416.1 [M+H]⁺

Example 134. Synthesis of 3-(2-chloro-3-(5-fluoro-6-(oxazol-2-ylmethyl)pyridin-3-yl)phenyl)piperidine-2,6-dione (Compound 370)

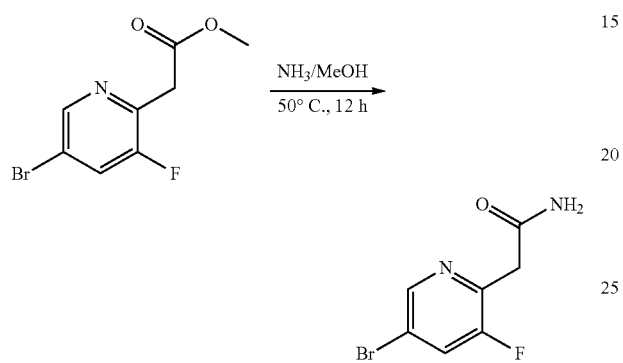

A mixture of methyl 2-(5-bromo-3-fluoropyridin-2-yl)acetate (720 mg, 2.90 mmol, 1.00 eq) in ammonia methanol (50.0 mL) was stirred at 50° C. for 12 h. The reaction was concentrated under reduced pressure to give a residue. The residue was purified by column chromatography (SiO₂, Petroleum ether/Ethyl acetate=1/1 to 0/1) to afford 2-(5-bromo-3-fluoropyridin-2-yl)acetamide (340 mg, 1.46 mmol, 50% yield) as a white solid.

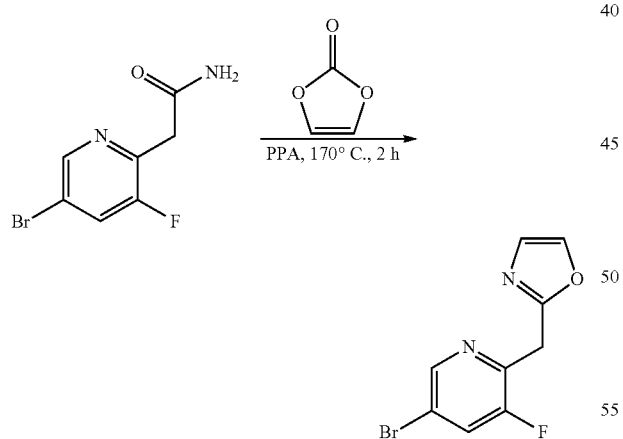

A mixture of 2-(5-bromo-3-fluoropyridin-2-yl)acetamide (570 mg, 2.45 mmol, 1.00 eq) and 1,3-dioxol-2-one (294 mg, 3.42 mmol, 1.40 eq) in polyphosphoric acid (5.00 mL) was stirred at 170° C. for 2 h. The reaction was cooled down to 25° C. and diluted with water (10 mL) to give a residue. The residue was purified by reversed-phase column (0.1% formic acid condition) to afford 2-((5-bromo-3-fluoropyridin-2-yl)methyl)oxazole (200 mg, 778 μmol, 32% yield) as a brown oil.

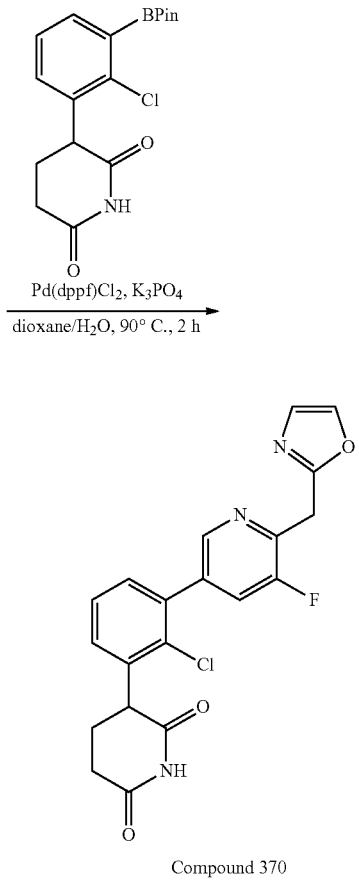

3-(2-chloro-3-(5-fluoro-6-(oxazol-2-ylmethyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 2-((5-bromo-3-fluoropyridin-2-yl)methyl)oxazole according to General Scheme 1.

¹H NMR (400 MHz, DMSO-d₆) δ=10.94 (br s, 1H), 8.42 (t, J=1.6 Hz, 1H), 8.07 (d, J=0.8 Hz, 1H), 7.90 (dd, J=1.6, 10.6 Hz, 1H), 7.53-7.42 (m, 3H), 7.16 (d, J=0.8 Hz, 1H), 4.43 (d, J=1.6 Hz, 2H), 4.37 (dd, J=5.2, 12.4 Hz, 1H), 2.87-2.75 (m, 1H), 2.60-2.55 (m, 1H), 2.34 (br dd, J=4.0 12.4 Hz, 1H), 2.09-2.01 (m, 1H); MS (ESI) m/z 400.0 [M+H]⁺

Example 135. Synthesis of 3-(2-chloro-4'-(2-methyl-6-oxo-2,5-diazaspiro[3.4]octan-5-yl)-[1,1'-biphenyl]-3-yl)piperidine-2,6-dione (Compound 371)

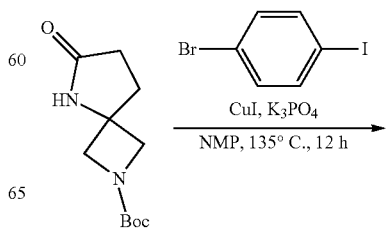

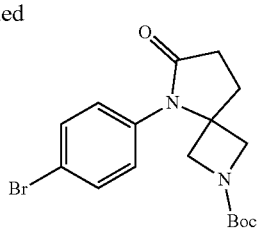

tert-butyl 5-(4-bromophenyl)-6-oxo-2,5-diazaspiro[3.4]octane-2-carboxylate was prepared from tert-butyl 6-oxo-2,5-diazaspiro[3.4]octane-2-carboxylate and 1-bromo-4-iodobenzene according to General Scheme 7.

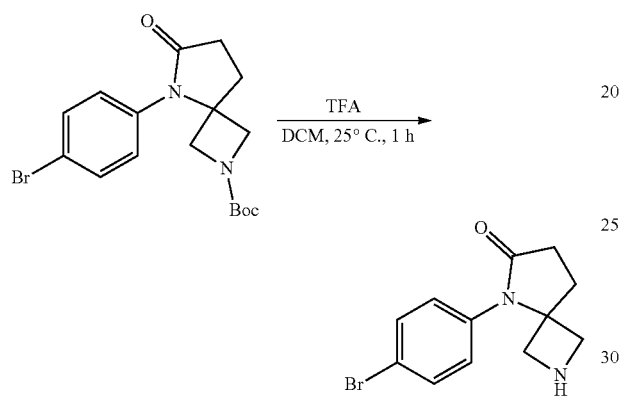

A solution of tert-butyl 5-(4-bromophenyl)-6-oxo-2,5-diazaspiro[3.4]octane-2-carboxylate (200 mg, 524 μmol, 1.00 eq) in trifluoroacetic acid (0.4 mL) and dichloromethane (2 mL) was stirred at 25° C. for 1 h. The reaction mixture was concentrated in vacuum to give 5-(4-bromophenyl)-2,5-diazaspiro[3.4]octan-6-one (200 mg, crude) as a yellow solid.

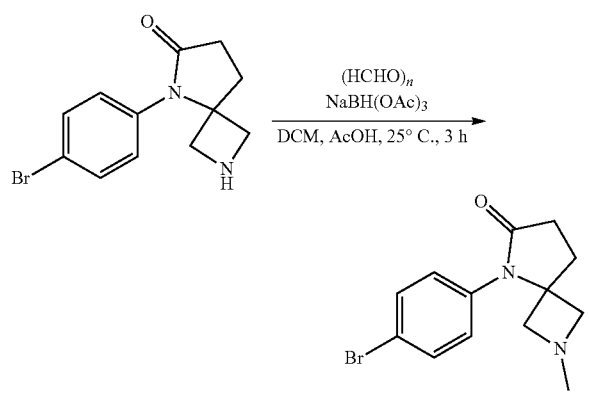

To a solution of 5-(4-bromophenyl)-2,5-diazaspiro[3.4]octan-6-one (200 mg, 711 μmol, 1.00 eq) in dichloromethane (2 mL) was added formaldehyde (42.7 mg, 1.42 mmol, 39.1 μL, 2.00 eq) and acetic acid (21.3 mg, 355 μmol, 20.3 μL, 0.500 eq). Then the reaction mixture was stirred at 25° C. for 1 h. Then the reaction mixture was added sodium triacetoxyhydroborate (452 mg, 2.13 mmol, 3.00 eq). Then the reaction mixture was stirred at 25° C. for 2 h. The reaction mixture was diluted with water (100 mL) and extracted with ethyl acetate (3×50 mL). The combined organic layers were washed with brine (3×20 mL), dried over sodium sulfate, filtered and concentrated under reduced pressure to gave 5-(4-bromophenyl)-2-methyl-2,5-diazaspiro 3.4 octan-6-one (160 mg, 542 μmol, 76% yield) as a white solid.

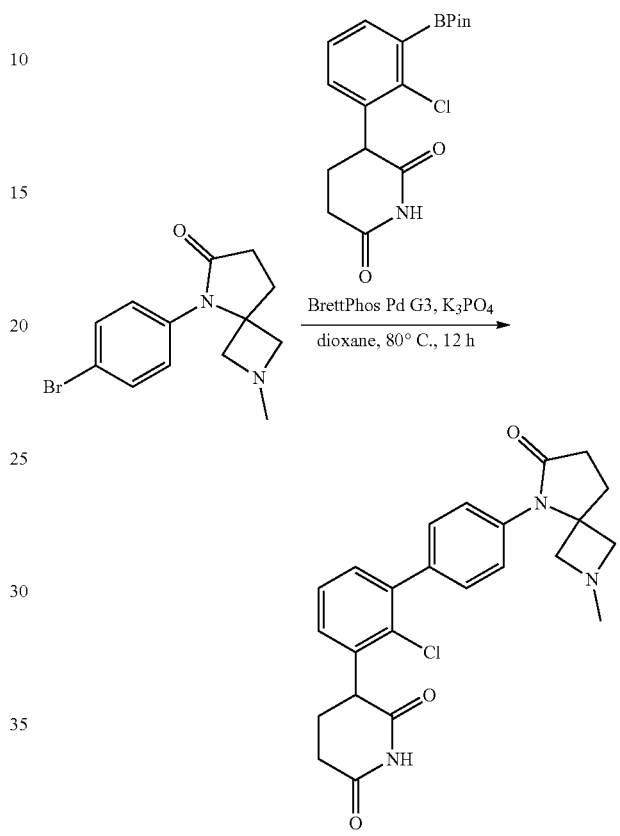

Compound 371

3-(2-chloro-4'-(2-methyl-6-oxo-2,5-diazaspiro[3.4]octan-5-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5-(4-bromophenyl)-2-methyl-2,5-diazaspiro[3.4]octan-6-one according to General Scheme 1.

$^1$H NMR (400 MHz, DMSO-d$_6$) δ=10.93 (br s, 1H), 8.29 (s, 0.6H), 7.78 (d, J=8.6 Hz, 2H), 7.45-7.41 (m, 2H), 7.39 (d, J=7.6 Hz, 1H), 7.37-7.34 (m, 1H), 7.33-7.29 (m, 1H), 4.35 (dd, J=12.0, 4.8 Hz, 1H), 3.82 (t, J=6.8 Hz, 2H), 3.32 (d, J=7.6 Hz, 2H), 3.23 (d, J=7.6 Hz, 2H), 2.78 (br d, J=12.0 Hz, 1H), 2.61-2.54 (m, 1H), 2.43 (t, J=6.8 Hz, 2H), 2.34 (br dd, J=12.8, 4.0 Hz, 1H), 2.25 (s, 3H), 2.09-2.01 (m, 1H); MS (ESI) m/z. 437.9 [M+H]$^+$

Example 136. Synthesis of 3-(2-chloro-4'-(2-oxotetrahydropyrimidin-1(2H)-yl)-[1,1'-biphenyl]-3-yl)piperidine-2,6-dione (Compound 372)

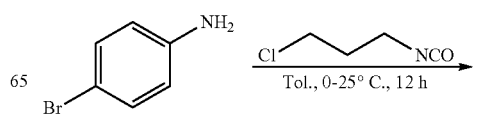

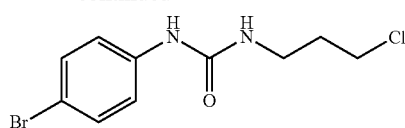

To a solution of 4-bromoaniline (1.00 g, 5.81 mmol, 1.00 eq) in toluene (8 mL) was added 1-chloro-3-isocyanatopropane (1.04 g, 8.72 mmol, 1.50 eq) at 0° C. The mixture was stirred at 25° C. for 12 h. The reaction mixture was filtered and the filter cake was used into the next step without further purification to get 1-(4-bromophenyl)-3-(3-chloropropyl)urea (1.50 g, 5.14 mmol, 88% yield, 100% purity) as a white solid.

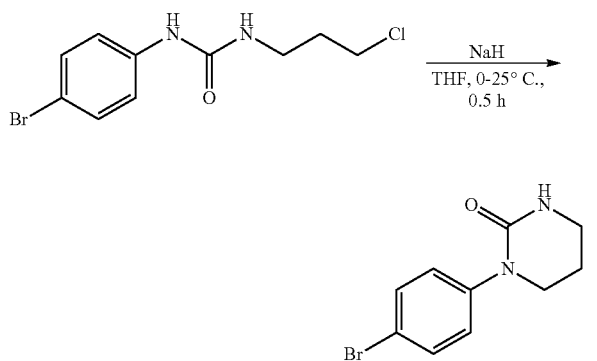

To a mixture of 1-(4-bromophenyl)-3-(3-chloropropyl) urea (200 mg, 686 μmol, 1.00 eq) in tetrahydrofuran (2 mL) was added sodium hydride (82.3 mg, 2.06 mmol, 60% purity, 3.00 eq) at 0° C. The mixture was stirred at 25° C. for 0.5 h. The mixture was quenched with saturated ammonium chloride solution (15 mL) and extracted with ethyl acetate (3×10 mL). The combined organic layers were dried over sodium sulfate and concentrated under vacuum. The crude product was used into the next step without further purification to get 1-(4-bromophenyl)hexahydropyrimidin-2-one (1.00 g, crude) as a white solid.

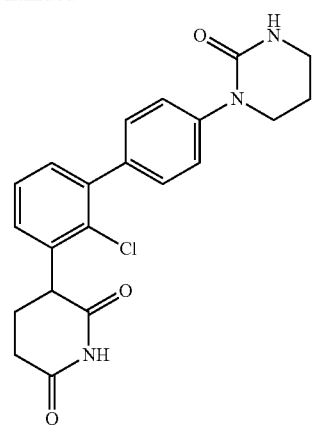

Compound 372

3-(2-chloro-4'-(2-oxotetrahydropyrimidin-1(2H)-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)hexahydropyrimidin-2-one according to General Scheme 1.

$^1$H NMR (400 MHz, DMSO-$d_6$) δ=10.93 (s, 1H), 7.41-7.34 (m, 3H), 7.34-7.29 (m, 4H), 6.67 (s, 1H), 4.35 (dd, J=12.0, 5.2 Hz, 1H), 3.68 (t, J=5.6 Hz, 2H), 3.28-3.20 (m, 2H), 2.84-2.74 (m, 1H), 2.56 (br d, J=3.6 Hz, 1H), 2.38-2.29 (m, 1H), 2.08-2.02 (m, 1H), 1.97 (quin, J=5.6 Hz, 2H); MS (ESI) m/z 398.0 [M+H]$^+$ Example 137. Synthesis of 3-(2-chloro-4'-(furan-2-ylmethyl)-[1,1'-biphenyl]-3-yl)piperidine-2,6-dione (Compound 373)

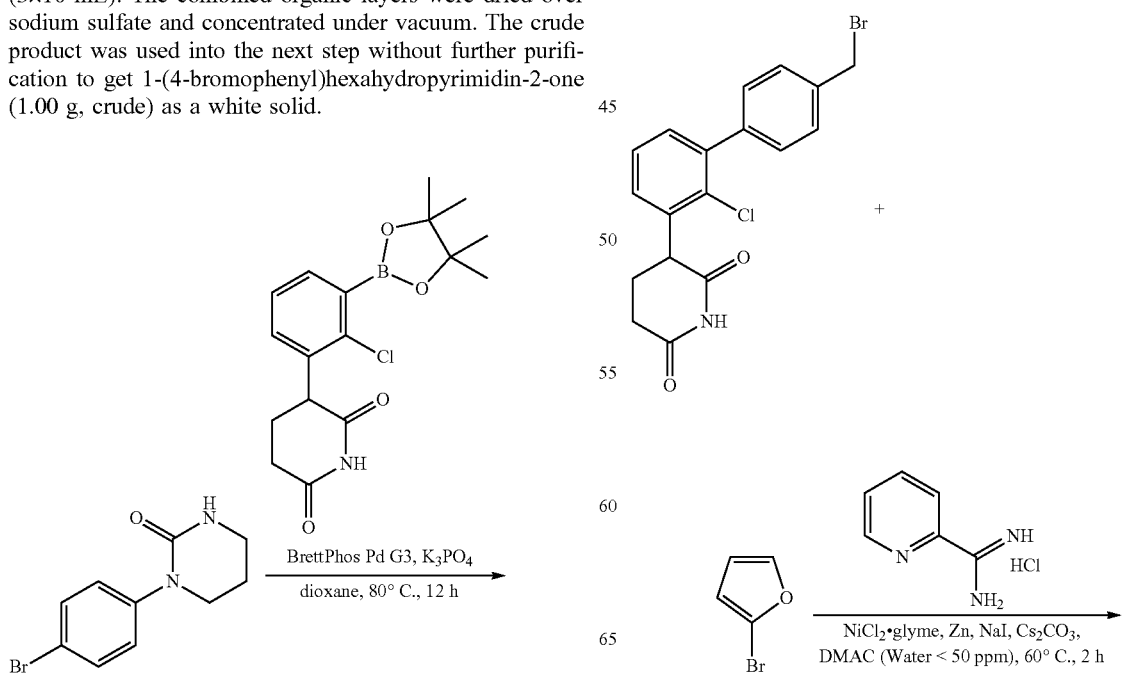

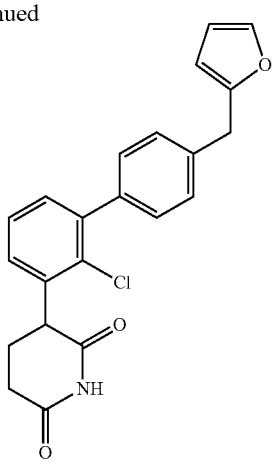

Compound 373

3-(4'-(bromomethyl)-2-chloro-[1,1'-biphenyl]-3-yl)piperidine-2,6-dione (intermediate B) was synthesized as described above. To a mixture of 3-[3-[4-(bromomethyl)phenyl]-2-chloro-phenyl]piperidine-2,6-dione (50.0 mg, 127 μmol, 1.00 eq), 2-bromofuran (28.1 mg, 191 μmol, 1.50 eq) and cesium carbonate (82.9 mg, 255 μmol, 2.00 eq), sodiumiodide (7.25 mg, 48.4 μmol, 0.380 eq), nickel(II) chloride ethylene glycol dimethyl ether complex (7.27 mg, 33.1 μmol, 0.260 eq) and pyridine-2-carboxamidine; hydrochloride (5.22 mg, 33.1 μmol, 0.260 eq) in N,N-dimethylacetamide (1.00 mL) was added zinc (20.8 mg, 318 μmol, 2.50 eq) under nitrogen. The reaction was heated to 60° C. stirred for 4 h. The reaction mixture was cooled to room temperature and filtered. The cake was washed with 1M hydrogen chloride for quenching the zinc dust, and the filtrate was poured into water (20 mL). The aqueous phase was extracted with ethyl acetate (3×20 mL). The combined extracts was dried over sodium sulfate, filtered, and concentrated under vacuum. The crude product was purified by Prep-HPLC (column: C18 150×30 mm; mobile phase: [water(formic acid)-acetonitrile]; gradient: 52%-82% B over 7 min) to afford 3-(2-chloro-4'-(furan-2-ylmethyl)-[1,1'-biphenyl]-3-yl)piperidine-2,6-dione (9.90 mg, 26.1 mol, 20% yield, 99% purity) as a white solid.

MS (ESI) m/z 380.1 [M+H]⁺

Example 138. Synthesis of 3-(2-chloro-4'-(pyridin-3-ylmethyl)-[1,1'-biphenyl]-3-yl)piperidine-2,6-dione (Compound 374)

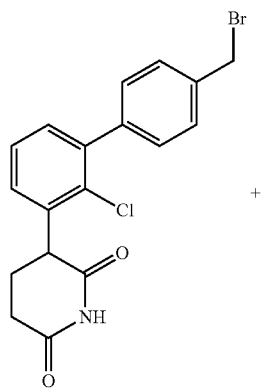

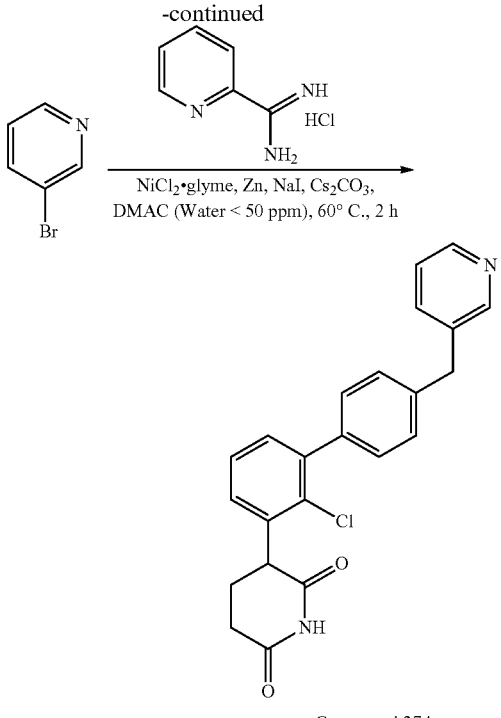

Compound 374

3-[2-chloro-3-[4-(3-pyridylmethyl)phenyl]phenyl]piperidine-2,6-dione was prepared from 3-(4'-(bromomethyl)-2-chloro-[1,1'-biphenyl]-3-yl)piperidine-2,6-dione and 3-bromopyridine analogously to Example 137.

MS (ESI) m/z 391.0 [M+H]⁺

Example 139. Synthesis of methyl 5-((2'-chloro-3'-(2,6-dioxopiperidin-3-yl)-[1,1'-biphenyl]-4-yl)methyl)-1-methyl-1H-pyrrole-2-carboxylate (Compound 375)

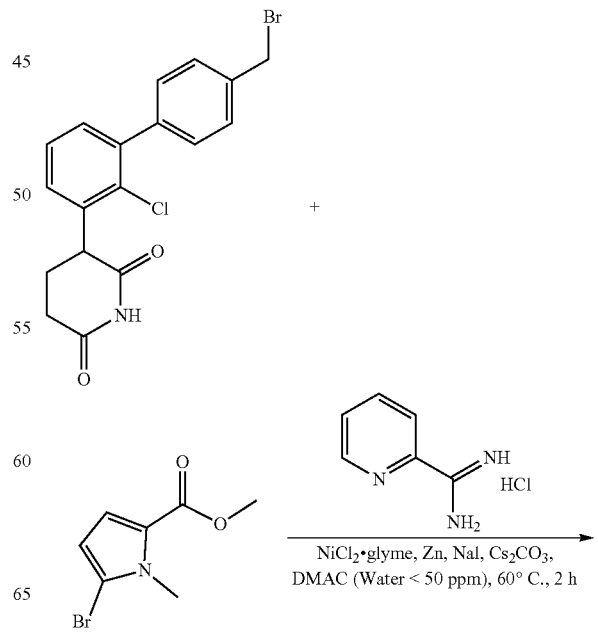

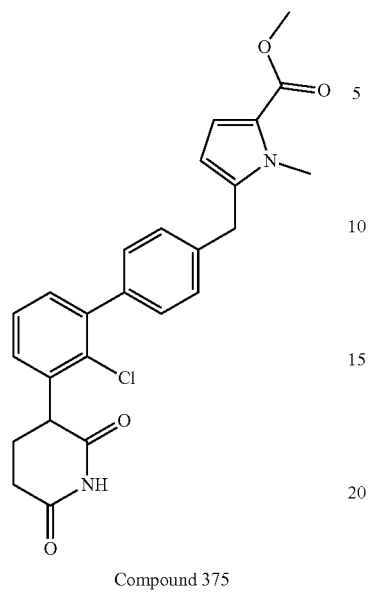

Compound 375

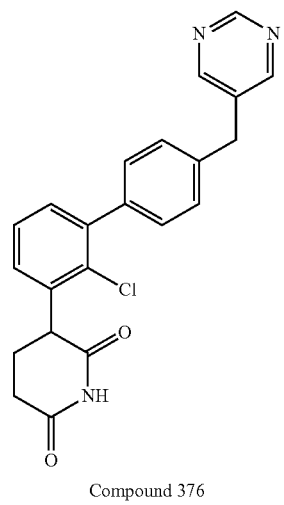

Compound 376 methyl 5-((2'-chloro-3'-(2,6-dioxopiperidin-3-yl)-[1,1'-biphenyl]-4-yl)methyl)-1-methyl-1H-pyrrole-2-carboxylate was prepared from 3-(4'-(bromomethyl)-2-chloro-[1,1'-biphenyl]-3-yl)piperidine-2,6-dione and methyl 5-bromo-1-methyl-1h-pyrrole-2-carboxylate analogously to Example 137.

MS (ESI) m/z 451.2 [M+H]$^+$ 3-(2-chloro-4'-(pyrimidin-5-ylmethyl)-[1,1'-biphenyl]-3-yl)piperidine-2,6-dione was prepared from 3-(4'-(bromomethyl)-2-chloro-[1,1'-biphenyl]-3-yl)piperidine-2,6-dione and 5-bromopyrimidine analogously to Example 137.

MS (ESI) m/z 392.1 [M+H]$^+$

Example 140. Synthesis of 3-(2-chloro-4'-(pyrimidin-5-ylmethyl)-[1,1'-biphenyl]-3-yl)piperidine-2,6-dione (Compound 376)

Example 141. Synthesis of 3-(2-chloro-4'-(thiophen-2-ylmethyl)-[1,1'-biphenyl]-3-yl)piperidine-2, 6-dione (Compound 377)

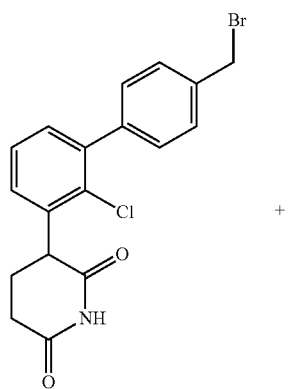 +

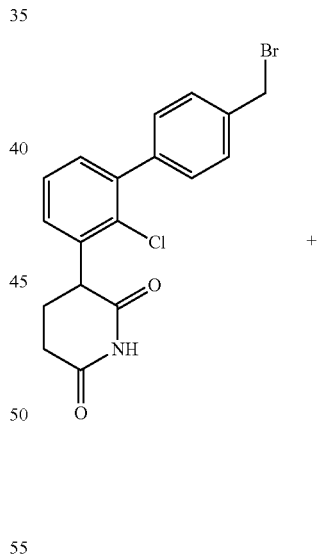 +

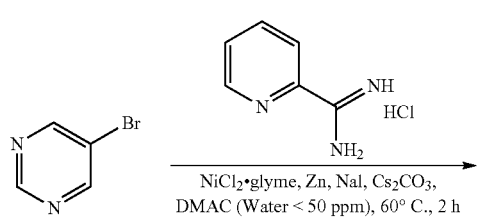

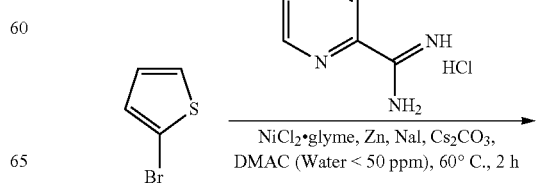

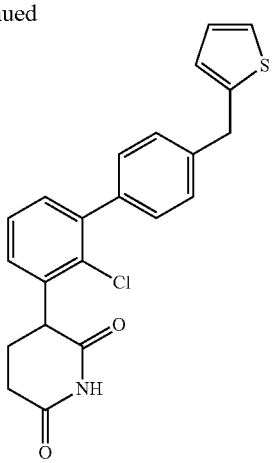

Compound 377

3-(2-chloro-4'-(thiophen-2-ylmethyl)-[1,1'-biphenyl]-3-yl)piperidine-2,6-dione was prepared from 3-(4'-(bromomethyl)-2-chloro-[1,1'-biphenyl]-3-yl)piperidine-2,6-dione and 2-bromothiophene analogously to Example 137.

MS (ESI) m/z 396.1 [M+H]$^+$

Example 142. Synthesis of 3-(2-chloro-4'-(3,6,6-trimethyl-2-oxotetrahydropyrimidin-1(2H)-yl)-[1,1'-biphenyl]-3-yl)piperidine-2,6-dione (Compound 378)

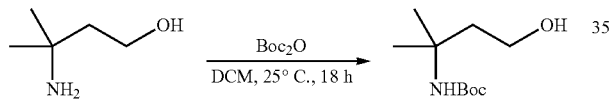

To a solution of 3-amino-3-methylbutan-1-ol (3.00 g, 29.1 mmol, 1.00 eq) in dichloromethane (80 mL) was added di-tert-butyl dicarbonate (7.62 g, 34.9 mmol, 1.20 eq). The mixture was stirred at 25° C. for 18 h. The reaction mixture was concentrated in vacuo to give tert-butyl (4-hydroxy-2-methylbutan-2-yl)carbamate (10.0 g, crude) as colorless oil.

$^1$H NMR (400 MHz, DMSO-d$_6$) δ=6.41 (s, 1H), 4.41 (t, J=4.8 Hz, 1H), 3.45 (dt, J=5.2, 6.8 Hz, 2H), 1.71 (t, J=7.2 Hz, 2H), 1.36 (s, 9H), 1.18 (s, 6H)

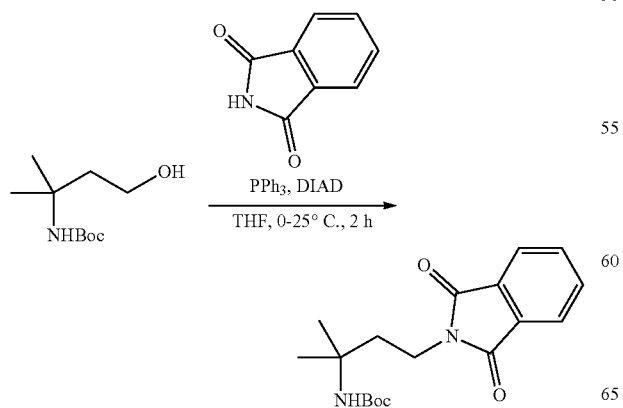

Under nitrogen atmosphere, to a solution of tert-butyl (4-hydroxy-2-methylbutan-2-yl)carbamate (4.00 g, 19.7 mmol, 1.00 eq), isoindoline-1,3-dione (3.76 g, 25.6 mmol, 1.30 eq) and triphenylphosphine (6.70 g, 25.5 mmol, 1.30 eq) in tetrahydrofuran (50 mL) was added diisopropyl azodicarboxylate (5.18 g, 25.6 mmol, 1.30 eq) at 0° C. The mixture was stirred at 25° C. for 2 h. Ethyl acetate (80 mL) and water (80 mL) were added and layers were separated. The aqueous phase was extracted with ethyl acetate (3×80 mL). Combined extracts were washed with brine (120 mL), dried over sodium sulfate, filtered, and concentrated under vacuum. The residue was purified by flash silica gel chromatography (ISCO®; 120 g SepaFlash® Silica Flash Column, eluent of 0%-100% ethyl acetate/petroleum ether gradient @ 100 mL/min) to give tert-butyl (4-(1,3-dioxoisoindolin-2-yl)-2-methylbutan-2-yl)carbamate (10.0 g, crude) as a white solid.

$^1$H NMR (400 MHz, DMSO-d$_6$) δ=7.85-7.82 (m, 4H), 4.79-4.75 (m, 1H), 3.59-3.50 (m, 2H), 1.96-1.90 (m, 2H), 1.32 (s, 9H), 1.21 (s, 6H)

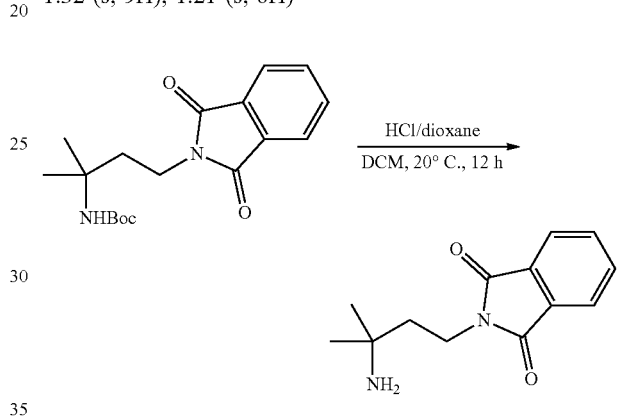

To a solution of tert-butyl (4-(1,3-dioxoisoindolin-2-yl)-2-methylbutan-2-yl)carbamate (10.0 g, 30.1 mmol, 1.00 eq) in dichloromethane (50 mL) was added hydrochloric acid/dioxane (4 M, 5.00 mL). The mixture was stirred at 20° C. for 12 h. The mixture was concentrated in vacuo to give 2-(3-amino-3-methylbutyl)isoindoline-1,3-dione (8.00 g, hydrochloride, crude) as a red solid.

$^1$H NMR (400 MHz, DMSO-d$_6$) δ=8.87 (s, 2H), 7.89-7.83 (m, 4H), 4.81-4.72 (m, 2H), 3.69-3.59 (m, 2H), 1.93-1.83 (m, 2H), 1.31 (s, 6H)

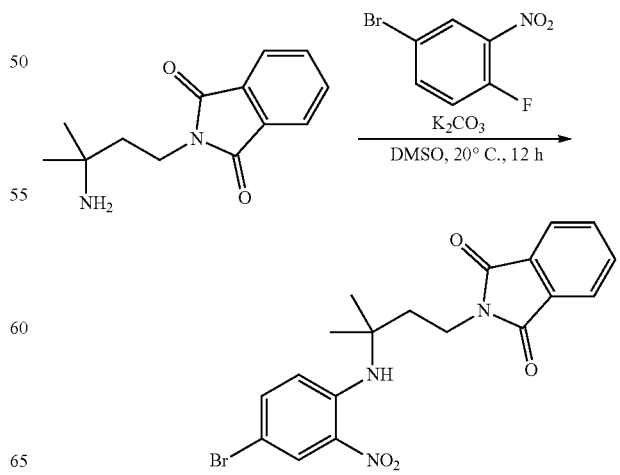

To a solution of 2-(3-amino-3-methylbutyl)isoindoline-1,3-dione (8.00 g, 34.4 mmol, 1.00 eq) and 4-bromo-1-fluoro-2-nitrobenzene (8.33 g, 37.9 mmol 1.10 eq) in dimethyl sulfoxide (50 mL) was added potassium carbonate (9.53 g, 68.9 mmol, 2.00 eq). The mixture was stirred at 20° C. for 12 h. Ethyl acetate (100 mL) and water (100 mL) were added and layers were separated. The aqueous phase was extracted with ethyl acetate (3×100 mL). Combined extracts were washed with brine (140 mL), dried over sodium sulfate, filtered, and concentrated under vacuum. The residue was purified by flash silica gel chromatography (ISCO®; 120 g SepaFlash® Silica Flash Column, eluent of 0%-100% ethyl acetate/petroleum ether gradient @ 120 mL/min) to give 2-(3-((4-bromo-2-nitrophenyl)amino)-3-methylbutyl)isoindoline-1,3-dione (1.20 g, 2.78 mmol, 8% yield) as a white solid.

$^1$H NMR (400 MHz, DMSO-d$_6$) δ=8.01 (s, 1H), 7.75 (dd, J=3.2, 5.2 Hz, 2H), 7.70 (d, J=2.4 Hz, 1H), 7.62 (dd, J=3.2, 5.6 Hz, 2H), 7.40 (dd, J=2.4, 9.2 Hz, 1H), 7.08 (d, J=9.2 Hz, 1H), 3.65 (t, J=6.4 Hz, 2H), 2.23 (t, J=6.4 Hz, 2H), 1.49 (s, 6H)

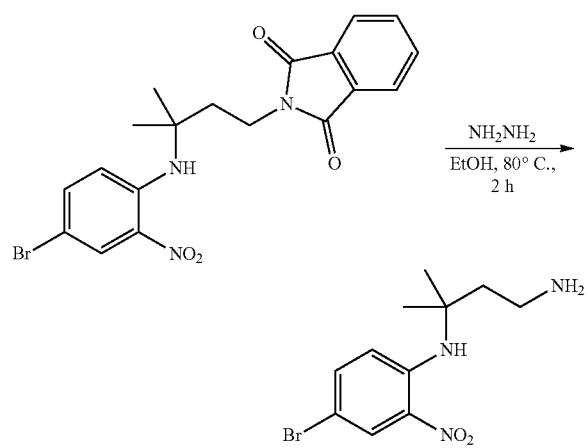

To a solution of 2-(3-((4-bromo-2-nitrophenyl)amino)-3-methylbutyl)isoindoline-1,3-dione (1.20 g, 2.78 mmol, 1.00 eq) in ethanol (20 mL) was added hydrazine monohydrate (818 mg, 13.9 mmol, 85% purity, 5.00 eq). The mixture was stirred at 80° C. for 2 h. After being cooled to room temperature, the mixture was diluted with water (50 mL) and extracted with ethyl acetate (3×50 mL). The combined organic layers were washed with brine (60 mL) and dried over anhydrous sodium sulfate, filtered and concentrated to give N$^3$-(4-bromo-2-nitrophenyl)-3-methylbutane-1,3-diamine (800 mg, crude) as a yellow solid.

$^1$H NMR (400 MHz, DMSO-d$_6$) δ=8.19 (d, J=2.4 Hz, 1H), 7.63-7.50 (m, 2H), 7.26 (d, J=9.2 Hz, 1H), 2.64-2.56 (m, 2H), 1.91-1.83 (m, 2H), 1.42 (s, 6H)

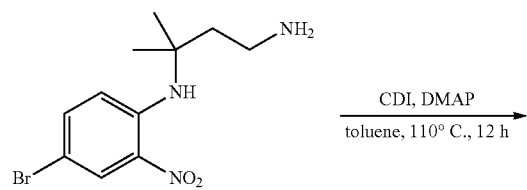

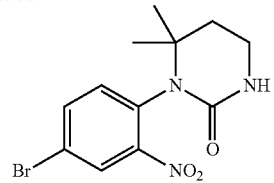

To a solution of N$^3$-(4-bromo-2-nitrophenyl)-3-methylbutane-1,3-diamine (800 mg, 2.65 mmol, 1.00 eq) in toluene (10 mL) was added 1,1'-carbonyldiimidazole (515 mg, 3.18 mmol, 1.20 eq) and 4-dimethylaminopyridin (80.0 mg, 0.655 mmol, 0.247 eq). The mixture was stirred at 110° C. for 12 h. After being cooled to room temperature, ethyl acetate (40 mL) and water (40 mL) were added and layers were separated. The aqueous phase was extracted with ethyl acetate (3×50 mL). Combined extracts were washed with brine (80 mL), dried over sodium sulfate, filtered and concentrated under vacuum. The residue was purified by flash silica gel chromatography (ISCO®; 10 g SepaFlash® Silica Flash Column, eluent of 0%-100% ethyl acetate/petroleum ether gradient @ 20 mL/min) to give 1-(4-bromo-2-nitrophenyl)-6,6-dimethyltetrahydropyrimidin-2(1H)-one (450 mg, 1.37 mmol, 52% yield) as a yellow solid.

$^1$H NMR (400 MHz, DMSO-d$_6$) δ=8.13 (d, J=2.4 Hz, 1H), 7.88 (dd, J=2.4, 8.4 Hz, 1H), 7.43 (d, J=8.4 Hz, 1H), 6.86 (d, J=3.2 Hz, 1H), 3.29-3.14 (m, 2H), 1.96-1.75 (m, 2H), 1.42 (s, 3H), 1.03 (s, 3H)

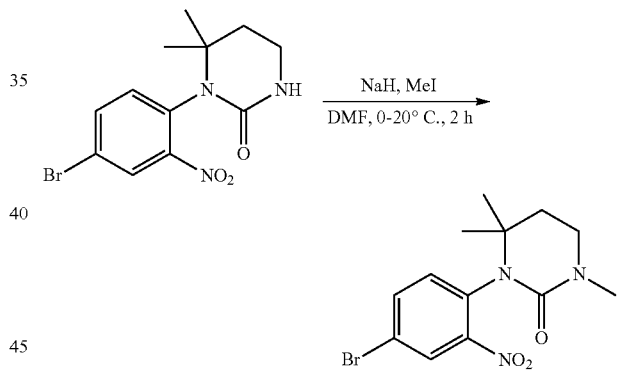

To a solution of 1-(4-bromo-2-nitrophenyl)-6,6-dimethyltetrahydropyrimidin-2(1H)-one (450 mg, 1.37 mmol, 1.00 eq) in tetrahydrofuran (6 mL) was added sodium hydride (66.0 mg, 1.65 mmol, 60% purity, 1.20 eq) and methyl iodide (234 mg, 1.65 mmol, 1.20 eq) at 0° C. The mixture was stirred at 20° C. for 2 h. The mixture was quenched with water (50 mL) in slow drops while stirring at 0° C. The mixture was extracted with ethyl acetate (3×60 mL). The combined organic layers were washed with brine (80 mL) and filtered and concentrated to give the residue. The residue was purified by flash silica gel chromatography (ISCO®; 10 g SepaFlash® Silica Flash Column, eluent of 0%-100% ethyl acetate/petroleum ether gradient @20 mL/min) to give 3-(4-bromo-2-nitrophenyl)-1,4,4-trimethyltetrahydropyrimidin-2(1H)-one (330 mg, 0.964 mmol, 70% yield) as a yellow solid.

$^1$H NMR (400 MHz, DMSO-d$_6$) δ=8.15 (d, J=2.4 Hz, 1H), 7.88 (dd, J=2.4, 8.4 Hz, 1H), 7.41 (d, J=8.4 Hz, 1H), 3.49-3.38 (m, 1H), 3.29-3.20 (m, 1H), 2.82 (s, 3H), 2.07-1.96 (m, 1H), 1.92-1.80 (m, 1H), 1.42 (s, 3H), 1.01 (s, 3H)

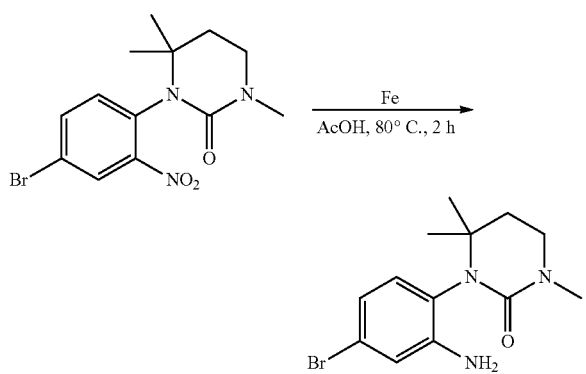

To a solution of 3-(4-bromo-2-nitrophenyl)-1,4,4-trimethyltetrahydropyrimidin-2(1H)-one (330 mg, 0.964 mmol, 1.00 eq) in acetic acid (5 mL) was added iron (269 mg, 4.82 mmol, 4.99 eq).

The mixture was stirred at 80° C. for 2 h. After being cooled to room temperature, the reaction mixture was concentrated in vacuo. The residue was purified by flash silica gel chromatography (ISCO®; 10 g SepaFlash® Silica Flash Column, eluent of 0%-100% ethyl acetate/petroleum ether gradient @ 20 mL/min) to give 3-(2-amino-4-bromophenyl)-1,4,4-trimethyltetrahydropyrimidin-2(1H)-one (200 mg, 0.641 mmol, 66% yield) as a white solid.

$^1$H NMR (400 MHz, DMSO-d$_6$) δ=6.84 (d, J=2.4 Hz, 1H), 6.72 (d, J=8.4 Hz, 1H), 6.60 (dd, J=2.4, 8.4 Hz, 1H), 5.06 (s, 2H), 3.41-3.35 (m, 1H), 3.27-3.18 (m, 1H), 2.84 (s, 3H), 2.19 (dt, J=5.6, 12.4 Hz, 1H), 1.84-1.72 (m, 1H), 1.23 (s, 3H), 0.99 (s, 3H)

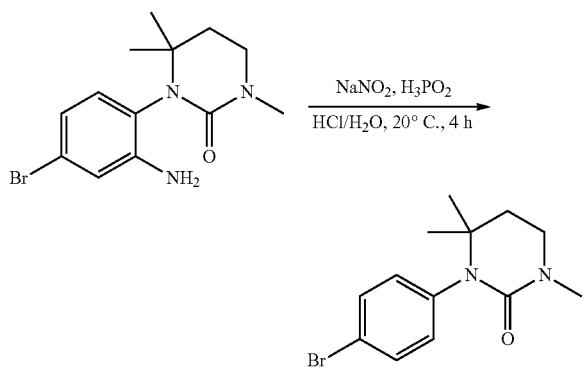

To a solution of 3-(2-amino-4-bromophenyl)-1,4,4-trimethyltetrahydropyrimidin-2(1H)-one (200 mg, 0.641 mmol, 1.00 eq) in hydrochloric acid (0.15 mL) and water (3 mL) was added sodium nitrite (54.0 mg, 0.783 mmol, 1.22 eq) and hypophosphorous acid (42.0 mg, 0.646 mmol, 1.01 eq) The mixture was stirred at 20° C. for 4 h. The mixture was diluted with water (40 mL) and extracted with ethyl acetate (3×40 mL). The combined organic layers were washed with brine (60 mL), dried over anhydrous sodium sulfate, filtered and concentrated in vacuo to give 3-(4-bromophenyl)-1,4,4-trimethyltetrahydropyrimidin-2(1H)-one (150 mg, crude) as a yellow solid.

$^1$H NMR (400 MHz, DMSO-d$_6$) δ=7.51 (d, J=7.6 Hz, 2H), 7.02 (d, J=8.0 Hz, 2H), 3.40 (br s, 1H), 3.31 (br s, 1H), 2.82 (s, 3H), 1.93 (t, J=6.4 Hz, 2H), 1.08 (s, 6H)

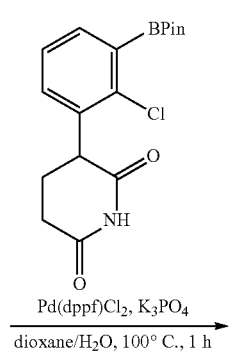

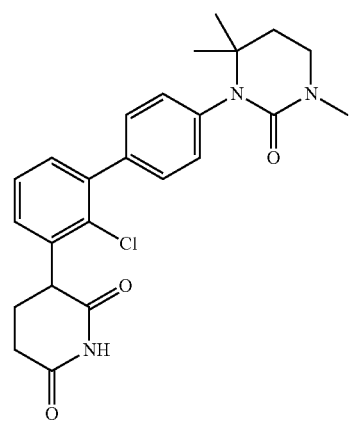

Compound 378

3-(2-chloro-3-(4,4,5,5-tetramethyl-1,3,2-dioxaborolan-2-yl)phenyl)piperidine-2,6-dione (intermediate A) was synthesized as described above. To a solution of 3-(4-bromophenyl)-1,4,4-trimethyltetrahydropyrimidin-2(1H)-one (130 mg, 0.437 mmol, 1.00 eq) and 3-(2-chloro-3-(4,4,5,5-tetramethyl-1,3,2-dioxaborolan-2-yl)phenyl)piperidine-2,6-dione (182 mg, 0.521 mmol, 1.20 eq) in dioxane (3 mL) and water (0.3 mL) was added [1,1'-bis(diphenylphosphino)ferrocene]dichloropalladium(II) (32.0 mg, 0.0438 mmol, 0.100 eq) and potassium phosphate (279 mg, 1.31 mmol, 3.00 eq). The mixture was stirred at 100° C. for 1 h under nitrogen atmosphere. After being cooled to room temperature, the reaction mixture was concentrated in vacuo. The residue was purified by flash silica gel chromatography (ISCO®; 10 g SepaFlash® Silica Flash Column, eluent of 0%-100% ethyl acetate/petroleum ether gradient @ 20 mL/min) and then re-purified by Prep-HPLC (column: Phenomenex luna C18 150 mm×25 mm×10 μm; mobile phase: [water (formic acid)-acetonitrile]; B %: 34%-64%, 10 min). The desired fraction was collected and lyophilized to afford 3-(2-chloro-4'-(3,6,6-trimethyl-2-oxotetrahydropyrimidin-1(2H)-yl)-[1,1'-biphenyl]-3-yl)piperidine-2,6-dione (82.16 mg, 185 mol, 42% yield, 99% purity) as an off-white solid.

$^1$H NMR (400 MHz, DMSO-d$_6$) δ=10.92 (s, 1H), 7.44-7.30 (m, 5H), 7.14 (d, J=8.4 Hz, 2H), 4.36 (dd, J=4.8, 12.0 Hz, 1H), 3.37-3.34 (m, 2H), 2.85 (s, 3H), 2.82-2.74 (m, 1H), 2.56 (d, J=3.6 Hz, 1H), 2.34 (dd, J=4.0, 12.8 Hz, 1H), 2.10-2.01 (m, 1H), 1.96 (t, J=6.4 Hz, 2H), 1.14 (s, 6H); MS (ESI) m/z 440.1 [M+H]$^+$

Example 143. Synthesis of 3-(2-chloro-3-(5-fluoro-6-(3-methyl-2-oxotetrahydropyrimidin-1(2H)-yl)pyridin-3-yl)phenyl)piperidine-2,6-dione (Compound 382)

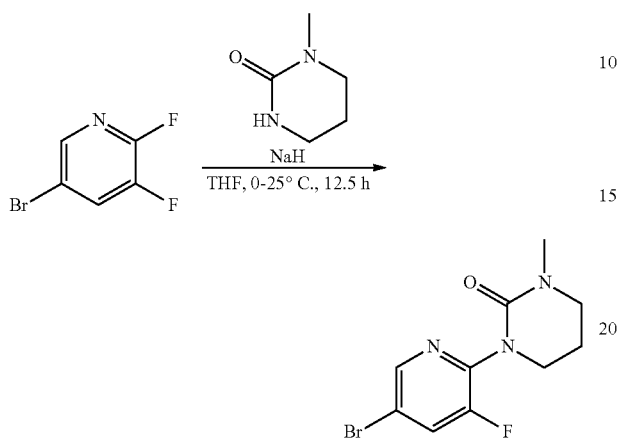

Sodium hydride (0.0250 g, 0.625 mmol, 60% purity, 1.21 eq) was added to a solution of 1-methyltetrahydropyrimidin-2(1H)-one (0.0710 g, 0.622 mmol, 1.21 eq) in tetrahydrofuran (4 mL) under nitrogen at 0° C. The mixture was stirred at 0° C. for 0.5 h. 5-bromo-2,3-difluoropyridine (0.100 g, 0.515 mmol, 1.00 eq) was added to the mixture under nitrogen at 0° C. The final mixture was stirred at 25° C. for 12 h. The reaction was quenched with ammonium chloride solution (10 mL) under nitrogen at 0° C. The mixture was then extracted with ethyl acetate (3×5 mL). Combined organics were dried over magnesium sulfate, filtered and concentrated under reduced pressure. The crude product was purified by flash silica gel chromatography (ISCO®; 12 g SepaFlash®Silica Flash Column, eluent of 20%-40% ethyl acetate/petroleum ether gradient at 80 mL/min) to give 1-(5-bromo-3-fluoropyridin-2-yl)-3-methyltetrahydropyrimidin-2(1H)-one (0.0300 g, 0.0916 mmol, 18% yield) as a white solid.

$^1$H NMR (400 MHz, DMSO-$d_6$) δ 8.38 (d, J=2.0 Hz, 1H), 8.12 (dd, J=2.0, 9.6 Hz, 1H), 3.69 (t, J=5.6 Hz, 2H), 3.38-3.34 (m, 2H), 2.85 (s, 3H), 2.07-1.99 (m, 2H)

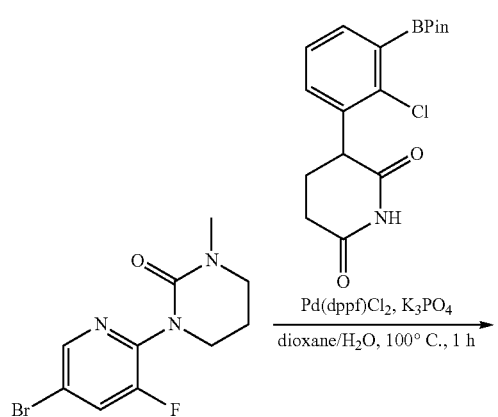

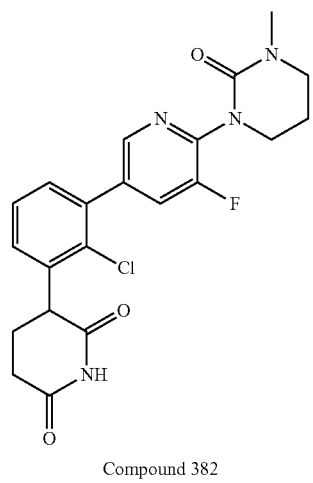

Compound 382

3-(2-chloro-3-(4,4,5,5-tetramethyl-1,3,2-dioxaborolan-2-yl)phenyl)piperidine-2,6-dione (intermediate A) was synthesized as described above. [1,1'-bis(diphenylphosphino)ferrocene]dichloropalladium(II) (0.00800 g, 0.0109 mmol, 0.100 eq) was added to a solution of 1-(5-bromo-3-fluoropyridin-2-yl)-3-methyltetrahydropyrimidin-2(1H)-one (0.0300 g, 0.104 mmol, 1.00 eq), 3-(2-chloro-3-(4,4,5,5-tetramethyl-1,3,2-dioxaborolan-2-yl)phenyl)piperidine-2,6-dione (0.0730 g, 0.208 mmol, 2.01 eq) and potassium phosphate (0.0660 g, 0.310 mmol, 2.99 eq) in dioxane (2 mL) and water (0.2 mL) under nitrogen. The mixture was stirred at 100° C. for 1 h. The mixture was cooled to 25° C. and concentrated under reduced pressure. The crude product was purified by Prep-HPLC (column: Phenomenex luna C18 150 mm×25 mm×10 μm; mobile phase: [water (formic acid)-acetonitrile]; gradient: 24%-44% B over 10 min). The desired fraction was collected and lyophilized to give 3-(2-chloro-3-(5-fluoro-6-(3-methyl-2-oxotetrahydropyrimidin-1(2H)-yl)pyridin-3-yl)phenyl)piperidine-2,6-dione (0.0227 g, 0.0515 mmol, 49% yield, 98% purity) as a white solid.

$^1$H NMR (400 MHz, DMSO-$d_6$) δ=10.94 (s, 1H), 8.28 (d, J=1.2 Hz, 1H), 7.82 (dd, J=2.0, 10.4 Hz, 1H), 7.49-7.38 (m, 3H), 4.37 (dd, J=5.2, 12.4 Hz, 1H), 3.76 (t, J=5.6 Hz, 2H), 3.38 (t, J=6.0 Hz, 2H), 2.89 (s, 3H), 2.86-2.75 (m, 1H), 2.57 (d, J=3.6 Hz, 1H), 2.34-2.28 (m, 1H), 2.07 (t, J=5.6 Hz, 3H)
MS (ESI) m/z 431.2 [M+H]$^+$

Example 144. Synthesis of 3-(2-chloro-3-(5-fluoro-6-((3-methyl-2-oxotetrahydropyrimidin-1(2H)-yl)methyl)pyridin-3-yl)phenyl)piperidine-2,6-dione (Compound 383)

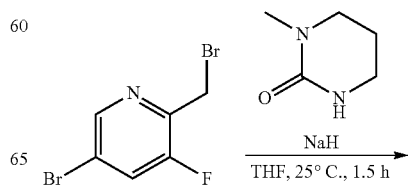

-continued

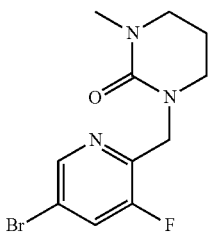

To a solution of 1-methyltetrahydropyrimidin-2(1H)-one (150.00 mg, 1.31 mmol, 1.18 eq) in tetrahydrofuran (3 mL) was added sodium hydride (54.0 mg, 1.35 mmol, 60% purity, 1.21 eq), the mixture was stirred at 25° C. for 30 min. Then the mixture was added. 5-bromo-2-(bromomethyl)-3-fluoropyridine (300 mg, 1.12 mmol, 1.00 eq). The mixture was stirred at 25° C. for 1 h. The mixture was quenched with water (60 mL) in slow drops while stirring at 0° C. The mixture extracted with ethyl acetate (3×40 mL). The combined organic layers were washed with brine (60 mL) and filtered and concentrated to give the residue. The residue was purified by flash silica gel chromatography (ISCO®; 10 g SepaFlash® Silica Flash Column, eluent of 0%-50% ethyl acetate/petroleum ether gradient at 40 mL/min) to give 1-((5-bromo-3-fluoropyridin-2-yl)methyl)-3-methyltetrahydropyrimidin-2(1H)-one (100 mg, 0.331 mmol, 30% yield) as a white solid.

3-(2-chloro-3-(5-fluoro-6-((3-methyl-2-oxotetrahydropyrimidin-1(2H)-yl)methyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-((5-bromo-3-fluoropyridin-2-yl)methyl)-3-methyltetrahydropyrimidin-2(1H)-one according to General Scheme 1.

¹H NMR (400 MHz, DMSO-d₆) δ=10.98 (s, 1H), 8.42 (s, 1H), 7.80 (dd, J=1.6, 10.8 Hz, 1H), 7.48-7.39 (m, 3H), 4.67 (s, 2H), 4.36 (dd, J=5.2, 12.0 Hz, 1H), 3.43 (br s, 2H), 3.26-3.24 (m, 2H), 3.13-3.13 (m, 1H), 2.82-2.77 (m, 4H), 2.58-2.55 (m, 1H), 2.34-2.30 (m, 1H), 2.09-2.00 (m, 1H), 1.94 (td, J=5.6, 11.6 Hz, 2H)

¹H NMR (400 MHz, METHANOL-d₄) δ=8.38 (s, 1H), 7.66 (dd, J=1.6, 10.4 Hz, 1H), 7.46-7.41 (m, 2H), 7.39-7.35 (m, 1H), 4.78 (s, 2H), 4.40 (dd, J=5.2, 12.0 Hz, 1H), 3.48 (t, J=5.6 Hz, 2H), 3.37 (t, J=6.0 Hz, 2H), 2.93 (s, 3H), 2.87-2.77 (m, 1H), 2.75-2.67 (m, 1H), 2.43 (dq, J=4.4, 12.4 Hz, 1H), 2.24-2.16 (m, 1H), 2.05 (td, J=6.0, 11.6 Hz, 2H); MS (ESI) m/z 445.1 [M+H]⁺

Example 145. Synthesis of 3-(2-chloro-3-(6-(5-oxo-4-azaspiro[2.4]heptan-4-yl)pyridin-3-yl)phenyl)piperidine-2,6-dione (Compound 384)

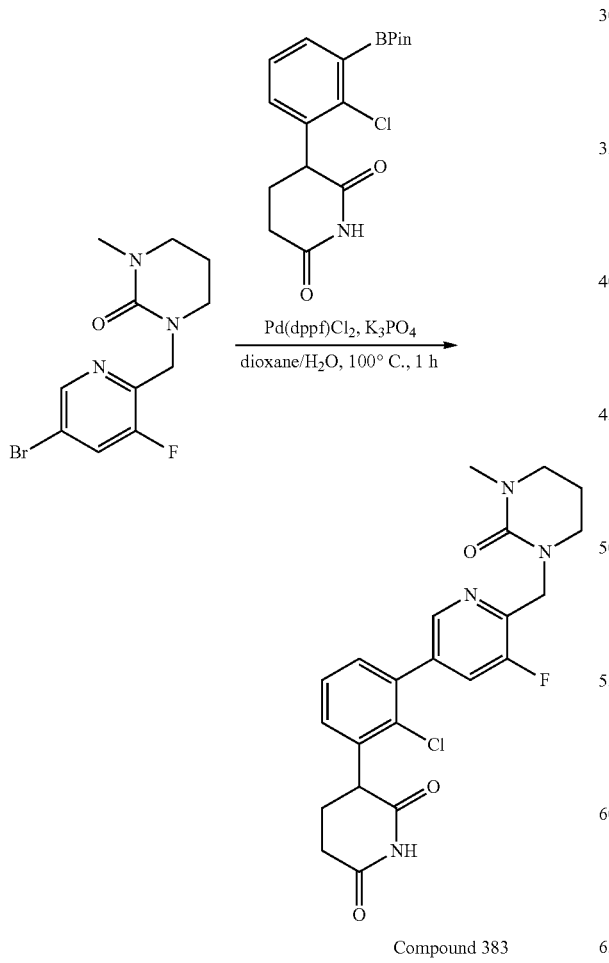

Compound 383

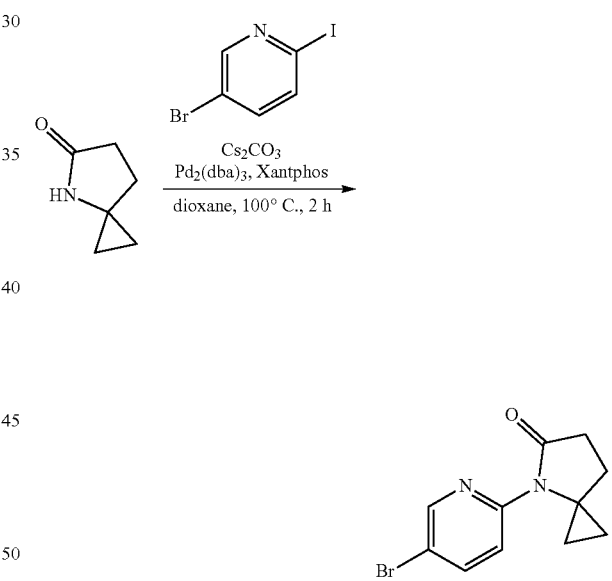

To a solution of 4-azaspiro[2.4]heptan-5-one (200 mg, 1.80 mmol, 1.00 eq) and 5-bromo-2-iodopyridine (511 mg, 1.80 mmol, 1.00 eq) in dioxane (10.0 mL) was added cesium carbonate (1.17 g, 3.60 mmol, 2.00 eq), tris(dibenzylideneacetone)dipalladium(0) (49.4 mg, 54.0 µmol, 0.0300 eq) and 4,5-bis(diphenylphosphino)-9,9-dimethylxanthene (104 mg, 180 µmol, 0.100 eq), the mixture was stirred at 100° C. for 2 h under nitrogen atmosphere. The reaction mixture was concentrated under reduced pressure to give a residue. The residue was purified by reversed-phase column (column: spherical C18, 20-45 um, 100 Å, SW 40, mobile phase: [water (0.1% Formic Acid)-acetonitrile) and lyophilized to afford 4-(5-bromopyridin-2-yl)-4-azaspiro[2.4]heptan-5-one (200 mg, 749 µmol, 21% yield) as brown oil.

467

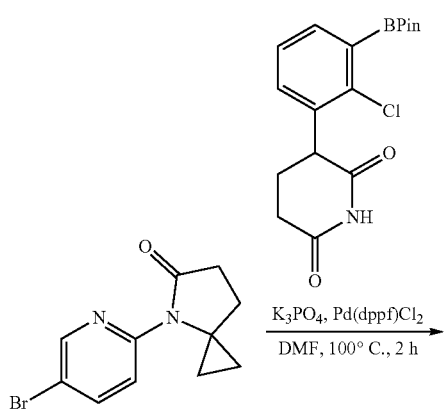

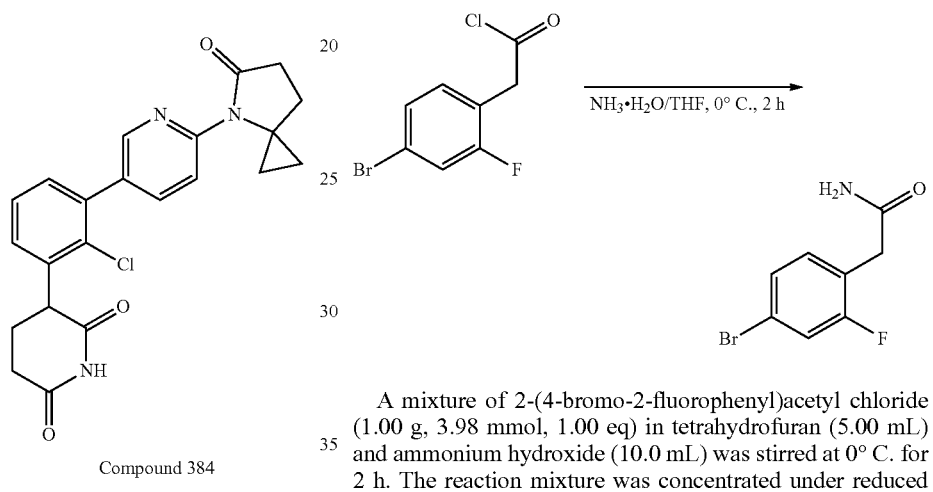

Compound 384

3-(2-chloro-3-(6-(5-oxo-4-azaspiro[2.4]heptan-4-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(5-bromopyridin-2-yl)-4-azaspiro[2.4]heptan-5-one according to General Scheme 1.

¹H NMR (400 MHz, DMSO-d₆) δ=11.03-10.84 (m, 1H), 8.42 (d, J=2.4 Hz, 1H), 7.93 (dd, J=2.4, 8.4 Hz, 1H), 7.62 (d, J=8.4 Hz, 1H), 7.47-7.37 (m, 3H), 4.40-4.32 (m, 1H), 2.88-2.76 (m, 1H), 2.63 (t, J=8.0 Hz, 2H), 2.57 (br d, J=3.6 Hz, 1H), 2.47-2.33 (m, 1H), 2.17 (t, J=7.6 Hz, 2H), 2.11-2.01 (m, 1H), 1.49-1.41 (m, 2H), 0.74-0.63 (m, 2H); MS (ESI) m/z 410.1 [M+H]⁺

Example 146. Synthesis of 3-(2-chloro-3'-fluoro-4'-(oxazol-2-ylmethyl)-[1,1'-biphenyl]-3-yl)piperidine-2,6-dione (Compound 385)

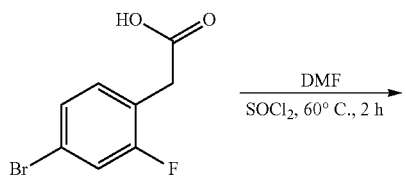

468

-continued

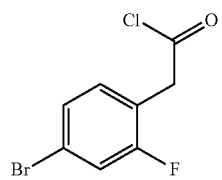

To a solution of 2-(4-bromo-2-fluorophenyl)acetic acid (1.00 g, 4.29 mmol, 1.00 eq) in thionyl chloride (20.0 mL) was added dimethylformamide (31.3 mg, 429 μmol, 33.0 μL, 0.100 eq), then the mixture was stirred at 60° C. for 2 h. The reaction mixture was concentrated under reduced pressure to afford 2-(4-bromo-2-fluorophenyl)acetyl chloride (1.00 g, 3.98 mmol, 92% yield) as yellow oil.

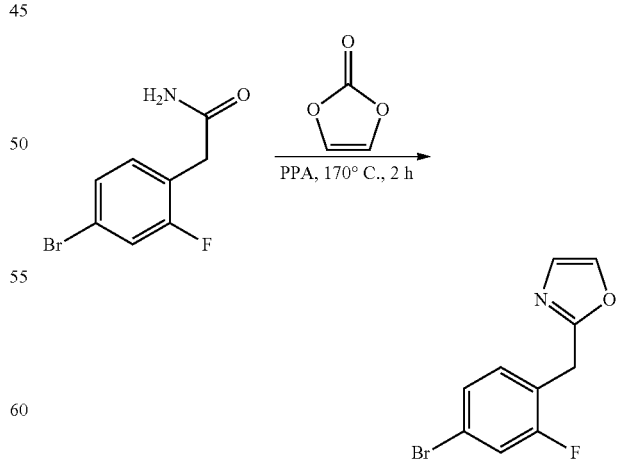

A mixture of 2-(4-bromo-2-fluorophenyl)acetyl chloride (1.00 g, 3.98 mmol, 1.00 eq) in tetrahydrofuran (5.00 mL) and ammonium hydroxide (10.0 mL) was stirred at 0° C. for 2 h. The reaction mixture was concentrated under reduced pressure to give a residue. The residue was diluted with water (100 mL) and extracted with ethyl acetate (3×50 mL). The combined organic phase was separated, washed with brine (80 mL), dried over anhydrous sodium sulfate and concentrated under reduced pressure to afford 2-(4-bromo-2-fluorophenyl)acetamide (820 mg, 3.53 mmol, 88% yield) as a white solid.

A mixture of 2-(4-bromo-2-fluorophenyl)acetamide (820 mg, 3.53 mmol, 1.00 eq) and 1,3-dioxol-2-one (365 mg, 4.24 mmol, 1.20 eq) in polyphosphoric acid (8.00 mL) was stirred at 170° C. for 2 h. The mixture was cool down to 25° C. and diluted with water (10 mL). The residue was purified by reversed-phase column (0.10% formic acid condition) and concentrated under reduced pressure to afford 2-(4-bromo-2-fluorobenzyl)oxazole (130 mg, 507 µmol, 14% yield) as yellow oil.

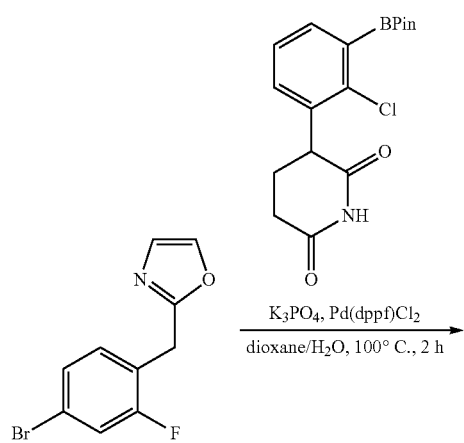

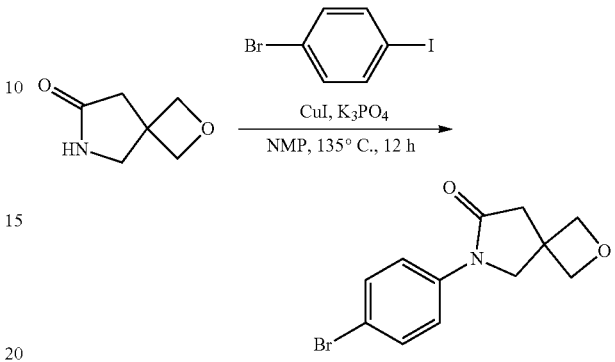

6-(4-bromophenyl)-2-oxa-6-azaspiro[3.4]octan-7-one was prepared from 2-oxa-7-azaspiro[3.4]octan-6-one and 1-bromo-4-iodo-benzene according to General Scheme 7.

Compound 385

3-(2-chloro-3'-fluoro-4'-(oxazol-2-ylmethyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 2-(4-bromo-2-fluorobenzyl)oxazole according to General Scheme 1.

¹H NMR (400 MHz, DMSO-d₆) δ=10.92 (br s, 1H), 8.04 (d, J=0.8 Hz, 1H), 7.47-7.38 (m, 3H), 7.36-7.32 (m, 1H), 7.28 (dd, J=1.6, 10.8 Hz, 1H), 7.23 (dd, J=1.6, 8.0 Hz, 1H), 7.15 (d, J=0.8 Hz, 1H), 4.35 (dd, J=5.2, 12.4 Hz, 1H), 4.23 (s, 2H), 2.85-2.73 (m, 1H), 2.56 (br d, J=3.6 Hz, 1H), 2.38-2.28 (m, 1H), 2.09-2.00 (m, 1H); MS (ESI) m/z 399.1 [M+H]⁺

Example 147. Synthesis of 3-(2-chloro-4'-(7-oxo-2-oxa-6-azaspiro[3.4]octan-6-yl)-[1,1'-biphenyl]-3-yl)piperidine-2,6-dione (Compound 386)

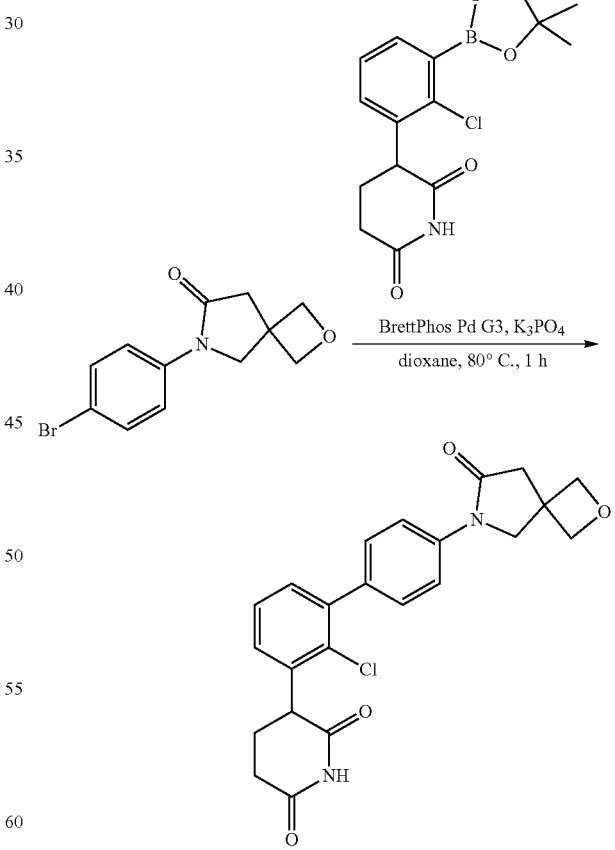

Compound 386

3-(2-chloro-4'-(7-oxo-2-oxa-6-azaspiro[3.4]octan-6-yl)-[1,1'-biphenyl]-3-yl)piperidine-2,6-dione was prepared from 3-(2-chloro-3-(4,4,5,5-tetramethyl-1,3,2-dioxaborolan-2-yl)

phenyl)piperidine-2,6-dione (intermediate A) and 6-(4-bromophenyl)-2-oxa-6-azaspiro[3.4]octan-7-one according to General Scheme 1.

¹H NMR (400 MHz, DMSO-d₆) δ=10.91 (s, 1H), 7.73 (d, J=8.4 Hz, 1H), 7.42 (d, J=8.8 Hz, 2H), 7.40-7.28 (m, 4H), 4.69-4.59 (m, 4H), 4.34 (dd, J=12.0, 4.8 Hz, 1H), 4.19 (s, 2H), 2.94 (s, 2H), 2.82-2.74 (m, 1H), 2.56 (br d, J=3.2 Hz, 1H), 2.37-2.29 (m, 1H), 2.08-2.01 (m, 1H); MS (ESI) m/z 425.0 [M+H]⁺

Example 148. Synthesis of 3-(2-chloro-4'-(3-methyl-2-oxoimidazolidin-1-yl)-[1,1'-biphenyl]-3-yl)piperidine-2,6-dione (Compound 387)

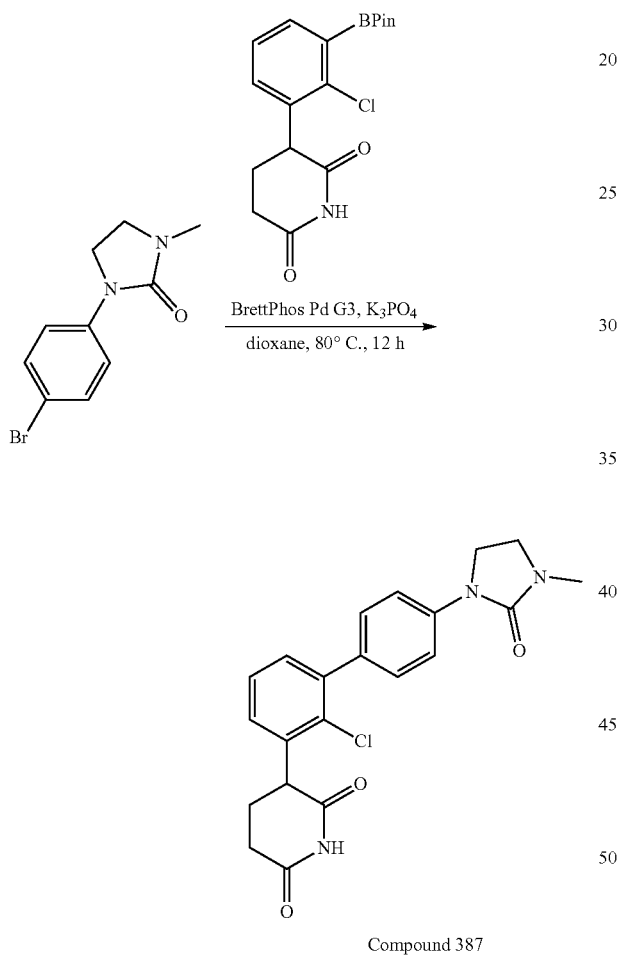

Compound 387

3-(2-chloro-4'-(3-methyl-2-oxoimidazolidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-3-methylimidazolidin-2-one according to General Scheme 1.

¹H NMR (400 MHz, DMSO-d₆) δ=10.92 (br s, 1H), 7.65 (d, J=8.8 Hz, 2H), 7.40-7.28 (m, 5H), 4.34 (dd, J=12.4, 5.2 Hz, 1H), 3.87-3.78 (m, 2H), 3.50-3.42 (m, 2H), 2.84-2.74 (m, 4H), 2.56 (br d, J=3.6 Hz, 1H), 2.36-2.28 (m, 1H), 2.09-2.00 (m, 1H); MS (ESI) m/z. 398.0 [M+H]⁺

Example 149. Synthesis of 3-(2-chloro-4'-((3-methyl-2-oxoimidazolidin-1-yl)methyl)-[1,1'-biphenyl]-3-yl)piperidine-2,6-dione (Compound 388)

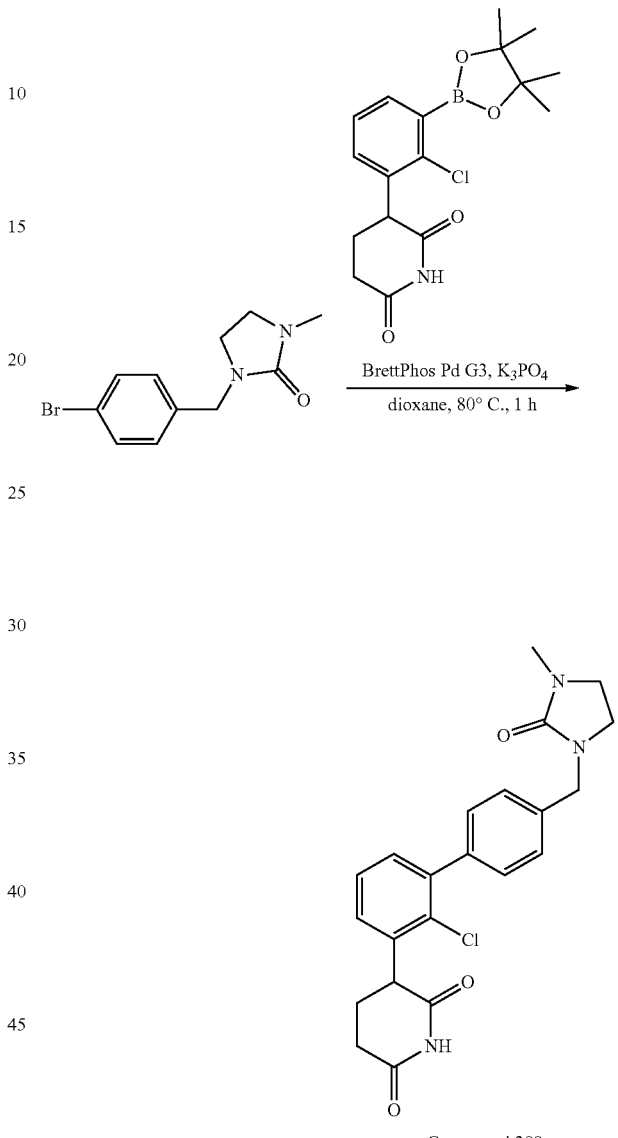

Compound 388

3-(2-chloro-4'-((3-methyl-2-oxoimidazolidin-1-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromobenzyl)-3-methylimidazolidin-2-one according to General Scheme 1.

¹H NMR (400 MHz, DMSO-d₆) δ=10.92 (s, 1H), 7.48-7.34 (m, 4H), 7.34-7.28 (m, 3H), 4.36 (br d, J=5.2 Hz, 1H), 4.32 (s, 2H), 3.30-3.25 (m, 2H), 3.23-3.17 (m, 2H), 2.84-2.74 (m, 1H), 2.70 (s, 3H), 2.56 (br d, J=3.6 Hz, 1H), 2.33 (dq, J=12.8, 4.0 Hz, 1H), 2.09-2.00 (m, 1H); MS (ESI) m/z 412.0 [M+H]⁺

Example 150. Synthesis of 3-(2-chloro-3-(6-(5-oxo-4-azaspiro[2.5]octan-4-yl)pyridin-3-yl)phenyl)piperidine-2,6-dione (Compound 389)

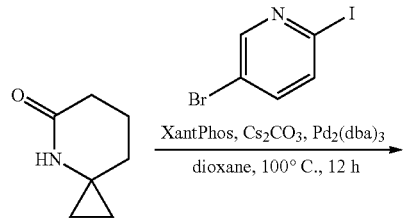

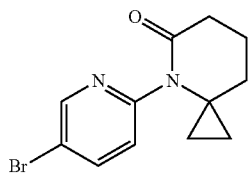

To a solution of 5-bromo-2-iodo-pyridine (0.680 g, 2.40 mmol, 1.20 eq) and 4-azaspiro[2.5]octan-5-one (0.250 g, 2.00 mmol, 1.00 eq) in dioxane (8 mL) were added 4,5-bis(diphenylphosphino)-9,9-dimethylxanthene (0.116 g, 0.200 mmol, 0.100 eq) and tris(dibenzylideneacetone)dipalladium(0) (0.0549 g, 0.0600 mmol, 0.0300 eq) followed by cesium carbonate (1.30 g, 3.99 mmol, 2.00 eq) at 25° C. under nitrogen atmosphere. The reaction was stirred at 100° C. for 12 h. After being cooled to room temperature, the mixture was diluted with saturated ammonium chloride aqueous (20 mL) and extracted with ethyl acetate (3×20 mL). The combined organic layers were washed with brine (3×20 mL), dried over anhydrous sodium sulfate and concentrated under vacuum. The residue was purified by column chromatography (silica, petroleum ether:ethyl acetate=5:1 to 1:2) to give 4-(5-bromopyridin-2-yl)-4-azaspiro[2.5]octan-5-one (0.0450 g, 0.160 mmol, 8% yield) as a yellow solid.

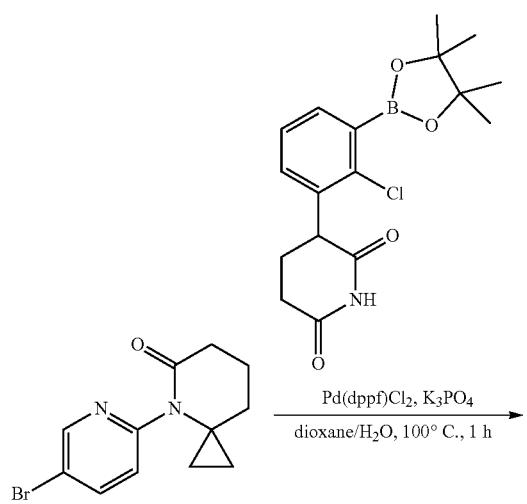

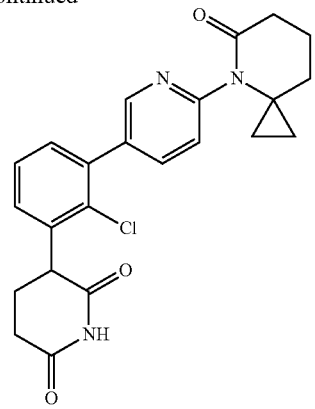

Compound 389

3-(2-chloro-3-(6-(5-oxo-4-azaspiro[2.5]octan-4-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(5-bromo-2-pyridyl)-4-azaspiro[2.5]octan-5-one according to General Scheme 1.

$^1$H NMR (400 MHz, DMSO-d$_6$) δ=10.94 (s, 1H), 8.51 (d, J=2.0 Hz, 1H), 7.90 (dd, J=2.4, 8.0 Hz, 1H), 7.48-7.38 (m, 3H), 7.31 (d, J=8.0 Hz, 1H), 4.37 (dd, J=4.8, 12.0 Hz, 1H), 2.86-2.75 (m, 1H), 2.61-2.57 (m, 3H), 2.42-2.34 (m, 1H), 2.10-2.02 (m, 1H), 2.00-1.93 (m, 2H), 1.91-1.85 (m, 2H), 0.81-0.72 (m, 2H), 0.68-0.60 (m, 2H); MS (ESI) m/z 424.1 [M+H]$^+$

Example 151. Synthesis of 3-(2-chloro-3-(6-(6-oxo-5-azaspiro[3.4]octan-5-yl)pyridin-3-yl)phenyl)piperidine-2,6-dione (Compound 394)

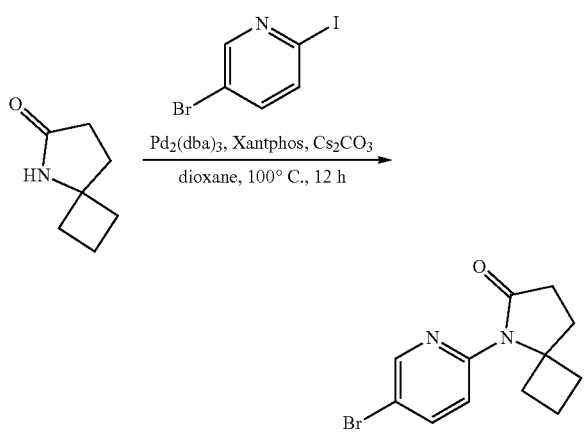

Under nitrogen atmosphere, to a solution of 5-azaspiro[3.4]octan-6-one (0.100 g, 0.799 mmol, 1.00 eq) in dioxane (2.0 mL) was added 5-bromo-2-iodopyridine (0.227 g, 0.800 mmol, 1.00 eq), 4,5-bis(diphenylphosphino)-9,9-dimethylxanthene (0.0460 g, 0.0800 mmol, 0.100 eq), cesium carbonate (0.520 g, 1.60 mmol, 2.00 eq) and tris(dibenzylideneacetone)dipalladium(0) (0.0220 g, 0.0240 mmol, 0.0300 eq). The mixture was stirred at 100° C. for 12 h. After being cooled to room temperature, the mixture was concentrated under reduced pressure. The residue was purified by flash silica gel chromatography (ISCO®; 20 g SepaFlash®Silica Flash Column, eluent of 50%-100% ethyl acetate/petroleum ether gradient at 30 mL/min to give 5-(5-bromopyridin-2-yl)-5-azaspiro[3.4]octan-6-one (0.0600 g, 0.213 mmol, 27% yield) as a white solid.

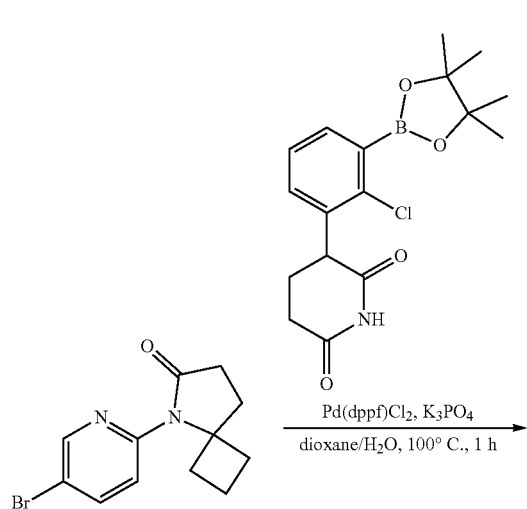

Compound 394

3-(2-chloro-3-(6-(6-oxo-5-azaspiro[3.4]octan-5-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5-(5-bromopyridin-2-yl)-5-azaspiro[3.4]octan-6-one according to General Scheme 1.

$^1$H NMR (400 MHz, DMSO-$d_6$) δ=10.94 (s, 1H), 8.54 (d, J=2.4 Hz, 1H), 7.94 (dd, J=2.4, 8.4 Hz, 1H), 7.67 (d, J=8.4 Hz, 1H), 7.47-7.42 (m, 3H), 4.37 (dd, J=5.2, 12.4 Hz, 1H), 3.01-2.98 (m, 2H), 2.89-2.72 (m, 1H), 2.57-2.53 (m, 3H), 2.42-2.32 (m, 1H), 2.31-2.24 (m, 2H), 2.11-2.03 (m, 1H), 2.00-1.98 (m, 2H), 1.81-1.76 (m, 2H); MS (ESI) m/z 424.1 [M+H]$^+$

Example 152. Synthesis of 3-(2-chloro-3-(6-(pyrimidin-2-ylmethyl)pyridin-3-yl)phenyl)piperidine-2,6-dione (Compound 400)

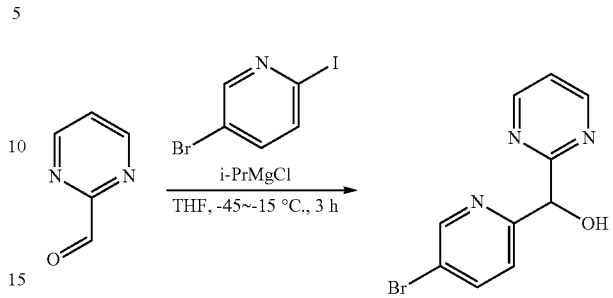

To a solution of 5-bromo-2-iodopyridine (2.49 g, 8.79 mmol, 0.950 eq) in tetrahydrofuran (10.0 mL) was added dropwise isopropylmagnesium chloride (2.00 M, 4.63 mL, 1.00 eq) at −15° C. under nitrogen atmosphere. After addition, the mixture was stirred at this temperature for 1 h, and then pyrimidine-2-carbaldehyde (1.00 g, 9.25 mmol, 1.00 eq) in tetrahydrofuran (10.0 mL) was added dropwise at −45° C. The resulting mixture was stirred at −45° C. for 2 h under nitrogen atmosphere. The reaction mixture was quenched by saturated ammonium chloride solution (200 mL) and extracted with ethyl acetate (3×100 mL). The combined organic layers were washed with brine (150 mL) and dried over sodium sulfate, filtered and concentrated under reduced pressure to give a residue. The residue was purified by silica gel chromatography (Petroleum ether/Ethyl acetate=3/1 to 0/1) and concentrated under reduced pressure to afford (5-bromopyridin-2-yl)(pyrimidin-2-yl)methanol (1.16 g, 4.36 mmol, 47% yield) as yellow oil.

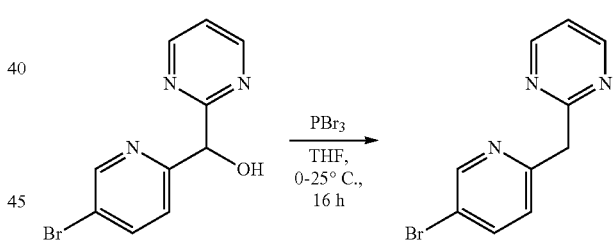

To a solution of (5-bromopyridin-2-yl)(pyrimidin-2-yl)methanol (100 mg, 376 μmol, 1.00 eq) in tetrahydrofuran (1.00 mL) was added phosphorus tribromide (305 mg, 1.13 mmol, 3.00 eq) at 0° C., then the mixture was stirred at 0° C. for 1 h. After addition, the mixture was stirred at 25° C. for 15 h. The reaction mixture was quenched by saturated aqueous sodium bicarbonate (50 mL), and then extracted with ethyl acetate (3×25 mL). The combined organic layers were washed with brine (50 mL), dried over sodium sulfate, filtered and concentrated under reduced pressure to give a residue. The residue was purified by reversed-phase column chromatography (0.1% formic acid condition) and lyophilized to afford 2-((5-bromopyridin-2-yl)methyl)pyrimidine (75.0 mg, 299 μmol, 16% yield) as a yellow solid.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(6-(pyrimidin-2-ylmethyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 2-((5-bromopyridin-2-yl)methyl)pyrimidine according to General Scheme 1.

MS (ESI) m/z 393.2 [M+H]$^+$

Example 153. Synthesis of 3-(2-chloro-4'-(pyrimidin-4-ylmethyl)-[1,1'-biphenyl]-3-yl)piperidine-2,6-dione (Compound 401)

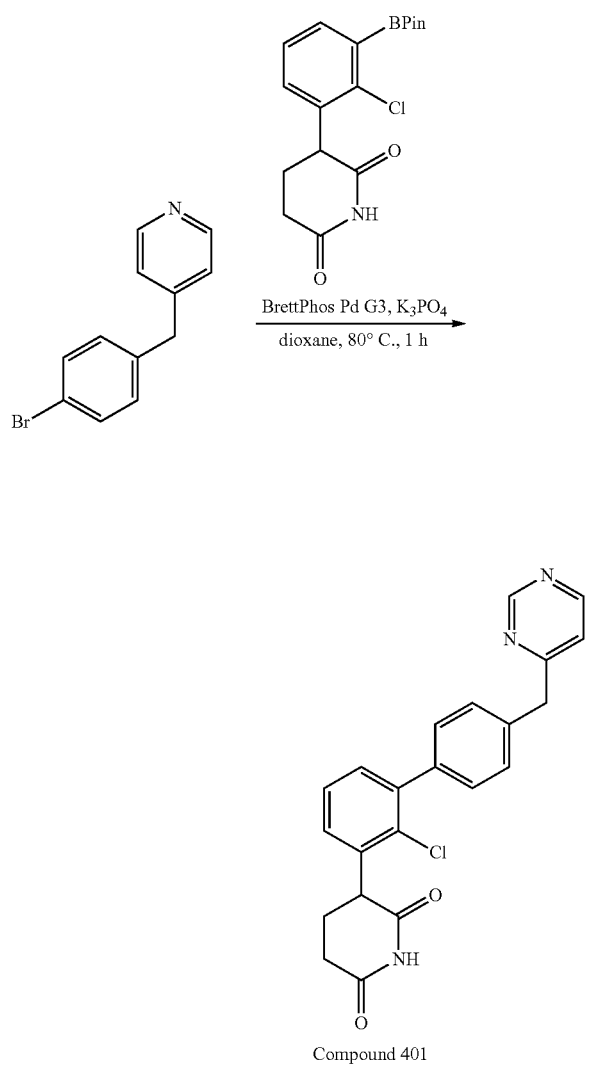

Compound 401

3-(2-chloro-4'-(pyrimidin-4-ylmethyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 4-(4-bromobenzyl)pyrimidine according to General Scheme 1.

$^1$H NMR (400 MHz, DMSO-d$_6$) δ=10.93 (br s, 1H), 9.11 (d, J=1.2 Hz, 1H), 8.72 (d, J=5.2 Hz, 1H), 7.51 (dd, J=1.2, 5.2 Hz, 1H), 7.41-7.33 (m, 6H), 7.31-7.27 (m, 1H), 4.33 (dd, J=5.2, 12.2 Hz, 1H), 4.15 (s, 2H), 2.84-2.73 (m, 1H), 2.58-2.54 (m, 1H), 2.32 (td, J=3.6, 8.8 Hz, 1H), 2.08-2.00 (m, 1H); MS (ESI) m/z 392.2 [M+H]$^+$

Example 154. Synthesis of 3-(2-chloro-4'-(3,3-dimethyl-5-oxomorpholino)-[1,1'-biphenyl]-3-yl)piperidine-2,6-dione (Compound 402)

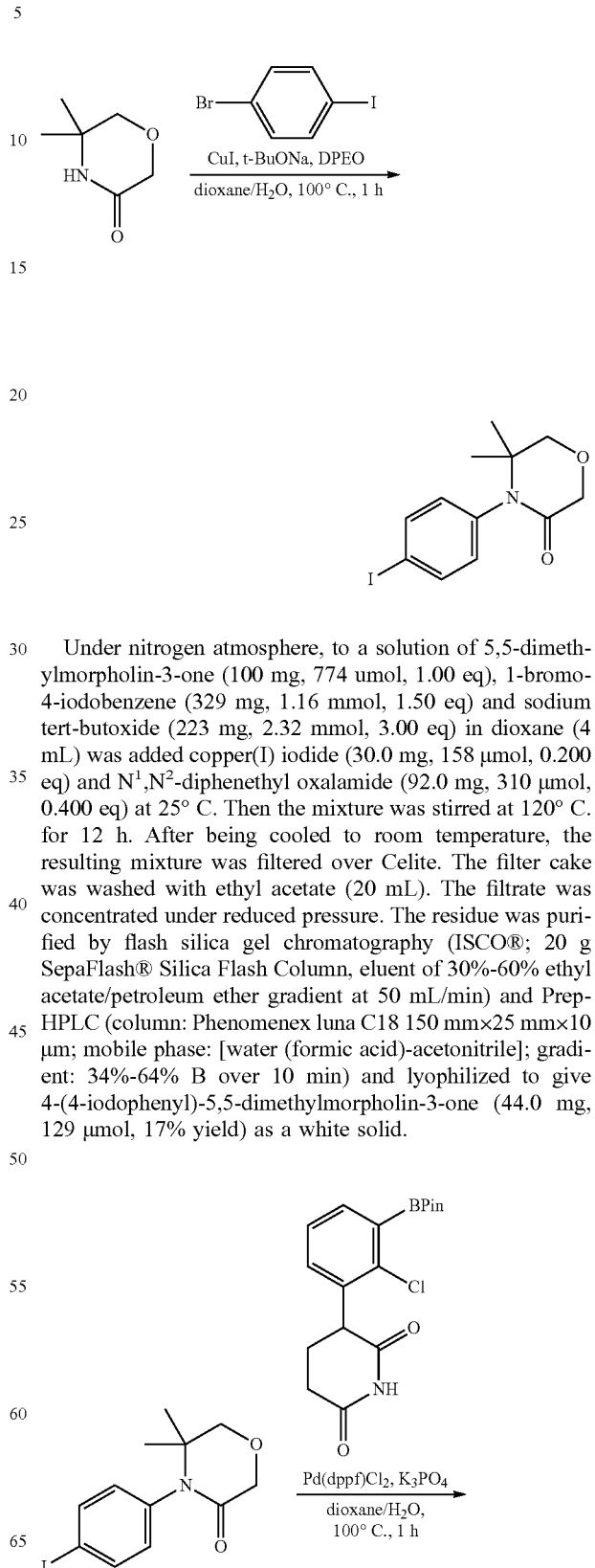

Under nitrogen atmosphere, to a solution of 5,5-dimethylmorpholin-3-one (100 mg, 774 umol, 1.00 eq), 1-bromo-4-iodobenzene (329 mg, 1.16 mmol, 1.50 eq) and sodium tert-butoxide (223 mg, 2.32 mmol, 3.00 eq) in dioxane (4 mL) was added copper(I) iodide (30.0 mg, 158 μmol, 0.200 eq) and N$^1$,N$^2$-diphenethyl oxalamide (92.0 mg, 310 μmol, 0.400 eq) at 25° C. Then the mixture was stirred at 120° C. for 12 h. After being cooled to room temperature, the resulting mixture was filtered over Celite. The filter cake was washed with ethyl acetate (20 mL). The filtrate was concentrated under reduced pressure. The residue was purified by flash silica gel chromatography (ISCO®; 20 g SepaFlash® Silica Flash Column, eluent of 30%-60% ethyl acetate/petroleum ether gradient at 50 mL/min) and Prep-HPLC (column: Phenomenex luna C18 150 mm×25 mm×10 μm; mobile phase: [water (formic acid)-acetonitrile]; gradient: 34%-64% B over 10 min) and lyophilized to give 4-(4-iodophenyl)-5,5-dimethylmorpholin-3-one (44.0 mg, 129 μmol, 17% yield) as a white solid.

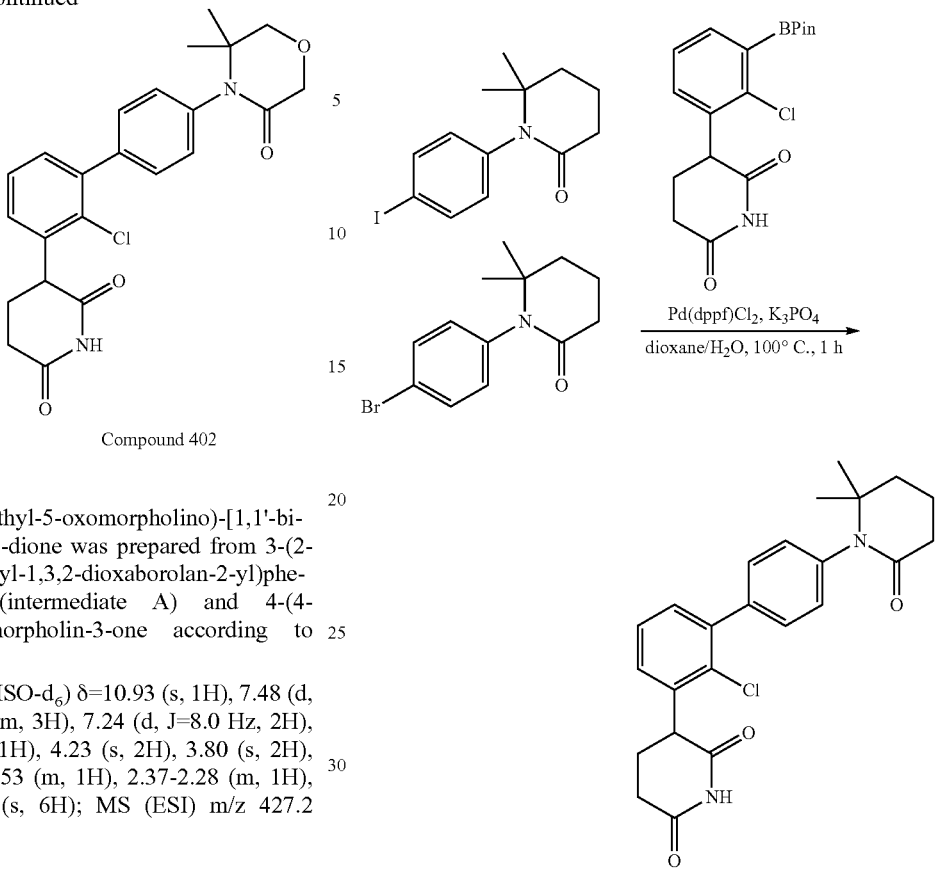

Compound 402

3-(2-chloro-4'-(3,3-dimethyl-5-oxomorpholino)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(4-iodophenyl)-5,5-dimethylmorpholin-3-one according to General Scheme 1.

$^1$H NMR (400 MHz, DMSO-d$_6$) δ=10.93 (s, 1H), 7.48 (d, J=8.0 Hz, 2H), 7.45-7.33 (m, 3H), 7.24 (d, J=8.0 Hz, 2H), 4.36 (dd, J=5.2, 12.4 Hz, 1H), 4.23 (s, 2H), 3.80 (s, 2H), 2.87-2.74 (m, 1H), 2.57-2.53 (m, 1H), 2.37-2.28 (m, 1H), 2.14-1.99 (m, 1H), 1.19 (s, 6H); MS (ESI) m/z 427.2 [M+H]$^+$

Example 155. Synthesis of 3-(2-chloro-4'-(2,2-dimethyl-6-oxopiperidin-1-yl)-[1,1'-biphenyl]-3-yl)piperidine-2,6-dione (Compound 403)

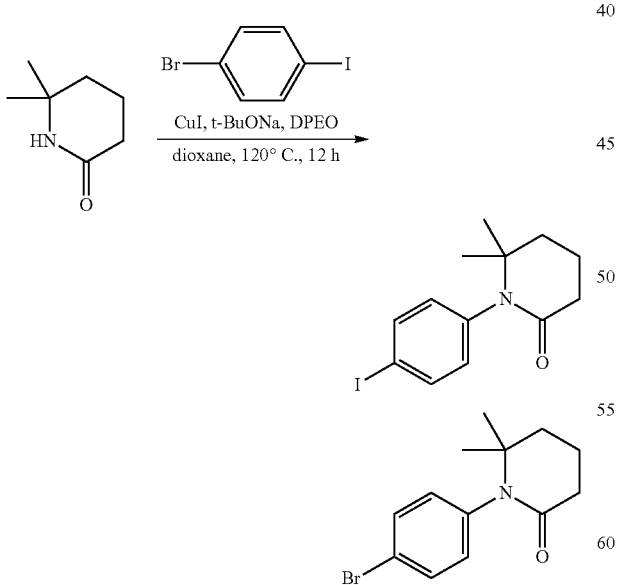

1-(4-bromophenyl)-6,6-dimethyl-piperidin-2-one and 1-(4-iodophenyl)-6,6-dimethylpiperidin-2-one were prepared from 6,6-dimethylpiperidin-2-one and 1-bromo-4-iodobenzene as in Example 154.

Compound 403

3-(2-chloro-4'-(2,2-dimethyl-6-oxopiperidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-6,6-dimethyl-piperidin-2-one and 1-(4-iodophenyl)-6,6-dimethylpiperidin-2-one according to General Scheme 1.

$^1$H NMR (400 MHz, DMSO-d$_6$) δ=10.93 (s, 1H), 7.46-7.39 (m, 3H), 7.16-7.14 (m, 2H), 7.15 (d, J=8.4 Hz, 2H), 4.36 (dd, J=5.2, 12.0 Hz, 1H), 2.85-2.75 (m, 1H), 2.57-2.55 (m, 1H), 2.44-2.25 (m, 3H), 2.14-1.99 (m, 1H), 1.87 (d, J=3.2 Hz, 4H), 1.19 (s, 6H); MS (ESI) m/z 425.2 [M+H]$^+$

Example 156. Synthesis of 3-(2-chloro-3-(6-((5-oxo-4-azaspiro[2.5]octan-4-yl)methyl)pyridin-3-yl)phenyl)piperidine-2,6-dione (Compound 404)

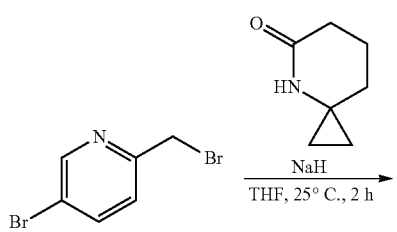

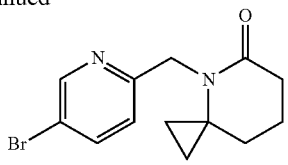

To a solution of 4-azaspiro[2.5]octan-5-one (125 mg, 0.999 mmol, 1.00 eq) in tetrahydrofuran (4 mL) was added sodium hydride (48.0 mg, 1.20 mmol, 60% purity, 1.20 eq) and 5-bromo-2-(bromomethyl)pyridine (250 mg, 0.996 mmol, 1.00 eq). The mixture was stirred at 25° C. for 2 h. The mixture was quenched with water (50 mL) while stirring at 0° C. The mixture extracted with ethyl acetate (3×30 mL). The combined organic layers were washed with brine (30 mL), dried over sodium sulfate, filtered and concentrated to give a residue. The residue was purified by flash silica gel chromatography (ISCO®; 10 g SepaFlash® Silica Flash Column, eluent of 40%-100% ethyl acetate/petroleum ether gradient @ 20 mL/min) to give 4-((5-bromopyridin-2-yl)methyl)-4-azaspiro[2.5]octan-5-one (150 mg, 0.508 mmol, 51% yield) as a yellow solid.

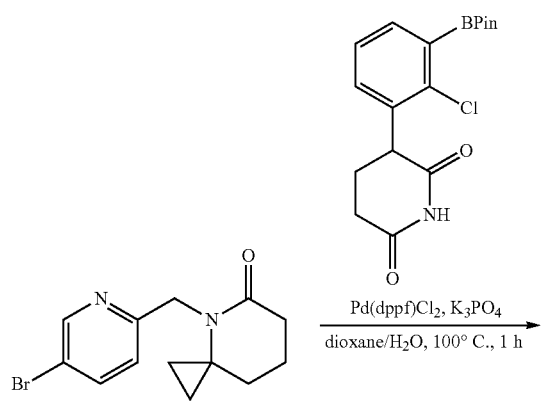

Compound 404

3-(2-chloro-3-(6-((5-oxo-4-azaspiro[2.5]octan-4-yl)methyl)pyridin-3-yl)phenyl)-piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-((5-bromopyridin-2-yl)methyl)-4-azaspiro[2.5]octan-5-one according to General Scheme 1.

$^1$H NMR (400 MHz, DMSO-$d_6$) δ=10.93 (s, 1H), 8.52 (d, J=2.0 Hz, 1H), 7.83 (dd, J=2.4, 8.4 Hz, 1H), 7.46-7.36 (m, 3H), 7.29 (d, J=8.2 Hz, 1H), 4.45 (s, 2H), 4.36 (dd, J=5.2, 12.0 Hz, 1H), 3.30 (s, 2H), 2.84-2.75 (m, 1H), 2.56 (d, J=3.6 Hz, 1H), 2.37-2.33 (m, 1H), 2.11-2.00 (m, 1H), 1.87 (t, J=6.8 Hz, 2H), 1.76-1.69 (m, 2H), 0.97-0.88 (m, 2H), 0.64-0.56 (m, 2H) $^1$H NMR (400 MHz, MeOD-$d_4$) δ=8.51 (d, J=1.6 Hz, 1H), 7.87 (dd, J=2.4, 8.0 Hz, 1H), 7.50-7.31 (m, 4H), 4.59 (s, 2H), 4.40 (dd, J=5.2, 12.0 Hz, 1H), 2.87-2.77 (m, 1H), 2.75-2.67 (m, 1H), 2.64 (t, J=7.2 Hz, 2H), 2.50-2.34 (m, 1H), 2.26-2.13 (m, 1H), 2.04-1.97 (m, 2H), 1.85-1.77 (m, 2H), 1.06-0.95 (m, 2H), 0.72-0.64 (m, 2H); MS (ESI) m/z 438.1 [M+H]$^+$

Example 157. Synthesis of 3-(2-chloro-4'-(2-oxo-1-azaspiro[3.3]-heptan-1-yl)-[1,1'-biphenyl]-3-yl)piperidine-2,6-dione (Compound 405)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(2-oxo-1-azaspiro[3.3]heptan-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 1-(4-bromophenyl)-1-azaspiro[3.3]heptan-2-one according to General Scheme 1.

MS (ESI) m/z 409.1 [M+H]$^+$

Example 158. Synthesis of 3-(2-chloro-4'-(2-methyl-1,1-dioxido-2,3-dihydrobenzo[d]isothiazol-7-yl)-[1,1'-biphenyl]-3-yl)piperidine-2,6-dione (Compound 406)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(2-methyl-1,1-dioxido-2,3-dihydrobenzo[d]isothiazol-7-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 4-(2-methyl-1,1-dioxido-2,3-dihydrobenzo[d]isothiazol-7-yl)phenyl trifluoromethanesulfonate according to General Scheme 1.

MS (ESI) m/z 481.2 [M+H]$^+$

Example 159. Synthesis of 3-(2-chloro-4'-(6-oxo-2-oxa-5-azaspiro[3.5]nonan-5-yl)-[1,1'-biphenyl]-3-yl)piperidine-2,6-dione (Compound 407)

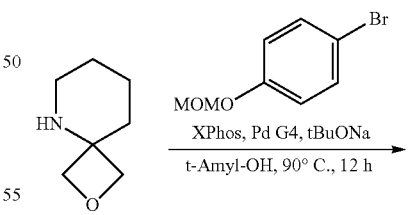

Under nitrogen atmosphere, to a solution of 2-oxa-5-azaspiro[3.5]nonane oxalate (750 mg, 3.45 mmol, 1.00 eq), 1-bromo-4-(methoxymethoxy)benzene (1.12 g, 5.18 mmol, 1.50 eq) and sodium tert-butoxide (1.33 g, 13.8 mmol, 4.00 eq) in 2-methylbutan-2-ol (10 mL) was added methanesulfonato(2-dicyclohexylphosphino-2,4,6-tri-i-propyl-1,1-biphenyl)(2-methylamino-1,1-biphenyl-2-yl)palladium(II) (596 mg, 693 µmol, 0.201 eq) at 25° C. Then the mixture was stirred at 90° C. for 12 h. After being cooled to room temperature, the mixture was concentrated under reduced pressure to give a residue, which was purified by flash silica gel chromatography (ISCO®; 50 g SepaFlash® Silica Flash Column, eluent of 0%-20% ethyl acetate/petroleum ether gradient at 70 mL/min) to give 5-[4-(methoxymethoxy)phenyl]-2-oxa-5-azaspiro[3.5]nonane (900 mg, 3.25 mmol, 87% yield) as a yellow solid.

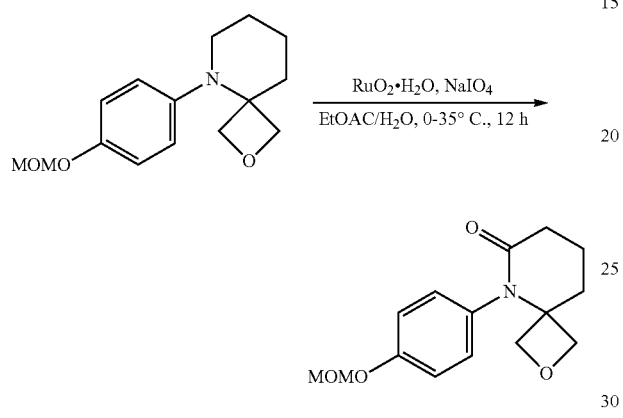

The reaction was performed in three batches (2×300 mg of compound 2). To a solution of sodium periodate (1.16 g, 5.44 mmol, 5.03 eq) in water (30 mL) was added ruthenium (IV) oxide hydrate (165 mg, 1.09 mmol, 1.01 eq) at 25° C. The mixture was stirred at 25° C. for 3 min. Then ethyl acetate (30 mL) and 5-[4-(methoxymethoxy)phenyl]-2-oxa-5-azaspiro[3.5]nonane (300 mg, 1.08 mmol, 1.00 eq) was added at 0° C. The mixture was stirred at 35° C. for 12 h. Then the mixture was poured into saturated aqueous disodium sulfite (20 mL) and extracted with ethyl acetate (3×20 mL). The combined organic layers were washed with brine (20 mL), dried over sodium sulfate, filtered and concentrated under reduced pressure to give a residue, which was purified by Prep-HPLC (column: Phenomenex luna C18 150 mm×25 mm×10 µm; mobile phase: [water (formic acid)-acetonitrile]; gradient: 17%-37% B over 9 min) to give 5-[4-(methoxymethoxy)phenyl]-2-oxa-5-azaspiro[3.5]nonan-6-one (140 mg, 480 mol, 22% yield) as a white solid.

To a solution of 5-(4-(methoxymethoxy)phenyl)-2-oxa-5-azaspiro[3.5]nonan-6-one (140 mg, 480 µmol, 1.00 eq) in dichloromethane (2 mL) was added trifluoroacetic acid (2.96 mL) at 0° C. Then the mixture was stirred at 0° C. for 2 h. The mixture was concentrated under reduced pressure to give a residue, which was lyophilized to give 5-(4-hydroxyphenyl)-2-oxa-5-azaspiro[3.5]nonan-6-one (110 mg, 424 µmol, 88% yield, 90% purity) as a white solid.

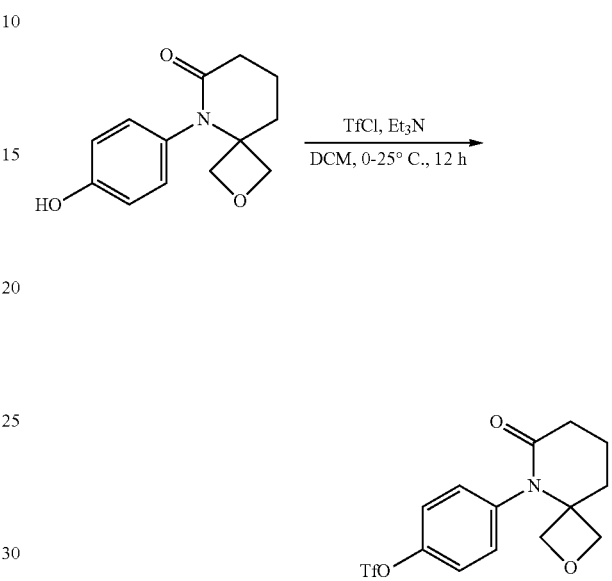

Under nitrogen atmosphere, to a solution of 5-(4-hydroxyphenyl)-2-oxa-5-azaspiro[3.5]nonan-6-one (110 mg, 424 µmol, 1.00 eq) and triethylamine (172 mg, 1.70 mmol, 4.01 eq) in dichloromethane (5 mL) was added trifluoromethanesulfonyl chloride (215 mg, 1.28 mmol, 3.01 eq) at 0° C. Then the mixture was stirred at 25° C. for 12 h. The reaction mixture was diluted with dichloromethane (20 mL). The organic layer was washed with brine (3×20 mL), dried over sodium sulfate and filtered. The filtrate was concentrated under reduced pressure to give a residue, which was purified by Prep-HPLC (column: Phenomenex luna C18 150 mm×25 mm×10 µm; mobile phase: [water (formic acid)-acetonitrile]; gradient: 31%-61% B over 10 min) to give [4-(6-oxo-2-oxa-5-azaspiro[3.5]nonan-5-yl)phenyl] trifluoromethanesulfonate (90.0 mg, 234 µmol, 55% yield) as a white solid.

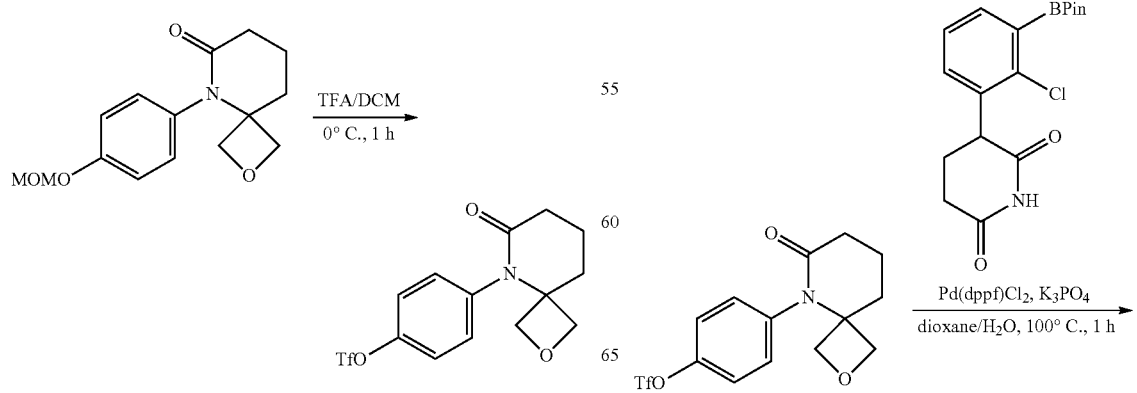

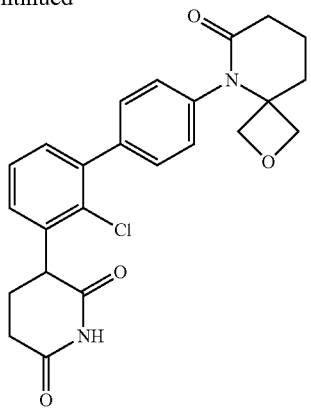

Compound 407

3-(2-chloro-4'-(6-oxo-2-oxa-5-azaspiro[3.5]nonan-5-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(6-oxo-2-oxa-5-azaspiro[3.5]nonan-5-yl)phenyl trifluoro-methanesulfonate according to General Scheme 1.

$^1$H NMR (400 MHz, DMSO-$d_6$) δ=10.93 (s, 1H), 7.53 (d, J=8.4 Hz, 2H), 7.46-7.36 (m, 3H), 7.29 (d, J=8.4 Hz, 2H), 4.61 (d, J=6.8 Hz, 2H), 4.44-4.27 (m, 3H), 2.88-2.74 (m, 1H), 2.60-2.51 (m, 1H), 2.47-2.40 (m, 2H), 2.39-2.29 (m, 3H), 2.12-2.02 (m, 1H), 1.90-1.81 (m, 2H).

MS (ESI) m/z 439.1 [M+H]$^+$

Example 160. Synthesis of 3-(2-chloro-4'-((1-methyl-1H-imidazol-4-yl)methyl)-[1,1'-biphenyl]-3-yl)piperidine-2,6-dione (Compound 408)

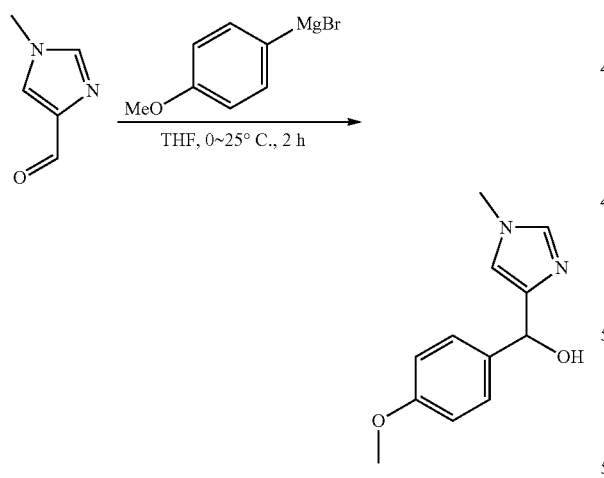

To a solution of 1-methyl-1H-imidazole-4-carbaldehyde (1.00 g, 9.08 mmol, 1.00 eq) in tetrahydrofuran (10.0 mL) was added (4-methoxyphenyl)magnesium bromide (2.88 g, 13.6 mmol, 3.01 mL, 1.50 eq) at 0° C. The mixture was stirred at 25° C. for 2 h. The reaction mixture was concentrated under reduced pressure to give a residue. The residue was purified by Prep-HPLC (column: Phenomenex Luna C18150×25 mm×10 m; mobile phase: [water (formic acid)-acetonitrile]; gradient: 1%-12% B over 9 min) to afford (4-methoxyphenyl)(1-methyl-1H-imidazol-4-yl)methanol (807 mg, 3.66 mmol, 40% yield) as yellow oil.

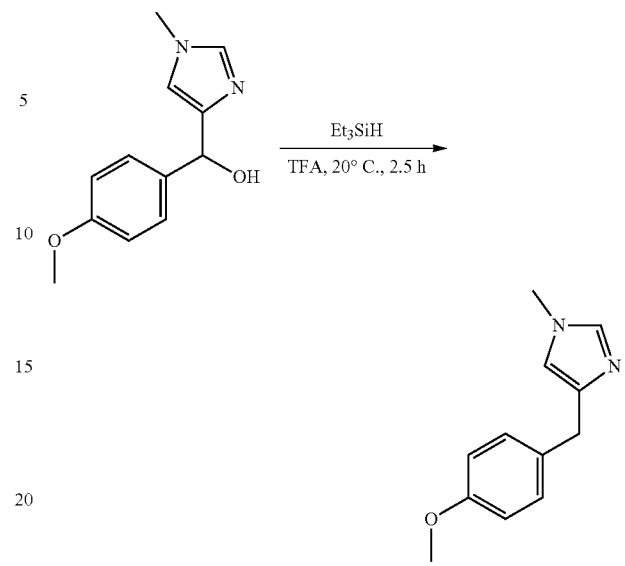

To a solution of (4-methoxyphenyl)(1-methyl-1H-imidazol-4-yl)methanol (800 mg, 3.67 mmol, 1.00 eq) in trifluoroacetic acid (9 mL) was added triethylsilane (852 mg, 7.33 mmol, 1.17 mL, 2.00 eq). The mixture was stirred at 20° C. for 2.5 h. The reaction solution was adjusted pH=7 with saturated aqueous sodium bicarbonate, poured into water (50 mL), and then extracted with ethyl acetate (3×40 mL). The combined organic layers were washed with brine (50 mL), dried over anhydrous sodium sulfate, filtered and concentrated under reduced pressure to give a residue. The residue was purified by column chromatography (SiO$_2$, Petroleum ether/Ethyl acetate=2/1 to 1/1) to afford 4-(4-methoxybenzyl)-1-methyl-1H-imidazole (607 mg, 2.79 mmol, 76% yield) as a yellow oil.

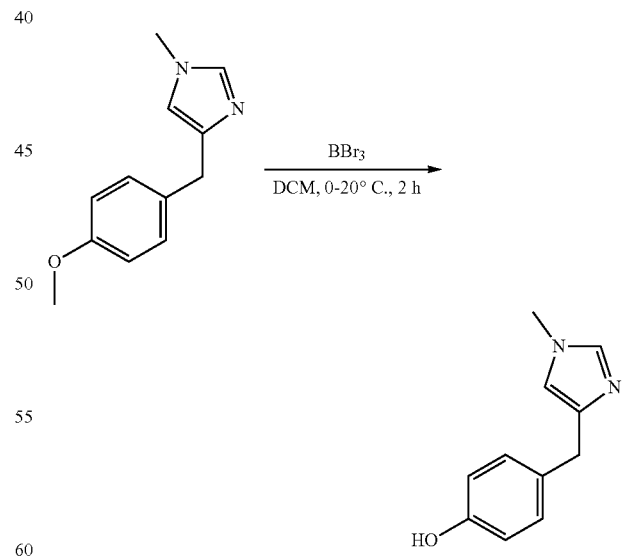

To a solution of 4-(4-methoxybenzyl)-1-methyl-1H-imidazole (300 mg, 1.40 mmol, 1.00 eq) in dichloromethane (1.00 mL) was added tribromoborane (1.49 g, 5.93 mmol, 571 μL, 4.00 eq) at 0° C. Then the mixture was stirred at 20° C. for 2 h. The reaction mixture was concentrated under reduced pressure to give a residue. The residue was purified by reversed-phase column (C18, 80 g; condition: water/acetonitrile=100:0 to 0:100, 0.1% formic acid) to afford 4-((1-methyl-1H-imidazol-4-yl)methyl)phenol (145 mg, 770 µmol, 52% yield) as a white solid.

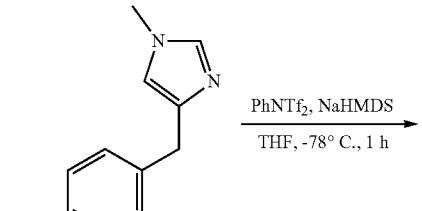

To a solution of 4-((1-methyl-1H-imidazol-4-yl)methyl)phenol (120 mg, 637 µmol, 1.00 eq) in tetrahydrofuran (3 mL) was added sodium hexamethyldisilazane (1 M, 956 µL, 1.50 eq) at −78° C., the mixture was stirred at −78° C. for 0.5 h, then 1,1,1-trifluoro-N-phenyl-N-((trifluoromethyl)sulfonyl)methanesulfonamide (284 mg, 796 µmol, 1.25 eq) in tetrahydrofuran (1.00 mL) was added, and the mixture was stirred at −78° C. for another 0.5 h. The reaction mixture was poured into water (60 mL) and extracted with ethyl acetate (3×40 mL). The combined organic layers were washed with brine (80 mL), dried over anhydrous sodium sulfate, filtered and concentrated in vacuum to give a residue. The residue was purified by Prep-HPLC (column: Phenomenex Luna C18 150×25 mm×10 m; mobile phase: [water (formic acid)-acetonitrile]; gradient: 16%-46% B over 9 min) to afford 4-((1-methyl-1H-imidazol-4-yl)methyl)phenyl trifluoromethanesulfonate (40.0 mg, 124 µmol, 19% yield) as colorless oil.

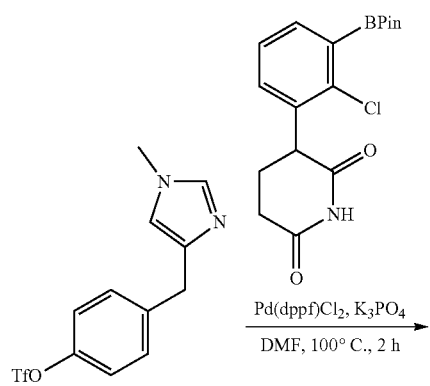

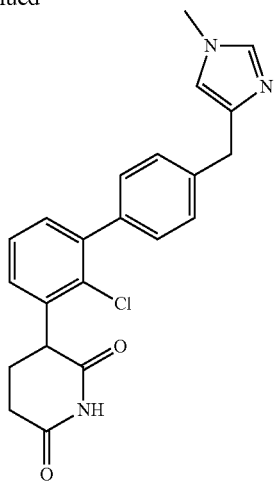

Compound 408

3-(2-chloro-4'-((1-methyl-1H-imidazol-4-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-((1-methyl-1H-imidazol-4-yl)methyl)phenyl trifluoromethanesulfonate according to General Scheme 1.

$^1$H NMR (400 MHz, DMSO-$d_6$) δ=10.92 (s, 1H), 8.29 (s, 1H), 7.47 (s, 1H), 7.41-7.25 (m, 7H), 6.88 (s, 1H), 4.34 (dd, J=5.2, 12.0 Hz, 1H), 3.83 (s, 2H), 3.60 (s, 3H), 2.88-2.75 (m, 1H), 2.61-2.53 (m, 1H), 2.39-2.32 (m, 1H), 2.10-2.01 (m, 1H); MS (ESI) m/z 394.1 [M+H]$^+$

Example 161. Synthesis of 3-(2-chloro-4'-((R)-1-methyl-2-oxopiperidin-3-yl)-[1,1'-biphenyl]-3-yl)piperidine-2,6-dione (Compound 409)

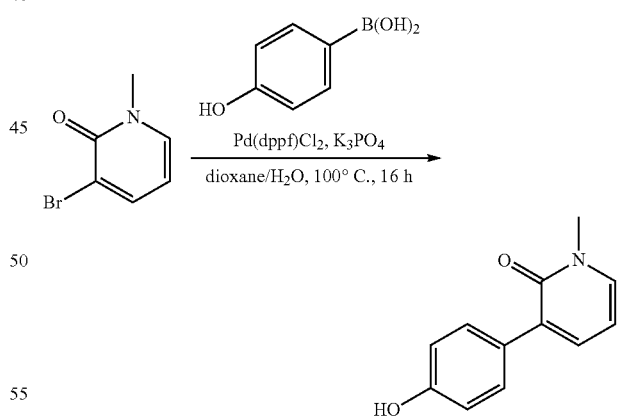

[1,1'-bis(diphenylphosphino)ferrocene]dichloropalladium (II) (0.973 g, 1.33 mmol, 0.100 eq) was added to a solution of 3-bromo-1-methylpyridin-2(1H)-one (2.50 g, 13.3 mmol, 1.00 eq), (4-hydroxyphenyl)boronic acid (2.20 g, 16.0 mmol, 1.20 eq) and potassium phosphate (8.47 g, 39.9 mmol, 3.00 eq) in water (5 mL) and dioxane (25 mL) under nitrogen atmosphere. The mixture was stirred at 100° C. for 16 h. Then the mixture was cooled to 25° C. and concentrated under reduced pressure to give a residue, which was purified by flash silica gel chromatography (ISCO®; 40 g SepaFlash®Silica Flash Column, eluent of 20%-40% ethyl acetate/petroleum ether gradient at 80 mL/min) to give 3-(4-hydroxyphenyl)-1-methylpyridin-2(1H)-one (1.50 g, 5.96 mmol, 45% yield) as a yellow solid.

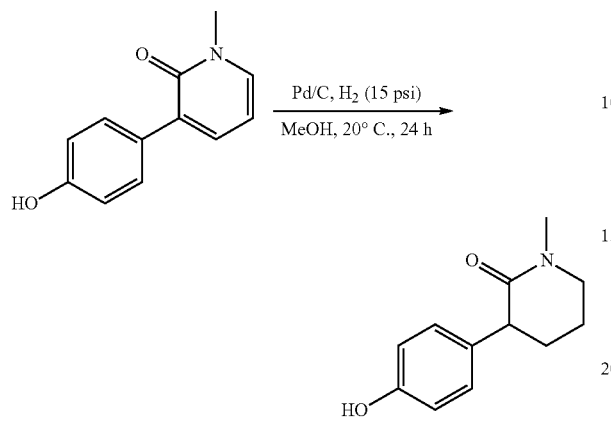

To a solution of 3-(4-hydroxyphenyl)-1-methylpyridin-2(1H)-one (1.10 g, 5.47 mmol, 1.00 eq) in methanol (50 mL) was added palladium on carbon (1.10 g, 1.03 mmol, 10 wt %, 1.00 eq) at 25° C. under argon atmosphere. The suspension was degassed and purged with hydrogen for three times. The mixture was stirred at 20° C. for 24 h under hydrogen atmosphere (15 psi). After completion of the reaction, the resulting mixture was filtered over Celite and the filter cake was washed with methanol (50 mL). The filtrate was concentrated under reduced pressure to give a residue, which was triturated with ethyl acetate (6 mL) at 20° C. for 1 h, then filtered. The filter cake was concentrated under reduced pressure to give 3-(4-hydroxyphenyl)-1-methylpiperidin-2-one (0.700 g, 3.14 mmol, 57% yield) as a white solid.

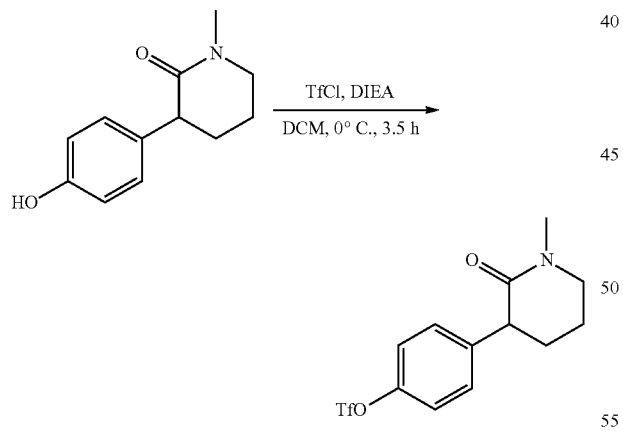

A solution of 3-(4-hydroxyphenyl)-1-methylpiperidin-2-one (0.300 g, 1.46 mmol, 1.00 eq) and N,N-diisopropylethylamine (0.223 g, 1.72 mmol, 1.18 eq) in dichloromethane (10 mL) was cooled to 0° C. and trifluoromethanesulfonyl chloride (0.287 g, 1.70 mmol, 1.16 eq) was added over 0.5 h, maintaining the temperature below 0° C. The reaction mixture was stirred at 0° C. for 3 h. The reaction was allowed to warm to room temperature and quenched with ammonium chloride solution (10 mL). The reaction mixture was then extracted with dichloromethane (3×5 mL). Combined organics were dried over magnesium sulfate, filtered and concentrated under reduced pressure to give a residue, which was purified by Prep-HPLC (column: Phenomenex luna C18 150 mm×25 mm×10 μm; mobile phase: [water (trifluoroacetic acid)-acetonitrile]; gradient: 48%-68% B over 7 min). The desired fraction was collected and lyophilized to give 4-(1-methyl-2-oxopiperidin-3-yl) phenyl trifluoromethanesulfonate (0.200 g, 0.593 mmol, 41% yield) as a white solid.

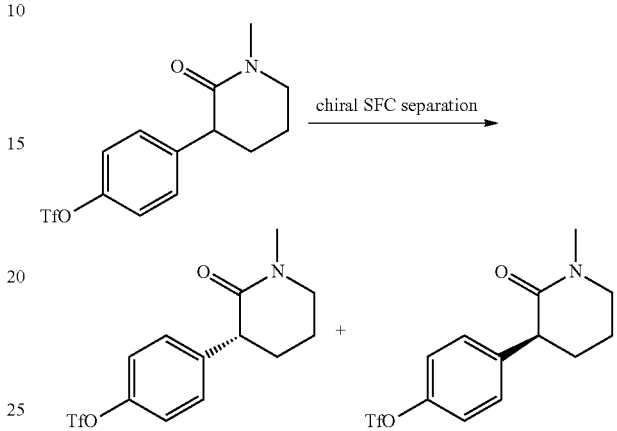

This experiment was used to isolate the two isomers by chiral SFC separation. 4-(1-methyl-2-oxopiperidin-3-yl) phenyl trifluoromethanesulfonate (0.260 g, 0.771 mmol, 1.00 eq) was purified by Chiral SFC (Instrument: waters 80Q Preparative SFC system; Daicel Chiral Pak AD column, 250 mm×30 mm I.D., 5 μm particle size; Mobile Phase: Phase A for Supercritical carbon dioxide, Phase B for ethanol (0.1% ammonium hydroxide); Isocratic elution: 25% Phase B in Supercritical carbon dioxide; Flowrate: 55 g/min; Retention; cycle time: 5.3 min; Back Pressure: 100 bar to keep the carbon dioxide in Supercritical flow; UV: 220 nm). The desired fraction was collected and evaporated under reduced pressure then lyophilized. Two peaks were separated. Peak 1 (Retention time=0.799 min): the desired fraction was evaporated under reduced pressure and lyophilized to afford (R)-4-(1-methyl-2-oxopiperidin-3-yl) phenyl trifluoromethanesulfonate (0.150 g, 0.436 mmol, 57% yield) as a white solid.

Peak 2 (Retention time=1.105 min): the desired fraction was evaporated under reduced pressure and lyophilized to afford (S)-4-(1-methyl-2-oxopiperidin-3-yl) phenyl trifluoromethane sulfonate (0.160 g, 0.460 mmol, 60% yield) as a white solid.

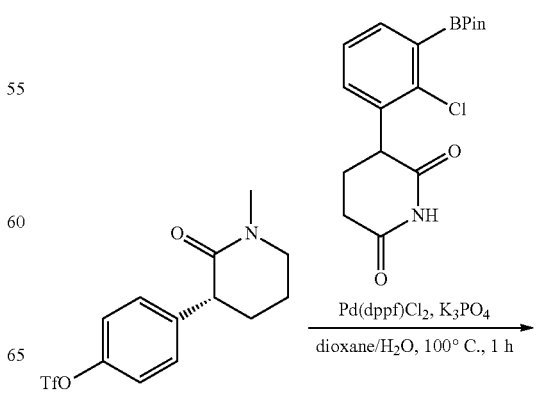

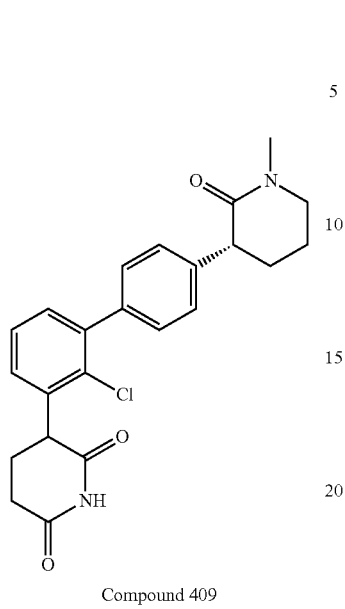

Compound 409

3-(2-chloro-4'-((R)-1-methyl-2-oxopiperidin-3-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and (R)-4-(1-methyl-2-oxopiperidin-3-yl) phenyl trifluoromethanesulfonate according to General Scheme 1.

$^1$H NMR (400 MHz, DMSO-d$_6$) δ=10.92 (s, 1H), 7.43-7.28 (m, 5H), 7.28-7.22 (m, 2H), 4.34 (dd, J=4.8, 12.0 Hz, 1H), 3.68-3.57 (m, 1H), 3.51-3.41 (m, 1H), 3.36 (s, 1H), 2.90 (s, 3H), 2.85-2.73 (m, 1H), 2.61-2.52 (m, 1H), 2.38-2.29 (m, 1H), 2.15-2.00 (m, 2H), 1.97-1.88 (m, 1H), 1.88-1.74 (m, 2H); MS (ESI) m/z 411.2/413.2 [M+H]$^+$

Example 162. Synthesis of 3-(2-chloro-4'-((S)-1-methyl-2-oxopiperidin-3-yl)-[1,1'-biphenyl]-3-yl)piperidine-2,6-dione (Compound 410)

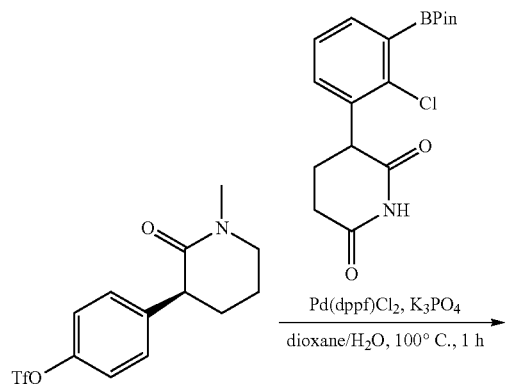

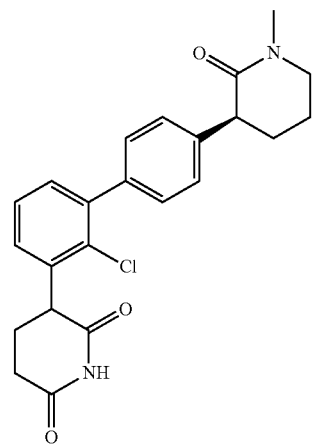

Compound 410

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-((S)-1-methyl-2-oxopiperidin-3-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and (S)-4-(1-methyl-2-oxopiperidin-3-yl)phenyl trifluoromethanesulfonate according to General Scheme 1.

$^1$H NMR (400 MHz, DMSO-d$_6$) δ=10.92 (s, 1H), 7.42-7.29 (m, 5H), 7.28-7.21 (m, 2H), 4.35 (dd, J=5.2, 12.0 Hz, 1H), 3.68-3.57 (m, 1H), 3.50-3.40 (m, 1H), 3.39-3.31 (m, 1H), 2.90 (s, 3H), 2.84-2.74 (m, 1H), 2.61-2.52 (m, 1H), 2.37-2.26 (m, 1H), 2.15-1.99 (m, 2H), 1.97-1.88 (m, 1H), 1.88-1.75 (m, 2H); MS (ESI) m/z 411.2, 413.2 [M+H]$^+$

Example 163. Synthesis of 3-(2-chloro-4'-(4-(methoxymethyl)-1-methyl-2-oxo-1,2-dihydropyridin-3-yl)-[1,1'-biphenyl]-3-yl)piperidine-2,6-dione (Compound 411)

Thionyl chloride (10.1 g, 84.6 mmol, 5.00 eq) was added to a solution of 3-bromo-2-chloroisonicotinic acid (4.00 g, 16.9 mmol, 1.00 eq) in methanol (40 mL) at 0° C. The mixture was stirred at 80° C. for 2.5 h. Then the mixture was cooled to 25° C. and concentrated under reduced pressure to give a residue, which was purified by flash silica gel chromatography (ISCO®; 40 g SepaFlash® Silica Flash Column, eluent of 30-50% ethyl acetate/petroleum ether gradient at 70 mL/min) to afford methyl 3-bromo-2-chloroisonicotinate (3.70 g, 13.3 mmol, 79% yield) as white oil.

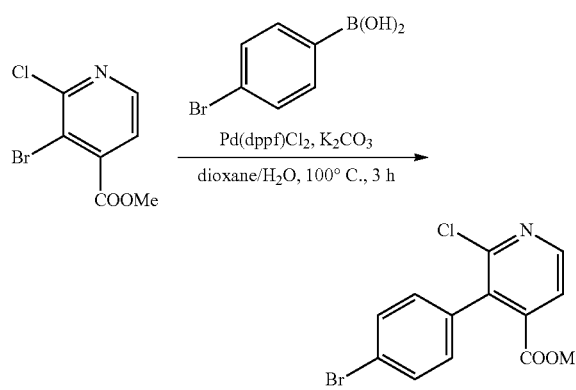

[1,1'-bis(diphenylphosphino)ferrocene]dichloropalladium(II) (1.08 g, 1.48 mmol, 0.100 eq) was added to a solution of methyl methyl 3-bromo-2-chloroisonicotinate (3.70 g, 14.8 mmol, 1.00 eq), (4-bromophenyl)-boronic acid (3.56 g, 17.7 mmol, 1.20 eq) and potassium carbonate (6.12 g, 44.3 mmol, 3.00 eq) in dioxane (35 mL) and water (7 mL) under nitrogen. The mixture was stirred at 100° C. for 3 h. The mixture was cooled to 25° C. and concentrated under reduced pressure. The crude product was purified by reversed-phase column (0.1% formic acid) and concentrated under reduced pressure to give methyl 3-(4-bromophenyl)-2-chloroisonicotinate (1.60 g, 4.90 mmol, 33% yield) as brown oil.

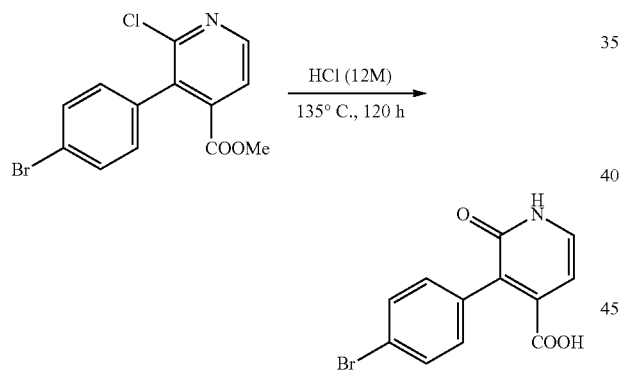

A solution of methyl methyl 3-(4-bromophenyl)-2-chloroisonicotinate (1.40 g, 4.29 mmol, 1.00 eq) in hydrochloric acid (12 M, 35.0 mL) was stirred at 135° C. for 120 h. The mixture was cooled to 25° C. and poured into ice water (15 mL). The mixture was filtered. The filter cake was dried under reduced pressure to afford 3-(4-bromophenyl)-2-oxo-1,2-dihydropyridine-4-carboxylic acid (1.10 g, 3.48 mmol, 81% yield) as a white solid.

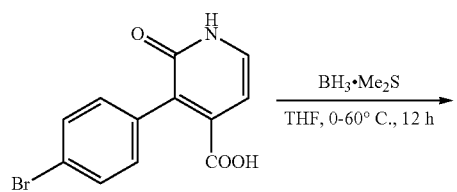

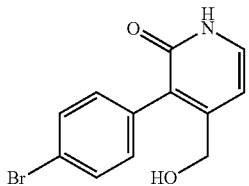

Borane dimethyl sulfide complex (10 M, 0.6 mL, 3.00 eq) was added to a solution of 3-(4-bromophenyl)-2-oxo-1,2-dihydropyridine-4-carboxylic acid (0.600 g, 2.04 mmol, 1.00 eq) in tetrahydrofuran (10 mL) at 0° C. under nitrogen atmosphere. The mixture was stirred at 60° C. for 12 h. After being cooled to room temperature, the reaction mixture was quenched with methanol (5 mL) and concentrated under reduced pressure to give a residue, which was purified by Prep-HPLC (column: Phenomenex luna C18 150 mm×40 mm×15 μm; mobile phase: [water (formic acid)-acetonitrile]; gradient: 13%-43% B over 15 min). The desired fraction was collected and lyophilized to give 3-(4-bromophenyl)-4-(hydroxymethyl) pyridin-2(1H)-one (0.350 g, 1.25 mmol, 61% yield) as a white solid.

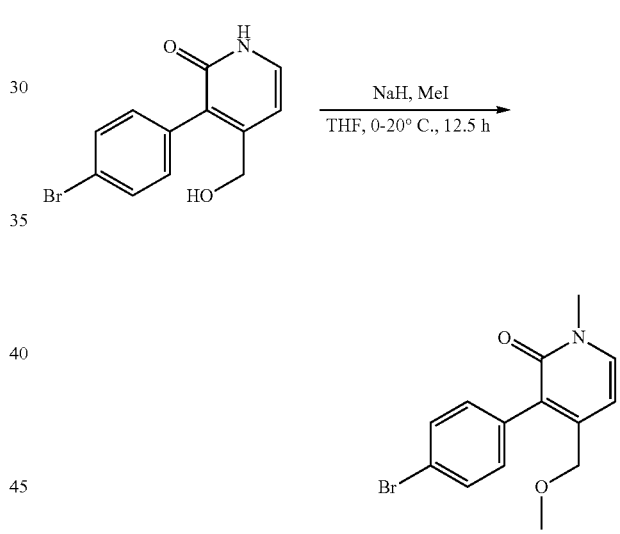

Sodium hydride (0.107 g, 2.68 mmol, 60% purity, 3.00 eq) was added to a solution of 3-(4-bromophenyl)-4-(hydroxymethyl)pyridin-2(1H)-one (0.250 g, 0.892 mmol, 1.00 eq) in tetrahydrofuran (8 mL) at 0° C. under nitrogen atmosphere. The mixture was stirred at 0° C. for 0.5 h. Then methyl iodide (0.443 g, 3.12 mmol, 3.50 eq) was added to the mixture at 25° C. The final mixture was stirred at 25° C. for 12 h. Then the reaction mixture was diluted with saturated aqueous ammonium chloride (15 mL) and extracted with ethyl acetate (2×15 mL). The combined organic layers were washed with brine (15 mL), dried over sodium sulfate, filtered and concentrated under reduced pressure to give a residue, which was purified by flash silica gel chromatography (ISCO®; 12 g SepaFlash®Silica Flash Column, eluent of 60-90% ethyl acetate/petroleum ether gradient at 80 mL/min) to give 3-(4-bromophenyl)-4-(methoxymethyl)-1-methylpyridin-2(1H)-one (0.220 g, 0.714 mmol, 80% yield) as a white solid.

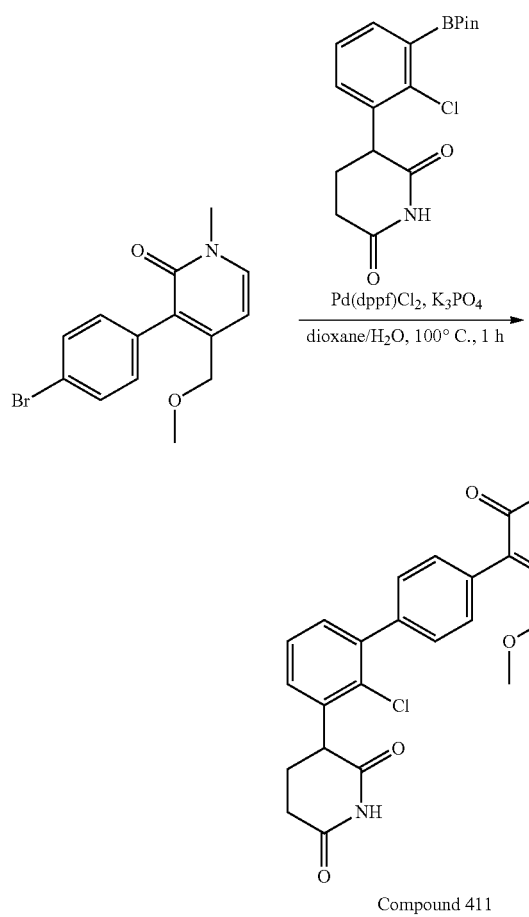

Compound 411

3-(2-chloro-4'-(4-(methoxymethyl)-1-methyl-2-oxo-1,2-dihydropyridin-3-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 3-(4-bromophenyl)-4-(methoxymethyl)-1-methylpyridin-2(1H)-one according to General Scheme 1.

$^1$H NMR (400 MHz, DMSO-d$_6$) δ=10.93 (s, 1H), 7.73 (d, J=7.2 Hz, 1H), 7.47-7.40 (m, 3H), 7.39-7.35 (m, 2H), 7.30 (d, J=8.0 Hz, 2H), 6.40 (d, J=7.2 Hz, 1H), 4.37 (dd, J=5.2, 12.0 Hz, 1H), 4.13 (s, 2H), 3.47 (s, 3H), 3.22 (s, 3H), 2.87-2.74 (m, 1H), 2.62-2.53 (m, 1H), 2.41-2.29 (m, 1H), 2.11-2.02 (m, 1H); MS (ESI) m/z 451.2, 453.2 [M+H]$^+$

Example 164. Synthesis of 3-(2-chloro-3-(5-fluoro-6-((2-oxopyridin-1(2H)-yl)methyl)pyridin-3-yl)phenyl)piperidine-2,6-dione (Compound 412)

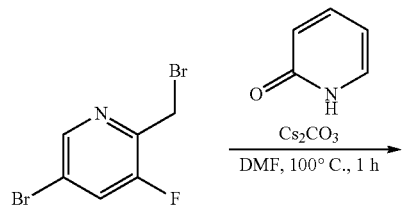

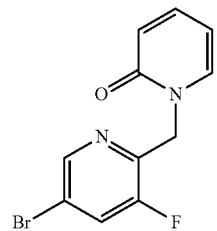

To a solution of 5-bromo-2-(bromomethyl)-3-fluoropyridine (300 mg, 1.12 mmol, 1.00 eq) and pyridin-2(1H)-one (128 mg, 1.35 mmol, 1.21 eq) in dimethyl formamide (3 mL) was added cesium carbonate (727 mg, 2.23 mmol, 2.00 eq). The mixture was stirred at 100° C. for 1 h. Ethyl acetate (40 mL) and water (40 mL) were added and layers were separated. The aqueous phase was extracted with ethyl acetate (3×40 mL). Combined extracts were washed with brine (60 mL), dried over sodium sulfate, filtered and concentrated under vacuum to give a residue, which was purified by flash silica gel chromatography (ISCO®; 10 g SepaFlash® Silica Flash Column, Eluent of 0%-100% Ethylacetate/Petroleum ethergradient @ 20 mL/min) to give 1-((5-bromo-3-fluoropyridin-2-yl)methyl)pyridin-2(1H)-one (170 mg, 0.601 mmol, 54% yield) as a white solid.

Compound 412

3-(2-chloro-3-(5-fluoro-6-((2-oxopyridin-1(2H)-yl)methyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-((5-bromo-3-fluoropyridin-2-yl)methyl)pyridin-2(1H)-one according to General Scheme 1.

¹H NMR (400 MHz, DMSO-d₆) δ=10.93 (s, 1H), 8.36 (s, 1H), 7.89 (dd, J=1.6, 10.4 Hz, 1H), 7.84 (dd, J=2.0, 6.8 Hz, 1H), 7.49-7.43 (m, 3H), 7.42-7.38 (m, 1H), 6.39 (d, J=9.2 Hz, 1H), 6.32-6.23 (m, 1H), 5.32 (s, 2H), 4.36 (dd, J=5.2, 12.4 Hz, 1H), 2.86-2.74 (m, 1H), 2.61-2.52 (m, 1H), 2.38-2.31 (m, 1H), 2.07-2.00 (m, 1H); MS (ESI) m/z 426.1 [M+H]⁺

Example 165. Synthesis of 3-(2-chloro-4'-(2,2-dimethyl-5-oxopyrrolidin-1-yl)-[1,1'-biphenyl]-3-yl)piperidine-2,6-dione (Compound 413)

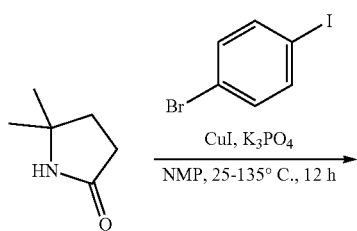

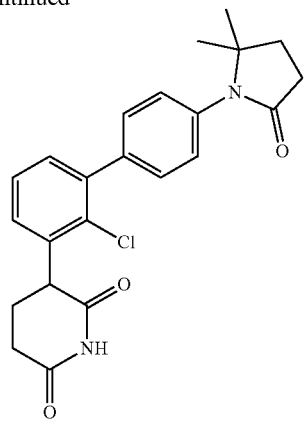

Compound 413

3-(2-chloro-4'-(2,2-dimethyl-5-oxopyrrolidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-5,5-dimethylpyrrolidin-2-one according to General Scheme 1.

¹H NMR (400 MHz, DMSO-d₆) δ=10.93 (s, 1H), 7.48 (d, J=8.4 Hz, 2H), 7.44-7.38 (m, 2H), 7.37-7.34 (m, 1H), 7.23 (d, J=8.4 Hz, 2H), 4.36 (dd, J=5.2, 12.4 Hz, 1H), 2.83-2.72 (m, 1H), 2.61-2.52 (m, 1H), 2.48-2.45 (m, 2H), 2.38-2.30 (m, 1H), 2.10-2.05 (m, 1H), 2.04-1.99 (m, 2H), 1.24 (s, 6H); MS (ESI) m/z 411.2 [M+H]⁺

Example 166. Synthesis of 3-(2-chloro-4'-(5-oxo-4-azaspiro[2.4]heptan-4-yl)-[1,1'-biphenyl]-3-yl)piperidine-2,6-dione (Compound 414)

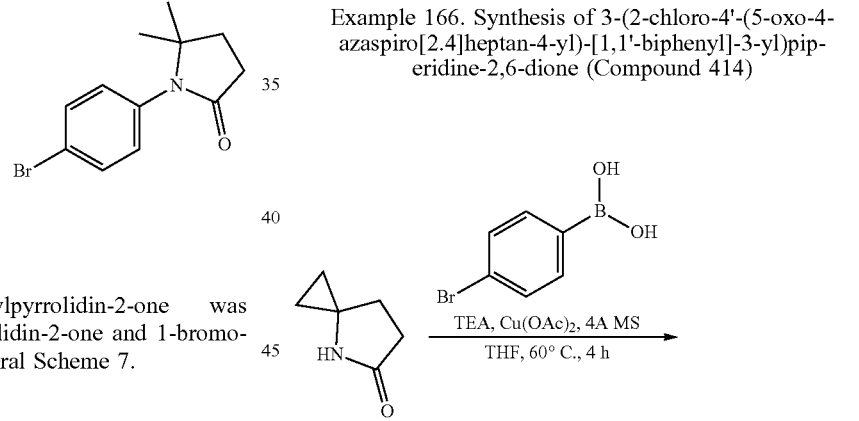

1-(4-bromophenyl)-5,5-dimethylpyrrolidin-2-one was prepared from 5,5-dimethylpyrrolidin-2-one and 1-bromo-4-iodobenzene according to General Scheme 7.

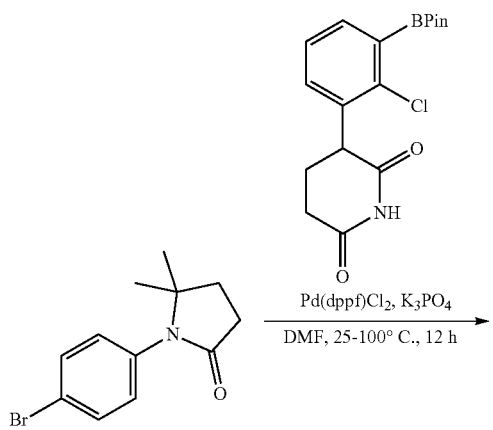

To a solution of 4-azaspiro[2.4]heptan-5-one (160 mg, 1.44 mmol, 1.00 eq) and (4-bromophenyl)boronic acid (723 mg, 3.60 mmol, 2.50 eq) in tetrahydrofuran (1 mL) was added triethylamine (437 mg, 4.32 mmol, 601 μL, 3.00 eq), copper(II)acetate (392 mg, 2.16 mmol, 1.50 eq) and 4 A molecular sieves (150 mg). The reaction mixture was stirred at 60° C. for 4 h under air. The reaction was concentrated to afford a residue. The residue was purified by column chromatography (SiO₂, Petroleum ether/Ethyl acetate=100/1 to 0/1) and concentrated to afford 4-(4-bromophenyl)-4-azaspiro[2.4]heptan-5-one (80.0 mg, 301 μmol, 21% yield) as a yellow solid.

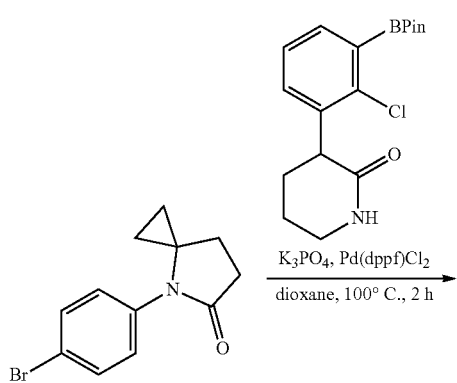

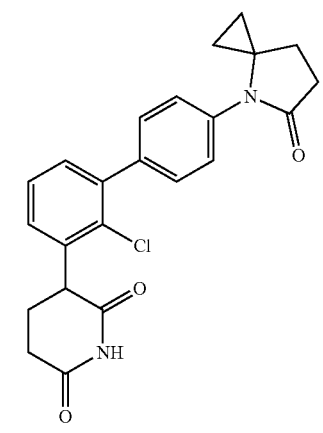

Compound 414

3-(2-chloro-4'-(5-oxo-4-azaspiro[2.4]heptan-4-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(4-bromophenyl)-4-azaspiro[2.4]heptan-5-one according to General Scheme 1.

$^1$H NMR (400 MHz, DMSO-d$_6$) δ=10.93 (s, 1H), 7.46 (d, J=8.4 Hz, 2H), 7.42-7.32 (m, 3H), 7.16 (d, J=8.4 Hz, 2H), 4.36 (dd, J=5.2, 12.0 Hz, 1H), 2.85-2.74 (m, 1H), 2.61-2.56 (m, 2H), 2.55-2.51 (m, 1H), 2.39-2.29 (m, 1H), 2.23 (t, J=8.0 Hz, 2H), 2.09-2.01 (m, 1H), 0.70-0.62 (m, 2H), 0.62-0.53 (m, 2H); MS (ESI) m/z 409.1 [M+H]$^+$

Example 167. Synthesis of 3-(2-chloro-4'-(4,4-dimethyl-2-oxooxazolidin-3-yl)-[1,1'-biphenyl]-3-yl)piperidine-2,6-dione (Compound 415)

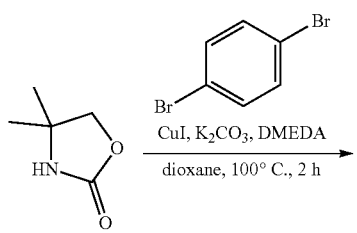

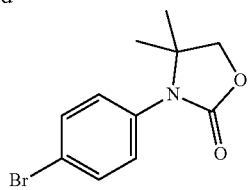

To a solution of 4,4-dimethyloxazolidin-2-one (500 mg, 4.34 mmol, 1.00 eq) and 1,4-dibromobenzene (1.02 g, 4.34 mmol, 557 μL, 1.00 eq) in dioxane (10 mL) was added copper iodide (827 mg, 4.34 mmol, 1.00 eq), N$^1$,N$^2$-dimethylethane-1,2-diamine (383 mg, 4.34 mmol, 467 μL, 1.00 eq) and potassium carbonate (1.80 g, 13.0 mmol, 3.00 eq), then the mixture was stirred at 100° C. for 2 h under nitrogen atmosphere. After being cooled to room temperature, the reaction mixture was filtered to give filtrate. Then the filtrate was concentrated under reduced pressure to give a residue. The residue was purified by silica gel chromatography (Petroleum ether/Ethyl acetate=5/1 to 2/1) and Prep-HPLC (column: Phenomenex Luna C18 150×25 mm×pm; mobile phase: [water (formic acid)-acetonitrile]; gradient: 30%-60% B over 10 min) and lyophilize to afford 3-(4-bromophenyl)-4,4-dimethyloxazolidin-2-one (200 mg, 740 μmol, 17% yield) as a white solid.

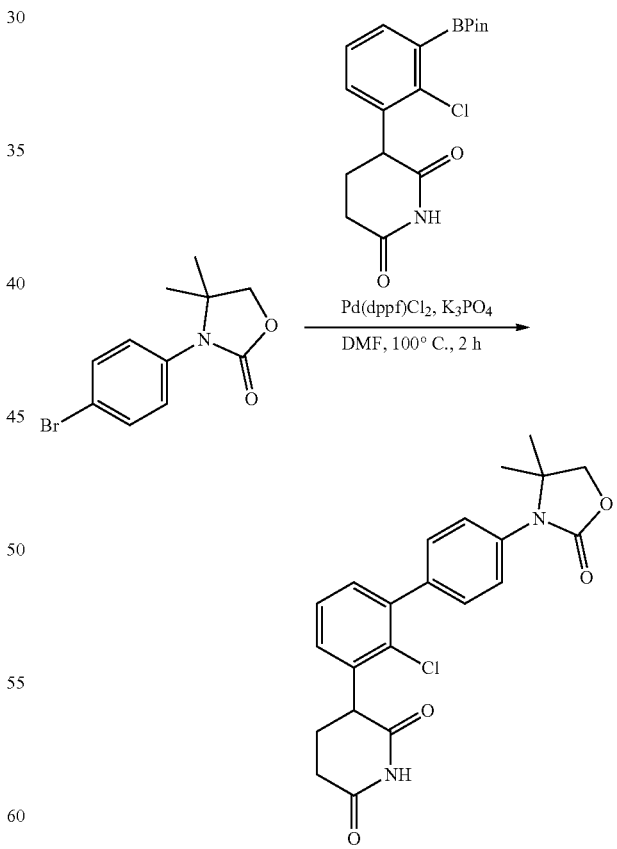

Compound 415

3-(2-chloro-4'-(4,4-dimethyl-2-oxooxazolidin-3-yl)-[1,1'-biphenyl]-3-yl)piperidine-2,6-dione was prepared from 3-(2-chloro-3-(4,4,5,5-tetramethyl-1,3,2-dioxaborolan-2-yl)

phenyl)piperidine-2,6-dione (intermediate A) and 3-(4-bromophenyl)-4,4-dimethyloxazolidin-2-one according to General Scheme 1.

¹HNMR (400 MHz, DMSO-d₆) δ=10.93 (s, 1H), 7.50 (d, J=8.4 Hz, 2H), 7.43-7.38 (m, 2H), 7.38-7.34 (m, 3H), 4.36 (dd, J=5.2, 12.4 Hz, 1H), 4.23 (s, 2H), 2.85-2.75 (m, 1H), 2.62-2.53 (in, 1H), 2.39-2.30 (m, 1H), 2.10-2.04 (m, 1H), 1.32 (s, 6H); MS (ESI) m/z 413.1 [M+H]⁺

Example 168. Synthesis of 3-(2-chloro-4'-(6-oxo-7-oxa-5-azaspiro[3.4] octan-5-yl)-[1,1'-biphenyl]-3-yl)piperidine-2,6-dione (Compound 416)

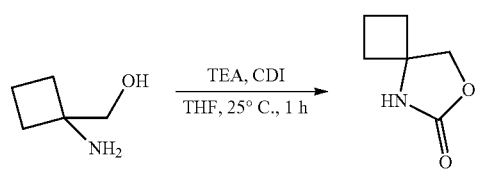 [SMILES: NC1(CO)CCC1 ; O=C1NC2(CCC2)CO1]

To a solution of (1-aminocyclobutyl)methanol in tetrahydrofuran (3 mL) was added triethylamine (662 mg, 6.54 mmol, 910 µL, 3.00 eq) and 1,1'-carbonyldiimidazole (707 mg, 4.36 mmol, 2.00 eq), the mixture was stirred at 25° C. for 1 h. Then the reaction mixture was diluted with water (30 mL) and exacted with ethyl acetate (3×30 mL). The combined organic phase was washed with brine (2×20 mL), dried over sodium sulfate, filtered and concentrated under reduced pressure to give a residue. The residue was purified by column chromatography (SiO₂, Petroleum ether/Ethyl acetate=5/1 to 1/1) to afford 7-oxa-5-azaspiro[3.4]octan-6-one (600 mg, 4.72 mmol, 72% yield) as a white solid.

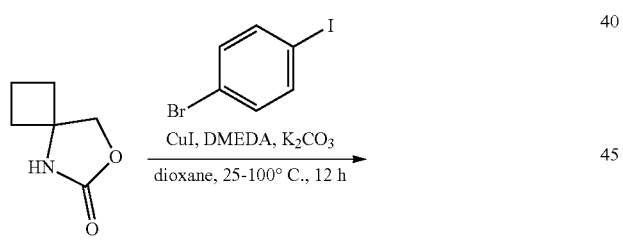

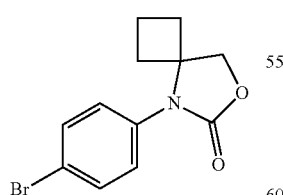

5-(4-bromophenyl)-7-oxa-5-azaspiro[3.4]octan-6-one was prepared from 7-oxa-5-azaspiro[3.4]octan-6-one and 1-bromo-4-iodobenzene according to General Scheme 7.

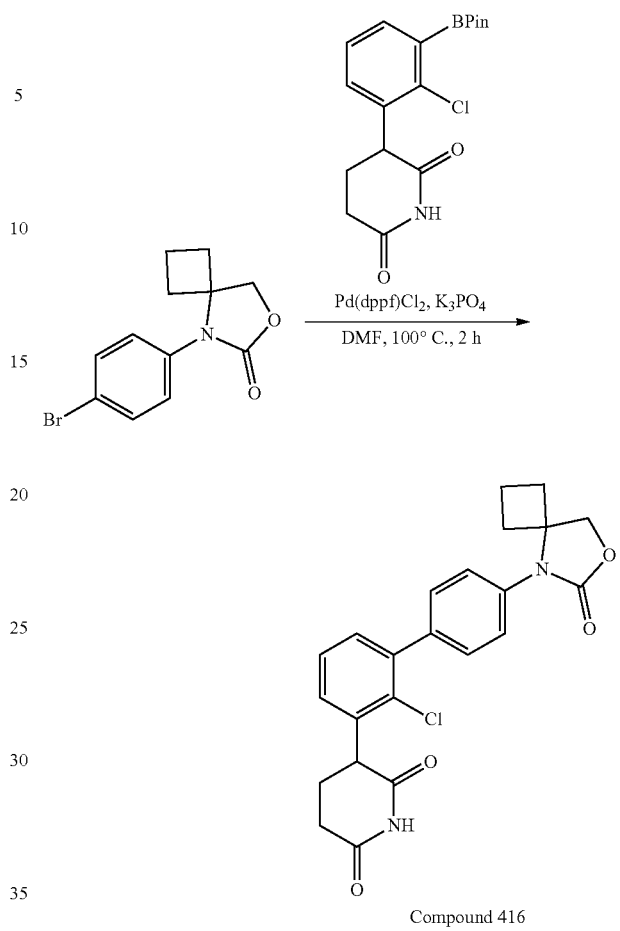

Compound 416

3-(2-chloro-4'-(6-oxo-7-oxa-5-azaspiro[3.4]octan-5-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5-(4-bromophenyl)-7-oxa-5-azaspiro[3.4]octan-6-one according to General Scheme 1.

¹H NMR (400 MHz, DMSO-d₆) δ=10.95 (s, 1H), 7.56 (d, J=8.0 Hz, 2H), 7.46-7.36 (m, 5H), 4.62 (s, 2H), 4.38 (dd, J=4.8, 12.4 Hz, 1H), 2.94-2.74 (m, 1H), 2.62-2.53 (m, 1H), 2.44-2.34 (m, 1H), 2.31-2.22 (m, 2H), 2.20-2.12 (m, 2H), 2.11-2.06 (m, 1H), 1.70-1.58 (m, 1H), 1.55-1.43 (m, 1H); MS (ESI) m/z 425.2 [M+H]⁺

Example 169. Synthesis of 3-(2-chloro-4'-(2-oxo-3-(2,2,2-trifluoroethyl)pyridin-1(2H)-yl)-[1,1'-biphenyl]-3-yl)piperidine-2,6-dione (Compound 417)

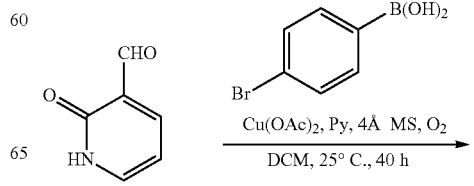

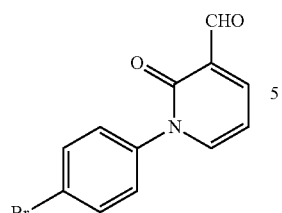

A mixture of 2-oxo-1,2-dihydropyridine-3-carbaldehyde (5.00 g, 40.6 mmol, 1.00 eq), (4-bromophenyl)boronic acid (8.97 g, 44.7 mmol, 1.10 eq), cupric acetate (738 mg, 4.06 mmol, 0.100 eq), pyridine (6.43 g, 81.2 mmol, 6.56 mL, 2.00 eq) and 4 Å molecular sieve (1.00 g) in dichloromethane (100 mL) was stirred at 25° C. for 40 h under oxygen atmosphere. The reaction mixture was filtered and the filtrate was concentrated under reduced pressure to give a residue. Then hydrochloric acid (1 M, 50 mL) was added to the residue and it was extracted with ethyl acetate (5×100 mL). The combined organic layers were dried over sodium sulfate, filtered and concentrated under reduced pressure to give a residue, which was purified by reversed phase column (C18, 80 g; condition: water/acetonitrile=100:0 to 0:100, 0.1% formic acid) and lyophilized to afford 1-(4-bromophenyl)-2-oxo-1,2-dihydropyridine-3-carbaldehyde (2.40 g, 8.20 mmol, 20% yield) as a yellow solid.

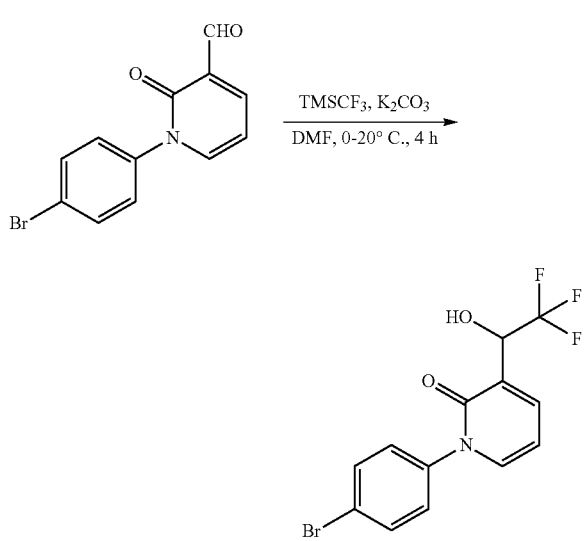

To a solution of 1-(4-bromophenyl)-2-oxo-1,2-dihydropyridine-3-carbaldehyde (450 mg, 1.62 mmol, 1.00 eq), potassium carbonate (671 mg, 4.85 mmol, 3.00 eq) in dimethyl formamide (5.00 mL) was added trimethyl(trifluoromethyl)silane (345 mg, 2.43 mmol, 1.50 eq) at 0° C. The mixture was stirred at 20° C. for 4 h. Then the reaction mixture was diluted with water (30 mL) and extracted with ethyl acetate (3×30 mL). The combined organic layers were washed with brine (3×10 mL), dried over sodium sulfate, filtered and concentrated to give a residue, which was purified by column chromatography (SiO$_2$, Petroleum ether/Ethyl acetate=5/1 to 1/1) and concentrated to afford 1-(4-bromophenyl)-3-(2,2,2-trifluoro-1-hydroxyethyl)pyridin-2(1H)-one (311 mg, 804 µmol, 50% yield) as a yellow solid.

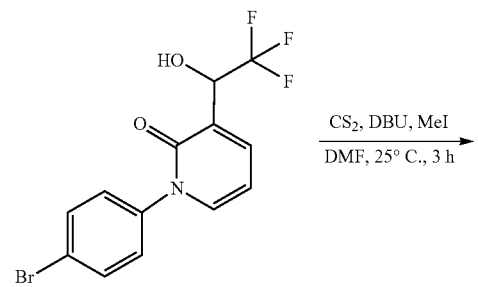

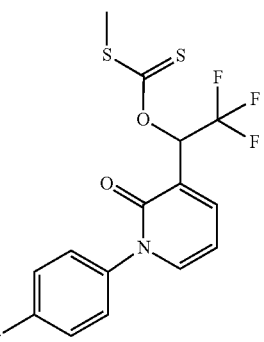

To a solution of 1-(4-bromophenyl)-3-(2,2,2-trifluoro-1-hydroxyethyl)pyridin-2(1H)-one (110 mg, 316 µmol, 1.00 eq) and 1,8-diazabicyclo[5.4.0]undec-7-ene (192 mg, 1.26 mmol, 190 µL, 4.00 eq) in dimethyl formamide (1 mL) was added dropwise carbon disulfide (241 mg, 3.16 mmol, 190 µL, 10.0 eq) under nitrogen atmosphere. The mixture was stirred at 25° C. for 1.5 h, then methyl iodide (448 mg, 3.16 mmol, 197 µL, 10.0 eq) was added dropwise. The resulting mixture was stirred at 25° C. for 1.5 h. The reaction mixture was then quenched by addition of saturated ammonium chloride solution (10 mL) and extracted with ethyl acetate (3×10 mL).

The combined organic layers were washed with brine (2×10 mL), dried over sodium sulfate, filtered and concentrated to give a residue, which was purified by column chromatography (SiO$_2$, Petroleum ether/Ethyl acetate=5/1 to 1/1) and concentrated to afford O-(1-(1-(4-bromophenyl)-2-oxo-1,2-dihydropyridin-3-yl)-2,2,2-trifluoroethyl) S-methyl carbonodithioate (120 mg, 274 µmol, 87% yield) as a yellow solid

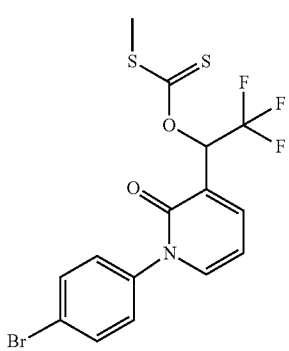

505
-continued

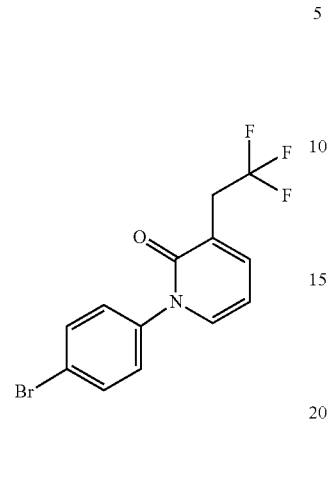

To a solution of O-(1-(1-(4-bromophenyl)-2-oxo-1,2-dihydropyridin-3-yl)-2,2,2-trifluoroethyl) S-methyl carbonodithioate (120 mg, 274 μmol, 1.00 eq) in toluene (5 mL) was added tributylstannane (239 mg, 821 μmol, 218 μL, 3.00 eq) at 25° C. under nitrogen atmosphere. Then the mixture was heated to 90° C. and 2,2-azobis(2-methylpropionitrile) (4.50 mg, 27.4 μmol, 0.100 eq) was added. The resulting mixture was stirred at 90° C. for 3 h under nitrogen atmosphere. The reaction mixture was then quenched by addition of potassium fluoride solution (1M, 10 mL), and extracted with ethyl acetate (3×10 mL). The combined organic layers were washed with brine (2×10 mL), dried over sodium sulfate, filtered and concentrated to give a residue, which was purified by reversed-phase column (C18, 20 g; condition: water/acetonitrile=100:0 to 0:100, 0.1% formic acid) and lyophilized to afford 1-(4-bromophenyl)-3-(2,2,2-trifluoroethyl)pyridin-2(1H)-one (32.0 mg, 96.4 μmol, 35% yield) was obtained as a white solid.

506
-continued

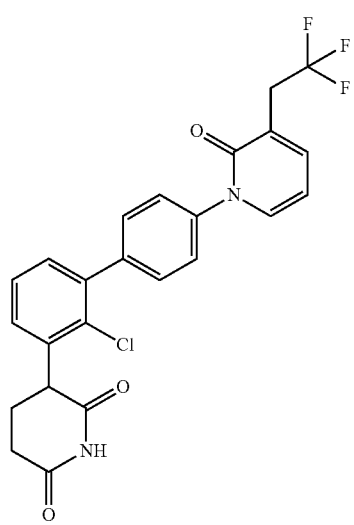

Compound 417

3-(2-chloro-4'-(2-oxo-3-(2,2,2-trifluoroethyl)pyridin-1 (2H)-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-3-(2,2,2-trifluoroethyl)pyridin-2 (1H)-one according to General Scheme 1.

$^1$H NMR (400 MHz, DMSO-d$_6$) δ=10.95 (s, 1H), 7.79 (dd, J=6.8, 1.6 Hz, 1H), 7.66 (d, J=7.2 Hz, 1H), 7.60-7.49 (m, 4H), 7.47-7.34 (m, 3H), 6.40 (t, J=6.8 Hz, 1H), 4.45-4.30 (m, 1H), 3.55 (q, J=11.2 Hz, 2H), 2.86-2.76 (m, 1H), 2.62-2.52 (m, 1H), 2.39-2.34 (m, 1H), 2.09-2.04 (m, 1H); MS (ESI) m/z 475.1 [M+H]$^+$

Example 170. Synthesis of 3-(2-chloro-4'-(2-oxo-7-oxa-1-azaspiro-[3.5]nonan-1-yl)-[1,1'-biphenyl]-3-yl)piperidine-2,6-dione (Compound 418)

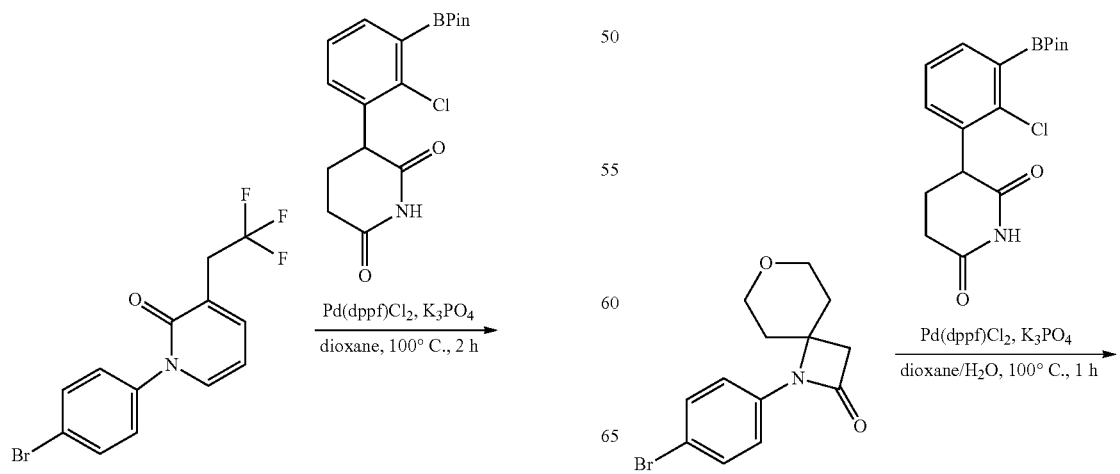

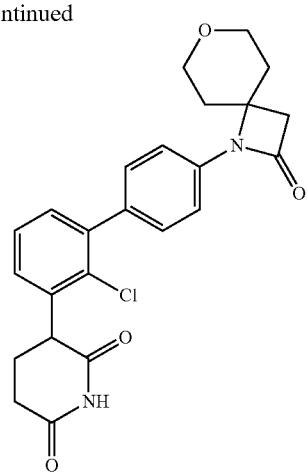

Compound 418

3-(2-chloro-4'-(2-oxo-7-oxa-1-azaspiro[3,5]nonan-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 1-(4-bromophenyl)-7-oxa-1-azaspiro[3.5]nonan-2-one according to General Scheme 1.

$^1$H NMR (400 MHz, DMSO-d$_6$) δ=10.92 (s, 1H), 7.62 (d, J=8.4 Hz, 2H), 7.43-7.37 (m, 3H), 7.36-7.32 (m, 1H), 7.30 (dd, J=7.2, 2.0 Hz, 1H), 4.34 (dd, J=12.0, 4.8 Hz, 1H), 3.99 (dd, J=11.2, 4.4 Hz, 2H), 3.40 (t, J=11.6 Hz, 2H), 3.08 (s, 2H), 2.79 (m, 1H), 2.58-2.51 (m, 2H), 2.49-2.43 (m, 1H), 2.41-2.26 (m, 1H), 2.12-1.99 (m, 1H), 1.75 (d, J=12.8 Hz, 2H).

$^1$H NMR (400 MHz, CDCl$_3$): δ=8.01 (s, 1H), 7.63 (d, J=8.4 Hz, 2H), 7.40 (d, J=8.4 Hz, 2H), 7.37-7.32 (m, 1H), 7.31-7.27 (m, 1H), 7.21 (dd, J=7.6, 1.6 Hz, 1H), 4.34 (dd, J=10.4, 5.6 Hz, 1H), 4.15 (dd, J=11.6, 4.8 Hz, 2H), 3.50 (t, J=11.6 Hz, 2H), 3.00 (s, 2H), 2.87-2.61 (m, 4H), 2.45-2.24 (m, 2H), 1.77 (d, J=12.8 Hz, 2H); MS (ESI) m/z 439.2 [M+H]$^+$

Example 171. Synthesis of 3-(2-chloro-3'-fluoro-4'-(2-oxopyrimidin-1(2H)-yl)-[1,1'-biphenyl]-3-yl)piperidine-2,6-dione (Compound 419)

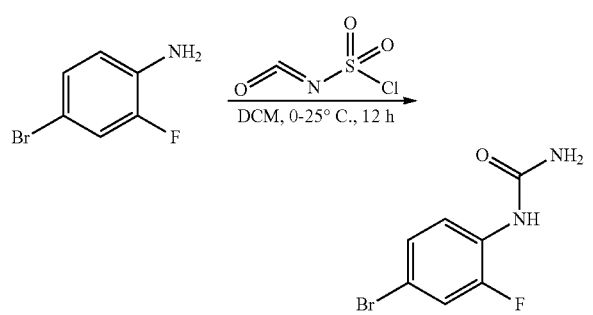

To a solution of 4-bromo-2-fluoroaniline (5.00 g, 26.3 mmol, 1.00 eq) in dichloromethane (10 mL) was added the solution of sulfurisocyanatidic chloride (2.75 mL, 31.6 mmol, 1.20 eq) in dichloromethane (30 mL) at 0° C. The mixture was stirred at 25° C. for 12 h. The reaction mixture was then diluted with ethyl acetate (30 mL) and water (30 mL). The mixture was extracted with ethyl acetate (3×30 mL). The combined organic extracts were washed with brine (30 mL), dried over sodium sulfate, filtered and concentrated under reduced pressure to give a residue, which was purified by column chromatography on silica gel (petroleum ether/ethyl acetate=2/1) to afford 1-(4-bromo-2-fluorophenyl)urea (1.30 g, 5.58 mmol, 21% yield) as a white solid.

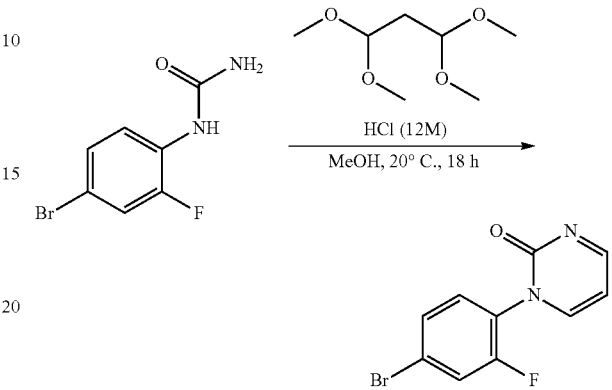

To a solution of 1-(4-bromo-2-fluorophenyl)urea (1.30 g, 5.58 mmol, 1.00 eq) in methanol (10 mL) was added 1,1,3,3-tetramethoxypropane (1.78 mL, 10.8 mmol, 2.00 eq) and hydrochloric acid (12 M in water, 2.32 mL, 5.00 eq). After addition, the mixture was resulted in the formation of an orange particulate suspension, which gradually became homogeneous and deep red in colour on stirring at 20° C. The mixture was stirred at 20° C. for 18 h. The pH was basified to 8 with saturated sodium bicarbonate aqueous solution. The reaction mixture was extracted with dichloromethane (3×20 mL). Hydrochloric acid (2.0 M, 20 mL) was added to the combined organic phase and then extracted with dichloromethane (3×20 mL). The aqueous layer was adjusted to pH=7 with saturated potassium carbonate aqueous solution and extracted with a further portion of dichloromethane (30 mL). The organic layer was dried over anhydrous sodium sulfate, filtrate and concentrated under reduced pressure to give a residue, which was purified by column chromatography on silica gel (100% ethyl acetate) to give 1-(4-bromo-2-fluorophenyl)pyrimidin-2(1H)-one (0.182 g, 0.676 mmol, 12% yield) as a yellow solid.

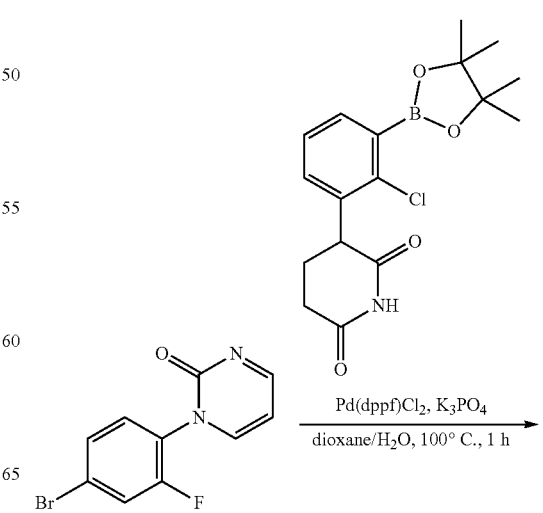

-continued

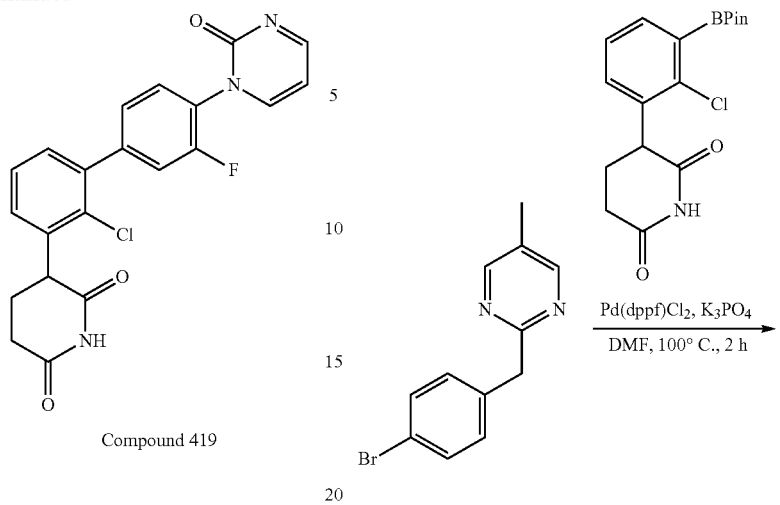

Compound 419

3-(2-chloro-3'-fluoro-4'-(2-oxopyrimidin-1(2H)-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromo-2-fluorophenyl)pyrimidin-2(1H)-one according to General Scheme 1.

$^1$H NMR (400 MHz, DMSO-$d_6$) δ=10.95 (s, 1H), 8.77-8.74 (m, 1H), 8.36-8.32 (m, 1H), 7.70 (t, J=8.0 Hz, 1H), 7.56 (d, J=10.8 Hz, 1H), 7.48-7.39 (m, 4H), 6.60 (dd, J=6.4, 4.0 Hz, 1H), 4.38 (dd, J=12.4, 4.8 Hz, 1H), 2.86-2.77 (m, 1H), 2.59-2.51 (m, 1H), 2.40-2.31 (m, 1H), 2.08-2.04 (m, 1H); MS (ESI) m/z 412.2 [M+H]$^+$

Example 172. Synthesis of 3-(2-chloro-4'-((5-methylpyrimidin-2-yl)methyl)-[1,1'-biphenyl]-3-yl)piperidine-2,6-dione (Compound 420)

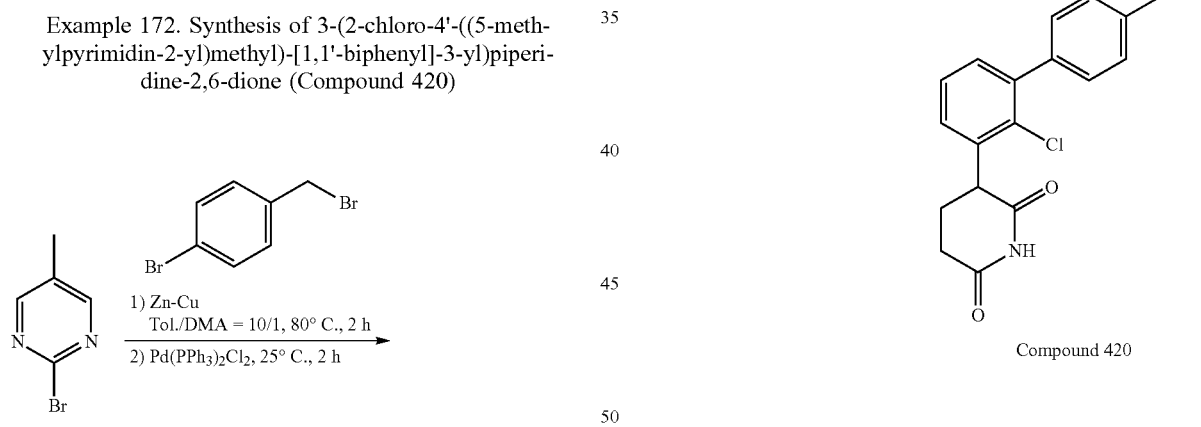

Compound 420

2-(4-bromobenzyl)-5-methylpyrimidine was prepared from 1-bromo-4-(bromomethyl)benzene and 2-bromo-5-methylpyrimidine according to General Scheme 12.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-((5-methylpyrimidin-2-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 2-(4-bromobenzyl)-5-methylpyrimidine according to General Scheme 1.

$^1$H NMR (400 MHz, DMSO-$d_6$) δ=10.92 (s, 1H), 8.61 (s, 2H), 7.40-7.26 (m, 7H), 4.34 (dd, J=12.0, 4.8 Hz, 1H), 4.22 (s, 2H), 2.84-2.75 (m, 1H), 2.61-2.52 (m, 1H), 2.39-2.29 (m, 1H), 2.25 (s, 3H), 2.09-2.00 (m, 1H); MS (ESI) m/z 406.2 [M+H]$^+$

Example 173. Synthesis of 3-(2-chloro-4'-((4-methoxypyrimidin-2-yl)methyl)-[1,1'-biphenyl]-3-yl)piperidine-2,6-dione (Compound 421)

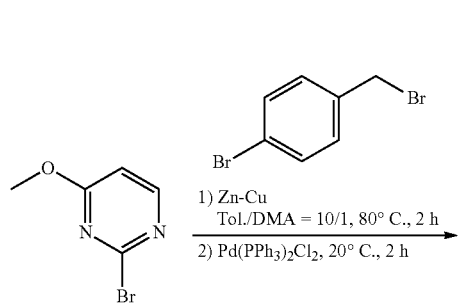

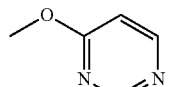

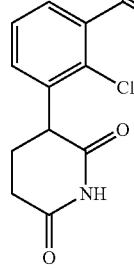

Compound 421

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-((4-methoxypyrimidin-2-yl)methyl)-[1,1'-biphenyl]-3-yl)piperidine-2,6-dione was prepared from 2-(4-bromobenzyl)-4-methoxypyrimidine and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.91 (s, 1H), 8.46 (d, J=5.6 Hz, 1H), 7.42-7.27 (m, 7H), 6.79 (d, J=6.0 Hz, 1H), 4.33 (dd, J=12.0, 5.2 Hz, 1H), 4.15 (s, 2H), 3.92 (s, 3H), 2.84-2.71 (m, 1H), 2.60-2.51 (m, 1H), 2.35-2.29 (m, 1H), 2.08-1.99 (m, 1H); MS (ESI) m/z 422.2 [M+H]$^+$

Example 174. Synthesis of 3-(2-chloro-4'-((5-methoxypyrimidin-2-yl)methyl)-[1,1'-biphenyl]-3-yl)piperidine-2,6-dione (Compound 422)

2-(4-bromobenzyl)-4-methoxypyrimidine was prepared from 1-bromo-4-(bromomethyl)benzene and 2-bromo-4-methoxypyrimidine according to General Scheme 12.

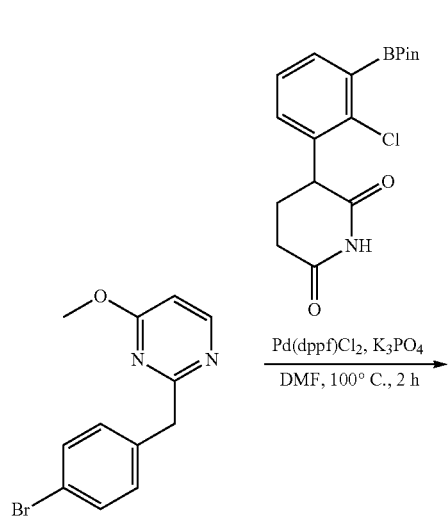

2-(4-bromobenzyl)-5-methoxypyrimidine was prepared from 1-bromo-4-(bromomethyl)benzene and 2-bromo-5-methoxypyrimidine according to General Scheme 12.

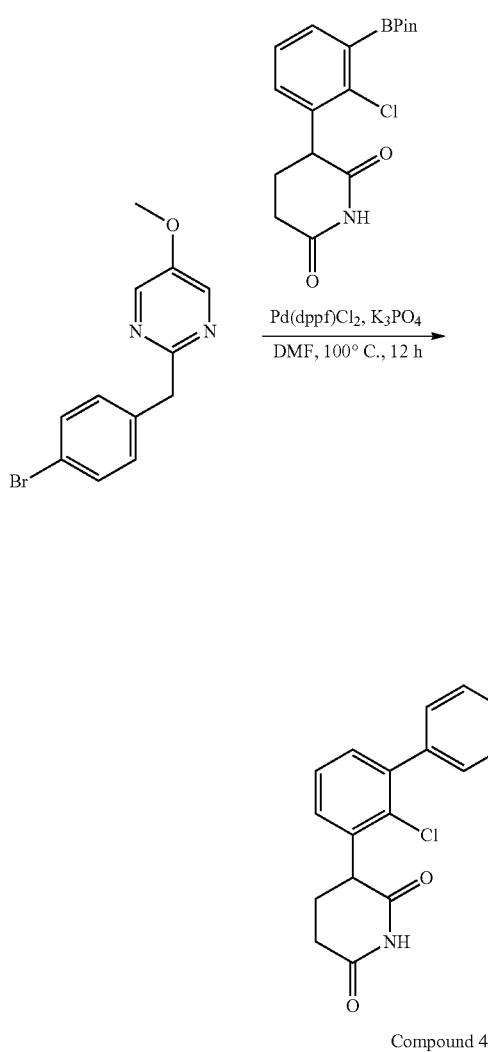

Compound 422

3-(2-chloro-4'-((5-methoxypyrimidin-2-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 2-(4-bromobenzyl)-5-methoxypyrimidine according to General Scheme 1.

$^1$H NMR (400 MHz, DMSO-$d_6$) δ=10.92 (s, 1H), 8.51 (s, 2H), 7.41-7.27 (m, 7H), 4.34 (dd, J=12.4, 4.8 Hz, 1H), 4.22 (s, 2H), 3.89 (s, 3H), 2.85-2.73 (m, 1H), 2.61-2.51 (m, 1H), 2.39-2.27 (m, 1H), 2.11-1.99 (m, 1H); MS (ESI) m/z 422.2 [M+H]$^+$

Example 175. Synthesis of 3-(2-chloro-4'-((pyrrolidin-1-ylsulfonyl)methyl)-[1,1'-biphenyl]-3-yl)piperidine-2,6-dione (Compound 423)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-((pyrrolidin-1-ylsulfonyl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 1-((4-bromobenzyl)sulfonyl)pyrrolidine according to General Scheme 1.
MS (ESI) m/z 445.0 [M−H]$^+$ Example 176. Synthesis of 3-(2-chloro-4'-((3-methyl-2-oxotetrahydropyrimidin-1(2H)-yl)methyl)-[1,1'-biphenyl]-3-yl)piperidine-2,6-dione (Compound 424)

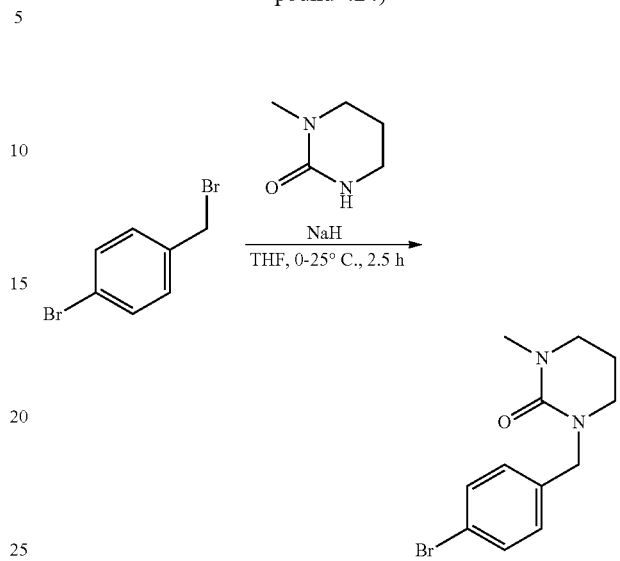

To a solution of 1-methylhexahydropyrimidin-2-one (0.168 g, 1.47 mmol, 1.23 eq) in tetrahydrofuran (12 mL) was added sodium hydride (0.0600 g, 1.50 mmol, 60% purity, 1.25 eq) under nitrogen atmosphere at 0° C. The mixture was stirred at 0° C. for 0.5 h. Then 1-bromo-4-(bromomethyl)benzene (0.300 g, 1.20 mmol, 1.00 eq) was added to the mixture under nitrogen atmosphere at 0° C. The mixture was stirred at 25° C. for another 2 h. Then the reaction mixture was quenched with saturated ammonium chloride solution (10 mL), extracted with ethyl acetate (3×5 mL). The combined organic layers were dried over magnesium sulfate, filtered and concentrated under reduced pressure to give a residue, which was purified by Prep-HPLC (column: Phenomenex luna C18 150 mm×25 mm×10 μm; mobile phase: [(formic acid)-acetonitrile]; gradient: 59%-79% B over 10 min). The desired fraction was collected and lyophilized to give 1-(4-bromobenzyl)-3-methyltetrahydropyrimidin-2(1H)-one (0.100 g, 0.353 mmol, 29% yield) as a white solid.

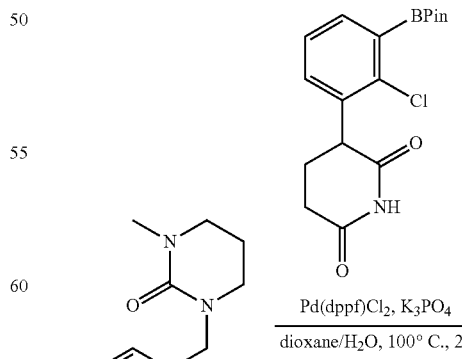

Compound 424

3-(2-chloro-4'-((3-methyl-2-oxotetrahydropyrimidin-1 (2H)-yl) methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromobenzyl)-3-methyltetrahydro pyrimidin-2(1H)-one according to General Scheme 1.

$^1$H NMR (400 MHz, DMSO-d$_6$) δ=10.92 (s, 1H), 7.56-7.07 (m, 7H), 4.48 (s, 2H), 4.39-4.29 (m, 1H), 3.29-3.18 (m, 4H), 2.83 (s, 3H), 2.80-2.72 (m, 1H), 2.56 (s, 1H), 2.38-2.28 (m, 1H), 2.10-1.98 (m, 1H), 1.96-1.81 (m, 2H); MS (ESI) m/z 426.2 [M+H]$^+$

Example 177. Synthesis of 3-(2-chloro-3'-fluoro-4'-((3-methyl-2-oxotetrahydropyrimidin-1(2H)-yl) methyl)-[1,1'-biphenyl]-3-yl)piperidine-2,6-dione (Compound 425)

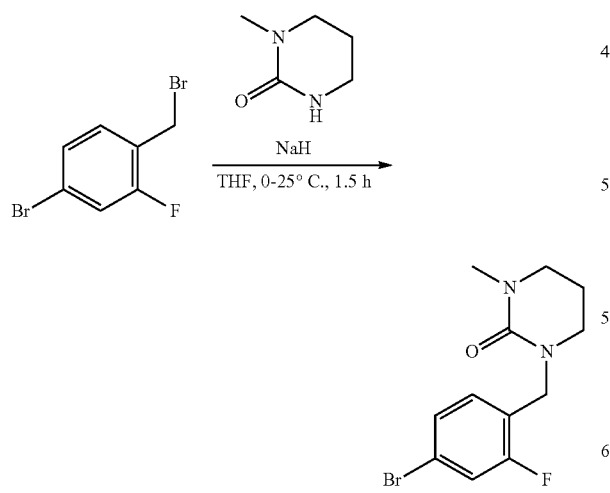

1-(4-bromo-2-fluorobenzyl)-3-methyltetrahydropyrimidin-2(1H)-one was prepared from 1-methyltetrahydropyrimidin-2(1H)-one and 4-bromo-1-(bromomethyl)-2-fluorobenzene analogously to Example 176.

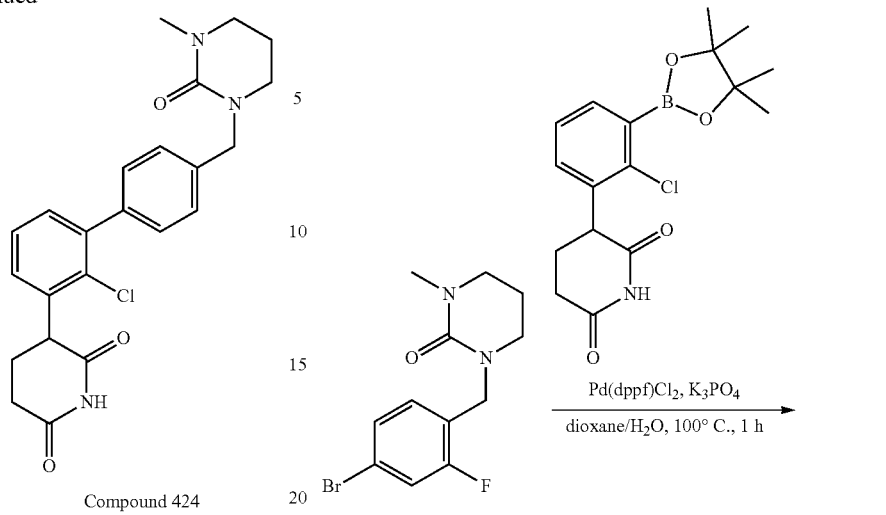

Compound 425

3-(2-chloro-3'-fluoro-4'-((3-methyl-2-oxotetrahydropyrimidin-1(2H)-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromo-2-fluorobenzyl)-3-methyltetrahydropyrimidin-2(1H)-one according to General Scheme 1.

$^1$H NMR (400 MHz, DMSO-d$_6$) δ=10.93 (s, 1H), 7.43-7.37 (m, 2H), 7.35-7.30 (m, 2H), 7.26-7.20 (m, 2H), 4.52 (s, 2H), 4.35 (dd, J=5.2, 12.0 Hz, 1H), 3.31-3.23 (m, 4H), 2.83 (s, 3H), 2.79-2.74 (m, 1H), 2.72-2.62 (m, 1H), 2.35-2.32 (m, 1H), 2.07-2.02 (m, 1H), 1.95-1.90 (m, 2H)

$^1$H NMR (400 MHz, MeOD) δ=7.41-7.33 (m, 3H), 7.33-7.28 (m, 1H), 7.24-7.15 (m, 1H), 7.17-7.13 (m, 1H), 4.64 (s, 2H), 4.39 (dd, J=11.6, 5.2 Hz, 1H), 3.41-3.32 (m, 4H), 2.95 (s, 3H), 2.84-2.73 (m, 1H), 2.74-2.65 (m, 1H), 2.47-2.36 (m, 1H), 2.24-2.15 (m, 1H), 2.06-1.95 (m, 2H).

MS (ESI) m/z 444.2 [M+H]$^+$

Example 178. Synthesis of 3-(2-chloro-4'-(5-oxo-6-oxa-4-azaspiro[2.4]heptan-4-yl)-[1,1'-biphenyl]-3-yl)piperidine-2,6-dione (Compound 426)

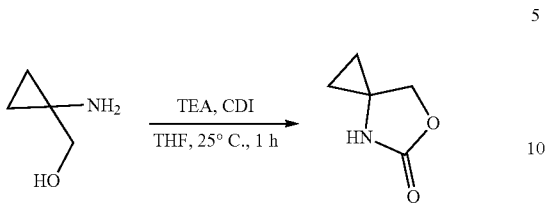

To a solution of (1-aminocyclopropyl)methanol (200 mg, 1.62 mmol, 1.00 eq, hydrochloric acid) and triethylamine (327 mg, 3.24 mmol, 450 μL, 2.00 eq) in tetrahydrofuran (2 mL) was added di(1H-imidazol-1-yl)methanone (315 mg, 1.94 mmol, 1.20 eq), the mixture was stirred at 25° C. for 1 h. Then the reaction mixture was poured into water (60 mL) and extracted with ethyl acetate (3×30 mL). The combined organic phase was washed with brine (60 mL), dried with anhydrous sodium sulfate, filtered and concentrated in vacuum to give a residue, which was purified by silica gel chromatography (Petroleum ether/Ethyl acetate=1/0 to 2/1) to afford 6-oxa-4-azaspiro[2.4]heptan-5-one (90.0 mg, 795 μmol, 49% yield) as a white solid.

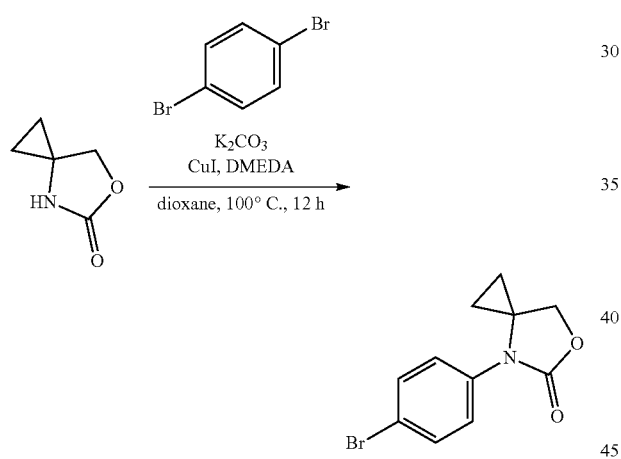

4-(4-bromophenyl)-6-oxa-4-azaspiro[2.4]heptan-5-one was prepared from 1,4-dibromobenzene and 6-oxa-4-azaspiro[2.4]heptan-5-one according to General Scheme 7.

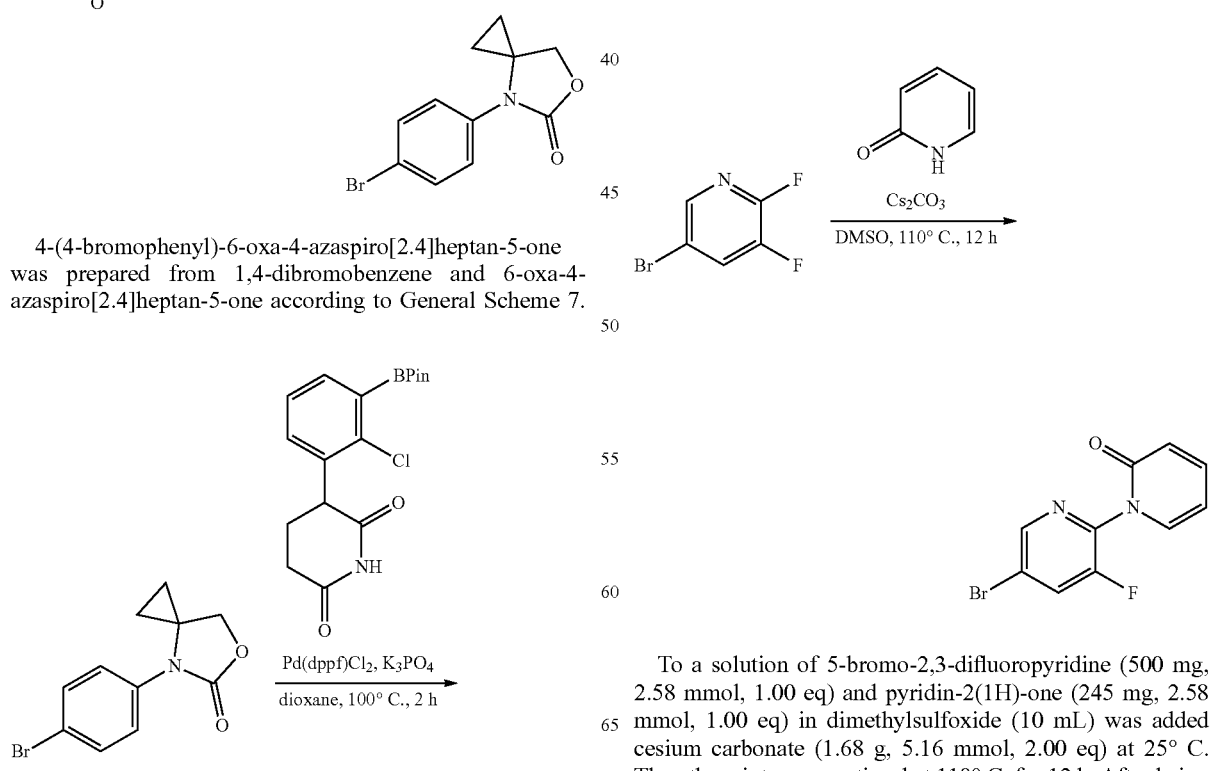

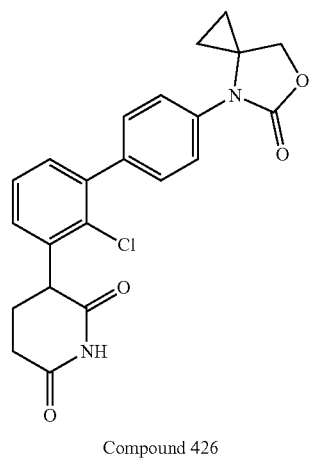

Compound 426

3-(2-chloro-4'-(5-oxo-6-oxa-4-azaspiro[2.4]heptan-4-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(4-bromophenyl)-6-oxa-4-azaspiro[2.4]heptan-5-one according to General Scheme 1.

$^1$H NMR (400 MHz, DMSO-$d_6$) δ=10.94 (s, 1H), 7.53-7.27 (m, 7H), 4.53 (s, 2H), 4.36 (dd, J=12.0, 5.2 Hz, 1H), 2.87-2.75 (m, 1H), 2.57 (s, 1H), 2.41-2.33 (m, 1H), 2.13-2.03 (m, 1H), 0.87-0.78 (m, 2H), 0.75-0.66 (m, 2H); MS (ESI) m/z 411.2 [M+H]$^+$

Example 179. Synthesis of 3-(2-chloro-3-(3'-fluoro-2-oxo-2H-[1,2'-bipyridin]-5'-yl)phenyl)piperidine-2,6-dione (Compound 427)

To a solution of 5-bromo-2,3-difluoropyridine (500 mg, 2.58 mmol, 1.00 eq) and pyridin-2(1H)-one (245 mg, 2.58 mmol, 1.00 eq) in dimethylsulfoxide (10 mL) was added cesium carbonate (1.68 g, 5.16 mmol, 2.00 eq) at 25° C. Then the mixture was stirred at 110° C. for 12 h. After being cooled to room temperature, the mixture was diluted with ethyl acetate (50 mL), washed with water (3×50 mL), dried over sodium sulfate, filtered and concentrated under reduced pressure to give a residue, which was purified by flash silica gel chromatography (ISCO®; 20 g SepaFlash® Silica Flash Column, eluent of 20-60% ethyl acetate/petroleum ether gradient at 70 mL/min) to give 5'-bromo-3'-fluoro-2H-[1,2'-bipyridin]-2-one (210 mg, 741 μmol, 29% yield) as a white solid.

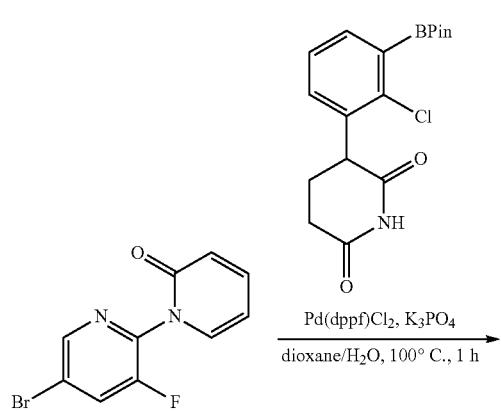

Compound 427

3-(2-chloro-3-(3'-fluoro-2-oxo-2H-[1,2'-bipyridin]-5'-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5'-bromo-3'-fluoro-2H-[1,2'-bipyridin]-2-one according to General Scheme 1.

$^1$H NMR (400 MHz, DMSO-$d_6$) δ=10.96 (s, 1H), 8.54 (d, J=1.2 Hz, 1H), 8.19 (dd, J=10.0, 1.6 Hz, 1H), 7.81 (dd, J=6.8, 1.6 Hz, 1H), 7.61 (m, 1H), 7.50 (s, 3H), 6.55 (d, J=9.2 Hz, 1H), 6.42 (t, J=6.8 Hz, 1H), 4.40 (dd, J=12.4, 5.2 Hz, 1H), 2.90-2.76 (m, 1H), 2.62-2.52 (m, 1H), 2.41-2.31 (m, 1H), 2.11-2.02 (m, 1H); MS (ESI) m/z 412.1 [M+H]$^+$

Example 180. Synthesis of 3-(2-chloro-4'-(1-methyl-2-oxo-4-(trifluoromethyl)-1,2-dihydropyridin-3-yl)-[1,1'-biphenyl]-3-yl)piperidine-2,6-dione (Compound 428)

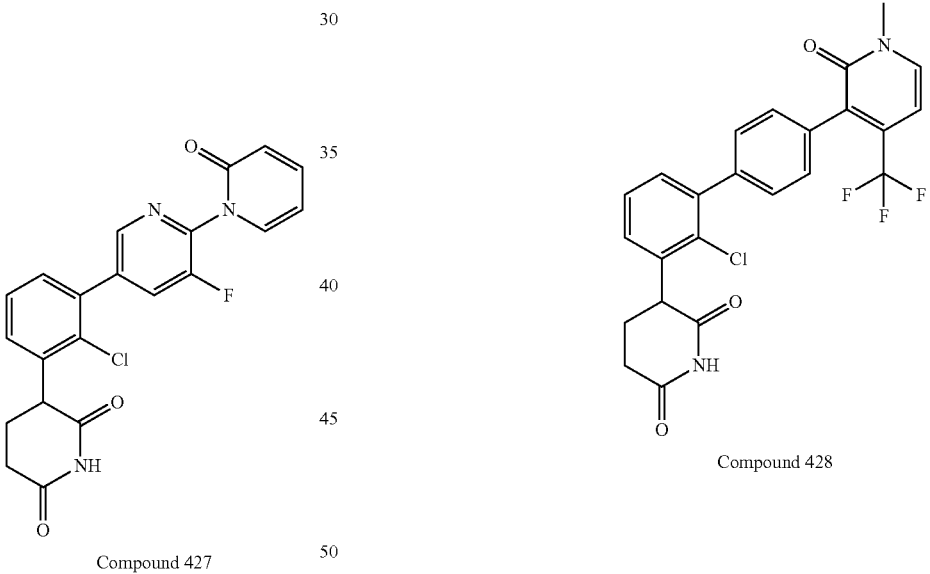

Compound 428

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(1-methyl-2-oxo-4-(trifluoromethyl)-1,2-dihydropyridin-3-yl)-[1,1'-biphenyl]-3-yl)piperidine-2,6-dione was prepared from 3-(4-bromophenyl)-1-methyl-4-(trifluoromethyl)pyridin-2(1H)-one and 3-(2-chloro-3-(4,4,5,5-tetramethyl-1,3,2-dioxaborolan-2-yl)phenyl)piperidine-2,6-dione according to General Scheme 1.

$^1$H NMR (400 MHz, DMSO-$d_6$) δ=10.93 (s, 1H), 8.01 (d, J=7.2 Hz, 1H), 7.45 (d, J=8.0 Hz, 2H), 7.42 (d, J=7.6 Hz, 1H), 7.40-7.34 (m, 2H), 7.28 (d, J=8.0 Hz, 2H), 6.57 (d, J=7.2 Hz, 1H), 4.42-4.32 (m, 1H), 3.53 (s, 3H), 2.85-2.76 (m, 1H), 2.59-2.55 (m, 1H), 2.39-2.29 (m, 1H), 2.11-2.03 (m, 1H); MS (ESI) m/z 475.1 [M+H]$^+$

Example 181. Synthesis of 3-(2-chloro-4'-(3-(2,2-difluoroethyl)-2-oxotetrahydropyrimidin-1(2H)-yl)-[1,1'-biphenyl]-3-yl)piperidine-2,6-dione (Compound 429)

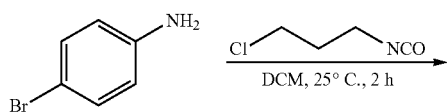

A mixture of 4-bromoaniline (3.00 g, 17.4 mmol, 1.00 eq) and 1-chloro-3-isocyanatopropane (2.50 g, 20.9 mmol, 1.20 eq) in dichloromethane (30 mL) was stirred at 25° C. for 2 h. The reaction mixture was concentrated to give a residue, which was triturated with petroleum ether (20 mL) to afford 1-(4-bromophenyl)-3-(3-chloropropyl)urea (4.00 g, 13.7 mmol, 79% yield) as a white solid.

$^1$H NMR (400 MHz, DMSO-$d_6$) δ=8.60 (s, 1H), 7.38 (s, 4H), 6.30 (t, J=5.6 Hz, 1H), 3.67 (t, J=6.4 Hz, 2H), 3.21 (q, J=6.4 Hz, 2H), 1.89 (quin, J=6.4 Hz, 2H).

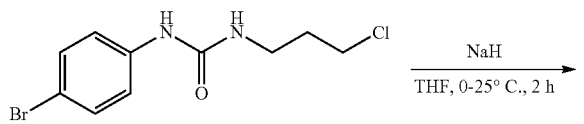

To a solution of 1-(4-bromophenyl)-3-(3-chloropropyl)urea (5.00 g, 17.2 mmol, 1.00 eq) in tetrahydrofuran (50 mL) was added sodium hydride (2.06 g, 51.5 mmol, 60% purity, 3.00 eq) at 0° C. The mixture was stirred at 25° C. for 2 h. The reaction mixture was poured into water (100 mL) and extracted with ethyl acetate (3×50 mL). The combined organic layers were washed with brine (100 mL), dried with anhydrous sodium sulfate, filtered and concentrated in vacuum to afford 1-(4-bromophenyl)tetrahydropyrimidin-2(1H)-one (4.85 g, crude) as a white solid.

$^1$H NMR (400 MHz, DMSO-$d_6$) δ=7.50-7.44 (m, 2H), 7.31-7.23 (m, 2H), 6.69 (s, 1H), 3.61 (t, J=5.6 Hz, 2H), 3.29-3.17 (m, 2H), 1.94 (quin, J=5.6 Hz, 2H).

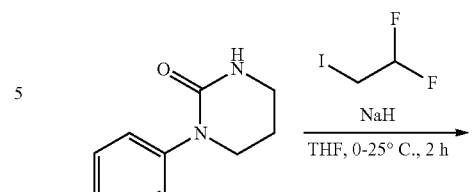

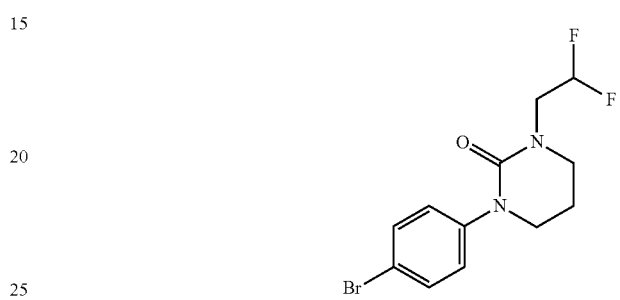

To a solution of 1-(4-bromophenyl)tetrahydropyrimidin-2(1H)-one (2.00 g, 7.84 mmol, 1.00 eq) and 1,1-difluoro-2-iodoethane (2.26 g, 11.8 mmol, 1.50 eq) in dimethylformamide (20 mL) was added sodium hydride (376 mg, 9.41 mmol, 60% purity, 1.20 eq) at 0° C., the mixture was stirred at 25° C. for 2 h. The reaction mixture was diluted with water (50 mL) and exacted with ethyl acetate (3×50 mL). The organic phase was separated, washed with brine (2×30 mL), dried over sodium sulfate, filtered and concentrated under reduced pressure to give a residue, which was purified by column chromatography (SiO$_2$, Petroleum ether/Ethyl acetate=5/1 to 0/1) to afford 1-(4-bromophenyl)-3-(2,2-difluoroethyl) tetrahydropyrimidin-2(1H)-one (200 mg, 627 mol, 8% yield) as a brown solid.

$^1$H NMR (400 MHz, DMSO-$d_6$) δ=7.50 (d, J=8.8 Hz, 2H), 7.26 (d, J=8.8 Hz, 2H), 6.35-5.90 (m, 1H), 3.70-3.63 (m, 4H), 3.47 (t, J=6.0 Hz, 2H), 2.10-1.95 (m, 2H).

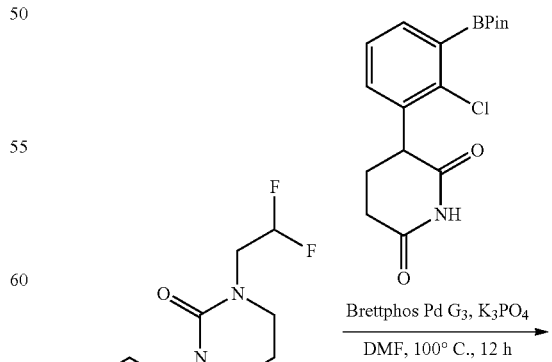

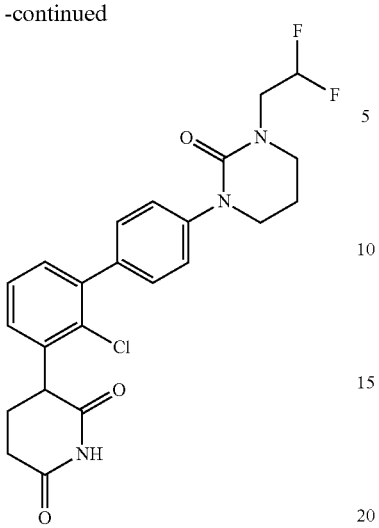

Compound 429

3-(2-chloro-3-(4,4,5,5-tetramethyl-1,3,2-dioxaborolan-2-yl)phenyl)piperidine-2,6-dione (intermediate A) was synthesized as described above. To a solution of 1-(4-bromophenyl)-3-(2,2-difluoroethyl)tetrahydropyrimidin-2(1H)-one (100 mg, 313 μmol, 1.00 eq) and 3-(2-chloro-3-(4,4,5,5-tetramethyl-1,3,2-dioxaborolan-2-yl)phenyl)piperidine-2,6-dione (164 mg, 376 μmol, 1.20 eq) in dimethylformamide (1.00 mL) was added potassium phosphate (200 mg, 940 μmol, 3.00 eq) and [(2-di-cyclohexylphosphino-3,6-dimethoxy-2',4',6'-triisopropyl-1,1'-biphenyl)-2-(2'-amino-1,1'-biphenyl)]palladium(II)methanesulfonate methanesulfonate (28.4 mg, 31.3 μmol, 0.100 eq), the mixture was stirred at 100° C. for 12 h under nitrogen atmosphere. After being cooled to room temperature, the mixture was filtered to give the filtrate, which was purified by Prep-HPLC (column: Phenomenex luna C18 150×25 mm×10 μm; mobile phase: [water (formic acid)-acetonitrile]; gradient: 34%-64% B over 10 min) to afford 3-(2-chloro-4'-(3-(2,2-difluoroethyl)-2-oxotetrahydropyrimidin-1(2H)-yl)-[1,1'-biphenyl]-3-yl)piperidine-2,6-dione (20.1 mg, 43.1 μmol, 14% yield) as an off-white solid.

$^{1}$H NMR (400 MHz, DMSO-d$_{6}$) δ=10.94 (s, 1H), 7.43-7.38 (m, 2H), 7.37 (d, J=1.2 Hz, 3H), 7.36-7.30 (m, 2H), 6.33-6.00 (m, 1H), 4.35 (dd, J=12.0, 5.2 Hz, 1H), 3.79-3.64 (m, 4H), 3.50 (t, J=5.6 Hz, 2H), 2.88-2.73 (m, 1H), 2.57 (m, 1H), 2.34 (m, 1H), 2.09-2.07 (m, 1H), 2.06 (m, 2H); MS (ESI) m/z 462.1 [M+H]$^{+}$

Example 182. Synthesis of 3-(2-chloro-3-(6-(oxazol-2-ylmethyl)pyridin-3-yl)phenyl)piperidine-2,6-dione (Compound 430)

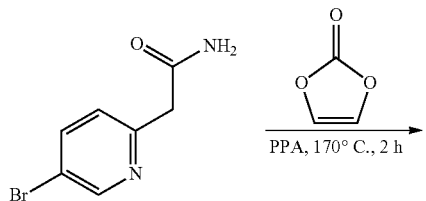

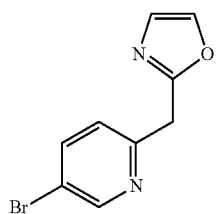

A mixture of 2-(5-bromopyridin-2-yl)acetamide (500 mg, 2.33 mmol, 1.00 eq) and 1,3-dioxol-2-one (240 mg, 2.79 mmol, 1.20 eq) in polyphosphoric acid (5 mL) was stirred at 170° C. for 2 h. The mixture was cool down to 25° C. and diluted with water (3 mL). Then the mixture was filtered to give the filtrate, and it was purified by reversed-phase column (0.1% formic acid condition) to afford 2-((5-bromopyridin-2-yl)methyl)oxazole (300 mg, 1.25 mmol, 54% yield) as brown oil.

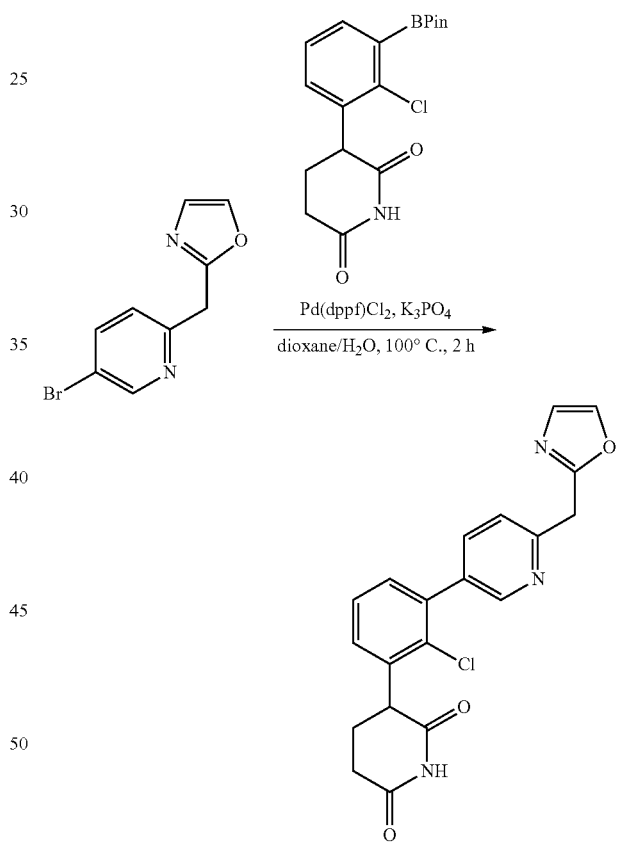

Compound 430

3-(2-chloro-3-(6-(oxazol-2-ylmethyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 2-((5-bromopyridin-2-yl)methyl)oxazole according to General Scheme 1.

$^{1}$H NMR (400 MHz, DMSO-d$_{6}$) δ=10.93 (s, 1H), 8.52 (s, 1H), 8.06 (s, 1H), 7.86 (dd, J=8.4, 1.6 Hz, 1H), 7.48-7.40 (m, 3H), 7.39-7.36 (m, 1H), 7.17 (s, 1H), 4.37 (s, 2H), 4.37-4.32 (m, 1H), 2.86-2.74 (m, 1H), 2.65-2.51 (m, 1H), 2.45-2.35 (m, 1H), 2.08-2.02 (m, 1H); MS (ESI) m/z 382.0 [M+H]$^{+}$

Example 183. Synthesis of 3-(2-chloro-3-(6-((2-oxo-1,3-oxazinan-3-yl)methyl)pyridin-3-yl)phenyl)piperidine-2,6-dione (Compound 431)

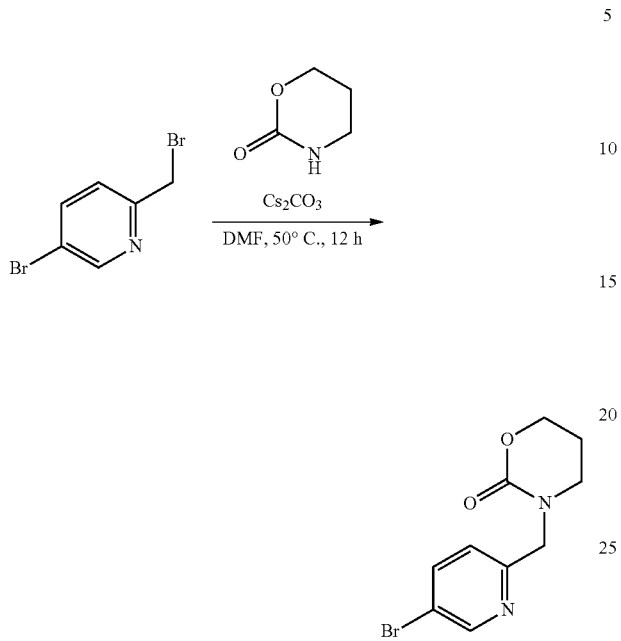

A solution of 5-bromo-2-(bromomethyl) pyridine (0.500 g, 1.99 mmol, 1.00 eq), 1,3-oxazinan-2-one (0.242 g, 2.39 mmol, 1.20 eq) and cesium carbonate (0.974 g, 2.99 mmol, 1.50 eq) in dimethyl formamide (10 mL) was stirred at 50° C. for 12 h. The mixture was cooled to 25° C. The reaction mixture was diluted with water (15 mL) and extracted with ethyl acetate (2×20 mL). The combined organic layers were washed with brine (20 mL), dried over sodium sulfate, filtered and concentrated under reduced pressure. The crude product was purified by flash silica gel chromatography (ISCO®; 20 g SepaFlash® Silica Flash Column, eluent of 40-60% ethyl acetate/petroleum ether gradient at 100 mL/min) to give 3-((5-bromopyridin-2-yl)methyl)-1,3-oxazinan-2-one (0.140 g, 0.516 mmol, 30% yield) as a brown solid.

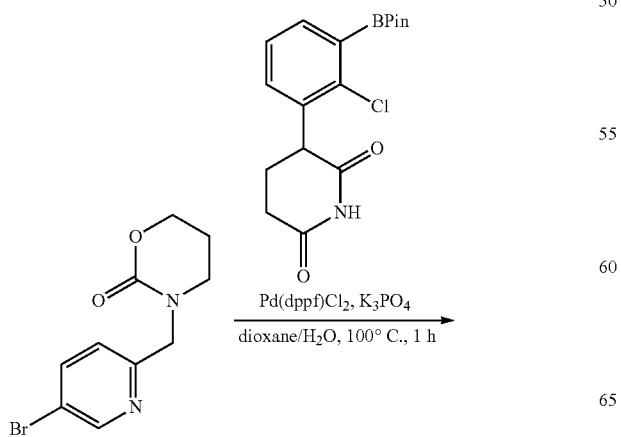

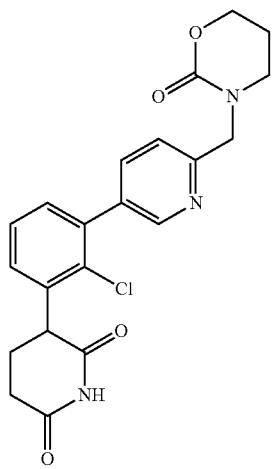

Compound 431

3-(2-chloro-3-(6-((2-oxo-1,3-oxazinan-3-yl)methyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 3-((5-bromopyridin-2-yl)methyl)-1,3-oxazinan-2-one according to General Scheme 1.

$^1$H NMR (400 MHz, DMSO-$d_6$) δ=10.94 (s, 1H), 8.56 (d, J=2.0 Hz, 1H), 7.86 (dd, J=8.0, 2.4 Hz, 1H), 7.48-7.42 (m, 2H), 7.42-7.34 (m, 2H), 4.59 (s, 2H), 4.36 (dd, J=12.4, 4.8 Hz, 1H), 4.31-4.21 (m, 2H), 3.43 (t, J=6.0 Hz, 2H), 2.87-2.74 (m, 1H), 2.59-2.55 (m, 1H), 2.36-2.32 (m, 1H), 2.08-1.98 (m, 3H); MS (ESI) m/z 414.2 [M+H]$^+$

Example 184. Synthesis of 3-(2-chloro-3-(6-((3-methyl-2-oxotetrahydropyrimidin-1(2H)-yl)methyl)pyridin-3-yl)phenyl)piperidine-2,6-dione (Compound 432)

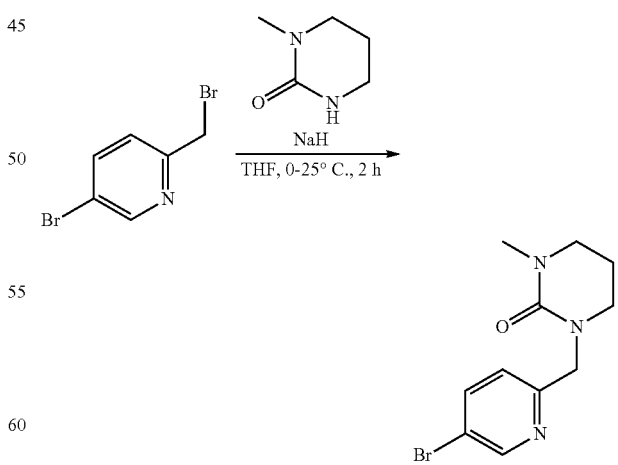

1-((5-bromopyridin-2-yl)methyl)-3-methyltetrahydropyrimidin-2(1H)-one was prepared from 1-methylhexahydropyrimidin-2-one and 5-bromo-2-(bromomethyl)pyridine analogously to Example 176.

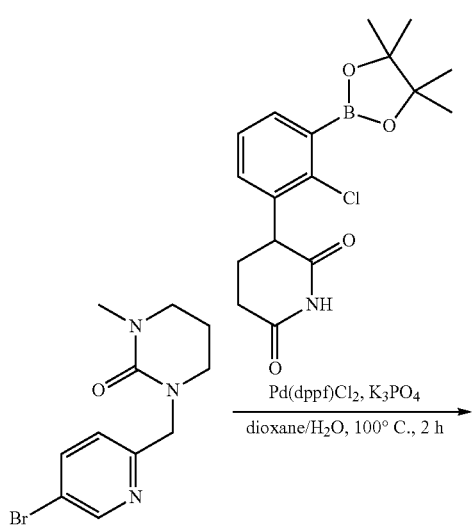

Compound 432

3-(2-chloro-3-(6-((3-methyl-2-oxotetrahydropyrimidin-1 (2H)-yl)methyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-[(5-bromo-2-pyridyl)methyl]-3-methyl-hexahydropyrimidin-2-one according to General Scheme 1.

$^1$H NMR (400 MHz, DMSO-$d_6$) δ=10.93 (s, 1H), 8.53 (d, J=2.0 Hz, 1H), 7.83 (dd, J=8.0, 2.4 Hz, 1H), 7.46-7.39 (m, 2H), 7.39-7.34 (m, 1H), 7.31 (d, J=8.0 Hz, 1H), 4.56 (s, 2H), 4.36 (dd, J=12.4, 5.2 Hz, 1H), 3.38-3.33 (m, 2H), 3.30-3.26 (m, 2H), 2.83 (s, 3H), 2.81-2.74 (m, 1H), 2.59-2.55 (m, 1H), 2.37-2.32 (m, 1H), 2.09-2.01 (m, 1H), 1.99-1.89 (m, 2H); MS (ESI) m/z 427.2 [M+H]$^+$

Example 185. Synthesis of 3-(2-chloro-3-(6-((2-oxopiperidin-1-yl)methyl)pyridin-3-yl)phenyl)piperidine-2,6-dione (Compound 433)

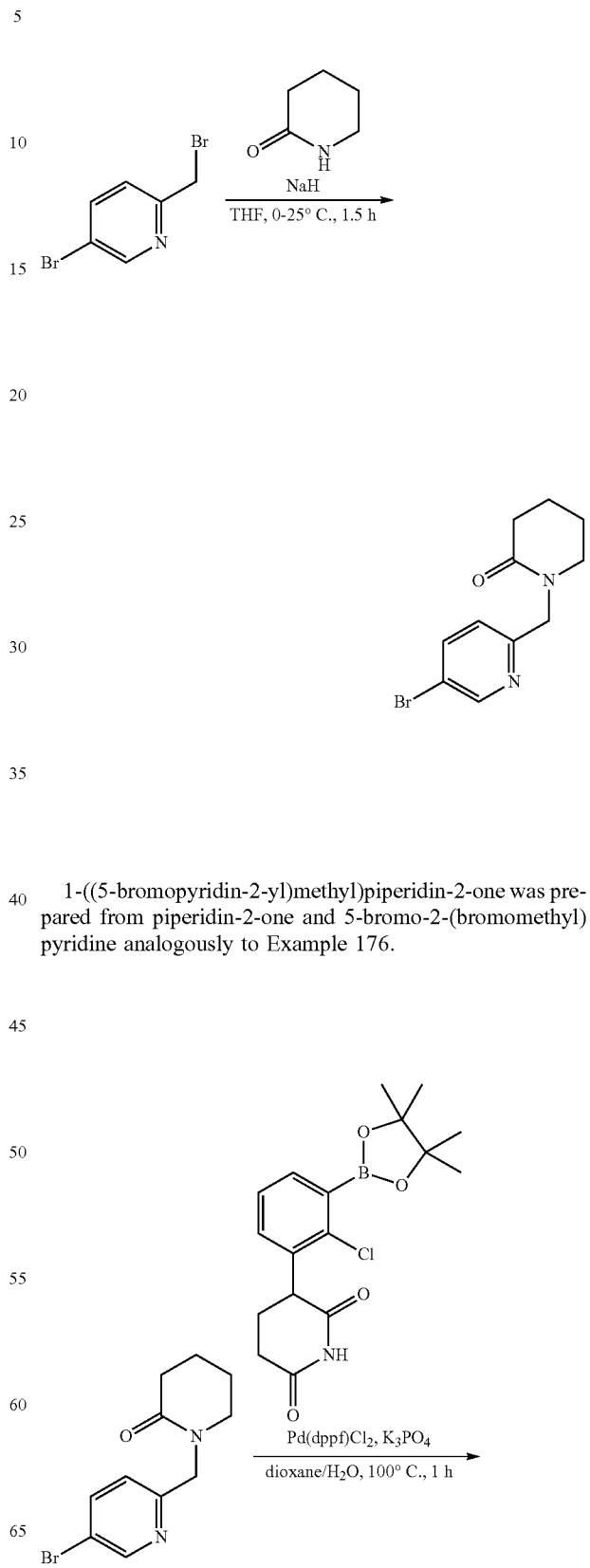

1-((5-bromopyridin-2-yl)methyl)piperidin-2-one was prepared from piperidin-2-one and 5-bromo-2-(bromomethyl) pyridine analogously to Example 176.

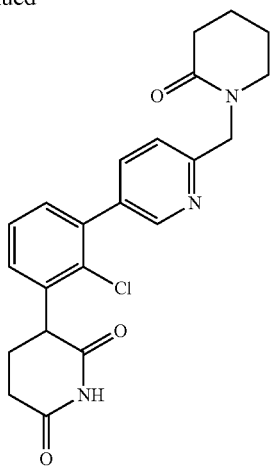

Compound 433

3-(2-chloro-3-(6-((2-oxopiperidin-1-yl)methyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-((5-bromopyridin-2-yl)methyl)piperidin-2-one according to General Scheme 1.

$^1$H NMR (400 MHz, DMSO-d$_6$) δ=10.94 (s, 1H), 8.54 (d, J=2.0 Hz, 1H), 7.84 (dd, J=8.0, 2.4 Hz, 1H), 7.47-7.40 (m, 2H), 7.39-7.35 (m, 1H), 7.31 (d, J=8.0 Hz, 1H), 4.63 (s, 2H), 4.36 (dd, J=12.4, 5.2 Hz, 1H), 3.37 (d, J=5.6 Hz, 2H), 2.86-2.73 (m, 1H), 2.59-2.53 (m, 1H), 2.39-2.28 (m, 3H), 2.10-1.99 (m, 1H), 1.84-1.73 (m, 4H).

$^1$H NMR (400 MHz, MeOD) δ=8.53 (s, 1H), 7.94-7.81 (m, 1H), 7.48-7.37 (m, 3H), 7.37-7.32 (m, 1H), 4.75 (s, 2H), 4.40 (dd, J=12.0, 5.2 Hz, 1H), 3.46 (s, 2H), 2.87-2.76 (m, 1H), 2.75-2.66 (m, 1H), 2.51-2.36 (m, 3H), 2.25-2.18 (m, 1H), 1.89 (s, 4H); MS (ESI) m/z 412.2 [M+H]$^+$

Example 186. Synthesis of 3-(2-chloro-3-(6-((2-oxopyrimidin-1(2H)-yl)methyl)pyridin-3-yl)phenyl)piperidine-2,6-dione (Compound 434)

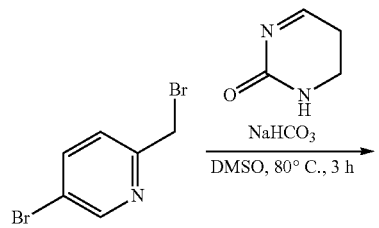

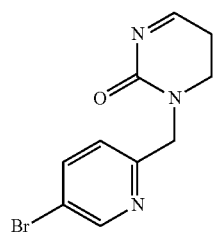

To a solution of pyrimidin-2(1H)-one (0.0460 g, 0.479 mmol, 1.20 eq) and 5-bromo-2-(bromomethyl)pyridine (0.100 g, 0.399 mmol, 1.00 eq) in dimethyl sulfoxide (1 mL) was added sodium bicarbonate (0.0670 g, 0.798 mmol, 2.00 eq). The mixture was stirred at 80° C. for 3 h. After being cooled to room temperature, ethyl acetate (40 mL) and water (40 mL) were added and layers were separated. The aqueous phase was extracted with ethyl acetate (3×40 mL). Combined extracts were washed with brine (50 mL), dried over sodium sulfate, filtered, and concentrated under vacuum to give a residue, which was purified by flash silica gel chromatography (ISCO®; 20 g SepaFlash® Silica Flash Column, Eluent of 0~100% ethyl acetate/petroleum ether gradient @ 40 mL/min) to give 1-((5-bromopyridin-2-yl)methyl)pyrimidin-2(1H)-one (70.0 mg, 0.263 mmol, 66% yield) as a yellow solid.

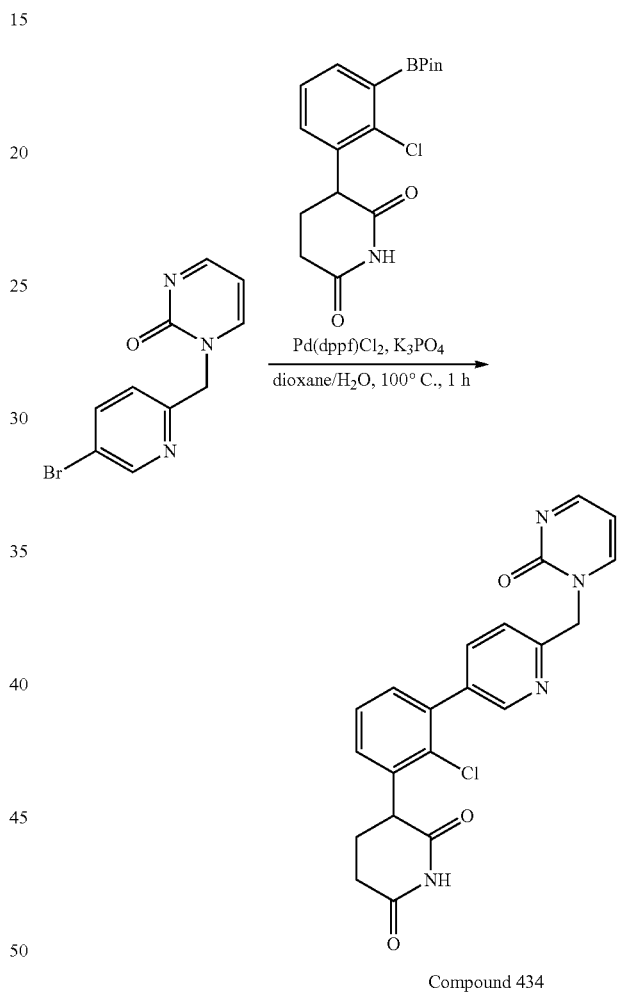

Compound 434

3-(2-chloro-3-(6-((2-oxopyrimidin-1(2H)-yl)methyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-((5-bromopyridin-2-yl)methyl)pyrimidin-2(1H)-one according to General Scheme 1.

$^1$H NMR (400 MHz, DMSO-d$_6$) δ=10.94 (s, 1H), 8.61 (dd, J=3.6, 2.8 Hz, 1H), 8.53 (d, J=2.0 Hz, 1H), 8.38 (dd, J=6.4, 2.8 Hz, 1H), 7.93-7.84 (m, 1H), 7.47-7.40 (m, 3H), 7.38 (s, 1H), 6.52 (dd, J=6.4, 4.4 Hz, 1H), 5.23 (s, 2H), 4.41-4.30 (m, 1H), 2.83-2.75 (m, 1H), 2.59-2.55 (m, 1H), 2.35-2.32 (m, 1H), 2.08-2.02 (m, 1H); MS (ESI) m/z 409.1 [M+H]$^+$

Example 187. Synthesis of 3-(2-chloro-3-(6-(3-methyl-2-oxotetrahydropyrimidin-1(2H)-yl)pyridin-3-yl)phenyl)piperidine-2,6-dione (Compound 435)

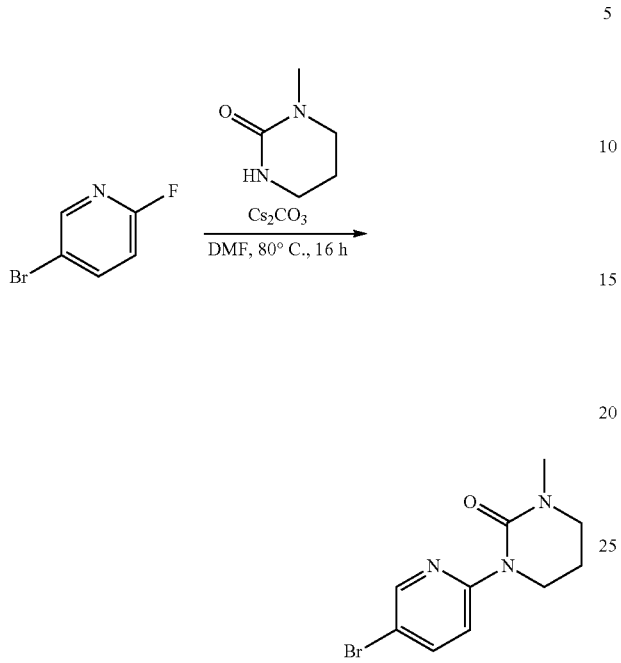

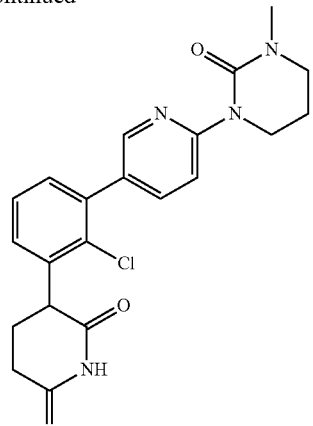

Compound 435

To a solution of 5-bromo-2-fluoropyridine (1.00 g, 5.68 mmol, 1.00 eq) and 1-methyltetrahydropyrimidin-2(1H)-one (0.778 g, 6.82 mmol, 1.20 eq) in dimethyl formamide (7 mL) was added cesium carbonate (3.70 g, 11.4 mmol, 2.00 eq). The mixture was stirred at 80° C. for 16 h. After being cooled to room temperature, ethyl acetate (40 mL) and water (40 mL) were added and layers were separated. The aqueous phase was extracted with ethyl acetate (3×40 mL), washed with brine (50 mL), dried over sodium sulfate, filtered and concentrated under vacuum to give a residue, which was purified by flash silica gel chromatography (ISCO®; 20 g SepaFlash® Silica Flash Column, Eluent of 0~100% ethyl acetate/petroleum ether gradient @ 40 mL/min) to give 1-(5-bromopyridin-2-yl)-3-methyltetrahydropyrimidin-2(1H)-one (50.0 mg, 0.185 mmol, 3% yield) as a yellow solid.

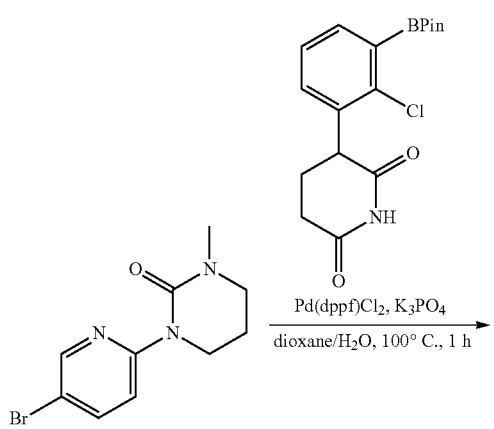

3-(2-chloro-3-(6-(3-methyl-2-oxotetrahydropyrimidin-1(2H)-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(5-bromopyridin-2-yl)-3-methyltetrahydropyrimidin-2(1H)-one according to General Scheme 1.

$^1$H NMR (400 MHz, DMSO-d$_6$) δ=10.93 (s, 1H), 8.34 (d, J=2.4 Hz, 1H), 7.86 (d, J=8.8 Hz, 1H), 7.74 (dd, J=8.8, 2.4 Hz, 1H), 7.46-7.33 (m, 3H), 4.35 (dd, J=12.4, 5.2 Hz, 1H), 4.00-3.89 (m, 2H), 3.38-3.35 (m, 2H), 2.92 (s, 3H), 2.84-2.75 (m, 1H), 2.59-2.55 (m, 1H), 2.36-2.31 (m, 1H), 2.07-1.99 (m, 3H).

$^1$H NMR (400 MHz, MeOD) δ=8.36 (d, J=2.0 Hz, 1H), 7.82-7.77 (m, 1H), 7.74-7.68 (m, 1H), 7.47-7.29 (m, 3H), 4.40 (dd, J=12.0, 5.2 Hz, 1H), 4.04-3.91 (m, 2H), 3.47 (t, J=6.4 Hz, 2H), 3.03 (s, 3H), 2.87-2.77 (m, 1H), 2.75-2.65 (m, 1H), 2.50-2.35 (m, 1H), 2.25-2.10 (m, 3H); MS (ESI) m/z 413.1 [M+H]$^+$

Example 188. Synthesis of 3-(2-chloro-3'-fluoro-4'-(3-methyl-2-oxotetrahydropyrimidin-1(2H)-yl)-[1,1'-biphenyl]-3-yl)piperidine-2,6-dione (Compound 436)

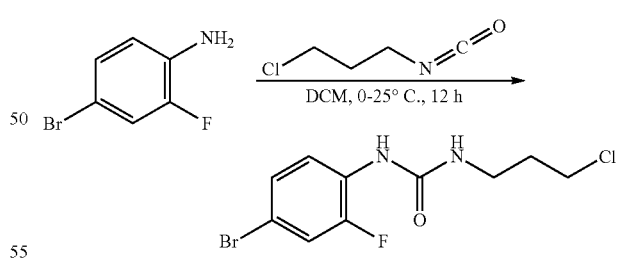

To a solution of 4-bromo-2-fluoroaniline (586 mg, 3.08 mmol, 1.00 eq) in dichloromethane (10 mL) was added 1-chloro-3-isocyanatopropane (420 mg, 3.52 mmol, 1.14 eq) at 0° C. under nitrogen atmosphere. Then the mixture was stirred at 25° C. for 12 h. The mixture was concentrated under reduced pressure to give a residue, which was purified by flash silica gel chromatography (ISCO®; 20 g SepaFlash® Silica Flash Column, eluent of 11-20% ethyl acetate/petroleum ether gradient at 50 mL/min) to give 1-(4-bromo-2-fluorophenyl)-3-(3-chloropropyl)urea (1.20 g, 2.71 mmol, 88% yield) as a white solid.

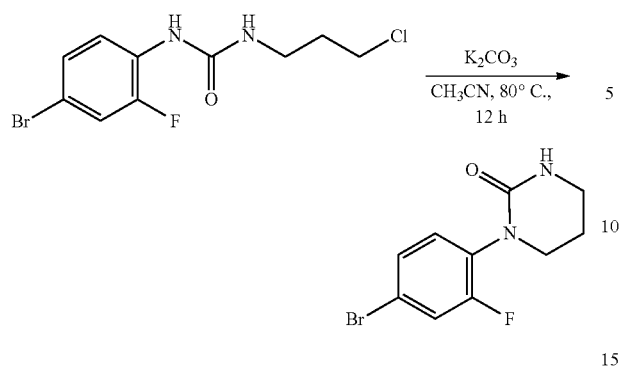

To a solution of 1-(4-bromo-2-fluorophenyl)-3-(3-chloropropyl)urea (600 mg, 1.36 mmol, 1.00 eq) in acetonitrile (6 mL) was added potassium carbonate (318 mg, 2.30 mmol, 1.70 eq) at 25° C. The mixture was stirred at 80° C. for 12 h. After being cooled to room temperature, the mixture was concentrated under reduced pressure to give a residue, which was purified by flash silica gel chromatography (ISCO®; 12 g SepaFlash® Silica Flash Column, eluent of 80-90% ethyl acetate/petroleum ether gradient at 50 mL/min) to afford 1-(4-bromo-2-fluorophenyl)tetrahydropyrimidin-2(1H)-one (376 mg, 1.24 mmol, 91% yield) as a white solid.

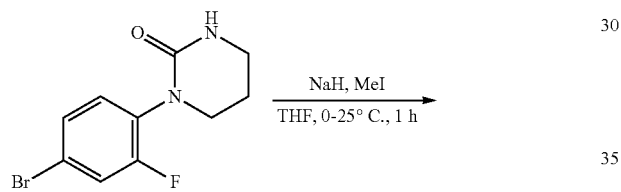

To a solution of 1-(4-bromo-2-fluorophenyl)tetrahydropyrimidin-2(1H)-one (376 mg, 1.24 mmol, 1.00 eq) in tetrahydrofuran (4 mL) was added sodium hydride (59.0 mg, 1.48 mmol, 1.19 eq) at 0° C. for 0.5 h under nitrogen atmosphere. Then methyl iodide (365 mg, 2.57 mmol, 2.08 eq) was added into the mixture at 0° C. The mixture was stirred at 25° C. for 0.5 h. Then the reaction mixture was poured into ice-water (50 mL), extracted with ethyl acetate (3×50 mL). The combined organic layers were washed with brine (50 mL), dried over sodium sulfate, filtered and concentrated to give a residue, which was purified by flash silica gel chromatography (ISCO®; 20 g SepaFlash® Silica Flash Column, eluent of 80-90% ethyl acetate/petroleum ether gradient at 50 mL/min) to give 1-(4-bromo-2-fluorophenyl)-3-methyltetrahydropyrimidin-2(1H)-one (318 mg, 986 μmol, 80% yield) as an off-white solid.

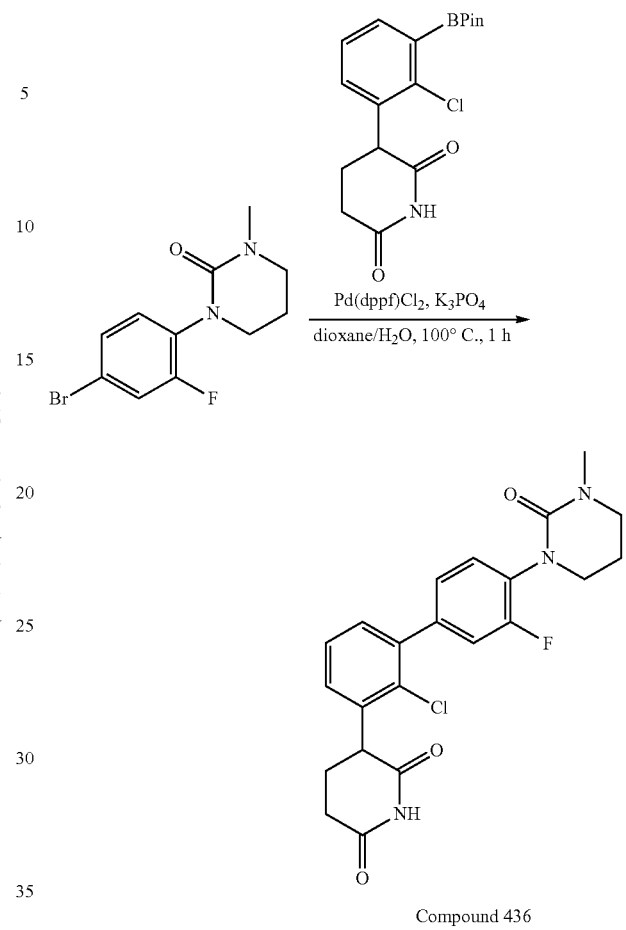

Compound 436

3-(2-chloro-3'-fluoro-4'-(3-methyl-2-oxotetrahydropyrimidin-1(2H)-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromo-2-fluorophenyl)-3-methyltetrahydropyrimidin-2(1H)-one according to General Scheme 1.

$^1$H NMR (400 MHz, DMSO-d$_6$) δ=10.93 (s, 1H), 7.44-7.32 (m, 4H), 7.31-7.19 (m, 2H), 4.35 (dd, J=12.4, 5.2 Hz, 1H), 3.60 (t, J=5.6 Hz, 2H), 3.37 (t, J=6.0 Hz, 2H), 2.86 (s, 3H), 2.84-2.73 (m, 1H), 2.59-2.55 (m, 1H), 2.35-2.31 (m, 1H), 2.11-1.99 (m, 3H); MS (ESI) m/z 430.1 [M+H]$^+$

Example 189. Synthesis of 3-(2-chloro-4'-((4-methylpyrimidin-2-yl)methyl)-[1,1'-biphenyl]-3-yl)piperidine-2,6-dione (Compound 437)

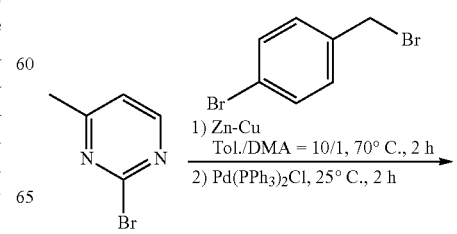

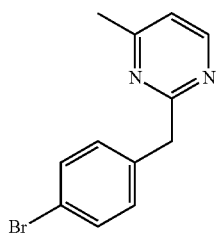

2-(4-bromobenzyl)-4-methylpyrimidine was prepared from 1-bromo-4-(bromomethyl)benzene and 2-bromo-4-methyl-pyrimidine according to General Scheme 12.

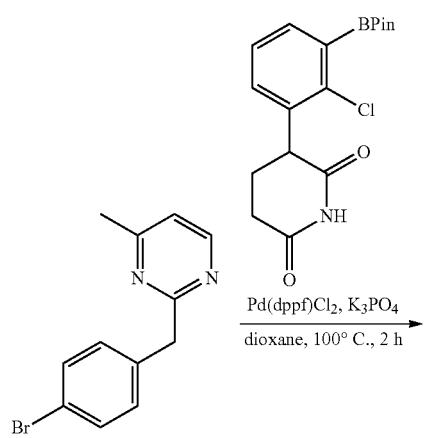

Compound 437

3-(2-chloro-4'-((4-methylpyrimidin-2-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 2-(4-bromobenzyl)-4-methylpyrimidine according to General Scheme 1.

$^1$H NMR (400 MHz, DMSO-$d_6$) δ=10.92 (s, 1H), 8.61 (d, J=5.2 Hz, 1H), 7.48-7.24 (m, 8H), 4.34 (dd, J=12.4, 5.2 Hz, 1H), 4.21 (s, 2H), 2.84-2.74 (m, 1H), 2.62-2.51 (m, 1H), 2.46 (s, 3H), 2.38-2.27 (m, 1H), 2.10-2.00 (m, 1H); MS (ESI) m/z 406.2 [M+H]$^+$

Example 190. Synthesis of 3-(2-chloro-4'-(pyrrolidin-1-ylsulfonyl)-[1,1'-biphenyl]-3-yl) piperidine-2, 6-dione (Compound 438)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(pyrrolidin-1-ylsulfonyl)-[1,1'-biphenyl]-3-yl) piperidine-2,6-dione was prepared from 3-(2-chloro-3-(4,4,5,5-tetramethyl-1,3,2-dioxaborolan-2-yl)phenyl)piperidine-2,6-dione and 1-((4-bromophenyl) sulfonyl) pyrrolidine according to General Scheme 1.

MS (ESI) m/z 433.1 [M+H]$^+$

Example 191. Synthesis of 3-(2-chloro-4'-(2-methyl-3-oxoisoindolin-4-yl)-[1,1'-biphenyl]-3-yl) piperidine-2,6-dione (Compound 439)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(2-methyl-3-oxoisoindolin-4-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 4-(2-methyl-3-oxoisoindolin-4-yl)phenyl trifluoromethanesulfonate according to General Scheme 1.

MS (ESI) m/z 445.2 [M+H]$^+$

Example 192. Synthesis of 3-(2-chloro-4'-((3-methyloxetan-3-yl) methyl)-[1,1'-biphenyl]-3-yl)piperidine-2,6-dione (Compound 440)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-((3-methyloxetan-3-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 3-[(4-bromophenyl)methyl]-3-methyl-oxetane according to General Scheme 1.

MS (ESI) m/z 384.2 [M+H]$^+$

Example 193. Synthesis of 3-(2-chloro-4'-((R)-3-methyl-5-oxomorpholino)-[1,1'-biphenyl]-3-yl)piperidine-2,6-dione (Compound 441)

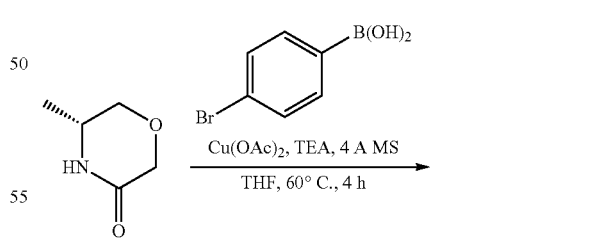

To a solution of (R)-5-methylmorpholin-3-one (565 mg, 4.91 mmol, 1.00 eq) and (4-bromophenyl)boronic acid (2.46 g, 12.3 mmol, 2.50 eq) in tetrahydrofuran (6 mL) was added cupric acetate (1.34 g, 7.36 mmol, 1.50 eq), triethylamine (1.49 g, 14.7 mmol, 2.05 mL, 3.00 eq) and 4 A molecular sieve (600 mg, 4.91 mmol, 1.00 eq), then the mixture was stirred at 60° C. for 4 h in air. The reaction mixture was filtered to give a filtrate and the filtrate was purified by reversed-phase column (0.10% formic acid condition) and concentrated under reduced pressure to afford (R)-4-(4-bromophenyl)-5-methylmorpholin-3-one (120 mg, 444 µmol, 9% yield) as yellow oil.

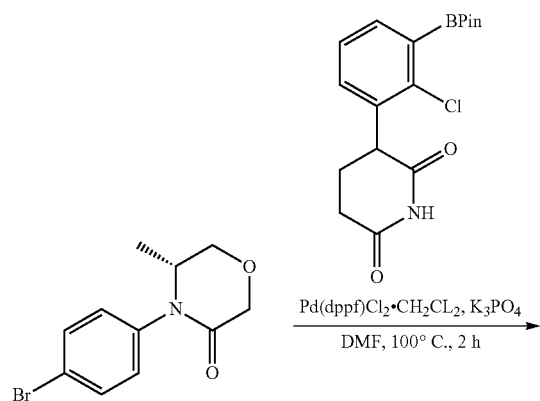

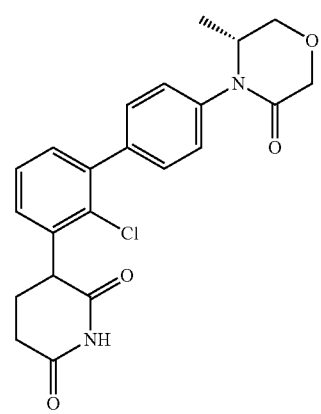

Compound 441

3-(2-chloro-4'-((R)-3-methyl-5-oxomorpholino)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and (R)-4-(4-bromophenyl)-5-methylmorpholin-3-one according to General Scheme 1.

$^1$H NMR (400 MHz, DMSO-d$_6$) δ=10.94 (s, 1H), 7.52-7.40 (m, 3H), 7.40-7.34 (m, 4H), 4.41-4.30 (m, 1H), 4.29-4.14 (m, 2H), 4.12-4.03 (m, 2H), 3.81-3.74 (m, 1H), 2.86-2.74 (m, 1H), 2.56-2.51 (m, 1H), 2.41-2.27 (m, 1H), 2.07-1.99 (m, 1H), 1.09 (d, J=6.4 Hz, 3H); MS (ESI) m/z 413.2 [M+H]$^+$

Example 194. Synthesis of 3-(2-chloro-4'-(oxazol-4-ylmethyl)-[1,1'-biphenyl]-3-yl)piperidine-2,6-dione (Compound 442)

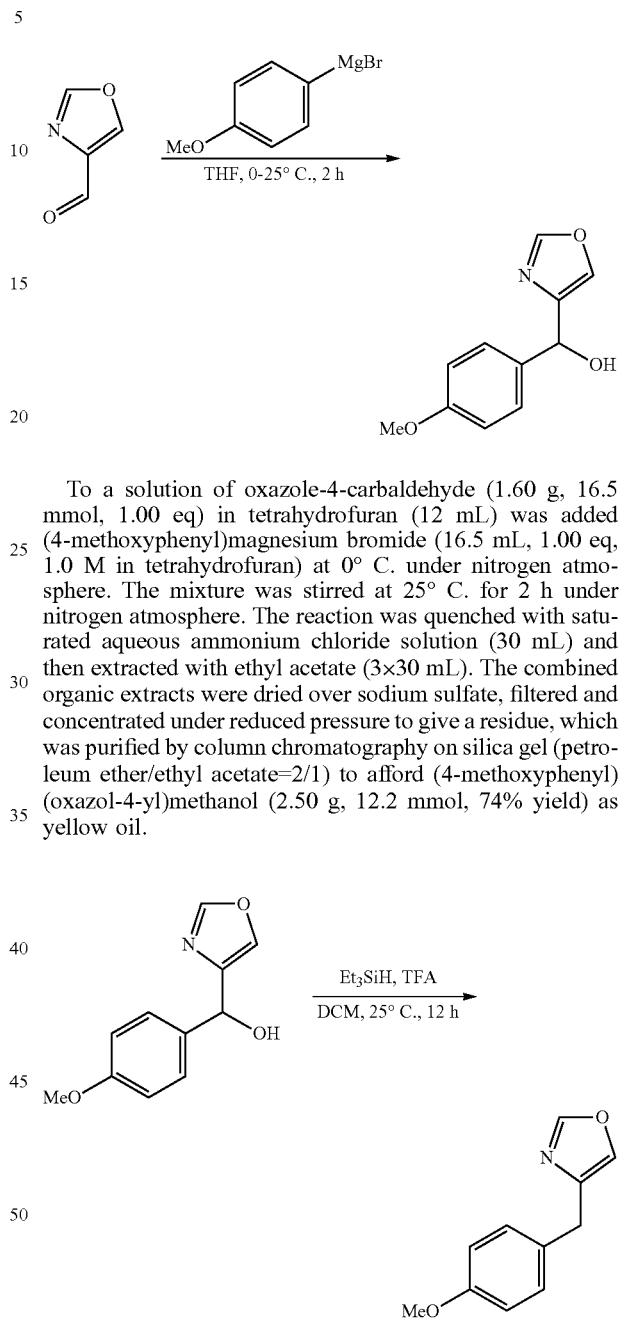

To a solution of oxazole-4-carbaldehyde (1.60 g, 16.5 mmol, 1.00 eq) in tetrahydrofuran (12 mL) was added (4-methoxyphenyl)magnesium bromide (16.5 mL, 1.00 eq, 1.0 M in tetrahydrofuran) at 0° C. under nitrogen atmosphere. The mixture was stirred at 25° C. for 2 h under nitrogen atmosphere. The reaction was quenched with saturated aqueous ammonium chloride solution (30 mL) and then extracted with ethyl acetate (3×30 mL). The combined organic extracts were dried over sodium sulfate, filtered and concentrated under reduced pressure to give a residue, which was purified by column chromatography on silica gel (petroleum ether/ethyl acetate=2/1) to afford (4-methoxyphenyl)(oxazol-4-yl)methanol (2.50 g, 12.2 mmol, 74% yield) as yellow oil.

To a solution of (4-methoxyphenyl)(oxazol-4-yl)methanol (2.50 g, 12.2 mmol, 1.00 eq) in dichloromethane (10 mL) was added triethylsilane (10 mL, 61.0 mmol, 5.00 eq) and trifluoroacetic acid (4.50 mL, 61.0 mmol, 5.00 eq). The mixture was stirred at 25° C. for 12 h. The reaction mixture was diluted with water (20 mL) and ethyl acetate (20 mL) and then extracted with ethyl acetate (3×20 mL). The combined organic extracts were washed with brine (20 mL), dried over sodium sulfate, filtered and concentrated under reduced pressure to give 4-(4-methoxybenzyl)oxazole (2.03 g, crude) as brown oil. The crude product was used for next step without further purification.

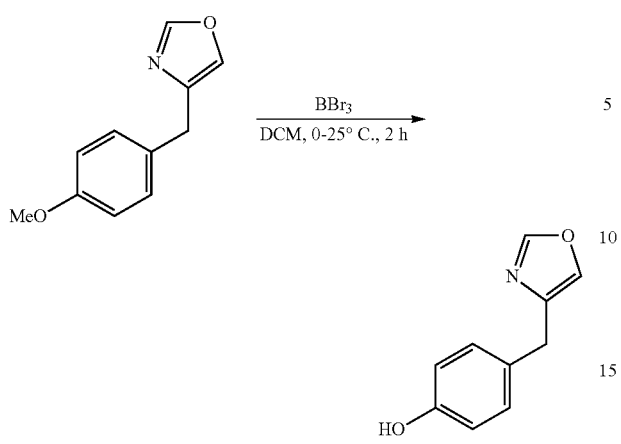

To a solution of 4-(4-methoxybenzyl)oxazole (2.10 g, crude) in dichloromethane (10 mL) was added tribromoborane (2.10 mL, 22.2 mmol, 2.00 eq) at 0° C. The mixture was stirred at 25° C. for 2 h under nitrogen atmosphere. The reaction was quenched with water (50 mL) while stirring at room temperature. The pH was adjusted to 7 with saturated sodium bicarbonate solution and then extracted with ethyl acetate (3×30 mL). The combined organic layers were washed with brine (30 mL), dried over sodium sulfate, filtered and concentrated under reduced pressure to give a residue. The residue was purified by column chromatography on silica gel (petroleum ether/ethyl acetate=0/1) to give 4-(oxazol-4-ylmethyl)phenol (0.970 g, 5.54 mmol, 50% yield) as a brown solid.

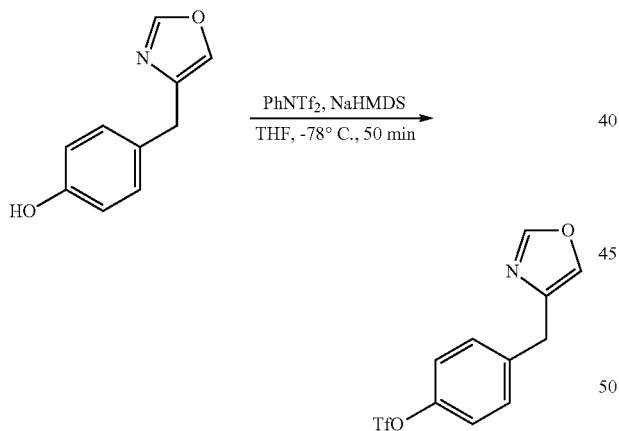

To a solution of 4-(oxazol-4-ylmethyl)phenol (0.300 g, 1.71 mmol, 1.00 eq) in tetrahydrofuran (3 mL) was added sodium hexamethyldisilazane (2.60 mL, 1.50 eq, 1.0 M in tetrahydrofuran) dropwise at −78° C. The mixture was stirred at −78° C. for 0.5 h and then 1,1,1-trifluoro-N-phenyl-N-((trifluoromethyl)sulfonyl)methanesulfonamide (0.765 g, 2.14 mmol, 1.25 eq) was added. The resulting mixture was stirred at −78° C. for 20 min. The reaction was allowed to warm to room temperature and then quenched with saturated ammonium chloride solution (10 mL). The mixture was extracted with ethyl acetate (3×20 mL). The combined organics were dried over sodium sulfate, filtered and concentrated under reduced pressure to give a residue, which was purified by column chromatography on silica gel (petroleum ether/ethyl acetate=2/1) to give 4-(oxazol-4-ylmethyl)phenyl trifluoromethanesulfonate (0.200 g, 0.651 mmol, 38% yield) as yellow oil.

3-(2-chloro-3-(4,4,5,5-tetramethyl-1,3,2-dioxaborolan-2-yl)phenyl)piperidine-2,6-dione (intermediate A) was synthesized as described above. 3-[2-chloro-3-[4-(oxazol-4-ylmethyl)phenyl]phenyl]piperidine-2,6-dione was prepared from 3-(2-chloro-3-(4,4,5,5-tetramethyl-1,3,2-dioxaborolan-2-yl)phenyl)piperidine-2,6-dione and 4-(oxazol-4-ylmethyl)phenyl trifluoromethanesulfonate according to General Scheme 1.

MS (ESI) m/z 381.0 [M+H]+

Example 195. Synthesis of 3-(2-chloro-4'-(2-oxo-6-(trifluoromethyl) pyridin-1(2H)-yl)-[1,1'-biphenyl]-3-yl)piperidine-2,6-dione (Compound 443)

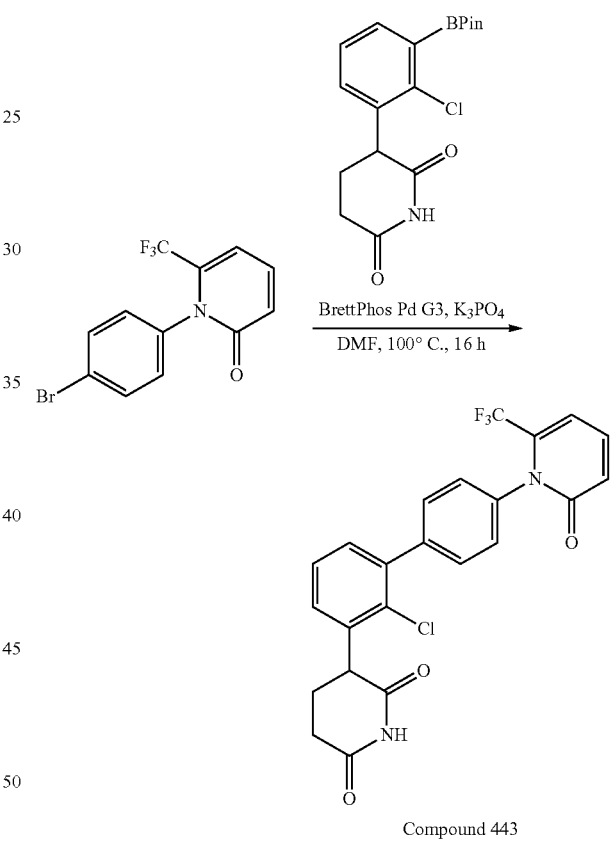

Compound 443

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(6-fluoro-2-oxopyridin-1(2H)-yl)-[1,1'-biphenyl]-3-yl)piperidine-2,6-dione was prepared from 1-(4-bromophenyl)-6-(trifluoromethyl) pyridin-2(1H)-one and 3-[2-chloro-3-(4,4,5,5-tetramethyl-1,3,2-dioxaborolan-2-yl)phenyl]piperidine-2,6-dione according to General Scheme 1.

1H NMR (400 MHz, DMSO-d6) δ=10.93 (s, 1H), 7.70-7.65 (m, 1H), 7.58-7.52 (m, 2H), 7.46-7.35 (m, 5H), 6.98 (d, J=6.8 Hz, 1H), 6.84 (d, J=9.6 Hz, 1H), 4.37 (dd, J=11.6, 5.2 Hz, 1H), 2.83-2.76 (m, 1H), 2.59-2.55 (m, 1H), 2.42-2.29 (m, 1H), 2.11-2.02 (m, 1H); MS (ESI) m/z 461.1 [M+H]+

Example 196. Synthesis of 3-(2-chloro-4'-(3-(2,2-difluoroethyl)-2-oxopyridin-1(2H)-yl)-[1,1'-biphenyl]-3-yl)piperidine-2,6-dione (Compound 444)

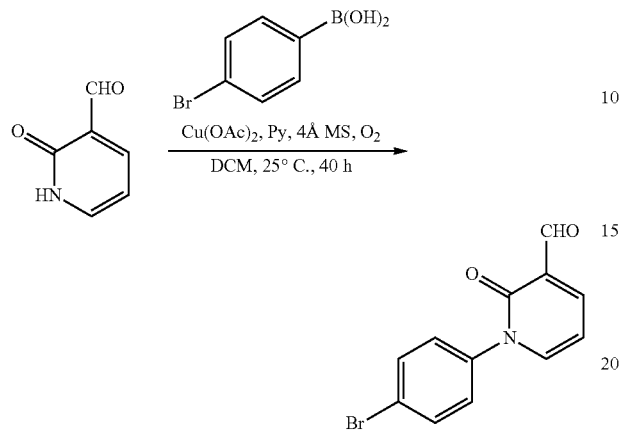

A mixture of 2-oxo-1,2-dihydropyridine-3-carbaldehyde (5.00 g, 40.6 mmol, 1.00 eq), (4-bromophenyl)boronic acid (8.97 g, 44.7 mmol, 1.10 eq), cupric acetate (738 mg, 4.06 mmol, 0.100 eq), pyridine (6.43 g, 81.2 mmol, 6.56 mL, 2.00 eq) and 4 Å molecular sieve (1.00 g) in dichloromethane (100 mL) was stirred at 25° C. for 40 h under oxygen atmosphere. The reaction mixture was filtered and the filtrate was concentrated under reduced pressure to give a residue. Then hydrochloric acid (1 M, 50 mL) was added to the residue and it was extracted with ethyl acetate (5×100 mL). The combined organic layers were dried over sodium sulfate, filtered and concentrated under reduced pressure to give a residue, which was purified by reversed phase column (C18, 80 g; condition: water/acetonitrile=100:0 to 0:100, 0.1% formic acid) and lyophilized to afford 1-(4-bromophenyl)-2-oxo-1,2-dihydropyridine-3-carbaldehyde (2.40 g, 8.20 mmol, 20% yield) as a yellow solid.

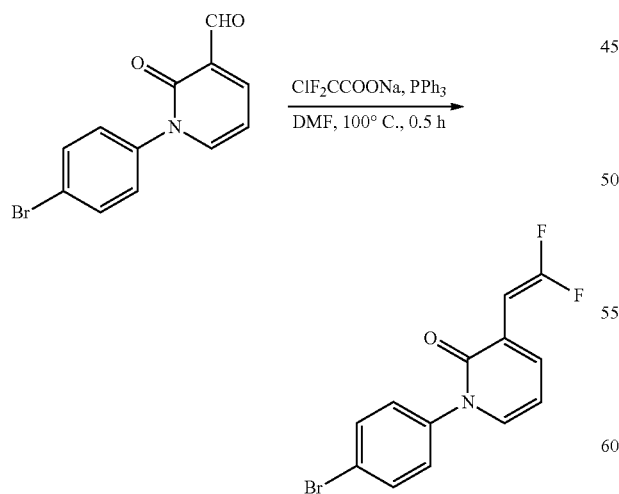

To a solution of 1-(4-bromophenyl)-2-oxo-1,2-dihydropyridine-3-carbaldehyde (100 mg, 360 mol, 1.00 eq) in dimethyl formamide (1.5 mL) was added triphenylphosphine (188 mg, 719 mol, 2.00 eq) and sodium chlorodifluoroacetate (110 mg, 719 μmol, 2.00 eq). The reaction mixture was stirred at 100° C. for 0.5 h. After being cooled to room temperature, the mixture was extracted with ethyl acetate (3×15 mL), wash with brine (20 mL), dried over sodium sulfate, filtered and concentrated under reduced pressure to give the residue, which was purified by column chromatography (SiO$_2$, Petroleum ether/Ethyl acetate=100/1 to 0/1) to afford 1-(4-bromophenyl)-3-(2,2-difluorovinyl)pyridin-2(1H)-one (80.0 mg, 256 μmol, 71% yield) as a white solid.

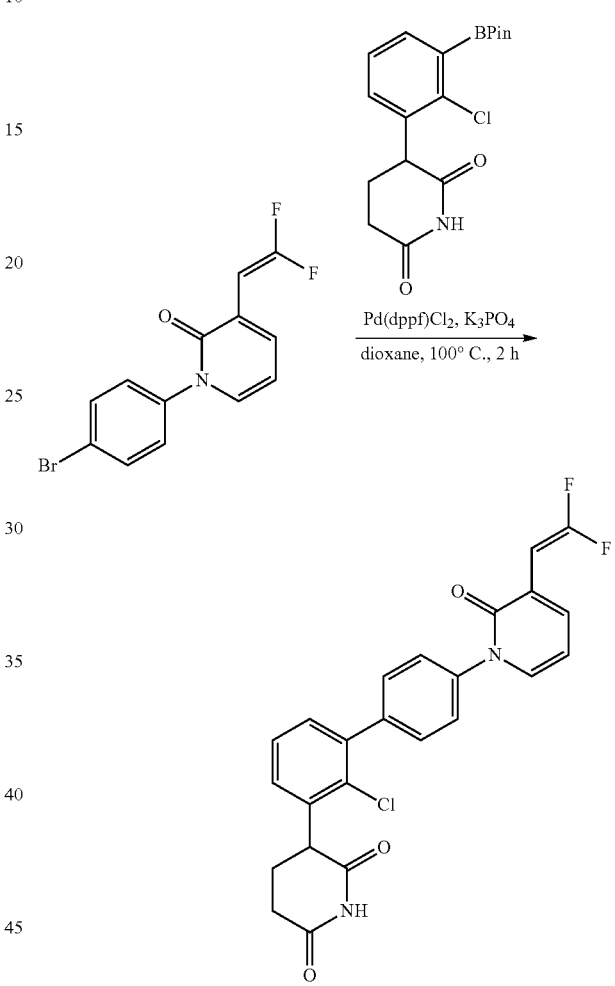

3-(2-chloro-3-(4,4,5,5-tetramethyl-1,3,2-dioxaborolan-2-yl)phenyl)piperidine-2,6-dione (intermediate A) was synthesized as described above. To a solution of 1-(4-bromophenyl)-3-(2,2-difluorovinyl)pyridin-2(1H)-one (50.0 mg, 160 μmol, 1.00 eq) in dioxane (1.5 mL) was added 3-(2-chloro-3-(4,4,5,5-tetramethyl-1,3,2-dioxaborolan-2-yl)phenyl)piperidine-2,6-dione (98.8 mg, 240 μmol, 1.50 eq), potassium phosphate (102 mg, 481 μmol, 3.00 eq) and 1,1'-bis(diphenylphosphino)ferrocene]dichloropalladium(II) (11.7 mg, 16.0 μmol, 0.100 eq) under nitrogen atmosphere. The reaction mixture was stirred at 100° C. for 2 h. After being cooled to room temperature, the reaction mixture was filtered through a plug of Celite, and the filtrate was concentrated under reduced pressure to give a residue, which was purified by reversed-phase column (C18, 20 g; condition: water/acetonitrile=100:0 to 0:100, 0.1% formic acid) and lyophilized to afford 3-(2-chloro-4'-(3-(2,2-difluorovinyl)-2-oxopyridin-1(2H)-yl)-[1,1'-biphenyl]-3-yl)piperidine-2,6-dione (35.0 mg, 69.3 μmol, 43% yield) as a white solid.

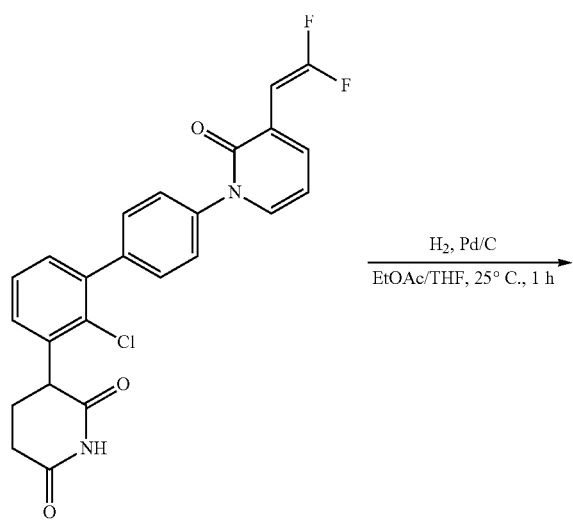

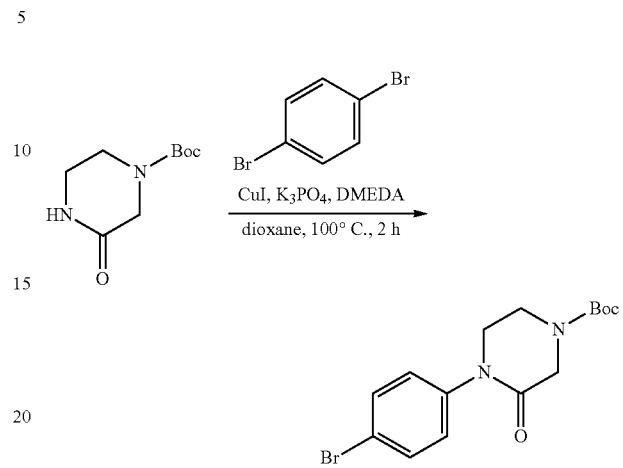

Example 197. Synthesis of 3-(2-chloro-4'-(2-oxo-4-(2,2,2-trifluoroethyl)piperazin-1-yl)-[1,1'-biphenyl]-3-yl)piperidine-2,6-dione (Compound 445)

tert-butyl 4-(4-bromophenyl)-3-oxopiperazine-1-carboxylate was prepared from tert-butyl 3-oxopiperazine-1-carboxylate and 1,4-dibromobenzene according to General Scheme 7.

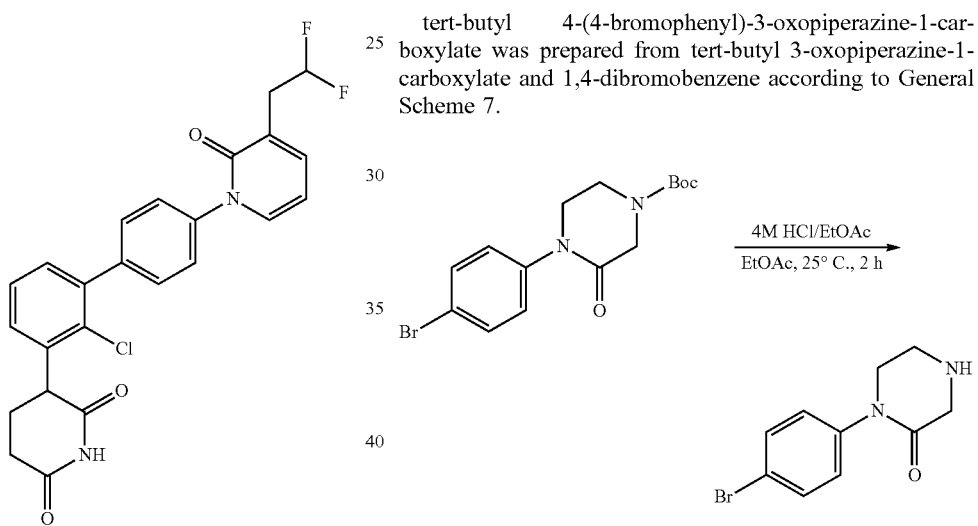

Compound 444

To a solution of 3-(2-chloro-4'-(3-(2,2-difluorovinyl)-2-oxopyridin-1(2H)-yl)-[1,1'-biphenyl]-3-yl)piperidine-2,6-dione (30.0 mg, 66.0 µmol, 1.00 eq) in ethyl acetate (5 mL) and tetrahydrofuran (0.5 mL) was added palladium on carbon (30.0 mg, 10% purity) under nitrogen atmosphere. The suspension was degassed and purged with hydrogen for three times. The reaction mixture was stirred at 25° C. for 1 h under hydrogen atmosphere. The reaction was filtered, and the filtrate was concentrated under reduced pressure to a residue, which was purified by Prep-HPLC (column: Phenomenex luna C18 150×25 mm×10 m; mobile phase: [water (formic acid)-acetonitrile]; gradient: 44%-60% B over 8 min) and lyophilized to afford 3-(2-chloro-4'-(3-(2,2-difluoroethyl)-2-oxopyridin-1(2H)-yl)-[1,1'-biphenyl]-3-yl)piperidine-2,6-dione (11.1 mg, 23.2 µmol, 35% yield) as a white solid $^1$H NMR (400 MHz, DMSO-d$_6$) δ=10.95 (s, 1H), 7.82-7.70 (m, 1H), 7.61-7.51 (m, 5H), 7.47-7.36 (m, 3H), 6.47-6.11 (m, 2H), 4.38 (dd, J=12.0, 4.8 Hz, 1H), 3.18-3.03 (m, 2H), 2.86-2.78 (m, 1H), 2.63-2.52 (m, 1H), 2.40-2.35 (m, 1H), 2.10-2.04 (m, 1H); MS (ESI) m/z 457.1 [M+H]$^+$ To a solution of tert-butyl 4-(4-bromophenyl)-3-oxopiperazine-1-carboxylate (700 mg, 1.58 mmol, 1.00 eq) in ethyl acetate (4 mL) was added hydrochloric acid/ethyl acetate (4 M, 4 mL, 10.2 eq). The mixture was stirred at 25° C. for 2 h. Then the mixture was concentrated under reduced pressure to give a residue, which was purified by reversed-phase column (C18, 80 g; condition: water/acetonitrile=1/0-0/1, 0.1% formic acid) and lyophilized to afford 1-(4-bromophenyl)piperazin-2-one (270 mg, 783 µmol, 49% yield, 74% purity) as a white solid.

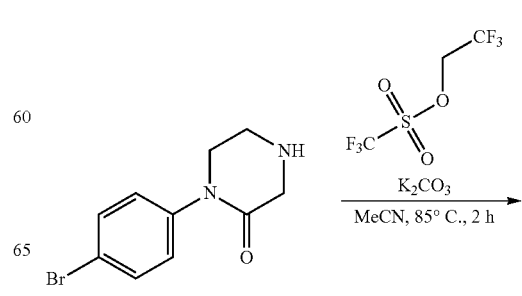

545
-continued

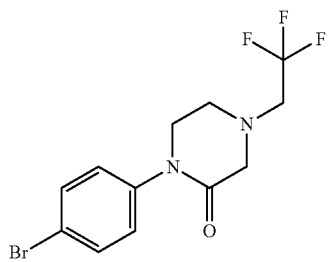

To a solution of 1-(4-bromophenyl)piperazin-2-one (130 mg, 377 μmol, 1.00 eq) and 2,2,2-trifluoroethyl trifluoromethanesulfonate (175 mg, 754 μmol, 2.00 eq) in acetonitrile (1 mL) was added potassium carbonate (104 mg, 754 μmol, 2.00 eq). The mixture was stirred at 85° C. for 2 h. After being cooled to room temperature, the mixture was concentrated under reduced pressure to give a residue, which was purified by Prep-HPLC (column: Phenomenex Luna C18 150×25 mm×10 m; mobile phase: [water (formic acid)-acetonitrile]; gradient: 43%-73% B over 9 min) and lyophilized to afford 1-(4-bromophenyl)-4-(2,2,2-trifluoroethyl)piperazin-2-one (40.0 mg, 118 μmol, 31% yield) as a white solid.

3-(2-chloro-4'-(2-oxo-4-(2,2,2-trifluoroethyl)piperazin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-4-(2,2,2-trifluoroethyl)piperazin-2-one according to General Scheme 1.

$^1$H NMR (400 MHz, DMSO-d$_6$) δ=10.93 (s, 1H), 7.47-7.32 (m, 7H), 4.35 (dd, J=12.0, 5.2 Hz, 1H), 3.79-3.69 (m, 2H), 3.47-3.37 (m, 4H), 3.07 (t, J=5.2 Hz, 2H), 2.84-2.75 (m, 1H), 2.61-2.52 (m, 1H), 2.39-2.29 (m, 1H), 2.10-1.99 (m, 1H); MS (ESI) m/z 480.2 [M+H]$^+$

Example 198. Synthesis of 3-(2-chloro-4'-(4-(2,2-difluoroethyl)-2-oxopiperazin-1-yl)-[1,1'-biphenyl]-3-yl)piperidine-2,6-dione (Compound 446)

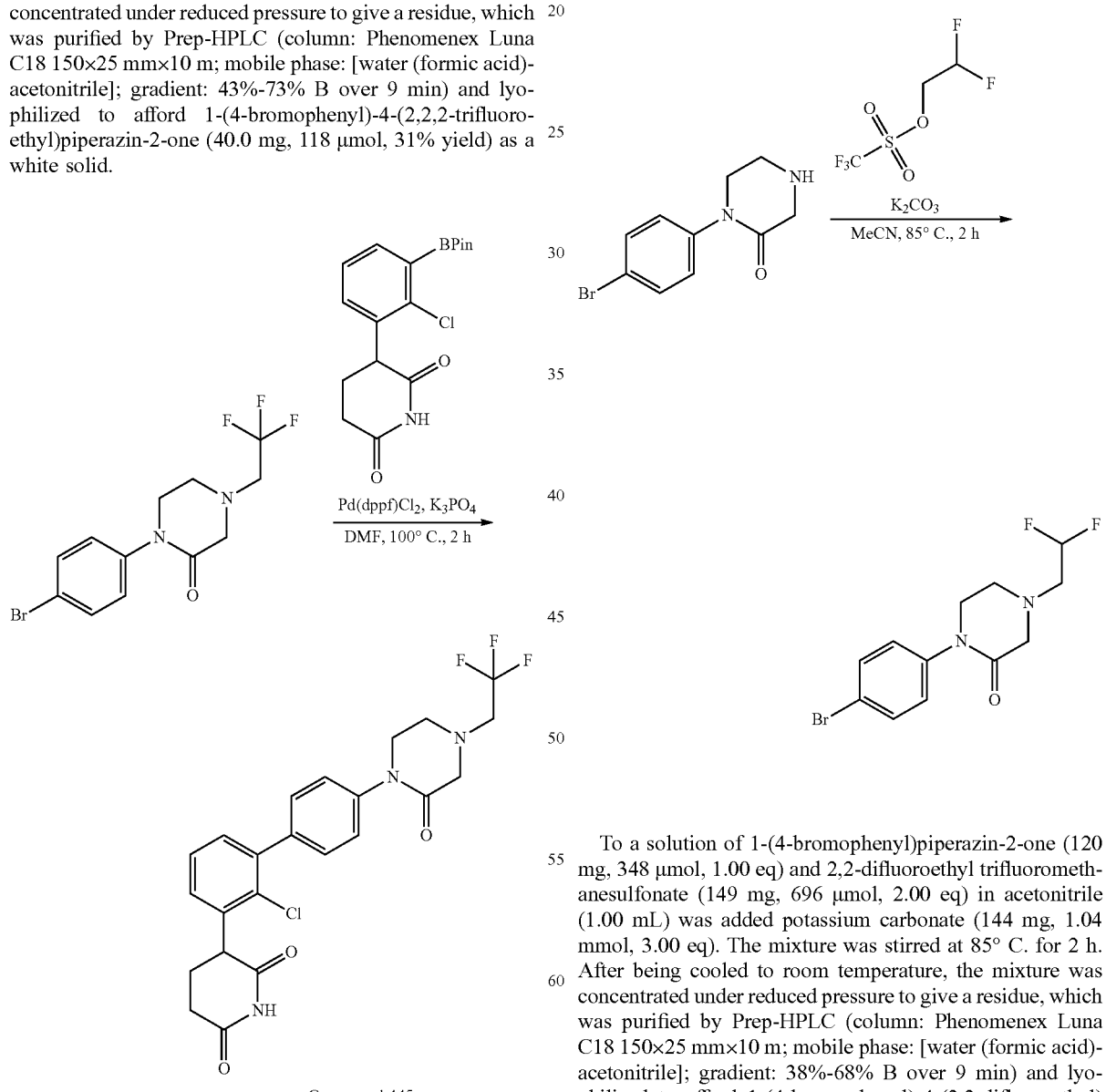

Compound 445

To a solution of 1-(4-bromophenyl)piperazin-2-one (120 mg, 348 μmol, 1.00 eq) and 2,2-difluoroethyl trifluoromethanesulfonate (149 mg, 696 μmol, 2.00 eq) in acetonitrile (1.00 mL) was added potassium carbonate (144 mg, 1.04 mmol, 3.00 eq). The mixture was stirred at 85° C. for 2 h. After being cooled to room temperature, the mixture was concentrated under reduced pressure to give a residue, which was purified by Prep-HPLC (column: Phenomenex Luna C18 150×25 mm×10 m; mobile phase: [water (formic acid)-acetonitrile]; gradient: 38%-68% B over 9 min) and lyophilized to afford 1-(4-bromophenyl)-4-(2,2-difluoroethyl)piperazin-2-one (25.0 mg, 78.3 μmol, 22% yield) as a white solid.

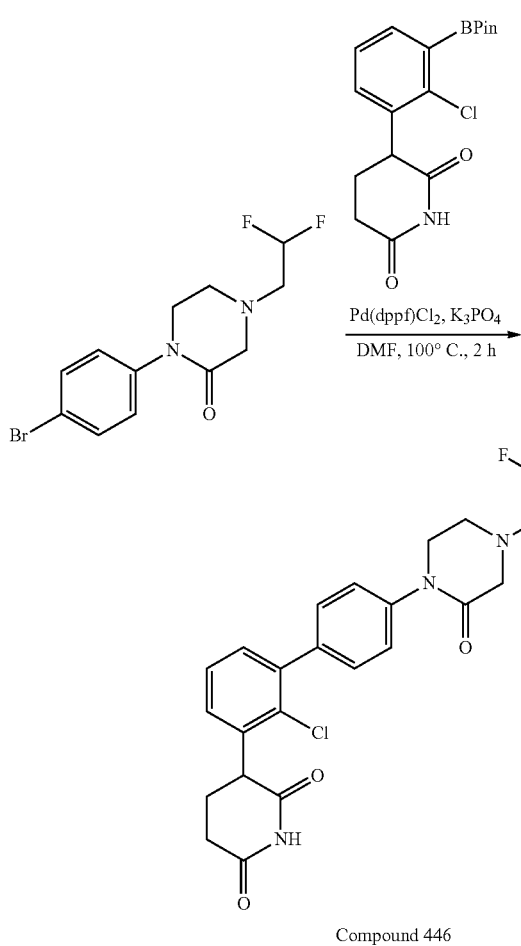

Compound 446

3-(2-chloro-4'-(4-(2,2-difluoroethyl)-2-oxopiperazin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-4-(2,2-difluoroethyl)piperazin-2-one according to General Scheme 1.

$^1$H NMR (400 MHz, DMSO-d$_6$) δ=10.92 (s, 1H), 7.44-7.31 (m, 7H), 6.29-6.18 (m, 1H), 4.35 (dd, J=12.4, 5.2, Hz, 1H), 3.77-3.66 (m, 2H), 3.39 (s, 2H), 3.00-2.88 (m, 4H), 2.84-2.72 (m, 1H), 2.61-2.50 (m, 1H), 2.40-2.28 (m, 1H), 2.14-1.96 (m, 1H); MS (ESI) m/z 462.1 [M+H]$^+$

Example 199. Synthesis of 3-(2-chloro-3-(6-((2-oxopyridin-1(2H)-yl)methyl)pyridin-3-yl)phenyl)piperidine-2,6-dione (Compound 447)

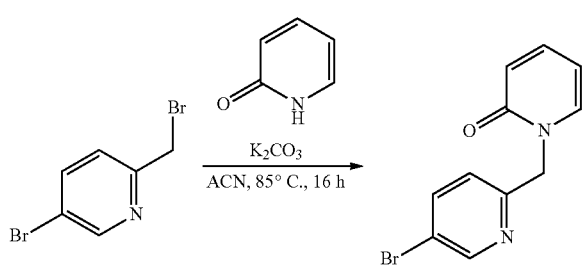

To a solution of 5-bromo-2-(bromomethyl)pyridine (0.850 g, 3.39 mmol, 1.00 eq) and 1H-pyridin-2-one (0.483 g, 5.08 mmol, 1.50 eq) in acetonitrile (10 mL) was added potassium carbonate (0.936 g, 6.78 mmol, 2.00 eq). The mixture was stirred at 85° C. for 16 h. The reaction mixture was cooled to room temperature and filtered through a plug of Celite. The filtrate was concentrated under reduced pressure to give a residue, which was purified by Prep-HPLC (column: Phenomenex luna C18 150 mm×25 mm×10 μm; mobile phase: [water (formic acid)-acetonitrile]; gradient: 15%-45% B over 10 min). The desired fraction was collected and lyophilized to give 1-((5-bromopyridin-2-yl)methyl)pyridin-2(1H)-one (0.400 g, 1.51 mmol, 45% yield) as a white solid.

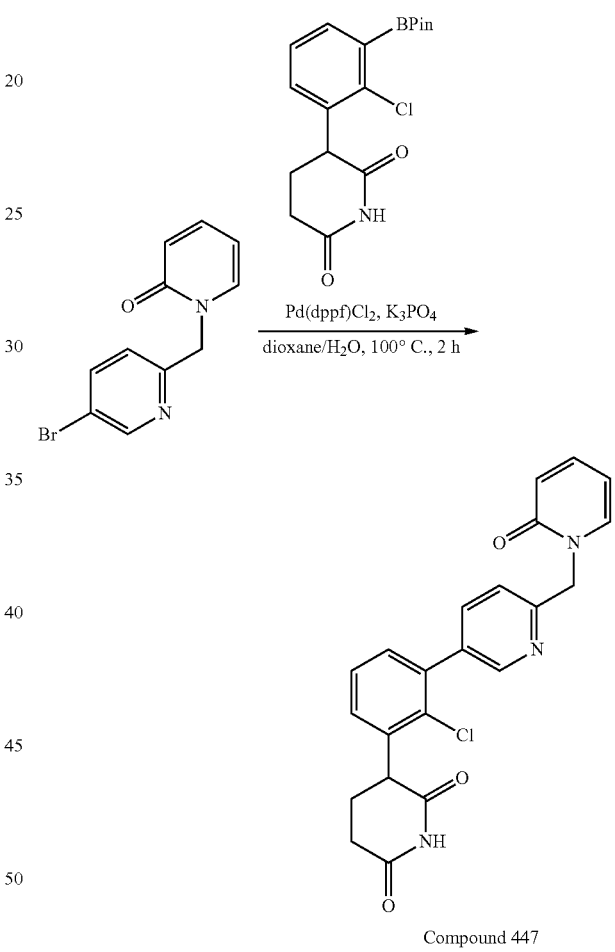

Compound 447

3-(2-chloro-3-(6-((2-oxopyridin-1(2H)-yl)methyl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-((5-bromopyridin-2-yl)methyl)pyridin-2(1H)-one according to General Scheme 1.

$^1$H NMR (400 MHz, DMSO-d$_6$) δ=10.93 (s, 1H), 8.54 (d, J=1.6 Hz, 1H), 7.91-7.81 (m, 2H), 7.51-7.40 (m, 3H), 7.39-7.34 (m, 1H), 7.29 (d, J=8.0 Hz, 1H), 6.46-6.40 (m, 1H), 6.33-6.26 (m, 1H), 5.25 (s, 2H), 4.39-4.32 (m, 1H), 2.85-2.73 (m, 1H), 2.61-2.56 (m, 1H), 2.37-2.30 (m, 1H), 2.09-2.00 (m, 1H); MS (ESI) m/z 408.1 [M+H]$^+$

Example 200. Synthesis of 3-(2-chloro-4'-(1,4-dimethyl-2-oxo-1,2-dihydropyridin-3-yl)-[1,1'-biphenyl]-3-yl)piperidine-2,6-dione (Compound 448)

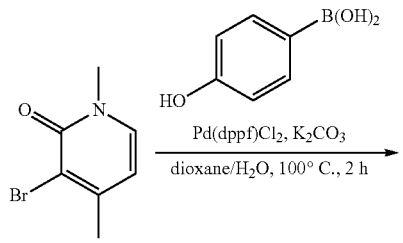

To a solution of 3-bromo-1,4-dimethylpyridin-2(1H)-one (0.300 g, 1.48 mmol, 1.00 eq) and (4-hydroxyphenyl)boronic acid (0.246 g, 1.78 mmol, 1.20 eq) in dioxane (3 mL) and water (0.3 mL) was added [1,1'-bis(diphenylphosphino)ferrocene]dichloropalladium(II) (0.109 g, 0.148 mmol, 0.100 eq) and potassium carbonate (0.616 g, 4.45 mmol, 3.00 eq). The mixture was stirred at 100° C. for 2 h under nitrogen atmosphere. After being cooled to room temperature, the reaction mixture was concentrated in vacuo to give a residue, which was purified by flash silica gel chromatography (ISCO®; 10 g SepaFlash® Silica Flash Column, Eluent of 0~100% ethyl acetate/petroleum ether gradient @ 20 mL/min) to afford 3-(4-hydroxyphenyl)-1,4-dimethylpyridin-2(1H)-one (0.225 g, 0.941 mmol, 63% yield, 90% purity) as a white solid.

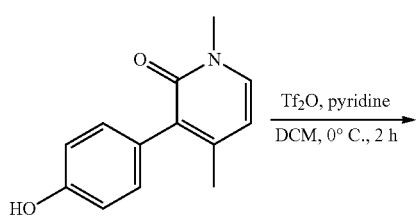

To a solution of 3-(4-hydroxyphenyl)-1,4-dimethylpyridin-2(1H)-one (0.200 g, 0.929 mmol, 1.00 eq) in dichloromethane (3 mL) was added pyridine (0.110 g, 1.39 mmol, 1.50 eq) and trifluoromethanesulfonic anhydride (0.260 g, 0.922 mmol, 1.00 eq) at 0° C. The mixture was stirred at 0° C. for 2 h. The reaction was diluted with water (40 mL) and then extracted with ethyl acetate (3×40 mL). Combined extracts were washed with brine (30 mL), dried over sodium sulfate, filtered, and concentrated under vacuum to afford 4-(1,4-dimethyl-2-oxo-1,2-dihydropyridin-3-yl)phenyl trifluoromethanesulfonate (0.300 g, crude) as a black solid. The crude product was used for next step without further purification.

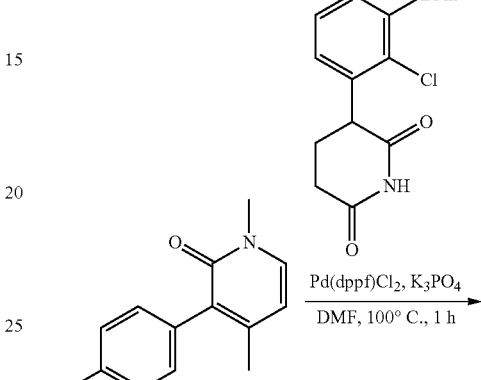

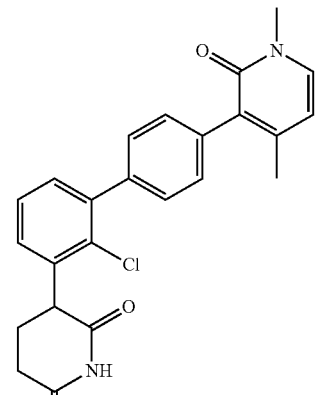

Compound 448

3-[2-chloro-3-[4-(1,4-dimethyl-2-oxo-3-pyridyl)phenyl]phenyl]piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(1,4-dimethyl-2-oxo-1,2-dihydropyridin-3-yl)phenyl trifluoromethanesulfonate according to General Scheme 1.

$^1$H NMR (400 MHz, DMSO-$d_6$) δ=10.94 (s, 1H), 7.63 (d, J=7.2 Hz, 1H), 7.46-7.40 (m, 3H), 7.39-7.35 (m, 2H), 7.30 (d, J=8.4 Hz, 2H), 6.23 (d, J=6.8 Hz, 1H), 4.37 (dd, J=11.6, 5.2 Hz, 1H), 3.44 (s, 3H), 2.87-2.75 (m, 1H), 2.59-2.56 (m, 1H), 2.39-2.32 (m, 1H), 2.11-2.07 (m, 1H), 2.04 (s, 3H); MS (ESI) m/z 421.1 [M+H]$^+$

Example 201. Synthesis of (2-chloro-4'-(2-oxo-3-(2,2,2-trifluoroethyl) tetrahydropyrimidin-1(2H)-yl)-[1,1'-biphenyl]-3-yl)piperidine-2,6-dione (Compound 449)

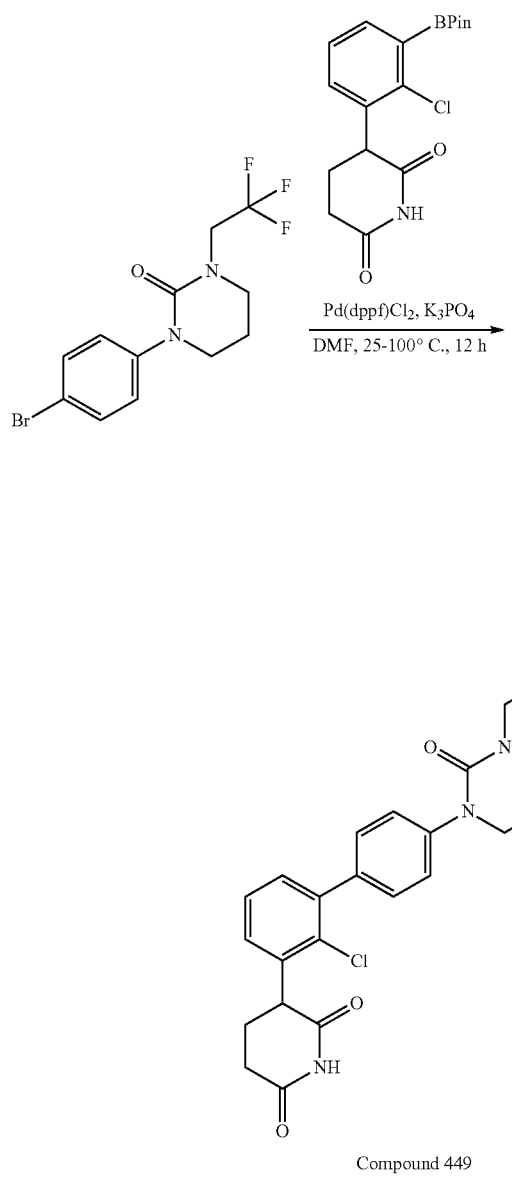

Compound 449

3-(2-chloro-4'-(2-oxo-3-(2,2,2-trifluoroethyl)tetrahydropyrimidin-1(2H)-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-3-(2,2,2-trifluoroethyl)tetrahydropyrimidin-2(1H)-one according to General Scheme 1.

$^1$H NMR (400 MHz, DMSO-d$_6$) δ=10.92 (s, 1H), 7.40 (s, 1H), 7.38-7.36 (m, 4H), 7.36-7.30 (m, 2H), 4.35 (dd, J=12.4, 5.2 Hz, 1H), 4.17 (q, J=9.6 Hz, 2H), 3.74 (t, J=5.6 Hz, 2H), 3.53 (t, J=5.6 Hz, 2H), 2.84-2.72 (m, 1H), 2.61-2.53 (m, 1H), 2.41-2.34 (m, 1H), 2.14-2.05 (m, 1H), 2.08-2.04 (m, 2H); MS (ESI) m/z 480.1 [M+H]$^+$

Example 202. Synthesis of 3-(2-chloro-3-(6-(2-oxopiperidin-1-yl)pyridin-3-yl)phenyl)piperidine-2,6-dione (Compound 450)

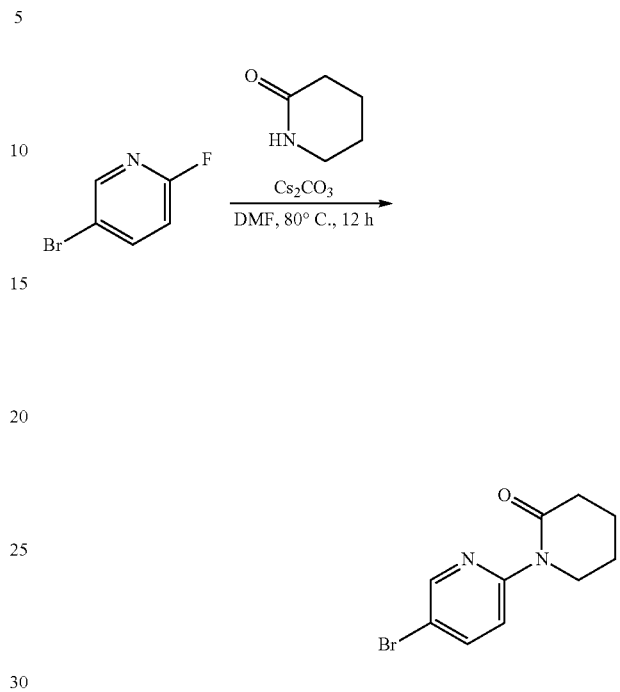

To a solution of piperidin-2-one (2.25 g, 22.7 mmol, 2.00 eq) and cesium carbonate (7.42 g, 22.8 mmol, 2.00 eq) in dimethyl formamide (20 mL) was added 5-bromo-2-fluoropyridine (2.00 g, 11.4 mmol, 1.00 eq) at 25° C. Then the mixture was stirred at 80° C. for 12 h. After being cooled to room temperature, the reaction mixture was diluted with ethyl acetate (20 mL), washed with brine (3×20 mL), dried over sodium sulfate, filtered and concentrated under reduced pressure to give a residue, which was purified by flash silica gel chromatography (ISCO®; 20 g SepaFlash® Silica Flash Column, eluent of 0-50% ethyl acetate/petroleum ether gradient at 70 mL/min) to give 1-(5-bromopyridin-2-yl)piperidin-2-one (380 mg, 1.42 mmol, 12% yield) as a white solid.

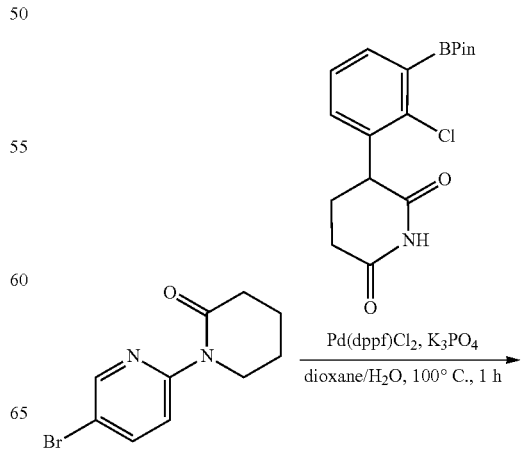

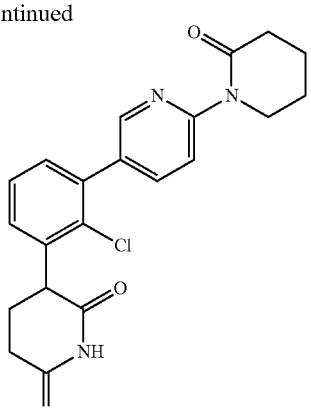

Compound 450

3-(2-chloro-3-(6-(2-oxopiperidin-1-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(5-bromopyridin-2-yl)piperidin-2-one according to General Scheme 1.

$^1$H NMR (400 MHz, DMSO-d$_6$) δ=10.94 (s, 1H), 8.46 (dd, J=2.4, 1.2 Hz, 1H), 8.00-7.75 (m, 2H), 7.55-7.27 (m, 3H), 4.37 (dd, J=12.4, 5.2 Hz, 1H), 3.92 (t, J=6.0 Hz, 2H), 2.91-2.72 (m, 1H), 2.59-2.51 (m, 3H), 2.42-2.26 (m, 1H), 2.12-2.00 (m, 1H), 1.96-1.77 (m, 4H) $^1$H NMR (400 MHz, MeOD-d$_4$) δ 8.48 (d, J=2.4 Hz, 1H), 7.90 (dd, J=8.4, 2.4 Hz, 1H), 7.70 (d, J=8.4 Hz, 1H), 7.51-7.31 (m, 3H), 4.41 (dd, J=12.0, 5.2 Hz, 1H), 4.00-3.85 (m, 2H), 2.88-2.76 (m, 1H), 2.75-2.66 (m, 1H), 2.60 (t, J=6.4 Hz, 2H), 2.48-2.37 (m, 1H), 2.28-2.14 (m, 1H), 2.05-1.94 (m, 4H); MS (ESI) m/z 398.1 [M+H]$^+$

Example 203. Synthesis of 3-(2-chloro-3-(6-(2-oxo-1,3-oxazinan-3-yl)pyridin-3-yl)phenyl)piperidine-2,6-dione (Compound 451)

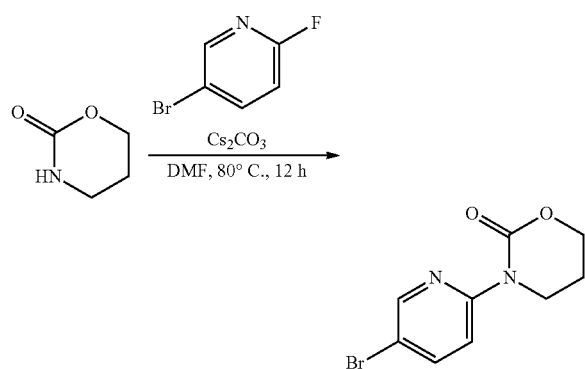

To a mixture of 1,3-oxazinan-2-one (0.200 g, 1.98 mmol, 1.20 eq) and 5-bromo-2-fluoropyridine (0.291 g, 1.65 mmol, 1.00 eq) in dimethyl formamide (5 mL) was added cesium carbonate (0.539 g, 1.65 mmol, 1.00 eq). The mixture was stirred at 80° C. for 12 h. Then the mixture was cooled to 25° C., diluted with water (5 mL) and extracted with ethyl acetate (2×10 mL). The combined organic layers were washed with brine (10 mL), dried over sodium sulfate, filtered and concentrated under reduced pressure to give a residue, which was purified by Prep-HPLC (column: Phenomenex luna C18 150 mm×25 mm×10 µm; mobile phase: [water (formic acid)-acetonitrile]; gradient: 20%-50% B over 10 min). The desired fraction was collected and lyophilized to give 3-(5-bromopyridin-2-yl)-1,3-oxazinan-2-one (0.0600 g, 0.229 mmol, 12% yield) as a white solid.

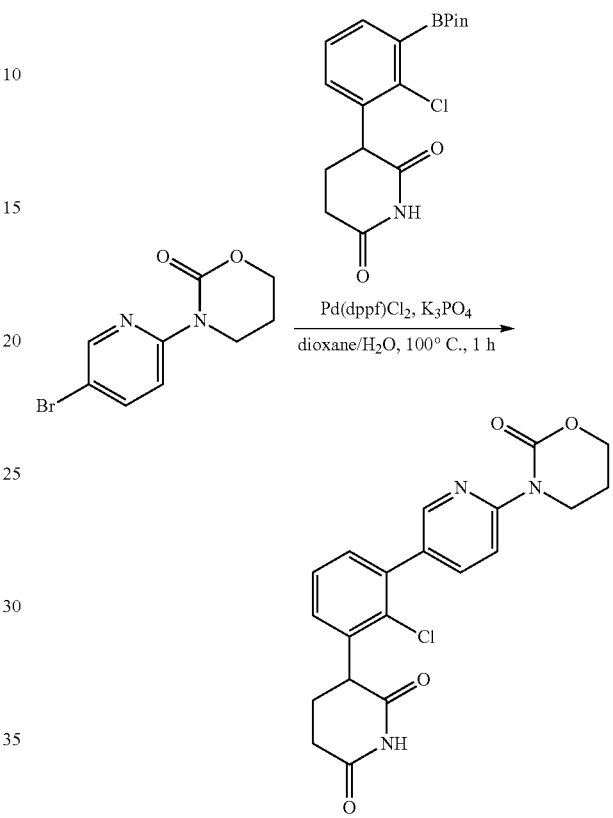

Compound 451

3-(2-chloro-3-(6-(2-oxo-1,3-oxazinan-3-yl)pyridin-3-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 3-(5-bromo-2-pyridyl)-1,3-oxazinan-2-one according to General Scheme 1.

$^1$H NMR (400 MHz, DMSO-d$_6$) δ=10.94 (s, 1H), 8.44 (s, 1H), 7.95-7.85 (m, 2H), 7.49-7.36 (m, 3H), 4.45-4.30 (m, 3H), 4.10-3.92 (m, 2H), 2.86-2.73 (m, 1H), 2.58-2.55 (m, 1H), 2.35-2.27 (m, 1H), 2.19-2.10 (m, 2H), 2.08-2.05 (m, 1H); MS (ESI) m/z 400.2 [M+H]$^+$

Example 204. Synthesis of 3-(2-chloro-3'-fluoro-4'-(2-oxo-1,3-oxazinan-3-yl)-[1,1'-biphenyl]-3-yl)piperidine-2,6-dione (Compound 452)

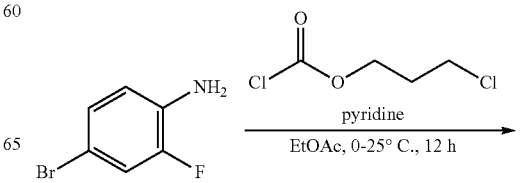

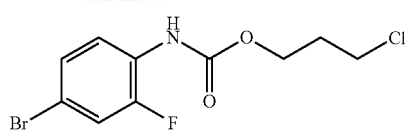

To a solution of 4-bromo-2-fluoroaniline (100 mg, 526 µmol, 1.00 eq) and pyridine (49.0 mg, 619 µmol, 1.18 eq) in ethyl acetate (1 mL) was added 3-chloropropyl carbonochloridate (91.0 mg, 579 µmol, 1.10 eq) at 0° C. under nitrogen atmosphere. The mixture was stirred at 25° C. for 12 h. Then the mixture was concentrated under reduced pressure to give a residue, which was purified by flash silica gel chromatography (ISCO®; 12 g SepaFlash® Silica Flash Column, eluent of 0-15% ethyl acetate/petroleum ether gradient at 50 mL/min) to give 3-chloropropyl (4-bromo-2-fluorophenyl)carbamate (150 mg, 435 µmol, 83% yield) as colorless oil.

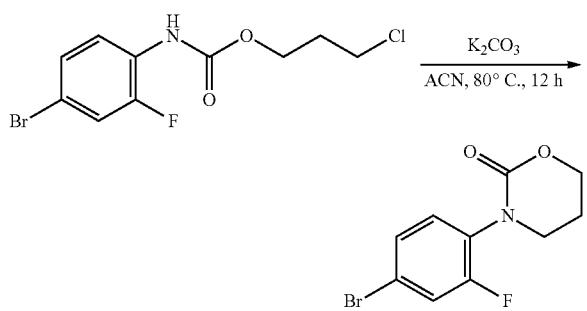

To a solution of 3-chloropropyl (4-bromo-2-fluorophenyl)carbamate (150 mg, 434 µmol, 1.00 eq) in acetonitrile (4 mL) was added potassium carbonate (102 mg, 738 µmol, 1.70 eq) at 25° C. The mixture was stirred at 80° C. for 12 h. After being cooled to room temperature, the mixture was concentrated under reduced pressure to give a residue, which was purified by flash silica gel chromatography (ISCO®; 12 g SepaFlash® Silica Flash Column, eluent of 80-90% ethyl acetate/petroleum ether gradient at 50 mL/min) to afford 3-(4-bromo-2-fluorophenyl)-1,3-oxazinan-2-one (97.0 mg, 343 µmol, 79% yield) as a white solid.

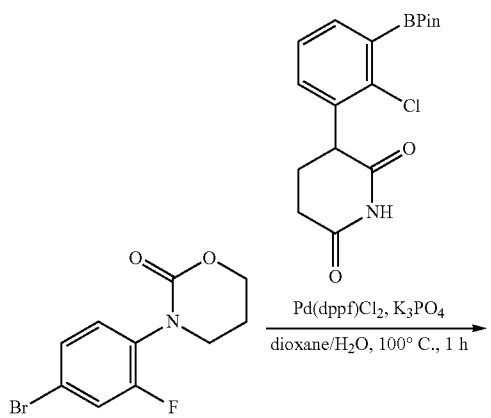

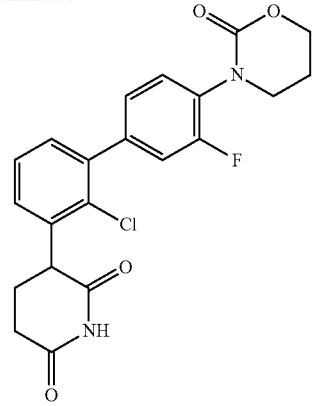

Compound 452

3-(2-chloro-3'-fluoro-4'-(2-oxo-1,3-oxazinan-3-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 3-(4-bromo-2-fluorophenyl)-1,3-oxazinan-2-one according to General Scheme 1.

$^1$H NMR (400 MHz, DMSO-$d_6$) δ=10.94 (s, 1H), 7.56 (t, J=8.4 Hz, 1H), 7.48-7.34 (m, 4H), 7.29 (dd, J=8.4, 1.6 Hz, 1H), 4.53-4.26 (m, 3H), 3.65 (t, J=6.0 Hz, 2H), 2.87-2.73 (m, 1H), 2.58-2.55 (m, 1H), 2.37-2.30 (m, 1H), 2.20-2.09 (m, 2H), 2.09-1.99 (m, 1H); MS (ESI) m/z 417.1 [M+H]$^+$

Example 205. Synthesis of 3-(2-chloro-4'-(pyridazin-3-ylmethyl)-[1,1'-biphenyl]-3-yl)piperidine-2,6-dione (Compound 453)

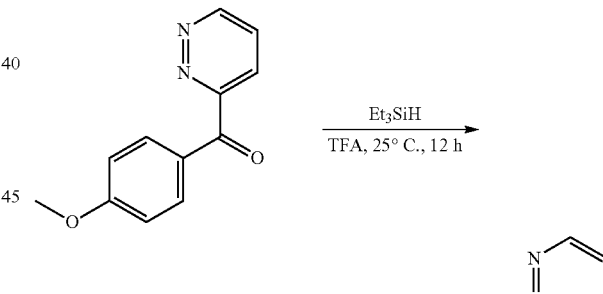

To a solution of (4-methoxyphenyl)(pyridazin-3-yl)methanone (3.39 g, 14.3 mmol, 1.00 eq) in trifluoroacetic acid (30 mL) was added triethylsilane (4.55 mL, 28.5 mmol, 2.00 eq) at 25° C. Then the mixture was stirred at 25° C. for 12 h. The mixture was poured into saturated aqueous sodium bicarbonate solution (150 mL) and extracted with ethyl acetate (3×100 mL). The combined organic layers were washed with brine (50 mL), dried over sodium sulfate, filtered and concentrated under reduced pressure to give a residue, which was purified by flash silica gel chromatography (ISCO®; 40 g SepaFlash® Silica Flash Column, eluent of 60-80% ethyl acetate/petroleum ether gradient @ 80 mL/min) to afford 3-(4-methoxybenzyl)pyridazine (1.70 g, 7.22 mmol, 51% yield) as red oil.

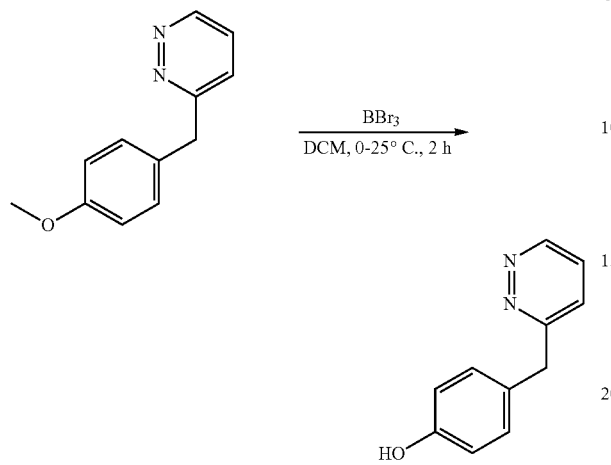

To a solution of 3-(4-methoxybenzyl)pyridazine (1.00 g, 4.99 mmol, 1.00 eq) in dichloromethane (10 mL) was added tribromoborane (1.00 mL, 10.4 mmol, 2.10 eq) at 0° C. under nitrogen atmosphere. The mixture was stirred at 25° C. for 2 h. Then the mixture was poured into saturated aqueous sodium bicarbonate solution (50 mL), extracted with ethyl acetate (3×50 mL), washed with brine (20 mL), dried over sodium sulfate, filtered and concentrated under reduced pressure to give a residue, which was purified by flash silica gel chromatography (ISCO®; 20 g SepaFlash® Silica Flash Column, eluent of 80-100% ethyl acetate/petroleum ether gradient @ 60 mL/min) to afford 4-(pyridazin-3-ylmethyl)-phenol (508 mg, 2.67 mmol, 54% yield) as a yellow solid.

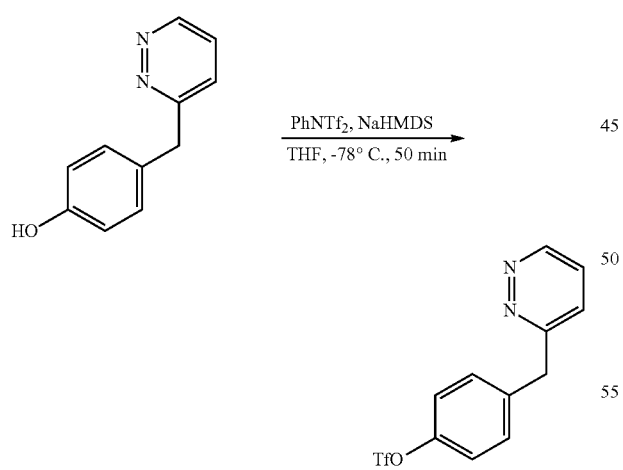

4-(pyridazin-3-ylmethyl)phenol (508 mg, 2.67 mmol, 1.00 eq) was dissolved in tetrahydrofuran (5 mL) and cooled to −78° C. under nitrogen atmosphere. Then sodium bis(trimethylsilyl)amide (4.10 mL, 1.0 M in tetrahydrofuran, 1.53 eq) was added dropwise to the mixture and the reaction mixture was stirred for 0.5 h. Then 1,1,1-trifluoro-N-phenyl-N-((trifluoromethyl)sulfonyl)methanesulfonamide (1.19 g, 3.34 mmol, 1.25 eq) was added and the reaction mixture was stirred at −78° C. for an additional 20 min. The mixture was then allowed to warm to room temperature and quenched with water (50 mL). The mixture was then extracted with dichloromethane (3×50 mL), dried over sodium sulfate, filtered and concentrated under reduced pressure to give a residue, which was purified by flash silica gel chromatography (ISCO®; 20 g SepaFlash® Silica Flash Column, eluent of 90-100% ethyl acetate/petroleum ether gradient @ 50 mL/min) to afford 4-(pyridazin-3-ylmethyl)phenyl trifluoromethanesulfonate (457 mg, 1.28 mmol, 48% yield) as a white solid.

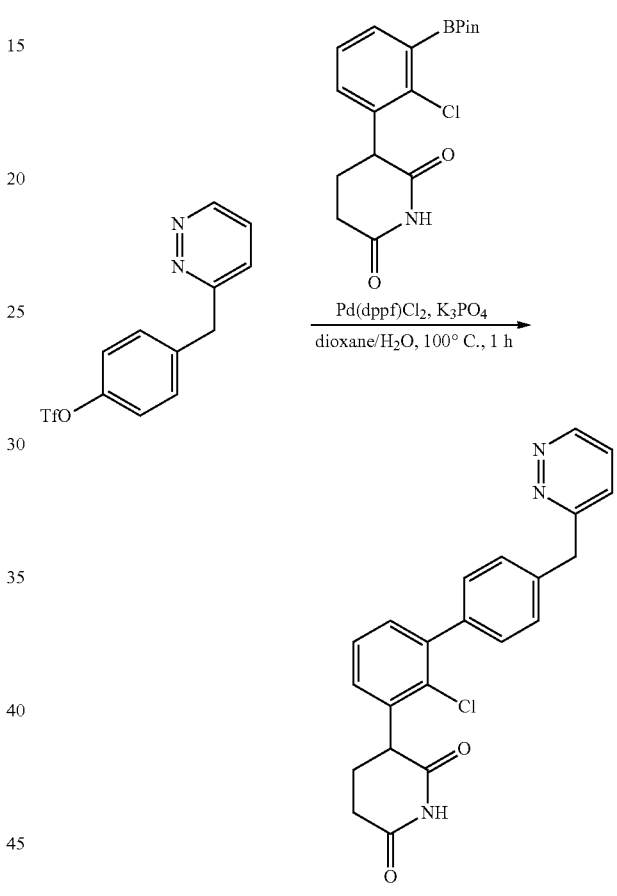

Compound 453

3-(2-chloro-4'-(pyridazin-3-ylmethyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 4-(pyridazin-3-ylmethyl)phenyl trifluoromethanesulfonate according to General Scheme 1.

$^1$H NMR (400 MHz, DMSO-$d_6$) δ=10.91 (s, 1H), 9.12 (dd, J=4.4, 2.0 Hz, 1H), 7.73-7.59 (m, 2H), 7.40-7.35 (m, 6H), 7.35-7.33 (m, 1H), 4.34 (s, 2H), 3.30 (s, 1H), 2.84-2.72 (m, 1H), 2.58-2.54 (m, 1H), 2.36-2.30 (m, 1H), 2.08-1.99 (m, 1H); MS (ESI) m/z 392.1 [M+H]$^+$

Example 206. Synthesis of 3-(2-chloro-4'-((3-methyl-2-oxooxazolidin-5-yl)methyl)-[1,1'-biphenyl]-3-yl)piperidine-2,6-dione (Compound 454)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-((3-methyl-2-oxooxazolidin-5-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 4-((3-methyl-2-oxooxazolidin-5-yl)methyl)phenyl trifluoromethanesulfonate according to General Scheme 1.

MS (ESI) m/z 413.1 [M+H]+

Example 207. Synthesis of 3-(2-chloro-4'-(isoxazol-3-ylmethyl)-[1,1'-biphenyl]-3-yl)piperidine-2,6-dione (Compound 455)

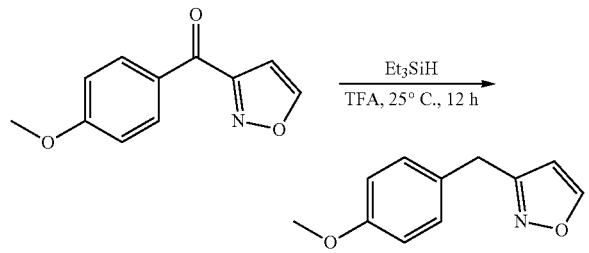

To a solution of isoxazol-3-yl(4-methoxyphenyl)methanone (2.00 g, 9.84 mmol, 1.00 eq) in trifluoroacetic acid (20 mL) was added triethylsilane (4.58 g, 39.4 mmol, 4.00 eq). The mixture was stirred at 25° C. for 12 h. The reaction was quenched with water (50 mL) and then extracted with ethyl acetate (3×50 mL). The combined organic extracts were dried over sodium sulfate, filtered and concentrated under vacuum to give a residue, which was purified by flash silica gel chromatography (ISCO®; 40 g SepaFlash® Silica Flash Column, Eluent of 0-100% ethyl acetate/petroleum ether gradient @ 100 mL/min) to give 3-[(4-methoxyphenyl)methyl]isoxazole (1.90 g, 9.04 mmol, 92% yield) as colorless oil.

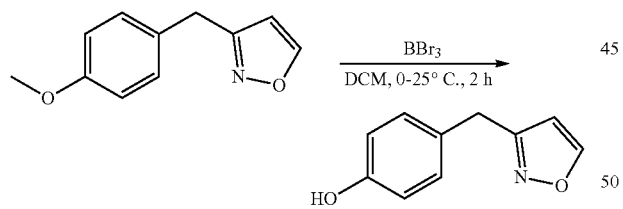

To a solution of 3-[(4-methoxyphenyl)methyl]isoxazole (1.90 g, 10.0 mmol, 1.00 eq) in dichloromethane (20 mL) was added tribromoborane (5.03 g, 20.1 mmol, 2.00 eq) at 0° C. The mixture was stirred at 25° C. for 2 h. The mixture was quenched with water (50 mL) and then the pH was adjusted to 7 with saturated aqueous sodium bicarbonate solution. Then the mixture was extracted with ethyl acetate (3×50 mL), washed with brine (60 mL), dried over sodium sulfate, filtered and concentrated under vacuum to give a residue, which was purified by flash silica gel chromatography (ISCO®; 40 g SepaFlash® Silica Flash Column, eluent of 0~100% ethyl acetate/petroleum ether gradient at 100 mL/min) to give 4-(isoxazol-3-ylmethyl)phenol (0.800 g, 4.11 mmol, 41% yield) as colorless oil.

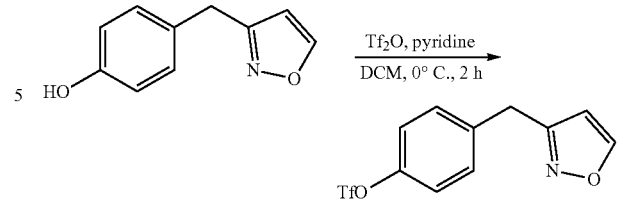

To a solution of 4-(isoxazol-3-ylmethyl)phenol (0.800 g, 4.57 mmol, 1.00 eq) in dichloromethane (10 mL) was added trifluoromethylsulfonic anhydride (1.29 g, 4.57 mmol, 1.00 eq) and pyridine (0.542 g, 6.85 mmol, 1.50 eq). The mixture was stirred at 0° C. for 2 h. Then the mixture was diluted with ethyl acetate (50 mL) and water (50 mL). The layers were separated and the aqueous phase was extracted with ethyl acetate (3×50 mL). The organic layer was dried over sodium sulfate, filtered and concentrated in vacuum to give a residue, which was purified by flash silica gel chromatography (ISCO®; 20 g SepaFlash® Silica Flash Column, Eluent of 0~100% ethyl acetate/petroleum ether gradient @ 40 mL/min) to afford [4-(isoxazol-3-ylmethyl)phenyl] trifluoromethanesulfonate (1.40 g, 4.10 mmol, 90% yield) as a white solid. 3-(2-chloro-3-(4,4,5,5-tetramethyl-1,3,2-dioxaborolan-2-yl)phenyl)piperidine-2,6-dione (intermediate A) was synthesized as described above. 3-[2-chloro-3-[4-(isoxazol-3-ylmethyl)phenyl]phenyl]piperidine-2,6-dione was prepared from 3-(2-chloro-3-(4,4,5,5-tetramethyl-1,3,2-dioxaborolan-2-yl)phenyl)piperidine-2,6-dione and [4-(isoxazol-3-ylmethyl)phenyl] trifluoromethanesulfonate according to General Scheme 1.

MS (ESI) m/z 381.1 [M+H]+

Example 208. Synthesis of 3-(2-chloro-4'-(1-oxoisoindolin-2-yl)-[1,1'-biphenyl]-3-yl)piperidine-2,6-dione (Compound 456)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(1-oxoisoindolin-2-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 2-(4-bromophenyl)isoindolin-1-one according to General Scheme 1.

MS (ESI) m/z 431.2 [M+H]+

Example 209. Synthesis of 3-(2-chloro-4'-(6-oxo-5-azaspiro[3.4]octan-5-yl)-[1,1'-biphenyl]-3-yl)piperidine-2,6-dione (Compound 457)

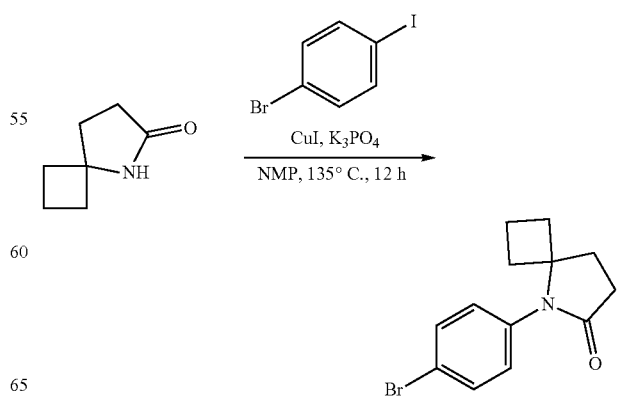

5-(4-bromophenyl)-5-azaspiro [3.4] octan-6-one was prepared from 5-azaspiro [3.4] octan-6-one and 1-bromo-4-iodobenzene according to General Scheme 7.

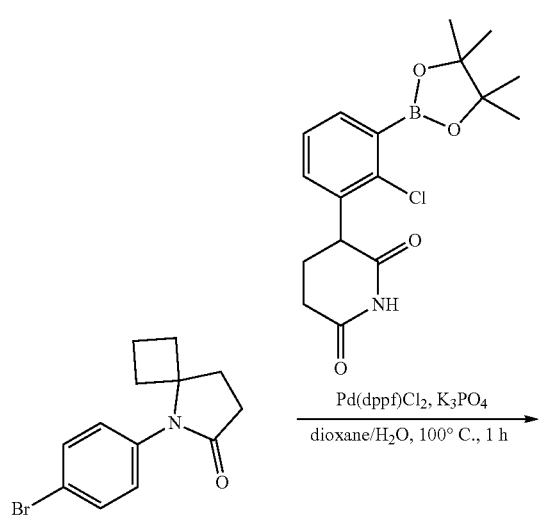

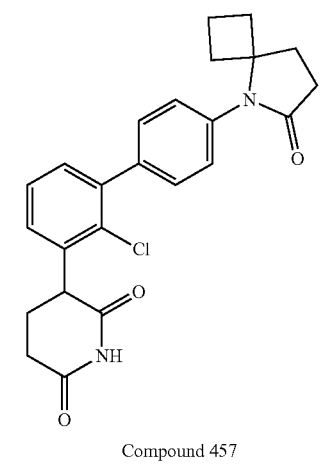

Compound 457

3-(2-chloro-4'-(6-oxo-5-azaspiro [3.4] octan-5-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5-(4-bromophenyl)-5-azaspiro[3.4]octan-6-one according to General Scheme 1.

$^1$H NMR (400 MHz, DMSO-$d_6$) δ=10.94 (s, 1H), 7.52 (d, J=8.4 Hz, 2H), 7.47-7.34 (m, 3H), 7.22 (d, J=8.4 Hz, 2H), 4.37 (dd, J=12.0, 4.8 Hz, 1H), 2.91-2.72 (m, 1H), 2.57 (m, 1H), 2.46-2.41 (m, 2H), 2.38-2.28 (m, 3H), 2.20-2.10 (m, 2H), 2.10-2.04 (m, 1H), 2.03-1.95 (m, 2H), 1.76-1.62 (m, 1H), 1.55-1.35 (m, 1H); MS (ESI) m/z 423.2 [M+H]$^+$

Example 210. Synthesis of 3-(2-chloro-4'-(2-oxo-1-(2,2,2-trifluoroethyl)-1,2-dihydropyridin-3-yl)-[1,1'-biphenyl]-3-yl)piperidine-2,6-dione (Compound 458)

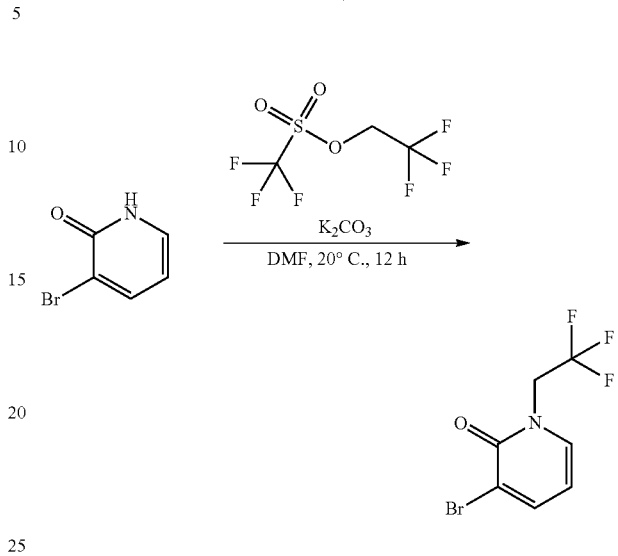

To a solution of 3-bromo-1H-pyridin-2-one (1.00 g, 5.75 mmol, 1.00 eq) in dimethyl formamide (10 mL) was added potassium carbonate (1.59 g, 11.5 mmol, 2.00 eq) and 2,2,2-trifluoroethyl trifluoromethanesulfonate (2.67 g, 11.5 mmol, 2.00 eq). The mixture was stirred at 20° C. for 12 h. The reaction mixture was diluted with water (10 mL) and extracted with ethyl acetate (2×20 mL). The combined organic layers were washed with brine (10 mL), dried over sodium sulfate, filtered and concentrated under reduced pressure to give a residue, which was purified by flash silica gel chromatography (ISCO®; 40 g SepaFlash® Silica Flash Column, eluent of 20~40% ethyl acetate/petroleum ether gradient at 80 mL/min) to give 3-bromo-1-(2,2,2-trifluoroethyl)pyridin-2(1H)-one (0.800 g, 2.81 mmol, 53% yield) as a yellow solid.

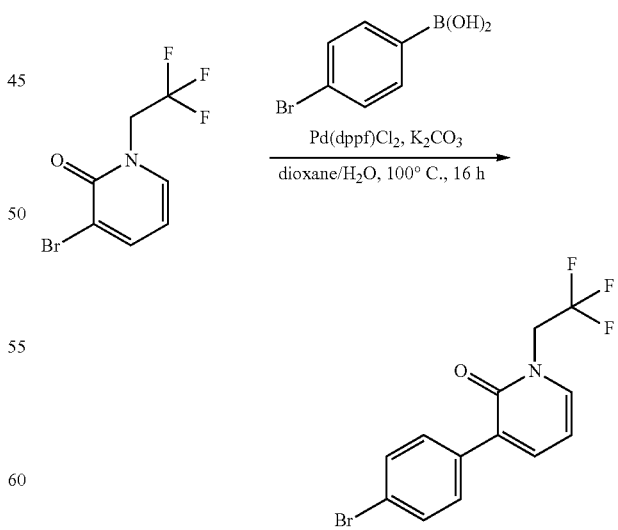

[1,1'-bis(diphenylphosphino)ferrocene]dichloropalladium(II) (0.171 g, 0.234 mmol, 0.100 eq) was added to a solution of 3-bromo-1-(2,2,2-trifluoroethyl)pyridin-2(1H)-one (0.600 g, 2.34 mmol, 1.00 eq), (4-bromophenyl)boronic acid (0.565 g, 2.81 mmol, 1.20 eq) and potassium carbonate (0.972 g, 7.03 mmol, 3.00 eq) in water (1.5 mL) and dioxane (7.5 mL) under nitrogen. The mixture was stirred at 100° C. for 16 h. The mixture was cooled to 25° C. and concentrated under reduced pressure to give a residue, which was purified by flash silica gel chromatography (ISCO®; 12 g SepaFlash®Silica Flash Column, eluent of 20~40% ethyl acetate/petroleum ether gradient at 80 mL/min), followed by Prep-HPLC (column: Phenomenex luna C18 150×25 mm×10 μm; mobile phase: [water (formic acid)-acetonitrile]; gradient: 52%-76% B over 8 min). The desired fraction was collected and lyophilized to afford 3-(4-bromophenyl)-1-(2,2,2-trifluoroethyl)pyridin-2(1H)-one (0.100 g, 0.271 mmol, 13% yield) as a yellow solid.

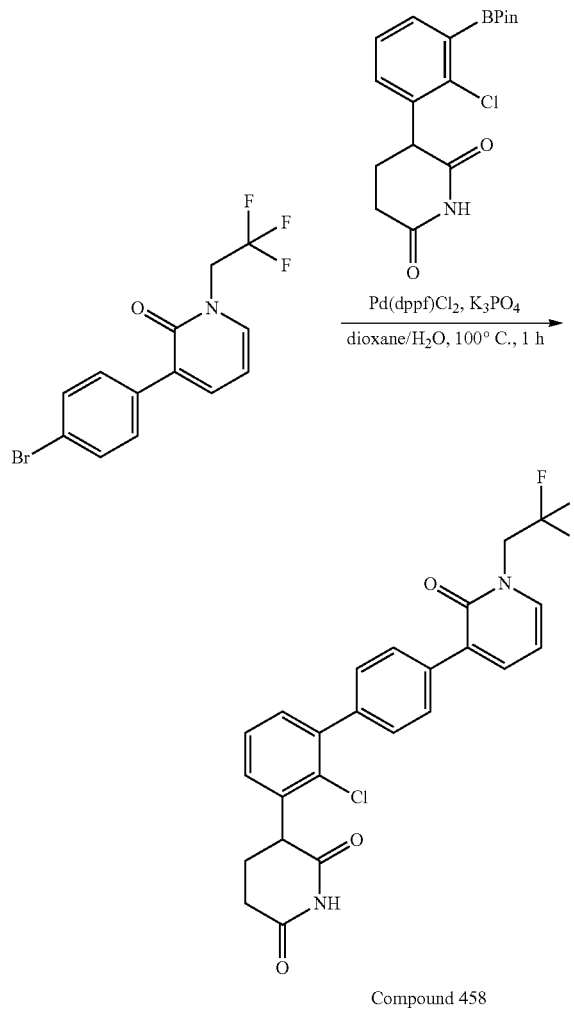

Compound 458

3-(2-chloro-4'-(2-oxo-1-(2,2,2-trifluoroethyl)-1,2-dihydropyridin-3-yl)-[1,1'-biphenyl]-3-yl) piperidine-2,6-dione was prepared from 3-(2-chloro-3-(4,4,5,5-tetramethyl-1,3,2-dioxaborolan-2-yl)phenyl)piperidine-2,6-dione (intermediate A) and 3-(4-bromophenyl)-1-(2,2,2-trifluoroethyl)pyridin-2(1H)-one according to General Scheme 1.

¹H NMR (400 MHz, DMSO-d₆) δ=10.94 (s, 1H), 7.82-7.71 (m, 4H), 7.45 (s, 1H), 7.43 (s, 1H), 7.41 (d, J=7.2 Hz, 1H), 7.39-7.36 (m, 1H), 7.36-7.32 (m, 1H), 6.47 (t, J=6.8 Hz, 1H), 4.98 (q, J=9.2 Hz, 2H), 4.36 (dd, J=12.4, 5.2 Hz, 1H), 2.87-2.73 (m, 1H), 2.58-5.55 (m, 1H), 2.38-2.27 (m, 1H), 2.11-2.00 (m, 1H); MS (ESI) m/z 475.2 [M+H]⁺

Example 211. Synthesis of 3-(2-chloro-4'-(piperidin-1-yl)-[1,1'-biphenyl]-3-yl)piperidine-2,6-dione (Compound 459)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(piperidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 1-(4-bromophenyl)piperidine according to General Scheme 1.

MS (ESI) m/z 383.2 [M+H]⁺

Example 212. Synthesis of 3-(4'-(benzo[d]oxazol-4-yl)-2-chloro-[1,1'-biphenyl]-3-yl)piperidine-2,6-dione (Compound 460)

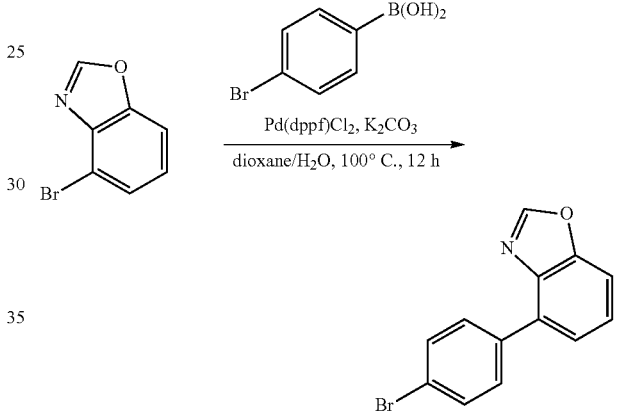

To a solution of 4-bromo-1,3-benzoxazole (1.50 g, 7.58 mmol, 1.00 eq) in dioxane (60 mL) and water (6 mL) were added (4-bromophenyl)boronic acid (1.83 g, 9.09 mmol, 1.20 eq) and potassium carbonate (3.14 g, 22.7 mmol, 3.00 eq), followed by [1,1'-bis(diphenylphosphino)ferrocene]dichloropalladium(II) (0.560 g, 0.758 mmol, 0.100 eq) at 25° C. under nitrogen atmosphere. The reaction was stirred at 100° C. for 12 h. After being cooled to room temperature, the mixture was diluted with water (80 mL) and extracted with ethyl acetate (3×80 mL). The combined organic layers were washed with brine (3×80 mL), dried over anhydrous sodium sulfate, filtered and concentrated under vacuum to give a residue, which was purified by column chromatography (silica, petroleum ether:ethyl acetate=5:1 to 1:2), followed by Prep-HPLC (column: Phenomenex Synergi Max-RP 250 mm×50 mm×10 μm; mobile phase: [water (trifluoroacetic acid)-acetonitrile]; gradient: 50-80% B over 23 min) and lyophilized to give 4-(4-bromophenyl)benzo[d]oxazole (0.500 g, 1.64 mmol, 22% yield) as a white solid.

3-(2-chloro-3-(4,4,5,5-tetramethyl-1,3,2-dioxaborolan-2-yl)phenyl)piperidine-2,6-dione (intermediate A) was synthesized as described above. 3-(4'-(benzo[d]oxazol-4-yl)-2-chloro-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 4-(4-bromophenyl)benzo[d]oxazole according to General Scheme 1.

MS (ESI) m/z 417.1 [M+H]⁺

Example 213. Synthesis of 3-(2-chloro-3'-fluoro-4'-(2-oxopiperidin-1-yl)-[1,1'-biphenyl]-3-yl)piperidine-2,6-dione (Compound 461)

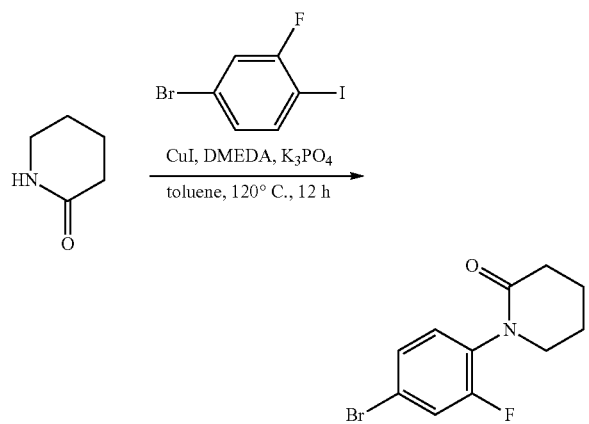

1-(4-bromo-2-fluorophenyl)piperidin-2-one was prepared from piperidin-2-one and 4-bromo-2-fluoro-1-iodobenzene according to General Scheme 7.

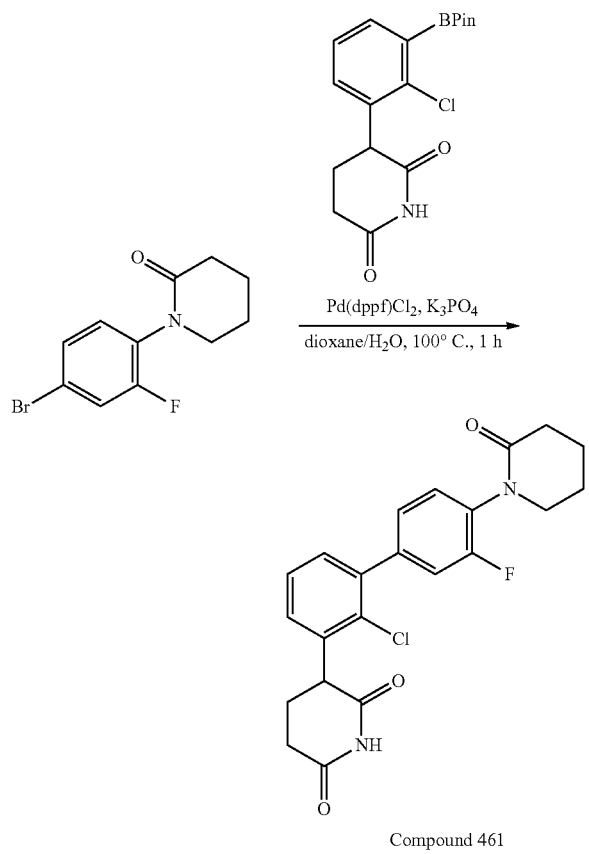

Compound 461

3-(2-chloro-3'-fluoro-4'-(2-oxopiperidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromo-2-fluorophenyl)piperidin-2-one according to General Scheme 1.

$^1$H NMR (400 MHz, DMSO-$d_6$) δ=10.93 (s, 1H), 7.49-7.32 (m, 5H), 7.28 (dd, J=8.0, 1.6 Hz, 1H), 4.36 (dd, J=12.0, 5.2 Hz, 1H), 3.59 (t, J=5.2 Hz, 2H), 2.87-2.73 (m, 1H), 2.61-2.52 (m, 1H), 2.43 (t, J=6.4 Hz, 2H), 2.40-2.26 (m, 1H), 2.10-1.98 (m, 1H), 1.95-1.78 (m, 4H).

MS (ESI) m/z 415.1 [M+H]$^+$

Example 214. Synthesis of 3-(2-chloro-3-(2,3,5,6-tetradeuterio-4-(2-oxo-1-pyridyl)phenyl)phenyl)piperidine-2,6-dione (Compound 462)

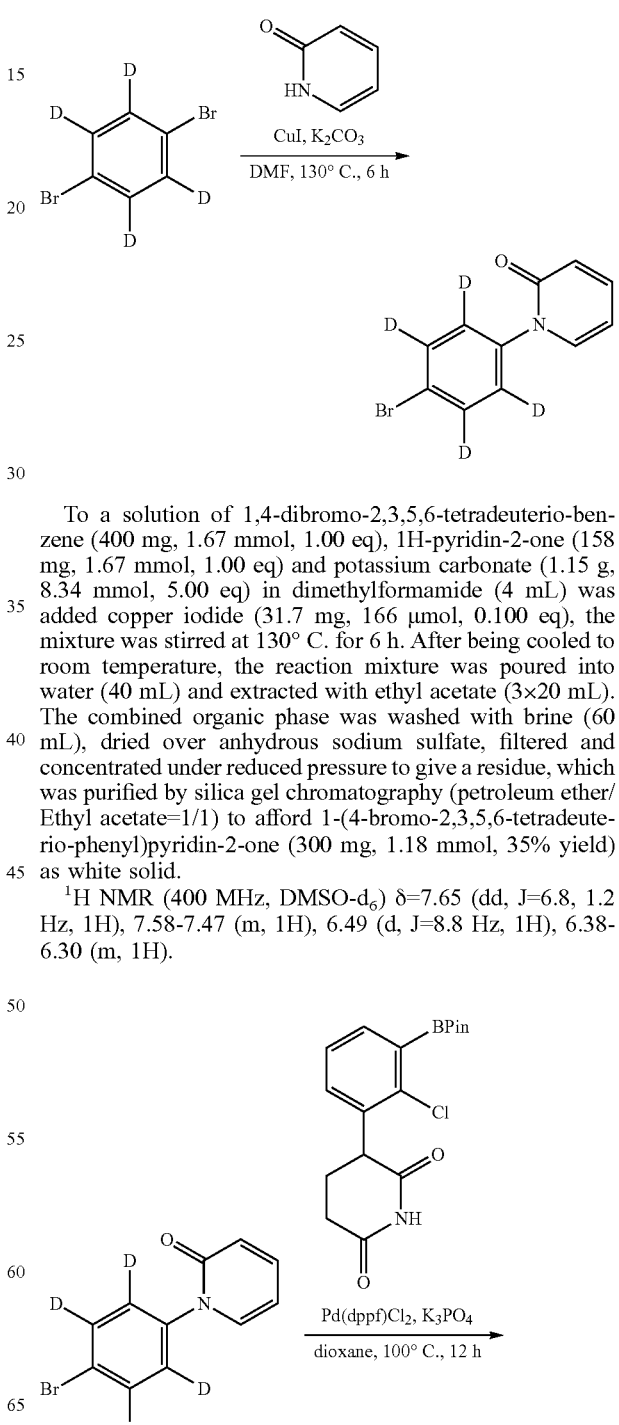

To a solution of 1,4-dibromo-2,3,5,6-tetradeuterio-benzene (400 mg, 1.67 mmol, 1.00 eq), 1H-pyridin-2-one (158 mg, 1.67 mmol, 1.00 eq) and potassium carbonate (1.15 g, 8.34 mmol, 5.00 eq) in dimethylformamide (4 mL) was added copper iodide (31.7 mg, 166 μmol, 0.100 eq), the mixture was stirred at 130° C. for 6 h. After being cooled to room temperature, the reaction mixture was poured into water (40 mL) and extracted with ethyl acetate (3×20 mL). The combined organic phase was washed with brine (60 mL), dried over anhydrous sodium sulfate, filtered and concentrated under reduced pressure to give a residue, which was purified by silica gel chromatography (petroleum ether/Ethyl acetate=1/1) to afford 1-(4-bromo-2,3,5,6-tetradeuterio-phenyl)pyridin-2-one (300 mg, 1.18 mmol, 35% yield) as white solid.

$^1$H NMR (400 MHz, DMSO-$d_6$) δ=7.65 (dd, J=6.8, 1.2 Hz, 1H), 7.58-7.47 (m, 1H), 6.49 (d, J=8.8 Hz, 1H), 6.38-6.30 (m, 1H).

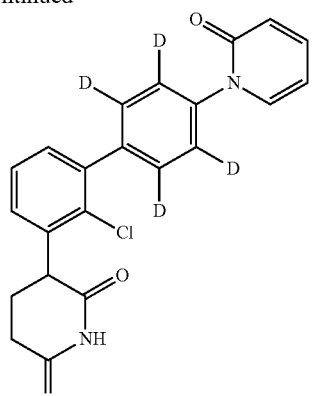

Compound 462

3-(2-chloro-3-(4,4,5,5-tetramethyl-1,3,2-dioxaborolan-2-yl)phenyl)piperidine-2,6-dione (intermediate A) was synthesized as described above. To a solution of 3-(2-chloro-3-(4,4,5,5-tetramethyl-1,3,2-dioxaborolan-2-yl)phenyl)piperidine-2,6-dione (416 mg, 952 µmol, 1.10 eq), 1-(4-bromo-2,3,5,6-tetradeuterio-phenyl)pyridin-2-one (220 mg, 865 µmol, 1.00 eq) and potassium phosphate (551 mg, 2.60 mmol, 3.00 eq) in dioxane (5 mL) was added [1,1-bis(diphenylphosphino)ferrocene]dichloropalladium(II) (63.0 mg, 86.5 µmol, 0.100 eq) under nitrogen atmosphere, the mixture was stirred at 100° C. for 12 h under nitrogen atmosphere. After being cooled to room temperature, the reaction mixture was concentrated to give a residue, which was purified by silica gel chromatography (Petroleum ether/Ethyl acetate=1/0 to 1/1) to afford a crude product, and the crude product was purified by Prep-HPLC (column: Phenomenex luna C18 150×25 mm×10 m; mobile phase: [water (formic acid)-acetonitrile]; gradient: 30%-50% B over 9 min) twice to afford 3-(2-chloro-3-(2,3,5,6-tetradeuterio-4-(2-oxo-1-pyridyl)phenyl)phenyl)piperidine-2,6-dione (190 mg, 478 µmol, 18% yield) as a white solid.

$^1$H NMR (400 MHz, DMSO-$d_6$) δ=10.95 (s, 1H), 7.82-7.72 (m, 1H), 7.59-7.50 (m, 1H), 7.48-7.31 (m, 3H), 6.52 (d, J=9.2 Hz, 1H), 6.40-6.30 (m, 1H), 4.38 (dd, J=12.4, 5.2 Hz, 1H), 2.89-2.76 (m, 1H), 2.60-2.56 (m, 1H), 2.42-2.31 (m, 1H), 2.14-2.03 (m, 1H).

MS (ESI) m/z 397.1 [M+H]$^+$

Example 215. Synthesis of 3-(2-chloro-4'-(2-(difluoromethyl)-6-oxopiperidin-1-yl)-[1,1'-biphenyl]-3-yl)piperidine-2,6-dione (Compound 463)

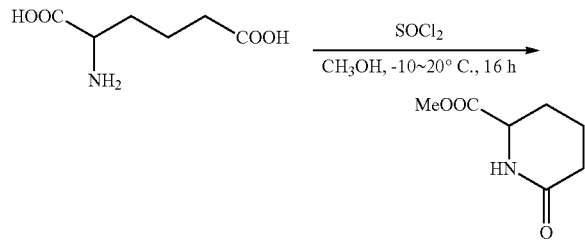

Methanol (30 mL) was cooled to −10° C. before adding dropwise thionyl chloride (7.38 g, 62.1 mmol, 4.51 mL, 2.50 eq), followed by the addition of 2-aminohexanedioic acid (4.00 g, 24.8 mmol, 1.00 eq). The mixture was stirred at 20° C. for 16 h. The reaction mixture was concentrated under reduced pressure to remove methanol, and then diluted with saturated sodium bicarbonate aqueous solution (30 mL) and extracted with ethyl acetate (3×50 mL). The organic layers were dried over sodium sulfate, filtered and concentrated under reduced pressure to afford methyl 6-oxopiperidine-2-carboxylate (2.70 g, crude) as yellow oil. The product was used into the next step without further purification.

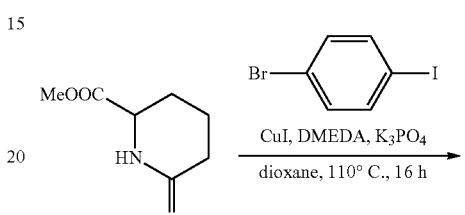

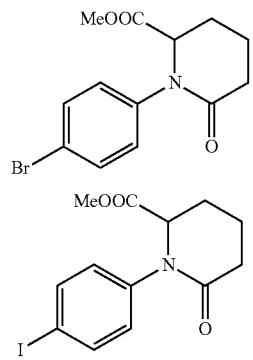

1-(4-bromophenyl)-6-oxopiperidine-2-carboxylate and methyl 1-(4-iodophenyl)-6-oxopiperidine-2-carboxylate were prepared from methyl 6-oxopiperidine-2-carboxylate and 1-bromo-4-iodobenzene according to General Scheme 7.

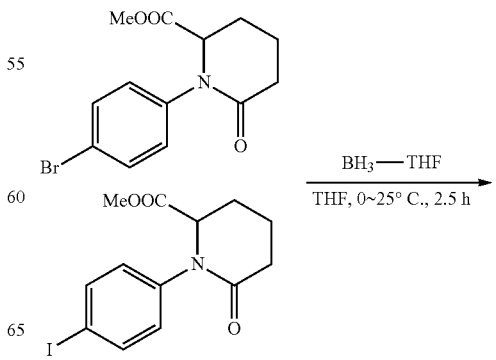

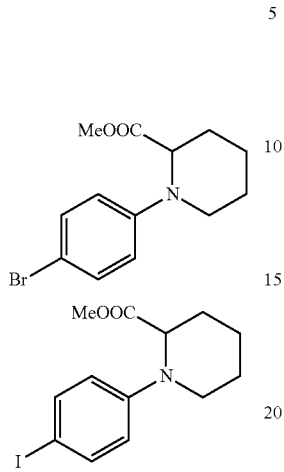

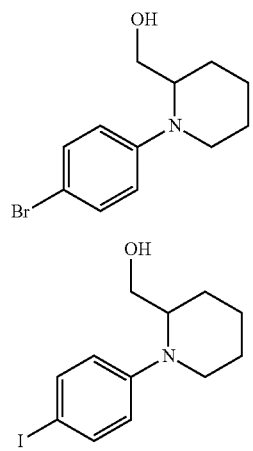

Borane tetrahydrofuran complex (1 M, 21.8 mL, 4.00 eq) was added dropwise in tetrahydrofuran (30 mL) at 0° C. under nitrogen atmosphere. After addition, the mixture was stirred at this temperature for 30 min, and then the mixture (2.50 g, crude) of methyl 1-(4-bromophenyl)-6-oxopiperidine-2-carboxylate and methyl 1-(4-iodophenyl)-6-oxopiperidine-2-carboxylate in tetrahydrofuran (5 mL) was dropwise added at 0° C. The resulting mixture was stirred at 25° C. for 2 h under nitrogen atmosphere. The reaction mixture was quenched by addition ice water (100 mL) at 0° C., and then extracted with ethyl acetate (3×150 mL). The combined organic layers were dried over sodium sulfate, filtered and concentrated under reduced pressure to give a residue. The residue was purified by flash silica gel chromatography (ISCO®; 40 g SepaFlash® Silica Flash Column, Eluent of 0-7% Ethyl acetate/Petroleum ether gradient @ 35 mL/min) to afford the mixture (2.00 g, crude) of methyl 1-(4-bromophenyl)piperidine-2-carboxylate and methyl 1-(4-iodophenyl)piperidine-2-carboxylate in a ratio of approximately 1:2.

lithium tetrahydroborate (2 M, 10.1 mL, 5.00 eq) was dropwise added in tetrahydrofuran (35 mL) at 0° C. under nitrogen atmosphere. After addition, the mixture was stirred at this temperature for 30 min, and then the mixture (2.00 g, crude) of methyl 1-(4-bromophenyl)piperidine-2-carboxylate and methyl 1-(4-iodophenyl)piperidine-2-carboxylate in tetrahydrofuran (5 mL) was added dropwise at 0° C. The resulting mixture was stirred at 20° C. for 15.5 h under nitrogen atmosphere. The reaction mixture was quenched by addition ice water (60 mL) at 0° C. under nitrogen, and then extracted with ethyl acetate (3×100 mL). The combined organic layers were dried over sodium sulfate, filtered and concentrated under reduced pressure to give a residue. The residue was purified by flash silica gel chromatography (ISCO®; 40 g SepaFlash® Silica Flash Column, Eluent of 0-15% Ethyl acetate/Petroleum ether gradient @ 30 mL/min) to afford the mixture (1.50 g, crude) of (1-(4-bromophenyl)piperidin-2-yl)methanol and (1-(4-iodophenyl)piperidin-2-yl)methanol in a ratio of approximately 3:4.

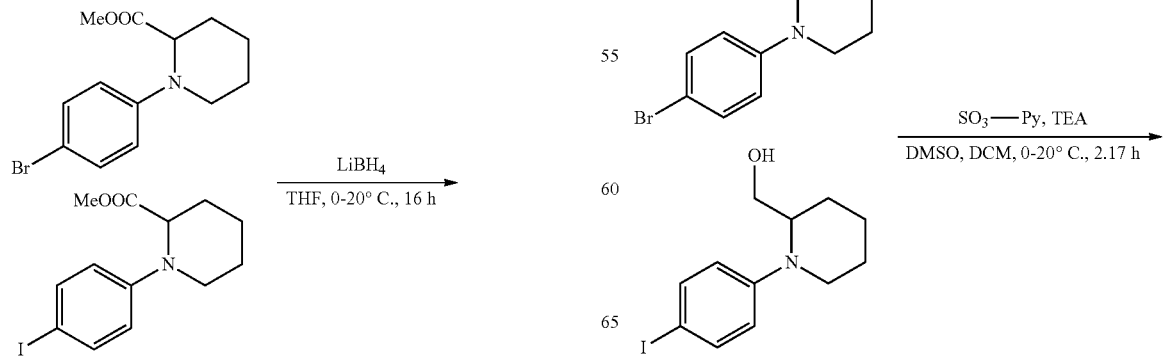

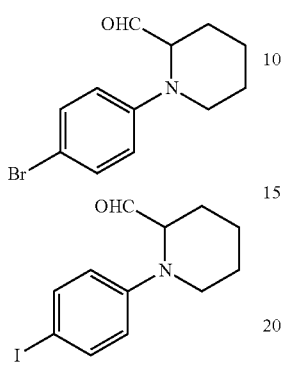

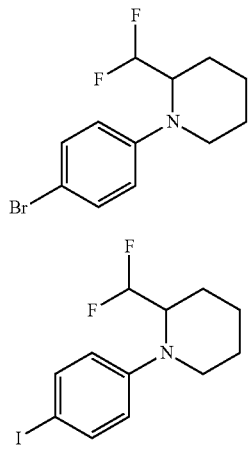

To a solution of the mixture (500 mg, crude) of (1-(4-bromophenyl)piperidin-2-yl)methanol and (1-(4-iodophenyl)piperidin-2-yl)methanol in dichloromethane (8 mL) and dimethylsulfoxide (1 mL) were added dropwise triethylamine (390 mg, 3.85 mmol, 536 μL, 4.00 eq) at 0° C. And then pyridine sulfur trioxide complex (460 mg, 2.89 mmol, 3.00 eq) as a solution in dimethylsulfoxide (1.5 mL) was added dropwise to the reaction mixture at 0° C. over 10 min.

The mixture was stirred at 20° C. for 2 h. The reaction mixture was quenched by addition of saturated sodium bicarbonate aqueous solution (20 mL), and then diluted with water (10 mL) and extracted with ethyl acetate (4×20 mL). The combined organic layers were dried over sodium sulfate, filtered and concentrated under reduced pressure to give a residue, which was purified by flash silica gel chromatography (ISCO®; 4 g SepaFlash® Silica Flash Column, Eluent of 0-10% Ethyl acetate/Petroleum ether gradient @ 10 mL/min) to afford the mixture (420 mg, crude) of 1-(4-bromophenyl)piperidine-2-carbaldehyde and 1-(4-iodophenyl)piperidine-2-carbaldehyde in a ratio of approximately 1:2.

To a solution of the mixture (420 mg, crude) of 1-(4-bromophenyl)piperidine-2-carbaldehyde and 1-(4-iodophenyl)piperidine-2-carbaldehyde in dichloromethane (6 mL) was added dropwise a solution of N,N-diethyl-1,1,1-trifluoro-$\lambda^4$-sulfanamine (439 mg, 2.72 mmol, 360 μL, 4.00 eq) in dichloromethane (4 mL) at 0° C. The resulting mixture was stirred at 25° C. for 2 h under nitrogen atmosphere. The reaction mixture was quenched by addition of saturated sodium bicarbonate aqueous solution (10 mL), and then diluted with water (10 mL) and extracted with ethyl acetate (3×50 mL). The combined organic layers were dried over sodium sulfate, filtered and concentrated under reduced pressure to give a residue. The residue was purified by reversed phase column (C18, flow: 35 mL/min; gradient: from 0-100% acetonitrile (0.1% formic acid) in water over 40 min) to afford the mixture (118 mg, crude) of 1-(4-bromophenyl)-2-(difluoromethyl)piperidine and 2-(difluoromethyl)-1-(4-iodophenyl)piperidine in a ratio of approximately 1:2.

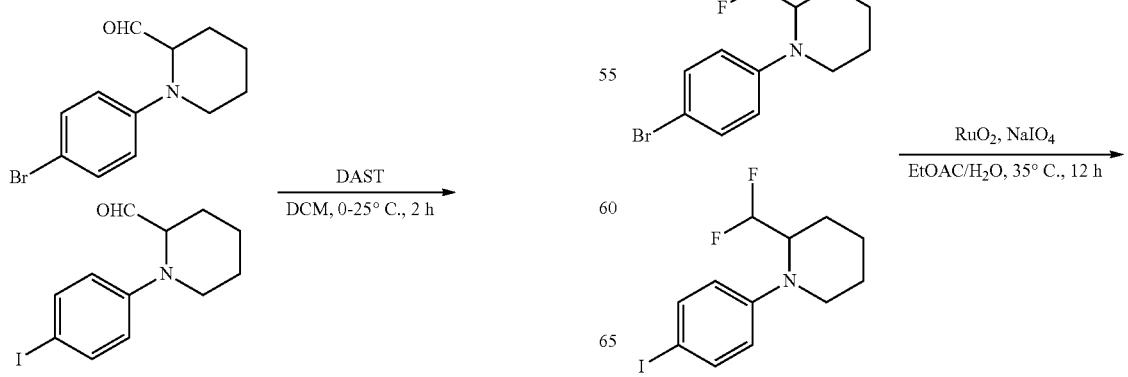

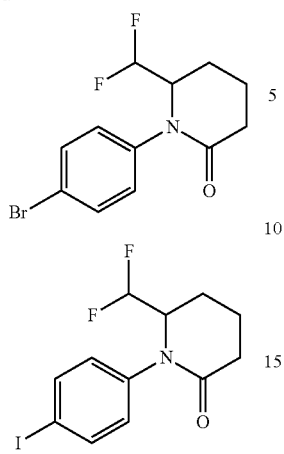

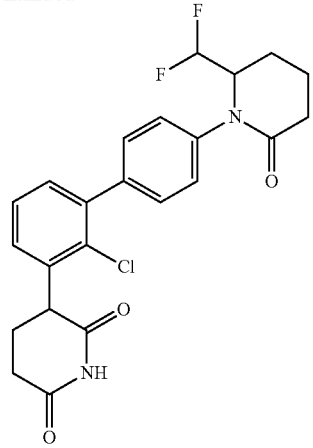

Compound 463

To a solution of sodium periodate (243 mg, 1.13 mmol, 62.8 μL, 5.00 eq) in water (2 mL) was added ruthenium(IV) oxide hydrate (17.1 mg, 113 μmol, 0.500 eq). After addition, ethyl acetate (1 mL) was added, and then the mixture (118 mg, crude) of 1-(4-bromophenyl)-2-(difluoromethyl)piperidine and 2-(difluoromethyl)-1-(4-iodophenyl)piperidine in ethyl acetate (1 mL) was added dropwise at 25° C. The resulting mixture was stirred at 35° C. for 12 h. The reaction mixture was cooled to 25° C., then filtered and quenched by addition sodium sulfurothioate (5 mL) at 0° C., and then diluted with water (5 mL) and extracted with ethyl acetate (3×10 mL). The combined organic layers were dried over sodium sulfate, filtered and concentrated under reduced pressure to give a residue, which was purified by flash silica gel chromatography (ISCO®; 5 g SepaFlash® Silica Flash Column, Eluent of 0-50% Ethyl acetate/Petroleum ether gradient @ 30 mL/min) to afford the mixture (100 mg, crude) of 1-(4-bromophenyl)-6-(difluoromethyl)piperidin-2-one and 6-(difluoromethyl)-1-(4-iodophenyl)piperidin-2-one in a ratio of approximately 1:2.

3-(2-chloro-4'-(2-(difluoromethyl)-6-oxopiperidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-6-(difluoromethyl)piperidin-2-one and 6-(difluoromethyl)-1-(4-iodophenyl)piperidin-2-one according to General Scheme 1.

$^1$H NMR (400 MHz, DMSO-d$_6$) δ=10.92 (s, 1H), 7.46-7.32 (m, 7H), 6.25-5.93 (m, 1H), 4.37-4.33 (m, 2H), 2.85-2.74 (m, 1H), 2.56-2.55 (m, 1H), 2.48-2.46 (m, 1H), 2.45-2.27 (m, 2H), 2.16-1.88 (m, 4H), 1.88-1.72 (m, 1H)

$^1$H NMR (400 MHz, MeOD) δ=7.52-7.46 (m, 2H), 7.42-7.31 (m, 5H), 5.88 (dt, J=55.2, 2.8 Hz, 1H), 4.45-4.26 (m, 2H), 2.87-2.75 (m, 1H), 2.74-2.54 (m, 3H), 2.48-2.37 (m, 1H), 2.28-2.05 (m, 4H), 2.04-1.87 (m, 1H); MS (ESI) m/z 447.1 [M+H]$^+$

Example 216. Synthesis of 3-(2-chloro-4'-(4,4-difluoro-2-oxopiperidin-1-yl)-[1,1'-biphenyl]-3-yl)piperidine-2,6-dione (Compound 464)

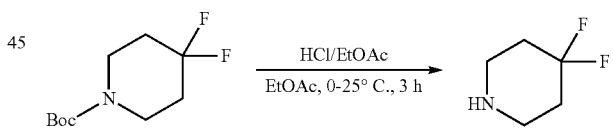

To a solution of tert-butyl 4,4-difluoropiperidine-1-carboxylate (3.60 g, 16.3 mmol, 1.00 eq) in ethyl acetate (10 mL) was added hydrogen chloride/ethyl acetate (4 M, 36 mL) at 0° C. The mixture was stirred at 25° C. for 3 h. The reaction mixture was concentrated under reduced pressure to give compound 4,4-difluoropiperidine hydrochloride (2.51 g, 15.5 mmol, 95% yield) as a yellow solid.

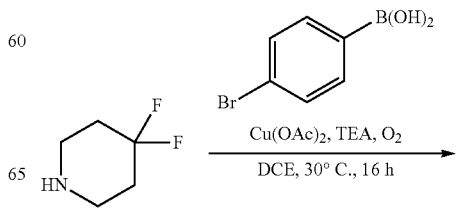

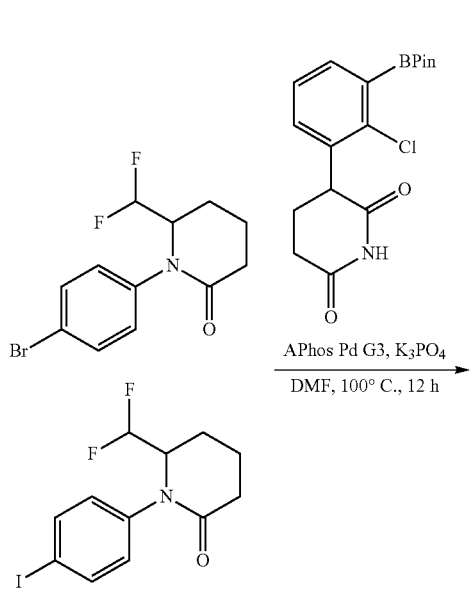

-continued

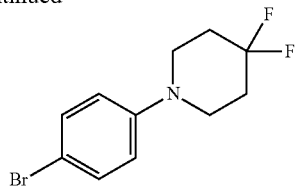

A mixture of 4,4-difluoropiperidine hydrochloride (2.50 g, 15.9 mmol, 1.00 eq), (4-bromophenyl)boronic acid (7.96 g, 39.7 mmol, 2.50 eq), copper acetate (2.88 g, 15.9 mmol, 1.00 eq), triethylamine (8.03 g, 79.3 mmol, 11.0 mL, 5.00 eq) and 4 A MS (100 mg) in 1,2-dichloroethane (100 mL) was degassed and purged with oxygen for three times, and then the mixture was stirred at 30° C. for 16 h under oxygen atmosphere (15 psi). The reaction mixture was filtered and concentrated under reduced pressure to give a residue. The residue was purified by flash silica gel chromatography (ISCO®; 12 g SepaFlash® Silica Flash Column, Eluent of 0-10% Ethyl acetate/Petroleum ether gradient @ 25 mL/min) to afford compound 1-(4-bromophenyl)-4,4-difluoropiperidine (950 mg, 3.27 mmol, 21% yield) as a white solid.

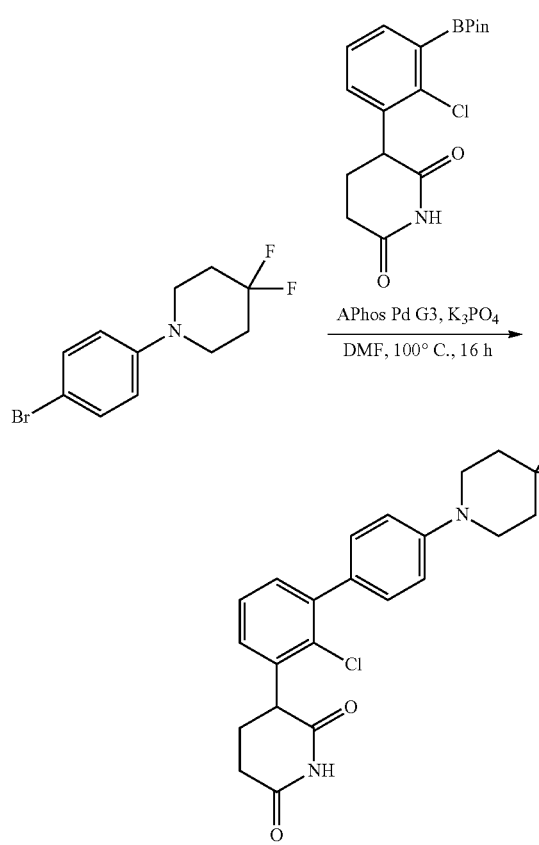

3-(2-chloro-3-(4,4,5,5-tetramethyl-1,3,2-dioxaborolan-2-yl)phenyl)piperidine-2,6-dione (intermediate A) was synthesized as described above. A mixture of 1-(4-bromophenyl)-4,4-difluoropiperidine (300 mg, 1.09 mmol, 1.00 eq), 3-(2-chloro-3-(4,4,5,5-tetramethyl-1,3,2-dioxaborolan-2-yl)phenyl)piperidine-2,6-dione (457 mg, 1.10 mmol, 84% purity, 1.01 eq), methanesulfonato[[4-(N,N-dimethylamino)phenyl]di-tert-butylphosphino](2'-amino-1,1'-biphenyl-2-yl) palladium(II) (69.0 mg, 109 µmol, 0.100 eq) and potassium phosphate (692 mg, 3.26 mmol, 3.00 eq) in dimethylformamide (10 mL) was degassed and purged with nitrogen for three times, and then the mixture was stirred at 100° C. for 16 h under nitrogen atmosphere. The reaction mixture was cooled to 25° C., then filtered and concentrated under reduced pressure to give a residue, which was purified by flash silica gel chromatography (ISCO®; 12 g SepaFlash® Silica Flash Column, Eluent of 0~50% ethyl acetate/petroleum ether gradient @ 25 mL/min) to afford 3-(2-chloro-4'-(4,4-difluoropiperidin-1-yl)-[1,1'-biphenyl]-3-yl)piperidine-2,6-dione (320 mg, 649 µmol, 60% yield) as a gray solid.

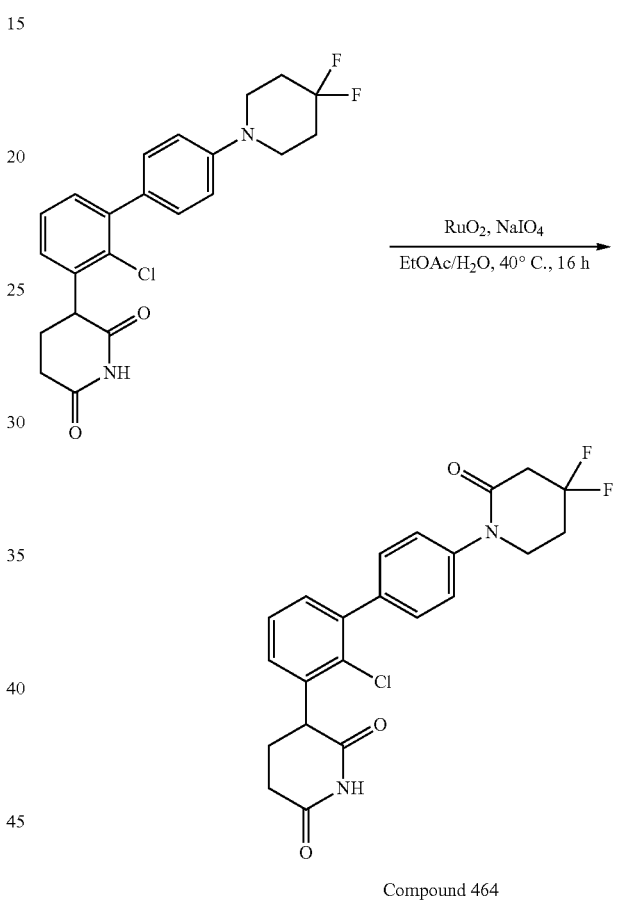

Compound 464

To a solution of dioxoruthenium hydrate (28.9 mg, 191 µmol, 0.400 eq) in water (4 mL) was added sodium periodate (511 mg, 2.39 mmol, 5.00 eq), followed by addition of a solution of 3-(2-chloro-4'-(4,4-difluoropiperidin-1-yl)-[1,1'-biphenyl]-3-yl)piperidine-2,6-dione (200 mg, 477 mol, 1.00 eq) in ethyl acetate (4 mL). The mixture was stirred at 40° C. for 16 h. The reaction mixture was filtered and concentrated under reduced pressure to give a residue, which was purified by flash silica gel chromatography (ISCO®; 4 g SepaFlash® Silica Flash Column, Eluent of 0~50% ethyl acetate/petroleum ether gradient @ 18 mL/min), followed by Prep-HPLC (column: Phenomenex luna C18 150×25 mm×10 m; mobile phase: [water (formic acid)-acetonitrile]; gradient: 30%-60% B over 10 min) to afford 3-(2-chloro-4'-(4,4-difluoro-2-oxopiperidin-1-yl)-[1,1'-biphenyl]-3-yl)piperidine-2,6-dione (39.2 mg, 89.8 µmol, 19% yield) as a white solid.

¹H NMR (400 MHz, DMSO-d₆) δ=10.93 (s, 1H), 7.55-7.28 (m, 7H), 4.36 (dd, J=12.0, 4.8 Hz, 1H), 3.81 (t, J=6.0 Hz, 2H), 3.16 (t, J=14.8 Hz, 2H), 2.88-2.74 (m, 1H), 2.64-2.53 (m, 3H), 2.40-2.29 (m, 1H), 2.13-1.97 (m, 1H).

¹H NMR (400 MHz, CDCl₃) δ=8.14 (s, 1H), 7.47 (d, J=8.0 Hz, 2H), 7.39-7.27 (m, 4H), 7.21 (d, J=6.8 Hz, 1H), 4.32 (dd, J=10.4, 5.6 Hz, 1H), 3.85 (t, J=6.0 Hz, 2H), 3.13 (t, J=14.4 Hz, 2H), 2.87-2.63 (m, 2H), 2.59-2.17 (m, 4H); MS (ESI) m/z 433.2 [M+H]⁺

Example 217. Synthesis of 3-(2-chloro-4'-(7-oxo-5,7-dihydro-6H-pyrrolo[3,4-b]pyridin-6-yl)-[1,1'-biphenyl]-3-yl)piperidine-2,6-dione (Compound 465)

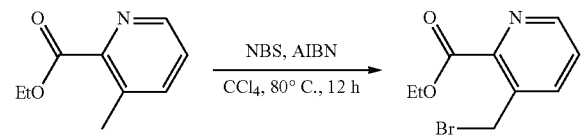

To a solution of ethyl 3-methylpicolinate (2.00 g, 12.1 mmol, 1.00 eq) in carbon tetrachloride (40 mL) was added N-bromosuccinimide (5.39 g, 30.3 mmol, 2.50 eq) and 2,2'-azobis(isobutyronitrile) (4.97 g, 30.3 mmol, 2.50 eq). The mixture was stirred at 80° C. for 12 h.

The reaction mixture was filtered and concentrated under reduced pressure to give a residue, which was purified by column chromatography (SiO₂, petroleum ether/ethyl acetate=100/1 to 15/1) to afford ethyl 3-(bromomethyl)picolinate (1.00 g, 3.07 mmol, 25% yield) as yellow oil.

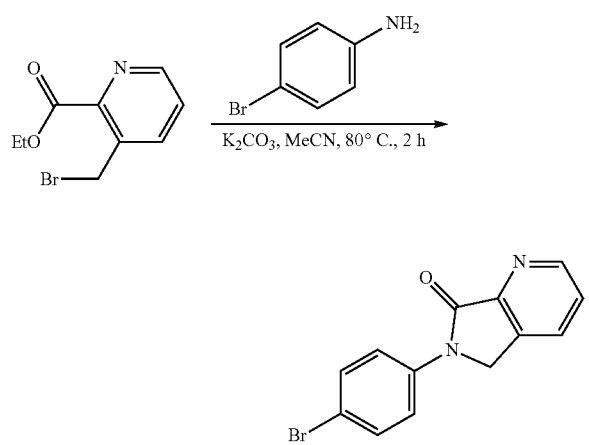

To a solution of ethyl 3-(bromomethyl)picolinate (1.00 g, 3.07 mmol, 1.00 eq) in acetonitrile (10 mL) was added potassium carbonate (1.27 g, 9.22 mmol, 3.00 eq) and 4-bromoaniline (529 mg, 3.07 mmol, 1.00 eq). The mixture was stirred at 80° C. for 2 h. The reaction mixture was filtered and concentrated under reduced pressure to give a residue. The residue was purified by reversed-phase HPLC (C18, 120 g; condition: water/acetonitrile=1/0 to 0/1, 0.1% formic acid) and lyophilized to afford 6-(4-bromophenyl)-5,6-dihydro-7H-pyrrolo[3,4-b]pyridin-7-one (180 mg, 567 μmol, 18% yield) as a brown solid.

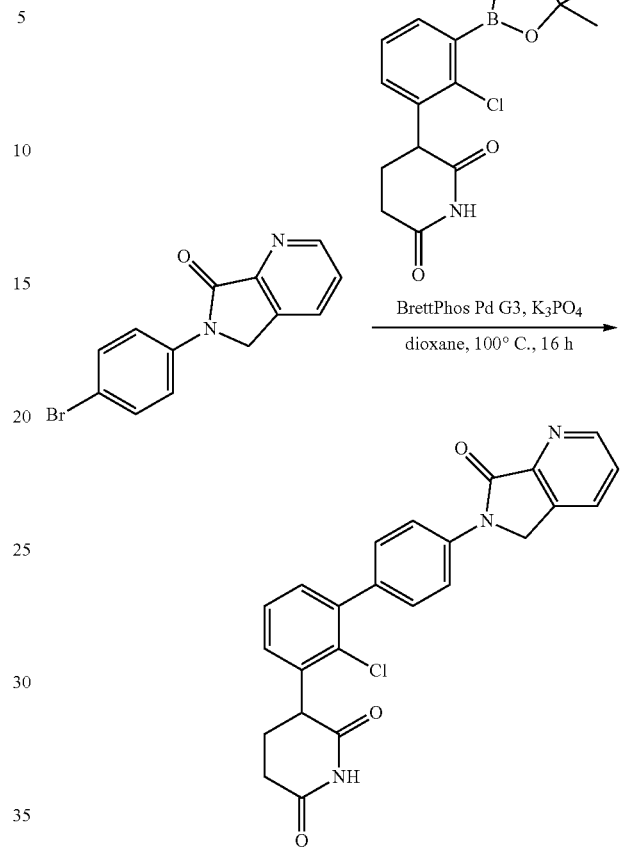

Compound 465

3-(2-chloro-4'-(7-oxo-5,7-dihydro-6H-pyrrolo[3,4-b]pyridin-6-yl)-[1,1'-biphenyl]-3-yl) piperidine-2,6-dione was prepared from 3-(2-chloro-3-(4,4,5,5-tetramethyl-1,3,2-dioxaborolan-2-yl)phenyl)piperidine-2,6-dione (intermediate A) and 6-(4-bromophenyl)-5,6-dihydro-7H-pyrrolo[3,4-b]pyridin-7-one according to General Scheme 1.

¹H NMR (400 MHz, DMSO-d₆) δ=10.95 (s, 1H), 8.81-8.77 (m, 1H), 8.20-8.14 (m, 1H), 8.07-8.01 (m, 2H), 7.67 (dd, J=7.6, 4.8 Hz, 1H), 7.53 (d, J=8.8 Hz, 2H), 7.45-7.40 (m, 1H), 7.39-7.34 (m, 2H), 5.11 (s, 2H), 4.36 (dd, J=12.0, 4.8 Hz, 1H), 2.86-2.75 (m, 1H), 2.58-2.53 (m, 1H), 2.42-2.32 (m, 1H), 2.10-2.02 (m, 1H); MS (ESI) m/z 432.2 [M+H]⁺

Example 218. Synthesis of 3-(2-chloro-4'-(5-oxo-5,7-dihydro-6H-pyrrolo[3,4-b]pyridin-6-yl)-[1,1'-biphenyl]-3-yl)piperidine-2,6-dione (Compound 466)

6-(4-bromophenyl)-6,7-dihydro-5H-pyrrolo[3,4-b]pyridin-5-one was prepared from 6,7-dihydro-5H-pyrrolo[3,4-b]pyridin-5-one and 1,4-dibromobenzene according to General Scheme 7. 3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(5-oxo-5,7-dihydro-6H-pyrrolo[3,4-b]pyridin-6-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 6-(4-bromophenyl)-6,7-dihydro-5H-pyrrolo[3,4-b]pyridin-5-one according to General Scheme 1.

MS (ESI) m/z 432.1 [M+H]+

Example 219. Synthesis of 3-(2-chloro-4'-(4-oxo-1,3-oxazinan-3-yl)-[1,1'-biphenyl]-3-yl)piperidine-2,6-dione (Compound 467)

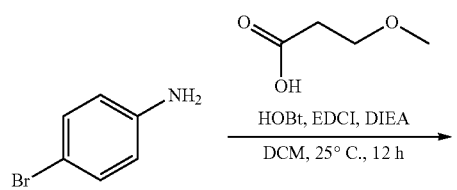

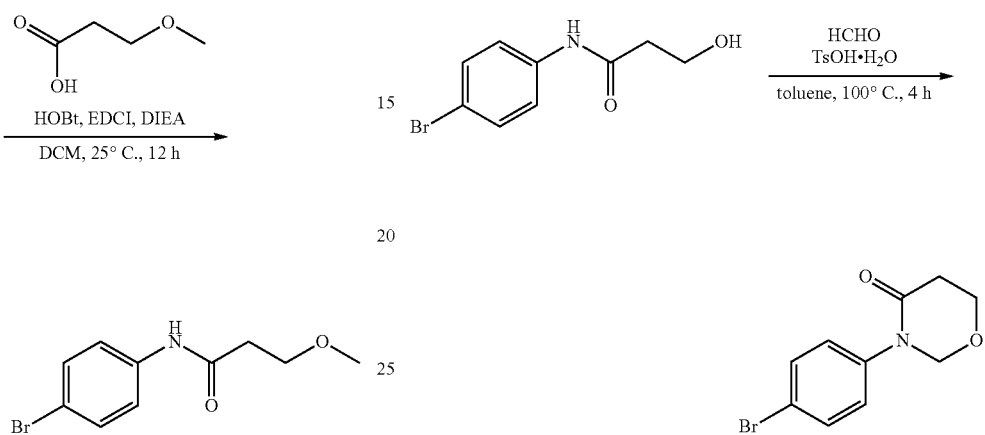

To a solution of 4-bromoaniline (500 mg, 2.91 mmol, 1.00 eq) and 3-methoxypropanoic acid (333 mg, 3.20 mmol, 1.10 eq) in dichloromethane (10 mL) was added 1-hydroxybenzotriazole (471 mg, 3.49 mmol, 1.20 eq), 1-(3-dimethylaminopropyl)-3-ethylcarbodiimide hydrochloride (669 mg, 3.49 mmol, 1.20 eq) and N,N-diisopropylethylamine (1.13 g, 8.72 mmol, 1.52 mL, 3.00 eq). The mixture was stirred at 25° C. for 12 h. Ethyl acetate (40 mL) and water (40 mL) were added and layers were separated. The aqueous phase was extracted with ethyl acetate (3×30 mL). The combined extracts were washed with brine (60 mL), dried over sodium sulfate, filtered and concentrated under vacuum. The residue was purified by flash silica gel chromatography (ISCO®; 10 g SepaFlash® Silica Flash Column, Eluent of 0-100% ethyl acetate/petroleum ether gradient @ 18 mL/min) to give N-(4-bromophenyl)-3-methoxypropanamide (500 mg, 1.74 mmol, 60% yield) as a yellow solid.

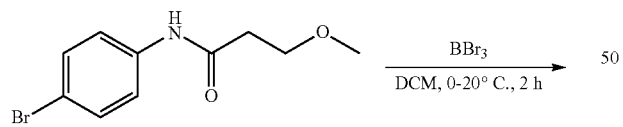

To a solution of N-(4-bromophenyl)-3-methoxypropanamide (400 mg, 1.55 mmol, 1.00 eq) in dichloromethane (4 mL) was added boron tribromide (776 mg, 3.10 mmol, 299 μL, 2.00 eq) at 0° C. The mixture was stirred at 20° C. for 2 h. The reaction was quenched with water (20 mL) and then extracted with ethyl acetate (3×30 mL). The combined extracts were washed with brine (30 mL), dried over sodium sulfate, filtered and concentrated under vacuum to give a residue, which was purified by flash silica gel chromatography (ISCO®; 10 g SepaFlash® Silica Flash Column, Eluent of 0~100% ethyl acetate/petroleum ether gradient @ 20 mL/min) to give N-(4-bromophenyl)-3-hydroxypropanamide (220 mg, 0.901 mmol, 58% yield) as a white solid.

To a solution of N-(4-bromophenyl)-3-hydroxypropanamide (250 mg, 1.02 mmol, 1.00 eq) and polyformaldehyde (250 mg, 8.33 mmol, 8.13 eq) in toluene (5 mL) was added 4-methylbenzenesulfonic acid hydrate (195 mg, 1.02 mmol, 1.00 eq). The mixture was stirred at 100° C. for 4 h. After being cooled to room temperature, ethyl acetate (20 mL) and water (20 mL) were added and layers were separated. The aqueous phase was extracted with ethyl acetate (3×30 mL). The combined extracts were washed with brine (40 mL), dried over sodium sulfate, filtered and concentrated under vacuum to give a residue, which was purified by flash silica gel chromatography (ISCO®; 10 g SepaFlash® Silica Flash Column, Eluent of 0-100% ethyl acetate/petroleum ether gradient @ 20 mL/min) to give 3-(4-bromophenyl)-1,3-oxazinan-4-one (130 mg, 0.508 mmol, 50% yield) as a white solid.

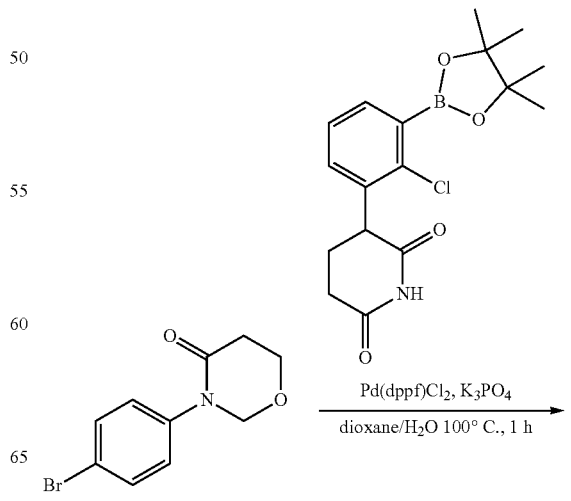

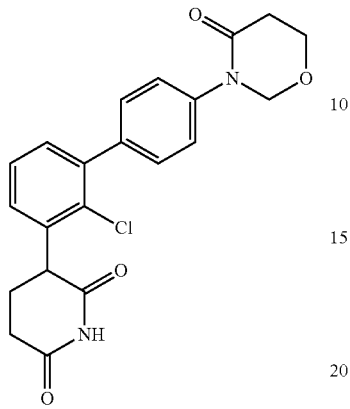

Compound 467

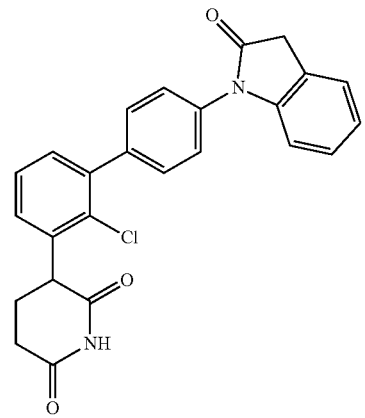

Compound 468

3-(2-chloro-4'-(4-oxo-1,3-oxazinan-3-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 3-(4-bromophenyl)-1,3-oxazinan-4-one according to General Scheme 1.

$^1$H NMR (400 MHz, DMSO-d$_6$) δ=10.91 (s, 1H), 7.44-7.32 (m, 7H), 5.11 (s, 2H), 4.33 (dd, J=12.0, 4.8 Hz, 1H), 4.08 (t, J=6.4 Hz, 2H), 2.71 (d, J=2.0 Hz, 1H), 2.60-2.53 (m, 3H), 2.34-2.33 (m, 1H), 2.05-2.02 (m, 1H).

$^1$H NMR (400 MHz, METHANOL-d$_4$) δ=7.49-7.47 (m, 2H), 7.39-7.36 (m, 5H), 5.14 (s, 2H), 4.44-4.34 (m, 1H), 4.18 (t, J=6.4 Hz, 2H), 2.79 (dd, J=12.4, 5.2 Hz, 1H), 2.72-2.68 (m, 3H), 2.42 (dd, J=12.8, 4.4 Hz, 1H), 2.22 (d, J=3.6 Hz, 1H); MS (ESI) m/z 399.1 [M+H]$^+$

Example 220. Synthesis of 3-(2-chloro-4'-(2-oxoindolin-1-yl)-[1,1'-biphenyl]-3-yl)piperidine-2,6-dione (Compound 468)

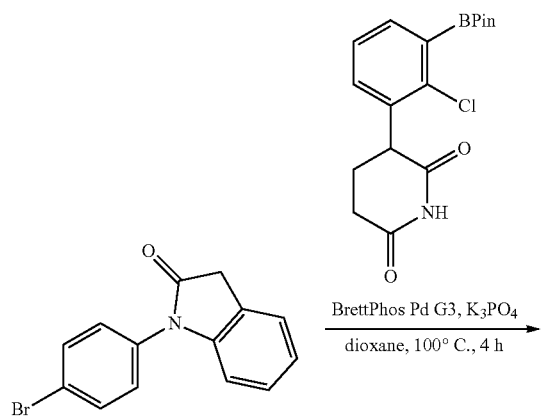

3-(2-chloro-4'-(2-oxoindolin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)indolin-2-one according to General Scheme 1.

$^1$H NMR (400 MHz, DMSO-d$_6$) δ=10.95 (s, 1H), 7.64-7.59 (m, 2H), 7.57-7.51 (m, 2H), 7.48-7.36 (m, 4H), 7.26 (t, J=7.6 Hz, 1H), 7.14-7.06 (m, 1H), 6.83 (d, J=8.0 Hz, 1H), 4.39 (dd, J=12.0, 5.2 Hz, 1H), 3.80 (s, 2H), 2.88-2.76 (m, 1H), 2.60-2.55 (m, 1H), 2.44-2.30 (m, 1H), 2.13-2.04 (m, 1H); MS (ESI) m/z 431.2 [M+H]$^+$

Example 221. Synthesis of 3-(2-chloro-4'-(2-(difluoromethyl)piperidin-1-yl)-[1,1'-biphenyl]-3-yl)piperidine-2,6-dione (Compound 469)

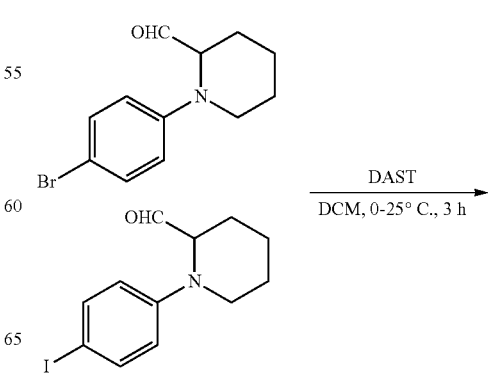

583
-continued

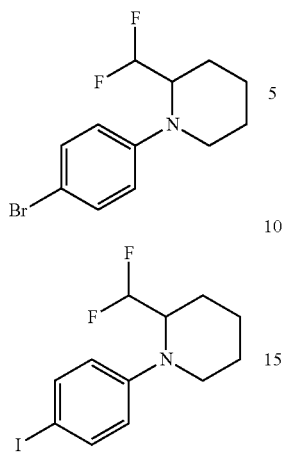

To a solution of the mixture (400 mg, crude) of 1-(4-bromophenyl)piperidine-2-carbaldehyde and 1-(4-iodophenyl)piperidine-2-carbaldehyde in dichloromethane (3 mL) was added dropwise N,N-diethyl-1,1,1-trifluoro-4-sulfanamine (260 mg, 1.61 mmol, 213 µL, 2.00 eq) as a solution in dichloromethane (2 mL) at 0° C. The resulting mixture was stirred at 25° C. for 3 h under nitrogen atmosphere. The reaction mixture was quenched by addition of saturated sodium bicarbonate aqueous solution (10 mL), and then diluted with water (10 mL) and extracted with ethyl acetate (3×50 mL). The combined organic layers were dried over sodium sulfate, filtered and concentrated under reduced pressure to give a residue. The residue was purified by reversed phase column (formic acid condition; C18, flow: 35 mL/min; gradient: from 0-80% acetonitrile (0.1% formic acid) in water over 40 min) to afford the mixture (100 mg, crude) of 1-(4-bromophenyl)-2-(difluoromethyl)piperidine and 2-(difluoromethyl)-1-(4-iodophenyl)piperidine in a ratio of approximately 1:2.

584
-continued

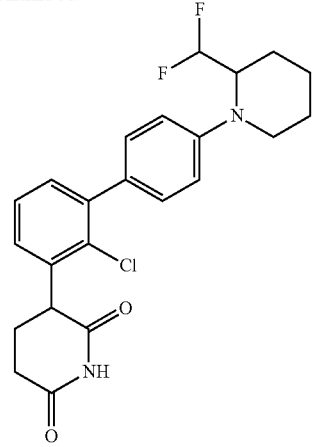

Compound 469

3-(2-chloro-4'-(2-(difluoromethyl)piperidin-1-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)-2-(difluoromethyl)piperidine and 2-(difluoromethyl)-1-(4-iodophenyl)piperidine according to General Scheme 1.

$^1$H NMR (400 MHz, DMSO-d$_6$) δ=10.89 (s, 1H), 7.40-7.31 (m, 1H), 7.30-7.22 (m, 4H), 7.00 (d, J=8.8 Hz, 2H), 6.34 (dt, J=55.6, 5.2 Hz, 1H), 4.32 (dd, J=12.0, 5.2 Hz, 1H), 4.30-4.20 (m, 1H), 3.60 (d, J=13.2 Hz, 1H), 3.15 (t, J=11.2 Hz, 1H), 2.88-2.71 (m, 1H), 2.61-2.53 (m, 1H), 2.35-2.24 (m, 1H), 2.11-2.00 (m, 1H), 1.93-1.82 (m, 1H), 1.77-1.52 (m, 5H); MS (ESI) m/z 433.1 [M+H]$^+$

Example 222. Synthesis of 3-(2-chloro-3'-fluoro-4'-(2-oxopyridin-1(2H)-yl)-[1,1'-biphenyl]-3-yl)piperidine-2,6-dione (Compound 470)

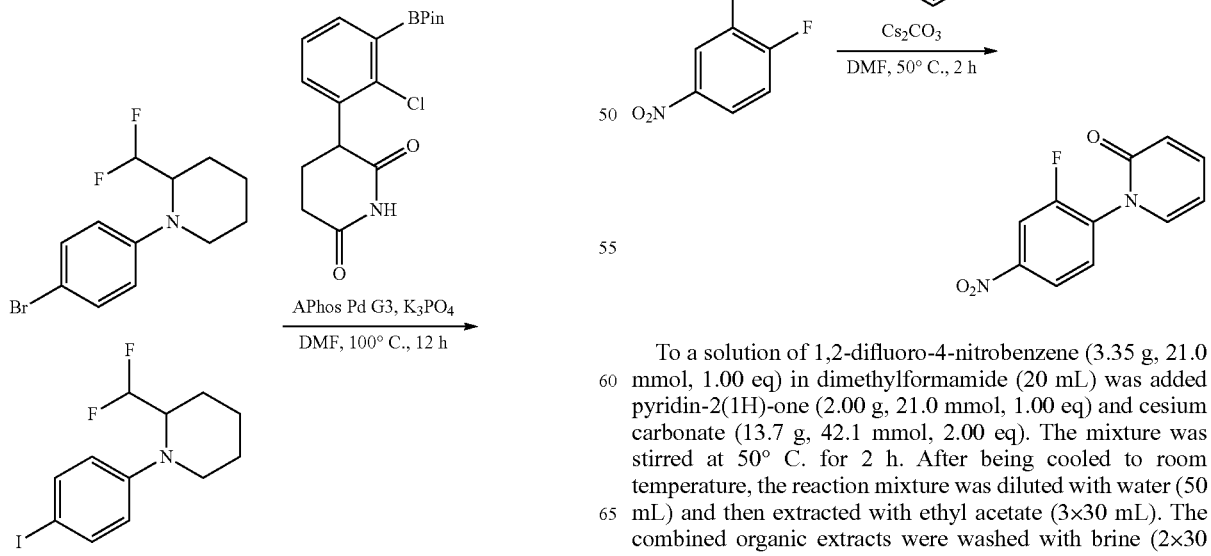

To a solution of 1,2-difluoro-4-nitrobenzene (3.35 g, 21.0 mmol, 1.00 eq) in dimethylformamide (20 mL) was added pyridin-2(1H)-one (2.00 g, 21.0 mmol, 1.00 eq) and cesium carbonate (13.7 g, 42.1 mmol, 2.00 eq). The mixture was stirred at 50° C. for 2 h. After being cooled to room temperature, the reaction mixture was diluted with water (50 mL) and then extracted with ethyl acetate (3×30 mL). The combined organic extracts were washed with brine (2×30 mL), dried over sodium sulfate and filtered. The filtrate was concentrated under reduced pressure. The residue was purified by column chromatography on silica gel (petroleum ether:ethyl acetate=1:1) to give 1-(2-fluoro-4-nitrophenyl)pyridin-2(1H)-one (1.60 g, 5.88 mmol, 28% yield) as a yellow solid.

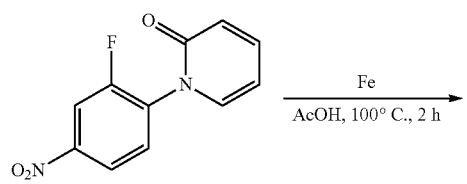

To a solution of 1-(2-fluoro-4-nitrophenyl)pyridin-2(1H)-one (1.00 g, 4.27 mmol, 1.00 eq) in acetic acid (20 mL) was added iron powder (0.715 g, 12.8 mmol, 3.00 eq). The mixture was stirred at 100° C. for 2 h. After being cooled to room temperature, the pH was adjusted to 7 with sodium bicarbonate. The reaction mixture was diluted with water (50 mL) and then extracted with ethyl acetate (3×30 mL). The combined organic extracts were washed with brine (2×30 mL), dried over sodium sulfate and filtered. The filtrate was concentrated under reduced pressure. The residue was purified by Prep-HPLC (column: Phenomenex Luna C18 150 mm×25 mm×10 µm; mobile phase: [water (formic acid)-acetonitrile]; gradient: 13%-43% B over 9 min). The desired fraction was collected and lyophilized to give 1-(4-amino-2-fluorophenyl)pyridin-2(1H)-one (0.400 g, 1.76 mmol, 41% yield) as a yellow solid.

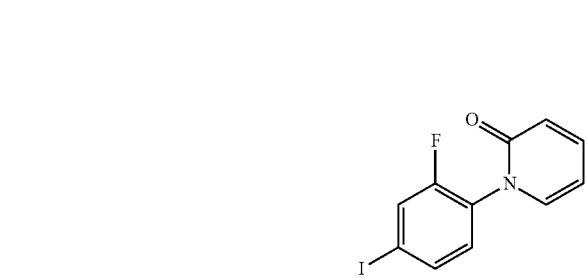

To a solution of 1-(4-amino-2-fluorophenyl)pyridin-2(1H)-one (0.100 g, 0.489 mmol, 1.00 eq) in hydrochloric acid (5 M, 2 mL, 20.4 eq) was added sodium nitrite (0.0510 g, 0.734 mmol, 1.50 eq) in water (0.4 mL) at 0° C. The reaction mixture was stirred for 30 min at the same temperature. A solution of potassium iodide (0.163 g, 0.979 mmol, 2.00 eq) in water (0.4 mL) was added slowly to the above reaction mixture over a period of 30 min at 0° C. The resulting reaction mixture was allowed to warm to 25° C. and stirred for 4 h. Ethyl acetate (20 mL) and water (20 mL) were added and layers were separated. The aqueous phase was extracted with ethyl acetate (3×20 mL). Combined extracts were washed with brine (30 mL), dried over sodium sulfate, filtered, and concentrated under vacuum. The residue was purified by flash silica gel chromatography (ISCO®; 4 g SepaFlash® Silica Flash Column, Eluent of 0~100% ethyl acetate/petroleum ether gradient @ 20 mL/min) to give 1-(2-fluoro-4-iodophenyl)pyridin-2(1H)-one (0.0900 g, 0.285 mmol, 58% yield) as a yellow solid.

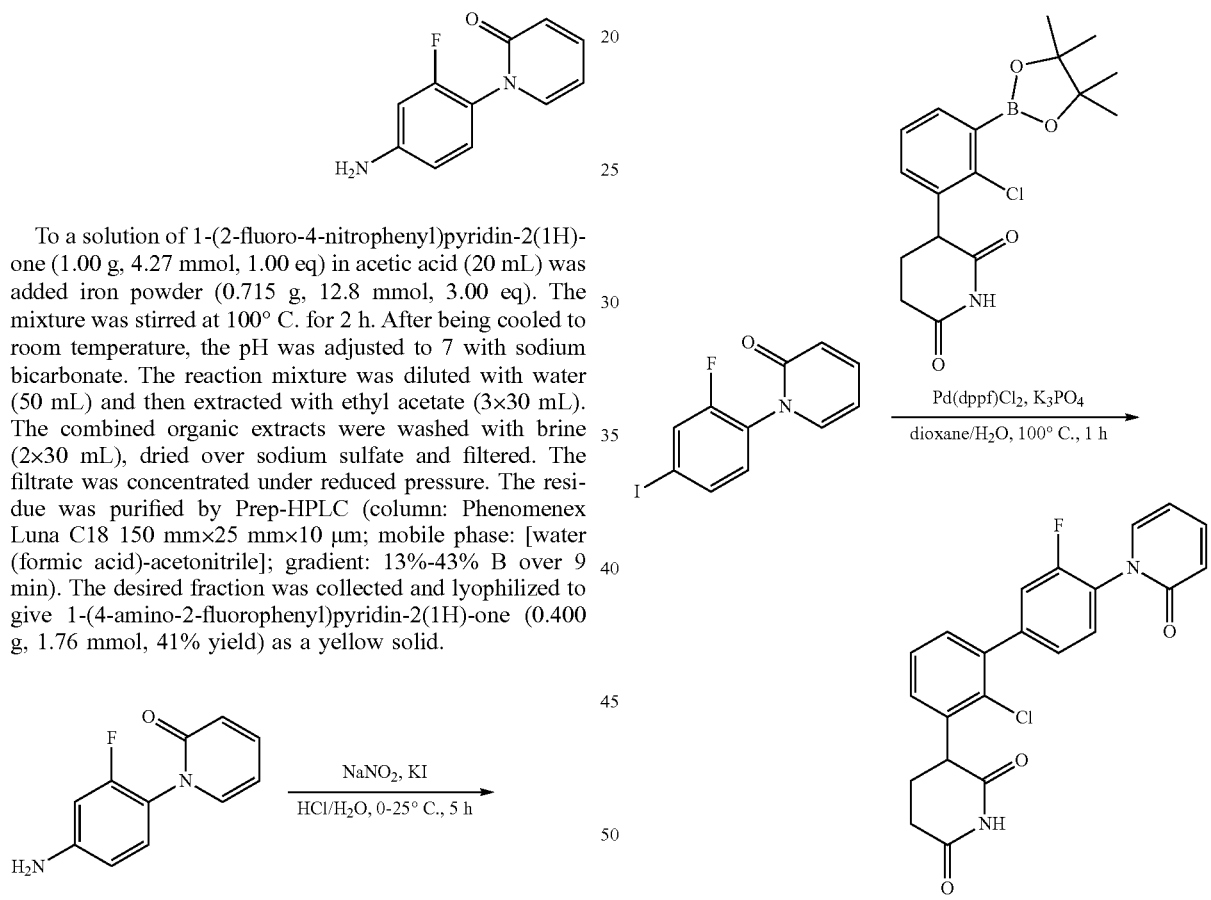

Compound 470

3-(2-chloro-3'-fluoro-4'-(2-oxopyridin-1(2H)-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(2-fluoro-4-iodophenyl)pyridin-2(1H)-one according to General Scheme 1.

$^1$H NMR (400 MHz, DMSO-d$_6$) δ=10.94 (s, 1H), 7.73 (dd, J=6.8, 1.6 Hz, 1H), 7.62-7.50 (m, 3H), 7.48-7.38 (m, 4H), 6.54 (d, J=9.2 Hz, 1H), 6.41-6.32 (m, 1H), 4.38 (dd, J=12.0, 5.2 Hz, 1H), 2.87-2.75 (m, 1H), 2.55-2.52 (m, 1H), 2.40-2.30 (m, 1H), 2.11-2.00 (m, 1H) MS (ESI) m/z 411.1 [M+H]$^+$

Example 223. Synthesis of 3-(2-chloro-4'-(2-oxopyrimidin-1(2H)-yl)-[1,1'-biphenyl]-3-yl)piperidine-2,6-dione (Compound 471)

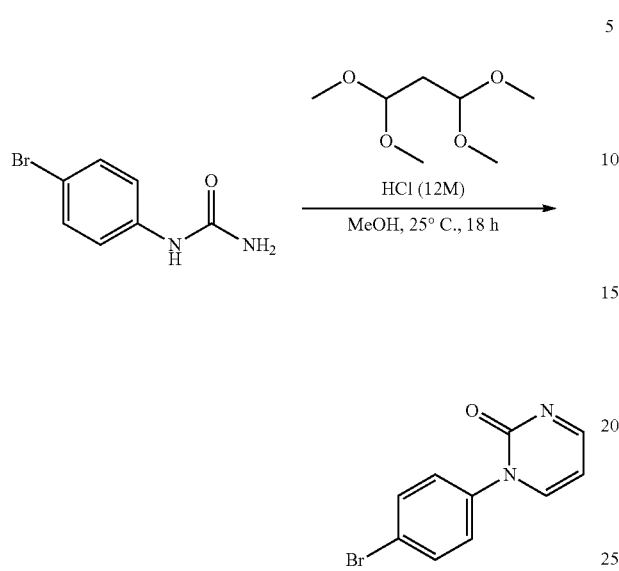

To a solution of 1-(4-bromophenyl)urea (5.00 g, 23.3 mmol, 1.00 eq) in methyl alcohol (20 mL) were added 1,1,3,3-tetramethoxypropane (7.64 g, 46.5 mmol, 7.70 mL, 2.00 eq) and hydrochloric acid (12 M, 9 mL, 4.65 eq). The mixture was stirred at 25° C. for 18 h. The pH was basified to 8 with saturated sodium bicarbonate aqueous solution. The reaction mixture was extracted with dichloromethane (3×20 mL). Hydrochloric acid (2M, 20 ml) was added to the combined organic phase and then extracted with dichloromethane (3×20 mL). The aqueous layer was adjust to pH=7 with saturated potassium carbonate aqueous solution and extracted with a further portion of dichloromethane (30 ml). The organic layer was dried over anhydrous sodium sulfate, filtrate and concentrated under reduced pressure to give a residue, which was purified by column chromatography on silica gel (100% ethyl acetate) to give 1-(4-bromophenyl)pyrimidin-2(1H)-one (0.500 g, 1.59 mmol, 7% yield, 80% purity) as a yellow solid.

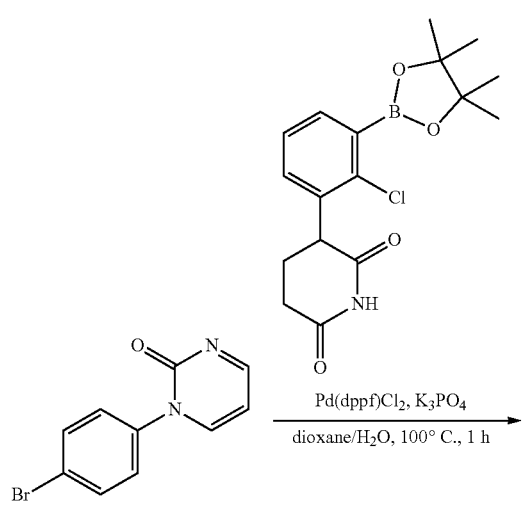

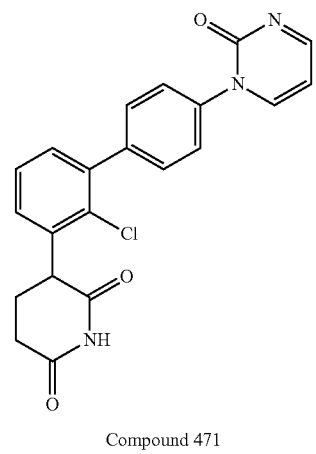

Compound 471

3-(2-chloro-4'-(2-oxopyrimidin-1(2H)-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(4-bromophenyl)pyrimidin-2(1H)-one according to General Scheme 1.

$^1$H NMR (400 MHz, DMSO-$d_6$) δ=10.93 (s, 1H), 8.69 (dd, J=4.0, 2.8 Hz, 1H), 8.29 (dd, J=6.4, 2.8 Hz, 1H), 7.61-7.56 (m, 4H), 7.43-7.36 (m, 3H), 6.56 (dd, J=6.4, 4.0 Hz, 1H), 4.37 (dd, J=12.0, 5.2 Hz, 1H), 2.85-2.76 (m, 1H), 2.59-2.57 (m, 1H), 2.37-2.33 (m, 1H), 2.10-2.03 (m, 1H).

MS (ESI) m/z 394.0 [M+H]$^+$

Example 224. Synthesis of 3-(2-chloro-4'-(oxazol-2-ylmethyl)-[1,1'-biphenyl]-3-yl)piperidine-2,6-dione (Compound 472)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(oxazol-2-ylmethyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 2-(4-bromobenzyl)oxazole according to General Scheme 1.

MS (ESI) m/z 381.0 [M+H]$^+$

Example 225. Synthesis of 3-(2-chloro-4'-((5-methyl-1,2,4-oxadiazol-3-yl)methyl)-[1,1'-biphenyl]-3-yl)piperidine-2,6-dione (Compound 473)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-((5-methyl-1,2,4-oxadiazol-3-yl)methyl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione and 3-[(4-bromophenyl)-methyl]-5-methyl-1,2,4-oxadiazole according to General Scheme 1.

MS (ESI) m/z 396.1 [M+H]$^+$

Example 226. Synthesis of 3-(2-chloro-3-(2-(2-oxopyridin-1(2H)-yl)pyrimidin-5-yl)phenyl)piperidine-2,6-dione (Compound 474)

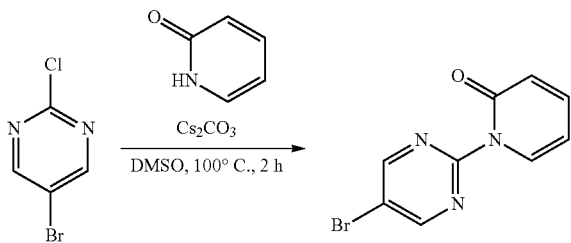

To a solution of 5-bromo-2-chloro-pyrimidine (1.00 g, 5.17 mmol, 1.00 eq) in dimethyl sulfoxide (20 mL) was added 1H-pyridin-2-one (0.541 g, 5.69 mmol, 1.10 eq), followed by addition of cesium carbonate (3.37 g, 10.3 mmol, 2.00 eq) at 25° C. The reaction was stirred at 100° C. for 2 h under nitrogen atmosphere. After being cooled to room temperature, the mixture was diluted with water (20 mL) and extracted with ethyl acetate (3×20 mL). The combined organic layers were washed with brine (3×20 mL), dried over anhydrous sodium sulfate and concentrated under vacuum to give a residue, which was purified by column chromatography (silica, petroleum ether:ethyl acetate=5:1 to 1:2) to give 1-(5-bromopyrimidin-2-yl)pyridin-2(1H)-one (0.450 g, 1.70 mmol, 33% yield) as a white solid.

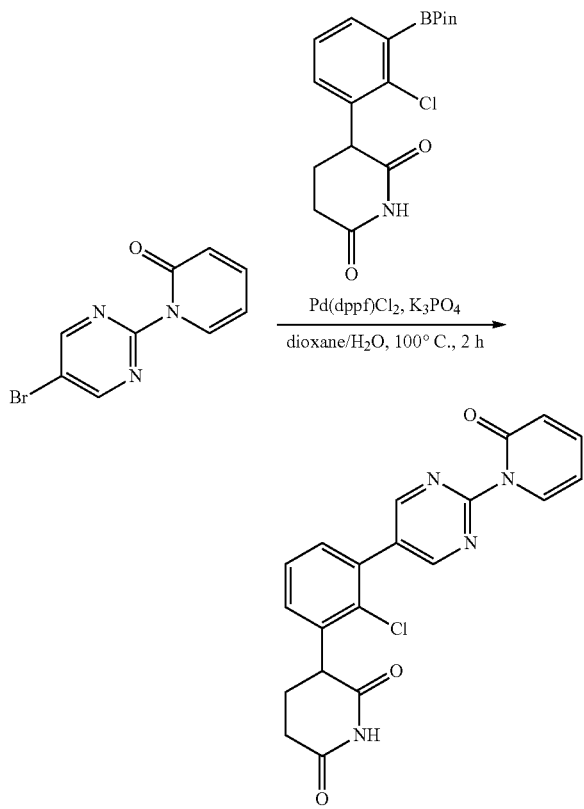

Compound 474

3-(2-chloro-3-(2-(2-oxopyridin-1(2H)-yl)pyrimidin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 1-(5-bromopyrimidin-2-yl)pyridin-2-one according to General Scheme 1.
$^1$H NMR (400 MHz, DMSO-$d_6$) δ=10.96 (s, 1H), 9.13 (s, 2H), 7.86 (dd, J=8.4, 2.0 Hz, 1H), 7.58-7.51 (m, 4H), 6.54 (d, J=9.2 Hz, 1H), 6.37 (dt, J=6.8, 1.2 Hz, 1H), 4.41 (dd, J=12.4, 5.2 Hz, 1H), 2.88-2.77 (m, 1H), 2.60-2.57 (m, 1H), 2.43-2.37 (m, 1H), 2.12-2.07 (m, 1H); MS (ESI) m/z 395.1 [M+H]$^+$ Example 227. Synthesis of N-(2'-chloro-3'-(2,6-dioxopiperidin-3-yl)-[1,1'-biphenyl]-4-yl)-N, 1-dimethyl-1H-pyrazole-3-carboxamide (Compound 475)

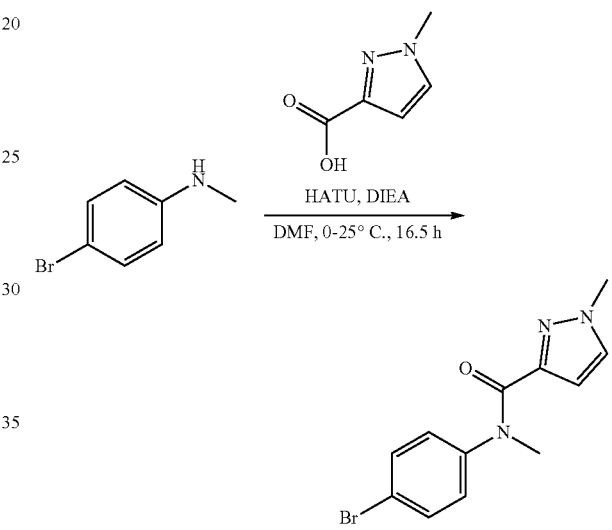

To a solution of 1-methyl-1H-pyrazole-3-carboxylic acid (746 mg, 5.92 mmol, 1.10 eq) in N,N-dimethylformamide (10 mL) was added 2-(3H-[1,2,3]triazolo[4,5-b]pyridin-3-yl)-1,1,3,3-tetramethyluronium hexafluorophosphate(V) (2.35 g, 6.18 mmol, 1.15 eq) and N-ethyl-N-isopropylpropan-2-amine (799 mg, 6.18 mmol, 1.15 eq) at 0° C. The mixture was stirred at 25° C. for 0.5 h. Then 4-bromo-N-methylaniline (1.00 g, 5.37 mmol, 1.00 eq) was added. The mixture was stirred at 25° C. for 16 h. The mixture was diluted with water (30 mL) and extracted with ethyl acetate (3×30 mL). The combined organic layers were washed with saturated sodium hydrogen carbonate (3×30 mL), dried over sodium sulfate, filtered and concentrated under reduced pressure to give a residue, which was purified by flash silica gel chromatography (ISCO®; 20 g SepaFlash® Silica Flash Column, Eluent of 50-60% Ethyl acetate/Petroleum ether gradient @ 60 mL/min) followed by reversed phase column (C18: 80 g, flow: 80 mL/min; gradient: from 60-70% water (0.1% formic acid) in acetonitrile over 65 min) and concentrated under reduced pressure to afford N-(4-bromophenyl)-N, 1-dimethyl-1H-pyrazole-3-carboxamide (650 mg, 2.17 mmol, 40% yield) as colorless oil.

3-(2-chloro-3-(4,4,5,5-tetramethyl-1,3,2-dioxaborolan-2-yl)phenyl)piperidine-2,6-dione (intermediate A) was synthesized as described above. N-(2'-chloro-3'-(2,6-dioxopiperidin-3-yl)-[1,1'-biphenyl]-4-yl)-N, 1-dimethyl-1H-pyrazole-3-carboxamide was prepared from 3-(2-chloro-3-(4,4,5,5- tetramethyl-1,3,2-dioxaborolan-2-yl)phenyl)piperidine-2,6-dione and N-(4-bromophenyl)-N, 1-dimethyl-1H-pyrazole-3-carboxamide according to General Scheme 1.

MS (ESI) m/z. 437.0 [M+H]+

Example 228. Synthesis of 3-(2-chloro-4'-(2-(trifluoromethyl)piperidin-1-yl)-[1,1'-biphenyl]-3-yl)piperidin-2-one (Compound 476)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-4'-(2-(trifluoromethyl)piperidin-1-yl)-[1,1'-biphenyl]-3-yl)piperidin-2-one was prepared from 3-(2-chloro-3-(4,4,5,5-tetramethyl-1,3,2-dioxaborolan-2-yl)phenyl)piperidine-2,6-dione and 1-(4-bromophenyl)-2-(trifluoromethyl)piperidine according to General Scheme 1.

MS (ESI) m/z 451.2 [M+H]+

Example 229. Synthesis of 3-(2-chloro-3-(2-oxo-2H-[1,2'-bipyridin]-5'-yl)phenyl)piperidine-2,6-dione (Compound 477)

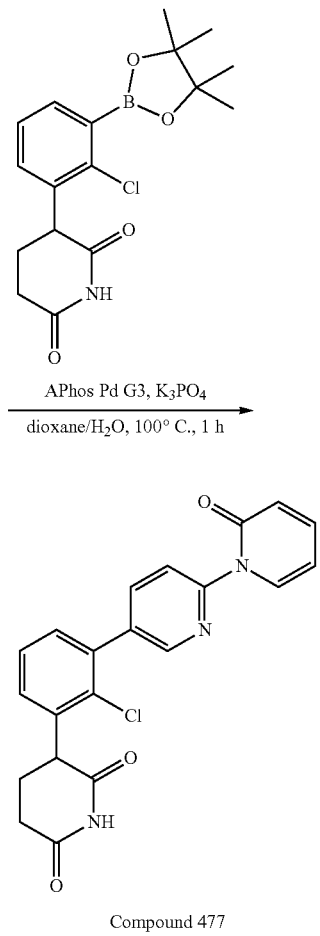

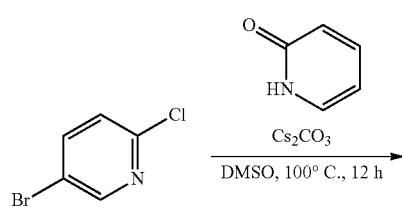

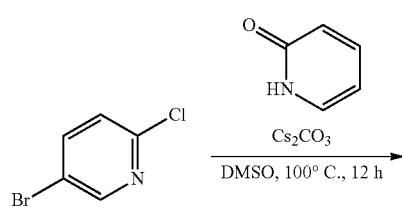

To a solution of 5-bromo-2-chloropyridine (500 mg, 2.60 mmol, 1.00 eq) and pyridin-2(1H)-one (272 mg, 2.86 mmol, 1.10 eq) in dimethylsulfoxide (10 mL) was added cesium carbonate (1.69 g, 5.20 mmol, 2.00 eq), then the mixture was stirred at 100° C. for 12 h. After being cooled to room temperature, ethyl acetate (40 mL) and water (40 mL) were added and layers were separated. The aqueous phase was extracted with ethyl acetate (3×30 mL). The combined extracts were washed with brine (30 mL), dried over anhydrous sodium sulfate, filtered, and concentrated under vacuum. The residue was purified by flash silica gel chromatography (ISCO®; 20 g SepaFlash® Silica Flash Column, eluent of 0-100% ethyl acetate/petroleum ether gradient at 40 mL/min) to give 5'-bromo-2H-[1,2'-bipyridin]-2-one (340 mg, 1.34 mmol, 52% yield) as a white solid.

Compound 477

3-(2-chloro-3-(2-oxo-2H-[1,2'-bipyridin]-5'-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5'-bromo-2H-[1,2'-bipyridin]-2-one according to General Scheme 1.

1H NMR (400 MHz, DMSO-$d_6$) δ=10.95 (s, 1H), 8.65 (d, J=2.4 Hz, 1H), 8.08 (dd, J=8.4, 2.4 Hz, 1H), 7.98 (dd, J=7.2, 1.6 Hz, 1H), 7.91 (d, J=8.4 Hz, 1H), 7.56 (ddd, J=9.2, 6.8, 2.0 Hz, 1H), 7.50-7.42 (m, 3H), 6.55 (d, J=9.2 Hz, 1H), 6.45-6.35 (m, 1H), 4.39 (dd, J=12.0, 5.2 Hz, 1H), 2.79 (dd, J=12.4, 5.2 Hz, 1H), 2.61-2.53 (m, 1H), 2.39-2.35 (m, 1H), 2.12-2.02 (m, 1H).

MS (ESI) m/z 394.1 [M+H]+

Example 230. Synthesis of 3-(2-chloro-4'-(3-oxo-2-azabicyclo[3.1.0]hexan-2-yl)-[1,1'-biphenyl]-3-yl)piperidine-2,6-dione (Compound 478)

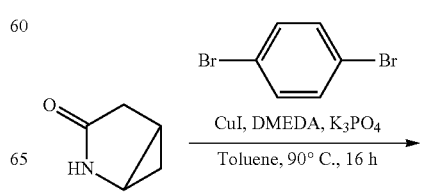

-continued

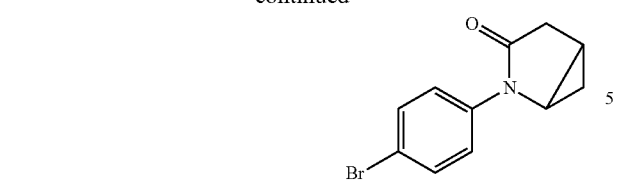

2-(4-bromophenyl)-2-azabicyclo[3.1.0]hexan-3-one was prepared from 2-azabicyclo[3.1.0]hexan-3-one and 1,4-dibromobenzene according to General Scheme 7.

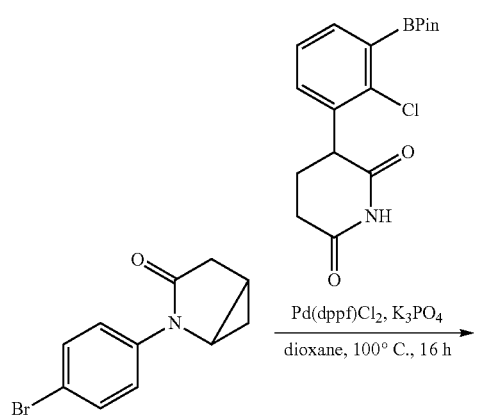

Compound 478

3-(2-chloro-4'-(3-oxo-2-azabicyclo[3.1.0]hexan-2-yl)-[1,1'-biphenyl]-3-yl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 2-(4-bromophenyl)-2-azabicyclo[3.1.0]hexan-3-one according to General Scheme 1.

¹H NMR (400 MHz, DMSO-$d_6$) δ 10.92 (s, 1H), 7.77 (d, J=8.4 Hz, 2H), 7.46-7.42 (m, 2H), 7.42-7.28 (m, 3H), 4.40-4.28 (m, 1H), 3.62 (t, J=5.6 Hz, 1H), 3.01 (dd, J=18.0, 7.2, Hz, 1H), 2.85-2.71 (m, 1H), 2.59-2.52 (m, 1H), 2.46 (s, 1H), 2.40-2.27 (m, 1H), 2.10-1.98 (m, 1H), 1.69-1.54 (m, 1H), 1.11 (td, J=8.4, 5.6, Hz, 1H), 0.52 (dt, J=5.6, 2.4 Hz, 1H); MS (ESI) m/z 395.2 [M+H]⁺

Example 231. Synthesis of 3-(2-chloro-3-(2-((1-methyl-1H-pyrazol-3-yl)methoxy)pyrimidin-5-yl)phenyl)piperidine-2,6-dione (Compound 479)

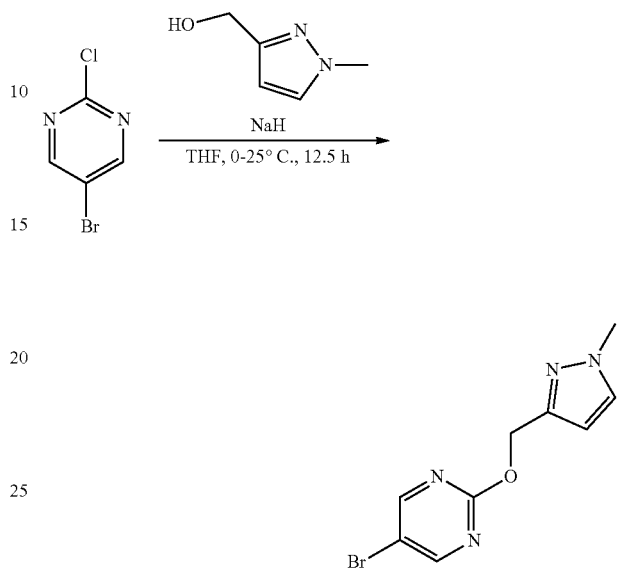

Under nitrogen atmosphere, to a mixture of (1-methyl-1H-pyrazol-3-yl)methanol (500 mg, 4.46 mmol, 1.00 eq) in tetrahydrofuran (12.5 mL) was added sodium hydride (268 mg, 6.70 mmol, 60% purity, 1.50 eq) at 0° C., and then the mixture was stirred at 25° C. for 0.5 h. 5-bromo-2-chloropyrimidine (1.04 g, 5.35 mmol, 1.20 eq) was added to the reaction mixture at 0° C., then the mixture was stirred at 25° C. for 12 h. The reaction mixture was poured into water (100 mL), extracted with ethyl acetate (3×100 mL). The combined organic layers were washed with brine (100 mL), dried over sodium sulfate, filtered and concentrated under reduced pressure. The residue was purified by flash silica gel chromatography (ISCO®; 40 g SepaFlash® Silica Flash Column, eluent of 50-80% ethyl acetate/petroleum ether gradient @ 70 mL/min) to give 5-bromo-2-((1-methyl-1H-pyrazol-3-yl)methoxy)pyrimidine (968 mg, 3.56 mmol, 80% yield) as a white solid.

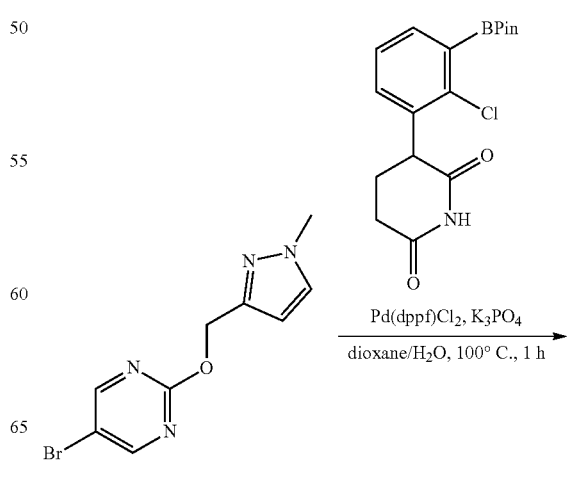

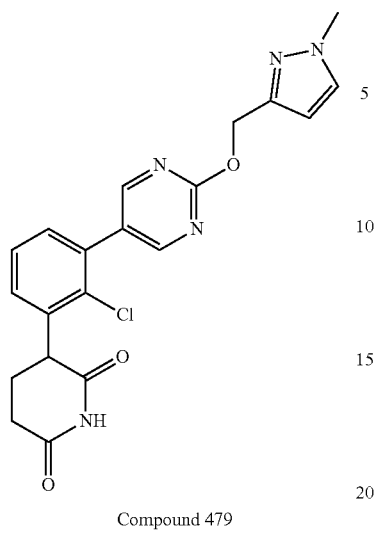

Compound 479

3-(2-chloro-3-(2-((1-methyl-1H-pyrazol-3-yl)methoxy)pyrimidin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione (intermediate A) and 5-bromo-2-((1-methyl-1H-pyrazol-3-yl)methoxy)pyrimidine according to General Scheme 1.

$^1$H NMR (400 MHz, DMSO-d$_6$) δ=10.94 (s, 1H), 8.72 (s, 2H), 7.68 (d, J=2.0 Hz, 1H), 7.51-7.37 (m, 3H), 6.34 (d, J=2.0 Hz, 1H), 5.36 (s, 2H), 4.36 (dd, J=12.4, 5.2 Hz, 1H), 3.84 (s, 3H), 2.87-2.74 (m, 1H), 2.68-2.65 (m, 1H), 2.58-2.55 (m, 1H), 2.36-2.28 (m, 1H), 2.09-1.99 (m, 1H).

MS (ESI) m/z 412.1 [M+H]$^+$

Example 232. Synthesis of 3-(2-chloro-4'-{3-oxo-2-azabicyclo[2.1.1]hexan-2-yl}-[1,1'-biphenyl]-3-yl)piperidine-2,6-dione (Compound 481)

Compounds similar to Compound 481 may be prepared according to the following scheme.

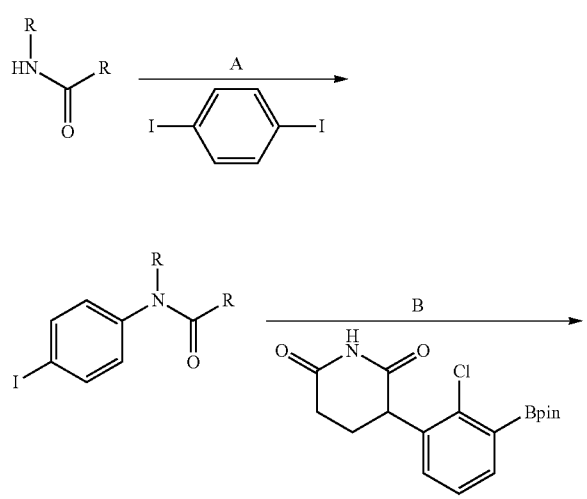

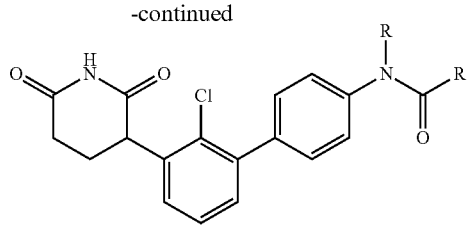

Step a (Scale on 1 g of Intermediate 3):

An appropriate lactam (1 eq.) was dissolved in dioxane (15 ml). 1,4-Diiodobenzene 2 (1 eq.), potassium phosphate (K$_3$PO$_4$) (1.2 eq.), rac-(1R,2R)—N1,N2-dimethylcyclohexane-1,2-diamine (0.2 eq.), and copper iodide (CuI) (0.1 eq.) under an argon atmosphere. The reaction mixture was sealed and heated with stirring at 90° C. for 15 hours (overnight). The resulting mixture was cooled to a room temperature and filtered. The solution was concentrated under reduced pressure. Then water (40 ml) and dichloromethane (CH$_2$Cl2) (40 ml) were added to the residue. The organic layer was separated, washed with water, dried over sodium sulphate (Na$_2$SO$_4$) and evaporated in vacuo. Crude products 3 were purified by flash chromatography (mobile phases: A —CHCl$_3$, B—CH$_3$CN).

Step B (Scale of 120 mg of Final Product):

3-[2-Chloro-3-(4,4,5,5-tetramethyl-1,3,2-dioxaborolan-2-yl)phenyl]piperidine-2,6-dione (1 eq.) was dissolved in dioxane/water 10:1 (1.5 ml). Appropriate iodide from Step A (1.2 eq.), potassium fluoride (KF) (3 eq.), and Pd(dppf)Cl$_2$ (0.1 eq.) were added in one portion under an argon atmosphere. The reaction mixture was sealed and heated with stirring at 85° C. for 3-48 hours. The resulting mixture was cooled to the room temperature and filtered. The solution was concentrated under reduced pressure. The residue was diluted with water (5 ml) and dichloromethane (CH$_2$Cl2) (5 ml). The organic layer was separated, washed with water, dried over sodium sulphate (Na$_2$SO4) and evaporated in vacuo. The solvent was evaporated under reduced pressure and the residue was dissolved in the DMSO (0.7 ml). DMSO solution was treated with scavenger SiliaMetS DMT, filtered, analyzed by LCMS, and transferred for HPLC purification.

3-(2-chloro-4'-{3-oxo-2-azabicyclo[2.1.1]hexan-2-yl}-[1,1'-biphenyl]-3-yl)piperidine-2,6-dione was obtained by the synthetic procedure described above. Yield of intermediate: 300.0 mg (30.0%). Final compound was purified by HPLC (gradient: from A-75%: B-25% to A-45%: B-55%). Yield: 45.8 mg (38.2%). Beige powder. LCMS purity: 100% (LCMS procedure outlined below, Rf=0.62, run time=2 min). EI MS m/z: pos. 395.0 (MH+).

Example 233. Synthesis of 3-(2-chloro-3-(1H-indol-5-yl)phenyl)piperidine-2,6-dione (Compound 482)

3-(2-chloro-3-(1H-indol-5-yl)phenyl)piperidine-2,6-dione was prepared from (1H-indol-5-yl)boronic acid and 3-(3-bromo-2-chloro-phenyl)-piperidine-2,6-dione analogously to General Scheme 1. MS (ESI) m/z 339.0, 341.0 [M+H]$^+$ Example 234. Synthesis of 3-(2-chloro-3-(1H-indol-6-yl)phenyl) piperidine-2,6-dione (Compound 483)

3-(2-chloro-3-(1H-indol-6-yl)phenyl)piperidine-2,6-dione was prepared from (1H-indol-6-yl)boronic acid and 3-(3-bromo-2-chlorophenyl) piperidine-2,6-dione analogously to General Scheme 1. MS (ESI) m/z 339.2 [M+H]$^+$

Example 235. Synthesis of 3-(2-chloro-3-(1H-indazol-6-yl)phenyl) piperidine-2,6-dione (Compound 484)

3-(2-chloro-3-(1H-indazol-6-yl)phenyl)piperidine-2,6-dione was prepared from (1H-indazol-6-yl)boronic acid and 3-(3-bromo-2-chlorophenyl) piperidine-2,6-dione analogously to General Scheme 1. MS (ESI) m/z 340.1 [M+H]$^+$

Example 236. Synthesis of 3-(2-chloro-3-(1H-indazol-5-yl)phenyl) piperidine-2,6-dione (Compound 485)

3-[2-chloro-3-(1H-indazol-5-yl)phenyl]piperidine-2,6-dione was prepared from (1H-indazol-5-yl)boronic acid and 3-(3-bromo-2-chlorophenyl) piperidine-2,6-dione analogously to General Scheme 1. MS (ESI) m/z 340.0 [M+H]$^+$

Example 237. Synthesis of 3-(2-chloro-3-(1,2,3,4-tetrahydroquinolin-6-yl)phenyl)piperidine-2,6-dione (Compound 486)

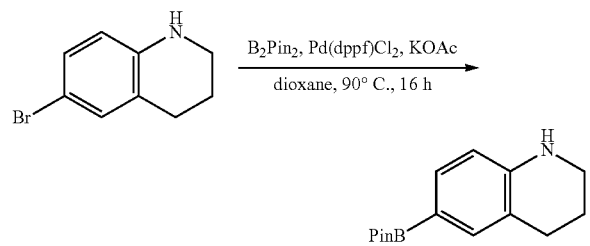

To a solution of 6-bromo-1,2,3,4-tetrahydroquinoline (200 mg, 943 μmol, 1.00 eq) and 4,4,4',4',5,5,5',5'-octamethyl-2,2'-bi(1,3,2-dioxaborolane) (290 mg, 1.14 mmol, 1.21 eq) in dioxane (4 mL) were added potassium acetate (280 mg, 2.85 mmol, 3.03 eq) and [1,1-bis(diphenylphosphino)ferrocene]-dichloropalladium(II) (138 mg, 189 μmol, 0.20 eq) under nitrogen atmosphere. The reaction mixture was stirred at 90° C. for 16 h. The mixture was filtered and the filtration was concentrated under vacuum. The residue was purified by flash silica gel chromatography (eluent of 0~16% ethyl acetate/petroleum ether) to afford 6-(4,4,5,5-tetramethyl-1,3,2-dioxaborolan-2-yl)-1,2,3,4-tetrahydroquinoline (90.0 mg, 323 μmol, 34% yield) as a yellow oil.

3-(2-chloro-3-(1,2,3,4-tetrahydroquinolin-6-yl)phenyl) piperidine-2,6-dione was prepared from 6-(4,4,5,5-tetramethyl-1,3,2-dioxaborolan-2-yl)-1,2,3,4-tetrahydroquinoline and 3-(3-bromo-2-chlorophenyl)piperidine-2,6-dione analogously to General Scheme 1. MS (ESI) m/z 355.1 [M+H]$^+$

Example 238. Synthesis of 3-(2-chloro-3-(3,4-dihydro-2H-benzo[b][1,4]oxazin-7-yl)phenyl)piperidine-2,6-dione (Compound 487)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(3,4-dihydro-2H-benzo[b][1,4]oxazin-7-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 7-bromo-3,4-dihydro-2H-benzo[b][1,4]oxazine analogously to General Scheme 1. MS (ESI) m/z 357.0 [M+H]$^+$

Example 239. Synthesis of 3-(2-chloro-3-(1-methylindolin-5-yl)phenyl)piperidine-2,6-dione (Compound 488)

3-(2-chloro-3-(1-methylindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-methylindoline analogously to General Scheme 1. 3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-methylindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-methylindoline analogously to General Scheme 1. MS (ESI) m/z 355.0 [M+H]$^+$

Example 240. Synthesis of 3-(2-chloro-3-(1-((1-methyl-1H-pyrazol-3-yl)methyl)indolin-5-yl)phenyl) piperidine-2,6-dione (Compound 489)

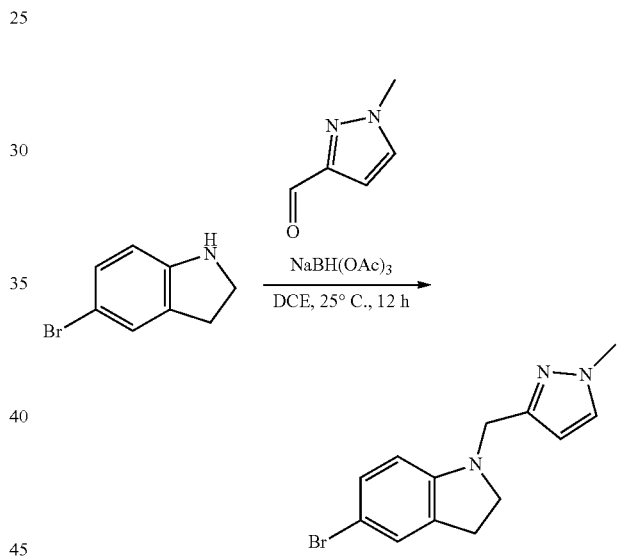

To a solution of 5-bromoindoline (100 mg, 505 μmol, 1.00 eq) in dichloromethane (2 mL) were added sodium triacetoxyhydroborate (270 mg, 1.27 mmol, 2.52 eq) and 1-methyl-1H-pyrazole-3-carbaldehyde (70.0 mg, 636 μmol, 1.26 eq). The mixture was stirred at 25° C. for 12 h. The reaction mixture was concentrated under reduced pressure. The residue was purified by flash silica gel chromatography (ISCO®; 12 g SepaFlash® Silica Flash Column, Eluent of 38~40% Ethyl acetate/Petroleum ether gradient @ 40 mL/min) to afford 5-bromo-1-((1-methyl-1H-pyrazol-3-yl)methyl)indoline (120 mg, 370 μmol, 73% yield) as yellow oil.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-pyrazol-3-yl)methyl)indolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-pyrazol-3-yl)methyl) indoline analogously to General Scheme 1.

$^1$H NMR (400 MHz, DMSO-d$_6$) δ=10.90 (s, 1H), 7.60 (d, J=2.0 Hz, 1H), 7.38-7.29 (m, 1H), 7.28-7.20 (m, 2H), 7.09-6.99 (m, 2H), 6.67 (d, J=8.0 Hz, 1H), 6.15 (d, J=2.0 Hz, 1H), 4.31 (dd, J=5.2, 12.0 Hz, 1H), 4.24 (s, 2H), 3.80 (s, 3H), 3.37 (t, J=8.4 Hz, 2H), 2.91 (t, J=8.4 Hz, 2H), 2.84-2.71 (m, 1H), 2.55 (d, J=3.7 Hz, 1H), 2.39-2.25 (m, 1H), 2.10-1.97 (m, 1H); MS (ESI) m/z 435.2/437.2 [M+H]$^+$

Example 241. Synthesis of 3-(2-chloro-3-(indolin-5-yl)phenyl)piperidine-2,6-dione (Compound 490)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(indolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromoindoline analogously to General Scheme 1. MS (ESI) m/z 341.0 [M+H]$^+$.

Example 242. Synthesis of 3-(2-fluoro-3-(indolin-5-yl)phenyl)piperidine-2,6-dione (Compound 491)

3-(3-bromo-2-chloro-6-fluorophenyl)piperidine-2,6-dione was prepared from 2-(3-bromo-2-fluoro-phenyl)acetonitrile according to General Scheme 2.
3-(2-fluoro-3-(indolin-5-yl)phenyl)piperidine-2,6-dione was prepared from 3-(3-bromo-2-chloro-6-fluorophenyl)piperidine-2,6-dione and 5-(4,4,5,5-tetramethyl-1,3,2-dioxaborolan-2-yl)indoline analogously to General Scheme 1. MS (ESI) m/z 325.0 [M+H]$^+$ Example 243. Synthesis of 3-(2-chloro-3-(2-oxo-1,2,3,4-tetrahydroquinolin-6-yl)phenyl)piperidine-2,6-dione (Compound 492)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(2-oxo-1,2,3,4-tetrahydroquinolin-6-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 6-bromo-3,4-dihydroquinolin-2(1H)-one analogously to General Scheme 1. MS (ESI) m/z 369.2 [M+H]$^+$ Example 244. Synthesis of 3,5-dichloro-4-(2,6-dioxopiperidin-3-yl)benzyl cyclohexyl(methyl)carbamate (Compound 493)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(2-oxoindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromoindolin-2-one analogously to General Scheme 1. MS (ESI) m/z 355.1 [M+H]$^+$ Example 245. Synthesis of 3-(2-chloro-3-(3,4-dihydro-2H-pyrido[3,2-b][1,4]oxazin-7-yl)phenyl)piperidine-2,6-dione (Compound 494)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(3,4-dihydro-2H-pyrido[3,2-b][1,4]oxazin-7-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 7-bromo-3,4-dihydro-2H-pyrido[3,2-b][1,4]oxazine analogously to General Scheme 1. MS (ESI) m/z 358.1 [M+H]$^+$ Example 246. Synthesis of 3-(2-chloro-3-(1-((1-methyl-1H-pyrazol-3-yl)methyl)-1H-indol-5-yl)phenyl)piperidine-2,6-dione (Compound 495)

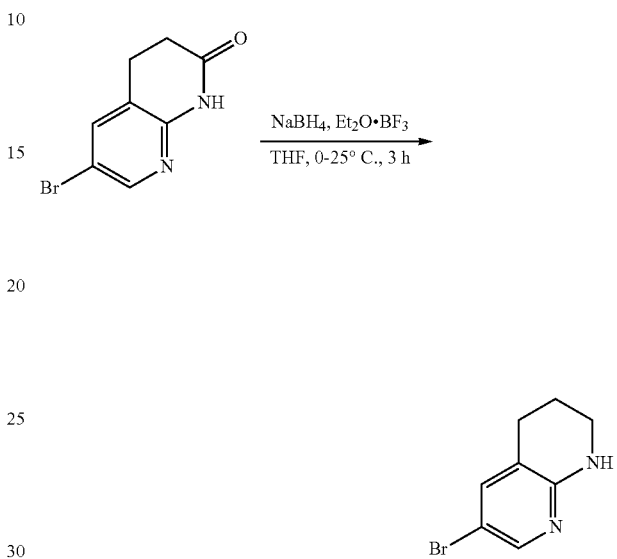

To a dry three-neck round bottom flask was added sodium borohydride (1.00 g, 26.4 mmol, 6.00 eq), followed by a solution of 6-bromo-3,4-dihydro-1,8-naphthyridin-2(1H)-one (1.00 g, 4.40 mmol, 1.00 eq) in anhydrous tetrahydrofuran (40 mL). Then a solution of boron trifluoride diethyl etherate (9.31 g, 30.8 mmol, 8.10 mL, 47% purity, 7.00 eq) was added dropwise under nitrogen at 0° C. Then the reaction mixture was stirred at 25° C. for 3 h. The reaction mixture was quenched by addition saturated ammonium chloride (50 mL) at 0° C. and extracted with ethyl acetate (3×50 mL). The pH of combined organic extracts was adjusted to 5 with 12 N hydrochloric acid, followed by the pH of mixture was adjusted to 8-9 with saturated sodium bicarbonate. The combined organic layers were dried over sodium sulfate, filtered and concentrated under reduced pressure to give a residue. The residue was purified by flash silica gel chromatography (ISCO®; 12 g SepaFlash® Silica Flash Column, Eluent of 0~100% ethyl acetate/petroleum ether gradient @ 30 mL/min) to afford 6-bromo-1,2,3,4-tetrahydro-1,8-naphthyridine (380 mg, 1.64 mmol, 37% yield) as yellow oil.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-pyrazol-3-yl)methyl)-1H-indol-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 6-bromo-1,2,3,4-tetrahydro-1,8-naphthyridine analogously to General Scheme 1 MS (ESI) m/z 356.0 [M+H]$^+$ Example 247. Synthesis of 3-(2-chloro-3-(1-((1-methyl-1H-pyrazol-3-yl)methyl)-2-oxoindolin-5-yl)phenyl)piperidine-2,6-dione (Compound 496)

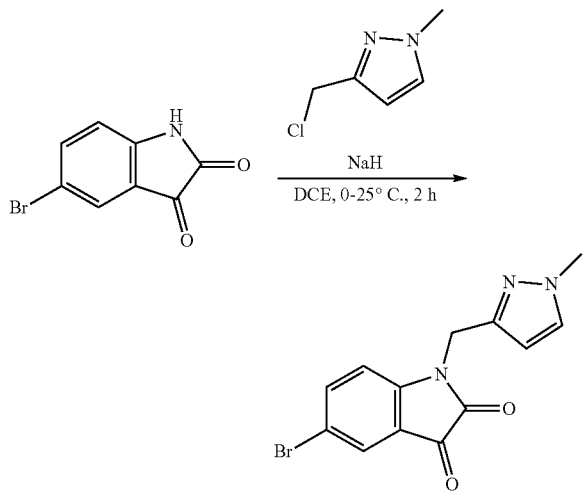

5-bromo-1-((1-methyl-1H-pyrazol-3-yl)methyl)indoline-2,3-dione was prepared from 5-bromoindoline-2,3-dione and 3-(chloromethyl)-1-methyl-1H-pyrazole analogously to General Scheme 11.

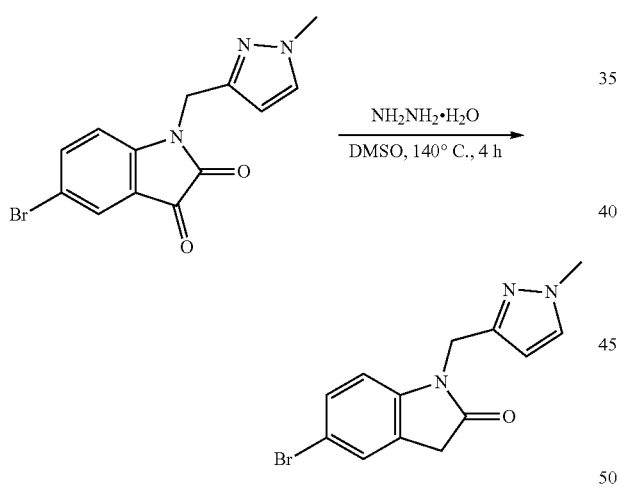

A mixture of 5-bromo-1-((1-methyl-1H-pyrazol-3-yl)methyl)indoline-2,3-dione (300 mg, 937 umol, 1.00 eq) and hydrazine hydrate (1.08 g, 18.3 mmol, 1.05 mL, 85% purity, 19.5 eq) in dimethylsulfoxide (5.00 mL) was stirred at 140° C. for 4 h. The mixture was diluted with water (50.0 mL) and extracted with ethyl acetate (3×30.0 mL). The combined organic layers were washed with brine (20 mL) and dried over anhydrous sodium sulfate, filtered and concentrated to give crude product. The crude product was purified by silica gel chromatography (petroleum ether/ethyl acetate=20/1 to 2/1) to give 5-bromo-1-((1-methyl-1H-pyrazol-3-yl)methyl)indolin-2-one (240 mg, 784 umol, 83% yield) as a yellow solid.

3-(2-chloro-3-(1-((1-methyl-1H-pyrazol-3-yl)methyl)-2-oxoindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-pyrazol-3-yl)methyl)indolin-2-one analogously to General Scheme 1.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-pyrazol-3-yl)methyl)-2-oxoindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-pyrazol-3-yl)methyl)indolin-2-one analogously to General Scheme 1.

$^1$H NMR (400 MHz, DMSO-$d_6$) δ=10.91 (br s, 1H), 7.60 (d, J=1.6 Hz, 1H), 7.39-7.31 (m, 2H), 7.30-7.19 (m, 3H), 7.02 (d, J=8.0 Hz, 1H), 6.13 (d, J=1.6 Hz, 1H), 4.82 (s, 2H), 4.33 (br dd, J=5.2, 12.0 Hz, 1H), 3.78 (s, 3H), 3.66 (s, 2H), 2.84-2.73 (m, 1H), 2.61-2.53 (m, 1H), 2.39-2.26 (m, 1H), 2.09-1.99 (m, 1H); MS (ESI) m/z 449.2 [M+H]$^+$

Example 248. Synthesis of 3-(2-chloro-3-(2,2-dimethylindolin-5-yl)phenyl)piperidine-2,6-dione (Compound 497)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(2,2-dimethylindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-2,2-dimethylindoline analogously to General Scheme 1. MS (ESI) m/z 369.1 [M+H]$^+$ Example 249. Synthesis of 3-(2-chloro-3-(1-((1-methyl-1H-pyrazol-3-yl)methyl)-1H-indazol-5-yl)phenyl)piperidine-2,6-dione (Compound 498)

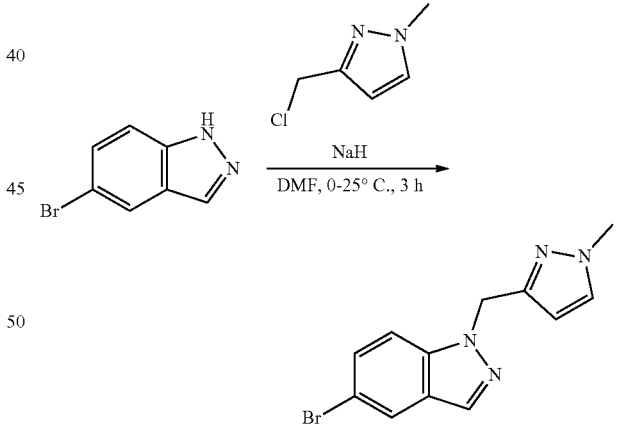

5-bromo-1-((1-methyl-1H-pyrazol-3-yl)methyl)-1H-indazole was prepared from 5-bromo-1H-indazole and 3-(chloromethyl)-1-methyl-1H-pyrazole according to General Scheme 11. 3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-pyrazol-3-yl)methyl)-1H-indazol-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-pyrazol-3-yl)methyl)-1H-indazole analogously to General Scheme 1. MS (ESI) m/z 434.2 [M+H]$^+$ Example 250. Synthesis of 3-(2-chloro-3-(1-((1-methyl-1H-pyrazol-3-yl)methyl)-1H-indol-5-yl)phenyl)piperidine-2,6-dione (Compound 499)

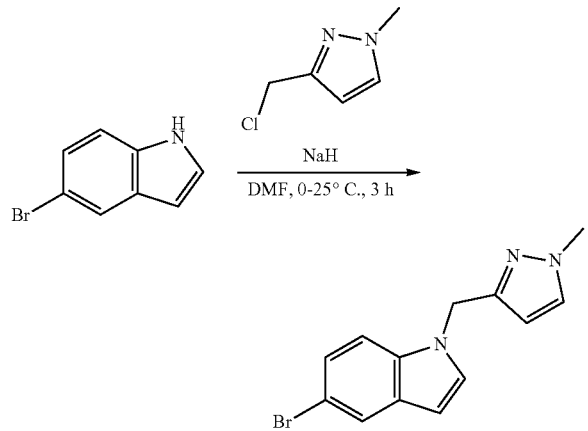

5-bromo-1-((1-methyl-1H-pyrazol-3-yl)methyl)-1H-indole was prepared from 5-bromo-1H-indole and 3-chloromethyl)-1-methyl-1H-pyrazole according to General Scheme 11. 3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-pyrazol-3-yl)methyl)-1H-indol-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-pyrazol-3-yl)methyl)-1H-indole analogously to General Scheme 1. MS (ESI) m/z 433.1 [M+H]$^+$ Example 251. Synthesis of 3-(2-chloro-3-(2-methylindolin-5-yl)phenyl)piperidine-2,6-dione (Compound 500)

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(2-methylindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-2-methylindoline analogously to General Scheme 1. MS (ESI) m/z 355.0 [M+H]$^+$ Example 252. Synthesis of 3-(2-chloro-3-(1-((1-methyl-1H-pyrazol-3-yl)methyl)-2-oxo-1,2,3,4-tetrahydroquinolin-6-yl)phenyl)piperidine-2,6-dione (Compound 501)

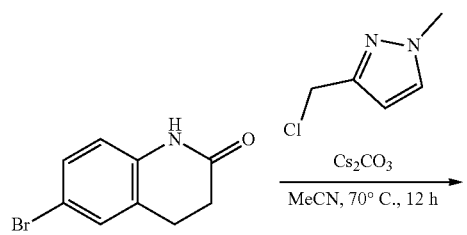

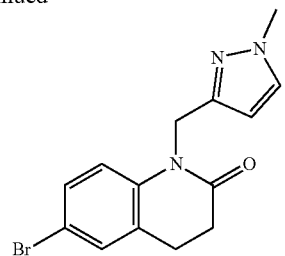

6-bromo-1-((1-methyl-1H-pyrazol-3-yl)methyl)-3,4-dihydroquinolin-2(1H)-one was prepared from 6-bromo-3,4-dihydroquinolin-2(1H)-one and 3-(chloromethyl)-1-methyl-1H-pyrazole according to General Scheme 11. 3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-pyrazol-3-yl)methyl)-2-oxo-1,2,3,4-tetrahydroquinolin-6-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 6-bromo-1-((1-methyl-1H-pyrazol-3-yl)methyl)-3,4-dihydroquinolin-2(1H)-one analogously to General Scheme 1.
$^1$H NMR (400 MHz, DMSO-d$_6$) δ=10.90 (s, 1H), 7.57 (d, J=2.0 Hz, 1H), 7.39-7.30 (m, 2H), 7.29-7.25 (m, 2H), 7.22 (s, 2H), 6.05 (d, J=2.4 Hz, 1H), 5.02 (s, 2H), 4.32 (dd, J=5.2, 12.4 Hz, 1H), 3.78 (s, 3H), 2.94 (t, J=7.2 Hz, 2H), 2.85-2.71 (m, 1H), 2.65 (dd, J=6.4, 8.4 Hz, 2H), 2.55 (d, J=3.6 Hz, 1H), 2.32 (dd, J=4.0, 12.8 Hz, 1H), 2.08-1.97 (m, 1H); MS (ESI) m/z 463.0 [M+H]$^+$ Example 253. Synthesis of 3-(2-chloro-3-(4-((1-methyl-1H-pyrazol-3-yl)methyl)-3-oxo-3,4-dihydro-2H-benzo[b][1,4]oxazin-7-yl)phenyl)piperidine-2,6-dione (Compound 502)

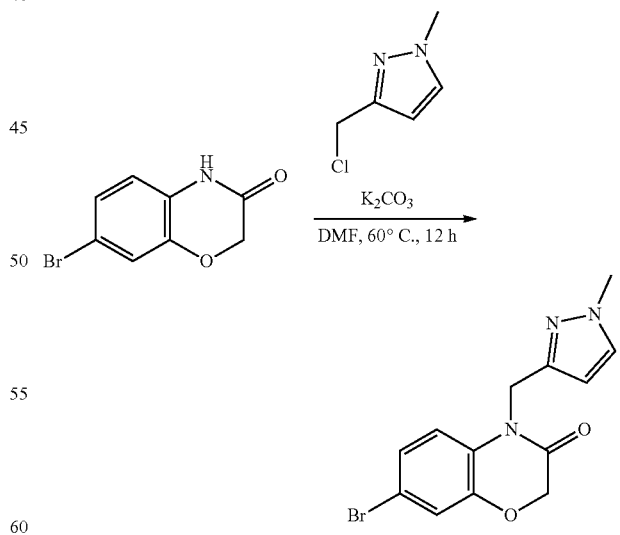

7-bromo-4-((1-methyl-1H-pyrazol-3-yl)methyl)-2H-benzo[b][1,4]oxazin-3(4H)-one was prepared from 7-bromo-2H-benzo[b][1,4]oxazin-3(4H)-one and 3-(chloromethyl)-1-methyl-1H-pyrazole according to General Scheme 11. 3-(2-chloro-3-(4,4,5,5-tetramethyl-1,3,2-dioxaborolan-2-yl)phenyl)piperidine-2,6-dione (intermediate A)

was synthesized as described above. 3-(2-chloro-3-(4-((1-methyl-1H-pyrazol-3-yl)methyl)-3-oxo-3,4-dihydro-2H-benzo[b][1,4]oxazin-7-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 7-bromo-4-((1-methyl-1H-pyrazol-3-yl)methyl)-2H-benzo[b][1,4]oxazin-3(4H)-one analogously to General Scheme 1. MS (ESI) m/z 465.1 [M+H]+

Example 254. Synthesis of 3-(2-chloro-3-(3-methyl-1-((1-methyl-1H-pyrazol-3-yl)methyl)-2-oxo-1,2,3,4-tetrahydroquinazolin-6-yl)phenyl)piperidine-2,6-dione (Compound 503)

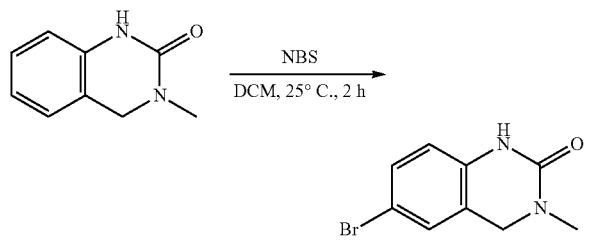

To a solution of 3-methyl-3,4-dihydroquinazolin-2(1H)-one (5.00 g, 30.8 mmol, 1.00 eq) in dichloromethane (50 mL) was added N-bromosuccinimide (6.58 g, 37.0 mmol, 1.20 eq) at 25° C. Then the mixture was stirred at 25° C. for 2 h. The reaction mixture was diluted with dichloromethane (50 mL). The mixture was washed with 10% aqueous sodium bicarbonate (2×50 mL), dried over sodium sulfate and filtered. The filtrate was concentrated under reduced pressure. The residue was purified by flash silica gel chromatography (ISCO®; 80 g SepaFlash® Silica Flash Column, eluent of 0-90% ethyl acetate/petroleum ether gradient at 100 mL/min) to give 6-bromo-3-methyl-3,4-dihydroquinazolin-2(1H)-one (2.00 g, 7.88 mmol, 26% yield) as a white solid.

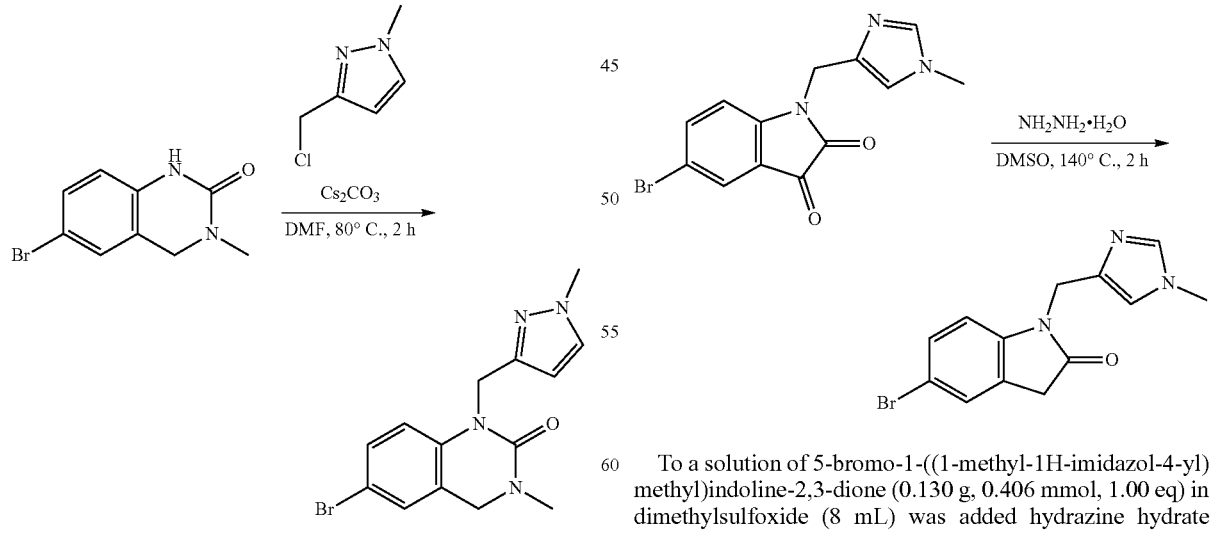

6-bromo-3-methyl-1-((1-methyl-1H-pyrazol-3-yl)methyl)-3,4-dihydroquinazolin-2(1H)-one was prepared from 6-bromo-3-methyl-3,4-dihydroquinazolin-2(1H)-one and 3-(chloromethyl)-1-methyl-1H-pyrazole according to General Scheme 11. 3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(3-methyl-1-((1-methyl-1H-pyrazol-3-yl)methyl)-2-oxo-1,2,3,4-tetrahydroquinazolin-6-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 6-bromo-3-methyl-1-((1-methyl-1H-pyrazol-3-yl)methyl)-3,4-dihydroquinazolin-2(1H)-one analogously to General Scheme 1. MS (ESI) m/z 478.1 [M+H]+

Example 255. Synthesis of 3-(2-chloro-3-(1-((1-methyl-1H-imidazol-4-yl)methyl)-2-oxoindolin-5-yl)phenyl)piperidine-2,6-dione (Compound 504)

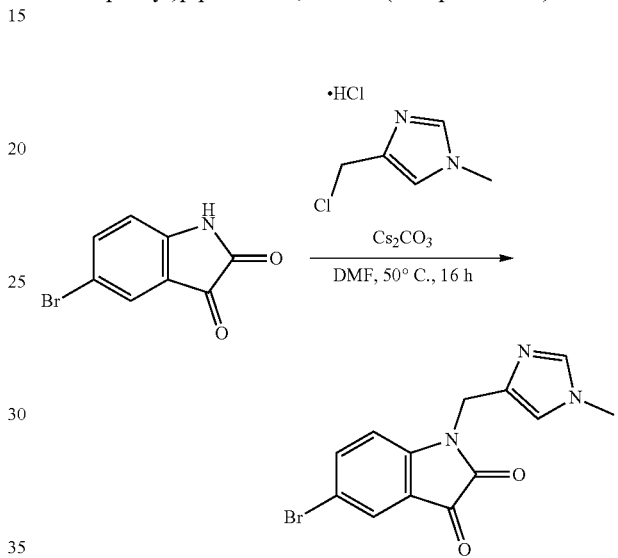

5-bromo-1-((1-methyl-1H-imidazol-4-yl)methyl)indoline-2,3-dione was prepared from 5-bromoindoline-2,3-dione and 4-(chloromethyl)-1-methyl-1H-imidazole hydrochloride according to General Scheme 11.

To a solution of 5-bromo-1-((1-methyl-1H-imidazol-4-yl)methyl)indoline-2,3-dione (0.130 g, 0.406 mmol, 1.00 eq) in dimethylsulfoxide (8 mL) was added hydrazine hydrate (0.0410 g, 0.812 mmol, 2.00 eq). The mixture was stirred at 140° C. for 2 h. The mixture was diluted with water (20 mL) and then extracted with ethyl acetate (3×30 mL). The combined organic layers were washed with brine (20 mL) and dried over anhydrous sodium sulfate, filtered and concentrated under reduced pressure. The crude product was purified by silica gel chromatography (100% ethyl acetate) to give 5-bromo-1-((1-methyl-1H-imidazol-4-yl)methyl)indolin-2-one (0.120 g, 0.368 mmol, 91% yield, 94% purity) as a yellow oil.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-imidazol-4-yl)methyl)-2-oxoindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-imidazol-4-yl)methyl)indolin-2-one analogously to General Scheme 1. MS (ESI) m/z 449.1 [M+H]$^+$ Example 256. Synthesis of 3-(2-chloro-3-(1-(oxazol-4-ylmethyl)-2-oxoindolin-5-yl)phenyl)piperidine-2,6-dione (Compound 505)

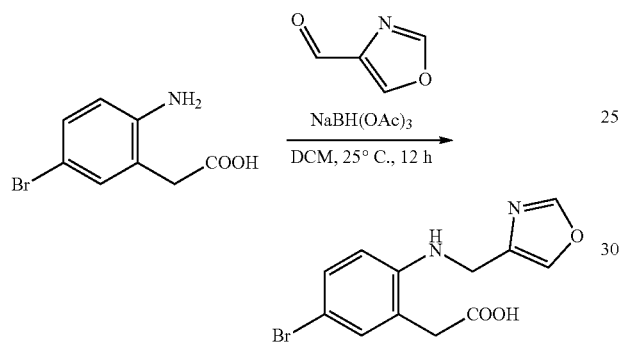

To a solution of 2-(2-amino-5-bromophenyl)acetic acid (700 mg, 3.04 mmol, 1.00 eq) and oxazole-4-carbaldehyde (325 mg, 3.35 mmol, 1.10 eq) in dichloromethane (10 mL) was added sodium triacetoxy borohydride (903 mg, 4.26 mmol, 1.40 eq). The mixture was stirred at 25° C. for 12 h. Ethyl acetate (40 mL) and water (40 mL) were added and layers were separated. The aqueous phase was extracted with ethyl acetate (3×30 mL). The combined extracts were washed with brine (30 mL), dried over sodium sulfate, filtered and concentrated under vacuum to give a residue, which was purified by flash silica gel chromatography (ISCO®; 10 g SepaFlash® Silica Flash Column, Eluent of 0-100% ethyl acetate/petroleum ether gradient @ 18 mL/min) to give 2-(5-bromo-2-((oxazol-4-ylmethyl)amino)phenyl)acetic acid (650 mg, 1.88 mmol, 62% yield, 90% purity) as a white solid.

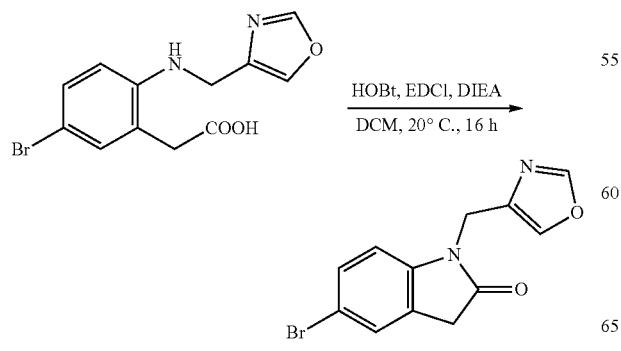

To a solution of 2-(5-bromo-2-((oxazol-4-ylmethyl)amino)phenyl)acetic acid (590 mg, 1.90 mmol, 1.00 eq) in dichloromethane (15 mL) was added N,N-diisopropylethylamine (735 mg, 5.69 mmol, 991 µL, 3.00 eq), 1-hydroxybenzotriazole (282 mg, 2.09 mmol, 1.10 eq) and 1-(3-dimethylaminopropyl)-3-ethylcarbodiimide hydrochloride (400 mg, 2.09 mmol, 1.10 eq). The mixture was stirred at 20° C. for 16 h. Ethyl acetate (50 mL) and water (50 mL) were added and layers were separated. The aqueous phase was extracted with ethyl acetate (3×50 mL). The combined extracts were washed with brine (40 mL), dried over sodium sulfate, filtered and concentrated under vacuum to give a residue, which was purified by flash silica gel chromatography (ISCO®; 12 g SepaFlash® Silica Flash Column, Eluent of 0~100% ethyl acetate/petroleum ether gradient @ 40 mL/min) to give 5-bromo-1-(oxazol-4-ylmethyl)indolin-2-one (300 mg, 1.02 mmol, 54% yield) as a white solid.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-(oxazol-4-ylmethyl)-2-oxoindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-(oxazol-4-ylmethyl)indolin-2-one analogously to General Scheme 1. MS (ESI) m/z 436.1 [M+H]$^+$ Example 257. Synthesis of 3-(2-chloro-3-(1-(cyclopropylmethyl)-2-oxoindolin-5-yl)phenyl)piperidine-2,6-dione (Compound 506)

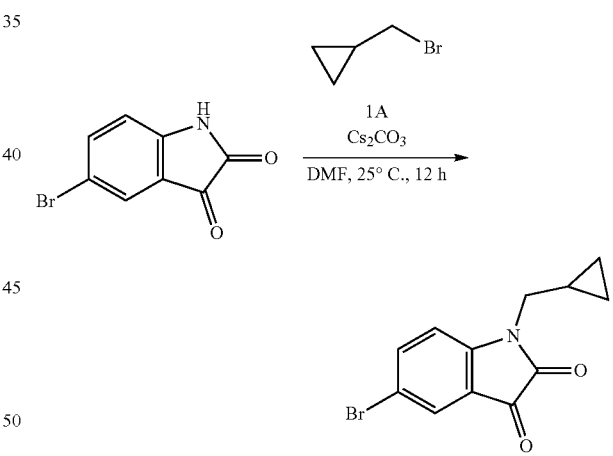

5-bromo-1-(cyclopropylmethyl)indoline-2,3-dione was prepared from 5-bromoindoline-2,3-dione and (bromomethyl)cyclopropane according to General Scheme 11.

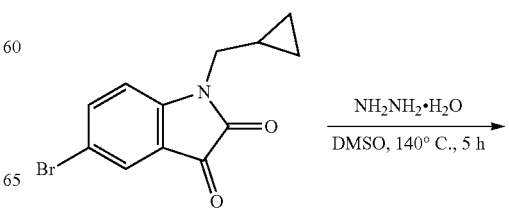

-continued

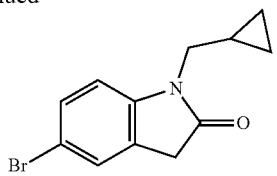

To a solution of 5-bromo-1-(cyclopropylmethyl)indoline-2,3-dione (1.10 g, crude) in dimethylsulfoxide (10 mL) was added hydrazine hydrate (4.63 g, 78.5 mmol, 4.48 mL, 85% purity, 20.0 eq). The mixture was stirred at 140° C. for 5 h. The mixture was diluted with water (50 mL) and extracted with ethyl acetate (3×50 mL). The combined organic layers were washed with brine (60 mL) and dried over anhydrous sodium sulfate, filtered and concentrated under reduced pressure to give 5-bromo-1-(cyclopropylmethyl)indolin-2-one (1.00 g, crude) as a white solid.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-(cyclopropylmethyl)-2-oxoindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-(cyclopropylmethyl)indolin-2-one analogously to General Scheme 1. MS (ESI) m/z 409.1 [M+H]+

Example 258. Synthesis of 3-(2-chloro-3-(3-((1-methyl-1H-pyrazol-3-yl)methyl)-2-oxo-2,3-dihydrobenzo[d]oxazol-6-yl)phenyl)piperidine-2,6-dione (Compound 507)

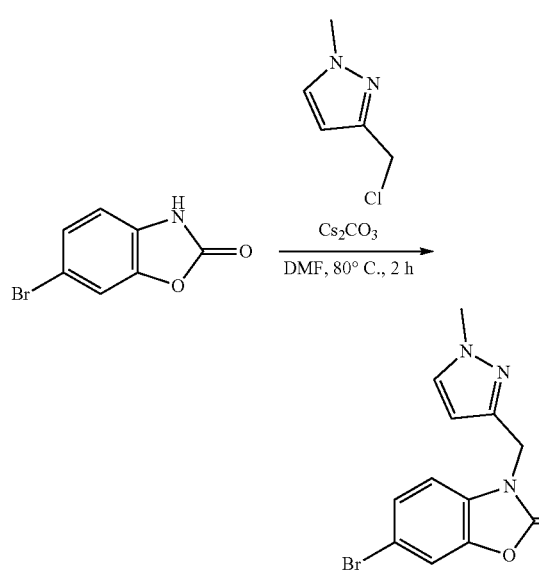

6-bromo-3-((1-methyl-1H-pyrazol-3-yl)methyl)benzo[d]oxazol-2(3H)-one was prepared from 6-bromobenzo[d]oxazol-2(3H)-one and 3-(chloromethyl)-1-methyl-1H-pyrazole according to General Scheme 11.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(3-((1-methyl-1H-pyrazol-3-yl)methyl)-2-oxo-2,3-dihydrobenzo[d]oxazol-6-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 6-bromo-3-((1-methyl-1H-pyrazol-3-yl)methyl)benzo[d]oxazol-2(3H)-one analogously to General Scheme 1. MS (ESI) m/z 451.1, 453.1 [M+H]+

Example 259. Synthesis of 3-(2-chloro-3-(1-((1-methyl-1H-imidazol-5-yl)methyl)-1H-indazol-5-yl)phenyl)piperidine-2,6-dione (Compound 508)

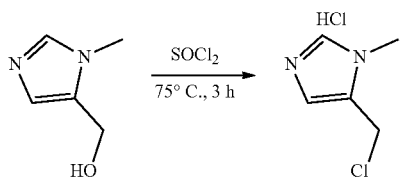

The solution of (1-methyl-1H-imidazol-5-yl) methanol (1.00 g, 8.92 mmol, 1.00 eq) in sulfurous dichloride (10 mL) was degassed and purged with nitrogen for 3 times, and then the mixture was stirred at 75° C. for 3 h under nitrogen atmosphere. The reaction mixture was cooled to 25° C. and concentrated under reduced pressure to give a residue. Petroleum ether was added to the residue and sonicate for 5 min, filter and dry to give a crude product 5-(chloromethyl)-1-methyl-1H-imidazole hydrochloride as a yellow solid (1.13 g, 6.43 mmol, 72% yield).

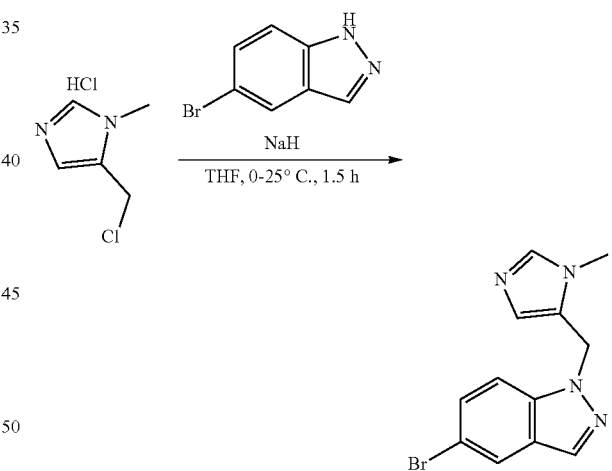

5-bromo-1-((1-methyl-1H-imidazol-5-yl)methyl)-1H-indazole was prepared from 5-bromo-1H-indazole and 5-(chloromethyl)-1-methyl-1H-imidazole hydrochloride analogously to General Scheme 11.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-imidazol-5-yl)methyl)-1H-indazol-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-imidazol-5-yl)methyl)-1H-indazole analogously to General Scheme 1. MS (ESI) m/z 434.2 [M+H]+

Example 260. Synthesis of 3-(2-chloro-3-(1-(1-methyl-2-oxo-1,2-dihydropyridin-3-yl)indolin-5-yl)phenyl)piperidine-2,6-dione (Compound 509)

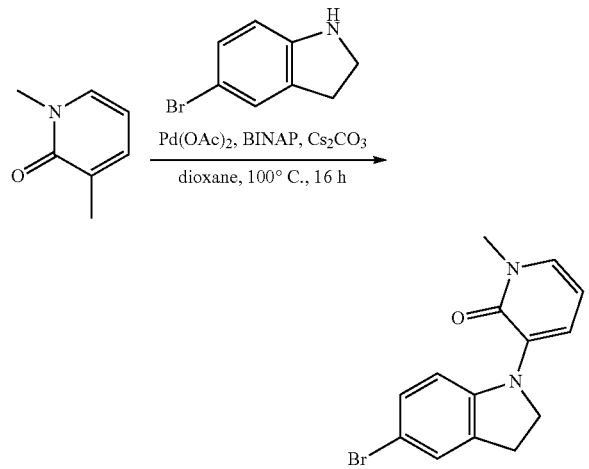

A mixture of 3-iodo-1-methylpyridin-2(1H)-one (653 mg, 2.78 mmol, 1.10 eq), 5-bromoindoline (500 mg, 2.52 mmol, 1.00 eq), palladium diacetate (56.7 mg, 252 μmol, 0.100 eq), (±)-2,2'-bis(diphenylphosphino)-1,1'-binaphthyl (314 mg, 505 μmol, 0.200 eq), cesium carbonate (2.47 g, 7.57 mmol, 3.00 eq) in dioxane (10 mL) was degassed and purged with nitrogen for 3 times, and then the mixture was stirred at 100° C. for 16 h under nitrogen atmosphere. The reaction mixture was cooled to 25° C., filtered and concentrated under reduced pressure to give a residue. The residue was purified by flash silica gel chromatography (ISCO®; 4 g SepaFlash® Silica Flash Column, Eluent of 0-100% Ethyl acetate/Petroleum ether gradient @ 18 mL/min) to give 3-(5-bromoindolin-1-yl)-1-methylpyridin-2(1H)-one (334 mg, 1.03 mmol, 41% yield) as an off-white solid.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-(1-methyl-2-oxo-1,2-dihydropyridin-3-yl)indolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 3-(5-bromoindolin-1-yl)-1-methylpyridin-2(1H)-one analogously to General Scheme 1. MS (ESI) m/z 448.3 [M+H]$^+$

Example 261. Synthesis of 3-(2-chloro-3-(3-((1-methyl-1H-pyrazol-3-yl)methyl)benzo[d]isoxazol-6-yl)phenyl)piperidine-2,6-dione (Compound 510)

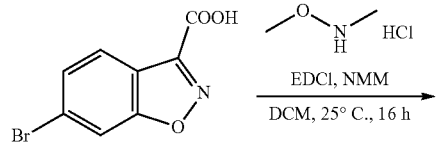

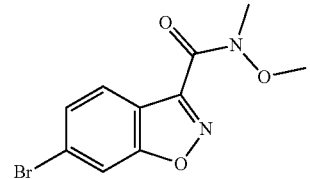

To a solution of 6-bromo-1,2-benzoxazole-3-carboxylic acid (1.00 g, 4.13 mmol, 1.00 eq) in dichloromethane (10 mL) were added 3-(ethyliminomethyleneamino)-N,N-dimethyl-propan-1-amine hydrochloride (0.792 g, 4.13 mmol, 1.00 eq), N-methyl morpholine (0.418 g, 4.13 mmol, 1.00 eq) and N-methoxymethanamine hydrochloride (0.403 g, 4.13 mmol, 1.00 eq). The mixture was stirred at 25° C. for 16 h. Then the reaction mixture was diluted with dichloromethane (15 mL) and water (20 mL). The mixture was extracted with dichloromethane (3×20 mL). The combined organic extracts were washed with brine (20 mL), dried over sodium sulfate, filtered and concentrated under reduced pressure to give a residue, which was purified by flash silica gel chromatography (ISCO®; 20 g SepaFlash® Silica Flash Column, Eluent of 0-30% ethyl acetate/petroleum ether gradient at 60 mL/min). The desired fraction was collected and concentrated under reduced pressure to give 6-bromo-N-methoxy-N-methylbenzo[d]isoxazole-3-carboxamide (0.900 g, 3.16 mmol, 76% yield) as a white solid.

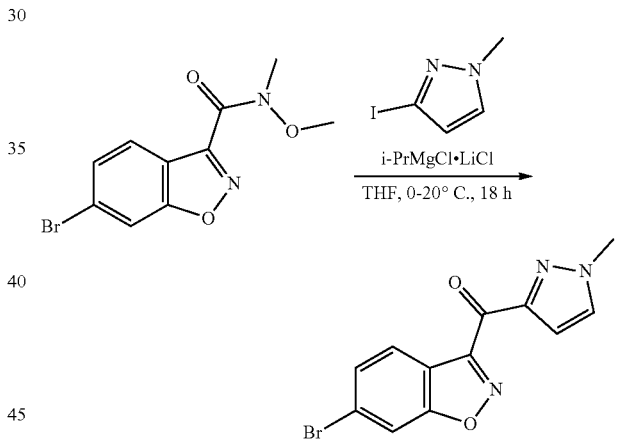

To a solution of 3-iodo-1-methyl-pyrazole (3.65 g, 17.5 mmol, 5.00 eq) in tetrahydrofuran (20 mL) was added isopropylmagnesium chloride-lithium chloride complex (1.30 M, 13.5 mL, 5.00 eq) dropwise at 0° C. under nitrogen atmosphere. The mixture was stirred at 20° C. for 1 h. Then 6-bromo-N-methoxy-N-methylbenzo[d]isoxazole-3-carboxamide (1.00 g, 3.51 mmol, 1.00 eq) in tetrahydrofuran (10 mL) was added. The resulting mixture was stirred at 20° C. for 17 h. The reaction was quenched with saturated aqueous ammonium chloride solution (30 mL). Then the mixture was extracted with ethyl acetate (3×30 mL), washed with brine (30 mL), dried over anhydrous sodium sulfate, filtered and concentrated under reduced pressure to give a residue, which was purified by flash silica gel chromatography (ISCO®; 20 g SepaFlash® Silica Flash Column, Eluent of 0-30% ethyl acetate/petroleum ether gradient at 60 mL/min). The desired fraction was collected and concentrated under reduced pressure to give (6-bromobenzo[d]isoxazol-3-yl)(1-methyl-1H-pyrazol-3-yl)methanone (0.800 g, 2.61 mmol, 75% yield) as a white solid.

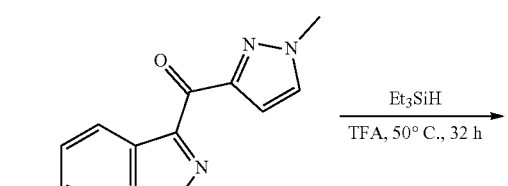

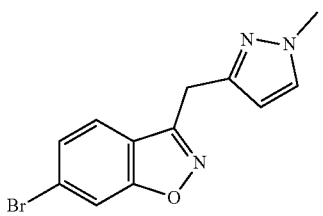

To a solution of (6-bromobenzo[d]isoxazol-3-yl)(1-methyl-1H-pyrazol-3-yl)methanone (0.400 g, 1.31 mmol, 1.00 eq) in trifluoroacetic acid (5 mL) was added triethylsilane (5.00 mL, 31.30 mmol, 24.0 eq). The mixture was stirred at 50° C. for 16 h. Then the triethylsilane (5.00 mL, 31.3 mmol, 24.0 eq) and trifluoroacetic acid (5 mL) were added to the mixture and stirred at 50° C. for another 16 h. After being cooled to room temperature, the reaction mixture was concentrated under reduced pressure to give a residue, which was purified by Prep-HPLC (column: Phenomenex luna C18 150 mm×25 mm×10 μm; mobile phase: [water (formic acid)-acetonitrile]; gradient: 40%-60% B over 10 min). The desired fraction was collected and lyophilized to afford 6-bromo-3-((1-methyl-1H-pyrazol-3-yl)methyl)benzo[d]isoxazole (0.206 g, 0.705 mmol, 54% yield) as a white solid.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(3-((1-methyl-1H-pyrazol-3-yl)methyl)benzo[d]isoxazol-6-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 6-bromo-3-((1-methyl-1H-pyrazol-3-yl)methyl)benzo[d]isoxazole analogously to General Scheme 1. MS (ESI) m/z 435.1 [M+H]⁺

Example 262. Synthesis of 3-(2-chloro-3-(1-methyl-3-((1-methyl-1H-pyrazol-3-yl)methyl)-1H-indazol-6-yl)phenyl)piperidine-2,6-dione (Compound 480)

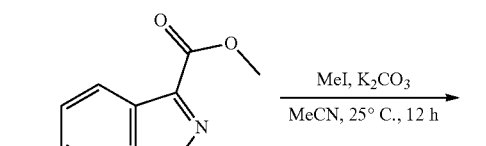

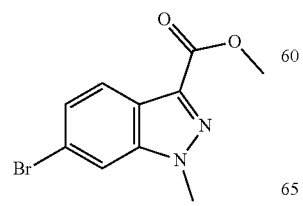

To a suspension of methyl 6-bromo-1H-indazole-3-carboxylate (2.00 g, 7.84 mmol, 1.00 eq) and potassium carbonate (5.12 g, 37.1 mmol, 4.72 eq) in acetonitrile (80 mL) was added iodomethane (2.30 mL, 36.9 mmol, 4.71 eq) at 25° C. The mixture was stirred at 25° C. for 12 h. The reaction mixture was filtered, and then the filtrate was concentrated under reduced pressure to give a residue, which was purified by flash silica gel chromatography (ISCO®; 40 g SepaFlash® Silica Flash Column, Eluent of 10~29% Ethyl acetate/Petroleum ether gradient @60 mL/min) to afford methyl 6-bromo-1-methyl-1H-indazole-3-carboxylate (1.35 g, 4.97 mmol, 63% yield) as a white solid.

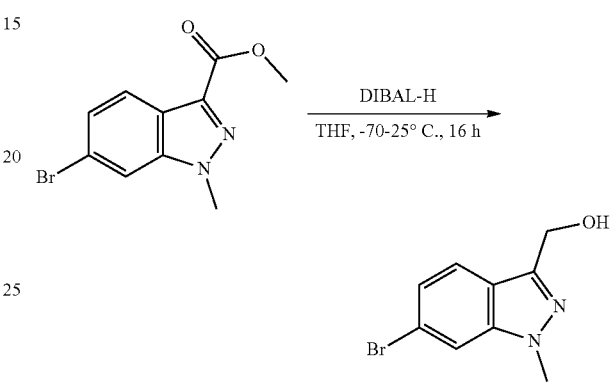

To a solution of methyl 6-bromo-1-methyl-1H-indazole-3-carboxylate (1.25 g, 4.65 mmol, 1.00 eq) in tetrahydrofuran (15 mL) was added diisobutylaluminum hydride (1 M in tetrahydrofuran, 18.6 mL, 4.00 eq) at −70° C. under nitrogen atmosphere. The mixture was stirred at 25° C. for 16 h under nitrogen atmosphere. The reaction was quenched with saturated ammonium chloride (40 mL) at 0° C. under nitrogen atmosphere. The mixture was adjusted to pH=3 with 1 M hydrochloric acid at 0° C. under nitrogen atmosphere. The mixture was extracted with ethyl acetate (2×50 mL). The combined organic extracts were dried over sodium sulfate, filtered and concentrated under reduced pressure to give a residue, which was purified by flash silica gel chromatography (ISCO®; 120 g SepaFlash® Silica Flash Column, Eluent of 20~75% Ethyl acetate/Petroleum ether gradient @ 60 mL/min) to afford (6-bromo-1-methyl-1H-indazol-3-yl)methanol (860 mg, 3.35 mmol, 72% yield) as a white solid.

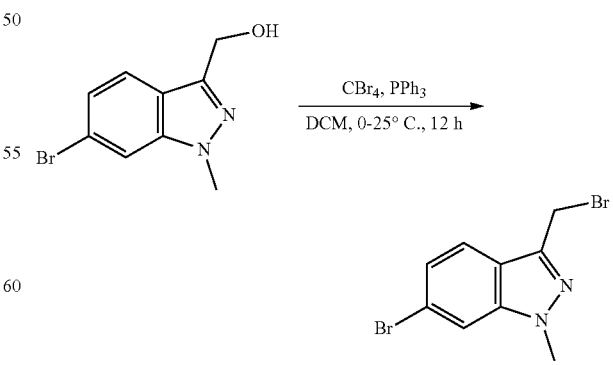

To a solution of (6-bromo-1-methyl-1H-indazol-3-yl)methanol (860 mg, 3.57 mmol, 1.00 eq) in dichloromethane (20 mL) were added perbromomethane (1.70 g, 5.13 mmol, 1.44 eq) and triphenylphosphane (1.35 g, 5.14 mmol, 1.44 eq) at 0° C. The mixture was stirred at 25° C. for 12 h. The reaction mixture was concentrated under reduced pressure to give a residue, which was purified by flash silica gel chromatography (ISCO®; 20 g SepaFlash® Silica Flash Column, Eluent of 100-100% Dichloromethane/Petroleum ether gradient @ 30 mL/min) to afford 6-bromo-3-(bromomethyl)-1-methyl-1H-indazole (1.12 g, 3.32 mmol, 93% yield) as a white solid.

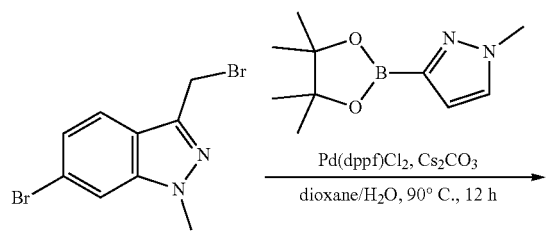

To a solution of 6-bromo-3-(bromomethyl)-1-methyl-1H-indazole (900 mg, 2.96 mmol, 1.00 eq) and 1-methyl-3-(4,4,5,5-tetramethyl-1,3,2-dioxaborolan-2-yl)-1H-pyrazole (720 mg, 3.46 mmol, 1.17 eq) in water (4 mL) and dioxane (20 mL) were added cesium carbonate (2.97 g, 9.12 mmol, 3.08 eq) and [1,1-bis(diphenylphosphino)ferrocene]dichloropalladium(II) (450 mg, 615 μmol, 0.200 eq). The mixture was stirred at 90° C. for 12 h under nitrogen atmosphere. The reaction mixture was diluted with water (20 mL) and extracted with ethyl acetate (2×30 mL). The combined organic layers were dried over sodium sulfate, filtered and concentrated under reduced pressure to give a residue, which was purified by flash silica gel chromatography (ISCO®; 12 g SepaFlash® Silica Flash Column, Eluent of 100~100% Ethyl acetate/Petroleum ether gradient @40 mL/min) followed by Prep-HPLC (column: Phenomenex Luna C18 150×25 mm×10 m; mobile phase: [water (formic acid)-acetonitrile]; gradient: 32%-62% B over 10 min) and concentrated under reduced pressure to afford 6-bromo-1-methyl-3-((1-methyl-1H-pyrazol-3-yl)methyl)-1H-indazole (80.0 mg, 260 μmol, 9% yield) as colorless oil.

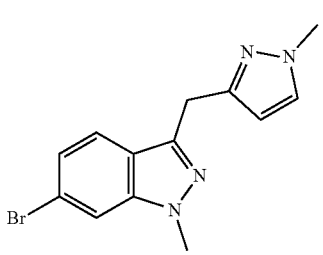

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-methyl-3-((1-methyl-1H-pyrazol-3-yl)methyl)-1H-indazol-6-yl)phenyl) piperidine-2,6-dione was prepared from 3-(2-chloro-3-(4,4,5,5-tetramethyl-1,3,2-dioxaborolan-2-yl)phenyl)piperidine-2,6-dione and 6-bromo-1-methyl-3-((1-methyl-1H-pyrazol-3-yl)methyl)-1H-indazole analogously to General Scheme 1. MS (ESI) m/z 448.0 [M+H]$^+$ Example 263. Synthesis of 3-(2-chloro-3-(3-methyl-1-((1-methyl-1H-pyrazol-3-yl)methyl)-2-oxo-2,3-dihydro-1H-benzo[d]imidazol-5-yl)phenyl)piperidine-2,6-dione (Compound 363)

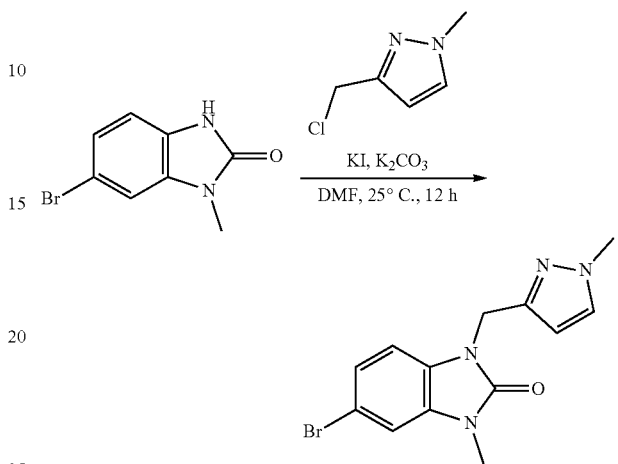

5-bromo-3-methyl-1-((1-methyl-1H-pyrazol-3-yl)methyl)-1,3-dihydro-2H-benzo[d]imidazol-2-one was prepared from 6-bromo-1-methyl-1,3-dihydro-2H-benzo[d]imidazol-2-one and 3-(chloromethyl)-1-methyl-1H-pyrazole according to General Scheme 11. 3-(2-chloro-3-(4,4,5,5-tetramethyl-1,3,2-dioxaborolan-2-yl)phenyl) piperidine-2,6-dione (intermediate A) was synthesized as described above. 3-(2-chloro-3-(3-methyl-1-((1-methyl-1H-pyrazol-3-yl)methyl)-2-oxo-2,3-dihydro-1H-benzo[d]imidazol-5-yl)phenyl)piperidine-2,6-dione was prepared from 3-(2-chloro-3-(4,4,5,5-tetramethyl-1,3,2-dioxaborolan-2-yl) phenyl)piperidine-2,6-dione and 5-bromo-3-methyl-1-((1-methyl-1H-pyrazol-3-yl)methyl)-1,3-dihydro-2H-benzo[d]imidazol-2-one according to General Scheme 1.
MS (ESI) m/z 464.4 [M+H]$^+$ Example 264. Synthesis of 3-(2-chloro-3-(1-((1-methyl-1H-imidazol-4-yl)methyl)-1H-indazol-5-yl) phenyl)piperidine-2,6-dione (Compound 397)

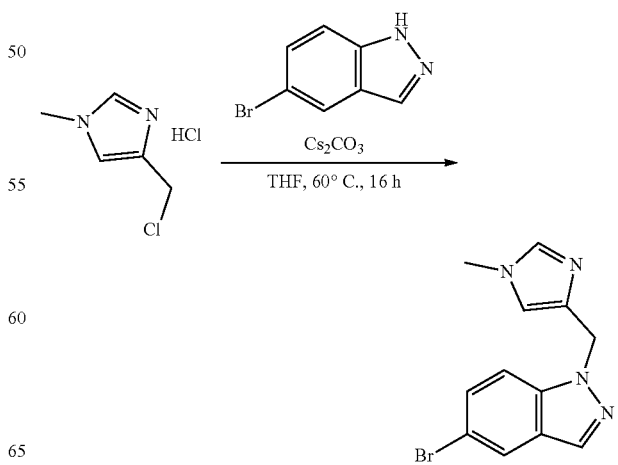

5-bromo-1-((1-methyl-1H-imidazol-4-yl)methyl)-1H-indazole was prepared from 4-(chloromethyl)-1-methyl-1H-imidazole hydrogen chloride and 5-bromo-1H-indazole analogously to General Scheme 11.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methyl-1H-imidazol-4-yl)methyl)-1H-indazol-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methyl-1H-imidazol-4-yl)methyl)-1H-indazole analogously to General Scheme 1. MS (ESI) m/z 434.1 [M+H]+

Example 265. Synthesis of 3-(2-chloro-3-(1-(pyrimidin-2-ylmethyl)-1H-indazol-5-yl)phenyl)piperidine-2,6-dione (Compound 396)

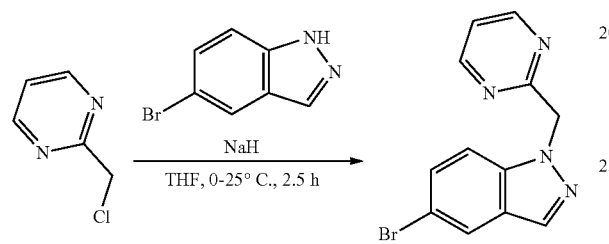

5-bromo-1-(pyrimidin-2-ylmethyl)-1H-indazole was prepared from 5-bromo-1H-indazole and 2-(chloromethyl)pyrimidine analogously to General Scheme 11.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-(pyrimidin-2-ylmethyl)-1H-indazol-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-(pyrimidin-2-ylmethyl)-1H-indazole analogously to General Scheme 1. MS (ESI) m/z 432.0 [M+H]+

Example 266. Synthesis of 3-(2-chloro-3-(2-oxo-1-(pyridazin-3-ylmethyl)indolin-5-yl)phenyl)piperidine-2,6-dione (Compound 395)

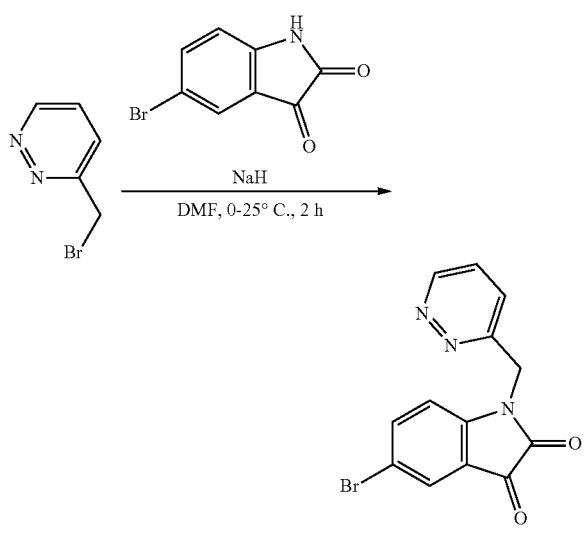

5-bromo-1-(pyridazin-3-ylmethyl)indoline-2,3-dione was prepared from 5-bromoindoline-2,3-dione and 3-(bromomethyl)pyridazine according to General Scheme 11.

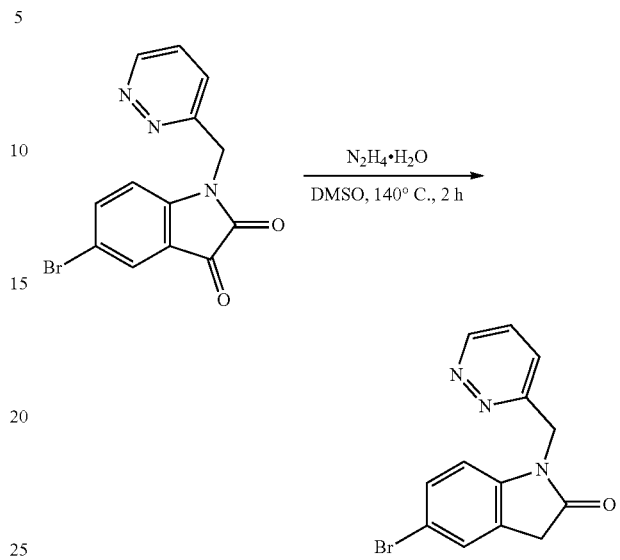

To a solution of 5-bromo-1-(pyridazin-3-ylmethyl)indoline-2,3-dione (236 mg, 742 µmol, 1.00 eq) in dimethylsulfoxide (6 mL) was added hydrazine hydrate (874 mg, 14.8 mmol, 846 µL, 85% purity, 20.0 eq). The mixture was stirred at 140° C. for 2 h. After being cooled to room temperature, the mixture was quenched with water (30 mL) and extracted with ethyl acetate (3×30 mL). The combined organic layers were washed with brine (30 mL), dried over anhydrous sodium sulfate, filtered and concentrated to give a residue, which was purified by column chromatography (SiO2, petroleum ether/ethyl acetate=100/1 to 1/10) to afford 5-bromo-1-(pyridazin-3-ylmethyl)indolin-2-one (134 mg, 441 µmol, 59% yield) as a yellow solid. 3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(2-oxo-1-(pyridazin-3-ylmethyl)indolin-5-yl)phenyl)piperidine-2,6-dione was prepared from 5-bromo-1-(pyridazin-3-ylmethyl)indolin-2-one and 3-(2-chloro-3-(4,4,5,5-tetramethyl-1,3,2-dioxaborolan-2-yl)phenyl)piperidine-2,6-dione analogously General Scheme 1.MS (ESI) m/z 447.2 [M+H]+

Example 267. Synthesis of 3-(2-chloro-3-(2-oxo-1-(pyrimidin-2-ylmethyl)indolin-5-yl)phenyl)piperidine-2,6-dione (Compound 393)

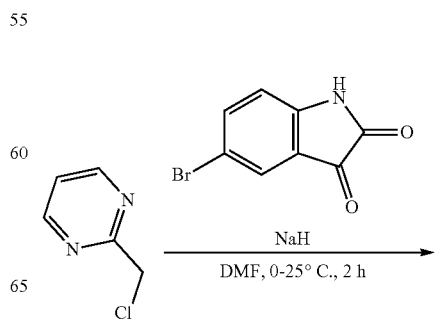

-continued

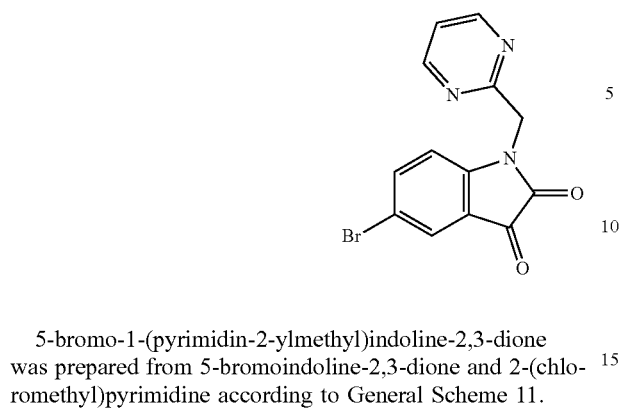

5-bromo-1-(pyrimidin-2-ylmethyl)indoline-2,3-dione was prepared from 5-bromoindoline-2,3-dione and 2-(chloromethyl)pyrimidine according to General Scheme 11.

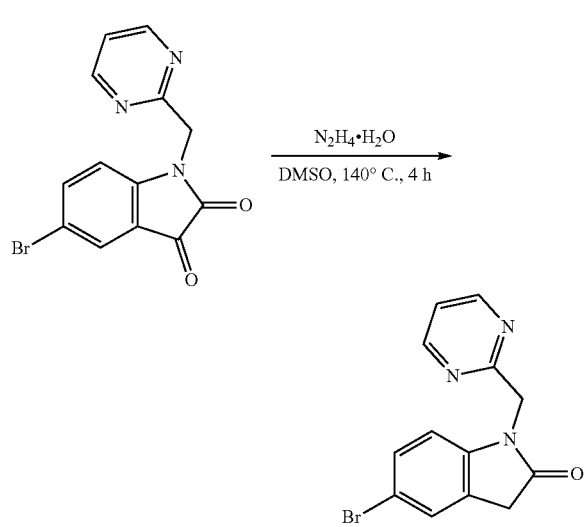

A mixture of 5-bromo-1-(pyrimidin-2-ylmethyl)indoline-2,3-dione (704 mg, 1.55 mmol, 1.00 eq) and hydrazine hydrate (1.94 g, 32.9 mmol, 1.88 mL, 85% purity, 21.3 eq) in dimethylsulfoxide (15 mL) was stirred at 140° C. for 4 h. The mixture was diluted with water (50 mL) and extracted with ethyl acetate (3×50 mL). The combined organic layers were washed with brine (50 mL) and dried over anhydrous sodium sulfate, filtered and concentrated to give a residue, which was purified by column chromatography (SiO$_2$, Petroleum ether/Ethyl acetate=10/0 to 3/7) to afford 5-bromo-1-(pyrimidin-2-ylmethyl)indolin-2-one (337 mg, 1.11 mmol, 72% yield) as a yellow solid.

3-(2-chloro-3-(4,4,5,5-tetramethyl-1,3,2-dioxaborolan-2-yl)phenyl)piperidine-2,6-dione (intermediate A) was synthesized as described above. 3-[2-chloro-3-[2-oxo-1-(pyrimidin-2-ylmethyl)indolin-5-yl]phenyl]piperidine-2,6-dione was prepared from 5-bromo-1-(pyrimidin-2-ylmethyl)indolin-2-one and 3-[2-chloro-3-(4,4,5,5-tetramethyl-1,3,2-dioxaborolan-2-yl)phenyl]piperidine-2,6-dione analogously to General Scheme 1.

$^1$H NMR (400 MHz, DMSO-d$_6$) δ=10.92 (s, 1H), 8.78 (d, J=4.8 Hz, 2H), 7.44 (t, J=4.8 Hz, 1H), 7.40-7.35 (m, 1H), 7.34-7.27 (m, 3H), 7.21 (d, J=8.0 Hz, 1H), 6.90 (d, J=8.0 Hz, 1H), 5.13 (s, 2H), 4.33 (dd, J=12.0, 4.8 Hz, 1H), 3.73 (s, 2H), 2.84-2.73 (m, 1H), 2.56 (s, 1H), 2.39-2.27 (m, 1H), 2.08-2.01 (m, 1H); MS (ESI) m/z 447.1 [M+H]$^+$

Example 268. Synthesis of 3-(2-chloro-3-(3-((1-methyl-1H-imidazol-4-yl)methyl)-2-oxo-2,3-dihydrobenzo[d]oxazol-6-yl)phenyl)piperidine-2,6-dione (Compound 392)

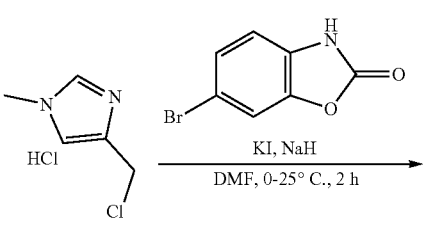

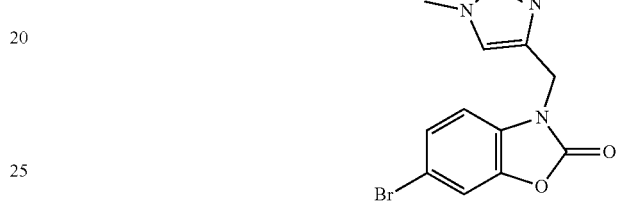

6-bromo-3-((1-methyl-1H-imidazol-4-yl)methyl)benzo[d]oxazol-2(3H)-one was prepared from 6-bromobenzo[d]oxazol-2(3H)-one and 4-(chloromethyl)-1-methyl-1H-imidazole according to General Scheme 11.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(3-((1-methyl-1H-imidazol-4-yl)methyl)-2-oxo-2,3-dihydrobenzo[d]oxazol-6-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 6-bromo-3-((1-methyl-1H-imidazol-4-yl)methyl)benzo[d]oxazol-2(3H)-one analogously to General Scheme 1. MS (ESI) m/z 451.0 [M+H]$^+$ Example 269. Synthesis of 3-(2-chloro-3-(1-((1-methoxycyclopropyl)methyl)-2-oxoindolin-5-yl)phenyl)piperidine-2,6-dione (Compound 391)

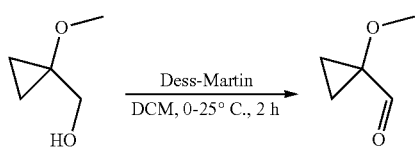

To a solution of (1-methoxycyclopropyl)methanol (1.00 g, 9.79 mmol, 1.00 eq) in dichloromethane (10 mL) was added Dess-Martin (4.15 g, 9.79 mmol, 3.03 mL, 1.00 eq) at 0° C. The reaction was stirred at 25° C. for 2 h. Then the reaction was filtered to give a residue. The residue was purified by column chromatography (SiO$_2$, Petroleum ether/Ethyl acetate=10/1 to 5/1) to afford 1-methoxycyclopropane-1-carbaldehyde (500 mg, 1.50 mmol, 15% yield, 30% purity) as colorless oil.

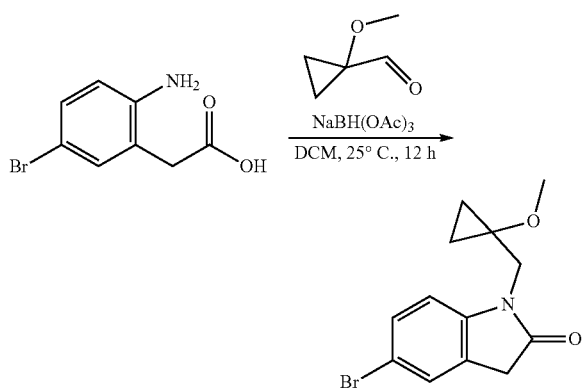

To a solution of 1-methoxycyclopropane-1-carbaldehyde (500 mg, 4.99 mmol, 3.00 eq) and 2-(2-amino-5-bromophenyl)acetic acid (383 mg, 1.66 mmol, 1.00 eq) in dichloromethane (5 mL) was added sodium triacetoxyhydroborate (635 mg, 3.00 mmol, 1.80 eq). The reaction was stirred at 25° C. for 12 h. Then the reaction was concentrated under reduced pressure to give a residue. The residue was purified by reversed-phase column (0.1% formic acid condition) to afford 5-bromo-1-((1-methoxycyclopropyl)methyl)indolin-2-one (250 mg, 844 µmol, 51% yield) as a yellow solid.

3-(2-chloro-3-(4,4,5,5-tetramethyl-1,3,2-dioxaborolan-2-yl)phenyl)piperidine-2,6-dione (intermediate A) was synthesized as described above. 3-(2-chloro-3-(1-((1-methoxycyclopropyl)methyl)-2-oxoindolin-5-yl)phenyl)piperidine-2,6-dione was prepared from 3-(2-chloro-3-(4,4,5,5-tetramethyl-1,3,2-dioxaborolan-2-yl)phenyl)piperidine-2,6-dione and 5-bromo-1-((1-methoxycyclopropyl)methyl)indolin-2-one analogously to General Scheme 1.

Example 270. Synthesis of 1-((5-(2-chloro-3-(2,6-dioxopiperidin-3-yl)phenyl)-2-oxoindolin-1-yl)methyl)cyclopropane-1-carbonitrile (Compound 390)

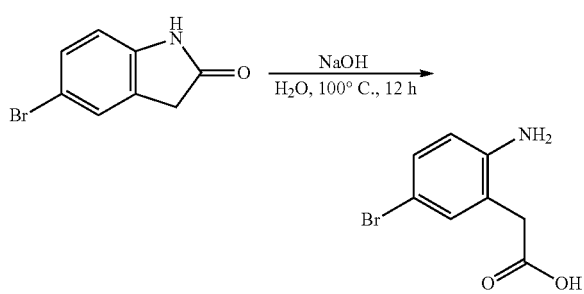

To a solution of 5-bromoindolin-2-one (1.00 g, 4.72 mmol, 1.00 eq) in water (10 mL) was added sodium hydroxide (2 M, 11.7 mL, 5.00 eq). The reaction was stirred at 100° C. for 12 h. After being cooled to room temperature, the reaction was adjust pH<7, then diluted with water (100 mL) and extracted with ethyl acetate (3×50 mL), then the organic layers were wash with brine (100 mL), dried over sodium sulfate, filtered and concentrated under reduced pressure to afford 2-(2-amino-5-bromophenyl)acetic acid (350 mg, 1.52 mmol, 32% yield) as a yellow solid.

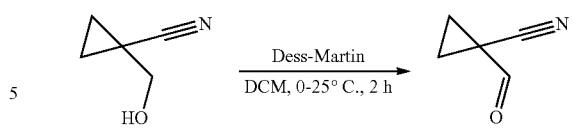

To a solution of 1-(hydroxymethyl)cyclopropane-1-carbonitrile (1.00 g, 10.3 mmol, 1.00 eq) in dichloromethane (10.0 mL) was added Dess-Martin (4.37 g, 10.3 mmol, 3.19 mL, 1.00 eq) at 0° C. The reaction was stirred at 25° C. for 2 h. The reaction was quenched with aqueous sodium bicarbonate solution (50 mL) and extracted with ethyl acetate (3×50 mL), then the organic layers were wash with brine (100 mL), dried over sodium sulfate, filtered and concentrated under reduced pressure to give a residue, which was purified by column chromatography (SiO$_2$, Petroleum ether/Ethyl acetate=5/1 to 3/1) to afford 1-formylcyclopropane-1-carbonitrile (500 mg, 5.26 mmol, 51% yield) as colorless oil.

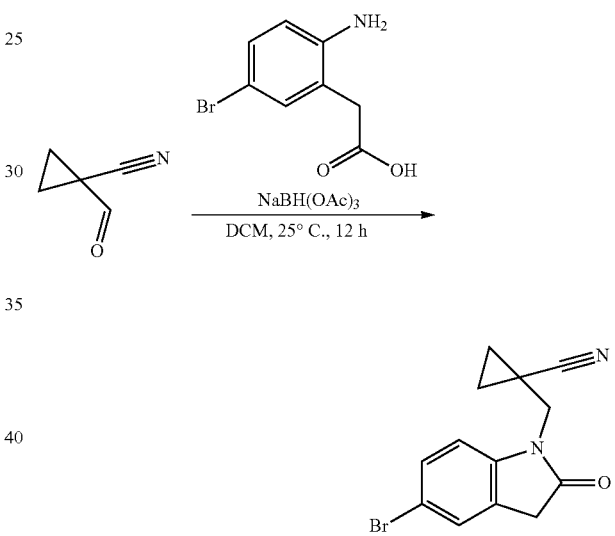

To a solution of 1-formylcyclopropane-1-carbonitrile (50.0 mg, 525 µmol, 1.00 eq) and 2-(2-amino-5-bromophenyl)acetic acid (181 mg, 788 µmol, 1.50 eq) in dichloromethane (2.00 mL) was added sodium triacetoxyhydroborate (200 mg, 946 µmol, 1.80 eq). The reaction was stirred at 25° C. for 12 h. Then the reaction was diluted with water (50 mL), extracted with dichloromethane (3×50 mL), wash with brine (50 mL), dried over sodium sulfate, filtered and concentrated under reduced pressure to give a residue, which was purified by reversed-phase column (0.1% formic acid condition) to afford 1-((5-bromo-2-oxoindolin-1-yl)methyl)cyclopropane-1-carbonitrile (100 mg, 343 µmol, 65% yield) as a white solid. 3-(2-chloro-3-(4,4,5,5-tetramethyl-1,3,2-dioxaborolan-2-yl)phenyl)piperidine-2,6-dione (intermediate A) was synthesized as described above. 1-((5-(2-chloro-3-(2,6-dioxopiperidin-3-yl)phenyl)-2-oxoindolin-1-yl)methyl)cyclopropane-1-carbonitrile was prepared from 1-((5-bromo-2-oxoindolin-1-yl)methyl)cyclopropane-1-carbonitrile and 3-(2-chloro-3-(4,4,5,5-tetramethyl-1,3,2-dioxaborolan-2-yl)phenyl)piperidine-2,6-dione analogously to General Scheme 1. MS (ESI) m/z 434.2 [M+H]$^+$

Example 271. Synthesis of 3-[2-chloro-3-(3,4-dihydro-2H-1-benzopyran-6-yl)phenyl]piperidine-2,6-dione (Compound 381)

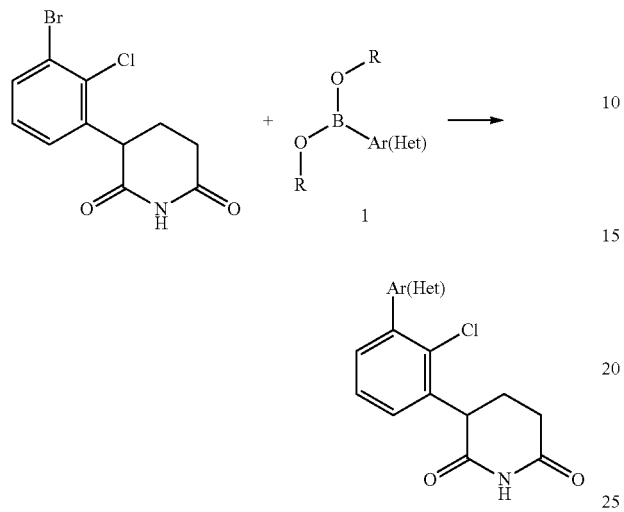

3-(3-Bromo-2-chlorophenyl)piperidine-2,6-dione (1 eq.), appropriate boronic acid or pinacolate 1 (appr. 1.5-2 eq.), were mixed in DMF-water 20:1 (appr. 0.7 ml) and then cataCXium A Pd G3 (0.05 eq.), RuPhos Pd G4 (0.05 eq.), and sodium bicarbonate ($NaHCO_3$) were added in one portion in an inert atmosphere. The reaction mixture was sealed and heated for 15 hours at 90° C. Then the mixture was cooled to the ambient temperature and trifluoroaceticacid (TFA) was added dropwise until neutral pH. The mixture was evaporated under reduced pressure and the residue was dissolved in the DMSO (appr. 0.7 ml). DMSO solution was treated with scavenger SiliaMetS DMT, filtered, analyzed by LCMS, and purified by HPLC purification. 3-[2-chloro-3-(3,4-dihydro-2H-1-benzopyran-6-yl)phenyl]piperidine-2,6-dione was obtained by the synthetic procedure above with using 65 mg (0,215 mmol) of 3-(3-bromo-2-chlorophenyl)piperidine-2,6-dione, 58 mg (0,326 mmol) of (3,4-dihydro-2H-1-benzopyran-6-yl)boronic acid, 46 mg (0,548 mmol) of $NaHCO_3$, 7.8 mg (0,011 mmol) of cataCXium A Pd G3, and 9.1 mg (0,011 mmol) of RuPhos Pd G4. Purified by the HPLC procedure described below (gradient: from A-55%: B-45% to A-45%: B-55%). Yield: 10.1 mg (13.2%). EI MS m/z: pos. 356.0 ($MH^+$).

Example 272. Synthesis of 3-{2-chloro-[1,1'-biphenyl]-3-yl}piperidine-2,6-dione (Compound 380)

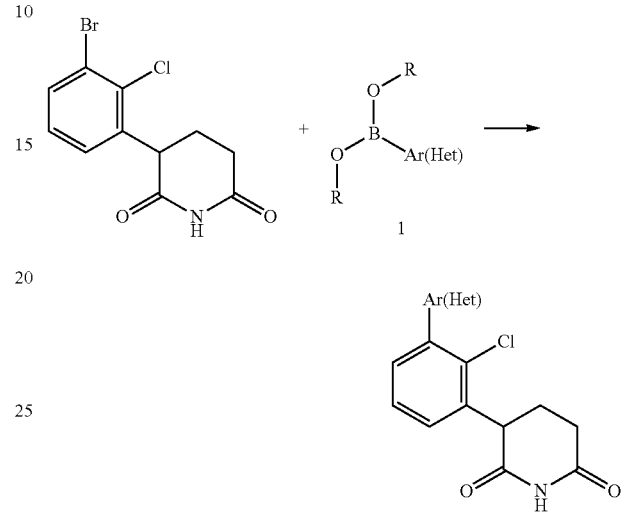

3-{2-chloro-[1,1'-biphenyl]-3-yl}piperidine-2,6-dione was obtained by the synthetic procedure described for Example 271 with using 72 mg (0.239 mmol) of 3-(3-bromo-2-chlorophenyl)piperidine-2,6-dione, 58 mg (0.475 mmol) of phenylboronic acid, 68 mg (0.81 mmol) of $NaHCO_3$, 8.7 mg (0.012 mmol) of cataCXium A Pd G3, and 10.1 mg (0.012 mmol) of RuPhos Pd G4. Purified by the HPLC (gradient: from A-65%: B-35% to A-45%: B-55%). Yield: 7 mg (9.8%). White powder. LCMS purity: 100% (LCMS procedure described below, Rf=0.66, run time=2 min). EI MS m/z: pos. 300.0 ($MH^+$).

Example 273. Synthesis of 3-(2-chloro-3-{1H-pyrrolo[2,3-b]pyridin-5-yl}phenyl)piperidine-2,6-dione (Compound 379)

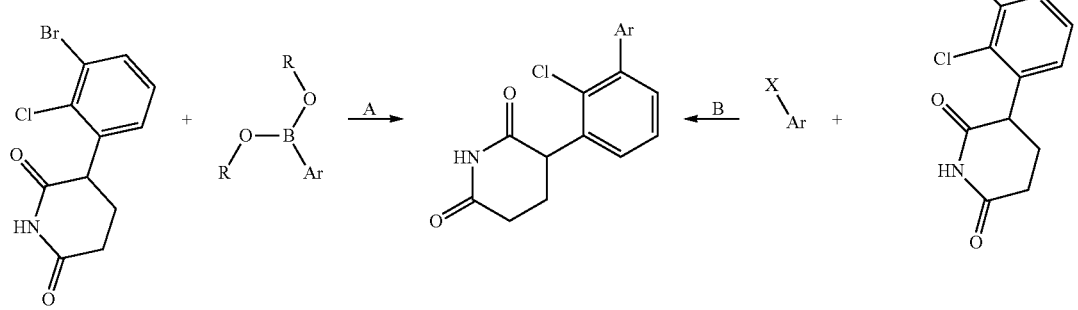

Appropriate halogenide (1 eq.) and appropriate boronic acid or pinacolate (appr. 1-2 eq.) were mixed in DMF-water 20:1 (appr. 0.7 ml) and then cataCXium A Pd G3 (0.05 eq.), RuPhos Pd G4 (0.05 eq.), and sodium bicarbonate (NaHCO$_3$) (appr. 3-3.5 eq.) were added in one portion in an inert atmosphere. The reaction mixture was sealed and heated for 15 hours at 90° C. Then the mixture was cooled to the ambient temperature and trifluoroaceticacid (TFA) was added dropwise until neutral pH. The mixture was evaporated under reduced pressure and the residue was dissolved in DMSO (appr. 0.7 ml). DMSO solution was treated with scavenger SiliaMetS DMT, filtered, analyzed by LCMS, and purified by HPLC.

3-(2-chloro-3-{1H-pyrrolo[2,3-b]pyridin-5-yl}phenyl)piperidine-2,6-dione; trifluoroacetic acid was obtained by the above synthetic procedure with using 51 mg (0.26 mmol) of 5-bromo-1H-pyrrolo[2,3-b]pyridine, 74 mg (0.212 mmol) of 3-[2-chloro-3-(4,4,5,5-tetramethyl-1,3,2-dioxaborolan-2-yl) phenyl]piperidine-2,6-dione, 76 mg (0.905 mmol) of NaHCO$_3$, 7.9 mg (0.011 mmol) of cataCXium A Pd G3, and 9.2 mg (0.011 mmol) of RuPhos Pd G4. Purified by the HPLC (gradient: from A-75%: B-25% to A-50%: B-50%). Yield: 10.4 mg (14.2%). Light brown sticky oil. LCMS purity: 97.2% EI MS m/z: pos. 340.0 (MH$^+$).

Example 274. Synthesis of (S)-3-(2-chloro-4'-(2-oxopiperidin-1-yl)-[1,1'-biphenyl]-3-yl)-3-fluoropiperidine-2,6-dione and (R)-3-(2-chloro-4'-(2-oxopiperidin-1-yl)-[1,1'-biphenyl]-3-yl)-3-fluoropiperidine-2,6-dione (Compounds 367 and 368)

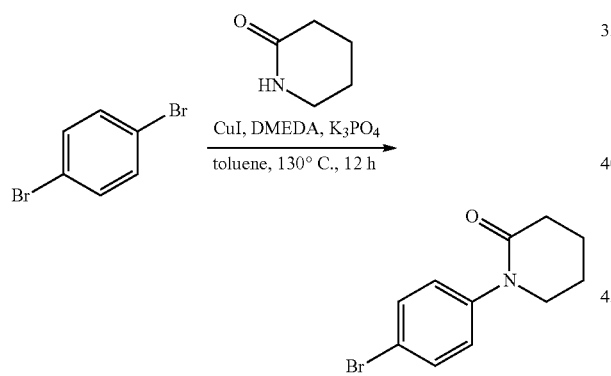

To a solution of piperidin-2-one (1.00 g, 10.1 mmol, 1.00 eq) and 1,4-dibromobenzene (2.38 g, 10.1 mmol, 1.29 mL, 1.00 eq) in toluene (20 mL) was added potassium phosphate (4.28 g, 20.2 mmol, 2.00 eq) and cuprous iodide (0.0960 g, 0.504 mmol, 0.0500 eq) followed by N$^1$,N$^2$-dimethylethane-1,2-diamine (0.0440 g, 0.499 mmol, 0.0500 eq) at 25° C. under nitrogen atmosphere. The reaction was stirred at 130° C. for 12 h. After being cooled to room temperature, the mixture was diluted with water (40 mL) and extracted with ethyl acetate (3×40 mL). The combined organic layers were washed with brine (3×40 mL), dried over anhydrous sodium sulfate and concentrated under vacuum. The residue was purified by column chromatography (silica, petroleum ether: ethyl acetate=5:1 to 1:2) to give 1-(4-bromophenyl)piperidin-2-one (0.900 g, 3.54 mmol, 35% yield) as a yellow solid.

$^1$H NMR (400 MHz, DMSO-d$_6$) δ=7.59-7.52 (m, 2H), 7.29-7.20 (m, 2H), 3.59 (t, J=5.2 Hz, 2H), 2.38 (t, J=6.8 Hz, 2H), 1.92-1.77 (m, 4H)

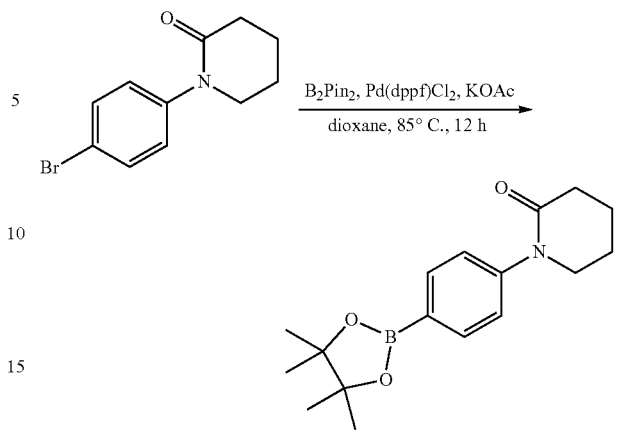

To a solution of 1-(4-bromophenyl)piperidin-2-one (0.700 g, 2.75 mmol, 1.00 eq) in dioxane (10 mL) was added potassium acetate (0.812 g, 8.27 mmol, 3.00 eq) and 4,4,4', 4',5,5,5',5'-octamethyl-2,2'-bi(1,3,2-dioxaborolane) (0.840 g, 3.31 mmol, 1.20 eq) followed by [1,1'-bis(diphenylphosphino)ferrocene]-dichloropalladium(II) (0.202 g, 0.275 mmol, 0.100 eq) at 25° C. under nitrogen atmosphere. The reaction was stirred at 85° C. for 12 h. After being cooled to room temperature, the mixture was diluted with water (30 mL) and extracted with ethyl acetate (3×30 mL). The combined organic layers were washed with brine (3×30 mL), dried over anhydrous sodium sulfate and concentrated under vacuum. The residue was purified by column chromatography (silica, petroleum ether:ethyl acetate=5:1 to 1:2) to give 1-(4-(4,4,5,5-tetramethyl-1,3,2-dioxaborolan-2-yl) phenyl)piperidin-2-one (650 mg, 1.62 mmol, 59% yield) as a white solid.

$^1$H NMR (400 MHz, DMSO-d$_6$) δ=7.66 (d, J=8.4 Hz, 2H), 7.30 (d, J=8.4 Hz, 2H), 3.66-3.55 (m, 2H), 2.45-2.32 (m, 2H), 1.91-1.77 (m, 4H), 1.29 (s, 12H)

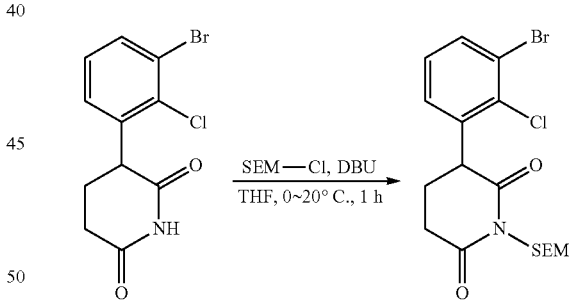

To a solution of 3-(3-bromo-2-chlorophenyl)piperidine-2,6-dione (500 mg, 1.65 mmol, 1.00 eq) in tetrahydrofuran (5.00 mL) was added 1,8-diazabicyclo[5.4.0]undec-7-ene (503 mg, 3.31 mmol, 498 uL, 2.00 eq) and 2-(trimethylsilyl) ethoxymethyl chloride (495 mg, 2.97 mmol, 526 uL, 1.80 eq) at 0° C. The mixture was stirred at 20° C. for 1 h. The mixture was quenched with saturated sodium bicarbonate solution (20 mL), extracted with ethyl acetate (3×20 mL), washed with brine (3×20 mL), and dried over anhydrous sodium sulfate, filtered and concentrated under reduced pressure to give a residue. The residue was purified by column chromatography (SiO$_2$, petroleum ether/ethyl acetate=10/1 to 1/1) to afford 3-(3-bromo-2-chlorophenyl)-1-((2-(trimethylsilyl)ethoxy)methyl)piperidine-2,6-dione (600 mg, 1.39 mmol, 83% yield) as light yellow oil.

¹H NMR (400 MHz, DMSO-d₆) δ=7.74 (dd, J=1.4, 7.9 Hz, 1H), 7.40-7.34 (m, 1H), 7.32-7.26 (m, 1H), 5.09 (s, 2H), 4.47 (dd, J=5.0, 12.6 Hz, 1H), 3.56-3.50 (m, 2H), 3.01-2.90 (m, 1H), 2.74 (td, J=3.5, 17.1 Hz, 1H), 2.35 (dd, J=4.2, 13.1 Hz, 1H), 2.05-1.99 (m, 1H), 0.87-0.81 (m, 2H), -0.02 (s, 9H).

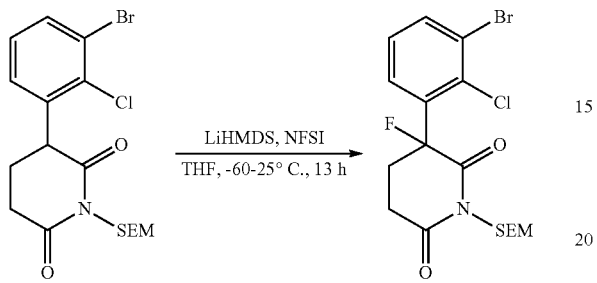

To a solution of 3-(3-bromo-2-chlorophenyl)-1-((2-(trimethylsilyl)ethoxy)methyl)piperidine-2,6-dione (0.600 g, 1.39 mmol, 1.00 eq) in tetrahydrofuran (18 mL) was added lithium bis(trimethylsilyl)amide (1 M in tetrahydrofuran, 2.08 mL, 1.50 eq) at −60° C. under nitrogen atmosphere. The reaction was stirred at −60° C. for 1 h. N-fluoro-N-(phenylsulfonyl)benzenesulfonamide (0.656 g, 2.08 mmol, 1.50 eq) in tetrahydrofuran (2 mL) was added at −60° C. The reaction was stirred at 25° C. for 12 h. The mixture was diluted with water (30 mL) and extracted with ethyl acetate (3×40 mL). The combined organic layers were washed with brine (3×40 mL), dried over anhydrous sodium sulfate and concentrated under vacuum. The residue was purified by column chromatography (silica, petroleum ether:ethyl acetate=5:1 to 1:2) to give 3-(3-bromo-2-chlorophenyl)-3-fluoro-1-((2-(trimethylsilyl)ethoxy)methyl)piperidine-2,6-dione (0.190 g, 0.421 mmol) as a yellow solid.

¹H NMR (400 MHz, DMSO-d₆) δ=7.94-7.87 (m, 1H), 7.71-7.64 (m, 1H), 7.50-7.42 (m, 1H), 5.28-5.04 (m, 2H), 3.63-3.51 (m, 2H), 3.10-2.74 (m, 3H), 2.35-2.24 (m, 1H), 0.88-0.81 (m, 2H), 0.01-0.03 (m, 9H)

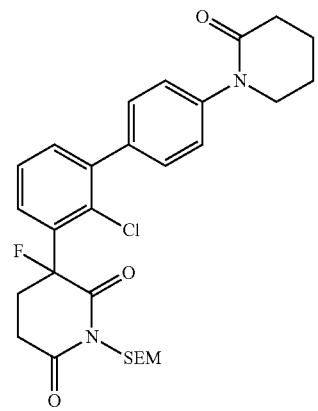

To a solution of 3-(3-bromo-2-chloro-phenyl)-3-fluoro-1-(2-trimethylsilylethoxymethyl)piperidine-2,6-dione (0.100 g, 0.222 mmol, 1.00 eq) in dioxane (10 mL) and water (1 mL) was added 1-(4-(4,4,5,5-tetramethyl-1,3,2-dioxaborolan-2-yl)phenyl)piperidin-2-one (0.130 g, 0.432 mmol, 1.95 eq) and potassium phosphate (0.141 g, 0.665 mmol, 3.00 eq) followed by [1,1'-bis(diphenylphosphino)ferrocene]dichloropalladium(II) (0.0162 g, 0.022 mmol, 0.100 eq) at 25° C. under nitrogen atmosphere. The reaction was stirred at 100° C. for 12 h. After being cooled to room temperature, the mixture was diluted with water (20 mL) and extracted with ethyl acetate (3×30 mL). The combined organic layers were washed with brine (3×30 mL), dried over anhydrous sodium sulfate and concentrated under vacuum. The residue was purified by column chromatography (silica, petroleum ether:ethyl acetate=5:1 to 1:2) to give 3-(2-chloro-4'-(2-oxopiperidin-1-yl)-[1,1'-biphenyl]-3-yl)-3-fluoro-1-((2-(trimethylsilyl)ethoxy)methyl)piperidine-2,6-dione (0.0850 g, 0.156 mmol, 70% yield) as a yellow solid.

¹H NMR (400 MHz, DMSO-d₆) δ=7.68 (d, J=8.0 Hz, 1H), 7.58 (t, J=8.0 Hz, 1H), 7.53-7.47 (m, 1H), 7.44-7.34 (m, 4H), 5.20 (d, J=9.6 Hz, 1H), 5.10 (d, J=10.0 Hz, 1H), 3.65 (t, J=5.2 Hz, 2H), 3.60-3.53 (m, 2H), 3.10-2.75 (m, 3H), 2.52-2.51 (m, 1H), 2.41 (t, J=6.4 Hz, 2H), 1.93-1.81 (m, 4H), 0.88-0.77 (m, 2H), 0.044 (s, 9H)

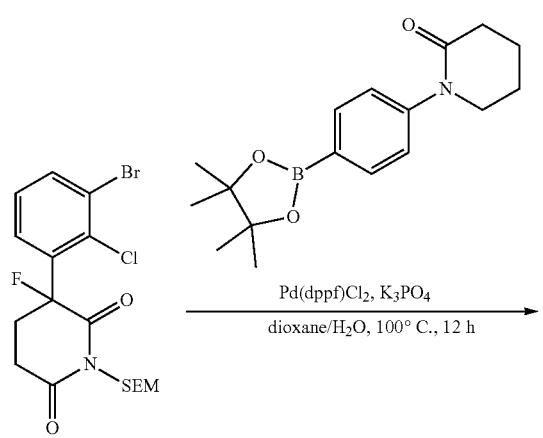

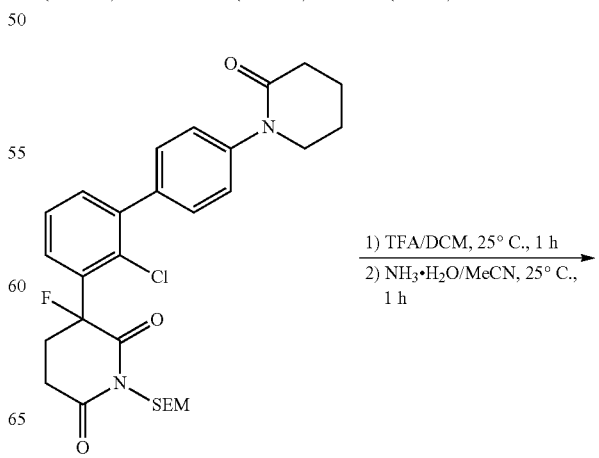

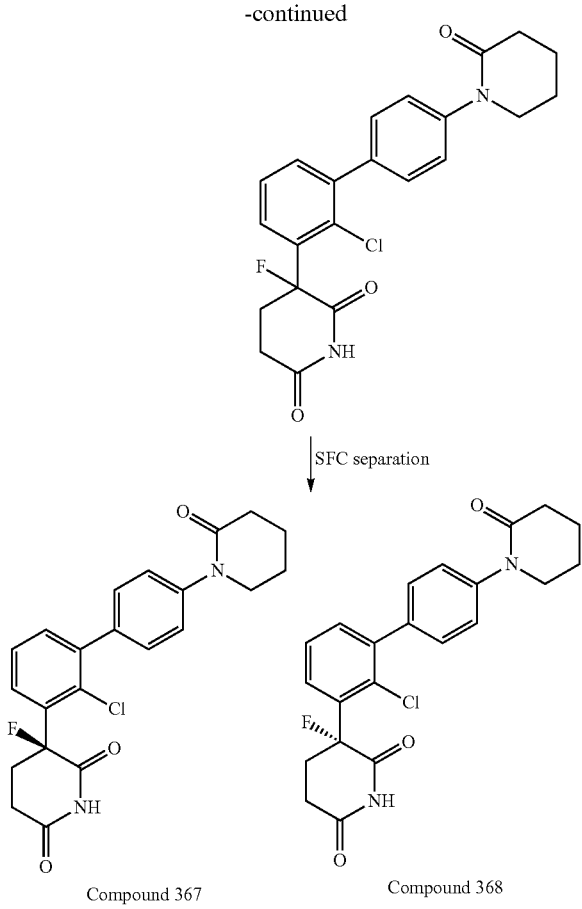

To a solution of 3-(2-chloro-4'-(2-oxopiperidin-1-yl)-[1,1'-biphenyl]-3-yl)-3-fluoro-1-((2-(trimethylsilyl)-ethoxy)methyl)piperidine-2,6-dione (0.160 g, 0.294 mmol, 1.00 eq) in dichloromethane (3 mL) was added trifluoroacetic acid (0.750 ml) at 25° C. The reaction was stirred at 25° C. for 1 h. The reaction mixture was concentrated under reduced pressure. The residue was suspended in acetonitrile (4 mL) and ammonium hydroxide (0.2 mL, 26% purity) at 25° C. The reaction was stirred at 25° C. for 1 h. The mixture was adjusted pH to 4 with hydrochloric acid (2 M) and concentrated under vacuum. The residue was purified by column chromatography (silica, petroleum ether:ethyl acetate=5:1 to 1:2) to give 3-(2-chloro-4'-(2-oxopiperidin-1-yl)-[1,1'-biphenyl]-3-yl)-3-fluoropiperidine-2,6-dione (0.0900 g, 0.216 mmol, 74% yield) as a white solid.

$^1$H NMR (400 MHz, DMSO-$d_6$) δ=11.52 (s, 1H), 7.67 (d, J=8.0 Hz, 1H), 7.57 (t, J=7.6 Hz, 1H), 7.48 (dd, J=1.2, 7.2 Hz, 1H), 7.43-7.35 (m, 4H), 3.66 (t, J=5.2 Hz, 2H), 3.03-2.82 (m, 2H), 2.66-2.59 (m, 1H), 2.52-2.52 (m, 1H), 2.41 (t, J=6.8 Hz, 2H), 2.35-2.28 (m, 1H), 1.91-1.80 (m, 4H)

The product was separated by chiral SFC (column: DAICEL CHIRALPAK AD (250 mm×30 mm, 10 μm); mobile phase: [carbon dioxide-isopropanol/acetonitrile]; B %: 60%, isocratic elution mode). The desired fraction was collected and evaporated under reduced pressure, then lyophilized. Two peaks were separated.

Peak 1 (Retention time=0.903 min): the desired fraction was evaporated under reduced pressure and lyophilized to afford (R)-3-(2-chloro-4'-(2-oxopiperidin-1-yl)-[1,1'-biphenyl]-3-yl)-3-fluoropiperidine-2,6-dione (30.84 mg, 0.0736 mmol, 25% yield) as an off-white solid.

$^1$H NMR (400 MHz, DMSO-$d_6$) δ=11.52 (s, 1H), 7.67 (d, J=8.0 Hz, 1H), 7.57 (t, J=7.6 Hz, 1H), 7.48 (dd, J=1.2, 7.2 Hz, 1H), 7.43-7.35 (m, 4H), 3.66 (t, J=5.2 Hz, 2H), 3.03-2.82 (m, 2H), 2.66-2.59 (m, 1H), 2.52-2.52 (m, 1H), 2.41 (t, J=6.8 Hz, 2H), 2.35-2.28 (m, 1H), 1.91-1.80 (m, 4H)

MS (ESI) m/z 415.2 [M+H]$^+$

Peak 2 (Retention time=1.846 min): the desired fraction was evaporated under reduced pressure and lyophilized to afford (S)-3-(2-chloro-4'-(2-oxopiperidin-1-yl)-[1,1'-biphenyl]-3-yl)-3-fluoropiperidine-2,6-dione (35.09 mg, 0.0837 mmol, 29% yield) as a white solid.

1H NMR (400 MHz, DMSO-$d_6$) δ=11.52 (s, 1H), 7.67 (d, J=8.0 Hz, 1H), 7.57 (t, J=7.6 Hz, 1H), 7.48 (dd, J=1.2, 7.2 Hz, 1H), 7.43-7.35 (m, 4H), 3.66 (t, J=5.2 Hz, 2H), 3.03-2.82 (m, 2H), 2.66-2.59 (m, 1H), 2.52-2.52 (m, 1H), 2.41 (t, J=6.8 Hz, 2H), 2.35-2.28 (m, 1H), 1.91-1.80 (m, 4H); MS (ESI) m/z 415.1 [M+H]$^+$

Biological Assay

Example A: VAV1 Degradation Activity

A heterozygous VAV1 C-terminal HiBiT knock-in pool was generated at Monte Rosa Therapeutics from a clonal Jurkat cell stably expressing LgBiT and possessing a homozygous GSPT1-G575N mutation. Cells were plated at 10,000 cells per well using Multiflo (BioTek) or Multi Drop Combi (Thermo Fisher) in 384-well white solid bottom plates (Corning, 3570BC) in 25 ul volume in RPMI 1640 media (Thermo Fischer, 22400105) containing 10% FBS (Corning, 35-075-CV), 1% Penicillin/Streptomycin (ThermoFisher Scientific, 15140-122), and 1% Endurazine (Nano-Glo Endurazine Live Cell Substrate (Promega, N2571)). Cells were incubated for ~16 hours at 37° C., 5% CO2. 25 nL of a compound at 10 μM were dosed into the plate using an Echo® 650 liquid handler (Labcyte). Cells were incubated at 37° C., 5% CO2 and signal was read at 6 and 24 hours after compound addition on a Pherastar FSX using "LUM plus" optic module.

Analysis was performed in Scinamic (Scinamic, Cambridge, MA). Luminescence response (R) was calculated by the formula: response=100*(S−N)/(P−N) where S is the signal of the well, N and P the mean negative and positive control values respectively of the same plate. The luminescence response was then fitted in Scinamic using a 3-parameter agonist logistic fit (hillslope=1, EC50>0, top/bottom unconstrained).

The result of this study are presented in in Table 1.

TABLE 1

| VAV1 Degradation Activity | | | | |
|---|---|---|---|---|
| Compound No. | VAV1 DC50 (nM) | VAV1 DC50 (nM) | VAV1 Dmax % | VAV1 Dmax % |
| 101 | 12.33 | A | 95.98 | A |
| 102 | 239.72 | B | 84.09 | B |
| 103 | 45.42 | A | 93.6 | A |
| 104 | 59.69 | A | 81.73 | B |

TABLE 1-continued

| Compound No. | VAV1 DC50 (nM) | VAV1 DC50 (nM) | VAV1 Dmax % | VAV1 Dmax % |
|---|---|---|---|---|
| 105 | 18.07 | A | 97.68 | A |
| 106 | 10000 | C | 13.98 | C |
| 107 | 10000 | C | 27.04 | C |
| 108 | 10000 | C | 47.81 | C |
| 109 | 677.53 | B | 66.39 | B |
| 110 | 22.28 | A | 89.2 | B |
| 111 | 49.24 | A | 87.83 | B |
| 112 | 119.41 | B | 78.18 | B |
| 113 | 481.73 | B | 64.6 | B |
| 115 | 125.39 | B | 80.9 | B |
| 116 | 22.28 | A | 96.05 | A |
| 117 | 353.44 | B | 72.04 | B |
| 118 | 39.71 | A | 89.66 | B |
| 119 | 69.31 | A | 87.09 | B |
| 120 | 15.11 | A | 93.95 | A |
| 121 | 11 | A | 94.03 | A |
| 122 | 48.81 | A | 81.31 | B |
| 123 | 11.56 | A | 96.3 | A |
| 124 | 4.04 | A | 98.83 | A |
| 125 | 1531.83 | C | 75.87 | B |
| 126 | 127.27 | B | 91.38 | A |
| 127 | 39.02 | A | 92.38 | A |
| 128 | 67.37 | A | 81.08 | B |
| 129 | 240.06 | B | 68.15 | B |
| 130 | 37.15 | A | 84.61 | B |
| 131 | 7.27 | A | 94.93 | A |
| 132 | 474.95 | B | 84.48 | B |
| 133 | 427.07 | B | 79.01 | B |
| 134 | 127.78, 90.85 | C | 85.69, 76.45 | A |
| 135 | 10000 | C | 34.86 | C |
| 136 | 10000 | C | 40.91 | C |
| 137 | 7437.48 | C | 63.84 | B |
| 138 | 604.04 | B | 84.62 | B |
| 139 | 10000 | C | 25.23 | C |
| 140 | 52.23 | A | 83.77 | B |
| 141 | 99.19 | A | 87.56 | B |
| 142 | 705.15 | B | 69.91 | B |
| 143 | 6160.87 | C | 54.96 | C |
| 144 | 247.98 | B | 65.29 | B |
| 145 | 13797.78 | C | 55.51 | C |
| 146 | 8404.11 | C | 81.5 | B |
| 147 | 10000.0, 10000.0 | C | 33.26, 33.28 | C |
| 148 | 10000 | C | 21.41 | C |
| 149 | 91.46 | A | 89.62 | B |
| 150 | 47.99 | A | 84.15 | B |
| 151 | 10000 | C | 39.78 | C |
| 152 | 10000 | C | 8.11 | C |
| 153 | 10000 | C | 1.26 | C |
| 154 | 18.75 | A | 97 | A |
| 155 | 14.95 | A | 92.66 | A |
| 156 | 26 | A | 92 | A |
| 157 | 10000 | C | 20.02 | C |
| 158 | 74.33 | A | 81.72 | B |
| 159 | 14.76 | A | 96.03 | A |
| 160 | 18.46 | A | 94.53 | A |
| 161 | 10.12 | A | 95.38 | A |
| 162 | 283.15 | B | 73.12 | B |
| 163 | 10000 | C | 44.67 | C |
| 164 | 542.43 | B | 71.9 | B |
| 165 | 47.72 | A | 90.21 | A |
| 166 | 516.62 | B | 61.54 | B |
| 167 | 38.46 | A | 87.35 | B |
| 168 | 18.83 | A | 91.49 | A |
| 169 | 5.59 | A | 98.05 | A |
| 170 | 69.74 | A | 94.19 | A |
| 171 | 93.82 | A | 94.93 | A |
| 172 | 10000 | C | 24.73 | C |
| 173 | 40.15 | A | 88.07 | B |
| 174 | 27.39 | A | 92.22 | A |
| 175 | 31.63 | A | 87.11 | B |
| 176 | 4.41 | A | 98.01 | A |
| 177 | 10000 | C | 29.18 | C |
| 178 | 238.94 | B | 81.12 | B |
| 179 | 10000 | C | 32.79 | C |
| 180 | 11.5 | A | 88.81 | B |
| 181 | 33.95 | A | 85.88 | B |

TABLE 1-continued

VAV1 Degradation Activity

| Compound No. | VAV1 DC50 (nM) | VAV1 DC50 (nM) | VAV1 Dmax % | VAV1 Dmax % |
|---|---|---|---|---|
| 182 | 11.75 | A | 89.35 | B |
| 183 | 5.55 | A | 95.71 | A |
| 184 | 11.62 | A | 92.07 | A |
| 185 | 7 | A | 97 | A |
| 186 | 13.64 | A | 95.3 | A |
| 187 | 9.75 | A | 94.24 | A |
| 188 | 7.16 | A | 95.01 | A |
| 189 | 33.65 | A | 91.36 | A |
| 190 | 3333.33 | C | 21.47 | C |
| 193 | 13.3 | A | 91.72 | A |
| 194 | 18.45 | A | 94.13 | A |
| 195 | 551.63 | B | 79.43 | B |
| 196 | 9.34 | A | 95.61 | A |
| 197 | 33.05 | A | 88.77 | B |
| 198 | 4843.6 | C | 54.64 | C |
| 199 | 1280.27 | C | 66.75 | B |
| 200 | 5.14 | A | 97.02 | A |
| 201 | 203.43 | B | 88.74 | B |
| 202 | 14.57 | A | 94.61 | A |
| 203 | 29.29 | A | 94.62 | A |
| 204 | 12.19 | A | 95.84 | A |
| 205 | 16.36 | A | 90.42 | A |
| 206 | 42.71 | A | 87.47 | B |
| 207 | 34.71 | A | 88.7 | B |
| 208 | 4.54 | A | 97.2 | A |
| 209 | 7.35 | A | 93.34 | A |
| 210 | 40.93 | A | 96.86 | A |
| 211 | 3.07 | A | 97.94 | A |
| 212 | 7987.28 | C | 47.29 | C |
| 213 | 101.4 | B | 91.99 | A |
| 214 | 3.61 | A | 97.49 | A |
| 215 | 14.15 | A | 96.82 | A |
| 216 | 48.99 | A | 86.59 | B |
| 217 | 43.03 | A | 84.59 | B |
| 218 | 9.71 | A | 96.05 | A |
| 219 | 105.1 | B | 81.17 | B |
| 220 | 103.86 | B | 77.17 | B |
| 221 | 210.91 | B | 77.36 | B |
| 222 | 127.13 | B | 90.95 | A |
| 223 | 10.7 | A | 96.62 | A |
| 224 | 7798.33 | C | 51.51 | C |
| 225 | 14.44 | A | 93.69 | A |
| 226 | 9.8 | A | 96.77 | A |
| 227 | 81.85 | A | 77.37 | B |
| 228 | 190.42 | B | 73.55 | B |
| 229 | 79.32 | A | 82.74 | B |
| 230 | 2088.95 | C | 58.53 | C |
| 231 | 18.37 | A | 90.07 | A |
| 232 | 2.8 | A | 98.47 | A |
| 233 | 16.13 | A | 91.99 | A |
| 234 | 127.17 | B | 75.8 | B |
| 235 | 3.87 | A | 97.12 | A |
| 236 | 31.26 | A | 93.47 | A |
| 237 | 35.76 | A | 92.72 | A |
| 238 | 2.24 | A | 98.74 | A |
| 239 | 341.08 | B | 63.35 | B |
| 240 | 77.09 | A | 94.36 | A |
| 241 | 919.91 | B | 77.02 | B |
| 242 | 68.42 | A | 91.48 | A |
| 243 | 4221.27 | C | 56.79 | C |
| 244 | 8.36 | A | 96.53 | A |
| 245 | 17.54 | A | 95.21 | A |
| 246 | 17.54 | A | 94.34 | A |
| 247 | 5.38 | A | 95.43 | A |
| 248 | 26.31 | A | 84.43 | B |
| 249 | 7396.75 | C | 48.85 | C |
| 251 | 354.32 | B | 73.78 | B |
| 252 | 54.82 | A | 82.84 | B |
| 253 | 29.6 | A | 87.68 | B |
| 254 | 11.25 | A | 96.16 | A |
| 255 | 10.96 | A | 89.47 | B |
| 256 | 212.98 | B | 75.83 | B |
| 257 | 9.66 | A | 94.22 | A |
| 258 | 12.6 | A | 94.52 | A |
| 259 | 28.07 | A | 90.01 | A |
| 260 | 193.4 | B | 83.94 | B |

TABLE 1-continued

| Compound No. | VAV1 DC50 (nM) | VAV1 DC50 (nM) | VAV1 Dmax % | VAV1 Dmax % |
|---|---|---|---|---|
| 261 | 100.95 | B | 84.85 | B |
| 262 | 32.61 | A | 90.22 | A |
| 263 | 29.28 | A | 87.47 | B |
| 264 | 39.46 | A | 84.62 | B |
| 265 | 32.5 | A | 88.02 | B |
| 266 | 14.05 | A | 93.22 | A |
| 267 | 11.51 | A | 96.4 | A |
| 268 | 12.8 | A | 94.46 | A |
| 269 | 6.83 | A | 96.87 | A |
| 270 | 31.32 | A | 89.63 | B |
| 271 | 50.94 | A | 83.75 | B |
| 272 | 13.61 | A | 96.8 | A |
| 273 | 118.33 | B | 78.05 | B |
| 274 | 269.24 | B | 69.46 | B |
| 275 | 37.22 | A | 87.61 | B |
| 276 | 47.6 | A | 88.6 | B |
| 277 | 646.83 | B | 76.77 | B |
| 278 | 5.33 | A | 95.86 | A |
| 279 | 4.83 | A | 98.52 | A |
| 280 | 44.89 | A | 83.31 | B |
| 28 | 33.25 | A | 92.45 | A |
| 282 | 3.88 | A | 97.99 | A |
| 283 | 11.09 | A | 93.26 | A |
| 284 | 3.48 | A | 97.97 | A |
| 285 | 10.17 | A | 95.25 | A |
| 286 | 15.86 | A | 94 | A |
| 287 | 12.53 | A | 95.55 | A |
| 288 | 6.09 | A | 96.65 | A |
| 289 | 43.28 | A | 86.65 | B |
| 290 | 16.9 | A | 92.9 | A |
| 291 | 21.29 | A | 93.09 | A |
| 292 | 12.68 | A | 93.74 | A |
| 293 | 6.99 | A | 95.76 | A |
| 294 | 8.3 | A | 95.69 | A |
| 295 | 9.84 | A | 94.77 | A |
| 296 | 10.1 | A | 93.79 | A |
| 297 | 13.43 | A | 93.48 | A |
| 298 | 11.75 | A | 95.44 | A |
| 299 | 91.52 | A | 91.56 | A |
| 300 | 17.06 | A | 94.29 | A |
| 301 | 71.2 | A | 86.23 | B |
| 302 | 92.11 | A | 77.95 | B |
| 303 | 13.91 | A | 93.45 | A |
| 304 | 274.03 | B | 71.96 | B |
| 305 | 19.55 | A | 92.99 | A |
| 306 | 49.23 | A | 89.09 | B |
| 307 | 9.64 | A | 95.99 | A |
| 308 | 22.53 | A | 93.8 | A |
| 309 | 39.38 | A | 89.59 | B |
| 310 | 22.97 | A | 90.53 | A |
| 311 | 21.9 | A | 92.7 | A |
| 312 | 7.99 | A | 96.1 | A |
| 313 | 7.02 | A | 95.31 | A |
| 314 | 9.68 | A | 96.08 | A |
| 315 | 21.99 | A | 89.85 | B |
| 316 | 11.78 | A | 93.3 | A |
| 317 | 13.6 | A | 93.22 | A |
| 318 | 5.24 | A | 97.21 | A |
| 319 | 103.83 | B | 80.84 | B |
| 320 | 101.9 | B | 84.9 | B |
| 321 | 22.46 | A | 88.08 | B |
| 322 | 17.69 | A | 93.91 | A |
| 323 | 10.55 | A | 95.04 | A |
| 324 | 3.46 | A | 97.85 | A |
| 325 | 6.66 | A | 96.2 | A |
| 326 | 16.2 | A | 90.92 | A |
| 327 | 30.07 | A | 89.29 | B |
| 328 | 15 | A | 90.8 | A |
| 329 | 6.62 | A | 95.85 | A |
| 330 | 130.41 | B | 72.12 | B |
| 331 | 17.22 | A | 91.64 | A |
| 332 | 10.62 | A | 95.53 | A |
| 333 | 3.17 | A | 98.24 | A |
| 334 | 11.14 | A | 93.54 | A |
| 335 | 5.87 | A | 97.35 | A |
| 336 | 17.39 | A | 93.55 | A |

TABLE 1-continued

| Compound No. | VAV1 DC50 (nM) | VAV1 DC50 (nM) | VAV1 Dmax % | VAV1 Dmax % |
|---|---|---|---|---|
| 337 | 5771 | C | 40 | C |
| 338 | 2170.07 | C | 57.75 | C |
| 339 | 1.96 | A | 98.2 | A |
| 340 | 5.86 | A | 96.6 | A |
| 341 | 2.46 | A | 98.25 | A |
| 342 | 4.56 | A | 97.65 | A |
| 343 | 161.46 | B | 86.3 | B |
| 344 | 6.97 | A | 97.95 | A |
| 345 | 3.53 | A | 97.9 | A |
| 346 | 10000 | C | 29.45 | C |
| 347 | 17.07 | A | 96.4 | A |
| 348 | 11.67 | A | 95.2 | A |
| 349 | 2.21 | A | 98.3 | A |
| 350 | 7.18 | A | 97.3 | A |
| 351 | 82.45 | A | 86.95 | B |
| 352 | 65.34 | A | 82.3 | B |
| 353 | 62.14 | A | 90.7 | A |
| 354 | 13.26 | A | 97.4 | A |
| 355 | 15.90 | A | 91.8 | A |
| 356 | 71.40 | A | 86.05 | B |
| 357 | 35.85 | A | 90.8 | A |
| 358 | 10000 | C | 44.3 | C |
| 359 | 13.30 | A | 94.95 | A |
| 360 | 6.85 | A | 96.55 | A |
| 361 | 76.36 | A | 84.4 | B |
| 362 | 69.56 | A | 87.55 | B |
| 363 | 4.86 | A | 97.13 | A |
| 364 | 234.05 | B | 71.7 | B |
| 365 | 55.03 | A | 88.05 | B |
| 366 | 1.87 | A | 97.75 | A |
| 367 | 705.76 | B | 90.63 | A |
| 368 | 1.845 | A | 98.52 | A |
| 369 | 331.25 | B | 69.45 | B |
| 370 | 1571.62 | C | 58.1 | C |
| 371 | 10000 | C | 37.8 | C |
| 372 | 10.03 | A | 94.4 | A |
| 373 | 25.60 | A | 97.2 | A |
| 374 | 10.20 | A | 97.4 | A |
| 375 | 14.20 | A | 98 | A |
| 376 | 15.20 | A | 95.8 | A |
| 377 | 17.20 | A | 98.8 | A |
| 378 | 1.56 | A | 98.3 | A |
| 379 | 40.1 | A | 88.2 | B |
| 380 | 1068.83 | C | 91.1 | A |
| 381 | 35.88 | A | 96.45 | A |
| 382 | 167.37 | B | 76 | B |
| 383 | 112.64 | B | 80.25 | B |
| 384 | 121.64 | B | 75.45 | B |
| 385 | 7.00 | A | 97.85 | A |
| 386 | 10000 | C | 29.2 | C |
| 387 | 864.58 | B | 58.35 | C |
| 388 | 16.24 | A | 91 | A |
| 389 | 41.37 | A | 88.55 | B |
| 390 | 615.45 | B | 71.15 | B |
| 391 | 5105.88 | C | 53.95 | C |
| 392 | 12.84 | A | 94.8 | A |
| 393 | 29.26 | A | 86.7 | B |
| 394 | 36.19 | A | 88.7 | B |
| 395 | 55.67 | A | 83.90 | B |
| 396 | 4.98 | A | 96.87 | A |
| 397 | 3.01 | A | 99.1 | A |
| 400 | 77.03 | A | 81.45 | B |
| 401 | 15.04 | A | 94.425 | A |
| 402 | 5.30 | A | 97.4 | A |
| 403 | 3.26 | A | 98.2 | A |
| 404 | 261.64 | B | 65.5 | B |
| 405 | 382.98 | B | 76.3 | B |
| 406 | 25.93 | A | 82.4 | B |
| 407 | 6.17 | A | 95.55 | A |
| 408 | 30.80 | A | 96.05 | A |
| 409 | 7.82 | A | 95.25 | A |
| 410 | 17.00 | A | 92.1 | A |
| 411 | 1.99 | A | 98.2 | A |
| 412 | 418.00 | B | 67.35 | B |
| 413 | 4.87 | A | 97.5 | A |
| 414 | 5.85 | A | 97.7 | A |

TABLE 1-continued

VAV1 Degradation Activity

| Compound No. | VAV1 DC50 (nM) | VAV1 DC50 (nM) | VAV1 Dmax % | VAV1 Dmax % |
|---|---|---|---|---|
| 415 | 4.87 | A | 97.15 | A |
| 416 | 3.54 | A | 98 | A |
| 417 | 6.68 | A | 98.55 | A |
| 418 | 10000 | C | 45.25 | C |
| 419 | 43.09 | A | 90.7 | A |
| 420 | 2.43 | A | 98.8 | A |
| 421 | 6.96 | A | 97.85 | A |
| 422 | 4.35 | A | 98.4 | A |
| 423 | 144.11 | B | 74.6 | B |
| 424 | 9.94 | A | 95.3 | A |
| 425 | 10.65 | A | 96.5 | A |
| 426 | 8.90 | A | 96.55 | A |
| 427 | 245.91 | B | 79.6 | B |
| 428 | 2.25 | A | 98.75 | A |
| 429 | 5.19 | A | 96.9 | A |
| 430 | 261.26 | B | 72.6 | B |
| 431 | 10000 | C | 23.5 | C |
| 432 | 181.72 | B | 71.9 | B |
| 433 | 10000 | C | 33.65 | C |
| 434 | 10000 | C | 46.25 | C |
| 435 | 330.04 | B | 70.75 | B |
| 436 | 8.75 | A | 95.95 | A |
| 437 | 5.92 | A | 96.45 | A |
| 438 | 91.69 | A | 90.45 | A |
| 439 | 4.48 | A | 89.35 | B |
| 440 | 21.71 | A | 94.35 | A |
| 441 | 14.20 | A | 90.5 | A |
| 442 | 34.52 | A | 95.8 | A |
| 443 | 2.27 | A | 99.35 | A |
| 444 | 7.10 | A | 97.65 | A |
| 445 | 11.46 | A | 96.05 | A |
| 446 | 9.83 | A | 95.25 | A |
| 447 | 741.44 | B | 61.9 | B |
| 448 | 1.63 | A | 98.7 | A |
| 449 | 6.45 | A | 97 | A |
| 450 | 172.90 | B | 75.9 | B |
| 451 | 542.25 | B | 63.95 | B |
| 452 | 21.52 | A | 94.05 | A |
| 453 | 13.38 | A | 97.85 | A |
| 454 | 139.68 | B | 68.35 | B |
| 455 | 15.23 | A | 95.5 | A |
| 456 | 1562.40 | C | 61.05 | B |
| 457 | 2.78 | A | 98.2 | A |
| 458 | 4.79 | A | 98.6 | A |
| 459 | 122.33 | B | 84.4 | B |
| 460 | 277.09 | B | 89.9 | B |
| 461 | 10.14 | A | 96.15 | A |
| 462 | 14.79 | A | 95.47 | A |
| 463 | 7.16 | A | 95.65 | A |
| 464 | 9.46 | A | 94.75 | A |
| 465 | 10000 | C | 39.85 | C |
| 466 | 10000 | C | 35.25 | C |
| 467 | 11.53 | A | 94.95 | A |
| 468 | 24.79 | A | 96.175 | A |
| 469 | 266.17 | B | 79.42 | B |
| 470 | 9.19 | A | 97.1 | A |
| 471 | 24.12 | A | 92.78 | A |
| 472 | 8.25 | A | 96.74 | A |
| 473 | 9.34 | A | 96.17 | A |
| 474 | 10000 | C | 35.3 | C |
| 475 | 98.91 | A | 73.25 | B |
| 476 | 397.12 | B | 83.97 | B |
| 477 | 65.59 | A | 88.68 | B |
| 478 | 291.39 | B | 70.55 | B |
| 479 | 10000 | C | 31 | C |
| 480 | 8.08 | A | 96.65 | A |
| 481 | 10000 | C | 46 | C |
| 482 | 18.74 | A | 91.74 | A |
| 483 | 59.95 | A | 88.07 | B |
| 484 | 220.22 | B | 78.42 | B |
| 485 | 40.97 | A | 89.74 | B |
| 486 | 6.51 | A | 96.15 | A |
| 487 | 23.72 | A | 82.84 | B |
| 488 | 17.25 | A | 90.96 | A |
| 489 | 2.84 | A | 97.78 | A |
| 490 | 130.75 | B | 74.55 | B |

TABLE 1-continued

VAV1 Degradation Activity

| Compound No. | VAV1 DC50 (nM) | VAV1 DC50 (nM) | VAV1 Dmax % | VAV1 Dmax % |
|---|---|---|---|---|
| 491 | 15.74 | A | 88.53 | B |
| 492 | 10.70 | A | 94.33 | A |
| 493 | 502.35 | B | 75.7 | B |
| 494 | 929.16 | B | 61.23 | B |
| 495 | 61.78 | A | 89.3 | B |
| 496 | 12.65 | A | 95.6 | A |
| 497 | 18.01 | A | 95.83 | A |
| 498 | 11.83 | A | 98.05 | A |
| 499 | 5.45 | A | 97.9 | A |
| 500 | 7.51 | A | 98.55 | A |
| 501 | 8.19 | A | 97.7 | A |
| 502 | 3.95 | A | 97.77 | A |
| 503 | 4.73 | A | 89.95 | B |
| 504 | 5.50 | A | 96.68 | A |
| 505 | 86.93 | A | 80.7 | B |
| 506 | 1765.43 | C | 63.7 | B |
| 507 | 28.62 | A | 91.85 | A |
| 508 | 63.25 | A | 91.95 | A |
| 509 | 3.85 | A | 97.8 | A |
| 510 | 78.61 | A | 89.2 | B |

For DC50, A represents a $DC_{50}$ value of ≤100 nM; B represents a $DC_{50}$ value >100 nM and ≤1000 nM; C represents a $DC_{50}$ value of >1000 nM.
For Dmax %, A represents a Dmax % >90%; B represents Dmax % >60% and <=90%; C represents a Dmax % value of <60%.

Examples B-J

Examples B-J present biological activity data generated using compound 185 from Table 1. The same compound ("the selected VAV1 MGD") was used in Examples B-J.

Example B: VAV1 Degradation in T Cells

Figure 2A:
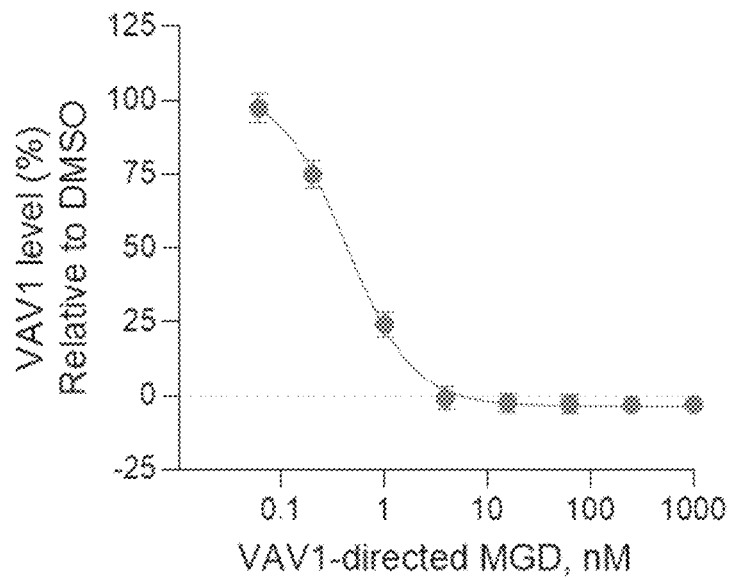
FIG. 2A shows dose-dependent decrease in VAV1 levels in primary human T-cells upon 24 h treatment with a compound presented in Table 1 ("selected VAV1 MGD") relative to DMSO control as assessed by flow cytometry (y-axis represents normalized VAV1 levels to DMSO control; x-axis depicts doses of the selected VAV1 MGD).

Frozen human Pan T cells purchased from STEMCELL technologies were thawed, washed with 1×PBS & resuspended in complete cell culture medium (RPMI+10% FBS). Cells were plated at optimized cell density in U-bottom 96 well plate (Costar, catalog number Z707899) and treated with the selected VAV1 MGD using a serial dilution ranging from 0.1 nM to 1000 nM and including a DMSO control. Plates were incubated for 24 hrs at 5% $CO_2$, 37° C. Cells were fixed and permeabilized and then washed 2× with BD stain buffer and stained with anti-VAV1 antibody (CST #2502) for 30 minutes at 4° C. Following staining with VAV1 antibody cells were washed with PBS and incubated with PE conjugated Anti-rabbit IgG (H+L), F(ab')$_2$ Fragment (CST #79408) secondary antibody for 20 minutes at 4° C. Following 2×PBS washes, the PE fluorophore signal intensity (VAV1) was evaluated by flow cytometry and data reported as Geometric Mean and normalized to DMSO control levels. The result of this study are shown in FIG. 2A.

Example C: Selectivity of VAV1 Degradation in a Human T-lymphocyte Cell Line Jurkat cells (ATCC #TIB-152) were treated with either DMSO or the selected VAV1 MGD at 10 µM for 24 hr (2 replicates per condition). Proteins were extracted with the PreOmics iST-NHS lysis buffer (PreOmics #P.O. 00030). The samples were then processed using the PreOmics kit following their recommended protocol with minor modifications. In brief, the proteins were reduced, alkylated and digested for 2 h at 37° C. The peptides were then labelled with TMT reagent (1:4; peptide: TMT label) (Thermo Fisher Scientific). After quenching, the peptides were purified, and the 16 samples were combined to a 1:1 ratio. Mixed and labeled peptides were subjected to high-pH reversed-phase HPLC fractionation on an Agilent X-bridge C18 column (2.1 mm ID, 3.5 µm particles and 15 cm in length). Using an Agilent 1260 Infinity II LC system, a 60 min linear gradient from 0% to 45% 10 mM ammonium formate in 90% acetonitrile separated the peptide mixture into a total of 60 fractions, which were then consolidated into 24 fractions. The dried 24 fractions were reconstituted in 0.1% formic acid for LC-MS3 analysis.

Labelled peptides were loaded onto an Aurora column from Ionopticks (75 µm ID, 1.6 µm particles, 25 cm in length) in an EASY-nLC 1200 system. The peptides were separated using a 168 min gradient from 4% to 30% buffer B (80% acetonitrile in 0.1% formic acid) equilibrated with buffer A (0.1% formic acid) at a flow rate of 400 nl/min. Eluted TMT peptides were analyzed on an Orbitrap Eclipse mass spectrometer (Thermo Fisher Scientific). MS1 scans were acquired at resolution 120,000 with 400-1400 m/z scan range, AGC target 4×105, maximum injection time 50 ms. Then, MS2 precursors were isolated using the quadrupole (0.7 m/z window) with AGC 1×104 and maximum injection time 50 ms. Precursors were fragmented by CID at a normalized collision energy (NCE) of 35% and analyzed in the ion trap.

Following MS2, synchronous precursor selection (SPS) MS3 scans were collected by using high energy collision-induced dissociation (HCD) and fragments were analyzed using the Orbitrap (NCE 55%, AGC target 1×105, maximum injection time 120 ms, resolution 60,000). The real-time search algorithm was used to trigger MS3 quantification scans. Protein identification and quantification were performed using Proteome Discoverer 2.4.0.305 with the SEQUEST algorithm and Uniprot human database (2021-01-29, 20614 protein sequences). Mass tolerance was set at 10 ppm for precursors and at 0.6 Da for fragment. Maximum of 3 missed cleavages were allowed. Methionine oxidation was set as dynamic modification, while TMT tags on peptide N termini/lysine residues and cysteine alkylation (+113.084) were set as static modifications. The list of identified peptide spectrum matches (PSMs) was filtered to respect a 1% False Discovery Rate (FDR) after excluding PSMs with TMT reporter ion signal-to-noise value lower than S and a precursor interference level value higher than 100%.

Figure 2B:
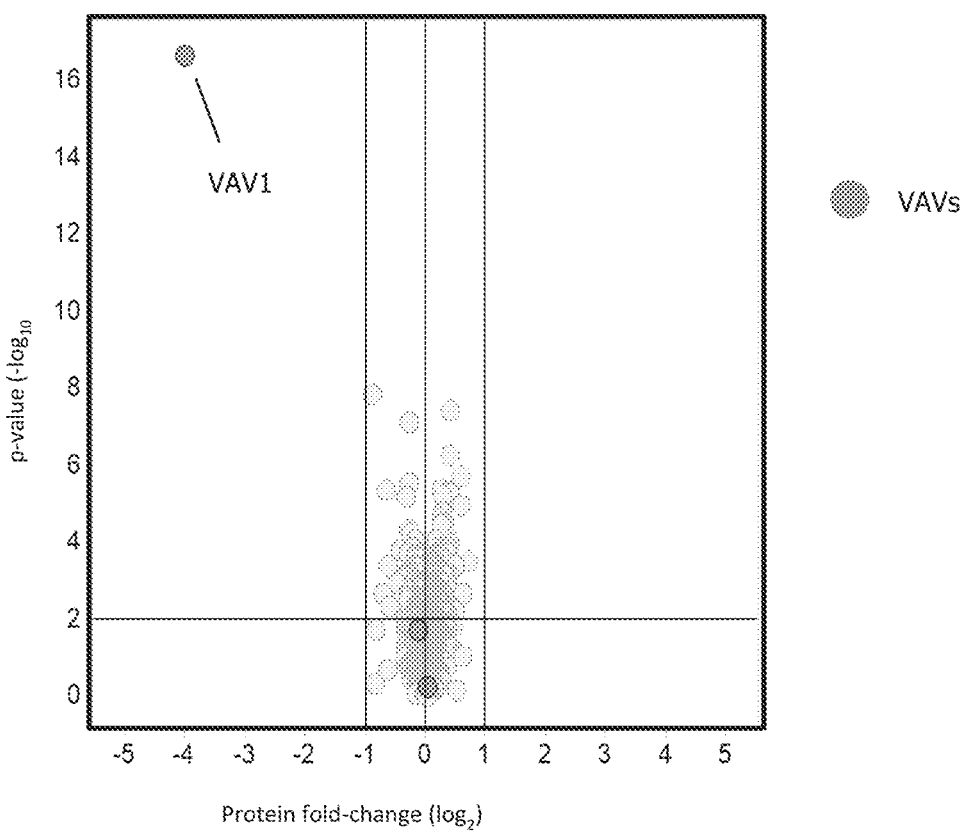
FIG. 2B shows that VAV1 is significantly and selectively degraded by the selected VAV1 MGD in Jurkat cells following 24 h treatment as assessed by quantitative TMT proteomics (y-axis represents confidence p-value [−$\log_{10}$]; x-axis represents protein fold-change [$\log_2$] relative to DMSO control samples).

Subsequently, protein identifications were inferred from protein specific peptides, i.e. peptides matching multiple protein entries were excluded. Protein relative quantification was performed using an in-house developed java script. This analysis included multiple steps; adjustment of reporter ion intensities for isotopic impurities according to the manufacturer's instructions, global data normalization by equalizing the total reporter ion intensity across all channels, summation of reporter ion intensities per protein and channel, calculation of protein abundance log 2 fold changes (L2FC) and testing for differential abundance using moderated t-statistics where the resulting p-values reflect the probability of detecting a given L2FC across sample conditions by chance alone. The results of this study are shown in FIG. 2B.

Figure 3A:
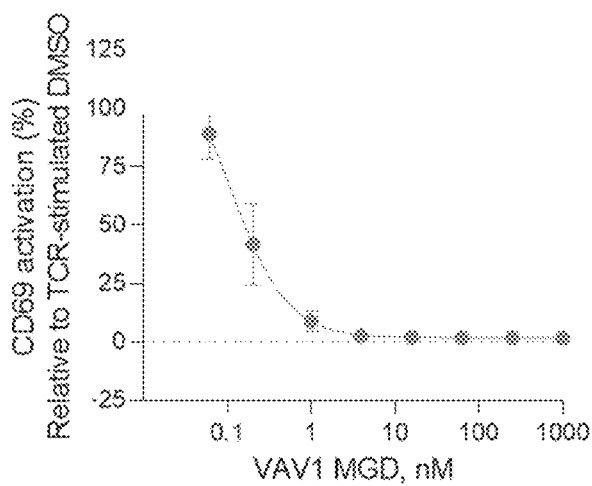
FIGS. 3A-3C show that VAV1 degradation results in inhibition of various hallmarks of TCR-mediated activity following TCR stimulation of primary human T-cells. Cells were treated with the selected VAV1 MGD for 24 h followed by TCR stimulation (anti-CD3/anti-CD28 antibodies). CD69 surface expression (24 hr), IL-2 secretion (48 hr), and proliferation (96 hr) were evaluated at various timepoints following TCR stimulation (y-axis depicts percent of CD69 activation, IL-2 secretion, or proliferation relative to TCR-stimulated DMSO control; x-axis depicts doses of the selected VAV1 MGD).
Figure 3B:
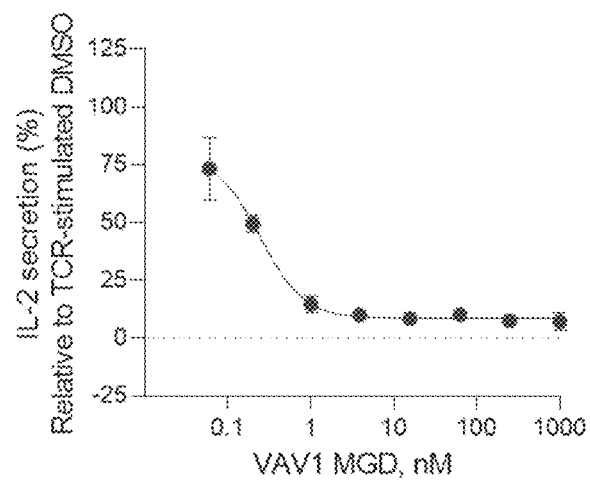
Figure 3C:
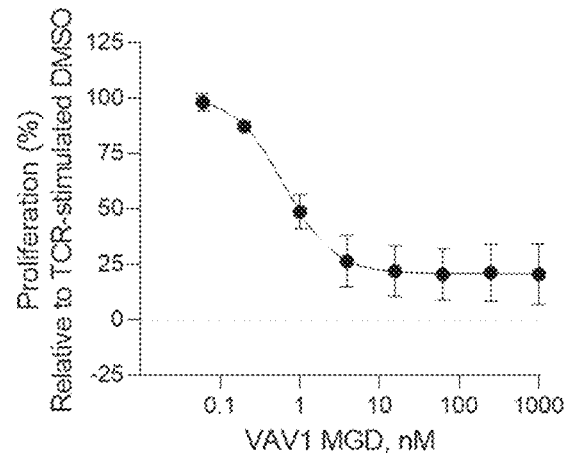

Example D: Degradation of VAV1 Results in Inhibition of TCR-Mediated CD69 Activation, IL-2 Secretion, and Proliferation of Primary T-Cells Frozen human Pan T cells purchased from STEMCELL technologies were thawed, washed with 1×PBS & resuspended in complete cell culture medium (RPMI+10% FBS). Cells were plated at optimized cell density in U-bottom 96 well plate (Costar, Z707899) and treated with the selected VAV1 MGD using a serial dilution ranging from 0.1 nM to 1000 nM and including a DMSO control and incubated for 24 hrs at 5% $CO_2$, 37° C. Cells were transferred from treatment plate to anti-CD3 coated plate (5 ug/mL anti-CD3 antibody, clone OKT3) and co-stimulated with anti-CD28 (1 ug/mL, clone CD28.2). Cells were incubated at 5% $CO_2$, 37° C. and cells and/or supernatants harvested at various timepoints following anti-CD3/anti-CD28 co-stimulation for various readouts (24 h, CD69; 48 h, IL-2; 96 h, proliferation). For CD69 surface evaluation, cells were washed with PBS and stained for 20 minutes at 4 C with anti-CD69 allophycocyanin (APC) antibody. Cells washed with PBS and evaluated by flow cytometry. APC fluorophore signal intensity (CD69) reported as Geometric Mean. IL-2 was evaluated within cellular supernatants using an IL-2 ELISA kit (Abcam, ab270883) according to manufacturer protocol. Optical density (O.D.) values (IL-2) were obtained at 450 nM. For proliferation assays, cells were labeled with cell trace violet (final dye concentration 12.5 uM). Cells were analyzed as a percentage of cell trace violet dye dilution (relative to unstimulated cells) by flow cytometry. For all assays, data were normalized to anti-CD3/anti-CD28 co-stimulated DMSO control levels. The results of this study are shown in FIGS. 3A-3C.

Example E: VAV1 Degradation by a MGD in PBMCs after a Single Oral Dose in Mice

Mice were treated orally with a single dose of the selected VAV1 MGD at 10 mg/kg and blood samples were collected pre-dose and at 2, 6 and 24 hours post-dose. Compound formulation was prepared fresh the day of administration in 50% PEG400+50% (20% Captisol in water) by first dissolving the selected VAV1 MGD in PEG400 followed by vortex and sonication, then adding 50% of 20% captisol in water with vortex until a clear solution or a uniform suspension was obtained. Plasma samples collected pre and post dosed were analyzed by Mass spectrometry to evaluate the compound concentration in ng/ml and blood samples were used to assess VAV1 protein levels and b-actin as loading control by western blotting (WB).

Briefly, cells were rinsed with PBS and lysed using 30 μL RIPA lysis buffer (Pierce 89901), supplemented with EDTA and PhosStop (Roche 04906845001). Samples were run on 4-15% precast gels (Bio-Rad 161-0732) at 10-15 μg/lane and transferred to pre-activated PVDF membranes (Millipore IPVH00010). Primary antibodies (mouse VAV1, CST 2502S and b-actin, CST 3700S) was diluted in blocking buffer (dil. 1/1000) and incubated with the membranes overnight at 4° C. After three washes with 1×TBST (5 minutes each), secondary antibodies (anti-rabbit IgG, CST 7074, dil. 1/1000 and IRDye® 680RD Goat anti-Mouse IgG (H+L), Licor 926-68070, dil. 1/5000) were diluted in blocking buffer, added to membranes and incubated for 1 hour at room temperature. Signals were detected using an WB image systems.

Figure 4:
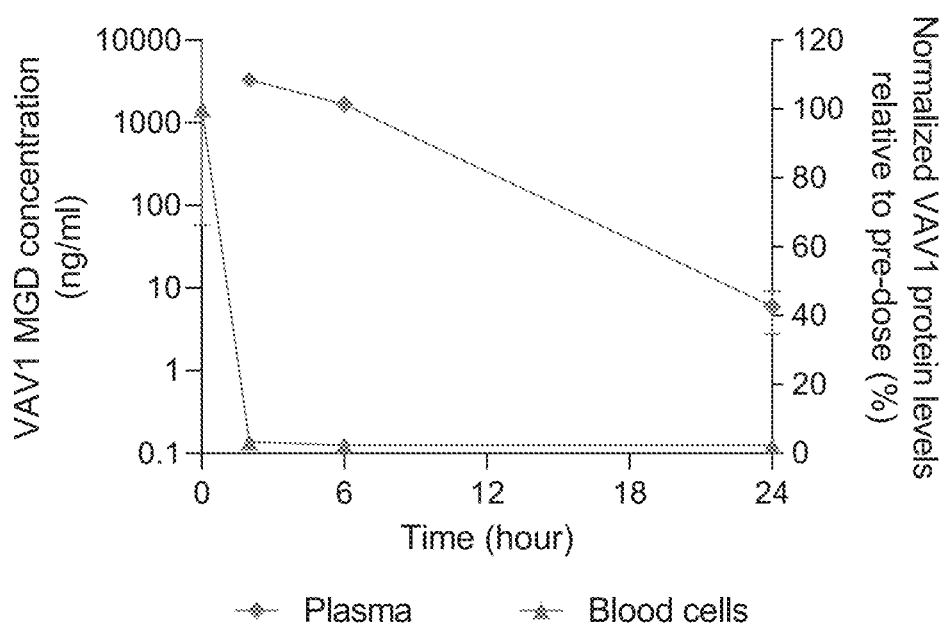
FIG. 4 shows the concentration of the selected VAV1 MGD in plasma over time and associated decrease in normalized VAV1 to b-actin protein levels relative to pre-treatment after a single oral dose of the selected VAV1 MGD at 10 mg/kg (y-axis represents hours post one single oral dose of the selected VAV1 MGD [hour]; left y-axis represents the selected VAV1 MGD concentration in ng/ml in plasma, filled *rhombi*; right y-axis represents percentage [%] VAV1 protein levels normalized to b-actin protein levels and relative to pre-dose in blood cells, filled triangles).

First the VAV1 protein levels were normalized to b-actin levels within the same samples than the ratio between the normalized VAV1 protein levels and the pre-dose levels were calculated and used for representation. The results of this study are shown in FIG. 4.

Example F: Inhibition of Disease Progression in a $MOG_{35-55}$-Induced Multiple Sclerosis Experimental Autoimmune Encephalomyelitis (EAE) Mouse Model To induce experimental autoimmune encephalomyelitis (EAE), C57BL/6J mice were injected subcutaneously with an emulsified mixture consisting of 100 μg of the synthetic peptide derived from myelin oligodendrocyte glycoprotein ($MOG_{35-55}$) and 200 μg M. tuberculosis mixed with incomplete Freund's adjuvant. Mice were additionally injected intraperitoneally with 200 ng pertussis toxin at 0 and 48 hours post immunization. This immunization induces the activation and expansion of peripheral myelin-specific encephalitogenic T cells and their migration into the CNS.

Figure 5:
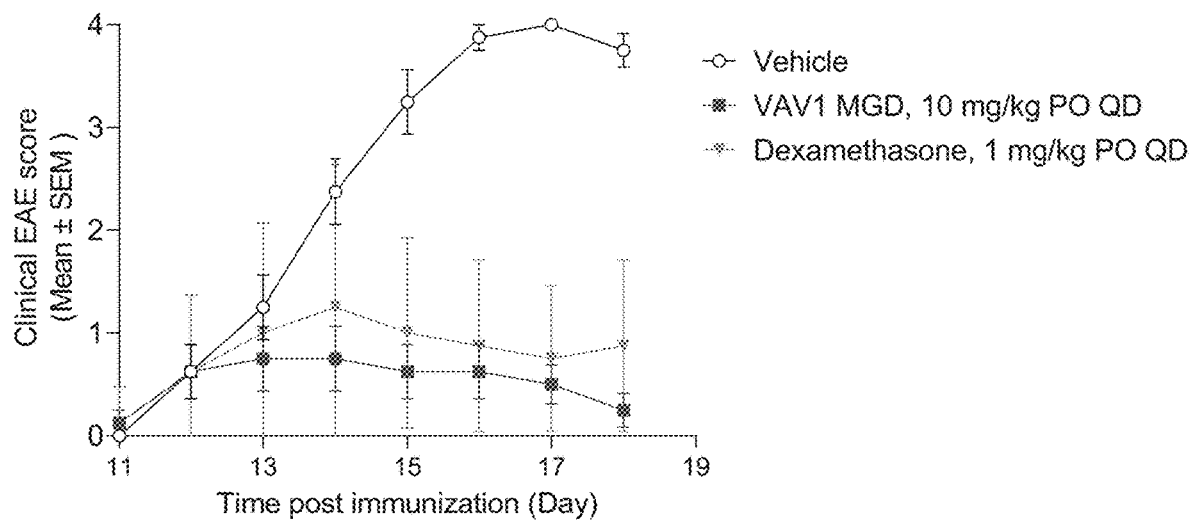
FIG. 5 shows that oral administration of the selected VAV1 MGD in a $MOG_{35-55}$-induced experimental autoimmune encephalomyelitis (EAE) model led to inhibition of disease progression. Mice were immunized by subcutaneous injection at day 0 with an emulsified mixture consisting of the synthetic peptide derived from myelin oligodendrocyte glycoprotein ($MOG_{35-55}$) and *M. tuberculosis* mixed with incomplete Freund's adjuvant. Additionally, mice were injected intraperitoneally with pertussis toxin at 0 and 48 hours. Mice were followed for development of symptoms and scored for EAE clinical signs disease (0=no signs of disease; 1=limp tail or hind limb weakness; 2=limp tail and hind limb weakness; 3=partial hind limb paralysis; 4=complete hind limb paralysis; 5=moribund), once a day (QD) dosing started at day 12 and ended at day 18. Dexamethasone dosed QD orally from day 12 to day 18 was used as comparative treatment. 10 mg/kg the selected VAV1 MGD prevented the progression of EAE disease as it was observed for the mice treated with Dexamethasone at 1 mg/kg (x-axis represents days post immunization initiation [days]; y-axis represents clinical EAE score, [mean±SEM]; empty circle: vehicle, PO, QD; filled triangles inverted, VAV1 MGD 10 mg/kg, PO, QD; filled square, Dexamethasone 1 mg/kg, PO, QD).

Once in the CNS, the activated T-cells initiate an inflammatory cascade, which ultimately leads to myelin destruction and symptoms of paralysis. From the day before disease induction (day −1), the mice were monitored daily and scored for clinical signs of EAE disease as follows: 0=no signs of disease; 1=limp tail or hind limb weakness; 2=limp tail and hind limb weakness; 3=partial hind limb paralysis; 4=complete hind limb paralysis; 5=moribund. Mice were then treated with vehicle (50/50 (v/v) PEG400 and 20% captisol in water) or once daily (QD) orally (PO) at 10 mg/kg with VAV1 MGD (resuspended in 50/50 (v/v) PEG400 and 20% captisol in water) or QD PO at 1 mg/kg with Dexamethasone from day 12 to day 18. A VAV1 MGD formulation was prepared fresh the day of administration by first dissolving the selected VAV1 MGD in PEG400 followed by vortex and sonification, then adding 50% of 20% captisol in water with vortex until a clear solution or a uniform suspension was obtained. The results of this study are shown in FIG. 5.

Example G: Oral Dosing of a VAV1 MGD Inhibits EAE Disease Progression in a Dose-Dependent Manner To induce experimental autoimmune encephalomyelitis (EAE), twelve C57BL/6 (Beijing Vital River Laboratory Animal Co; #213) mice were injected subcutaneously with an emulsified mixture consisting of 100 μg of the synthetic peptide derived from myelin oligodendrocyte glycoprotein ($MOG_{35-55}$; GL Biochem Ltd; #51716)) and 200 μg M. tuberculosis (Fifco; #231141) mixed with incomplete Freund's adjuvant (Sigma-Alrich; #F5506). Mice were additionally injected intraperitoneally with 200 ng pertussis toxin (List Biological Laboratories; #180235AIA) at 0 and 48 hours post immunization. This immunization induces the activation and expansion of peripheral myelin-specific encephalitogenic T cells and their migration into the CNS. Once in the CNS, the activated T-cells initiate an inflammatory cascade, which ultimately leads to myelin destruction and symptoms of paralysis. From the day of disease induction (day −12), the mice were monitored every 3 days for clinical signs of EAE disease as follows: 0=no signs of disease; 1=limp tail or hind limb weakness; 2=limp tail and hind limb weakness; 3=partial hind limb paralysis; 4=complete hind limb paralysis; 5=moribund. On day 0, at disease onset, mice were treated with vehicle (10% captisol in water) VAV1 MGD at 1, 0.1, or 0.01 mg/kg with VAV1 MGD (resuspended in 10% captisol in water), or QD PO at 1 mg/kg with Dexamethasone (dissolved in saline; Shanghai SPH Sine Pharmaceutical Co; #H31020793) from day 12 to day 24 and monitored every 3 days for clinical signs of EAE disease as described above. A VAV1 MGD formulation was prepared fresh the day of administration by dissolving the VAV1 MGD in 10% captisol in water then vortexed until a clear solution or a uniform suspension was obtained. At peak of disease (day 6 post-treatment start), spinal cords of four mice per group were excised and VAV1 levels (normalized to β-actin and relative to vehicle-treated mice) were measured by western blot.

Figure 6A:
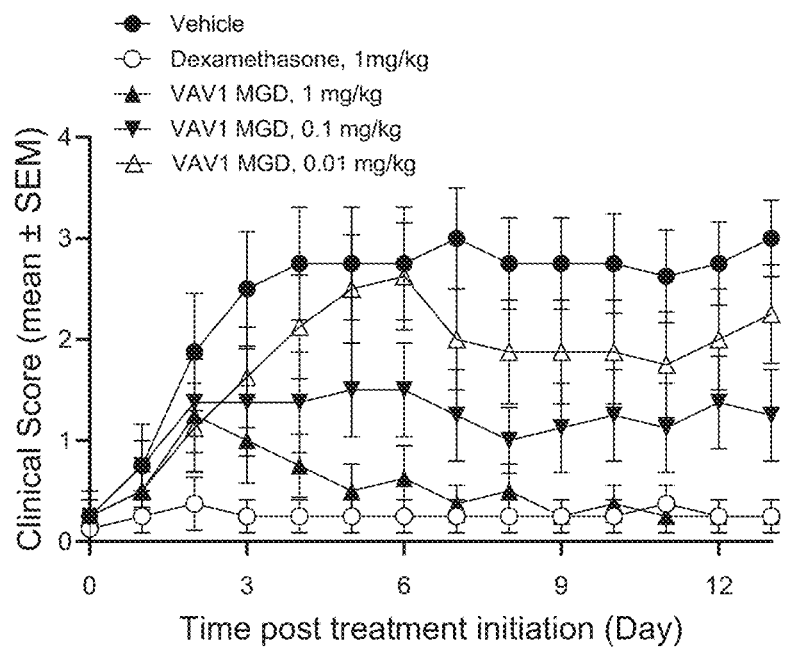
FIG. 6A shows that oral administration of VAV1 MGD in a $MOG_{35-55}$-induced experimental autoimmune encephalomyelitis (EAE) model led to inhibition of disease progression in a dose-dependent manner. Mice were immunized by subcutaneous injection at day −12 with an emulsified mixture consisting of the synthetic peptide derived from myelin oligodendrocyte glycoprotein ($MOG_{35-55}$) and *M. tuberculosis* mixed with incomplete Freund's adjuvant. Additionally, mice were injected intraperitoneally with pertussis toxin at day −12 and −10. Mice were followed for development of symptoms and scored for EAE clinical signs disease (0=no signs of disease; 1=limp tail or hind limb weakness; 2=limp tail and hind limb weakness; 3=partial hind limb paralysis; 4=complete hind limb paralysis; 5=moribund) every 3 days until day 0. Dosing started at day 0 and ended at day 13 with vehicle (PO, QD), dexamethasone (1 mg/kg, PO QD), and VAV1 MGD (1, 0.1, 0.01 mg/kg, PO, QD). 1 mg/kg VAV1 MGD prevented the progression of EAE disease as it was observed for the mice treated with Dexamethasone at 1 mg/kg (x-axis represents days post immunization initiation [days]; y-axis represents clinical EAE score, [mean SEM]; closed circle: vehicle; solid up triangle, VAV1 MGD 1 mg/kg; closed down triangle, VAV1 MGD 0.1 mg/kg; Open up triangle, VAV1 MGD 0.01 mg/kg; open circle, Dexamethasone 1 mg/kg).
Figure 6B:
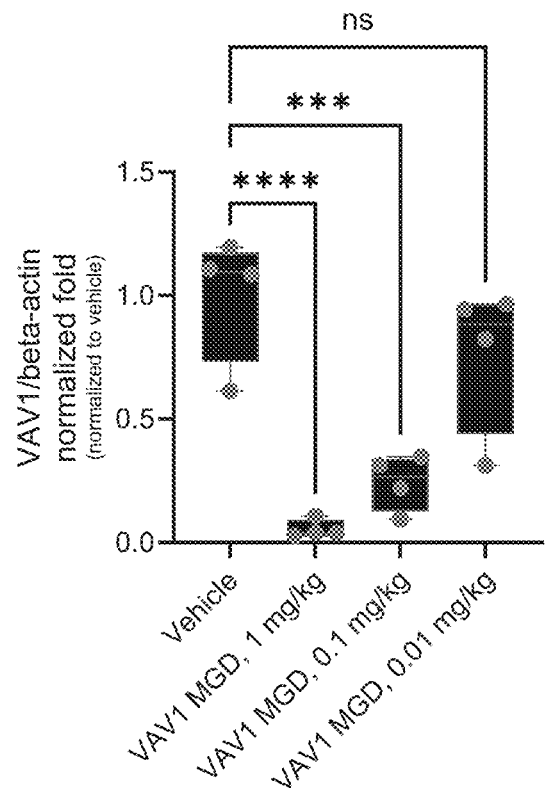
FIG. 6B shows that oral administration of VAV1 MGD degraded VAV1 in the spinal cord in a dose-dependent manner commensurate with reduction in clinical scores. On day 6, 4 mice per group were euthanized, spinal cords were excised and homogenized, and western blot was then used to assess VAV1 levels normalized to β-actin and shown relative to vehicle treated mice. Statistical analysis was performed using a one-way ANOVA with Dunnett's multiple comparisons. ns=not significant, \*\*\*$p<0.001$, \*\*\*\*$p<0.0001$.

To determine the levels of Vav1 in the spinal cord, tissues were excised after euthanasia and snap frozen. For sample preparation, frozen samples were defrosted, 30-100 mg of tissue was placed in a 2 mL microcentrifuge tube, and 400 μL RIPA buffer (Sigma; #R0278) containing 1% protease inhibitor cocktail (Roche; #04693124001) and 1% phosphatase inhibitor cocktail 2 (Sigma; #P5726) was added to each tube. Tissues were ground using a Tissuelyser (Shanghai Jingzin; #JXSTPRP-CL) at 50 hZ for 5 mins. Samples were then incubated on ice for 30 mins. After incubation, samples were centrifuged at 13, 523×g for 10 mins at 4° C., then transferred into new, pre-chilled microcentrifuge tubes. Protein concentrations was determined using a BCA assay kit (Thermo Fisher; #23225)) and samples were diluted to a final concentration of 2 μg/L in RIPA buffer containing 4×LDS sample buffer (Invitrogen; #NP0007) and 10× sample reducing agent (Invitrogen; #NP0009). Once diluted, samples were boiled at 100° C. for 10 mins. Denatured samples were then stored at −80° C. For western blotting, protein samples were defrosted and 15 μL of each sample was loaded in 4-12% Bis-Tris gels (Invitrogen; #WG1402BOX). Electrophoresis was then run in MES running buffer (Invitrogen; #NP0002) at 80 V for 30 mins then 120 V for 90 mins. Proteins were transferred to a nitrocellulose membrane with an iBlot 2 Gel Transfer Device (Invitrogen) using P3 for 7 mins. After transfer, membranes were washed (10 mL 1×TBST, 5 mins, 3 times), blocked (TBS Blocking Buffer (LI-COR; #927-60001), 1 h with agitation, room temperature), and washed again (1×TBST (Bio-Serve; #BS-P-15), 10 mins, 3 times). Vav1 and β-actin were detected by incubation with anti-Vav1 (CST; 2502) and β-actin (CST; #4967) antibodies (1:1000 or 1:2000 respectively in TBS Blocking Buffer containing 0.1% Tween-20 (Sigma; #P2287) at 4° C. overnight with gentle agitation). Membranes were then washed (10 mL 1×TBST, 10 mins, 3 times) and then incubated with secondary detection goat anti-mouse IgG-IRDye 860RD (LI-COR; #926-68070) and goat anti-rabbit IgG-IRDye 800CW (LI-COR; #926-32211) antibodies (both 1:10000 in TBD Blocking Buffer containing 0.1% Tween-20 for 1 h at room temperature with gentle agitation, protected from light). Membranes were then washed (10 mL 1×TBST, 5 mins, 5 times) and protein levels were detected by fluorescence signal using an Odessey CLx Imaging System (LI-COR). Vav1 protein levels were quantified by fluorescence intensity relative to β-actin and normalized to the vehicle treatment group. The results of this study are shown in FIGS. 6A and 6B.

Figure 7:
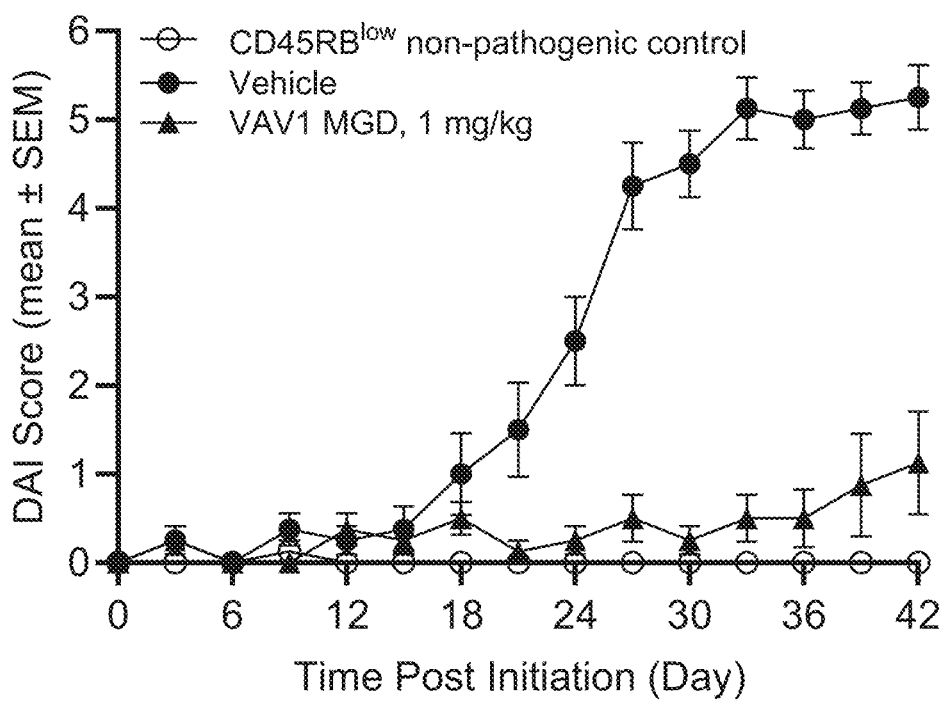
FIG. 7 shows that oral administration of VAV1 MGD in a T-cell transfer induced model of colitis led to inhibition of disease progression. CD17-SCID mice were injected intraperitoneally with $0.5 \times 10^6$ non-pathogenic activated $CD45RB^{low}$ (no disease control group) or pathogenic naïve CD45RBhigh (treatment groups) CD4+ T cells. From the day of cell transfer (day 0), the mice were monitored daily for disease activity index (DAI) comprising weight loss and stool consistency assessment. On day 0, two hours post-cell transfer, mice were treated orally (PO) daily (QD) with vehicle or VAV1 MGD 1 mg/kg for 42 days. 1 mg/kg VAV1 MGD prevented the progression of colitis (x-axis represents days post disease induction and treatment start [days]; y axis represents DAI score [mean±SEM]; open circles, non-pathogenic control; closed black circles, vehicle; closed triangles, VAV1 MGD 1 mg/kg).

Example H: Oral Dosing of VAV1 MGD Inhibits Disease Progression in a T Cell Transfer-Induced Model of Colitis and Reduces Expression of Calprotectin Subunits (S100a8/S100a9) within Colon Tissue in a T Cell Transfer-Induced Model of Colitis To induce colitis, eight CD17-SCID mice were injected intraperitoneally with $0.5 \times 10^6$ non-pathogenic activated CD45RB$^{low}$ (no disease control group) or pathogenic naïve CD45RB$^{high}$ (treatment groups) CD4+ T cells isolated from Balb/c mice. To isolate T cells, spleens were collected, homogenized, and CD4+ T cells were enriched using negative magnetic selection (Stemcell; #19852) as per the manufacturer's instructions. After enrichment, cells were stained with viability stain 780 (BD; #BD-565388), blocked with rat anti-CD16/32 (BD; #BD-553141), stained with rat anti-mouse CD4-APC (BD; #BD-553051) and rat anti-mouse CD45RB-PE (BD; #BD-553101), and then sorted based on CD45RB expression using fluorescence activated cell sorting (FACS). Transfer of naïve CD4+ T cells induced microbe peptide-specific immune responses in the colon leading to colitis-like inflammation. From the day of cell transfer (day 0), the mice were monitored daily for disease activity index (DAI) comprising weight loss and stool consistency assessment. On day 0, two hours post-cell transfer, mice were treated orally (PO) daily with vehicle (10% captisol in water) or VAV1 MGD at 10 or 1 mg/kg with VAV1 MGD (resuspended in 10% captisol in water) for 42 days. A VAV1 MGD formulation was prepared fresh the day of administration by dissolving the VAV1 MGD in 10% captisol in water then vortexed until a clear solution or a uniform suspension was obtained. The results of this study are shown in FIG. 7.

To determine gene expression changes, at the end of the study colons from each group were excised and stored in RNAlater (Sigma; #R0901) at −80° C. Samples were then defrosted, and RNA was extracted using an Rneasy Mini Kit (Qiagen; 74104) as per the manufacturer's instructions. RNA samples were then assessed by NanoDrop (Thermo; #AZY1705823) and Qubit (Inviitrogen; #2322618036279). After RNA quality assessment, samples were assessed using the Nanostring Autoimmune Panel as per the manufacturer's instruction. Briefly, ~100 ng RNA was processed in a hybridization reaction (65° C. for 20 hours) and loaded onto an nCounter Prep Station (NanoString Technologies; #1609D0496) for automated purification and RNA immobilization on an nCounter Master Kit cartridge (NanoString; #NAA-AKIT-012). Cartridges were then transferred to an nCounter Digital Analyzer (NanoString; #1804C0565) and assessed using the nCounter Mouse Autoimmune Profiling Panel (NanoString; #XT-CSO-MAIPI1-12). Quality control (QC) included image QC, binding density, positive control linearity, and positive control limit of detection. Background signal was calculated as twice the standard deviation above the mean of the negative control. The limit of detection was determined by detection of a 0.5 fM positive control probe. For normalization of gene counts, 8 of 20 standard housekeeping genes were assessed using common normalization methods including the mean, geomean, median of ratio. Counts in each sample were then normalized using these parameters. Differential expression of genes (DEG) was then determined on normalized gene counts to provide significant variance between the selected VAV1 MGD and vehicle treated groups. The results of this study are shown in Table 3.

TABLE 3

| Gene | Log2 fold change | Adjusted p value |
| --- | --- | --- |
| S100a9 | −3.40 | $3.67 \times 10^{-9}$ |
| S100a8 | −3.24 | $8.56 \times 10^{-7}$ |

Table 3 shows that expression of the calprotectin subunit genes (S100a9 S100a8) were significantly decreased in VAV1 MGD treated mice compared to vehicle. At the end of the study, colons were excised, homogenized, and assessed for gene expression using the Nanostring Autoimmune Panel. Gene expression was normalized to house keeping genes and differential expression of genes was compared between VAV1 MGD and vehicle treated mice (table shows log 2 fold change and adjusted p value of gene expression in VAV1 MGD compared to vehicle treated mice).

Figure 8A:
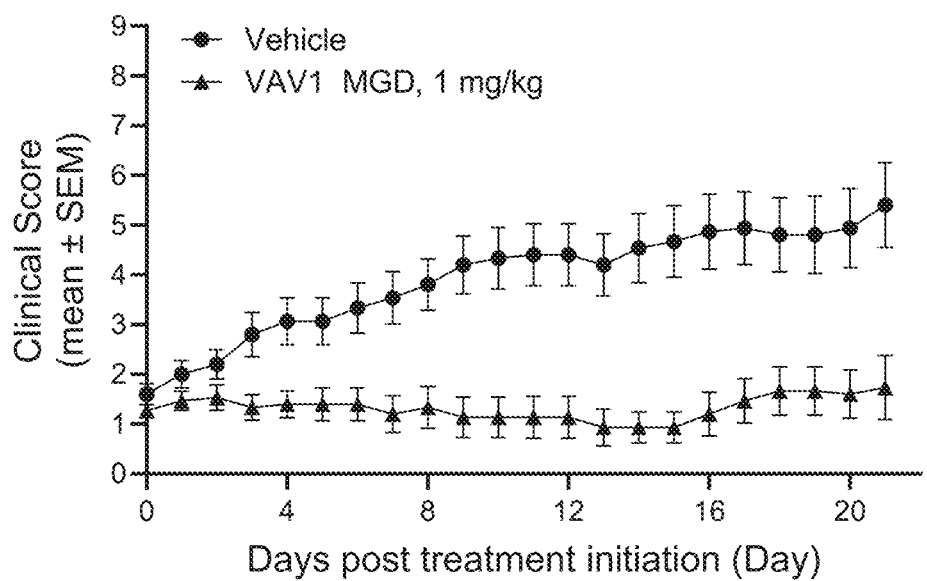
FIG. 8A shows that oral administration of VAV1 MGD in a collagen-induced arthritis model led to inhibition of disease progression. To induce collagen-induced arthritis (CIA), fifteen DBA/1 mice were injected intravenously with an emulsified mixture consisting of 100 μg of chicken collagen II emulsified in incomplete Freund's adjuvant then 18 days later injected subcutaneously with chicken collagen II emulsified in complete Freund's adjuvant. This immunization induces the activation and expansion of collagen specific T- and B-cells that migrate into the paw joints. Once in the paw joints, the activated T-cells induce destruction of the joint and bone tissue, leading to redness and swelling of the phalanges, and B-cells produce antibodies against collagen II. Following the second immunization, mice were monitored daily for clinical signs of disease as follows: 0=erythema and redness; 1=Erythema or mild redness near ear the tarsal, ankle, or metatarsal or one toe with erythema and redness; 2=Ankles and metatarsals are slightly erythematous and swollen with two or more toes with erythema and redness; 3=Moderate erythema and swelling of the ankle, wrists, and metatarsals; 4=Ankles, wrists, metatarsals, and toes are severely red and swollen. Upon disease onset, mice were randomly enrolled into treatment groups: vehicle (PO, QD), anti-TNF (10 mg/kg, IP, Q3D), or VAV1 MGD (1 mg/kg, PO, QD) and treated for 21 days. 1 mg/kg VAV1 MGD prevented the progression of arthritis (x-axis represents days post disease onset and treatment start [days]; y axis represents clinical score [mean±SEM]; circles, vehicle; triangles, VAV1 MGD 1 mg/kg).
Figure 8B:
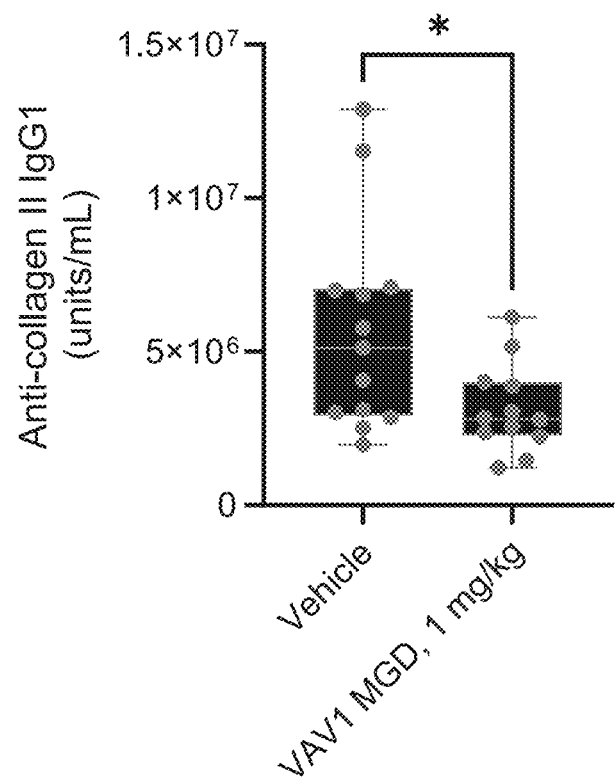
FIG. 8B shows that oral administration of VAV1 MGD in a collagen-induced arthritis model led to decreased production of anti-collagen II IgG1 antibodies. At the end of the study, serum was collected and the amount of anti-collagen II IgG1 antibodies was measured by ELISA. Statistical analysis was performed using an unpaired two-tailed t-test. \*$p<0.05$.

Example I: Oral Dosing of VAV1 MGD Attenuates Disease Progression in a CIA Mouse Model To induce collagen-induced arthritis (CIA), fifteen DBA/1 mice (Shanghai Vital River Laboratory Animal Technology Co; #218) were injected intravenously on days 0 and 21 with a mixture consisting of 100 µg of bovine collagen II (Sichuan University) dissolved in 100 mM acetic acid (Sigma; #A8976) emulsified in complete Freund's adjuvant (CFA; Sigma; #F5881) 2-3 cm from the base of the tail. This immunization induces the activation and expansion of collagen specific T- and B-cells that migrate into the paw joints. Once in the paw joints, the activated T-cells induce destruction of the joint and bone tissue, leading to redness and swelling of the phalanges, and B-cells produce antibodies against collagen II. Following the second immunization, mice were monitored daily for clinical signs of disease as follows: 0=erythema and redness; 1=Erythema or mild redness near ear the tarsal, ankle, or metatarsal or one toe with erythema and redness; 2=Ankles and metatarsals are slightly erythematous and swollen with two or more toes with erythema and redness; 3=Moderate erythema and swelling of the ankle, wrists, and metatarsals; 4=Ankles, wrists, metatarsals, and toes are severely red and swollen. Upon disease onset, mice were randomly enrolled into treatment groups: vehicle (10% captisol in water; PO, QD) or VAV1 MGD (1 mg/kg, PO, QD) and treated for 21 days. VAV1 MGD formulation was prepared fresh the day of administration by dissolving the VAV1 MGD in 10% captisol in water then vortexed until a clear solution or a uniform suspension was obtained. At the end of the study, serum was collected from each mouse and assessed by ELISA for levels of anti-collagen II IgG1 antibodies. ELISA plates containing 100 µL/well of 40 µg/mL bovine collagen II in acetic acid were incubated overnight at 4° C. The solution was then aspirated and washed 3 times with 400 µL Wash Buffer (0.001% Tween-20 in PBS) with 1 min soaking between each wash step. Wells were then blocked using 1% BSA in 1×PBS for 2 hours at room temperature. Well were then washed as previously. A 2-fold serial dilution of IgG1 standard (starting at 2000 units/mL) or prediluted serum (1:5000) were then added to individual wells and incubated for 2 hours at room temperature. Wells were then washed 4 times as described above. To detect antibody binding, 100 µL of secondary antibody (goat anti-mouse IgG1-HRP; Invitrogen; #PA1-74424) was added to watch well and incubated at room temperature for 1 hour. After incubation, 100 µL of TMB substrate (Abcam; #ab171523) was added to each well, incubated for 5-30 mins, then quenced by addition of 100 µL Stop Solution (Abcam; #ab171529). Plates were then read at 450 nm with 570 nm values subtracted from those of 450 nm and analyzed. Using standards, concentrations of each group were calculated at units/mL. The results of this study are shown in FIGS. 8A-8B.

Example J: VAV1 MGD Attenuates BCR-Mediated Activity in Primary Human B-Cells

Figure 10A:
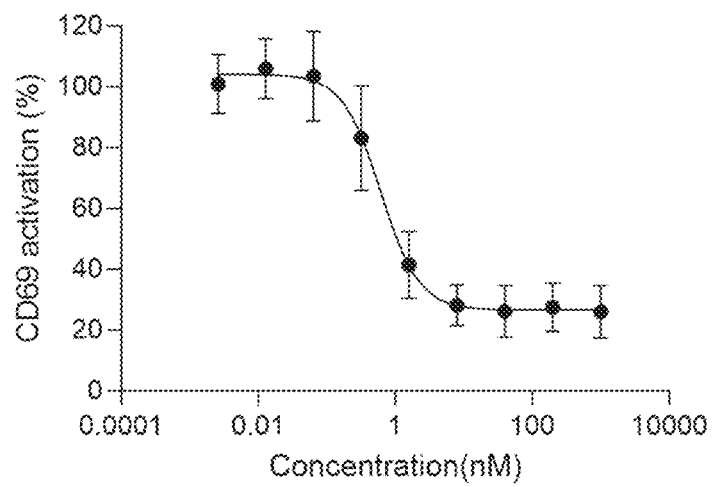
FIGS. 10A-10C show that VAV1 MGD-mediated degradation of VAV1 reduces BCR-mediated CD69 expression and secretion of IL-6 and IgG of primary human B cells. Purified human primary B-cells were treated with VAV1 MGD 24 hrs followed by stimulation with anti-IgM and recombinant human IL-4 for 24 hours (for CD69 expression and IL-6 secretion) or with anti-IgM, BAFF, IL-21, and sCD40L for 5 days (for IgG secretion).
Figure 10B:
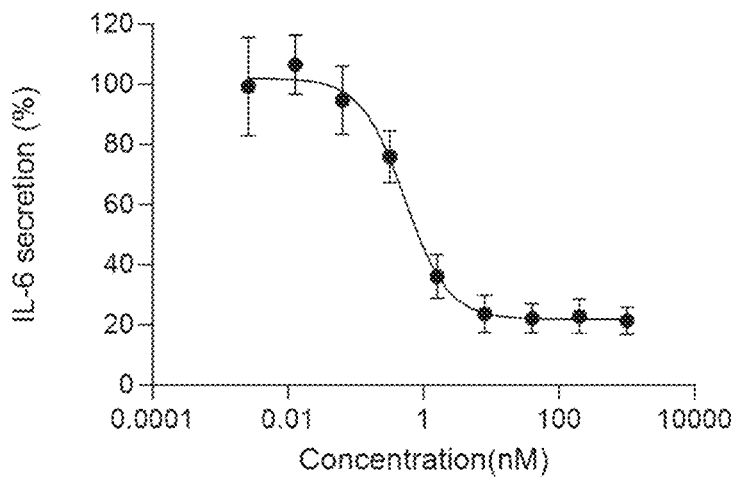
Figure 10C:
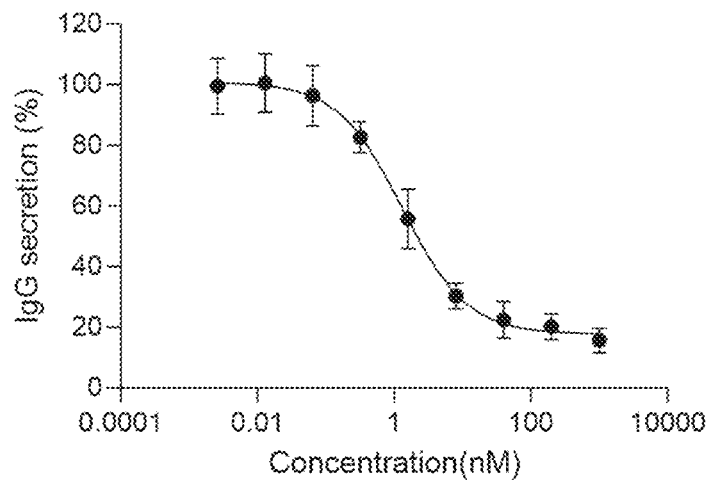

Peripheral blood mononuclear cells (PBMC) were first isolated from human blood leukopaks. Each leukopak was diluted by adding 40 mL of the leukopak contents into 60 mL of 1×PBS into a disposable Nalgene 150 mL bottle. The diluted blood mixture was transferred evenly among three Accupsin tubes (~30 mL/tube). The mixture in Accupsin tubes was centrifuged at 720×g for 20 minutes without brake at room temperature. Peripheral blood mononuclear cells) (PBMC) were collected from the interphase with a sterile transfer pipette and transferred into new 50 mL tubes. PBMCs were washed with 1×PBS and counted using Nexcelom cell counter. From the isolated PBMCs, B cells were isolated using EasySep B cell isolation kit (Stemcell; #17954) following the manufacturer's manual magnetic isolation technique. Cells were treated with VAV1 MGD at the indicated final concentrations or DMSO control and incubated at 37° C. in a humidified incubator with 5% $CO_2$. After treatment, B cells were cultured in RPMI 1640 (Gibco; #22400089) supplemented with 10% fetal bovine serum (Gibco; #A31605-01; Lot #2408990P), 2 mM L-glutamine (Gibco; #35050061), 100 IU/mL penicillin/streptomycin (Gibco; Ser. No. 15/140,122), 1 mM sodium pyruvate (Gibco, #11360070), 0.01 M HEPES (Gibco, #15630080), 1% non-essential amino acids (Gibco; Ser. No. 11/140,050), and 55 µM β-mercaptoethanol (Gibco; #21985023), and stimulated with assay-dependent stimuli. For CD69 expression and IL-6 secretion, B cells were stimulated with anti-IgM (1 µg/mL; Southern Biotech; #2022-14) and recombinant human IL-4 (10 ng/mL; R&D Systems; #305-IL-010) for 24 hrs. For IgG secretion, B cells were stimulated with anti-IgM (1 µg/mL), BAFF (30 ng/mL; R&D Systems; #7537-BF-025), IL-21 (100 ng/mL; PeproTech; #200-2), and soluble CD40L (50 ng/mL; R&D Systems; #6245-C) for 5 days. For CD69 expression, cells were blocked with TruStain FcX (BioLegend; #422302), stained with mouse anti-human CD19-BV421 (BD; #562440; Clone HIB19) and anti-human CD69-APC (BioLegend; 310910; Clone FN50) then, then assessed by flow cytometry. For IL-6 and IgG, supernatants were assessed by Alphalisa as per the manufacturer's instructions. Mean fluorescence intensity (MFI) of CD69-APC was calculated on the CD19+ population using FlowJo (BD). MFI of CD69 for VAV1 MGD treated samples was normalized to DMSO stimulated and unstimulated control. Normalized data were transferred to Prism 9.3.1 (GraphPad) and fitted with a four-parameter model ([Inhibitor] vs. response—Variable slope). The results of this study are shown in FIGS. 10A-10C.

Examples K-L

Examples K-L present biological activity data generated using compound 161 from Table 1. The same compound ("the selected VAV1 MGD") was used in Examples K-L.

Example K: VAV1 MGD Attenuates B-Cell Lymphoma Cell Line Growth

Figure 11:
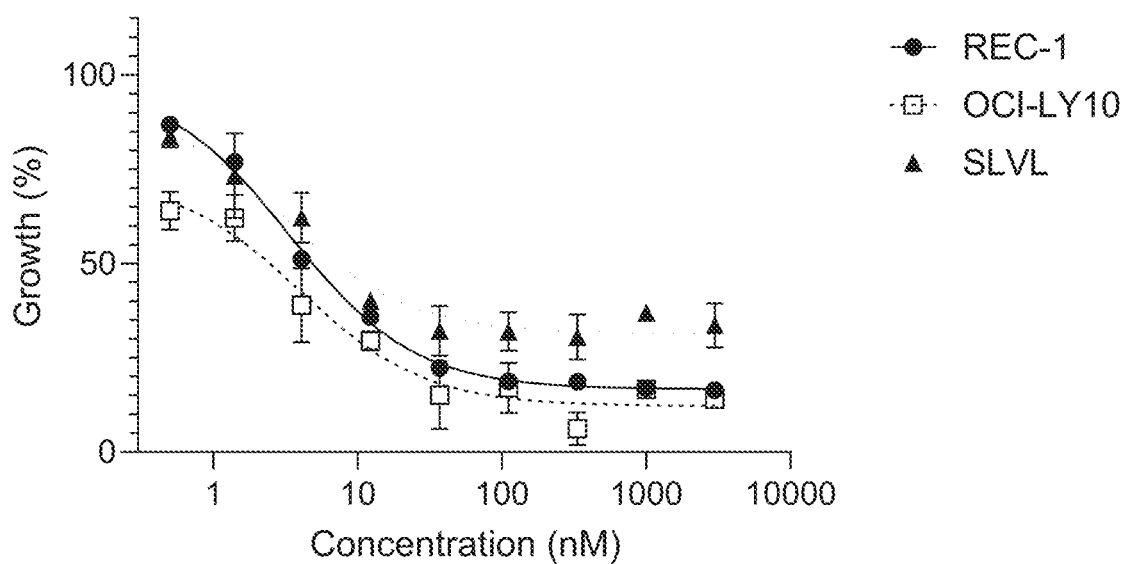
FIG. 11 shows that VAV1 MGD treatment of selected B-cell lymphoma cell lines decrease growth with increasing concentration. REC-1, OCI-LY10, and SLVL cells were treated for 5 days with the indicated concentrations of VAV1 MGD. At 5 days of treatment, cell growth was measured by cell titer glow and normalized to $T_0$ and DMSO.

REC1 (ATCC; #CRL-3004) was cultured in RPMI 1640 (Invitrogen; #11875-093) supplemented with 10% FBS (Invitrogen; #10091-148) and an optimum number of cells were plated in black walled clear bottom 96 well plates (Corning; #3903) at 100 μL per well and grown overnight. OCI-LY10 was cultured in IMDM (HyClone; #SH30228.018) supplemented with 20% FBS (HyClone; #SH30406.05) and 1× Penicillin-Streptomycin (SolarBio; #P1400) and an optimum number of cells were plated into 384 black wall clear bottom well plates (Corning: #3903) at 40 μL per well and grown overnight. SLVL was cultured in alpha-MEM supplemented with 10% FBS and an optimum number of cells were plated into a 384 black wall clear bottom well plates (Corning; #3764). For all cell lines, cell quantification was performed on 8 wells with CellTiter Glo (Promega; #G7573) to determine $Read_0$. Wells were treated in duplicate with the indicated concentrations of the selected VAV1 MGD with a final DMSO concentration of 0.1% and grown for 5 days. At day 5, cell quantification was performed with CellTiter Glo. For calculating growth %, blank read control was subtracted from all wells, then calculated as $100*(Read_{compound}-Read_0)/(Read_{DMSO}-Read_0)$. The results of this study are shown in FIG. 11.

Figure 12:
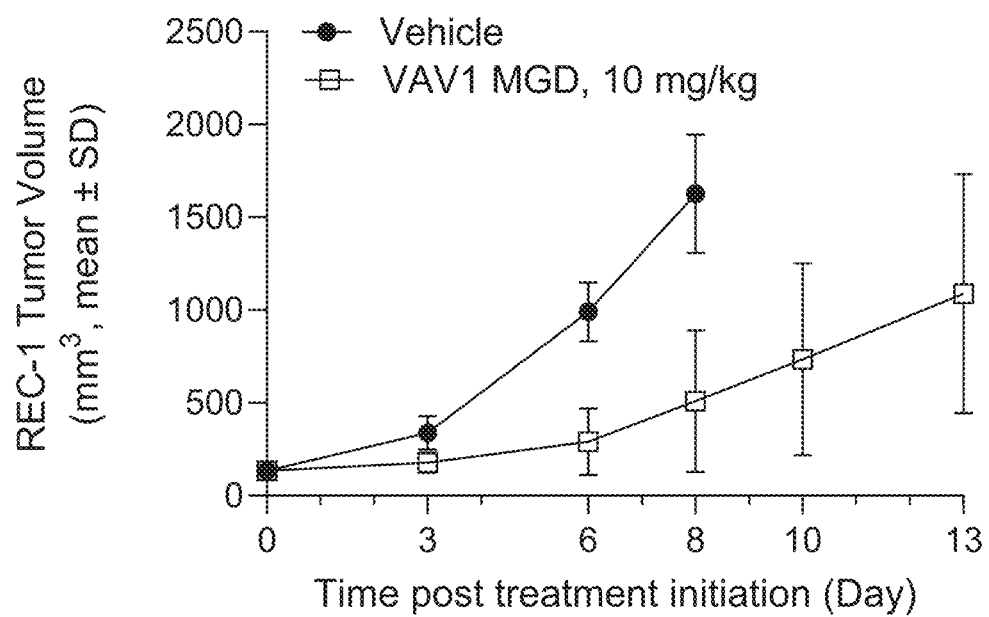
FIG. 12 shows that VAV1 MGD treatment of subcutaneously implanted REC-1 CDX decreases growth in vivo. CB17 SCID mice (10 per group) were inoculated subcutaneously on the right flank with 5×10⁶ REC-1 cells. After the average tumor volume of all mice reached 100-150 mm³, mice were treated with either vehicle or 10 mg/kg VAV1 MGD PO QD. At indicated days post treatment initiation, tumor volume was measured. Mice were sacrificed when tumor volume reached 2000 mm³.

Example L: VAV1 MGD Elicits Anti-Tumor Activity in REC-1 Xenograft Mouse Model To measure growth inhibition of REC-1 cell line (ATCC; #CRL-3004) derived xenograft, CB17 SCID mice (Shanghai Lingchang BioTech Co., Ltd.) were inoculated subcutaneously at the right flank with $5\times10^6$ REC-1 cells in 0.2 ml mixture of base medium with BD Matrigel (BD; 354234) mixed at 1:1. The tumors were grown until the average size was 100-150 mm³, after which 10 mice were chosen for the vehicle group and 10 mice for the VAV1 MGD group through using randomized block design based mainly upon their tumor volumes. For VAV1 MGD, mice were orally dosed daily with 10 mg/kg of VAV1 MGD within the vehicle formulation of 1% methyl cellulose (Sigma; #64632)+0.4% cremaphor (BASF). Tumor volume was measured at days 0, 3, 6, 8, and 10 post treatment initiation. Euthanization was performed when tumor volume exceeded 2000 mm³ and the associated group's analysis was stopped (day 8 for vehicle and day 13 for VAV1 MGD treatment). The results of this study are shown in FIG. 12.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound represented by the formula:

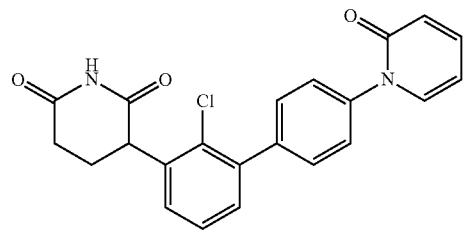

or a pharmaceutically acceptable salt or stereoisomer thereof.

2. A pharmaceutical composition comprising the compound of claim 1, or pharmaceutically acceptable salt or stereoisomer thereof, and a pharmaceutically acceptable excipient.

3. A method of treating a disorder selected from the group consisting of multiple sclerosis, rheumatoid arthritis, myasthenia gravis, Sjogren's syndrome, Grave's disease, asthma, allergic contact dermatitis, rhinitis, contact dermatitis, biliary sclerosis, sclerosing cholangitis, chronic inflammatory demyelinating polyradiculoneuropathy, macular degeneration, systemic lupus erythematosus, Hashimoto's thyroiditis, amyloidosis, inflammatory eye diseases, pemphigus, Chronic Graft vs. Host Disease, lupus nephritis, pulmonary arterial hypertension, vasculitis, ulcerative colitis, psoriasis, cutaneous lupus, axial spondylarthritis, juvenile idiopathic arthritis, and systemic sclerosis in a subject in need thereof, comprising administering to the subject a therapeutically effective amount of the compound of claim 1 or a pharmaceutically acceptable salt or stereoisomer thereof.

4. The method of claim 3, wherein the disorder is selected from the group consisting of ulcerative colitis, rheumatoid arthritis, psoriasis, multiple sclerosis, myasthenia gravis, cutaneous lupus, axial spondylarthritis, and Sjogren's syndrome.

5. The method of claim 3, wherein the disorder is ulcerative colitis or Sjogren's syndrome.

6. A method of treating an autoimmune disorder selected from the group consisting of allergic asthma, atopic dermatitis, allergic rhinitis, conjunctivitis, allergic contact dermatitis, inflammatory bowel disease, Crohn's disease or ulcerative colitis, intrinsic asthma, inflammatory lung injury, inflammatory liver injury, and inflammatory glomerular injury in a subject in need thereof, comprising administering to the subject a therapeutically effective amount of the compound of claim 1 or a pharmaceutically acceptable salt or stereoisomer thereof.

7. The method of claim 6, wherein the autoimmune disorder is selected from the group consisting of inflammatory bowel disease, Crohn's disease or ulcerative colitis, intrinsic asthma, inflammatory lung injury, inflammatory liver injury, and inflammatory glomerular injury.

8. The method of claim 3, wherein the disorder is selected from the group consisting of multiple sclerosis, rheumatoid arthritis, myasthenia gravis, Sjogren's syndrome, Grave's disease, asthma, allergic contact dermatitis, rhinitis, contact dermatitis, biliary sclerosis, sclerosing cholangitis, chronic inflammatory demyelinating polyradiculoneuropathy, macular degeneration, systemic lupus erythematosus, Hashimoto's thyroiditis, amyloidosis, inflammatory eye diseases, pemphigus, Chronic Graft vs. Host Disease, lupus nephritis, pulmonary arterial hypertension, and vasculitis.

9. The method of claim 6, wherein the autoimmune disorder is selected from the group consisting of allergic asthma, atopic dermatitis, allergic rhinitis, conjunctivitis, and allergic contact dermatitis.

10. The compound of claim 1, wherein the compound is represented by:

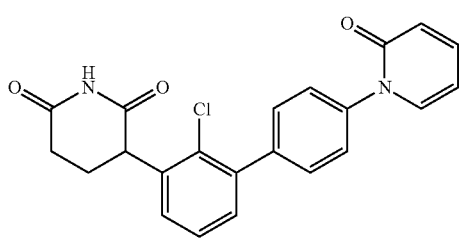

or a pharmaceutically acceptable salt thereof.

11. The compound of claim 1, wherein the compound is represented by:

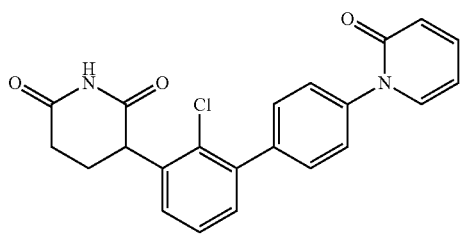 [SMILES: O=C1CCC(c2cccc(-c3ccc(-n4ccccc4=O)cc3)c2Cl)C(=O)N1]

or a pharmaceutically acceptable salt thereof.

12. The compound of claim 1, wherein the compound is in racemic mixture and represented by:

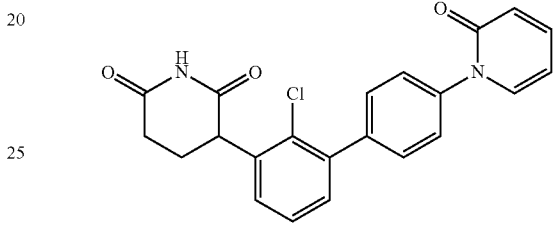

or a pharmaceutically acceptable salt thereof.

* * * * *

UNITED STATES PATENT AND TRADEMARK OFFICE
CERTIFICATE OF CORRECTION

PATENT NO. : 12,257,247 B2
APPLICATION NO. : 18/633272
DATED : March 25, 2025
INVENTOR(S) : Laura Ann McAllister et al.

Page 1 of 1

It is certified that error appears in the above-identified patent and that said Letters Patent is hereby corrected as shown below:

In the Claims

At Claim 10, Column 651, Lines 20-30, replace " 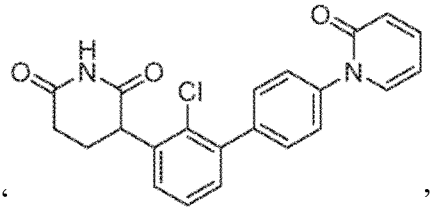 " with

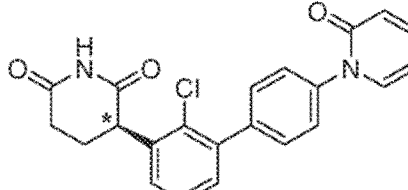

-- 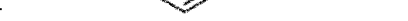 --.

At Claim 11, Column 652, Lines 4-14, replace " 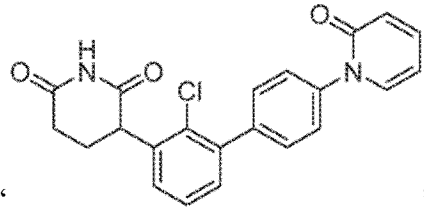 " with

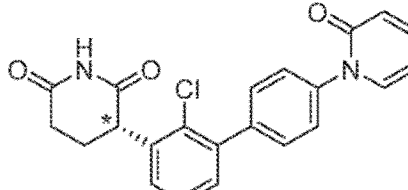

-- 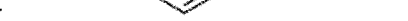 --.

Signed and Sealed this
Twenty-first Day of October, 2025

John A. Squires
*Director of the United States Patent and Trademark Office*